US012758643B2

(12) United States Patent
Liu et al.

(10) Patent No.: US 12,758,643 B2
(45) Date of Patent: Oct. 13, 2026

(54) MODIFIED PROTEINS AND PROTEIN DEGRADERS

(71) Applicant: Cullgen (Shanghai), Inc., Shanghai (CN)

(72) Inventors: Jing Liu, Oradell, NJ (US); Michael Bruno Plewe, San Diego, CA (US); Matthew Randolph Lee, Del Mar, CA (US); Xiaoran Han, Shanghai (CN); Liqun Chen, Shanghai (CN); Chengwei Zhang, Shanghai (CN); Jialiang Wang, Nashville, TN (US)

(73) Assignee: CULLGEN (SHANGHAI), INC., Shanghai (CN)

( * ) Notice: Subject to any disclaimer, the term of this patent is extended or adjusted under 35 U.S.C. 154(b) by 0 days.

(21) Appl. No.: 18/361,422

(22) Filed: Jul. 28, 2023

(65) Prior Publication Data

US 2024/0066136 A1 Feb. 29, 2024

Related U.S. Application Data

(63) Continuation of application No. 17/496,628, filed on Oct. 7, 2021, now abandoned, which is a continuation of application No. PCT/CN2021/096782, filed on May 28, 2021.

(30) Foreign Application Priority Data

May 28, 2020 (WO) ................ PCT/CN2020/092941
Mar. 18, 2021 (WO) ................ PCT/CN2021/081554

(51) Int. Cl.
*A61K 47/64* (2017.01)
*A61K 47/54* (2017.01)

(52) U.S. Cl.
CPC ............ *A61K 47/64* (2017.08); *A61K 47/545* (2017.08)

(58) Field of Classification Search
CPC ...... A61K 47/00; A61K 47/64; A61K 47/545; A61K 38/00; C07K 14/47
See application file for complete search history.

(56) References Cited

U.S. PATENT DOCUMENTS

| | | | | |
|---|---|---|---|---|
| 5,846,514 | A | 12/1998 | Foster et al. | |
| 6,334,997 | B1 | 1/2002 | Foster et al. | |
| 10,816,544 | B2 * | 10/2020 | Chamberlain | C07K 14/47 |
| 11,691,984 | B2 * | 7/2023 | Cravatt | C07D 211/60 435/183 |
| 2002/0103146 | A1 | 8/2002 | Popoff et al. | |
| 2011/0044921 | A1 | 2/2011 | Zhou | |
| 2015/0374678 | A1 | 12/2015 | Chamberlain et al. | |
| 2018/0224435 | A1 | 8/2018 | Chamberlain et al. | |
| 2021/0002296 | A1 | 1/2021 | Mainolfi et al. | |
| 2022/0378923 | A1 | 12/2022 | Yamamoto et al. | |
| 2023/0057177 | A1 | 2/2023 | Liu et al. | |

FOREIGN PATENT DOCUMENTS

| | | | |
|---|---|---|---|
| CN | 1896136 | A | 1/2007 |
| CN | 106177906 | A | 12/2016 |
| CN | 111347747 | A | 6/2020 |
| CN | 112409376 | A | 2/2021 |
| FR | 3015679 | A1 | 6/2015 |
| NO | 20120885 | A1 | 2/2014 |
| RU | 2012151377 | A | 6/2014 |
| WO | WO-2017089763 | A1 | 6/2017 |
| WO | WO-2017185031 | A1 | 10/2017 |
| WO | WO-2018106870 | A1 | 6/2018 |
| WO | WO-2018144832 | A1 | 8/2018 |
| WO | WO-2019034332 | A1 | 2/2019 |
| WO | WO-2019238817 | A1 | 12/2019 |
| WO | WO-2020077278 | A1 | 4/2020 |
| WO | WO-2020079103 | A1 | 4/2020 |
| WO | WO-2020092662 | A1 | 5/2020 |
| WO | WO-2020132189 | A1 | 6/2020 |
| WO | WO-2020169838 | A1 | 8/2020 |
| WO | WO-2020169840 | A1 | 8/2020 |
| WO | WO-2020173440 | A1 | 9/2020 |
| WO | WO-2020207396 | A1 | 10/2020 |
| WO | WO-2020219650 | A1 | 10/2020 |
| WO | WO-2020247537 | A1 | 12/2020 |
| WO | WO-2021055530 | A1 | 3/2021 |
| WO | WO-2021061151 | A1 | 4/2021 |
| WO | WO-2021074414 | A1 | 4/2021 |
| WO | WO-2021074418 | A1 | 4/2021 |
| WO | WO-2021239117 | A1 | 12/2021 |
| WO | WO-2023061440 | A1 | 4/2023 |

OTHER PUBLICATIONS

Yeh et al, PNAS, pp. E2337-E2746. (Year: 2012).*
AbCam product page and datasheet for Anti-DDB1 antibody (ab9194) (2002).
Abramic et al. Purification of an ultraviolet-inducible, damage-specific DNA-binding protein from primate cells. J Biol Chem 266:22493-22500 (1991).
Behan et al. Prioritization of cancer therapeutic targets using CRISPR-Cas9 screens. Nature 568:511-516 (2019).
Berge et al. Pharmaceutical Salts. Journal of Pharmaceutical Sciences 66(1):1-19 (Jan. 1977).

(Continued)

*Primary Examiner* — D. L. Jones
(74) *Attorney, Agent, or Firm* — WILSON SONSINI GOODRICH & ROSATI

(57) ABSTRACT

Provided herein are compounds, pharmaceutical compositions, and methods for binding or degrading target proteins. Further provided herein are compounds having a DNA damage-binding protein 1 (DDB1) binding moiety. Some such embodiments include a linker. Some such embodiments include a target protein binding moiety. Further provided herein are ligand-DDB1 complexes. Further provided herein are in vivo modified DDB1 proteins.

20 Claims, 19 Drawing Sheets

Specification includes a Sequence Listing.

(56) References Cited

OTHER PUBLICATIONS

Brennan et al. The somatic genomic landscape of glioblastoma. Cell 155:462-477 (2013).
Casimiro et al. Kinase-independent role of cyclin D1 in chromosomal instability and mammary tumorigenesis. Oncotarget 6:8525-8538 (2015).
Chauvin et al. Involvement of human release factors eRF3a and eRF3b in translation termination and regulation of the termination complex formation. Mol. Cell Biol. 25:5801-5811 (2005).
Chen et al. USP15 suppresses tumor immunity via deubiquitylation and inactivation of TET2. Sci Adv 6:eabc9730 (2020).
Coqueret. Linking cyclins to transcriptional control. Gene 299:35-55 (2002).
Diaz-Rodriguez et al., Modulation of cereblon levels by anti-myeloma agents. Leuk Lymphoma. 57(1):167-176 (2016).
Evans. Synthesis of radiolabeled compounds. J Radioanal Chem 64(1-2):9-32 (1981).
Groh et al. The antiobesity factor WDTC1 suppresses adipogenesis via the CRL4WDTC1 E3 ligase. EMBO Report 17(5):638-647 (2016).
Guan et al. Growth suppression by p18, a p16INK4/MTS1- and p14INK4B/MTS2-related CDK6 inhibitor, correlates with wild-type pRb function. Genes Dev 8:2939-2952 (1994).
Guo et al. DCAF1 controls T-cell function via p53-dependent and -independent mechanisms. Nat Commun. 7:10307 (2016).
Han et al. CRL4 DCAF1/VprBP E3 ubiquitin ligase controls ribosome biogenesis, cell proliferation, and development. Sci Adv 6:eabd6078 (2020).
He et al. DDB1 functions as a linker to recruit receptor WD40 proteins to CUL4-ROC1 ubiquitin ligases. Genes Dev. 20:2949-2954 (2006).
Hirschfeld et al. A constitutive damage-specific DNA-binding protein is synthesized at higher levels in UV-irradiated primate cells. Mol Cell Biol 10:2041-2048 (1990).
Hsu et al. EED-Targeted PROTACs Degrade EED, EZH2, and SUZ12 in the PRC2 Complex. Cell Chemical Biol. 27:p. 41-46.e17 (2019).
Hu et al. An evolutionarily conserved function of proliferating cell nuclear antigen for Cdt1 degradation by the Cul4-Ddb1 ubiquitin ligase in response to DNA damage. J Biol Chem 281(7):3753-3756 (2006).
Hu et al. Targeted ubiquitination of CDT1 by the DDB1-CUL4A-ROC1 ligase in response to DNA damage. Nat Cell Biol 6(10):1003-1009 (2004).
Hu et al. WD40 protein FBW5 promotes ubiquitination of tumor suppressor TSC2 by DDB1-CUL4-ROC1 ligase. Genes Dev. 22:866-871 (2008).
Jackson et al. CRL4s: the CUL4-RING E3 ubiquitin ligases. Trends Biochem Sci 34(11):562-570 (2009).
Jirawatnotai et al. A function for cyclin D1 in DNA repair uncovered by protein interactome analyses in human cancers. Nature 474:230-234 (2011). 10.1038/nature10155.
Kabalka et al. The Synthesis of Radiolabeled Compounds via Organometallic Intermediates. Tetrahedron 45(21):6601-6621 (1989).
Kassmeier et al. VprBP binds full-length RAG1 and is required for B-cell development and V(D)J recombination fidelity. EMBO J. 31:945-958 (2012).
Kim et al. CRL4A-FBXW5-mediated degradation of DLC1 Rho GTPase-activating protein tumor suppressor promotes non-small cell lung cancer cell growth. PNAS USA 110(42):16868-16873 (2013).
Kim et al. Targeted disruption of the EZH2-EED complex inhibits EZH2-dependent cancer. Nat. Chem. Biol. 9:643-650 (2013).
Kim et al. Vpr-binding protein antagonizes p53-mediated transcription via direct interaction with H3 tail. Mol Cell Biol. 32(4):783-796 (2012).
Koboldt et al. Comprehensive molecular portraits of human breast tumours. Nature 490:61-70 (2012).
Kotake et al. DDB1-CUL4 and MLL1 mediate oncogene-induced p16INK4a activation. Cancer Res. 69:1809-1814 (2009).
Lee et al. Cell type-dependent requirement for PIP box-regulated Cdt1 destruction during S phase. Mol Biol Cell 21:3639-3653 (2010).
Lee et al. Characterization of *Arabidopsis* and rice DWD proteins and their roles as substrate receptors for CUL4-RING E3 ubiquitin ligases. Plant Cell 20:152-157 (2008).
Liu et al., TTF-1/NKX2-1 binds to DDB1 and confers replication stress resistance to lung adenocarcinomas. Oncogene 36(26):3740-3748 (2017).
Lv et al., Discovery of a molecular glue promoting CDK12-DDB1 interaction to trigger cyclin K degradation. Elife 9:e59994 [1-34] (2020).
Lv et al. Vpr Targets TET2 for Degradation by CRL4(VprBP) E3 Ligase to Sustain IL-6 Expression and Enhance HIV-1 Replication. Mol Cell 70:961-970 (2018).
Ma et al. Discovery of a first-in-class EZH2 selective degrader. Nat. Chem. Biol. 16:214-222 (2020).
Matsushime et al. Colony-stimulating factor 1 regulates novel cyclins during the G1 phase of the cell cycle. Cell 65:701-713 (1991).
Matsushime et al. Identification and properties of an atypical catalytic subunit (p34PSK-J3/cdk4) for mammalian D type G1 cyclins. Cell 71:323-334 (1992).
Mayor-Ruiz et al., Rational discovery of molecular glue degraders via scalable chemical profiling. Nat. Chem. Biol. 16:1199-1207 (2020).
McCall et al. Human immunodeficiency virus type 1 Vpr-binding protein VprBP, a WD40 protein associated with the DDB1-CUL4 E3 ubiquitin ligase, is essential for DNA replication and embryonic development. Mol Cell Biol 28(18):5621-5633 (2008).
Mo et al. SIRT7 deacetylates DDB1 and suppresses the activity of the CRL4 E3 ligase complexes. FEBS J. 284(21):3619-3636 (2017).
Motokura et al. A novel cyclin encoded by a bcl1-linked candidate oncogene. Nature 350:512-515 (1991).
Murphy et al. Hepatitis B Virus X Protein Promotes Degradation of SMC5/6 to Enhance HBV Replication. Cell Reports 16(11):2846-2854 (2016).
Musgrove et al. Cyclin D as a therapeutic target in cancer. Nat Rev Cancer 11:558-572 (2011).
Nakagawa et al. CRL4(VprBP) E3 ligase promotes monoubiquitylation and chromatin binding of TET dioxygenases. Mol Cell 57(2):247-260 (2015).
Nakagawa et al. X-linked mental retardation gene CUL4B targets ubiquitylation of H3K4 methyltransferase component WDR5 and regulates neuronal gene expression. Mol Cell 43(3):381-391 (2011).
PCT/CN2021/096782 International Search Report and Written Opinion dated Aug. 13, 2021.
PCT/CN2022/125080 International Search Report and Written Opinion dated Jan. 18, 2023.
Ran et al. Genome engineering using the CRISPR-Cas9 system. Nat Protoc 8:2281-2308 (2013).
Sekiba et al., Inhibition of HBV transcription from cccDNA with nitazoxanide by targeting the HBx-DDB1 interaction. Cell Mol Gastroenterol Hepatol. 7(2):297-312 (2019).
Serrano et al. A new regulatory motif in cell-cycle control causing specific inhibition of cyclin D/CDK4. Nature 366:704-707 (1993).
Sherr. Cancer cell cycles. Science 274:1672-1677 (1996).
Silfhout et al. Variants in CUL4B are Associated with Cerebral Malformations. Human Mutat 36(1):106-117 (2015).
Slabicki et al. The CDK inhibitor CR8 acts as a molecular glue degrader that depletes cyclin K. Nature 585:293-297 (2020).
Stabicki et al., The CDK inhibitor CR8 acts as a molecular glue degrader that depletes cyclin K. Nature 585(7824):293-297 (2020).
Su. Disruption of HBx-DDB1 by NTZ: new mechanistic insight into an old drug with broad anti-infective activities. Cell Mol Gastroenterol Hepatol. 7(2):289-290 (2019).
The Cancer Genome Atlas Network. Comprehensive genomic characterization of head and neck squamous cell carcinomas. Nature 517:576-582 (2015a).

(56) References Cited

OTHER PUBLICATIONS

The Cancer Genome Atlas Network. Comprehensive molecular characterization of urothelial bladder carcinoma. Nature 507:315-322 (2014a).
The Cancer Genome Atlas Network. Comprehensive molecular profiling of lung adenocarcinoma. Nature 511:543-550 (2014b).
The Cancer Genome Atlas Network et al. Comprehensive and Integrative Genomic Characterization of Hepatocellular Carcinoma. Cell 169:1327-1341e23 (2017).
The Cancer Genome Atlas Network et al. Integrated genomic characterization of oesophageal carcinoma. Nature 541:169-175 (2017).
The Cancer Genome Atlas Network. Genomic Classification of Cutaneous Melanoma. Cell 161:1681-1696 (2015b).
The Cancer Genome Atlas Network. Integrated genomic analyses of ovarian carcinoma. Nature 474:609-615 (2011).
U.S. Appl. No. 17/496,628 Office Action dated Jun. 14, 2022.
U.S. Appl. No. 17/496,628 Office Action dated Mar. 1, 2022.
U.S. Appl. No. 17/496,628 Office Action dated Mar. 30, 2023.
Wang et al. Histone H3 and H4 ubiquitylation by the CUL4-DDB-ROC1 ubiquitin ligase facilitates cellular response to DNA damage. Mol Cell 22(3):383-394 (2006).
WEINBERG. The retinoblastoma protein and cell cycle control. Cell 81:323-330 (1995).
Xie et al., Pyruvate kinase M2 interacts with DNA damage-binding protein 2 and reduces cell survival upon UV irradiation. Biochem Biophys Res Commun. 467(2):427-433 (2015).
Xiong et al. D type cyclins associate with multiple protein kinases and the DNA replication and repair factor PCNA. Cell 71:505-514 (1992).
Xiong et al. Human D-type cyclin. Cell 65:691-699 (1991).
Yang et al., Small molecule NSC1892 targets the CUL4A/4B-DDB1 interactions and causes impairment of CRL4DCAF4 E3 ligases to inhibit colorectal cancer cell growth. Int J Biol Sci. 16(6):1059-1070 (2020).
Yeh et al. Damaged DNA induced UV-damaged DNA-binding protein (UV-DDB) dimerization and its roles in chromatinized DNA repair. Pnas USA 109(41):E2737-E2746 (2012).
Yu et al. Single subunit degradation of WIZ, a lenalidomide- and pomalidomide-dependent substrate of E3 ubiquitin ligase CRL4CRBN. BioRxiv 2019:595389 (2019).
Zha et al. A Non-Canonical Function of Gβ as a Subunit of E3 Ligase in Targeting GRK2 Ubiquitylation. Mol Cell 58(5):794-803 (2015).
Zha et al. Hypertension-associated C825T polymorphism impairs the function of Gβ3 to target GRK2 ubiquitination. Cell Discovery 2:16005 (2016).
Zhang et al. *Arabidopsis* DDB1-CUL4 Associated FACTOR1 Forms a Nuclear E3 Ubiquitin Ligase with DDB1 and CUL4 That Is Involved in Multiple Plant Developmental Processes. Plant Cell 20:1437-1455 (2008).
Zou et al. The novel protein homeostatic modulator BTX306 is active in myeloma and overcomes bortezomib and lenalidomide resistance. J. Mol. Med. 98:1161-1173 (2020).
Berge, S M et al. Pharmaceutical Salts. Journal of Pharmaceutical Sciences 66(1):1-19 (1977).
Dean, et al. Recent Advances in the Synthesis and Applications of Radiolabeled Compounds for Drug Discovery and Development. Current Pharmaceutical Design 6(10):1-2 (2000).
Matyskiela et al. A cereblon modulator (CC-220) with improved degradation of Ikaros and Aiolos. J Med Chem 61(2):535-542 (2018).
Rodriguez-Gonzalez, A. et al. Targeting steroid hormone receptors for ubiquitination and degradation in breast and prostate cancer. 27(57):7201-7211 (2008).
Schapira, Matthieu et al. Targeted protein degradation: expanding the toolbox. Nat Rev Drug Discovery 18(12):949-963 (2019).
Stahl, Heinrich P et al. Usage frequency of acids and bases for forming drug salts. Handbook of Pharmaceutical Salts. Verlag Helvetica Chimica Acta, Zurich: pp. 329-350 (2002).
Wang, Yang et al. Degradation of proteins by PROTACs and other strategies. Acta Pharm Sin B. 10(2):207-238 (2020).
Watson, Edmond R. et al. Molecular glue CELMOD compounds are regulators of cereblon conformation. Science 378(6619):549-553 (2022).
Co-pending U.S. Appl. No. 18/700,898, inventors Liu; Jing et al., filed Apr. 12, 2024.
Qui, Xing et al. Chemoselective Synthesis of Lenalidomide-Based PROTAC Library Using Alkylation Reaction. Org Lett 21(10):3838-3841 (2019) (With Supplemental Information).

* cited by examiner

Compound D-2

Compound D-7

Compound D-13

Compound D-48

Compound D-49

| Cell line | LNCaP | | | | | | | | | | | | | |
|---|---|---|---|---|---|---|---|---|---|---|---|---|---|---|
| Compound | Compound D-2 (500nM) | | | | | | | Compound D-13 (500nM) | | | | | | |
| Time (h) | 0 | 1 | 2 | 4 | 8 | 16 | 24 | 0 | 1 | 2 | 4 | 8 | 16 | 24 |
| Lane | 1 | 2 | 3 | 4 | 5 | 6 | 7 | 8 | 9 | 10 | 11 | 12 | 13 | 14 |

MODIFIED PROTEINS AND PROTEIN DEGRADERS

CROSS-REFERENCE

This application is a continuation of U.S. application Ser. No. 17/496,628, filed Oct. 7, 2021, which is a continuation of International Application No. PCT/CN2021/096782, filed May 28, 2021, which claims the benefit of International Application No. PCT/CN2020/092941, filed May 28, 2020, and International Application No. PCT/CN2021/081554, filed Mar. 18, 2021, each of which are incorporated herein by reference in their entireties.

SEQUENCE LISTING

The instant application contains a Sequence Listing which has been submitted electronically in XML format and is hereby incorporated by reference in its entirety. Said XML copy, created on Jul. 27, 2023, is named 54922-705_302_SL.xml and is 11,283 bytes in size.

BACKGROUND

A need exists for ligands for binding to, or modifying proteins. A need exists in the medicinal arts for selective degradation of target proteins.

SUMMARY

Described herein are modified proteins and protein-ligand complexes. The modified proteins and protein-ligand complexes of some embodiments are useful for biotechnology applications such as selective degradation of a target protein, molecular glues, or anti-microbial drugs.

Described herein are ligands that can bind to DD1. The DDB1 binding ligands are useful for biotechnology applications such as selective degradation of a target protein, molecular glues, or anti-microbial drugs Disclosed herein, in some embodiments, are ligand-DNA damage-binding protein 1 (DDB1) complexes formed by binding a DDB1 protein directly to a ligand, the ligand comprising a DDB1 binding moiety. In some embodiments, the DDB1 binding moiety is bound to a binding region on the DDB1 protein. In some embodiments, the binding region on the DDB1 protein comprises a beta propeller C (BPC) domain. In some embodiments, the binding region on the DDB1 protein comprises atop face of the BPC domain. In some embodiments, the binding region on the DDB1 protein comprises one or more of the following DDB1 residues: ARG327, LEU328, PRO358, ILE359, VAL360, ASP361, GLY380, ALA381, PHE382, SER720, ARG722, LYS723, SER738, ILE740, GLU787, TYR812, LEU814, SER815, ALA834, VAL836, ALA841, ALA869, TYR871, SER872, MET910, LEU912, TYR913, LEU926, TRP953, SER955, ALA956, ASN970, ALA971, PHE972, PHE1003, ASN1005, VAL1006, or VAL1033. In some embodiments, one or more of the following DDB1 residues are involved in the binding between the DDB1 protein and the ligand: ARG327, LEU328, PRO358, ILE359, VAL360, ASP361, GLY380, ALA381, PHE382, SER720, ARG722, LYS723, SER738, ILE740, GLU787, TYR812, LEU814, SER815, ALA834, VAL836, ALA841, ALA869, TYR871, SER872, MET910, LEU912, TYR913, LEU926, TRP953, SER955, ALA956, ASN970, ALA971. PHE972, PHE1003, ASN1005, VAL1006, or VAL1033. In some embodiments, the binding between the DDB1 binding moiety and the DDB1 protein is non-covalent. In some embodiments, the binding between the DDB1 protein and the ligand comprises a binding affinity with an equilibrium dissociation constant (Kd) below 100 μM, a Kd below 90 μM, a Kd below 80 μM, a Kd below 70 μM, a Kd below 60 μM, below 50 μM, a Kd below 45 μM, a Kd below 40 μM, a Kd below 35 μM, a Kd below 30 μM, a Kd below 25 μM, a Kd below 20 μM, a Kd below 15 μM, a Kd below 14 μM, a Kd below 13 μM, a Kd below 12 μM, a Kd below 11 μM, a Kd below 10 μM, a Kd below 9 μM, a Kd below 8 μM, a Kd below 7 μM, a Kd below 6 μM, a Kd below 5 μM, a Kd below 4 μM, a Kd below 3 μM, a Kd below 2 μM, or a Kd below 1 μM. In some embodiments, the binding between the DDB1 protein and the ligand comprises a binding affinity with a $Kd<20$ uM, a Kd from 20-100 uM, or a $Kd>100$ uM. In some embodiments, the binding between the DDB1 binding moiety and the DDB1 protein is covalent. In some embodiments, the DDB1 ligand is a small molecule. In some embodiments, the DDB1 ligand is synthetic. In some embodiments, the DDB1 binding moiety comprises a structure of Formula (II):

Formula (II)

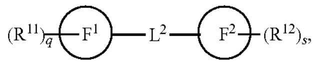

wherein $F^1$ is aryl, heteroaryl, carbocyclyl, or heterocyclyl; $F^2$ is aryl, heteroaryl, carbocyclyl, or heterocyclyl; $L^2$ is a bond, —C(═O)$NR^{13}$—, —$NR^{13}$C(═O)—, —C(═O)—, —C(═S)—, —S—, —S(═O), —$S(═O)_2$—, —S(═O)$NR^{13}$—, —$NR^{13}$S(═O)—, —$S(═O)_2NR^{13}$—, —$NR^{13}S(═O)_2$—, —O—, $C_1$-$C_4$ alkyl, $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —$S(═O)_2R^d$, —$S(═O)_2NR^cR^d$, —C(═O)$R^b$, —$CO_2R^a$, —C(═O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$; each $R^{11}$ and $R^{12}$ is independently a bond, hydrogen, halogen, —CN, —$R^a$, —$OR^a$, —$SR^a$, —S(═O)$R^b$, —$NO_2$, —$NR^cR^d$, —$S(═O)_2R^d$, —$NR^aS(═O)_2R^d$, —$S(═O)_2NR^cR^d$, —C(═O)$R^b$, —OC(═O)$R^b$, —$CO_2R^a$, —$OCO_2R^a$, —C(═O)$NR^cR^d$, —OC(═O)$NR^cR^d$, —$NR^a$C(═O)$NR^cR^d$, —$NR^a$C(═O)$R^b$, —$NR^a$C(═O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$, and optionally wherein at least one $R^{11}$ is a bond attached to a linker; each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$; each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe. or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$; each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen. $C_1$-$C_6$ alkyl, $C_1$-$C_6$ haloalkyl, —OH, —OMe, or —$NH_2$; each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$; q is 1-5; and s is 1-5; or a pharmaceutically acceptable salt thereof. In some embodiments, the DDB1 binding moiety comprises a structure of Formula (IIa):

Formula (IIa)

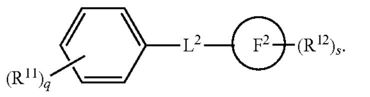

In some embodiments, $F^2$ is heteroaryl. In some embodiments, $F^2$ is a five membered or six membered ring heteroaryl. In some embodiments, $F^2$ is triazolyl, tetrazolyl, furanyl, pyrrolyl, thiazolyl, oxazolyl, isoxazolyl, imidazolyl, pyrazolyl, thiadiazolyl, or oxadiazolyl. In some embodiments, the DDB1 binding moiety comprises a structure of Formula (IIb):

Formula (IIb)

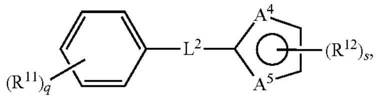

wherein $A^4$ and $A^5$ are each independently $CR^{12}$, S, N, or O, wherein at least one of $A^4$ or $A^5$ is N, O, or S. In some embodiments, $A^4$ is N and $A^5$ is S. In some embodiments, the DDB1 binding moiety comprises the structure

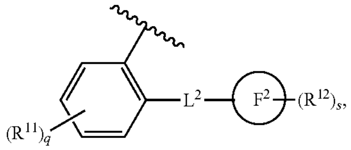

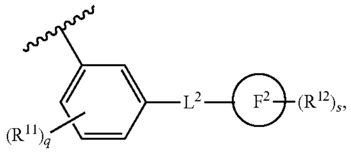

or

-continued

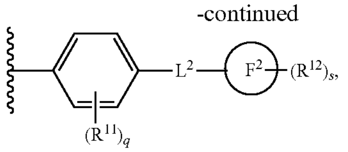

wherein the wavy line indicates an optional point of attachment to a linker or a target protein binding moiety. In some embodiments, $R^{12}$, at each occurrence, is independently selected from —$NO_2$, halogen, methyl, halomethyl, phenyl, isopropyl, cyclopropyl, $SO_2CH_3$, or —CN. In some embodiments, $L^2$ is —$NR^cC$(═O)— or —C(═O)$NR^c$—. In some embodiments, $R^c$ is H, $CH_3$, isopropyl, or cyclopropyl. In some embodiments, q is 1 or 2. In some embodiments, s is 1 or 2. In some embodiments, the DDB1 binding moiety comprises any of compounds B-1 to B-176 as shown in Table 1. In some embodiments, the DDB1 binding moiety comprises

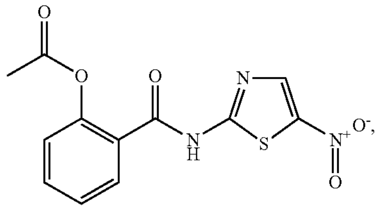

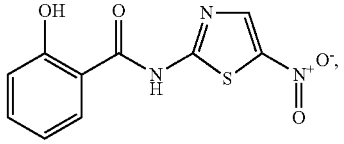

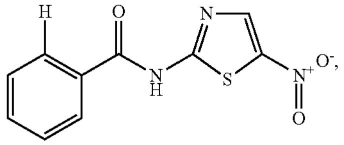

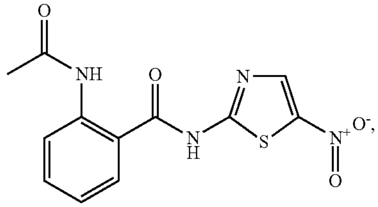

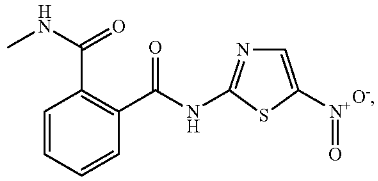

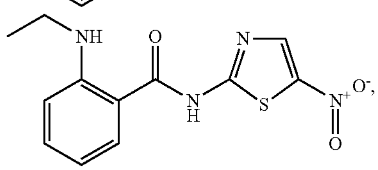

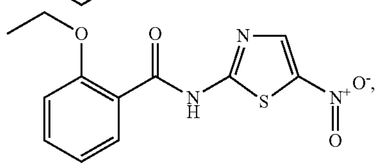

-continued
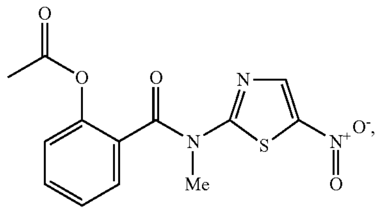
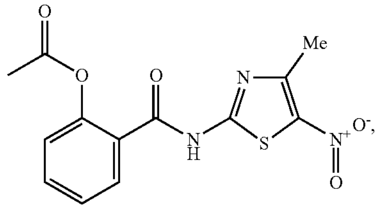
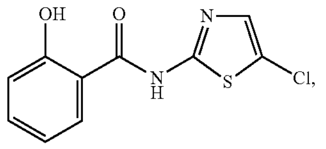
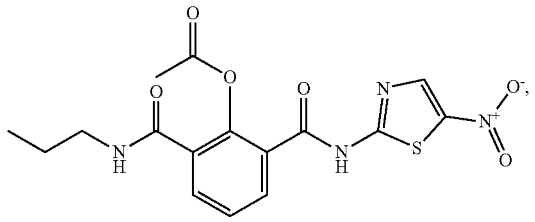
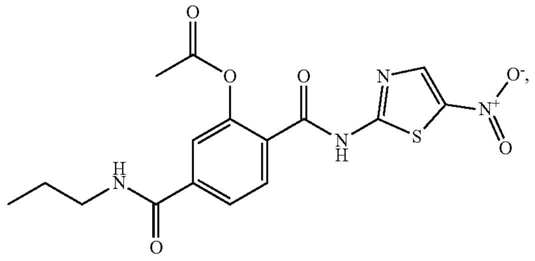
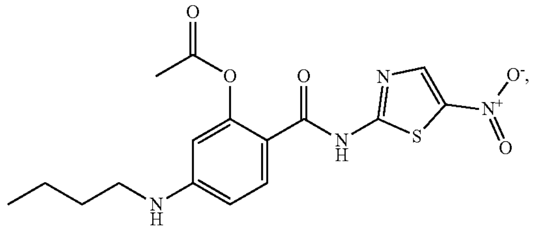
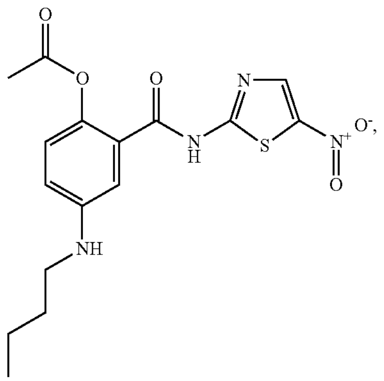
-continued
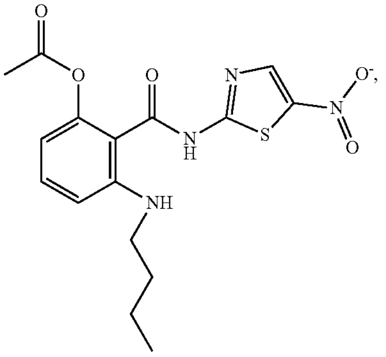
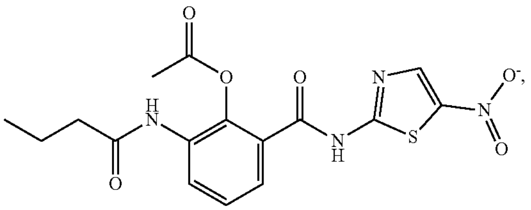
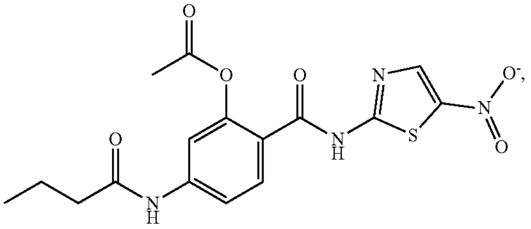
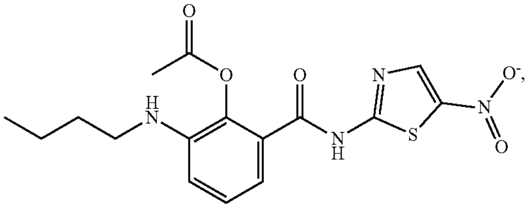
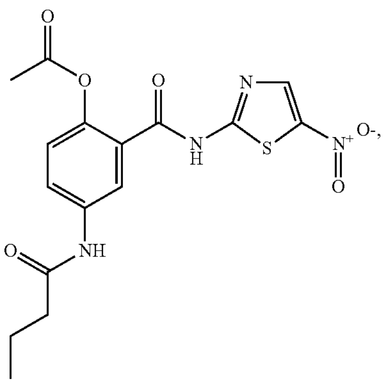

-continued
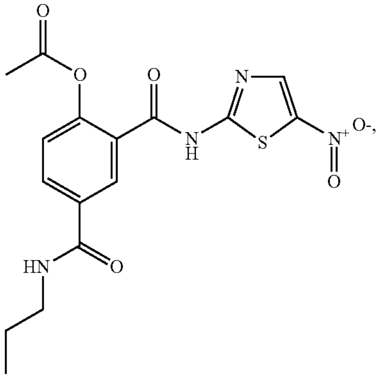
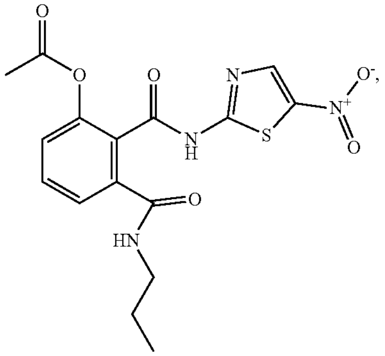
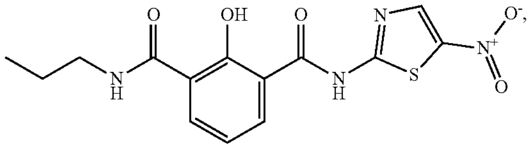
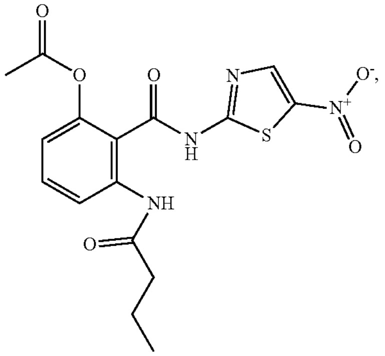
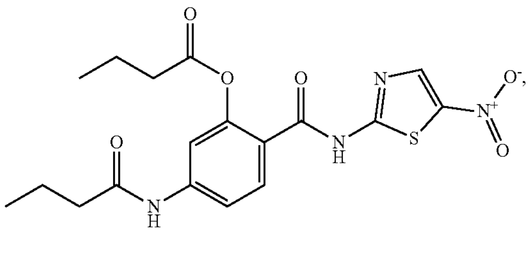
-continued
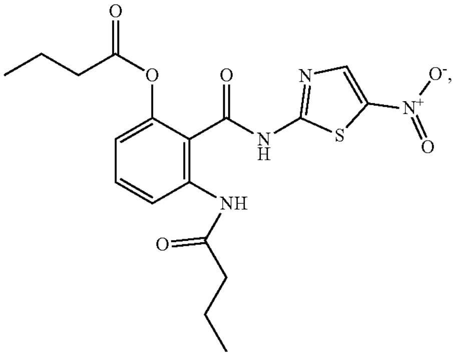
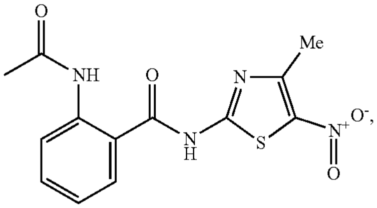
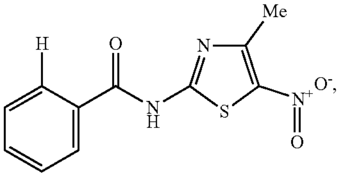
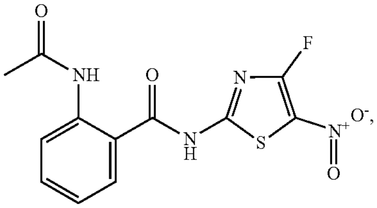
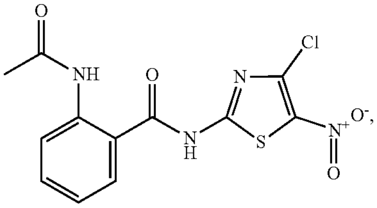
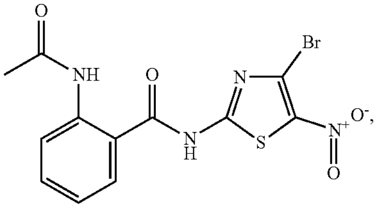
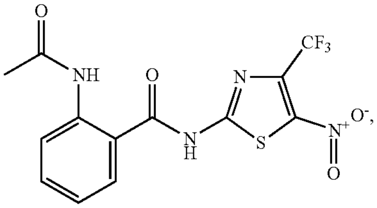

-continued
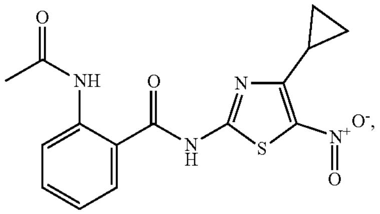
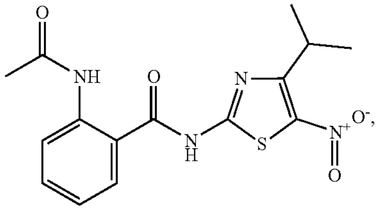
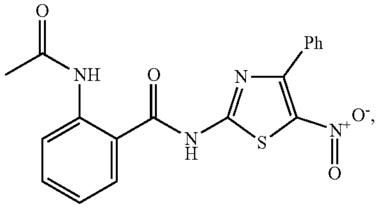
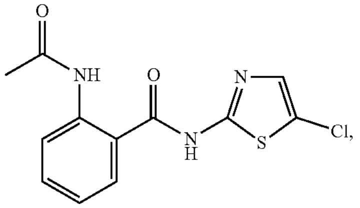
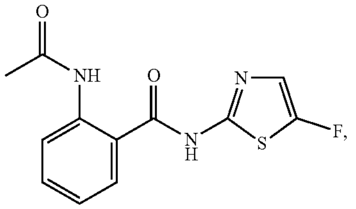
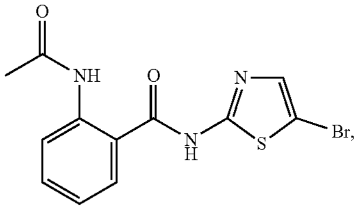
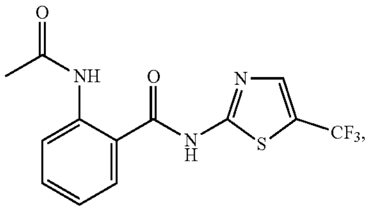
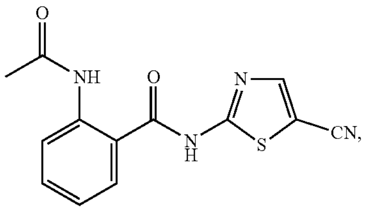
-continued
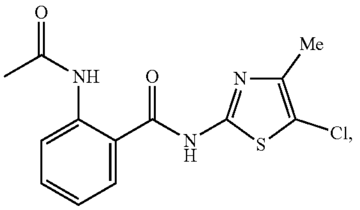
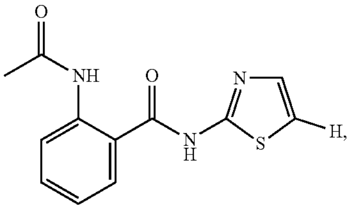
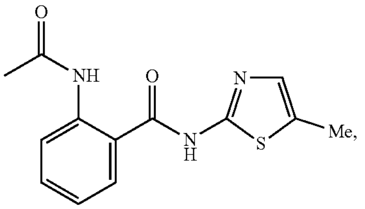
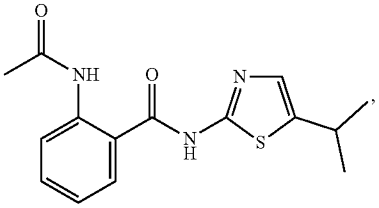
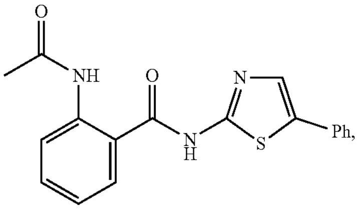
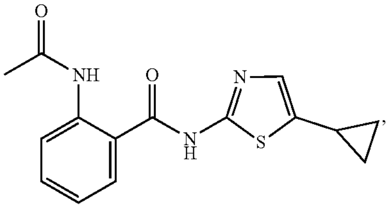
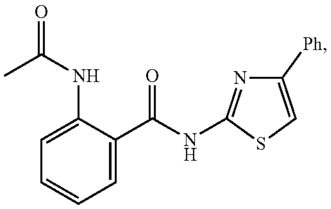
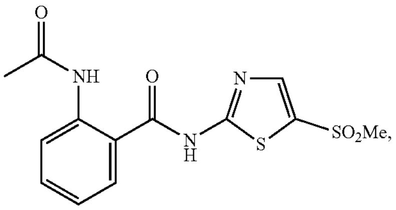

-continued
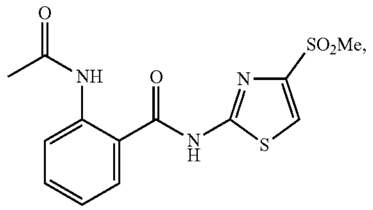
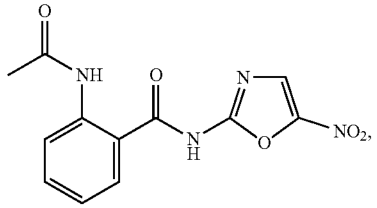
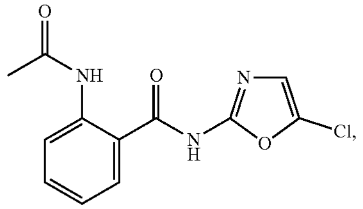
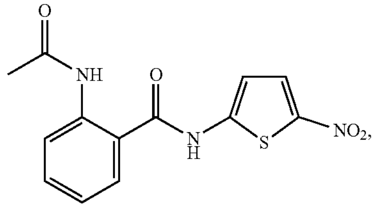
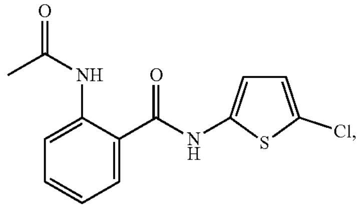
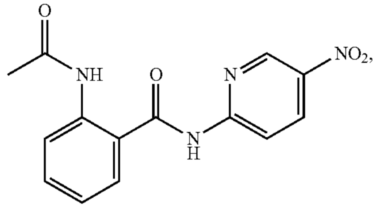
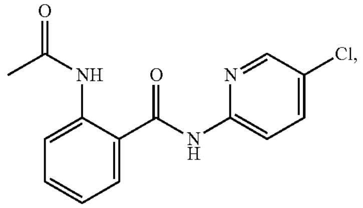
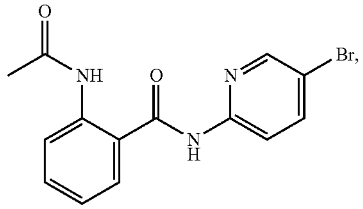
-continued
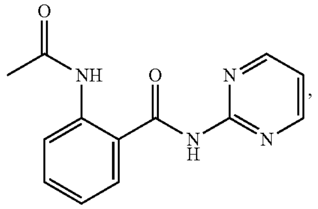
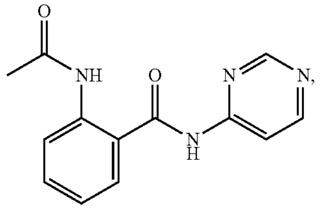
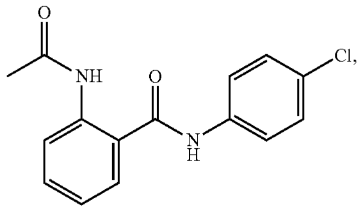
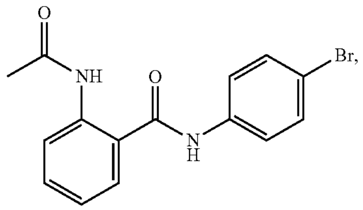
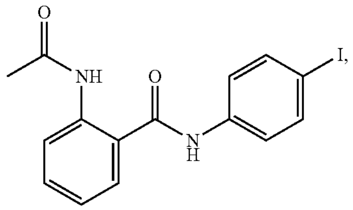
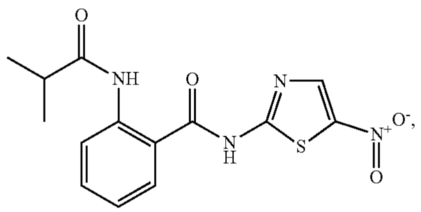
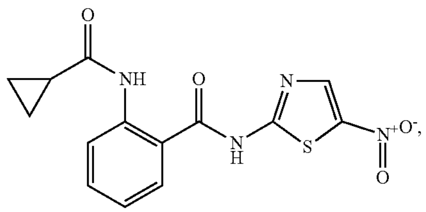

-continued
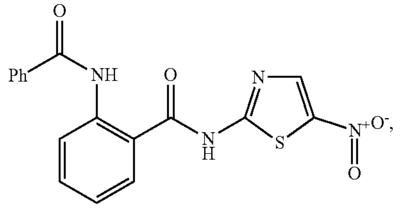
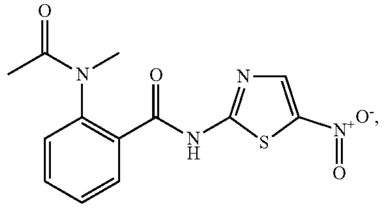
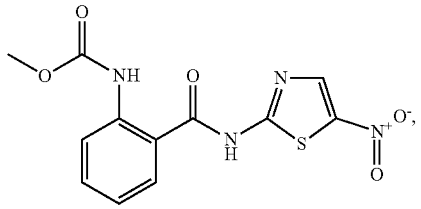
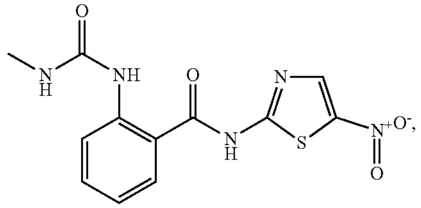
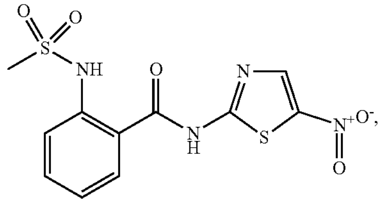
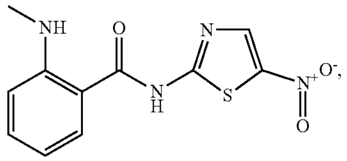
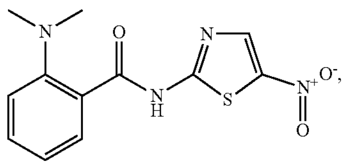
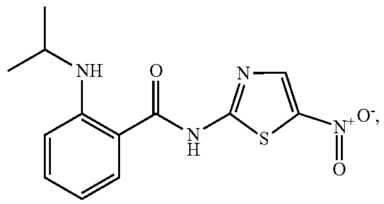
-continued
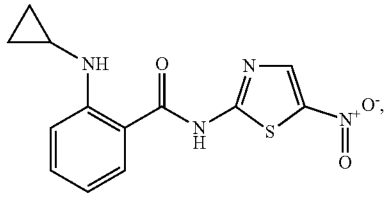
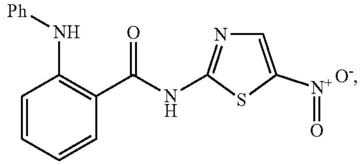
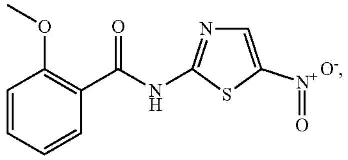
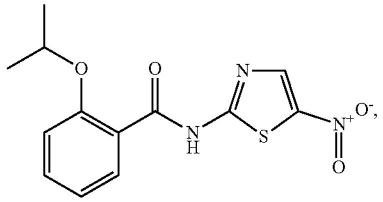
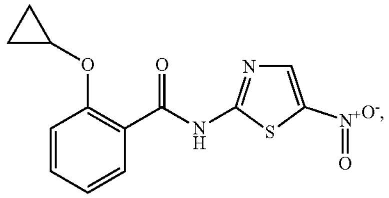
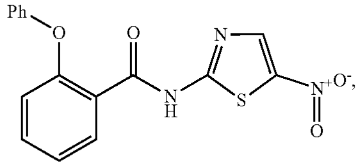
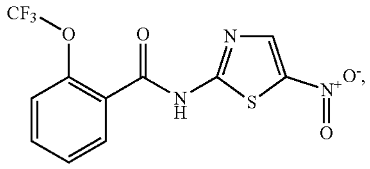
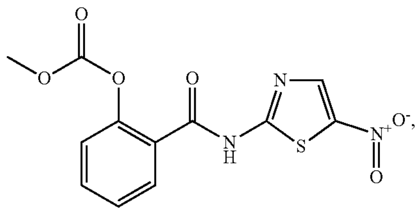
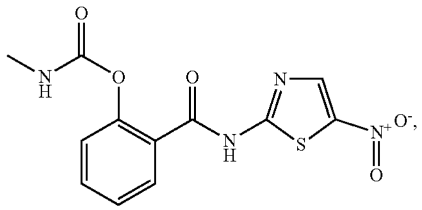

-continued
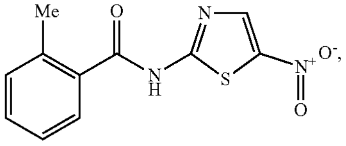
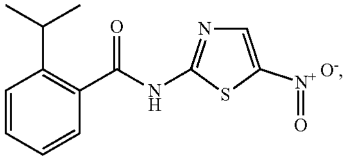
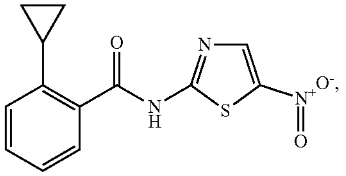
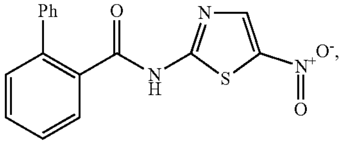
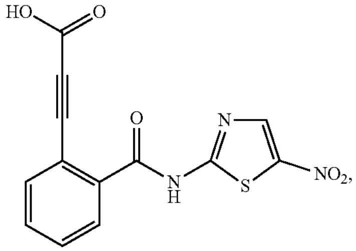
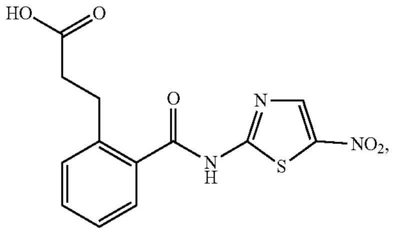
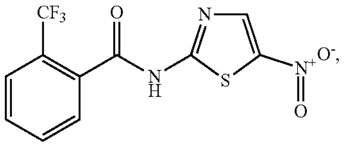
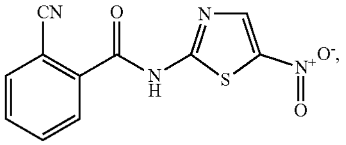
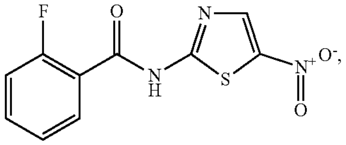
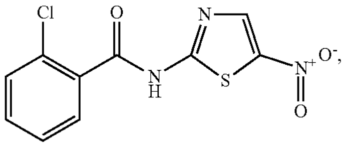
-continued
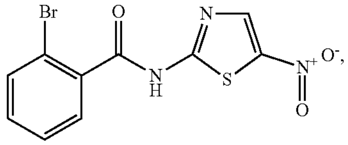
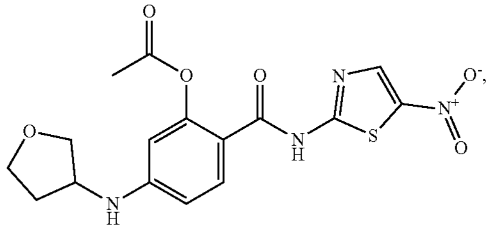
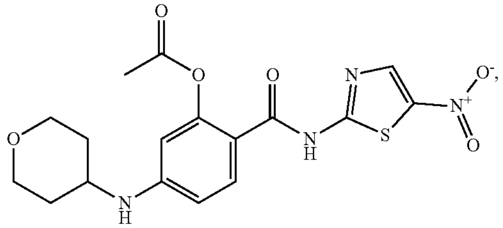
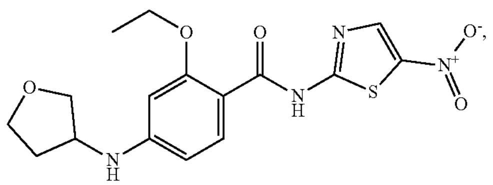
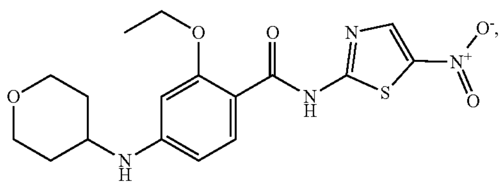
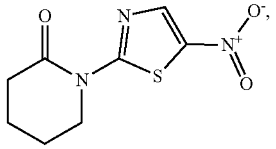
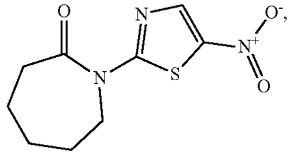
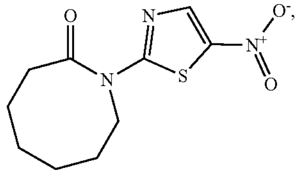
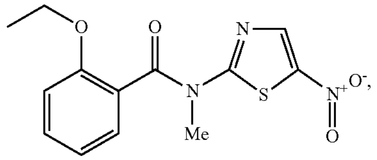

-continued
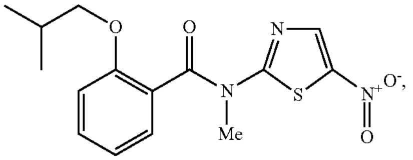
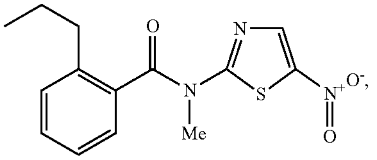
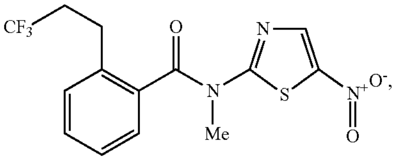
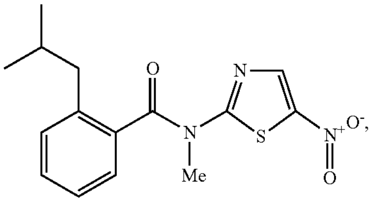
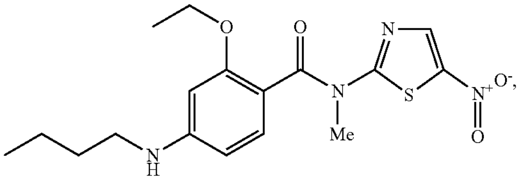
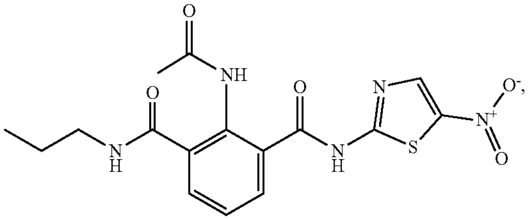
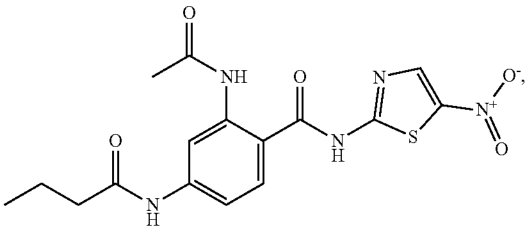
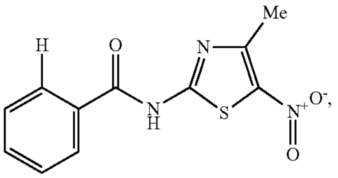
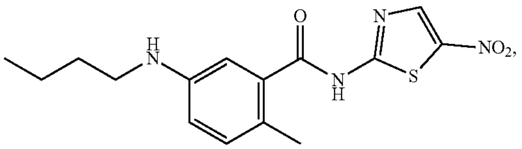
-continued
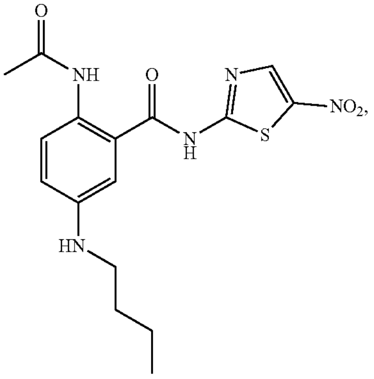
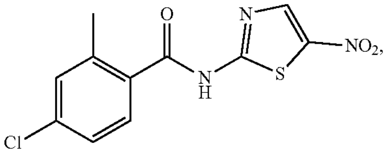
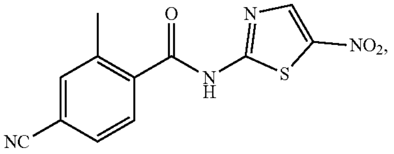
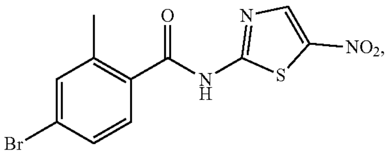
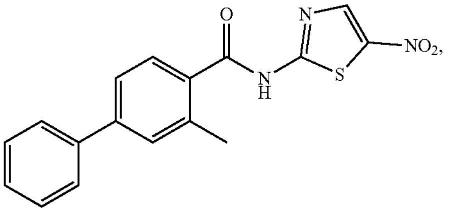
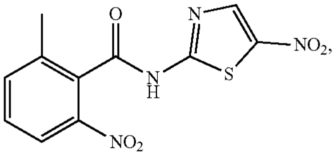
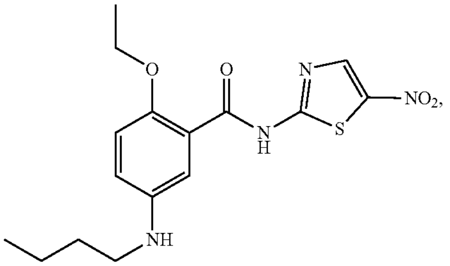
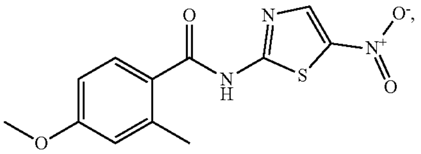

-continued
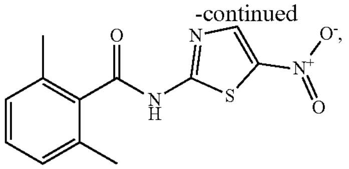
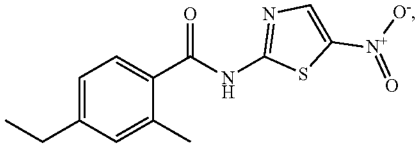
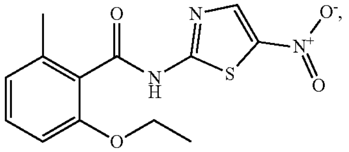
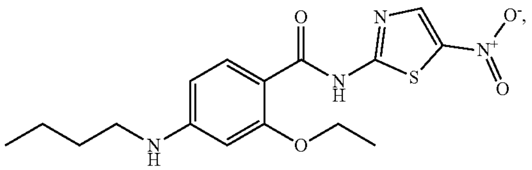
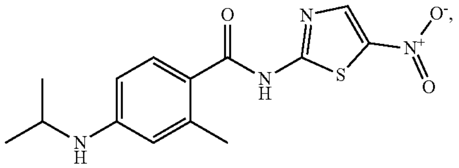
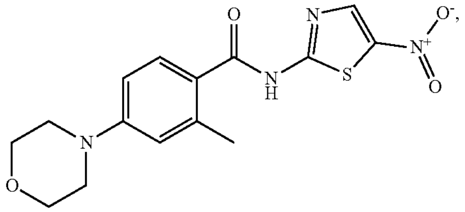
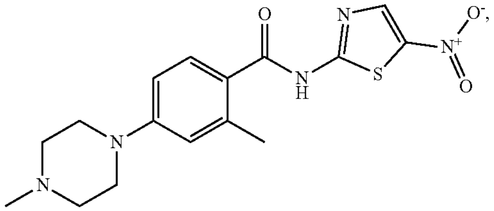
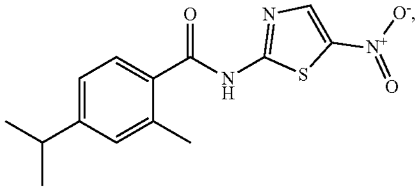
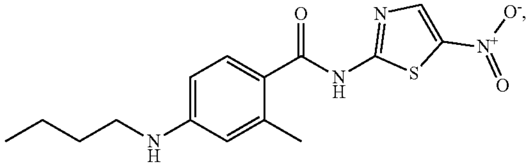
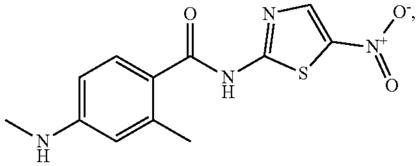
-continued
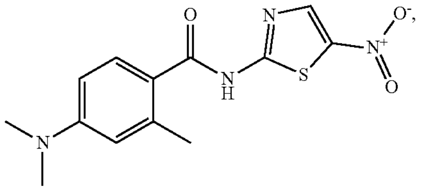
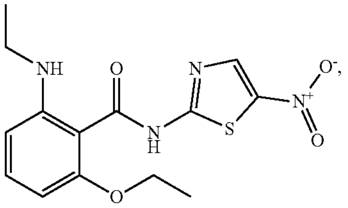
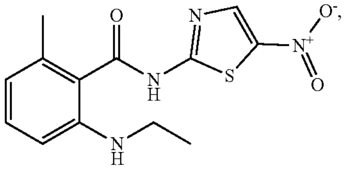
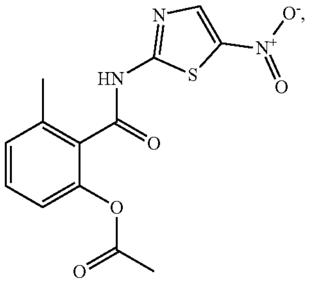
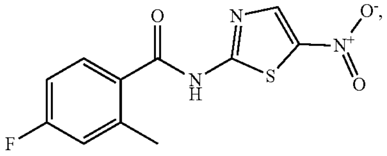
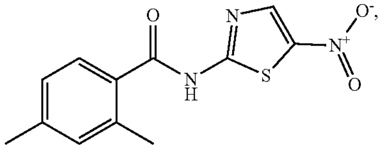
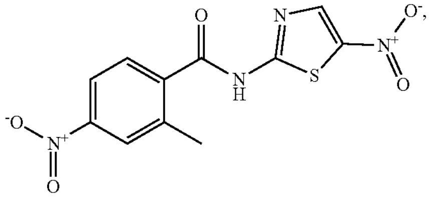
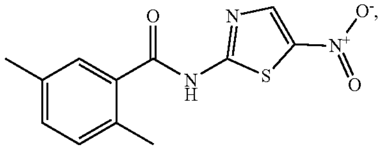
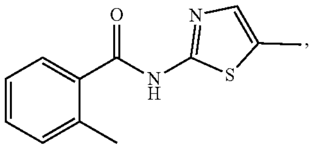

-continued
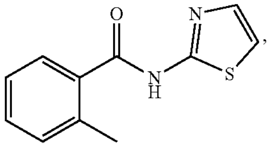
or a pharmaceutically acceptable salt thereof. In some embodiments, the DDB1 binding moiety comprises
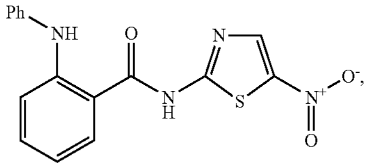
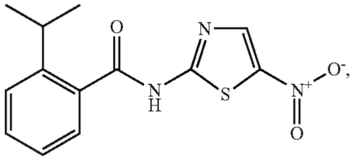
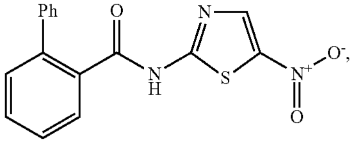
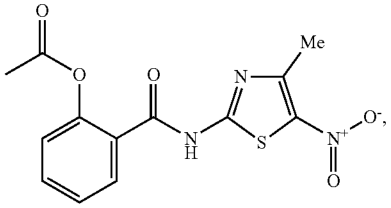
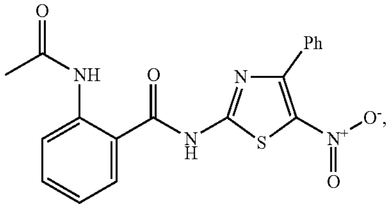
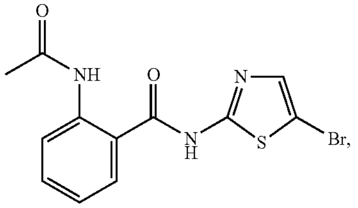
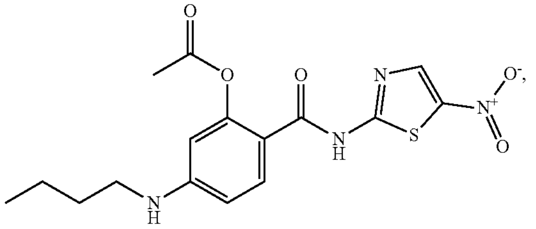
-continued
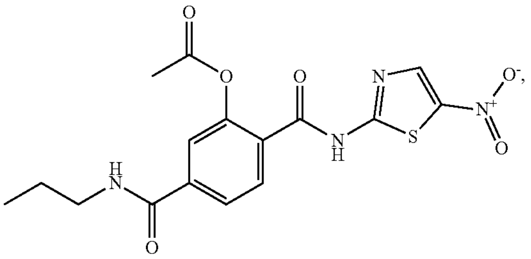
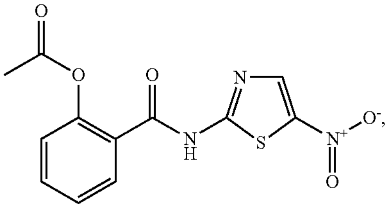
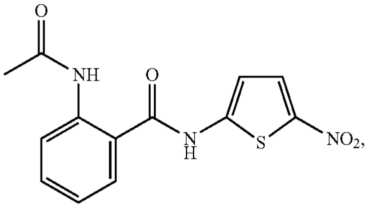
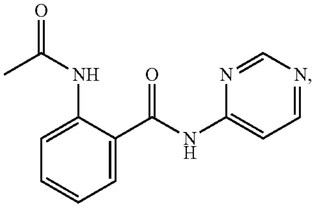
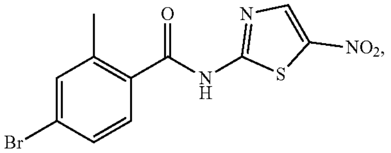
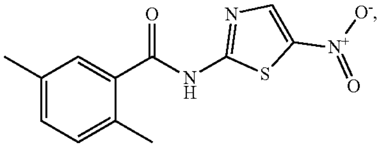
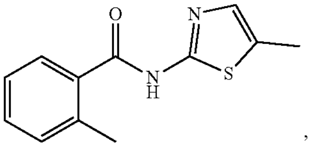
,
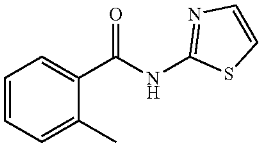
,
or a pharmaceutically acceptable salt thereof. In some embodiments, the DDB1 binding moiety comprises

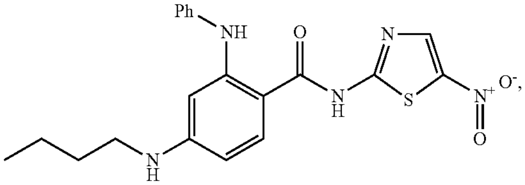
,
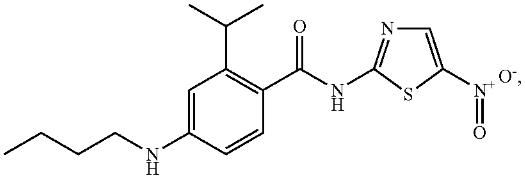
,
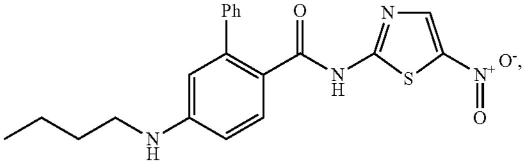
,
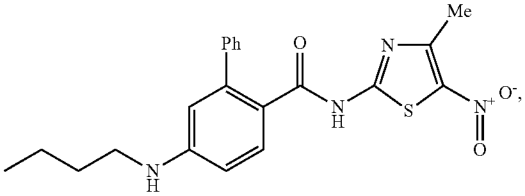
,
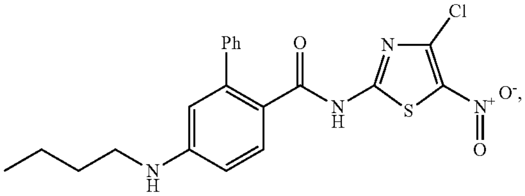
,
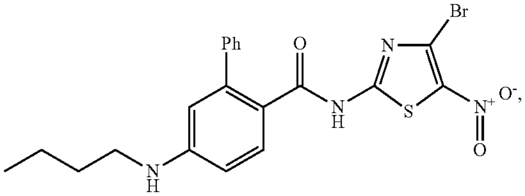
,
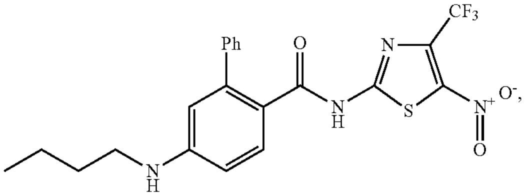
,
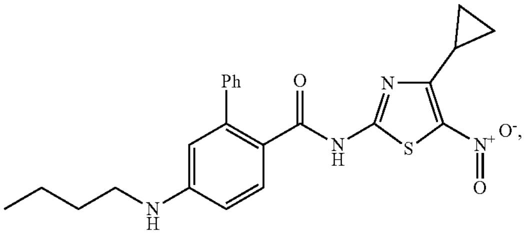
,
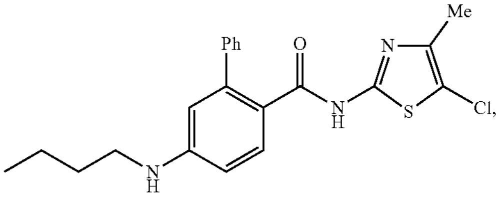
,
-continued
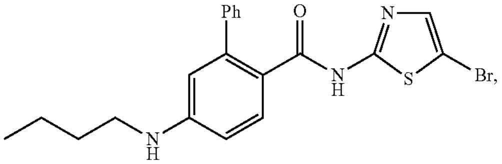
,
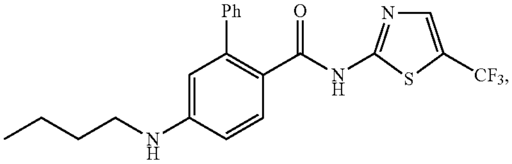
,
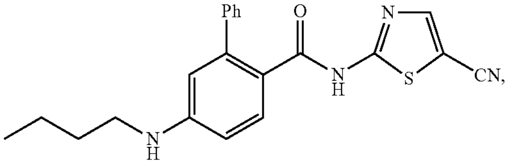
,
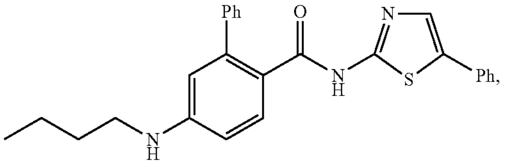
,
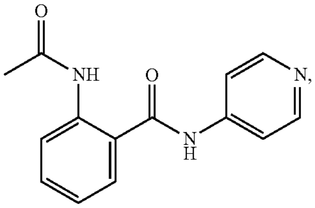
,
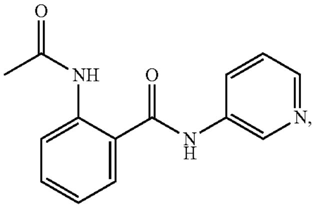
,
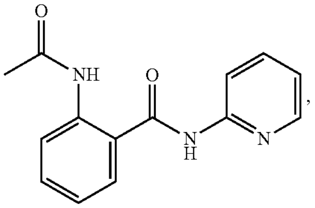
,
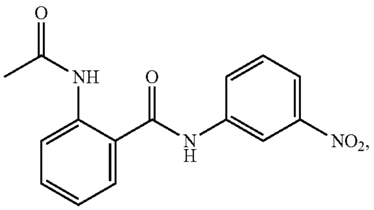
,
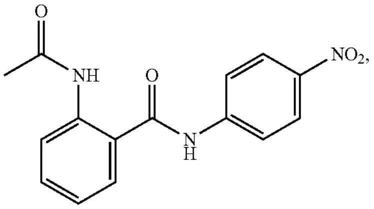
, -continued
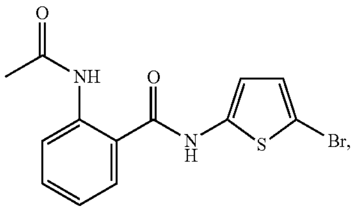
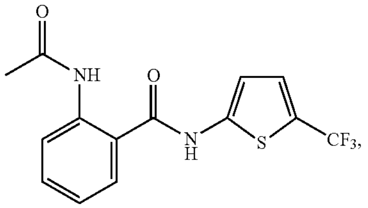
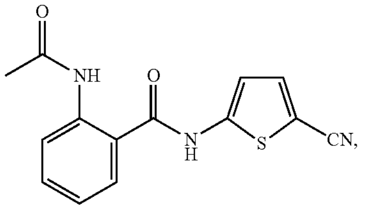
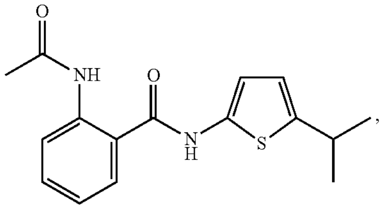
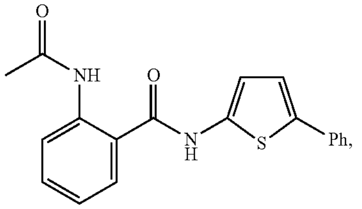
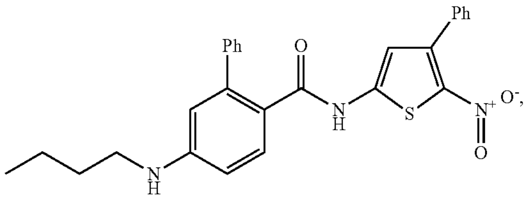
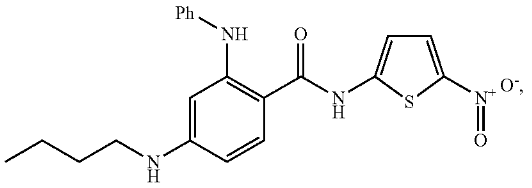
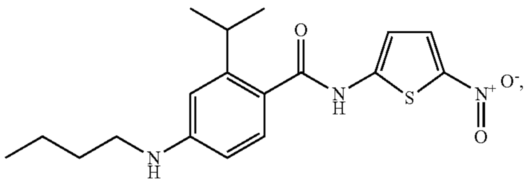
-continued
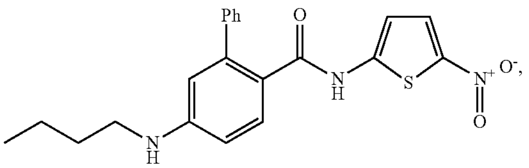
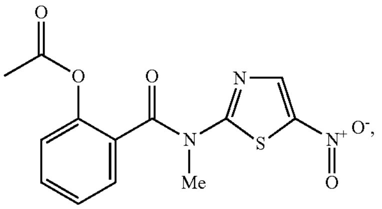
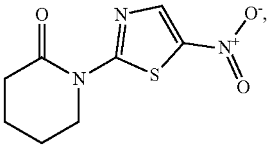
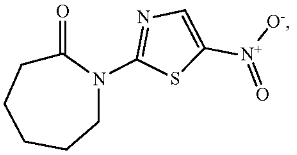
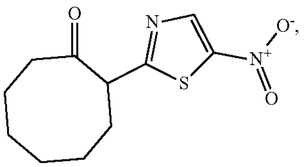
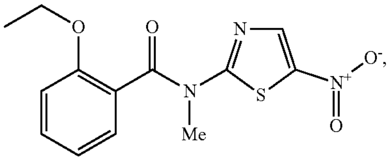
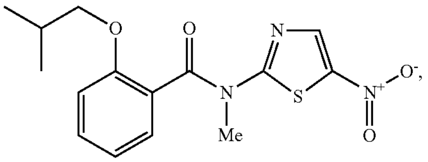
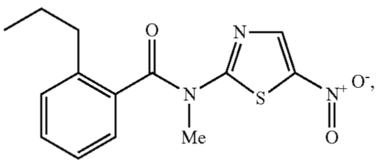
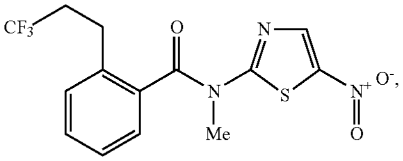
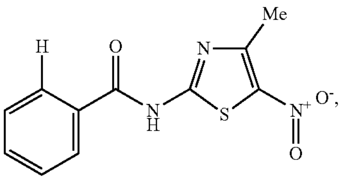

-continued
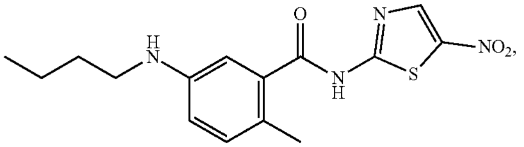
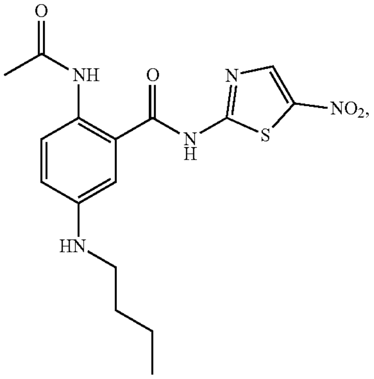
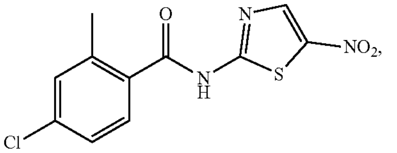
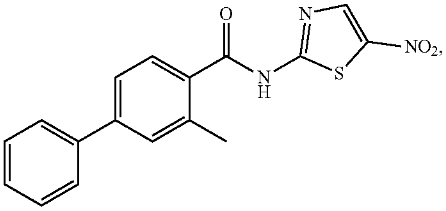
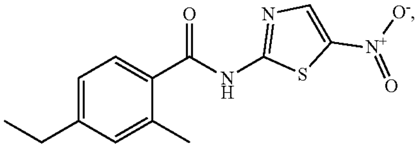
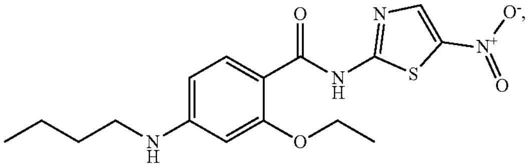
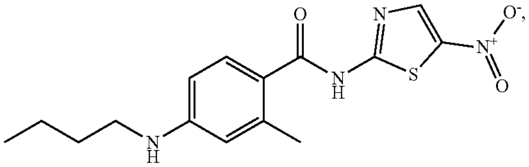
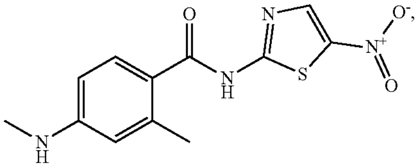
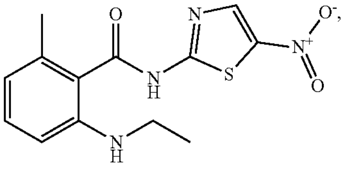
-continued
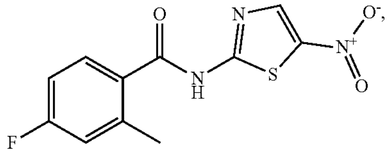
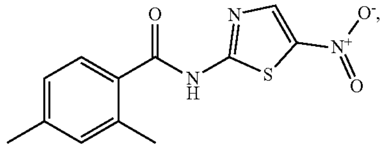
or a pharmaceutically acceptable salt thereof. In some embodiments, the DDB1 binding moiety comprises
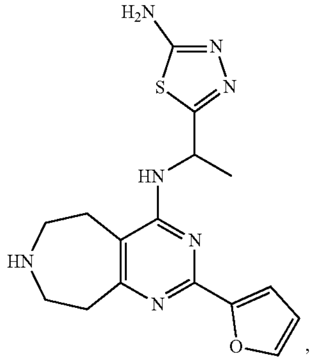
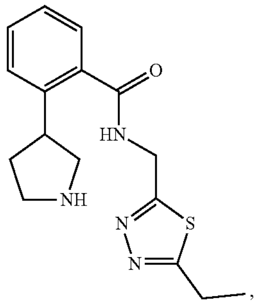
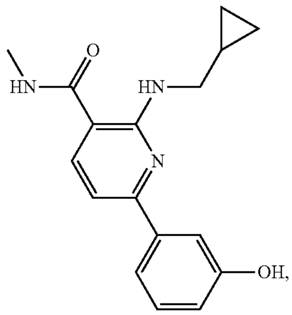
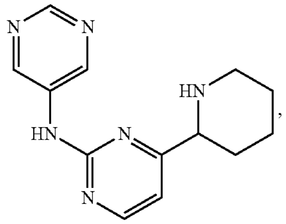

-continued

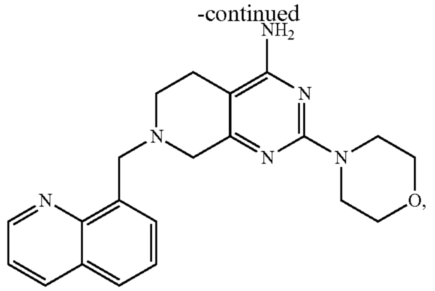,

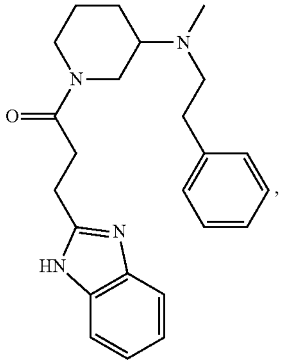,

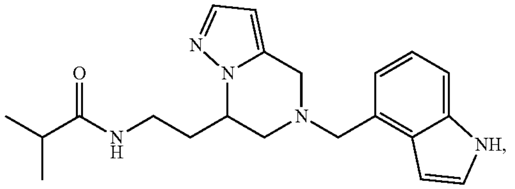,

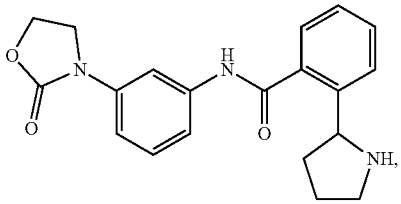,

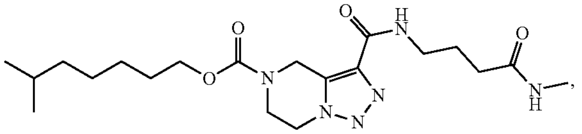, or a pharmaceutically acceptable salt thereof. In some embodiments, a DDB1 binding moiety comprises a peptide of Table 3. In some embodiments, a DDB1 binding moiety comprises any one of SEQ ID NOs: 1-7 (e.g. SEQ ID NO: 1, SEQ ID NO: 2, SEQ ID NO: 3, SEQ ID NO: 4, SEQ ID NO: 5, SEQ ID NO: 6, or SEQ ID NO: 7), or a pharmaceutically acceptable salt thereof. In some embodiments, the DDB1 binding moiety is covalently connected to a linker. In some embodiments, the linker is a bond. In some embodiments, the linker is not a bond. In some embodiments, the linker is more than just a bond. Some embodiments include a linker attached DDB1 binding moiety. In some embodiments, the linker attached DDB1 binding moiety comprises any of compounds BL-1 to BL-71 as shown in Table 2. In some embodiments, the linker is further connected to a target protein binding moiety. In some embodiments, the target protein binding moiety binds to a target protein. In some embodiments, the target protein binding moiety comprises any of compounds A-1 to A-69 as shown in Table 4. In some embodiments, the DDB1 ligand is a heterobifunctional compound comprising a DDB1 binding moiety covalently connected through a linker to a target protein binding moiety. In some embodiments, the heterobifunctional compound comprises any of compounds D-1 to D-130 as shown in Table 5. In some embodiments, the complex is formed in vivo. In some embodiments, the complex is formed in vitro.

Disclosed herein, in some embodiments, are in vivo modified proteins comprising: a DNA damage-binding protein 1 (DDB1) protein directly bound to a ligand comprising a DDB1 binding moiety. In some embodiments, the DDB1 binding moiety binds to a binding region on the DDB1 protein. In some embodiments, the binding region on the DDB1 protein comprises a beta propeller C (BPC) domain. In some embodiments, the binding region on the DDB1 protein comprises a top face of the BPC domain. In some embodiments, the binding region on the DDB1 protein comprises one or more of the following DDB1 residues: ARG327, LEU328, PRO358, ILE359, VAL360, ASP361, GLY380, ALA381, PHE382, SER720, ARG722, LYS723, SER738, ILE740, GLU787, TYR812, LEU814, SER815, ALA834, VAL836, ALA841, ALA869, TYR871, SER872, MET910, LEU912, TYR913, LEU926, TRP953, SER955, ALA956, ASN970, ALA971, PHE972, PHE1003, ASN1005, VAL1006, or VAL1033. In some embodiments, the DDB1 protein is directly bound to the ligand by a non-covalent interaction between the DDB1 protein and the ligand. In some embodiments, one or more of the following DDB1 residues are involved in the non-covalent interaction between the DDB1 protein and the ligand: ARG327, LEU328, PRO358, ILE359, VAL360, ASP361, GLY380, ALA381, PHE382, SER720, ARG722, LYS723, SER738, ILE740, GLU787, TYR812, LEU814, SER815, ALA834, VAL836, ALA841, ALA869, TYR871, SER872, MET910, LEU912, TYR913, LEU926, TRP953, SER955, ALA956, ASN970, ALA971, PHE972, PHE1003, ASN1005, VAL1006, or VAL1033. In some embodiments, the binding between the DDB1 protein and the ligand comprises a binding affinity with an equilibrium dissociation constant (Kd) below 100 μM, a Kd below 90 μM, a Kd below 80 μM, a Kd below 70 μM, a Kd below 60 μM, below 50 μM, a Kd below 45 μM, a Kd below 40 μM, a Kd below 35 μM, a Kd below 30 μM, a Kd below 25 μM, a Kd below 20 μM, a Kd below 15 μM, a Kd below 14 μM, a Kd below 13 μM, a Kd below 12 μM, a Kd below 11 μM, a Kd below 10 μM, a Kd below 9 μM, a Kd below 8 μM, a Kd below 7 μM, a Kd below 6 μM, a Kd below 5 μM, a Kd below 4 μM, a Kd below 3 μM, a Kd below 2 μM, or a Kd below 1 μM. In some embodiments, the binding between the DDB1 protein and the ligand comprises a binding affinity with a Kd<20 uM, a Kd from 20-100 uM, or a Kd>100 uM. In some embodiments, the ligand is a small molecule. In some embodiments, the ligand comprises a targeted protein degrader. In some embodiments, the ligand is synthetic. In some embodiments, the ligand and/or the DDB1 binding moiety comprises the structure described herein. In some embodiments, the DDB1 binding moiety is covalently connected to a linker. In some embodiments, the linker is a bond. In some embodiments, the linker is more than just a bond. In some embodiments, the linker is further connected to a target protein binding moiety. In some embodiments, the target protein binding moiety binds to a target protein. Disclosed herein, in some embodiments, are ligands comprising a DNA damage-binding protein 1 (DDB1) binding moiety. In some embodiments, the DDB1 binding moiety is covalently connected through a linker to a target protein binding moiety. In some embodiments, the DDB1 binding moiety binds to a DDB1 protein. In some embodiments, the DDB1 binding moiety binds to a binding region on the DDB1 protein. In some embodiments, the binding between the DDB1 binding moiety and the DDB1 protein is non-covalent. In some embodiments, the binding between the DDB1 protein and the ligand comprises a binding affinity with a Kd<20 uM, a Kd from 20-100 uM, or a Kd>100 uM. In some embodiments, the ligand is a small molecule. In some embodiments, the ligand comprises a targeted protein degrader. In some embodiments, the ligand is synthetic. In some embodiments, the DDB1 binding moiety comprises a structure of Formula (II):

Formula (II)

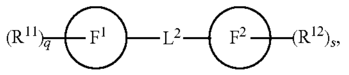

wherein $F^1$ is aryl, heteroaryl, carbocyclyl, or heterocyclyl; $F^2$ is aryl, heteroaryl, carbocyclyl, or heterocyclyl; $L^2$ is a bond, —C(═O)NR$^{13}$—, —NR$^{13}$C(═O)—, —C(═O)—, —C(═S)—, —S—, —S(═O), —S(═O)$_2$—, —S(═O)NR$^{13}$—, —NR$^{13}$S(═O)—, —S(═O)$_2$NR$^{13}$—, —NR$^{13}$S(═O)$_2$—, —O—, $C_1$-$C_4$ alkyl, or $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —S(═O)$_2R^d$, —S(═O)$_2$NR$^c$R$^d$, —C(═O)$R^b$, —CO$_2R^a$, —C(═O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —OR$^a$, or —NR$^c$R$^d$; and the carbocyclyl, heterocyclyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$; each $R^{11}$ and $R^{12}$ is independently a bond, hydrogen, halogen, —CN, —R$^a$, —OR, —SR$^a$, —S(═O)R$^b$, —NO$_2$, —NR$^c$R$^d$, —S(═O)$_2$R$^d$, —NR$^a$S(═O)$_2$R$^d$, —S(═O)$_2$NR$^c$R$^d$, —C(═O)R$^b$, —OC(═O)R$^b$, —CO$_2$R$^a$, —OCO$_2$R$^a$, —C(═O)NR$^c$R$^d$, —OC(═O)NR$^c$R$^d$, —NR$^a$C(═O)NR$^c$R$^d$, —NR$^a$C(═O)R$^b$, —NR$^a$C(═O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —R$^a$, —OR$^a$, or NR$^c$R$^d$; and the carbocyclyl, heterocyclyl, aryl, and heteroaryl is optionally substituted with one, two, or three of halogen, $C_1$-$C_6$ alkyl, $C_1$-$C_6$ haloalkyl, —R$^a$, —OR$^a$, or —NR$^c$R$^d$, and wherein at least one $R^{11}$ is a bond attached to the linker; each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —NH$_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —NH$_2$; each $R^b$ is independently hydrogen, $C_1$-$C_6$ alkyl, $C_1$-$C_6$ alkenyl, $C_1$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe. or —NH$_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —NH$_2$; each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —NH$_2$; and the carbocyclyl, heterocyclyl, aryl, and heteroaryl is optionally substituted with one, two, or three of halogen. $C_1$-$C_6$ alkyl, $C_1$-$C_6$ haloalkyl, —OH, —OMe, or —NH$_2$; each $R^c$ and $R^d$, together with the nitrogen atom to which they are attached, form a heterocyclyl or heteroaryl; wherein the heterocyclyl and heteroaryl is optionally substituted with one, two, or three of halogen, $C_1$-$C_6$ alkyl, $C_1$-$C_6$ haloalkyl, —OH, —OMe, or —NH$_2$; q is 1-5; and s is 1-5; or a pharmaceutically acceptable salt thereof. In some embodiments, the DDB1 binding moiety comprises a structure of Formula (IIa):

Formula (IIa)

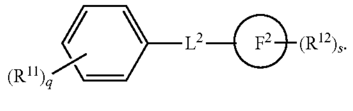

In some embodiments, $F^2$ is heteroaryl. In some embodiments, $F^2$ is a five membered or six membered ring heteroaryl. In some embodiments, F2 is triazolyl, tetrazolyl, furanyl, pyrrolyl, thiazolyl, oxazolyl, isoxazolyl, imidazolyl, pyrazolyl, thiadiazolyl, or oxadiazolyl. In some embodiments, the DDB1 binding moiety comprises a structure of Formula (IIb):

Formula (IIb)

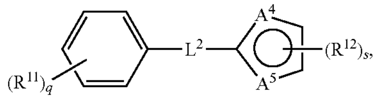

wherein $A^4$ and $A^5$ are each independently CR$^{12}$, S, N, or O, wherein at least one of $A^4$ or $A^5$ is N, O, or S. In some embodiments, $A^4$ is N and $A^5$ is S. In some embodiments, the DDB1 binding moiety comprises the structure

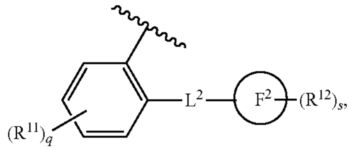

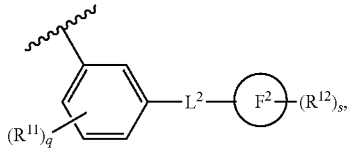

or

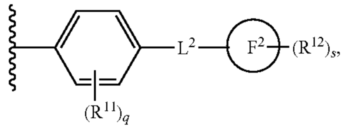

wherein the wavy line indicates a point of attachment to the linker or target protein binding moiety. In some embodiments, $R^{12}$, at each occurrence, is independently selected from —NO$_2$, halogen, methyl, halomethyl, phenyl, isopropyl, cyclopropyl. SO$_2$CH$_3$, or —CN. In some embodiments, $L^2$ is —NR$^c$C(═O)— or —C(═O)NR$^c$—. In some embodiments, $R^c$ is H, CH$_3$, isopropyl, or cyclopropyl. In some embodiments, q is 1 or 2. In some embodiments, s is 1 or 2. In some embodiments, the DDB1 binding moiety comprises any of compounds B-1 to B-176 as shown in Table 1. In some embodiments, the DDB1 binding moiety comprises
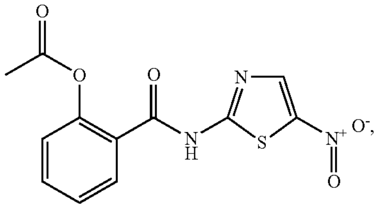
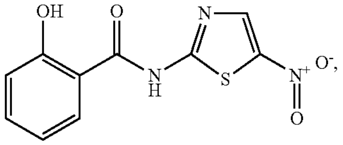
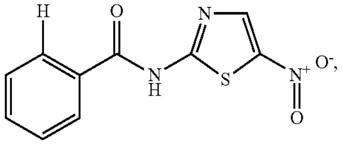
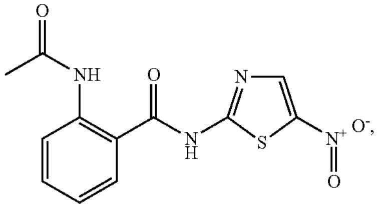
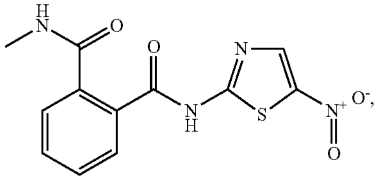
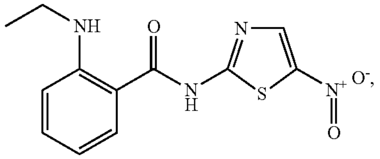
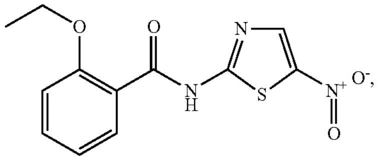
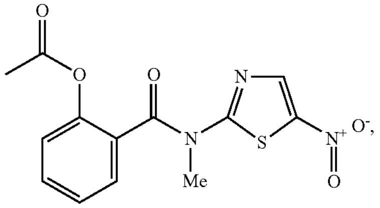
-continued
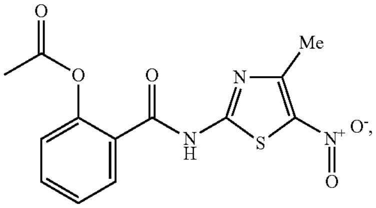
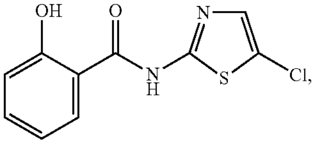
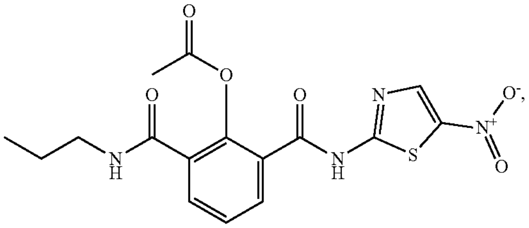
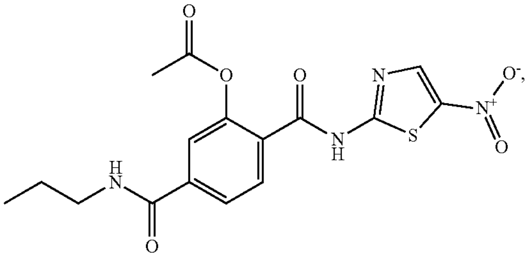
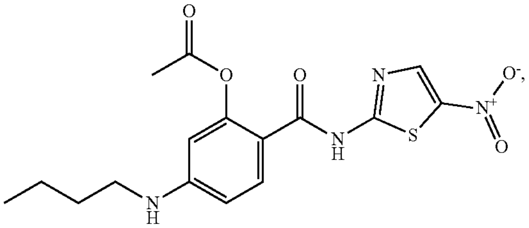
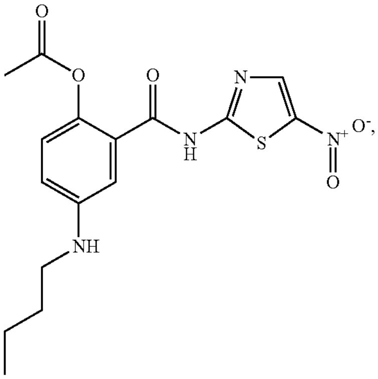

-continued
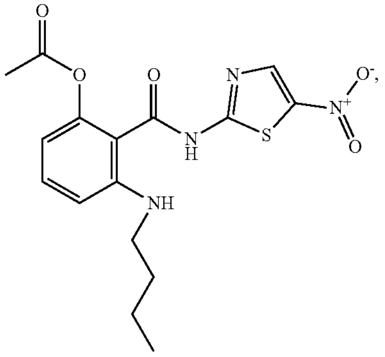
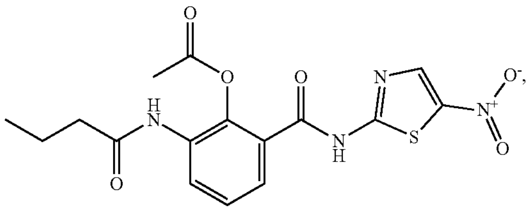
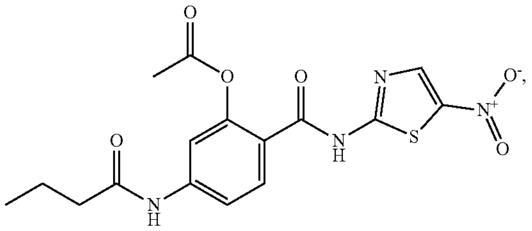
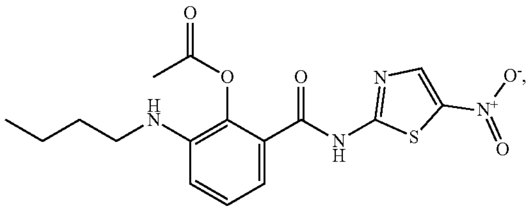
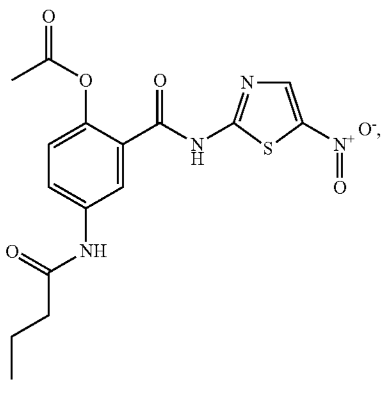
-continued
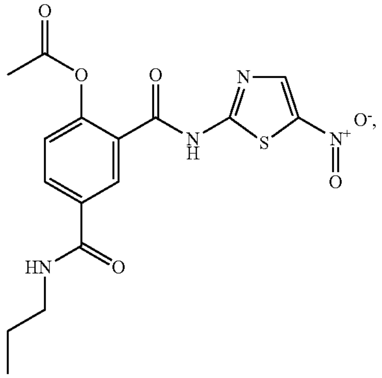
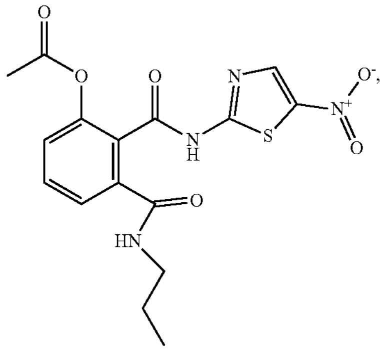
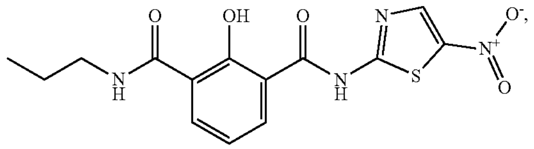
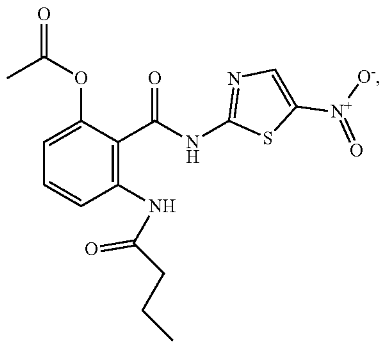
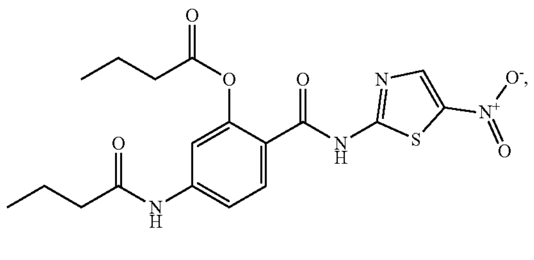

-continued
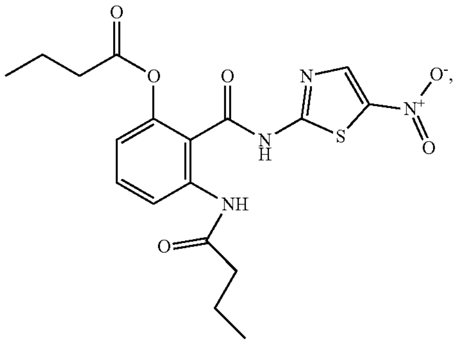
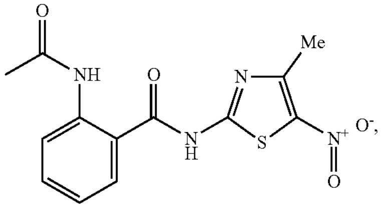
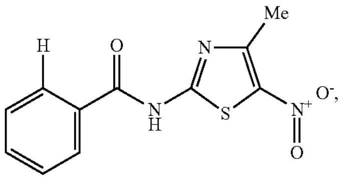
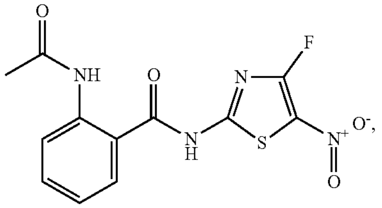
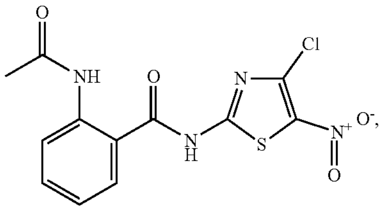
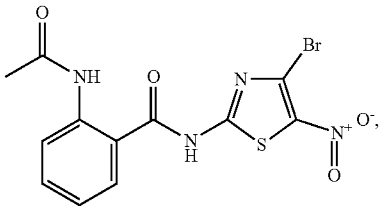
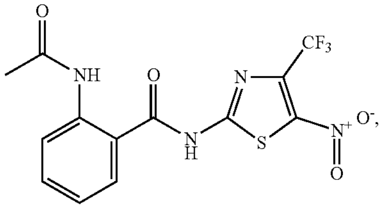
-continued
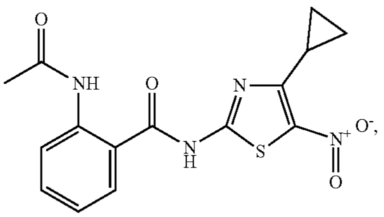
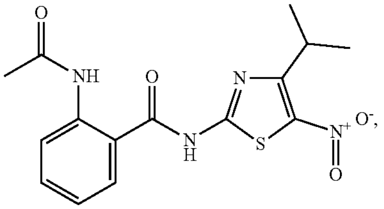
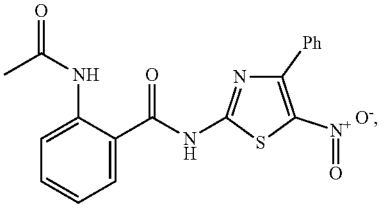
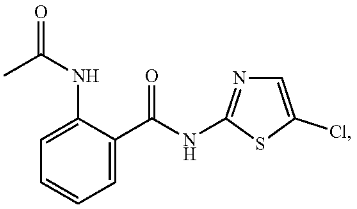
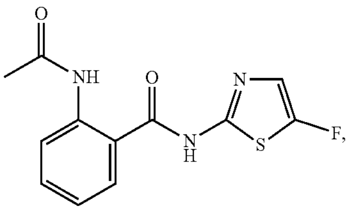
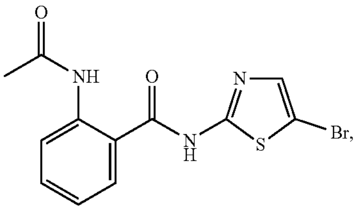
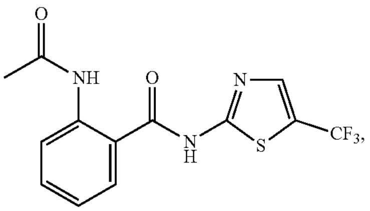
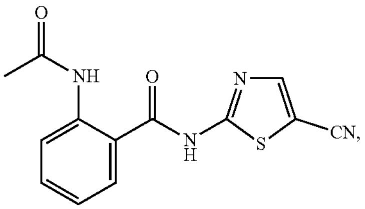

-continued
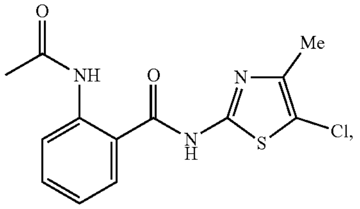
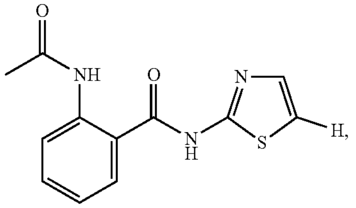
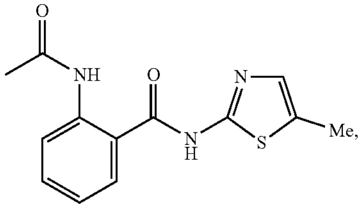
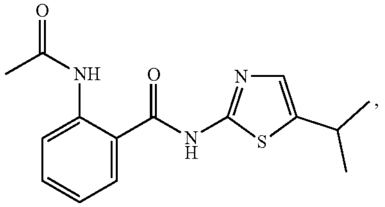
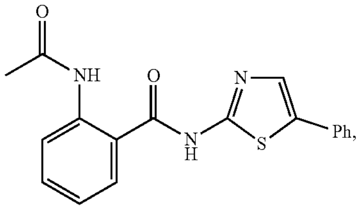
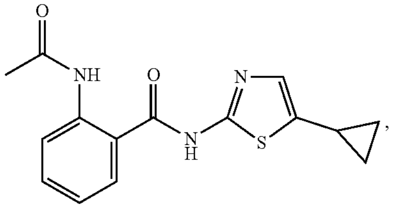
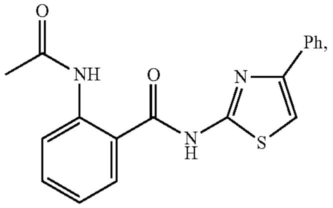
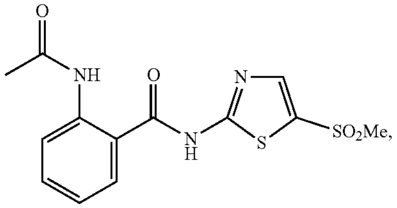
-continued
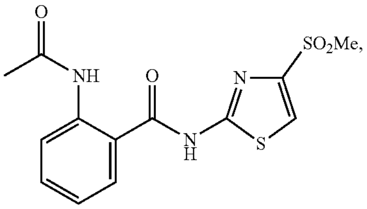
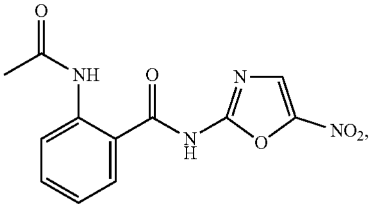
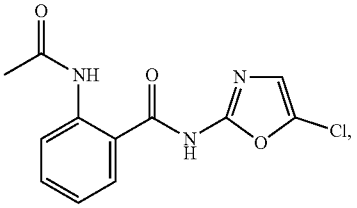
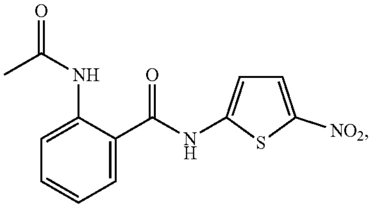
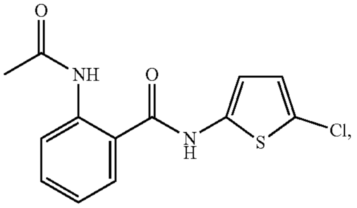
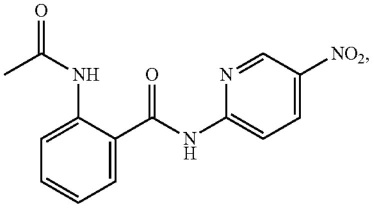
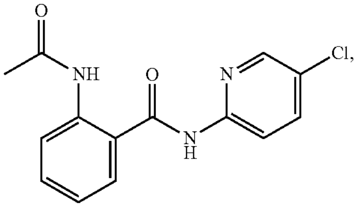
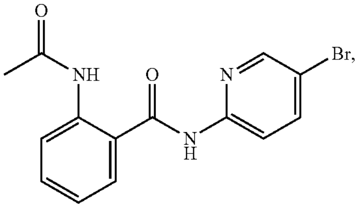

-continued
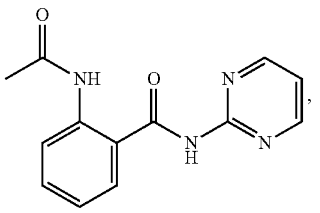
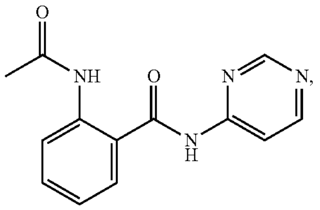
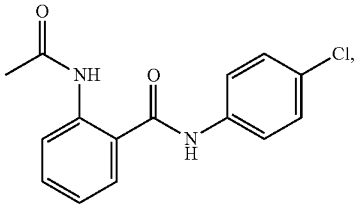
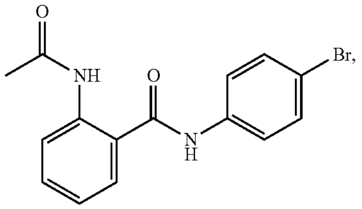
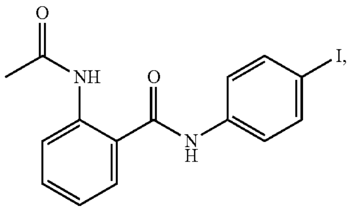
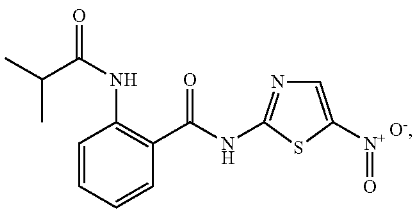
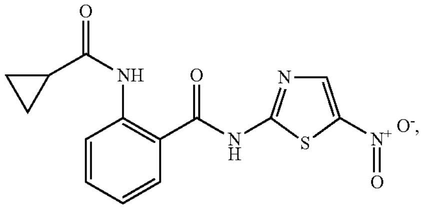
-continued
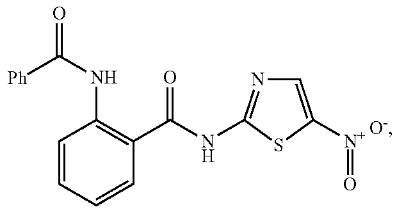
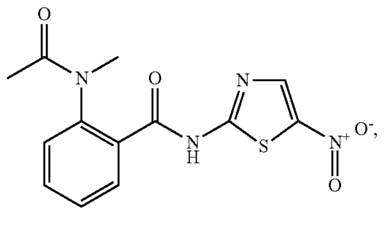
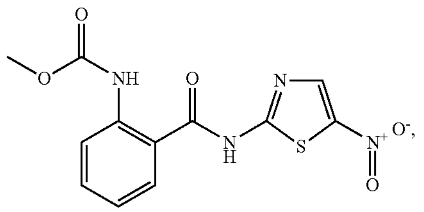
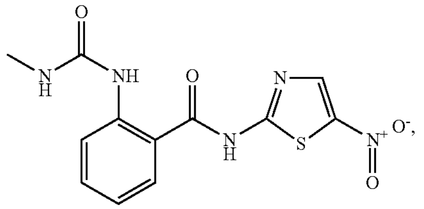
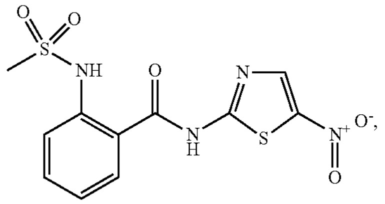
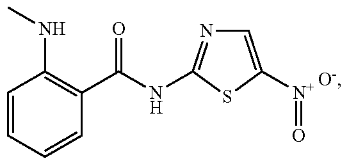
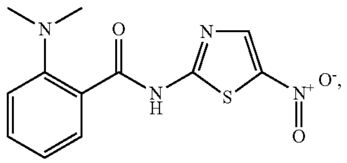
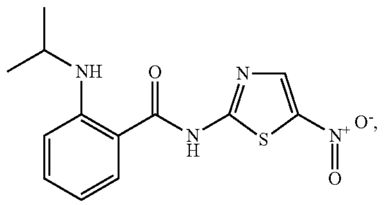

-continued
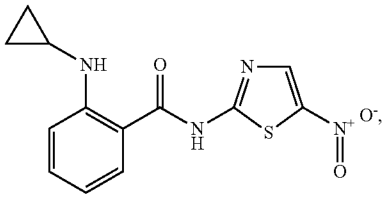
,
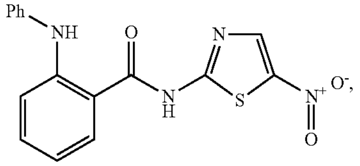
,
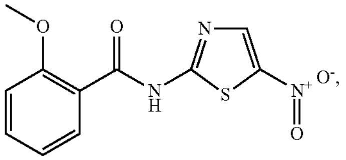
,
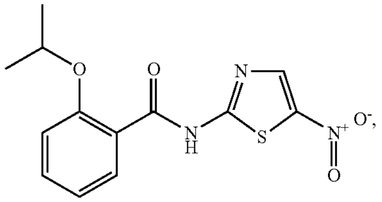
,
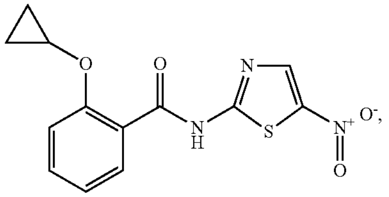
,
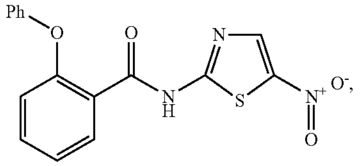
,
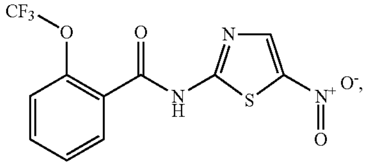
,
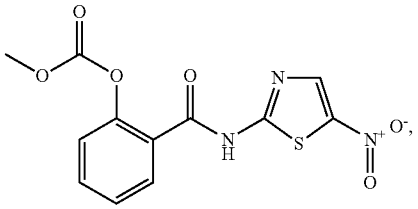
,
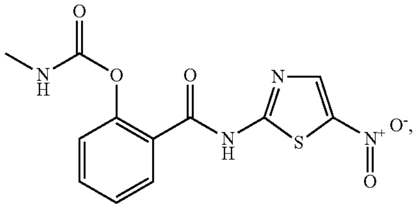
,
-continued
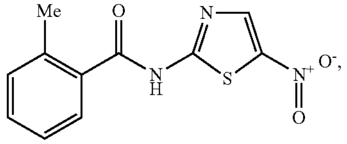
,
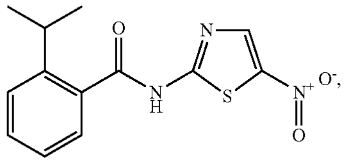
,
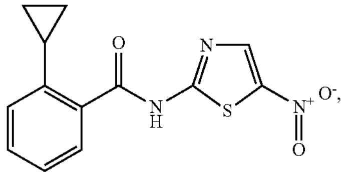
,
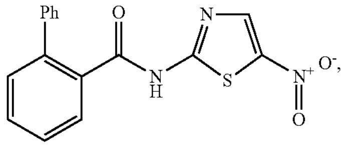
,
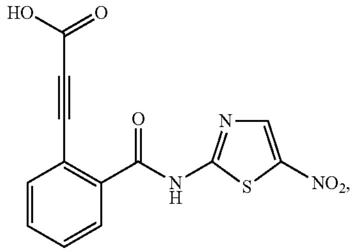
,
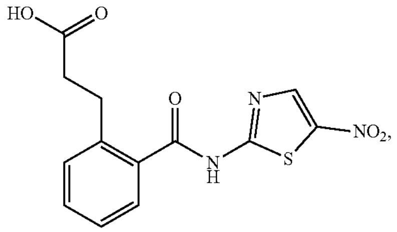
,
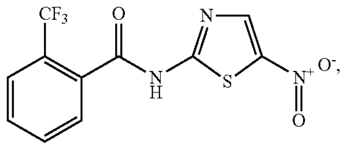
,
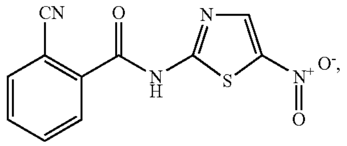
,
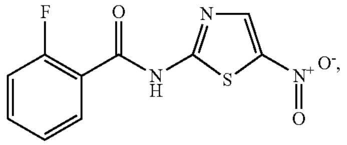
,
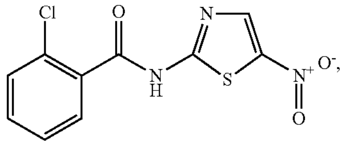
, -continued
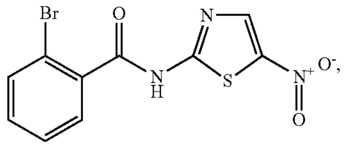
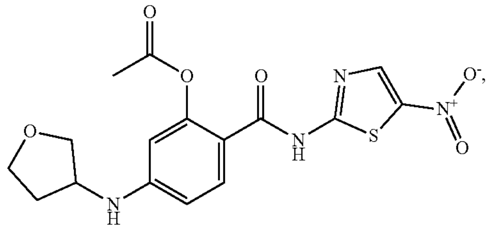
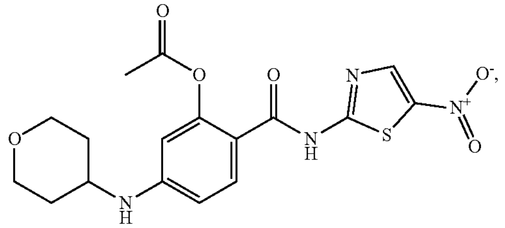
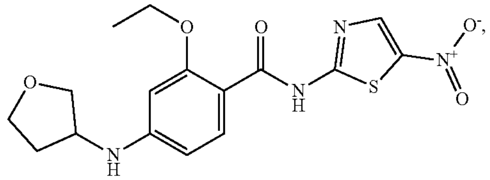
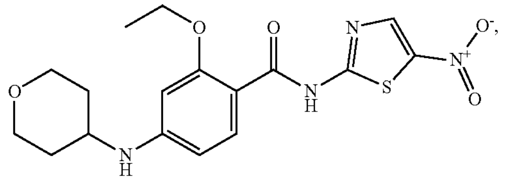
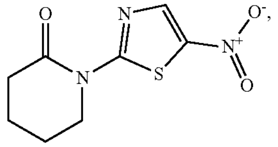
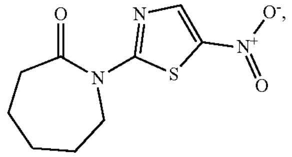
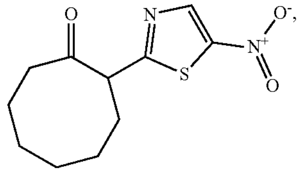
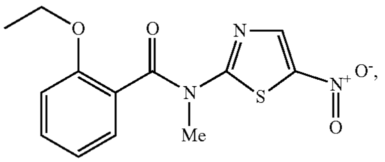
-continued
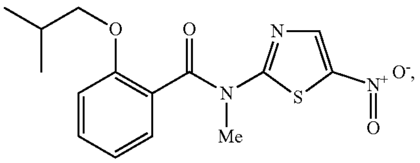
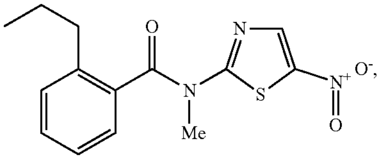
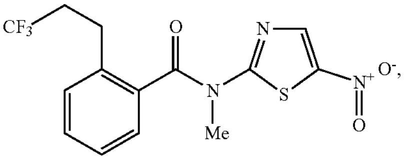
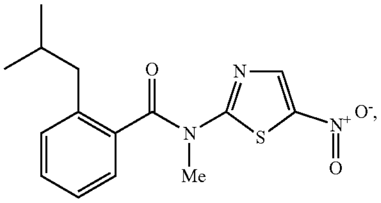
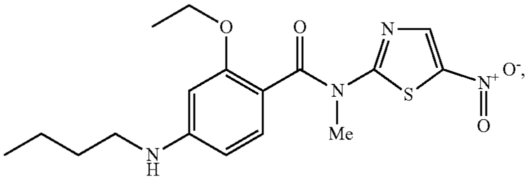
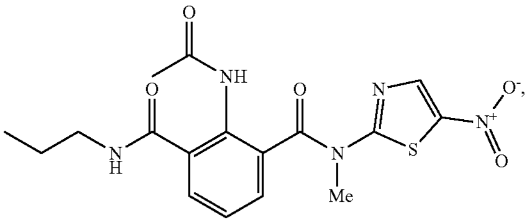
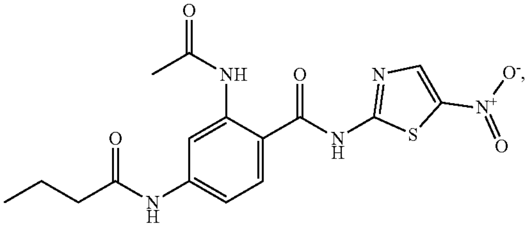
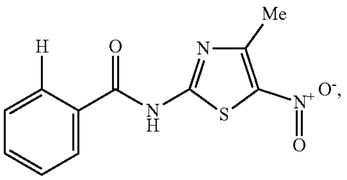
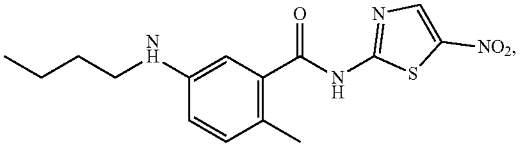

-continued
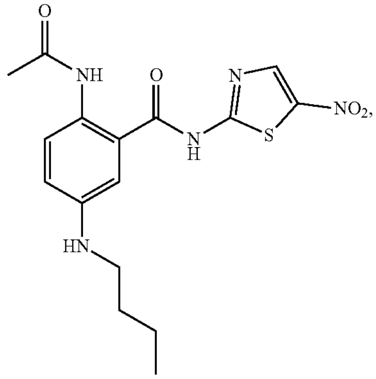
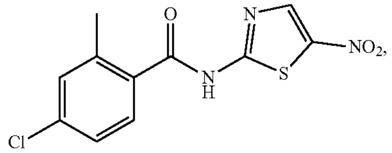
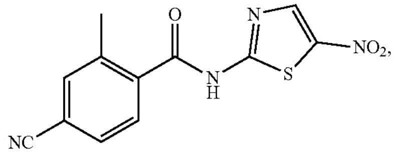
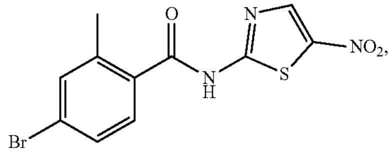
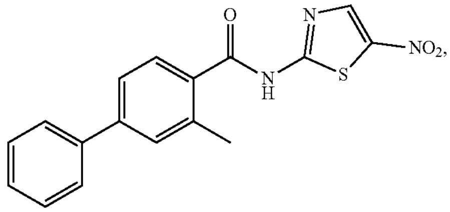
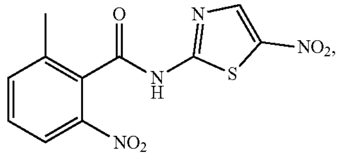
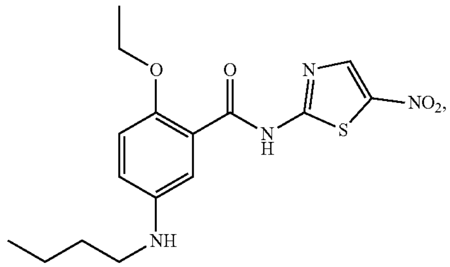
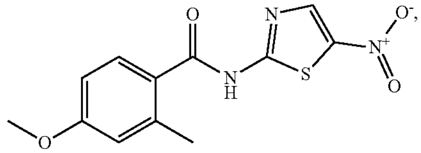
-continued
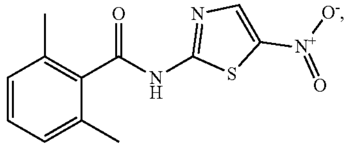
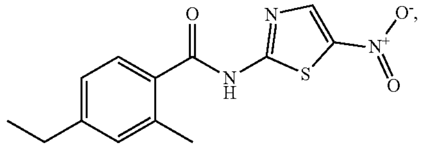
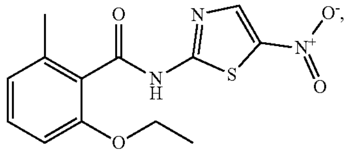
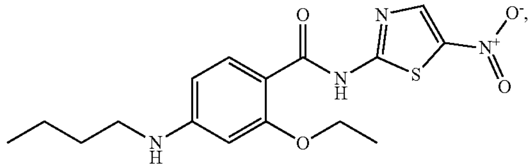
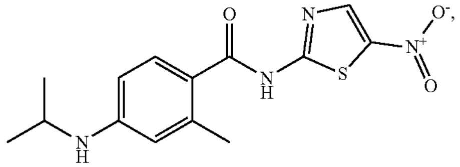
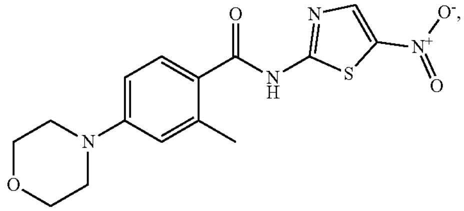
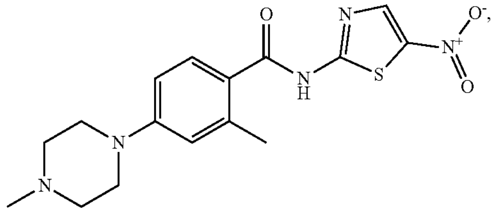
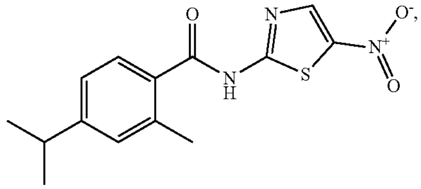
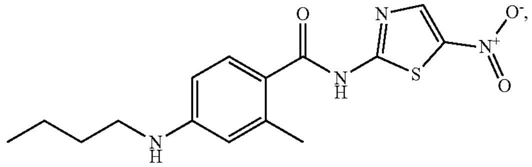
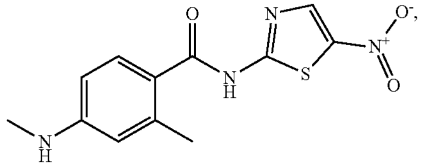

-continued
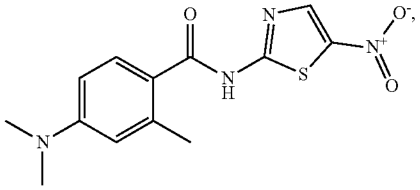
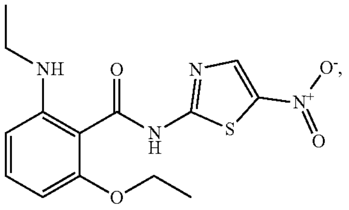
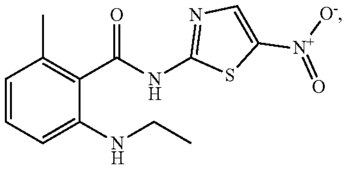
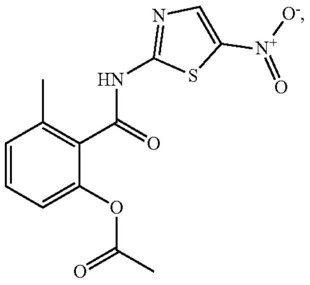
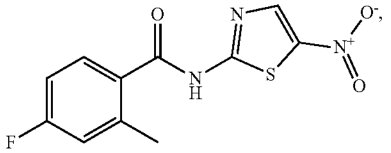
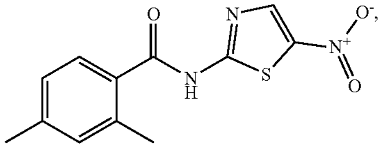
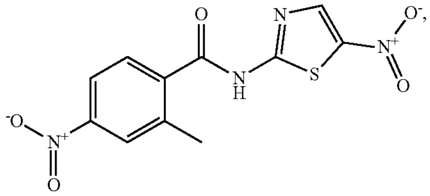
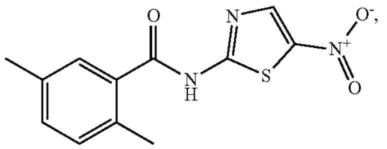
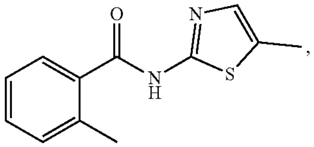
-continued
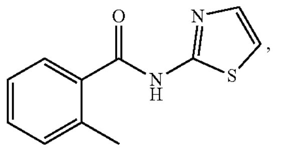
or a pharmaceutically acceptable salt thereof. In some embodiments, the DDB1 binding moiety
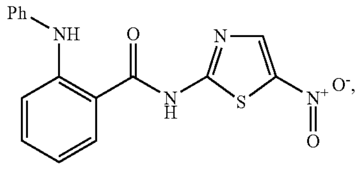
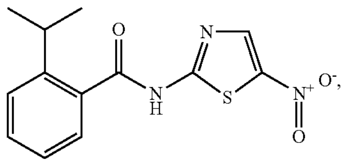
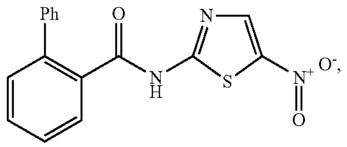
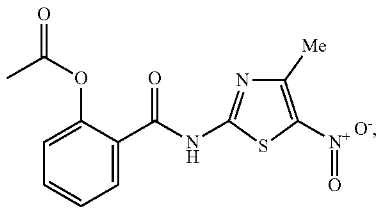
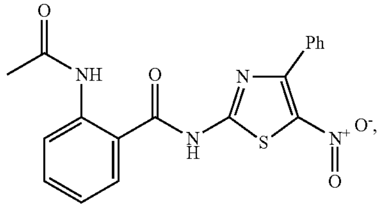
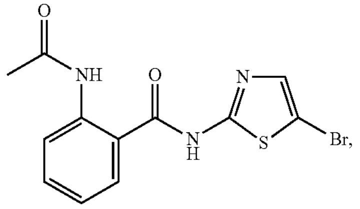
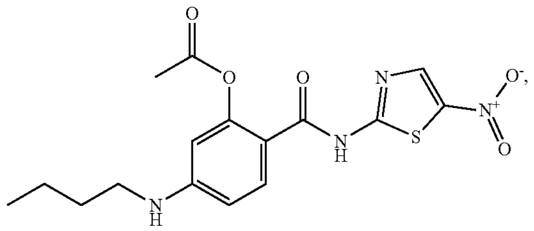

-continued
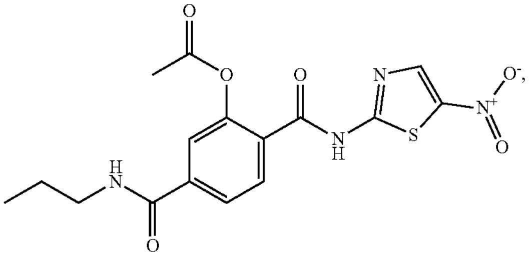
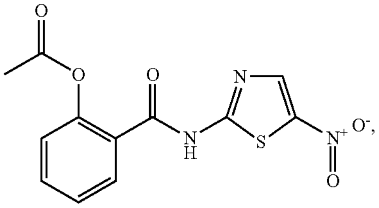
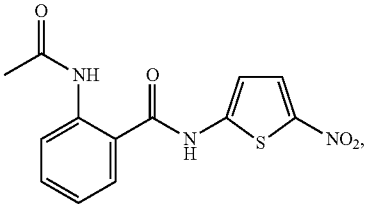
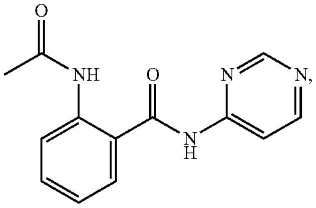
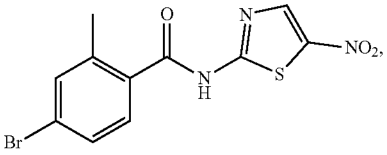
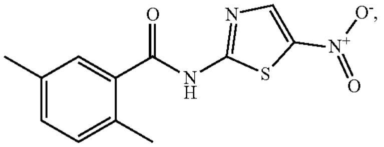
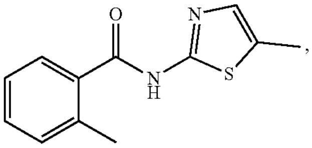
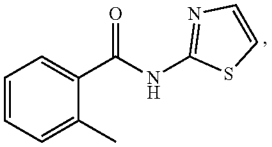
or a pharmaceutically acceptable salt thereof. In some embodiments, the DDB1 binding moiety comprises
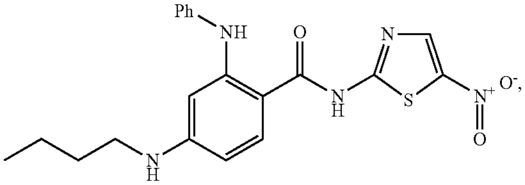
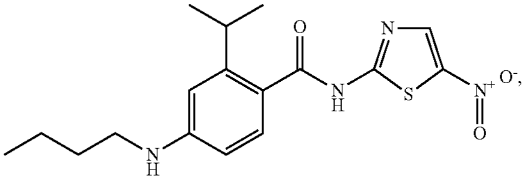
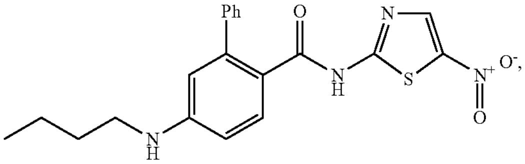
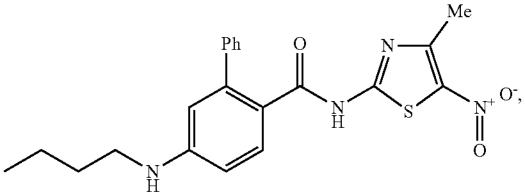
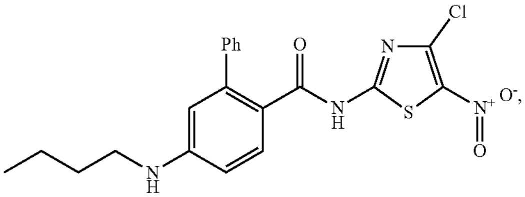
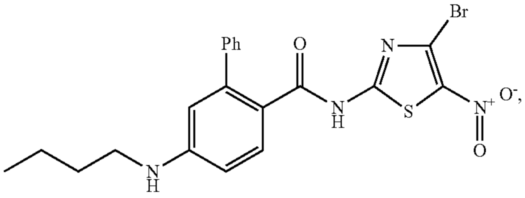
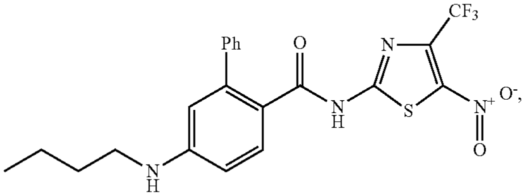
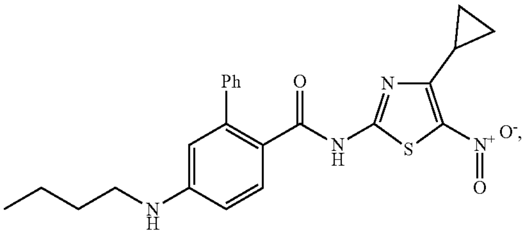

-continued
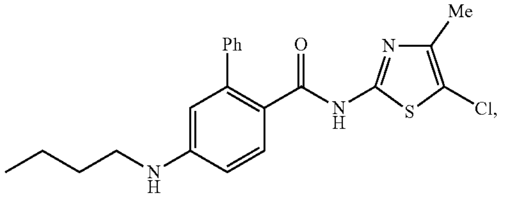
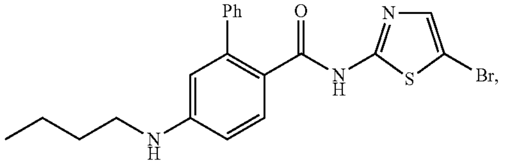
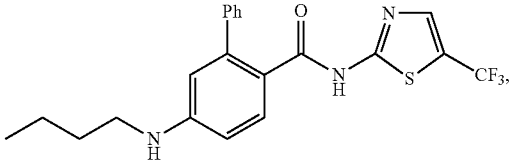
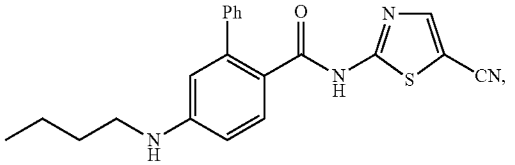
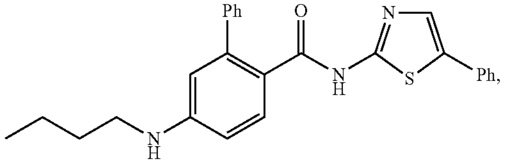
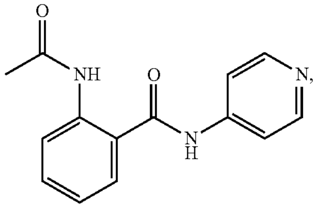
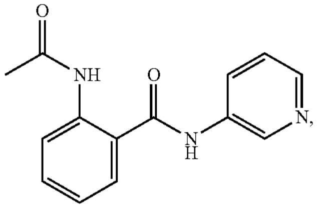
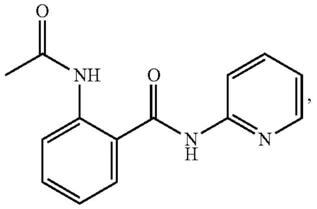
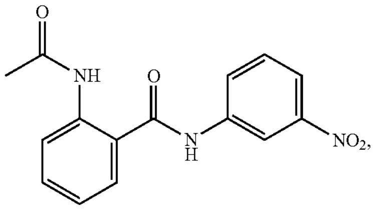
-continued
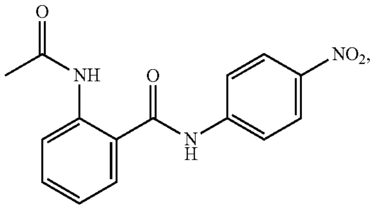
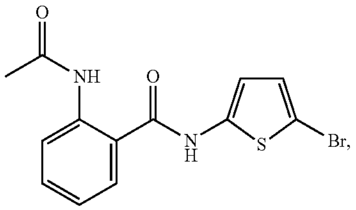
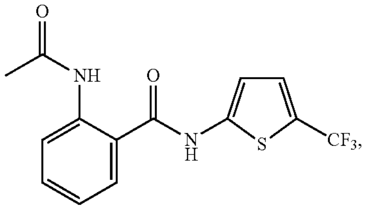
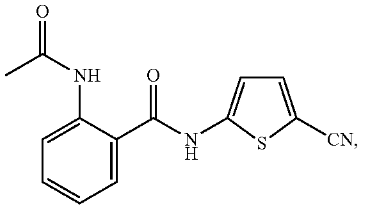
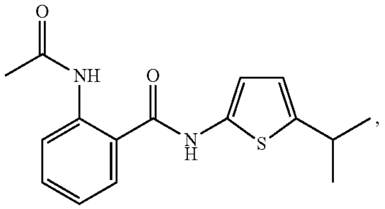
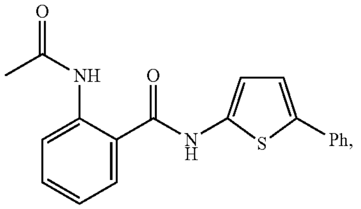
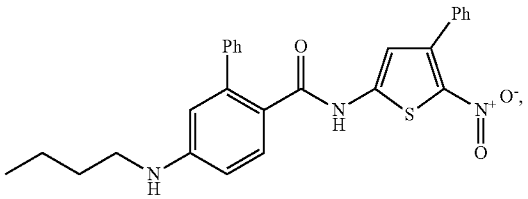
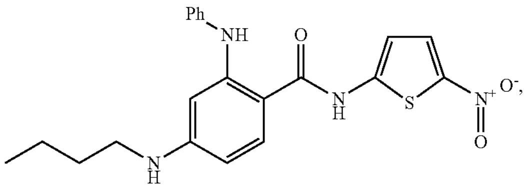

-continued
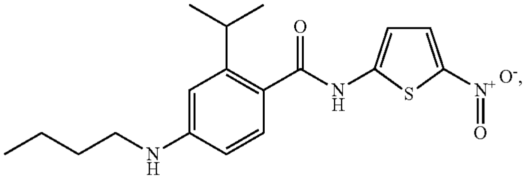
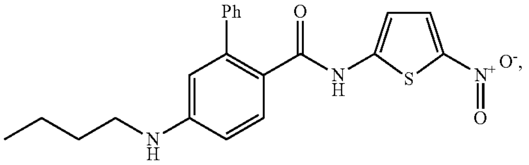
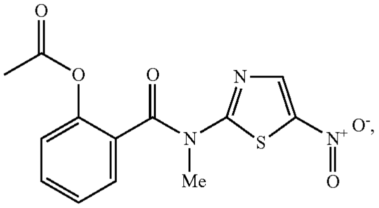
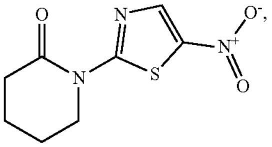
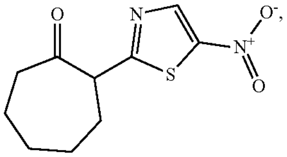
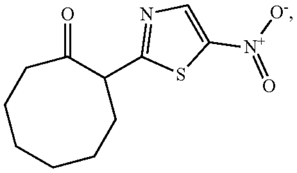
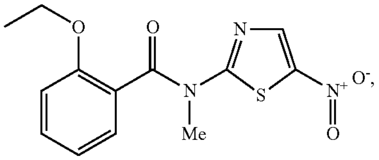
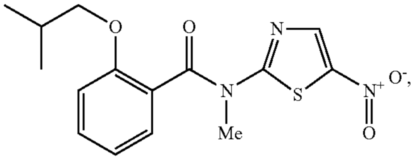
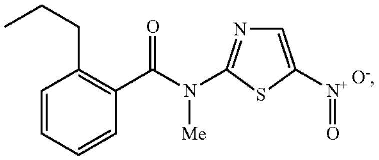
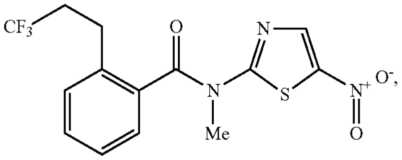
-continued
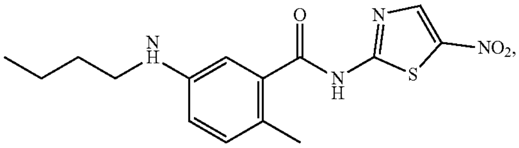
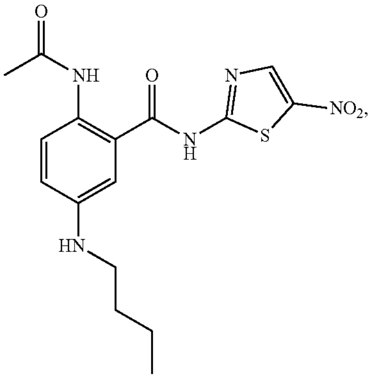
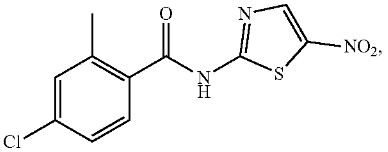
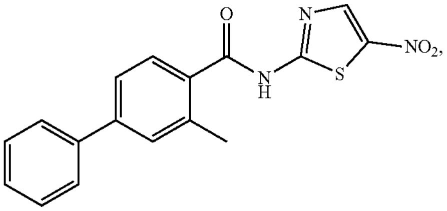
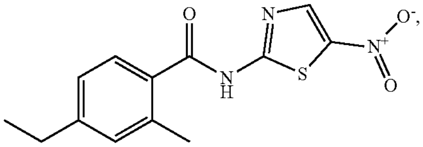
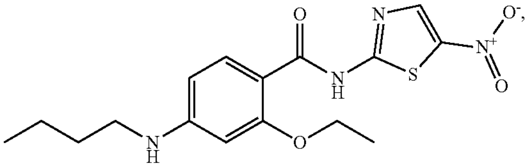
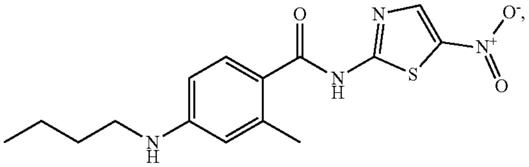
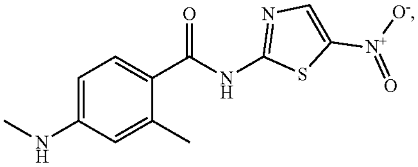
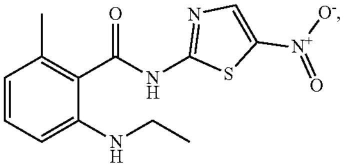

-continued

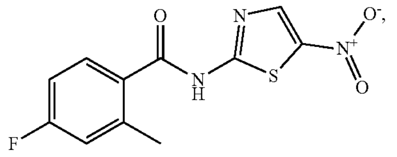

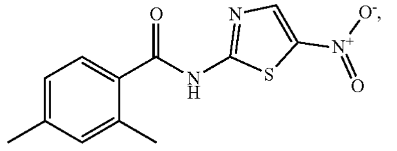

or a pharmaceutically acceptable salt thereof. In some embodiments, the DDB1 binding moiety comprises

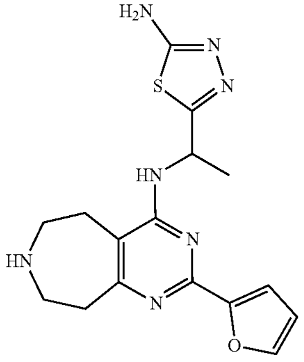

,

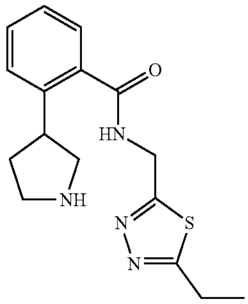

,

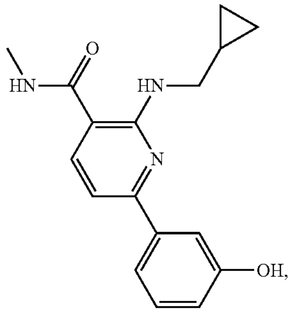

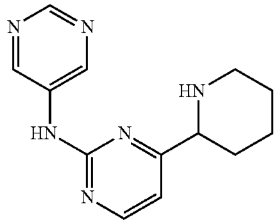

,

-continued

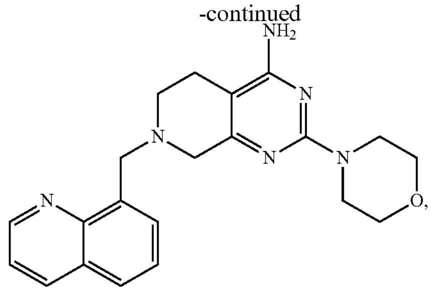

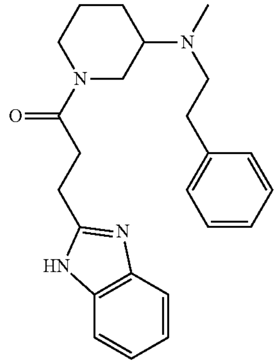

,

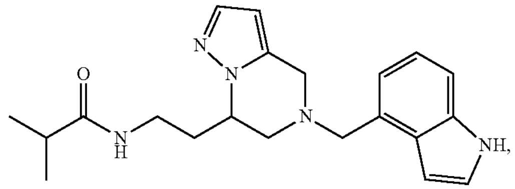

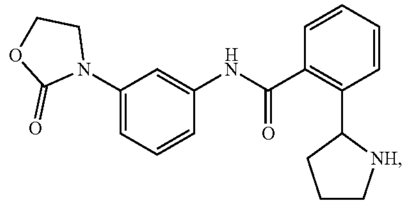

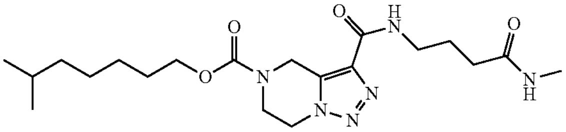

, or a pharmaceutically acceptable salt thereof. In some embodiments, the linker comprises $-(CH_2)_{p2}NH(CH_2)_{p1}NH-$, $-(CH_2)_{p2}NH(CH_2)_{p1}C(=O)NH-$, $-(CH_2)_{p2}NH(CH_2)_{p1}NHC(=O)-$, $-(CH_2)_{p2}NH(CH_2CH_2)(OCH_2CH_2)_{p1}NH-$, $-(CH_2)_{p2}NH(CH_2CH_2)(OCH_2CH_2)_{p1}C(=O)NH-$, or $-(CH_2)_{p2}NH(CH_2CH_2)(OCH_2CH_2)_{p1}NHC(=O)-$, wherein p1 is 1-15, and p2 is 0-15. In some embodiments, the target protein binding moiety binds to a target protein. In some embodiments, the target protein binding moiety comprises any of compounds A-1 to A-69 as shown in Table 4. In some embodiments, the DDB1 ligand is a heterobifunctional compound comprising a DDB1 binding moiety covalently connected through a linker to a target protein binding moiety. In some embodiments, the heterobifunctional compound comprises any of compounds D-1 to D-130 as shown in Table 5. In some embodiments, the heterobifunctional compound is a degrader of the target protein. In some embodiments, in vivo contact of the ligand with the target protein results in degradation of the target protein.

Disclosed herein, in some embodiments, are methods for degrading a target protein in a subject, comprising: administering, to the subject, a heterobifunctional ligand comprising a DNA damage-binding protein 1 (DDB1) binding moiety covalently connected through a linker to a target protein binding moiety. In some embodiments, the subject is a mammal. In some embodiments, the subject is a human. In some embodiments, the administration is intravenous. In some embodiments, the administration is intramuscular. In some embodiments, the administration is intrathecal. In some embodiments, the administration is subcutaneous. In some embodiments, the administration comprises an injection. In some embodiments, the administration is oral. In some embodiments, the administration is sublingual. In some embodiments, the administration is buccal. In some embodiments, the administration is rectal. In some embodiments, the administration is vaginal. In some embodiments, the administration is ocular. In some embodiments, the administration is otic. In some embodiments, the administration is nasal. In some embodiments, the administration is inhalation. In some embodiments, the administration is nebulization. In some embodiments, the administration is cutaneous. In some embodiments, the administration is topical. In some embodiments, the administration is transdermal. In some embodiments, the administration is systemic. In some embodiments, administering the ligand to the subject comprises administering an effective amount of the ligand sufficient to degrade the target protein. In some embodiments, upon administration of the ligand to the subject, the target protein is ubiquitinated to form a ubiquitinated target protein. Disclosed herein, in some embodiments, are methods for degrading a target protein in a sample, comprising: contacting a target protein with a ligand comprising a DNA damage-binding protein 1 (DDB1) binding moiety covalently connected through a linker to a target protein binding moiety. In some embodiments, the sample is a biological sample. In some embodiments, the biological sample comprises a tissue, a cell, or a biological fluid. In some embodiments, the contact is in vitro. In some embodiments, the contact is in vivo. In some embodiments, upon being contacted with the ligand, the target protein is ubiquitinated to form a ubiquitinated target protein. In some embodiments, the ubiquitinated target protein is degraded. In some embodiments, the degradation of the target protein is specific to the target protein. In some embodiments, the degradation of the target protein comprises proteasomal degradation. In some embodiments, the target protein is degraded by a proteasome. In some embodiments, the ligand binds to a DDB1 protein to form a ligand-DDB1 complex. In some embodiments, the ligand directly binds to the DDB1 protein through the DDB1 binding moiety of the ligand. In some embodiments, the binding between the DDB1 binding moiety and the DDB1 protein is non-covalent. In some embodiments, the binding between the DDB1 binding moiety and the DDB1 protein is covalent. In some embodiments, the target protein is ubiquitinated by a ubiquitin E3 ligase complex comprising the DDB1 protein. In some embodiments, the ligand (e.g. a DDB1 ligand) recruits the ubiquitin E3 ligase complex to the target protein via the DDB1 binding moiety. In some embodiments, the ligand is a small molecule. In some embodiments, the DDB1 ligand is a heterobifunctional compound comprising a DDB1 binding moiety covalently connected through a linker to a target protein binding moiety. In some embodiments, the heterobifunctional compound induces the target protein degradation. In some embodiments, the ligand comprises a ligand described herein. In some embodiments, the target protein comprises any one of a transcription factor, CBP, p300, a kinase, a receptor, a TRK, TrkA, TrkB, TrkC, a cyclin dependent kinase, CDK, CDK1, CDK2, CDK3, CDK4, CDK6, CDK7, CDK8, CDK9, CDK10, CDK11, CDK12, CDK13, a cyclin, cyclin A, cyclin B, cyclin C, cyclin D, cyclin D1, cyclin D2, cyclin D3, cyclin E, cyclin H, cyclin K, cyclin T, cyclin T1, p25, p35, B7.1, B7, TINFRlm, TNFR2, NADPH oxidase, a partner in an apoptosis pathway, BclIBax, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide synthase, cyclo-oxygenase 1, cyclo-oxygenase 2, a receptor, a 5HT receptor, a dopamine receptor, a G-protein, Gq, a histamine receptor, 5-lipoxygenase, tryptase serine protease, thymidylate synthase, purine nucleoside phosphorylase, GAPDH, a trypanosomal protein, glycogen phosphorylase, carbonic anhydrase, a chemokine receptor, JAK, STAT, RXR, RAR, HIV 1 protease, HIV 1 integrase, influenza, neuramimidase, hepatitis B reverse transcriptase, sodium channel, multi drug resistance, protein P-glycoprotein, MRP, a tyrosine kinase, CD23, CD124, tyrosine kinase p56 lck, CD4, CD5, IL-2 receptor, IL-1 receptor, TNF-alphaR, ICAM1, a Ca+ channel, VCAM, an integrin, a VLA-4 integrin, a selectin, CD40, CD40L, a neurokinin, a neurokinin receptor, inosine monophosphate dehydrogenase, p38 MAP Kinase, Ras, Raf, Mek, Erk, interleukin-1 converting enzyme, a caspase, HCV. NS3 protease, HCV NS3 RNA helicase, glycinamide ribonucleotide formyl transferase, rhinovirus 3C protease, herpes simplex virus-1, a protease, cytomegalovirus protease, poly ADP-ribose polymerase, vascular endothelial growth factor, oxytocin receptor, microsomal transfer protein inhibitor, bile acid transport inhibitor, a 5 alpha reductase inhibitor, angiotensin II, a glycine receptor, a noradrenaline reuptake receptor, an endothelin receptor, neuropeptide Y, a neuropeptide Y receptor, an estrogen receptor, an androgen receptor, an adenosine receptor, an adenosine kinase, AMP deaminase, a purinergic receptor, P2Y1, P2Y2, P2Y4, P2Y6, P2X1-7, a farnesyltransferase, geranylgeranyl transferase, an NGF receptor, beta-amyloid, a tyrosine kinase, Flk-IIKDR, vitronectin receptor, an integrin receptor, Her2 neu, telomerase inhibition, cytosolic phospholipaseA2. EGF receptor tyrosine kinase, ecdysone 20-monooxygenase, ion channel of the GABA gated chloride channel, acetylcholinesterase, voltage-sensitive sodium channel protein, calcium release channel, a chloride channel, acetyl-CoA carboxylase, adenylosuccinate synthetase, protoporphyrinogen oxidase, enolpyruvylshikimate-phosphate synthase, an HSP, Hsp90, a kinase, an MDM, MDM2, a Human BET Bromodomain-containing protein, an HDAC, a lysine methyltransferase, an angiogenesis protein, an immunomodulatory protein, AHR, VEGFR3, Alk, Abl, a Janus kinase, JAK2, Met, B-Raf, a phosphatase, FKBP, a thyroid hormone receptor, acyl-protein thioesterase-1, acyl-protein thioesterase-2, an HIV protein, an HIV protease, an HIV integrase, an HCV protein, or an HCV protease.

Disclosed herein, in some embodiments, are methods of treatment, comprising: administering to a subject having an infection, a therapeutically effective amount of a heterobifunctional compound comprising a DNA damage-binding protein 1 (DDB1) binding moiety covalently connected to a target protein binding moiety. In some embodiments, the infection comprises a viral infection, and the target protein comprises a viral protein. In some embodiments, the compound comprises a ligand described herein. In some embodiments, the administration results in ubiquitination and degradation of the target protein. In some embodiments, the subject is a human.

Disclosed herein, in some embodiments, are methods of modulating a DNA damage-binding protein 1 (DDB1) protein, comprising: contacting a DDB1 protein with a compound comprising a DDB1 binding moiety. In some embodiments, the DDB1 binding moiety comprises a structure of Formula (II), a structure of Formula (IIa), or a structure of Formula (IIb), or a salt thereof. In some embodiments, the compound comprises a compound in Table 1, or a salt thereof. In some embodiments, the compound comprises a peptide in Table 3, or a peptide having an amino acid sequence at least 70% identical, at least 75% identical, at least 80% identical, at least 85% identical, at least 90% identical, or at least 95% identical, to a peptide in Table 3. In some embodiments, contacting the DDB1 protein with the compound comprises contacting the DDB1 protein with the compound in vitro. In some embodiments, contacting the DDB1 protein with the compound comprises delivering the compound to a cell expressing the DDB1 protein. In some embodiments, contacting the DDB1 protein with the compound comprises contacting the DDB1 protein with the compound in vivo. In some embodiments, contacting the DDB1 protein with the compound comprises administering the compound to a subject. In some embodiments, the subject is a human. In some embodiments, the compound binds to the DDB1 protein. In some embodiments, the contact results in an increase in an amount of the DDB1 protein, relative to a baseline amount. In some embodiments, the contact results in a decrease in an amount of the DDB1 protein, relative to a baseline amount. In some embodiments, the contact results in an increase in an activity of the DDB1 protein, relative to a baseline activity. In some embodiments, the contact results in a decrease in an activity of the DDB1 protein, relative to a baseline activity.

Disclosed herein, in some embodiments, are methods of bringing a DNA damage-binding protein 1 (DDB1) protein into proximity with a target protein, comprising: contacting a DDB1 protein and a target protein with a compound comprising a DDB1 binding moiety and a target protein binding moiety. In some embodiments, the compound comprises a ligand described herein. In some embodiments, the contact is in vitro. In some embodiments, the contact is in vivo. In some embodiments, contacting the DDB1 protein and the target protein with the compound comprises delivering the compound to a cell expressing the DDB1 protein and the target protein. In some embodiments, contacting the DDB1 protein and the target protein with the compound comprises administering the compound to a subject. In some embodiments, the subject is a human. In some embodiments, the compound binds to the DDB1 protein and to the target protein. In some embodiments, the contact results in an increase in an amount of the target protein, relative to a baseline amount. In some embodiments, the contact results in a decrease in an amount of the target protein, relative to a baseline amount. In some embodiments, the contact results in an increase in an activity of the target protein, relative to a baseline activity. In some embodiments, the contact results in a decrease in an activity of the target protein, relative to a baseline activity.

INCORPORATION BY REFERENCE

All publications, patents, and patent applications mentioned in this specification are herein incorporated by reference for the specific purposes identified herein.

DETAILED DESCRIPTION OF THE INVENTION

Described herein are compounds and methods for binding DNA damage-binding protein 1 (DDB1), for binding and/or degrading target proteins, for inducing subsequent cellular effects, and/or for inhibiting microbes such as a virus or a bacteria. Disclosed are compositions comprising a DBB1 binding moiety, a DBB1 binding moiety covalently connected to a linker, and/or a DDB1 binding moiety covalently connected through a linker to a target protein binding moiety. Compounds described herein may be useful for several purposes, including but not limited to use as: 1) antiviral drugs; 2) DDB1 protein level modulators (e.g. increasing or decreasing DDB1 protein levels); 3) DDB1 function modulators (e.g. DDB1 activators or inhibitors); or 4) molecular glues (e.g. increasing a protein-protein interaction between DDB1 and a second protein). The molecular glue function may be useful for affecting activity or protein levels of the second protein.

Figure 1A:
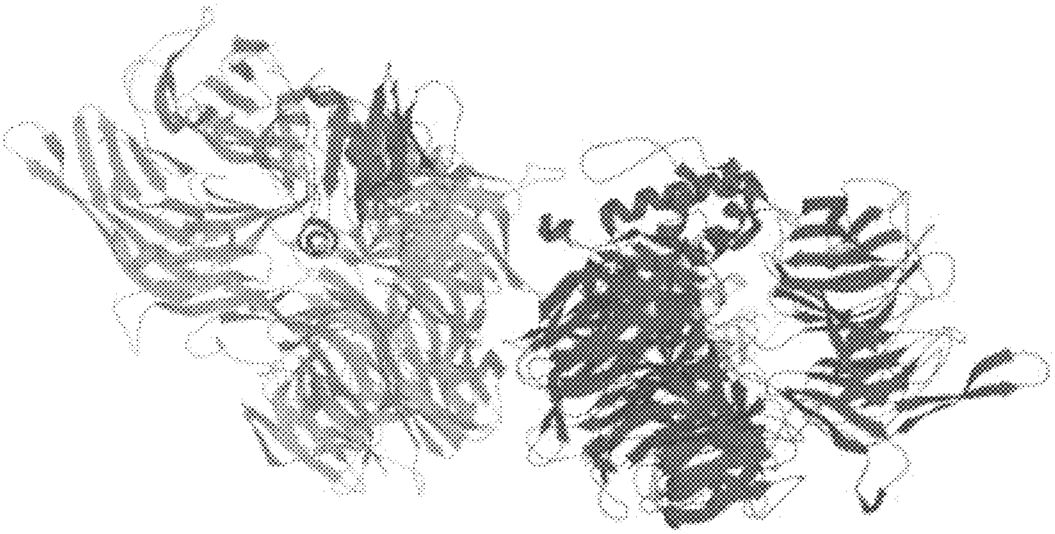
FIG. 1A shows a three-dimensional conformation of protein that includes a DNA damage-binding protein 1 (DDB1) protein in accordance with some embodiments described herein.

An example of a DDB1 protein is included in the protein structure shown in FIG. 1A. In some embodiments, the DDB1 protein contains 1140 amino acids, and has a mass of 127 kDa. The DDB1 protein may function as a component of an E3 ubiquitin ligase complex. The E3 ubiquitin ligase complex may include CUL4A and CUL4B. The DDB1 protein may serve as a bridge or adaptor and interact with other proteins such as DDB1 and CUL4-associated factors (DCAFs). The DCAFs may be ubiquitin ligase substrates.

Disclosed herein, in some embodiments, are ligand-DDB1 complexes. In some embodiments, the ligand-DDB1 complex is formed by non-covalently binding a DDB1 protein directly to a ligand. In some embodiments, the ligand comprises a DDB1 binding moiety. In some embodiments, the ligand is a heterobifunctional compound comprising a DDB1 binding moiety covalently connected through a linker to a target protein binding moiety.

Disclosed herein, in some embodiments, are modified proteins such as n vivo modified proteins. In some embodiments, the modified protein comprises a DDB1 protein directly bound to a ligand. In some embodiments, the ligand comprises a DDB1 binding moiety. In some embodiments, the ligand is a heterobifunctional compound comprising a DDB1 binding moiety covalently connected through a linker to a target protein binding moiety.

Disclosed herein, in some embodiments, are ligands. In some embodiments, the ligand comprises a DDB1 binding moiety. In some embodiments, the DDB1 binding moiety is covalently connected through a linker to a target protein binding moiety.

Disclosed herein, in some embodiments, are methods of degrading a target protein. Some embodiments comprise administering, to the subject, a ligand comprising a DDB1 binding moiety covalently connected through a linker to a target protein binding moiety.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Characterization of Exemplary Heterobifunctional Compounds

Figure 1B:
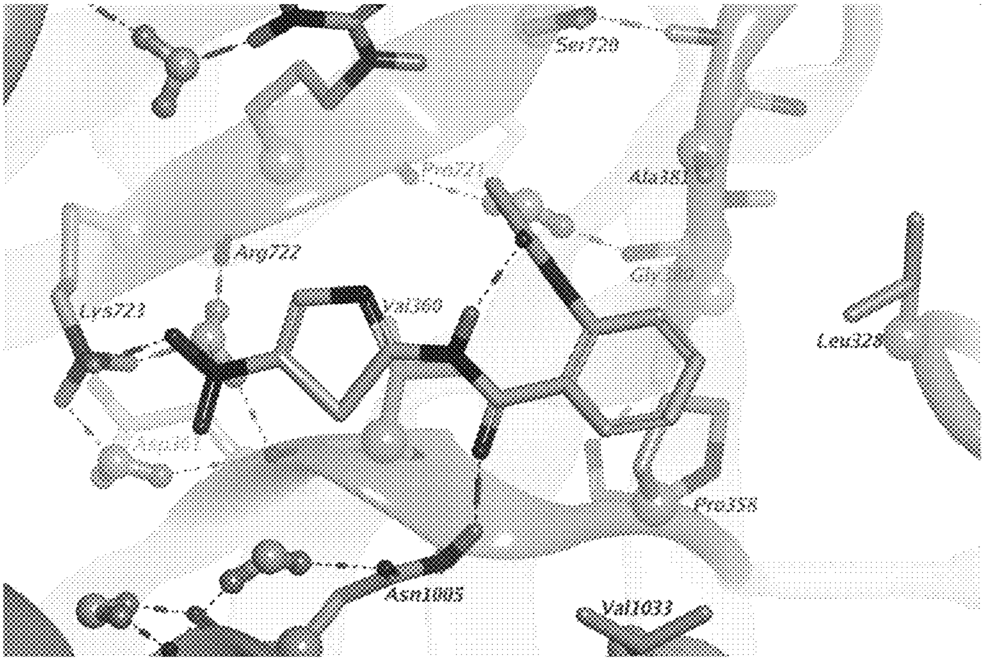
FIG. 1B shows a DDB1 protein bound to a ligand, in accordance with some embodiments.
Figure 2A:
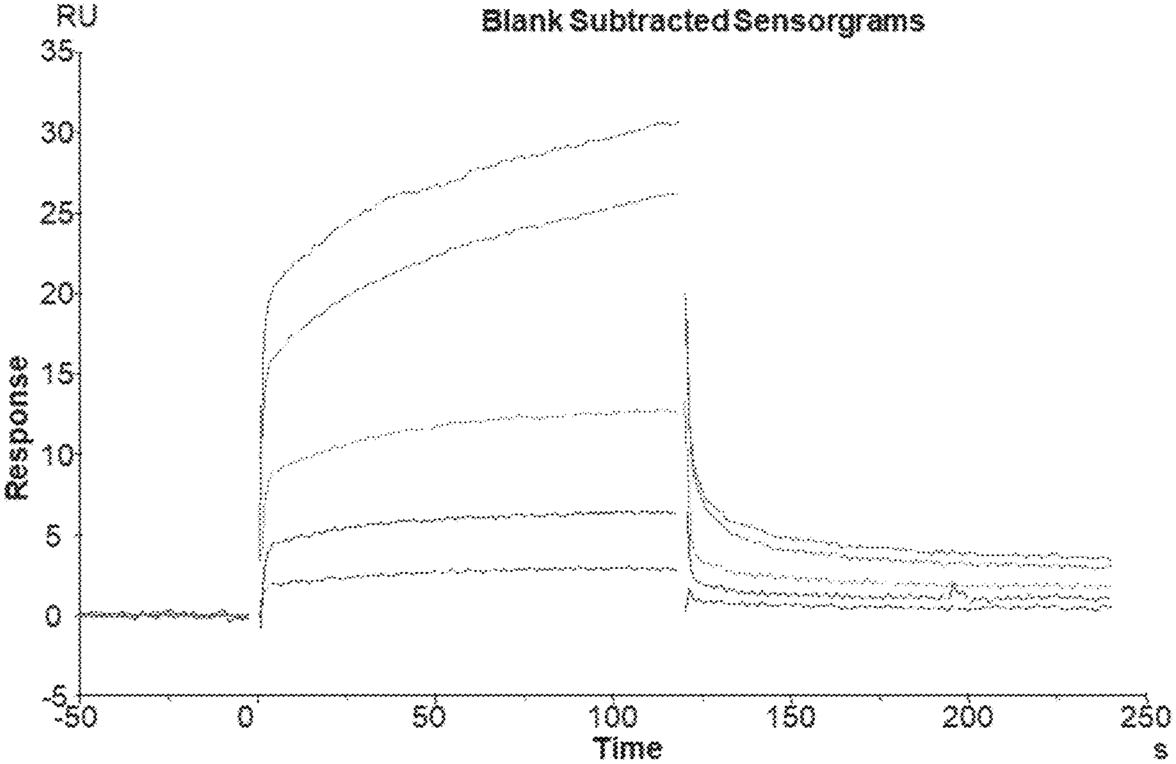
FIG. 2A shows SPR sensorgrams of heterobifunctional compound D-2 binding to DDB1.
Figure 2A:
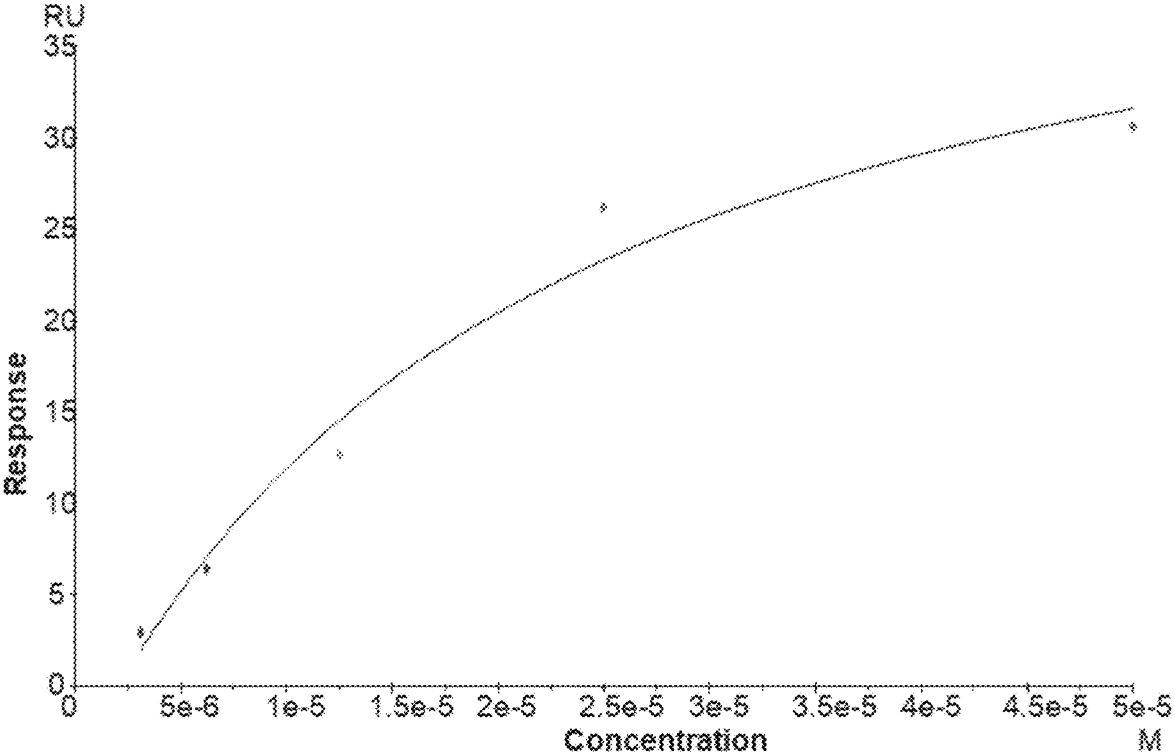
Figure 2B:
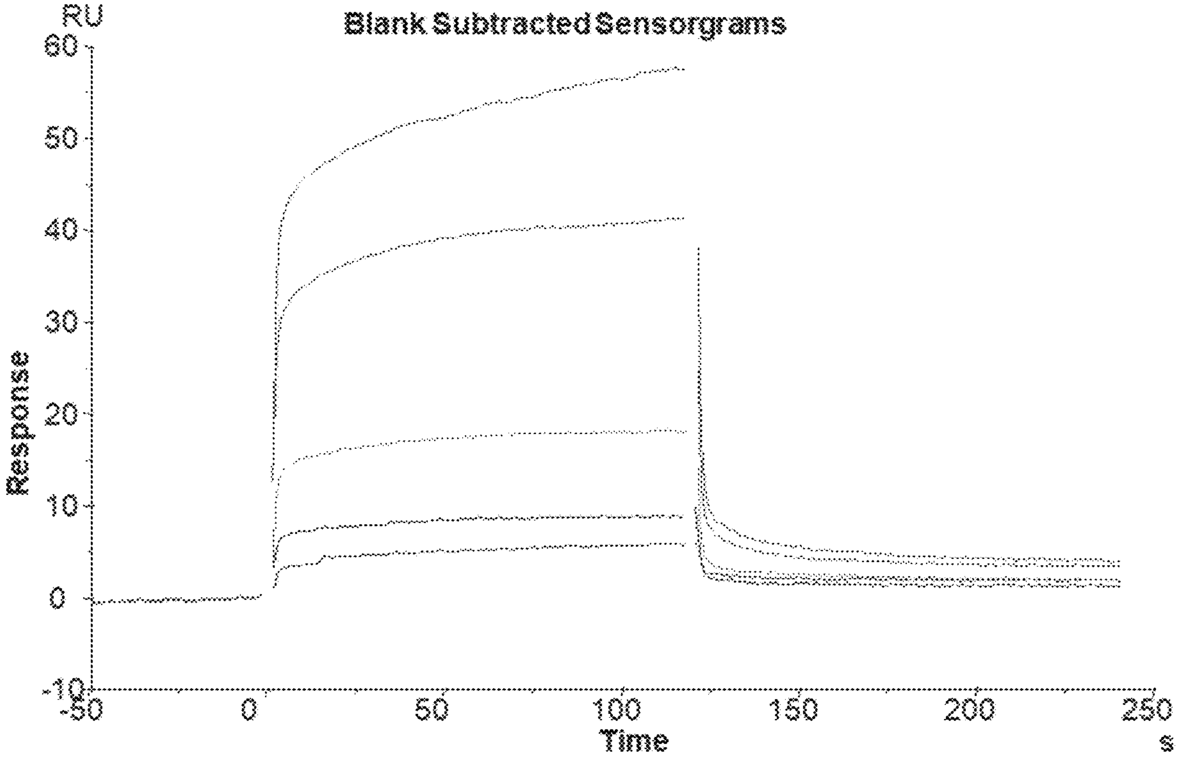
FIG. 2B shows SPR sensorgrams of heterobifunctional compound D-7 binding to DDB1.
Figure 2B:
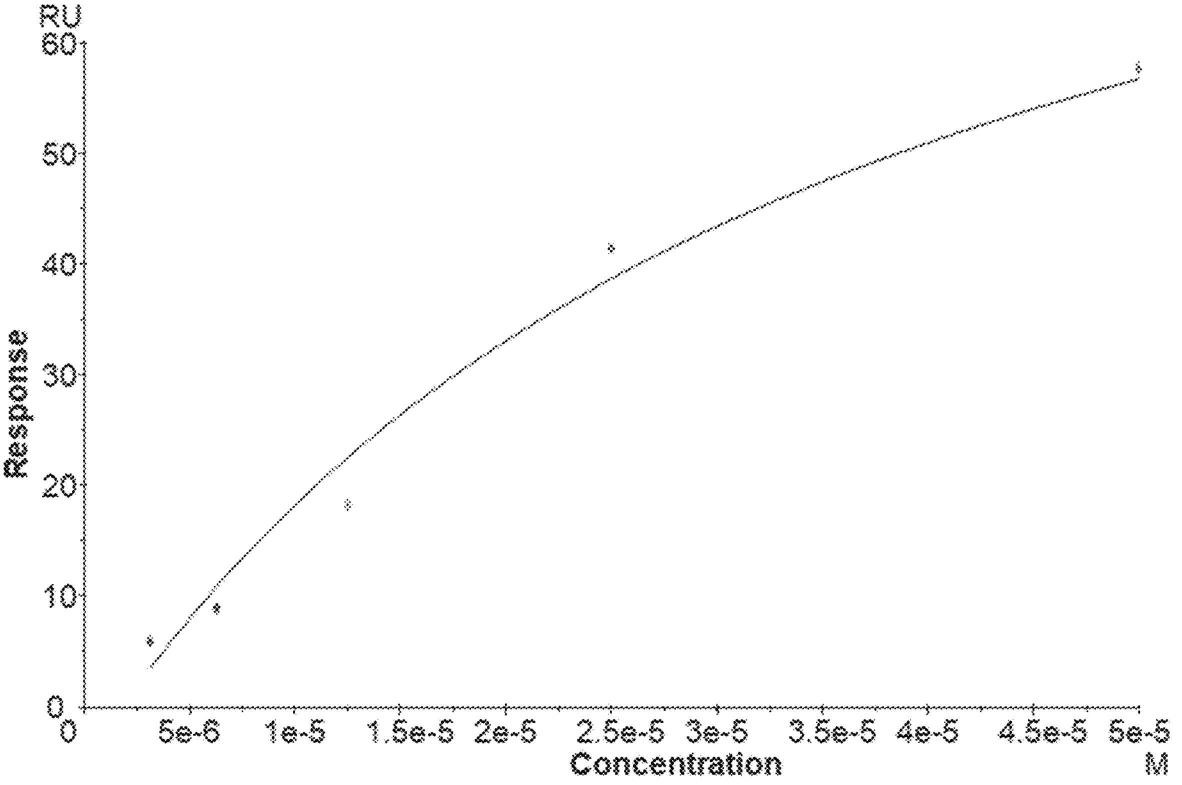
Figure 2C:
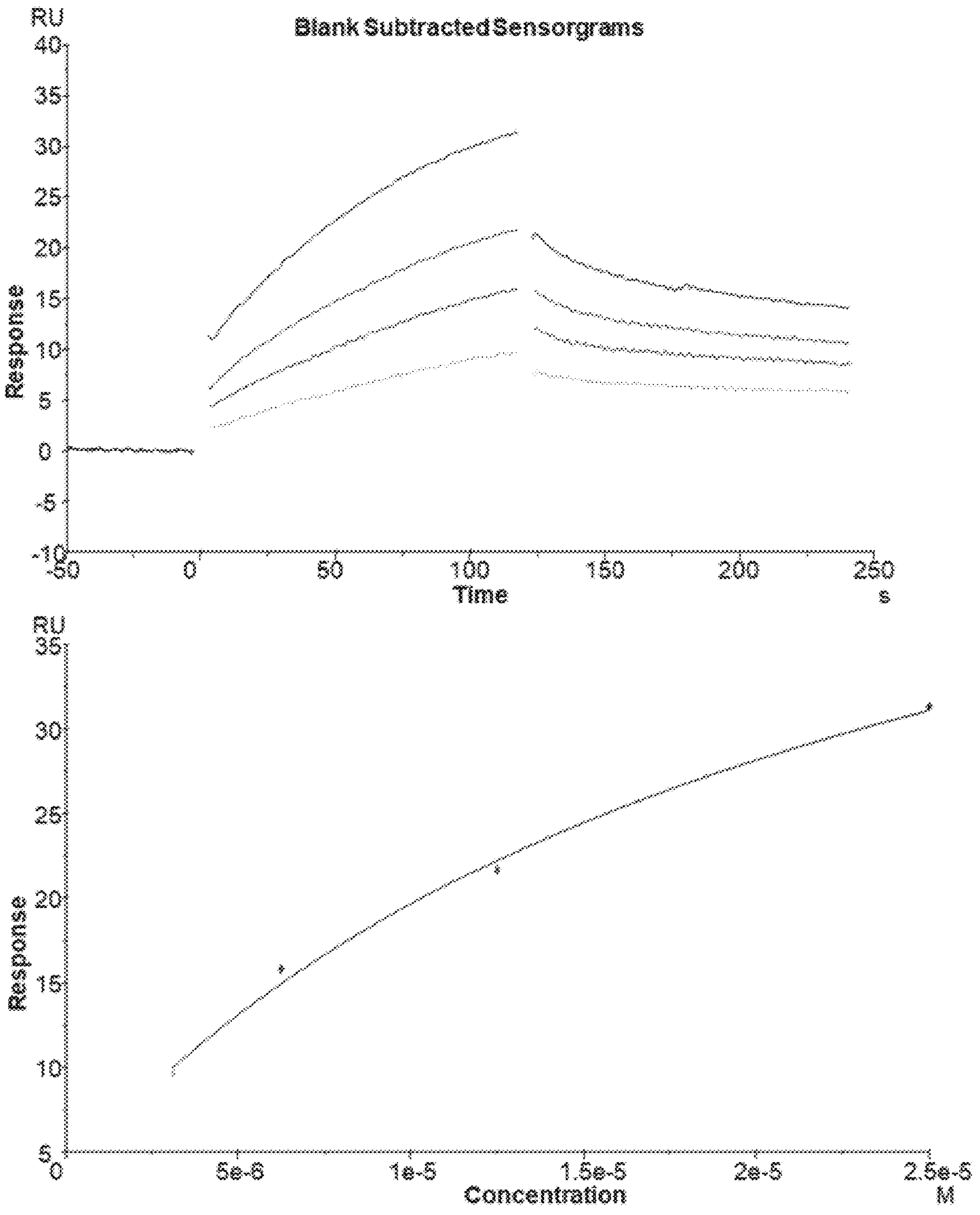
FIG. 2C shows SPR sensorgrams of heterobifunctional compound D-13 binding to DDB1.
Figure 2D:
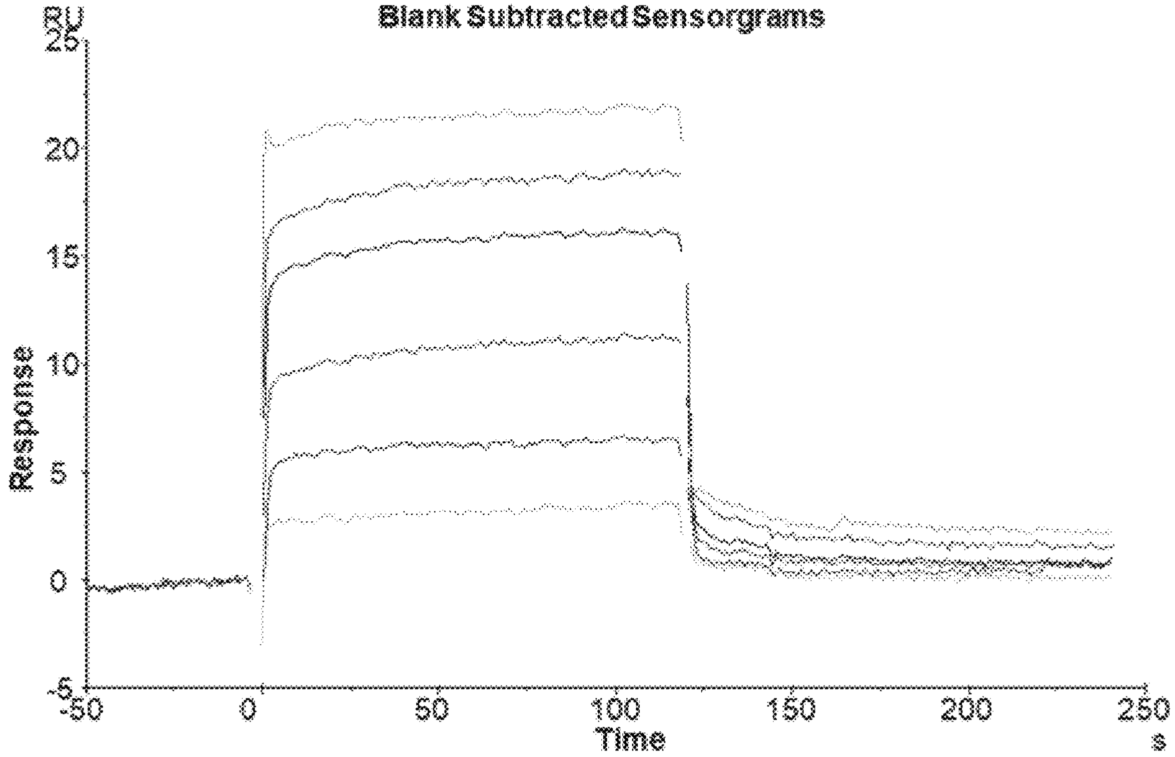
FIG. 2D shows SPR sensorgrams of heterobifunctional compound D-48 binding to DDB1.
Figure 2D:
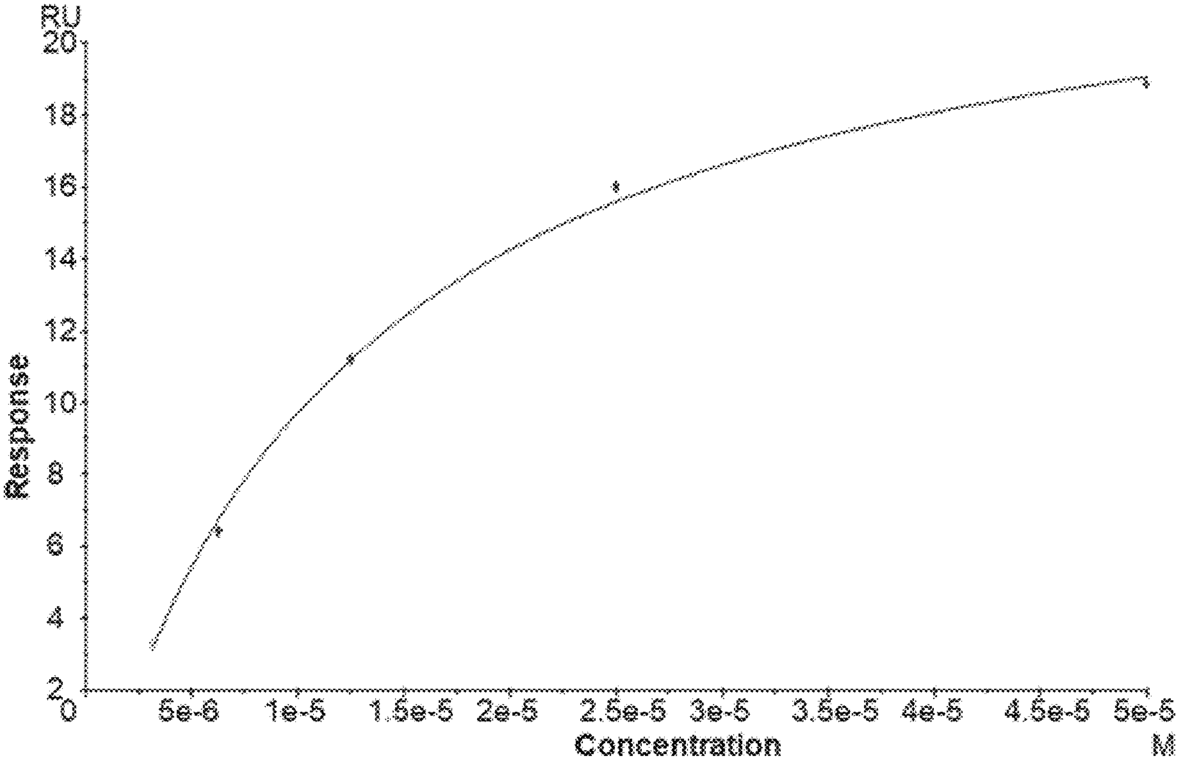
Figure 2E:
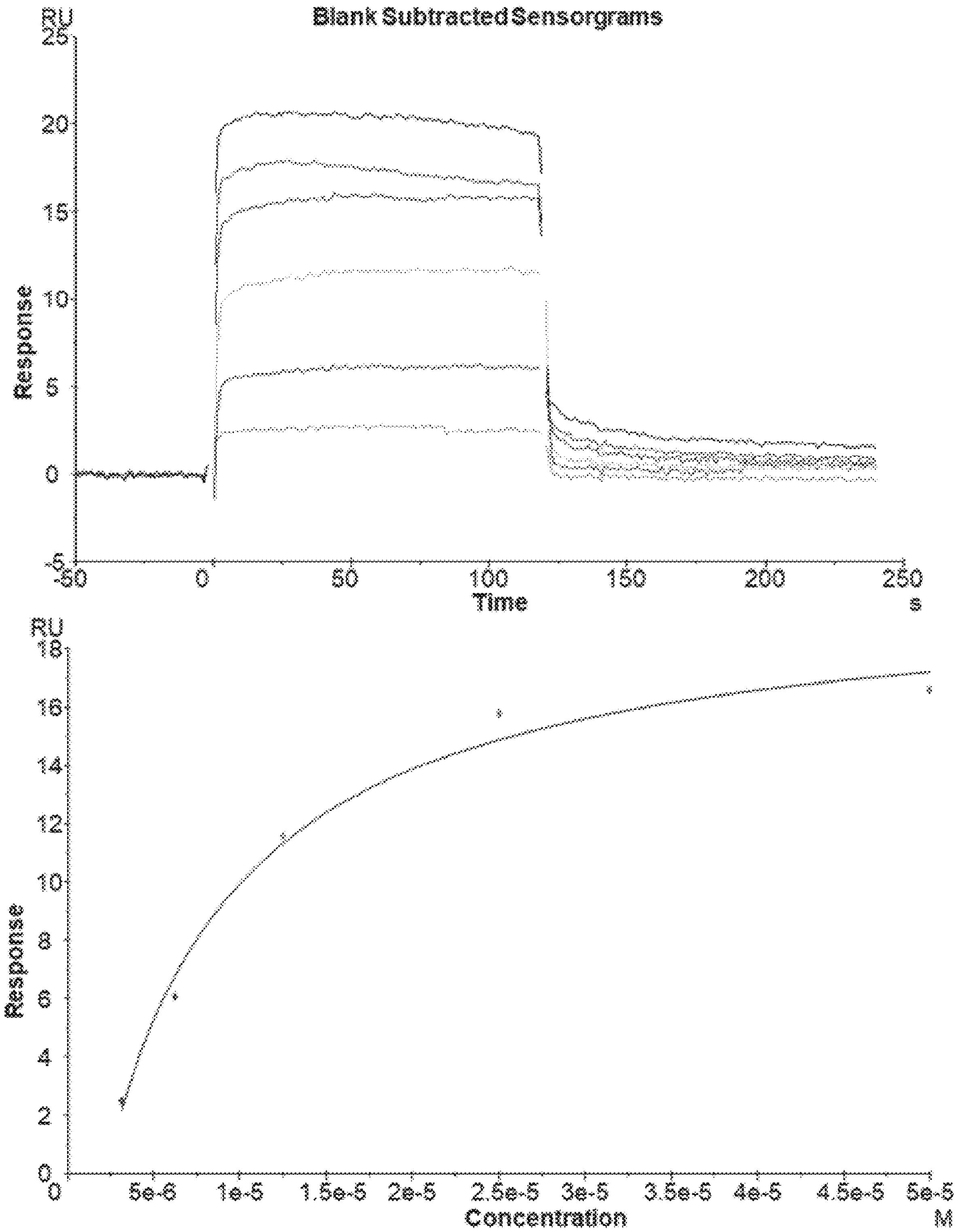
FIG. 2E shows SPR sensorgrams of heterobifunctional compound D-49 binding to DDB1.

A non-limiting example of a DDB1 protein bound to a ligand is included in FIG. 1B, which shows a docking model of a DDB1 protein in a complex with a ligand comprising compound B-1 in accordance with some embodiments. In the model, the ligand occupies a central cavity of a BPC domain of a DDB1 protein, anchored towards the center of a WD40-motif by a salt-bridge between the primary amine of LYS723 and a nitro group of the ligand and through a Coulombic interaction between the electron-deficient nitrogen of the nitro group and a lone-pair of a nearby water, which is ordered between the backbone carbonyl oxygen atoms of ARG722 and VAL360 as well as the primary amine of LYS723. In the model, the pi-faces of the thiazole and amide rest over the VAL360 sidechain, while the amide forms an intermolecular hydrogen bond with the sidechain of ASN1005 and an intramolecular hydrogen bond with the acetate. In the model, the sulfur of the thiophene is believed to be geometrically stabilized through a stereoelectronic interaction with the ASN1005 sidechain. In the model, the acetate methyl forms dispersion contacts with the ARG722 sidechain and an ordered water. In the model, the benzene ring forms dispersion contacts with the sidechains of ALA381, LEU328, PRO358 and VAL1033. Although the docking model includes compound B-1, other ligands may bind to the DDB1 protein in a similar manner as compound B-1.

The binding affinities of specific, non-limiting exemplary heterobifunctional compounds to DDB1 were determined by a surface plasmon resonance (SPR) assay. In short, purified His-DDB1 proteins were immobilized by amine coupling to a density of 11,000-13,000 resonance units (RUs) on a CM5 sensor chip. Sensorgrams were recorded at different concentrations of heterobifunctional compounds in multi-cycle kinetic format. All data were fit to steady state affinity model using Biacore Evaluation Software and gave equivalent dissociation constants ($K_D$). Data showed that all exemplary heterobifunctional compounds bind to DDB1 in a concentration-dependent manner, and the binding affinities ($K_D$) are from 5 μM to 60 μM (see FIG. 2, Table 6 and Table 7).

Figure 3A:
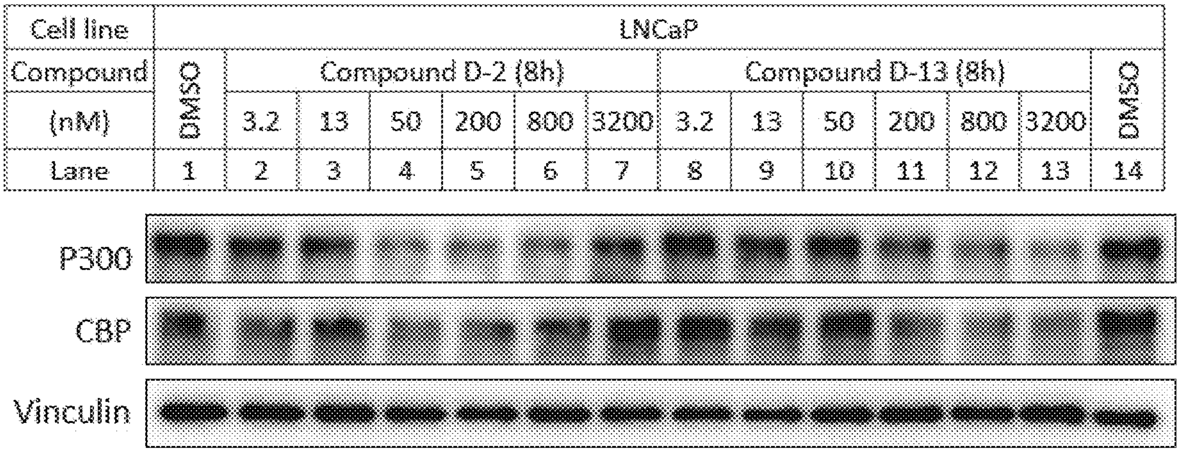
FIG. 3A shows immunoblots of P300 and CBP protein expressed by LNCaP cells after treatment with heterobifunctional compound D-2 or D-13 at indicated concentrations for 8 hours.
Figure 3B:
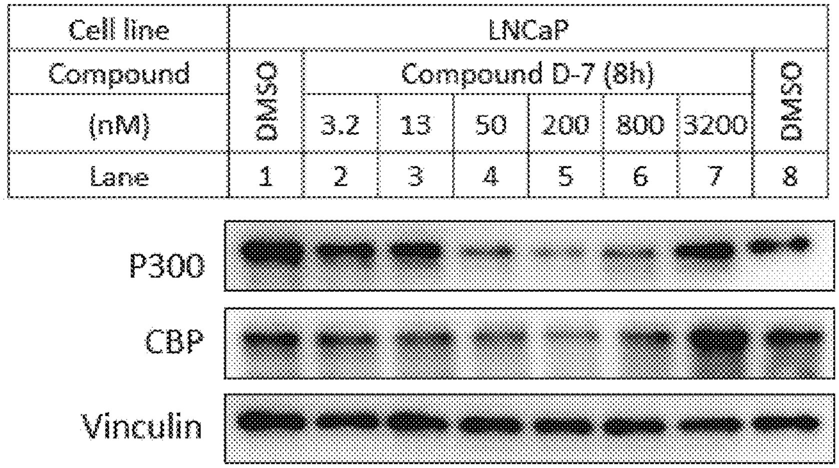
FIG. 3B shows immunoblots of P300 and CBP protein expressed by LNCaP cells after treatment with heterobifunctional compound D-7 at indicated concentrations for 8 hours.
Figure 4:
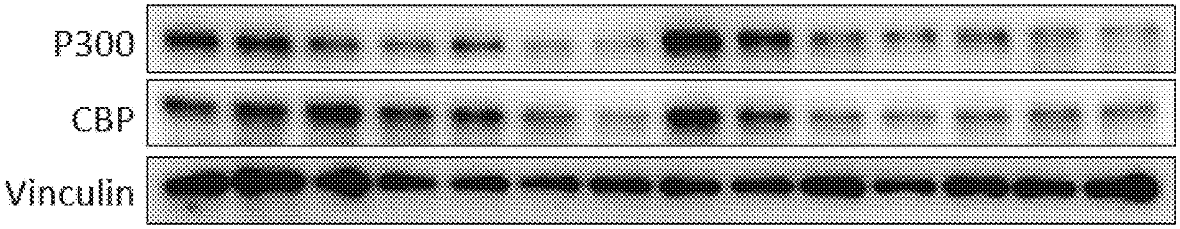
FIG. 4 shows immunoblots of P300 and CBP protein expressed by LNCaP cells after treatment with heterobifunctional compound D-2 or D-13 at various time points.

Experiments were performed to see if heterobifunctional compounds as described herein could degrade target proteins. Specific exemplary heterobifunctional compounds were characterized in LNCaP and Calu-1 cells. LNCaP cells that express P300/CBP proteins were treated with heterobifunctional compounds disclosed herein (D-2, D-13, or D-7)

at indicated concentrations for 8 hours. Cells were collected, lysed and subject to immunoblotting using an antibody specific to P300 or CBP proteins. Vinculin was included as the loading control. DMSO treatment was used as the negative control. Following treatment with D-2, D-13, or D-7, P300 and CBP protein levels in LNCaP cells were significantly decreased in a concentration-dependent manner (FIG. 3A and FIG. 3B). These results highlight the abilities of three non-limiting examples of heterobifunctional degrader compounds to degrade the targeted proteins. In addition, LNCaP cells were treated with 500 nM of D-2, or D-13 for indicated period of time. Subsequently, changes in P300 and CBP protein levels were measured by immunoblotting. Significant degradation of P300 and CBP were readily detected as early as 2-4 hours following administration of the compounds (FIG. 4).

The heterobifunctional compound-mediated p300 and CBP degradation was dependent on the ubiquitin-proteasome system and cullin E3 ligase. The degradation induced by D-2 or D-13 was compromised by co-administration of a proteasome inhibitor, MG-132 or bortezomib (BTZ), or a cullin RING E3 ubiquitin ligase (CRL) neddylation inhibitor, MLN4924, as demonstrated in FIG. 5A and FIG. 5B. The binding with DDB1 also played a role in the heterobifunctional compounds ability to induce degradation of P300 and CBP proteins. The D-13 mediated degradation could be partially neutralized by co-administration with excess DDB1 ligand, BL-11, that competed for DDB1 binding, as demonstrated in FIG. 5B. These findings collectively demonstrate that heterobifunctional compounds induce degradation of P300/CBP proteins via a mechanism specifically mediated by DDB1, cullin E3 ligase, and the proteasome.

Figure 6:
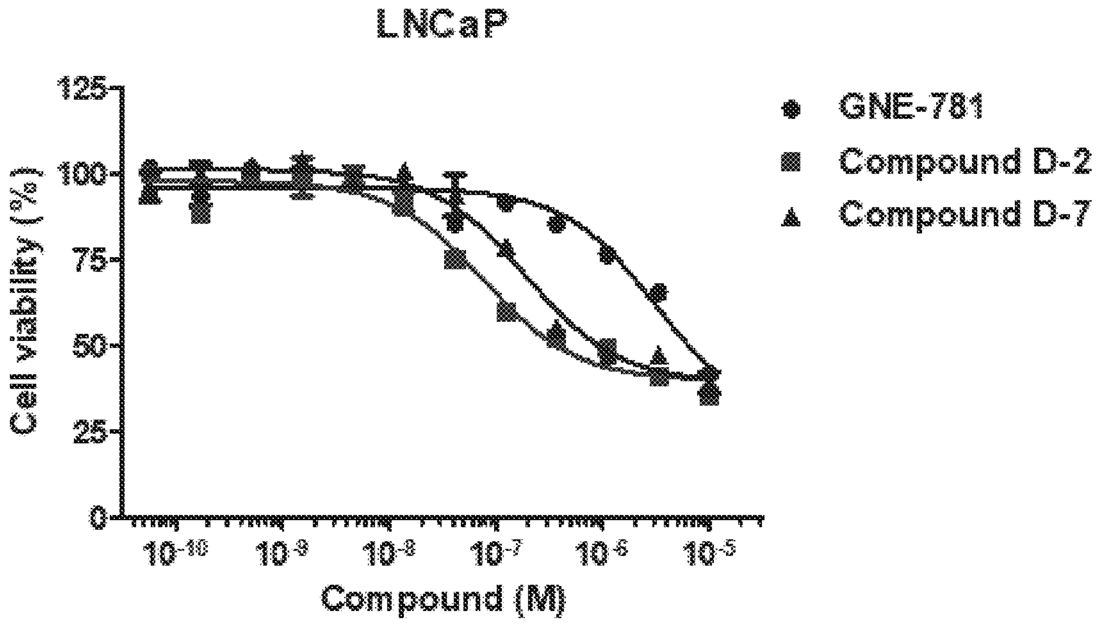
FIG. 6 shows a graph of LNCaP cell viability vs. concentrations of GNE-781, D-2, or D-7.

Targeting CBP/P300 using ligands to their bromodomains or lysine acetyltransferase domains has been shown to compromise cancer cell proliferation and survival. LNCaP cells seeded in 96-well plates were treated with 10 μM GNE-781 or selected heterobifunctional compounds, following a 12-point 3-fold serial dilution. Three days after treatment, cell viability was determined using the CellTiter-Glo Kit (Promega). Cell viability was normalized to the mean values of 3 replicates of untreated cells. Dose-dependent response was analyzed following the least-squares non-linear regression method using the GraphPad Prism software. Heterobifunctional compounds dose-dependently suppressed viability of LNCaP cells, as exemplified by D-2, or D-7 (FIG. 6). These results demonstrated that downregulation of CBP/P300 proteins levels by using heterobifunctional compounds described herein induced antiproliferation activities. Compared to the p300/CBP inhibitor GNE-781, the exemplified heterobifunctional p300/CBP degrader compounds D-2 and D-7 induced more potent inhibitory effects on the growth of LNCaP cells. Overall, the heterobifunctional degrader compounds described herein could be more potent for inducing cellular effects such as inhibiting cell growth or viability than target protein inhibitors.

Figure 7A:
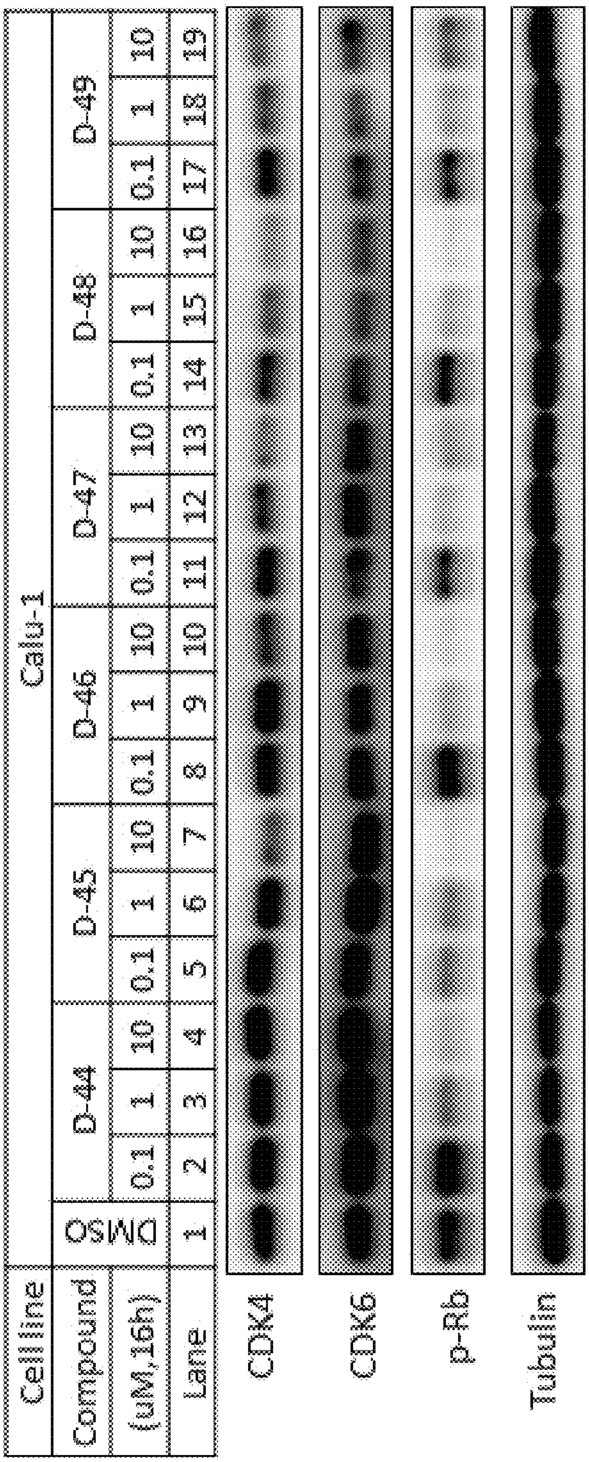
FIG. 7A shows immunoblots of CDK4 and CDK6 protein expressed by Calu-1 cells after treatment with heterobifunctional compound D-44, D-45, D-46, D-47, D-48, or D-49 at indicated concentrations for 16 hours.
Figure 7B:
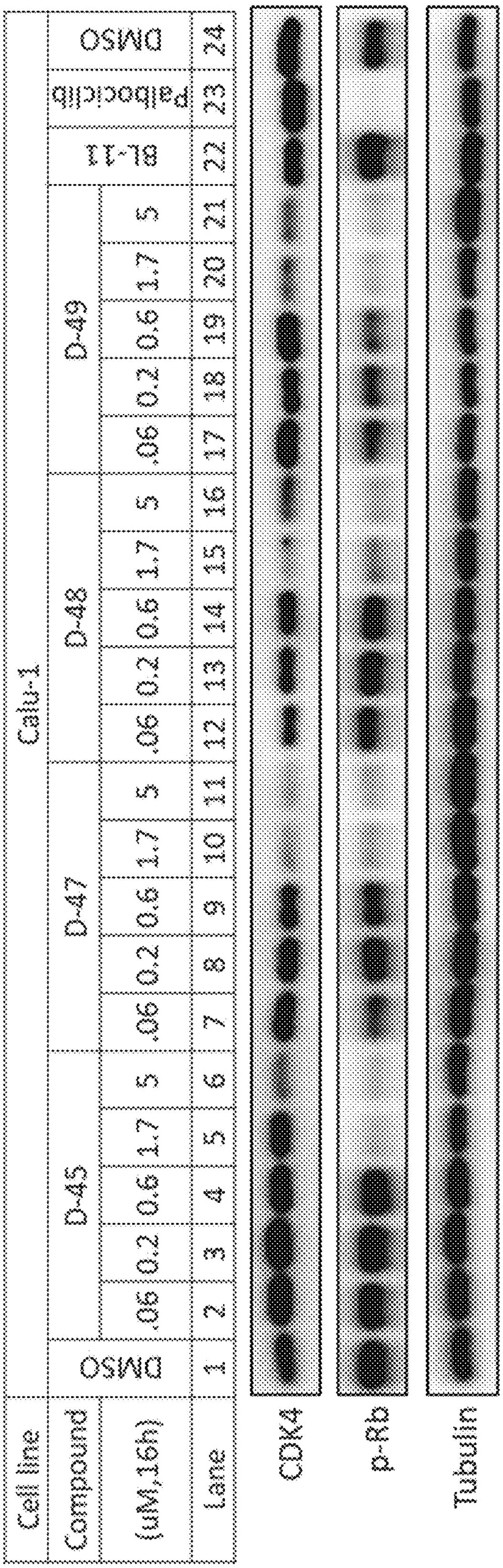
FIG. 7B shows immunoblots of CDK4 protein expressed by Calu-1 cells after treatment with heterobifunctional compound D-45, D-47, D-48, or D-49 at indicated concentrations for 16 hours.
Figure 8:
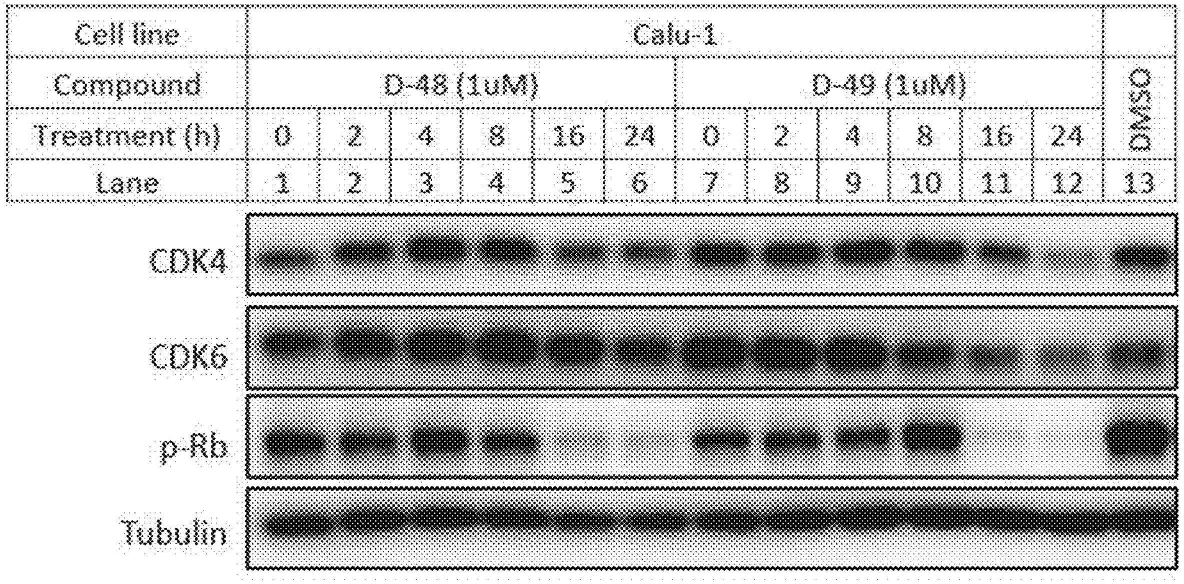
FIG. 8 shows immunoblots of CDK4 and CDK6 protein expressed by Calu-1 cells after treatment with heterobifunctional compound D-48 or D-49 at various time points.

Additional heterobifunctional compounds were designed and tested for their ability to target and degrade another two target proteins, CDK4 and CDK6. Calu-1 cells that express CDK4/6 proteins were treated with heterobifunctional compounds disclosed herein (D-44 to D-49) at indicated concentrations for 16 hours. Cells were collected, lysed and subject to immunoblotting using an antibody specific to CDK4, CDK6 or phosphorylated Rb proteins. Tubulin was included as the loading control. DMSO treatment was used as the negative control. Following treatment with various heterobifunctional compounds, CDK4 and CDK6 protein levels in Calu-1 cells were significantly decreased in a concentration-dependent manner, along with the decreased downstream Rb phosphorylation accordingly (FIG. 7A and FIG. 7B). Whereas palbociclib, a CDK4/6 inhibitor, or BL-11, a linker attached DDB1 ligand that doesn't have CDK4/6 binding moiety, didn't have a significant effect on CDK4 protein levels (FIG. 7B). In addition, Calu-1 cells were treated with 1 μM D-48 or D-49 for an indicated period of time. Subsequently, changes in CDK4 and CDK6 protein levels were measured by immunoblotting. Significant degradation of CDK4 and CDK6 were detected 16 hours after administration of the compounds (FIG. 8). These experiments highlight the ability of DDB1 binder derived heterobifunctional compounds to degrade multiple different target proteins, including but not limited to epigenetic target proteins, such as CBP and p300, and kinases, such as CDK4 and CDK6.

FIGS. 10, 11, 13 and 14 include western blots of various proteins including cyclin D1, cyclin D2, cyclin D3, CDK4, CDK6, or phospho-Rb after treatment with heterobifunctional compounds. Some heterobifunctional compounds were more potent or effective than others at reducing expression of proteins shown in these figures. For example, some heterobifunctional compounds were more effective at lower doses than others. These data show that heterobifunctional compounds in accordance with this disclosure may be effective at binding, inhibiting, or degrading a target protein. These compounds may be effective in multiple cell types.

Figure 12:
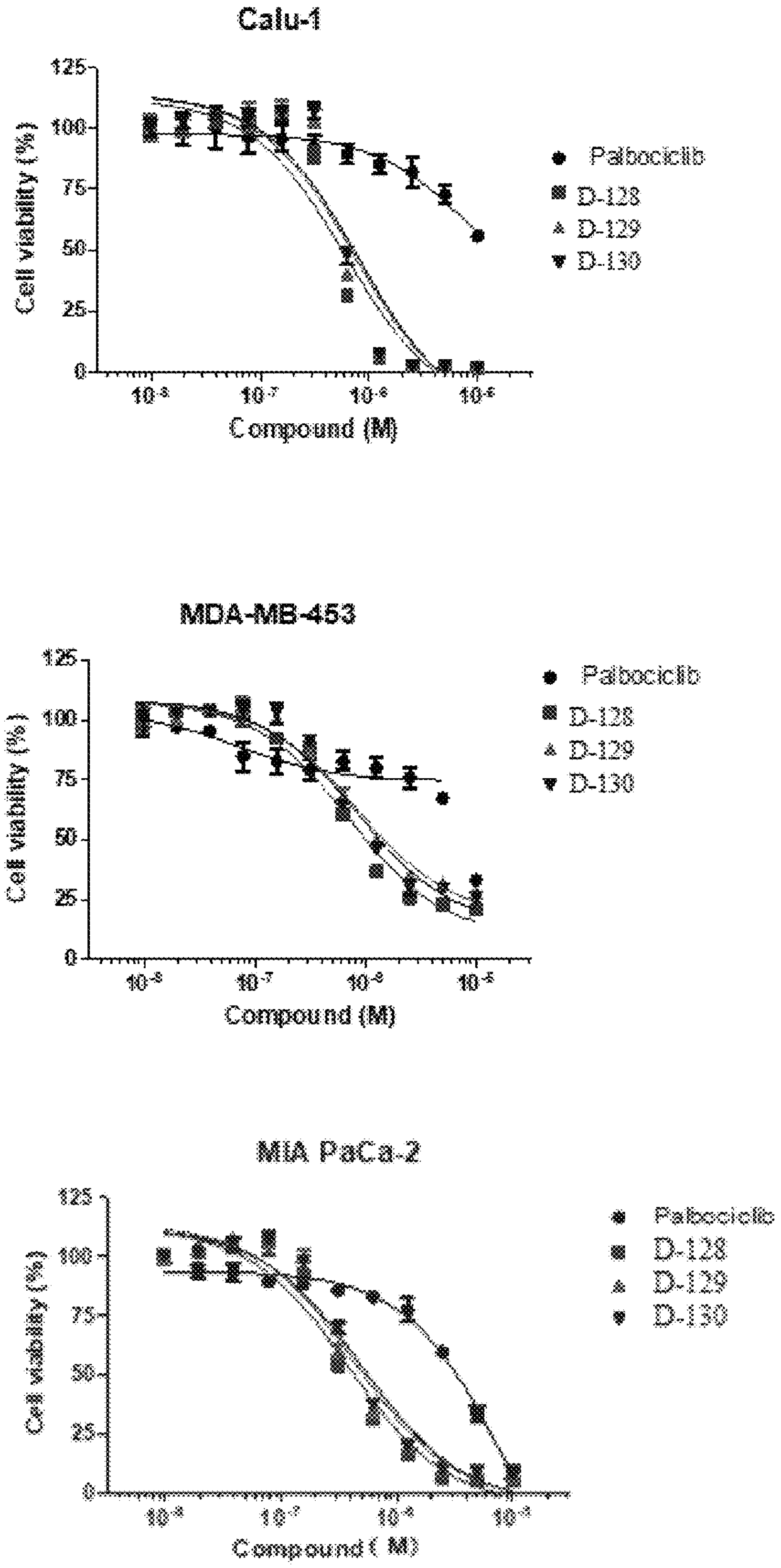
FIG. 12 shows plots showing cell viability of Calu-1, MDA-MB-453, and MIA PaCa-2 cell lines after treatment with various amounts of compound D-128, D-129, D-130, or Palbociclib for 5 days.

FIG. 12 and Table 8 include cell viability data after treatment with heterobifunctional compound D-128, D129, or D-130. These heterobifunctional compounds were more potent or effective than palbociclib at reducing viability in a variety of different cell types. For example, D-128, D129, or D-130 were more effective at lower doses than palbociclib. The data show that heterobifunctional compounds in accordance with this disclosure may be effective at inhibiting cell viability. The compounds may be effective in multiple cell types.

Definitions

As used in the specification and appended claims, unless specified to the contrary, the following terms have the meaning indicated below.

"Amino" refers to the $—NH_2$ radical.

"Cyano" refers to the —CN radical.

"Nitro" refers to the $—NO_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Hydrazino" refers to the $=N—NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_8$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, $R^a$, —$OR^a$, —$SR^a$, —OC(O)—$R^a$, —$N(R^a)_2$, —C(O)$R^a$, —C(O)$OR^a$, —C(O)$N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)R^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Haloalkyl" refers to an alkyl group that is substituted by one or more halogens. Exemplary haloalkyl groups include trifluoromethyl, difluoromethyl, trichloromethyl, 2,2,2 trifluoroethyl, 1,2 difluoroethyl, 3 bromo 2 fluoropropyl, and 1,2 dibromoethyl.

"Heteroalkyl", "heteroalkenyl" and "heteroalkynyl" refer to substituted or unsubstituted alkyl, alkenyl and alkynyl groups which respectively have one or more skeletal chain atoms selected from an atom other than carbon. Exemplary skeletal chain atoms selected from an atom other than carbon include, e.g., O, N, P, Si, S, or combinations thereof, wherein the nitrogen, phosphorus, and sulfur atoms may optionally be oxidized and the nitrogen heteroatom may optionally be quaternized. If given, a numerical range refers to the chain length in total. For example, a 3- to 8-membered heteroalkyl has a chain length of 3 to 8 atoms. Connection to the rest of the molecule may be through either a heteroatom or a carbon in the heteroalkyl, heteroalkenyl or heteroalkynyl chain. Unless stated otherwise specifically in the specification, a heteroalkyl, heteroalkenyl, or heteroalkynyl group is optionally substituted by one or more substituents such as those substituents described herein.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, $R^a$, —$OR^a$, —$SR^a$, —OC(O)—$R^a$, —$N(R^a)_2$, —C(O)$R^a$, —C(O)$OR^a$, —C(O)$N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, $R^a$, —$OR^a$, —$SR^a$, —OC(O)—$R^a$, —$N(R^a)_2$, —C(O)$R^a$, —C(O)$OR^a$, —C(O)$N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_8$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, $R^a$, —$OR^a$, —$SR^a$, —OC(O)—$R^a$, —$N(R^a)_2$, —C(O)$R^a$, —C(O)O$R^a$, —C(O)$N(R^a)_2$, —N($R^a$)C(O)O$R^a$, —OC(O)—$N(R^a)_2$, —N($R^a$)C(O)$R^a$, —N($R^a$)$S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $R^a$, —$R^b$—O$R^a$, —$R^b$—OC(O)—$R^a$, —$R^b$—OC(O)—O$R^a$, —$R^b$—OC(O)—$N(R^a)_2$, —$R^b$—$N(R^a)_2$, —$R^b$—C(O)$R^a$, —$R^b$—C(O)O$R^a$, —$R^b$—C(O)$N(R^a)_2$, —$R^b$—O—$R^c$—C(O)$N(R^a)_2$, —$R^b$—N($R^a$)C(O)O$R^a$, —$R^b$—N($R^a$)C(O)$R^a$, —$R^b$—N($R^a$)$S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" or "cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $R^a$, —$R^b$—O$R^a$, —$R^b$—OC(O)—$R^a$, —$R^b$—OC(O)—O$R^a$, —$R^b$—OC(O)—$N(R^a)_2$, —$R^b$—$N(R^a)_2$, —$R^b$—C(O)$R^a$, —$R^b$—C(O)O$R^a$, —$R^b$—C(O)$N(R^a)_2$, —$R^b$—O—$R^c$—C(O)$N(R^a)_2$, —$R^b$—N($R^a$)C(O)O$R^a$, —$R^b$—N($R^a$)C(O)$R^a$, —$R^b$—N($R^a$)$S(O)_tR^a$ (where t is 1 or 2), —$R^b$—$S(O)_tR^a$ (where t is 1 or 2), —$R^b$—S(O)O$R^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical are optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" or "heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $R^a$, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, I-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]

quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $R^a$, $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)_tR^a$ (where t is 1 or 2), $—R^b—S(O)_tOR^a$ (where t is 1 or 2) and $—R^b—S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

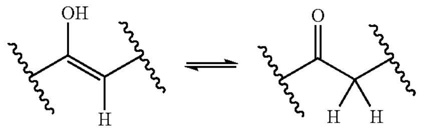

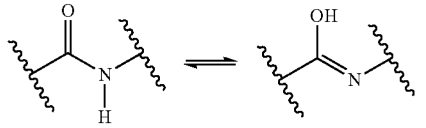

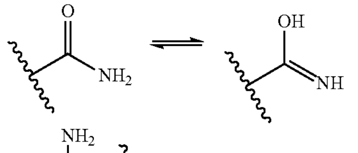

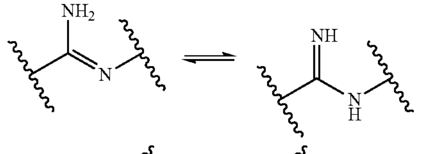

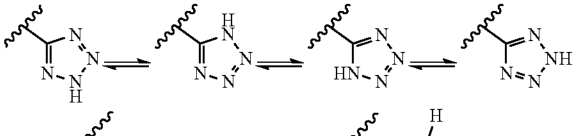

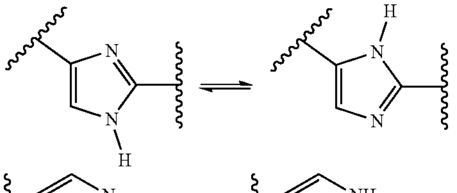

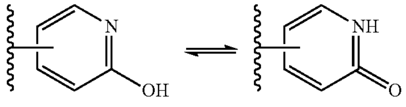

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6 (10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64 (1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

Modified or Engineered Proteins

Disclosed herein, in some embodiments, are modified proteins such as in vivo modified proteins. Disclosed herein, in some embodiments, are in vivo modified proteins. In some embodiments, the in vivo modified protein comprises a DNA damage-binding protein 1 (DDB1) protein. In some embodiments, the DDB1 protein is bound to a ligand. In some embodiments, the ligand is a DDB1 ligand. In some embodiments, the DDB1 protein is directly bound to the ligand. In some embodiments, the binding between the DDB1 protein and the ligand is non-covalent. In some embodiments, the binding between the DDB1 protein and the ligand is covalent. The ligand may be any ligand described herein. In some embodiments, the ligand comprises a DDB1 binding moiety such as a DDB1 binding moiety described herein. In some embodiments, the DDB1 ligand is a heterobifunctional compound comprising a DDB1 binding moiety covalently connected through a linker to a target protein binding moiety described herein. In some embodiments, a DDB1 protein is modified in vivo by being bound to a ligand administered to a subject.

A modified protein may include an engineered protein. Disclosed herein, in some embodiments, are engineered DDB1 proteins such as an in vivo engineered DDB1 protein. The engineered DDB1 protein may be bound to a ligand. The engineered DDB1 protein may bind to the ligand in vivo. For example, the ligand may be administered to a subject, and bind to a DDB1 protein or engineered DDB1 protein in vivo.

Disclosed herein, in some embodiments, are in vivo modified proteins. In some embodiments, the in vivo modified protein comprises a DDB1 protein directly bound to a ligand comprising a DDB1 binding moiety. In some embodiments, the in vivo modified protein comprises a DDB1 protein directly bound to a ligand, the ligand comprising a DDB1 binding moiety. In some embodiments, the in vivo modified protein comprises a DDB1 protein directly bound to a heterobifunctional compound, the heterobifunctional compound comprising a DDB1 binding moiety covalently connected through a linker to a target protein binding moiety.

Disclosed herein, in some embodiments, are in vivo modified proteins. In some embodiments, the ligand comprises a DDB1 binding moiety. In some embodiments, the ligand comprises a linker. In some embodiments, the ligand comprises a target protein binding moiety. In some embodiments, the DDB1 binding moiety is covalently connected to a linker. In some embodiments, the linker is further connected to a target protein binding moiety. In some embodiments, the DDB1 binding moiety is covalently connected through a linker to a target protein binding moiety. In some embodiments, the DDB1 binding moiety is covalently connected to a target protein binding moiety without a linker. In some embodiments, target protein binding moiety binds to a target protein such as a target protein described herein. In some embodiments, the ligand comprises a compound described herein. For example, the ligand may comprise a DDB1 binding moiety disclosed herein, or the ligand may comprise a linker disclosed herein, or the ligand may comprise a target protein binding moiety disclosed herein. In some embodiments, a linker is a bond. In some embodiments, the linker is more than just a bond. In some embodiments, the ligand is a small molecule. In some embodiments, the ligand is a heterobifunctional compound comprising a DDB1 binding moiety covalently connected through a linker to a target protein binding moiety.

Disclosed herein, in some embodiments, are in vivo modified proteins. In some embodiments, the DDB1 binding moiety is bound to a binding region on the DDB1 protein. In some embodiments, the binding region on the DDB1 protein comprises a beta propeller domain. In some embodiments, the beta propeller domain comprises a beta propeller C (BPC) domain. In some embodiments, the binding region on the DDB1 protein comprises a BPC domain. In some embodiments, the binding region on the DDB1 protein comprises a top face of the BPC domain. Disclosed herein, in some embodiments, are in vivo modified proteins. In some embodiments, the binding region on the DDB1 protein comprises one or more of the following DDB1 residues: ARG327, LEU328, PRO358, ILE359, VAL360, ASP361, GLY380, ALA381, PHE382, SER720, ARG722, LYS723, SER738, ILE740, GLU787, TYR812, LEU814, SER815, ALA834, VAL836. ALA841, ALA869, TYR871, SER872, MET910. LEU912, TYR913, LEU926, TRP953, SER955, ALA956, ASN970, ALA971, PHE972, PHE1003, ASN1005, VAL1006, or VAL1033. In some embodiments, one or more of the following DDB1 residues are involved in the non-covalent binding between the DDB1 protein and the ligand: ARG327, LEU328, PRO358, ILE359, VAL360, ASP361, GLY380, ALA381, PHE382, SER720. ARG722, LYS723, SER738, ILE740. GLU787, TYR812, LEU814, SER815, ALA834, VAL836, ALA841, ALA869, TYR871, SER872, MET910, LEU912, TYR913, LEU926, TRP953, SER955, ALA956, ASN970, ALA971, PHE972, PHE1003, ASN1005, VAL1006, or VAL1033. An in vivo engineered DDB1 protein may include a DDB1 protein bound to a ligand at any of the aforementioned residues.

Disclosed herein, in some embodiments, are in vivo modified proteins. In some embodiments, the binding region on the DDB1 protein comprises ARG327 of the DDB1 protein. In some embodiments, the binding region on the DDB1 protein comprises LEU328 of the DDB1 protein. In some embodiments, the binding region on the DDB1 protein comprises PRO358 of the DDB1 protein. In some embodiments, the binding region on the DDB1 protein comprises ILE359 of the DDB1 protein. In some embodiments, the binding region on the DDB1 protein comprises VAL360 of the DDB1 protein. In some embodiments, the binding region on the DDB1 protein comprises ASP361 of the DDB1 protein. In some embodiments, the binding region on the DDB1 protein comprises GLY380 of the DDB1 protein. In some embodiments, the binding region on the DDB1 protein comprises ALA381 of the DDB1 protein. In some embodiments, the binding region on the DDB1 protein comprises PHE382 of the DDB1 protein. In some embodiments, the binding region on the DDB1 protein comprises SER720 of the DDB1 protein. In some embodiments, the binding region on the DDB1 protein comprises ARG722 of the DDB1 protein. In some embodiments, the binding region on the DDB1 protein comprises LYS723 of the DDB1 protein. In some embodiments, the binding region on the DDB1 protein comprises SER738 of the DDB1 protein. In some embodiments, the binding region on the DDB1 protein comprises ILE740 of the DDB1 protein. In some embodiments, the binding region on the DDB1 protein comprises GLU787 of the DDB1 protein. In some embodiments, the binding region on the DDB1 protein comprises TYR812 of the DDB1 protein. In some embodiments, the binding region on the DDB1 protein comprises LEU814 of the DDB1 protein. In some embodiments, the binding region on the DDB1 protein comprises SER815 of the DDB1 protein. In some embodiments, the binding region on the DDB1 protein comprises ALA834 of the DDB1 protein. In some embodiments, the binding region on the DDB1 protein comprises VAL836 of the DDB1 protein. In some embodiments, the binding region on the DDB1 protein comprises ALA841 of the DDB1 protein. In some embodiments, the binding region on the DDB1 protein comprises ALA869 of the DDB1 protein. In some embodiments, the binding region on the DDB1 protein comprises TYR871 of the DDB1 protein. In some embodiments, the binding region on the DDB1 protein comprises SER872 of the DDB1 protein. In some embodiments, the binding region on the DDB1 protein comprises MET910 of the DDB1 protein. In some embodiments, the binding region on the DDB1 protein comprises LEU912 of the DDB1 protein. In some embodiments, the binding region on the DDB1 protein comprises TYR913 of the DDB1 protein. In some embodiments, the binding region on the DDB1 protein comprises LEU926 of the DDB1 protein. In some embodiments, the binding region on the DDB1 protein comprises TRP953 of the DDB1 protein. In some embodiments, the binding region on the DDB1 protein comprises SER955 of the DDB1 protein. In some embodiments, the binding region on the DDB1 protein comprises ALA956 of the DDB1 protein. In some embodiments, the binding region on the DDB1 protein comprises ASN970 of the DDB1 protein. In some embodiments, the binding region on the DDB1 protein comprises ALA971 of the DDB1 protein. In some embodiments, the binding region on the DDB1 protein comprises PHE972 of the DDB1 protein. In some embodiments, the binding region on the DDB1 protein comprises PHE1003 of the DDB1 protein. In some embodiments, the binding region on the DDB1 protein comprises ASN1005 of the DDB1 protein. In some embodiments, the binding region on the DDB1 protein comprises VAL1006 of the DDB1 protein. In some embodiments, the binding region on the DDB1 protein comprises VAL1033 of the DDB1 protein.

In some embodiments, the binding between the DDB1 protein and the ligand comprises one or more of a salt-bridge, a Coulombic interaction, a hydrogen bond, a stereoelectronic interaction, and a dispersion contact. In some embodiments, the binding between the DDB1 protein and the ligand comprises a salt-bridge. In some embodiments, the binding between the DDB1 protein and the ligand comprises a Coulombic interaction. In some embodiments, the binding between the DDB1 protein and the ligand comprises one or more hydrogen bonds. In some embodiments, the binding between the DDB1 protein and the ligand comprises a stereoelectronic interaction. In some embodiments, the binding between the DDB1 protein and the ligand comprises a dispersion contacts.

In some embodiments, the DDB1 protein comprises a BPC domain comprising a central cavity. In some embodiments, the ligand binds the DDB1 protein in the central cavity of the BPC domain. In some embodiments, the DDB1 protein comprises a WD40-motiff. In some embodiments, the WD40-motiff comprises a center. In some embodiments, the ligand is anchored toward the center of the WD40-motiff. In some embodiments, the ligand is anchored toward the center of the WD40-motiff by a salt-bridge. In some embodiments, the ligand includes a nitro group. In some embodiments, the salt-bridge is between the primary amine of an amino acid of the DDB1 protein and the ligand's nitro group. In some embodiments, the salt-bridge is between the primary amine of a lysine (e.g. LYS723) of the DDB1 protein and the ligand's nitro group.

In some embodiments, the ligand is anchored toward the center of the WD40-motiff by a Coulombic interaction. In some embodiments, the ligand includes an electron deficient nitrogen. In some embodiments, the nitro group includes an electron deficient nitrogen. In some embodiments, the Coulombic interaction is between the electron-deficient nitrogen and a lone-pair of a nearby water. In some embodiments, the nearby water is ordered between a backbone carbonyl oxygen atom of one or more amino acids of the DDB1 protein. In some embodiments, the nearby water is ordered between a backbone carbonyl oxygen atom of an arginine (e.g. ARG722) of the DDB1 protein. In some embodiments, the nearby water is ordered between a backbone carbonyl oxygen atom of a valine (e.g. VAL360) of the DDB1 protein. In some embodiments, the nearby water is ordered between the primary amine of a lysine such as LYS723. In some embodiments, the nearby water is ordered between the backbone carbonyl oxygen atom of the arginine, and the backbone carbonyl oxygen atom of the valine, and/or the primary amine of the lysine. In some embodiments, the nearby water is ordered between the backbone carbonyl oxygen atoms of ARG722 and VAL360 as well as the primary amine of LYS723. In some embodiments, the ligand is anchored toward the center of the WD40-motiff by the Coulombic interaction and the salt-bridge.

In some embodiments, the ligand includes a thiazole. In some embodiments, the ligand includes an amide. In some embodiments, the ligand includes an acetate. In some embodiments, the ligand includes one or more pi-faces. In some embodiments, the ligand includes a pi-face of a thiazole. In some embodiments, the ligand includes a pi-face of an amide. In some embodiments, the pi-faces of the thiazole and the amide rest over an amino acid sidechain. In some embodiments, the pi-faces of the thiazole and the amide rest over a valine (e.g. VAL360) sidechain. In some embodiments, the amide forms an intermolecular hydrogen bond with a sidechain of an amino acid of the DDB1 protein. In some embodiments, the amide forms a hydrogen bond with a sidechain of an asparginine (e.g. ASN1005) of the DDB1 protein. In some embodiments, the amide forms an intramolecular hydrogen bond with the acetate. In some embodiments, the amide forms an intermolecular hydrogen bond with a sidechain of the asparagine and an intramolecular hydrogen bond with the acetate. In some embodiments, the ligand includes thiophene comprising a sulfur. In some embodiments, the sulfur of the thiophene is geometrically stabilized through a stereoelectronic interaction with an amino acid sidechain of the DDB1 protein. In some embodiments, the sulfur of the thiophene is geometrically stabilized through a stereoelectronic interaction with the sidechain of the asparginine (e.g, ASN1005). In some embodiments, the acetate comprises a methyl group that forms a dispersion contact with an ordered water. In some embodiments, the acetate comprises a methyl group that forms a dispersion contact with an amino acid sidechain of the DDB1 protein. In some embodiments, the acetate comprises a methyl group that forms a dispersion contact with an arginine (e.g. ARG722) sidechain of the DDB1 protein. In some embodiments, the acetate comprises a methyl group that forms dispersion contacts with the arginine sidechain of the DDB1 protein and an ordered water. In some embodiments, the ligand includes a benzene ring. In some embodiments, the benzene ring forms dispersion contacts with amino acid sidechains of the DDB1 protein. In some embodiments, the benzene ring forms a dispersion contact with an alanine (e.g. ALA381) sidechain of the DDB1 protein. In some embodiments, the benzene ring forms a dispersion contact with a leucine (e.g. LEU328) sidechain of the DDB1 protein. In some embodiments, the benzene ring forms a dispersion contact with a proline (e.g. PRO358) sidechain of the DDB1 protein. In some embodiments, the benzene ring forms a dispersion contact with a valine (e.g. VAL1033) sidechain of the DDB1 protein. In some embodiments, the benzene ring forms dispersion contacts with the alanine, leucine, proline, and valine sidechains of the DDB1 protein. In some embodiments, the benzene ring forms dispersion contacts with ALA381, LEU328, PRO358 and VAL1033 sidechains of the DDB1 protein.

Disclosed herein, in some embodiments, are in vivo modified proteins. In some embodiments, the binding between the DDB1 protein and the ligand comprises a binding affinity with an equilibrium dissociation constant (Kd) below 100 μM, a Kd below 90 μM, a Kd below 80 μM, a Kd below 70 μM, a Kd below 60 μM, below 50 μM, a Kd below 45 μM, a Kd below 40 μM, a Kd below 35 μM, a Kd below 30 μM, a Kd below 25 μM, a Kd below 20 μM, a Kd below 15 μM, a Kd below 14 μM, a Kd below 13 μM, a Kd below 12 μM, a Kd below 11 μM, a Kd below 10 μM, a Kd below 9 μM, a Kd below 8 μM, a Kd below 7 μM, a Kd below 6 μM, a Kd below 5 μM, a Kd below 4 μM, a Kd below 3 μM, a Kd below 2 μM, or a Kd below 1 μM. In some embodiments, the binding between the DDB1 protein and the ligand comprises a binding affinity with a Kd<20 uM, a Kd from 20-100 uM, or a Kd>100 uM. In some embodiments, the binding between the DDB1 protein and the ligand comprises a binding affinity disclosed herein (e.g. a binding affinity described in the section titled, "DDB1 Binding Moieties," or in Table 6 or Table 7). An in vivo engineered DDB1 protein may include a DDB1 protein bound to a ligand with any of the aforementioned binding affinities.

Disclosed herein, in some embodiments, are in vivo modified proteins. In some embodiments, the binding between the DDB1 binding moiety and the DDB1 protein is non-covalent. The binding may include a non-covalent bond. The binding may include more than one non-covalent bond. Some non-limiting examples of non-covalent bonds include a salt-bridge, a Coulombic interaction, a hydrogen bond, a stereoelectronic interaction, or a dispersion contact. The binding may include a combination of non-covalent bonds. In some embodiments, the binding between the DDB1 binding moiety and the DDB1 protein is covalent.

Ligand-Protein Complexes

Disclosed herein, in some embodiments, are ligand-protein complexes. In some embodiments, the ligand-protein complex comprises a ligand-DNA damage-binding protein 1 (DDB1) complex. In some embodiments, the ligand-DDB1 complex is formed by binding a DDB1 protein to a ligand. In some embodiments, the ligand is a DDB1 ligand. In some embodiments, the binding is directly between the DDB1 protein and the ligand. In some embodiments, the DDB1 protein is directly bound to the ligand. In some embodiments, the binding is non-covalent. In some embodiments, the binding is covalent. In some embodiments, the DDB1 is directly bound to the ligand. The ligand may be any ligand described herein. In some embodiments, the ligand comprises a DDB1 binding moiety such as a DDB1 binding moiety described herein. In some embodiments, the DDB1 ligand is a heterobifunctional compound comprising a DDB1 binding moiety covalently connected through a linker to a target protein binding moiety described herein.

Disclosed herein, in some embodiments, are ligand-protein complexes. In some embodiments, the ligand-DDB1 complex is formed by non-covalently binding a DDB1 protein directly to a ligand, the ligand comprising a DDB1 binding moiety. In some embodiments, the ligand-DDB1 complex is formed by covalently binding a DDB1 protein directly to a ligand, the ligand comprising a DDB1 binding moiety. In some embodiments, the ligand-DDB1 complex is formed by non-covalently binding a DDB1 protein directly to a heterobifunctional compound, the heterobifunctional compound comprising a DDB1 binding moiety covalently connected through a linker to a target protein binding moiety. In some embodiments, the ligand-DDB1 complex is formed by covalently binding a DDB1 protein directly to a heterobifunctional compound, the heterobifunctional compound comprising a DDB1 binding moiety covalently connected through a linker to a target protein binding moiety.

Disclosed herein, in some embodiments, are ligand-protein complexes. In some embodiments, the ligand comprises a DDB1 binding moiety. In some embodiments, the ligand comprises a linker. In some embodiments, the ligand comprises a target protein binding moiety. In some embodiments, the DDB1 binding moiety is covalently connected to a linker. In some embodiments, the linker is further connected to a target protein binding moiety. In some embodiments, the DDB1 binding moiety is covalently connected through a linker to a target protein binding moiety. In some embodiments, the DDB1 binding moiety is covalently connected to a target protein binding moiety without a linker. In some embodiments, target protein binding moiety binds to a target protein such as a target protein described herein. In some embodiments, the ligand comprises a compound described herein. For example, the ligand may comprise a DDB1 binding moiety disclosed herein, or the ligand may comprise a linker disclosed herein, or the ligand may comprise a target protein binding moiety disclosed herein. In some embodiments, the ligand is a small molecule. In some embodiments, the ligand is a heterobifunctional compound comprising a DDB1 binding moiety covalently connected through a linker to a target protein binding moiety.

Disclosed herein, in some embodiments, are ligand-protein complexes. In some embodiments, the DDB1 binding moiety is bound to a binding region on the DDB1 protein. In some embodiments, the binding region on the DDB1 protein comprises a beta propeller domain. In some embodiments, the beta propeller domain comprises a beta propeller C (BPC) domain. In some embodiments, the binding region on the DDB1 protein comprises a BPC domain. In some embodiments, the binding region on the DDB1 protein comprises a top face of the BPC domain.

Disclosed herein, in some embodiments, are ligand-protein complexes. In some embodiments, the binding region on the DDB1 protein comprises one or more of the following DDB1 residues: ARG327, LEU328, PRO358, ILE359, VAL360, ASP361, GLY380, ALA381, PHE382, SER720, ARG722, LYS723, SER738, ILE740, GLU787. TYR812, LEU814, SER815, ALA834, VAL836, ALA841, ALA869, TYR871, SER872, MET910, LEU912, TYR913, LEU926, TRP953, SER955, ALA956, ASN970, ALA971, PHE972, PHE1003, ASN1005, VAL1006, or VAL1033. In some embodiments, one or more of the following DDB1 residues are involved in the non-covalent binding between the DDB1 protein and the ligand: ARG327, LEU328, PRO358, ILE359, VAL360, ASP361, GLY380, ALA381, PHE382, SER720, ARG722, LYS723, SER738, ILE740, GLU787, TYR812, LEU814, SER815, ALA834, VAL836, ALA841, ALA869, TYR871, SER872, MET910, LEU912, TYR913, LEU926, TRP953, SER955, ALA956, ASN970, ALA971, PHE972, PHE1003, ASN1005, VAL1006, or VAL1033. In some embodiments, the binding region on the DDB1 protein comprises an amino acid residue described herein, such as in the section titled "Modified Proteins."

In some embodiments, the binding between the DDB1 protein and the ligand comprises one or more of a salt-bridge, a Coulombic interaction, a hydrogen bond, a stereoelectronic interaction, and a dispersion contact. In some embodiments, the binding between the DDB1 protein and the ligand comprises a salt-bridge. In some embodiments, the binding between the DDB1 protein and the ligand comprises a Coulombic interaction. In some embodiments, the binding between the DDB1 protein and the ligand comprises one or more hydrogen bonds. In some embodiments, the binding between the DDB1 protein and the ligand comprises a stereoelectronic interaction. In some embodiments, the binding between the DDB1 protein and the ligand comprises a dispersion contacts.

In some embodiments, the DDB1 protein comprises a BPC domain comprising a central cavity. In some embodiments, the ligand binds the DDB1 protein in the central cavity of the BPC domain. In some embodiments, the DDB1 protein comprises a WD40-motiff. In some embodiments, the WD40-motiff comprises a center. In some embodiments, the ligand is anchored toward the center of the WD40-motiff. In some embodiments, the ligand is anchored toward the center of the WD40-motiff by a salt-bridge. In some embodiments, the ligand includes a nitro group. In some embodiments, the salt-bridge is between the primary amine of an amino acid of the DDB1 protein and the ligand's nitro group. In some embodiments, the salt-bridge is between the primary amine of a lysine (e.g. LYS723) of the DDB1 protein and the ligand's nitro group.

In some embodiments, the ligand is anchored toward the center of the WD40-motiff by a Coulombic interaction. In some embodiments, the ligand includes an electron deficient nitrogen. In some embodiments, the nitro group includes an electron deficient nitrogen. In some embodiments, the Coulombic interaction is between the electron-deficient nitrogen and a lone-pair of a nearby water. In some embodiments, the nearby water is ordered between a backbone carbonyl oxygen atom of one or more amino acids of the DDB1 protein. In some embodiments, the nearby water is ordered between a backbone carbonyl oxygen atom of an arginine (e.g. ARG722) of the DDB1 protein. In some embodiments, the nearby water is ordered between a backbone carbonyl oxygen atom of a valine (e.g. VAL360) of the DDB1 protein. In some embodiments, the nearby water is ordered between the primary amine of a lysine such as LYS723. In some embodiments, the nearby water is ordered between the backbone carbonyl oxygen atom of the arginine, and the backbone carbonyl oxygen atom of the valine, and/or the primary amine of the lysine. In some embodiments, the nearby water is ordered between the backbone carbonyl oxygen atoms of ARG722 and VAL360 as well as the primary amine of LYS723. In some embodiments, the ligand is anchored toward the center of the WD40-motiff by the Coulombic interaction and the salt-bridge.

In some embodiments, the ligand includes a thiazole. In some embodiments, the ligand includes an amide. In some embodiments, the ligand includes an acetate. In some embodiments, the ligand includes one or more pi-faces. In some embodiments, the ligand includes a pi-face of a thiazole. In some embodiments, the ligand includes a pi-face of an amide. In some embodiments, the pi-faces of the thiazole and the amide rest over an amino acid sidechain. In some embodiments, the pi-faces of the thiazole and the amide rest over a valine (e.g. VAL360) sidechain. In some embodiments, the amide forms an intermolecular hydrogen bond with a sidechain of an amino acid of the DDB1 protein. In some embodiments, the amide forms a hydrogen bond with a sidechain of an asparginine (e,g, ASN1005) of the DDB1 protein. In some embodiments, the amide forms an intramolecular hydrogen bond with the acetate. In some embodiments, the amide forms an intermolecular hydrogen bond with a sidechain of the asparagine and an intramolecular hydrogen bond with the acetate. In some embodiments, the ligand includes thiophene comprising a sulfur. In some embodiments, the sulfur of the thiophene is geometrically stabilized through a stereoelectronic interaction with an amino acid sidechain of the DDB1 protein. In some embodiments, the sulfur of the thiophene is geometrically stabilized through a stereoelectronic interaction with the sidechain of the asparginine (e,g, ASN1005). In some embodiments, the acetate comprises a methyl group that forms a dispersion contact with an ordered water. In some embodiments, the acetate comprises a methyl group that forms a dispersion contact with an amino acid sidechain of the DDB1 protein. In some embodiments, the acetate comprises a methyl group that forms a dispersion contact with an arginine (e.g. ARG722) sidechain of the DDB1 protein. In some embodiments, the acetate comprises a methyl group that forms dispersion contacts with the arginine sidechain of the DDB1 protein and an ordered water. In some embodiments, the ligand includes a benzene ring. In some embodiments, the benzene ring forms dispersion contacts with amino acid sidechains of the DDB1 protein. In some embodiments, the benzene ring forms a dispersion contact with an alanine (e.g. ALA38l) sidechain of the DDB1 protein. In some embodiments, the benzene ring forms a dispersion contact with a leucine (e.g. LEU328) sidechain of the DDB1 protein. In some embodiments, the benzene ring forms a dispersion contact with a proline (e.g. PRO358) sidechain of the DDB1 protein. In some embodiments, the benzene ring forms a dispersion contact with a valine (e.g. VAL1033) sidechain of the DDB1 protein. In some embodiments, the benzene ring forms dispersion contacts with the alanine, leucine, proline, and valine sidechains of the DDB1 protein. In some embodiments, the benzene ring forms dispersion contacts with ALA381, LEU328, PRO358 and VAL1033 sidechains of the DDB1 protein.

Disclosed herein, in some embodiments, are ligand-protein complexes. In some embodiments, the binding between the DDB1 protein and the ligand comprises a binding affinity with an equilibrium dissociation constant (Kd) below 100 μM, a Kd below 90 μM, a Kd below 80 μM, a Kd below 70 μM, a Kd below 60 μM, a Kd below 50 μM, a Kd below 45 μM, a Kd below 40 μM, a Kd below 35 μM, a Kd below 30 μM, a Kd below 25 μM, a Kd below 20 μM, a Kd below 15 μM, a Kd below 14 μM, a Kd below 13 μM, a Kd below 12 μM, a Kd below 11 μM, a Kd below 10 μM, a Kd below 9 μM, a Kd below 8 μM, a Kd below 7 μM, a Kd below 6 μM, a Kd below 5 μM, a Kd below 4 μM, a Kd below 3 μM, a Kd below 2 μM, or a Kd below 1 μM. In some embodiments, the binding between the DDB1 protein and the ligand comprises a binding affinity with a Kd<20 uM, a Kd from 20-100 uM, or a Kd>100 uM. In some embodiments, the binding between the DDB1 protein and the ligand comprises a binding affinity disclosed herein (e.g. a binding affinity described in the section titled, "DDB1 Binding Moieties," or in Table 6 or Table 7).

Disclosed herein, in some embodiments, are ligand-protein complexes. In some embodiments, the binding between the DDB1 binding moiety and the DDB1 protein is non-covalent. In some embodiments, the binding between the DDB1 binding moiety and the DDB1 protein is covalent.

Disclosed herein, in some embodiments, are ligand-protein complexes. In some embodiments, the complex is formed in vivo. In some embodiments, the complex is formed in vitro.

Compounds

Disclosed herein, in some embodiments, are compounds. The compound may be or include a DDB1 ligand. The compound may comprise a DDB1 binding moiety. The compound may comprise a linker. The compound may comprise a target protein binding moiety. The ligand may be a heterobifunctional compound. The heterobifunctional compound may comprise a DDB1 binding moiety covalently connected through a linker to a target protein binding moiety. The compound may comprise a ligand. The ligand may comprise a DDB1 binding moiety. The ligand may comprise a linker. The ligand may comprise a target protein binding moiety. The DDB1 binding moiety may be connected via the linker to the target protein binding moiety. The ligand may be a heterobifunctional compound. The heterobifunctional compound may comprise a DDB1 binding moiety covalently connected through a linker to a target protein binding moiety.

Disclosed herein, in some embodiments, are DDB1 ligands. The ligand may include a small molecule. An example of a small molecule is an organic compound having a molecular weight of less than 900 daltons. The ligand may have a molecular weight below 2500 daltons, below 2250 daltons, below 2000 daltons, below 1750 daltons, below 1500 daltons, or below 1250 daltons. The ligand may have a molecular weight below 1000 daltons, below 900 daltons, below 800 daltons, below 700 daltons, below 600 daltons, or below 500 daltons. The ligand may have a molecular weight greater than 2500 daltons, greater than 2250 daltons, greater than 2000 daltons, greater than 1750 daltons, greater than 1500 daltons, or greater than 1250 daltons. The ligand may have a molecular weight greater than 1000 daltons, greater than 900 daltons, greater than 800 daltons, greater than 700 daltons, greater than 600 daltons, or greater than 500 daltons.

Disclosed herein, in some embodiments, are compounds for use in a method such as a method of treatment. Some embodiments include a compound for use in a method of degrading, inhibiting, or modulating a protein or a target protein. The compound may be or include a compound described herein. Some embodiments include a method of making a compound disclosed herein.

DDB1 Binding Moieties

Described herein are compounds comprising a DDB1 binding moiety. Some such compounds may be useful as an antiviral drug, as a DDB1 protein level or function modulator, as part of a molecular glue, or as part of a targeted protein degrader. In some embodiments, the DDB1 binding moiety is included as part of a heterobifunctional compound.

Described herein are compounds comprising a DDB1 binding moiety. In some embodiments, the DDB1 binding moiety binds to a DDB1 protein. In some embodiments, the DDB1 binding moiety is bound to a DDB1 protein. In some embodiments, the compound binds to a DDB1 protein via the DDB1 binding moiety. In some embodiments, the compound is bound to a DDB1 protein via the DDB1 binding moiety. In some instances, a compound of Formula (I) comprises a structure of any one of Formula (II), Formula (IIa), or Formula (Jib). In some embodiments, the compound or the DDB1 binding moiety does not inhibit DDB1 function. For example, binding of DDB1 to the DDB1 binding moiety may, in some embodiments, not prevent or reduce associations between DDB1 and a cullin protein such as Cullin 4A or Cullin 4B. In some embodiments, a DDB1 binding moiety is a small molecule.

In some embodiments, a DDB1 binding moiety described herein comprises the structure of Formula (II):

Formula (II)

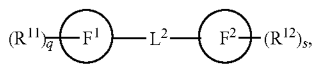

wherein $F^1$ is aryl, heteroaryl, carbocyclyl, or heterocyclyl;

$F^2$ is aryl, heteroaryl, carbocyclyl, or heterocyclyl;

$L^2$ is a bond, —C(═O)$NR^{13}$—, —$NR^{13}$C(═O)—, —C(═O)—, —C(═S)—, —S—, —S(═O), —S(═O)$_2$—, —S(═O)$NR^{13}$—, —$NR^{13}$S(═O)—, —S(═O)$_2NR^{13}$—, —$NR^{13}$S(═O)$_2$—, —O—, $C_1$-$C_4$ alkyl, $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —S(═O)$_2R^d$, —S(═O)$_2NR^cR^d$, —C(═O)$R^b$, —$CO_2R^a$, —C(═O)$NR^cR^d$, $C_1$-$C_6$ alkyl, $C_1$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen. —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{11}$ and $R^{12}$ is independently a bond, hydrogen, halogen, —CN, —$R^a$, —$OR^a$, —$SR^a$, —S(═O)$R^b$, —$NO_2$, —$NR^cR^d$, —S(═O)$_2R^d$, —$NR^a$S(═O)$_2R^d$, —S(═O)$_2NR^cR^d$, —C(═O)$R^b$, —OC(═O)$R^b$, —$CO_2R^a$, —$OCO_2R^a$, —C(═O)$NR^cR^d$, —OC(═O)$NR^cR^d$, —$NR^a$C(═O)$NR^cR^d$, —$NR^a$C(═O)$R^b$, —$NR^a$C(═O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$;

each $R^a$ is independently hydrogen, $C_1$-$C_6$ alkyl, $C_1$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen. $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_1$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$:

each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-5; and s is 1-5.

In some embodiments of a compound of Formula (II), $F^1$ is aryl. In some embodiments of a compound of Formula (II), $F^1$ is heteroaryl. In some embodiments of a compound of Formula (II), $F^1$ is 5-12 membered heteroaryl. In some embodiments of a compound of Formula (II), $F^1$ is phenyl. In some embodiments of a compound of Formula (II), $F^1$ is phenyl and q is 1. In some embodiments of a compound of Formula (II), $F^2$ is aryl. In some embodiments of a compound of Formula (II), $F^2$ is $C_6$-$C_{12}$ aryl. In some embodiments of a compound of Formula (II), $F^2$ is heteroaryl. In some embodiments of a compound of Formula (II), $F^2$ is 5-12 membered heteroaryl. In some embodiments of a compound of Formula (II), $F^2$ is a five membered ring heteroaryl. In some embodiments of a compound of Formula (II), $F^2$ is a six membered ring heteroaryl. In some embodiments of a compound of Formula (II), $F^2$ is an N-heterocyclyl ring. In some embodiments, $F^2$ is triazolyl, tetrazolyl, furanyl, pyrrolyl, thiazolyl, oxazolyl, isoxazolyl, imidazolyl, pyrazolyl, thiadiazolyl, or oxadiazolyl. In some embodiments, $F^2$ is triazolyl, tetrazolyl, furanyl, pyrrolyl, thiazolyl, oxazolyl, isoxazolyl, imidazolyl, pyrazolyl, thiadiazolyl, or oxadiazolyl, and q is 1. In some embodiments, $F^2$ is 5-6 membered heteroaryl. In some embodiments, $F^2$ is heteroaryl, wherein the heteroaryl group has at least one nitrogen atom in the ring. In some embodiments, $F^2$ is heteroaryl, wherein the heteroaryl group has at least two nitrogen atoms in the ring. In some embodiments. $F^2$ is pyridyl, pyrimidinyl, or pyrazinyl. In some embodiments, $F^2$ is heteroaryl, wherein the heteroaryl group has at least one sulfur atom in the ring. In some embodiments, $F^2$ is heteroaryl, wherein the heteroaryl group has at least one oxygen atom in the ring. In some embodiments, $F^2$ is thiazolyl, oxazolyl, furyl, or thiophenyl. In some embodiments, $F^2$ is thiazolyl. In some embodiments, $R^{12}$, at each occurrence, is $—NO_2$, halogen, methyl, halomethyl, phenyl, cyclopropyl, $SO_2CH_3$, or —CN. In some embodiments, $R^{12}$ is $—NO_2$. In some embodiments of a compound of Formula (IIb), $R^{12}$, at each occurrence, is chloro or bromo. In some embodiments, IV is —NHC(═O) or —C(═O)NH—. In some embodiments, $L^2$ is —C(═O)NH—. In some embodiments, $L^2$ is —C(═O)N($C_1$-$C_8$ alkyl)-. In some embodiments, a DDB1 binding moiety comprises nitazoxanide or a pharmaceutically acceptable salt thereof.

In some instances, a DDB1 binding moiety described herein comprises the structure of Formula (IIa):

Formula (IIa)

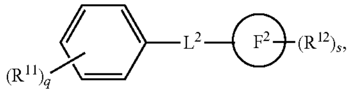

wherein $F^2$ is aryl, heteroaryl, carbocyclyl, or heterocyclyl;

$L^2$ is a bond, —C(═O)$NR^{13}$—, —$NR^{13}$C(═O)—, —C(═O)—, —C(═S)—, —S—, —S(═O), —S(═O)$_2$—, —S(═O)$NR^{13}$—, —$NR^{13}$S(═O)—, —S(═O)$_2NR^{13}$—, —$NR^{13}$S(═O)$_2$—, —O—, $C_1$-$C_4$ alkyl, or $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —S(═O)$_2R^d$, —S(═O)$_2NR^cR^d$, —C(═O)$R^b$, —$CO_2R^a$, —C(═O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{11}$ and $R^{12}$ is independently a bond, hydrogen, halogen, —CN, —$R^a$, —$OR^a$, —$SR^a$, —S(═O)$R^b$, —$NO_2$, —$NR^cR^d$, —S(═O)$_2R^d$, —$NR^a$S(═O)$_2R^d$, —S(═O)$_2NR^cR^d$, —C(═O)$R^b$, —OC(═O)$R^b$, —$CO_2R^a$, —$OCO_2R^a$, —C(═O)$NR^cR^d$, —OC(═O)$NR^cR^d$, —$NR^a$C(═O)$NR^cR^d$, —$NR^a$C(═O)$R^b$, —$NR^a$C(═O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$:

each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-5; and s is 1-5.

In some embodiments of a compound of Formula (IIa), $F^2$ is aryl. In some embodiments of a compound of Formula (IIa), $F^2$ is $C_6$-$C_{12}$ aryl. In some embodiments of a compound of Formula (IIa), $F^2$ is heteroaryl. In some embodiments of a compound of Formula (IIa), $F^2$ is 5-12 membered heteroaryl. In some embodiments of a compound of Formula (IIa) $F^2$ is triazolyl, tetrazolyl, furanyl, pyrrolyl, thiazolyl, oxazolyl, isoxazolyl, imidazolyl, pyrazolyl, thiadiazolyl, or oxadiazolyl. In some embodiments of a compound of Formula (IIa) $F^2$ is triazolyl, tetrazolyl, furanyl, pyrrolyl, thiazolyl, oxazolyl, isoxazolyl, imidazolyl, pyrazolyl, thiadiazolyl, or oxadiazolyl, and p is 1. In some embodiments of a compound of Formula (IIa) $F^2$ is 5-6 membered heteroaryl. In some embodiments of a compound of Formula (IIa) $F^2$ is heteroaryl, wherein the heteroaryl group has at least one nitrogen atom in the ring. In some embodiments of a compound of Formula (IIa) $F^2$ is heteroaryl, wherein the heteroaryl group has at least two nitrogen atoms in the ring. In some embodiments of a compound of Formula (IIa) $F^2$ is pyridyl, pyrimidinyl, or pyrazinyl. In some embodiments, $F^2$ is heteroaryl, wherein the heteroaryl group has at least one sulfur atom in the ring. In some embodiments, $F^2$ is heteroaryl, wherein the heteroaryl group has at least one oxygen atom in the ring. In some embodiments of a compound of Formula (IIa) $F^2$ is thiazolyl, oxazolyl, furyl, or thiophenyl. In some embodiments of a compound of Formula (IIa) $F^2$ is thiazolyl. In some embodiments of a compound of Formula (IIa) $R^{12}$, at each occurrence, is —$NO_2$, halogen, methyl, halomethyl, phenyl, cyclopropyl, $SO_2CH_3$, or —CN. In some embodiments of a compound of Formula (IIa) $R^2$ is —$NO_2$. In some embodiments of a compound of Formula (IIb), $R^{12}$, at each occurrence, is chloro or bromo. In some embodiments of a compound of Formula (IIa) $L^2$ is —NHC(═O) or —C(═O)NH—. In some embodiments of a compound of Formula (IIa), $L^2$ is —C(═O)NH—. In some embodiments of a compound of Formula (IIa), $L^2$ is —C(═O)N($C_1$-$C_8$ alkyl)-. In some embodiments of a compound of Formula (IIa), q is 1. In some embodiments of a compound of Formula (IIa), q is 2.

In some instances, a compound described herein comprises the structure of Formula (IIb):

Formula (IIb)

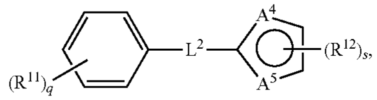

wherein $A^4$ and $A^5$ are each independently S, N, or O, wherein at least one of $A^4$ or $A^5$ is N;

$L^2$ is a bond, —C(═O)$NR^{13}$—, —$NR^{13}$C(═O)—, —C(═O)—, —C(═S)—, —S—, —S(═O), —S(═O)$_2$—, —S(═O)$NR^{13}$—, —$NR^{13}$S(═O)—, —S(═O)$_2NR^{13}$—, —$NR^{13}$S(═O)$_2$—, —O—, $C_1$-$C_4$ alkyl, $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —S(═O)$_2R^d$, —S(═O)$_2NR^cR^d$, —C(═O)$R^b$, —$CO_2R^a$, —C(═O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{11}$ and $R^{12}$ is independently a bond, hydrogen, halogen, —CN, —$R^a$, —$OR^a$, —$SR^a$, —S(═O)$R^b$, —$NO_2$, —$NR^cR^d$, —S(═O)$_2R^d$, —$NR^a$S(═O)$_2R^d$, —S(═O)$_2NR^cR^d$, —C(═O)$R^b$, —OC(═O)$R^a$, —$CO_2R^a$, —$OCO_2R^a$, —C(═O)$NR^cR^d$, —OC(═O)$NR^cR^d$, —$NR^a$C(═O)$NR^cR^d$, —$NR^a$C(═O)$R^b$, —$NR^a$C(═O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_1$-$C_8$ heterocyclyl, aryl, or heteroaryl, wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$;

each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen. $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_1$-$C_6$ alkenyl, $C_1$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-5; and s is 1-3.

In some embodiments of a compound of Formula (IIb) $R^{12}$, at each occurrence, is —$NO_2$, halogen, methyl, halomethyl, phenyl, isopropyl, cyclopropyl, $SO_2CH_3$, or —CN. In some embodiments of a compound of Formula (IIb) $R^{12}$ is —$NO_2$. In some embodiments of a compound of Formula (IIb), $R^{12}$, at each occurrence, is chloro or bromo. In some embodiments of a compound of Formula (IIb) $L^2$ is —NHC(═O) or —C(═O)NH—. In some embodiments of a compound of Formula (IIb), $L^2$ is —C(═O)NH—. In some embodiments of a compound of Formula (IIb), $L^2$ is —C(═O)N($C_1$-$C_8$ alkyl)-. In some embodiments of a compound of Formula (IIb), q is 1. In some embodiments of a compound of Formula (IIb), q is 2.

In some embodiments, the DDB1 binding moiety is incorporated into a ligand described herein. In some embodiments, the DDB1 binding moiety is part of a modified protein described herein. In some embodiments, the DDB1 binding moiety is part of a ligand-protein complex described herein. In some embodiments, the DDB1 binding moiety is attached to a linker such as a linker described herein. In some embodiments, the DDB1 binding moiety is covalently connected through the linker to a target protein binding moiety described herein.

Described herein are compounds comprising a DDB1 binding moiety. In some embodiments, the DDB1 binding moiety comprises a compound of Table 1.

TABLE 1

| DDB1 binding moieties | | |
|---|---|---|
| Compound | Structure | Name |
| B-1 | 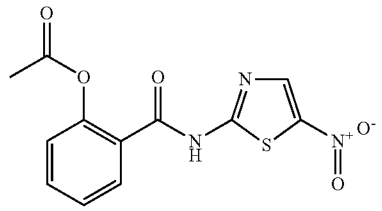 | 2-((5-nitrothiazol-2-yl)carbamoyl)phenyl acetate |
| B-2 | 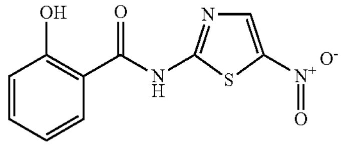 | 2-hydroxy-N-(5-nitrothiazol-2-yl)benzamide |
| B-3 | 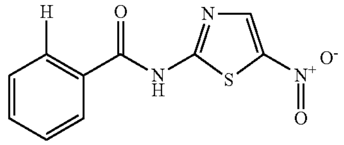 | N-(5-nitrothiazol-2-yl)benzamide |
| B-4 | 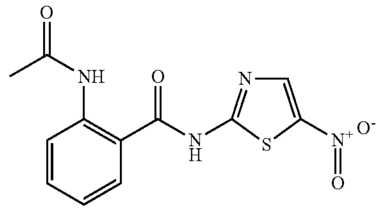 | 2-acetamido-N-(5-nitrothiazol-2-yl)benzamide |
| B-5 | 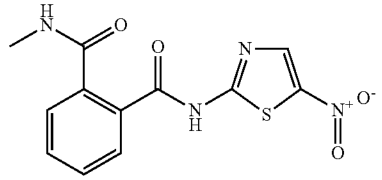 | N1-methyl-N2-(5-nitrothiazol-2-yl)phthalamide |
| B-6 | 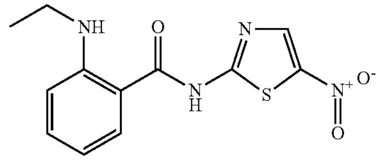 | 2-(ethylamino)-N-(5-nitrothiazol-2-yl)benzamide |
| B-7 | 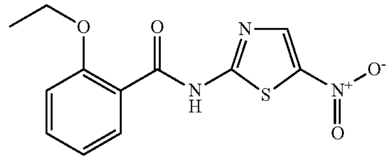 [SMILES: CCOc1ccccc1C(=O)Nc1ncc([N+](=O)[O-])s1] | 2-ethoxy-N-(5-nitrothiazol-2 yl)benzamide |
| B-8 | 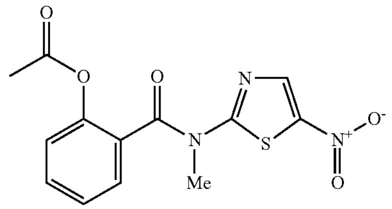 [SMILES: CC(=O)Oc1ccccc1C(=O)N(C)c1ncc([N+](=O)[O-])s1] | 2-(methyl(5-nitrothiazol-2-yl)carbamoyl)phenyl acetate |

TABLE 1-continued
| DDB1 binding moieties | | |
|---|---|---|
| Compound | Structure | Name |
| B-9 | 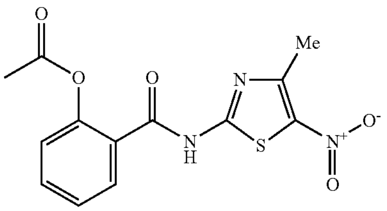 [SMILES: CC(=O)Oc1ccccc1C(=O)Nc1nc(C)c([N+](=O)[O-])s1] | 2-((4-methyl-5-nitrothiazol-2-yl)carbamoyl)phenyl acetate |
| B-10 | 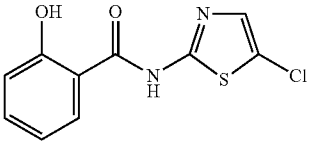 [SMILES: O=C(Nc1ncc(Cl)s1)c1ccccc1O] | N-(5-chlorothiazol-2-yl)-2-hydroxybenzamide |
| B-11 | 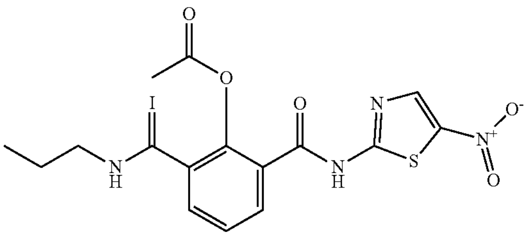 | 2-(ethylcarbamoyl)-6-((5-nitrothiazol-2-yl)carbamoyl)phenyl acetate |
| B-12 | 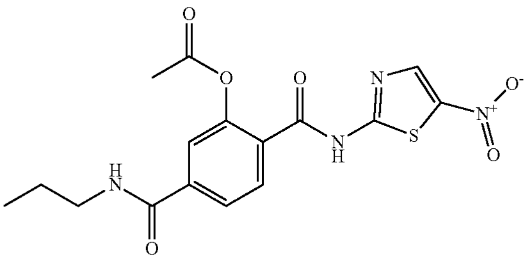 [SMILES: CCCNC(=O)c1ccc(C(=O)Nc2ncc([N+](=O)[O-])s2)c(OC(C)=O)c1] | 2-((5-nitrothiazol-2-yl)carbamoyl)-5-(propylcarbamoyl)phenyl acetate |
| B-13 | 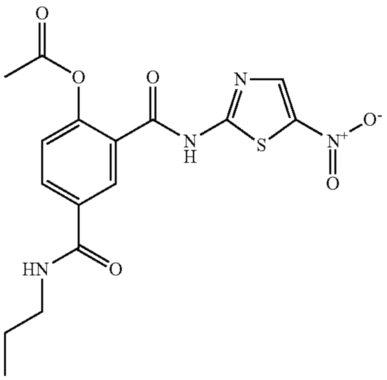 [SMILES: CCCNC(=O)c1ccc(OC(C)=O)c(C(=O)Nc2ncc([N+](=O)[O-])s2)c1] | 2-((5-nitrothiazol-2-yl)carbamoyl)-4-(propylcarbamoyl)phenyl acetate |

TABLE 1-continued
| DDB1 binding moieties | | |
|---|---|---|
| Compound | Structure | Name |
| B-14 | 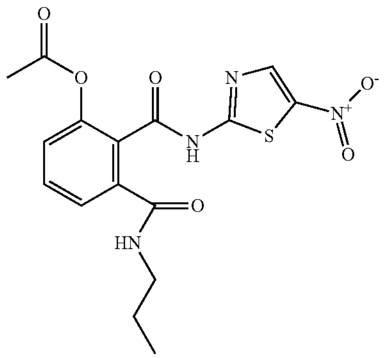 [SMILES: CCCNC(=O)c1cccc(OC(C)=O)c1C(=O)Nc1ncc([N+](=O)[O-])s1] | 2-((5-nitrothiazol-2-yl)carbamoyl)-3-(propylcarbamoyl)phenyl acetate |
| B-15 | 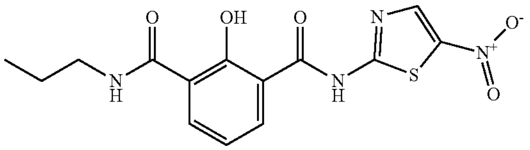 [SMILES: CCCNC(=O)c1cccc(C(=O)Nc2ncc([N+](=O)[O-])s2)c1O] | 2-hydroxy-N1-(5-nitrothiazol-2-yl)-N3-propylisophthalamide |
| B-16 | 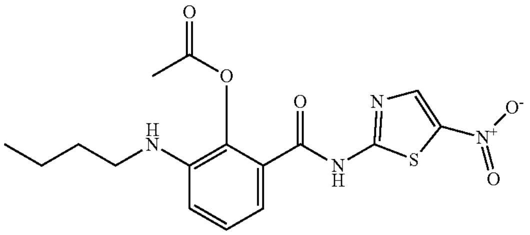 [SMILES: CCCCNc1cccc(C(=O)Nc2ncc([N+](=O)[O-])s2)c1OC(C)=O] | 2-(butylamino)-6-((5-nitrothiazol-2-yl)carbamoyl)phenyl acetate |
| B-17 | 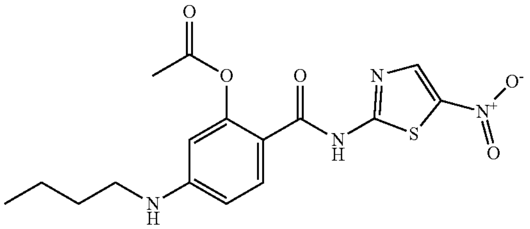 [SMILES: CCCCNc1ccc(C(=O)Nc2ncc([N+](=O)[O-])s2)c(OC(C)=O)c1] | 5-(butylamino)-2-((5-nitrothiazol-2-yl)carbamoyl)phenyl acetate |
| B-18 | 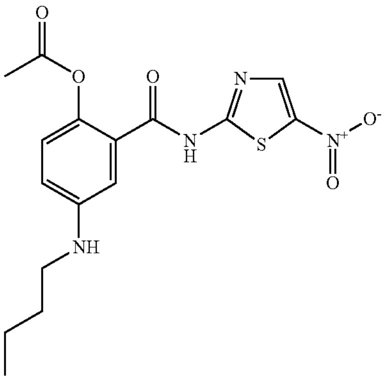 [SMILES: CCCCNc1ccc(OC(C)=O)c(C(=O)Nc2ncc([N+](=O)[O-])s2)c1] | 4-(butylamino)-2-((5-nitrothiazol-2-yl)carbamoyl)phenyl acetate |

TABLE 1-continued
| DDB1 binding moieties | | |
|---|---|---|
| Compound | Structure | Name |
| B-19 | 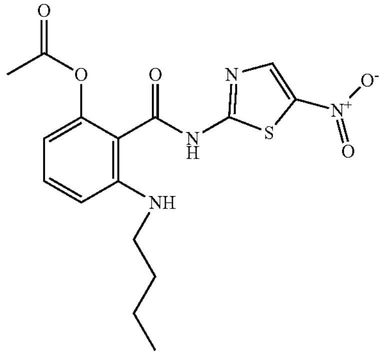 [SMILES: CCCCNc1cccc(OC(C)=O)c1C(=O)Nc1ncc([N+](=O)[O-])s1] | 3-(butylamino)-2-((5-nitrothiazol-2-yl)carbamoyl)phenyl acetate |
| B-20 | 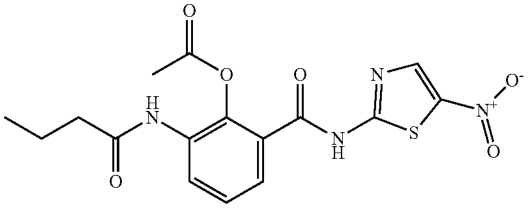 [SMILES: CCCC(=O)Nc1cccc(C(=O)Nc2ncc([N+](=O)[O-])s2)c1OC(C)=O] | 2-butyramido-6-((5-nitrothiazol-2-yl)carbamoyl)phenyl acetate |
| B-21 | 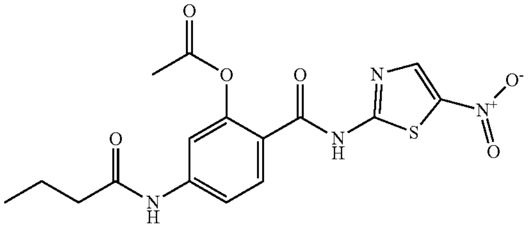 [SMILES: CCCC(=O)Nc1ccc(C(=O)Nc2ncc([N+](=O)[O-])s2)c(OC(C)=O)c1] | 5-butyramido-2-((5-nitrothiazol-2-yl)carbamoyl)phenyl acetate |
| B-22 | 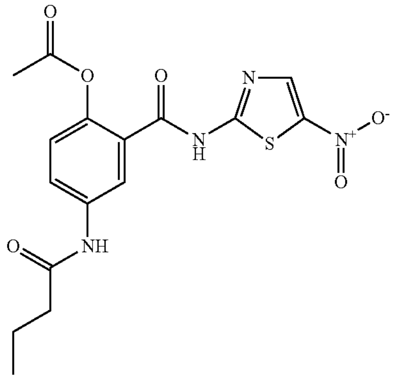 [SMILES: CCCC(=O)Nc1ccc(OC(C)=O)c(C(=O)Nc2ncc([N+](=O)[O-])s2)c1] | 4-butyramido-2-((5-nitrothiazol-2-yl)carbamoyl)phenyl acetate |
| B-23 | 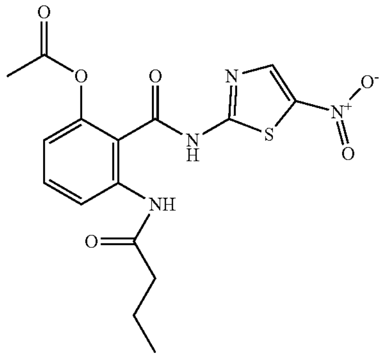 [SMILES: CCCC(=O)Nc1cccc(OC(C)=O)c1C(=O)Nc1ncc([N+](=O)[O-])s1] | 3-butyramido-2-((5-nitrothiazol-2-yl)carbamoyl)phenyl acetate |

TABLE 1-continued

| DDB1 binding moieties | | |
|---|---|---|
| Compound | Structure | Name |
| B-24 | 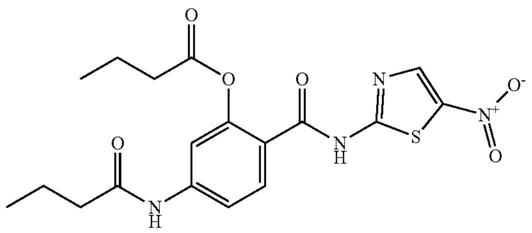 [SMILES: CCCC(=O)Nc1ccc(C(=O)Nc2ncc([N+](=O)[O-])s2)c(OC(=O)CCC)c1] | 5-butyramido-2-((5-nitrothiazol-2-yl)carbamoyl)phenyl butyrate |
| B-25 | 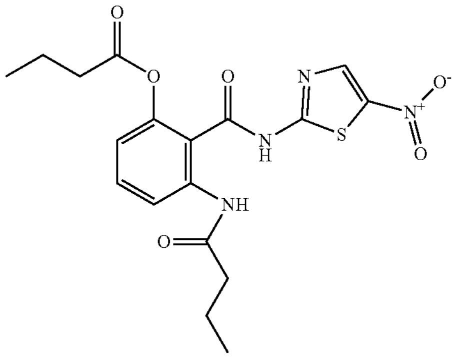 [SMILES: CCCC(=O)Nc1cccc(OC(=O)CCC)c1C(=O)Nc1ncc([N+](=O)[O-])s1] | 3-butyramido-2-((5-nitrothiazol-2-yl)carbamoyl)phenyl butyrate |
| B-26 | 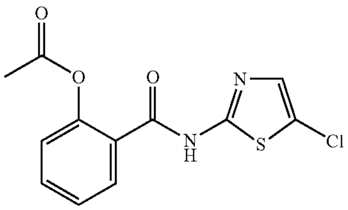 [SMILES: CC(=O)Oc1ccccc1C(=O)Nc1ncc(Cl)s1] | 2-((5-chlorothiazol-2-yl)carbamoyl)phenyl acetate |
| B-27 | 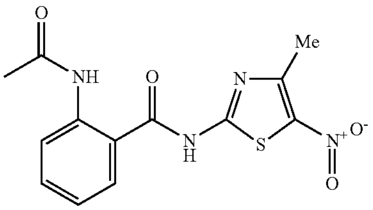 | 2-acetamido-N-(4-methyl-5-nitrothiazol-2-yl)benzamide |
| B-28 | 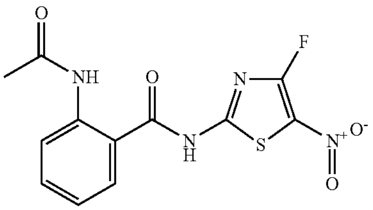 | 2-acetamido-N-(4-fluoro-5-nitrothiazol-2-yl)benzamide |
| B-29 | 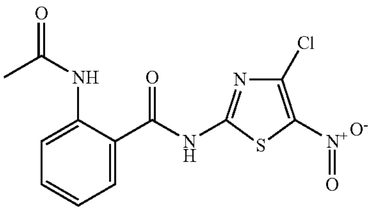 | 2-acetamido-N-(4-chloro-5-nitrothiazol-2-yl)benzamide |

TABLE 1-continued

| DDB1 binding moieties | | |
|---|---|---|
| Compound | Structure | Name |
| B-30 | 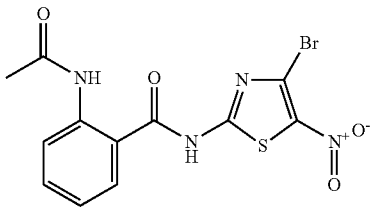 | 2-acetamido-N-(4-bromo-5-nitrothiazol-2-yl)benzamide |
| B-31 | 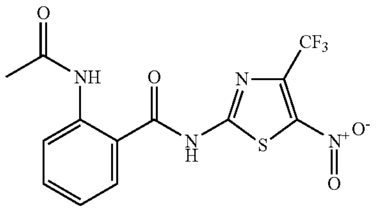 | 2-acetamido-N-(5-nitro-4-(trifluoromethyl)thiazol-2-yl)benzamide |
| B-32 | 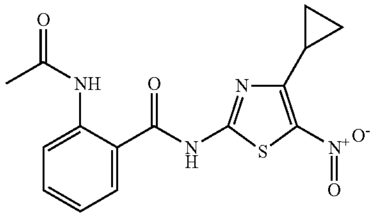 | 2-acetamido-N-(4-cyclopropyl-5-nitrothiazol-2-yl)benzamide |
| B-33 | 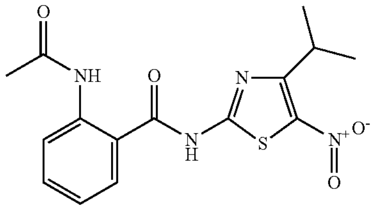 | 2-acetamido-N-(4-isopropyl-5-nitrothiazol-2-yl)benzamide |
| B-34 | 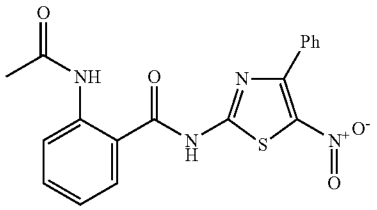 | 2-acetamido-N-(5-nitro-4-phenylthiazol-2-yl)benzamide |
| B-35 | 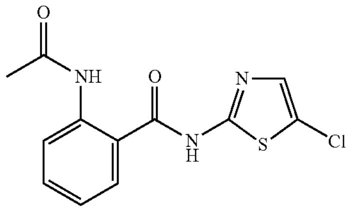 [SMILES: CC(=O)Nc1ccccc1C(=O)Nc1ncc(Cl)s1] | 2-acetamido-N-(5-chlorothiazol-2-yl)benzamide |
| B-36 | 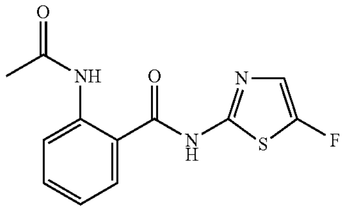 [SMILES: CC(=O)Nc1ccccc1C(=O)Nc1ncc(F)s1] | 2-acetamido-N-(5-fluorothiazol-2-yl)benzamide |

TABLE 1-continued

| DDB1 binding moieties | | |
|---|---|---|
| Compound | Structure | Name |
| B-37 | 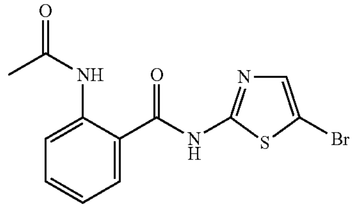 [SMILES: CC(=O)Nc1ccccc1C(=O)Nc1ncc(Br)s1] | 2-acetamido-N-(5-bromothiazol-2-yl)benzamide |
| B-38 | 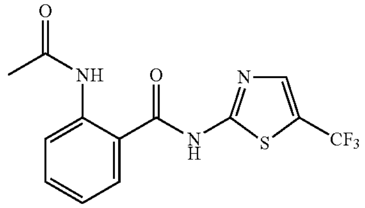 [SMILES: CC(=O)Nc1ccccc1C(=O)Nc1ncc(C(F)(F)F)s1] | 2-acetamido-N-(5-(trifluoromethyl)thiazol-2-yl)benzamide |
| B-39 | 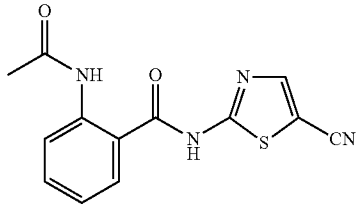 [SMILES: CC(=O)Nc1ccccc1C(=O)Nc1ncc(C#N)s1] | 2-acetamido-N-(5-cyanothiazol-2-yl)benzamide |
| B-40 | 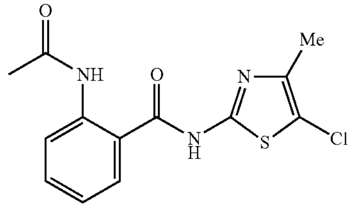 [SMILES: CC(=O)Nc1ccccc1C(=O)Nc1nc(C)c(Cl)s1] | 2-acetamido-N-(5-chloro-4-methylthiazol-2-yl)benzamide |
| B-41 | 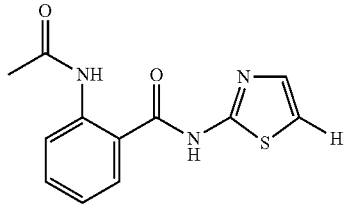 [SMILES: CC(=O)Nc1ccccc1C(=O)Nc1nccs1] | 2-acetamido-N-(thiazol-2-yl)benzamide |
| B-42 | 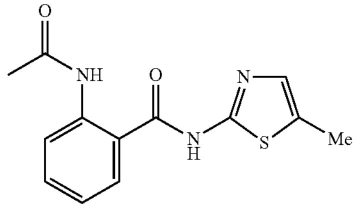 [SMILES: CC(=O)Nc1ccccc1C(=O)Nc1ncc(C)s1] | 2-acetamido-N-(5-methylthiazol-2-yl)benzamide |
| B-43 | 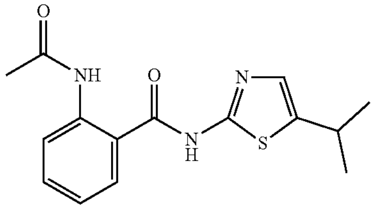 [SMILES: CC(=O)Nc1ccccc1C(=O)Nc1ncc(C(C)C)s1] | 2-acetamido-N-(5-isopropylthiazol-2-yl)benzamide |

TABLE 1-continued

| DDB1 binding moieties | | |
|---|---|---|
| Compound | Structure | Name |
| B-44 | 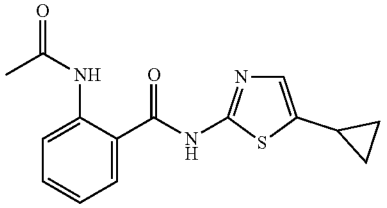 [SMILES: CC(=O)Nc1ccccc1C(=O)Nc1ncc(C2CC2)s1] | 2-acetamido-N-(5-cyclopropylthiazol-2-yl)benzamide |
| B-45 | 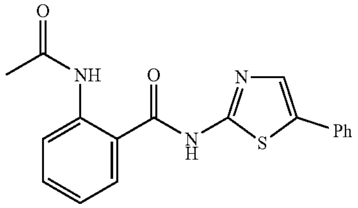 [SMILES: CC(=O)Nc1ccccc1C(=O)Nc1ncc(-c2ccccc2)s1] | 2-acetamido-N-(5-phenylthiazol-2-yl)benzamide |
| B-46 | 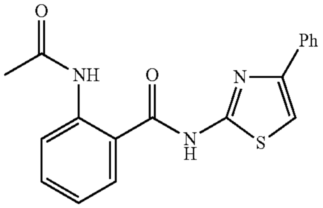 [SMILES: CC(=O)Nc1ccccc1C(=O)Nc1nc(-c2ccccc2)cs1] | 2-acetamido-N-(4-phenylthiazol-2-yl)benzamide |
| B-47 | 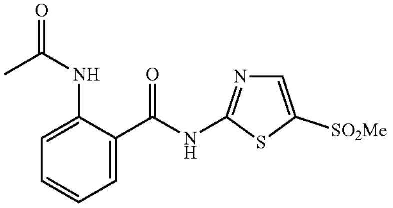 [SMILES: CC(=O)Nc1ccccc1C(=O)Nc1ncc(S(C)(=O)=O)s1] | 2-acetamido-N-(5-(methylsulfonyl)thiazol-2-yl)benzamide |
| B-48 | 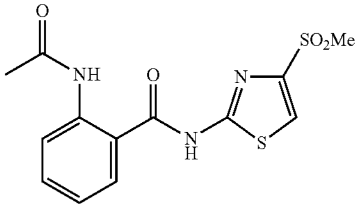 [SMILES: CC(=O)Nc1ccccc1C(=O)Nc1nc(S(C)(=O)=O)cs1] | 2-acetamido-N-(4-(methylsulfonyl)thiazol-2-yl)benzamide |
| B-49 | 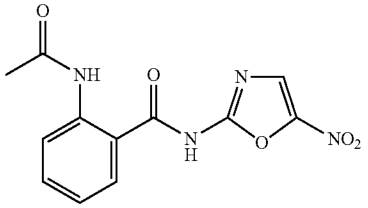 [SMILES: CC(=O)Nc1ccccc1C(=O)Nc1ncc([N+](=O)[O-])o1] | 2-acetamido-N-(5-nitrooxazol-2-yl)benzamide |
| B-50 | 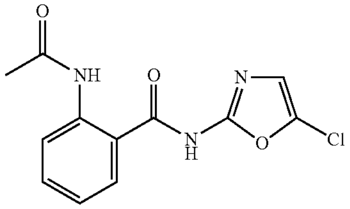 [SMILES: CC(=O)Nc1ccccc1C(=O)Nc1ncc(Cl)o1] | 2-acetamido-N-(5-chlorooxazol-2-yl)benzamide |

TABLE 1-continued
DDB1 binding moieties
| Compound | Structure | Name |
|---|---|---|
| B-51 | 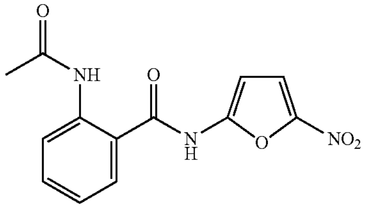 [SMILES: CC(=O)Nc1ccccc1C(=O)Nc1ccc([N+](=O)[O-])o1] | 2-acetamido-N-(5-nitrothiophen-2-yl)benzamide |
| B-52 | 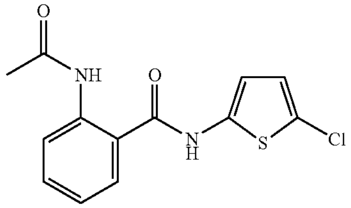 [SMILES: CC(=O)Nc1ccccc1C(=O)Nc1ccc(Cl)s1] | 2-acetamido-N-(5-chlorothiophen-2-yl)benzamide |
| B-53 | 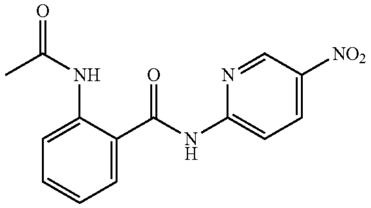 [SMILES: CC(=O)Nc1ccccc1C(=O)Nc1ccc([N+](=O)[O-])cn1] | 2-acetamido-N-(5-nitropyridin-2-yl)benzamide |
| B-54 | 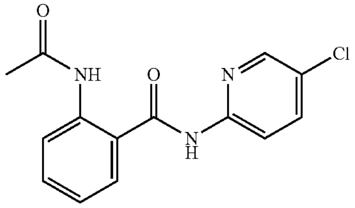 [SMILES: CC(=O)Nc1ccccc1C(=O)Nc1ccc(Cl)cn1] | 2-acetamido-N-(5-chloropyridin-2-yl)benzamide |
| B-55 | 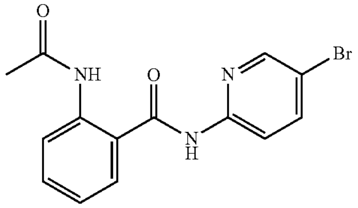 [SMILES: CC(=O)Nc1ccccc1C(=O)Nc1ccc(Br)cn1] | 2-acetamido-N-(5-bromopyridin-2-yl)benzamide |
| B-56 | 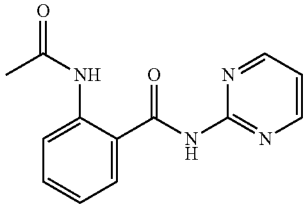 [SMILES: CC(=O)Nc1ccccc1C(=O)Nc1ncccn1] | 2-acetamido-N-(pyrimidin-2-yl)benzamide |
| B-57 | 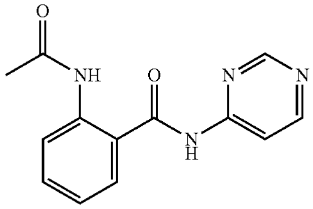 [SMILES: CC(=O)Nc1ccccc1C(=O)Nc1ccncn1] | 2-acetamido-N-(pyrimidin-4-yl)benzamide |

TABLE 1-continued

| DDB1 binding moieties | | |
|---|---|---|
| Compound | Structure | Name |
| B-58 | 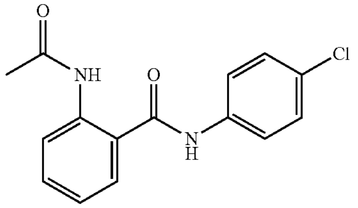 [SMILES: CC(=O)Nc1ccccc1C(=O)Nc1ccc(Cl)cc1] | 2-acetamido-N-(4-chlorophenyl)benzamide |
| B-59 | 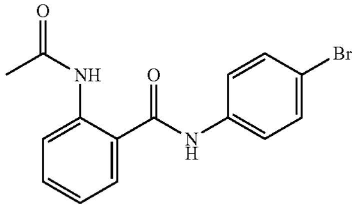 [SMILES: CC(=O)Nc1ccccc1C(=O)Nc1ccc(Br)cc1] | 2-acetamido-N-(4-bromophenyl)benzamide |
| B-60 | 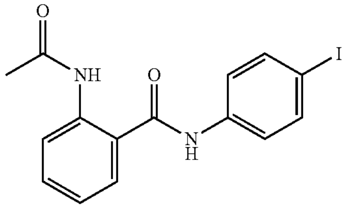 [SMILES: CC(=O)Nc1ccccc1C(=O)Nc1ccc(I)cc1] | 2-acetamido-N-(4-iodophenyl)benzamide |
| B-61 | 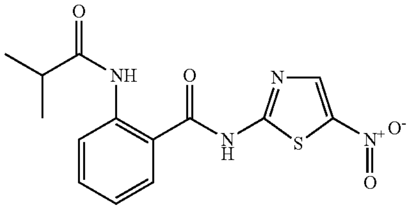 | 2-isobutyramido-N-(5-nitrothiazol-2-yl)benzamide |
| B-62 | 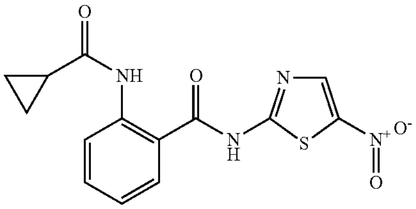 | 2-(cyclopropanecarboxamido)-N-(5-nitrothiazol-2-yl)benzamide |
| B-63 | 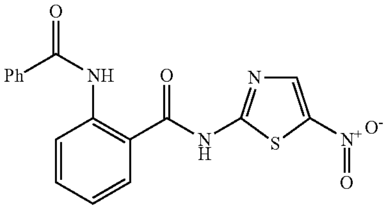 | 2-benzamido-N-(5-nitrothiazol-2-yl)benzamide |
| B-64 | 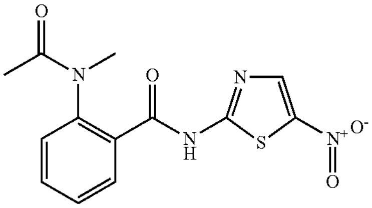 | 2-(N-methylacetamido)-N-(5-nitrothiazol-2-yl)benzamide |

TABLE 1-continued

DDB1 binding moieties

| Compound | Structure | Name |
| --- | --- | --- |
| B-65 | 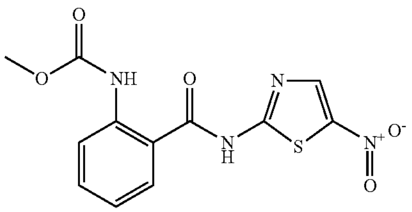 | methyl(2-((5-nitrothiazol-2-yl)carbamoyl)phenyl)carbamate |
| B-66 | 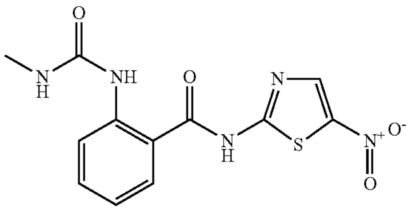 | 2-(3-methylureido)-N-(5-nitrothiazol-2-yl)benzamide |
| B-67 | 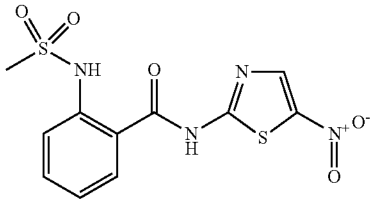 | 2-(methylsulfonamido)-N-(5-nitrothiazol-2-yl)benzamide |
| B-68 | 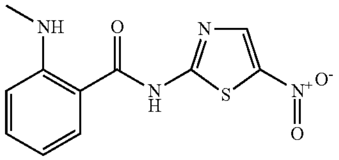 | 2-(methylamino)-N-(5-nitrothiazol-2-yl)benzamide |
| B-69 | 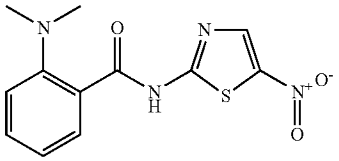 | 2-(dimethylamino)-N-(5-nitrothiazol-2-yl)benzamide |
| B-70 | 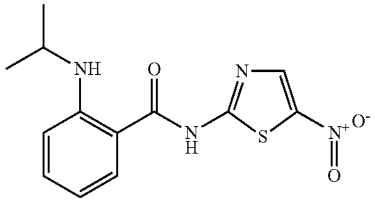 | 2-(isopropylamino)-N-(5-nitrothiazol-2-yl)benzamide |
| B-71 | 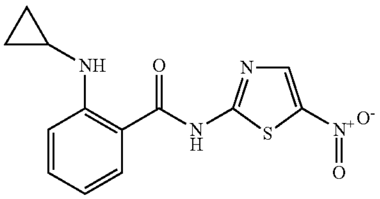 | 2-(cyclopropylamino)-N-(5-nitrothiazol-2-yl)benzamide |

TABLE 1-continued

| DDB1 binding moieties | | |
|---|---|---|
| Compound | Structure | Name |
| B-72 | 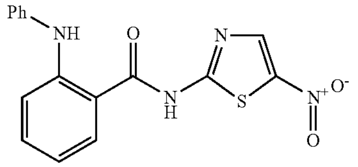 | N-(5-nitrothiazol-2-yl)-2-(phenylamino)benzamide |
| B-73 | 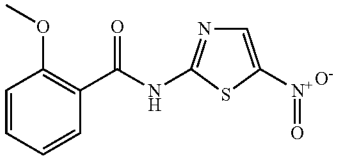 | 2-methoxy-N-(5-nitrothiazol-2-yl)benzamide |
| B-74 | 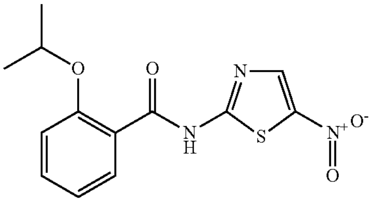 | 2-isopropoxy-N-(5-nitrothiazol-2-yl)benzamide |
| B-75 | 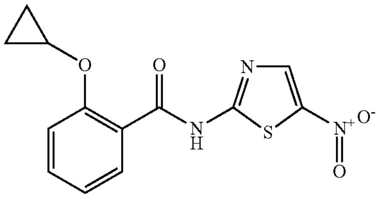 | 2-cyclopropoxy-N-(5-nitrothiazol-2-yl)benzamide |
| B-76 | 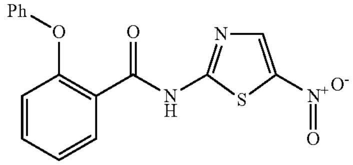 | N-(5-nitrothiazol-2-yl)-2-phenoxybenzamide |
| B-77 | 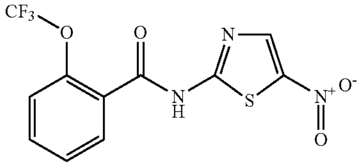 | N-(5-nitrothiazol-2-yl)-2-(trifluoromethoxy)benzamide |
| B-78 | 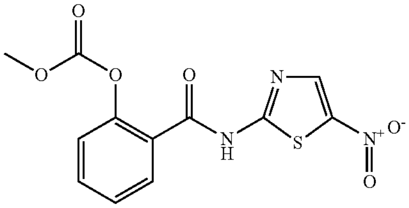 | methyl(2-((5-nitrothiazol-2-yl)carbamoyl)phenyl)carbonate |
| B-79 | 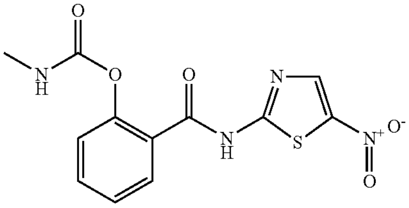 | 2-((5-nitrothiazol-2-yl)carbamoyl)phenyl methylcarbamate |

TABLE 1-continued

| DDB1 binding moieties | | |
|---|---|---|
| Compound | Structure | Name |
| B-80 | 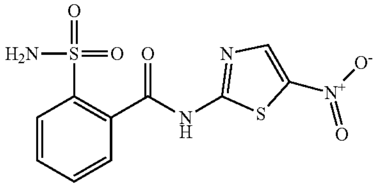 [SMILES: NS(=O)(=O)c1ccccc1C(=O)Nc1ncc([N+](=O)[O-])s1] | N-(5-nitrothiazol-2-yl)-2-sulfamoylbenzamide |
| B-81 | 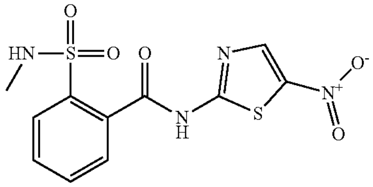 [SMILES: CNS(=O)(=O)c1ccccc1C(=O)Nc1ncc([N+](=O)[O-])s1] | 2-(N-methylsulfamoyl)-N-(5-nitrothiazol-2-yl)benzamide |
| B-82 | 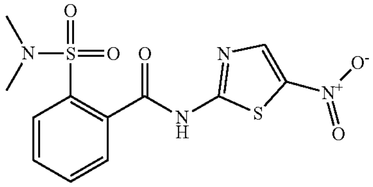 [SMILES: CN(C)S(=O)(=O)c1ccccc1C(=O)Nc1ncc([N+](=O)[O-])s1] | 2-(N,N-dimethylsulfamoyl)-N-(5-nitrothiazol-2-yl)benzamide |
| B-83 | 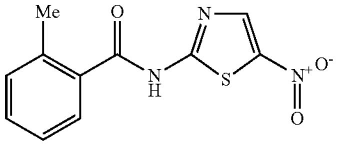 | 2-methyl-N-(5-nitrothiazol-2-yl)benzamide |
| B-84 | 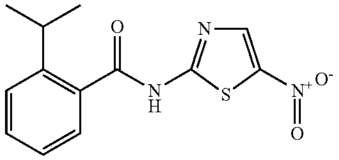 | 2-isopropyl-N-(5-nitrothiazol-2-yl)benzamide |
| B-85 | 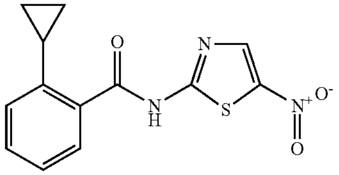 | 2-cyclopropyl-N-(5-nitrothiazol-2-yl)benzamide |
| B-86 | 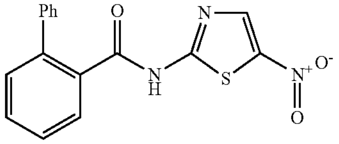 | N-(5-nitrothiazol-2-yl)-[1,1'-biphenyl]-2-carboxamide |
| B-87 | 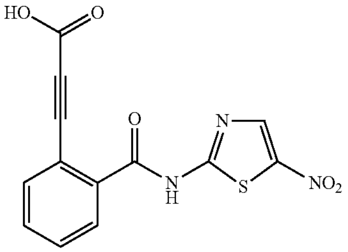 [SMILES: O=C(O)C#Cc1ccccc1C(=O)Nc1ncc([N+](=O)[O-])s1] | 3-(2-((5-nitrothiazol-2-yl)carbamoyl)phenyl)propiolic acid |

TABLE 1-continued

| DDB1 binding moieties | | |
|---|---|---|
| Compound | Structure | Name |
| B-88 | 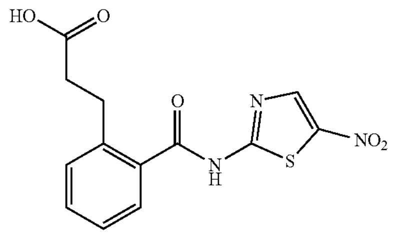 [SMILES: O=C(O)CCc1ccccc1C(=O)Nc1ncc([N+](=O)[O-])s1] | 3-(2-((5-nitrothiazol-2-yl)carbamoyl)phenyl)propanoic acid |
| B-89 | 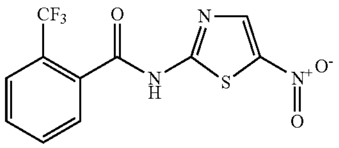 | N-(5-nitrothiazol-2-yl)-2-(trifluoromethyl)benzamide |
| B-90 | 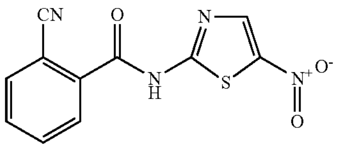 | 2-cyano-N-(5-nitrothiazol-2-yl)benzamide |
| B-91 | 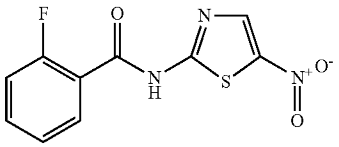 | 2-fluoro-N-(5-nitrothiazol-2-yl)benzamide |
| B-92 | 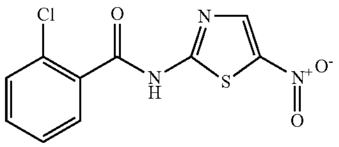 | 2-chloro-N-(5-nitrothiazol-2-yl)benzamide |
| B-93 | 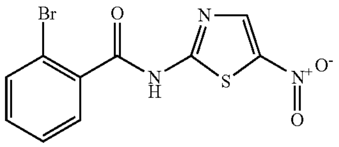 | 2-bromo-N-(5-nitrothiazol-2-yl)benzamide |
| B-94 | 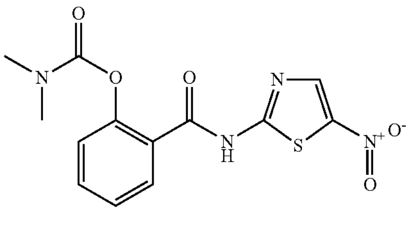 | 2-((5-nitrothiazol-2-yl)carbamoyl)phenyl dimethylcarbamate |
| B-95 | 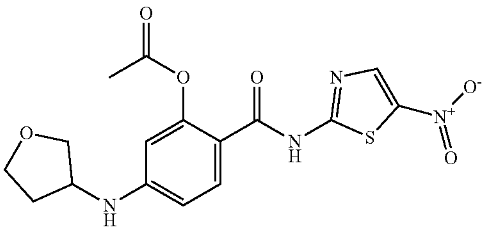 [SMILES: CC(=O)Oc1cc(NC2CCOC2)ccc1C(=O)Nc1ncc([N+](=O)[O-])s1] | 2-((5-nitrothiazol-2-yl)carbamoyl)-5-((tetrahydrofuran-3-yl)amino)phenyl acetate |

TABLE 1-continued

| DDB1 binding moieties | | |
|---|---|---|
| Compound | Structure | Name |
| B-96 | 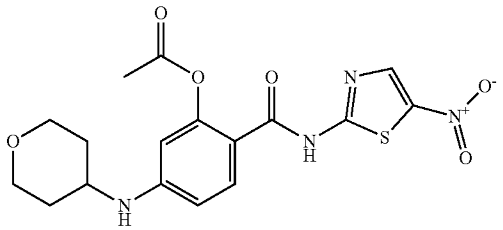 [SMILES: CC(=O)Oc1cc(NC2CCOCC2)ccc1C(=O)Nc1ncc([N+](=O)[O-])s1] | 2-((5-nitrothiazol-2-yl)carbamoyl)-5-((tetrahydro-2H-pyran-4-yl)amino)phenyl acetate |
| B-97 | 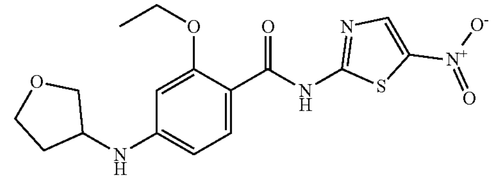 [SMILES: CCOc1cc(NC2CCOC2)ccc1C(=O)Nc1ncc([N+](=O)[O-])s1] | 2-ethoxy-N-(5-nitrothiazol-2-yl)-4-((tetrahydrofuran-3-yl)amino)benzamide |
| B-98 | 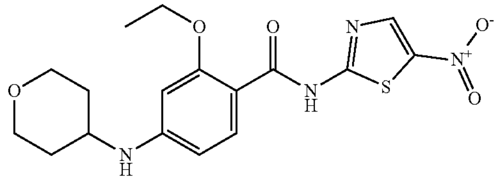 [SMILES: CCOc1cc(NC2CCOCC2)ccc1C(=O)Nc1ncc([N+](=O)[O-])s1] | 2-ethoxy-N-(5-nitrothiazol-2-yl)-4-((tetrahydro-2H-pyran-4-yl)amino)benzamide |
| B-99 | 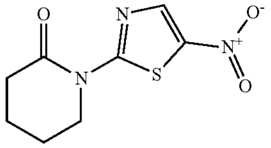 [SMILES: O=C1CCCCN1c1ncc([N+](=O)[O-])s1] | 1-(5-nitrothiazol-2-yl)piperidin-2-one |
| B-100 | 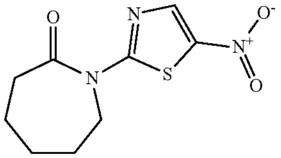 [SMILES: O=C1CCCCCN1c1ncc([N+](=O)[O-])s1] | 1-(5-nitrothiazol-2-yl)azepan-2-one |
| B-101 | 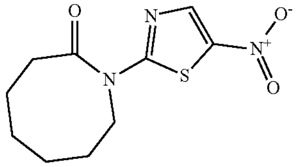 [SMILES: O=C1CCCCCCN1c1ncc([N+](=O)[O-])s1] | 1-(5-nitrothiazol-2-yl)azocan-2-one |
| B-102 | 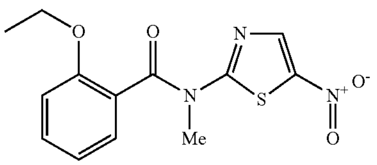 | 2-ethoxy-N-methyl-N-(5-nitrothiazol-2-yl)benzamide |
| B-103 | 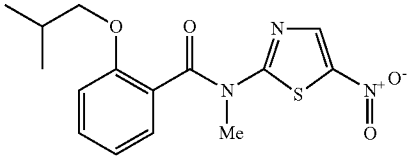 | 2-isobutoxy-N-methyl-N-(5-nitrothiazol-2-yl)benzamide |

TABLE 1-continued

| DDB1 binding moieties | | |
|---|---|---|
| Compound | Structure | Name |
| B-104 | 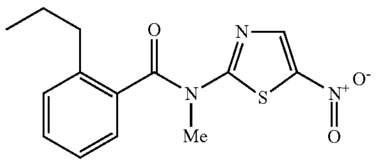 | N-methyl-N-(5-nitrothiazol-2-yl)-2-propylbenzamide |
| B-105 | 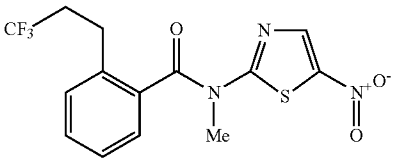 | N-methyl-N-(5-nitrothiazol-2-yl)-2-(3,3,3-trifluoropropyl)benzamide |
| B-106 | 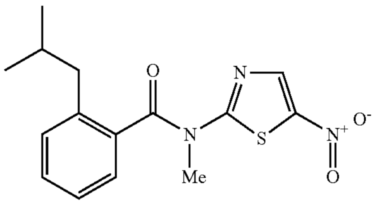 | 2-isobutyl-N-methyl-N-(5-nitrothiazol-2-yl)benzamide |
| B-107 | 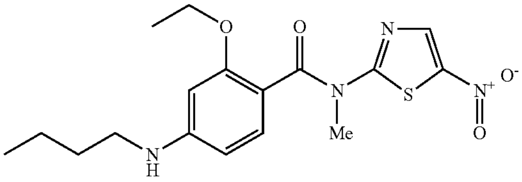 | 4-(butylamino)-2-ethoxy-N-methyl-N-(5-nitrothiazol-2-yl)benzamide |
| B-108 | 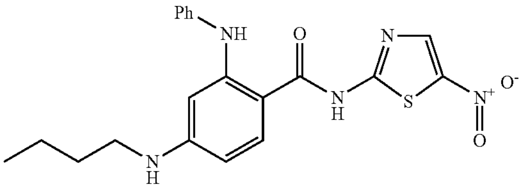 | 4-(butylamino)-N-(5-nitrothiazol-2-yl)-2-(phenylamino)benzamide |
| B-109 | 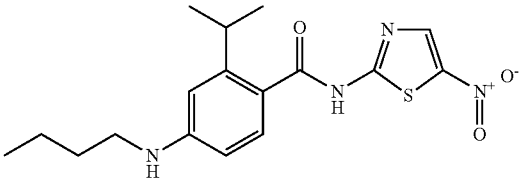 | 4-(butylamino)-2-isopropyl-N-(5-nitrothiazol-2-yl)benzamide |
| B-110 | 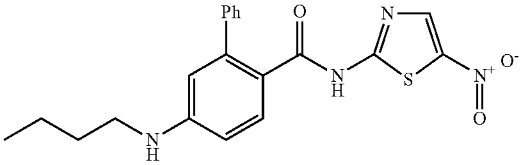 | 5-(butylamino)-N-(5-nitrothiazol-2-yl)-[1,1'-biphenyl]-2-carboxamide |
| B-111 | 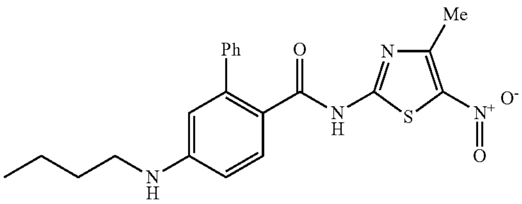 | N-(4-methyl-5-nitrothiazol-2-yl)-5-(butylamino)-[1,1'-biphenyl]-2-carboxamide |

TABLE 1-continued

| DDB1 binding moieties | | |
|---|---|---|
| Compound | Structure | Name |
| B-112 | 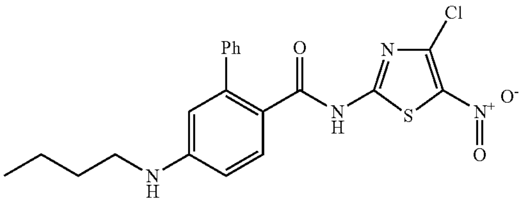 | N-(4-chloro-5-nitrothiazol-2-yl)-5-(butylamino)-[1,1'-biphenyl]-2-carboxamide |
| B-113 | 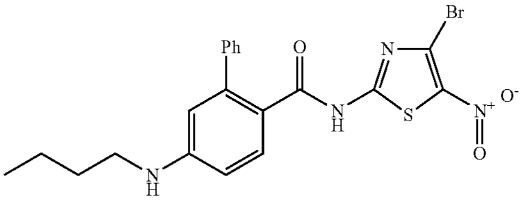 | N-(4-bromo-5-nitrothiazol-2-yl)-5-(butylamino)-[1,1'-biphenyl]-2-carboxamide |
| B-114 | 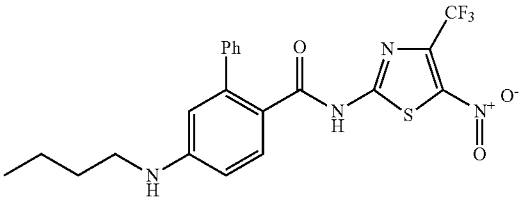 | 5-(butylamino)-N-(5-nitro-4-(trifluoromethyl)thiazol-2-yl)-[1,1'-biphenyl]-2-carboxamide |
| B-115 | 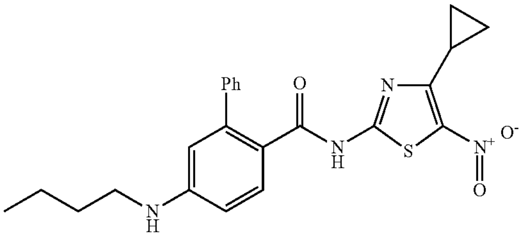 | 5-(butylamino)-N-(4-cyclopropyl-5-nitrothiazol-2-yl)-[1,1'-biphenyl]-2-carboxamide |
| B-116 | 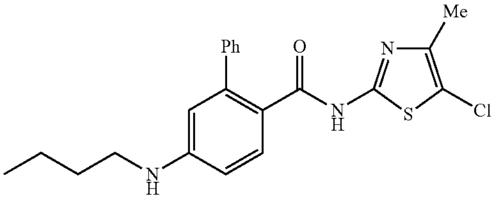 [SMILES: CCCCNc1ccc(C(=O)Nc2nc(C)c(Cl)s2)c(-c2ccccc2)c1] | N-(5-chlorothiazol-2-yl)-5-(butylamino)-[1,1'-biphenyl]-2-carboxamide |
| B-117 | 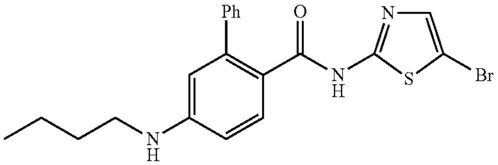 [SMILES: CCCCNc1ccc(C(=O)Nc2ncc(Br)s2)c(-c2ccccc2)c1] | N-(5-bromothiazol-2-yl)-5-(butylamino)-[1,1'-biphenyl]-2-carboxamide |
| B-118 | 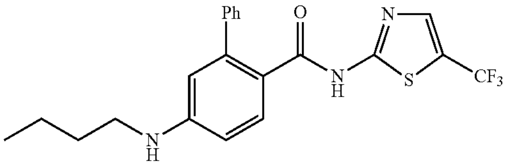 [SMILES: CCCCNc1ccc(C(=O)Nc2ncc(C(F)(F)F)s2)c(-c2ccccc2)c1] | 5-(butylamino)-N-(5-(trifluoromethyl)thiazol-2-yl)-[1,1'-biphenyl]-2-carboxamide |

TABLE 1-continued
| DDB1 binding moieties | | |
|---|---|---|
| Compound | Structure | Name |
| B-119 | 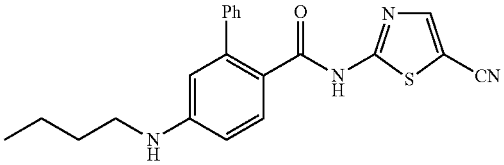 [SMILES: CCCCNc1ccc(C(=O)Nc2ncc(C#N)s2)c(-c2ccccc2)c1] | 5-(butylamino)-N-(5-cyanothiazol-2-yl)-[1,1'-biphenyl]-2-carboxamide |
| B-120 | 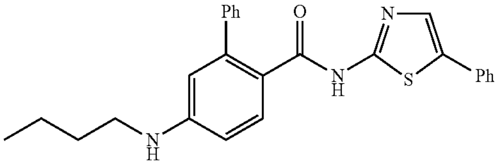 [SMILES: CCCCNc1ccc(C(=O)Nc2ncc(-c3ccccc3)s2)c(-c2ccccc2)c1] | 5-(butylamino)-N-(5-phenylthiazol-2-yl)-[1,1'-biphenyl]-2-carboxamide |
| B-121 | 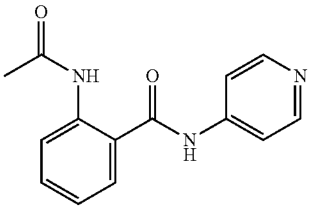 [SMILES: CC(=O)Nc1ccccc1C(=O)Nc1ccncc1] | 2-acetamido-N-(pyridin-4-yl)benzamide |
| B-122 | 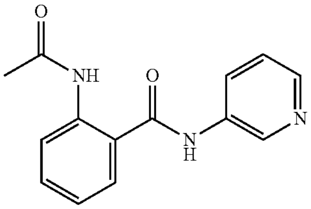 [SMILES: CC(=O)Nc1ccccc1C(=O)Nc1cccnc1] | 2-acetamido-N-(pyridin-3-yl)benzamide |
| B-123 | 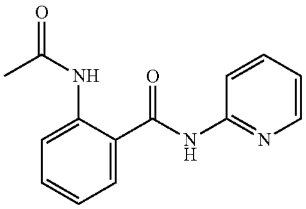 [SMILES: CC(=O)Nc1ccccc1C(=O)Nc1ccccn1] | 2-acetamido-N-(pyridin-2-yl)benzamide |
| B-124 | 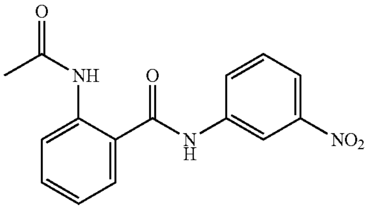 [SMILES: CC(=O)Nc1ccccc1C(=O)Nc1cccc([N+](=O)[O-])c1] | 2-acetamido-N-(3-nitrophenyl)benzamide |
| B-125 | 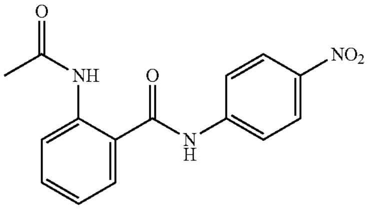 [SMILES: CC(=O)Nc1ccccc1C(=O)Nc1ccc([N+](=O)[O-])cc1] | 2-acetamido-N-(4-nitrophenyl)benzamide |

TABLE 1-continued

| DDB1 binding moieties | | |
|---|---|---|
| Compound | Structure | Name |
| B-126 | 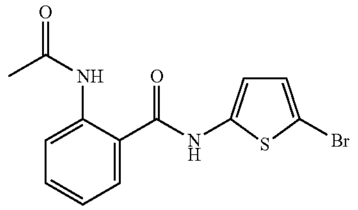 [SMILES: CC(=O)Nc1ccccc1C(=O)Nc1ccc(Br)s1] | 2-acetamido-N-(5-bromothiophen-2-yl)benzamide |
| B-127 | 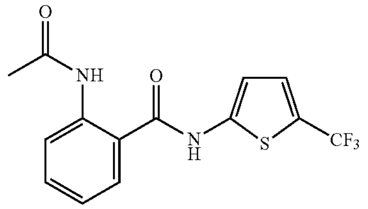 [SMILES: CC(=O)Nc1ccccc1C(=O)Nc1ccc(C(F)(F)F)s1] | 2-acetamido-N-(5-(trifluoromethyl)thiophen-2-yl)benzamide |
| B-128 | 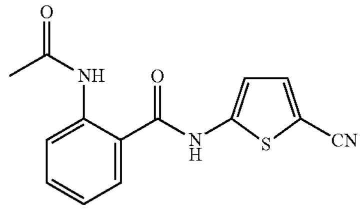 [SMILES: CC(=O)Nc1ccccc1C(=O)Nc1ccc(C#N)s1] | 2-acetamido-N-(5-cyanothiophen-2-yl)benzamide |
| B-129 | 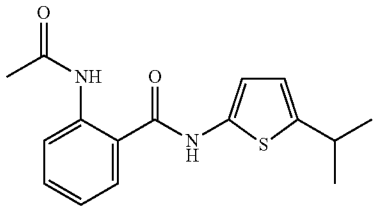 [SMILES: CC(=O)Nc1ccccc1C(=O)Nc1ccc(C(C)C)s1] | 2-acetamido-N-(5-isopropylthiophen-2-yl)benzamide |
| B-130 | 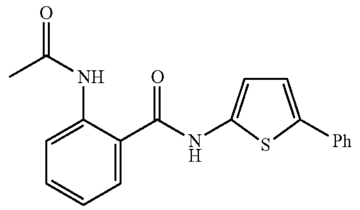 [SMILES: CC(=O)Nc1ccccc1C(=O)Nc1ccc(-c2ccccc2)s1] | 2-acetamido-N-(5-phenylthiophen-2-yl)benzamide |
| B-131 | 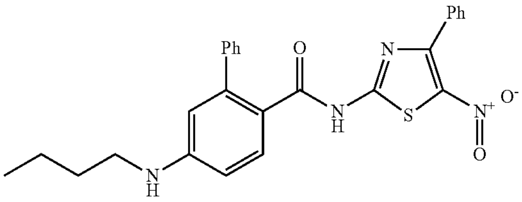 | 5-(butylamino)-N-(5-nitro-4-phenylthiazol-2-yl)-[1,1'-biphenyl]-2-carboxamide |
| B-132 | 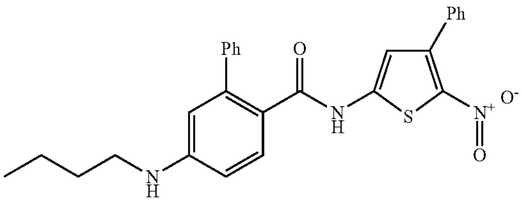 | 5-(butylamino)-N-(5-nitro-4-phenylthiophen-2-yl)-[1,1'-biphenyl]-2-carboxamide |

TABLE 1-continued

| DDB1 binding moieties | | |
|---|---|---|
| Compound | Structure | Name |
| B-133 | 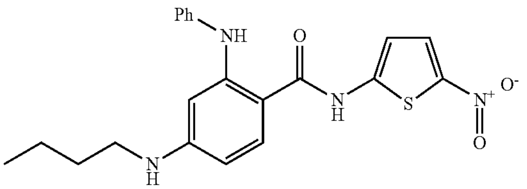 | 4-(butylamino)-N-(5-nitrothiophen-2-yl)-2-(phenylamino)benzamide |
| B-134 | 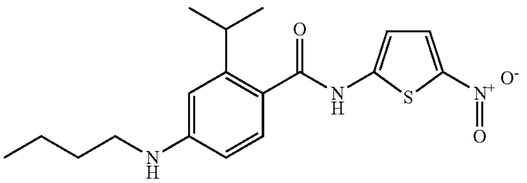 | 4-(butylamino)-2-isopropyl-N-(5-nitrothiophen-2-yl)benzamide |
| B-135 | 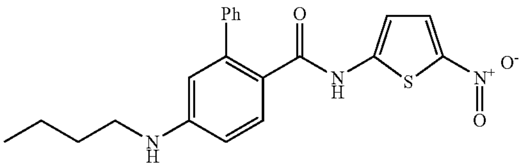 | 5-(butylamino)-N-(5-nitrothiophen-2-yl)-[1,1'-biphenyl]-2-carboxamide |
| B-136 | 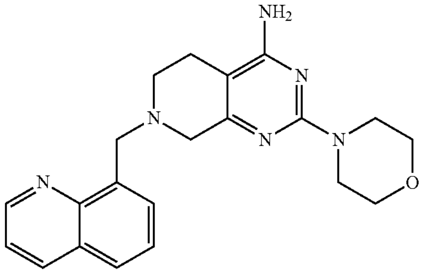 [SMILES: Nc1nc(N2CCOCC2)nc2c1CCN(Cc1cccc3cccnc13)C2] | 2-morpholino-7-(quinolin-8-ylmethyl)-5,6,7,8-tetrahydropyrido[3,4-d]pyrimidin-4-amine |
| B-137 | 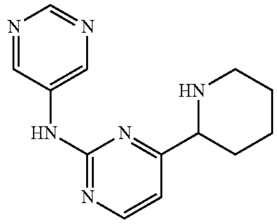 [SMILES: c1ncc(Nc2nccc(C3CCCCN3)n2)cn1] | 4-(piperidin-2-yl)-N-(pyrimidin-5-yl)pyrimidin-2-amine |
| B-138 | 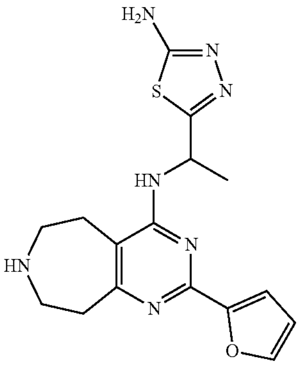 [SMILES: CC(Nc1nc(-c2ccco2)nc2c1CCNCC2)c1nnc(N)s1] | 5-(1-((2-(furan-2-yl)-6,7,8,9-tetrahydro-5H-pyrimido[4,5-d]azepin-4-yl)amino)ethyl)-1,3,4-thiadiazol-2-amine |

TABLE 1-continued

| DDB1 binding moieties | | |
|---|---|---|
| Compound | Structure | Name |
| B-139 | 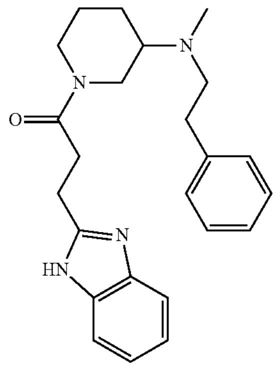 [SMILES: CN(CCc1ccccc1)C1CCCN(C(=O)CCc2nc3ccccc3[nH]2)C1] | 3-(1H-benzo[d]imidazol-2-yl)-1-(3-(methyl(phenethyl)amino)piperidin-1-yl)propan-1-one |
| B-140 | 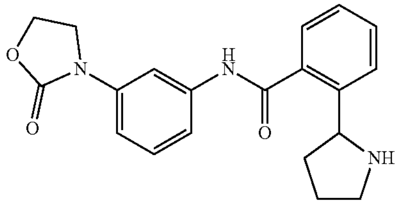 [SMILES: O=C(Nc1cccc(N2CCOC2=O)c1)c1ccccc1C1CCCN1] | N-(3-(2-oxooxazolidin-3-yl)phenyl)-2-(pyrrolidin-2-yl)benzamide |
| B-141 | 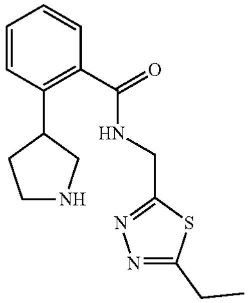 [SMILES: CCc1nnc(CNC(=O)c2ccccc2C2CCNC2)s1] | N-((5-ethyl-1,3,4-thiadiazol-2-yl)methyl)-2-(pyrrolidin-3-yl)benzamide |
| B-142 | 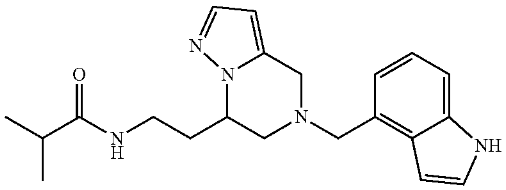 [SMILES: CC(C)C(=O)NCCC1CN(Cc2cccc3[nH]ccc23)Cc2ccnn21] | N-(2-(5-((1H-indol-4-yl)methyl)-4,5,6,7-tetrahydropyrazolo[1,5-a]pyrazin-7-yl)ethyl)isobutyramide |
| B-143 | 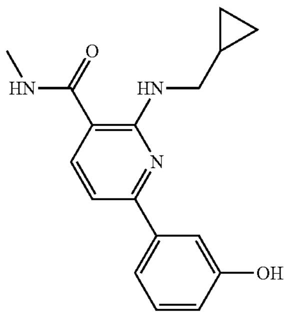 [SMILES: CNC(=O)c1ccc(-c2cccc(O)c2)nc1NCC1CC1] | 2-((cyclopropylmethyl)amino)-6-(3-hydroxyphenyl)-N-methylnicotinamide |

TABLE 1-continued

| Compound | Structure | Name |
|---|---|---|
| DDB1 binding moieties | | |
| B-144 | 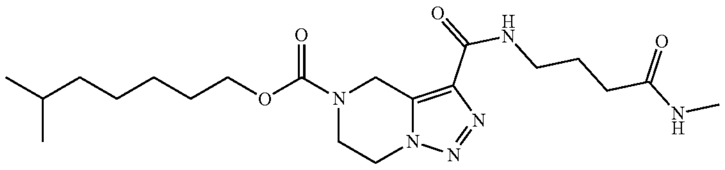 [SMILES: CNC(=O)CCCNC(=O)c1nnn2c1CN(C(=O)OCCCCCC(C)C)CC2] | 6-methylheptyl3-((4-(methylamino)-4-oxobutyl)carbamoyl)-6,7-dihydro-[1,2,3]triazolo[1,5-a]pyrazine-5(4H)-carboxylate |
| B-145 | 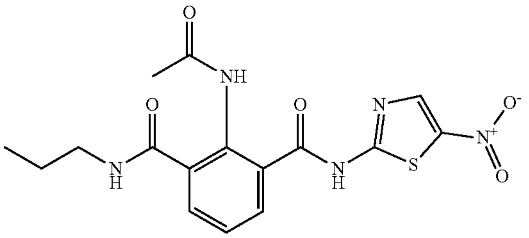 [SMILES: CCCNC(=O)c1cccc(C(=O)Nc2ncc([N+](=O)[O-])s2)c1NC(C)=O] | 2-acetamido-$N^1$-(5-nitrothiazol-2-yl)-$N^3$-propylisophthalamide |
| B-146 | 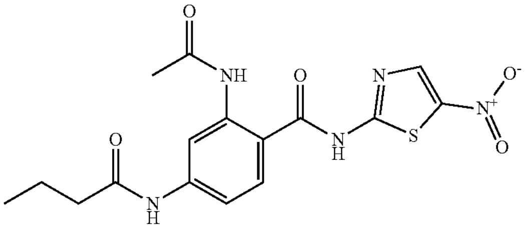 [SMILES: CCCC(=O)Nc1ccc(C(=O)Nc2ncc([N+](=O)[O-])s2)c(NC(C)=O)c1] | 2-acetamido-4-butyramido-N-(5-nitrothiazol-2-yl)benzamide |
| B-147 | 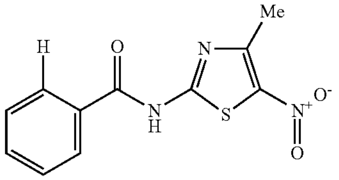 | N-(4-methyl-5-nitrothiazol-2-yl)benzamide |
| B-148 | 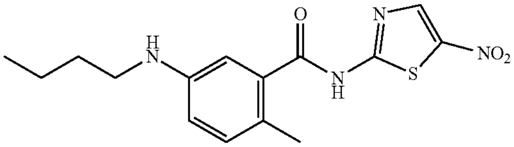 [SMILES: CCCCNc1ccc(C)c(C(=O)Nc2ncc([N+](=O)[O-])s2)c1] | 5-(butylamino)-2-methyl-N-(5-nitrothiazol-2-yl)benzamide |
| B-149 | 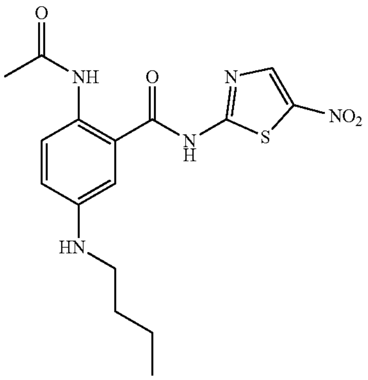 [SMILES: CCCCNc1ccc(NC(C)=O)c(C(=O)Nc2ncc([N+](=O)[O-])s2)c1] | 2-acetamido-5-(butylamino)-N-(5-nitrothiazol-2-yl)benzamide |
| B-150 | 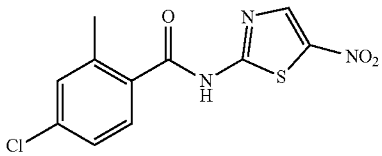 [SMILES: Cc1cc(Cl)ccc1C(=O)Nc1ncc([N+](=O)[O-])s1] | 4-chloro-2-methyl-N-(5-nitrothiazol-2-yl)benzamide |

TABLE 1-continued

| DDB1 binding moieties | | |
|---|---|---|
| Compound | Structure | Name |
| B-151 | 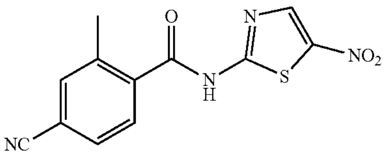 [SMILES: Cc1cc(C#N)ccc1C(=O)Nc1ncc([N+](=O)[O-])s1] | 4-cyano-2-methyl-N-(5-nitrothiazol-2-yl)benzamide |
| B-152 | 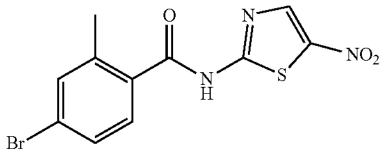 | 4-bromo-2-methyl-N-(5-nitrothiazol-2-yl)benzamide |
| B-153 | 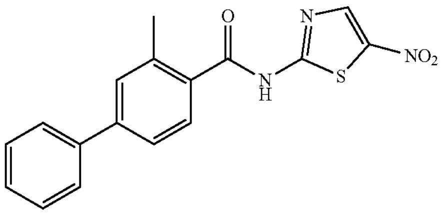 [SMILES: Cc1cc(-c2ccccc2)ccc1C(=O)Nc1ncc([N+](=O)[O-])s1] | 3-methyl-N-(5-nitrothiazol-2-yl)-[1,1'-biphenyl]-4-carboxamide |
| B-154 | 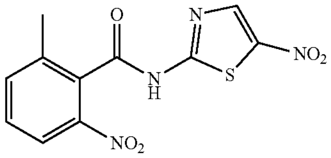 [SMILES: Cc1cccc([N+](=O)[O-])c1C(=O)Nc1ncc([N+](=O)[O-])s1] | 2-methyl-6-nitro-N-(5-nitrothiazol-2-yl)benzamide |
| B-155 | 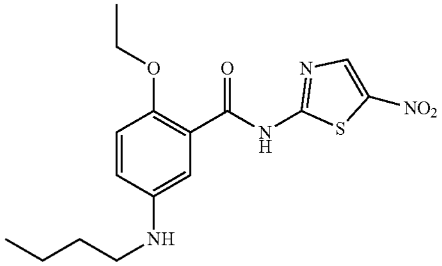 [SMILES: CCCCNc1ccc(OCC)c(C(=O)Nc2ncc([N+](=O)[O-])s2)c1] | 5-(butylamino)-2-ethoxy-N-(5-nitrothiazol-2-yl)benzamide |
| B-156 | 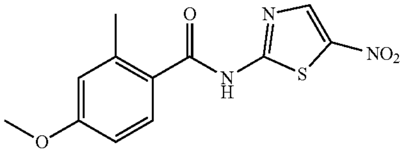 [SMILES: COc1ccc(C(=O)Nc2ncc([N+](=O)[O-])s2)c(C)c1] | 4-methoxy-2-methyl-N-(5-nitrothiazol-2-yl)benzamide |
| B-157 | 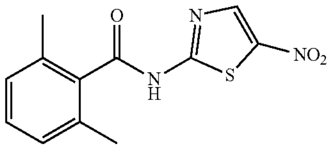 [SMILES: Cc1cccc(C)c1C(=O)Nc1ncc([N+](=O)[O-])s1] | 2,6-dimethyl-N-(5-nitrothiazol-2-yl)benzamide |
| B-158 | 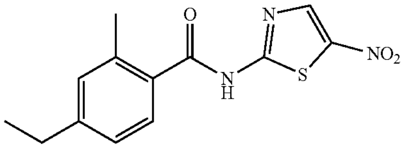 [SMILES: CCc1ccc(C(=O)Nc2ncc([N+](=O)[O-])s2)c(C)c1] | 4-ethyl-2-methyl-N-(5-nitrothiazol-2-yl)benzamide |

TABLE 1-continued

| DDB1 binding moieties | | |
|---|---|---|
| Compound | Structure | Name |
| B-159 | 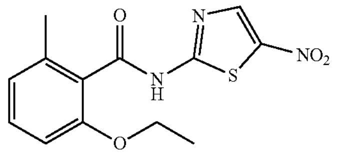 [SMILES: CCOc1cccc(C)c1C(=O)Nc1ncc([N+](=O)[O-])s1] | 2-ethoxy-6-methyl-N-(5-nitrothiazol-2-yl)benzamide |
| B-160 | 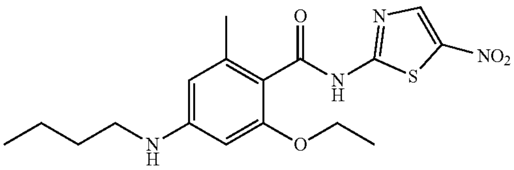 [SMILES: CCCCNc1cc(C)c(C(=O)Nc2ncc([N+](=O)[O-])s2)c(OCC)c1] | 4-(butylamino)-2-ethoxy-N-(5-nitrothiazol-2-yl)benzamide |
| B-161 | 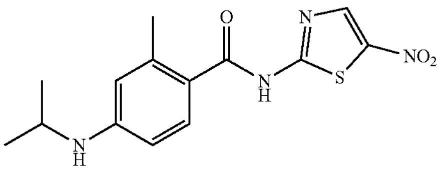 [SMILES: Cc1cc(NC(C)C)ccc1C(=O)Nc1ncc([N+](=O)[O-])s1] | 4-(isopropylamino)-2-methyl-N-(5-nitrothiazol-2-yl)benzamide |
| B-162 | 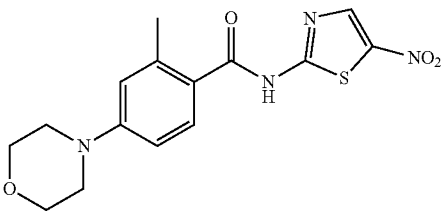 [SMILES: Cc1cc(N2CCOCC2)ccc1C(=O)Nc1ncc([N+](=O)[O-])s1] | 2-methyl-4-morpholino-N-(5-nitrothiazol-2-yl)benzamide |
| B-163 | 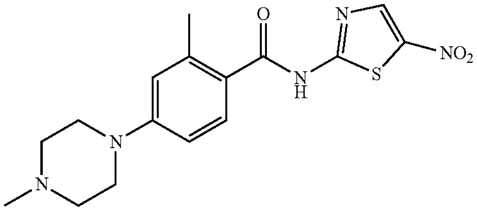 [SMILES: Cc1cc(N2CCN(C)CC2)ccc1C(=O)Nc1ncc([N+](=O)[O-])s1] | 2-methyl-4-(4-methylpiperazin-1-yl)-N-(5-nitrothiazol-2-yl)benzamide |
| B-164 | 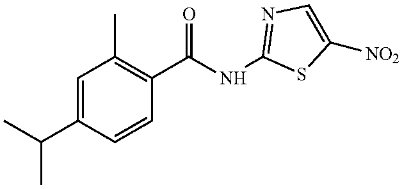 [SMILES: Cc1cc(C(C)C)ccc1C(=O)Nc1ncc([N+](=O)[O-])s1] | 4-isopropyl-2-methyl-N-(5-nitrothiazol-2-yl)benzamide |
| B-165 | 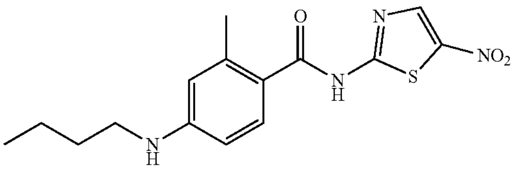 [SMILES: CCCCNc1ccc(C(=O)Nc2ncc([N+](=O)[O-])s2)c(C)c1] | 4-(butylamino)-2-methyl-N-(5-nitrothiazol-2-yl)benzamide |
| B-166 | 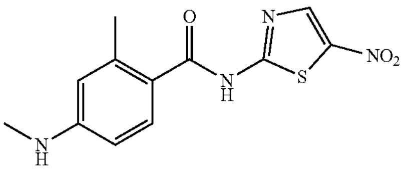 [SMILES: CNc1ccc(C(=O)Nc2ncc([N+](=O)[O-])s2)c(C)c1] | 2-methyl-4-(methylamino)-N-(5-nitrothiazol-2-yl)benzamide |

TABLE 1-continued

| DDB1 binding moieties | | |
|---|---|---|
| Compound | Structure | Name |
| B-167 | 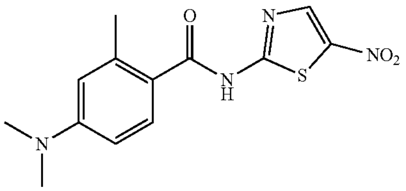 [SMILES: Cc1cc(N(C)C)ccc1C(=O)Nc1ncc([N+](=O)[O-])s1] | 4-(dimethylamino)-2-methyl-N-(5-nitrothiazol-2-yl)benzamide |
| B-168 | 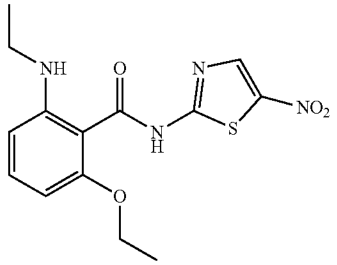 [SMILES: CCNc1cccc(OCC)c1C(=O)Nc1ncc([N+](=O)[O-])s1] | 2-ethoxy-6-(ethylamino)-N-(5-nitrothiazol-2-yl)benzamide |
| B-169 | 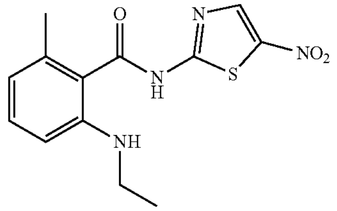 [SMILES: CCNc1cccc(C)c1C(=O)Nc1ncc([N+](=O)[O-])s1] | 2-(ethylamino)-6-methyl-N-(5-nitrothiazol-2-yl)benzamide |
| B-170 | 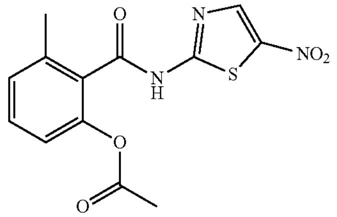 [SMILES: CC(=O)Oc1cccc(C)c1C(=O)Nc1ncc([N+](=O)[O-])s1] | 3-methyl-2-((5-nitrothiazol-2-yl)carbamoyl)phenyl acetate |
| B-171 | 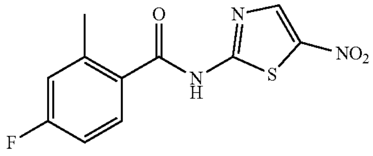 [SMILES: Cc1cc(F)ccc1C(=O)Nc1ncc([N+](=O)[O-])s1] | 4-fluoro-2-methyl-N-(5-nitrothiazol-2-yl)benzamide |
| B-172 | 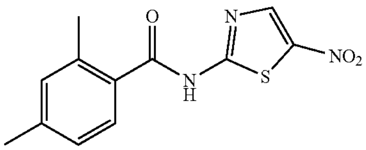 [SMILES: Cc1ccc(C(=O)Nc2ncc([N+](=O)[O-])s2)c(C)c1] | 2,4-dimethyl-N-(5-nitrothiazol-2-yl)benzamide |
| B-173 | 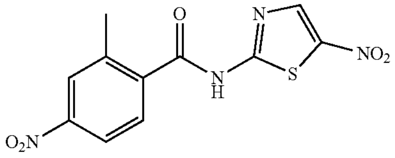 [SMILES: Cc1cc([N+](=O)[O-])ccc1C(=O)Nc1ncc([N+](=O)[O-])s1] | 2-methyl-4-nitro-N-(5-nitrothiazol-2-yl)benzamide |

TABLE 1-continued

| DDB1 binding moieties | | |
|---|---|---|
| Compound | Structure | Name |
| B-174 | 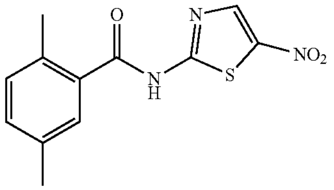 [SMILES: Cc1ccc(C)c(C(=O)Nc2ncc([N+](=O)[O-])s2)c1] | 2,5-dimethyl-N-(5-nitrothiazol-2-yl)benzamide |
| B-175 | 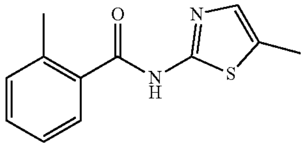 [SMILES: Cc1cnc(NC(=O)c2ccccc2C)s1] | 2-methyl-N-(5-methylthiazol-2-yl)benzamide |
| B-176 | 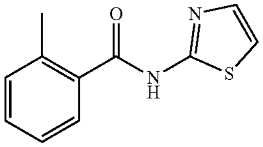 | 2-methyl-N-(thiazol-2-yl)benzamide |

In some embodiments, a compound of Table 1 is capped with a capping group to simulate a linker. In some instances, capping group comprises a substituted amino group. In some instances, a capping group comprises an N-alkyl or N-dialkyl group, an acetamide, an alkyl or haloalkyl group, a lactam, an aminofuran, or an aminopyran group. Without being bound by theory, in some instances capping groups are used to approximate the effect on activity from a similar linker. For example, a DDB1 binding moiety comprising the structure:

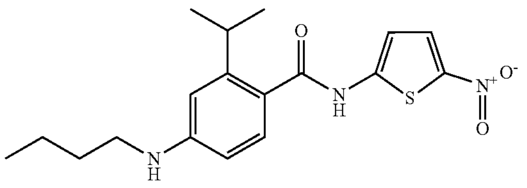

in some embodiments is incorporated into a compound comprising

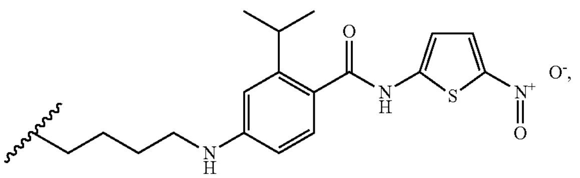

wherein the wavy line indicates a point of attachment to a target protein binding moiety and/or linker. In another example, a DDB1 binding moiety comprising the structure:

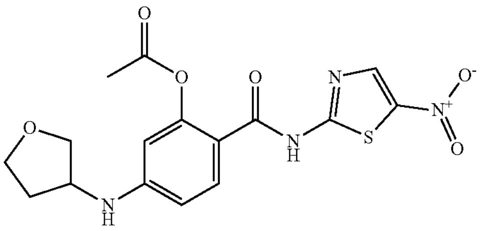

in some embodiments is incorporated into a compound comprising

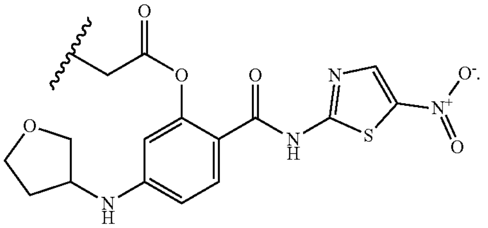

wherein the wavy line indicates a point of attachment to a target protein binding moiety and/or linker.

Disclosed herein, in some embodiments, are ligands comprising a DDB1 binding moiety that binds or is bound to a DDB1 protein. In some embodiments, the binding between the DDB1 protein and the ligand comprises a binding affinity with an equilibrium dissociation constant (Kd) below 100 μM, a Kd below 90 μM, a Kd below 80 μM, a Kd below 70 μM, a Kd below 60 μM, below 50 μM, a Kd below 45 μM, a Kd below 40 μM, a Kd below 35 μM, a Kd below 30 μM, a Kd below 25 μM, a Kd below 20 μM, a Kd below 15 μM, a Kd below 14 μM, a Kd below 13 μM, a Kd below 12 μM, a Kd below 11 μM, a Kd below 10 μM, a Kd below 9 μM, a Kd below 8 μM, a Kd below 7 μM, a Kd below 6 μM, a Kd below 5 μM, a Kd below 4 μM, a Kd below 3 μM, a Kd below 2 μM, or a Kd below 1 μM. In some embodiments, the binding between the DDB1 protein and the ligand comprises a binding affinity with a Kd value of about 100 μM, about 90 μM, about 80 μM, about 70 μM, about 60 μM, about 50 μM, about 45 μM, about 40 μM, about 35 μM, about 30 μM, about 25 μM, about 20 μM, about 15 μM, about 14 μM, about 13 μM, about 12 μM, about 11 μM, about 10 μM, about 9 μM, about 8 μM, about 7 μM, about 6 μM, about 5 μM, about 4 μM, about 3 μM, about 2 μM, or about 1 μM, or a range of Kd values defined by any two of the aforementioned Kd values. In some embodiments, the binding between the DDB1 protein and the ligand comprises a binding affinity with a Kd value of 100 μM, 90 μM, 80 μM, 70 μM, 60 μM, 50 μM, 45 μM, 40 μM, 35 μM, 30 μM, 25 μM, 20 μM, 15 μM, 14 μM, 13 μM, 12 μM, 11 μM, 10 μM, 9 μM, 8 μM, 7 μM, 6 μM, 5 μM, 4 μM, 3 μM, 2 μM, or 1 μM, or a range of Kd values defined by any two of the aforementioned Kd values.

In some embodiments, the binding between the DDB1 protein and the ligand comprises a binding affinity with a Kd below 100 μM. In some embodiments, the binding between the DDB1 protein and the ligand comprises a binding affinity with a Kd below 90 μM. In some embodiments, the binding between the DDB1 protein and the ligand comprises a binding affinity with a Kd below 80 μM. In some embodiments, the binding between the DDB1 protein and the ligand comprises a binding affinity with a Kd below 70 μM. In some embodiments, the binding between the DDB1 protein and the ligand comprises a binding affinity with a Kd below 60 μM. In some embodiments, the binding between the DDB1 protein and the ligand comprises a binding affinity with a Kd below 50 μM. In some embodiments, the binding between the DDB1 protein and the ligand comprises a binding affinity with a Kd below 45 μM. In some embodiments, the binding between the DDB1 protein and the ligand comprises a binding affinity with a Kd below 40 μM. In some embodiments, the binding between the DDB1 protein and the ligand comprises a binding affinity with a Kd below 35 μM. In some embodiments, the binding between the DDB1 protein and the ligand comprises a binding affinity with a Kd below 30 μM. In some embodiments, the binding between the DDB1 protein and the ligand comprises a binding affinity with a Kd below 25 μM. In some embodiments, the binding between the DDB1 protein and the ligand comprises a binding affinity with a Kd below 20 μM. In some embodiments, the binding between the DDB1 protein and the ligand comprises a binding affinity with a Kd below 15 μM. In some embodiments, the binding between the DDB1 protein and the ligand comprises a binding affinity with a Kd below 14 μM. In some embodiments, the binding between the DDB1 protein and the ligand comprises a binding affinity with a Kd below 13 μM. In some embodiments, the binding between the DDB1 protein and the ligand comprises a binding affinity with a Kd below 12 μM. In some embodiments, the binding between the DDB1 protein and the ligand comprises a binding affinity with a Kd below 11 μM. In some embodiments, the binding between the DDB1 protein and the ligand comprises a binding affinity with a Kd below 10 μM. In some embodiments, the binding between the DDB1 protein and the ligand comprises a binding affinity with a Kd below 9 μM. In some embodiments, the binding between the DDB1 protein and the ligand comprises a binding affinity with a Kd below 8 μM. In some embodiments, the binding between the DDB1 protein and the ligand comprises a binding affinity with a Kd below 7 μM. In some embodiments, the binding between the DDB1 protein and the ligand comprises a binding affinity with a Kd below 6 μM. In some embodiments, the binding between the DDB1 protein and the ligand comprises a binding affinity with a Kd below 5 μM. In some embodiments, the binding between the DDB1 protein and the ligand comprises a binding affinity with a Kd below 4 μM. In some embodiments, the binding between the DDB1 protein and the ligand comprises a binding affinity with a Kd below 3 μM. In some embodiments, the binding between the DDB1 protein and the ligand comprises a binding affinity with a Kd below 2 μM. In some embodiments, the binding between the DDB1 protein and the ligand comprises a binding affinity with a Kd below 1 μM.

In some embodiments, the binding between the DDB1 protein and the ligand comprises a binding affinity with a Kd above 100 μM. In some embodiments, the binding between the DDB1 protein and the ligand comprises a binding affinity with a Kd above 90 μM. In some embodiments, the binding between the DDB1 protein and the ligand comprises a binding affinity with a Kd above 80 μM. In some embodiments, the binding between the DDB1 protein and the ligand comprises a binding affinity with a Kd above 70 μM. In some embodiments, the binding between the DDB1 protein and the ligand comprises a binding affinity with a Kd above 60 μM. In some embodiments, the binding between the DDB1 protein and the ligand comprises a binding affinity with a Kd above 50 μM. In some embodiments, the binding between the DDB1 protein and the ligand comprises a binding affinity with a Kd above 45 μM. In some embodiments, the binding between the DDB1 protein and the ligand comprises a binding affinity with a Kd above 40 μM. In some embodiments, the binding between the DDB1 protein and the ligand comprises a binding affinity with a Kd above 35 μM. In some embodiments, the binding between the DDB1 protein and the ligand comprises a binding affinity with a Kd above 30 μM. In some embodiments, the binding between the DDB1 protein and the ligand comprises a binding affinity with a Kd above 25 μM. In some embodiments, the binding between the DDB1 protein and the ligand comprises a binding affinity with a Kd above 20 μM. In some embodiments, the binding between the DDB1 protein and the ligand comprises a binding affinity with a Kd above 15 μM. In some embodiments, the binding between the DDB1 protein and the ligand comprises a binding affinity with a Kd above 14 μM. In some embodiments, the binding between the DDB1 protein and the ligand comprises a binding affinity with a Kd above 13 μM. In some embodiments, the binding between the DDB1 protein and the ligand comprises a binding affinity with a Kd above 12 μM. In some embodiments, the binding between the DDB1 protein and the ligand comprises a binding affinity with a Kd above 11 μM. In some embodiments, the binding between the DDB1 protein and the ligand comprises a binding affinity with a Kd above 10 μM. In some embodiments, the binding between the DDB1 protein and the ligand comprises a binding affinity with a Kd above 9 μM. In some embodiments, the binding between the DDB1 protein and the ligand comprises a binding affinity with a Kd above 8 μM. In some embodiments, the binding between the DDB1 protein and the ligand comprises a binding affinity with a Kd above 7 μM. In some embodiments, the binding between the DDB1 protein and the ligand comprises a binding affinity with a Kd above 6 μM. In some embodiments, the binding between the DDB1 protein and the ligand comprises a binding affinity with a Kd above 5 μM. In some embodiments, the binding between the DDB1 protein and the ligand comprises a binding affinity with a Kd above 4 μM. In some embodiments, the binding between the DDB1 protein and the ligand comprises a binding affinity with a Kd above 3

μM. In some embodiments, the binding between the DDB1 protein and the ligand comprises a binding affinity with a Kd above 2 μM. In some embodiments, the binding between the DDB1 protein and the ligand comprises a binding affinity with a Kd above 1 μM.

In some embodiments, the binding between the DDB1 protein and the ligand comprises a binding affinity with a Kd<20 uM, a Kd from 20-100 uM, or a Kd>100 uM. In some embodiments, the binding between the DDB1 protein and the ligand comprises a binding affinity with a Kd<20 uM. In some embodiments, the binding between the DDB1 protein and the ligand comprises a binding affinity with a Kd from 20-100 uM. In some embodiments, the binding between the DDB1 protein and the ligand comprises a binding affinity with a Kd>100 uM.

In some embodiments, the ligand comprises a compound in Table 6, or a derivative or salt thereof. The compound may include a peptide or non-peptide compound. In some embodiments, the ligand in Table 6 has category A binding, as defined in the table. In some embodiments, the ligand in Table 6 has category B binding, as defined in the table. In some embodiments, the ligand in Table 6 has category C binding, as defined in the table. In some embodiments, the ligand comprises a compound in Table 7, or a derivative or salt thereof. In some embodiments, the ligand in Table 7 has category A binding, as defined in the table. In some embodiments, the ligand in Table 7 has category B binding, as defined in the table.

In some embodiments, the binding between the DDB1 binding moiety and DDB1 is non-covalent. In some embodiments, the binding between the DDB1 binding moiety and DDB1 is covalent.

Described herein are compounds of Table 2 comprising a DDB1 binding moiety and a linker. The linker may include any linker described herein. In some embodiments, the compound is bound to DDB1 via the DDB1 binding moiety. In some embodiments, a linker is a bond. In some embodiments a linker is not a bond (e.g. more than just a bond).

TABLE 2

DDB1 binding moieties with linkers

| Compound | Structure | Name |
| --- | --- | --- |
| BL-1 | 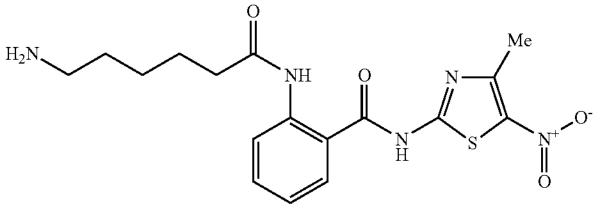 [SMILES: Cc1nc(NC(=O)c2ccccc2NC(=O)CCCCCN)sc1[N+](=O)[O-]] | 2-(6-aminohexanamido)-N-(4-methyl-5-nitrothiazol-2-yl)benzamide |
| BL-2 | 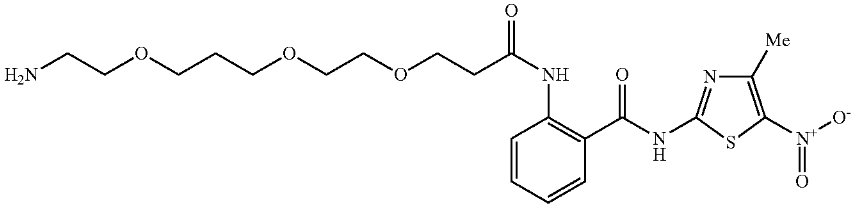 [SMILES: Cc1nc(NC(=O)c2ccccc2NC(=O)CCOCCOCCCOCCN)sc1[N+](=O)[O-]] | 2-(3-(2-(3-(2-aminoethoxy)propoxy)ethoxy)propanamido)-N-(4-methyl-5-nitrothiazol-2-yl)benzamide |
| BL-3 | 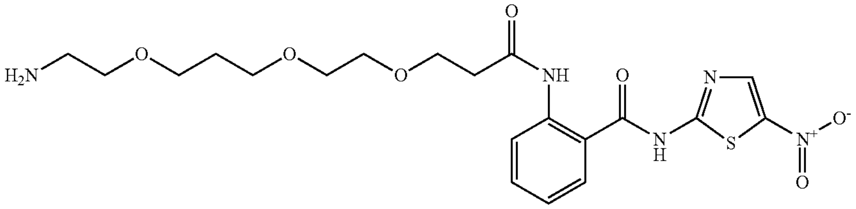 [SMILES: NCCOCCCOCCOCCC(=O)Nc1ccccc1C(=O)Nc1ncc([N+](=O)[O-])s1] | 2-(3-(2-(3-(2-aminoethoxy)propoxy)ethoxy)propanamido)-N-(5-nitrothiazol-2-yl)benzamide |
| BL-4 | 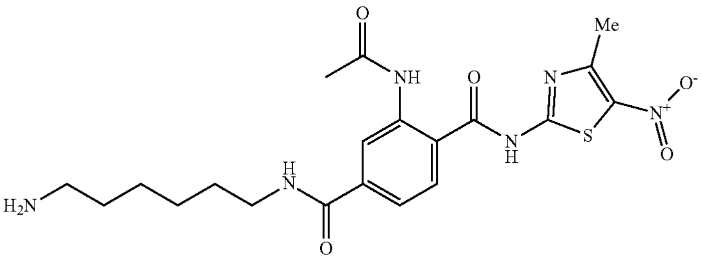 [SMILES: CC(=O)Nc1cc(C(=O)NCCCCCCN)ccc1C(=O)Nc1nc(C)c([N+](=O)[O-])s1] | 2-acetamido-N4-(6-aminohexyl)-N1-(4-methyl-5-nitrothiazol-2-yl)terephthalamide |

TABLE 2-continued

| DDB1 binding moieties with linkers | | |
|---|---|---|
| Compound | Structure | Name |
| BL-5 | 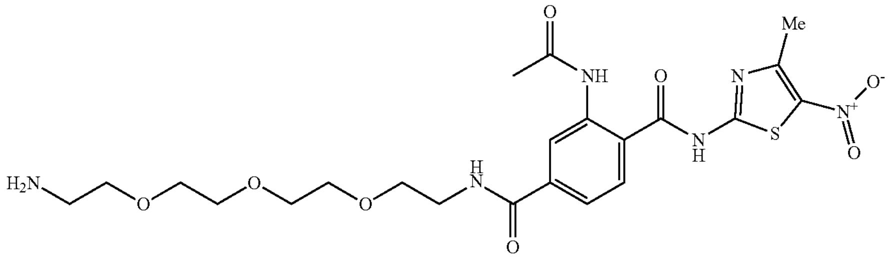 [SMILES: CC(=O)Nc1cc(C(=O)NCCOCCOCCOCCN)ccc1C(=O)Nc1nc(C)c([N+](=O)[O-])s1] | 2-acetamido-N4-(2-(2-(2-(2-aminoethoxy)ethoxy)ethoxy)ethyl)-N1-(4-methyl-5-nitrothiazol-2-yl)terephthalamide |
| BL-6 | 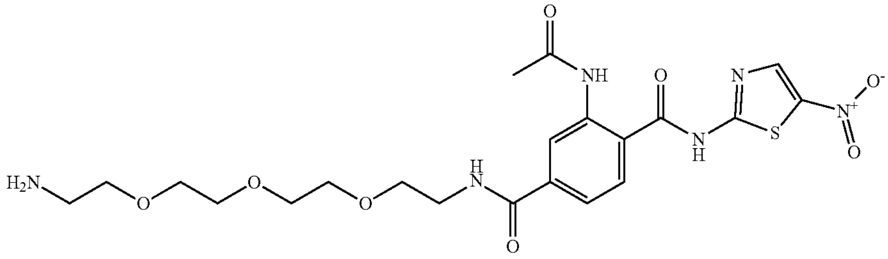 [SMILES: CC(=O)Nc1cc(C(=O)NCCOCCOCCOCCN)ccc1C(=O)Nc1ncc([N+](=O)[O-])s1] | 2-acetamido-N4-(2-(2-(2-(2-aminoethoxy)ethoxy)ethoxy)ethyl)-N1-(5-nitrothiazol-2-yl)terephthalamide |
| BL-7 | 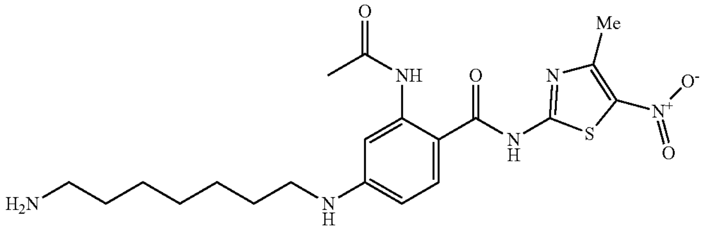 [SMILES: CC(=O)Nc1cc(NCCCCCCCN)ccc1C(=O)Nc1nc(C)c([N+](=O)[O-])s1] | 2-acetamido-4-((7-aminoheptyl)amino)-N-(4-methyl-5-nitrothiazol-2-yl)benzamide |
| BL-8 | 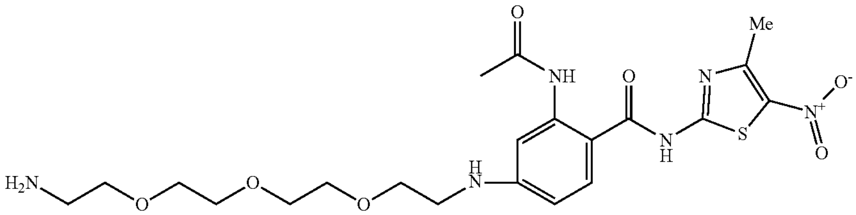 [SMILES: CC(=O)Nc1cc(NCCOCCOCCOCCN)ccc1C(=O)Nc1nc(C)c([N+](=O)[O-])s1] | 2-acetamido-4-((2-(2-(2-(2-aminoethoxy)ethoxy)ethoxy)ethyl)amino)-N-(4-methyl-5-nitrothiazol-2-yl)benzamide |
| BL-9 | 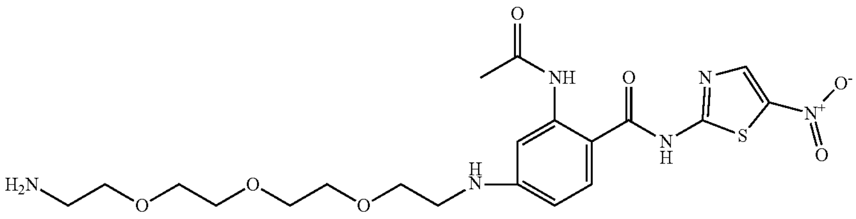 [SMILES: CC(=O)Nc1cc(NCCOCCOCCOCCN)ccc1C(=O)Nc1ncc([N+](=O)[O-])s1] | 2-acetamido-4-((2-(2-(2-(2-aminoethoxy)ethoxy)ethoxy)ethyl)amino)-N-(5-nitrothiazol-2-yl)benzamide |
| BL-10 | 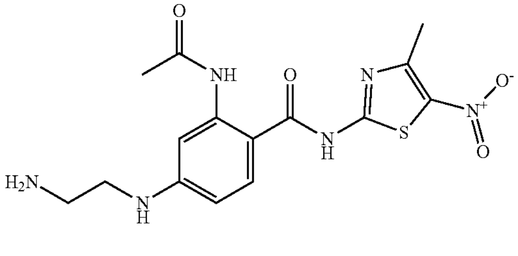 [SMILES: CC(=O)Nc1cc(NCCN)ccc1C(=O)Nc1nc(C)c([N+](=O)[O-])s1] | 2-acetamido-4-((2-aminoethyl)amino)-N-(4-methyl-5-nitrothiazol-2-yl)benzamide |

TABLE 2-continued

| DDB1 binding moieties with linkers | | |
|---|---|---|
| Compound | Structure | Name |
| BL-11 | 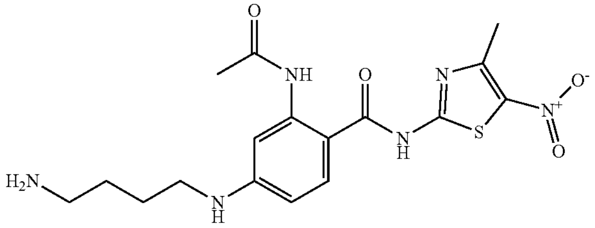 [SMILES: CC(=O)Nc1cc(NCCCCN)ccc1C(=O)Nc1nc(C)c([N+](=O)[O-])s1] | 2-acetamido-4-((4-aminobutyl)amino)-N-(4-methyl-5-nitrothiazol-2-yl)benzamide |
| BL-12 | 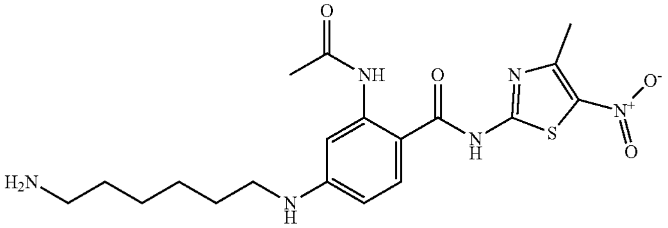 [SMILES: CC(=O)Nc1cc(NCCCCCCN)ccc1C(=O)Nc1nc(C)c([N+](=O)[O-])s1] | 2-acetamido-4-((6-aminohexyl)amino)-N-(4-methyl-5-nitrothiazol-2-yl)benzamide |
| BL-13 | 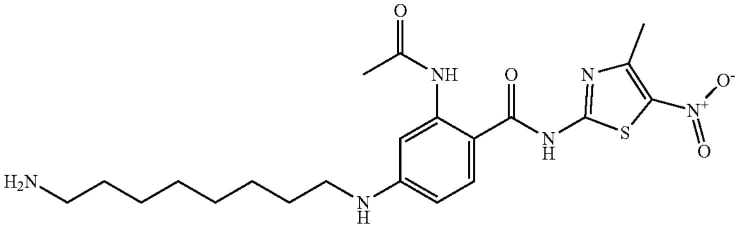 [SMILES: CC(=O)Nc1cc(NCCCCCCCCN)ccc1C(=O)Nc1nc(C)c([N+](=O)[O-])s1] | 2-acetamido-4-((8-aminooctyl)amino)-N-(4-methyl-5-nitrothiazol-2-yl)benzamide |
| BL-14 | 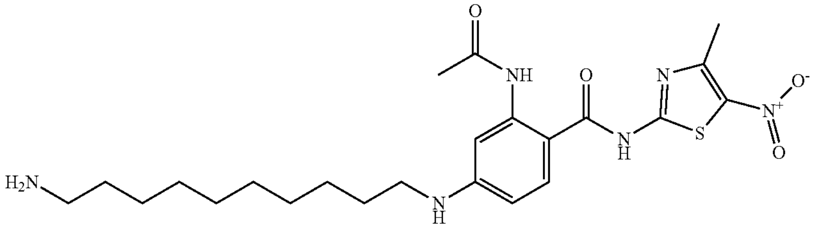 [SMILES: CC(=O)Nc1cc(NCCCCCCCCCCN)ccc1C(=O)Nc1nc(C)c([N+](=O)[O-])s1] | 2-acetamido-4-((10-aminodecyl)amino)-N-(4-methyl-5-nitrothiazol-2-yl)benzamide |
| BL-15 | 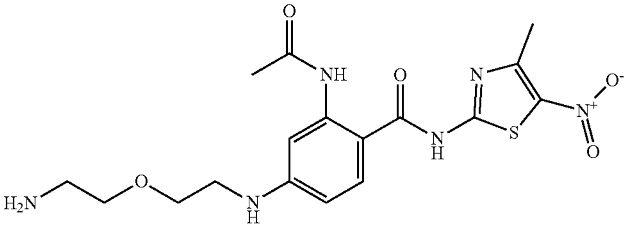 [SMILES: CC(=O)Nc1cc(NCCOCCN)ccc1C(=O)Nc1nc(C)c([N+](=O)[O-])s1] | 2-acetamido-4-((2-(2-aminoethoxy)ethyl)-amino)-N-(4-methyl-5-nitrothiazol-2-yl)benzamide |
| BL-16 | 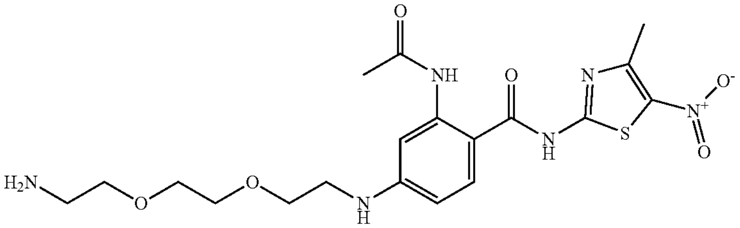 [SMILES: CC(=O)Nc1cc(NCCOCCOCCN)ccc1C(=O)Nc1nc(C)c([N+](=O)[O-])s1] | 2-acetamido-4-((2-(2-(2-aminoethoxy)ethoxy)-ethyl)amino)-N-(4-methyl-5-nitrothiazol-2-yl)benzamide |

TABLE 2-continued

| DDB1 binding moieties with linkers | | |
|---|---|---|
| Compound | Structure | Name |
| BL-17 | 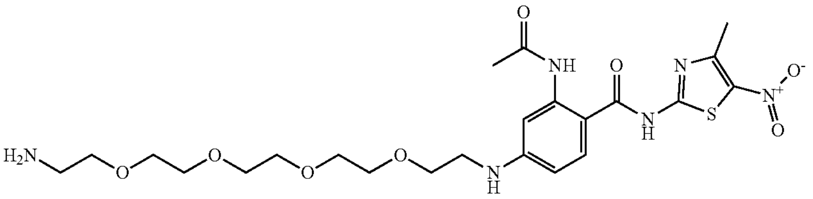 [SMILES: CC(=O)Nc1cc(NCCOCCOCCOCCOCCN)ccc1C(=O)Nc1nc(C)c([N+](=O)[O-])s1] | 2-acetamido-4-((14-amino-3,6,9,12-tetraoxatetradecyl)amino)-N-(4-methyl-5-nitrothiazol-2-yl)benzamide |
| BL-18 | 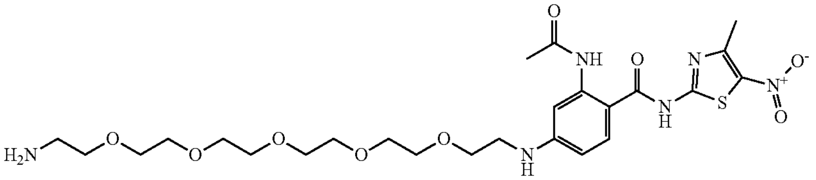 [SMILES: CC(=O)Nc1cc(NCCOCCOCCOCCOCCOCCN)ccc1C(=O)Nc1nc(C)c([N+](=O)[O-])s1] | 2-acetamido-4-((17-amino-3,6,9,12,15-pentaoxaheptadecyl)amino)-N-(4-methyl-5-nitrothiazol-2-yl)benzamide |
| BL-19 | 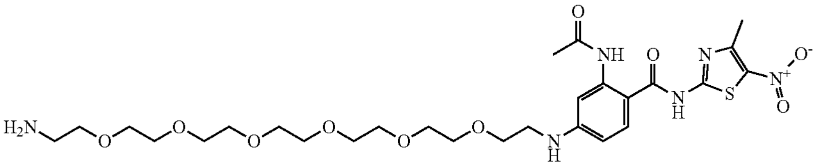 [SMILES: CC(=O)Nc1cc(NCCOCCOCCOCCOCCOCCOCCN)ccc1C(=O)Nc1nc(C)c([N+](=O)[O-])s1] | 2-acetamido-4-((20-amino-3,6,9,12,15,18-hexaoxaicosyl)amino)-N-(4-methyl-5-nitrothiazol-2-yl)benzamide |
| BL-20 | 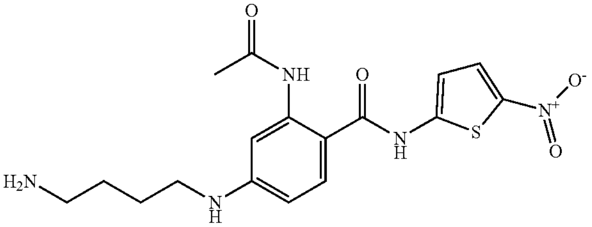 [SMILES: CC(=O)Nc1cc(NCCCCN)ccc1C(=O)Nc1ccc([N+](=O)[O-])s1] | 2-acetamido-4-((4-aminobutyl)amino)-N-(5-nitrothiophen-2-yl)benzamide |
| BL-21 | 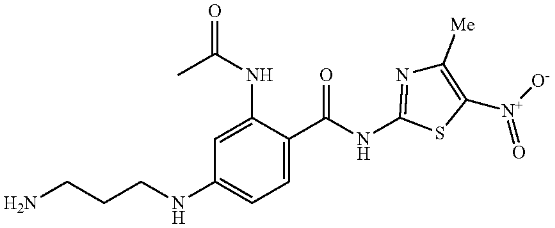 [SMILES: CC(=O)Nc1cc(NCCCN)ccc1C(=O)Nc1nc(C)c([N+](=O)[O-])s1] | 2-acetamido-4-((3-aminopropyl)amino)-N-(4-methyl-5-nitrothiazol-2-yl)benzamide |
| BL-22 | 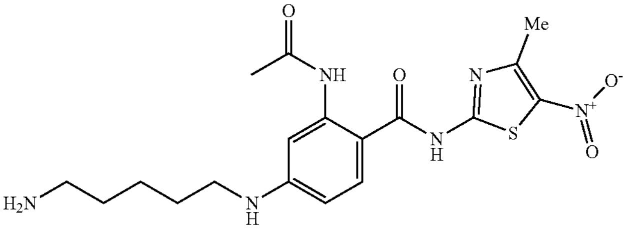 [SMILES: CC(=O)Nc1cc(NCCCCCN)ccc1C(=O)Nc1nc(C)c([N+](=O)[O-])s1] | 2-acetamido-4-((5-aminopentyl)amino)-N-(4-methyl-5-nitrothiazol-2-yl)benzamide |
| BL-23 | 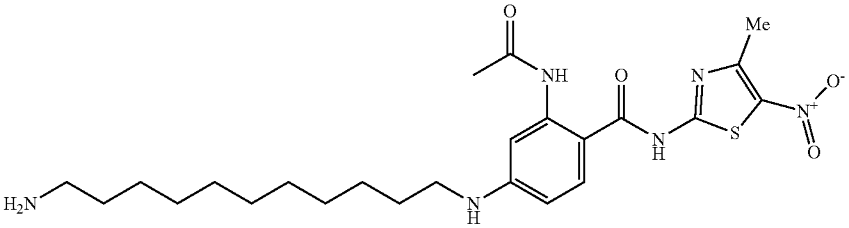 [SMILES: CC(=O)Nc1cc(NCCCCCCCCCCCN)ccc1C(=O)Nc1nc(C)c([N+](=O)[O-])s1] | 2-acetamido-4-((11-aminoundecyl)amino)-N-(4-methyl-5-nitrothiazol-2-yl)benzamide |

TABLE 2-continued

| DDB1 binding moieties with linkers | | |
|---|---|---|
| Compound | Structure | Name |
| BL-24 | 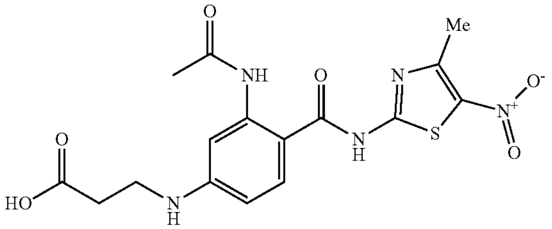 [SMILES: CC(=O)Nc1cc(NCCC(=O)O)ccc1C(=O)Nc1nc(C)c([N+](=O)[O-])s1] | 3-((3-acetamido-4-((4-methyl-5-nitrothiazol-2-yl)carbamoyl)phenyl)amino)propanoic acid |
| BL-25 | 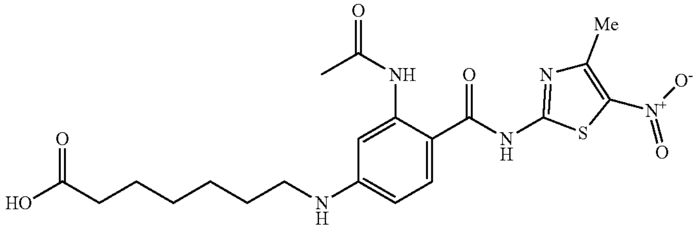 [SMILES: CC(=O)Nc1cc(NCCCCCCC(=O)O)ccc1C(=O)Nc1nc(C)c([N+](=O)[O-])s1] | 7-((3-acetamido-4-((4-methyl-5-nitrothiazol-2-yl)carbamoyl)phenyl)amino)propanoic acid |
| BL-26 | 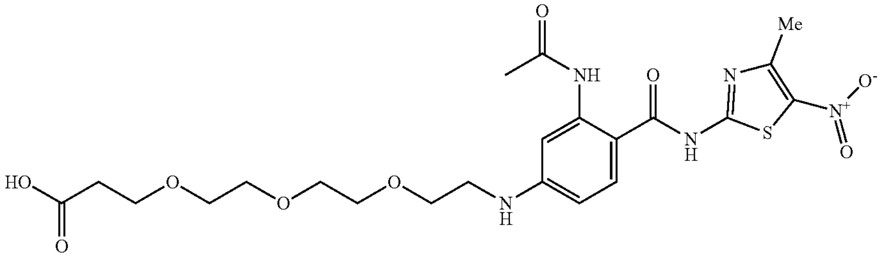 [SMILES: CC(=O)Nc1cc(NCCOCCOCCOCCC(=O)O)ccc1C(=O)Nc1nc(C)c([N+](=O)[O-])s1] | 3-(2-(2-(2-((3-acetamido-4-((4-methyl-5-nitrothiazol-2-yl)carbamoyl)phenyl)amino)ethoxy)ethoxy)ethoxy)propanoic acid |
| BL-27 | 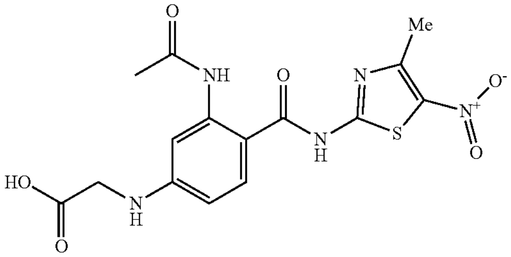 [SMILES: CC(=O)Nc1cc(NCC(=O)O)ccc1C(=O)Nc1nc(C)c([N+](=O)[O-])s1] | (3-acetamido-4-((4-methyl-5-nitrothiazol-2-yl)carbamoyl)phenyl)glycine |
| BL-28 | 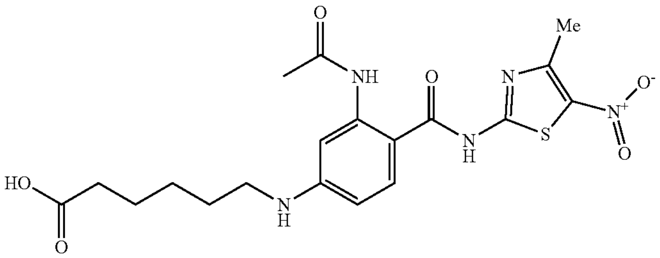 [SMILES: CC(=O)Nc1cc(NCCCCCC(=O)O)ccc1C(=O)Nc1nc(C)c([N+](=O)[O-])s1] | 6-((3-acetamido-4-((4-methyl-5-nitrothiazol-2-yl)carbamoyl)phenyl)amino)hexanoic acid |
| BL-29 | 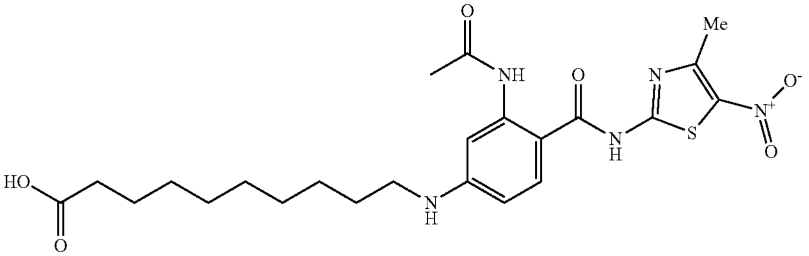 [SMILES: CC(=O)Nc1cc(NCCCCCCCCCC(=O)O)ccc1C(=O)Nc1nc(C)c([N+](=O)[O-])s1] | 10-((3-acetamido-4-((4-methyl-5-nitrothiazol-2-yl)carbamoyl)phenyl)amino)decanoic acid |

TABLE 2-continued

| DDB1 binding moieties with linkers | | |
|---|---|---|
| Compound | Structure | Name |
| BL-30 | 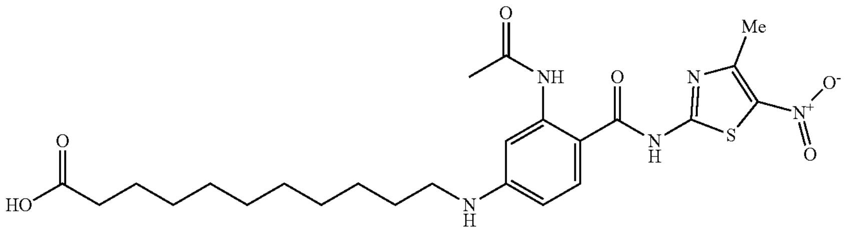 [SMILES: CC(=O)Nc1cc(NCCCCCCCCCCC(=O)O)ccc1C(=O)Nc1nc(C)c([N+](=O)[O-])s1] | 11-((3-acetamido-4-((4-methyl-5-nitrothiazol-2-yl)carbamoyl) phenyl)amino) undecanoic acid |
| BL-31 | 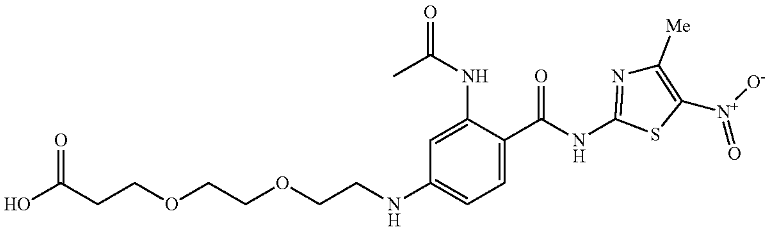 [SMILES: CC(=O)Nc1cc(NCCOCCOCCC(=O)O)ccc1C(=O)Nc1nc(C)c([N+](=O)[O-])s1] | 3-(2-(2-((3-acetamido-4-((4-methyl-5-nitrothiazol-2-yl)carbamoyl) phenyl)amino)ethoxy) ethoxy)propanoic acid |
| BL-32 | 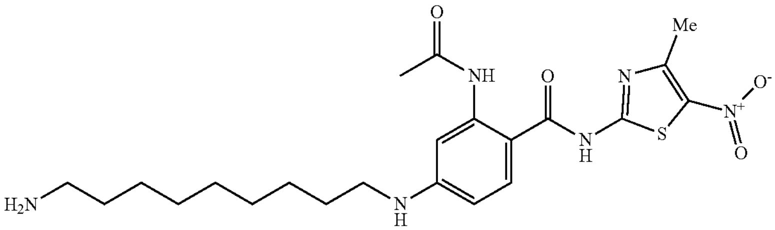 [SMILES: CC(=O)Nc1cc(NCCCCCCCCCN)ccc1C(=O)Nc1nc(C)c([N+](=O)[O-])s1] | 2-acetamido-4-((9-aminononyl)amino)-N-(4-methyl-5-nitrothiazol-2-yl)benzamide |
| BL-33 | 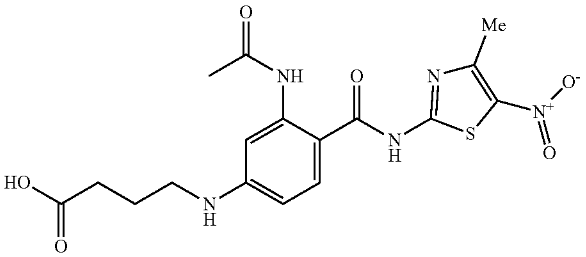 [SMILES: CC(=O)Nc1cc(NCCCC(=O)O)ccc1C(=O)Nc1nc(C)c([N+](=O)[O-])s1] | 4-((3-acetamido-4-((4-methyl-5-nitrothiazol-2-yl)carbamoyl) phenyl)amino)butanoic acid |
| BL-34 | 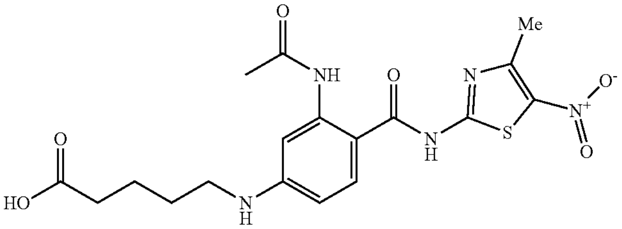 [SMILES: CC(=O)Nc1cc(NCCCCC(=O)O)ccc1C(=O)Nc1nc(C)c([N+](=O)[O-])s1] | 5-((3-acetamido-4-((4-methyl-5-nitrothiazol-2-yl)carbamoyl) phenyl)amino)butanoic acid |
| BL-35 | 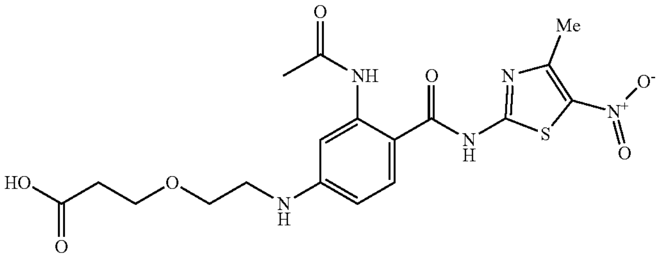 [SMILES: CC(=O)Nc1cc(NCCOCCC(=O)O)ccc1C(=O)Nc1nc(C)c([N+](=O)[O-])s1] | 3-(2-((3-acetamido-4-((4-methyl-5-nitrothiazol-2-yl)carbamoyl) phenyl)amino)ethoxy) propanoic acid |

TABLE 2-continued

| DDB1 binding moieties with linkers | | |
|---|---|---|
| Compound | Structure | Name |
| BL-36 | 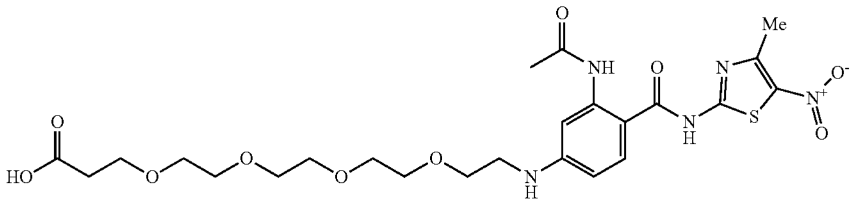 [SMILES: CC(=O)Nc1cc(NCCOCCOCCOCCOCCC(=O)O)ccc1C(=O)Nc1nc(C)c([N+](=O)[O-])s1] | 1-((3-acetamido-4-((4-methyl-5-nitrothiazol-2-yl)carbamoyl)phenyl)amino)-3,6,9,12-tetraoxapentadecan-15-oic acid |
| BL-37 | 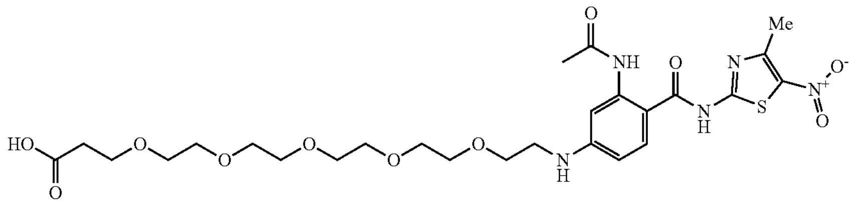 [SMILES: CC(=O)Nc1cc(NCCOCCOCCOCCOCCOCCC(=O)O)ccc1C(=O)Nc1nc(C)c([N+](=O)[O-])s1] | 1-((3-acetamido-4-((4-methyl-5-nitrothiazol-2-yl)carbamoyl)phenyl)amino)-3,6,9,12,15-pentaoxaoctadecan-18-oic acid |
| BL-38 | 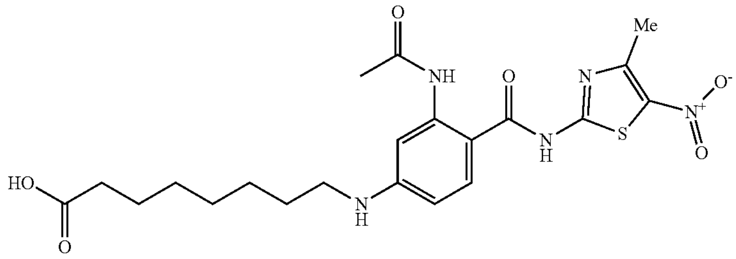 [SMILES: CC(=O)Nc1cc(NCCCCCCCC(=O)O)ccc1C(=O)Nc1nc(C)c([N+](=O)[O-])s1] | 8-((3-acetamido-4-((4-methyl-5-nitrothiazol-2-yl)carbamoyl)phenyl)amino)octanoic acid |
| BL-39 | 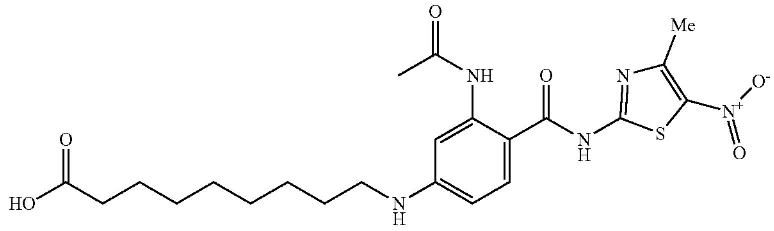 [SMILES: CC(=O)Nc1cc(NCCCCCCCCC(=O)O)ccc1C(=O)Nc1nc(C)c([N+](=O)[O-])s1] | 9-((3-acetamido-4-((4-methyl-5-nitrothiazol-2-yl)carbamoyl)phenyl)amino)nonanoic acid |
| BL-40 | 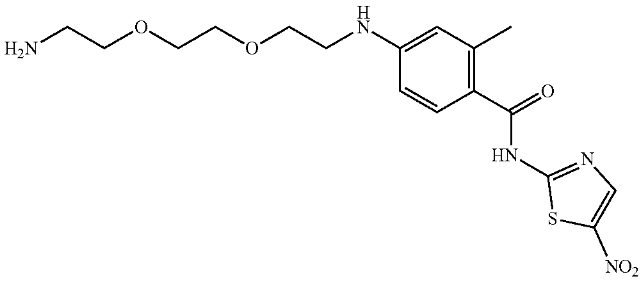 [SMILES: Cc1cc(NCCOCCOCCN)ccc1C(=O)Nc1ncc([N+](=O)[O-])s1] | 4-((2-(2-(2-aminoethoxy)ethoxy)ethyl)amino)-2-methyl-N-(5-nitrothiazol-2-yl)benzamide |
| BL-41 | 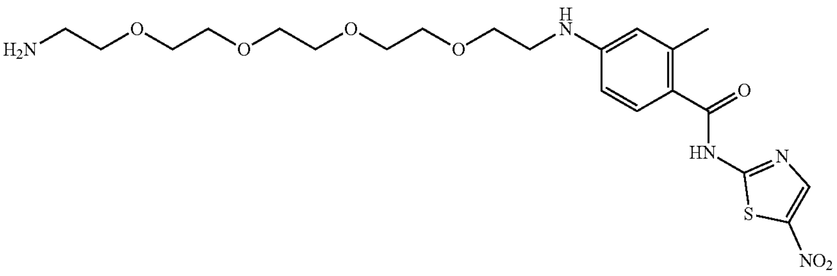 [SMILES: Cc1cc(NCCOCCOCCOCCOCCN)ccc1C(=O)Nc1ncc([N+](=O)[O-])s1] | 4-((14-amino-3,6,9,12-tetraoxatetradecyl)amino)-2-methyl-N-(5-nitrothiazol-2-yl)benzamide |

TABLE 2-continued

| DDB1 binding moieties with linkers | | |
|---|---|---|
| Compound | Structure | Name |
| BL-42 | 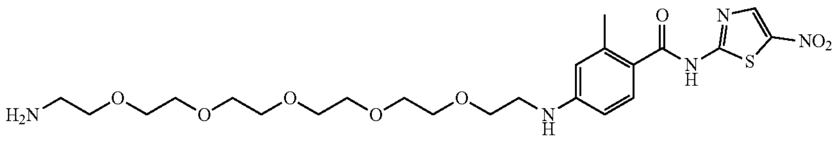 [SMILES: Cc1cc(NCCOCCOCCOCCOCCOCCN)ccc1C(=O)Nc1ncc([N+](=O)[O-])s1] | 4-((17-amino-3,6,9,12,15-pentaoxaheptadecyl)amino)-2-methyl-N-(5-nitrothiazol-2-yl)benzamide |
| BL-43 | 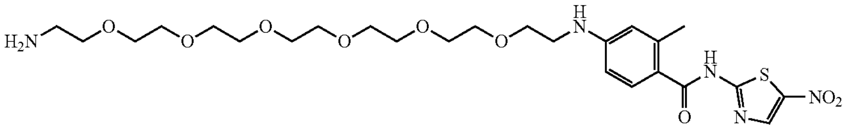 [SMILES: Cc1cc(NCCOCCOCCOCCOCCOCCOCCN)ccc1C(=O)Nc1ncc([N+](=O)[O-])s1] | 4-((20-amino-3,6,9,12,15,18-hexaoxaicosyl)amino)-2-methyl-N-(5-nitrothiazol-2-yl)benzamide |
| BL-44 | 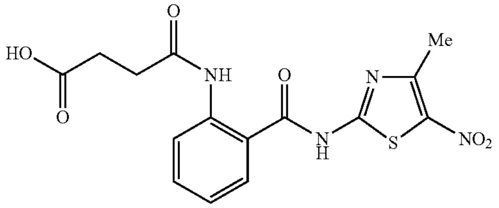 [SMILES: Cc1nc(NC(=O)c2ccccc2NC(=O)CCC(=O)O)sc1[N+](=O)[O-]] | 4-((2-((4-methyl-5-nitrothiazol-2-yl)carbmoyl)phenyl)amino)-4-oxobutanoic acid |
| BL-45 | 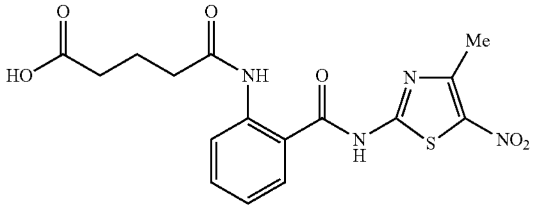 [SMILES: Cc1nc(NC(=O)c2ccccc2NC(=O)CCCC(=O)O)sc1[N+](=O)[O-]] | 5-((2-((4-methyl-5-nitrothiazol-2-yl)carbmoyl)phenyl)amino)-5-oxopentanoic acid |
| BL-46 | 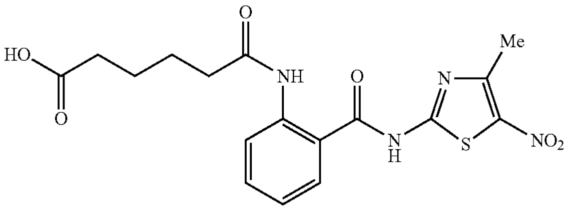 [SMILES: Cc1nc(NC(=O)c2ccccc2NC(=O)CCCCC(=O)O)sc1[N+](=O)[O-]] | 6-((2-((4-methyl-5-nitrothiazol-2-yl)carbmoyl)phenyl)amino)-6-oxohexanoic acid |
| BL-47 | 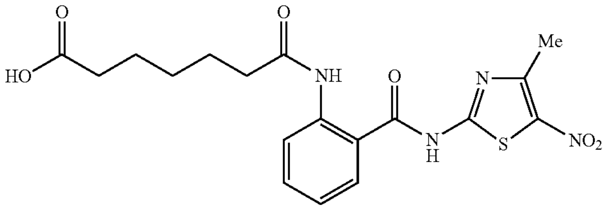 [SMILES: Cc1nc(NC(=O)c2ccccc2NC(=O)CCCCCC(=O)O)sc1[N+](=O)[O-]] | 7-((2-((4-methyl-5-nitrothiazol-2-yl)carbmoyl)phenyl)amino)-7-oxoheptanoic acid |
| BL-48 | 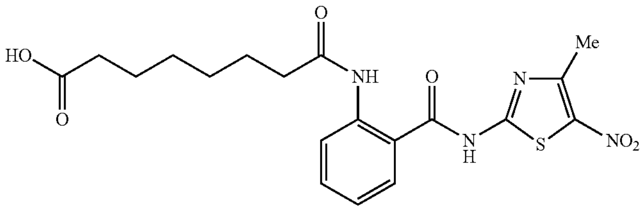 [SMILES: Cc1nc(NC(=O)c2ccccc2NC(=O)CCCCCCC(=O)O)sc1[N+](=O)[O-]] | 8-((2-((4-methyl-5-nitrothiazol-2-yl)carbmoyl)phenyl)amino)-8-oxooctanoic acid |

TABLE 2-continued

| DDB1 binding moieties with linkers | | |
|---|---|---|
| Compound | Structure | Name |
| BL-49 | 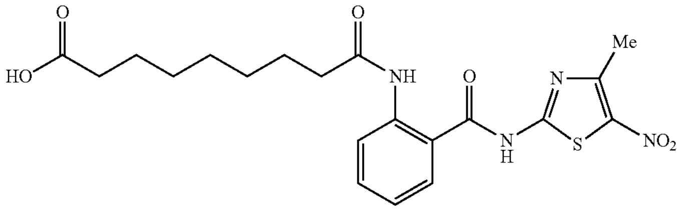 [SMILES: Cc1nc(NC(=O)c2ccccc2NC(=O)CCCCCCCC(=O)O)sc1[N+](=O)[O-]] | 9-((2-((4-methyl-5-nitrothiazol-2-yl)carbmoyl)phenyl)amino)-9-oxononanoic acid |
| BL-50 | 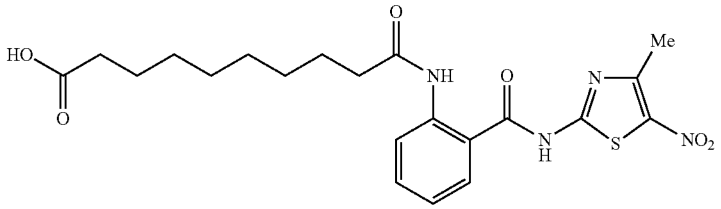 [SMILES: Cc1nc(NC(=O)c2ccccc2NC(=O)CCCCCCCCC(=O)O)sc1[N+](=O)[O-]] | 10-((2-((4-methyl-5-nitrothiazol-2-yl)carbamoyl)phenyl)amino)-10-oxodecanoic acid |
| BL-51 | 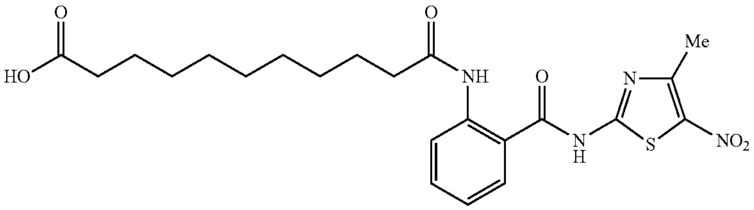 [SMILES: Cc1nc(NC(=O)c2ccccc2NC(=O)CCCCCCCCCC(=O)O)sc1[N+](=O)[O-]] | 11-((2-((4-methyl-5-nitrothiazol-2-yl)carbamoyl)phenyl)amino)-11-oxoundecanoic acid |
| BL-52 | 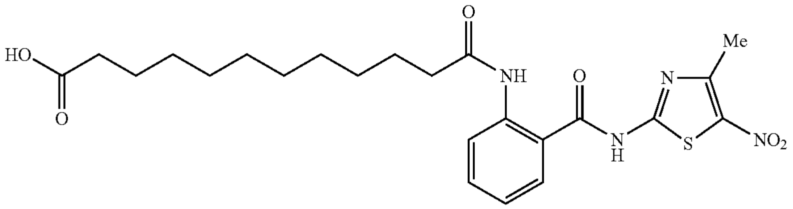 [SMILES: Cc1nc(NC(=O)c2ccccc2NC(=O)CCCCCCCCCCC(=O)O)sc1[N+](=O)[O-]] | 12-((2-((4-methyl-5-nitrothiazol-2-yl)carbamoyl)phenyl)amino)-12-oxododecanoic acid |
| BL-53 | 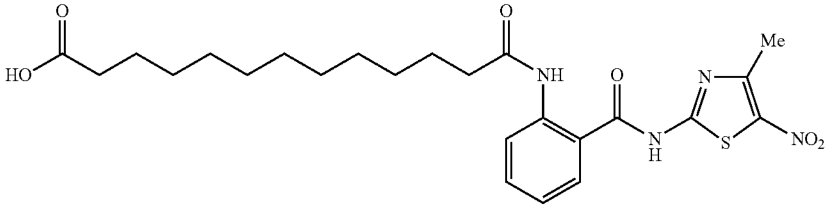 [SMILES: Cc1nc(NC(=O)c2ccccc2NC(=O)CCCCCCCCCCCC(=O)O)sc1[N+](=O)[O-]] | 13-((2-((4-methyl-5-nitrothiazol-2-yl)carbamoyl)phenyl)amino)-13-oxotridecanoic acid |
| BL-54 | 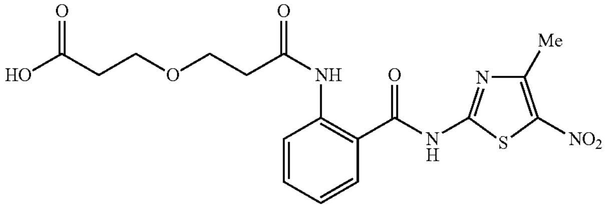 [SMILES: Cc1nc(NC(=O)c2ccccc2NC(=O)CCOCCC(=O)O)sc1[N+](=O)[O-]] | 3-(3-((2-((4-methyl-5-nitrothiazol-2-yl)carbamoyl)phenyl)amino)-3-oxopropoxy)propanoic acid |
| BL-55 | 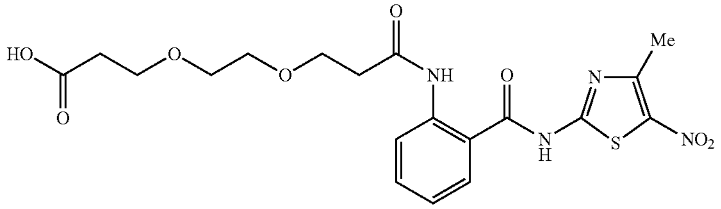 [SMILES: Cc1nc(NC(=O)c2ccccc2NC(=O)CCOCCOCCC(=O)O)sc1[N+](=O)[O-]] | 3-(2-(3-((2-((4-methyl-5-nitrothiazol-2-yl)carbamoyl)phenyl)amino)-3-oxopropoxy)ethoxy)propanoic acid |

TABLE 2-continued

DDB1 binding moieties with linkers

| Compound | Structure | Name |
| --- | --- | --- |
| BL-56 | 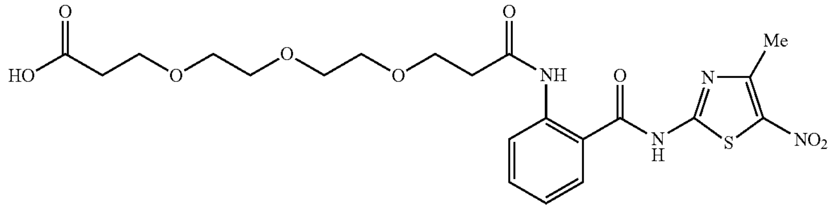 [SMILES: Cc1nc(NC(=O)c2ccccc2NC(=O)CCOCCOCCOCCC(=O)O)sc1[N+](=O)[O-]] | 3-(2-(2-(3-((2-((4-methyl-5-nitrothiazol-2-yl)carbamoyl)phenyl) amino)-3-oxopropoxy)ethoxy) propanoic acid |
| BL-57 | 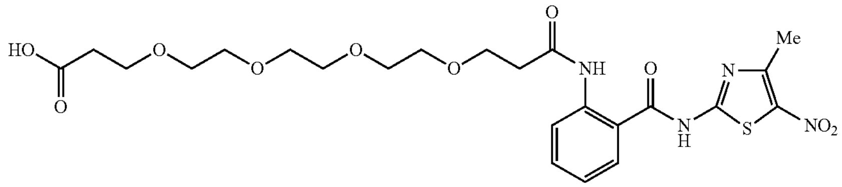 [SMILES: Cc1nc(NC(=O)c2ccccc2NC(=O)CCOCCOCCOCCOCCC(=O)O)sc1[N+](=O)[O-]] | 16-((2-((4-methyl-5-nitrothiazol-2-yl)carbamoyl)phenyl) amino)-16-oxo-4,7,10,13-tetraoxahexadecanoic acid |
| BL-58 | 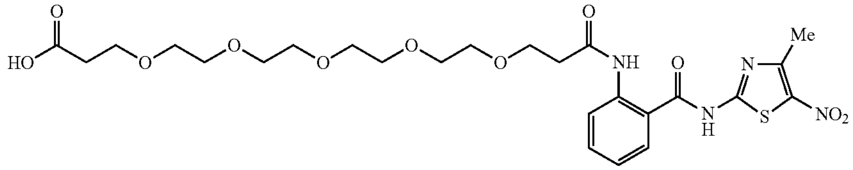 [SMILES: Cc1nc(NC(=O)c2ccccc2NC(=O)CCOCCOCCOCCOCCOCCC(=O)O)sc1[N+](=O)[O-]] | 19-((2-((4-methyl-5-nitrothiazol-2-yl)carbamoyl)phenyl) amino)-19-oxo-4,7,10,13,16-pentaoxanonadecanoic acid |
| BL-59 | 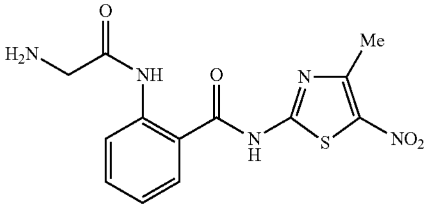 [SMILES: Cc1nc(NC(=O)c2ccccc2NC(=O)CN)sc1[N+](=O)[O-]] | 2-(2-aminoacetamido)-N-(4-methyl-5-nitrothiazol-2-yl)benzamide |
| BL-60 | 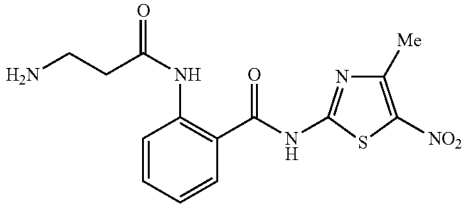 [SMILES: Cc1nc(NC(=O)c2ccccc2NC(=O)CCN)sc1[N+](=O)[O-]] | 2-(3-aminopropanamido)-N-(4-methyl-5-nitrothiazol-2-yl)benzamide |
| BL-61 | 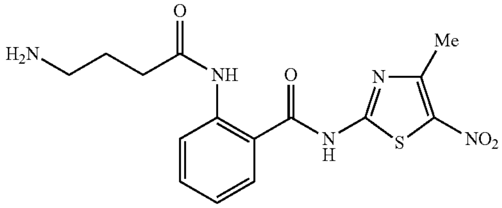 [SMILES: Cc1nc(NC(=O)c2ccccc2NC(=O)CCCN)sc1[N+](=O)[O-]] | 2-(4-aminobutanamido)-N-(4-methyl-5-nitrothiazol-2-yl)benzamide |
| BL-62 | 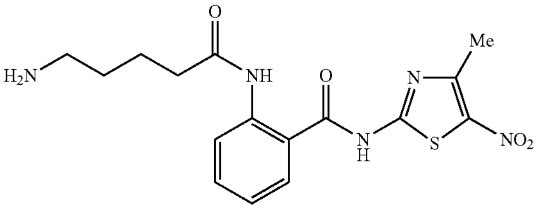 [SMILES: Cc1nc(NC(=O)c2ccccc2NC(=O)CCCCN)sc1[N+](=O)[O-]] | 2-(5-aminopentanamido)-N-(4-methyl-5-nitrothiazol-2-yl)benzamide |

TABLE 2-continued

| DDB1 binding moieties with linkers | | |
|---|---|---|
| Compound | Structure | Name |
| BL-63 | 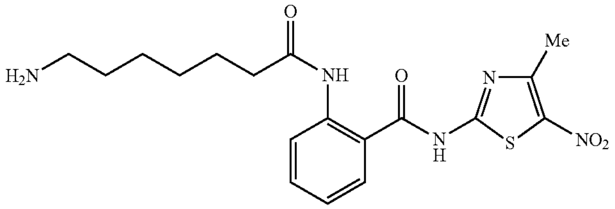 [SMILES: Cc1nc(NC(=O)c2ccccc2NC(=O)CCCCCCN)sc1[N+](=O)[O-]] | 2-(7-aminoheptanamido)-N-(4-methyl-5-nitrothiazol-2-yl)benzamide |
| BL-64 | 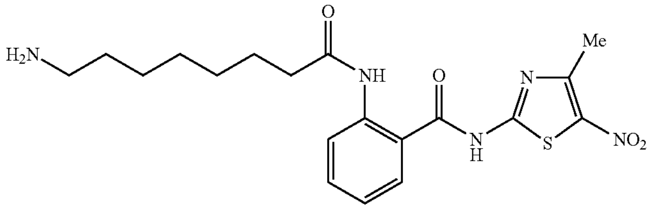 [SMILES: Cc1nc(NC(=O)c2ccccc2NC(=O)CCCCCCCN)sc1[N+](=O)[O-]] | 2-(8-aminooctanamido)-N-(4-methyl-5-nitrothiazol-2-yl)benzamide |
| BL-65 | 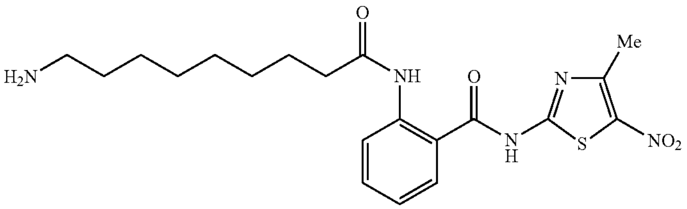 [SMILES: Cc1nc(NC(=O)c2ccccc2NC(=O)CCCCCCCCN)sc1[N+](=O)[O-]] | 2-(9-aminononanamido)-N-(4-methyl-5-nitrothiazol-2-yl)benzamide |
| BL-66 | 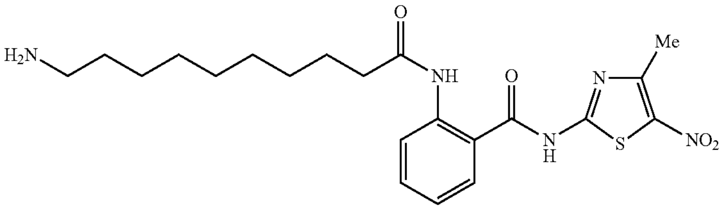 [SMILES: Cc1nc(NC(=O)c2ccccc2NC(=O)CCCCCCCCCN)sc1[N+](=O)[O-]] | 2-(10-aminodecanamido)-N-(4-methyl-5-nitrothiazol-2-yl)benzamide |
| BL-67 | 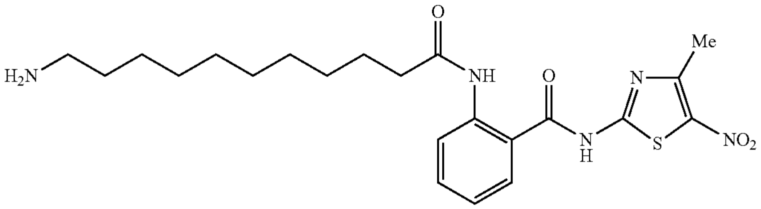 [SMILES: Cc1nc(NC(=O)c2ccccc2NC(=O)CCCCCCCCCCN)sc1[N+](=O)[O-]] | 2-(11-aminoundecanamido)-N-(4-methyl-5-nitrothiazol-2-yl)benzamide |
| BL-68 | 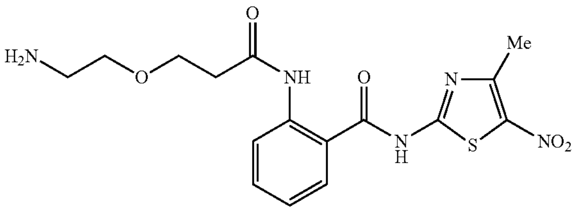 [SMILES: Cc1nc(NC(=O)c2ccccc2NC(=O)CCOCCN)sc1[N+](=O)[O-]] | 2-(3-(2-aminoethoxy)propanamido)-N-(4-methyl-5-nitrothiazol-2-yl)benzamide |
| BL-69 | 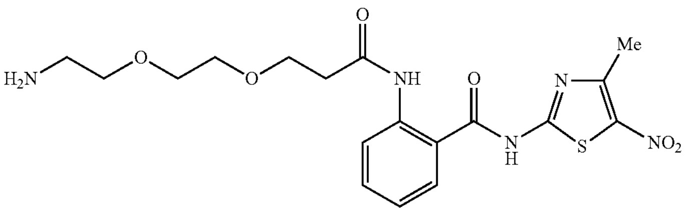 [SMILES: Cc1nc(NC(=O)c2ccccc2NC(=O)CCOCCOCCN)sc1[N+](=O)[O-]] | 2-(3-(2-(2-aminoethoxy)ethoxy)propanamido)-N-(4-methyl-5-nitrothiazol-2-yl)benzamide |

TABLE 2-continued

| DDB1 binding moieties with linkers | | |
|---|---|---|
| Compound | Structure | Name |
| BL-70 | 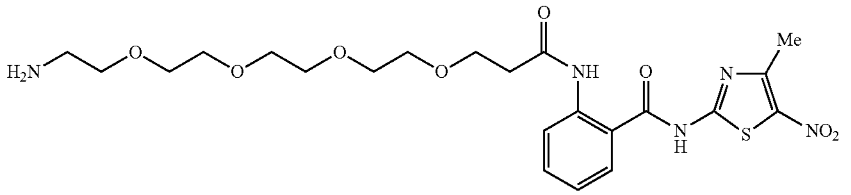 [SMILES: Cc1nc(NC(=O)c2ccccc2NC(=O)CCOCCOCCOCCOCCN)sc1[N+](=O)[O-]] | 1-amino-N-(2-((4-methyl-5-nitrothiazol-2-yl)carbamoyl)phenyl)-3,6,9,12-tetraoxapentadecan-15-amide |
| BL-71 | 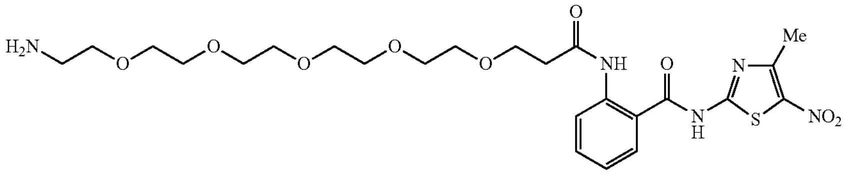 [SMILES: Cc1nc(NC(=O)c2ccccc2NC(=O)CCOCCOCCOCCOCCOCCN)sc1[N+](=O)[O-]] | 1-amino-N-(2-((4-methyl-5-nitrothiazol-2-yl)carbamoyl)phenyl)-3,6,9,12,15-pentaoxaoctadecan-18-amide |

In some embodiments, a DDB1 binding moiety comprises a peptide. In some embodiments, a DDB1 binding moiety comprises no more than 30, 25, 20, 19, 18, 17, 16, 15, 14, 13, 12, 11, 10, 9, or no more than 8 amino acids. In some embodiments, a DDB1 binding moiety comprises at least 30, 25, 20, 19, 18, 17, 16, 15, 14, 13, 12, 11, 10, 9, or at least 8 amino acids. In some embodiments, a DDB1 binding moiety comprises about 30, 25, 20, 19, 18, 17, 16, 15, 14, 13, 12, 11, 10, 9, or about 8 amino acids. In some embodiments, a DDB1 binding moiety comprises 30, 25, 20, 19, 18, 17, 16, 15, 14, 13, 12, 11, 10, 9, or 8 amino acids, or a range defined by any two of the aforementioned numbers of amino acids. In some embodiments, a DDB1 binding moiety comprises a peptide derived from a virus. In some embodiments, a DDB1 binding moiety comprises a peptide of Table 3. In some embodiments, a DDB1 binding moiety comprises the amino acid sequence of any one of SEQ ID NOs:1-7 (e.g. SEQ ID NO: 1, SEQ ID NO: 2, SEQ ID NO: 3, SEQ ID NO: 4, SEQ ID NO: 5, SEQ ID NO: 6, or SEQ ID NO: 7). In some embodiments, the DDB1 binding moiety comprises the amino acid sequence of SEQ ID NO: 1, or a variant thereof. In some embodiments, the DDB1 binding moiety comprises the amino acid sequence of SEQ ID NO: 2, or a variant thereof. In some embodiments, the DDB1 binding moiety comprises the amino acid sequence of SEQ ID NO: 3, or a variant thereof. In some embodiments, the DDB1 binding moiety comprises the amino acid sequence of SEQ ID NO: 4, or a variant thereof. In some embodiments, the DDB1 binding moiety comprises the amino acid sequence of SEQ ID NO: 5, or a variant thereof. In some embodiments, the DDB1 binding moiety comprises the amino acid sequence of SEQ ID NO: 6, or a variant thereof. In some embodiments, the DDB1 binding moiety comprises the amino acid sequence of SEQ ID NO: 7, or a variant thereof. In some embodiments, a DDB1 binding moiety has at least 99% sequence identity to any one of SEQ ID NOs:1-7. In some embodiments, a DDB1 binding moiety has at least 98% sequence identity to any one of SEQ ID NOs:1-7. In some embodiments, a DDB1 binding moiety has at least 97% sequence identity to any one of SEQ ID NOs:1-7. In some embodiments, a DDB1 binding moiety has at least 96% sequence identity to any one of SEQ ID NOs:1-7. In some embodiments, a DDB1 binding moiety has at least 95% sequence identity to any one of SEQ ID NOs:1-7. In some embodiments, a DDB1 binding moiety has at least 94% sequence identity to any one of SEQ ID NOs:1-7. In some embodiments, a DDB1 binding moiety has at least 93% sequence identity to any one of SEQ ID NOs:1-7. In some embodiments, a DDB1 binding moiety has at least 92% sequence identity to any one of SEQ ID NOs:1-7. In some embodiments, a DDB1 binding moiety has at least 91% sequence identity to any one of SEQ ID NOs:1-7. In some embodiments, a DDB1 binding moiety has at least 90% sequence identity to any one of SEQ ID NOs:1-7. In some embodiments, a DDB1 binding moiety has at least 89% sequence identity to any one of SEQ ID NOs:1-7. In some embodiments, a DDB1 binding moiety has at least 88% sequence identity to any one of SEQ ID NOs:1-7. In some embodiments, a DDB1 binding moiety has at least 87% sequence identity to any one of SEQ ID NOs:1-7. In some embodiments, a DDB1 binding moiety has at least 86% sequence identity to any one of SEQ ID NOs:1-7. In some embodiments, a DDB1 binding moiety has at least 85% sequence identity to any one of SEQ ID NOs:1-7. In some embodiments, a DDB1 binding moiety has at least 80% sequence identity to any one of SEQ ID NOs:1-7. In some embodiments, a DDB1 binding moiety has at least 75% sequence identity to any one of SEQ ID NOs:1-7. In some embodiments, a DDB1 binding moiety has at least 70% sequence identity to any one of SEQ ID NOs:1-7. In some embodiments, a DDB1 binding moiety has at least 65% sequence identity to any one of SEQ ID NOs:1-7. In some embodiments, a DDB1 binding moiety comprises a variant of any one of SEQ ID NOs:1-7, wherein at least one residue has been modified. In some embodiments, modification comprises insertion, deletion, or substitution. In some embodiments, a DDB1 binding moiety comprises a variant of any one of SEQ ID NOs:1-7, wherein the peptide comprises at least one non-canonical amino acid.

TABLE 3

| Peptide DDB1 binding moieties | |
|---|---|
| SEQ ID NO: | Peptide Sequence |
| 1 | ILPKVLHKRTLGLS |
| 2 | ILPKVWHKRELGLS |
| 3 | ILPKVLHKRTLGL |

TABLE 3-continued

Peptide DDB1 binding moieties

| SEQ ID NO: | Peptide Sequence |
|---|---|
| 4 | ILPKVLHKRTFGL |
| 5 | KVLHKRTLG |
| 6 | NFTSRLNRRASFP |
| 7 | SRLNRRASF |

Peptides (e.g., DDB1 binding moieties) may comprise non-canonical amino acids (e.g. an amino acids other than the 20 canonical amino acids normally encoded by triplet codons). In some embodiments, a non-canonical amino acid has an (S) configuration at the alpha position. In some embodiments, a non-canonical amino acid has an (R) configuration at the alpha position. In some embodiments, a non-canonical amino acid is an alpha amino acid. In some embodiments, a non-canonical amino acid is a beta or gamma amino acid. In some embodiments, a non-canonical amino acid is selected from the group consisting of: an aromatic side chain amino acid; a non-aromatic side chain amino acid; an aliphatic side chain amino acid; a side chain amide amino acid; a side chain ester amino acid; a heteroaromatic side chain amino acid; a side chain thiol amino acid; a beta amino acid; and a backbone-modified amino acid. In some embodiments, a non-canonical amino acid is a derivative of tyrosine, histidine, tryptophan, or phenylalanine. In some embodiments, a derivative of an amino acid comprises an ester, amide, disulfide, carbamate, urea, phosphate, ether of the amino acid. In some embodiments, a non-aromatic side chain amino acid is a derivative of serine, threonine, cysteine, methionine, arginine, asparagine, glutamine, aspartic acid, glutamic acid, lysine, proline, glycine, alanine, valine, isoleucine, or leucine. In some embodiments, a non-canonical amino acid is selected from the group consisting of 2-aminoadipic acid; 3-aminoadipic acid; beta-alanine; beta-aminoproprionic acid; 2-aminobutyric acid; 4-aminobutyric acid; piperidinic acid; 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminoproprionic acid; N-ethylglycine; N-ethylasparagine; hydroxylysine; allo-hydroxylysine; 3-hydroxyproline; 4-hydroxyproline; isodesmosine; allo-isoleucine; N-methylglycine; sarcosine; n-methylisoleucine; 6-N-methyllysine; N-methylvaline; norvaline; norleucine; and omithine. In some embodiments, a non-canonical amino acid is a proline derivative. In some embodiments, a proline derivative is 3-fluoroproline, 4-fluoroproline, 3-hydroxyproline, 4-hydroxyproline, 3-aminoproline, 4-aminoproline, 3,4-dehydroproline, aziridine-2-carboxylic acid, azetidine-2-carboxylic acid, pipecolic acid, 4-oxa-proline, 3-thiaproline, or 4-thiaproline. In some embodiments, a non-canonical amino acid comprises a lipid.

Peptides (e.g., DDB1 binding moieties) may comprise modifications to the N terminus amino group (N-terminal modifications), C terminus acid group (C-terminal modifications), or both. In some embodiments, an unmodified N terminus comprises hydrogen. In some embodiments, an unmodified C terminus comprises a —OH. In some embodiments, an N-terminal modification comprises $C_1$-$C_6$ acyl, $C_1$-$C_8$ alkyl, $C_6$-$C_{12}$ aralkyl, $C_5$-$C_{10}$ aryl, $C_4$-$C_8$ heteroaryl, formyl, or a lipid. In some embodiments, an N-terminal modification comprises $C_6$-$C_{12}$ aralkyl. In some embodiments, an N-terminal modification comprises $C_1$-$C_6$ acyl. In some embodiments, an N-terminal modification comprises acetyl. In some embodiments, an N-terminal modification comprises methyl, ethyl, propyl, or tert-butyl. In some embodiments, an N-terminal modification comprises benzyl. In some embodiments, an N-terminal modification comprises formyl. In some embodiments, an N-terminal modification comprises a lipid. In some embodiments, a C-terminal modification comprises an amino group, wherein the amino group is optionally substituted. In some embodiments, a C-terminal modification comprises an amino group, wherein the amino group is unsubstituted (—$NH_2$). In some embodiments, a C-terminal modification comprises an amino group, wherein the amino group is substituted. In some embodiments, a C-terminal modification comprises —$NH_2$, -amino-acyl, -amino-$C_1$-$C_8$ alkyl, -amino-$C_6$-$C_{12}$-aralkyl, -amino-$C_5$-$C_{10}$ aryl, or -amino-$C_4$-$C_8$ heteroaryl, -amino-$C_4$-$C_8$ heteroaryl, or —O—($C_1$-$C_8$ alkyl). In some embodiments, a C-terminal modification comprises -amino-$C_6$-$C_{12}$-aralkyl. In some embodiments, a C-terminal modification comprises —O—($C_1$-$C_8$ alkyl). In some embodiments, a C-terminal modification comprises -amino-$C_6$-$C_{12}$-aralkyl. In some embodiments, a C-terminal modification comprises —NH—$CH_2$Ph. In some embodiments, a C-terminal modification comprises —OEt. In some embodiments, a C-terminal modification comprises —OMe.

Peptides (e.g., DDB1 binding moieties) may comprise lipids. Such lipids are covalently attached to an amino acid in the peptide. In some embodiments, a lipid is attached to the N-terminus. In some embodiments, a lipid is attached to cysteine, serine, lysine, threonine or tyrosine. In some embodiments, a lipid is attached to cysteine, lysine. In some embodiments, a lipid is attached to a non-canonical amino acid. In some embodiments, a lipid comprises a hydrophobic group. In some embodiments, a lipid comprises a fatty acid group. In some embodiments, a lipid comprises a $C_6$-$C_{20}$ fatty acid group. In some embodiments, a lipid comprises a steroid. In some embodiments, a lipid comprises a wax. In some embodiments, a lipid comprises an alkyl group. In some embodiments, a lipid comprises a $C_6$-$C_{20}$ alkyl group. In some embodiments, a lipid comprises a $C_6$-$C_{20}$ alkenyl group. In some embodiments, a lipid comprises a $C_6$-$C_{20}$ alkyl, $C_6$-$C_{20}$ alkenyl, $C_6$-$C_{20}$ alkynyl, or $C_6$-$C_{20}$ acyl group. In some embodiments, a lipid comprises a geranyl, farnesyl, or geranylgeranyl group. In some embodiments, a lipid comprises a undecyloyl, lauroyl, tridecyloyl, myristoyl, palmitoyl, or stearoyl group. In some embodiments, a lipid is attached to a cysteine through palmitoylation or prenylation. In some embodiments, a peptide described herein comprises an ester, amide, or thioester of a fatty acid.

Disclosed herein, in some embodiments, are DDB1 binding moieties. In some embodiments, the DDB1 binding moiety binds to a DDB1 protein. In some embodiments, the DDB1 binding moiety binds to a binding region on the DDB1 protein. In some embodiments, the DDB1 binding moiety is bound to a DDB1 protein. In some embodiments, the DDB1 binding moiety is bound to a binding region on the DDB1 protein. In some embodiments, the binding region on the DDB1 protein comprises a beta propeller domain. In some embodiments, the binding region on the DDB1 protein comprises a beta propeller C (BPC) domain. In some embodiments, the binding region on the DDB1 protein comprises a top face of the BPC domain. In some embodiments, the binding region on the DDB1 protein comprises one or more of the following DDB1 protein residues: ARG327, LEU328, PRO358, ILE359, VAL360, ASP361, GLY380, ALA381, PHE382, SER720, ARG722, LYS723, SER738, ILE740, GLU787, TYR812. LEU814, SER815, ALA834, VAL836. ALA841, ALA869, TYR871, SER872, MET910, LEU912, TYR913, LEU926, TRP953, SER955, ALA956, ASN970, ALA971, PHE972, PHE1003, ASN1005, VAL1006, and/or VAL1033. In some embodiments, one or more of the following DDB1 protein residues are involved in the non-covalent binding between the DDB1 protein and the ligand: ARG327, LEU328, PRO358, ILE359, VAL360, ASP361, GLY380. ALA381, PHE382, SER720, ARG722, LYS723, SER738, ILE740, GLU787, TYR812, LEU814, SER815, ALA834, VAL836, ALA841, ALA869, TYR871, SER872, MET910, LEU912, TYR913, LEU926, TRP953, SER955, ALA956, ASN970, ALA971, PHE972, PHE1003, ASN1005, VAL1006, and/or VAL1033. In some embodiments, the binding region on the DDB1 protein comprises an amino acid residue described herein, such as in the section titled "Modified Proteins."

Linkers

Described herein are compounds comprising a linker. In some embodiments, the linker is connected to a DDB1 binding moiety described herein. In some embodiments, the linker is connected to a target protein binding moiety described herein. In some embodiments, the linker is connected to a DDB1 binding moiety and to a target protein binding moiety. In some embodiments, the connection is covalent. In some embodiments, the linker is incorporated into a ligand described herein. In some embodiments, a compound described herein of Formula (I) comprises a linker of Formula (III), Formula (IIIa), Formula (IIIb), Described herein are compounds comprising a DDB1 binding moiety and a linker. In some embodiments, the linker comprises optionally substituted polyethylene glycol (PEG). In some embodiments, the linker comprises an optionally substituted alkyl chain. In some embodiments, the linker is a straight chain alkane. In some embodiments, the linker comprises optionally substituted $C_2$-$C_{30}$, $C_2$-$C_{25}$, $C_3$-$C_{25}$, $C_4$-$C_{10}$, $C_6$-$C_{12}$, $C_6$-$C_{18}$, or $C_4$-$C_{20}$ alkyl units. In some embodiments, the linker comprises an optionally substituted carbocycle ring. In some embodiments, the linker comprises an optionally substituted heterocycle ring. In some embodiments, the linker comprises an optionally substituted aryl ring. In some embodiments, the linker comprises an optionally substituted heteroaryl ring. In some embodiments, the linker comprises ethers. In some embodiments, the linker is comprises a $C_2$-$C_{30}$, $C_2$-$C_{25}$, $C_3$-$C_{25}$, $C_4$-$C_{10}$, $C_6$-$C_{12}$, $C_6$-$C_{18}$, or $C_4$-$C_{20}$ alkylether units. In some embodiments, the PEG is optionally substituted 1-5, 2-7, 2-10, 2-20, 5-25, or 4-30 —(O—$CH_2CH_2$)— units in length. In some embodiments, the linker comprises amines. In some embodiments, the linker is comprises a $C_2$-$C_{30}$, $C_2$-$C_{25}$, $C_3$-$C_{25}$, $C_4$-$C_{10}$, $C_6$-$C_{12}$, $C_6$-$C_{18}$, or $C_4$-$C_{20}$ alkylamino units. In some embodiments, the linker comprises optionally substituted 1-5, 2-7, 2-10, 2-20, 5-25, or 4-30 —(NH—$CH_2CH_2$)— units. In some embodiments, the linker comprises amides. In some embodiments, the linker comprises sulfonamides. In some embodiments, the linker comprises carbamides. In some embodiments, the linker comprises carbamates. In some embodiments, the linker comprises carbonates. In some embodiments, a compound comprises a DDB1 binding moiety, a linker, and/or a target protein binding moiety. In some embodiments, the linker is of Formula (III):

Formula (III)

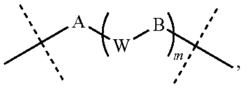

wherein

A, W, and B, at each occurrence, are independently selected from null, or bivalent moiety selected from R'—R", R'COR", R"$CO_2$R", R'C(O)N($R^1$)R", R'C(S)N($R^1$)R", R'OR", R'OC(O)R", R'OC(O)OR", R'OCON($R^1$)R", R'SR", R'SOR", R'$SO_2$R", R'$SO_2$N($R^1$)R", R'N($R^1$)R", R'N($R^1$)COR", R'N($R^1$)C(O)OR", R'N($R^1$)CON($R^2$)R", R'N($R^1$)C(S)R", R'N($R^1$)S(O)R", R'N($R^1$)S(O)$_2$R", R'N($R^1$)S(O)$_2$N($R^2$)R", optionally substituted $C_1$-$C_8$ alkylene, optionally substituted $C_2$-$C_8$ alkenylene, optionally substituted $C_2$-$C_8$ alkynylene, optionally substituted $C_1$-$C_8$ heteroalkylene, optionally substituted $C_2$-$C_8$ heteroalkenylene, optionally substituted $C_2$-$C_8$ heteroalkynylene, optionally substituted $C_1$-$C_8$alkoxy$C_1$-$C_8$alkylene, optionally substituted $C_1$-$C_8$ haloalkylene, optionally substituted $C_1$-$C_8$ hydroxyalkylene, optionally substituted $C_4$-$C_{13}$ fused carbocyclyl, optionally substituted $C_5$-$C_{13}$ fused heterocyclyl, optionally substituted $C_5$-$C_{13}$ bridged carbocyclyl, optionally substituted $C_5$-$C_{13}$ bridged heterocyclyl, optionally substituted $C_5$-$C_{13}$ spiro carbocyclyl, optionally substituted $C_5$-$C_{13}$ spiro heterocyclyl, optionally substituted 3-10 membered carbocyclyl, optionally substituted 4-10 membered heterocyclyl, optionally substituted aryl, and optionally substituted heteroaryl, wherein R' and R", at each occurrence, are independently selected from null, optionally substituted ($C_1$-$C_8$ alkylene)-$R^r$ (preferably, $CH_2$—$R^r$), optionally substituted $R^r$—($C_1$-$C_8$ alkylene), optionally substituted ($C_1$-$C_8$ alkylene)-$R^r$—($C_1$-$C_8$ alkyl), or a bivalent moiety comprising of optionally substituted $C_1$-$C_8$ alkylene, optionally substituted $C_2$-$C_8$ alkenylene, optionally substituted $C_2$-$C_8$ alkynylene, optionally substituted $C_1$-$C_8$ heteroalkylene, optionally substituted $C_2$-$C_8$ heteroalkenylene, optionally substituted $C_2$-$C_8$ heteroalkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_4$-$C_{13}$ fused carbocyclyl, optionally substituted $C_5$-$C_{13}$ fused heterocyclyl, optionally substituted $C_5$-$C_{13}$ bridged carbocyclyl, optionally substituted $C_5$-$C_{13}$ bridged heterocyclyl, optionally substituted $C_5$-$C_{13}$ spiro carbocyclyl, optionally substituted $C_5$-$C_{13}$ spiro heterocyclyl, optionally substituted aryl, and optionally substituted heteroaryl;

$R^r$, at each occurrence, is selected from optionally substituted 3-10 membered carbocyclyl, optionally substituted 4-10 membered heterocyclyl, optionally substituted $C_4$-$C_{13}$ fused carbocyclyl, optionally substituted $C_5$-$C_{13}$ fused heterocyclyl, optionally substituted $C_5$-$C_{13}$ bridged carbocyclyl, optionally substituted $C_5$-$C_{13}$ bridged heterocyclyl, optionally substituted $C_5$-$C_{13}$ spiro carbocyclyl, optionally substituted $C_5$-$C_{13}$ spiro heterocyclyl, optionally substituted aryl, and optionally substituted heteroaryl;

$R^1$ and $R^2$, at each occurrence, are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ heteroalkyl, optionally substituted $C_2$-$C_8$ hetroalkenyl, optionally substituted $C_2$-$C_8$ hetroalkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl; or R' and R", $R^1$ and $R^2$, R' and $R^1$, R' and $R^2$, R" and $R^1$, R" and $R^2$ together with the atom to which they are connected optionally form a 3-20 membered carbocyclyl or 4-20 membered heterocyclyl ring; and m is 0 to 15.

In some embodiments of linker of Formula (III), A is $(CH_2)_{0-12}N(R^1)$, B is null, and W is alkylene. In some embodiments of linker of Formula (III), A is $(CH_2)_{0-12}OC(O)$, B is null, and W is alkylene. In some embodiments of linker of Formula (III), A is $(CH_2)_{0-12}N(R^1)C(O)$, B is null, and W is alkylene. In some embodiments of linker of Formula (III), A is $(CH_2)_{0-12}C(O)O$, B is null, and W is alkylene. In some embodiments of linker of Formula (III), A is $(CH_2)_{0-12}C(O)N(R^1)$, B is null, and W is alkylene. In some embodiments of linker of Formula (III), m is 2-10. In some embodiments of linker of Formula (III), m is 2-7. In some embodiments of linker of Formula (III), m is 5-10.

In some embodiments of linker of Formula (III), A is $(CH_2)_{0-12}N(R^1)$, B is O, and W is alkylene. In some embodiments of linker of Formula (III), A is $(CH_2)_{0-12}OC(O)$, B is O, and W is alkylene. In some embodiments of linker of Formula (III), A is $(CH_2)_{0-12}N(R^1)C(O)$, B is O, and W is alkylene. In some embodiments of linker of Formula (III), A is $(CH_2)_{0-12}C(O)O$, B is O, and W is alkylene. In some embodiments of linker of Formula (III), A is $(CH_2)_{0-12}C(O)N(R^1)$, B is O, and W is alkylene. In some embodiments of linker of Formula (III), m is 2-12. In some embodiments of linker of Formula (III), m is 2-7. In some embodiments of linker of Formula (III), m is 5-12.

In some embodiments of linker of Formula (III), A is $(CH_2)_{0-12}N(R^1)$, B is $N(R^2)$, and W is alkylene. In some embodiments of linker of Formula (III), A is $(CH_2)_{0-12}OC(O)$, B is $N(R^2)$, and W is alkylene. In some embodiments of linker of Formula (III), A is $(CH_2)_{0-12}N(R^1)C(O)$, B is $N(R^2)$, and W is alkylene. In some embodiments of linker of Formula (III), A is $(CH_2)_{0-12}C(O)O$, B is $N(R^2)$, and W is alkylene. In some embodiments of linker of Formula (III), A is $(CH)_{0-12}C(O)N(R^1)$, B is $N(R^2)$, and W is alkylene. In some embodiments of linker of Formula (III), m is 2-12. In some embodiments of linker of Formula (III), m is 2-7. In some embodiments of linker of Formula (III), m is 5-12.

In some embodiments, the linker is of Formula (IIIa):

Formula (IIIa)

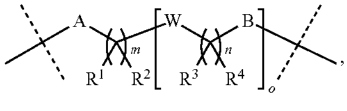

wherein $R^1$, $R^2$, $R^3$ and $R^4$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ heteroalkyl, optionally substituted $C_2$-$C_8$ hetroalkenyl, optionally substituted $C_2$-$C_8$ hetroalkynyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl, optionally substituted 3-10 membered carbocyclyl, optionally substituted 3-8 membered cycloalkoxy, optionally substituted 3-10 membered carbocyclylamino, optionally substituted 4-8 membered heterocyclyl, optionally substituted aryl, and optionally substituted heteroaryl, or $R^1$ and $R^2$, $R^3$ and $R^4$ together with the atom to which they are connected optionally form a 3-20 membered carbocyclyl or 4-20 membered heterocyclyl ring;

A, W, and B, at each occurrence, are independently selected from null, or bivalent moiety selected from R'—R", R'COR", R'$CO_2$R", R'C(O)N($R^5$)R", R'C(S)N($R^5$)R", R'OR", R'OC(O)R", R'OC(O)OR", R'OCON($R^5$)R", R'SR", R'SOR", R'$SO_2$R", R'$SO_2$N($R^5$)R", R'N($R^5$)R", R"N($R^5$)COR", R'N($R^5$)C(O)OR", R'N($R^5$)CON($R^6$)R", R'N($R^5$)C(S)R", R'N($R^5$)S(O)R", R'N($R^5$)$S(O)_2$R", R'N($R^5$)$S(O)_2$N($R^6$)R", optionally substituted $C_1$-$C_8$ alkylene, optionally substituted $C_2$-$C_8$ alkenylene, optionally substituted $C_2$-$C_8$ alkynylene, optionally substituted $C_1$-$C_8$ heteroalkylene, optionally substituted $C_2$-$C_8$ heteroalkenylene, optionally substituted $C_2$-$C_8$ heteroalkynylene, optionally substituted $C_1$-$C_8$alkoxy$C_1$-$C_8$alkylene, optionally substituted $C_1$-$C_8$ haloalkylene, optionally substituted $C_1$-$C_8$ hydroxyalkylene, optionally substituted $C_4$-$C_{13}$ fused carbocyclyl, optionally substituted $C_5$-$C_{13}$ fused heterocyclyl, optionally substituted $C_5$-$C_{13}$ bridged carbocyclyl, optionally substituted $C_5$-$C_{13}$ bridged heterocyclyl, optionally substituted $C_5$-$C_{13}$ spiro carbocyclyl, optionally substituted $C_5$-$C_{13}$ spiro heterocyclyl, optionally substituted 3-10 membered carbocyclyl, optionally substituted 4-10 membered heterocyclyl, optionally substituted aryl, and optionally substituted heteroaryl, wherein R' and R", at each occurrence, are independently selected from null, optionally substituted ($C_1$-$C_8$ alkylene)-$R^r$ (preferably, $CH_2$—$R^r$), optionally substituted $R^r$—($C_1$-$C_8$ alkylene), optionally substituted ($C_1$-$C_8$ alkylene)-$R^r$—($C_1$-$C_8$ alkylene), or a bivalent moiety comprising of optionally substituted $C_1$-$C_8$ alkylene, optionally substituted $C_2$-$C_8$ alkenylene, optionally substituted $C_2$-$C_8$ alkynylene, optionally substituted $C_1$-$C_8$ heteroalkylene, optionally substituted $C_2$-$C_8$ heteroalkenylene, optionally substituted $C_2$-$C_8$ heteroalkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$ alkylene, optionally substituted $C_1$-$C_8$ haloalkylene, optionally substituted 3-10 membered carbocyclyl, optionally substituted 4-10 membered heterocyclyl, optionally substituted $C_4$-$C_{13}$ fused carbocyclyl, optionally substituted $C_5$-$C_{13}$ fused heterocyclyl, optionally substituted $C_5$-$C_{13}$ bridged carbocyclyl, optionally substituted $C_5$-$C_{13}$ bridged heterocyclyl, optionally substituted $C_5$-$C_{13}$ spiro carbocyclyl, optionally substituted $C_5$-$C_{13}$ spiro heterocyclyl, optionally substituted aryl, and optionally substituted heteroaryl;

$R^{r}$, at each occurrence, is selected from optionally substituted 3-10 membered carbocyclyl, optionally substituted 4-10 membered heterocyclyl, optionally substituted $C_4$-$C_{13}$ fused carbocyclyl, optionally substituted $C_5$-$C_{13}$ fused heterocyclyl, optionally substituted $C_5$-$C_{13}$ bridged carbocyclyl, optionally substituted $C_5$-$C_{13}$ bridged heterocyclyl, optionally substituted $C_5$-$C_{13}$ spiro carbocyclyl, optionally substituted $C_5$-$C_{13}$ spiro heterocyclyl, optionally substituted aryl, and optionally substituted heteroaryl;

$R^5$ and $R^6$, at each occurrence, are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ heteroalkyl, optionally substituted $C_2$-$C_8$ hetroalkenyl, optionally substituted $C_2$-$C_8$ hetroalkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$ alkyl, optionally substituted 3-10 membered carbocyclyl, optionally substituted 4-10 membered heterocyclyl, optionally substituted aryl, and optionally substituted heteroaryl; or R' and R", $R^5$ and $R^6$, R' and $R^5$, R' and $R^6$, R" and $R^5$, R" and $R^6$ together with the atom to which they are connected form a 3-20 membered cycloalkyl or 4-20 membered heterocyclyl ring;

m is 0 to 15;

n, at each occurrence, is 0 to 15; and o is 0 to 15.

In some embodiments, the linker is of Formula (IIIb):

Formula (IIIb)

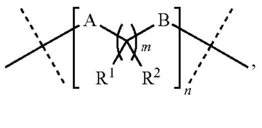

wherein $R^1$ and $R^2$, at each occurrence, are independently selected from hydrogen, halogen, hydroxyl, amino, cyano, nitro, and optionally substituted $C_1$-$C_8$ alkyl, optionally substituted $C_2$-$C_8$ alkenyl, optionally substituted $C_2$-$C_8$ alkynyl, optionally substituted $C_1$-$C_8$ heteroalkyl, optionally substituted $C_2$-$C_8$ hetroalkenyl, optionally substituted $C_2$-$C_8$ hetroalkynyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, $C_1$-$C_8$alkylamino$C_1$-$C_8$alkyl, optionally substituted 3-10 membered carbocyclyl, optionally substituted 3-8 membered cycloalkoxy, optionally substituted 3-10 membered carbocyclylamino, optionally substituted 4-10 membered heterocyclyl, optionally substituted aryl, and optionally substituted heteroaryl, or $R^1$ and $R^2$ together with the atom to which they are connected form a 3-20 membered cycloalkyl or 4-20 membered heterocyclyl ring;

A and B, at each occurrence, are independently selected from null, or bivalent moiety selected from R'—R", R'COR", R'$CO_2$R", R'C(O)N($R^3$)R", R'C(S)N($R^3$)R", R'OR", R'OC(O)R", R'OC(O)OR", R'OCON($R^3$)R", R'SR", R'SOR", R'$SO_2$R", R'$SO_2$NR"$R^3$, R'N($R^3$)R", R'N($R^3$)COR", R'N($R^3$)C(O)OR", R'N($R^3$)CON($R^4$)R", R'N($R^3$)C(S)R', R'N($R^3$)S(O)R", R'N($R^3$)S(O)$_2$R", R'N($R^3$)S(O)$_2$N($R^4$)R", optionally substituted $C_1$-$C_8$ alkylene, optionally substituted $C_2$-$C_8$ alkenylene, optionally substituted $C_2$-$C_8$ alkynylene, optionally substituted $C_1$-$C_8$ heteroalkylene, optionally substituted $C_2$-$C_8$ heteroalkenylene, optionally substituted $C_2$-$C_8$ heteroalkynylene, optionally substituted $C_1$-$C_8$alkoxy$C_1$-$C_8$alkylene, optionally substituted $C_1$-$C_8$ haloalkylene, optionally substituted $C_1$-$C_8$ hydroxyalkylene, optionally substituted $C_4$-$C_{13}$ fused carbocyclyl, optionally substituted $C_5$-$C_{13}$ fused heterocyclyl, optionally substituted $C_5$-$C_{13}$ bridged carbocyclyl, optionally substituted $C_5$-$C_{13}$ bridged heterocyclyl, optionally substituted $C_5$-$C_{13}$ spiro carbocyclyl, optionally substituted $C_5$-$C_{13}$ spiro heterocyclyl, optionally substituted 3-10 membered carbocyclyl, optionally substituted 4-10 membered heterocyclyl, optionally substituted aryl, and optionally substituted heteroaryl, wherein R' and R", at each occurrence, are independently selected from null, optionally substituted ($C_1$-$C_8$ alkylene)-$R^{r}$ (preferably, $CH_2$—$R^{r}$), optionally substituted $R^{r}$—($C_1$-$C_8$ alkylene), optionally substituted ($C_1$-$C_8$ alkylene)-$R^{r}$—($C_1$-$C_8$ alkylene), or a bivalent moiety comprising of optionally substituted $C_1$-$C_8$ alkylene, optionally substituted $C_2$-$C_8$ alkenylene, optionally substituted $C_2$-$C_8$ alkynylene, optionally substituted $C_1$-$C_8$ heteroalkylene, optionally substituted $C_2$-$C_8$ heteroalkenylene, optionally substituted $C_2$-$C_8$ heteroalkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_4$-$C_{13}$ fused carbocyclyl, optionally substituted $C_5$-$C_{13}$ fused heterocyclyl, optionally substituted $C_5$-$C_{13}$ bridged carbocyclyl, optionally substituted $C_5$-$C_{13}$ bridged heterocyclyl, optionally substituted $C_5$-$C_{13}$ spiro carbocyclyl, optionally substituted $C_5$-$C_{13}$ spiro heterocyclyl, optionally substituted aryl, and optionally substituted heteroaryl;

$R_{L}^{r}$, at each occurrence, is selected from optionally substituted 3-10 membered carbocyclyl, optionally substituted 4-10 membered heterocyclyl, optionally substituted $C_4$-$C_{13}$ fused carbocyclyl, optionally substituted $C_5$-$C_{13}$ fused heterocyclyl, optionally substituted $C_5$-$C_{13}$ bridged carbocyclyl, optionally substituted $C_5$-$C_{13}$ bridged heterocyclyl, optionally substituted $C_5$-$C_{13}$ spiro carbocyclyl, optionally substituted $C_5$-$C_{13}$ spiro heterocyclyl, optionally substituted aryl, and optionally substituted heteroaryl;

$R^3$ and $R^4$, at each occurrence, are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ heteroalkyl, optionally substituted $C_2$-$C_8$ hetroalkenyl, optionally substituted $C_2$-$C_8$ hetroalkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$ alkyl, optionally substituted 3-10 membered carbocyclyl, optionally substituted 4-10 membered heterocyclyl, optionally substituted aryl, and optionally substituted heteroaryl; or R' and R", $R^3$ and $R^4$, R' and $R^3$, R' and $R^4$, R" and $R^3$, R" and $R^4$ together with the atom to which they are connected optionally form a 3-20 membered carbocyclyl or 4-20 membered heterocyclyl ring;

each m is 0 to 15; and n is 0 to 15.

In some embodiments, the linker is of Formula (IIIc):

Formula (IIIc)

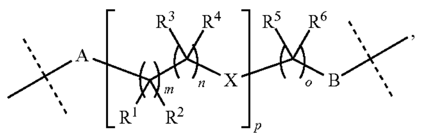

wherein

X, at each occurrence, is selected from O, NH, and $NR^7$;

$R^1$, $R^2$, $R^3$, $R^4$, $R^5$, and $R^6$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ heteroalkyl, optionally substituted $C_2$-$C_8$ hetroalkenyl, optionally substituted $C_2$-$C_8$ hetroalkynyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, optionally substituted $C_1$-$C_8$ alkylamino$C_1$-$C_8$ alkyl, optionally substituted 3-10 membered carbocyclyl, optionally substituted 3-8 membered cycloalkoxy, optionally substituted 4-10 membered heterocyclyl, optionally substituted aryl, and optionally substituted heteroaryl;

A and B are independently selected from null, or bivalent moiety selected from R'—R", R'COR", $R'CO_2R"$, R'C(O)N($R^8$)R", R'C(S)N($R^8$)R", R'OR", R'OC(O)R", R'OC(O)OR", R'OCON($R^8$)R", R'SR", R'SOR", $R'SO_2R"$, $R'SO_2N(R^8)R"$, R'N($R^8$)R", R'N(R')COR", R'N($R^8$)C(O)OR", R'N($R^8$)CON($R^9$)R", R'N($R^8$)C(S)R", R'N($R^8$)S(O)R", $R'N(R^8)S(O)_2R"$, $R'N(R^8)S(O)_2N(R^9)R"$, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ heteroalkylene, optionally substituted $C_2$-$C_8$ heteroalkenylene, optionally substituted $C_2$-$C_8$ heteroalkynylene, optionally substituted $C_1$-$C_8$ alkoxy$C_1$-$C_8$ alkylene, optionally substituted $C_1$-$C_8$ haloalkylene, optionally substituted $C_1$-$C_8$ hydroxyalkylene, optionally substituted $C_4$-$C_{13}$ fused carbocyclyl, optionally substituted $C_5$-$C_{13}$ fused heterocyclyl, optionally substituted $C_5$-$C_{13}$ bridged carbocyclyl, optionally substituted $C_5$-$C_{13}$ bridged heterocyclyl, optionally substituted $C_5$-$C_{13}$ spiro carbocyclyl, optionally substituted $C_5$-$C_{13}$ spiro heterocyclyl, optionally substituted 3-10 membered carbocyclyl, optionally substituted 4-10 membered heterocyclyl, optionally substituted aryl, and optionally substituted heteroaryl, wherein R' and R", at each occurrence, are independently selected from null, optionally substituted ($C_1$-$C_8$ alkylene)-$R^r$ (preferably, $CH_2$—$R^r$) optionally substituted $R^r$—($C_1$-$C_8$ alkylene), or a bivalent moiety comprising of optionally substituted $C_1$-$C_8$ alkylene, optionally substituted $C_2$-$C_8$ alkenylene, optionally substituted $C_2$-$C_8$ alkynylene, optionally substituted $C_1$-$C_8$ heteroalkylene, optionally substituted $C_2$-$C_8$ heteroalkenylene, optionally substituted $C_2$-$C_8$ heteroalkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_4$-$C_{13}$ fused carbocyclyl, optionally substituted $C_5$-$C_3$ fused heterocyclyl, optionally substituted $C_5$-$C_{13}$ bridged carbocyclyl, optionally substituted $C_5$-$C_{13}$ bridged heterocyclyl, optionally substituted $C_5$-$C_{13}$ spiro carbocyclyl, optionally substituted $C_5$-$C_{13}$ spiro heterocyclyl, optionally substituted aryl, and optionally substituted heteroaryl;

$R^r$, at each occurrence, is selected from optionally substituted 3-10 membered carbocyclyl, optionally substituted 4-10 membered heterocyclyl, optionally substituted $C_4$-$C_{13}$ fused carbocyclyl, optionally substituted $C_5$-$C_{13}$ fused heterocyclyl, optionally substituted $C_5$-$C_{13}$ bridged carbocyclyl, optionally substituted $C_5$-$C_{13}$ bridged heterocyclyl, optionally substituted $C_5$-$C_{13}$ spiro carbocyclyl, optionally substituted $C_5$-$C_{13}$ spiro heterocyclyl, optionally substituted aryl, and optionally substituted heteroaryl;

$R^7$, $R_8$ and $R^9$, at each occurrence, are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ heteroalkyl, optionally substituted $C_2$-$C_8$ hetroalkenyl, optionally substituted $C_2$-$C_8$ hetroalkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$ alkyl, optionally substituted 3-10 membered carbocyclyl, optionally substituted 4-10 membered heterocyclyl, optionally substituted aryl, and optionally substituted heteroaryl; or R' and R", $R^8$ and $R^9$, R' and $R^8$, R' and $R^9$, R" and $R^8$, R" and $R^9$ together with the atom to which they are connected optionally form a 3-20 membered carbocyclyl or 4-20 membered heterocyclyl ring;

m, at each occurrence, is 0 to 15;

n, at each occurrence, is 0 to 15;

o is 0 to 15; and p is 0 to 15.

In some embodiments, the linker is of Formula (IIId):

FORMULA (IIId)

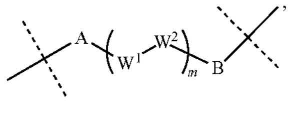

wherein

A, $W^1$, $W^2$, and B, at each occurrence, are bivalent moieties independently selected from the group consisting of null, R'—R", R'COR", R'C(O)OR", R'C(O)N($R^1$)R", R'C(S)N($R^1$)R", R'OR", R'SR", R'SOR", $R'SO_2R"$, $R'SO_2N(R^1)R"$, R'N(R")R", R'N($R^1$)COR", R'N($R^1$)CON($R^2$)R", R'N($R^1$)C(S)R", optionally substituted $C_1$-$C_8$ alkylene, optionally substituted $C_2$-$C_8$ alkenylene, optionally substituted $C_2$-$C_8$ alkynylene, optionally substituted $C_1$-$C_8$ heteroalkylene, optionally substituted $C_2$-$C_8$ heteroalkenylene, optionally substituted $C_2$-$C_8$ heteroalkynylene, optionally substituted $C_1$-$C_8$alkoxy$C_1$-$C_8$alkylene, optionally substituted $C_1$-$C_8$ haloalkylene, optionally substituted $C_1$-$C_8$ hydroxyalkylene, optionally substituted $C_3$-$C_{13}$ cycloalkyl, optionally substituted 3-13 membered heterocyclyl, optionally substituted aryl, and optionally substituted heteroaryl, wherein R' and R", at each occurrence, are independently selected from null, $R^r$, optionally substituted ($C_1$-$C_8$ alkylene)-$R^r$ (preferably, $CH_2$—$R^r$), optionally substituted R'—($C_1$-$C_8$ alkylene), optionally substituted ($C_1$-$C_8$ alkylene)-$R^r$—($C_1$-$C_8$ alkylene), or a bivalent moiety comprising of optionally substituted $C_1$-$C_8$ alkylene, optionally substituted $C_2$-$C_8$ alkenylene, optionally substituted $C_2$-$C_8$ alkynylene, optionally substituted $C_1$-$C_8$ heteroalkylene, optionally substituted $C_2$-$C_8$ heteroalkenylene, optionally substituted $C_2$-$C_8$ heteroalkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$ alkylene, optionally substituted $C_1$-$C_8$ haloalkylene, optionally substituted $C_3$-$C_{13}$ cycloalkyl, optionally substituted 3-13 membered, optionally substituted aryl, and optionally substituted heteroaryl;

$R^r$, at each occurrence, is selected from optionally substituted $C_3$-$C_{10}$ carbocyclyl, optionally substituted 3-10 membered heterocyclyl, optionally substituted aryl, and optionally substituted heteroaryl;

$R^1$ and $R^2$, at each occurrence, are independently selected from the group consisting of hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ heteroalkyl, optionally substituted $C_2$-$C_8$ heteroalkenyl, optionally substituted $C_2$-$C_8$ heteroalkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_{10}$ carbocyclyl, optionally substituted 3-10 membered heterocyclyl, optionally substituted aryl, and optionally substituted heteroaryl;

R' and R", $R^1$ and $R^2$, R' and $R^1$, R' and $R^2$, R" and $R^1$, or R" and $R^2$ together with the atom(s) to which they are connected optionally form a $C_3$-$C_{20}$ carbocyclyl or 3-20 membered heterocyclyl ring; and m is 0 to 15.

In some embodiments, A and B, at each occurrence, are independently selected from null, CO, NH, NH—CO, CO—NH, $CH_2$—NH—CO, $CH_2$—CO—NH, NH—CO—$CH_2$, CO—NH—$CH_2$, $CH_2$—NH—$CH_2$—CO—NH, $CH_2$—NH—$CH_2$—NH—CO, —CO—NH, CO—NH— $CH_2$—NH—$CH_2$, $CH_2$—NH—$CH_2$. In some embodiments, o is 0 to 5. In some embodiments, the linker comprises a ring selected from the group consisting of a 3 to 13 membered ring, a 3 to 13 membered fused ring, a 3 to 13 membered bridged ring, and a 3 to 13 membered spiro ring. In some embodiments, the linker comprises one or more rings selected from the group consisting of Formula (IIIC1a), Formula (IIIC2a), Formula (IIIC3a), Formula (IIIC4a) and Formula (IIIC5a)

Formula (IIIC1a)

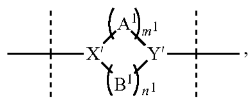

-continued

Formula (IIIC2a)

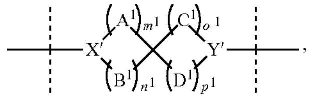

Formula (IIIC3a)

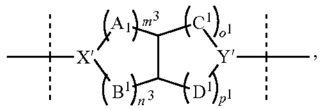

Formula (IIIC4a)

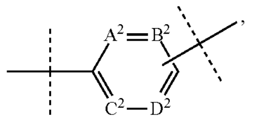

and

Formula (IIIC5a)

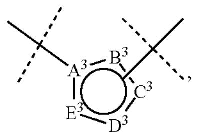

wherein

X' and Y' are independently selected from N, $CR^b$;

$A^1$, $B^1$, $C^1$ and $D^1$, at each occurrence, are independently selected from null, O, CO, SO, $SO_2$, $NR^b$, and $CR^bR^c$;

$A^2$, $B^2$, $C^2$, and $D^2$, at each occurrence, are independently selected from N, and $CR^b$;

$A^3$, $B^3$, $C^3$, $D^3$, and $E^3$, at each occurrence, are independently selected from N, O, S, $NR^b$, and $CR^b$;

$R^b$ and $R^c$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ heteroalkyl, optionally substituted $C_2$-$C_8$ heteroalkenyl, optionally substituted $C_2$-$C_8$ heteroalkynyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl, optionally substituted 3-10 membered carbocyclyl, optionally substituted 3-8 membered cycloalkoxy, optionally substituted 3-10 membered carbocyclylamino, optionally substituted 4-8 membered heterocyclyl, optionally substituted aryl, and optionally substituted heteroaryl; and $m^1$, $n^1$, $o^1$ and $p^1$ are independently selected from 0, 1, 2, 3, 4 and 5.

In some embodiments, the linker comprises one or more rings selected from the group consisting of Formula (IIIC1), Formula (IIIC2), Formula (IIIC3), Formula (IIIC4) and Formula (IIIC5):

Formula (IIIC1)

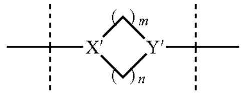

X' = N or CH
Y' = N or CH
m = 0-5
n = 0-5

-continued

Formula (IIIC2)

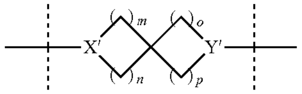

X′ = N or CH
Y′ = N or CH
m = 0-5
n = 0-5
o = 0-5
p = 0-5

Formula (IIIC3)

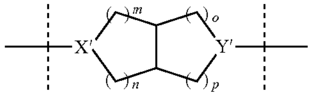

X′ = N or CH
Y′ = N or CH
m = 0-5
n = 0-5
o = 0-5
p = 0-5

Formula (IIIC4)

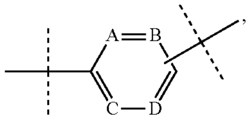

, and

A = CH, C($C_{1-3}$ alkyl), or N
B = CH, C($C_{1-3}$ alkyl), or N
C = CH, C($C_{1-3}$ alkyl), or N
D= CH, C($C_{1-3}$ alkyl), or N Formula (IIIC5)

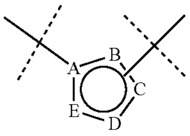

A = C, CH, C($C_{1-3}$ alkyl), N, NH, N($C_{1-3}$ alkyl), O, S
B = C, CH, C($C_{1-3}$ alkyl), N, NH, N($C_{1-3}$ alkyl), O, S
C = C, CH, C($C_{1-3}$ alkyl), N, NH, N($C_{1-3}$ alkyl), O, S
D = C, CH, C($C_{1-3}$ alkyl), N, NH, N($C_{1-3}$ alkyl), O, S
E = C, CH, C(C1-3 alkyl), N, NH, N(C1-3alkyl), O, S.

In some embodiments, the linker comprises one or more rings selected from:

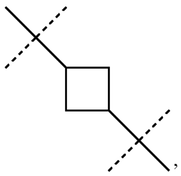
,
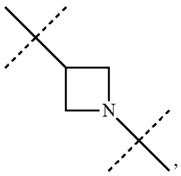
,
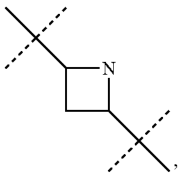
,
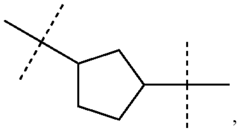
,

-continued

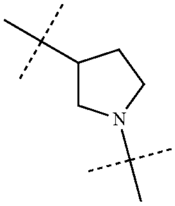
,
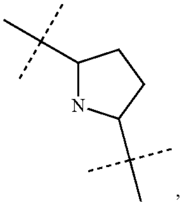
,
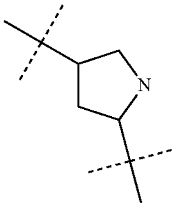
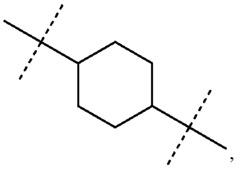
,
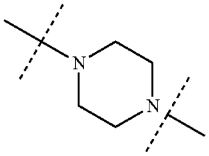
,
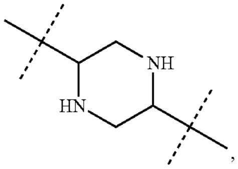
,
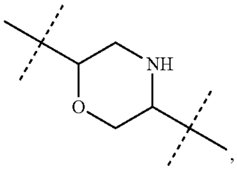
,
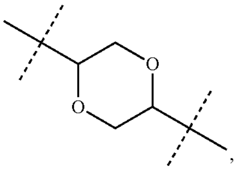
,
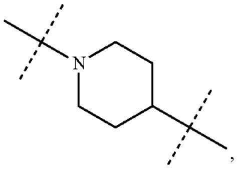
,
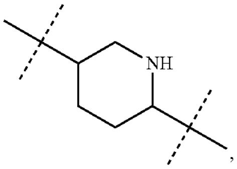
,
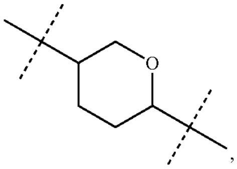
,
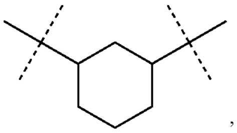
,
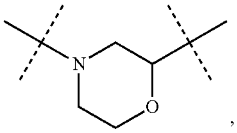
,
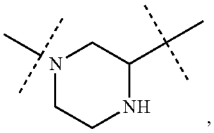
,
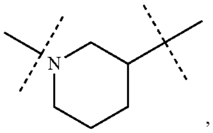
,
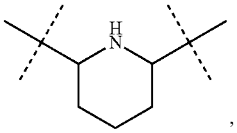
,
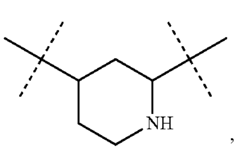
,
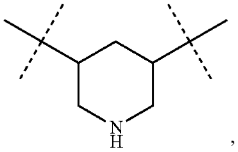
,
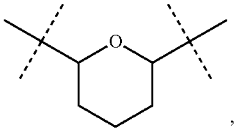
,
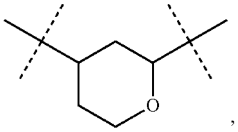
, -continued
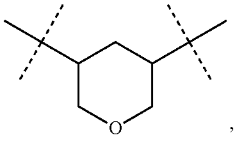,
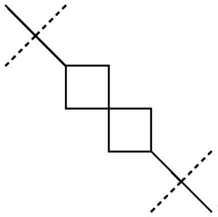,
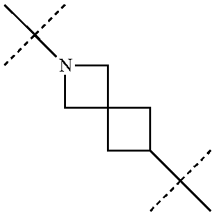,
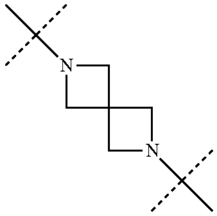,
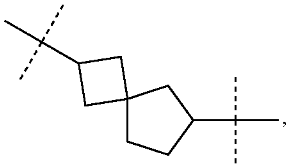,
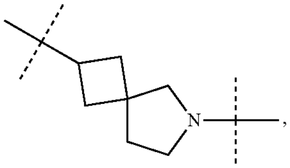,
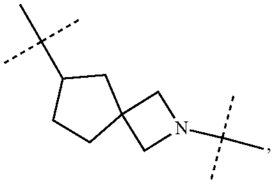,
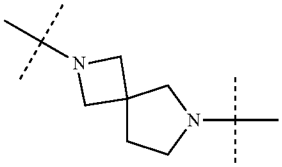,
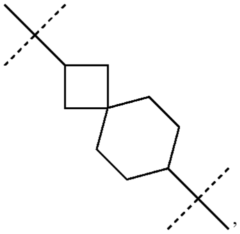,
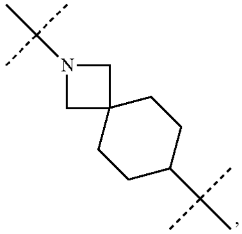,
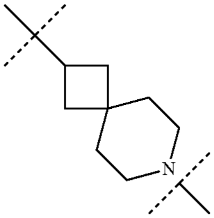,
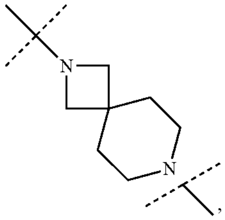,
-continued
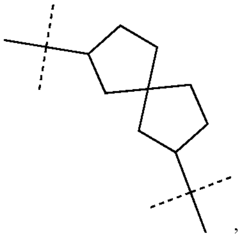,
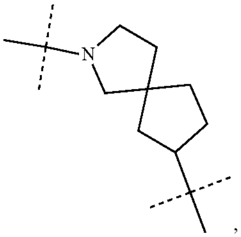,
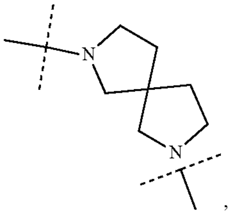,
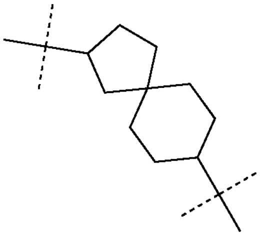,
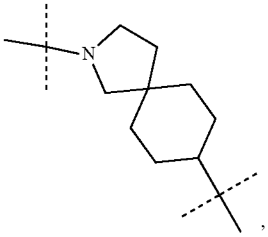,
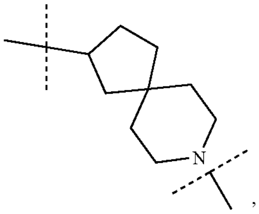,
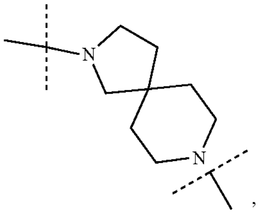,
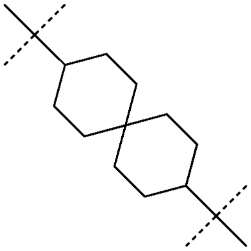,
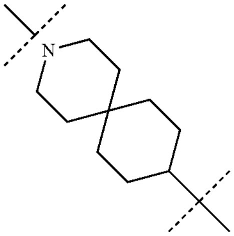,
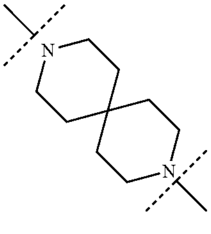,
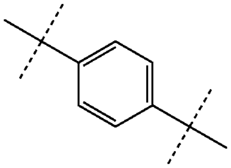,
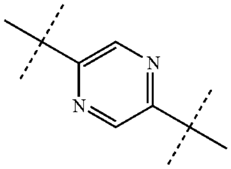, -continued
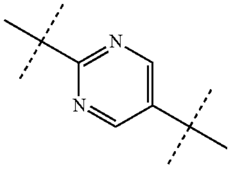, 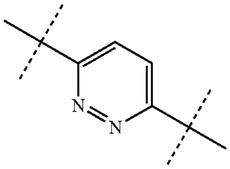,
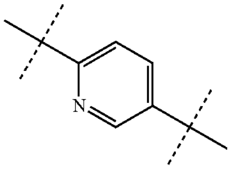, 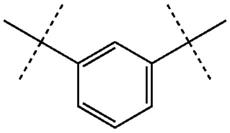,
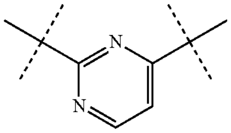, 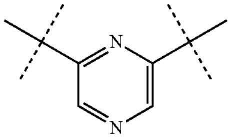,
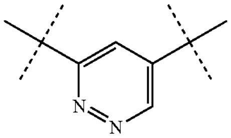, 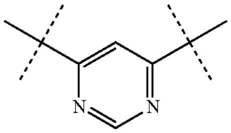,
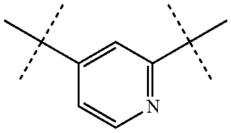, 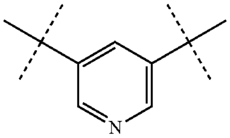,
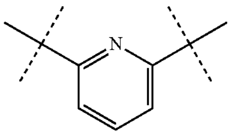, 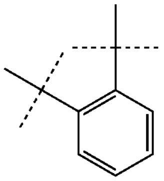,
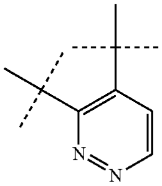, 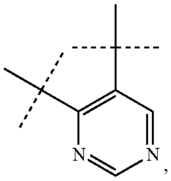,
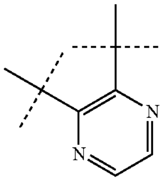, 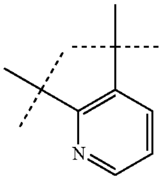,
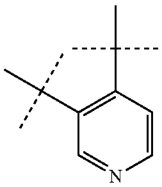, 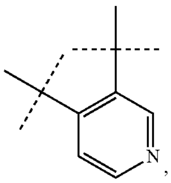,
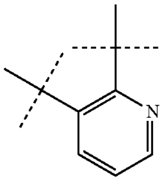, 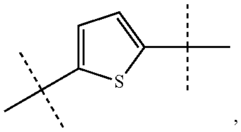,
-continued
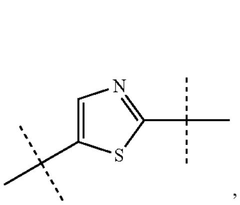, 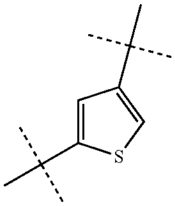,
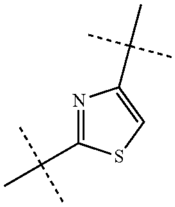, 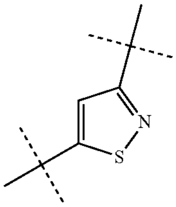,
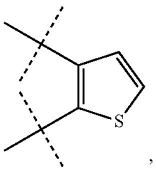, 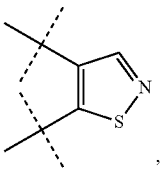, 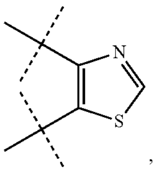,
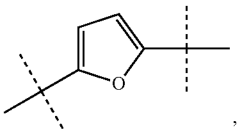, 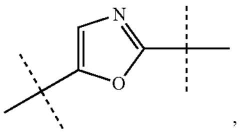,
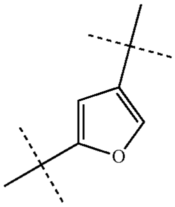, 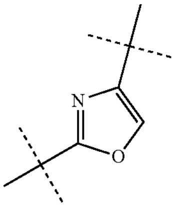,
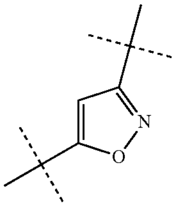, 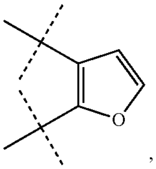, 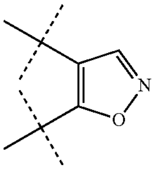,
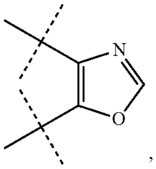, 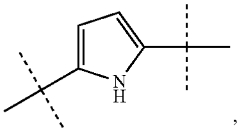,
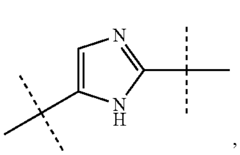, 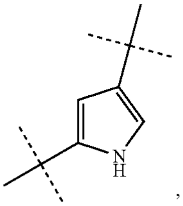,
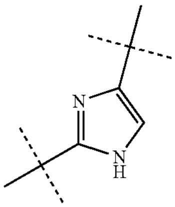, 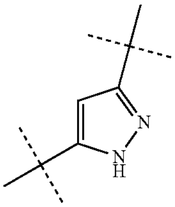, -continued

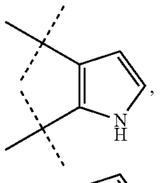 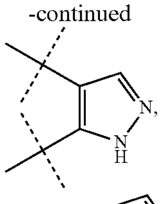 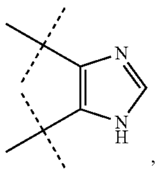,

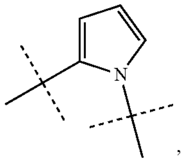, 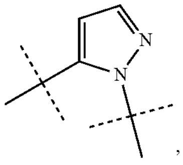,

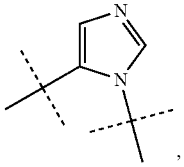, 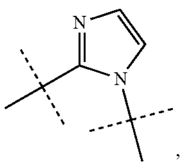, and

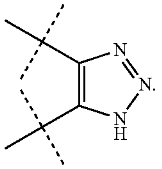

In some embodiments, a linker has the structure —$(CH_2)_{0-12}NH(CH_2)_{2-12}NH$—. In some embodiments, a linker has the structure —$NH(CH_2)_2NH$—, —$NH(CH_2)_3NH$—, —$NH(CH_2)_4NH$—, —$NH(CH_2)_5NH$—, —$NH(CH_2)_6NH$—, —$NH(CH_2)_7NH$—, —$NH(CH_2)_8NH$—, —$NH(CH_2)_9NH$—, —$NH(CH_2)_{10}NH$—, —$NH(CH_2)_{11}NH$—, or —$NH(CH_2)_{12}NH$—. In some embodiments, a linker has the structure —$(CH_2)_{0-12}NHC(=O)(CH_2)_{2-12}NH$—. In some embodiments, a linker has the structure —$NHC(=O)(CH_2)_2NH$—, —$NHC(=O)(CH_2)_3NH$—, —$NHC(=O)(CH_2)_4NH$—, —$NHC(=O)(CH_2)_5NH$—, —$NHC(=O)(CH_2)_6NH$—, —$NHC(=O)(CH_2)_7NH$—, —$NHC(=O)(CH_2)_8NH$—, —$NHC(=O)(CH_2)_9NH$—, —$NHC(=O)(CH_2)_{10}NH$—, —$NHC(=O)(CH_2)_{11}NH$—, or —$NHC(=O)(CH_2)_{12}NH$—. In some embodiments, a linker has the structure —$(CH_2)_{0-12}NH(CH_2)_{2-12}C(=O)NH$—. In some embodiments, a linker has the structure —$NH(CH_2)_2C(=O)NH$—, —$NH(CH_2)_3C(=O)NH$—, —$NH(CH_2)_4C(=O)NH$—, —$NH(CH_2)_5C(=O)NH$—, —$NH(CH_2)_6C(=O)NH$—, —$NH(CH_2)_7C(=O)NH$—, —$NH(CH_2)_8C(=O)NH$—, —$NH(CH_2)_9C(=O)NH$—, —$NH(CH_2)_{10}C(=O)NH$—, —$NH(CH_2)_{11}C(=O)NH$—, or —$NH(CH_2)_{12}(=O)NH$—. In some embodiments, a linker has the structure —$(CH_2)_{0-12}C(=O)NH(CH_2)_{2-12}C(=O)NH$—, In some embodiments, a linker has the structure —$C(=O)NH(CH_2)_2C(=O)NH$—, —$C(=O)NH(CH_2)_3C(=O)NH$—, —$C(=O)NH(CH_2)_4C(=O)NH$—, —$C(=O)NH(CH_2)_5C(=O)NH$—, —$C(=O)NH(CH_2)_6C(=O)NH$—, —$C(=O)NH(CH_2)_7C(=O)NH$—, —$C(=O)NH(CH_2)_8C(=O)NH$—, —$C(=O)NH(CH_2)_9C(=O)NH$—, —$C(=O)NH(CH_2)_{10}C(=O)NH$—, —$C(=O)NH(CH_2)_{11}C(=O)NH$—, or —$C(=O)NH(CH_2)_{12}(=O)NH$—. In some embodiments, a linker has the structure —$(CH_2)C(=O)NH(CH_2)_2C(=O)NH$—, —$(CH_2)C(=O)NH(CH_2)_3C(=O)NH$—, —$(CH_2)C(=O)NH(CH_2)_4C(=O)NH$—, —$(CH_2)C(=O)NH(CH_2)_5C(=O)NH$—, —$(CH_2)C(=O)NH(CH_2)_6C(=O)NH$—, —$(CH_2)C(=O)NH(CH_2)_7C(=O)NH$—, —$(CH_2)C(=O)NH(CH_2)_8C(=O)NH$—, —$(CH_2)C(=O)NH(CH_2)_9C(=O)NH$—, —$(CH_2)C(=O)NH(CH_2)_{10}C(=O)NH$—, —$(CH_2)C(=O)NH(CH_2)_{11}C(=O)NH$—, or —$(CH_2)C(=O)NH(CH_2)_{12}(=O)NH$—. In some embodiments, a linker has the structure —$(CH_2)_2C(=O)NH(CH_2)_2C(=O)NH$—, —$(CH_2)_2C(=O)NH(CH_2)_3C(=O)NH$—, —$(CH_2)_2C(=O)NH(CH_2)_4C(=O)NH$—, —$(CH_2)_2C(=O)NH(CH_2)_5C(=O)NH$—, —$(CH_2)_2C(=O)NH(CH_2)_6C(=O)NH$—, —$(CH_2)_2C(=O)NH(CH_2)_7C(=O)NH$—, —$(CH_2)_2C(=O)NH(CH_2)_8C(=O)NH$—, —$(CH_2)_2C(=O)NH(CH_2)_9C(=O)NH$—, —$(CH_2)_2C(=O)NH(CH_2)_{10}C(=O)NH$—, —$(CH_2)_2C(=O)NH(CH_2)_{11}C(=O)NH$—, or —$(CH_2)_2C(=O)NH(CH_2)_{12}(=O)NH$—. In some embodiments, a linker has the structure —$(CH_2)_3C(=O)NH(CH_2)_2C(=O)NH$—, —$(CH_2)_3C(=O)NH(CH_2)_3C(=O)NH$—, —$(CH_2)_3C(=O)NH(CH_2)_4C(=O)NH$—, —$(CH_2)_3C(=O)NH(CH_2)_5C(=O)NH$—, —$(CH_2)_3C(=O)NH(CH_2)_6C(=O)NH$—, —$(CH_2)_3C(=O)NH(CH_2)_7C(=O)NH$—, —$(CH_2)_3C(=O)NH(CH_2)_5C(=O)NH$—, —$(CH_2)_3C(=O)NH(CH_2)_9C(=O)NH$—, —$(CH_2)_3C(=O)NH(CH_2)_{10}C(=O)NH$—, —$(CH_2)_3C(=O)NH(CH_2)_{11}C(=O)NH$—, or —$(CH_2)_3C(=O)NH(CH_2)_{12}(=O)NH$—.

In some embodiments, a linker has the structure —$(CH_2)_{0-12}NH(CH_2CH_2O)_{1-12}(CH_2)_2NH$—. In some embodiments, a linker has the structure —$NH(CH_2CH_2O)(CH_2)_2NH$—, —$NH(CH_2CH_2O)_2(CH_2)_2NH$—, —$NH(CH_2CH_2O)_3(CH_2)_2NH$—, —$NH(CH_2CH_2O)_4(CH_2)_2NH$—, —$NH(CH_2CH_2O)_5(CH_2)_2NH$—, —$NH(CH_2CH_2O)_6(CH_2)_2NH$—, —$NH(CH_2CH_2O)_7(CH_2)_2NH$—, —$NH(CH_2CH_2O)_8(CH_2)_2NH$—, —$NH(CH_2CH_2O)_9(CH_2)_2NH$—, —$NH(CH_2CH_2O)_{10}(CH_2)_2NH$—, —$NH(CH_2CH_2O)_{11}(CH_2)_2NH$—, or —$NH(CH_2CH_2O)_{12}(CH_2)_2NH$—. In some embodiments, a linker has the structure —$(CH_2)_{0-12}NHC(=O)(CH_2CH_2O)_{1-12}(CH_2)_2NH$—. In some embodiments, a linker has the structure —$(CH_2)_{0-12}NH(CH_2CH_2O)_{1-12}(CH_2)_2C(=O)NH$—. In some embodiments, a linker has the structure —$NH(CH_2CH_2O)(CH_2)_2C(=O)NH$—, —$NH(CH_2CH_2O)_2(CH_2)_2C(=O)NH$—, —$NH(CH_2CH_2O)_3(CH_2)_2C(=O)NH$—, —$NH(CH_2CH_2O)_4(CH_2)_2C(=O)NH$—, —$NH(CH_2CH_2O)_5(CH_2)_2C(=O)NH$—, —$NH(CH_2CH_2O)_6(CH_2)_2C(=O)NH$—, —$NH(CH_2CH_2O)_7(CH_2)_2C(=O)NH$—, —$NH(CH_2CH_2O)_8(CH_2)_2C(=O)NH$—, —$NH(CH_2CH_2O)_9(CH_2)_2C(=O)NH$—, —$NH(CH_2CH_2O)_{10}(CH_2)_2C(=O)NH$—, —$NH(CH_2CHO)_{11}(CH_2)_2C(=O)NH$—, or —$NH(CH_2CH_2O)_{12}(CH_2)_2C(=O)NH$—. In some embodiments, a linker has the structure —$(CH_2)_{0-12}C(=O)NH(CH_2CH_2O)_{1-12}(CH_2)_2C(=O)NH$—. In some embodiments, a linker has the structure —$C(=O)NH(CH_2CH_2O)(CH_2)_2C(=O)NH$—, —$C(=O)NH(CH_2CH_2O)_2(CH_2)_2C(=O)NH$—, —$C(=O)NH(CH_2CHO)_3(CH_2)_2C(=O)NH$—, —$C(=O)NH(CH_2CH_2O)_4(CH_2)_2C(=O)NH$—, —$C(=O)NH(CH_2CH_2O)_5(CH_2)_2C(=O)NH$—, —$C(=O)NH(CH_2CH_2O)_6(CH_2)_2C(=O)NH$—, —$C(=O)NH(CH_2CH_2O)_7(CH_2)_2C(=O)NH$—, —$C(=O)NH(CH_2CH_2O)_8(CH_2)_2C(=O)NH$—, —$C(=O)NH(CH_2CH_2O)_9(CH_2)_2C(=O)NH$—, —$C(=O)NH(CH_2CH_2O)_{10}(CH_2)_2C(=O)NH$—, —$C(=O)NH(CH_2CH_2O)_{11}(CH_2)_2C(=O)NH$—, or —$C(=O)NH(CH_2CH_2O)_{12}(CH_2)_2C(=O)NH$—. In some embodiments, a linker has the structure —$(CH_2)C(=O)NH(CH_2CH_2O)(CH_2)_2C(=O)NH$—, —$(CH_2)C(=O)NH(CH_2CH_2O)_2(CH_2)_2C(=O)NH$—, —$(CH_2)C(=O)NH(CH_2CH_2O)_3(CH_2)_2C(=O)NH$—, —$(CH_2)C(=O)NH(CH_2CH_2O)_4(CH_2)_2C(=O)NH$—, —$(CH_2)C(=O)NH(CH_2CH_2O)_5(CH_2)_2C(=O)NH$—, —$(CH_2)C(=O)NH(CH_2CH_2O)_6(CH_2)_2C(=O)NH$—, —$(CH_2)C(=O)NH(CH_2CH_2O)_7(CH_2)_2C(=O)NH$—, —$(CH_2)C(=O)NH(CH_2CH_2O)_8(CH_2)_2C(=O)NH$—, —$(CH_2)C(=O)NH(CH_2CH_2O)_9$ $(CH_2)_2C(=O)NH-$, $-(CH_2)C(=O)NH(CH_2CH_2O)_{10}(CH_2)_2C(=O)NH-$, $-(CH_2)C(=O)NH(CH_2CH_2O)_{11}(CH_2)_2C(=O)NH-$, or $-(CH_2)C(=O)NH(CH_2CH_2O)_{12}(CH_2)_2C(=O)NH-$. In some embodiments, a linker has the structure $-(CH_2)_2C(=O)NH(CH_2CH_2O)(CH_2)_2C(=O)NH-$, $-(CH_2)_2C(=O)NH(CH_2CH_2O)_2(CH_2)_2C(=O)NH-$, $-(CH_2)_2C(=O)NH(CH_2CH_2O)_3(CH_2)_2C(=O)NH-$, $-(CH_2)_2C(=O)NH(CH_2CH_2O)_4(CH_2)_2C(=O)NH-$, $-(CH_2)_2C(=O)NH(CH_2CH_2O)_5(CH_2)_2C(=O)NH-$, $-(CH_2)_2C(=O)NH(CH_2CH_2O)_6(CH_2)_2C(=O)NH-$, $-(CH_2)_2C(=O)NH(CH_2CH_2O)_7(CH_2)_2C(=O)NH-$, $-(CH_2)_2C(=O)NH(CH_2CH_2O)_8(CH_2)_2C(=O)NH-$, $-(CH_2)_2C(=O)NH(CH_2CH_2O)_9(CH_2)_2C(=O)NH-$, $-(CH_2)_2C(=O)NH(CH_2CH_2O)_{10}(CH_2b)C(=O)NH-$, $-(CH_2)_2C(=O)NH(CH_2CH_2O)_{11}(CH_2)_2C(=O)NH-$, or $-(CH_2)_2C(=O)NH(CH_2CH_2O)_{12}(CH_2)_2C(=O)NH-$. In some embodiments, a linker has the structure $-(CH_2)_3C(=O)NH(CH_2CH_2O)(CH_2)_2C(=O)NH-$, $-(CH_2)_3C(=O)NH(CH_2CH_2O)_2(CH_2)_2C(=O)NH-$, $-(CH_2)_3C(=O)NH(CH_2CH_2O)_3(CH_2)_2C(=O)NH-$, $-(CH_2)_3C(=O)NH(CH_2CH_2O)_4(CH_2)_2C(=O)NH-$, $-(CH_2)_3C(=O)NH(CH_2CH_2O)_5(CH_2)_2C(=O)NH-$, $-(CH_2)_3C(=O)NH(CH_2CH_2O)_6(CH_2)_2C(=O)NH-$, $-(CH_2)_3C(=O)NH(CH_2CH_2O)_7(CH_2)_2C(=O)NH-$, $-(CH_2)_3C(=O)NH(CH_2CH_2O)_8(CH_2)_2C(=O)NH-$, $-(CH_2)_3C(=O)NH(CH_2CH_2O)_9(CH_2)_2C(=O)NH-$, $-(CH_2)_3C(=O)NH(CH_2CH_2O)_{10}(CH_2)_2C(=O)NH-$, $-(CH_2)_3C(=O)NH(CH_2CH_2O)_{11}(CH_2)_2C(=O)NH-$, or $-(CH_2)_3C(=O)NH(CH_2CH_2O)_{12}(CH_2)_2C(=O)NH-$.

Target Proteins and Target Protein Binding Moieties

Disclosed herein, in some embodiments, are target proteins. In some embodiments, a target protein comprises a transcription factor. In some embodiments, a target protein comprises an epigenetic modulator. In some embodiments, a target protein comprises p300 or CBP (CREB binding protein). In some embodiments, a target protein comprises p300. In some embodiments, a target protein comprises CBP. In some embodiments, a target protein comprises a bromodomain-containing protein. In some embodiments, a target protein comprises bromodomain-containing protein 4 (BRD4). In some embodiments, a target protein comprises a kinase. In some embodiments, a target protein comprises a cyclin-dependent kinase. In some embodiments, a target protein comprises a cyclin-dependent kinase (CDK). In some embodiments, a target protein comprises cyclin-dependent kinase 4 (CDK4) or cyclin-dependent kinase 6 (CDK6). In some embodiments, a target protein comprises CDK4. In some embodiments, a target protein comprises CDK6. In some embodiments, a target protein comprises CDK9. In some embodiments, a target protein comprises CDK, CDK1, CDK2, CDK3, CDK4, CDK6, CDK7, CDK8, CDK9, CDK10, CDK11, CDK12, or CDK13. In some embodiments, a target protein comprises a tyrosine receptor kinase (Trk). In some embodiments, a target protein comprises TrkA. In some embodiments, a target protein comprises TrkB. In some embodiments, a target protein comprises TrkC. In some embodiments, a target protein comprises mitogen-activated protein kinase kinase (MKK or MEK). In some embodiments, a target protein comprises MEK1. In some embodiments, a target protein comprises MEK2. In some embodiments, the heterobifunctional compound degrades the target protein.

Some non-limiting examples of target proteins include any one of B7.1, B7, TINFRlm, TNFR2, NADPH oxidase, a partner in an apoptosis pathway, BclIBax, C5a receptor, HMG-CoA reductase, PDE V phosphodiesterase type. PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, a receptor, a 5HT receptor, a dopamine receptor, a G-protein (e.g. Gq), a histamine receptor, 5-lipoxygenase, tryptase serine protease, thymidylate synthase, purine nucleoside phosphorylase, GAPDH, a trypanosomal protein, glycogen phosphorylase, carbonic anhydrase, a chemokine receptor, JAK, STAT, RXR, RAR, HIV 1 protease, HIV 1 integrase, influenza, neuramimidase, hepatitis B reverse transcriptase, sodium channel, multi drug resistance (MDR), protein P-glycoprotein, MRP, a tyrosine kinase, CD23, CD124, tyrosine kinase p56 lck, CD4, CD5, IL-2 receptor, IL-1 receptor, TNF-alphaR, ICAM1, a Ca+ channel, VCAM, an integrin, a VLA-4 integrin, a selectin, CD40, CD40L, a neurokinin, a neurokinin receptor, inosine monophosphate dehydrogenase, p38 MAP Kinase, Ras, Raf, Mek, Erk, interleukin-1 converting enzyme, a caspase, HCV, NS3 protease, HCV NS3 RNA helicase, glycinamide ribonucleotide formyl transferase, rhinovirus 3C protease, herpes simplex virus-1 (HSV-I), a protease, cytomegalovirus (CMV) protease, poly (ADP-ribose) polymerase, a cyclin dependent kinase, vascular endothelial growth factor, oxytocin receptor, microsomal transfer protein inhibitor, bile acid transport inhibitor, a 5 alpha reductase inhibitor, angiotensin II, a glycine receptor, a noradrenaline reuptake receptor, an endothelin receptor, neuropeptide Y, a neuropeptide Y receptor, an estrogen receptor, an androgen receptor, an adenosine receptor, an adenosine kinase, AMP deaminase, a purinergic receptor (e.g. P2Y1, P2Y2, P2Y4, P2Y6, or P2X1-7), a farnesyltransferase, geranylgeranyl transferase, TrkA, a receptor for NGF, beta-amyloid, tyrosine kinase Flk-IIKDR, vitronectin receptor, an integrin receptor, Hcr2 neu, telomerase inhibition, cytosolic phospholipaseA2, EGF receptor tyrosine kinase, ecdysone 20-monooxygenase, ion channel of the GABA gated chloride channel, acetylcholinesterase, voltage-sensitive sodium channel protein, calcium release channel, a chloride channel, acetyl-CoA carboxylase, adenylosuccinate synthetase, protoporphyrinogen oxidase, or enolpyruvylshikimate-phosphate synthase. The target protein may include p25 or p35.

The target protein may include a cyclin. In some embodiments, the cyclin is a cyclin D. The cyclin D may include cyclin D1. The cyclin D may include cyclin D2. The cyclin D may include cyclin D3. In some embodiments, the heterobifunctional compound degrades the cyclin. Some examples of cyclins include cyclin A, cyclin B, cyclin C, cyclin D, cyclin D1, cyclin D2, cyclin D3, cyclin E, cyclin H, cyclin K, cyclin T, or cyclin T1.

In some embodiments, a target protein comprises a protein associated with a disease state. For example, the target protein may be present or upregulated in the disease state. In some embodiments, a target protein comprises a pathogen protein. In some embodiments, a target protein comprises a viral protein. In some embodiments, a target protein comprises a bacterial protein.

Target proteins are numerous in kind and are selected from proteins that are expressed in a cell such that at least a portion of the sequences is found in the cell and may bind to a target protein binding moiety. The term "protein" may include oligopeptides and polypeptide sequences of sufficient length that they can bind to a target protein binding moiety. Any protein in a eukaryotic system or a microbial system, including a virus, bacteria or fungus, as otherwise described herein, may be a target protein for ubiquitination mediated by the compounds according to the present disclosure. The target protein may be a eukaryotic protein.

Any protein, which can bind to a protein target moiety and acted on or degraded by an ubiquitin ligase may be a target protein. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eukaryotes and prokaryotes including humans as targets for drug therapy, other animals, including domesticated animals, microbials for the determination of targets for antibiotics and other antimicrobials and plants, and even viruses, among numerous others.

In some embodiments, a target protein comprises any of Hsp90, a kinase, MDM2, a Human BET Bromodomain-containing protein, an HDAC, a lysine methyltransferase, an angiogenesis protein, an immunomodulatory protein, or aryl hydrocarbon receptor (AHR). In some embodiments, a target protein comprises a heat shock protein (HSP) such as HSP90. In some embodiments, a target protein comprises a kinase or a phosphatase. In some embodiments, the target protein includes a kinase. In some embodiments, the kinase is a tyrosine kinase. In some embodiments, the kinase is VEGFR3. In some embodiments, the kinase is an aurora kinase. In some embodiments, the kinase is ALK. In some embodiments, the kinase is JAK2. In some embodiments, the kinase is Alk. In some embodiments, the kinase is Met. In some embodiments, the kinase is Abl. In some embodiments, the kinase is B-Raf or Mek. In some embodiments, a target protein comprises a phosphatase. In some embodiments, the phosphatase is a protein tyrosine phosphatase. In some embodiments, the phosphatase includes a SHP-2 domain. In some embodiments, a target protein comprises an MDM. In some embodiments, the MDM is MDM2. In some embodiments, a target protein comprises an HDAC. In some embodiments, a target protein comprises a methyltransferase such as a lysine methyltransferase. In some embodiments, a target protein comprises an angiogenesis. In some embodiments, a target protein comprises an immunomodulatory or immunosuppressive protein. In some embodiments, a target protein comprises an aryl hydrocarbon receptor (AHR). In some embodiments, a target protein comprises RAF receptor In some embodiments, a target protein comprises FKBP. In some embodiments, the target protein comprises estrogen receptor or an androgen receptor. In some embodiments, a target protein comprises an androgen receptor. In some embodiments, a target protein comprises an estrogen receptor. In some embodiments, a target protein comprises a thyroid hormone receptor. In some embodiments, a target protein comprises an HIV protein such as an HIV protease or an HIV integrase. In some embodiments, a target protein comprises an HCV protein such as an HCV protease. In some embodiments, a target protein comprises acyl-protein thioesterase-1 or -2.

Disclosed herein, in some embodiments, are target protein binding moieties. For example, a ligand described herein may include a target protein binding moiety. In some embodiments, the target protein binds to or is bound by a target protein binding moiety. In some embodiments, the target protein binding moiety binds to a target protein. In some embodiments, binding of the ligand to the target protein in a cell results in degradation of the target protein. For example, the ligand may increase ubiquiting mediated target protein degradation, or proteasomal degradation of the target protein. The target protein binding moiety can be any molecule that binds to a target protein. For example, the target protein binding moiety can be any small molecule known to bind to a target protein.

Disclosed herein, in some embodiments, are compounds comprising a DDB1 binding moiety. In some embodiments, the DDB1 binding moiety binds to a DDB1 protein. In some embodiments, the DDB1 binding moiety is bound to a DDB1 protein. In some embodiments, the compound binds to a DDB1 protein via the DDB1 binding moiety. In some embodiments, the compound is bound to a DDB1 protein via the DDB1 binding moiety.

In some embodiments, the DDB1 binding moiety is incorporated into a ligand described herein. In some embodiments, the DDB1 binding moiety is part of a modified protein described herein. In some embodiments, the DDB1 binding moiety is part of a ligand-protein complex described herein. In some embodiments, the DDB1 binding moiety is attached to a linker such as a linker described herein. In some embodiments, the DDB1 binding moiety is covalently connected through the linker to a target protein binding moiety described herein. In some embodiments, the target protein binding moiety is incorporated into a molecular structure or formula disclosed herein.

Non-limiting examples of small molecule target protein binding moieties include Hsp90 inhibitors, kinase inhibitors, MDM2 inhibitors, compounds targeting Human BET Bromodomain-containing proteins. HDAC inhibitors, human lysine methyltransferase inhibitors, angiogenesis inhibitors, immunosuppressive compounds, and compounds targeting the aryl hydrocarbon receptor (AHR), among numerous others. By coupling a DDB1 binding moiety to a target protein binding moiety, the target protein may be ubiquitinated and/or degraded by a proteasome.

In certain aspects, the protein binding moiety is a haloalkane (preferably a C1-C10 alkyl group which is substituted with at least one halo group, preferably a halo group at the distal end of the alkyl group (i.e., away from the linker or DDB1 binding moiety), which may covalently bind to a dehalogenase enzyme in a patient or subject or in a diagnostic assay.

Target protein binding moieties according to the present disclosure may include any moiety which binds to a protein specifically (e.g. binds to a target protein) and may include the following non-limiting examples of small molecule target protein moieties: Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. Compositions described herein exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. These binding moieties may be linked to a DDB1 binding moiety through a linker to present a target protein (to which the protein target moiety is bound) in proximity to the ubiquitin ligase for ubiquitination and degradation.

In some embodiments, the target protein binding moiety includes a haloalkyl group, wherein said alkyl group generally ranges in size from about 1 or 2 carbons to about 12 carbons in length, often about 2 to 10 carbons in length, often about 3 carbons to about 8 carbons in length, more often about 4 carbons to about 6 carbons in length. The haloalkyl groups are generally linear alkyl groups (although branched-chain alkyl groups may also be used) and are end-capped with at least one halogen group, preferably a single halogen group, often a single chloride group. Haloalkyl target protein binding moieties for use in the present disclosure may be represented by the chemical structure-$(CH_2)$v-Halo where v is any integer from 2 to about 12, often about 3 to about 8, more often about 4 to about 6. Halo may be any halogen, but is preferably Cl or Br, more often Cl.

In some embodiments, the target protein binding moiety is a

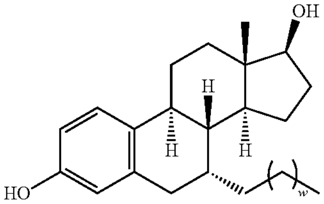

group, where w is 0 to 3, preferably 1 or 2. This group may bind selectively to a target protein comprising an estrogen receptor, and may be useful for treating diseases which are modulated through estrogen receptors, and in particular cancers, such as breast cancer, endometrial cancer, ovarian cancer and uterine cancer, among others.

Target protein binding moieties according to the present disclosure include, for example, haloalkane halogenase inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR). Some compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest.

In some embodiments, the target protein binding moiety includes a heat shock protein (HSP; e.g. HSP90) binder or inhibitor. HSP90 inhibitors as used herein include, but are not limited to: N-[4-(3H-imidazo[4,5-C]pyridin-2-yl)-9H-fluoren-9-yl]-succinamide, 8-[(2,4-dimethylphenyl)sulfanyl]-3-pent-4-yn-1-yl-3H-purin-6-amine, 5-[2,4-dihydroxy-5-(1-methylethyl)phenyl]-N-ethyl-4-[4-(morpholin-4-ylmethyl)phenyl]isoxazole-3-carboxamide, PU3, or (4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1] or any of its derivatives (e.g. 17-alkylamino-17-desmethoxygeldanamycin.

In some embodiments, N-[4-(3H-imidazo[4,5-C]pyridin-2-yl)-9H-fluoren-9-yl]-succinamide is attached via its terminal amide group to a linker described herein. In some embodiments, 8-[(2,4-dimethylphenyl)sulfanyl]-3-pent-4-yn-1-yl-3H-purin-6-amine is attached via its terminal acetylene group to a linker described herein. In some embodiments, 5-[2,4-dihydroxy-5-(1-methylethyl)phenyl]-N-ethyl-4-[4-(morpholin-4-ylmethyl)phenyl]isoxazole-3-carboxamide is attached via its amide group (e.g. at the amine or at the alkyl group on the amine) to a linker described herein. In some embodiments, PU3 is attached via its butyl group to a linker described herein. In some embodiments, (4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1] or any of its derivatives are attached by an amide group to a linker described herein.

In some embodiments, the target protein binding moiety includes a kinase inhibitor or a phosphatase inhibitor. In some embodiments, the target protein binding moiety includes a kinase inhibitor. In some embodiments, the kinase inhibitor is a tyrosine kinase inhibitor. In some embodiments, the kinase inhibitor is a VEGFR3 inhibitor. In some embodiments, the kinase inhibitor is an aurora kinase inhibitor. In some embodiments, the kinase inhibitor is an ALK inhibitor. In some embodiments, the kinase inhibitor is a JAK2 inhibitor. In some embodiments, the kinase inhibitor is an Alk inhibitor. In some embodiments, the kinase inhibitor is a Met inhibitor. In some embodiments, the kinase inhibitor is an Abl inhibitor. In some embodiments, the kinase inhibitor is a B-Raf/Mek inhibitor.

Non-limiting examples of kinase inhibitors include any one of erlotinib, sunitinib, sorafenib, desatinib, lapatinib, U09-CX-5279, Y1W, Y1X, 1-ethyl-3-(2-{[3-(1-methylethyl)[1,2,4]triazolo[4,3-a]pyridin-6-yl]sulfanyl}benzyl) urea, a 2,6-naphthyridine, 07U, YCF, XK9, NXP, N-{4-[(1E)-N—(N-hydroxycarbamimidoyl)ethanehydrazonoyl] phenyl}-7-nitro-1H-indole-2-carboxamide, afatinib, fostamatinib, gefitinib, lenvatinib, vandetanib, vemurafenib, gleevec, pazopanib, AT-9283, TAE684, nilotinib, NVP—BSK805, crizotinib, JNJ FMX, or foretinib.

In some embodiments, erlotinib is attached via its ether group to a linker described herein. In some embodiments, sunitinib is attached via its pyrrole moiety to a linker described herein. In some embodiments, sorafenib is attached via its phenyl moiety to a linker described herein. In some embodiments, desatinib is attached via its pyrimidine to a linker described herein. In some embodiments, lapatinib is attached via its terminal methyl of its sulfonyl methyl group to a linker described herein. In some embodiments, U09-CX-5279 is attached via its amine (aniline), carboxylic acid or amine alpha to cyclopropyl group, or cyclopropyl group to a linker described herein. In some embodiments, 1-ethyl-3-(2-{[3-(1-methylethyl)[1,2,4]triazolo[4,3-a]pyridin-6-yl]sulfanyl}benzyl)urea is attached via its propyl group to a linker described herein. In some embodiments, Y1W is attached via its propyl or butyl group to a linker described herein. In some embodiments, 6TP is attached via a terminal methyl group bound to an amide moiety to a linker described herein. In some embodiments, 07U is attached via its secondary amine or terminal amino group to a linker described herein. In some embodiments, YCF is attached via either of its terminal hydroxyl groups to a linker described herein. In some embodiments, XK9 is attached via its terminal hydroxyl group to a linker described herein. In some embodiments, NXP is attached via its terminal hydrazone group (NXP) to a linker described herein. In some embodiments, afatinib is attached via its aliphatic amine group to a linker described herein. In some embodiments, fostamatinib is attached via its methoxy group to a linker described herein. In some embodiments, gefitinib is attached via its methoxy group or its ether group to a linker described herein. In some embodiments, lenvatinib is attached via its cyclopropyl group to a linker described herein. In some embodiments, vandetanib is attached via its methoxy group or hydroxyl group to a linker described herein. In some embodiments, vemurafenib is attached via its sulfonyl propyl group to a linker described herein. In some embodiments, gleevec is attached via its amide group or via its aniline amine group to a linker described herein. In some embodiments, pazopanib is attached via its phenyl moiety or via its aniline amine group to a linker described herein. In some embodiments, AT-9283 is attached via its phenyl moiety to a linker described herein. In some embodiments, TAE684 is attached via its phenyl moiety to a linker described herein. In some embodiments, nilotinib is attached via its phenyl moiety or via its aniline amine group to a linker described herein. In some embodiments, crizotinib is attached via its phenyl moiety or diazole group to a linker described herein. In some embodiments, crizotinib is attached via its phenyl moiety or diazole group to a linker described herein. In some embodiments, JNJ FMX is attached via its phenyl moiety to a linker described herein.

In some embodiments, the target protein binding moiety includes a phosphatase inhibitor. In some embodiments, the phosphatase inhibitor is a protein tyrosine phosphatase inhibitor. In some embodiments, the phosphatase inhibitor is an inhibitor of a SHP-2 domain of a tyrosine phosphatase. A non-limiting example of a phosphatase inhibitors includes PTP1B. Non-limiting examples of phosphatase inhibitors are included in Table 4.

In some embodiments, the target protein binding moiety includes an MDM inhibitor. In some embodiments, the MDM inhibitor is an MDM2 inhibitor. Non-limiting examples of MDM2 inhibitors include any one of nutlin-3, nutlin-2, nutlin-1, or trans-4-iodo-4'-boranyl-chalcone. In some embodiments, nutlin-3, nutlin-2, or nutlin-1 is attached via a methoxy group or hydroxyl group to a linker described herein. In some embodiments, trans-4-iodo-4'-boranyl-chalcone is attached via its hydroxyl group to a linker described herein. Non-limiting examples of MDM2 inhibitors are included in Table 4.

In some embodiments, the target protein binding moiety includes a compound that targets a human BET bromodomain-containing protein. In some embodiments, the compound that targets a human BET bromodomain-containing protein is a 3,5-dimethylisoxazole. Non-limiting examples of compounds that target a human BET bromodomain-containing protein are included in Table 4.

In some embodiments, the target protein binding moiety includes a compound that inhibits an HDAC. Non-limiting examples of compounds that inhibit an HDAC are included in Table 4.

In some embodiments, the target protein binding moiety includes a compound that inhibits a methyltransferase such as a lysine methyltransferase. In some embodiments, the methyltransferase is a human lysine methyltransferase. In some embodiments, the lysine methyltransferase inhibitor is azacytidine. In some embodiments, azacytidine is attached via a hydroxy or amino group to a linker described herein. In some embodiments, the lysine methyltransferase inhibitor is decitabine. In some embodiments, decitabine is attached via a hydroxy or amino group to a linker described herein. Non-limiting examples of lysine methyltransferase inhibitors are included in Table 4.

In some embodiments, the target protein binding moiety includes an angiogenesis inhibitor. Non-limiting examples of angiogenesis inhibitors include GA-1, estradiol, testosterone, DHT, ovalicin, or fumagillin.

In some embodiments, the target protein binding moiety includes an immunosuppressive compound. Non-limiting examples of immunosuppressive compounds include AP21998, a glucocorticoid (e.g., hydrocortisone, prednisone, prednisolone, or methylprednisolone), beclomethasone dipropionate, methotrexate, ciclosporin, tacrolimus, rapamycin, or actinomycin. In some embodiments, the glucocorticoid is attached via a hydroxyl to a linker described herein. In some embodiments, the beclomethasone dipropionate is attached via a propionate to a linker described herein. In some embodiments, methotrexate is attached via either of its terminal hydroxyls to a linker described herein. In some embodiments, ciclosporin is attached via a butyl group to a linker described herein. In some embodiments, tacrolimus is attached via a methoxy group to a linker described herein. In some embodiments, rapamycin is attached via a methoxy group to a linker described herein. In some embodiments, actinomycin is attached via an isopropyl group to a linker described herein.

In some embodiments, the target protein binding moiety includes a compound that targets an aryl hydrocarbon receptor (AHR). Non-limiting examples of compounds that target an AHR include apigenin, SR1, or LGC006.

In some embodiments, the target protein binding moiety includes a compound that targets a RAF receptor. A non-limiting example of a compound that target a RAF receptor is included in Table 4.

In some embodiments, the target protein binding moiety includes a compound that targets FKBP. A non-limiting example of a compound that target FKBP is included in Table 4.

In some embodiments, the target protein binding moiety includes a compound that targets an androgen receptor. Non-limiting examples of compounds that target an androgen receptor include any one of RU59063, SARM, DHT, MDV3100, ARN-509, a hexahydrobenzisoxazole, or a tetramethylcyclobutane. Non-limiting examples of compounds that target an androgen receptor are included in Table 4.

In some embodiments, the target protein binding moiety includes a compound that targets an estrogen receptor. A non-limiting example of a compound that targets an estrogen receptor is included in Table 4.

In some embodiments, the target protein binding moiety includes a compound that targets a thyroid hormone receptor. A non-limiting example of a compound that target a thyroid hormone receptor is included in Table 4.

In some embodiments, the target protein binding moiety includes a compound that inhibits an HIV protease. Non-limiting examples of compounds that inhibit an HIV protease are included in Table 4.

In some embodiments, the target protein binding moiety includes a compound that inhibits an HIV integrase. Non-limiting examples of compounds that inhibit an HIV integrase are included in Table 4.

In some embodiments, the target protein binding moiety includes a compound that targets an HCV protease. A non-limiting example of a compound that targets an HCV protease is included in Table 4.

In some embodiments, the target protein binding moiety includes a compound that targets acyl-protein thioesterase-1 and/or -2. A non-limiting example of a compound that targets acyl-protein thioesterase-1 and/or -2 is included in Table 4.

In some embodiments, compounds comprising a target protein binding moiety are shown in Table 4. In the table. "R" or a wavy line indicates an optional point of attachment to a linker or other molecule such as a DDB1 binding moiety.

TABLE 4

Target protein binding moieties

| Compound | Structure | Notes (e.g. what target protein it may bind to) |
|---|---|---|
| A-1 | 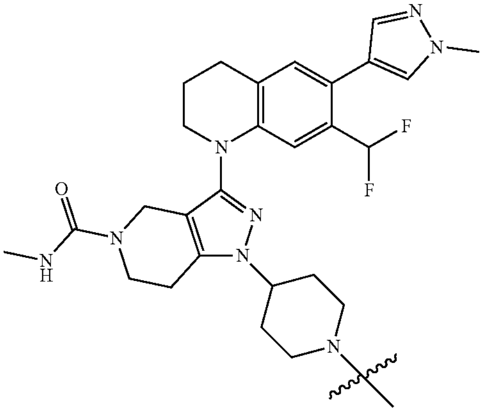 | Binds CBP and/or p300 |
| A-2 | 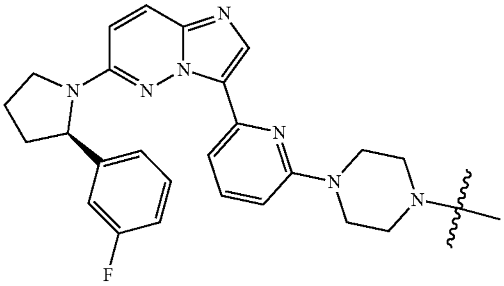 [SMILES: *N1CCN(c2cccc(-c3cnc4ccc(N5CCC[C@@H]5c5cccc(F)c5)nn34)n2)CC1] | Binds TrkA, TrkB, TrkC |
| A-3 | 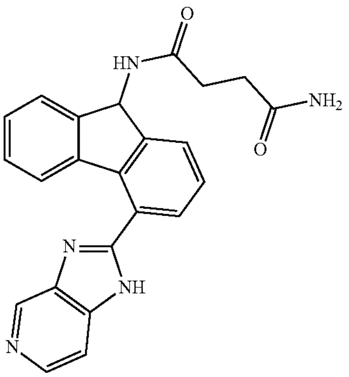 [SMILES: NC(=O)CCC(=O)NC1c2ccccc2-c2c(-c3nc4cnccc4[nH]3)cccc21] | Binds HSP90 |
| A-4 | 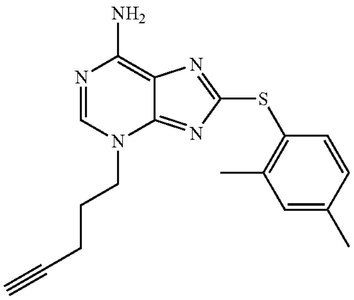 [SMILES: C#CCCCn1cnc(N)c2nc(Sc3ccc(C)cc3C)nc1-2] | Binds HSP90 |

TABLE 4-continued
| Target protein binding moieties | | |
|---|---|---|
| Compound | Structure | Notes (e.g. what target protein it may bind to) |
| A-5 | 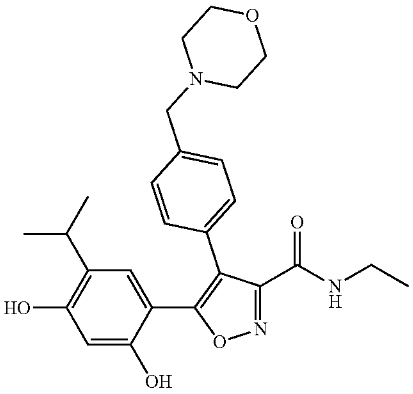 [SMILES: CCNC(=O)c1noc(-c2cc(C(C)C)c(O)cc2O)c1-c1ccc(CN2CCOCC2)cc1] | Binds HSP90 |
| A-6 | 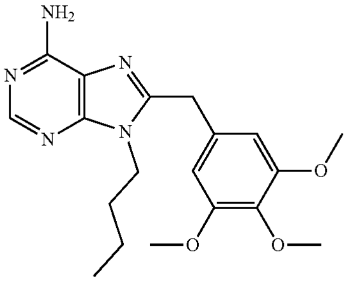 [SMILES: CCCCn1c(Cc2cc(OC)c(OC)c(OC)c2)nc2c(N)ncnc21] | Binds HSP90 |
| A-7 | 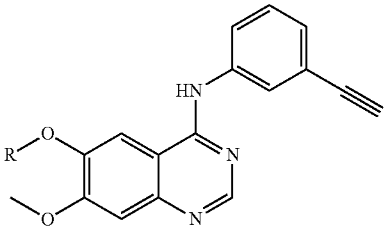 | Binds a kinase, binds a tyrosine kinase |
| A-8 | 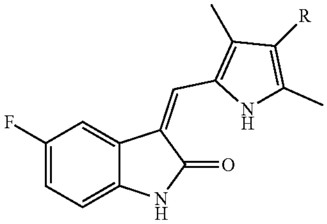 | Binds a kinase |
| A-9 | 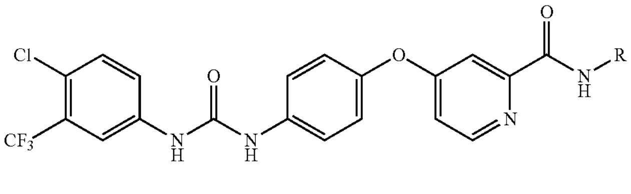 | Binds a kinase |

TABLE 4-continued
| Target protein binding moieties | | |
|---|---|---|
| Compound | Structure | Notes (e.g. what target protein it may bind to) |
| A-10 | 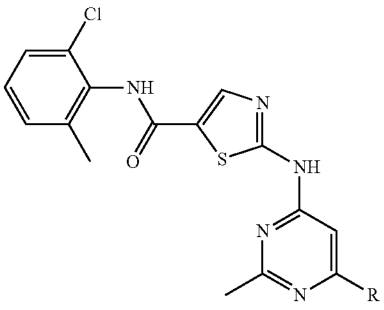 | Binds a kinase |
| A-11 | 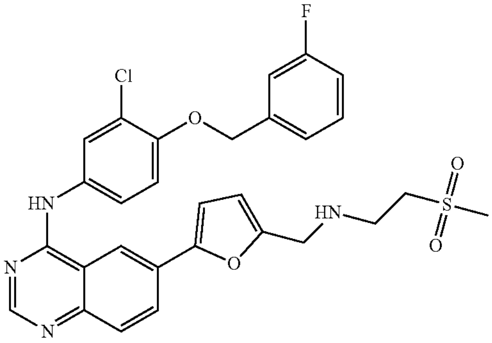 [SMILES: CS(=O)(=O)CCNCc1ccc(-c2ccc3ncnc(Nc4ccc(OCc5cccc(F)c5)c(Cl)c4)c3c2)o1] | Binds a kinase |
| A-12 | 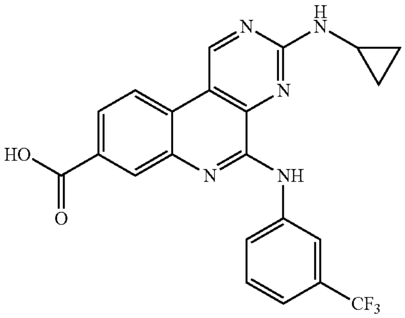 [SMILES: O=C(O)c1ccc2c(c1)nc(Nc1cccc(C(F)(F)F)c1)c1nc(NC3CC3)ncc12] | Binds a kinase |
| A-13 | 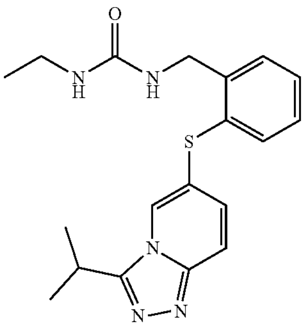 [SMILES: CCNC(=O)NCc1ccccc1Sc1ccc2nnc(C(C)C)n2c1] | Binds a kinase |

TABLE 4-continued
| Target protein binding moieties | | |
|---|---|---|
| Compound | Structure | Notes (e.g. what target protein it may bind to) |
| A-14 | 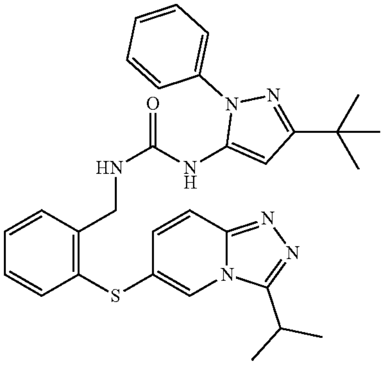 [SMILES: CC(C)c1nnc2ccc(Sc3ccccc3CNC(=O)Nc3cc(C(C)(C)C)nn3-c3ccccc3)cn12] | Binds a kinase |
| A-15 | 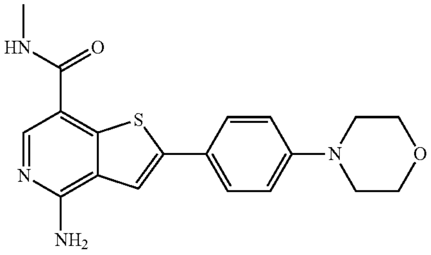 [SMILES: CNC(=O)c1cnc(N)c2cc(-c3ccc(N4CCOCC4)cc3)sc12] | Binds a kinase |
| A-16 | 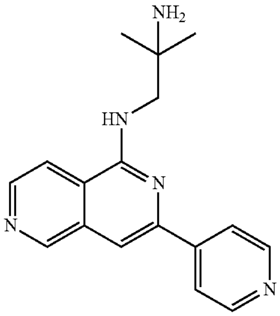 [SMILES: CC(C)(N)CNc1nc(-c2ccncc2)cc2cnccc12] | Binds a kinase |
| A-17 | 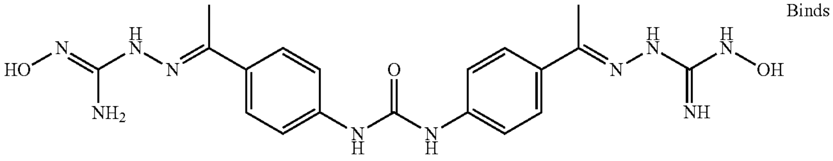 | Binds a kinase |
| A-18 | 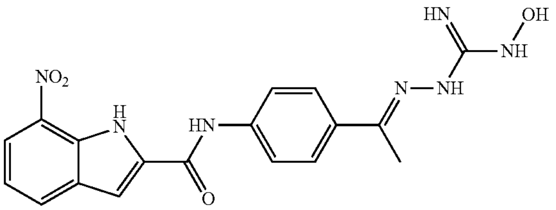 [SMILES: C/C(=N\NC(=N)NO)c1ccc(NC(=O)c2cc3cccc([N+](=O)[O-])c3[nH]2)cc1] | Binds a kinase |

TABLE 4-continued
| Target protein binding moieties | | |
|---|---|---|
| Compound | Structure | Notes (e.g. what target protein it may bind to) |
| A-19 | 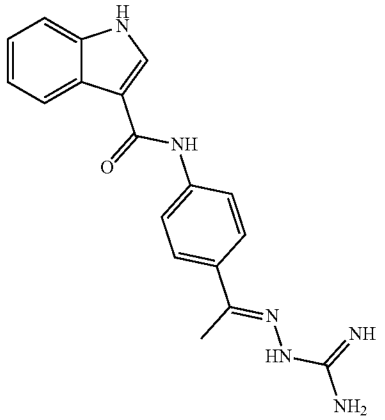 [SMILES: C/C(=N\NC(=N)N)c1ccc(NC(=O)c2c[nH]c3ccccc23)cc1] | Binds a kinase |
| A-20 | 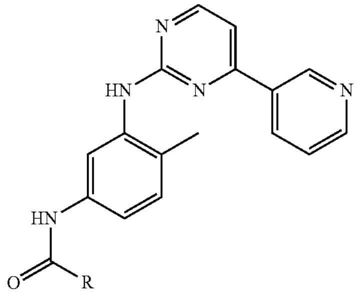 | Binds a kinase |
| A-21 | 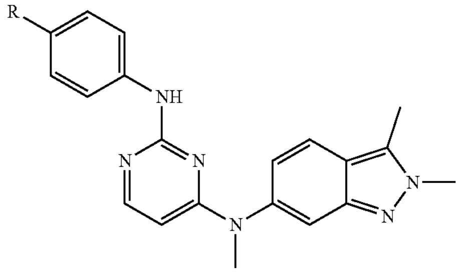 | Binds a kinase, binds VEGFR3 |
| A-22 | 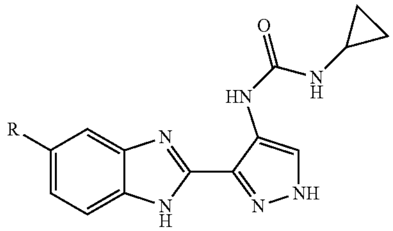 | Binds a kinase, binds aurora kinase |
| A-23 | 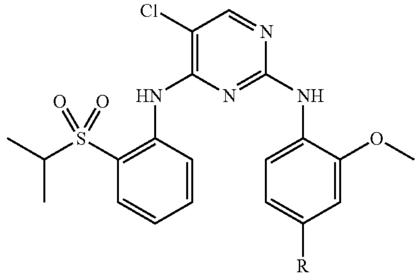 | Binds a kinase, binds ALK |

TABLE 4-continued
| Target protein binding moieties | | |
|---|---|---|
| Compound | Structure | Notes (e.g. what target protein it may bind to) |
| A-24 | 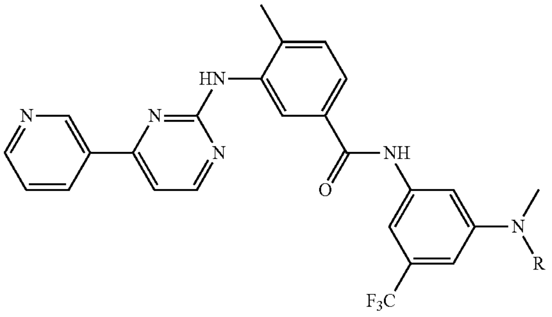 | Binds a kinase, binds Abl |
| A-25 | 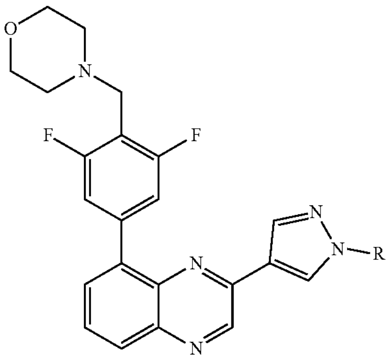 | Binds a kinase, binds JAK2 |
| A-26 | 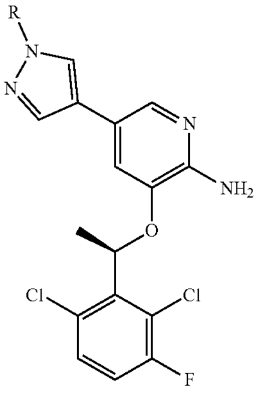 | Binds a kinase, binds Alk |
| A-27 | 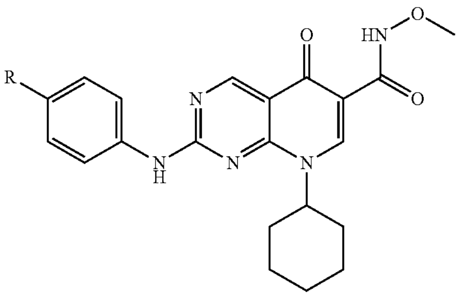 | Binds a kinase |

TABLE 4-continued
| Target protein binding moieties | | |
|---|---|---|
| Compound | Structure | Notes (e.g. what target protein it may bind to) |
| A-28 | 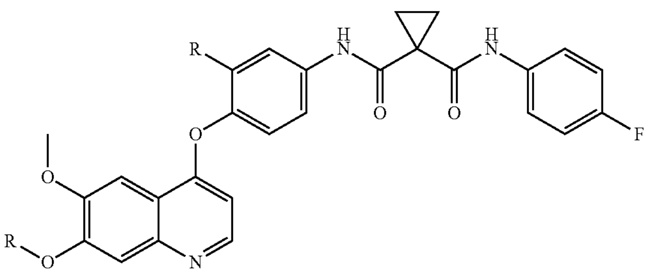 | Binds a kinase; binds Met |
| A-29 | 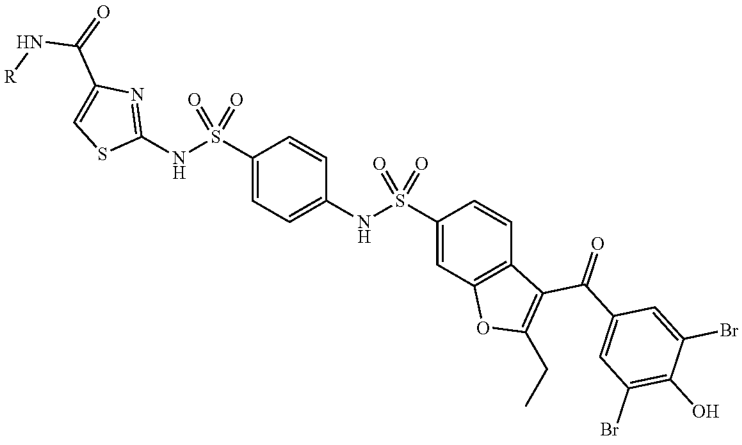 | Binds a phosphatase; binds a tyrosine phosphatase |
| A-30 | 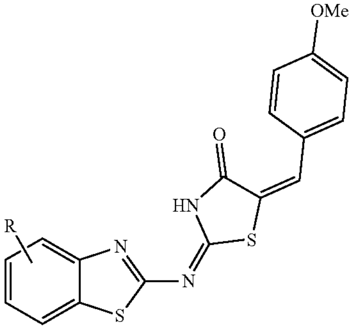 | Binds a phosphatase; binds a tyrosine phosphatase; binds an SHP-2 domain |
| A-31 | 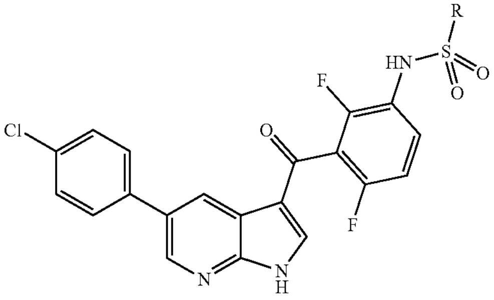 | Binds a kinase; binds B-Raf and/or Mek |

TABLE 4-continued
| Target protein binding moieties | | |
|---|---|---|
| Compound | Structure | Notes (e.g. what target protein it may bind to) |
| A-32 | 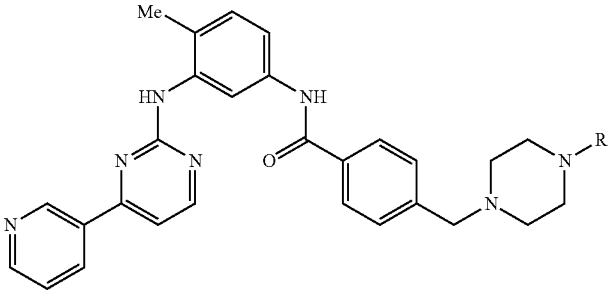 | Binds a kinase; binds a tyrosine kinase; binds ABL |
| A-33 | 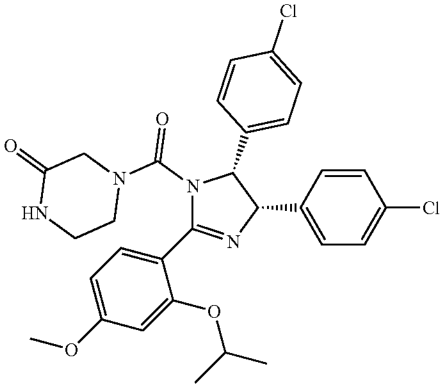 [SMILES: COc1ccc(C2=N[C@@H](c3ccc(Cl)cc3)[C@@H](c3ccc(Cl)cc3)N2C(=O)N2CCNC(=O)C2)c(OC(C)C)c1] | Binds MDM2 |
| A-34 | 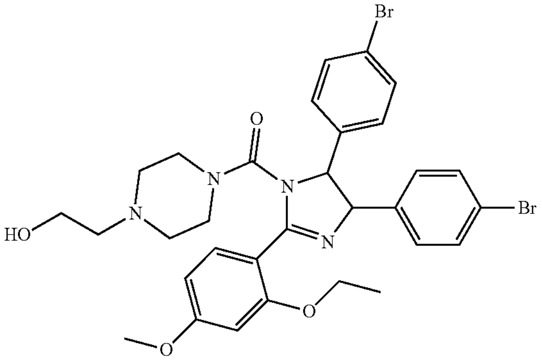 [SMILES: CCOc1cc(OC)ccc1C1=NC(c2ccc(Br)cc2)C(c2ccc(Br)cc2)N1C(=O)N1CCN(CCO)CC1] | Binds MDM2 |
| A-35 | 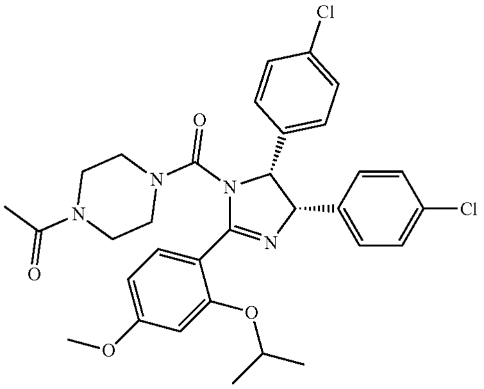 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1] | Binds MDM2 |

TABLE 4-continued

| Target protein binding moieties | | |
|---|---|---|
| Compound | Structure | Notes (e.g. what target protein it may bind to) |
| A-36 | 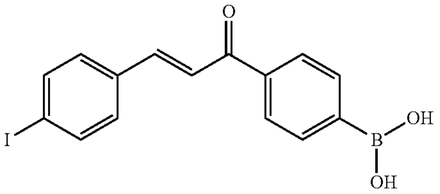 [SMILES: O=C(/C=C/c1ccc(I)cc1)c1ccc(B(O)O)cc1] | Binds MDM2 |
| A-37 | 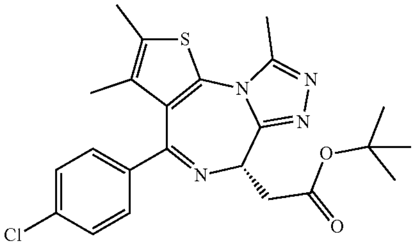 [SMILES: Cc1sc2c(c1C)C(c1ccc(Cl)cc1)=N[C@@H](CC(=O)OC(C)(C)C)c1nnc(C)n1-2] | Binds a human BET bromodomain-containing protein |
| A-38 | 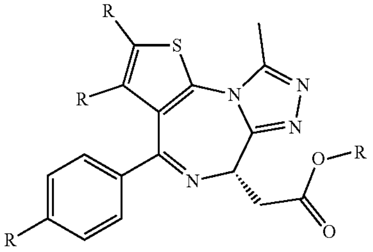 | Binds a human BET bromodomain-containing protein |
| A-39 | 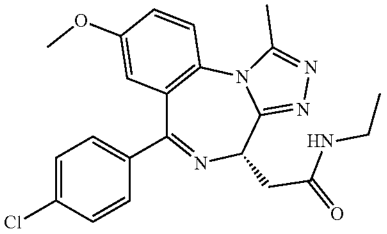 [SMILES: CCNC(=O)C[C@@H]1N=C(c2ccc(Cl)cc2)c2cc(OC)ccc2-n2c(C)nnc21] | Binds a human BET bromodomain-containing protein |
| A-40 | 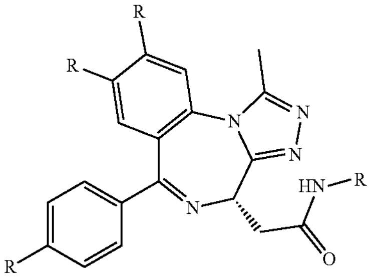 | Binds a human BET bromodomain-containing protein |
| A-41 | 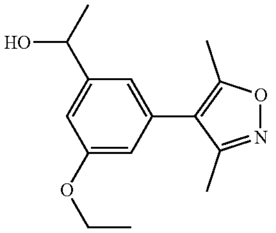 [SMILES: CCOc1cc(-c2c(C)noc2C)cc(C(C)O)c1] | Binds a human BET bromodomain-containing protein |

TABLE 4-continued
| Target protein binding moieties | | |
|---|---|---|
| Compound | Structure | Notes (e.g. what target protein it may bind to) |
| A-42 | 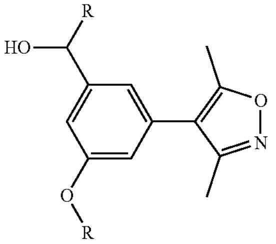 | Binds a human BET bromodomain-containing protein |
| A-43 | 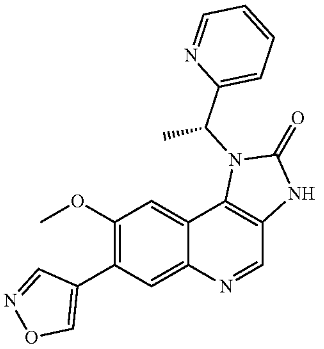 [SMILES: COc1cc2c(cc1-c1cnoc1)ncc1[nH]c(=O)n([C@H](C)c3ccccn3)c12] | Binds a human BET bromodomain-containing protein |
| A-44 | 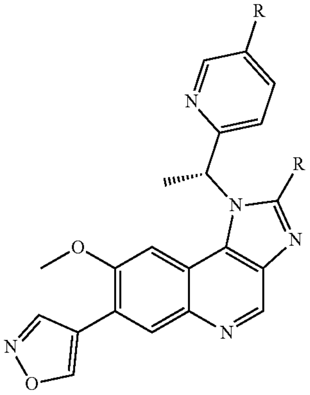 | Binds a human BET bromodomain-containing protein |
| A-45 | 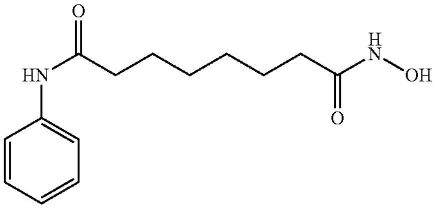 [SMILES: O=C(CCCCCCC(=O)Nc1ccccc1)NO] | Binds an HDAC |
| A-46 | 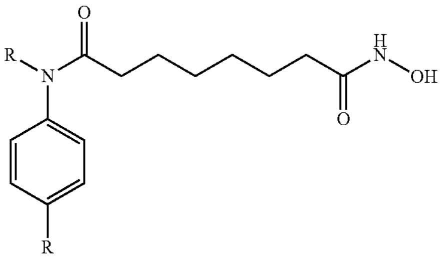 | Binds an HDAC |

TABLE 4-continued
| Target protein binding moieties | | |
|---|---|---|
| Compound | Structure | Notes (e.g. what target protein it may bind to) |
| A-47 | 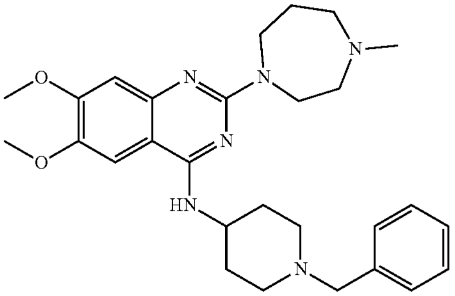 [SMILES: COc1cc2nc(N3CCCN(C)CC3)nc(NC3CCN(Cc4ccccc4)CC3)c2cc1OC] | Binds a lysine methyltransferase |
| A-48 | 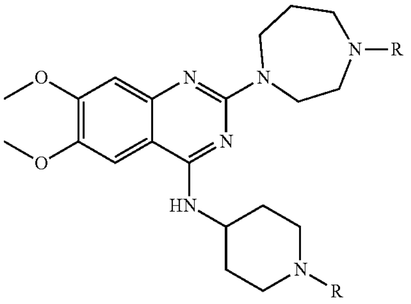 | Binds a lysine methyltransferase |
| A-49 | 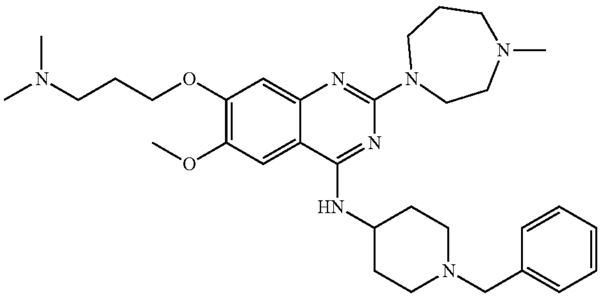 [SMILES: COc1cc2c(NC3CCN(Cc4ccccc4)CC3)nc(N3CCCN(C)CC3)nc2cc1OCCCN(C)C] | Binds a lysine methyltransferase |
| A-50 | 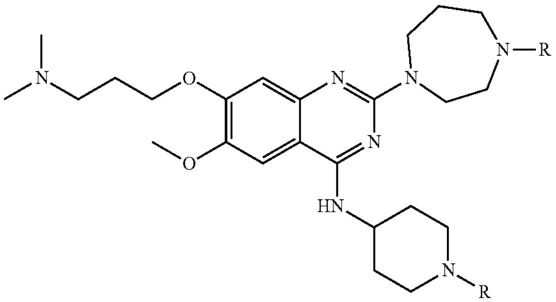 | Binds a lysine methyltransferase |
| A-51 | 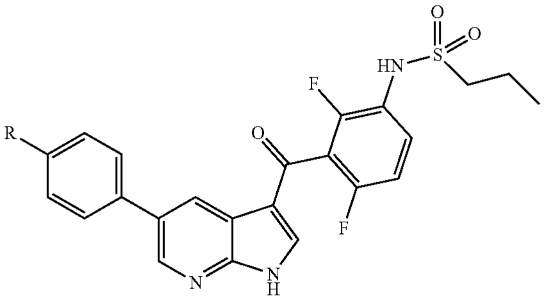 | Binds RAF receptor |

TABLE 4-continued
Target protein binding moieties
| Compound | Structure | Notes (e.g. what target protein it may bind to) |
|---|---|---|
| A-52 | 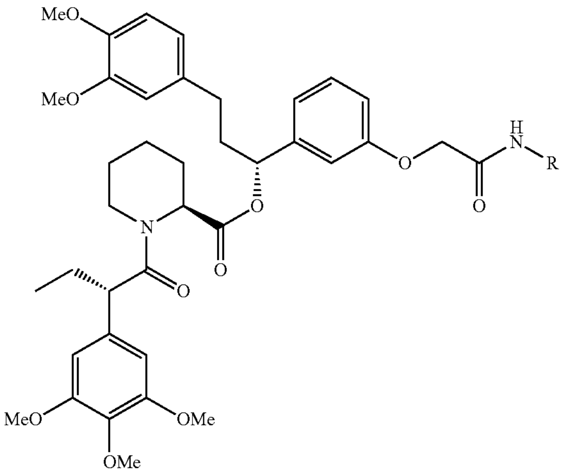 | Binds FKBP |
| A-53 | 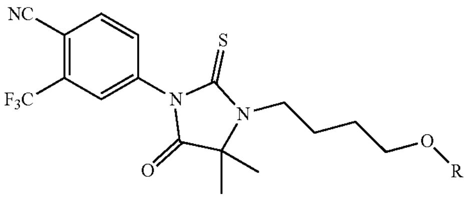 | Binds androgen receptor |
| A-54 | 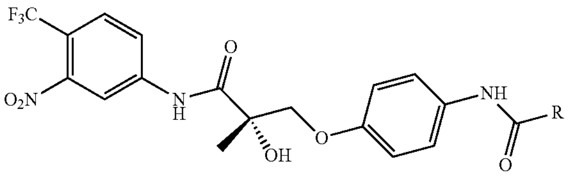 | Binds androgen receptor |
| A-55 | 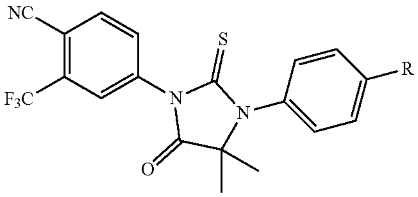 | Binds androgen receptor |
| A-56 | 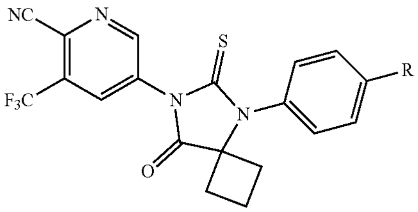 | Binds androgen receptor |
| A-57 | 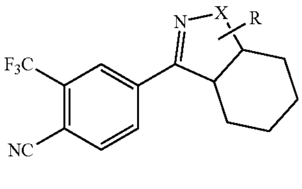 | Binds androgen receptor |

TABLE 4-continued
| Target protein binding moieties | | |
|---|---|---|
| Compound | Structure | Notes (e.g. what target protein it may bind to) |
| A-58 | 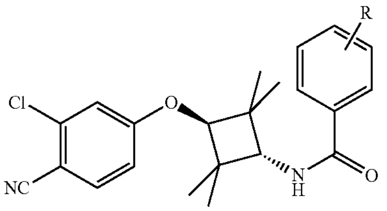 | Binds androgen receptor |
| A-59 | 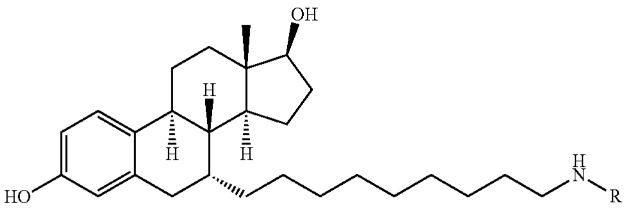 | Binds estrogen receptor |
| A-60 | 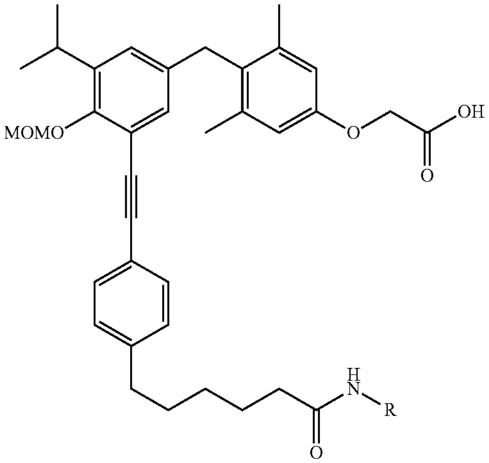 | Binds thyroid hormone receptor, MOMO indicates a methoxymethoxy group |
| A-61 | 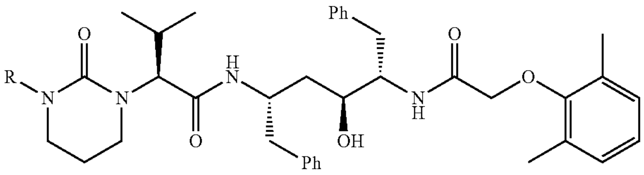 | Binds HIV protease |
| A-62 | 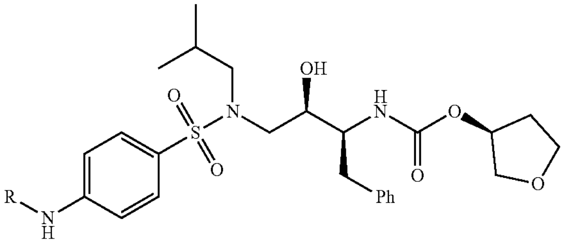 | Binds HIV protease |

TABLE 4-continued
| Target protein binding moieties | | |
|---|---|---|
| Compound | Structure | Notes (e.g. what target protein it may bind to) |
| A-63 | 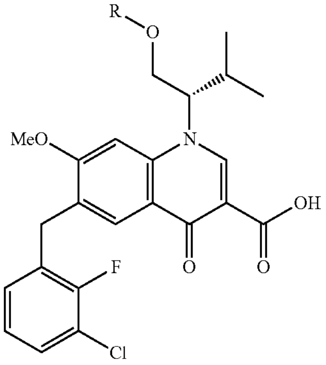 | Binds HIV integrase |
| A-64 | 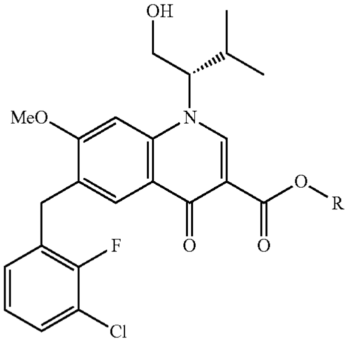 | Binds HIV integrase |
| A-65 | 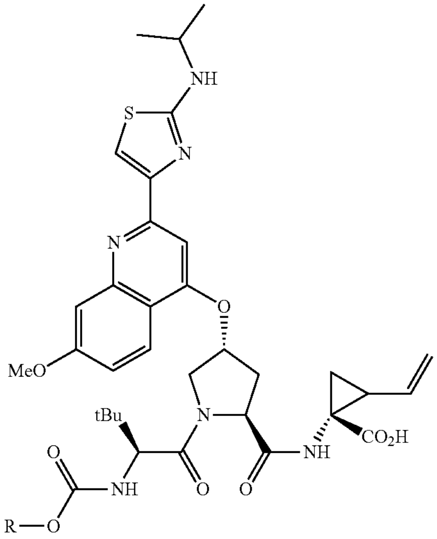 | Binds HCV protease |

TABLE 4-continued

| Target protein binding moieties | | |
|---|---|---|
| Compound | Structure | Notes (e.g. what target protein it may bind to) |
| A-66 | 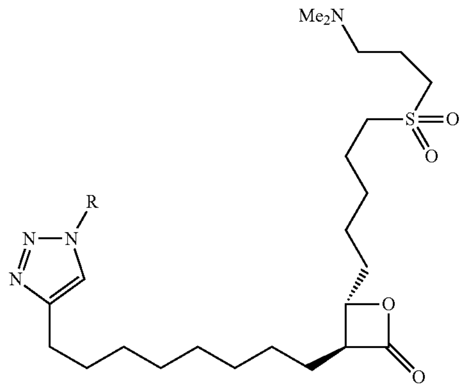 | Binds acyl-protein thioesterase-1 or -2 |
| A-67 | 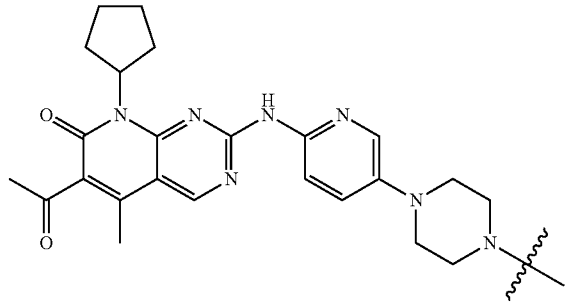 [SMILES: *N1CCN(c2ccc(Nc3ncc4c(C)c(C(C)=O)c(=O)n(C5CCCC5)c4n3)nc2)CC1] | Binds a kinase; binds CDK4/6 |
| A-68 | 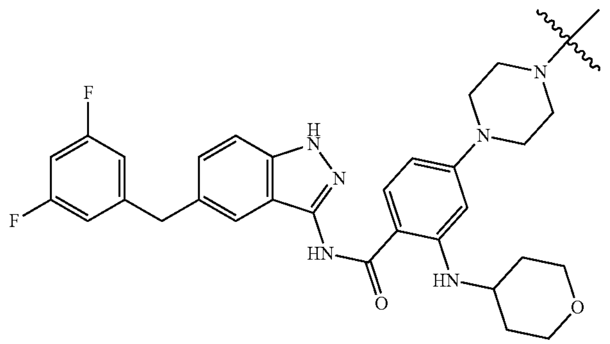 [SMILES: *N1CCN(c2ccc(C(=O)Nc3n[nH]c4ccc(Cc5cc(F)cc(F)c5)cc34)c(NC3CCOCC3)c2)CC1] | Binds a kinase; Binds TrkA, TrkB, TrkC |
| A-69 | 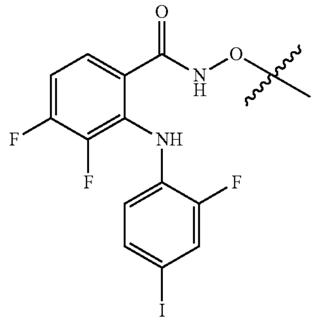 [SMILES: *ONC(=O)c1ccc(F)c(F)c1Nc1ccc(I)cc1F] | Binds a kinase; Binds MEK1, MEK2 |

Heterobifunctional Compounds

Described herein are heterobifunctional compounds. Such compounds may be useful for a variety of purposes, including use as molecular glues or targeted protein degraders. The heterobifunctional compound may be a small molecule. The heterobifunctional compound may be included in a method described herein. For example, the heterobifunctional compound may be included in a pharmaceutical composition and administered to a subject.

Provided herein in some embodiments are heterobifunctional compounds and pharmaceutical compositions comprising said compounds. In some embodiments a heterobifunctional compound described herein comprises a DNA damage-binding protein 1 (DDB11) binding moiety, a linker, and/or a target protein binding moiety. In some embodiments a heterobifunctional compound described herein comprises a DDB1 binding moiety and a target protein binding moiety. In some embodiments, the heterobifunctional compound comprising a DDB1 binding moiety covalently connected through a linker to a target protein binding moiety. In some embodiments, a DDB1 binding moiety is a natural product. In some embodiments, a DDB1 binding moiety is a synthetic product. In some embodiments, a target protein binding moiety is configured to bind a target protein. In some instances, a compound described herein comprises the structure of Formula (I):

Formula (I)

$$Z^1—L^1—Z^2,$$

wherein $Z^1$ is a target protein binding moiety $L^1$ is a linker; and $Z^2$ is a DDB1 binding moiety.

In some instances, a compound described herein comprises the structure of Formula (IIc):

Formula (IIc)

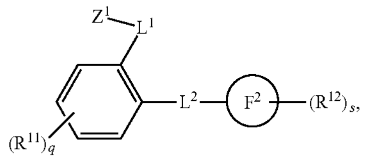

wherein $F^2$ is aryl, heteroaryl, carbocyclyl, or heterocyclyl;

$L^2$ is a bond, —C(═O)$NR^{13}$—, —$NR^{13}$C(═O)—, —C(═O)—, —C(═S)—, —S—, —S(═O), —$S(═O)_2$—, —S(═O)$NR^{13}$—, —$NR^{13}$S(═O)—, —$S(═O)_2NR^{13}$—, —$NR^{13}S(═O)_2$—, —O—, $C_1$-$C_4$ alkyl, or $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —$S(═O)_2R^d$, —$S(═O)_2NR^cR^d$, —C(═O)$R^b$, —$CO_2R^a$, —C(═O)$NR^cR^d$, $C_1$-$C_6$ alkyl, $C_2$-$C_6$ alkenyl, $C_1$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{11}$ and $R^{12}$ is independently hydrogen, halogen, —CN, —$R^a$, —$OR^a$, —$SR^a$, —S(═O)$R^b$, —$NO_2$, —$NR^cR^d$, —$S(═O)_2R^d$, —$NR^aS(═O)_2R^d$, —$S(═O)_2NR^cR^d$, —C(═O)$R^b$, —OC(═O)$R^b$, —$CO_2R^a$, —$CO_2R^a$, —C(═O)$NR^cR^d$, —OC(═O) $NR^cR^d$, —$NR^a$C(═O)$NR^cR^d$, —$NR^a$C(═O)$R^b$, —$NR^a$C(═O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$R^a$, —OR", or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$;

each $R^a$ is independently hydrogen, $C_1$-$C_6$ alkyl, $C_1$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe. or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-4;

s is 1-5;

$L^1$ is a linker; and $Z^1$ is a target protein binding moiety.

In some instances, a compound described herein comprises the structure of Formula (IId):

Formula (IId)

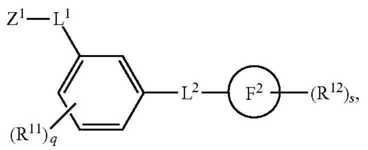

wherein $F^2$ is aryl, heteroaryl, carbocyclyl, or heterocyclyl;

$L^2$ is a bond, —C(═O)$NR^{13}$—, —$NR^{13}$C(═O)—, —C(═O)—, —C(═S)—, —S—, —S(═O), —$S(═O)_2$—, —S(═O)$NR^{13}$—, —$NR^{13}$S(═O)—, —$S(═O)_2NR^{13}$—, —$NR^{13}S(═O)_2$—, —O—, $C_1$-$C_4$ alkyl, $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —$S(═O)_2R^d$, —$S(═O)_2NR^cR^d$, —C(═O)$R^b$, —$CO_2R^a$, —C(═O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{11}$ and $R^{12}$ is independently hydrogen, halogen, —CN, —$R^a$, —$OR^a$, —$SR^a$, —S(═O)$R^b$, —$NO_2$, —$NR^cR^d$, —S(═O)$_2R^d$, —$NR^a$S(═O)$_2R^d$, —S(═O)$_2NR^cR^d$, —C(═O)$R^b$, —OC(═O)$R^b$, —$CO_2R^a$, —$OCO_2R^a$, —C(═O)$NR^cR^d$, —OC(═O)$NR^cR^d$, —$NR^a$C(═O)$NR^cR^d$, —$NR^a$C(═O)$R^b$, —$NR^a$C(═O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$;

each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-4;

s is 1-5;

$L^1$ is a linker; and $Z^1$ is a target protein binding moiety.

In some instances, a compound described herein comprises the structure of Formula (IIe):

Formula (IIe)

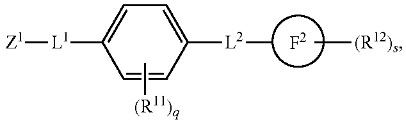

wherein $F^2$ is aryl, heteroaryl, carbocyclyl, or heterocyclyl;

$L^2$ is a bond, —C(═O)$NR^{13}$—, —$NR^{13}$C(═O)—, —C(═O)—, —C(═S)—, —S—, —S(═O), —S(═O)$_2$—, —S(═O)$NR^{13}$—, —$NR^{13}$S(═O)—, —S(═O)$_2NR^{13}$—, —$NR^{13}$S(═O)$_2$—, —O—, $C_1$-$C_4$ alkyl, $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —S(═O)$_2R^d$, —S(═O)$_2NR^cR^d$, —C(═O)$R^b$, —$CO_2R^a$, —C(═O)$NR^cR^d$, $C_1$-$C_6$, alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{11}$ and $R^{12}$ is independently hydrogen, halogen, —CN, —$R^a$, —$OR^a$, —$SR^a$, —S(═O)$R^b$, —$NO_2$, —$NR^cR^d$, —S(═O)$_2R^d$, —$NR^a$S(═O)$_2R^d$, —S(═O)$_2NR^cR^d$, —C(═O)$R^b$, —OC(═O)$R^b$, —$CO_2R^a$, —$OCO_2R^a$, —C(═O)$NR^cR^d$, —OC(═O)$NR^cR^d$, —$NR^a$C(═O)$NR^cR^d$, —$NR^a$C(═O)$R^b$, —$NR^a$C(═O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$;

each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_8$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe. or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$, haloalkyl, —OH, —OMe, or —$NH_2$;

each $R^c$ and $R^d$, together with the nitrogen atom to which they are attached, form a heterocyclyl or heteroaryl; wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-4;

s is 1-5;

$L^1$ is a linker; and $Z^1$ is a target protein binding moiety.

In some embodiments, each $R^{11}$ and $R^{12}$ is independently a bond, hydrogen, halogen, —CN, —$R^a$, —$OR^a$—, —$SR^a$, —S(=O)$R^b$, —$NO_2$, —$NR^cR^d$, —S(=O)$_2R^d$, —$NR^a$S(=O)$_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^a$C(=O)$NR^cR^d$, —$NR^a$C(=O)$R^b$, —$NR^a$C(=O)$OR^a$, $C_1$-$C_5$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$, and at least one $R^{11}$ is a bond attached to the linker.

In some embodiments of a compound of Formula (IIc-IIe), $F^2$ is aryl. In some embodiments of a compound of Formula (IIc-IIe), $F^2$ is $C_6$-$C_{12}$ aryl. In some embodiments of a compound of Formula (IIc-IIe), $F^2$ is heteroaryl. In some embodiments of a compound of Formula (IIc-IIe), $F^2$ is 5-12 membered heteroaryl. In some embodiments of a compound of Formula (IIa) $F^2$ is triazolyl, tetrazolyl, furanyl, pyrrolyl, thiazolyl, oxazolyl, isoxazolyl, imidazolyl, pyrazolyl, thiadiazolyl, or oxadiazolyl. In some embodiments of a compound of Formula (IIa) $F^2$ is triazolyl, tetrazolyl, furanyl, pyrrolyl, thiazolyl, oxazolyl, isoxazolyl, imidazolyl, pyrazolyl, thiadiazolyl, or oxadiazolyl, and p is 1. In some embodiments of a compound of Formula (IIa) $F^2$ is 5-6 membered heteroaryl. In some embodiments of a compound of Formula (IIa) $F^2$ is heteroaryl, wherein the heteroaryl group has at least one nitrogen atom in the ring. In some embodiments of a compound of Formula (IIa) $F^2$ is heteroaryl, wherein the heteroaryl group has at least two nitrogen atoms in the ring. In some embodiments of a compound of Formula (IIa) $F^2$ is pyridyl, pyrimidinyl, or pyrazinyl. In some embodiments, $F^2$ is heteroaryl, wherein the heteroaryl group has at least one sulfur atom in the ring. In some embodiments, $F^2$ is heteroaryl, wherein the heteroaryl group has at least one oxygen atom in the ring. In some embodiments of a compound of Formula (IIa) $F^2$ is thiazolyl, oxazolyl, furyl, or thiophenyl. In some embodiments of a compound of Formula (IIa) $F^2$ is thiazolyl. In some embodiments of a compound of Formula (IIa) $R^{12}$, at each occurrence, is —$NO_2$, halogen, methyl, halomethyl, phenyl, cyclopropyl, $SO_2CH_3$, or —CN. In some embodiments of a compound of Formula (IIa) $R^{12}$ is —$NO_2$. In some embodiments of a compound of Formula (IIb), $R^{12}$, at each occurrence, is chloro or bromo. In some embodiments of a compound of Formula (IIa) $L^2$ is —NHC(=O) or —C(=O)NH—. In some embodiments of a compound of Formula (IIc-IIe), $L^2$ is —C(=O)NH—. In some embodiments of a compound of Formula (IIc-IIe), $L^2$ is —C(=O)N($C_1$-$C_5$ alkyl)-. In some embodiments of a compound of Formula (IIc-IIe), q is 1. In some embodiments of a compound of Formula (IIc-IIe), q is 2. In some embodiments of a compound of Formula (IIc-IIe), the linker is a bond. In some embodiments of a compound of Formula (IIc-IIe), the linker is not a bond.

Described herein are compounds such as ligands comprising a DDB1 binding moiety, a linker, and a target protein binding moiety. In some embodiments, the compound binds to DDB1 via the DDB1 binding moiety. In some embodiments, the compound is bound to DDB1 via the DDB1 binding moiety. In some instances, a target protein binding moiety recruits a target protein which is ubiquitinated by a complex comprising DDB1. In some instances, the target protein is subsequently degraded. The target protein may, in some instances, be any protein desirable for protein binding or degradation. For example, the target protein may include any protein that may be subjected to proteasomal degradation, or may include any protein that is useful to be bound by a ligand described herein. In some embodiments, the target protein comprises a target protein described herein. In some embodiments, the target protein binding moiety comprises a CBP binding moiety. In some embodiments, the target protein binding moiety comprises a p300 binding moiety. In some embodiments, the target protein binding moiety is a TrkA binding moiety. In some embodiments, the target protein binding moiety is a TrkB binding moiety. In some embodiments, the target protein binding moiety is a TrkC binding moiety. In some embodiments, the target protein binding moiety is a CDK4 binding moiety. In some embodiments, the target protein binding moiety is a CDK6 binding moiety. In some embodiments, the target protein binding moiety is a MEK1 binding moiety. In some embodiments, the target protein binding moiety is a MEK2 binding moiety. In some embodiments, the target protein binding moiety is a transcriptional coactivator. In some embodiments, the target protein binding moiety is a BRD4 binding moiety.

A compound may include any aspect of a compound shown in Table 5, such as a DDB1 binding moiety, a linker, or a target protein binding moiety of a compound shown in Table 5. In some embodiments, compounds comprising a DDB1 binding moiety, a linker, and a target protein binding moiety are shown in Table 5.

TABLE 5
| DDB1 binding moieties attached to a target protein binding moiety | | |
|---|---|---|
| Compound | Structure | Name |
| D-1 | 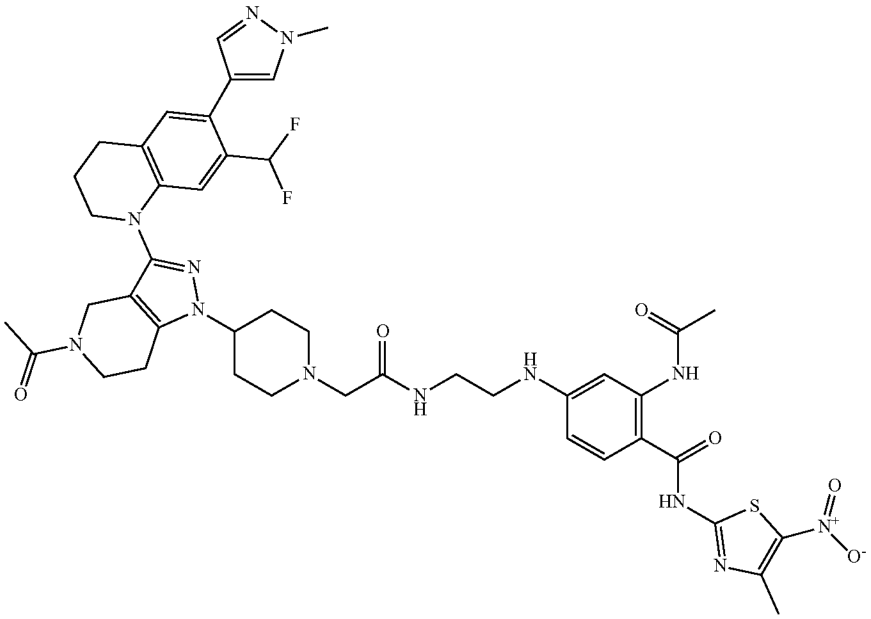 [SMILES: CC(=O)Nc1cc(NCCNC(=O)CN2CCC(n3nc(N4CCCc5cc(-c6cnn(C)c6)c(C(F)F)cc54)c4c3CCN(C(C)=O)C4)CC2)ccc1C(=O)Nc1nc(C)c([N+](=O)[O-])s1] | 2-acetamido-4-((2-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)ethyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-2 | 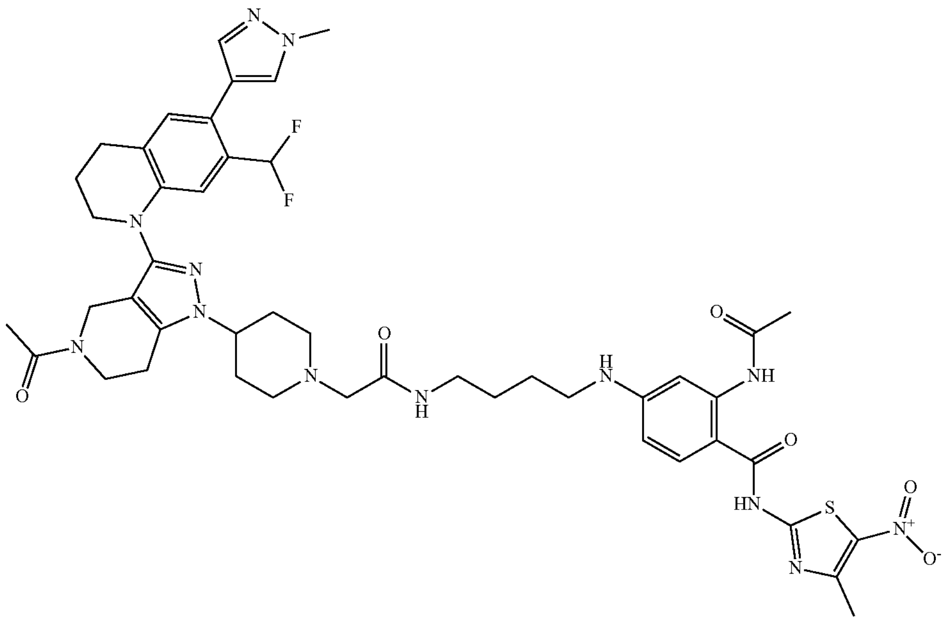 [SMILES: CC(=O)Nc1cc(NCCCCNC(=O)CN2CCC(n3nc(N4CCCc5cc(-c6cnn(C)c6)c(C(F)F)cc54)c4c3CCN(C(C)=O)C4)CC2)ccc1C(=O)Nc1nc(C)c([N+](=O)[O-])s1] | 2-acetamido-4-((4-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)butyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-3 | 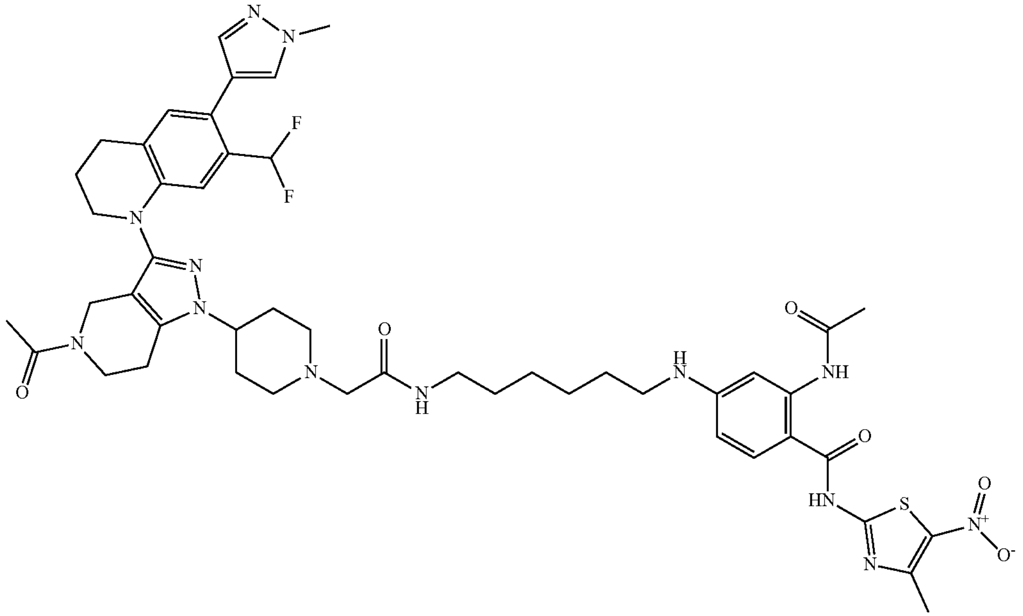 [SMILES: CC(=O)Nc1cc(NCCCCCCNC(=O)CN2CCC(n3nc(N4CCCc5cc(-c6cnn(C)c6)c(C(F)F)cc54)c4c3CCN(C(C)=O)C4)CC2)ccc1C(=O)Nc1nc(C)c([N+](=O)[O-])s1] | 2-acetamido-4-((6-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)hexyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-4 | 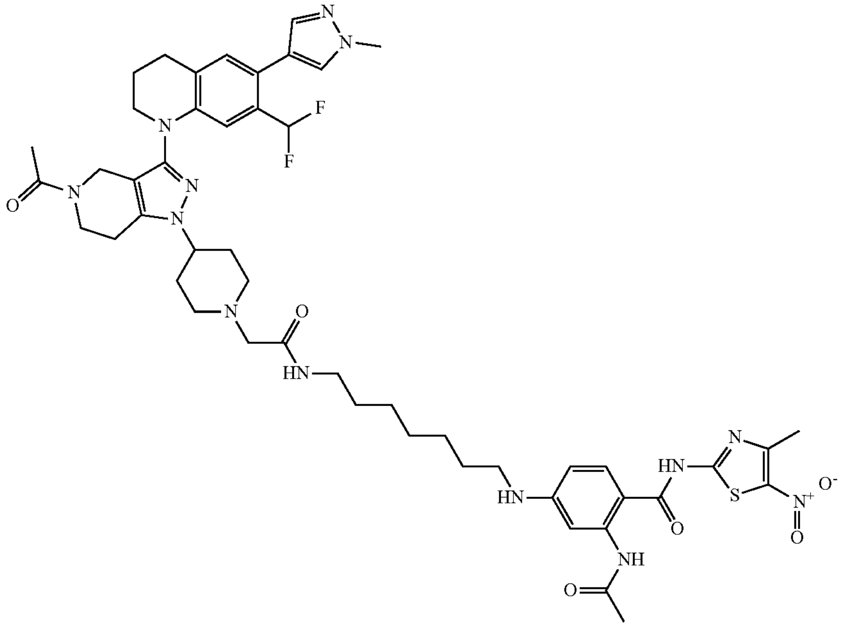 | 2-acetamido-4-((7-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)heptyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-5 | 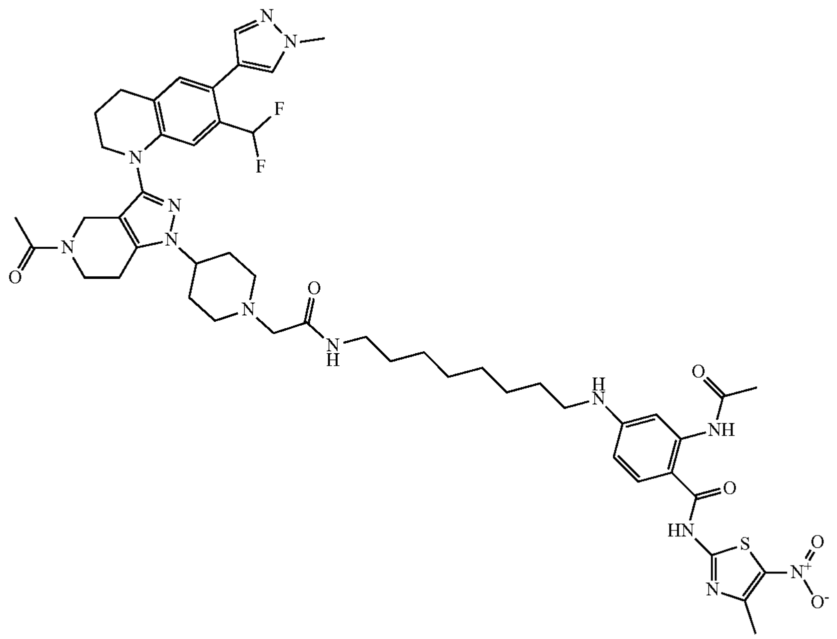 [SMILES: CC(=O)Nc1cc(NCCCCCCCCNC(=O)CN2CCC(n3nc(N4CCCc5cc(-c6cnn(C)c6)c(C(F)F)cc54)c4c3CCN(C(C)=O)C4)CC2)ccc1C(=O)Nc1nc(C)c([N+](=O)[O-])s1] | 2-acetamido-4-((8-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)octyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-6 | 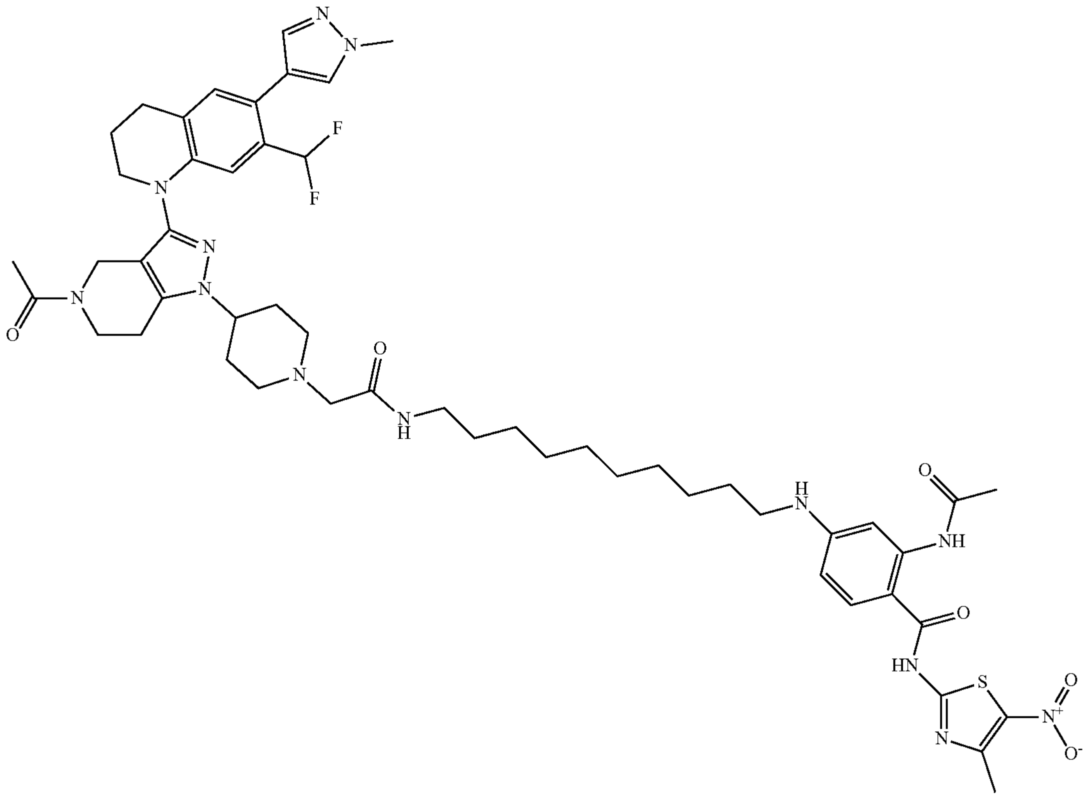 [SMILES: CC(=O)Nc1cc(NCCCCCCCCCCNC(=O)CN2CCC(n3nc(N4CCCc5cc(-c6cnn(C)c6)c(C(F)F)cc54)c4c3CCN(C(C)=O)C4)CC2)ccc1C(=O)Nc1nc(C)c([N+](=O)[O-])s1] | 2-acetamido-4-((10-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)decyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-7 | 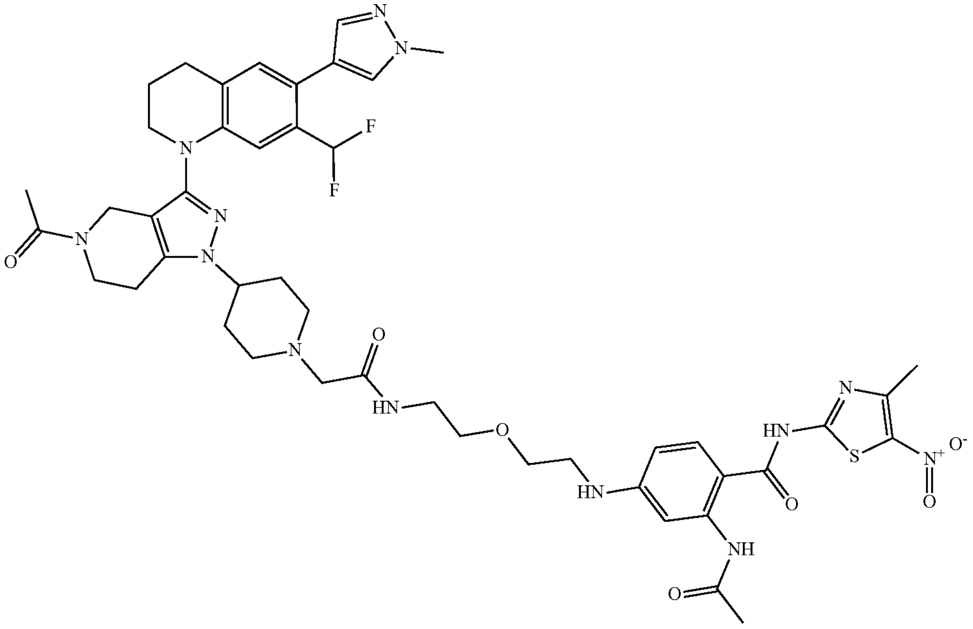 | 2-acetamido-4-((2-(2-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)ethoxy)ethyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-8 | 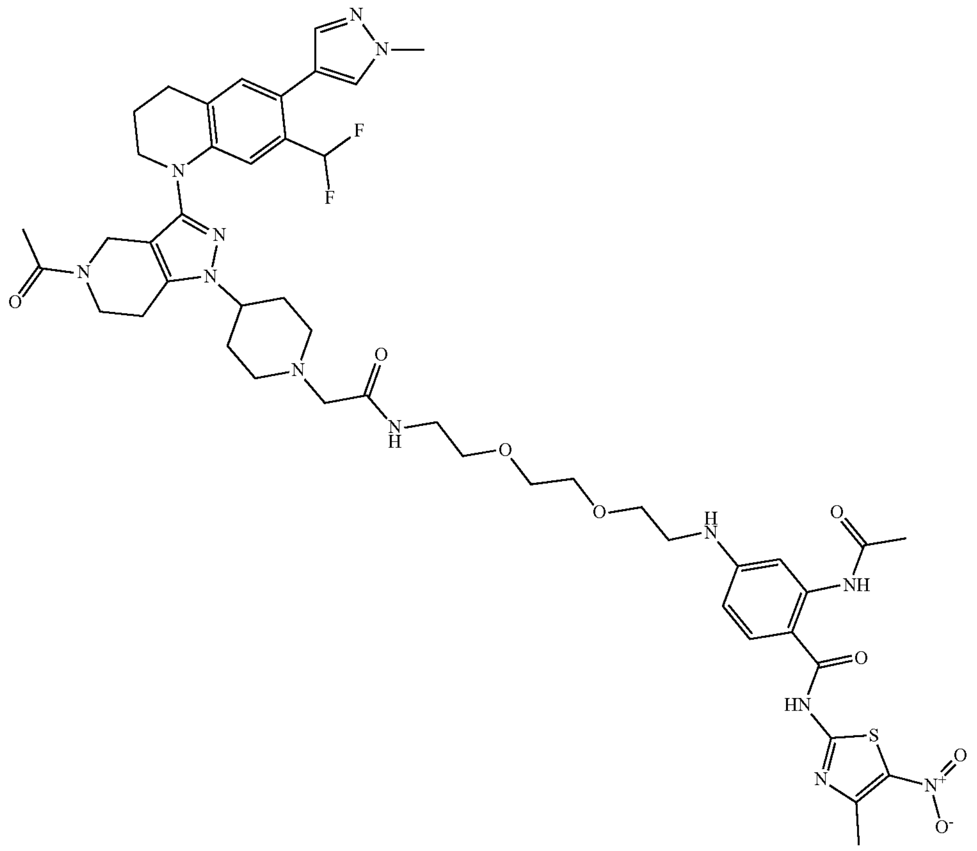 [SMILES: CC(=O)Nc1cc(NCCOCCOCCNC(=O)CN2CCC(n3nc(N4CCCc5cc(-c6cnn(C)c6)c(C(F)F)cc54)c4c3CCN(C(C)=O)C4)CC2)ccc1C(=O)Nc1nc(C)c([N+](=O)[O-])s1] | 2-acetamido-4-((2-(2-(2-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)ethoxy)ethoxy)ethyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-9 | 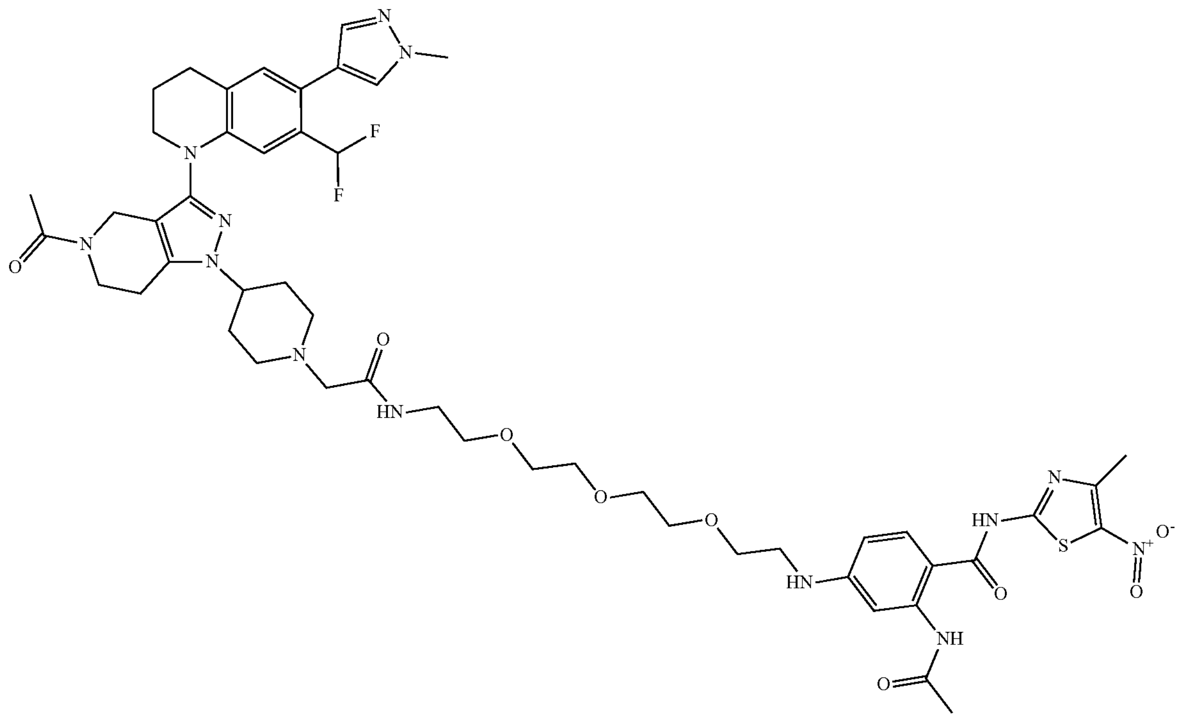 | 2-acetamido-4-((1-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)-2-oxo-6,9,12-trioxa-3-azatetradecan-14-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-10 | 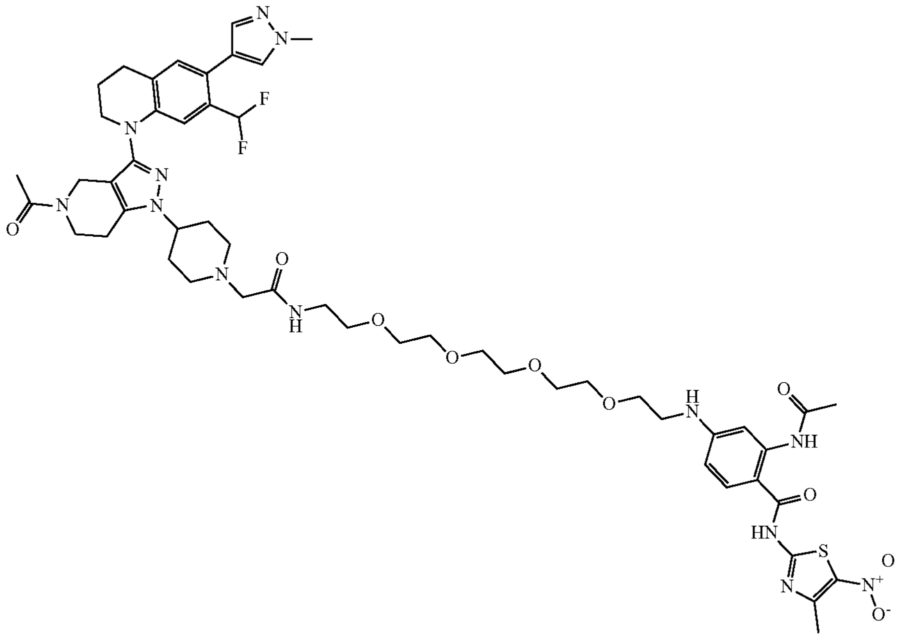 | 2-acetamido-4-((1-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)-2-oxo-6,9,12,15-tetraoxa-3-azaheptadecan-17-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-11 | 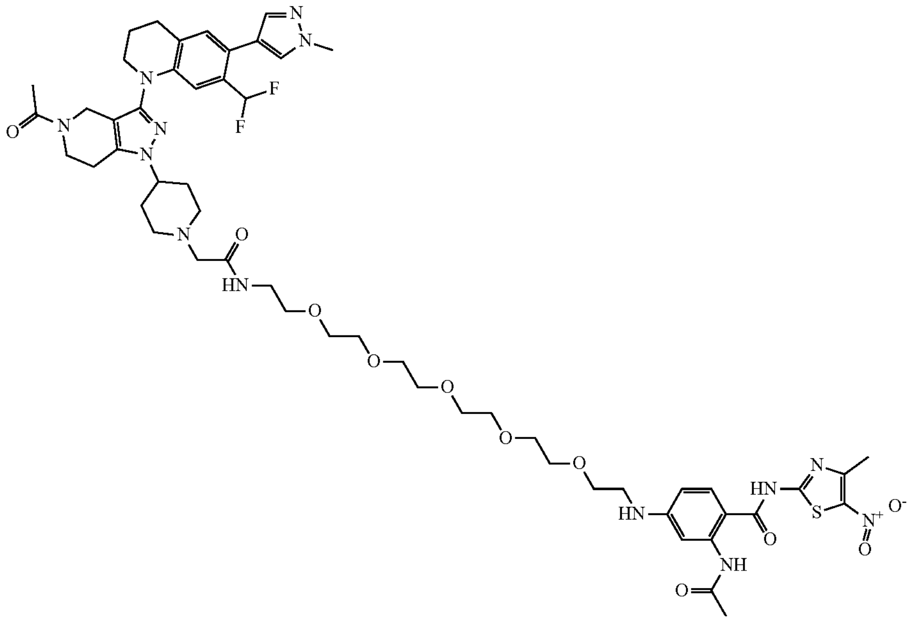 | 2-acetamido-4-((1-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)-2-oxo-6,9,12,15,18-pentaoxa-3-azaicosan-20-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-12 | 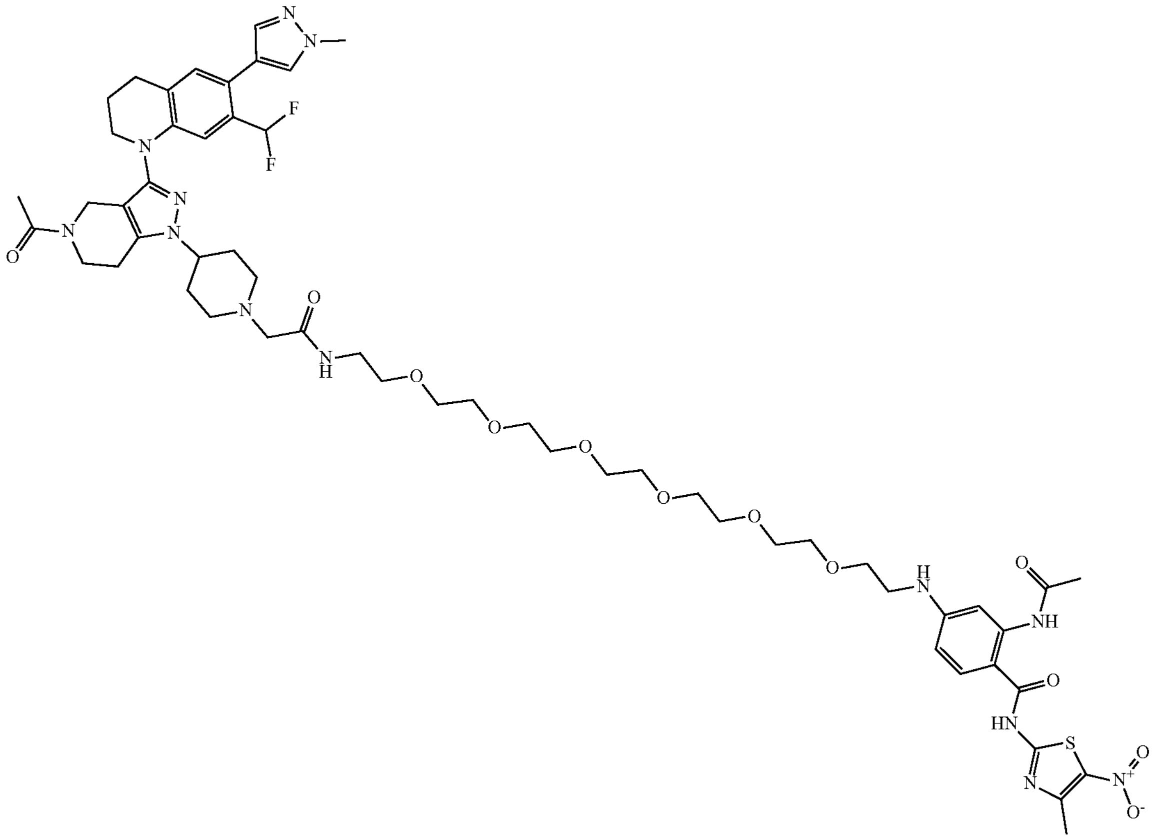 [SMILES: CC(=O)Nc1cc(NCCOCCOCCOCCOCCOCCOCCNC(=O)CN2CCC(n3nc(N4CCCc5cc(-c6cnn(C)c6)c(C(F)F)cc54)c4c3CCN(C(C)=O)C4)CC2)ccc1C(=O)Nc1nc(C)c([N+](=O)[O-])s1] | 2-acetamido-4-((1-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)-2-oxo-6,9,12,15,18,21-hexaoxa-3-azatricosan-23-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-13 | 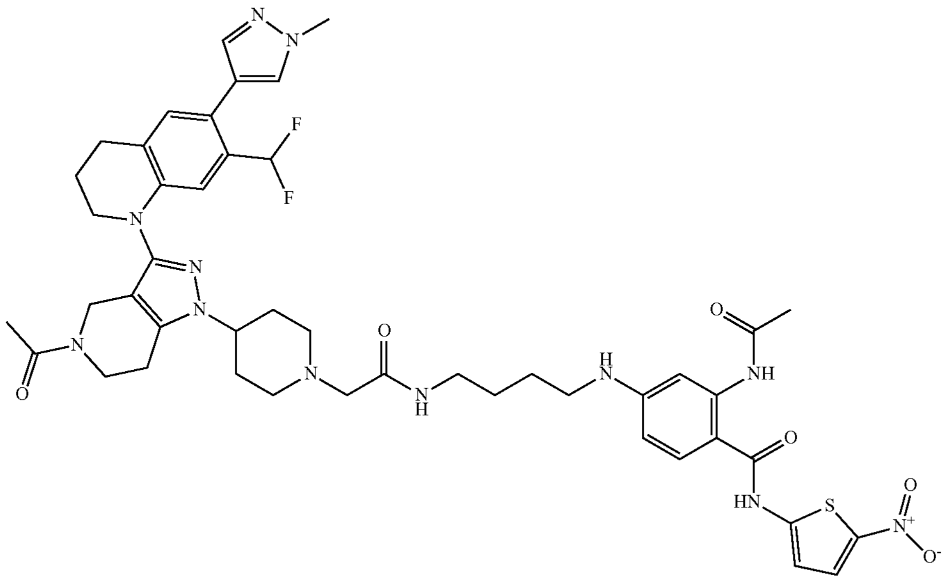 [SMILES: CC(=O)Nc1cc(NCCCCNC(=O)CN2CCC(n3nc(N4CCCc5cc(-c6cnn(C)c6)c(C(F)F)cc54)c4c3CCN(C(C)=O)C4)CC2)ccc1C(=O)Nc1ccc([N+](=O)[O-])s1] | 2-acetamido-4-((4-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)butyl)amino)-N-(5-nitrothiophen-2-yl)benzamide |

TABLE 5-continued
| DDB1 binding moieties attached to a target protein binding moiety | | |
|---|---|---|
| Compound | Structure | Name |
| D-14 | 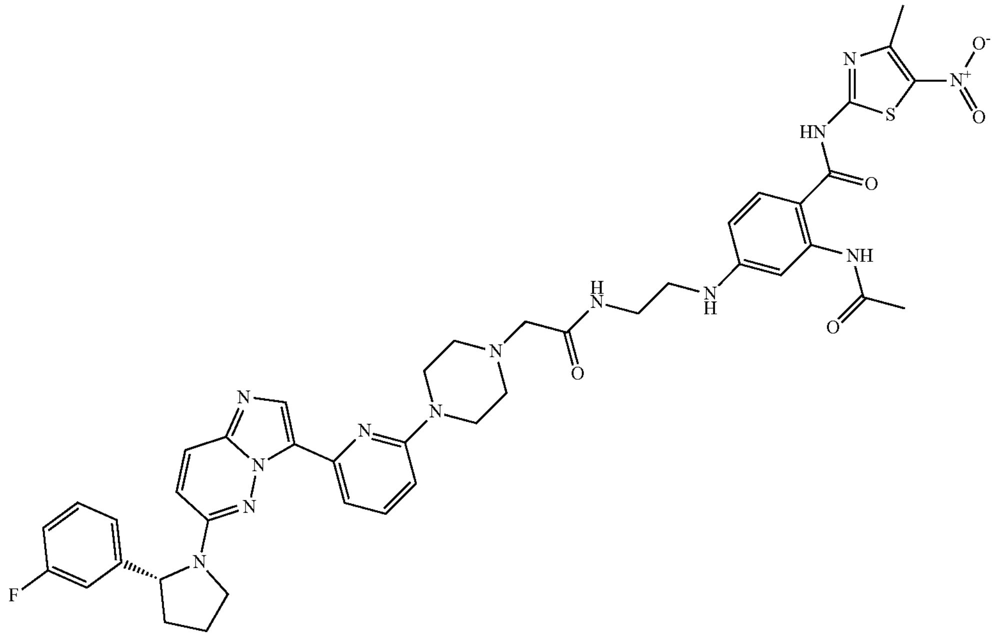 [SMILES: CC(=O)Nc1cc(NCCNC(=O)CN2CCN(c3cccc(-c4cnc5ccc(N6CCC[C@@H]6c6cccc(F)c6)nn45)n3)CC2)ccc1C(=O)Nc1nc(C)c([N+](=O)[O-])s1] | (R)-2-acetamido-4-((2-(2-(4-(6-(6-(2-(3-fluorophenyl)pyrrolidin-1-yl)imidazo[1,2-b]pyridazin-3-yl)pyridin-2-yl)piperazin-1-yl)acetamido)ethyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-15 | 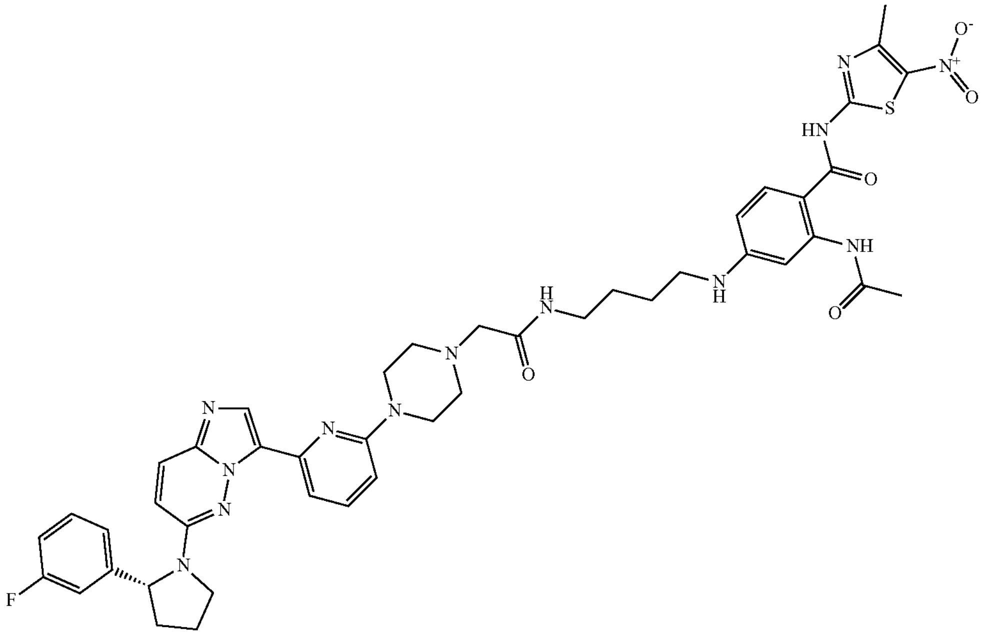 [SMILES: CC(=O)Nc1cc(NCCCCNC(=O)CN2CCN(c3cccc(-c4cnc5ccc(N6CCC[C@@H]6c6cccc(F)c6)nn45)n3)CC2)ccc1C(=O)Nc1nc(C)c([N+](=O)[O-])s1] | (R)-2-acetamido-4-((4-(2-(4-(6-(6-(2-(3-fluorophenyl)pyrrolidin-1-yl)imidazo[1,2-b]pyridazin-3-yl)pyridin-2-yl)piperazin-1-yl)acetamido)butyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-16 | 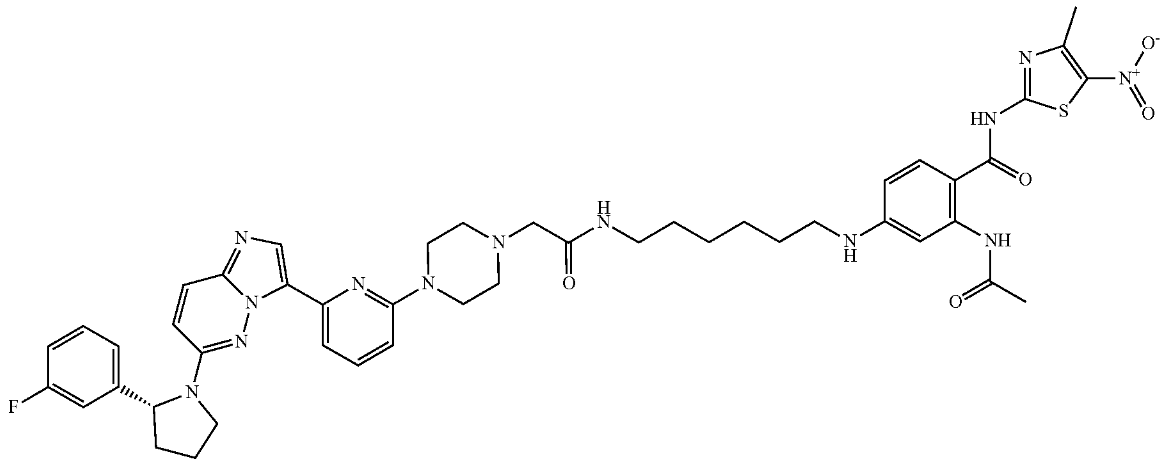 [SMILES: CC(=O)Nc1cc(NCCCCCCNC(=O)CN2CCN(c3cccc(-c4cnc5ccc(N6CCC[C@@H]6c6cccc(F)c6)nn45)n3)CC2)ccc1C(=O)Nc1nc(C)c([N+](=O)[O-])s1] | (R)-2-acetamido-4-((6-(2-(4-(6-(6-(2-(3-fluorophenyl) pyrrolidin-1-yl)imidazo[1,2-b]pyridazin-3-yl)pyridin-2-yl)piperazin-1-yl)acetamido)hexyl) amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-17 | 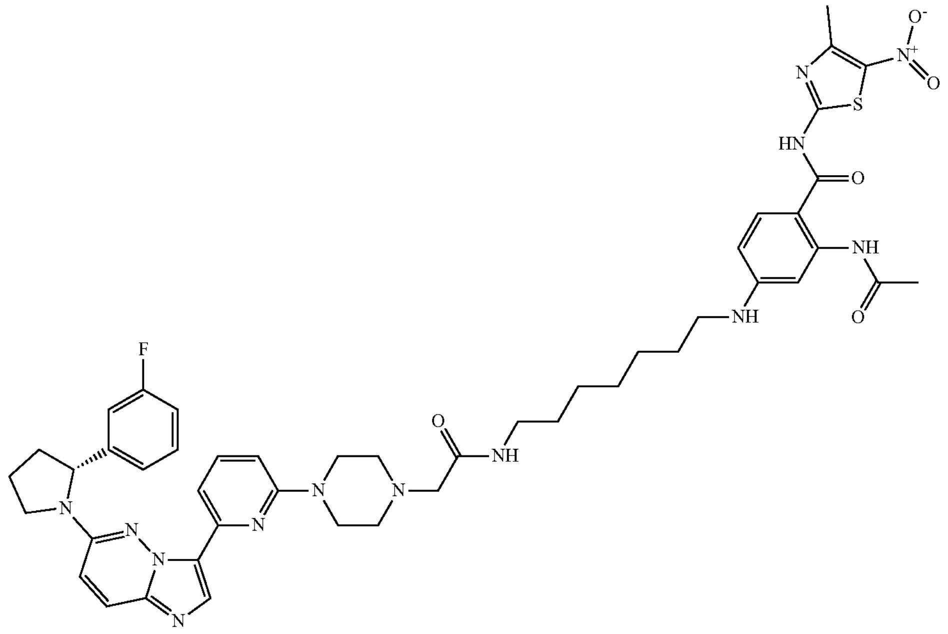 [SMILES: CC(=O)Nc1cc(NCCCCCCCNC(=O)CN2CCN(c3cccc(-c4cnc5ccc(N6CCC[C@@H]6c6cccc(F)c6)nn45)n3)CC2)ccc1C(=O)Nc1nc(C)c([N+](=O)[O-])s1] | (R)-2-acetamido-4-((7-(2-(4-(6-(6-(2-(3-fluorophenyl)pyrrolidin-1-yl)imidazo[1,2-b]pyridazin-3-yl)pyridin-2-yl)piperazin-1-yl)acetamido)heptyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-18 | 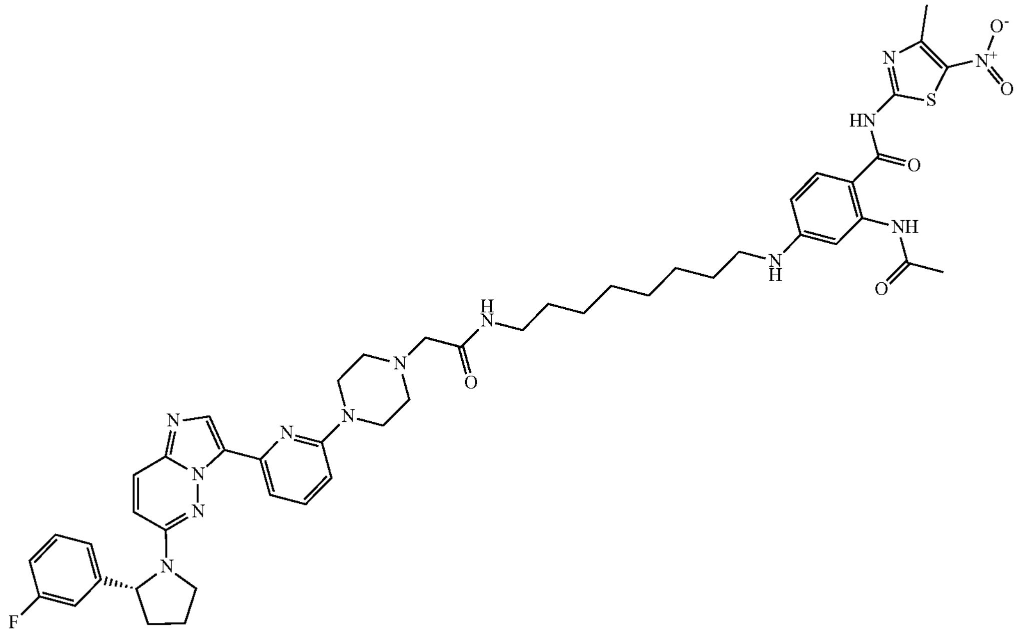 [SMILES: CC(=O)Nc1cc(NCCCCCCCCNC(=O)CN2CCN(c3cccc(-c4cnc5ccc(N6CCC[C@@H]6c6cccc(F)c6)nn45)n3)CC2)ccc1C(=O)Nc1nc(C)c([N+](=O)[O-])s1] | (R)-2-acetamido-4-((8-(2-(4-(6-(6-(2-(3-fluorophenyl)pyrrolidin-1-yl)imidazo[1,2-b]pyridazin-3-yl)pyridin-2-yl)piperazin-1-yl)acetamido)octyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-19 | 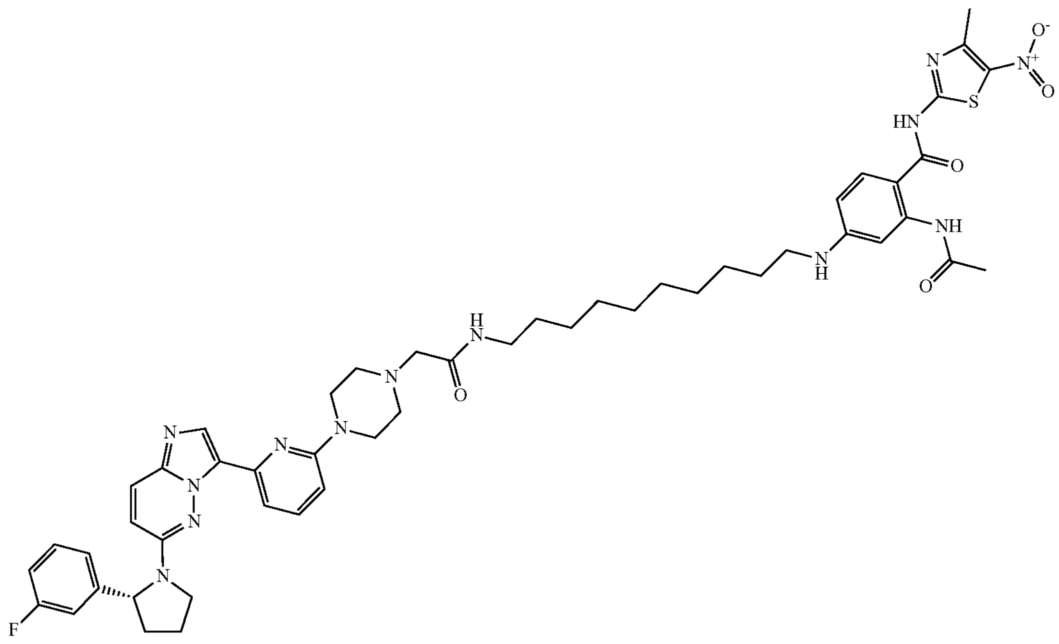 [SMILES: CC(=O)Nc1cc(NCCCCCCCCCCNC(=O)CN2CCN(c3cccc(-c4cnc5ccc(N6CCC[C@@H]6c6cccc(F)c6)nn45)n3)CC2)ccc1C(=O)Nc1nc(C)c([N+](=O)[O-])s1] | (R)-2-acetamido-4-((10-(2-(4-(6-(6-(2-(3-fluorophenyl)pyrrolidin-1-yl)imidazo[1,2-b]pyridazin-3-yl)pyridin-2-yl)piperazin-1-yl)acetamido)decyl)amino)-N-(4-methyl-5-nitrothiazol-2-yl)benzamide |

TABLE 5-continued
DDB1 binding moieties attached to a target protein binding moiety
| Compound | Structure | Name |
|---|---|---|
| D-20 | 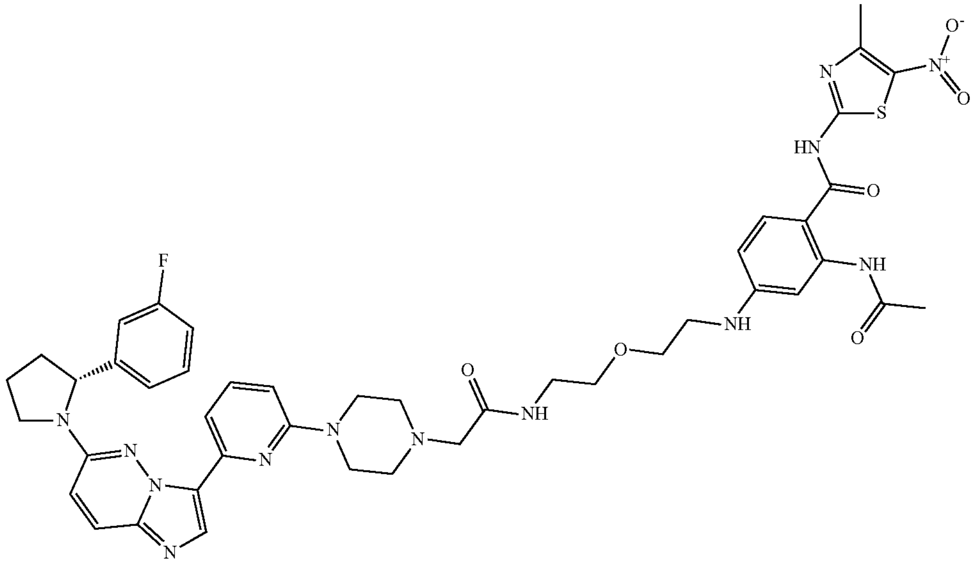 [SMILES: CC(=O)Nc1cc(NCCOCCNC(=O)CN2CCN(c3cccc(-c4cnc5ccc(N6CCC[C@@H]6c6cccc(F)c6)nn45)n3)CC2)ccc1C(=O)Nc1nc(C)c([N+](=O)[O-])s1] | (R)-2-acetamido-4-((2-(2-(2-(4-(6-(6-(2-(3-fluorophenyl)pyrrolidin-1-yl)imidazo[1,2-b]pyridazin-3-yl)pyridin-2-yl)piperazin-1-yl)acetamido)ethoxy)ethyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-21 | 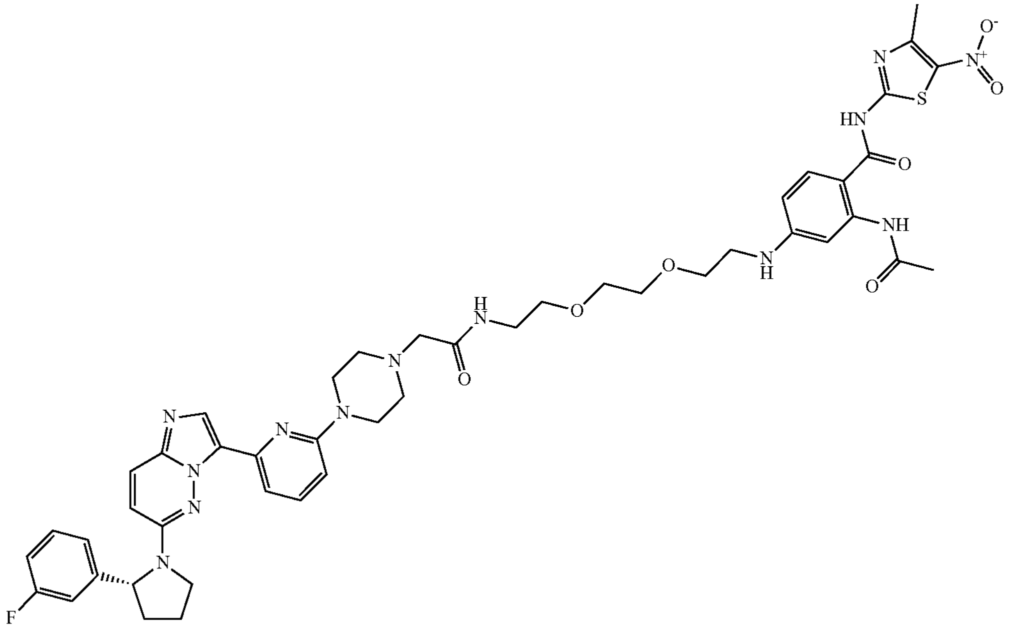 [SMILES: CC(=O)Nc1cc(NCCOCCOCCNC(=O)CN2CCN(c3cccc(-c4cnc5ccc(N6CCC[C@@H]6c6cccc(F)c6)nn45)n3)CC2)ccc1C(=O)Nc1nc(C)c([N+](=O)[O-])s1] | (R)-2-acetamido-4-((2-(2-(2-(2-(4-(6-(6-(2-(3-fluorophenyl)pyrrolidin-1-yl)imidazo[1,2-b]pyridazin-3-yl)pyridin-2-yl)piperazin-1-yl)acetamido)ethoxy)ethoxy)ethyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-22 | 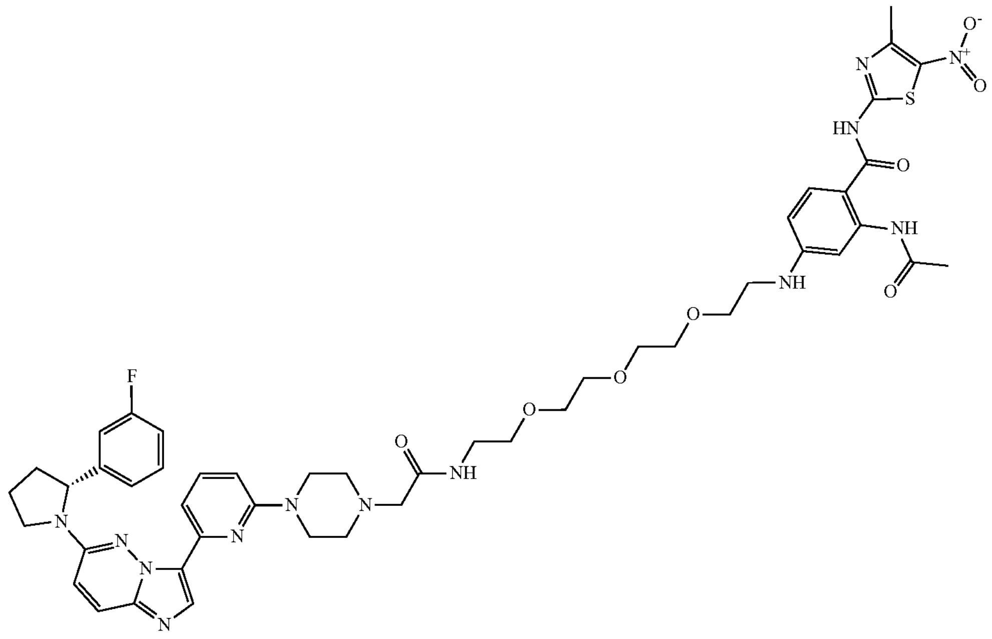 [SMILES: CC(=O)Nc1cc(NCCOCCOCCOCCNC(=O)CN2CCN(c3cccc(-c4cnc5ccc(N6CCC[C@@H]6c6cccc(F)c6)nn45)n3)CC2)ccc1C(=O)Nc1nc(C)c([N+](=O)[O-])s1] | (R)-2-acetamido-4-((1-(4-(6-(6-(2-(3-fluorophenyl)pyrrolidin-1-yl)imidazo[1,2-b]pyridazin-3-yl)pyridin-2-yl)piperazin-1-yl)-2-oxo-6,9,12-trioxa-3-azatetradecan-14-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-23 | 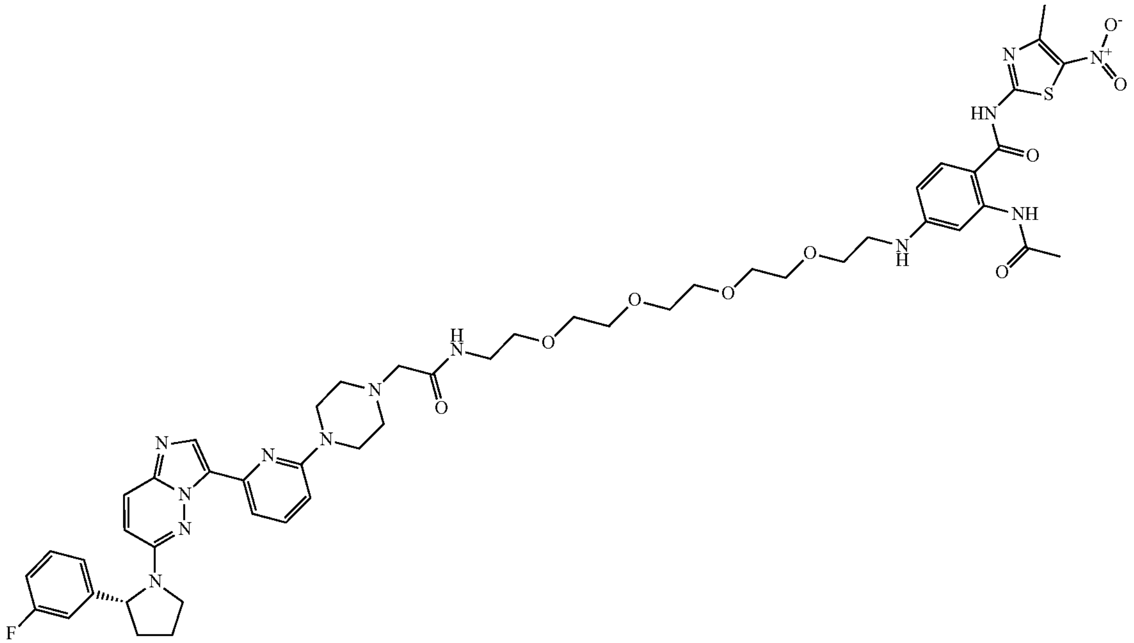 [SMILES: CC(=O)Nc1cc(NCCOCCOCCOCCOCCNC(=O)CN2CCN(c3cccc(-c4cnc5ccc(N6CCC[C@@H]6c6cccc(F)c6)nn45)n3)CC2)ccc1C(=O)Nc1nc(C)c([N+](=O)[O-])s1] | (R)-2-acetamido-4-((1-(4-(6-(6-(2-(3-fluorophenyl) pyrrolidin-1-yl)imidazo[1,2-b]pyridazin-3-yl)pyridin-2-yl)piperazin-1-yl)-2-oxo-6,9,12,15-tetraoxa-3-azaheptadecan-17-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-24 | 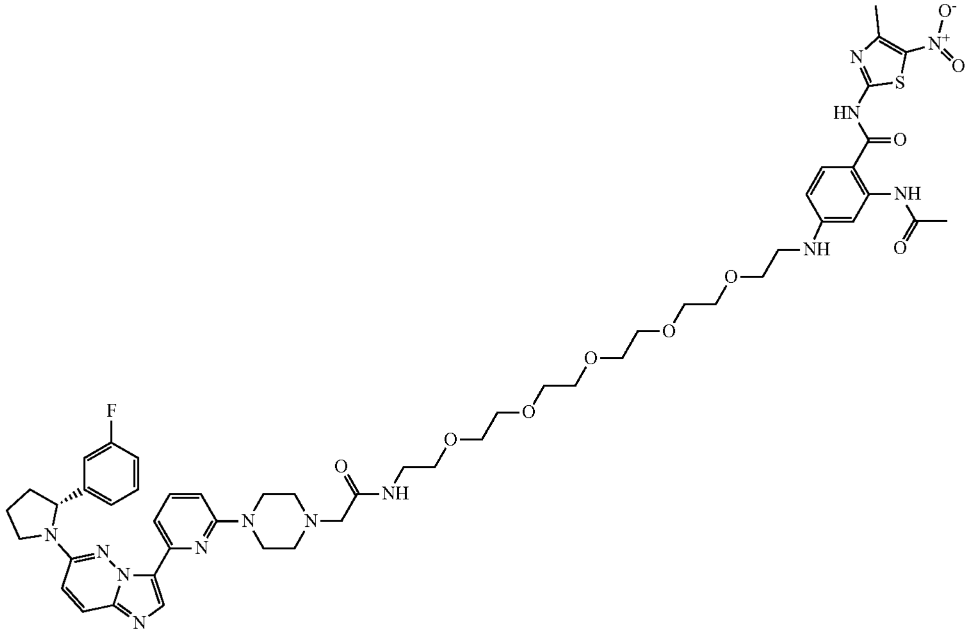 [SMILES: CC(=O)Nc1cc(NCCOCCOCCOCCOCCOCCNC(=O)CN2CCN(c3cccc(-c4cnc5ccc(N6CCC[C@@H]6c6cccc(F)c6)nn45)n3)CC2)ccc1C(=O)Nc1nc(C)c([N+](=O)[O-])s1] | (R)-2-acetamido-4-((1-(4-(6-(6-(2-(3-fluorophenyl) pyrrolidin-1-yl)imidazo[1,2-b]pyridazin-3-yl)pyridin-2-yl)piperazin-1-yl)-2-oxo-6,9,12,15,18-pentaoxa-3-azaicosan-20-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-25 | 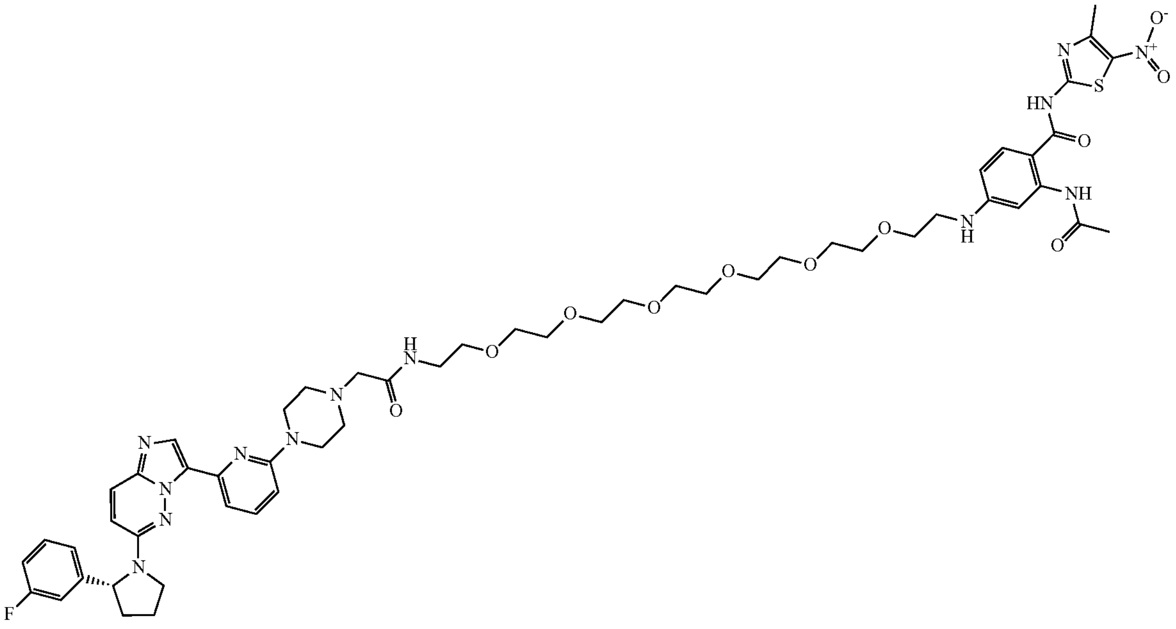 [SMILES: CC(=O)Nc1cc(NCCOCCOCCOCCOCCOCCOCCNC(=O)CN2CCN(c3cccc(-c4cnc5ccc(N6CCC[C@@H]6c6cccc(F)c6)nn45)n3)CC2)ccc1C(=O)Nc1nc(C)c([N+](=O)[O-])s1] | (R)-2-acetamido-4-((1-(4-(6-(6-(2-(3-fluorophenyl) pyrrolidin-1-yl)imidazo[1,2-b]pyridazin-3-yl)pyridin-2-yl)piperazin-1-yl)-2-oxo-6,9,12,15,18,21-hexaoxa-3-azatricosan-23-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-26 | 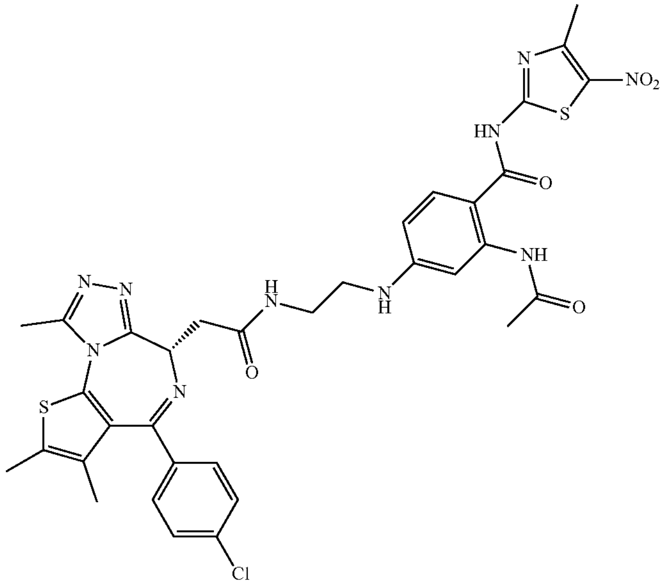 [SMILES: CC(=O)Nc1cc(NCCNC(=O)C[C@@H]2N=C(c3ccc(Cl)cc3)c3c(sc(C)c3C)-n3c(C)nnc32)ccc1C(=O)Nc1nc(C)c([N+](=O)[O-])s1] | (S)-2-acetamido-4-((2-(2-(4-(4-chlorophenyl)-2,3,9-trimethyl-6H-thieno[3,2-f][1,2,4]triazolo[4,3-a][1,4]diazepin-6-yl)acetamido)ethyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-27 | 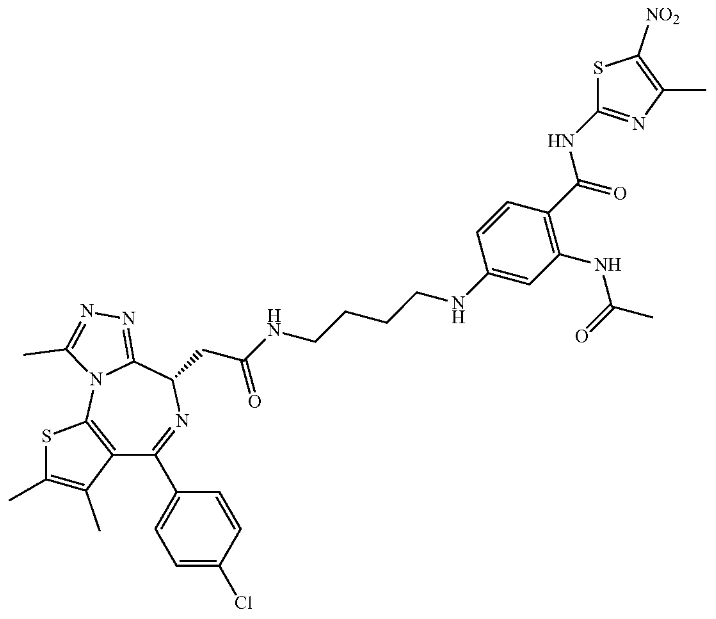 | (S)-2-acetamido-4-((4-(2-(4-(4-chlorophenyl)-2,3,9-trimethyl-6H-thieno[3,2-f][1,2,4]triazolo[4,3-a][1,4]diazepin-6-yl)acetamido)butyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-28 | 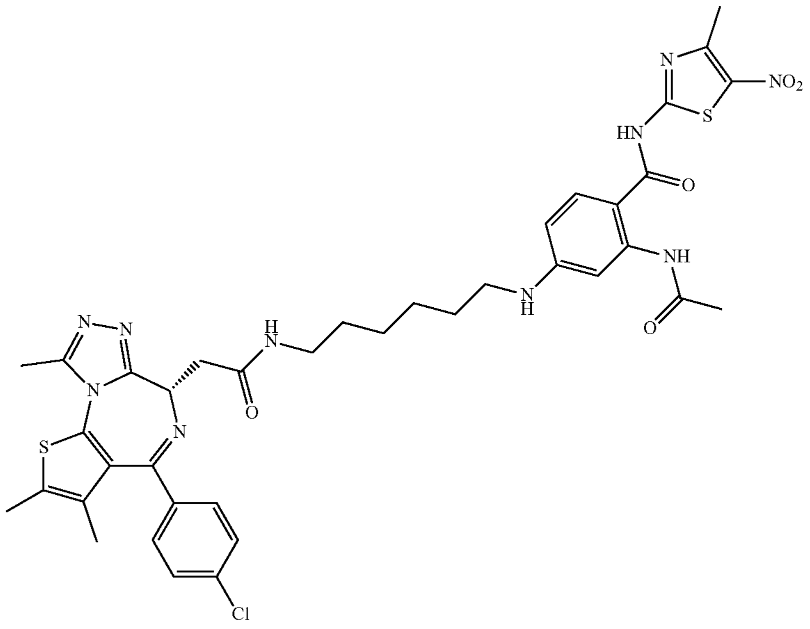 [SMILES: CC(=O)Nc1cc(NCCCCCCNC(=O)C[C@@H]2N=C(c3ccc(Cl)cc3)c3c(sc(C)c3C)-n3c(C)nnc32)ccc1C(=O)Nc1nc(C)c([N+](=O)[O-])s1] | (S)-2-acetamido-4-((6-(2-(4-(4-chlorophenyl)-2,3,9-trimethyl-6H-thieno[3,2-f][1,2,4]triazolo[4,3-a][1,4]diazepin-6-yl)acetamido)hexyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-29 | 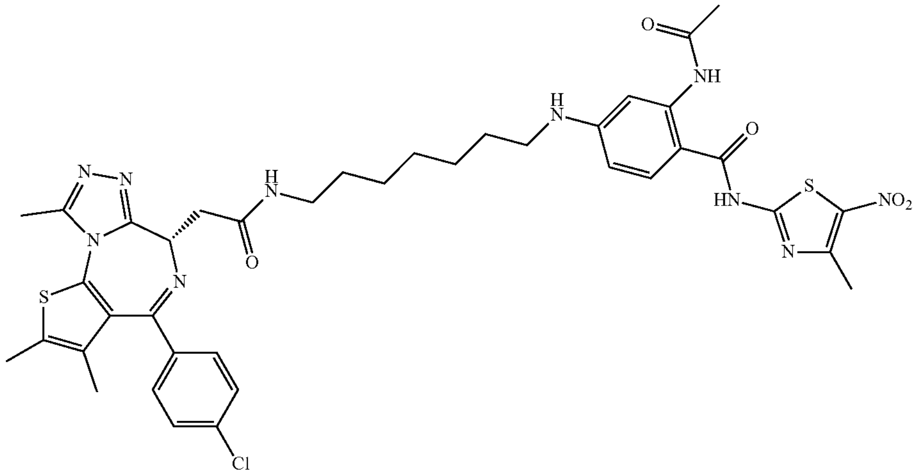 [SMILES: CC(=O)Nc1cc(NCCCCCCCNC(=O)C[C@@H]2N=C(c3ccc(Cl)cc3)c3c(sc(C)c3C)-n3c(C)nnc32)ccc1C(=O)Nc1nc(C)c([N+](=O)[O-])s1] | (S)-2-acetamido-4-((7-(2-(4-(4-chlorophenyl)-2,3,9-trimethyl-6H-thieno[3,2-f][1,2,4]triazolo[4,3-a][1,4]diazepin-6-yl)acetamido)heptyl)amino)-N-(4-methyl-5-nitrothiazol-2-yl)benzamide |

TABLE 5-continued
DDB1 binding moieties attached to a target protein binding moiety
| Compound | Structure | Name |
| --- | --- | --- |
| D-30 | 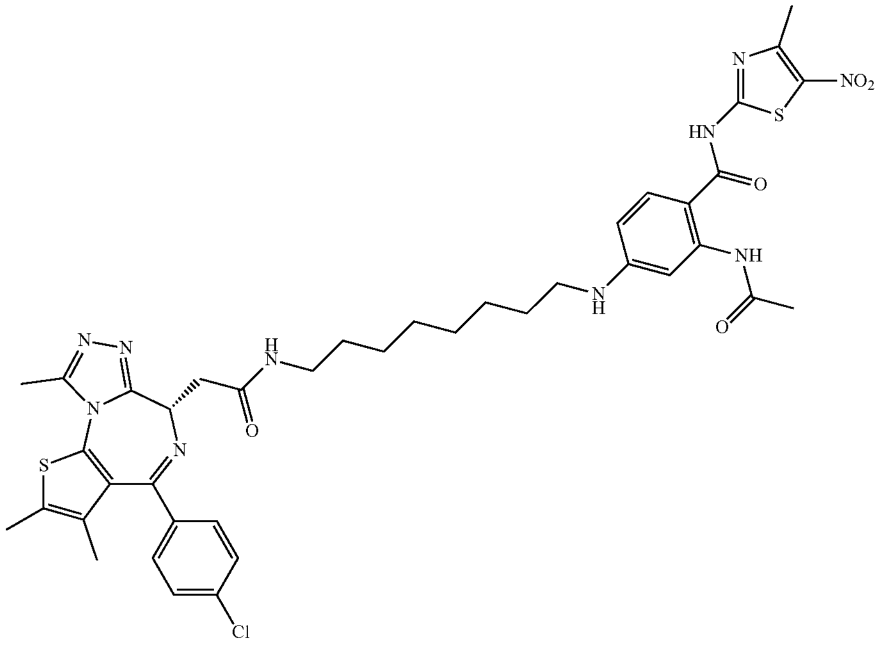 [SMILES: CC(=O)Nc1cc(NCCCCCCCCNC(=O)C[C@@H]2N=C(c3ccc(Cl)cc3)c3c(sc(C)c3C)-n3c(C)nnc32)ccc1C(=O)Nc1nc(C)c([N+](=O)[O-])s1] | (S)-2-acetamido-4-((8-(2-(4-(4-chlorophenyl)-2,3,9-trimethyl-6H-thieno[3,2-f][1,2,4]triazolo[4,3-a][1,4]diazepin-6-yl)acetamido)octyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-31 | 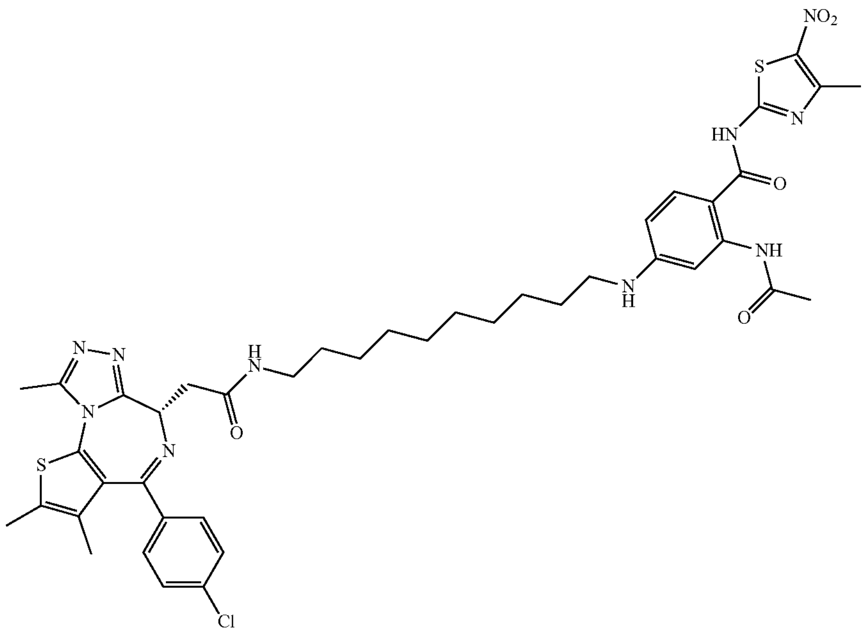 | (S)-2-acetamido-4-((10-(2-(4-(4-chlorophenyl)-2,3,9-trimethyl-6H-thieno[3,2-f][1,2,4]triazolo[4,3-a][1,4]diazepin-6-yl)acetamido)decyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-32 | 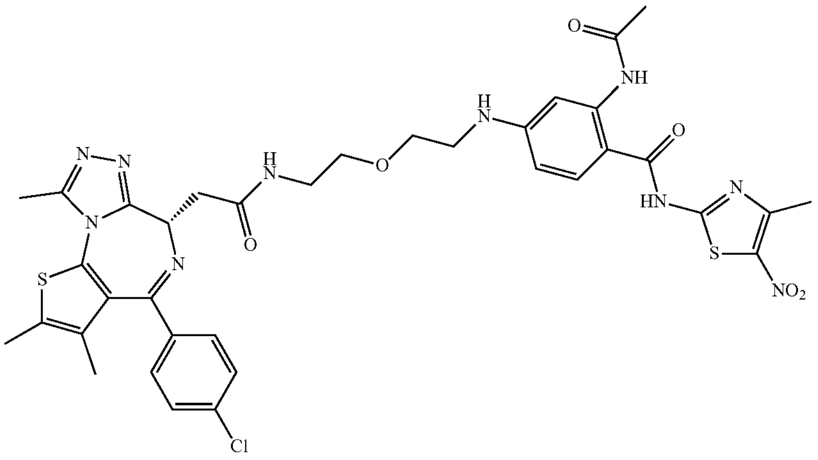 | (S)-2-acetamido-4-((2-(2-(2-(4-(4-chlorophenyl)-2,3,9-trimethyl-6H-thieno[3,2-f][1,2,4]triazolo[4,3-a][1,4]diazepin-6-yl)acetamido)ethoxy)ethyl)amino)-N-(4-methyl-5-D-34nitrothiazol-2-D-35yl)benzamide |

TABLE 5-continued
| DDB1 binding moieties attached to a target protein binding moiety | | |
|---|---|---|
| Compound | Structure | Name |
| D-33 | 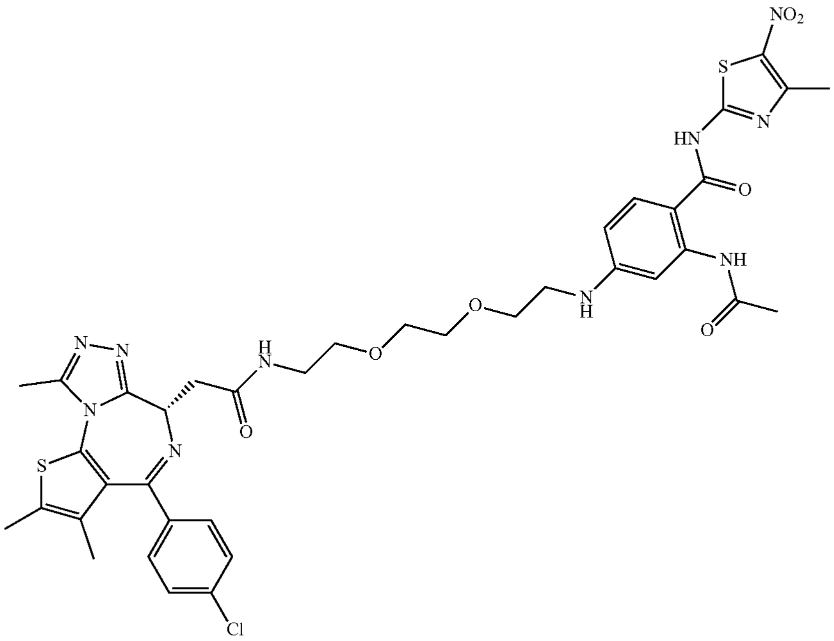 | (S)-2-acetamido-4-((2-(2-(2-(2-(4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-34 | 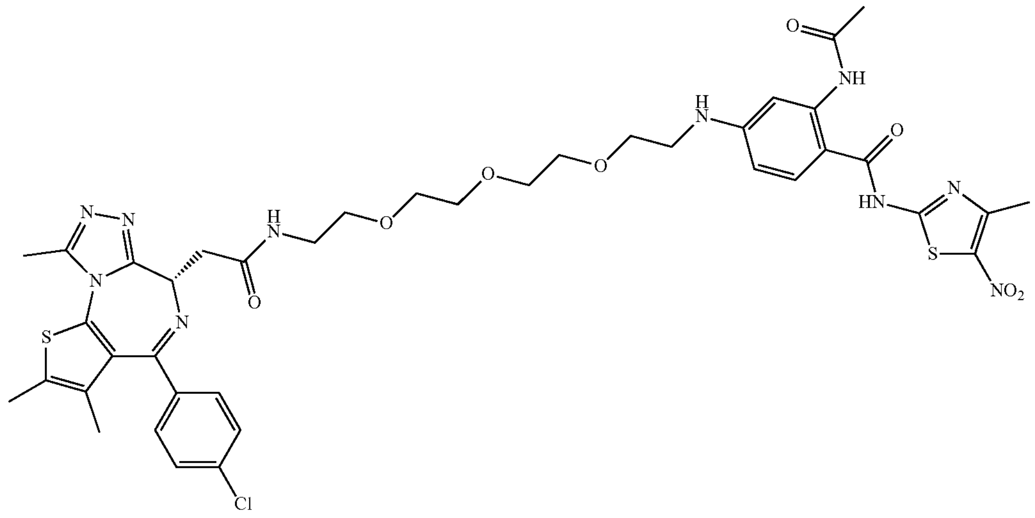 | (S)-2-acetamido-4-((1-(4-(4-chlorophenyl)-2,3,9-trimethyl-6H-thieno[3,2-f][1,2,4]triazolo[4,3-a][1,4]diazepin-6-yl)-2-oxo-6,9,12-trioxa-3-azatetradecan-14-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-35 | 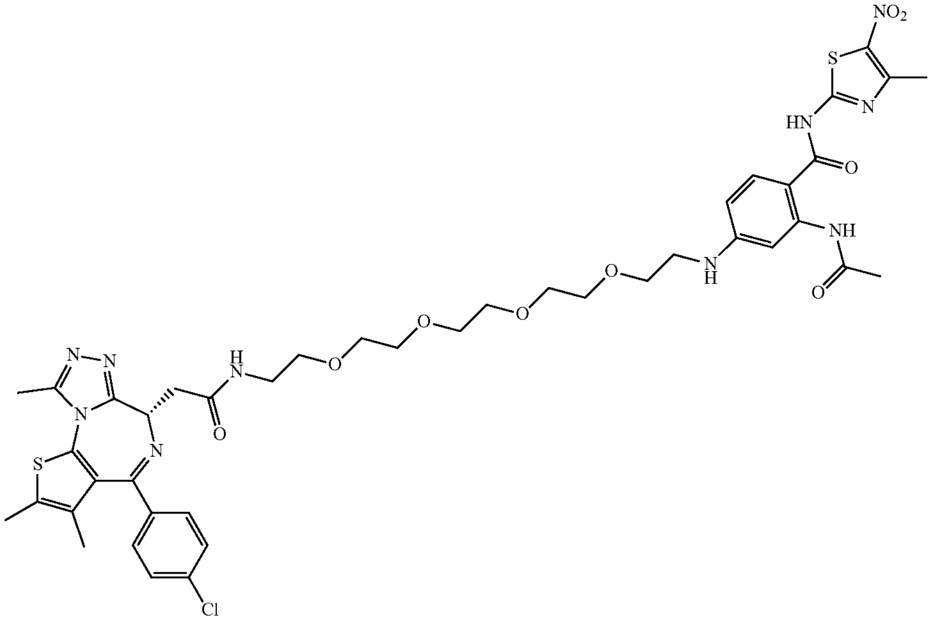 | (S)-2-acetamido-4-((1-(4-(4-chlorophenyl)-2,3,9-trimethyl-6H-thieno[3,2-f][1,2,4]triazolo[4,3-a][1,4]diazepin-6-yl)-2-oxo-6,9,12,15-tetraoxa-3-azaheptadecan-17-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-36 | 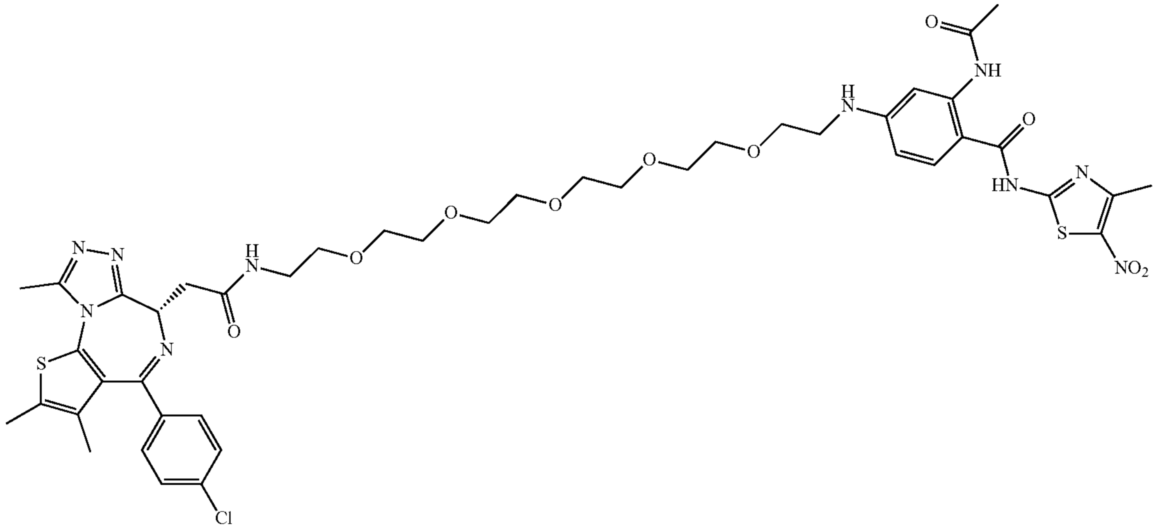 | (S)-2-acetamido-4-((1-(4-(4-chlorophenyl)-2,3,9-trimethyl-6H-thieno[3,2-f][1,2,4]triazolo[4,3-a][1,4]diazepin-6-yl)-2-oxo-6,9,12,15,18-pentaoxa-3-azaicosan-20-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-37 | 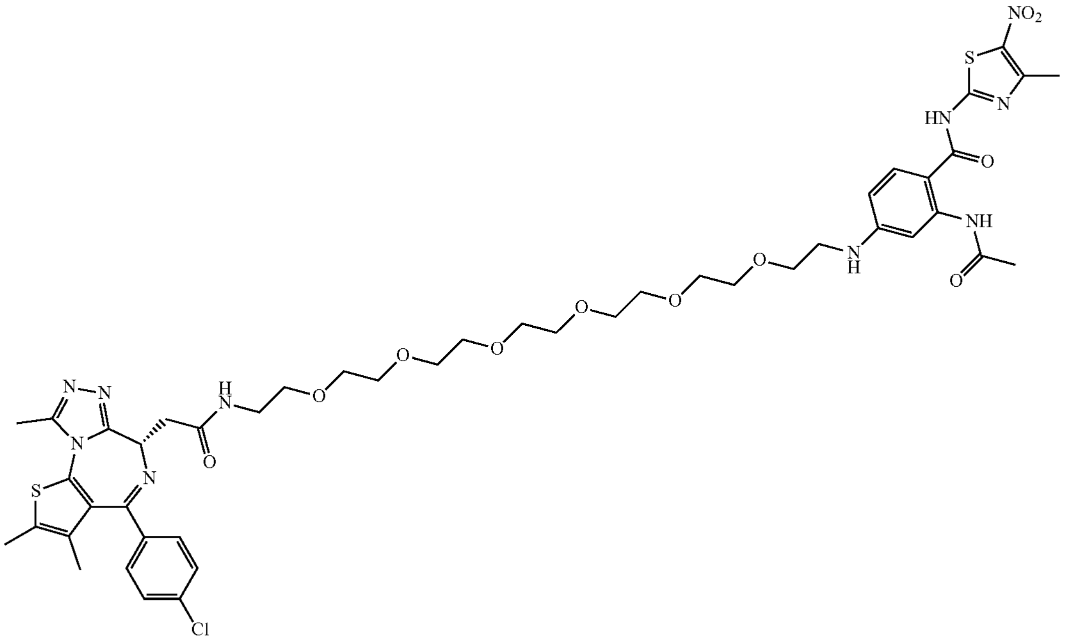 | (S)-2-acetamido-4-((1-(4-(4-chlorophenyl)-2,3,9-trimethyl-6H-thieno[3,2-f][1,2,4]triazolo[4,3-a][1,4]diazepin-6-yl)-2-oxo-6,9,12,15,18,21-hexaoxa-3-azatricosan-23-yl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-38 | 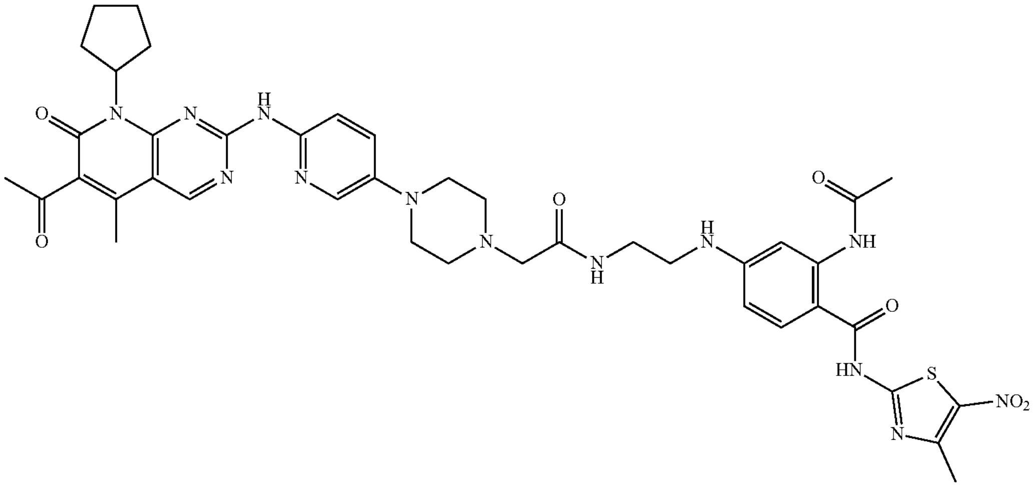 [SMILES: CC(=O)Nc1cc(NCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)ethyl)amino)-N-(4-methyl-5-nitrothiazol-2-yl)benzamide |
| D-39 | 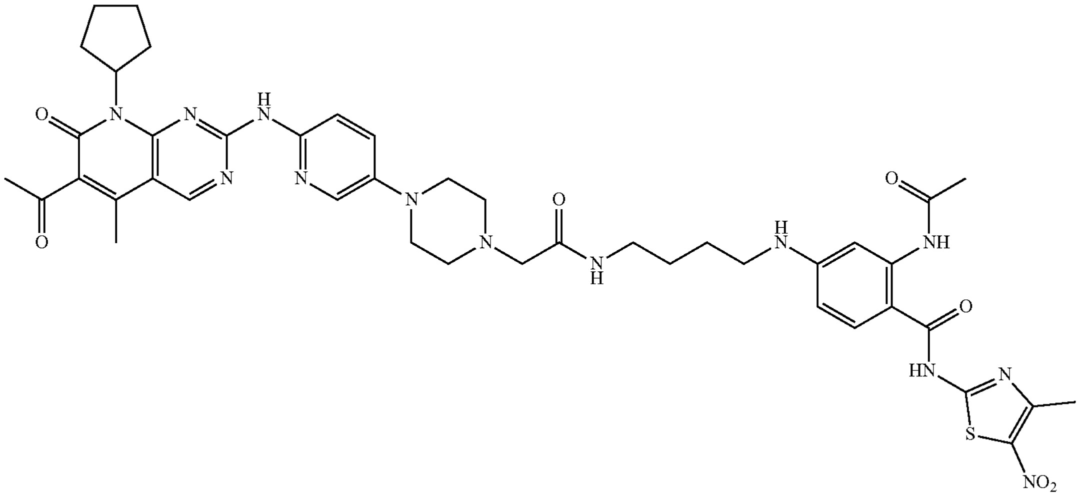 [SMILES: CC(=O)Nc1cc(NCCCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)butyl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-40 | 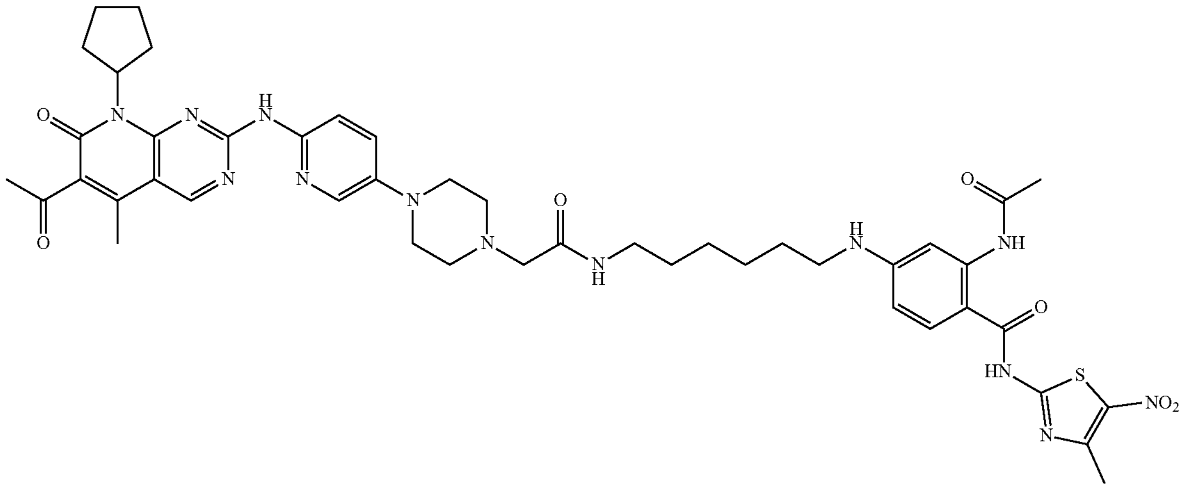 [SMILES: CC(=O)Nc1cc(NCCCCCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((6-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)hexyl)amino)-N-(4-methyl-5-nitrothiazol-2-yl)benzamide |
| D-41 | 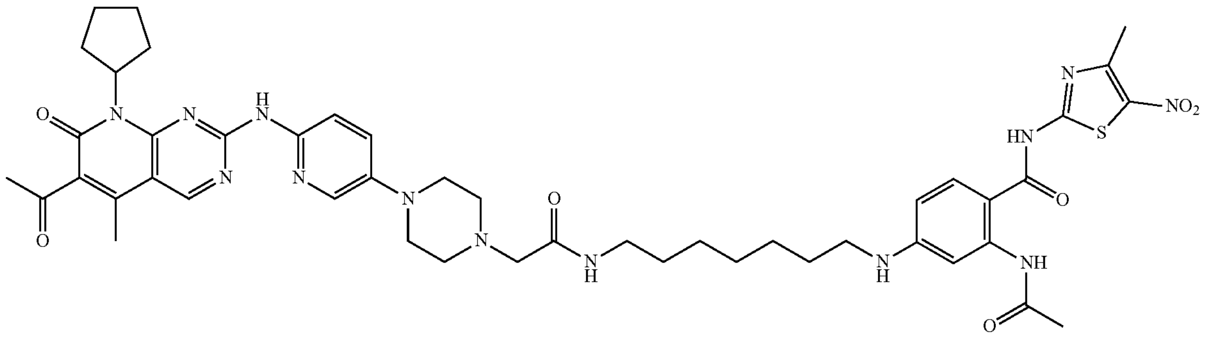 [SMILES: CC(=O)Nc1cc(NCCCCCCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((7-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)heptyl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-42 | 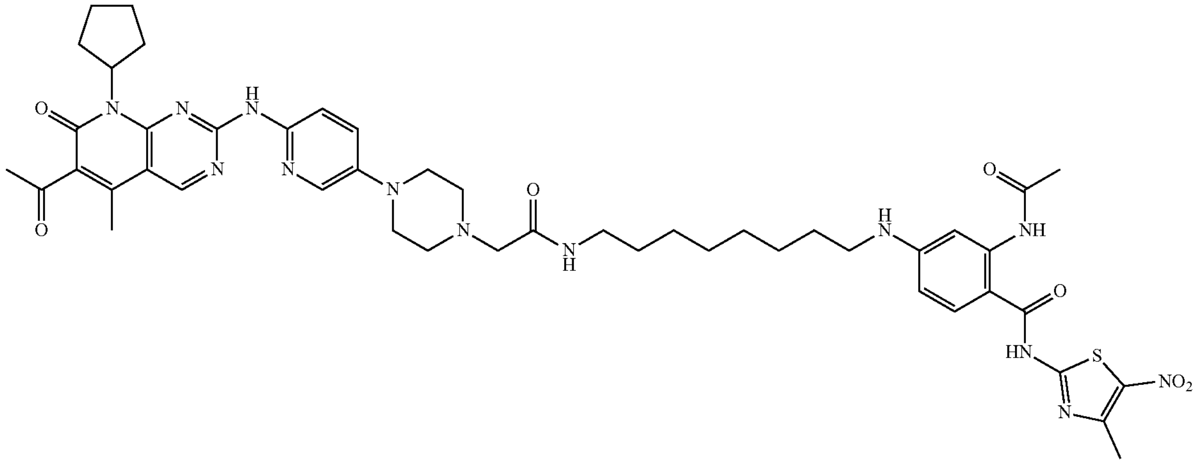 [SMILES: CC(=O)Nc1cc(NCCCCCCCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((8-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)octyl)amino)-N-(4-methyl-5-nitrothiazol-2-yl)benzamide |
| D-43 | 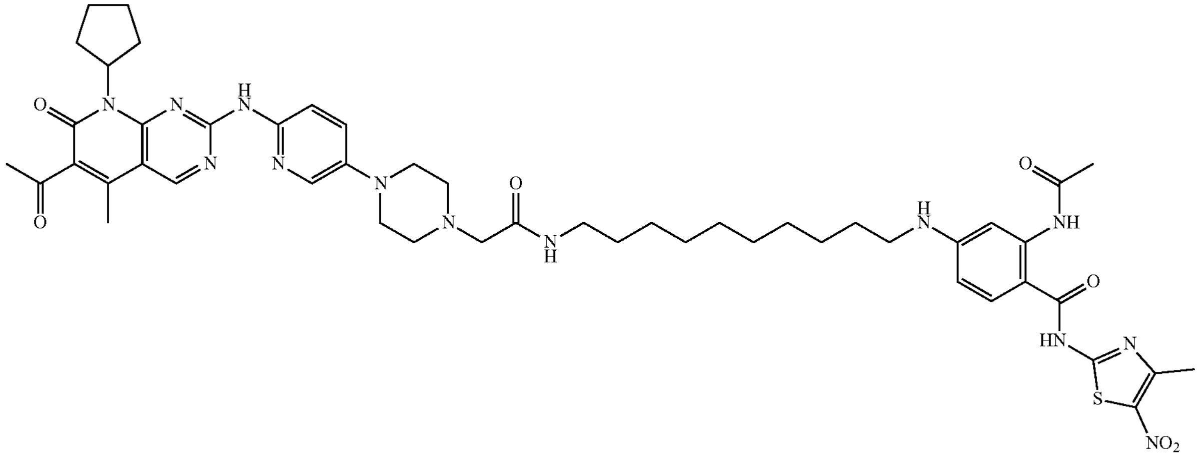 [SMILES: CC(=O)Nc1cc(NCCCCCCCCCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((10-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)decyl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-44 | 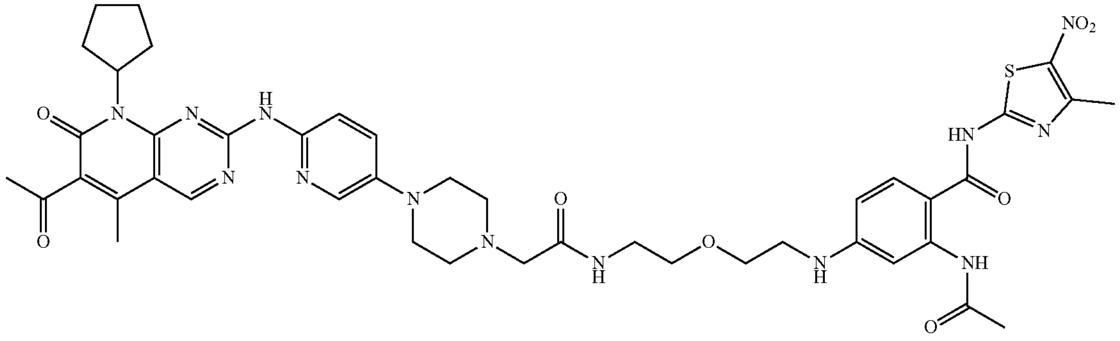 [SMILES: CC(=O)Nc1cc(NCCOCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((2-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)ethoxy)ethyl)amino)-N-(4-methyl-5-nitrothiazol-2-yl)benzamide |
| D-45 | 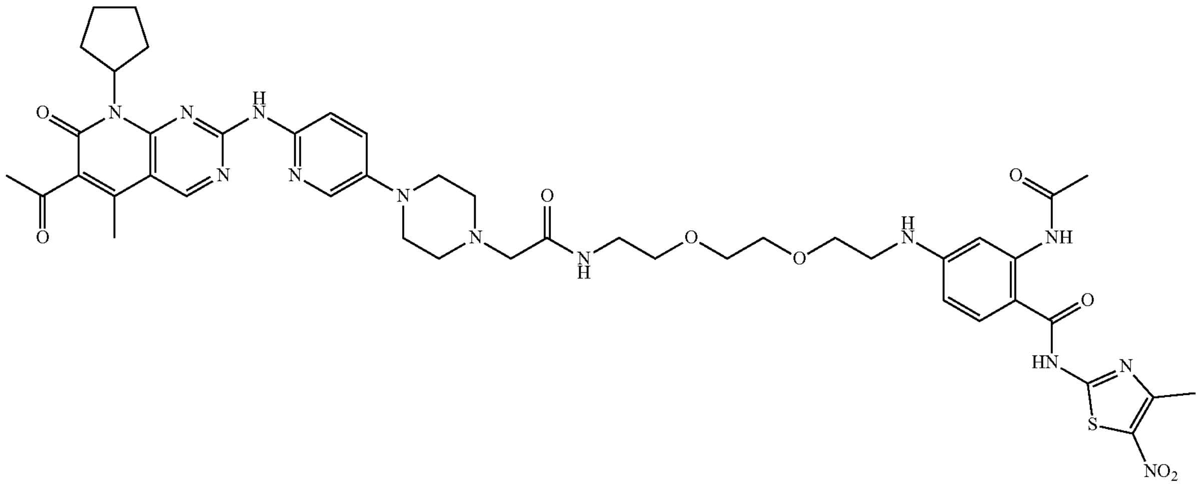 [SMILES: CC(=O)Nc1cc(NCCOCCOCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((2-(2-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)ethoxy)ethoxy)ethyl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-46 | 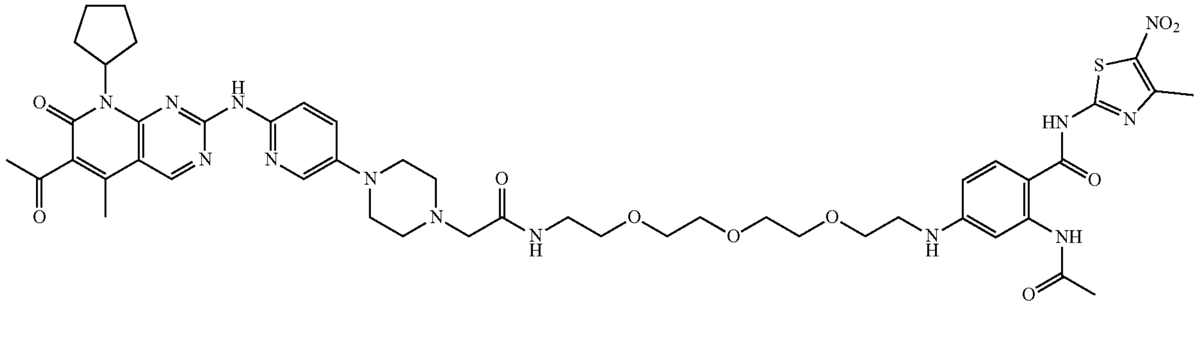 [SMILES: CC(=O)Nc1cc(NCCOCCOCCOCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12-trioxa-3-azatetradecan-14-yl)amino)-N-(4-methyl-5-nitrothiazol-2-yl)benzamide |
| D-47 | 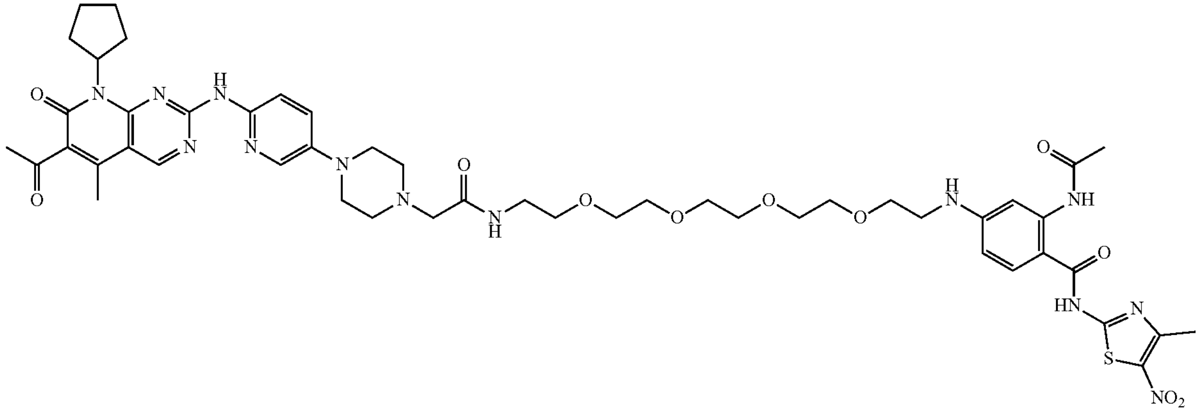 [SMILES: CC(=O)Nc1cc(NCCOCCOCCOCCOCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15-tetraoxa-3-azaheptadecan-17-yl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-48 | 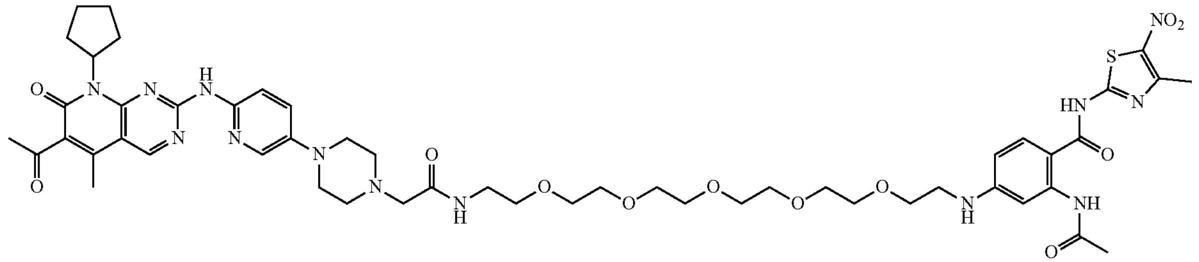 [SMILES: CC(=O)Nc1cc(NCCOCCOCCOCCOCCOCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15,18-pentaoxa-3-azaicosan-20-yl)amino)-N-(4-methyl-5-nitrothiazol-2-yl)benzamide |
| D-49 | 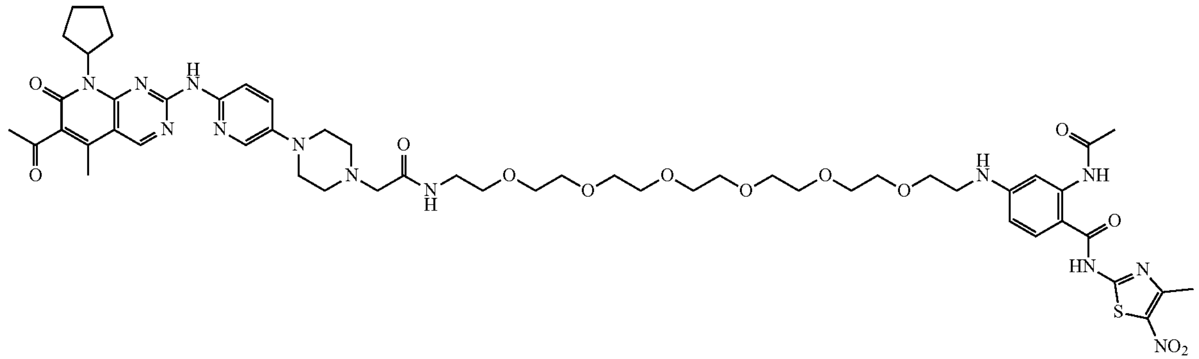 [SMILES: CC(=O)Nc1cc(NCCOCCOCCOCCOCCOCCOCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15,18,21-hexaoxa-3-azatricosan-23-yl)amino)-N-(4-methyl-5-nitrothiazol-2-yl)benzamide |

TABLE 5-continued
DDB1 binding moieties attached to a target protein binding moiety
| Compound | Structure | Name |
| --- | --- | --- |
| D-50 | 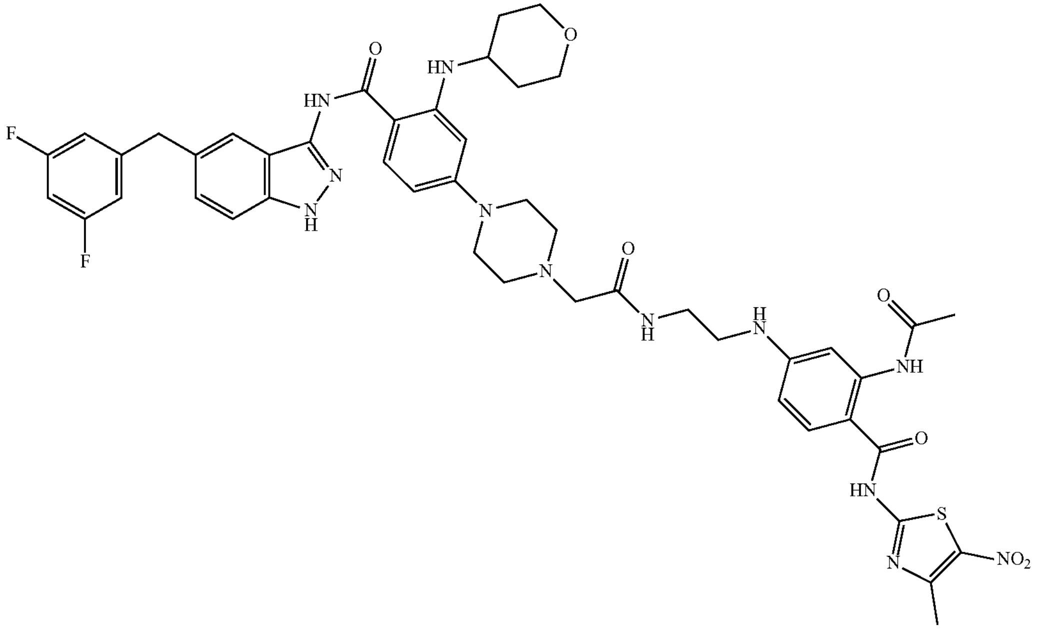 [SMILES: CC(=O)Nc1cc(NCCNC(=O)CN2CCN(c3ccc(C(=O)Nc4n[nH]c5ccc(Cc6cc(F)cc(F)c6)cc45)c(NC4CCOCC4)c3)CC2)ccc1C(=O)Nc1nc(C)c([N+](=O)[O-])s1] | 2-acetamido-4-((2-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)ethyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-51 | 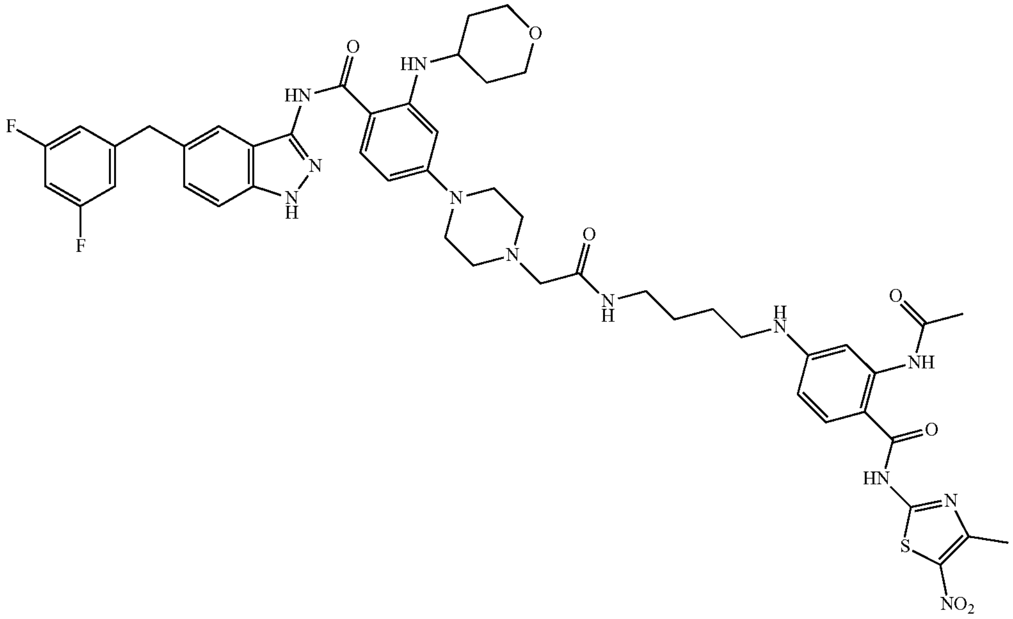 [SMILES: CC(=O)Nc1cc(NCCCCNC(=O)CN2CCN(c3ccc(C(=O)Nc4n[nH]c5ccc(Cc6cc(F)cc(F)c6)cc45)c(NC4CCOCC4)c3)CC2)ccc1C(=O)Nc1nc(C)c([N+](=O)[O-])s1] | 2-acetamido-4-((4-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)butyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-52 | 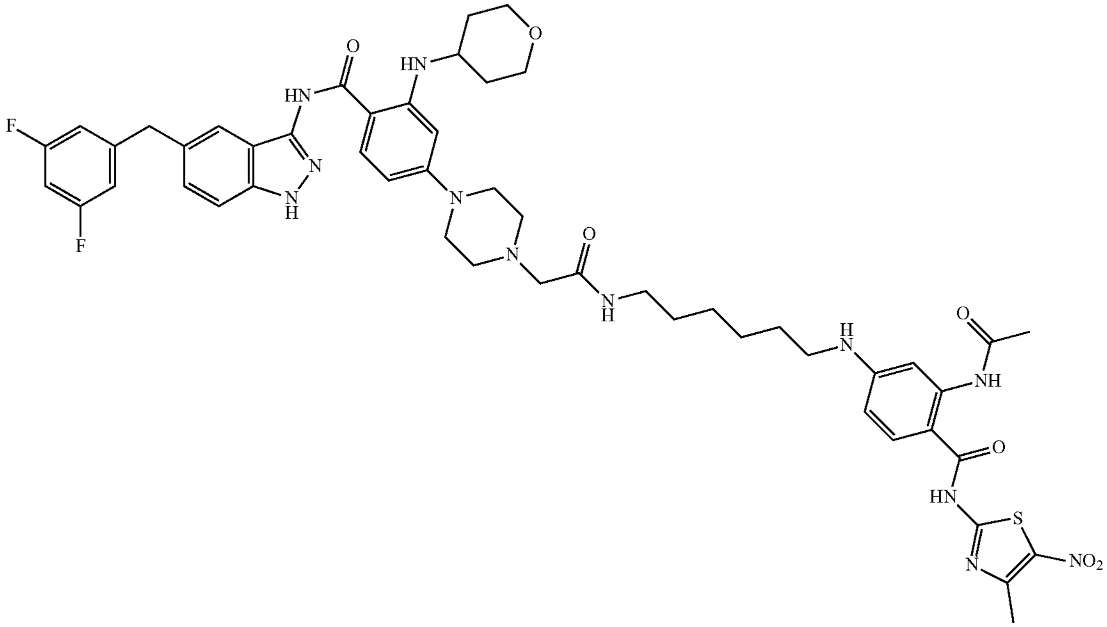 [SMILES: CC(=O)Nc1cc(NCCCCCCNC(=O)CN2CCN(c3ccc(C(=O)Nc4n[nH]c5ccc(Cc6cc(F)cc(F)c6)cc45)c(NC4CCOCC4)c3)CC2)ccc1C(=O)Nc1nc(C)c([N+](=O)[O-])s1] | 2-acetamido-4-((6-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)hexyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-53 | 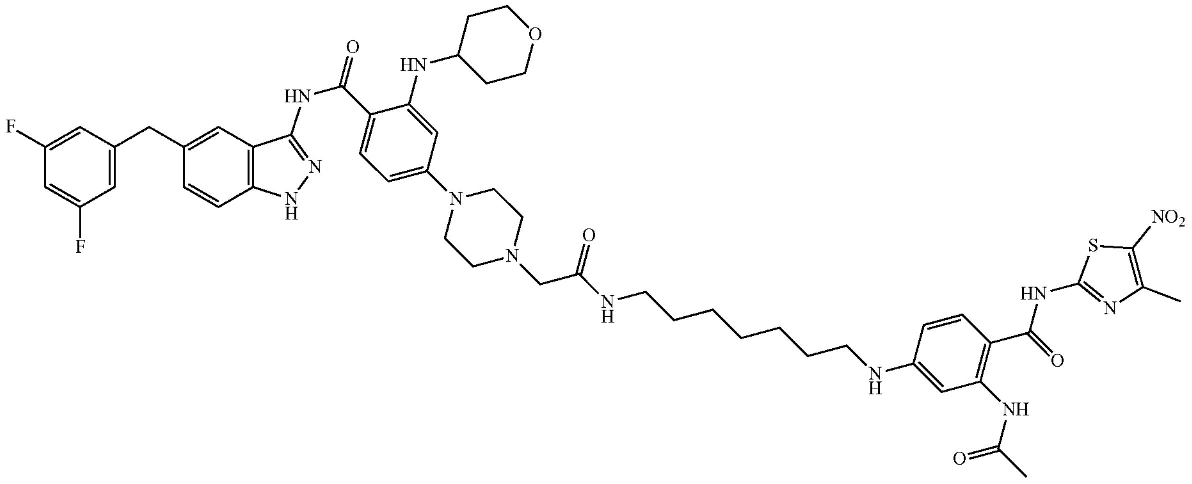 [SMILES: CC(=O)Nc1cc(NCCCCCCCNC(=O)CN2CCN(c3ccc(C(=O)Nc4n[nH]c5ccc(Cc6cc(F)cc(F)c6)cc45)c(NC4CCOCC4)c3)CC2)ccc1C(=O)Nc1nc(C)c([N+](=O)[O-])s1] | 2-acetamido-4-((7-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)heptyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-54 | 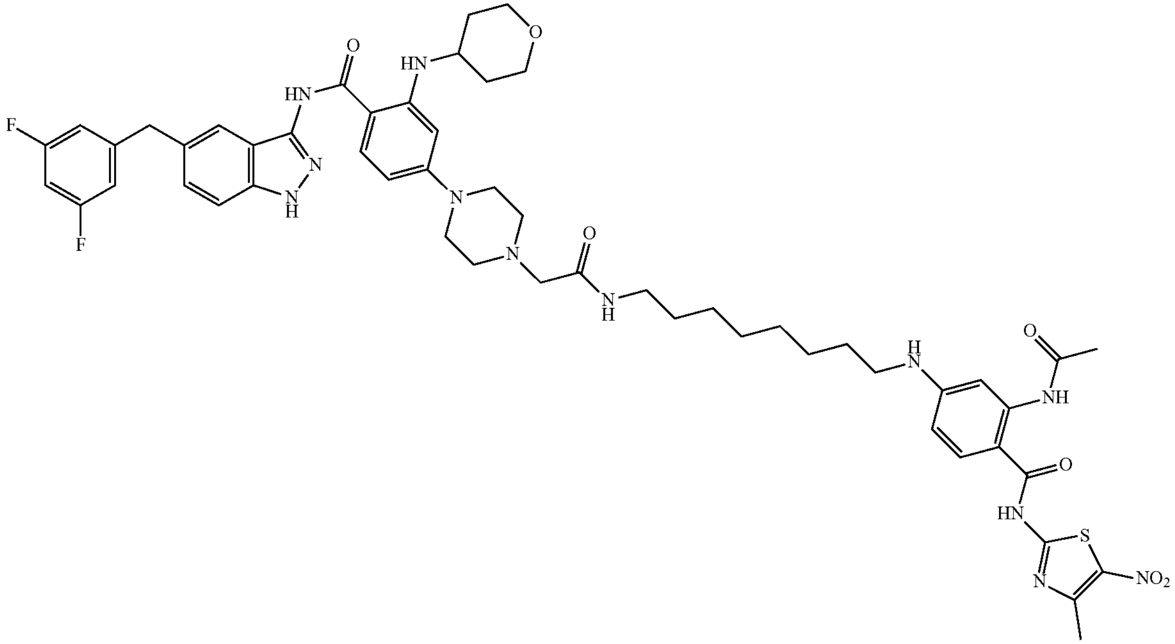 [SMILES: CC(=O)Nc1cc(NCCCCCCCCNC(=O)CN2CCN(c3ccc(C(=O)Nc4n[nH]c5ccc(Cc6cc(F)cc(F)c6)cc45)c(NC4CCOCC4)c3)CC2)ccc1C(=O)Nc1nc(C)c([N+](=O)[O-])s1] | 2-acetamido-4-((8-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)octyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-55 | 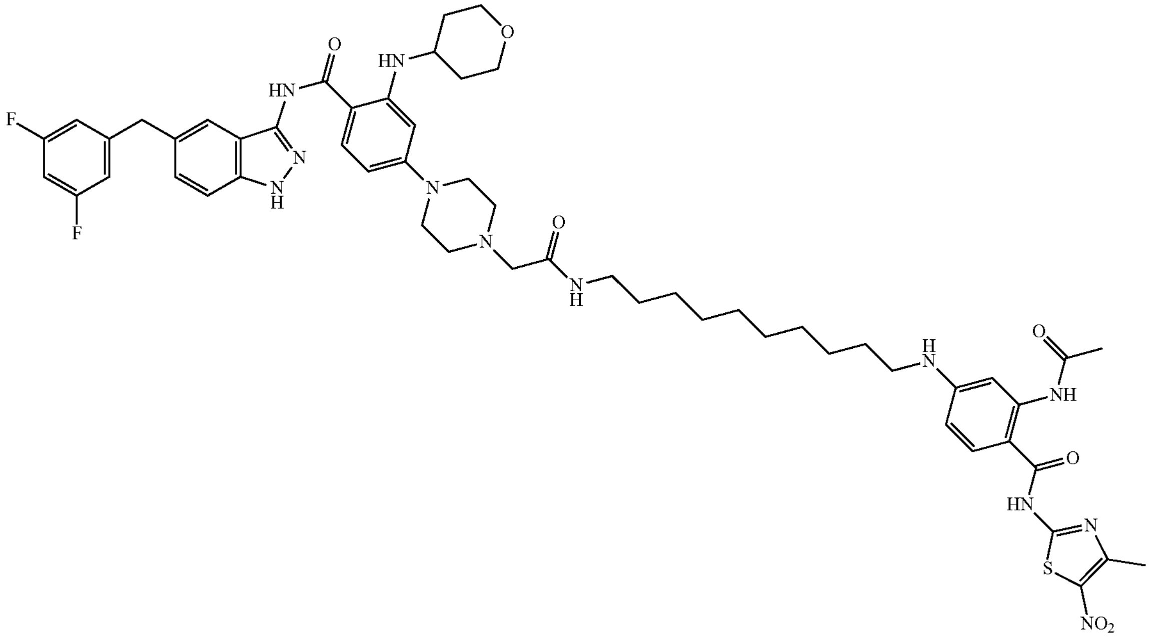 [SMILES: CC(=O)Nc1cc(NCCCCCCCCCCNC(=O)CN2CCN(c3ccc(C(=O)Nc4n[nH]c5ccc(Cc6cc(F)cc(F)c6)cc45)c(NC4CCOCC4)c3)CC2)ccc1C(=O)Nc1nc(C)c([N+](=O)[O-])s1] | 2-acetamido-4-((10-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)decyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-56 | 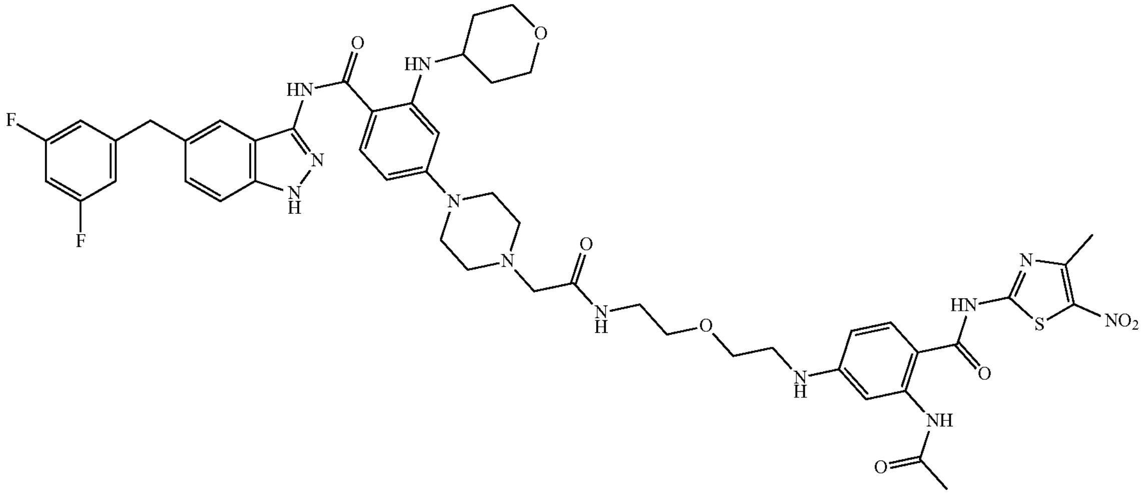 [SMILES: CC(=O)Nc1cc(NCCOCCNC(=O)CN2CCN(c3ccc(C(=O)Nc4n[nH]c5ccc(Cc6cc(F)cc(F)c6)cc45)c(NC4CCOCC4)c3)CC2)ccc1C(=O)Nc1nc(C)c([N+](=O)[O-])s1] | 2-acetamido-4-((2-(2-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)ethoxy)ethyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-57 | 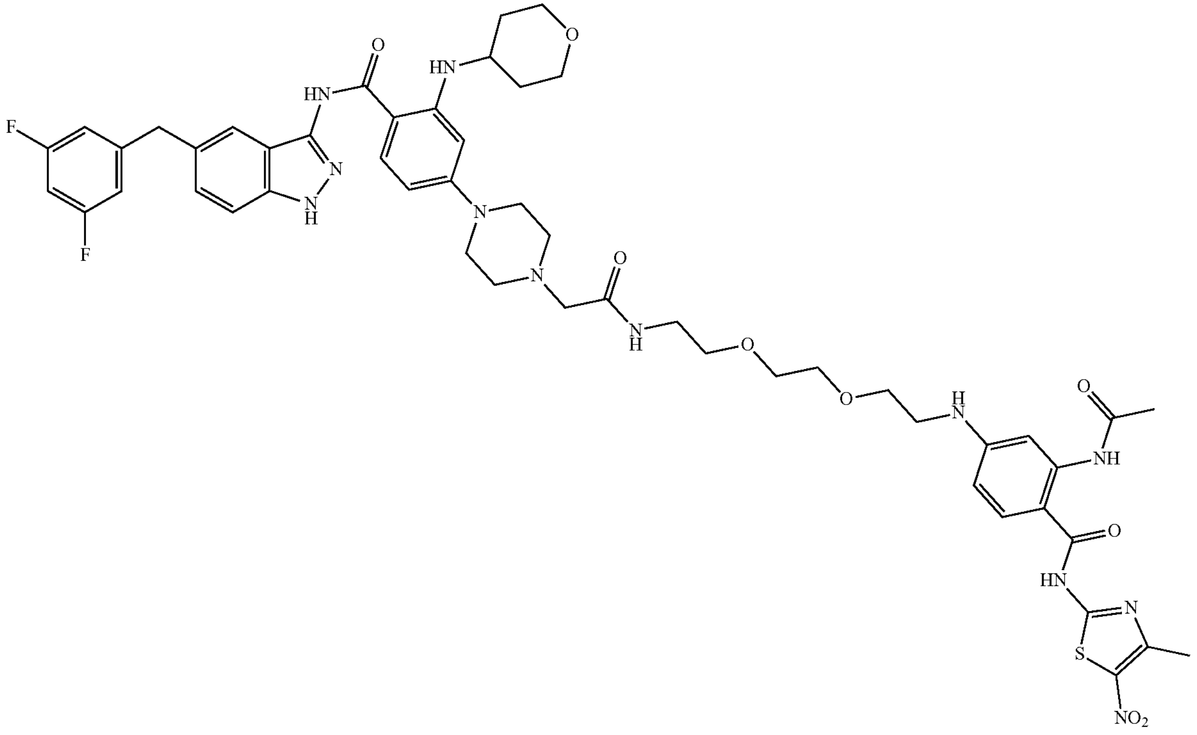 [SMILES: CC(=O)Nc1cc(NCCOCCOCCNC(=O)CN2CCN(c3ccc(C(=O)Nc4n[nH]c5ccc(Cc6cc(F)cc(F)c6)cc45)c(NC4CCOCC4)c3)CC2)ccc1C(=O)Nc1nc(C)c([N+](=O)[O-])s1] | 2-acetamido-4-((2-(2-(2-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)ethoxy)ethoxy)ethyl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-58 | 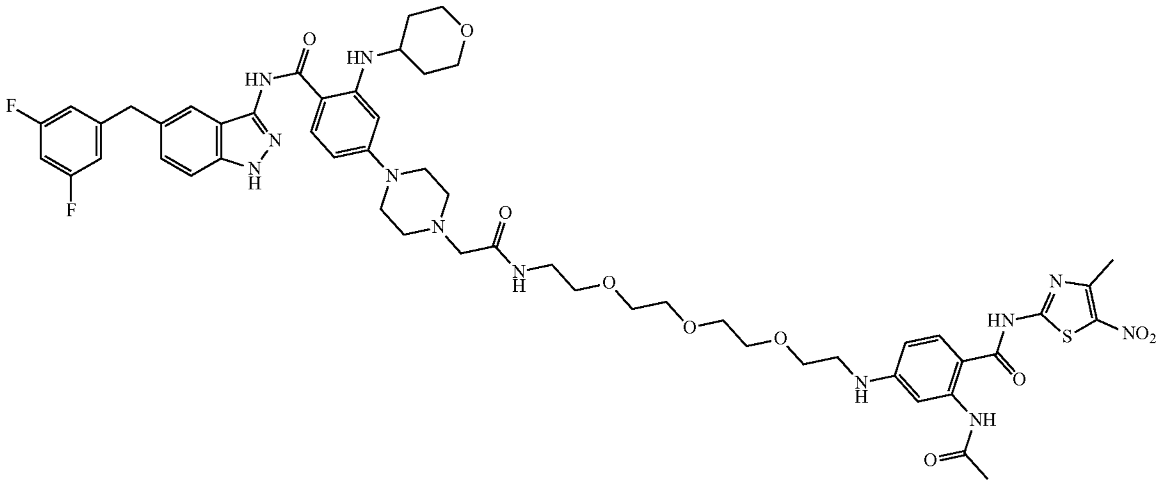 [SMILES: CC(=O)Nc1cc(NCCOCCOCCOCCNC(=O)CN2CCN(c3ccc(C(=O)Nc4n[nH]c5ccc(Cc6cc(F)cc(F)c6)cc45)c(NC4CCOCC4)c3)CC2)ccc1C(=O)Nc1nc(C)c([N+](=O)[O-])s1] | 2-acetamido-4-((1-(4-(4-((5-(3,5-difluorobenzyl)-1H-indazol-3-yl)carbamoyl)-3-((tetrahydro-2H-pyran-4-yl)amino)phenyl)piperazin-1-yl)-2-oxo-6,9,12-trioxa-3-azatetradecan-14-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-59 | 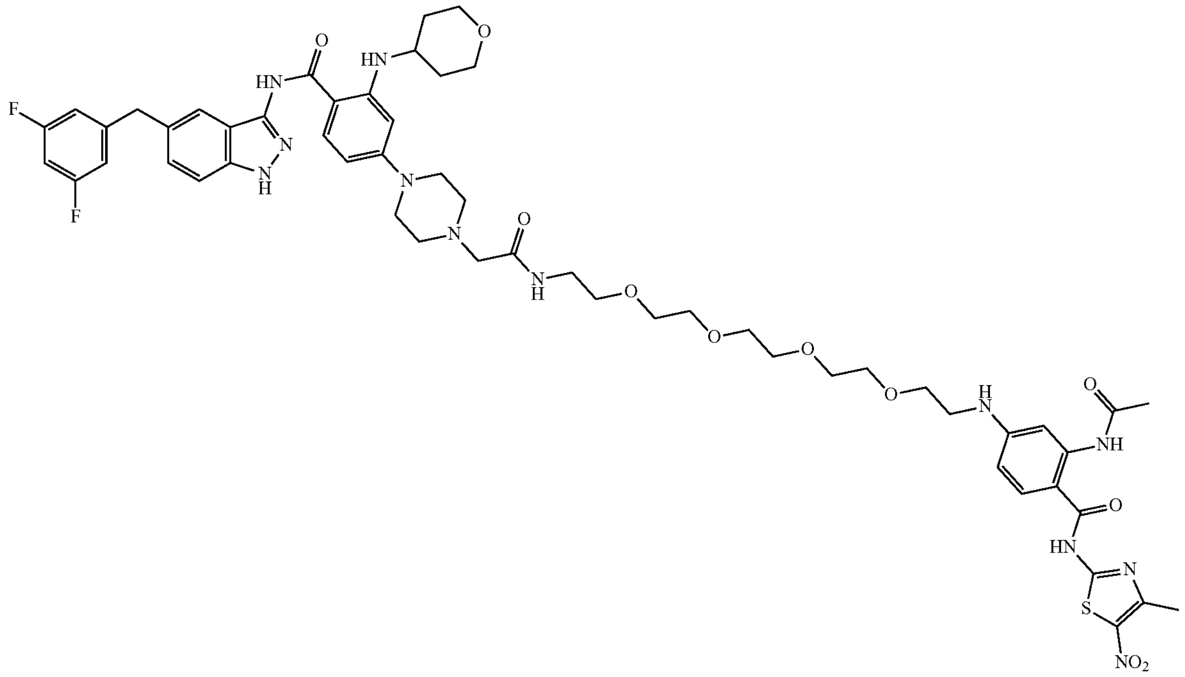 [SMILES: CC(=O)Nc1cc(NCCOCCOCCOCCOCCNC(=O)CN2CCN(c3ccc(C(=O)Nc4n[nH]c5ccc(Cc6cc(F)cc(F)c6)cc45)c(NC4CCOCC4)c3)CC2)ccc1C(=O)Nc1nc(C)c([N+](=O)[O-])s1] | 2-acetamido-4-((1-(4-(4-((5-(3,5-difluorobenzyl)-1H-indazol-3-yl)carbamoyl)-3-((tetrahydro-2H-pyran-4-yl)amino)phenyl)piperazin-1-yl)-2-oxo-6,9,12,15-tetraoxa-3-azaheptadecan-17-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-60 | 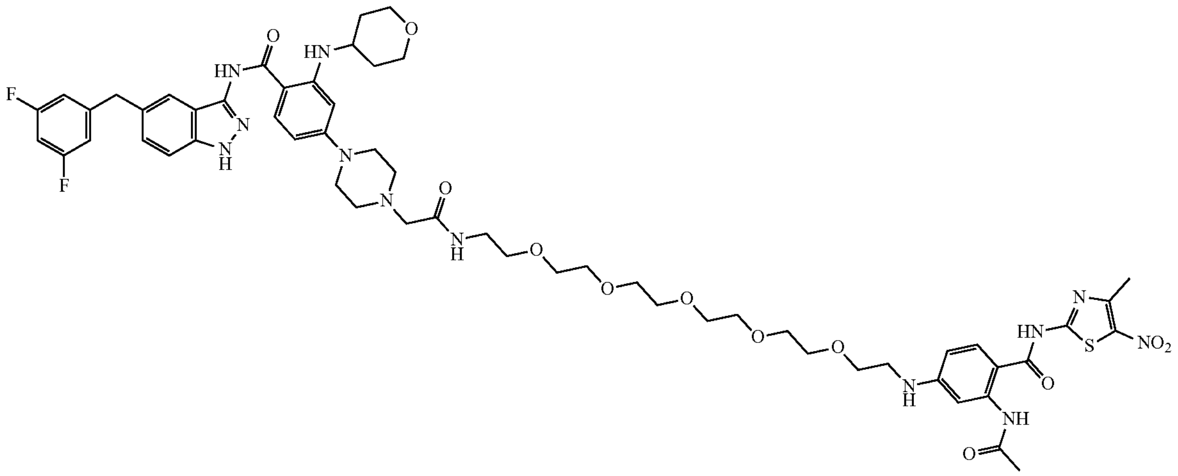 [SMILES: CC(=O)Nc1cc(NCCOCCOCCOCCOCCOCCNC(=O)CN2CCN(c3ccc(C(=O)Nc4n[nH]c5ccc(Cc6cc(F)cc(F)c6)cc45)c(NC4CCOCC4)c3)CC2)ccc1C(=O)Nc1nc(C)c([N+](=O)[O-])s1] | 2-acetamido-4-((1-(4-(4-((5-(3,5-difluorobenzyl)-1H-indazol-3-yl)carbamoyl)-3-((tetrahydro-2H-pyran-4-yl)amino)phenyl)piperazin-1-yl)-2-oxo-6,9,12,15,18-pentaoxa-3-azaicosan-20-yl)amino)-N-(4-methyl-5-nitrothiazol-2-yl)benzamide |

TABLE 5-continued
| DDB1 binding moieties attached to a target protein binding moiety | | |
|---|---|---|
| Compound | Structure | Name |
| D-61 | 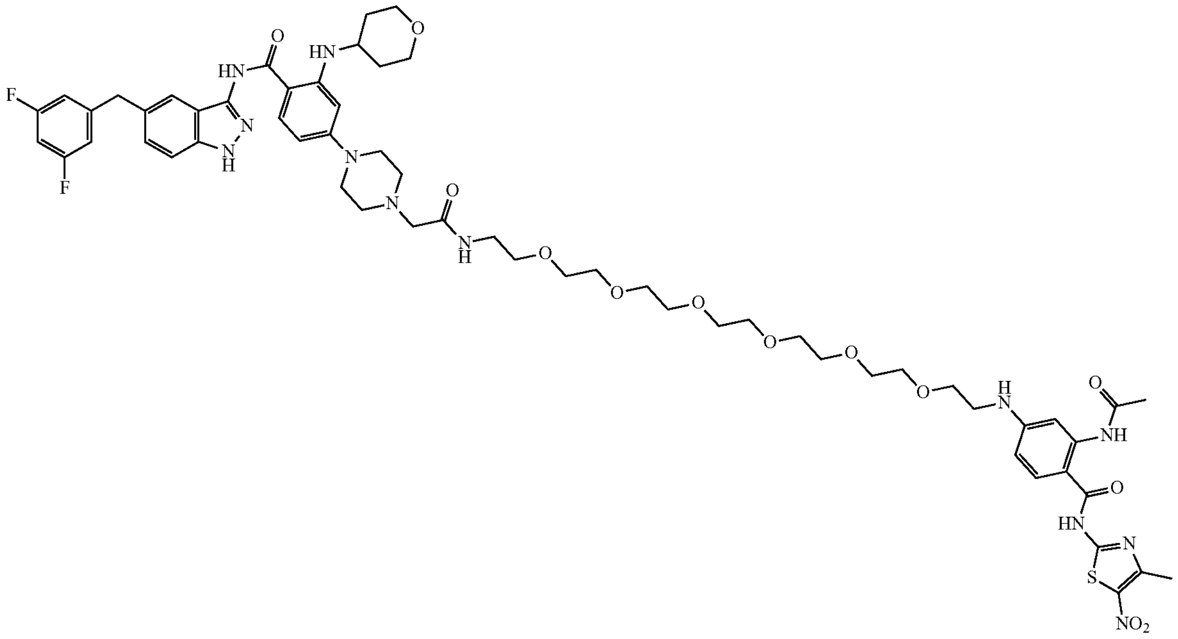 [SMILES: CC(=O)Nc1cc(NCCOCCOCCOCCOCCOCCOCCNC(=O)CN2CCN(c3ccc(C(=O)Nc4n[nH]c5ccc(Cc6cc(F)cc(F)c6)cc45)c(NC4CCOCC4)c3)CC2)ccc1C(=O)Nc1nc(C)c([N+](=O)[O-])s1] | 2-acetamido-4-((1-(4-(4-((5-(3,5-difluorobenzyl)-1H-indazol-3-yl)carbamoyl)-3-((tetrahydro-2H-pyran-4-yl)amino)phenyl)piperazin-1-yl)-2-oxo-6,9,12,15,18,21-hexaoxa-3-azatricosan-23-yl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-62 | 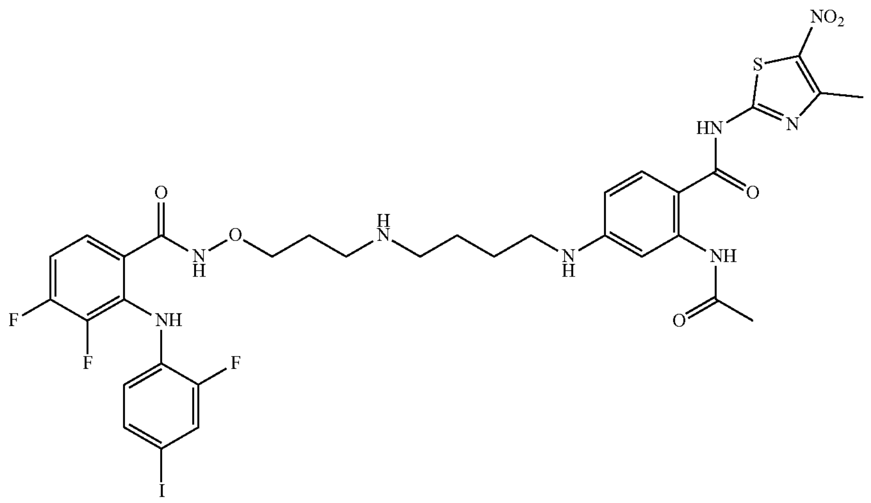 [SMILES: CC(=O)Nc1cc(NCCCCNCCCONC(=O)c2ccc(F)c(F)c2Nc2ccc(I)cc2F)ccc1C(=O)Nc1nc(C)c([N+](=O)[O-])s1] | N-(3-((4-((3-acetamido-4-((4-methyl-5-nitrothiazol-2-yl)carbamoyl)phenyl)amino)butyl)amino)propoxy)-3,4-difluoro-2-((2-fluoro-4-iodophenyl)amino)benzamide |
| D-63 | 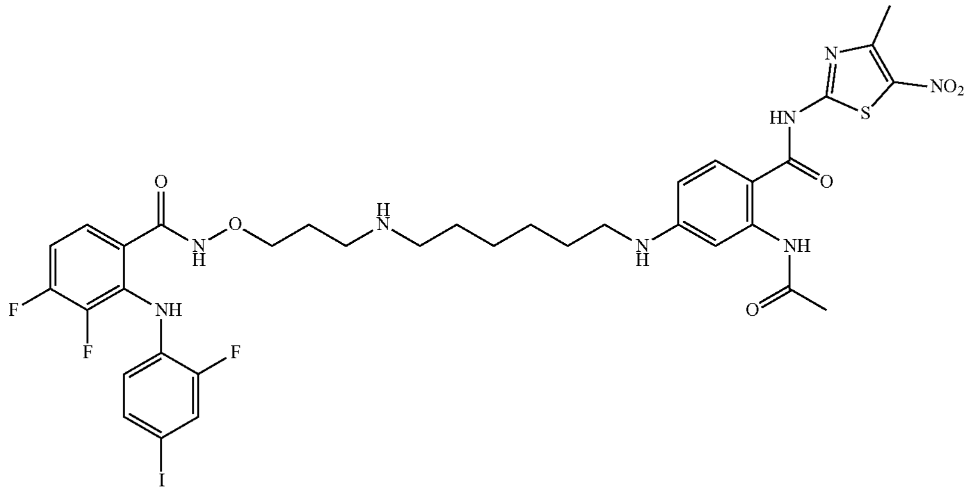 [SMILES: CC(=O)Nc1cc(NCCCCCCNCCCONC(=O)c2ccc(F)c(F)c2Nc2ccc(I)cc2F)ccc1C(=O)Nc1nc(C)c([N+](=O)[O-])s1] | N-(3-((6-((3-acetamido-4-((4-methyl-5-nitrothiazol-2-yl)carbamoyl)phenyl)amino)hexyl)amino)propoxy)-3,4-difluoro-2-((2-fluoro-4-iodophenyl)amino)benzamide |

TABLE 5-continued

| DDB1 binding moieties attached to a target protein binding moiety | | |
|---|---|---|
| Compound | Structure | Name |
| D-64 | 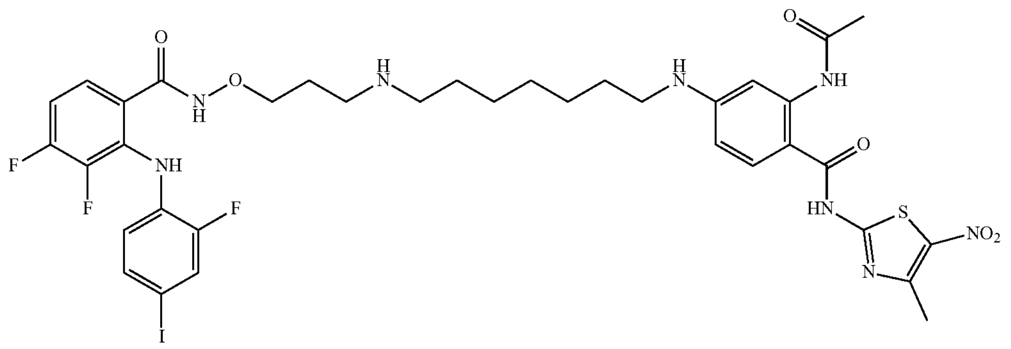 [SMILES: CC(=O)Nc1cc(NCCCCCCCNCCCONC(=O)c2ccc(F)c(F)c2Nc2ccc(I)cc2F)ccc1C(=O)Nc1nc(C)c([N+](=O)[O-])s1] | N-(3-((7-((3-acetamido-4-((4-methyl-5-nitrothiazol-2-yl)carbamoyl)phenyl)amino)heptyl)amino)propoxy)-3,4-difluoro-2-((2-fluoro-4-iodophenyl)amino)benzamide |
| D-65 | 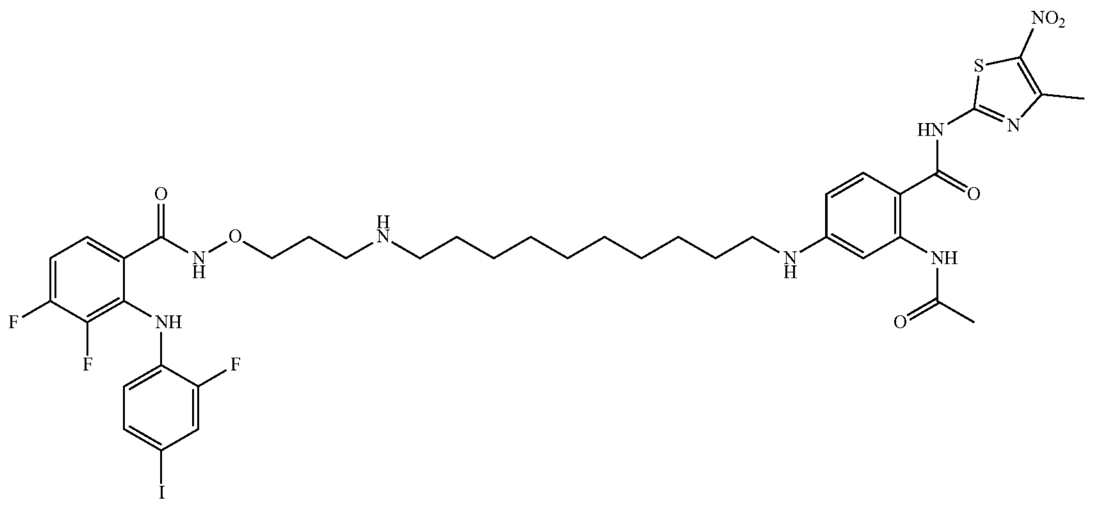 [SMILES: CC(=O)Nc1cc(NCCCCCCCCCCNCCCONC(=O)c2ccc(F)c(F)c2Nc2ccc(I)cc2F)ccc1C(=O)Nc1nc(C)c([N+](=O)[O-])s1] | N-(3-((10-((3-acetamido-4-((4-methyl-5-nitrothiazol-2-yl)carbamoyl)phenyl)amino)decyl)amino)propoxy)-3,4-difluoro-2-((2-fluoro-4-iodophenyl)amino)benzamide |

TABLE 5-continued

| DDB1 binding moieties attached to a target protein binding moiety | | |
|---|---|---|
| Compound | Structure | Name |
| D-66 | 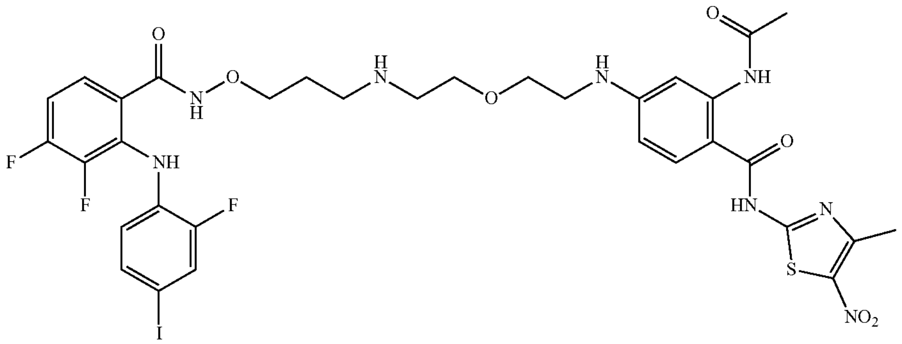 [SMILES: CC(=O)Nc1cc(NCCOCCNCCCONC(=O)c2ccc(F)c(F)c2Nc2ccc(I)cc2F)ccc1C(=O)Nc1nc(C)c([N+](=O)[O-])s1] | N-(3-((2-(2-((3-acetamido-4-((4-methyl-5-nitrothiazol-2-yl)carbamoyl)phenyl)amino)ethoxy)ethyl)amino)propoxy)-3,4-difluoro-2-((2-fluoro-4-iodophenyl)amino)benzamide |
| D-67 | 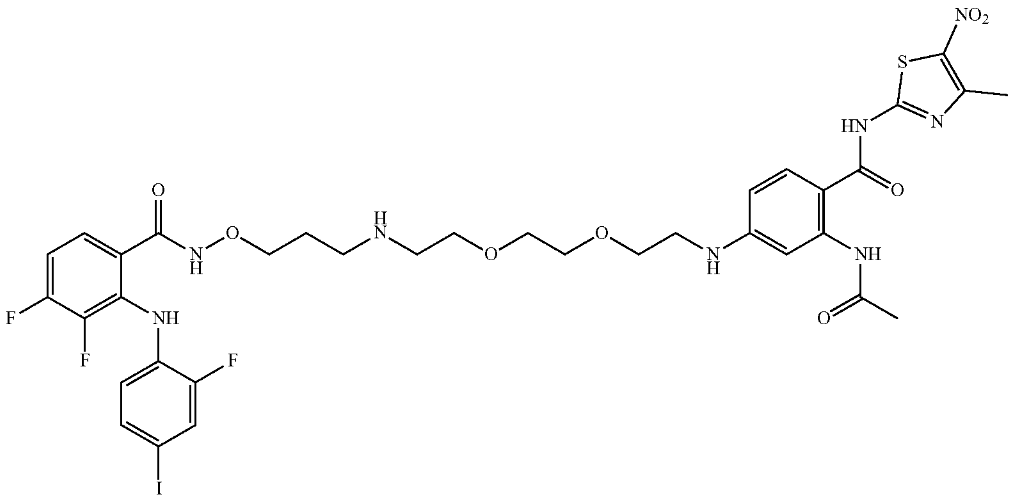 [SMILES: CC(=O)Nc1cc(NCCOCCOCCNCCCONC(=O)c2ccc(F)c(F)c2Nc2ccc(I)cc2F)ccc1C(=O)Nc1nc(C)c([N+](=O)[O-])s1] | N-(3-((2-(2-(2-((3-acetamido-4-((4-methyl-5-nitrothiazol-2-yl)carbamoyl)phenyl)amino)ethoxy)ethoxy)ethyl)amino)propoxy)-3,4-difluoro-2-((2-fluoro-4-iodophenyl)amino)benzamide |

TABLE 5-continued

| DDB1 binding moieties attached to a target protein binding moiety | | |
|---|---|---|
| Compound | Structure | Name |
| D-68 | 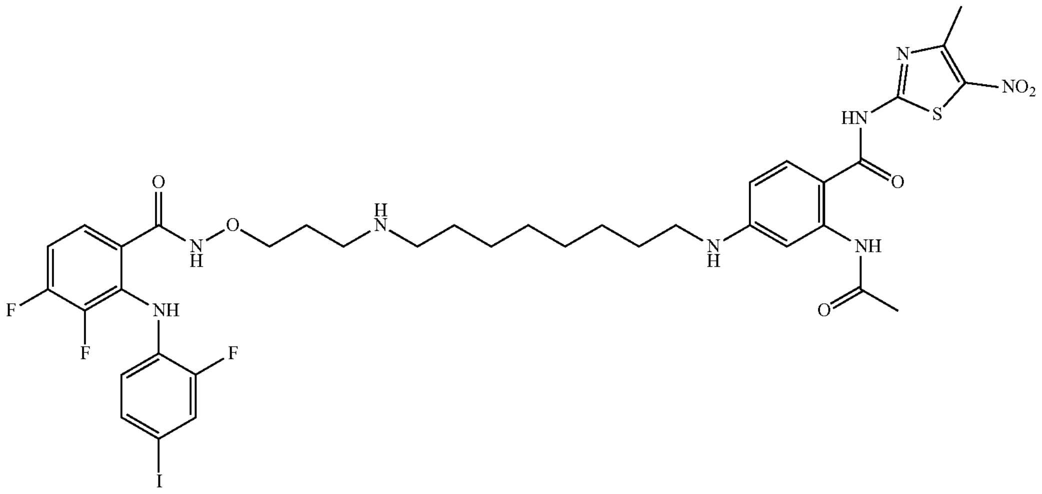 [SMILES: CC(=O)Nc1cc(NCCCCCCCCNCCCONC(=O)c2ccc(F)c(F)c2Nc2ccc(I)cc2F)ccc1C(=O)Nc1nc(C)c([N+](=O)[O-])s1] | N-(3-((8-((3-acetamido-4-((4-methyl-5-nitrothiazol-2-yl)carbamoyl)phenyl)amino)octyl)amino)propoxy)-3,4-difluoro-2-((2-fluoro-4-iodophenyl)amino)benzamide |
| D-69 | 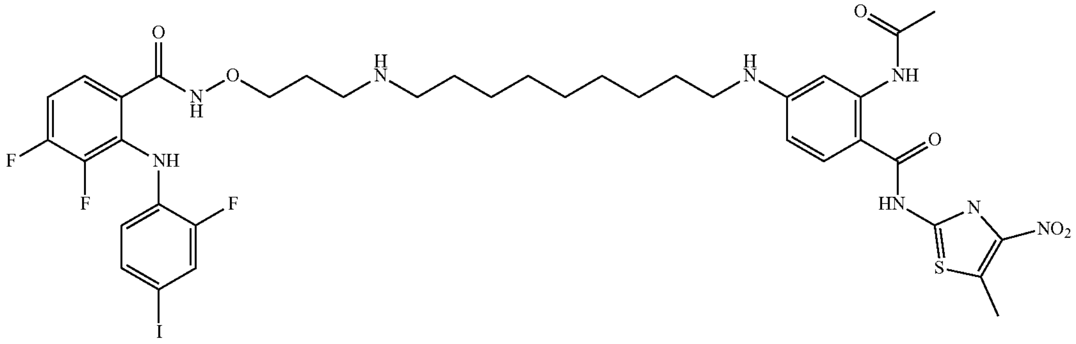 | N-(3-((9-((3-acetamido-4-((4-methyl-5-nitrothiazol-2-yl)carbamoyl)phenyl)amino)nonyl)amino)propoxy)-3,4-difluoro-2-((2-fluoro-4-iodophenyl)amino)benzamide |

TABLE 5-continued

| DDB1 binding moieties attached to a target protein binding moiety | | |
|---|---|---|
| Compound | Structure | Name |
| D-70 | 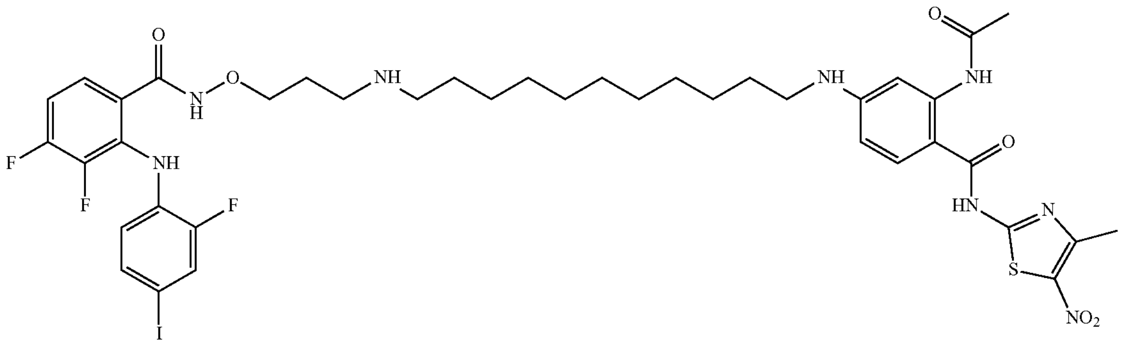 [SMILES: CC(=O)Nc1cc(NCCCCCCCCCCCNCCCONC(=O)c2ccc(F)c(F)c2Nc2ccc(I)cc2F)ccc1C(=O)Nc1nc(C)c([N+](=O)[O-])s1] | N-(3-((11-((3-acetamido-4-((4-methyl-5-nitrothiazol-2-yl)carbamoyl)phenyl)amino)undecyl)amino)propoxy)-3,4-difluoro-2-((2-fluoro-4-iodophenyl)amino)benzamide |
| D-71 | 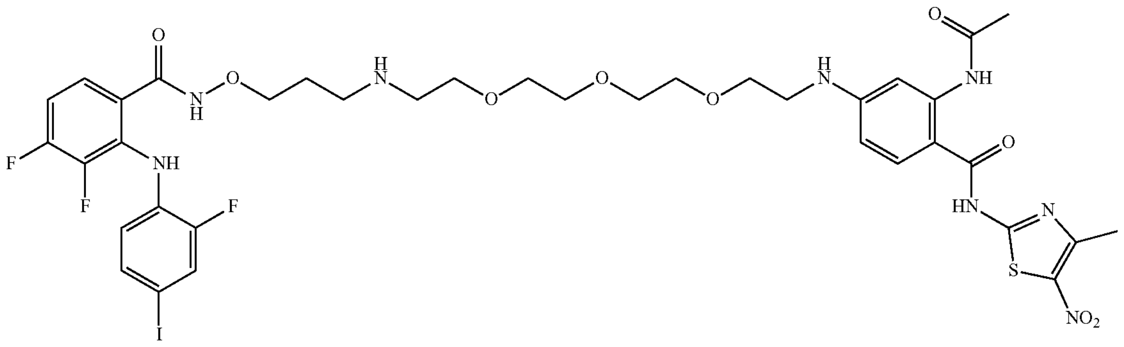 [SMILES: CC(=O)Nc1cc(NCCOCCOCCOCCNCCCONC(=O)c2ccc(F)c(F)c2Nc2ccc(I)cc2F)ccc1C(=O)Nc1nc(C)c([N+](=O)[O-])s1] | N-((1-((3-acetamido-4-((4-methyl-5-nitrothiazol-2-yl)carbamoyl)phenyl)amino)-3,6,9-trioxa-12-azapentadecan-15-yl)oxy)-3,4-difluoro-2-((2-fluoro-4-iodophenyl)amino)benzamide |

TABLE 5-continued

| DDB1 binding moieties attached to a target protein binding moiety | | |
|---|---|---|
| Compound | Structure | Name |
| D-72 | 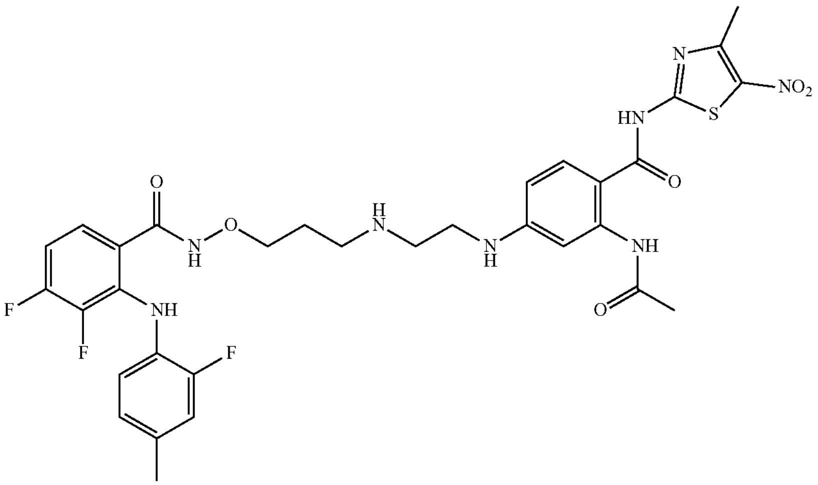 [SMILES: CC(=O)Nc1cc(NCCNCCCONC(=O)c2ccc(F)c(F)c2Nc2ccc(C)cc2F)ccc1C(=O)Nc1nc(C)c([N+](=O)[O-])s1] | N-(3-((2-((3-acetamido-4-((4-methyl-5-nitrothiazol-2-yl)carbamoyl)phenyl)amino)ethyl)amino)propoxy)-3,4-difluoro-2-((2-fluoro-4-iodophenyl)amino)benzamide |
| D-73 | 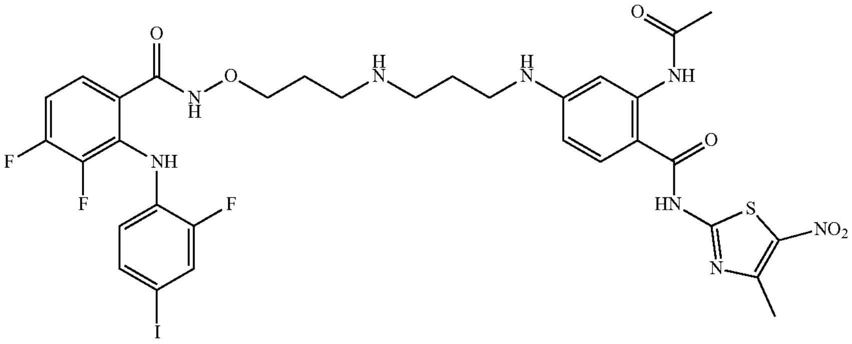 [SMILES: CC(=O)Nc1cc(NCCCNCCCONC(=O)c2ccc(F)c(F)c2Nc2ccc(I)cc2F)ccc1C(=O)Nc1nc(C)c([N+](=O)[O-])s1] | N-(3-((3-((3-acetamido-4-((4-methyl-5-nitrothiazol-2-yl)carbamoyl)phenyl)amino)propyl)amino)propoxy)-3,4-difluoro-2-((2-fluoro-4-iodophenyl)amino)benzamide |

TABLE 5-continued

| DDB1 binding moieties attached to a target protein binding moiety | | |
|---|---|---|
| Compound | Structure | Name |
| D-74 | 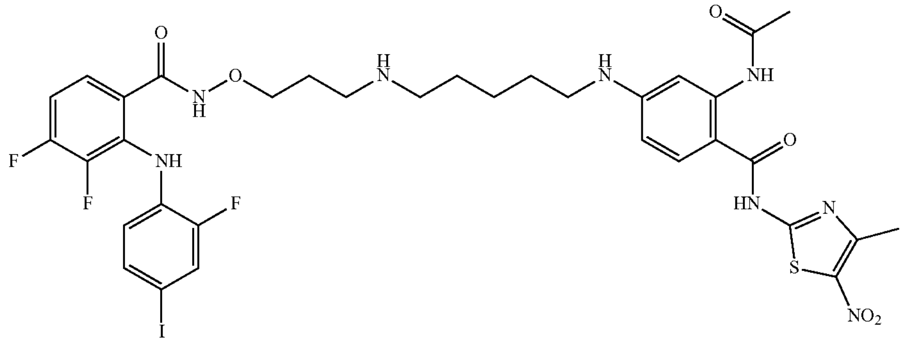 | N-(3-((5-((3-acetamido-4-((4-methyl-5-nitrothiazol-2-yl)carbamoyl)phenyl)amino)pentyl)amino)propoxy)-3,4-difluoro-2-((2-fluoro-4-iodophenyl)amino)benzamide |
| D-75 | 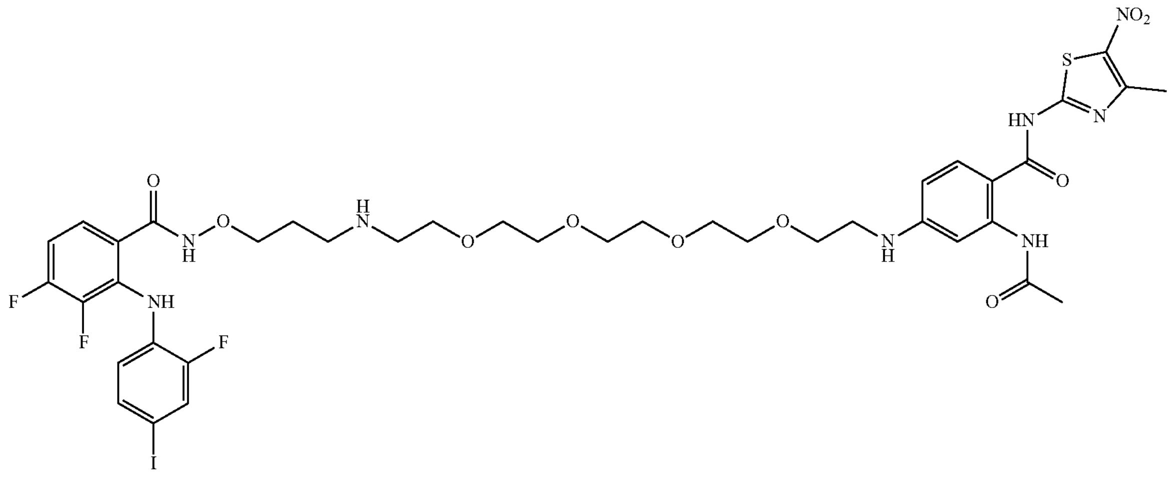 [SMILES: CC(=O)Nc1cc(NCCOCCOCCOCCOCCNCCCONC(=O)c2ccc(F)c(F)c2Nc2ccc(I)cc2F)ccc1C(=O)Nc1nc(C)c([N+](=O)[O-])s1] | N-((1-((3-acetamido-4-((4-methyl-5-nitrothiazol-2-yl)carbamoyl)phenyl)amino)-3,6,9,12-tetraoxa-15-azaoctadecan-18-yl)oxy)-3,4-difluoro-2-((2-fluoro-4-iodophenyl)amino)benzamide |

TABLE 5-continued

| DDB1 binding moieties attached to a target protein binding moiety | | |
|---|---|---|
| Compound | Structure | Name |
| D-76 | 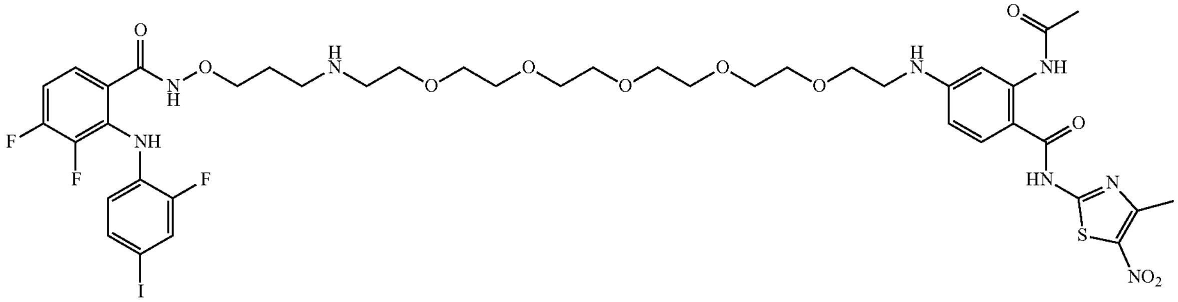 [SMILES: CC(=O)Nc1cc(NCCOCCOCCOCCOCCOCCNCCCONC(=O)c2ccc(F)c(F)c2Nc2ccc(I)cc2F)ccc1C(=O)Nc1nc(C)c([N+](=O)[O-])s1] | N-((1-((3-acetamido-4-((4-methyl-5-nitrothiazol-2-yl)carbamoyl)phenyl)amino)-3,6,9,12,15-pentaoxa-18-azahenicosan-21-yl)oxy)-3,4-difluoro-2-((2-fluoro-4-iodophenyl)amino)benzamide |
| D-77 | 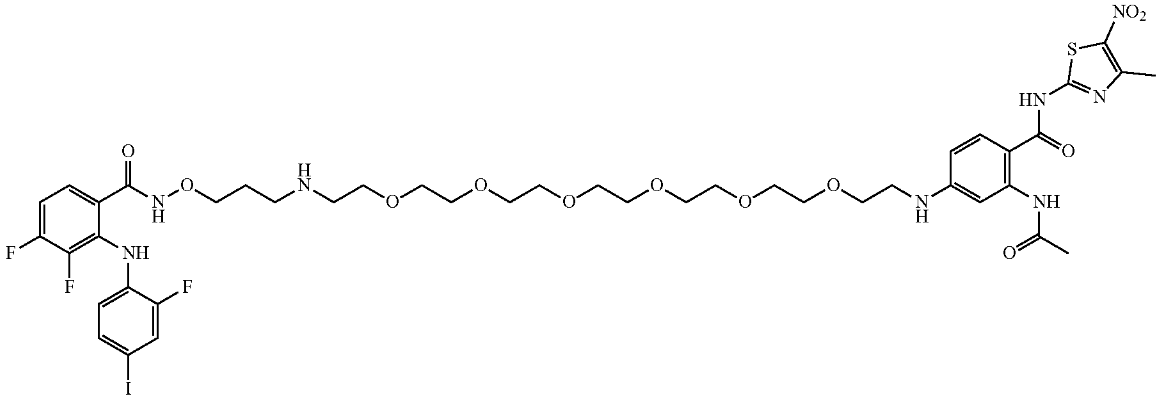 [SMILES: CC(=O)Nc1cc(NCCOCCOCCOCCOCCOCCOCCNCCCONC(=O)c2ccc(F)c(F)c2Nc2ccc(I)cc2F)ccc1C(=O)Nc1nc(C)c([N+](=O)[O-])s1] | N-((1-((3-acetamido-4-((4-methyl-5-nitrothiazol-2-yl)carbamoyl)phenyl)amino)-3,6,9,12,15,18-hexaoxa-21-azatetracosan-24-yl)oxy)-3,4-difluoro-2-((2-fluoro-4-iodophenyl)amino)benzamide |
| D-78 | 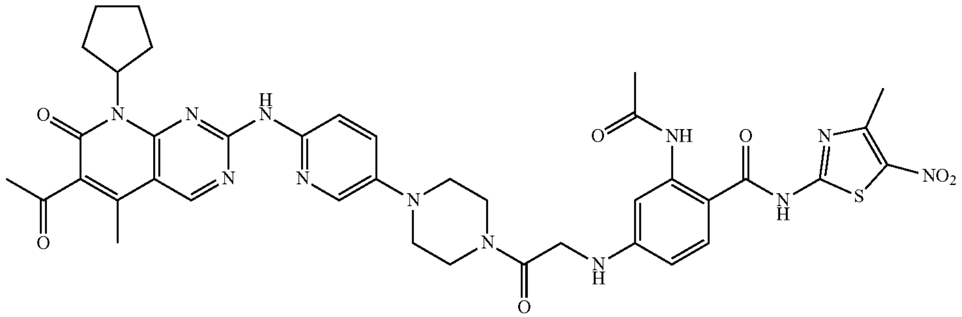 [SMILES: CC(=O)Nc1cc(NCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-79 | 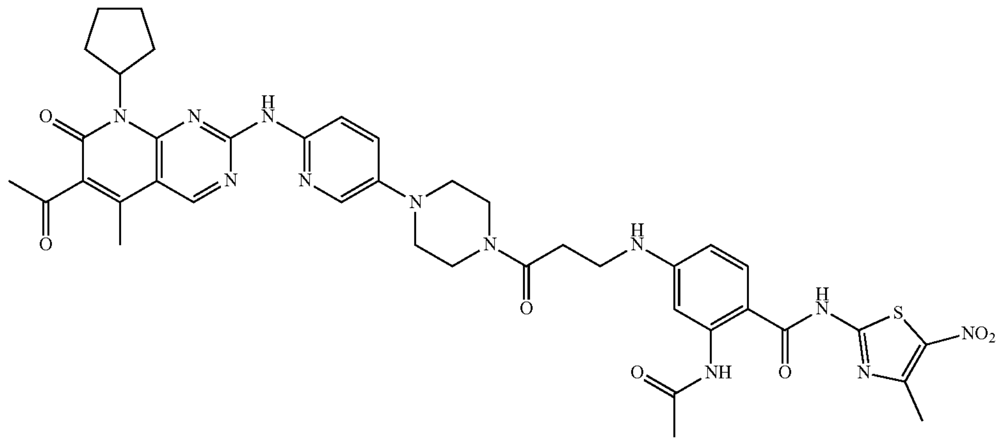 [SMILES: CC(=O)Nc1cc(NCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)amino)-N-(4-methyl-5-nitrothiazol-2-yl)benzamide |
| D-80 | 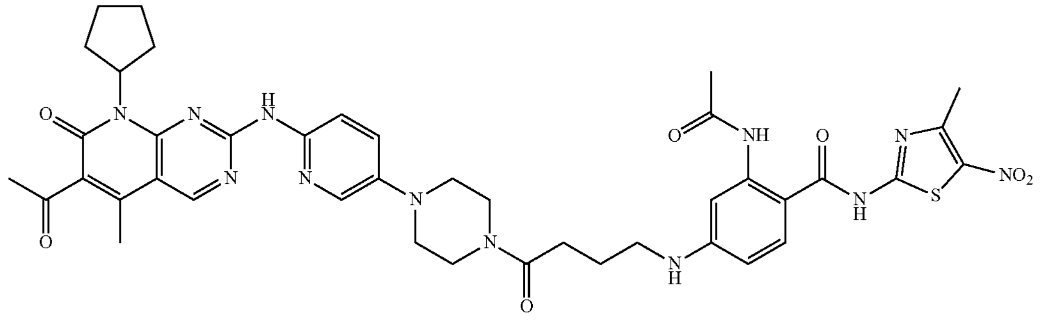 [SMILES: CC(=O)Nc1cc(NCCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((4-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-4-oxobutyl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-81 | 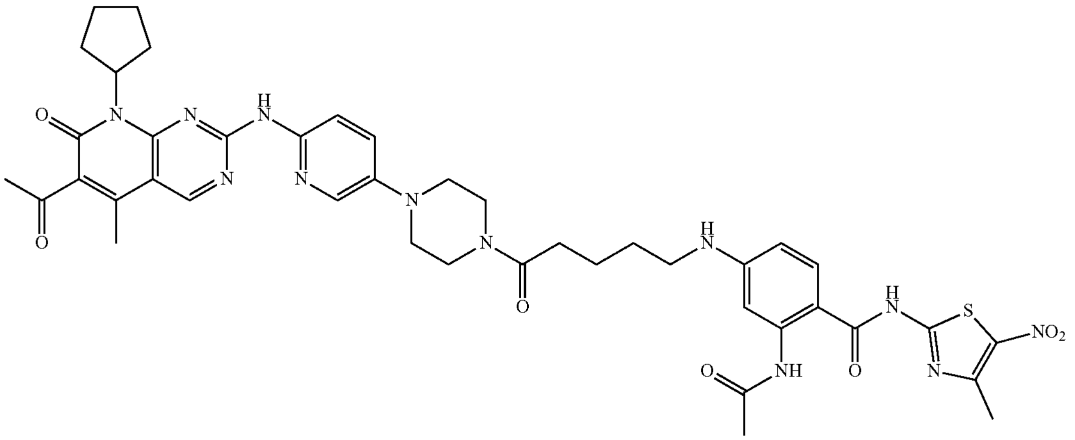 [SMILES: CC(=O)Nc1cc(NCCCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((5-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-5-oxopentyl)amino)-N-(4-methyl-5-nitrothiazol-2-yl)benzamide |
| D-82 | 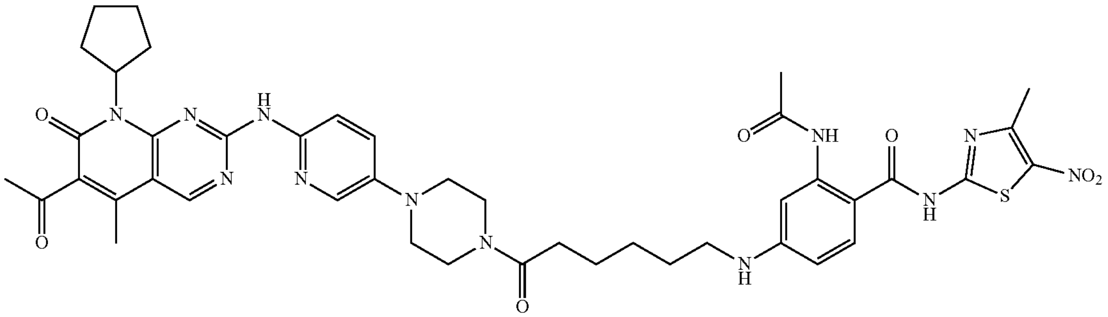 [SMILES: CC(=O)Nc1cc(NCCCCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((6-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-6-oxohexyl)amino)-N-(4-methyl-5-nitrothiazol-2-yl)benzamide |

TABLE 5-continued

DDB1 binding moieties attached to a target protein binding moiety

| Compound | Structure | Name |
| --- | --- | --- |
| D-83 | 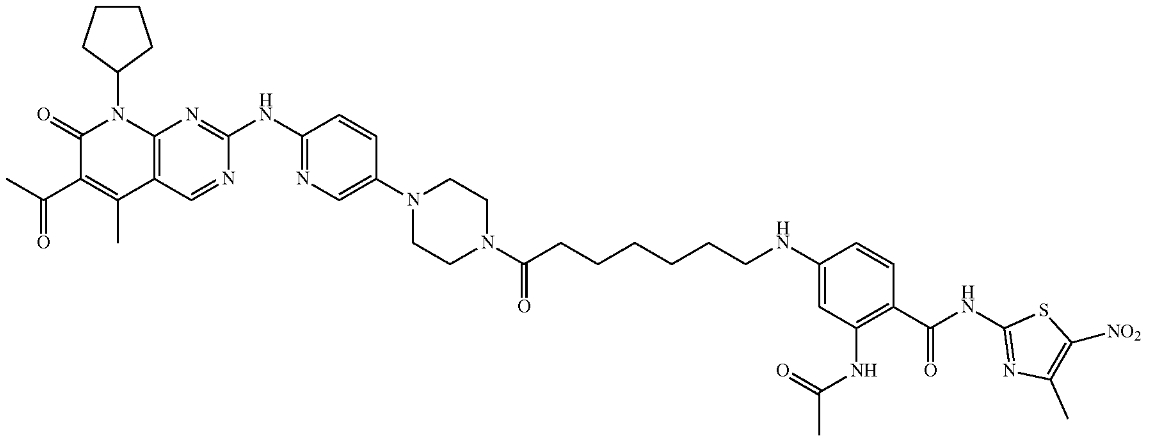 [SMILES: CC(=O)Nc1cc(NCCCCCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxoheptyl)amino)-N-(4-methyl-5-nitrothiazol-2-yl)benzamide |
| D-84 | 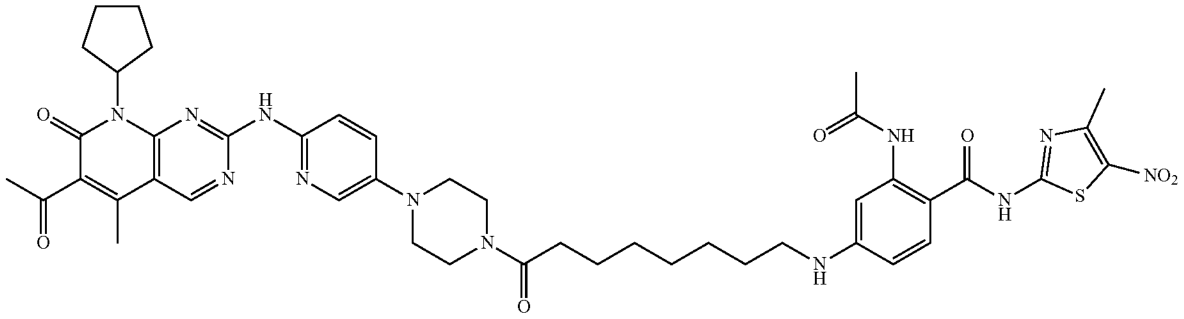 [SMILES: CC(=O)Nc1cc(NCCCCCCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((8-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-8-oxooctyl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-85 | 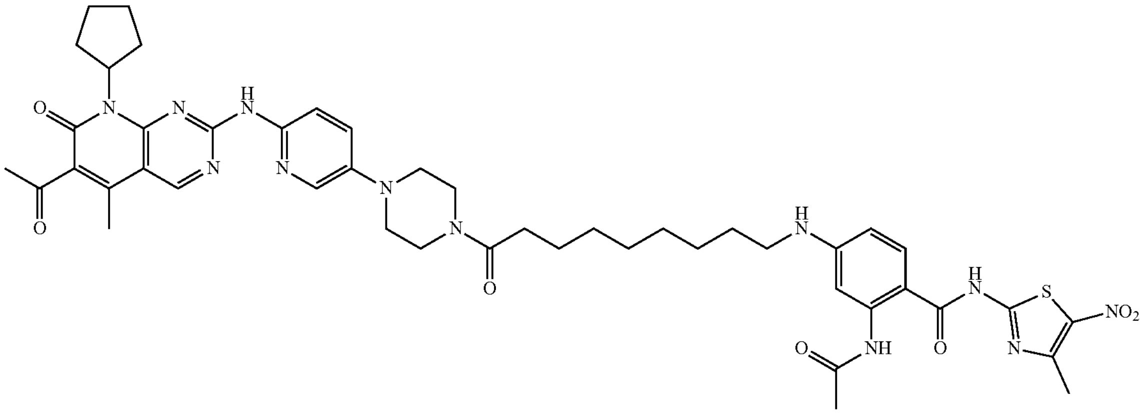 [SMILES: CC(=O)Nc1cc(NCCCCCCCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((9-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-9-oxononyl)amino)-N-(4-methyl-5-nitrothiazol-2-yl)benzamide |
| D-86 | 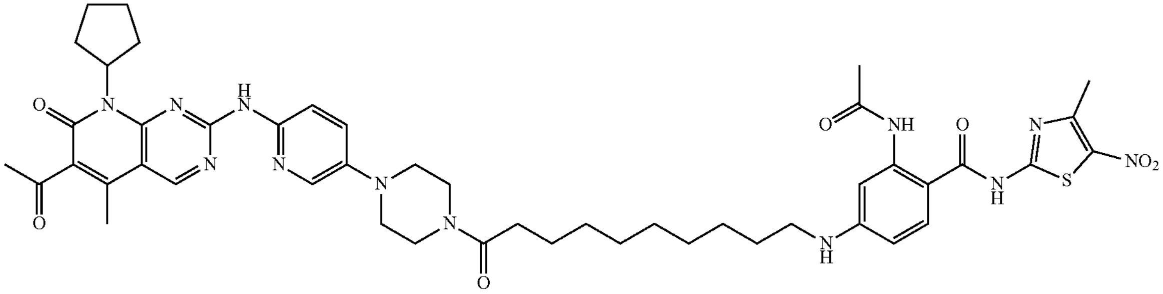 [SMILES: CC(=O)Nc1cc(NCCCCCCCCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((10-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-10-oxodecyl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-87 | 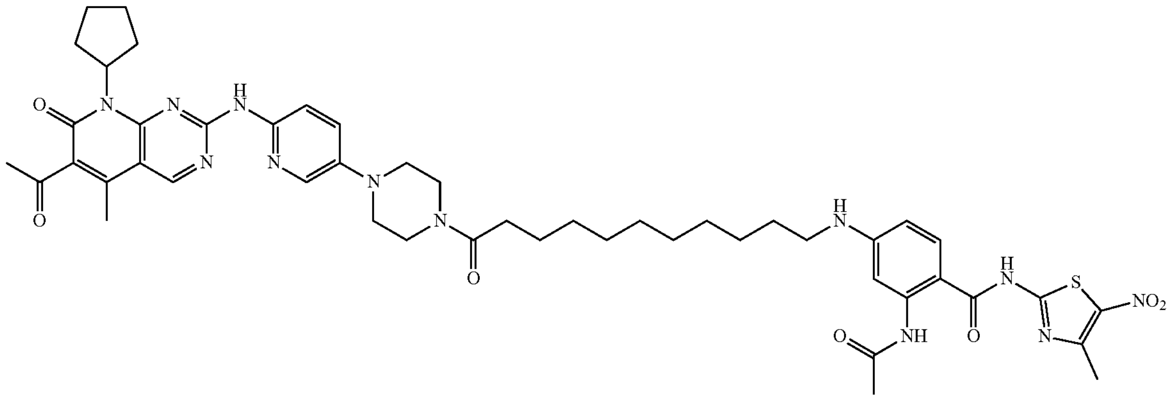 [SMILES: CC(=O)Nc1cc(NCCCCCCCCCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((11-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-11-oxoundecyl)amino)-N-(4-methyl-5-nitrothiazol-2-yl)benzamide |
| D-88 | 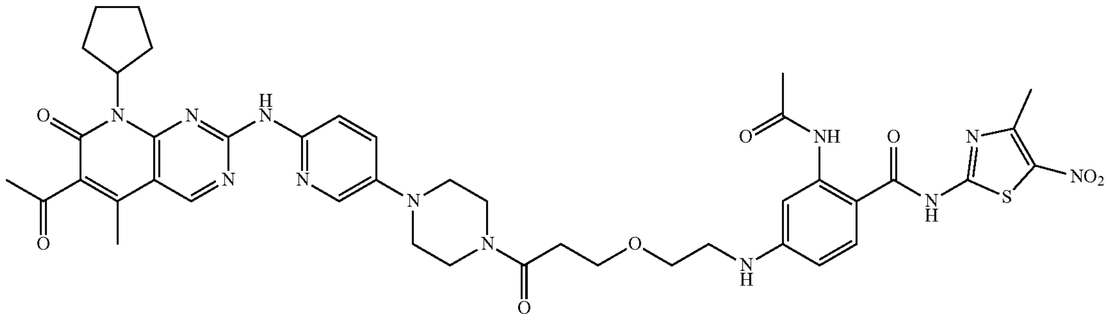 [SMILES: CC(=O)Nc1cc(NCCOCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethyl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-89 | 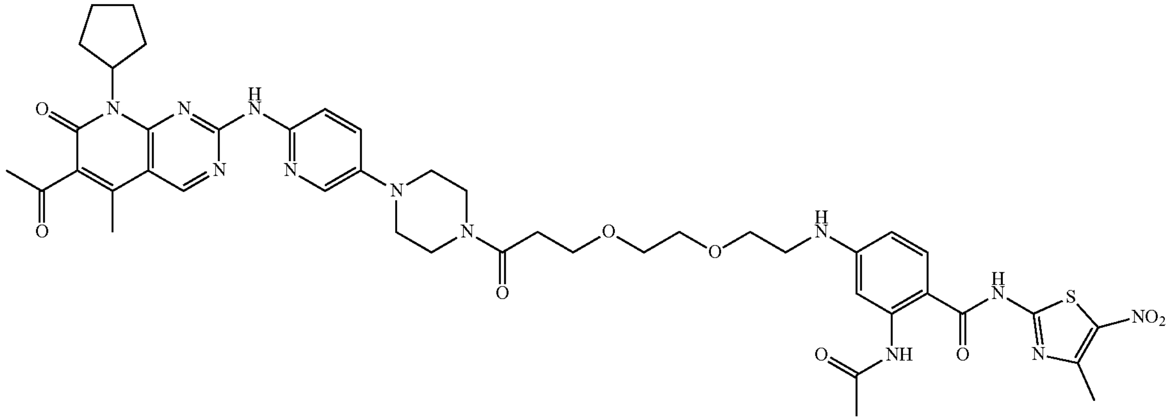 [SMILES: CC(=O)Nc1cc(NCCOCCOCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethyl)amino)-N-(4-methyl-5-nitrothiazol-2-yl)benzamide |
| D-90 | 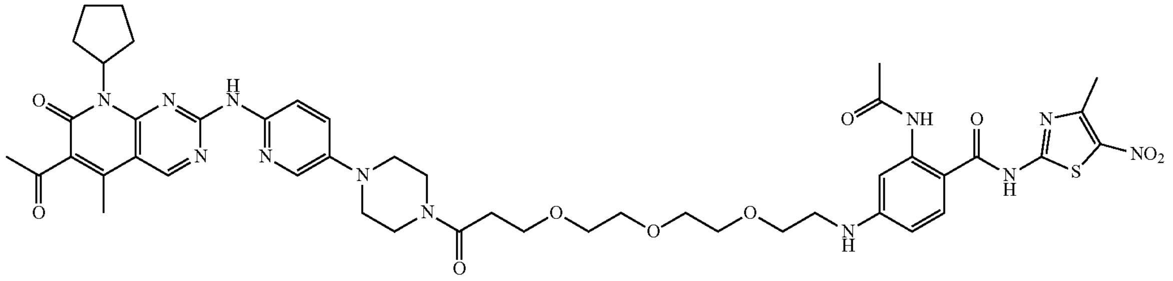 [SMILES: CC(=O)Nc1cc(NCCOCCOCCOCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((2-(2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethoxy)ethyl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-91 | 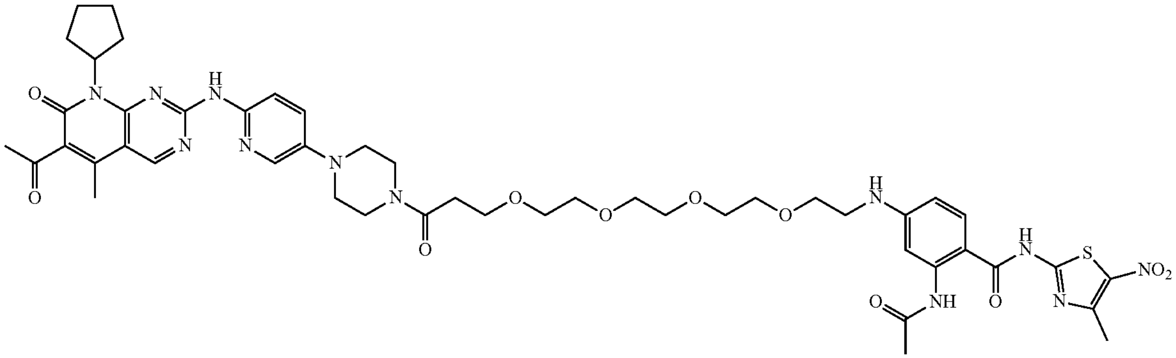 [SMILES: CC(=O)Nc1cc(NCCOCCOCCOCCOCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((15-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-15-oxo-3,6,9,12-tetraoxapentadecyl)amino)-N-(4-methyl-5-nitrothiazol-2-yl)benzamide |
| D-92 | 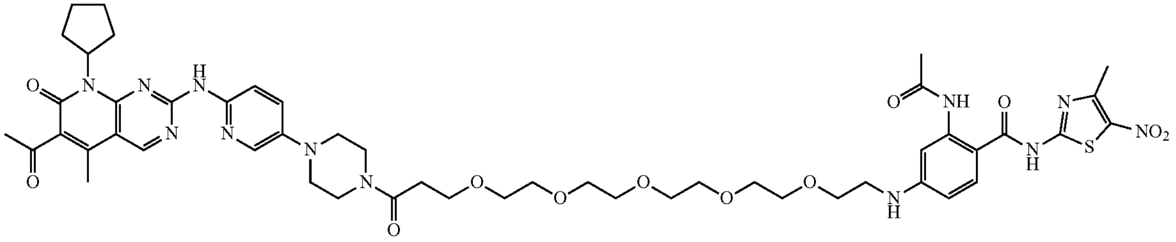 [SMILES: CC(=O)Nc1cc(NCCOCCOCCOCCOCCOCCC(=O)N2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((18-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-18-oxo-3,6,9,12,15-pentaoxaoctadecyl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-93 | 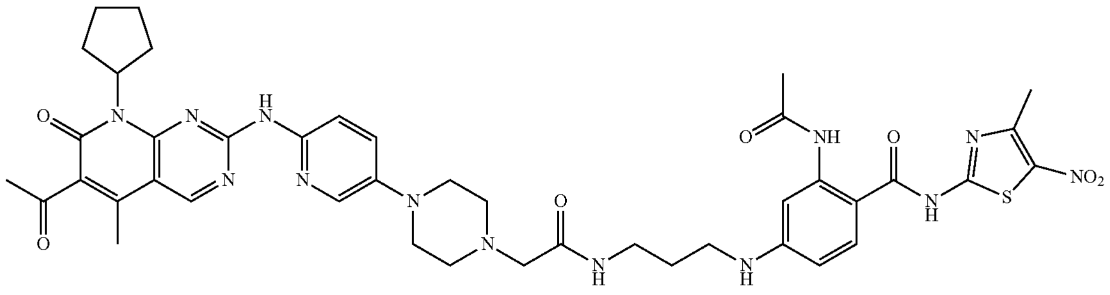 [SMILES: CC(=O)Nc1cc(NCCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((3-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)propyl)amino)-N-(4-methyl-5-nitrothiazol-2-yl)benzamide |
| D-94 | 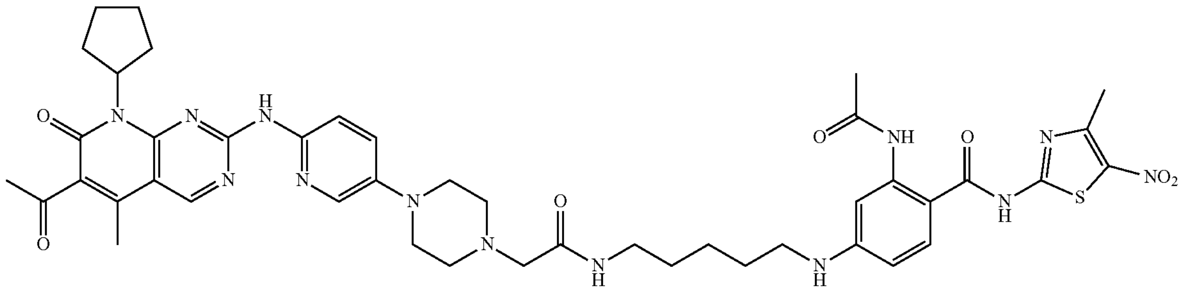 [SMILES: CC(=O)Nc1cc(NCCCCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((5-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)pentyl)amino)-N-(4-methyl-5-nitrothiazol-2-yl)benzamide |
| D-95 | 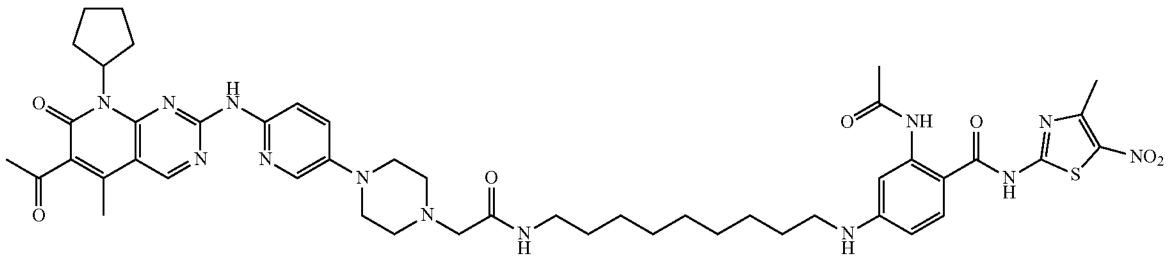 [SMILES: CC(=O)Nc1cc(NCCCCCCCCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((9-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)nonyl)amino)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-96 | 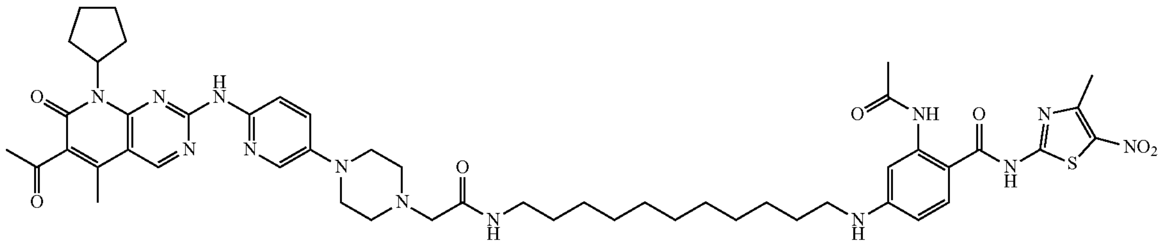 [SMILES: CC(=O)Nc1cc(NCCCCCCCCCCCNC(=O)CN2CCN(c3ccc(Nc4ncc5c(C)c(C(C)=O)c(=O)n(C6CCCC6)c5n4)nc3)CC2)ccc1C(=O)Nc1nc(C)c([N+](=O)[O-])s1] | 2-acetamido-4-((11-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)undecyl)amino)-N-(4-methyl-5-nitrothiazol-2-yl)benzamide |
| D-97 | 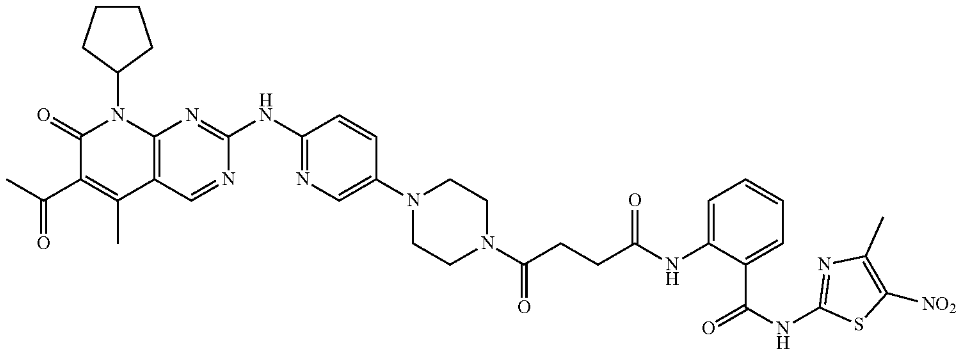 [SMILES: CC(=O)c1c(C)c2cnc(Nc3ccc(N4CCN(C(=O)CCC(=O)Nc5ccccc5C(=O)Nc5nc(C)c([N+](=O)[O-])s5)CC4)cn3)nc2n(C2CCCC2)c1=O] | 2-(4-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-4-oxobutanamido)-N-(4-methyl-5-nitrothiazol-2-yl)benzamide |

TABLE 5-continued

DDB1 binding moieties attached to a target protein binding moiety

| Compound | Structure | Name |
| --- | --- | --- |
| D-98 | 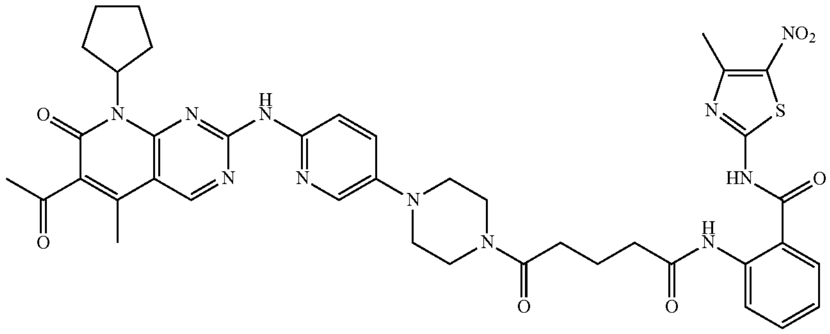 [SMILES: CC(=O)c1c(C)c2cnc(Nc3ccc(N4CCN(C(=O)CCCC(=O)Nc5ccccc5C(=O)Nc5nc(C)c([N+](=O)[O-])s5)CC4)cn3)nc2n(C2CCCC2)c1=O] | 2-(5-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-5-oxopentanamido)-N-(4-methyl-5-nitrothiazol-2-yl)benzamide |
| D-99 | 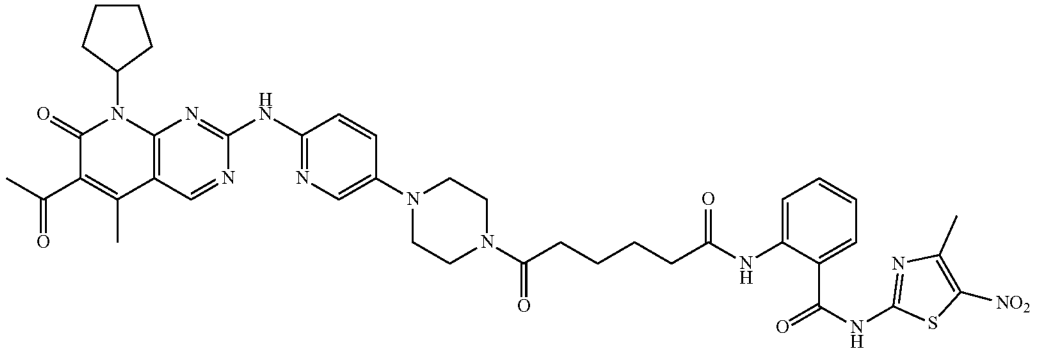 [SMILES: CC(=O)c1c(C)c2cnc(Nc3ccc(N4CCN(C(=O)CCCCC(=O)Nc5ccccc5C(=O)Nc5nc(C)c([N+](=O)[O-])s5)CC4)cn3)nc2n(C2CCCC2)c1=O] | 2-(6-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-6-oxohexanamido)-N-(4-methyl-5-nitrothiazol-2-yl)benzamide |
| D-100 | 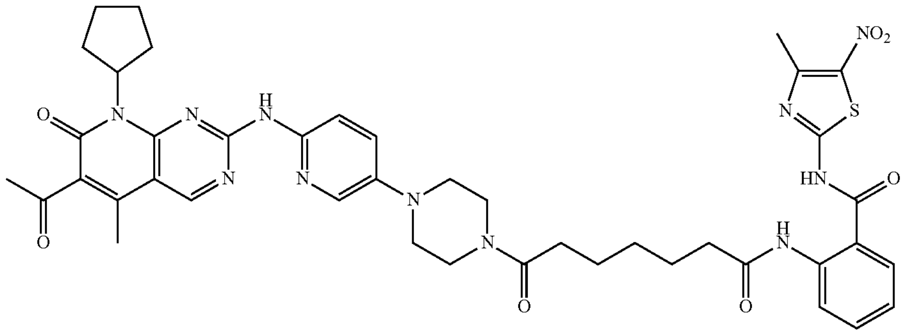 | 2-(7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxoheptanamido)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-101 | 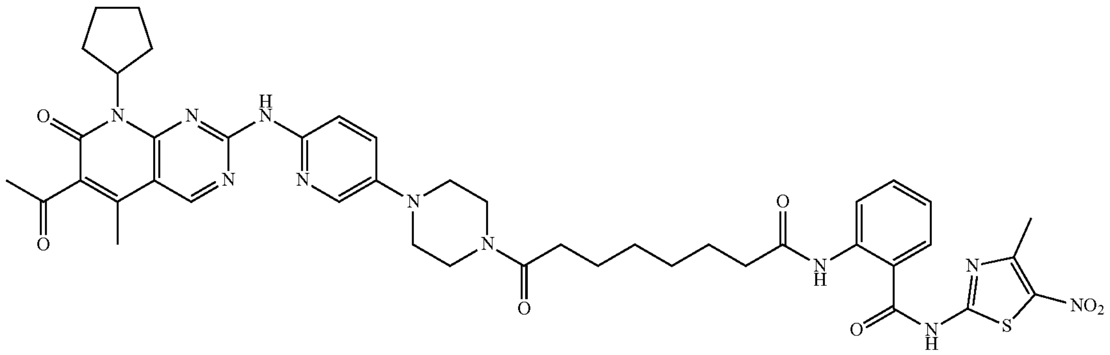 [SMILES: CC(=O)c1c(C)c2cnc(Nc3ccc(N4CCN(C(=O)CCCCCCC(=O)Nc5ccccc5C(=O)Nc5nc(C)c([N+](=O)[O-])s5)CC4)cn3)nc2n(C2CCCC2)c1=O] | 2-(8-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-8-oxooctanamido)-N-(4-methyl-5-nitrothiazol-2-yl)benzamide |
| D-102 | 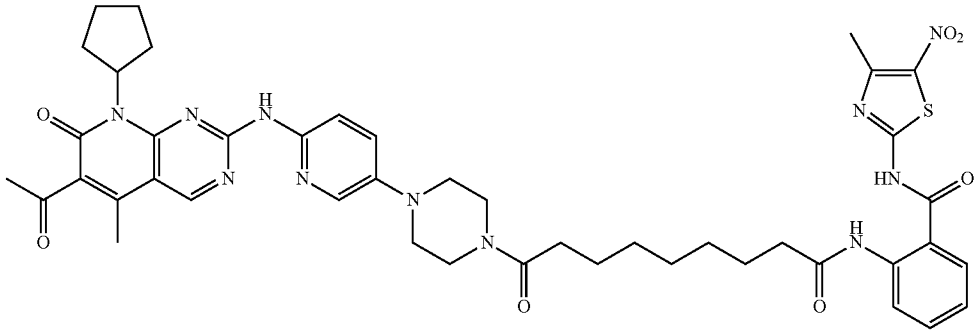 [SMILES: CC(=O)c1c(C)c2cnc(Nc3ccc(N4CCN(C(=O)CCCCCCCC(=O)Nc5ccccc5C(=O)Nc5nc(C)c([N+](=O)[O-])s5)CC4)cn3)nc2n(C2CCCC2)c1=O] | 2-(9-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-9-oxononanamido)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-103 | 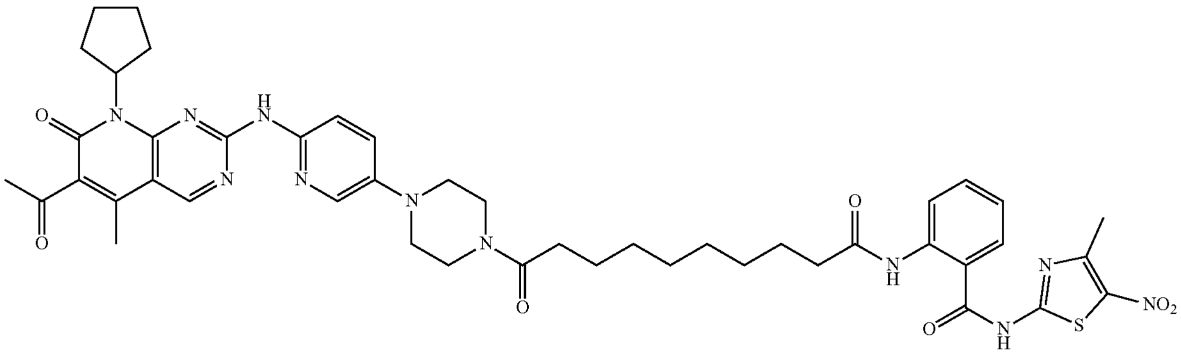 [SMILES: CC(=O)c1c(C)c2cnc(Nc3ccc(N4CCN(C(=O)CCCCCCCCC(=O)Nc5ccccc5C(=O)Nc5nc(C)c([N+](=O)[O-])s5)CC4)cn3)nc2n(C2CCCC2)c1=O] | 2-(10-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-10-oxodecanamido)-N-(4-methyl-5-nitrothiazol-2-yl)benzamide |
| D-104 | 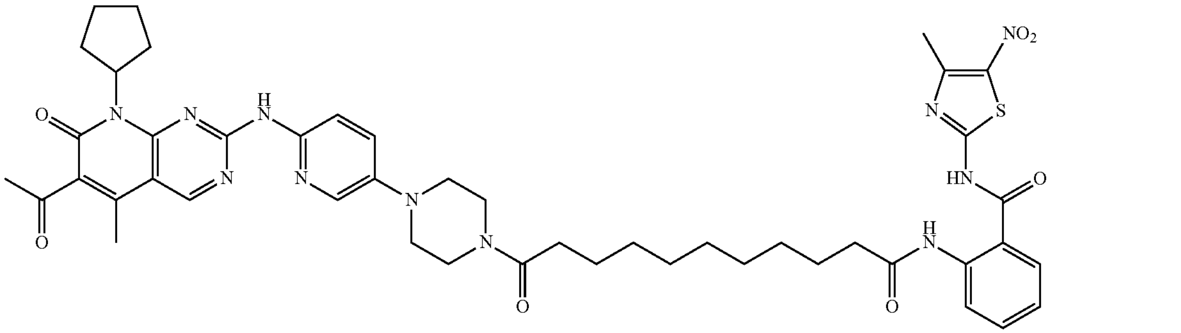 [SMILES: CC(=O)c1c(C)c2cnc(Nc3ccc(N4CCN(C(=O)CCCCCCCCCC(=O)Nc5ccccc5C(=O)Nc5nc(C)c([N+](=O)[O-])s5)CC4)cn3)nc2n(C2CCCC2)c1=O] | 2-(11-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-11-oxoundecanamido)-N-(4-methyl-5-nitrothiazol-2-yl)benzamide |
| D-105 | 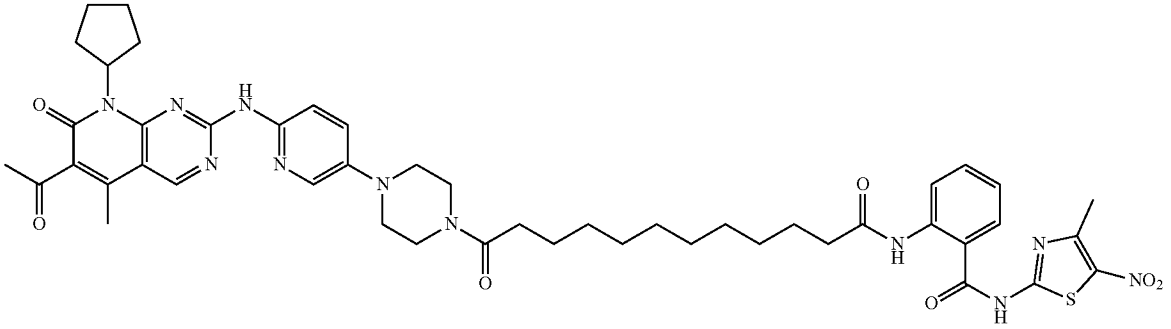 [SMILES: CC(=O)c1c(C)c2cnc(Nc3ccc(N4CCN(C(=O)CCCCCCCCCCC(=O)Nc5ccccc5C(=O)Nc5nc(C)c([N+](=O)[O-])s5)CC4)cn3)nc2n(C2CCCC2)c1=O] | 2-(12-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-12-oxododecanamido)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-106 | 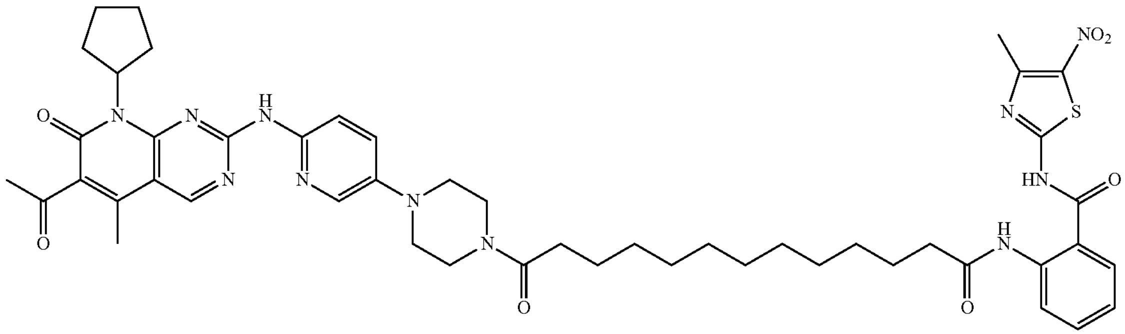 [SMILES: CC(=O)c1c(C)c2cnc(Nc3ccc(N4CCN(C(=O)CCCCCCCCCCCC(=O)Nc5ccccc5C(=O)Nc5nc(C)c([N+](=O)[O-])s5)CC4)cn3)nc2n(C2CCCC2)c1=O] | 2-(13-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-13-oxotridecanamido)-N-(4-methyl-5-nitrothiazol-2-yl)benzamide |
| D-107 | 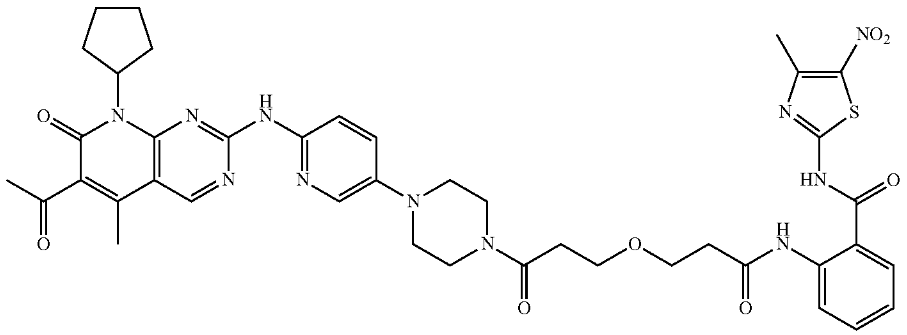 [SMILES: CC(=O)c1c(C)c2cnc(Nc3ccc(N4CCN(C(=O)CCOCCC(=O)Nc5ccccc5C(=O)Nc5nc(C)c([N+](=O)[O-])s5)CC4)cn3)nc2n(C2CCCC2)c1=O] | 2-(3-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)propanamido)-N-(4-methyl-5-nitrothiazol-2-yl)benzamide |
| D-108 | 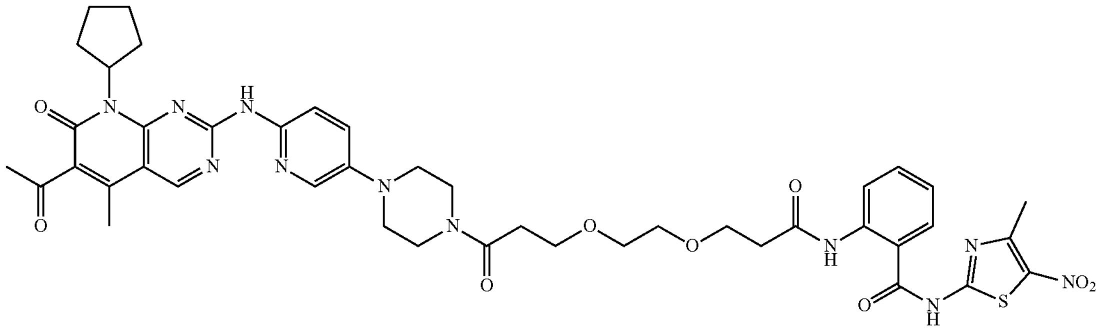 [SMILES: CC(=O)c1c(C)c2cnc(Nc3ccc(N4CCN(C(=O)CCOCCOCCC(=O)Nc5ccccc5C(=O)Nc5nc(C)c([N+](=O)[O-])s5)CC4)cn3)nc2n(C2CCCC2)c1=O] | 2-(3-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)propanamido)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-109 | 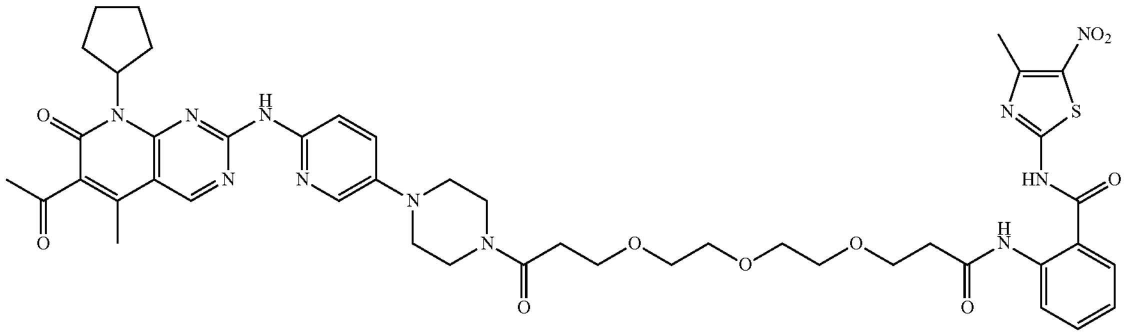 [SMILES: CC(=O)c1c(C)c2cnc(Nc3ccc(N4CCN(C(=O)CCOCCOCCOCCC(=O)Nc5ccccc5C(=O)Nc5nc(C)c([N+](=O)[O-])s5)CC4)cn3)nc2n(C2CCCC2)c1=O] | 2-(3-(2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethoxy)propanamido)-N-(4-methyl-5-nitrothiazol-2-yl)benzamide |
| D-110 | 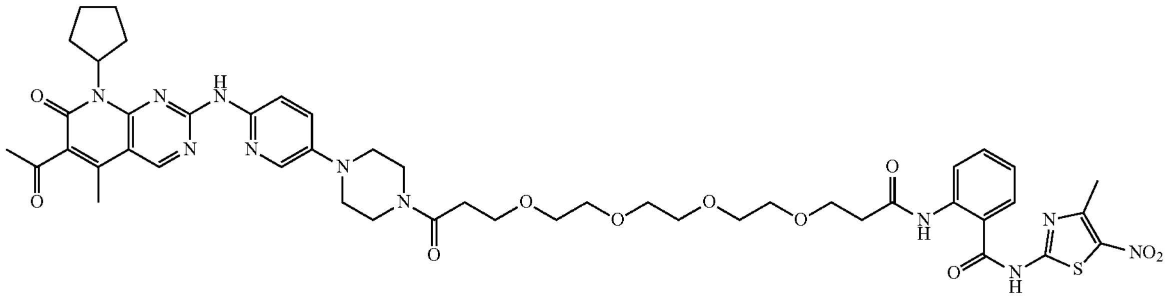 [SMILES: CC(=O)c1c(C)c2cnc(Nc3ccc(N4CCN(C(=O)CCOCCOCCOCCOCCC(=O)Nc5ccccc5C(=O)Nc5nc(C)c([N+](=O)[O-])s5)CC4)cn3)nc2n(C2CCCC2)c1=O] | 16-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-N-(2-((4-methyl-5-nitrothiazol-2-yl)carbamoyl)phenyl)-16-oxo-4,7,10,13-tetraoxahexadecanamide |

TABLE 5-continued

| DDB1 binding moieties attached to a target protein binding moiety | | |
|---|---|---|
| Compound | Structure | Name |
| D-111 | 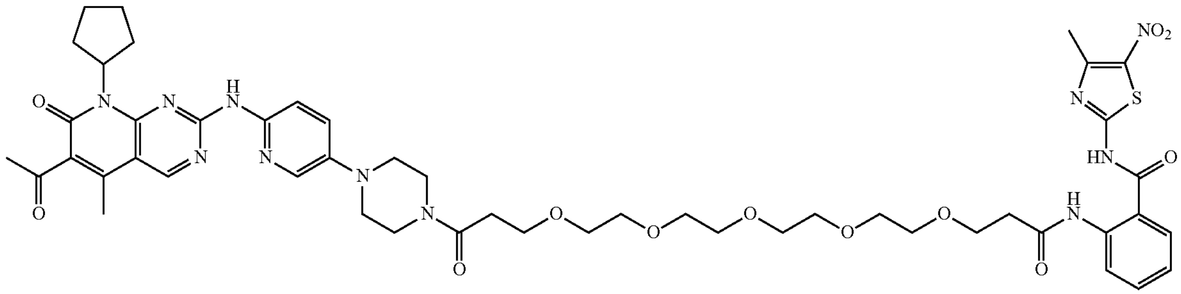 [SMILES: CC(=O)c1c(C)c2cnc(Nc3ccc(N4CCN(C(=O)CCOCCOCCOCCOCCOCCC(=O)Nc5ccccc5C(=O)Nc5nc(C)c([N+](=O)[O-])s5)CC4)cn3)nc2n(C2CCCC2)c1=O] | 19-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-N-(2-((4-methyl-5-nitrothiazol-2-yl)carbamoyl)phenyl)-19-oxo-4,7,10,13,16-pentaoxanonadecanamide |
| D-112 | 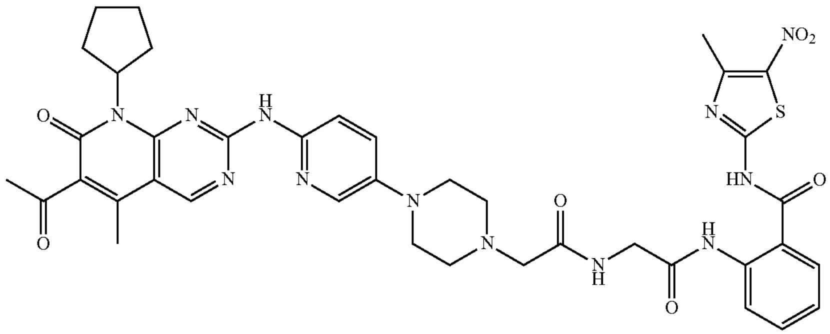 [SMILES: CC(=O)c1c(C)c2cnc(Nc3ccc(N4CCN(CC(=O)NCC(=O)Nc5ccccc5C(=O)Nc5nc(C)c([N+](=O)[O-])s5)CC4)cn3)nc2n(C2CCCC2)c1=O] | 2-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)acetamido)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-113 | 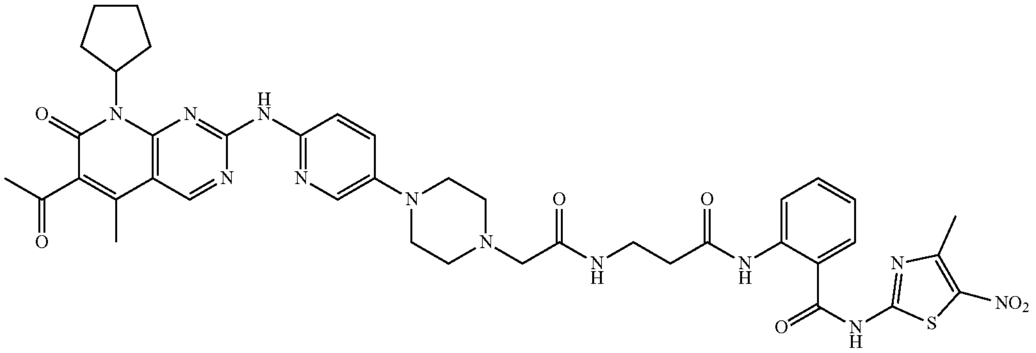 [SMILES: CC(=O)c1c(C)c2cnc(Nc3ccc(N4CCN(CC(=O)NCCC(=O)Nc5ccccc5C(=O)Nc5nc(C)c([N+](=O)[O-])s5)CC4)cn3)nc2n(C2CCCC2)c1=O] | 2-(3-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)panamido)-N-(4-methyl-5-nitrothiazol-2-yl)benzamide |
| D-114 | 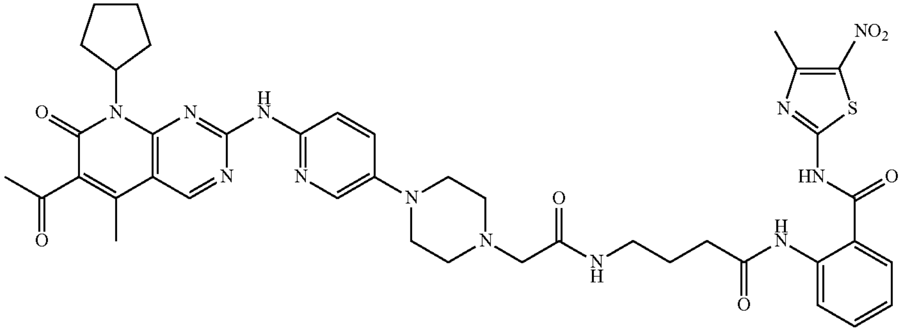 [SMILES: CC(=O)c1c(C)c2cnc(Nc3ccc(N4CCN(CC(=O)NCCCC(=O)Nc5ccccc5C(=O)Nc5nc(C)c([N+](=O)[O-])s5)CC4)cn3)nc2n(C2CCCC2)c1=O] | 2-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)butanamido)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-115 | 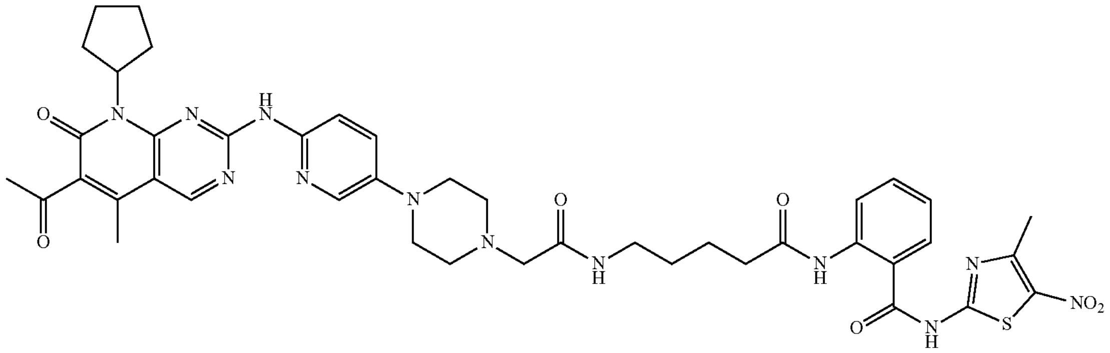 [SMILES: CC(=O)c1c(C)c2cnc(Nc3ccc(N4CCN(CC(=O)NCCCCC(=O)Nc5ccccc5C(=O)Nc5nc(C)c([N+](=O)[O-])s5)CC4)cn3)nc2n(C2CCCC2)c1=O] | 2-(5-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)pentanamido)-N-(4-methyl-5-nitrothiazol-2-yl)benzamide |
| D-116 | 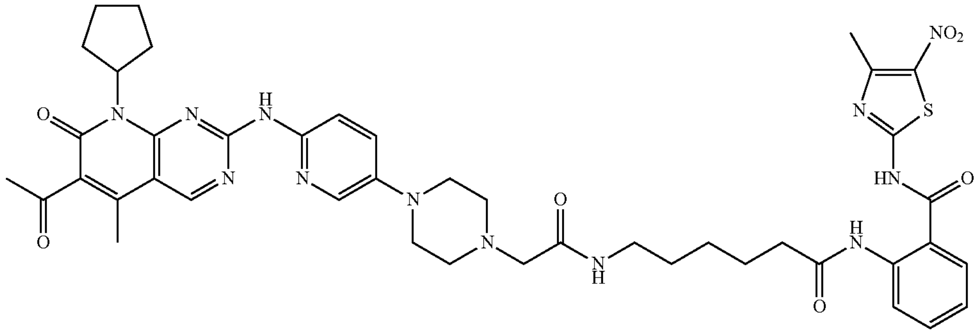 [SMILES: CC(=O)c1c(C)c2cnc(Nc3ccc(N4CCN(CC(=O)NCCCCCC(=O)Nc5ccccc5C(=O)Nc5nc(C)c([N+](=O)[O-])s5)CC4)cn3)nc2n(C2CCCC2)c1=O] | 2-(6-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)hexanamido)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-117 | 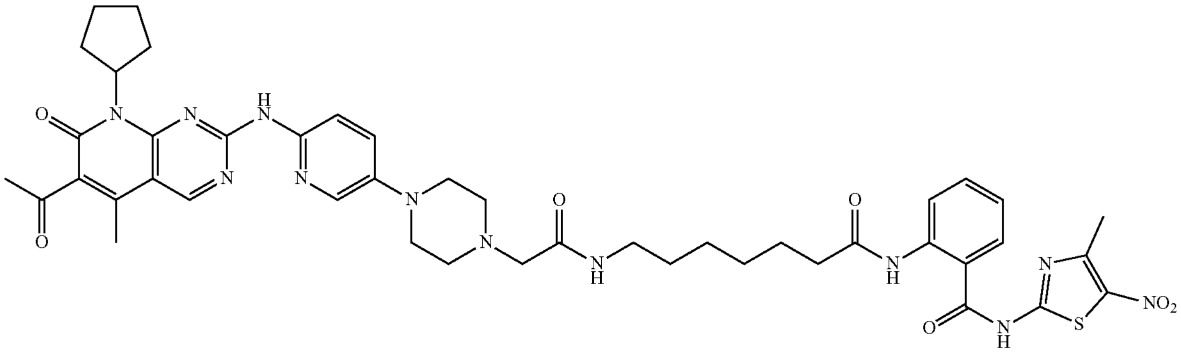 [SMILES: CC(=O)c1c(C)c2cnc(Nc3ccc(N4CCN(CC(=O)NCCCCCCC(=O)Nc5ccccc5C(=O)Nc5nc(C)c([N+](=O)[O-])s5)CC4)cn3)nc2n(C2CCCC2)c1=O] | 2-(7-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)heptanamido)-N-(4-methyl-5-nitrothiazol-2-yl)benzamide |
| D-118 | 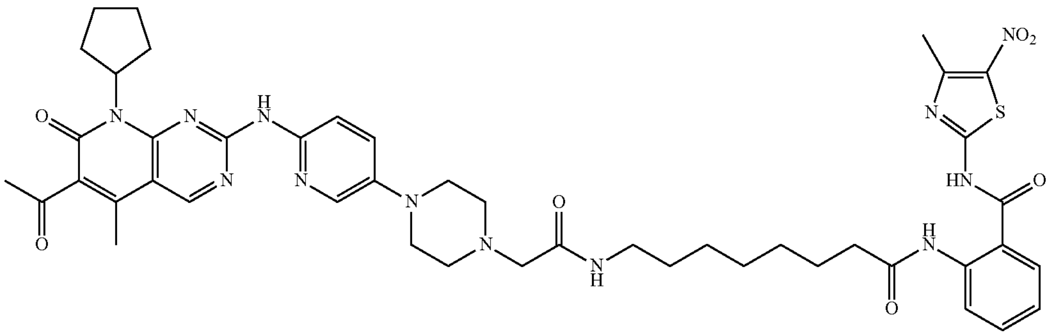 [SMILES: CC(=O)c1c(C)c2cnc(Nc3ccc(N4CCN(CC(=O)NCCCCCCCC(=O)Nc5ccccc5C(=O)Nc5nc(C)c([N+](=O)[O-])s5)CC4)cn3)nc2n(C2CCCC2)c1=O] | 2-(8-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)octanamido)-N-(4-methyl-5-nitrothiazol-2-yl)benzamide |
| D-119 | 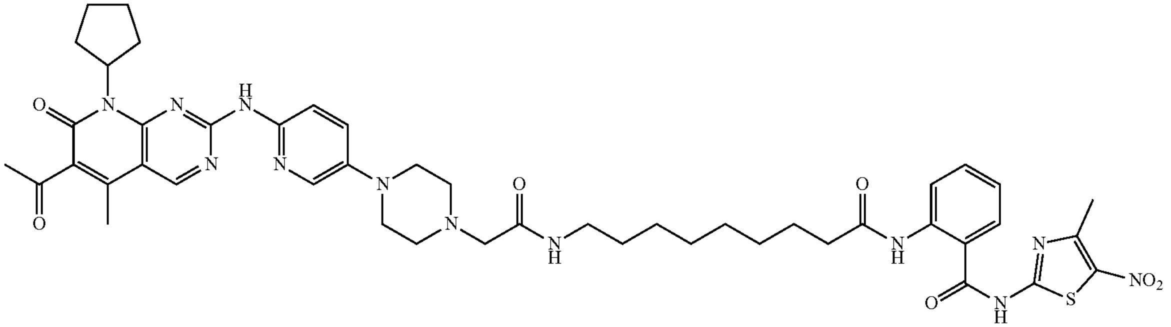 [SMILES: CC(=O)c1c(C)c2cnc(Nc3ccc(N4CCN(CC(=O)NCCCCCCCCC(=O)Nc5ccccc5C(=O)Nc5nc(C)c([N+](=O)[O-])s5)CC4)cn3)nc2n(C2CCCC2)c1=O] | 2-(9-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)nonanamido)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-120 | 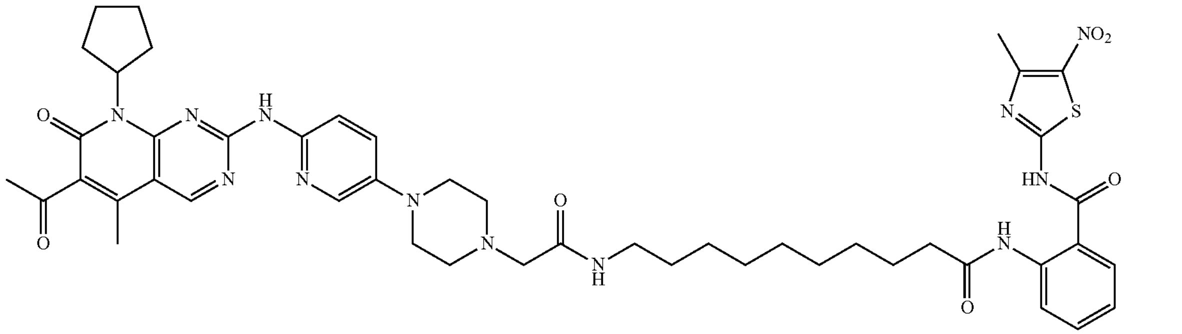 [SMILES: CC(=O)c1c(C)c2cnc(Nc3ccc(N4CCN(CC(=O)NCCCCCCCCCC(=O)Nc5ccccc5C(=O)Nc5nc(C)c([N+](=O)[O-])s5)CC4)cn3)nc2n(C2CCCC2)c1=O] | 2-(10-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)decanamido)-N-(4-methyl-5-nitrothiazol-2-yl)benzamide |
| D-121 | 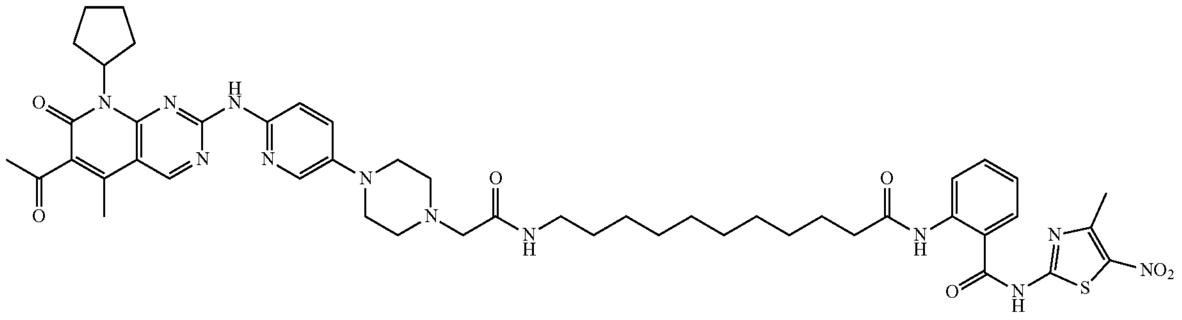 [SMILES: CC(=O)c1c(C)c2cnc(Nc3ccc(N4CCN(CC(=O)NCCCCCCCCCCC(=O)Nc5ccccc5C(=O)Nc5nc(C)c([N+](=O)[O-])s5)CC4)cn3)nc2n(C2CCCC2)c1=O] | 2-(11-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)undecanamido)-N-(4-methyl-5-nitrothiazol-2-yl)benzamide |
| D-122 | 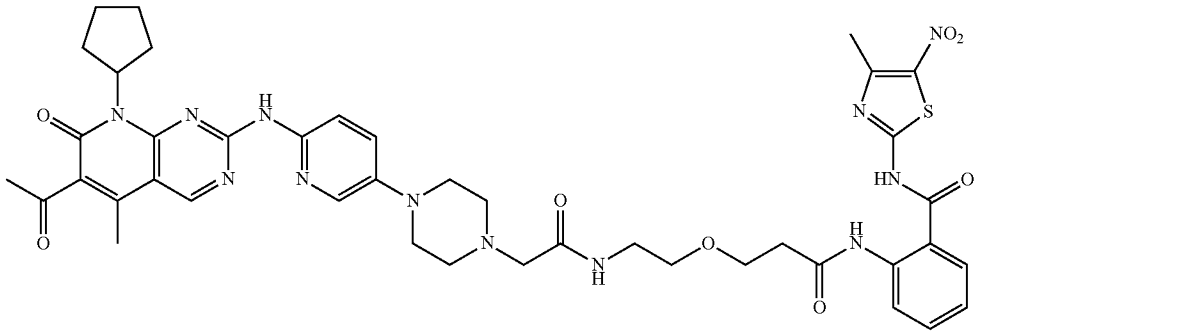 [SMILES: CC(=O)c1c(C)c2cnc(Nc3ccc(N4CCN(CC(=O)NCCOCCC(=O)Nc5ccccc5C(=O)Nc5nc(C)c([N+](=O)[O-])s5)CC4)cn3)nc2n(C2CCCC2)c1=O] | 2-(3-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)ethoxy)propanamido)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-123 | 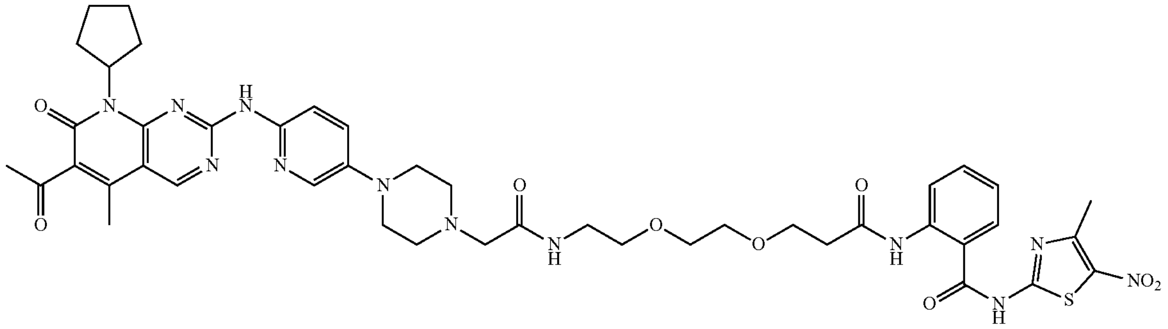 [SMILES: CC(=O)c1c(C)c2cnc(Nc3ccc(N4CCN(CC(=O)NCCOCCOCCC(=O)Nc5ccccc5C(=O)Nc5nc(C)c([N+](=O)[O-])s5)CC4)cn3)nc2n(C2CCCC2)c1=O] | 2-(3-(2-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)ethoxy)ethoxy)propanamido)-N-(4-methyl-5-nitrothiazol-2-yl)benzamide |
| D-124 | 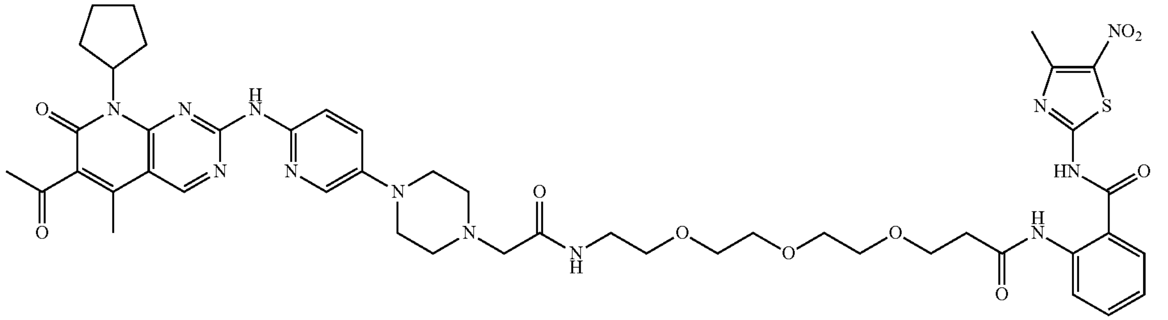 [SMILES: CC(=O)c1c(C)c2cnc(Nc3ccc(N4CCN(CC(=O)NCCOCCOCCOCCC(=O)Nc5ccccc5C(=O)Nc5nc(C)c([N+](=O)[O-])s5)CC4)cn3)nc2n(C2CCCC2)c1=O] | 2-(1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12-trioxa-3-azapentadecan-15-amido)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-125 | 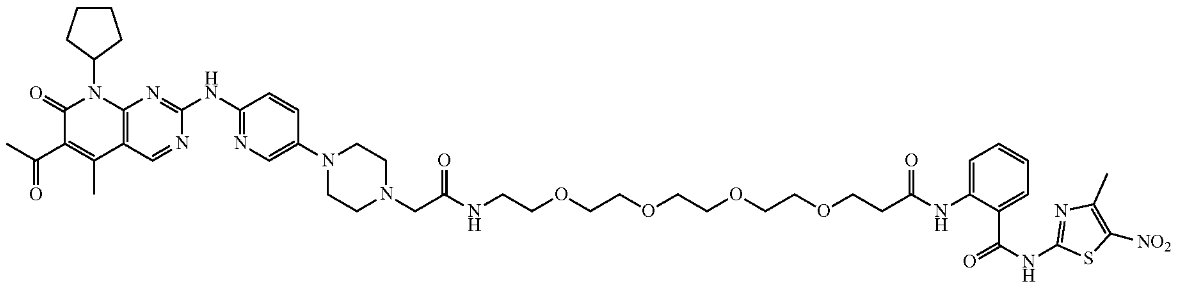 [SMILES: CC(=O)c1c(C)c2cnc(Nc3ccc(N4CCN(CC(=O)NCCOCCOCCOCCOCCC(=O)Nc5ccccc5C(=O)Nc5nc(C)c([N+](=O)[O-])s5)CC4)cn3)nc2n(C2CCCC2)c1=O] | 2-(1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15-tetraoxa-3-azaoctadecan-18-amido)-N-(4-methyl-5-nitrothiazol-2-yl)benzamide |
| D-126 | 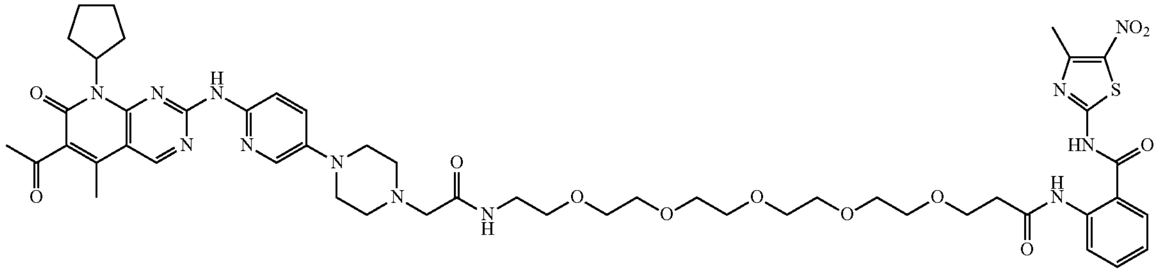 [SMILES: CC(=O)c1c(C)c2cnc(Nc3ccc(N4CCN(CC(=O)NCCOCCOCCOCCOCCOCCC(=O)Nc5ccccc5C(=O)Nc5nc(C)c([N+](=O)[O-])s5)CC4)cn3)nc2n(C2CCCC2)c1=O] | 2-(1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15,18-pentaoxa-3-azahenicosan-21-amido)-N-(4-methyl-5-nitrothiazol-2-yl)benzamide |

TABLE 5-continued

| DDB1 binding moieties attached to a target protein binding moiety | | |
|---|---|---|
| Compound | Structure | Name |
| D-127 | 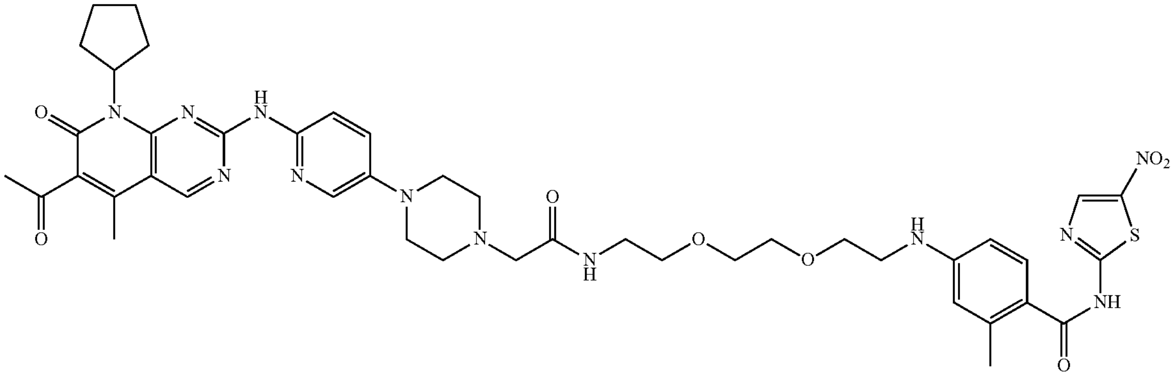 [SMILES: CC(=O)c1c(C)c2cnc(Nc3ccc(N4CCN(CC(=O)NCCOCCOCCNc5ccc(C(=O)Nc6ncc([N+](=O)[O-])s6)c(C)c5)CC4)cn3)nc2n(C2CCCC2)c1=O] | 4-((2-(2-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)ethoxy)ethoxy)ethyl)amino)-2-methyl-N-(5-nitrothiazol-2-yl)benzamide |
| D-128 | 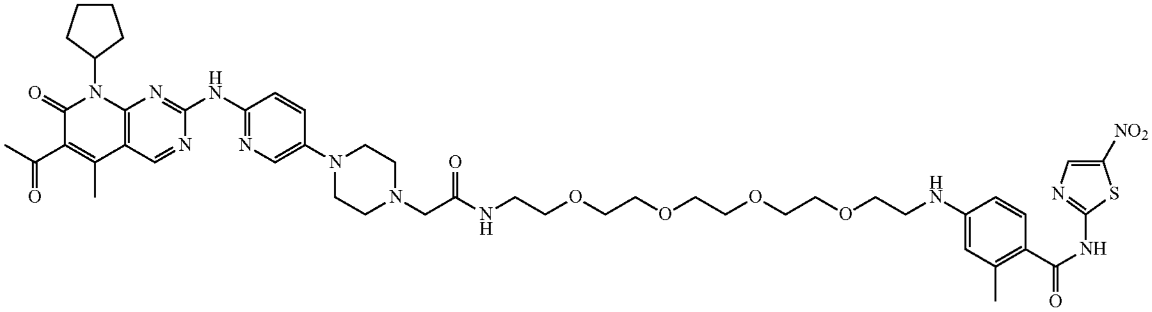 [SMILES: CC(=O)c1c(C)c2cnc(Nc3ccc(N4CCN(CC(=O)NCCOCCOCCOCCOCCNc5ccc(C(=O)Nc6ncc([N+](=O)[O-])s6)c(C)c5)CC4)cn3)nc2n(C2CCCC2)c1=O] | 4-((1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15-tetraoxa-3-azaheptadecan-17-yl)amino)-2-methyl-N-(5-nitrothiazol-2-yl)benzamide |

TABLE 5-continued

| DDB1 binding moieties attached to a target protein binding moiety | | |
|---|---|---|
| Compound | Structure | Name |
| D-129 | 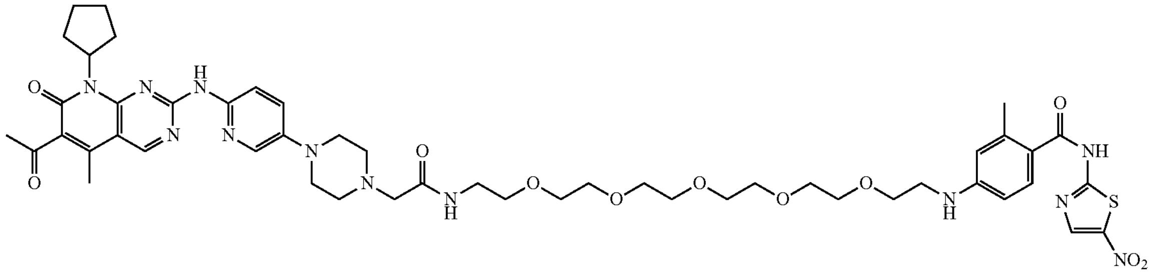 [SMILES: CC(=O)c1c(C)c2cnc(Nc3ccc(N4CCN(CC(=O)NCCOCCOCCOCCOCCOCCNc5ccc(C(=O)Nc6ncc([N+](=O)[O-])s6)c(C)c5)CC4)cn3)nc2n(C2CCCC2)c1=O] | 4-((1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15,18-pentaoxa-3-azaicosan-20-yl)amino)-2-methyl-N-(5-nitrothiazol-2-yl)benzamide |
| D-130 | 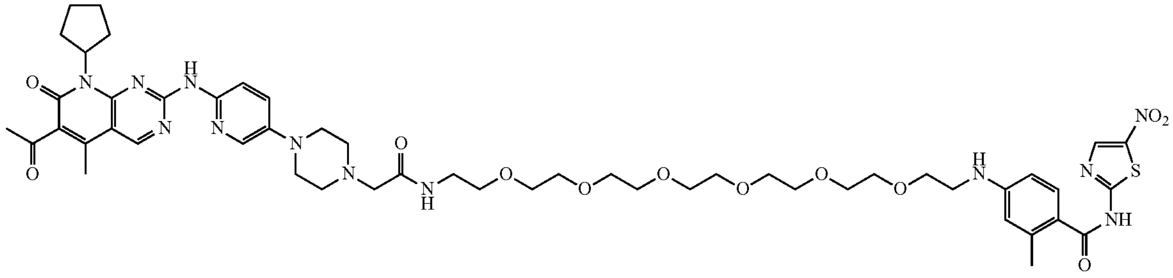 [SMILES: CC(=O)c1c(C)c2cnc(Nc3ccc(N4CCN(CC(=O)NCCOCCOCCOCCOCCOCCOCCNc5ccc(C(=O)Nc6ncc([N+](=O)[O-])s6)c(C)c5)CC4)cn3)nc2n(C2CCCC2)c1=O] | 4-((1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15,18,21-hexaoxa-3-azatricosan-23-yl)amino)-2-methyl-N-(5-nitrothiazol-2-yl)benzamide |

The compounds described herein may be useful for binding DNA damage-binding protein 1 (DDB1), binding and/or degrading target proteins, for inducing subsequent cellular effects, and/or for inhibiting microbes such as a virus or a bacteria. In some embodiments, the compound is used as an antiviral drug. For example, a compound such as compound comprising a ligand described herein may compete with one or more viral proteins. In some embodiments, the compound is used as an antiparasitic drug. In some embodiments, the compound is used as a molecular glue, for example, to hold two molecules together such as DDB1 proteins and/or target proteins. In some embodiments, the compound is used as a degrader. For example, a heterobifunctional compound described herein may be used as targeted protein degrader.

Preparation of Compounds

The compounds used in the chemical reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester. PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist. "Heterocyclic Chemistry", 2nd Ed., John Wiley & Sons. New York, 1992, J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0471-60180-2; Otera, J. (editor) "Modern Carbonyl Chemistry" (2000) Wiley-VCH, ISBN: 3-527-29871-1: Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Alternatively, specific and analogous reactants can be identified through the indices of known chemicals and reactions prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compound described herein is P. H. Stahl & C. G. Wermuth "Handbook of Pharmaceutical Salts", Vedlag Helvetica Chimica Acta, Zurich, 2002.

The compounds described herein are prepared using the general methods in the art of organic synthesis, as described in the Examples section. Alternative synthetic methods are also used to generate the compounds described herein. Some embodiments include a method of making a heterobifunctional compound disclosed herein.

Methods of Treatment and Pharmaceutical Compositions

In certain embodiments, the compounds described herein are used to treat a subject. In certain embodiments, the compounds described herein are used to degrade a target protein. Some embodiments include administering a compound described herein to a subject. The compound may be any ligand described herein. Some embodiments include administering a pharmaceutical composition comprising a compound described herein to a subject. Some embodiments include providing a compound or pharmaceutical composition described herein for administration to a subject.

In some embodiments, a modified protein disclosed herein is formed in vivo upon administration of the compound or pharmaceutical composition to the subject. In some embodiments, a ligand-protein complex disclosed herein is formed by administration of the compound or pharmaceutical composition to the subject.

In certain embodiments, the compound as described herein is administered as a pure chemical. In other embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, PA (2005)). One embodiment provides a pharmaceutical composition comprising a compound described herein, or a pharmaceutically acceptable salt thereof, and a pharmaceutically acceptable excipient.

Provided herein is a pharmaceutical composition comprising at least one compound described herein, or a stereoisomer, pharmaceutically acceptable salt, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject or patient) of the composition. In some embodiments, the excipient comprises a buffer or solution.

In certain embodiments, a compound described herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Some embodiments include use of a compound such as a ligand described herein, use of a ligand-DDB1 complex, or use of an in vivo modified DDB1 protein. The use may include a use as an anti-viral drug. The use may include a use as a molecule glue. The use may include a use as a targeted protein degrader. In some embodiments, the use comprises administration of the compound to a subject. In some embodiments, the use comprises contact of a sample with the compound.

Provided herein, in some embodiments, is a method for degrading a target protein in a subject. Some embodiments include administering, to the subject, a ligand described herein. Some embodiments include administering, to the subject, a ligand comprising a DNA damage-binding protein 1 (DDB1) binding moiety covalently connected through a linker to a target protein binding moiety. In some embodiments, the subject is a subject in need of administration of the ligand, or is in need of treatment with the ligand. Some embodiments include a method of modulating a target protein, comprising administering a therapeutically effective amount of a compound described herein (e.g., a heterobifunctional compound), to a subject in need thereof. In some embodiments, the target protein is decreased in the subject, relative to a baseline measurement. Following administration of a heterobifunctional compound described herein to a subject, a target protein measurement may be decreased in a tissue sample or fluid sample from the subject, relative to a baseline target protein measurement in a first tissue sample or fluid sample from the subject. Some embodiments include measuring a decrease in the CDK following the administration.

Some embodiments include obtaining a baseline measurement of a target protein. The baseline measurement may be obtained in a first sample obtained prior to administration of a compound described herein to a subject. The first sample may comprise a fluid sample. The first sample may comprise a tissue sample. The baseline measurement may be obtained directly in the subject. The baseline measurement may include a concentration. The baseline measurement may be normalized, for example to a sample weight, to a sample volume, to a total sample protein measurement, or to a housekeeping protein measurement.

Some embodiments include obtaining a measurement of a target protein. The measurement may be obtained in a second sample obtained after to administration of a compound described herein to a subject. The measurement may be obtained in a second sample obtained during to administration of a compound described herein to a subject. The second sample may comprise a fluid sample. The second sample may comprise a tissue sample. The measurement may be obtained directly in the subject. The measurement may be normalized, for example to a sample weight, to a sample volume, to a total sample protein measurement, or to a housekeeping protein measurement.

Measurements or baseline measurements of target proteins may include any method known in the art. For example, a measurement or baseline measurements may be obtained using an assay such as an immunoassay, a colorimetric assay, a lateral flow assay, a fluorescence assay, a proteomics assay, or a cell-based assay. The immunoassay may include an immunoblot such as a western blot or a dot blot, an enzyme-linked immunosorbent assay, or immunostaining. The proteomics assay may include mass spectrometry. A measurement or baseline measurements may be obtained using flow cytometry. A measurement or baseline measurements may be obtained using chromatography, for example high performance liquid chromatography.

The target protein may be or include any target protein included herein, as well as other target proteins not named. Some embodiments include a method of degrading a cyclin dependent kinase (CDK). Some embodiments include a method of degrading a target protein comprising a CDK. Some examples of such cyclin dependent kinases include, but are not limited to, CDK4 or CDK6. Some embodiments include a method of modulating a CDK, comprising administering a therapeutically effective amount of a compound described herein (e.g., a heterobifunctional compound), to a subject in need thereof. In some embodiments, the CDK is decreased in the subject, relative to a baseline measurement. Some embodiments include measuring a decrease in the CDK following the administration.

Some embodiments include a method of degrading a cyclin. Some embodiments include a method of degrading a target protein comprising a cyclin. Some examples of such cyclins include cyclin D such as cyclin D1, or cyclin D2, cyclin D3, or cyclin E. Some embodiments include a method of modulating a cyclin, comprising administering a therapeutically effective amount of a compound described herein (e.g., a heterobifunctional compound), to a subject in need thereof. Some embodiments include a method of modulating Cyclin D, comprising administering a therapeutically effective amount of a compound described herein (e.g., a heterobifunctional compound), to a subject in need thereof. In some embodiments, the cyclin is decreased in the subject, relative to a baseline measurement. Some embodiments include measuring a decrease in the cyclin following the administration.

Some embodiments include a method of degrading a transcription factor. Non-limiting examples of transcription factors include CBP and P300. Some embodiments include a method of degrading a target protein comprising CBP or P300. Some embodiments include a method of degrading a target protein comprising CBP. Some embodiments include a method of degrading a target protein comprising P300. Some embodiments include a method of modulating a transcription factor, comprising administering a therapeutically effective amount of a compound described herein (e.g., a heterobifunctional compound), to a subject in need thereof. In some embodiments, the transcription factor is decreased in the subject, relative to a baseline measurement. Some embodiments include measuring a decrease in the transcription factor following the administration. Additional examples of target proteins are included herein.

Examples of subjects include vertebrates, animals, mammals, dogs, cats, cattle, rodents, mice, rats, primates, monkeys, and humans. In some embodiments, the subject is a mammal. In some embodiments, the subject is a human.

In some embodiments, administering the ligand to the subject comprises administering an effective amount of the ligand sufficient to degrade the target protein. In some embodiments, upon administration of the ligand to the subject, the target protein is ubiquitinated to form a ubiquitinated target protein. In some embodiments, the administration is intravenous. In some embodiments, the administration comprises an injection. In some embodiments, the administration comprises cutaneous administration. In some embodiments, the administration comprises subcutaneous administration. In some embodiments, the administration comprises intraperitoneal administration. In some embodiments, the administration comprises oral administration. In some embodiments, the route of administration is intravenous, oral, subcutaneous, intraperitoneal, ocular, intraocular, intramuscular, interstitial, intraarterial, intracranial, intraventricular, intrasynovial, transepithelial, transdermal, by inhalation, ophthalmic, sublingual, buccal, topical, dermal, rectal, nasal, by insufflation, or by nebulization. In some embodiments, the administration is intramuscular. In some embodiments, the administration is intrathecal. In some embodiments, the administration is subcutaneous. In some embodiments, the administration is oral. In some embodiments, the administration is sublingual. In some embodiments, the administration is buccal. In some embodiments, the administration is rectal. In some embodiments, the administration is vaginal. In some embodiments, the administration is ocular. In some embodiments, the administration is otic. In some embodiments, the administration is nasal. In some embodiments, the administration is inhalation. In some embodiments, the administration is nebulization. In some embodiments, the administration is cutaneous. In some embodiments, the administration is topical. In some embodiments, the administration is transdermal. In some embodiments, the administration is systemic.

Provided herein, in some embodiments, is a method for degrading a target protein in a sample. Some embodiments include contacting a target protein with a ligand described herein. Some embodiments include contacting a target protein with a ligand comprising a DNA damage-binding protein 1 (DDB1) binding moiety covalently connected through a linker to a target protein binding moiety.

In some embodiments, the sample is a biological sample. In some embodiments, the biological sample comprises a tissue, a cell, or a biological fluid. In some embodiments, the contact is in vitro. In some embodiments, the contact is in vivo. In some embodiments, upon being contacted with the ligand, the target protein is ubiquitinated to form a ubiquitinated target protein.

In some embodiments, upon administration or contact, the ubiquitinated target protein is degraded. In some embodiments, the ubiquitinated target protein is degraded. In some embodiments, the degradation of the target protein is specific to the target protein. In some embodiments, the target protein comprises proteasomal degradation. In some embodiments, the target protein is degraded by a proteasome.

In some embodiments, upon administration or contact, the ligand binds to a DDB1 protein to form a ligand-DDB1 complex. In some embodiments, the ligand directly binds to the DDB1 protein through the DDB1 binding moiety of the ligand. In some embodiments, the binding between the DDB1 binding moiety and the DDB1 protein is non-covalent. In some embodiments, the binding between the DDB1 binding moiety and the DDB1 protein is covalent. In some embodiments, the target protein is ubiquitinated by a ubiquitin E3 ligase complex comprising the DDB1 protein. In some embodiments, the ligand (e.g. a DDB1 ligand) recruits the ubiquitin E3 ligase complex to the target protein via the DDB1 binding moiety. In some embodiments, the ligand is a small molecule. In some embodiments, the ligand comprises a targeted protein degrader. In some embodiments, the ligand is synthetic. In some embodiments, the ligand comprises a ligand described herein.

The target protein to degraded using a method described herein may be or include any target protein described herein. In some embodiments, the target protein comprises any one of a transcription factor, CBP, p300, a kinase, a receptor, a TRK, TrkA, TrkB, TrkC, a cyclin dependent kinase, CDK4, CDK6, B7.1, B7, TINFRlm, TNFR2, NADPH oxidase, a partner in an apoptosis pathway, BclIBax, $C_5$a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide synthase, cyclo-oxygenase 1, cyclo-oxygenase 2, a receptor, a 5HT receptor, a dopamine receptor, a G-protein, Gq, a histamine receptor, 5-lipoxygenase, tryptase serine protease, thymidylate synthase, purine nucleoside phosphorylase, GAPDH, a trypanosomal protein, glycogen phosphorylase, carbonic anhydrase, a chemokine receptor, JAK, STAT, RXR. RAR, HIV 1 protease, HIV 1 integrase, influenza, neuramimidase, hepatitis B reverse transcriptase, sodium channel, multi drug resistance, protein P-glycoprotein, MRP, a tyrosine kinase, CD23, CD124, tyrosine kinase p56 lck, CD4, CD5, IL-2 receptor, IL-1 receptor, TNF-alphaR, ICAM1, a Ca+ channel, VCAM, an integrin, a VLA-4 integrin, a selectin, CD40, CD40L, a neurokinin, a neurokinin receptor, inosine monophosphate dehydrogenase, p38 MAP Kinase, Ras, Raf, Mek, Erk, interleukin-1 converting enzyme, a caspase, HCV. NS3 protease, HCV NS3 RNA helicase, glycinamide ribonucleotide formyl transferase, rhinovirus 3C protease, herpes simplex virus-1, a protease, cytomegalovirus protease, poly ADP-ribose polymerase, vascular endothelial growth factor, oxytocin receptor, microsomal transfer protein inhibitor, bile acid transport inhibitor, a 5 alpha reductase inhibitor, angiotensin II, a glycine receptor, a noradrenaline reuptake receptor, an endothelin receptor, neuropeptide Y, a neuropeptide Y receptor, an estrogen receptor, an androgen receptor, an adenosine receptor, an adenosine kinase, AMP deaminase, a purinergic receptor. P2Y1, P2Y2, P2Y4, P2Y6, P2X1-7, a farnesyltransferase, geranylgeranyl transferase, an NGF receptor, beta-amyloid, tyrosine kinase Flk-IIKDR, vitronectin receptor, an integrin receptor, Hcr2 neu, telomerase inhibition, cytosolic phospholipaseA2, EGF receptor tyrosine kinase, ecdysone 20-monooxygenase, ion channel of the GABA gated chloride channel, acetylcholinesterase, voltage-sensitive sodium channel protein, calcium release channel, a chloride channel, acetyl-CoA carboxylase, adenylosuccinate synthetase, protoporphyrinogen oxidase, or enolpyruvylshikimate-phosphate synthase. Some embodiments include multiple target proteins, such as a combination of any two or more of the target proteins disclosed herein.

A compound (such as a compound comprising a DDB1 binding moiety) described herein may be useful 1) as an antiviral drug; 2) as a DDB1 protein level modulator (e.g. increasing or decreasing DDB1 protein levels); 3) as a DDB1 function modulator (e.g. activating or inhibiting DDB1); 4) as a molecular glue (e.g. increasing a protein-protein interaction between DDB1 and a second protein); 5) for affecting activity or protein levels of the second protein via the molecule glue function; 6) for decreasing protein levels of the second protein via the molecule glue function; 7) for increasing protein levels of the second protein via the molecule glue function; 8) for decreasing activity of the second protein via the molecule glue function; or 9) for increasing activity of the second protein via the molecule glue function.

A compound described herein may be useful for treating a disease or disorder. For example, the compound may be administered to a subject having the disease or disorder. The administration may reduce the severity of the disease or disorder in the subject, relative to a baseline measurement. The compound may bind a target protein involved in the disease or disorder, resulting in inhibition or degradation of the target protein. The compound may be a heterobifunctional compound, and comprise a DDB1 binding moiety and a target protein binding moiety, wherein the target protein is involved in the disease or disorder. The target protein may exacerbate the disease or disorder. The target protein may prevent or decrease inhibition of the disease or disorder.

In some embodiments, a compound described herein is used as an antimicrobial drug. For example, the compound may be administered to a subject having a microbial infection. The administration may reduce the severity of the microbial infection in the subject, relative to a baseline measurement. The compound may bind a target protein involved in the microbial infection, resulting in inhibition or degradation of the target protein. The microbial infection may include a virus infection. The microbial infection may include a bacterial infection. The compound may be a heterobifunctional compound, and comprise a DDB1 binding moiety and a target protein binding moiety, wherein the target protein is a microbial protein. The microbial protein may include a viral protein. The microbial protein may include a bacterial protein. The target protein may be a non-microbial protein that exacerbates the microbial infection. The target protein may be a non-microbial protein that prevents or decreases inhibition of the microbial infection. In some embodiments, the compound enters a cell of the subject, binds to a microbial protein in the cell via its target protein binding moiety, binds DDB1 via its DDB1 binding moiety, and induces ubiquitin-mediated degradation of the microbial protein. Such an action may be useful against microbes such as bacteria or viruses that infect or reside within the cell.

A compound described herein may be useful for modulating DDB1 protein levels. For example, the compound may be used to increase or decrease DDB1 protein levels. In some embodiments, a compound comprising a DDB1 binding moiety described herein, is used to increase DDB1 protein levels. For example, the compound may bind to DDB1 and prevent its degradation. In some embodiments, a compound comprising a DDB1 binding moiety described herein, is used to decrease DDB1 protein levels. For example, the compound may bind to DDB1 and increase its degradation. The compound may be a heterobifunctional compound, and include a DDB1 binding moiety coupled to (directly or through a linker) a second moiety that increases degradation of the DDB1 protein, or that decreases degradation of the DDB1 protein. The second moiety may accomplish this by binding to a target protein. In some such embodiments, the target protein may include an E3 ubiquitin ligase protein that enhances degradation of the DDB1 protein. In some embodiments, the compound is not a heterobifunctional compound. In some embodiments, the compound comprises or consists of a DDB1 binding moiety. In some embodiments, the compound comprises or consists of the structure of Formula (II), a compound provided in Table 1, or a derivative or salt thereof. In some embodiments, the compound is administered to a subject to increase a DDB1 protein level in the subject. The administration may increase DDB1 activity in the subject, relative to a baseline measurement. In some embodiments, the compound is administered to a subject to decrease a DDB1 protein level in the subject. The administration may decrease DDB1 activity in the subject, relative to a baseline measurement.

A compound described herein may be useful for modulating DDB1 function. For example, the compound may be used to activate or inhibit DDB1. In some embodiments, a compound comprising a DDB1 binding moiety described herein, is used to increase DDB1 activity. For example, the compound may bind to DDB1 and activate DDB1. The compound may allosterically activate DDB1. The compound may activate DDB1 by binding to a protein binding site on DDB1. In some embodiments, a compound comprising a DDB1 binding moiety described herein, is used to decrease DDB1 activity. For example, the compound may bind to DDB1 and inhibit DDB1. The compound may allosterically inhibit DDB1. The compound may inhibit DDB1 by binding to an active site of DDB1. The compound may inhibit DDB1 by binding to a protein binding site on DDB1. The compound may be a heterobifunctional compound, and include a DDB1 binding moiety coupled to (directly or through a linker) a second moiety that increases activity of the DDB1 protein, or that decreases activity of the DDB1 protein. The second moiety may accomplish this by binding to a target protein. In some embodiments, the compound is administered to a subject to increase DDB1 activity in the subject. The administration may increase DDB1 activity in the subject, relative to a baseline measurement. In some embodiments, the compound is administered to a subject to decrease DDB1 activity in the subject. The administration may decrease DDB1 activity in the subject, relative to a baseline measurement.

A compound described herein may be useful as a molecular glue. For example, the compound may bind multiple molecules and hold them together. In some embodiments, the molecular glue binds DDB1 and a target protein. The compound may accomplish this as a heterobifunctional compound that comprises a DDB1 binding moiety and a target protein binding moiety. The compound may increase a protein-protein interaction between DDB1 and a target protein. The compound may act as a molecular glue to modulate an activity or amount of the target protein. As a molecular glue, the compound may decrease an amount of the target protein. As a molecular glue, the compound may increase an amount of the target protein. As a molecular glue, the compound may decrease activity of the target protein. As a molecular glue, the compound may increase activity of the target protein.

Disclosed herein, in some embodiments, are methods for degrading a target protein in a cell. The method may include degrading the target protein through direct binding of an intermediate protein (e.g. a first protein) that interacts with the target protein. This may be referred to as bridged degradation. Some embodiments include administering a binding molecule to the cell. The binding molecule may include a ligand or compound disclosed herein. The ligand may be a heterobifunctional compound. The binding molecule may bind a first protein that interacts with the target protein. The target protein may be degraded before the first protein. In some embodiments, the first protein is not degraded. Some embodiments include administering, to the cell, a binding molecule that binds a first protein that interacts with the target protein, thereby degrading target protein, wherein the target protein is degraded before the first protein or wherein the first protein is not degraded. Some embodiments include measuring the target protein in the cell. Some embodiments include measuring the first protein in the cell. In some embodiments, the interaction between the target protein and the first protein is binding. In some embodiments, the interaction between the target protein and the first protein is dimerization. The target protein may include a target protein described herein. The first protein may include another target protein described herein. In some embodiments, the target protein comprises a cyclin. In some embodiments, the target protein comprises Cyclin D. In some embodiments, the Cyclin D comprises Cyclin D1, Cyclin D2, or Cyclin D3. The cyclin D may include Cyclin D1. The cyclin D may include Cyclin D2. The cyclin D may include Cyclin D3. In some embodiments, the first protein comprises a cyclin-dependent kinase (CDK). The CDK may include CDK4. The CDK may include CDK6. In some embodiments, the first protein comprises CDK4 or CDK6. In some embodiments, the binding molecule reduces viability of the cell. In some embodiments, the cell is a eukaryotic cell. In some embodiments, the cell is a mammalian cell. In some embodiments, the cell is a human cell. In some embodiments, the cell is a cancer cell. In some embodiments, administering the binding molecule to the cell comprises administering the binding molecule to a subject comprising the cell. In some embodiments, the binding molecule recruits a ubiquitin E3 ligase that ubiquitinates the target protein. In some embodiments, the E3 ubiquitin ligase comprises DNA damage-binding protein 1 (DDB1) or Von Hippel-Lindau tumor suppressor (VHL). The E3 ubiquitin ligase may include DDB1. The E3 ubiquitin ligase may include VHL. In some embodiments, the binding molecule comprises a heterobifunctional compound comprising an E3 ubiquitin ligase-binding moiety covalently connected through a linker to a first protein binding moiety. The first protein binding moiety may include a target protein binding moiety disclosed herein. In some embodiments, the binding molecule comprises a structure disclosed herein.

Disclosed herein, in some embodiments, are methods (e.g. a bridged degradation method) comprising administering to a cell a binding molecule that binds a cyclin-dependent kinase (CDK), thereby degrading a cyclin that interacts with the CDK. In some embodiments, the cyclin is degraded before the CDK, or wherein the CDK is not degraded. In some embodiments, the cyclin is degraded before the CDK. In some embodiments, the CDK is not degraded. Some embodiments include measuring the cyclin in the cell. Some embodiments include measuring the CDK in the cell. In some embodiments, the interaction between the cyclin and the CDK comprises binding or dimerization. The interaction may include binding. The interaction may include dimerization. In some embodiments, the cyclin comprises Cyclin D. In some embodiments, the Cyclin D comprises Cyclin D1, Cyclin D2, or Cyclin D3. The cyclin D may include Cyclin DL. The cyclin D may include Cyclin D2. The cyclin D may include Cyclin D3. In some embodiments, the CDK comprises CDK4 or CDK6. The CDK may include CDK4. The CDK may include CDK6. In some embodiments, the binding molecule reduces viability of the cell. In some embodiments, the cell is a eukaryotic cell. In some embodiments, the cell is a mammalian cell. In some embodiments, the cell is a human cell. In some embodiments, the cell is a cancer cell. In some embodiments, administering the binding molecule to the cell comprises administering the binding molecule to a subject comprising the cell. In some embodiments, the binding molecule recruits a ubiquitin E3 ligase that ubiquitinates the cyclin. In some embodiments, the E3 ubiquitin ligase comprises DNA damage-binding protein 1 (DDB1) or Von Hippel-Lindau tumor suppressor (VHL). The E3 ubiquitin ligase may include DDB1. The E3 ubiquitin ligase may include VHL. In some embodiments, the binding molecule comprises a heterobifunctional compound comprising an E3 ubiquitin ligase-binding moiety covalently connected through a linker to a CDK binding moiety. In some embodiments, the E3 ubiquitin ligase-binding moiety comprises a chemical structure disclosed herein. In some embodiments, the CDK binding moiety comprises a target protein binding moiety disclosed herein. In some embodiments, the binding molecule comprises a ligand disclosed herein.

NUMBERED EMBODIMENTS

Some embodiments include any one of the following:

1. A ligand-DNA damage-binding protein 1 (DDB1) complex formed by binding a DDB1 protein directly to a DDB1 ligand, the DDB1 ligand comprising a DDB1 binding moiety.
2. The ligand-DDB1 complex of embodiment 1, wherein the DDB1 binding moiety is bound to a binding region on the DDB1 protein.
3. The ligand-DDB1 complex of embodiment 2, wherein the beta binding region on the DDB1 protein comprises a beta propeller domain.
4. The ligand-DDB1 complex of embodiment 3, wherein the beta propeller domain comprises a beta propeller C (BPC) domain.
5. The ligand-DDB1 complex of embodiment 4, wherein the binding region on the DDB1 protein comprises a top face of the BPC domain.
6. The ligand-DDB1 complex of any one of embodiments 2-5, wherein the binding region on the DDB1 protein comprises one or more of the following DDB1 residues: ARG327, LEU328, PRO358, ILE359, VAL360, ASP361, GLY380, ALA381, PHE382, SER720, ARG722, LYS723, SER738, ILE740, GLU787, TYR812, LEU814, SER815, ALA834, VAL836, ALA841, ALA869, TYR871, SER872, MET9.10 LEU912, TYR913, LEU926, TRP953, SER955. ALA956, ASN970, ALA971, PHE972, PHE1003, ASN1005, VAL1006, or VAL1033.
7. The ligand-DDB1 complex of any one of embodiments 1-6, wherein one or more of the following DDB1 residues are involved in the binding between the DDB1 protein and the DDB1 ligand: ARG327, LEU328, PRO358, ILE359, VAL360, ASP361, GLY380, ALA381, PHE382, SER720, ARG722, LYS723, SER738, ILE740, GLU787, TYR812, LEU814, SER815, ALA834, VAL836, ALA841, ALA869, TYR871, SER872, MET910, LEU912, TYR913, LEU926, TRP953, SER955, ALA956, ASN970, ALA971, PHE972, PHE1003, ASN1005, VAL1006, or VAL1033.
8. The ligand-DDB1 complex of any one of embodiments 1-7, wherein the binding between the DDB1 binding moiety and the DDB1 protein is non-covalent.
9. The ligand-DDB1 complex of any one of embodiments 1-8, wherein the binding between the DDB1 protein and the DDB1 ligand comprises a binding affinity with an equilibrium dissociation constant (Kd) below 100 μM, a Kd below 90 μM, a Kd below 80 μM, a Kd below 70 μM, a Kd below 60 μM, a Kd below 50 μM, a Kd below 45 μM, a Kd below 40 μM, a Kd below 35 μM, a Kd below 30 μM, a Kd below 25 μM, a Kd below 20 μM, a Kd below 15 μM, a Kd below 14 μM, a Kd below 13 μM, a Kd below 12 μM, a Kd below 11 μM, a Kd below 10 μM, a Kd below 9 μM, a Kd below 8 μM, a Kd below 7 μM, a Kd below 6 μM, a Kd below 5 μM, a Kd below 4 μM, a Kd below 3 μM, a Kd below 2 μM, or a Kd below 1 μM.

10. The ligand-DDB1 complex of any one of embodiments 1-9, wherein the binding between the DDB1 protein and the DDB1 ligand comprises a binding affinity with a Kd<20 uM, a Kd from 20-100 uM, or a Kd>100 uM.

11. The ligand-DDB1 complex of any one of embodiments 1-7, wherein the binding between the DDB1 binding moiety and the DDB1 protein is covalent.

12. The ligand-DDB1 complex of any one of embodiments 1-11, wherein the DDB1 ligand is a small molecule.

13. The ligand-DDB1 complex of any one of embodiments 1-12, wherein the DDB1 ligand is a heterobifunctional compound comprising a DDB1 binding moiety covalently connected through a linker to a target protein binding moiety.

14. The ligand-DDB1 complex of any one of embodiments 1-13, wherein the DDB1 ligand is synthetic.

15. The ligand-DDB1 complex of any one of embodiments 1-14, wherein the DDB1 binding moiety comprises a structure of Formula (II):

Formula (II)

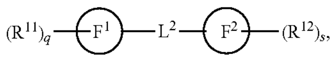

wherein $F^1$ is aryl, heteroaryl, carbocyclyl, or heterocyclyl:

$F^2$ is aryl, heteroaryl, carbocyclyl, or heterocyclyl:

$L^2$ is a bond, —C(═O)$NR^{13}$—, —$NR^{13}$C(═O)—, —C(═O)—, —C(═S)—, —S—, —S(═O), —$S(═O)_2$—, —S(═O)$NR^{13}$—, —$NR^{13}$S(═O)—, —$S(═O)_2NR^{13}$—, —$NR^{13}S(═O)_2$—, —O—, $C_1$-$C_4$ alkyl, or $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —$S(═O)_2R^d$, —$S(═O)_2NR^cR^d$, —C(═O)$R^b$, —$CO_2R^a$, —C(═O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen. $C_1$-$C_6$ alkyl, $C_1$-$C_6$ haloalkyl, —$OR^a$, or —$NR^cR^d$;

each $R^{11}$ and $R^{12}$ is independently a bond, hydrogen, halogen, —CN, —$R^a$, —$OR^a$, —$SR^a$, —S(═O)$R^b$, —$NO_2$, —$NR^cR^d$, —$S(═O)_2R^d$, —$NR^aS(═O)_2R^d$, —$S(═O)_2NR^cR^d$, —C(═O)$R^b$, —OC(═O)$R^b$, —$CO_2R^c$, —$OCO_2R^a$, —C(═O)$NR^cR^d$, —OC(═O) $NR^cR^d$, —$NR^a$C(═O)$NR^cR^d$, —$NR^a$C(═O)$R^b$, —$NR^a$C(═O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$R^a$, or —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$, and optionally wherein at least one $R^{11}$ is a bond attached to a linker;

each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-5; and s is 1-5;

or a pharmaceutically acceptable salt thereof.

16. The ligand-DDB1 complex of any one of embodiments 1-15, wherein the DDB1 binding moiety comprises a structure of Formula (IIa):

Formula (IIa)

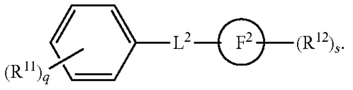

17. The ligand-DDB1 complex of embodiment 15 or 16, wherein $F^2$ is heteroaryl.

18. The ligand-DDB1 complex of any one of embodiments 15-17, wherein $F^2$ is a five membered or six membered ring heteroaryl.

19. The ligand-DDB1 complex of any one of embodiments 15-18, wherein $F^2$ is triazolyl, tetrazolyl, furanyl, pyrrolyl, thiazolyl, oxazolyl, isoxazolyl, imidazolyl, pyrazolyl, thiadiazolyl, or oxadiazolyl.

20. The ligand-DDB1 complex of any one of embodiments 1-19, wherein the DDB1 binding moiety comprises a structure of Formula (IIb):

Formula (IIb)

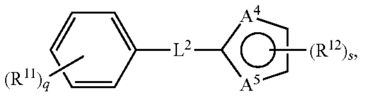

wherein $A^4$ and $A^5$ are each independently $CR^{12}$, S, N, or O, wherein at least one of $A^4$ or $A^5$ is N, S, or O.

21. The ligand-DDB1 complex of embodiment 20, wherein $A^4$ is N and $A^5$ is S.

22. The ligand-DDB1 complex of any one of embodiments 1-21, wherein the DDB1 binding moiety comprises the structure:

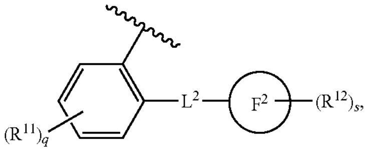

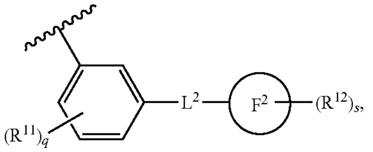

or

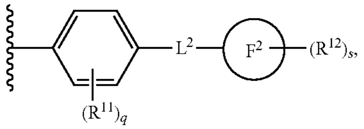

wherein the wavy line indicates an optional point of attachment to a linker or ligand.

23. The ligand-DDB1 complex of any one of embodiments 15-22, wherein $R^{12}$ is —$NO_2$, Cl, or Br.

24. The ligand-DDB1 complex of any one of embodiments 15-23, wherein $L^2$ is —$NR^cC(=O)$— or —$C(=O)NR^c$—.

25. The ligand-DDB1 complex of any one of embodiments 15-24, wherein $R^c$ is H or $CH_3$.

26. The ligand-DDB1 complex of any one of embodiments 15-25, wherein q is 1 or 2.

27. The ligand-DDB1 complex of any one of embodiments 15-26, wherein s is 1 or 2.

28. The ligand-DDB1 complex of any one of embodiments 1-27, wherein the DDB1 binding moiety comprises

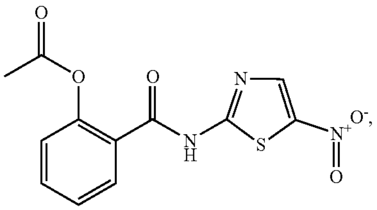

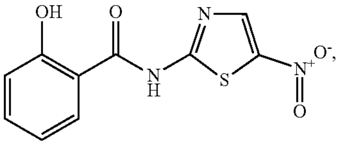

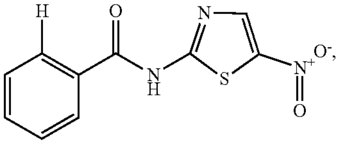

-continued

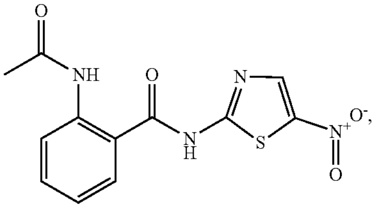

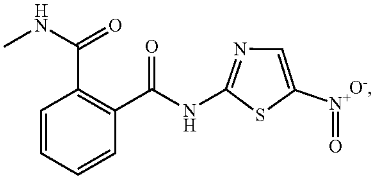

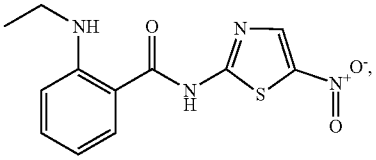

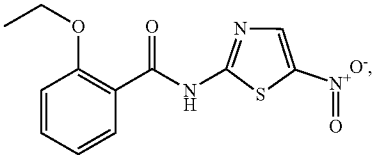

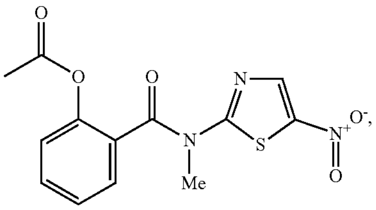

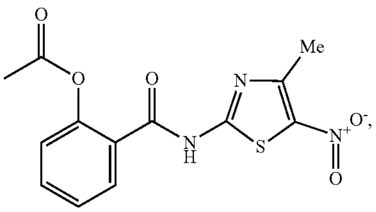

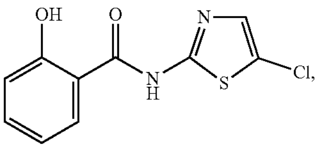

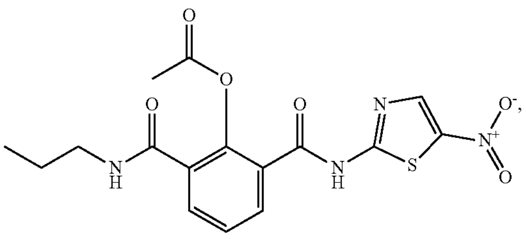

-continued
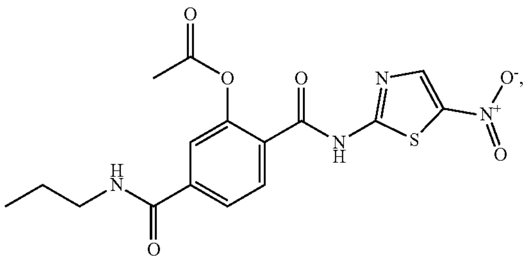
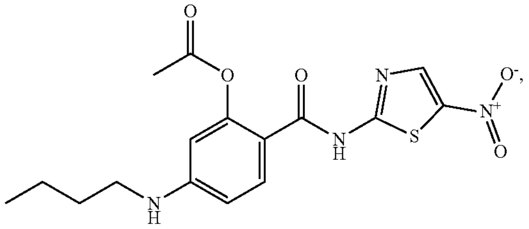
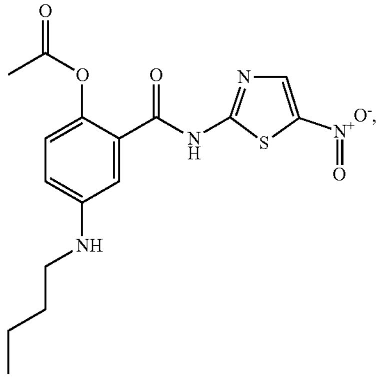
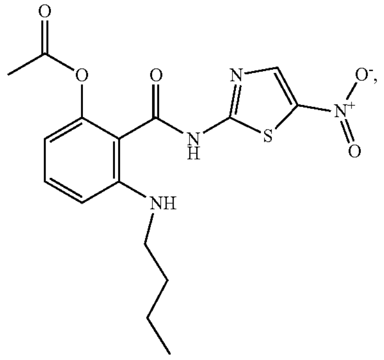
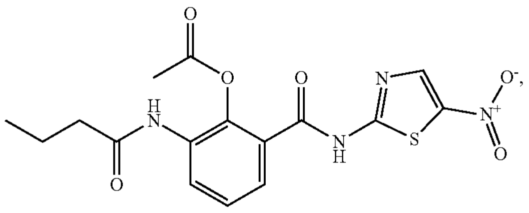
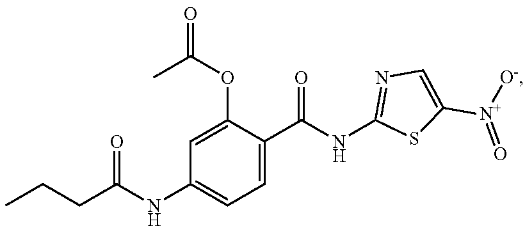
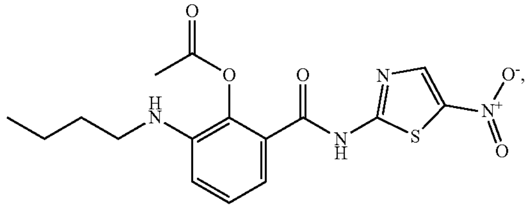
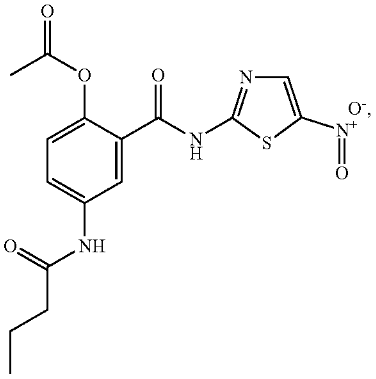
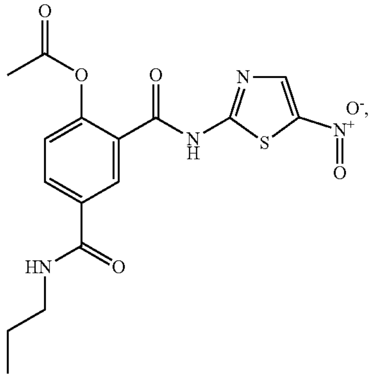
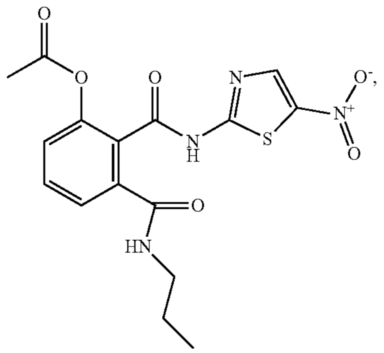
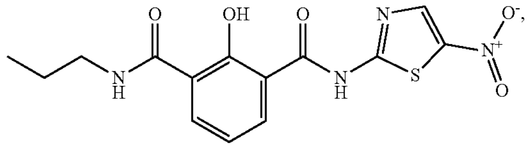

-continued
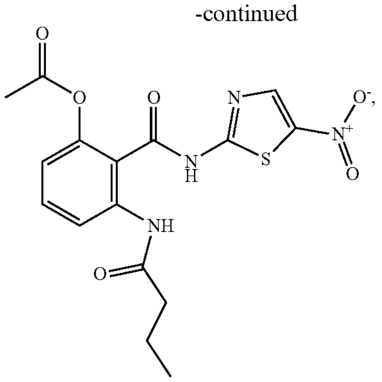
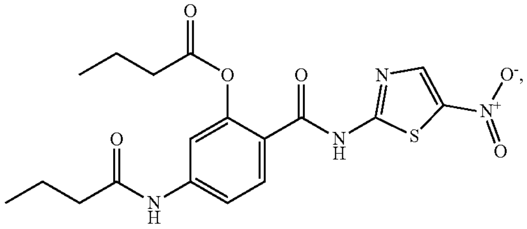
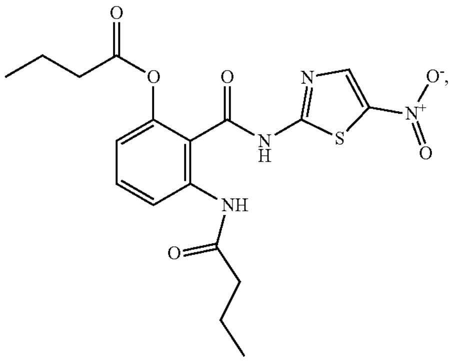
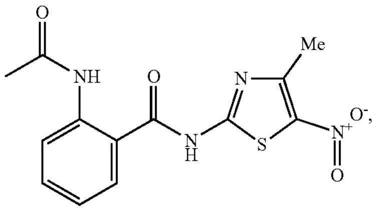
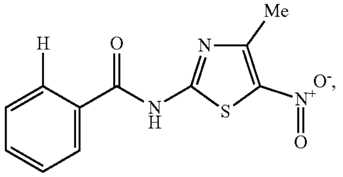
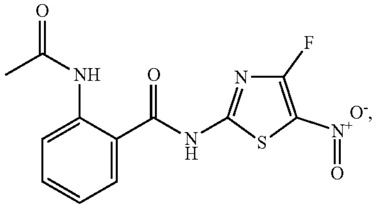
-continued
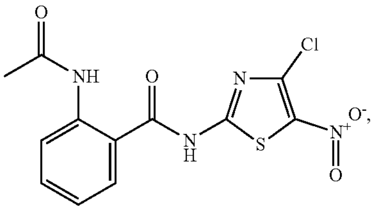
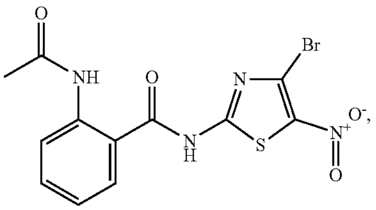
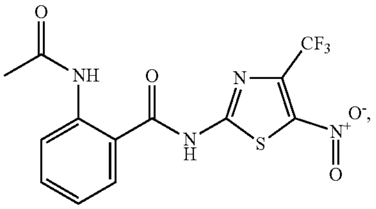
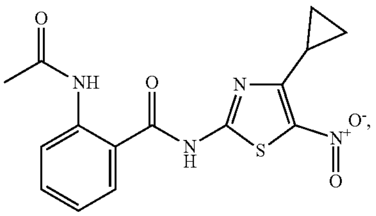
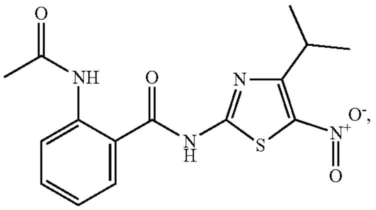
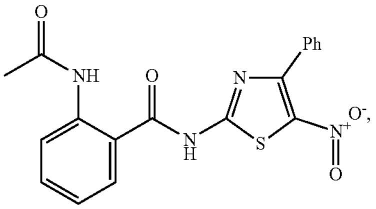
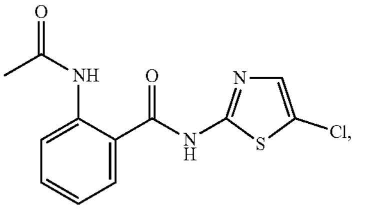
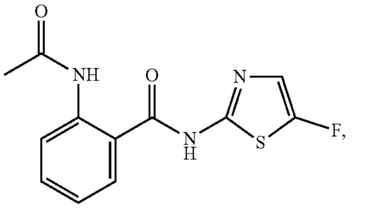

-continued
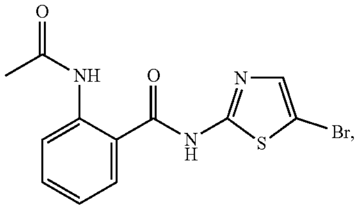
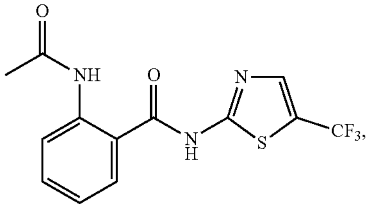
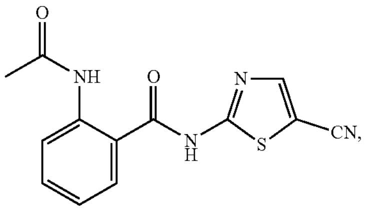
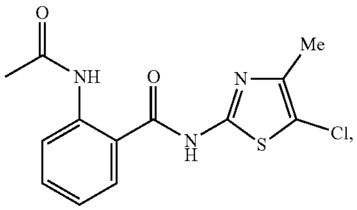
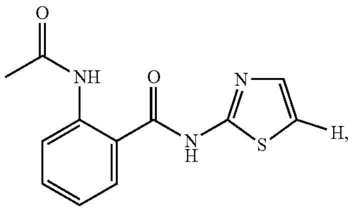
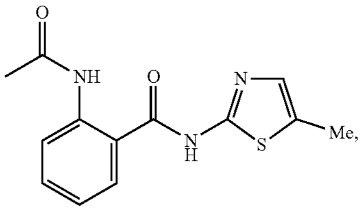
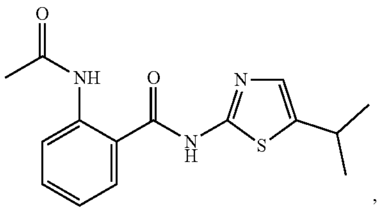
,
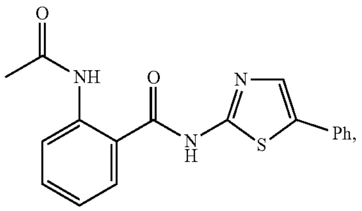
-continued
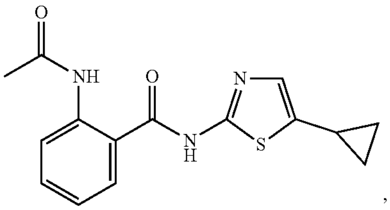
,
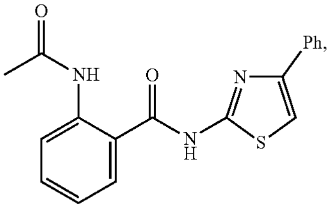
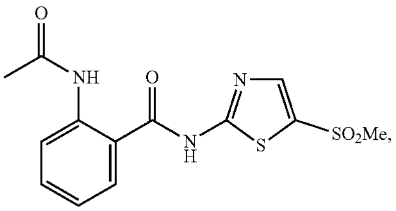
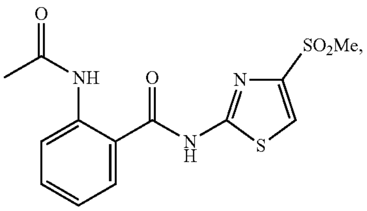
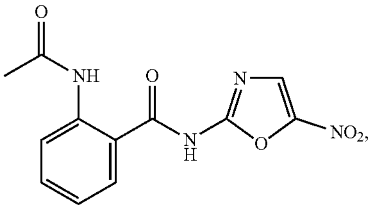
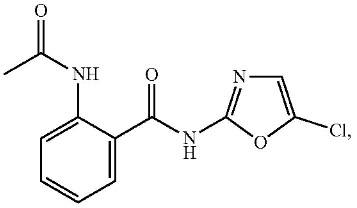
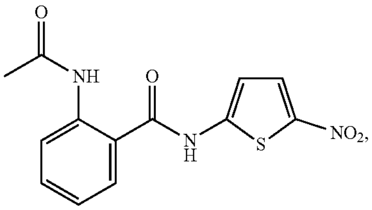
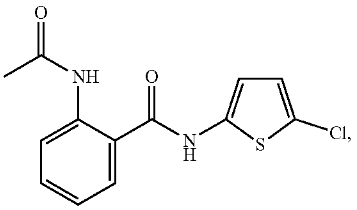

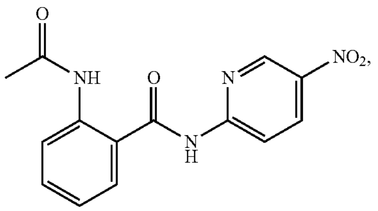
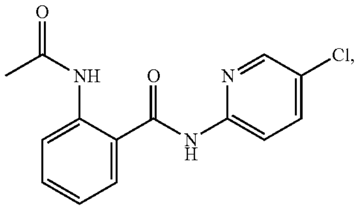
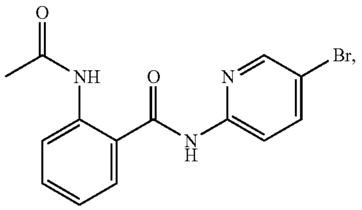
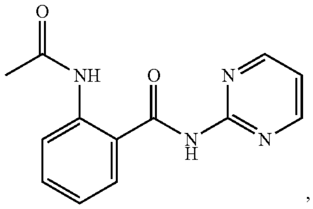
,
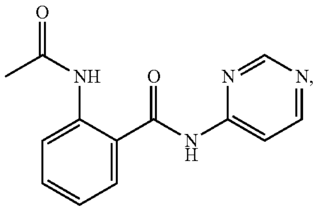
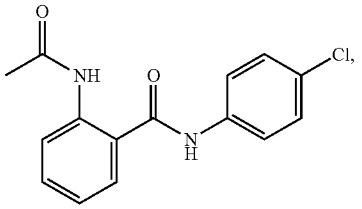
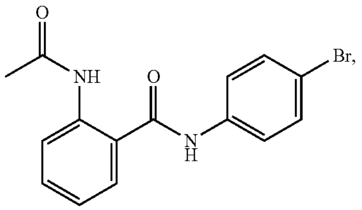
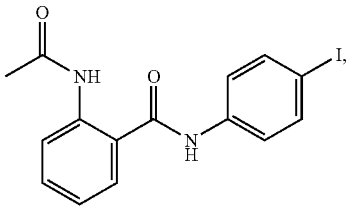
-continued
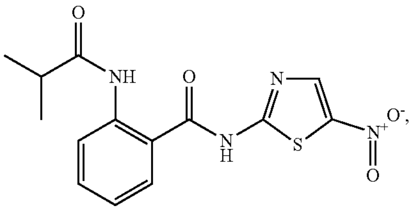
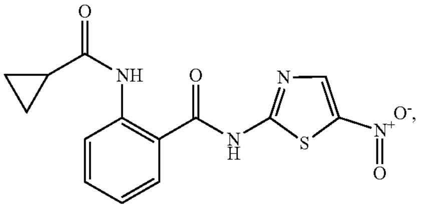
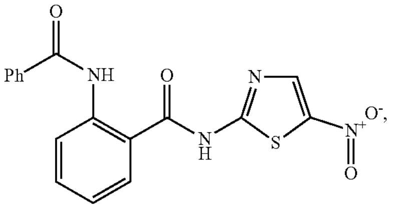
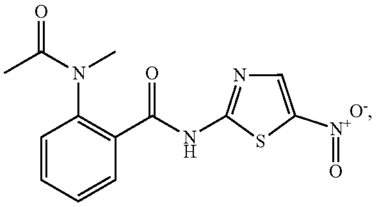
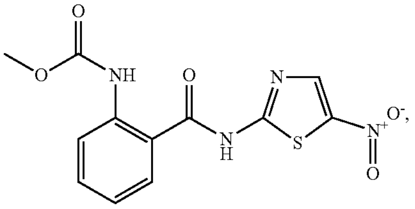
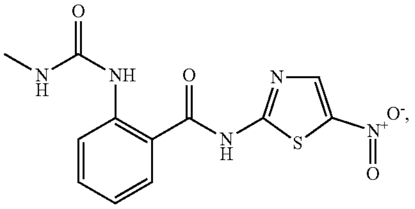
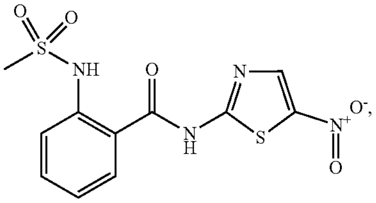
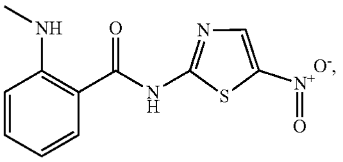

-continued
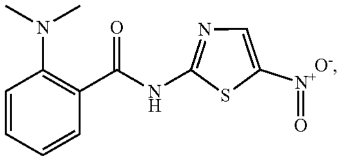
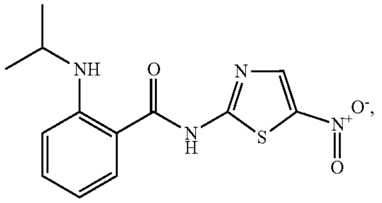
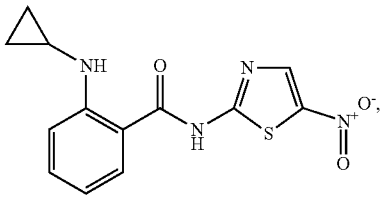
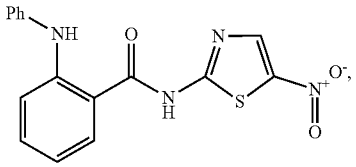
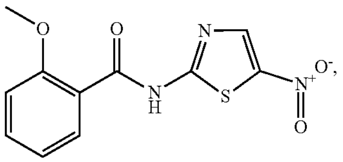
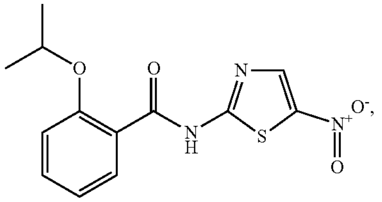
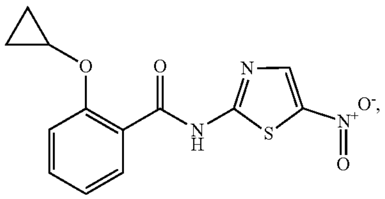
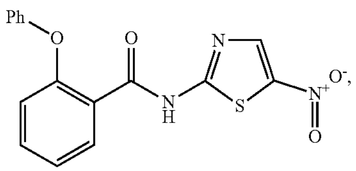
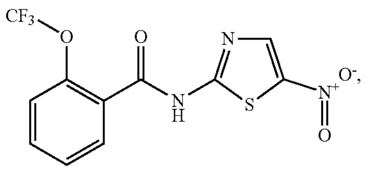
-continued
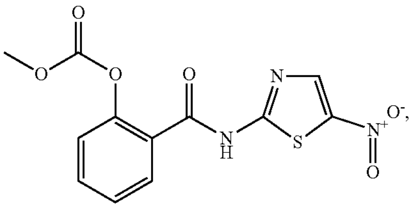
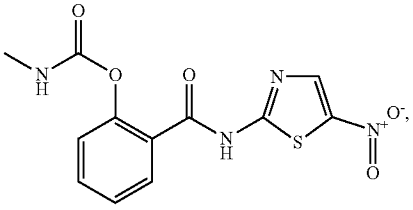
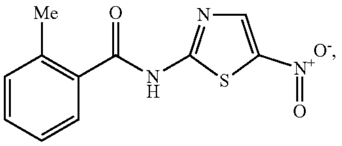
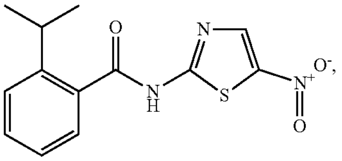
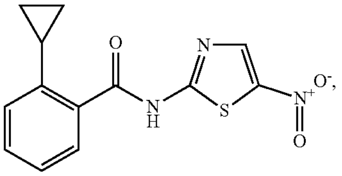
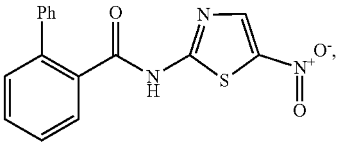
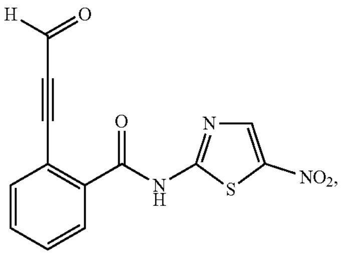
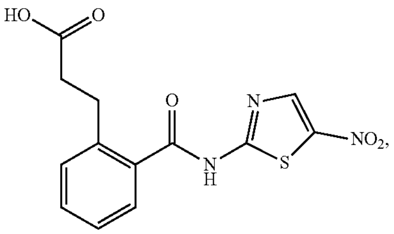
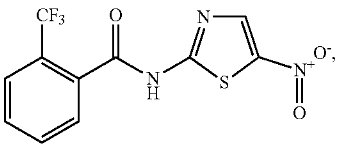

-continued
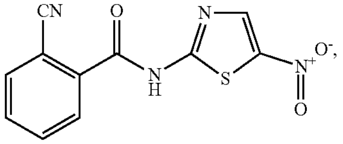
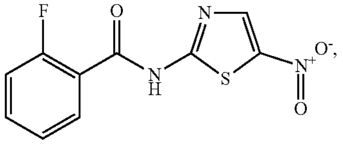
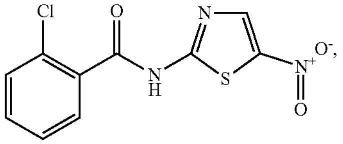
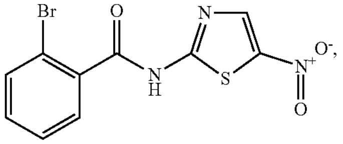
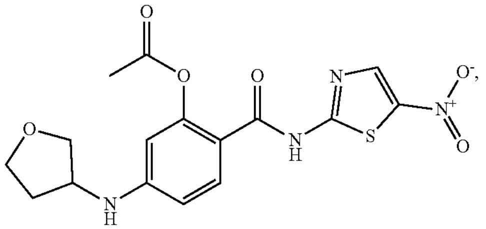
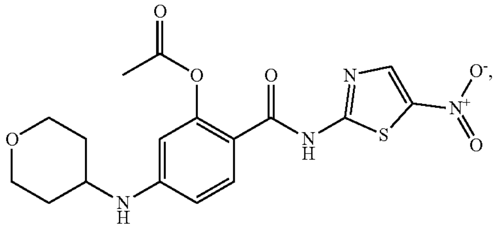
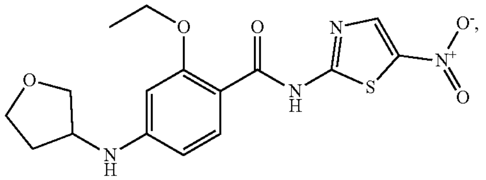
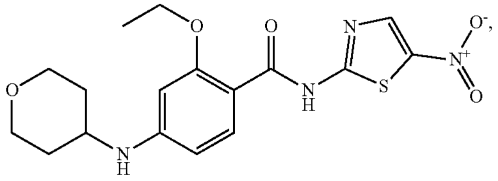
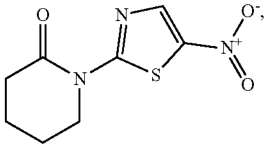
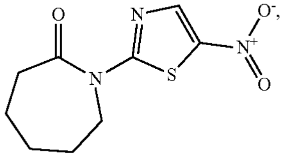
-continued
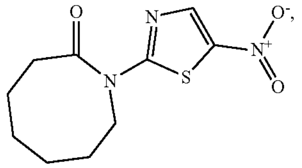
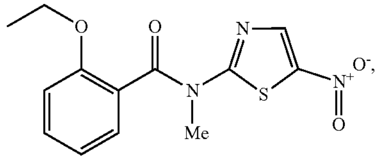
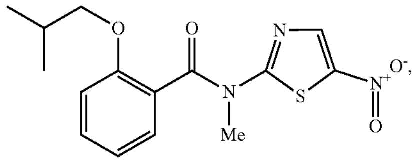
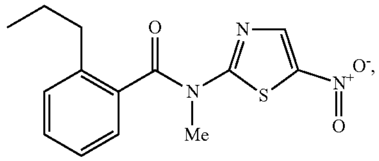
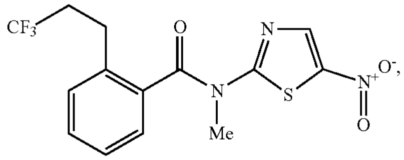
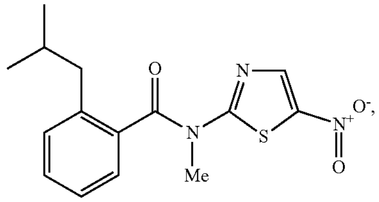
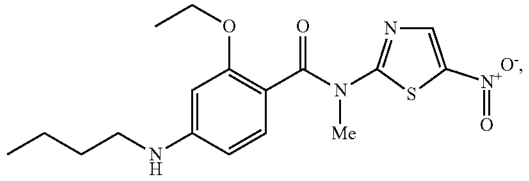
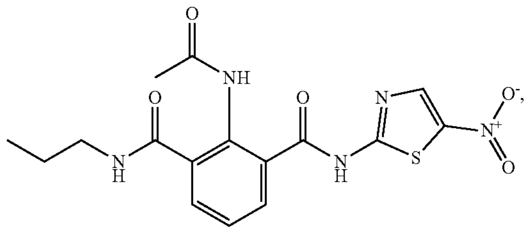
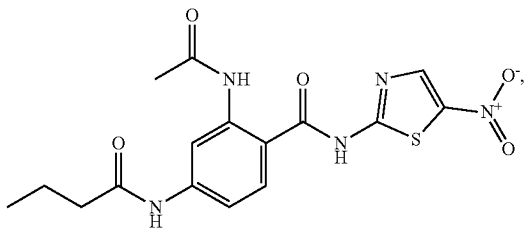

-continued
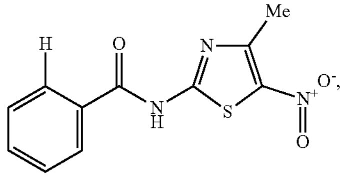
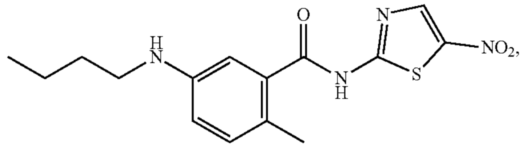
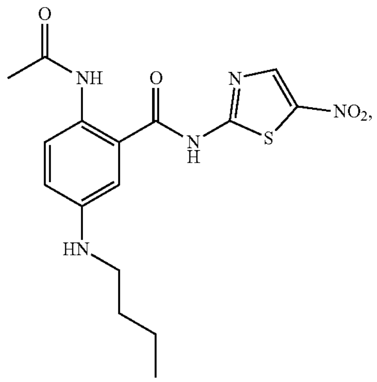
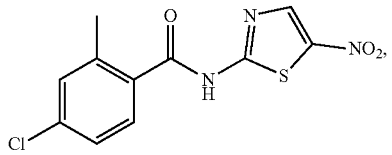
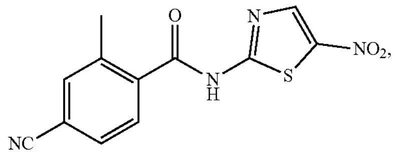
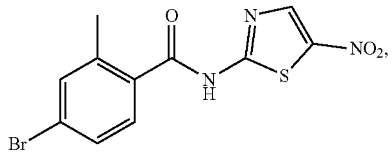
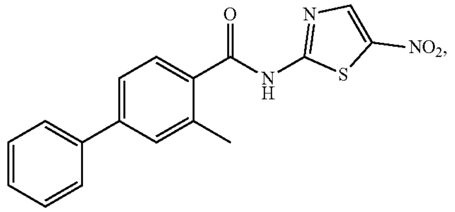
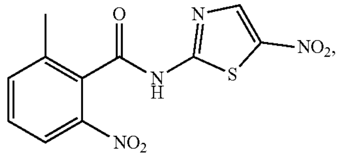
-continued
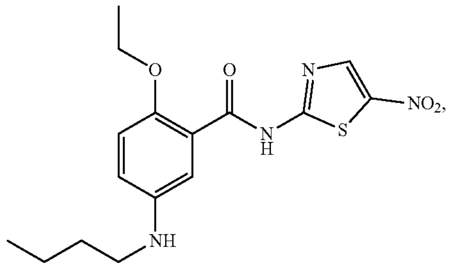
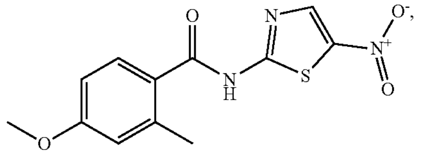
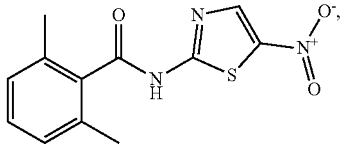
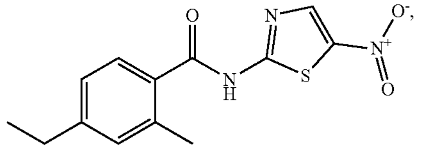
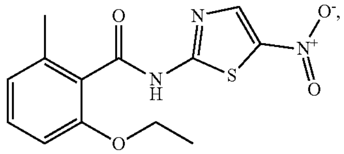
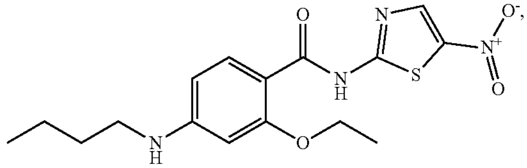
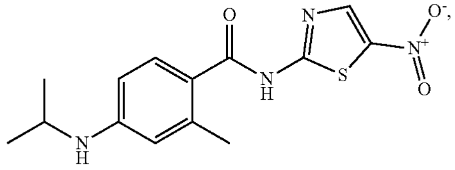
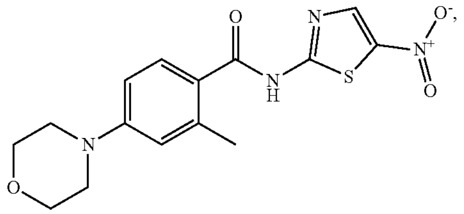
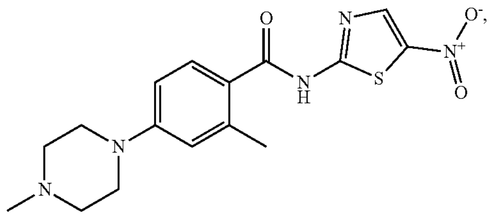

-continued
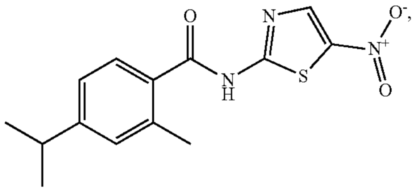
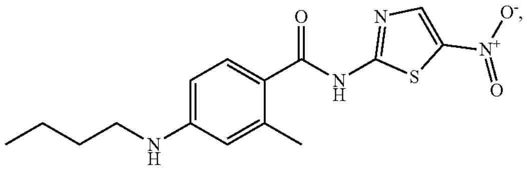
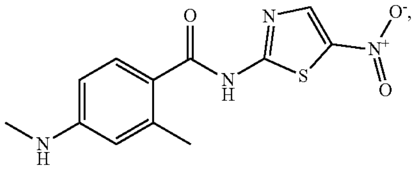
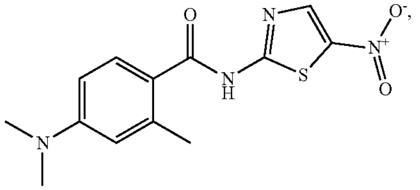
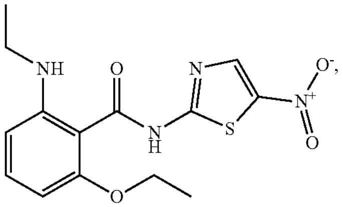
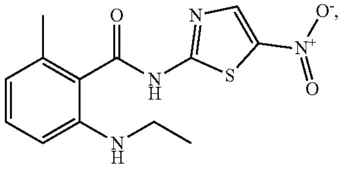
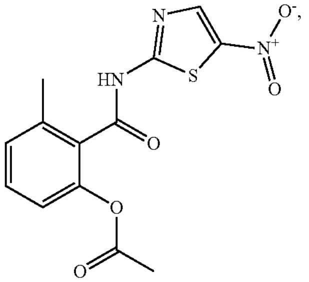
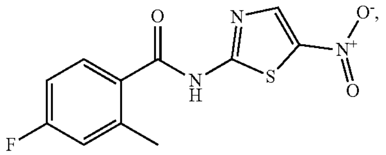
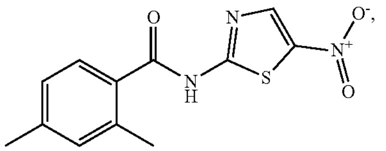
-continued
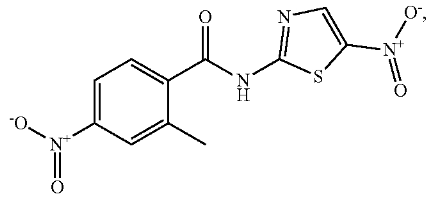
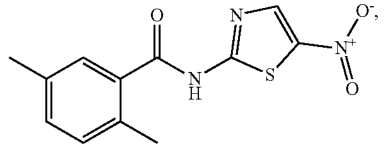
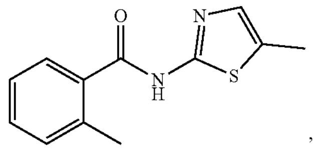
, or
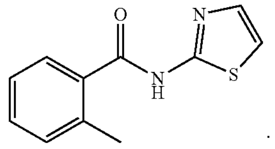
.
29. The ligand-DDB1 complex of any one of embodiments 1-28, wherein the DDB1 binding moiety comprises
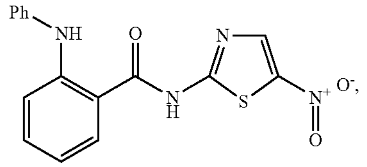
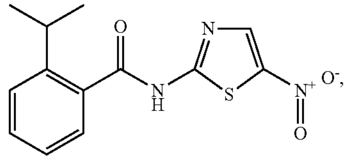
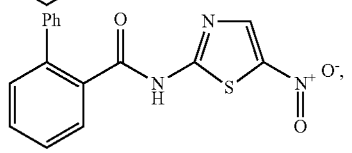
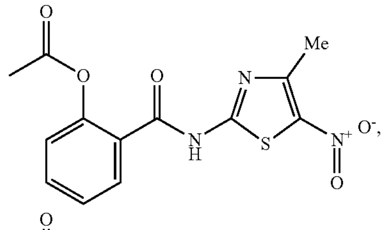
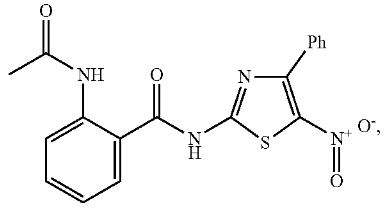

-continued
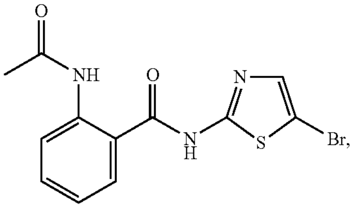
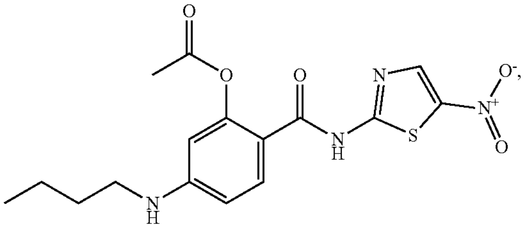
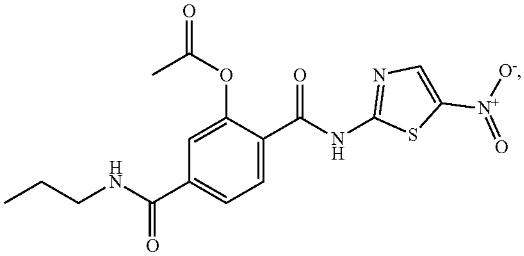
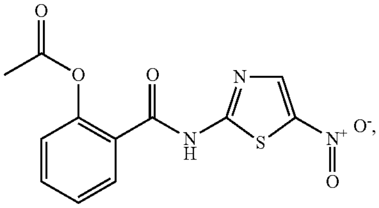
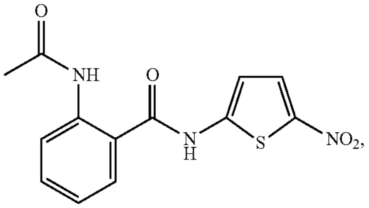
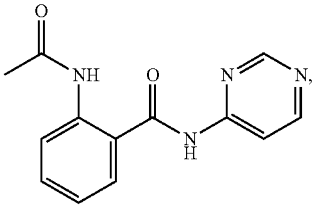
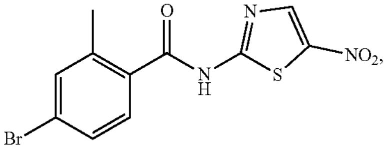
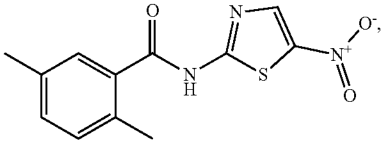
-continued
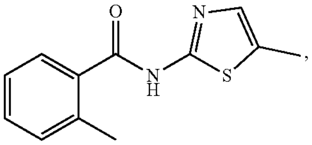
or
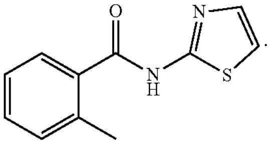
30. The ligand-DDB1 complex of any one of embodiments 1-29, wherein the DDB1 binding moiety comprises
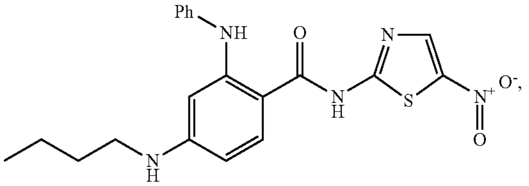
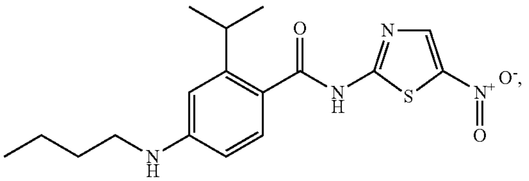
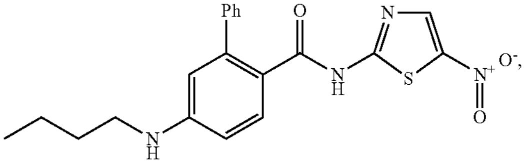
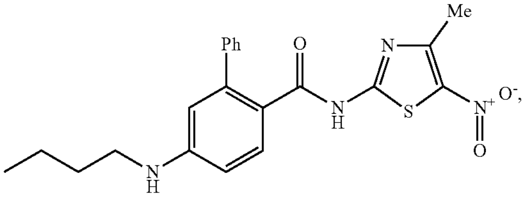
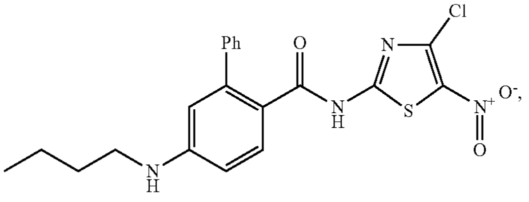
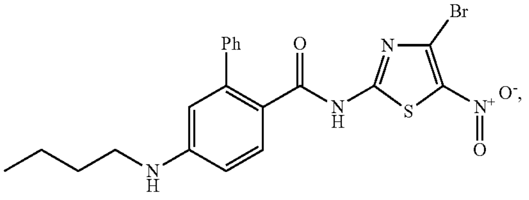

-continued
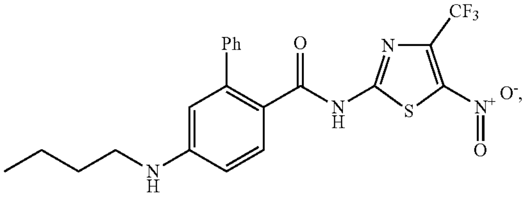
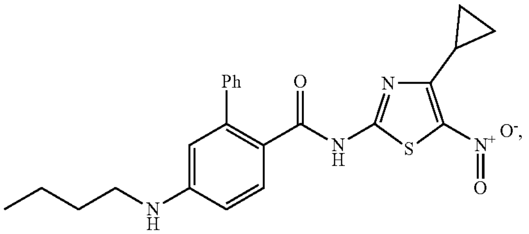
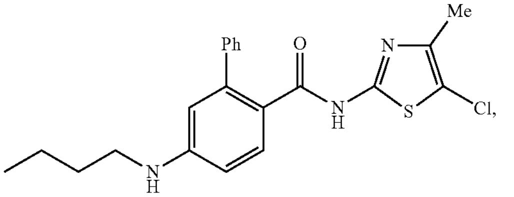
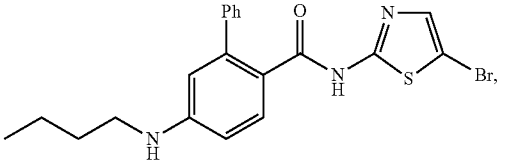
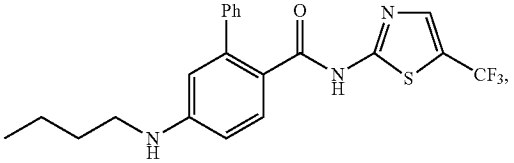
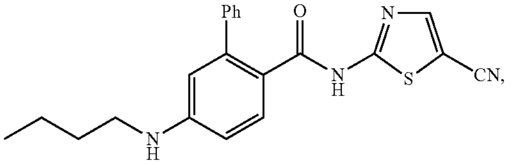
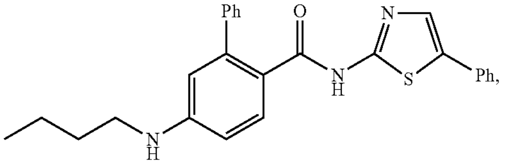
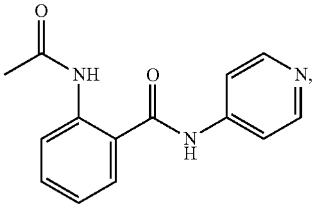
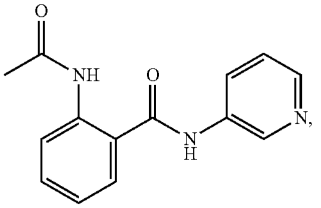
-continued
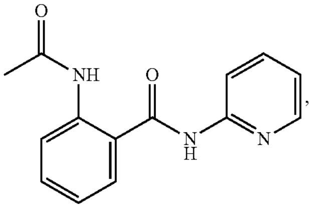
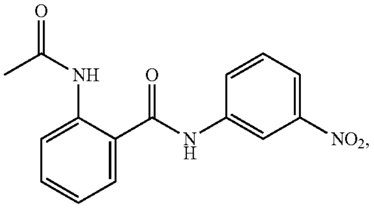
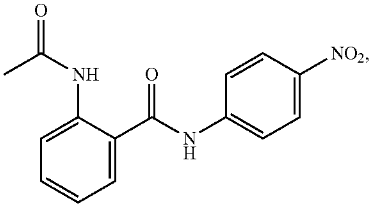
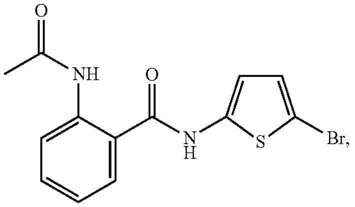
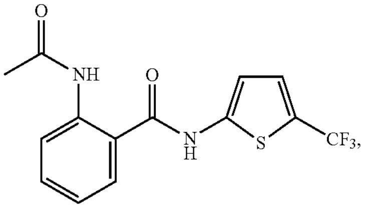
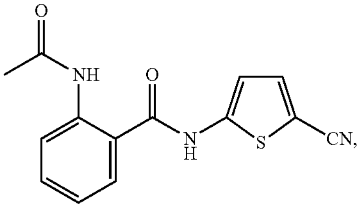
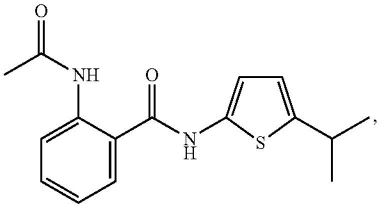
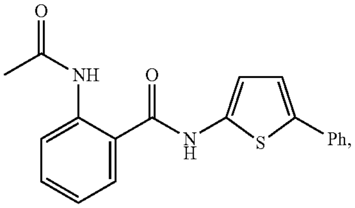

-continued
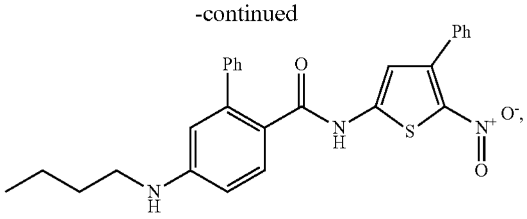
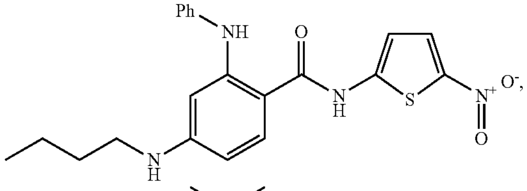
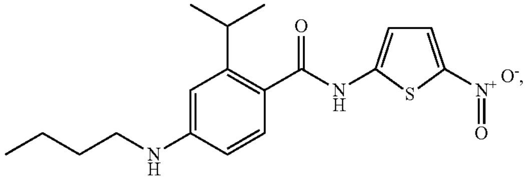
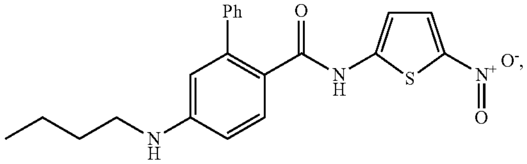
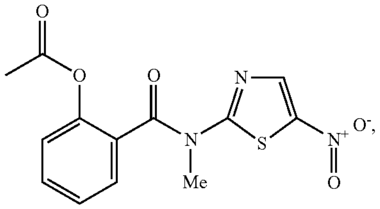
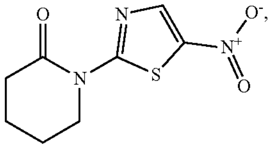
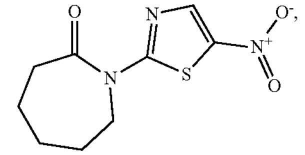
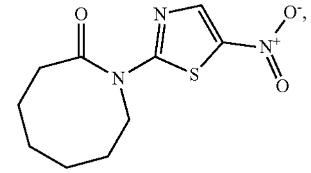
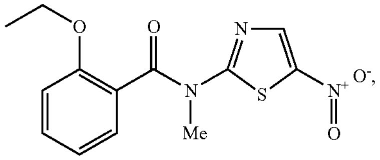
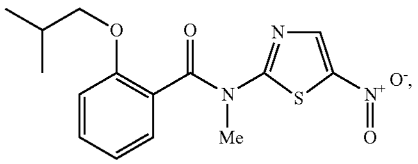
-continued
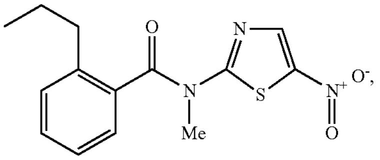
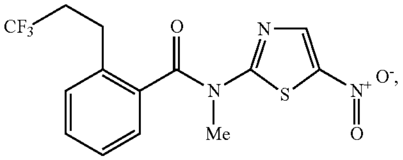
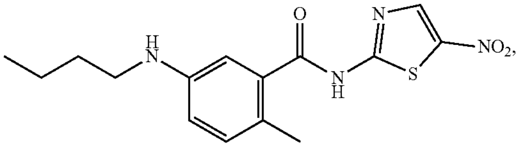
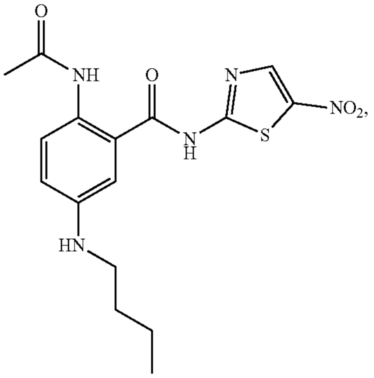
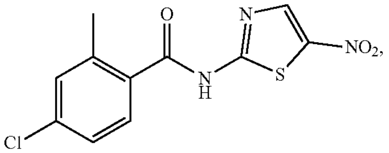
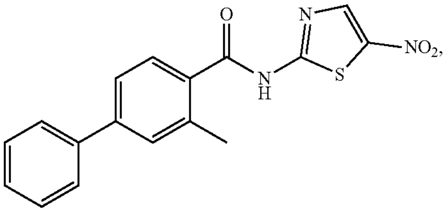
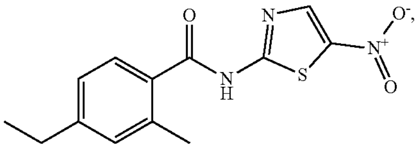
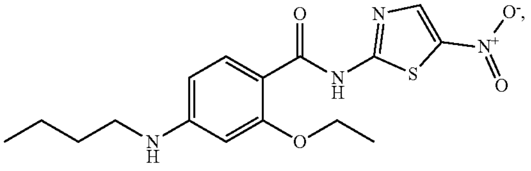
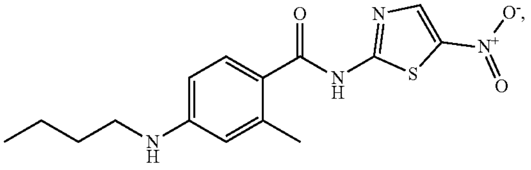

-continued
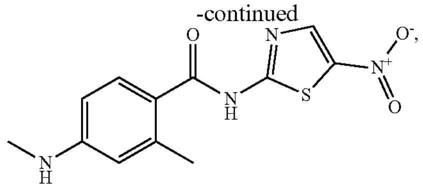
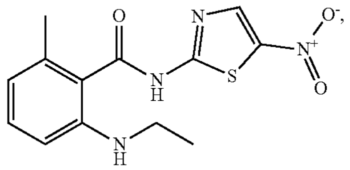
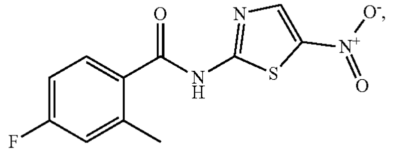
or
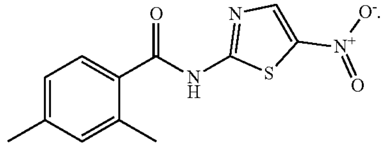
31. The ligand-DDB1 complex of any one of embodiments 1-30, wherein the DDB1 binding moiety comprises
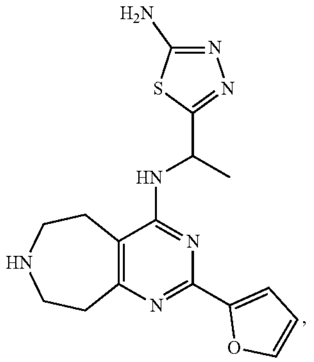
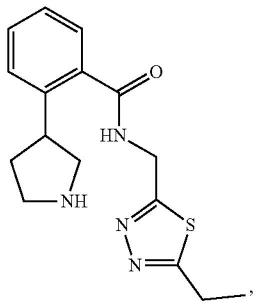
-continued
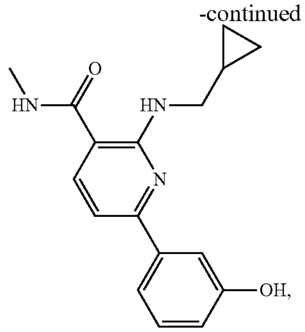
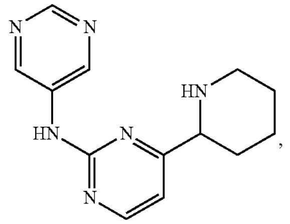
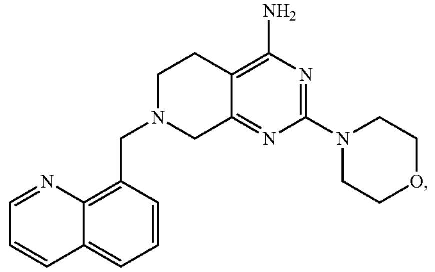
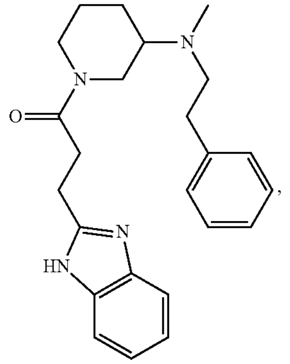
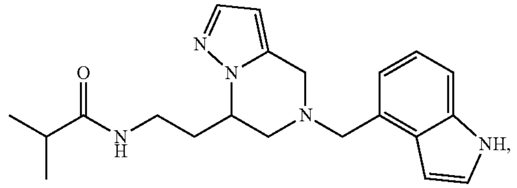
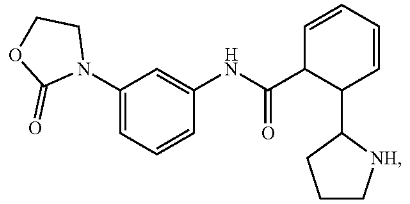
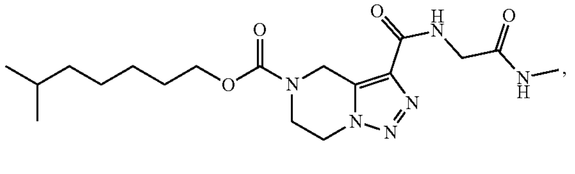
or a pharmaceutically acceptable salt thereof.

32. The ligand-DDB1 complex of any one of embodiments 1-31, wherein the DDB1 binding moiety is covalently connected to a linker.

33. The ligand-DDB1 complex of embodiment 32, wherein the linker is not bond.

34. The ligand-DDB1 complex of embodiment 32 or 33, wherein the linker is further connected to a target protein binding moiety.

35. The ligand-DDB1 complex of embodiment 34, wherein the target protein binding moiety binds to a target protein.

36. The ligand-DDB1 complex of embodiment 35, wherein the DDB1 ligand is a heterobifunctional ligand comprising the structure of Formula (I):

Formula (I)

$$Z^1—L^1—Z^2,$$

wherein $Z^1$ is a target protein binding moiety $L^1$ is a linker; and $Z^2$ is a DDB1 binding moiety.

37. The ligand-DDB1 complex of embodiment 36, wherein the DDB1 ligand is a heterobifunctional ligand comprising the structure of Formula (IIc):

Formula (IIc)

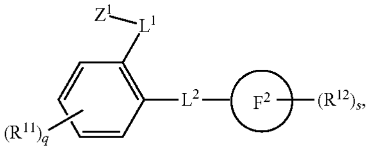

wherein $F^2$ is aryl, heteroaryl, carbocyclyl, or heterocyclyl;

$L^2$ is a bond, —C(=O)$NR^{13}$—, —$NR^{13}$C(=O)—, —C(=O)—, —C(=S)—, —S—, —S(=O), —$S(=O)_2$—, —S(=O)$NR^{13}$—, —$NR^{13}$S(=O)—, —$S(=O)_2NR^{13}$—, —$NR^{13}S(=O)_2$—, —O—, $C_1$-$C_4$ alkyl, or $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(=O)$R^b$, —$S(=O)_2R^d$, —$S(=O)_2NR^cR^d$, —C(=O)$R^b$, —$CO_2R^a$, —C(=O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{11}$ and $R^{12}$ is independently hydrogen, halogen, —CN, —$R^a$, —$OR^a$—, —$SR^a$, —S(=O)$R^b$, —$NO_2$, —$NR^cR^d$, —$S(=O)_2R^d$, —$NR^aS(=O)_2R^d$, —$S(=O)_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^a$C(=O)$NR^cR^d$, —$NR^a$C(=O)$R^b$, —$NR^a$C(=O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$;

each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-4;

s is 1-5:

$L^1$ is a linker; and $Z^1$ is a target protein binding moiety.

38. The ligand-DDB1 complex of embodiment 36, wherein the DDB1 ligand is a heterobifunctional ligand comprising the structure of Formula (IId):

Formula (IId)

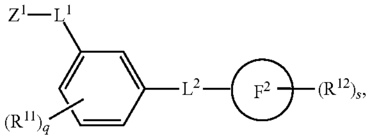

wherein $F^2$ is aryl, heteroaryl, carbocyclyl, or heterocyclyl;

$L^2$ is a bond, —C(=O)$NR^{13}$—, —$NR^{13}$C(=O)—, —C(=O)—, —C(=S)—, —S—, —S(=O), —$S(=O)_2$—, —S(=O)$NR^{13}$—, —$NR^{13}$S(=O)—, —$S(=O)_2NR^{13}$—, —$NR^{13}S(=O)_2$—, —O—, $C_1$-$C_4$ alkyl, $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(=O)$R^b$, —$S(=O)_2R^d$, —$S(=O)_2NR^cR^d$, —C(=O)$R^b$, —$CO_2R^a$, —C(=O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —OR$^a$, or —NR$^c$R$^d$; and the carbocyclyl, heterocyclyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{11}$ and $R^{12}$ is independently hydrogen, halogen, —CN. —R$^a$, —OR$^a$, —SR$^a$, —S(═O)R$^b$, —$NO_2$, —NR$^c$R$^d$, —S(═O)$_2$R$^d$, —NR$^a$S(═O)$_2$R$^d$, —S(═O)$_2$NR$^c$R$^d$, —C(═O)R$^b$, —OC(═O)R$^b$, —CO$_2$R$^a$, —OCO$_2$R$^a$, —C(═O)NR$^c$R$^d$, —OC(═O)NR$^c$R$^d$, —NR$^a$C(═O)NR$^c$R$^d$, —NR$^a$C(═O)R$^b$, —NR$^a$C(═O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —R$^a$, —OR$^a$, or NR$^c$R$^d$; and the carbocyclyl, heterocyclyl, aryl, and heteroaryl is optionally substituted with one, two, or three of halogen, $C_1$-$C_6$ alkyl, $C_1$-$C_6$ haloalkyl, —R$^a$, —OR$^a$, or —NR$^c$R$^d$;

each R$^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each R$^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each R$^c$ and R$^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each R$^c$ and R$^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-4;

s is 1-5;

$L^1$ is a linker; and $Z^1$ is a target protein binding moiety.

39. The ligand-DDB1 complex of embodiment 36, wherein the DDB1 ligand is a heterobifunctional ligand comprising the structure of Formula (IIe):

Formula (IIe)

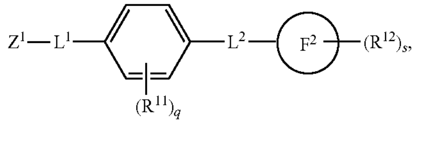

wherein $F^2$ is aryl, heteroaryl, carbocyclyl, or heterocyclyl;

$L^2$ is a bond, —C(═O)NR$^{13}$—, —NR$^{13}$C(═O)—, —C(═O)—, —C(═S)—, —S—, —S(═O), —S(═O)—, —S(═O)NR$^{13}$—, —NR$^{13}$S(═O)—, —S(═O)$_2$NR$^{13}$—, —NR$^{13}$S(═O)$_2$—, —O—, $C_1$-$C_4$ alkyl, $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)R$^b$, —S(═O)$_2$R$^d$, —S(═O)$_2$NR$^c$R$^d$, —C(═O)R$^b$, —CO$_2$R$^a$, —C(═O)NR$^c$R$^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OR$^a$, or —NR$^c$R$^d$; and the carbocyclyl, heterocyclyl, aryl, and heteroaryl is optionally substituted with one, two, or three of halogen, $C_1$-$C_6$ alkyl, $C_1$-$C_6$ haloalkyl, —OR$^a$, or —NR$^c$R$^d$;

each $R^{11}$ and $R^{12}$ is independently hydrogen, halogen, —CN, —R$^a$, —OR$^a$, —SR$^a$, —S(═O)R$^b$, —$NO_2$, —NR$^c$R$^d$, —S(═O)$_2$R$^d$, —NR$^a$S(═O)$_2$R$^d$, —S(═O)$_2$NR$^c$R$^d$, —C(═O)R$^b$, —OC(═O)R$^b$, —CO$_2$R$^a$, —OCO$_2$R$^a$, —C(═O)NR$^c$R$^d$, —OC(═O)NR$^c$R$^d$, —NR$^a$C(═O)NR$^c$R$^d$, —NR$^a$C(═O)R$^b$, —NR$^a$C(═O)OR$^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —R$^a$, —OR$^a$, or NR$^c$R$^d$; and the carbocyclyl, heterocyclyl, aryl, and heteroaryl is optionally substituted with one, two, or three of halogen, $C_1$-$C_6$ alkyl, $C_1$-$C_6$ haloalkyl, —R$^a$, —OR$^a$, or —NR$^c$R$^d$;

each R$^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each R$^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each R$^c$ and R$^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each R$^c$ and R$^d$, together with the nitrogen atom to which they are attached, form a heterocyclyl or heteroaryl; wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-4;

s is 1-5:

$L^1$ is a linker; and $Z^1$ is a target protein binding moiety.

40. The ligand-DDB1 complex of any one of embodiments 36-39, wherein $F^2$ is aryl.

41. The ligand-DDB1 complex of embodiment 40, wherein $F^2$ is $C_6$-$C_{12}$ aryl.

42. The ligand-DDB1 complex of embodiment 40, wherein $F^2$ is heteroaryl.

43. The ligand-DDB1 complex of embodiment 42, wherein $F^2$ is 5-12 membered heteroaryl.

44. The ligand-DDB1 complex of any one of embodiments 36-43, wherein $L^2$ is —C(═O)NH—.

45. The ligand-DDB1 complex of any one of embodiments 36-43, wherein $L^2$ is —C(═O)N($C_1$-$C_5$ alkyl)-.

46. The ligand-DDB1 complex of any one of embodiments 36-45, wherein q is 1.

47. The ligand-DDB1 complex of any one of embodiments 36-45, wherein q is 2.

48. The ligand-DDB1 complex of any one of embodiments 36-47, wherein the linker is a bond.

49. The ligand-DDB1 complex of any one of embodiments 36-47, wherein the linker the linker is not a bond.

50. The ligand-DDB1 complex of one of embodiments 1-49, wherein the complex is formed in vivo.

51. The ligand-DDB1 complex of one of embodiments 1-49, wherein the complex is formed in vitro.

52. An in vivo modified protein comprising:

a DNA damage-binding protein 1 (DDB1) protein directly bound to a DDB1 ligand comprising a DDB1 binding moiety.

53. The in vivo modified protein of embodiment 52, wherein the DDB1 binding moiety binds to a binding region on the DDB1 protein.

54. The in vivo modified protein of embodiment 53, wherein the binding region on the DDB1 protein comprises a beta propeller domain.

55. The in vivo modified protein of embodiment 54, wherein the beta propeller domain comprises a beta propeller C (BPC) domain.

56. The in vivo modified protein of embodiment 55, wherein the binding region on the DDB1 protein comprises a top face of the BPC domain.

57. The in vivo modified protein of any one of embodiments 53-56, wherein the binding region on the DDB1 protein comprises one or more of the following DDB1 residues: ARG327, LEU328, PRO358, ILE359, VAL360, ASP361, GLY380, ALA381, PHE382, SER720, ARG722, LYS723, SER738, ILE740, GLU787, TYR812, LEU814, SER815, ALA834, VAL836, ALA841, ALA869, TYR871, SER872. MET910, LEU912, TYR913, LEU926, TRP953, SER955, ALA956, ASN970, ALA971, PHE972, PHE1003, ASN1005, VAL1006, or VAL1033.

58. The in vivo modified protein of any one of embodiments 52-57, wherein the DDB1 protein is directly bound to the DDB1 ligand by a non-covalent interaction between the DDB1 protein and the DDB1 ligand.

59. The in vivo modified protein of embodiment 58, wherein one or more of the following DDB1 residues are involved in the non-covalent interaction between the DDB1 protein and the DDB1 ligand: ARG327, LEU328, PRO358, ILE359, VAL360, ASP361, GLY380, ALA381, PHE382, SER720, ARG722, LYS723, SER738, ILE740, GLU787, TYR812, LEU814, SER815. ALA834, VAL836, ALA841, ALA869, TYR871, SER872, MET910, LEU912, TYR913, LEU926, TRP953, SER955, ALA956, ASN970, ALA971, PHE972, PHE1003, ASN1005, VAL1006, or VAL1033.

60. The in vivo modified protein of any one of embodiments 52-59, wherein the binding between the DDB1 protein and the DDB1 ligand comprises a binding affinity with an equilibrium dissociation constant (Kd) below 100 μM, a Kd below 90 μM, a Kd below 80 μM, a Kd below 70 μM, a Kd below 60 μM, a Kd below 50 μM, a Kd below 45 μM, a Kd below 40 μM, a Kd below 35 μM, a Kd below 30 μM, a Kd below 25 μM, a Kd below 20 μM, a Kd below 15 μM, a Kd below 14 μM, a Kd below 13 μM, a Kd below 12 μM, a Kd below 11 μM, a Kd below 10 μM, a Kd below 9 μM, a Kd below 8 μM, a Kd below 7 μM, a Kd below 6 μM, a Kd below 5 μM, a Kd below 4 μM, a Kd below 3 μM, a Kd below 2 μM, or a Kd below 1 μM.

61. The in vivo modified protein of any one of embodiments 52-60, wherein the binding between the DDB1 protein and the DDB1 ligand comprises a binding affinity with a Kd<20 uM, a Kd from 20-100 uM, or a Kd>100 uM.

62. The in vivo modified protein of any one of embodiments 52-61, wherein the DDB1 ligand is a small molecule.

63. The in vivo modified protein of any one of embodiments 52-62, wherein the DDB1 ligand is a heterobifunctional compound comprising a DDB1 binding moiety covalently connected through a linker to a target protein binding moiety.

64. The in vivo modified protein of any one of embodiments 52-63, wherein the DDB1 ligand is synthetic.

65. The in vivo modified protein of any one of embodiments 52-64, wherein the DDB1 ligand and/or the DDB1 binding moiety comprises the structure of any one of embodiments 15-51.

66. The in vivo modified protein of any one of embodiments 52-65, wherein the DDB1 binding moiety is covalently connected to a linker.

67. The in vivo modified protein of embodiment 66, wherein the linker is not a bond.

68. The in vivo modified protein of embodiment 66 or 67, wherein the linker is further connected to a target protein binding moiety.

69. The in vivo modified protein of embodiment 68, wherein the target protein binding moiety binds to a target protein.

70. The in vivo modified protein of embodiment 69, wherein the DDB1 ligand is a heterobifunctional ligand comprising the structure of Formula (I):

Formula (I)

$$Z^1—L^1—Z^2,$$

wherein $Z^1$ is a target protein binding moiety $L^1$ is a linker; and $Z^2$ is a DDB1 binding moiety.

71. The in vivo modified protein of embodiment 70, wherein the DDB1 ligand is a heterobifunctional ligand comprising the structure of Formula (IIc):

Formula (IIc)

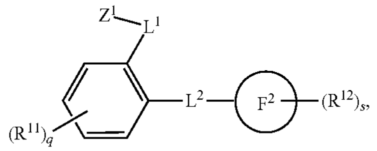

wherein $F^2$ is aryl, heteroaryl, carbocyclyl, or heterocyclyl;

$L^2$ is a bond, —C(=O)$NR^{13}$—, —$NR^{13}$C(=O)—, —C(=O)—, —C(=S)—, —S—, —S(=O), —$S(=O)_2$—, —S(=O)$NR^{13}$—, —$NR^{13}$S(=O)—, —$S(=O)_2NR^{13}$—, —$NR^{13}S(=O)_2$—, —O—, $C_1$-$C_4$ alkyl, or $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(=O)$R^b$, —$S(=O)_2R^d$, —$S(=O)_2NR^cR^c$, —C(=O)$R^b$, —$CO_2R^a$, —C(=O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{11}$ and $R^{12}$ is independently hydrogen, halogen, —CN, —$R^a$, —$OR^a$, —$SR^a$, —S(=O)$R^b$, —$NO_2$, —$NR^cR^d$, —$S(=O)_2R^d$, —$NR^aS(=O)_2R^d$, —$S(=O)_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^a$C(=O)$NR^cR^d$, —$NR^a$C(=O)$R^b$, —$NR^a$C(=O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$;

each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-4;

s is 1-5;

$L^1$ is a linker, and $Z^1$ is a target protein binding moiety.

72. The in vivo modified protein of embodiment 70, wherein the DDB1 ligand is a heterobifunctional ligand comprising the structure of Formula (IId):

Formula (IId)

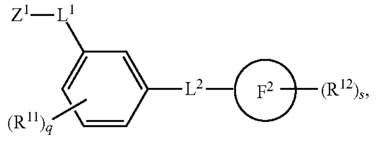

wherein $F^2$ is aryl, heteroaryl, carbocyclyl, or heterocyclyl;

$L^2$ is a bond, —C(=O)$NR^{13}$—, —$NR^{13}$C(=O)—, —C(=O)—, —C(=S)—, —S—, —S(=O), —$S(=O)_2$—, —S(=O)$NR^{13}$—, —$NR^{13}$S(=O)—, —$S(=O)_2NR^{13}$—, —$NR^{13}S(=O)_2$—, —O—, $C_1$-$C_4$ alkyl, $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(=O)$R^b$, —$S(=O)_2R^d$, —$S(=O)_2NR^cR^d$, —C(=O)$R^b$, —$CO_2R^a$, —C(=O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{11}$ and $R^{12}$ is independently hydrogen, halogen, —CN, —$R^a$, —$OR^a$, —$SR^a$, —S(=O)$R^b$, —$NO_2$, —$NR^cR^d$, —$S(=O)_2R^d$, —$NR^aS(=O)_2R^d$, —S(=O)$_2NR^cR^d$, —C(=O)$R^b$, —OC(=O)$R^b$, —$CO_2R^a$, —$OCO_2R^a$, —C(=O)$NR^cR^d$, —OC(=O)$NR^cR^d$, —$NR^a$C(=O)$NR^cR^d$, —$NR^a$C(=O)$R^b$, —$NR^a$C(=O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$;

each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_1$-$C_6$ alkenyl, $C_1$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-4;

s is 1-5;

$L^1$ is a linker, and $Z^1$ is a target protein binding moiety.

73. The in vivo modified protein of embodiment 70, wherein the DDB1 ligand is a heterobifunctional ligand comprising the structure of Formula (IIe):

Formula (IIe)

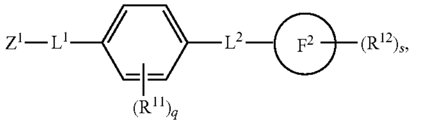

wherein $F^2$ is aryl, heteroaryl, carbocyclyl, or heterocyclyl;

$L^2$ is a bond, —C(═O)$NR^{13}$—, —$NR^{13}$C(═O)—, —C(═O)—, —C(═S)—, —S—, —S(═O), —S(═O)—, —S(═O)$NR^{13}$—, —$NR^{13}$S(═O)—, —S(═O)$_2NR^{13}$—, —$NR^{13}$S(═O)$_2$—, —O—, $C_1$-$C_4$ alkyl, $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —S(═O)$_2R^d$, —S(═O)$_2NR^cR^d$, —C(═O)$R^b$, —$CO_2R^a$, —C(═O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{11}$ and $R^{12}$ is independently hydrogen, halogen, —CN, —$R^a$, —$OR^a$, —$SR^a$, —S(═O)$R^b$, —$NO_2$, —$NR^cR^d$, —S(═O)$_2R^d$, —$NR^a$S(═O)$_2R^d$, —S(═O)$_2NR^cR^d$, —C(═O)$R^b$, —OC(═O)$R^b$, —$CO_2R^a$, —$OCO_2R^a$, —C(═O)$NR^cR^d$, —OC(═O)$NR^cR^d$, —$NR^a$C(═O)$NR^cR^d$, —$NR^a$C(═O)R, —$NR^a$C(═O)$OR^a$, $C_1$-$C_6$ alkyl, $C_1$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$;

each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_1$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$, together with the nitrogen atom to which they are attached, form a heterocyclyl or heteroaryl; wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-4;

s is 1-5;

$L^1$ is a linker, and $Z^1$ is a target protein binding moiety.

74. The in vivo modified protein of any one of embodiments 71-73, wherein $F^2$ is aryl.

75. The in vivo modified protein of embodiment 74, wherein $F^2$ is $C_6$-$C_{12}$ aryl.

76. The in vivo modified protein of embodiment 74, wherein $F^2$ is heteroaryl.

77. The in vivo modified protein of embodiment 76, wherein $F^2$ is 5-12 membered heteroaryl.

78. The in vivo modified protein of any one of embodiments 71-77, wherein $L^2$ is —C(═O)NH—.

79. The in vivo modified protein of any one of embodiments 71-77, wherein $L^2$ is —C(═O)N($C_1$-$C_5$ alkyl)-.

80. The in vivo modified protein of any one of embodiments 71-79, wherein q is 1.

81. The in vivo modified protein of any one of embodiments 71-79, wherein q is 2.

82. The in vivo modified protein of any one of embodiments 71-81, wherein the linker is a bond.

83. The in vivo modified protein of any one of embodiments 70-81, wherein the linker is not a bond (e.g. the linker may comprise —$(CH_2)_{p2}NH(CH_2)_{p1}NH$—, —$(CH_2)_{p2}NH(CH_2)_{p1}$C(═O)NH—, —$(CH_2)_{p2}NH(CH_2)_{p1}$NHC(═O)—, —$(CH_2)_{p2}NH(CH_2CH_2)$ $(OCH_2CH_2)_{p1}NH—$, $—(CH_2)_{p2}NH(CH_2CH_2)(OCH_2CH_2)_{p1}C(═O)NH—$, or $—(CH_2)_{p2}NH(CH_2CH_2)(OCH_2CH_2)_{p1}NHC(═O)—$, wherein p1 is 1-15, and p2 is 0-15).

84. A ligand comprising a DNA damage-binding protein 1 (DDB1) binding moiety.

85. The ligand of embodiment 84, wherein the DDB1 binding moiety is covalently connected through a linker to a target protein binding moiety.

86. The ligand of embodiment 84 or 85, wherein the DDB1 binding moiety binds to a DDB1 protein.

87. The ligand of embodiment 86, wherein the DDB1 binding moiety binds to a binding region on the DDB1 protein.

88. The ligand of embodiment 86 or 87, wherein the binding between the DDB1 binding moiety and the DDB1 protein is non-covalent.

89. The ligand of any one of embodiments 86-88, wherein the binding between the DDB1 protein and the ligand comprises a binding affinity with a Kd<20 uM, a Kd from 20-100 uM, or a Kd>100 uM.

90. The ligand of any one of embodiments 84-89, wherein the ligand is a small molecule.

91. The ligand of any one of embodiments 84-90, wherein the ligand is a heterobifunctional compound comprising a DDB1 binding moiety covalently connected through a linker to a target protein binding moiety.

92. The ligand of any one of embodiments 84-91, wherein the ligand is synthetic.

93. The ligand of any one of embodiments 84-92, wherein the ligand comprises a structure of Formula (II):

Formula (II)

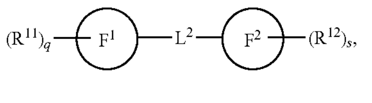

wherein $F^1$ is aryl, heteroaryl, carbocyclyl, or heterocyclyl;

$F^2$ is aryl, heteroaryl, carbocyclyl, or heterocyclyl;

$L^1$ is a bond, $—C(═O)NR^{13}—$, $—NR^{13}C(═O)—$, $—C(═O)—$, $—C(═S)—$, $—S—$, $—S(═O)$, $—S(═O)_2—$, $—S(═O)NR^{13}—$, $—NR^{13}S(═O)—$, $—S(═O)_2NR^{13}—$, $—NR^{13}S(═O)_2—$, $—O—$, $C_1$-$C_4$ alkyl, or $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, $—S(═O)R^b$, $—S(═O)_2R^d$, $—S(═O)_2NR^cR^d$, $—C(═O)R^b$, $—CO_2R^a$, $—C(═O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, $—OR^a$, or $—NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, $—OR^a$, or $—NR^cR^d$;

each $R^{11}$ and $R^{12}$ is independently a bond, hydrogen, halogen, —CN, $—R^a$, $—OR^a$, $—SR^a$, $—S(═O)R^b$, $—NO_2$, $—NR^cR^d$, $—S(═O)_2R^d$, $—NR^aS(═O)_2R^d$, $—S(═O)_2NR^cR^d$, $—C(═O)R^b$, $—OC(═O)R^b$, $—CO_2R^a$, $—OCO_2R^a$, $—C(═O)NR^cR^d$, $—OC(═O)NR^cR^d$, $—NR^aC(═O)NR^cR^d$, $—NR^aC(═O)R^b$, $—NR^aC(═O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, $—R^a$, $—OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, $—R^a$, $—OR^a$, or $—NR^cR^d$, and wherein at least one $R^{11}$ is a bond attached to the linker;

each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or $—NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or $—NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or $—NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or $—NH_2$;

each $R^c$ and $R^d$ is independently hydrogen, $C_1$-$C_6$ alkyl, $C_2$-$C_6$ alkenyl, $C_2$-$C_6$ alkynyl. $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or $—NH_2$; and the carbocyclyl, heterocyclyl, aryl, and heteroaryl is optionally substituted with one, two, or three of halogen, $C_1$-$C_6$, alkyl, $C_1$-$C_6$ haloalkyl, —OH, —OMe, or $—NH_2$;

each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —NH;

q is 1-5; and s is 1-5;

or a pharmaceutically acceptable salt thereof.

94. The ligand of any one of embodiments 84-93, wherein the ligand comprises a structure of Formula (IIa):

Formula (IIa)

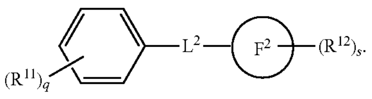

95. The ligand of embodiment 93 or 94, wherein $F^2$ is heteroaryl.

96. The ligand of any one of embodiments 93-95, wherein $F^2$ is a five membered or six membered ring heteroaryl.

97. The ligand of any one of embodiments 93-96, wherein $F^2$ is triazolyl, tetrazolyl, furanyl, pyrrolyl, thiazolyl, oxazolyl, isoxazolyl, imidazolyl, pyrazolyl, thiadiazolyl, or oxadiazolyl.

98. The ligand of any one of embodiments 84-97, wherein the ligand comprises a structure of Formula (IIb):

Formula (IIb)

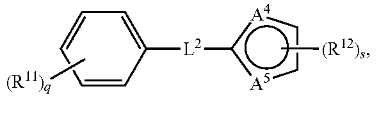

wherein $A^4$ and $A^5$ are each independently S, N, or O, wherein at least one of $A^4$ or $A^5$ is N.

99. The ligand of embodiment 98, wherein $A^4$ is N and $A^5$ is S.

100. The ligand of any one of embodiments 84-99, wherein the ligand comprises the structure:

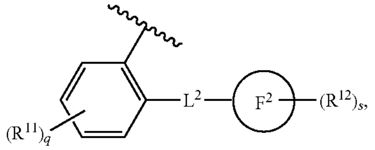

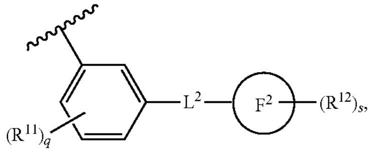

or

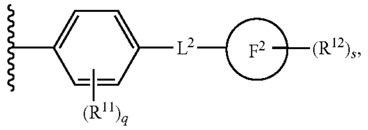

wherein the wavy line indicates a point of attachment to the linker or target protein binding moiety.

101. The ligand of any one of embodiments 93-100, wherein $R^{12}$ is —$NO_2$, Cl, or Br.

102. The ligand of any one of embodiments 93-101, wherein $L^2$ is —$NR^cC$(=O)— or —C(=O)$NR^c$—.

103. The ligand of any one of embodiments 93-102, wherein $R^c$ is H or $CH_3$.

104. The ligand of any one of embodiments 93-103, wherein q is 1 or 2.

105. The ligand of any one of embodiments 93-104, wherein s is 1 or 2.

106. The ligand of any one of embodiments 84-105, wherein the ligand comprises

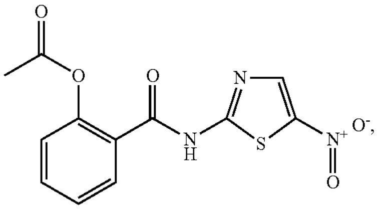

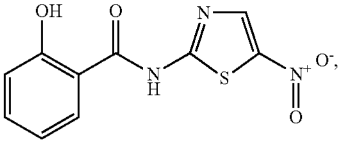

-continued

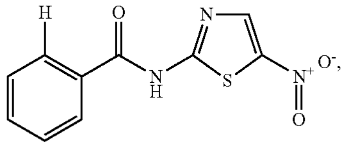

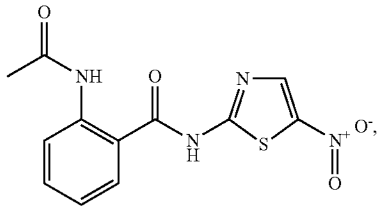

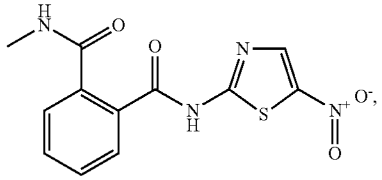

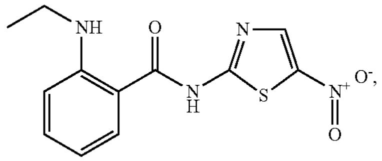

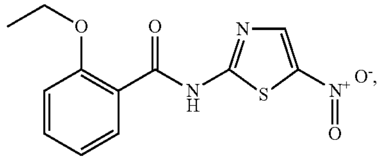

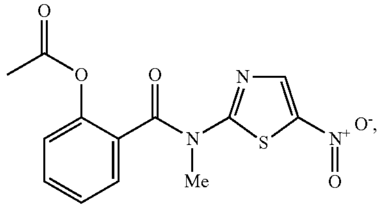

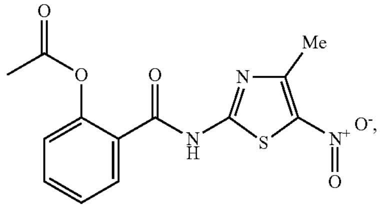

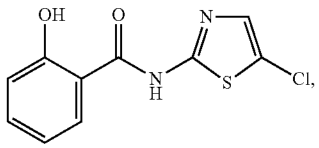

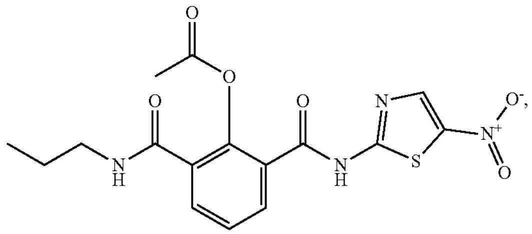

-continued
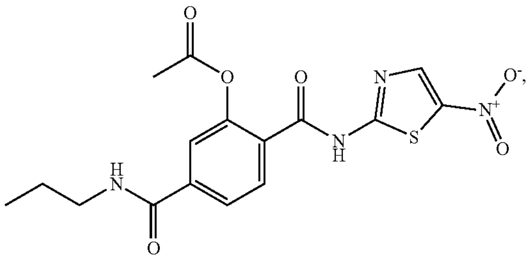
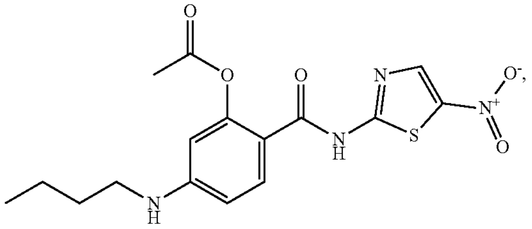
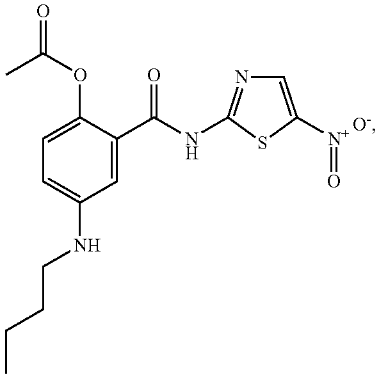
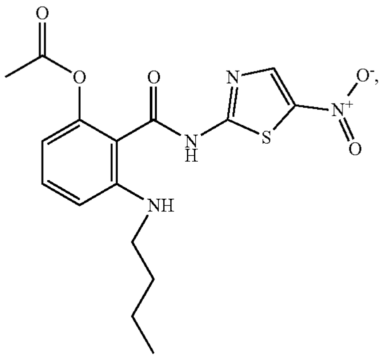
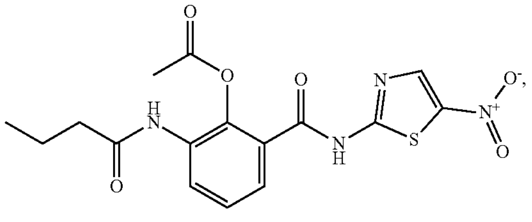
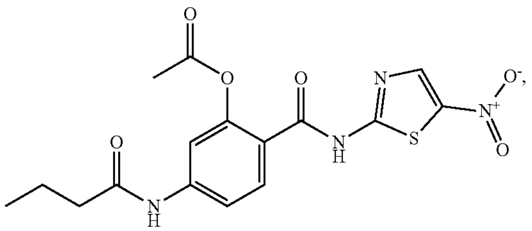
-continued
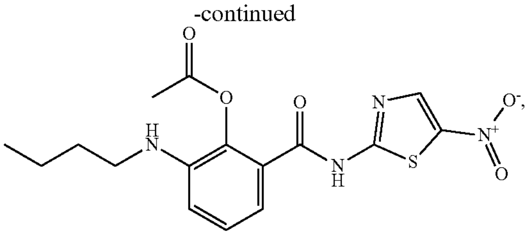
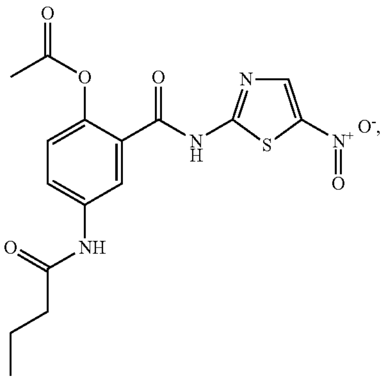
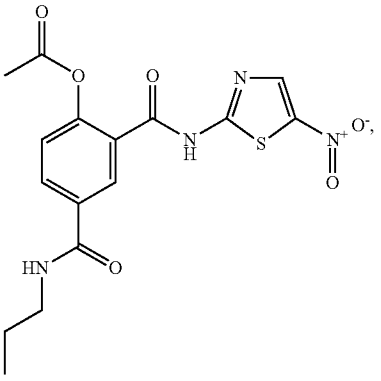
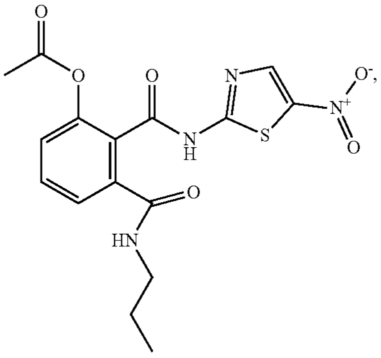
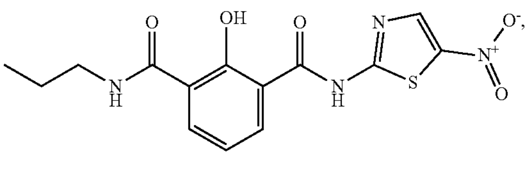

-continued
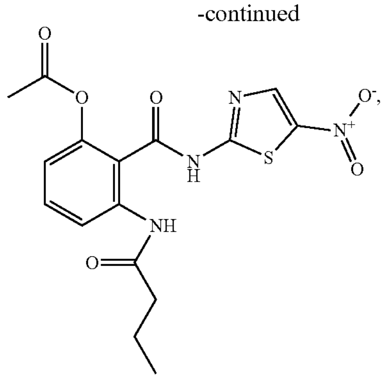
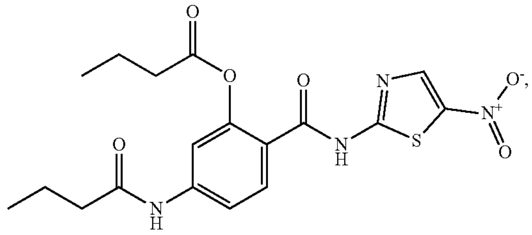
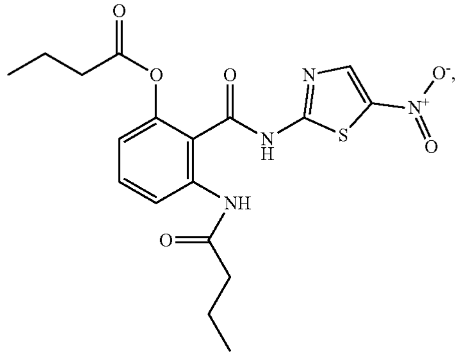
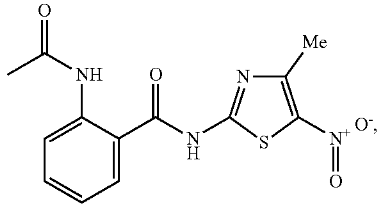
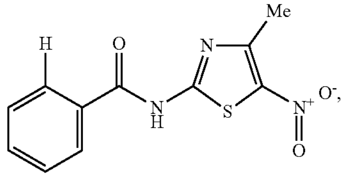
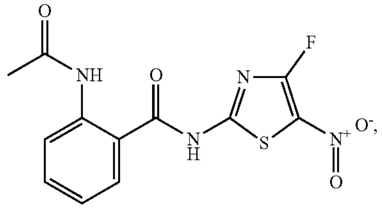
-continued
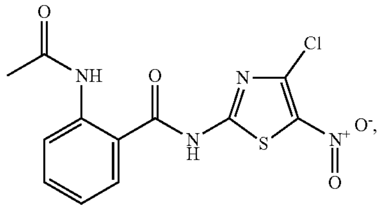
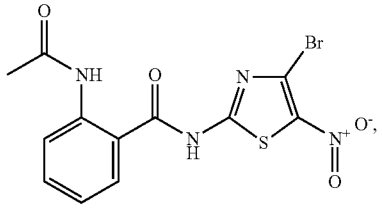
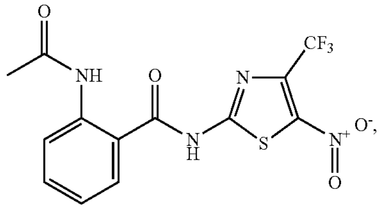
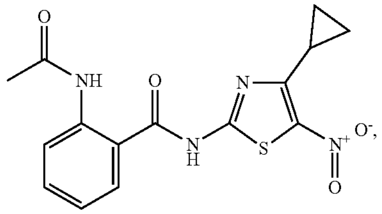
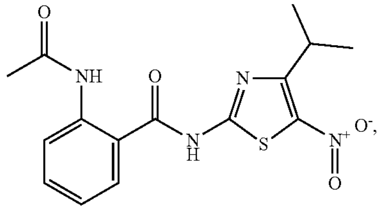
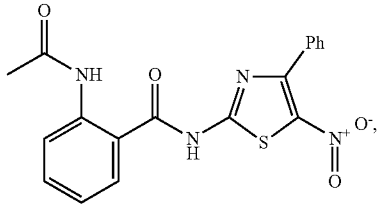
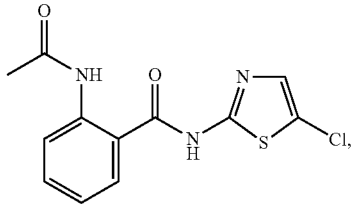
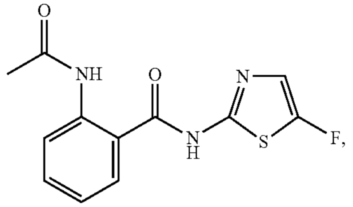

-continued
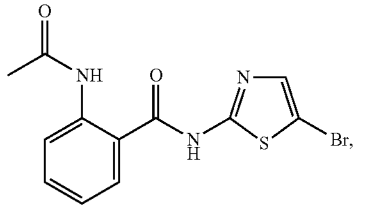
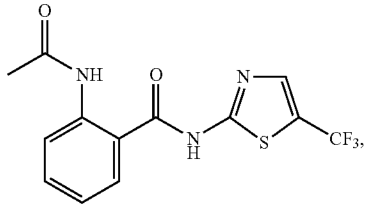
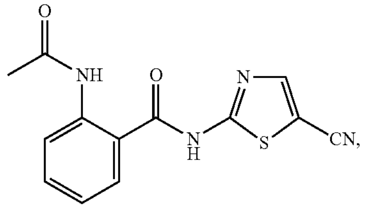
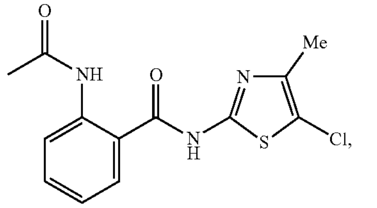
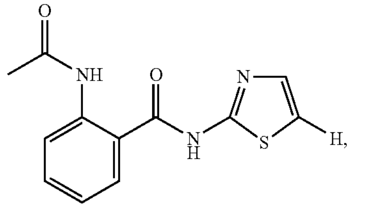
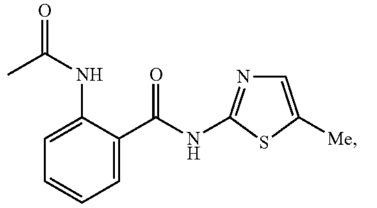
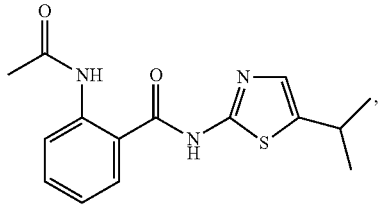
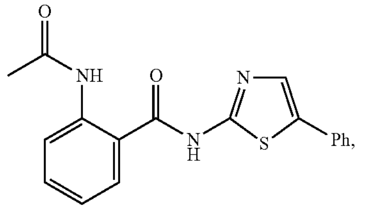
-continued
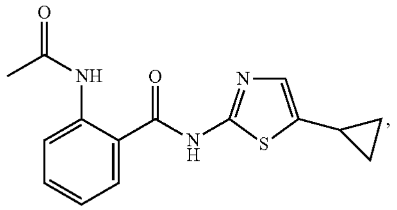
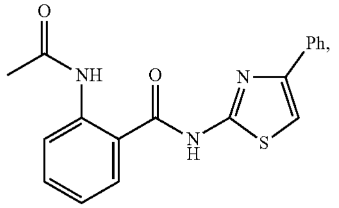
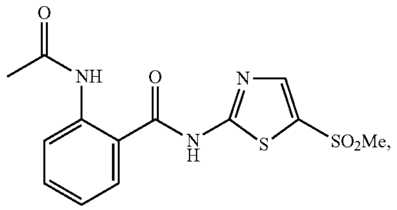
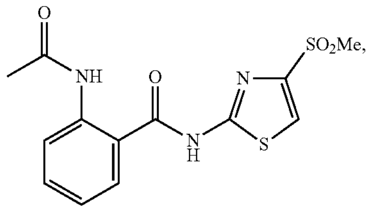
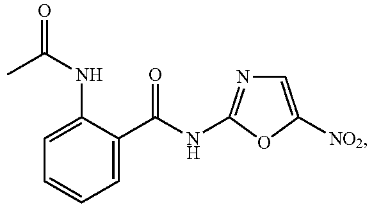
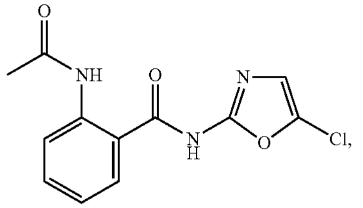
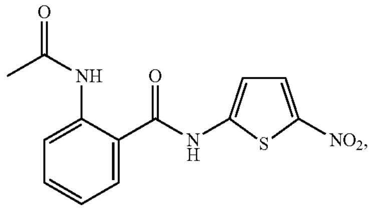

-continued
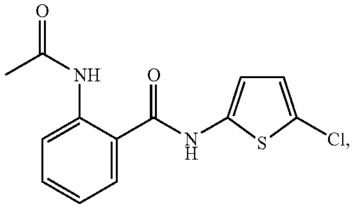
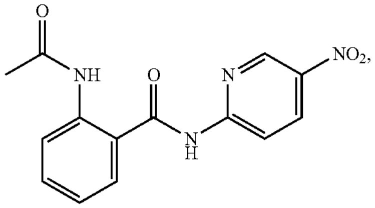
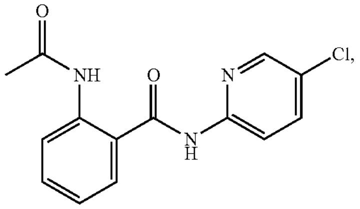
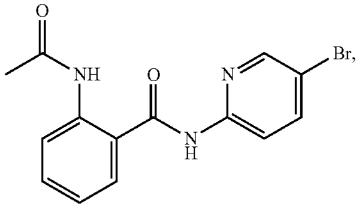
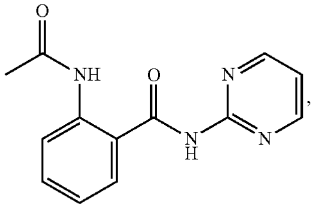
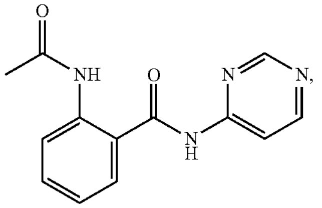
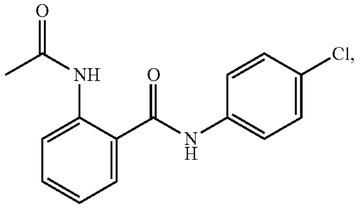
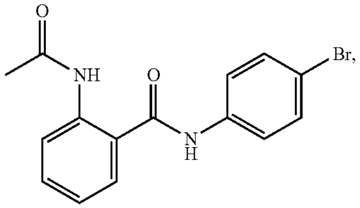
-continued
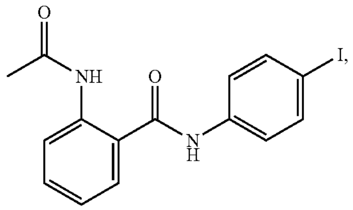
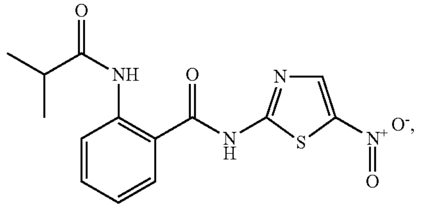
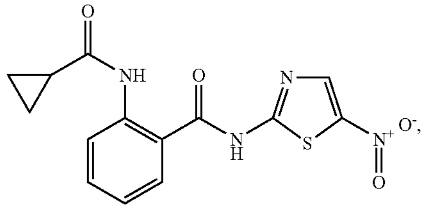
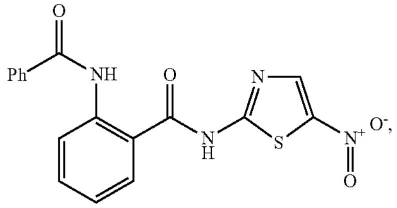
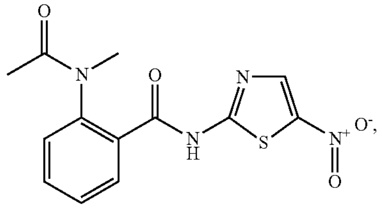
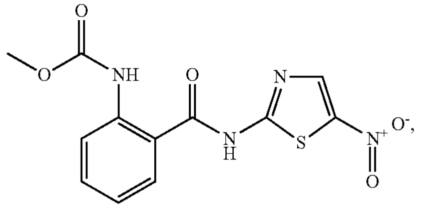
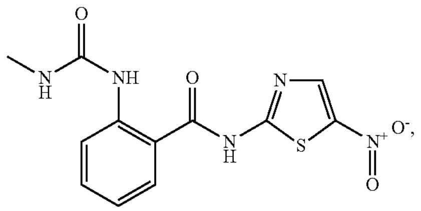
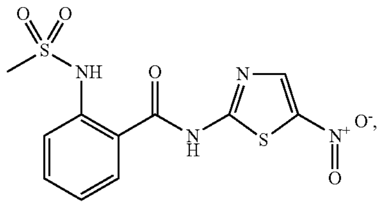

-continued
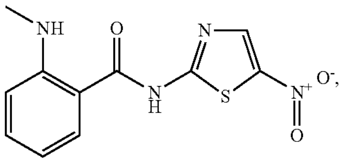
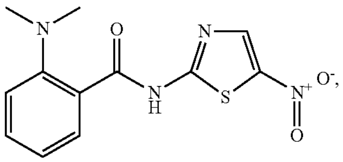
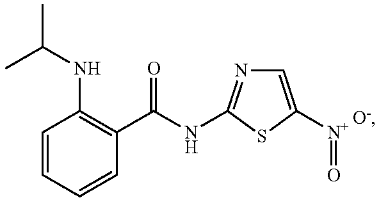
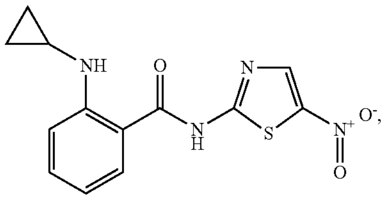
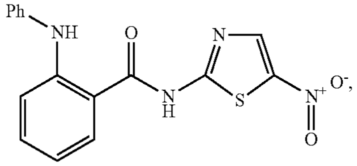
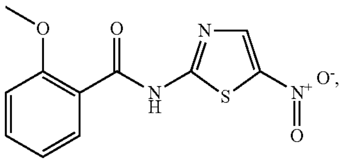
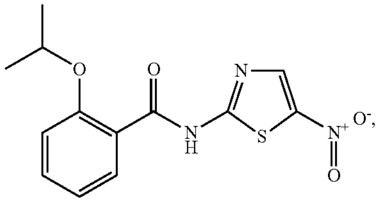
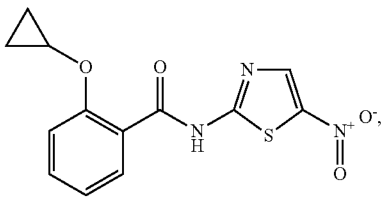
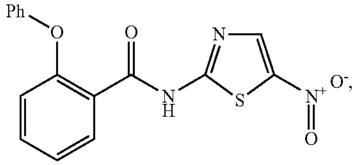
-continued
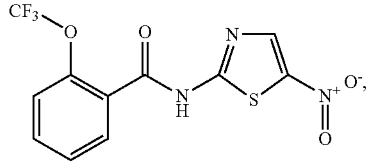
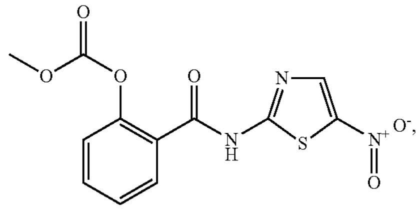
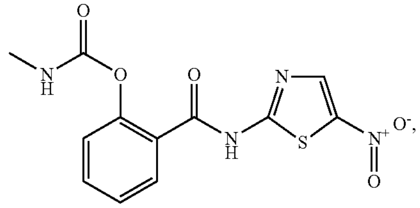
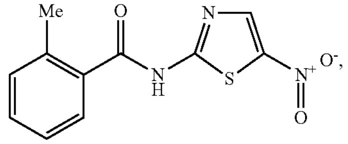
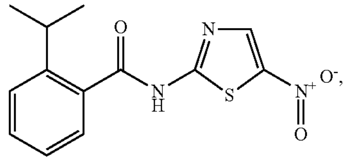
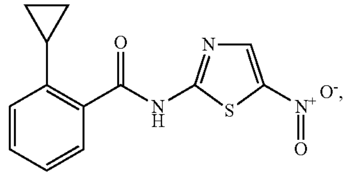
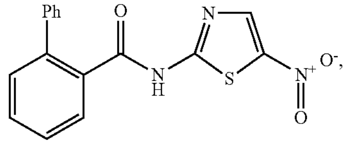
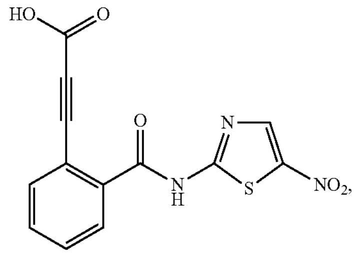
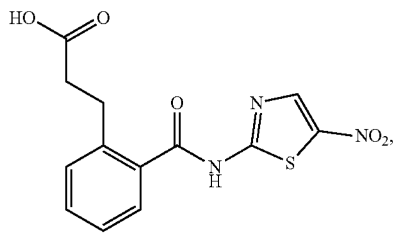

-continued
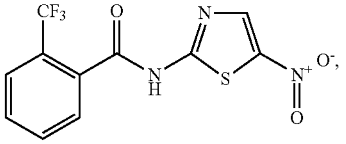
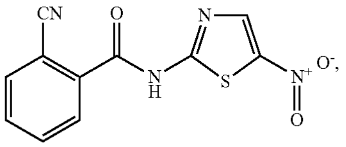
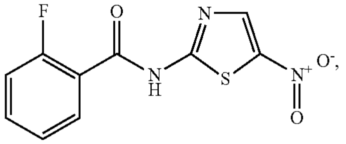
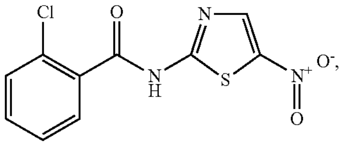
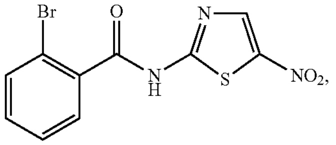
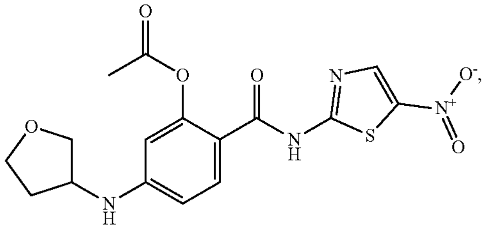
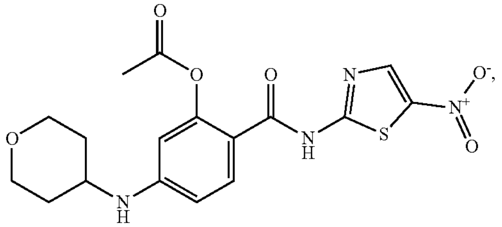
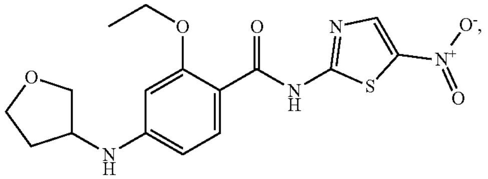
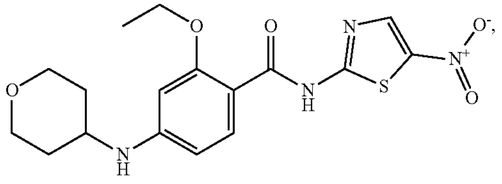
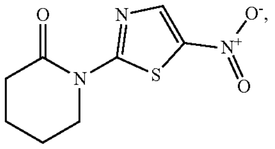
-continued
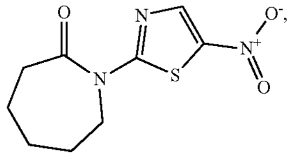
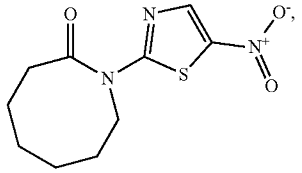
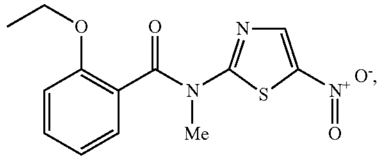
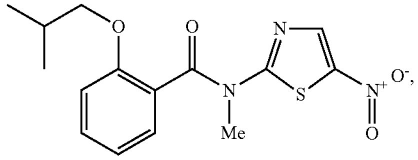
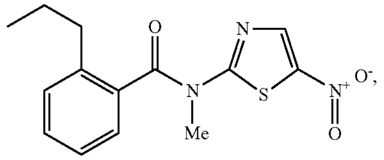
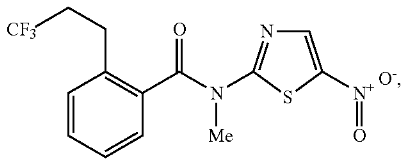
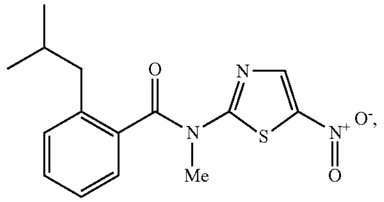
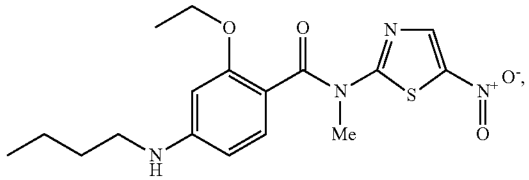
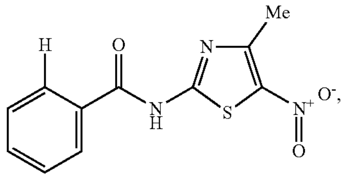
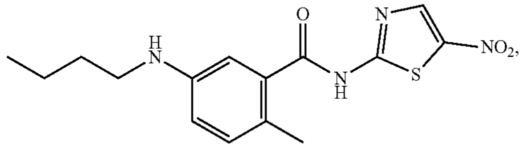

-continued
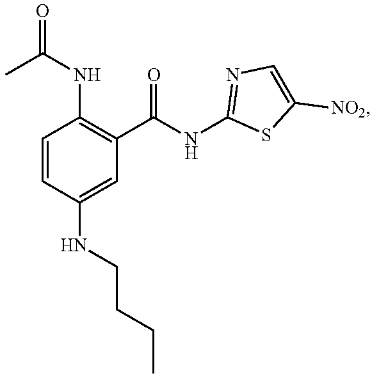
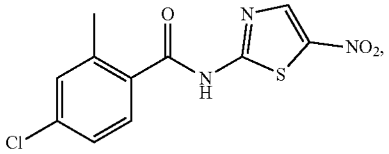
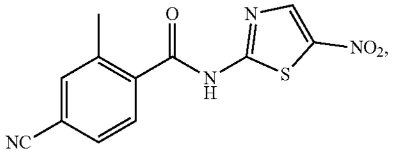
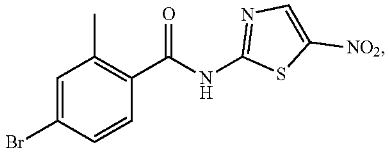
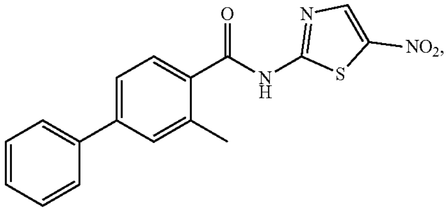
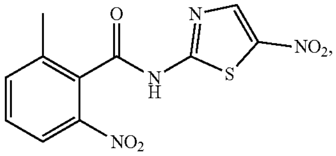
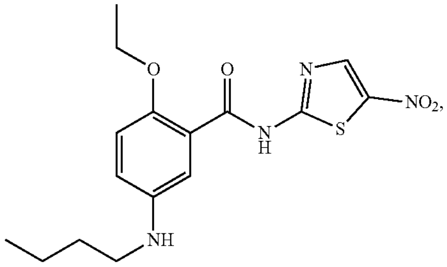
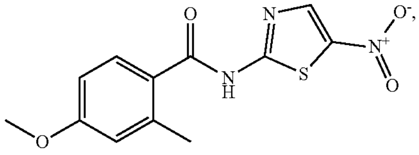
-continued
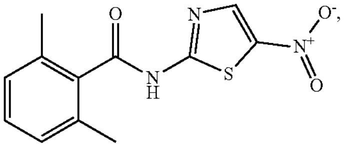
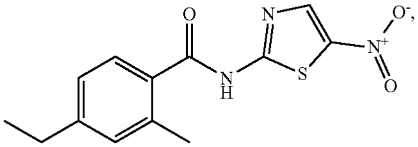
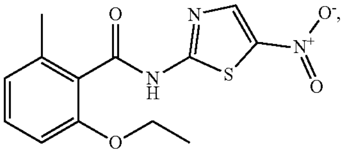
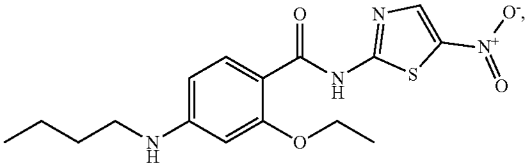
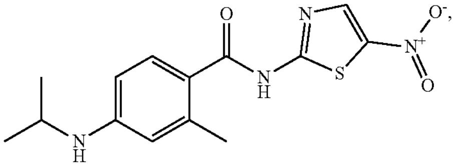
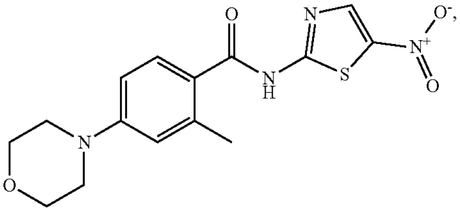
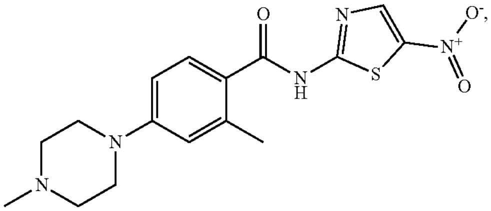
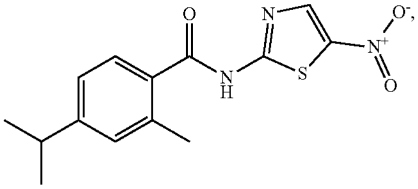
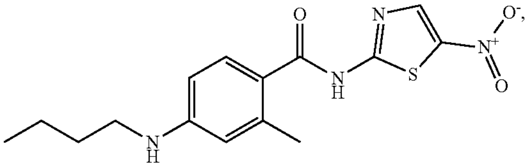
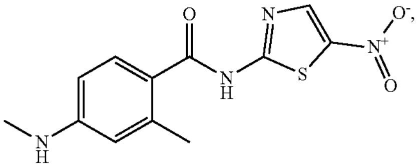

-continued
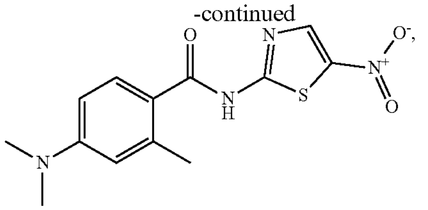
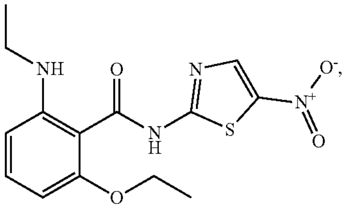
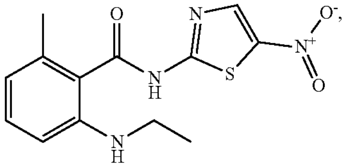
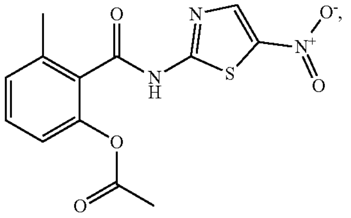
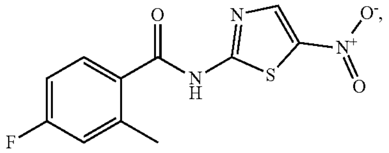
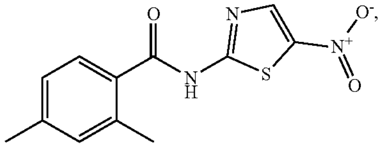
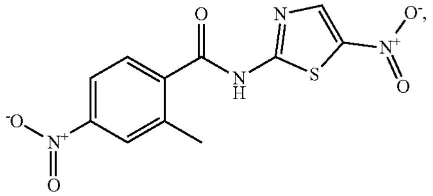
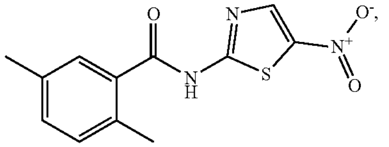
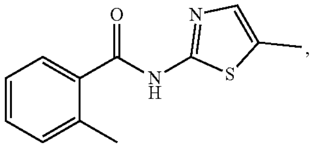
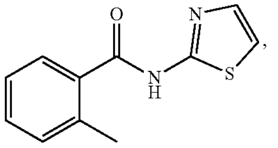
or a pharmaceutically acceptable salt thereof.
107. The ligand of any one of embodiments 84-106, wherein the ligand comprises
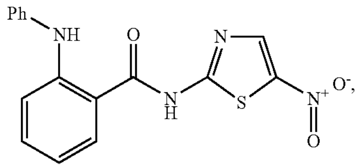
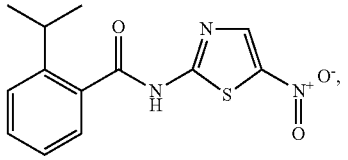
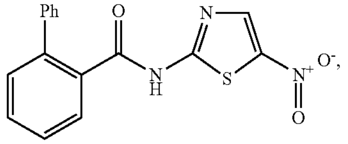
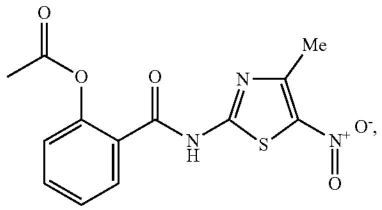
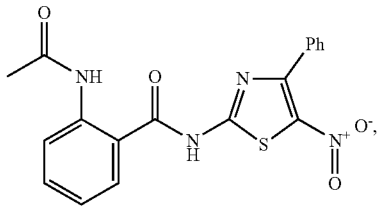
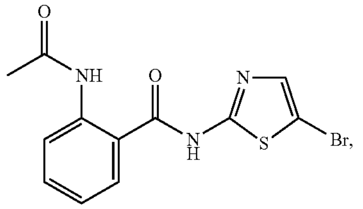
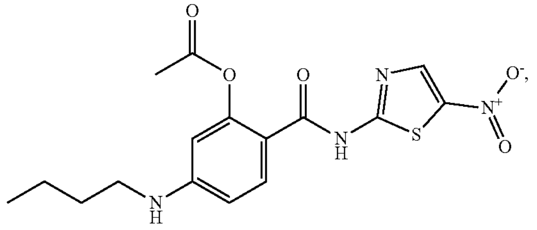
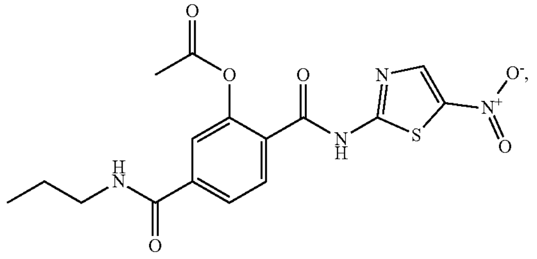

-continued
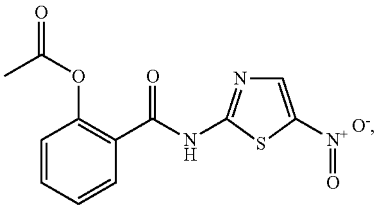
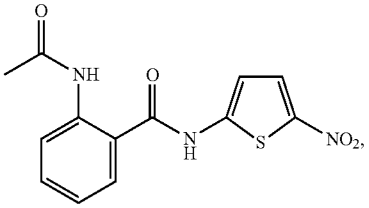
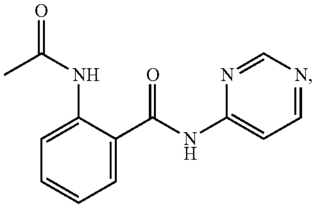
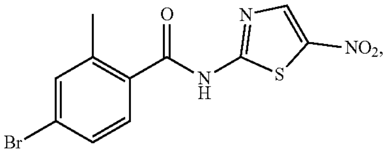
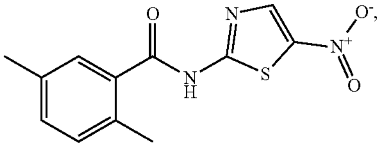
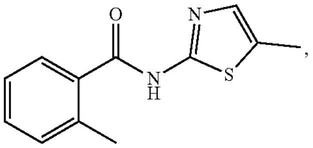
or
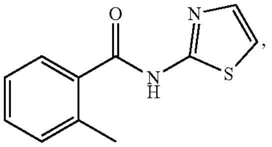
or a pharmaceutically acceptable salt thereof.
108. The ligand of any one of embodiments 84-107, wherein the ligand comprises
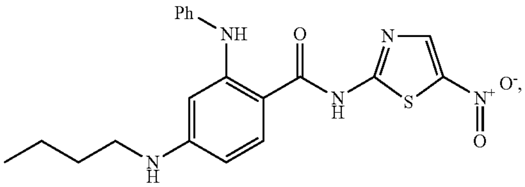
-continued
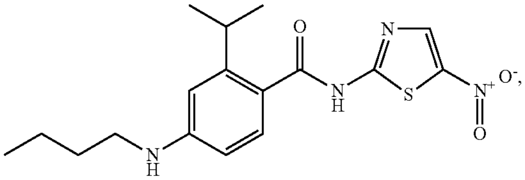
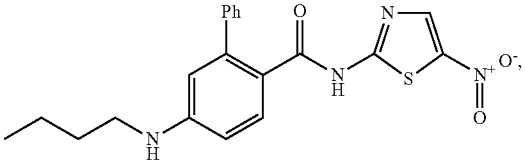
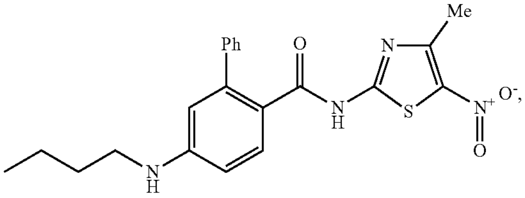
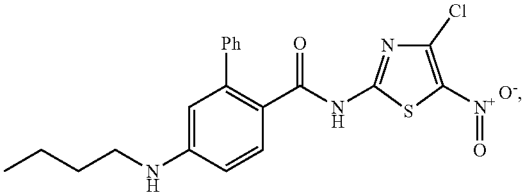
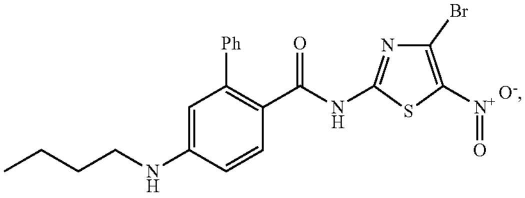
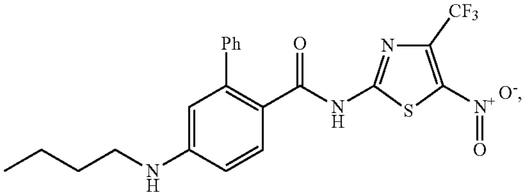
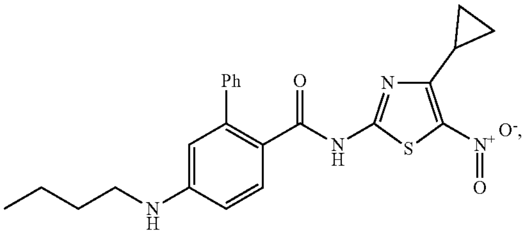
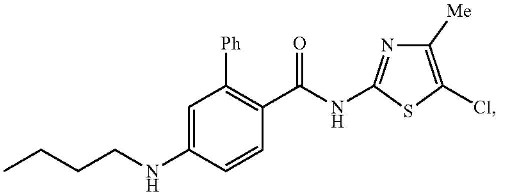
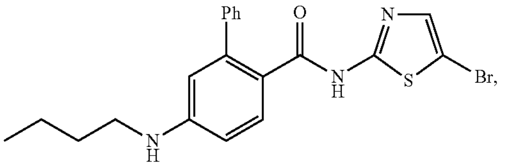

-continued
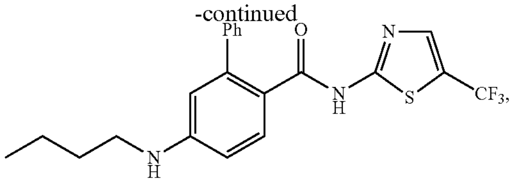
,
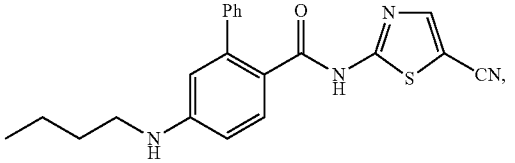
,
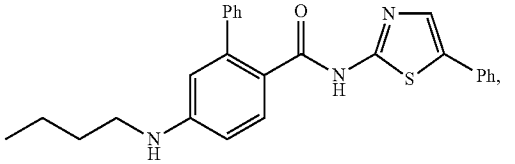
,
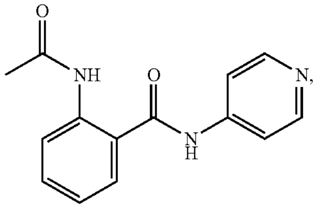
,
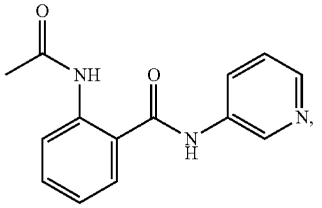
,
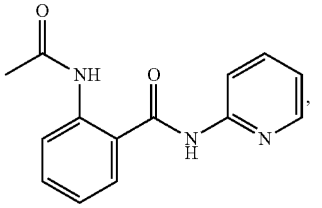
,
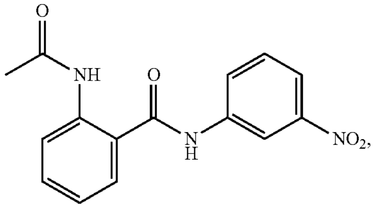
,
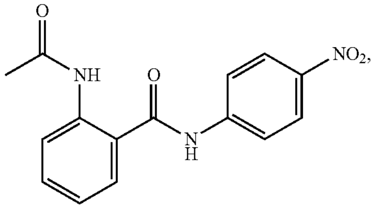
,
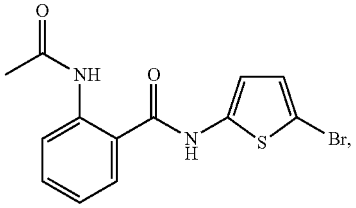
,
-continued
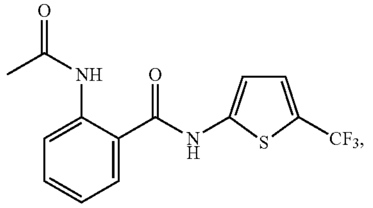
,
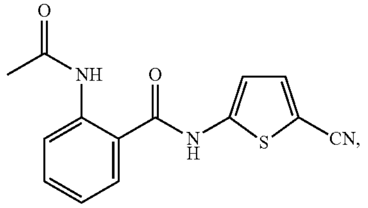
,
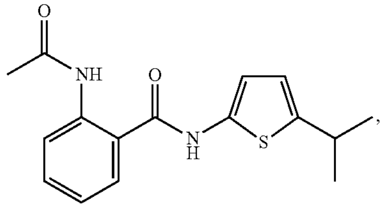
,
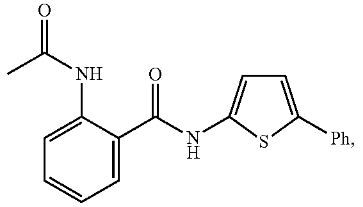
,
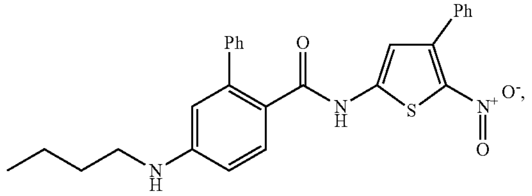
,
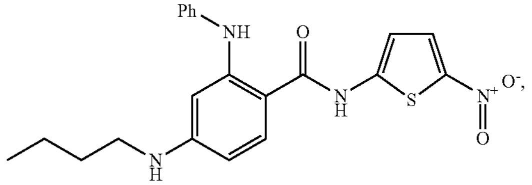
,
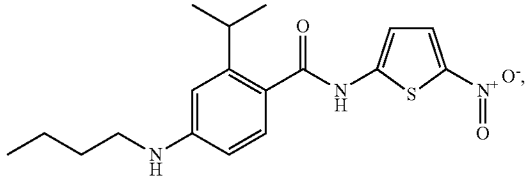
,
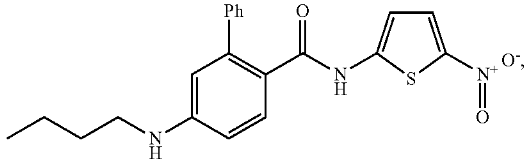
, -continued
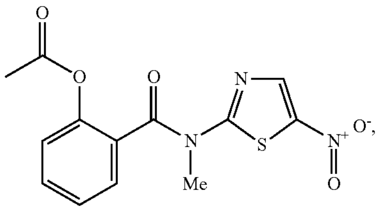
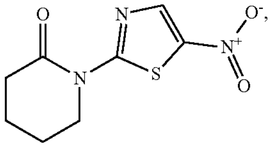
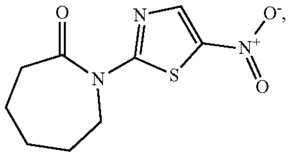
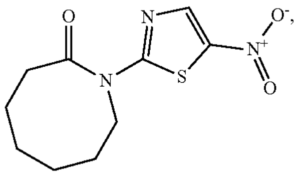
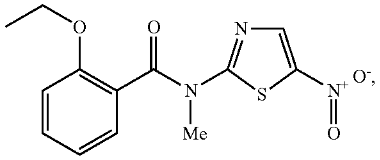
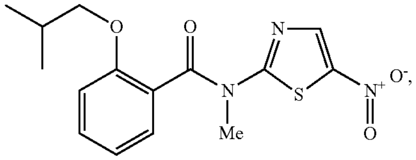
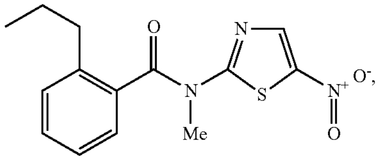
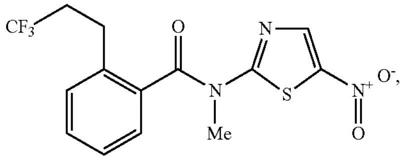
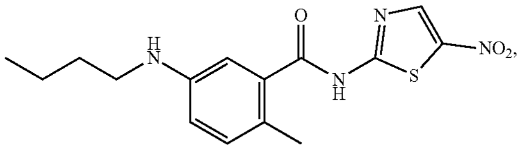
-continued
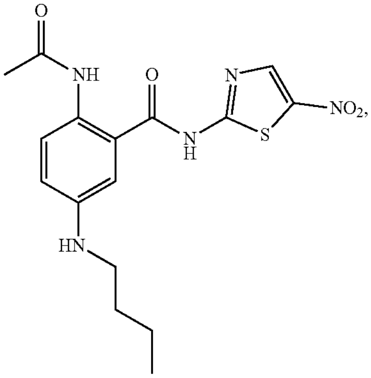
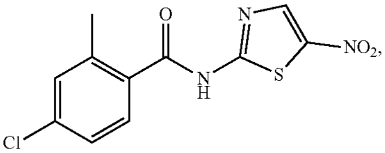
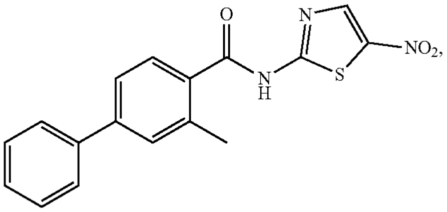
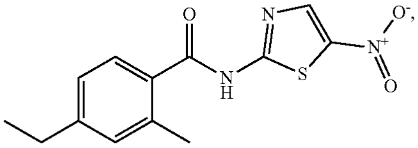
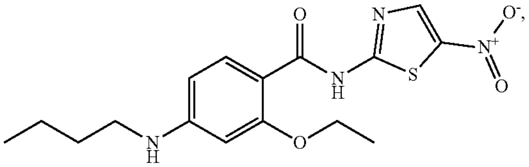
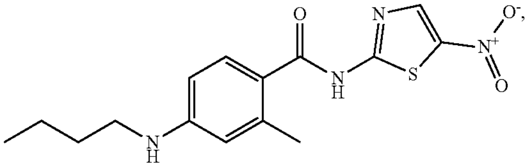
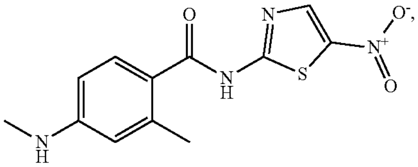
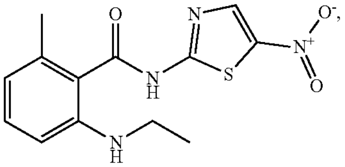
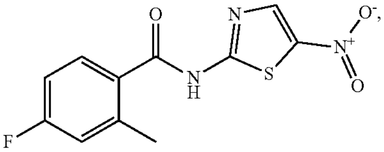

-continued

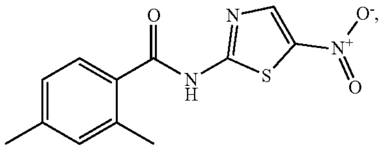

or a pharmaceutically acceptable salt thereof.

109. The ligand of any one of embodiments 84-108, wherein the ligand comprises

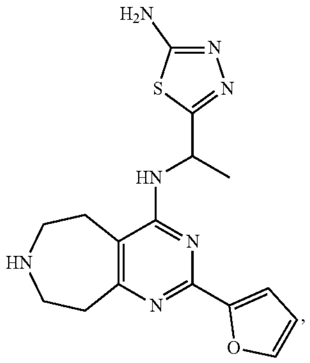

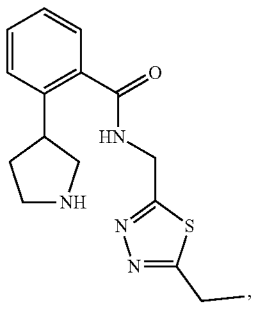

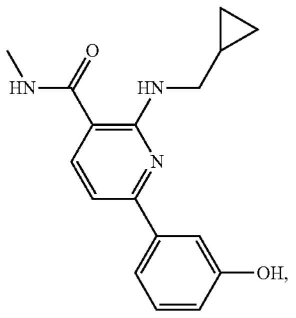

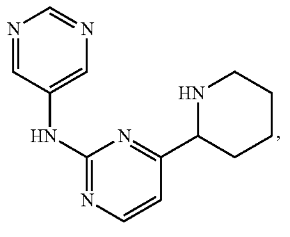

-continued

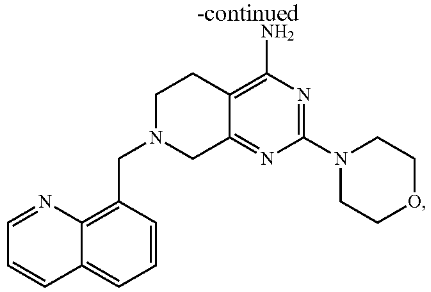

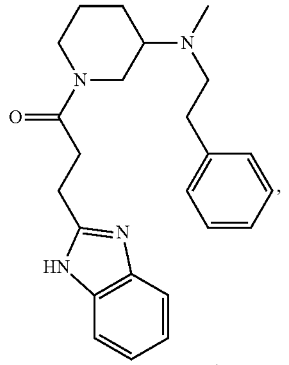

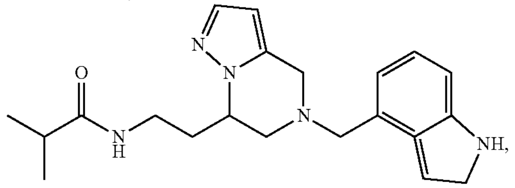

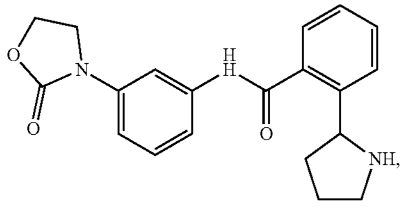

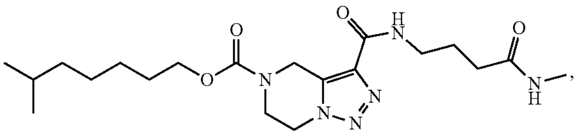

or a pharmaceutically acceptable salt thereof.

110. The ligand of any one of embodiments 91-109, wherein the linker comprises $-(CH_2)_{p2}NH(CH_2)_{p1}NH-$, $-(CH_2)_{p2}NH(CH_2)_{p1}C(=O)NH-$, $-(CH_2)_{p2}NH(CH_2)_{p1}NHC(=O)-$, $-(CH_2)_{p2}NH(CH_2CH_2)(OCH_2CH_2)_{p1}NH-$, $-(CH_2)_{p2}NH(CH_2CH_2)(OCH_2CH_2)_{p1}C(=O)NH-$, or $-(CH_2)_{p2}NH(CH_2CH_2)(OCH_2CH_2)_{p1}NHC(=O)-$, wherein p1 is 1-15, and p2 is 0-15.

111. The ligand of any one of embodiments 91-110, wherein the target protein binding moiety binds to a target protein.

112. The ligand of embodiment 111, wherein the ligand is a degrader of the target protein.

113. The ligand of embodiment 111 or 112, wherein in vivo contact of the ligand with the target protein results in degradation of the target protein.

114. The ligand of embodiment 113, wherein the ligand is a heterobifunctional ligand comprising the structure of Formula (I):

Formula (I)

$Z^1—L^1—Z^2$, wherein $Z^1$ is a target protein binding moiety $L^1$ is a linker; and $Z^2$ is a DDB1 binding moiety.

115. The ligand of embodiment 114, wherein the ligand is a heterobifunctional ligand comprising the structure of Formula (IIc):

Formula (IIc)

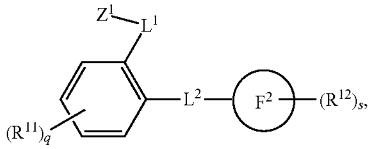

wherein $F^2$ is aryl, heteroaryl, carbocyclyl, or heterocyclyl;

$L^2$ is a bond, —C(═O)$NR^{13}$—, —$NR^{13}$C(═O)—, —C(═O)—, —C(═S)—, —S—, —S(═O), —S(═O)$_2$—, —S(═O)$NR^{13}$—, —$NR^{13}$S(═O)—, —S(═O)$_2NR^{13}$—, —$NR^1$S(═O)$_2$—, —O—, $C_1$-$C_4$ alkyl, or $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —S(═O)$_2R^d$, —S(═O)$_2NR^cR^d$, —C(═O)$R^b$, —$CO_2R^a$, —C(═O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —OR, or —$NR^cR^d$;

each $R^{11}$ and $R^{12}$ is independently hydrogen, halogen, —CN, —$R^a$, —$OR^a$—, —$SR^a$, —S(═O)$R^b$, —$NO_2$, —$NR^cR^d$, —S(═O)$_2R^d$, —$NR^a$S(═O)$_2R^d$, —S(═O)$_2NR^cR^d$, —C(═O)$R^b$, —OC(═O)$R^b$, —$CO_2R^a$, —$OCO_2R^a$, —C(═O)$NR^cR^d$, —OC(═O)$NR^cR^d$, —$NR^a$C(═O)$NR^cR^d$, —$NR^a$C(═O)$R^b$, —$NR^a$C(═O)$OR^a$, $C_1$-$C_6$ alkyl, $C_1$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$;

each $R^a$ is independently hydrogen, $C_1$-$C_6$ alkyl, $C_2$-$C_6$ alkenyl, $C_1$-$C_6$ alkynyl, $C_1$-$C_6$ heteroalkyl. $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-4;

s is 1-5;

$L^1$ is a linker; and $Z^1$ is a target protein binding moiety.

116. The ligand of embodiment 114, wherein the ligand is a heterobifunctional ligand comprising the structure of Formula (IId):

Formula (IId)

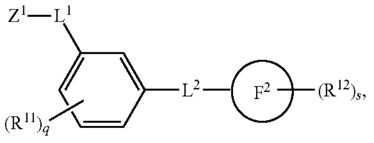

wherein $F^2$ is aryl, heteroaryl, carbocyclyl, or heterocyclyl;

$L^2$ is a bond, —C(═O)$NR^{13}$—, —$NR^{13}$C(═O)—, —C(═O)—, —C(═S)—, —S—, —S(═O), —S(═O)$_2$—, —S(═O)$NR^{13}$—, —$NR^{13}$S(═O)—, —S(═O)$_2NR^{13}$—, —$NR^{13}$S(═O)$_2$—, —O—, $C_1$-$C_4$ alkyl, $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —S(═O)$_2R^d$, —S(═O)$_2NR^cR^d$, —C(═O)$R^b$, —$CO_2R^a$, —C(═O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{11}$ and $R^{12}$ is independently hydrogen, halogen, —CN, —$R^a$, —OR, —$SR^a$, —S(═O)$R^b$, —$NO_2$, —$NR^cR^d$, —S(═O)$_2R^d$, —NRS(═O)$_2R^d$, —S(═O)$_2NR^cR^d$, —C(═O)$R^b$, —OC(═O)R, —$CO_2R^a$, —$OCO_2R^a$, —C(═O)$NR^cR^d$, —OC(═O)$NR^cR^d$, —$NR^a$C(═O)$NR^cR^d$, —$NR^a$C(═O)$R^b$, —$NR^a$C(═O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$;

each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-4:

s is 1-5:

$L^1$ is a linker; and $Z^1$ is a target protein binding moiety.

117. The ligand of embodiment 114, wherein the ligand is a heterobifunctional ligand comprising the structure of Formula (IIe):

Formula (IIe)

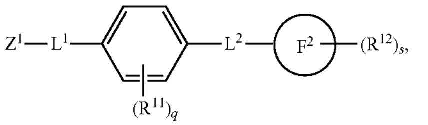

wherein $F^2$ is aryl, heteroaryl, carbocyclyl, or heterocyclyl;

$L^2$ is a bond, —C(═O)$NR^{13}$—, —$NR^{13}$C(═O)—, —C(═O)—, —C(═S)—, —S—, —S(═O), —S(═O)$_2$—, —S(═O)$NR^{13}$—, —$NR^{13}$S(═O)—, —S(═O)$_2NR^{13}$—, —$NR^{13}$S(═O)$_2$—, —O—, $C_1$-$C_4$ alkyl, $C_1$-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —S(═O)$_2R^d$, —S(═O)$_2NR^cR^d$, —C(═O)$R^b$, —$CO_2R^a$, —C(═O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{11}$ and $R^{12}$ is independently hydrogen, halogen, —CN, —$R^a$, —$OR^a$, —$SR^a$, —S(═O)$R^b$, —$NO_2$, —$NR^cR^d$, —S(═O)$_2R^d$, —$NR^a$S(═O)$_2R^d$, —S(═O)$_2NR^cR^d$, —C(═O)$R^b$, —OC(═O)$R^b$, —$CO_2R^a$, —$OCO_2R^a$, —C(═O)$NR^cR^d$, —OC(═O)$NR^cR^d$, —$NR^a$C(═O)$NR^cR^d$, —$NR^a$C(═O)$R^b$, —$NR^a$C(═O)$OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$;

each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen. $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH. —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$, together with the nitrogen atom to which they are attached, form a heterocyclyl or heteroaryl; wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is 1-4;

s is 1-5:

$L^1$ is a linker; and $Z^1$ is a target protein binding moiety.

118. The ligand of any one of embodiments 115-117, wherein $F^2$ is aryl.

119. The ligand of embodiment 118, wherein $F^2$ is $C_6$-$C_{12}$ aryl.

120. The ligand of embodiment 118, wherein $F^2$ is heteroaryl.

121. The ligand of embodiment 120, wherein $F^2$ is 5-12 membered heteroaryl.

122. The ligand of any one of embodiments 115-121, wherein $L^2$ is —C(═O)NH—.

123. The ligand of any one of embodiments 115-121, wherein $L^2$ is —C(═O)N($C_1$-$C_5$ alkyl)-.

124. The ligand of any one of embodiments 115-123, wherein q is 1.

125. The ligand of any one of embodiments 115-123, wherein q is 2.

126. The ligand of any one of embodiments 115-125, wherein the linker is a bond.

127. The ligand of any one of embodiments 115-125, wherein the linker the linker is not a bond (e.g. the linker may comprise $—(CH_2)_{p2}NH(CH_2)_{p1}NH—$, $—(CH_2)_{p2}NH(CH_2)_{p1}C(═O)NH—$, $—(CH_2)_{p2}NH(CH_2)_{p1}NHC(═O)—$, $—(CH_2)_{p2}NH(CH_2CH_2)(OCH_2CH_2)_{p1}NH—$, $—(CH_2)_{p2}NH(CH_2CH_2)(OCH_2CH_2)_{p1}C(═O)NH—$, or $—(CH_2)_{p2}NH(CH_2CH_2)(OCH_2CH_2)_{p1}NHC(═O)—$, wherein p1 is 1-15, and p2 is 0-15).

128. A method for degrading a target protein in a subject, comprising:

administering, to the subject, a heterobifunctional compound comprising a DNA damage-binding protein 1 (DDB1) binding moiety covalently connected through a linker to a target protein binding moiety.

129. The method of embodiment 128, wherein the subject is a mammal.

130. The method of embodiment 128 or 129, wherein the subject is a human.

131. The method of any one of embodiments 128-130, wherein the route of administration is intravenous, oral, subcutaneous, intraperitoneal, ocular, intraocular, intramuscular, interstitial, intraarterial, intracranial, intraventricular, intrasynovial, transepithelial, transdermal, by inhalation, ophthalmic, sublingual, buccal, topical, dermal, rectal, nasal, by insufflation, or by nebulization.

132. The method of any one of embodiments 128-131, wherein the administration comprises an injection.

133. The method of any one of embodiments 128-132, wherein administering the compound to the subject comprises administering an effective amount of the compound sufficient to degrade the target protein.

134. The method of any one of embodiments 128-133, wherein upon administration of the compound to the subject, the target protein is ubiquitinated to form a ubiquitinated target protein.

135. A method for degrading a target protein in a sample, comprising:

contacting a target protein with a heterobifunctional compound comprising a DNA damage-binding protein 1 (DDB1) binding moiety covalently connected through a linker to a target protein binding moiety.

136. The method of embodiment 135, wherein the sample is a biological sample.

137. The method of embodiment 136, wherein the biological sample comprises a tissue, a cell, or a biological fluid.

138. The method of any one of embodiments 135-137, wherein the contacting is in vitro.

139. The method of any one of embodiments 135-137, wherein the contacting is in vivo.

140. The method of any one of embodiments 135-139, wherein upon being contacted with the compound, the target protein is ubiquitinated to form a ubiquitinated target protein.

141. The method of embodiment 134 or 140, wherein the ubiquitinated target protein is degraded.

142. The method of any one of embodiments 128-141, wherein the degradation of the target protein is specific to the target protein.

143. The method of any one of embodiments 128-142, wherein the degradation of the target protein comprises proteasomal degradation.

144. The method of any one of embodiments 128-143, wherein the target protein is degraded by a proteasome.

145. The method of any one of embodiments 128-144, wherein the compound binds to a DDB1 protein to form a compound-DDB1 complex.

146. The method of any one of embodiments 128-145, wherein the compound directly binds to the DDB1 protein through the DDB1 binding moiety of the compound.

147. The method of any one of embodiments 128-146, wherein the binding between the DDB1 binding moiety and the DDB1 protein is non-covalent.

148. The method of any one of embodiments 128-146, wherein the binding between the DDB1 binding moiety and the DDB1 protein is covalent.

149. The method of any one of embodiments 128-148, wherein the target protein is ubiquitinated by a ubiquitin E3 ligase complex comprising the DDB1 protein.

150. The method of any one of embodiments 128-149, wherein the compound recruits the ubiquitin E3 ligase complex to the target protein via the DDB1 binding moiety.

151. The method of any one of embodiments 128-150, wherein the compound is a small molecule.

152. The method of any one of embodiments 128-151, wherein the compound comprises a targeted protein degrader.

153. The method of any one of embodiments 128-152, wherein the compound comprises the ligand of any one of embodiments 84-127.

154. The method of any one of embodiments 128-153, wherein the target protein comprises any one of a transcription factor, CBP, p300, a kinase, a receptor, a TRK, TrkA, a cyclin dependent kinase, CDK1, CDK2, CDK3, CDK4, CDK5, CDK6, CDK7, CDK8, CDK9, CDK10, CDK11, CDK12, CDK13, a cyclin, cyclin A, cyclin B, cyclin C, cyclin D, cyclin D1, cyclin D2, cyclin D3, cyclin E, cyclin H, cyclin K, cyclin T, cyclin T1, p25, p35, B7.1, B7, TINFRklm, TNFR2, NADPH oxidase, a partner in an apoptosis pathway, BclIBax, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide synthase, cyclo-oxygenase 1, cyclo-oxygenase 2, a receptor, a 5HT receptor, a dopamine receptor, a G-protein, Gq, a histamine receptor, 5-lipoxygenase, tryptase serine protease, thymidylate synthase, purine nucleoside phosphorylase, GAPDH, a trypanosomal protein, glycogen phosphorylase, carbonic anhydrase, a chemokine receptor, JAK, STAT, RXR, RAR, HIV 1 protease, HIV 1 integrase, influenza, neuramimidase, hepatitis B reverse transcriptase, sodium channel, multi drug resistance, protein P-glycoprotein, MRP, a tyrosine kinase, CD23, CD124, tyrosine kinase p56 lck, CD4, CD5, IL-2 receptor, IL-1 receptor, TNF-alphaR, ICAM1, a Ca+ channel, VCAM, an integrin, a VLA-4 integrin, a selectin, CD40, CD40L, a neurokinin, a neurokinin receptor, inosine monophosphate dehydrogenase, p38 MAP Kinase, Ras, Raf, Mek, Erk, interleukin-1 converting enzyme, a caspase, HCV, NS3 protease, HCV NS3

RNA helicase, glycinamide ribonucleotide formyl transferase, rhinovirus 3C protease, herpes simplex virus-1, a protease, cytomegalovirus protease, poly ADP-ribose polymerase, vascular endothelial growth factor, oxytocin receptor, microsomal transfer protein inhibitor, bile acid transport inhibitor, a 5 alpha reductase inhibitor, angiotensin 11, a glycine receptor, a noradrenaline reuptake receptor, an endothelin receptor, neuropeptide Y, a neuropeptide Y receptor, an estrogen receptor, an androgen receptor, an adenosine receptor, an adenosine kinase, AMP deaminase, a purinergic receptor, P2Y1, P2Y2, P2Y4, P2Y6. P2X1-7, a farnesyltransferase, geranylgeranyl transferase, an NGF receptor, beta-amyloid, a tyrosine kinase. Flk-IIKDR, vitronectin receptor, an integrin receptor, Her2 neu, telomerase inhibition, cytosolic phospholipaseA2, EGF receptor tyrosine kinase, ecdysone 20-monooxygenase, ion channel of the GABA gated chloride channel, acetylcholinesterase, voltage-sensitive sodium channel protein, calcium release channel, a chloride channel, acetyl-CoA carboxylase, adenylosuccinate synthetase, protoporphyrinogen oxidase, enolpyruvylshikimate-phosphate synthase, an HSP, Hsp90, a kinase, an MDM, MDM2, a Human BET Bromodomain-containing protein, an HDAC, a lysine methyltransferase, an angiogenesis protein, an immunomodulatory protein, AHR, VEGFR3, Alk, Abl, a Janus kinase, JAK2, Met, B-Raf, a phosphatase, FKBP, a thyroid hormone receptor, acyl-protein thioesterase-1, acyl-protein thioesterase-2, an HIV protein, an HIV protease, an HIV integrase, an HCV protein, or an HCV protease.

155. A method for degrading a target protein in a cell, comprising:

administering, to the cell, a binding molecule that binds a first protein that interacts with the target protein, thereby degrading target protein, wherein the target protein is degraded before the first protein or wherein the first protein is not degraded.

156. The method of embodiment 155, further comprising measuring the target protein in the cell.

157. The method of embodiment 155 or 156, further comprising measuring the first protein in the cell.

158. The method of any one of embodiments 155-157, wherein the interaction between the target protein and the first protein is dimerization.

159. The method of any one of embodiments 155-158, wherein the target protein comprises a cyclin.

160. The method of embodiment 159, wherein the cyclin comprises a Cyclin D.

161. The method of embodiment 169, wherein the Cyclin D comprises Cyclin D1, Cyclin D2, or Cyclin D3.

162. The method of any one of embodiments 155-161, wherein the first protein comprises a cyclin-dependent kinase (CDK).

163. The method of embodiment 162, wherein the CDK comprises CDK4 or CDK6.

164. The method of any one of embodiments 155-163, wherein the binding molecule reduces viability of the cell.

165. The method of any one of embodiments 155-164, wherein the cell comprises a eukaryotic cell.

166. The method of embodiment 165, wherein the eukaryotic cell comprises a mammalian cell.

167. The method of embodiment 166, wherein the mammalian cell comprises a human cell.

168. The method of any one of embodiments 155-167, wherein the cell is cancerous.

169. The method of any one of embodiments 155-168, wherein administering the binding molecule to the cell comprises administering the binding molecule to a subject comprising the cell.

170. The method of any one of embodiments 155-169, wherein the binding molecule recruits an E3 ubiquitin ligase that ubiquitinates the target protein.

171. The method of any one of embodiments 155-170, wherein the binding molecule comprises a heterobifunctional compound comprising an E3 ubiquitin ligase-binding moiety covalently connected through a linker to a first protein binding moiety.

172. The method of embodiment 170 or 171, wherein the E3 ubiquitin ligase comprises DNA damage-binding protein 1 (DDB1) or Von Hippel-Lindau tumor suppressor (VHL).

173. A method of treatment, comprising:

administering to a subject having an infection, a therapeutically effective amount of a heterobifunctional compound comprising a DNA damage-binding protein 1 (DDB1) binding moiety covalently connected through a linker to a target protein binding moiety.

174. The method of embodiment 173, wherein the infection comprises a viral infection, and the target protein comprises a viral protein.

175. The method of embodiment 173 or 174, wherein the compound comprises the ligand of any one of embodiments 84-127.

176. The method of any one of embodiments 173-175, wherein the administration results in ubiquitination and degradation of the target protein.

177. The method of any one of embodiments 173-176, wherein the subject is a human.

178. A method of modulating a DNA damage-binding protein 1 (DDB1) protein, comprising:

contacting a DDB1 protein with a compound comprising a DDB1 binding moiety.

179. The method of embodiment 178, wherein the DDB1 binding moiety comprises a structure of Formula (II), a structure of Formula (IIa), or a structure of Formula (IIb), or a salt thereof.

180. The method of embodiment 178, wherein the compound comprises a compound in Table 1, or a salt thereof.

181. The method of embodiment 178, wherein the compound comprises a peptide in Table 3, or a peptide having an amino acid sequence at least 70% identical, at least 75% identical, at least 80% identical, at least 85% identical, at least 90% identical, or at least 95% identical, to a peptide in Table 3.

182. The method of any one of embodiments 178-181, wherein contacting the DDB1 protein with the compound comprises contacting the DDB1 protein with the compound in vitro.

183. The method of any one of embodiments 178-181, wherein contacting the DDB1 protein with the compound comprises delivering the compound to a cell expressing the DDB1 protein.

184. The method of any one of embodiments 178-181, wherein contacting the DDB1 protein with the compound comprises contacting the DDB1 protein with the compound in vivo.

185. The method of embodiment 184, wherein contacting the DDB1 protein with the compound comprises administering the compound to a subject.

186. The method of embodiment 185, wherein the subject is a human.

187. The method of any one of embodiments 178-186, wherein the compound binds to the DDB1 protein.

188. The method of any one of embodiments 178-187, wherein the contact results in an increase in an amount of the DDB1 protein, relative to a baseline amount.

189. The method of any one of embodiments 178-187, wherein the contact results in a decrease in an amount of the DDB1 protein, relative to a baseline amount.

190. The method of any one of embodiments 178-187, wherein the contact results in an increase in an activity of the DDB1 protein, relative to a baseline activity.

191. The method of any one of embodiments 178-187, wherein the contact results in a decrease in an activity of the DDB1 protein, relative to a baseline activity.

192. A method of bringing a DNA damage-binding protein 1 (DDB1) protein into proximity with a target protein, comprising:

contacting a DDB1 protein and a target protein with a compound comprising a DDB1 binding moiety and a target protein binding moiety.

193. The method of embodiment 192, wherein the compound comprises the ligand of any one of embodiments 84-127.

194. The method of embodiment 192 or 193, wherein the contact is in vitro.

195. The method of embodiment 192 or 193, wherein contacting the DDB1 protein and the target protein with the compound comprises delivering the compound to a cell expressing the DDB1 protein and the target protein.

196. The method of embodiment 192 or 193, wherein the contact is in vivo.

197. The method of embodiment 196, wherein contacting the DDB1 protein and the target protein with the compound comprises administering the compound to a subject.

198. The method of embodiment 197, wherein the subject is a human.

199. The method of any one of embodiments 192-198, wherein the compound binds to the DDB1 protein and to the target protein.

200. The method of any one of embodiments 192-199, wherein the contact results in an increase in an amount of the target protein, relative to a baseline amount.

201. The method of any one of embodiments 192-199, wherein the contact results in a decrease in an amount of the target protein, relative to a baseline amount.

202. The method of any one of embodiments 192-199, wherein the contact results in an increase in an activity of the target protein, relative to a baseline activity.

203. The method of any one of embodiments 192-199, wherein the contact results in a decrease in an activity of the target protein, relative to a baseline activity.

EXAMPLES

The following examples are set forth to illustrate more clearly the principle and practice of instances disclosed herein to those skilled in the art and are not to be construed as limiting the scope of any claimed instances. Unless otherwise stated, all parts and percentages are on a weight basis.

The following are non-limiting examples of a synthesis of ligands.

Example 001. N-(5-Nitrothiazol-2-yl)benzamide (B-3)

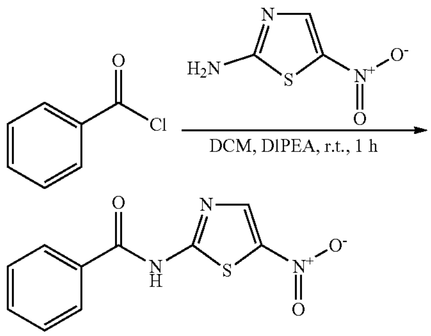

To a solution of 5-nitrothiazol-2-amine (341 mg, 2.35 mmol) and DIPEA (826 mg, 6.39 mmol) in DCM (10 mL) was added benzoyl chloride (300 mg, 2.13 mmol). After the reaction mixture was stirred at rt for 1 h, the mixture was concentrated. The resulting residue was purified by prep-HPLC to give the title compound (24.66 mg, 4.6% yield) as an off-yellow solid. $^1H$ NMR (400 MHz, DMSO-$d_6$): δ 13.61 (s, 1H), 8.72 (s, 1H), 8.14-8.12 (m, 2H), 7.71-7.68 (m, 1H), 7.60-7.57 (m, 2H). MS (ESI) m/z: 250.1 $[M+H]^+$.

Example 002. 2-Acetamido-N-(5-nitrothiazol-2-yl) benzamide (B-4)

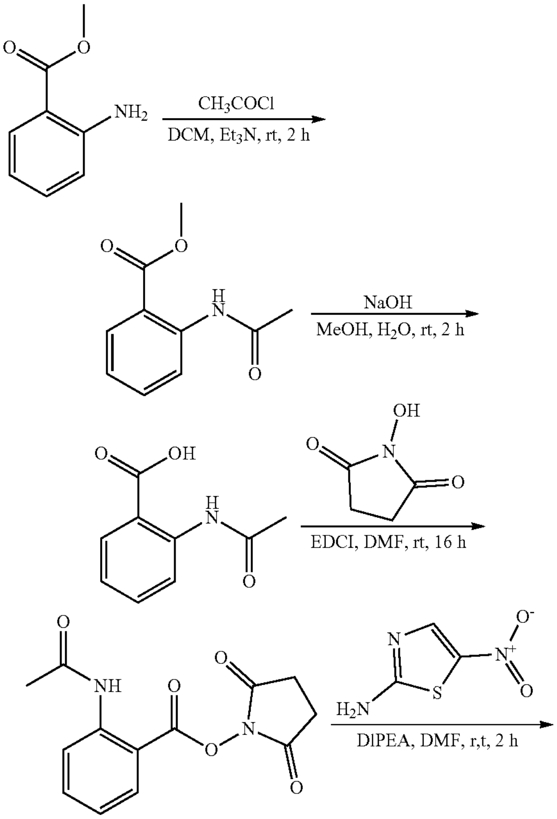

-continued

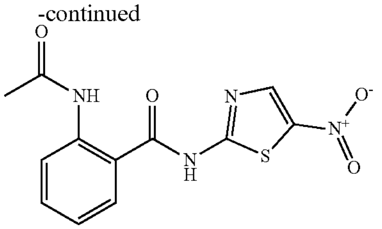

Step 1. Synthesis of methyl 2-acetamidobenzoate

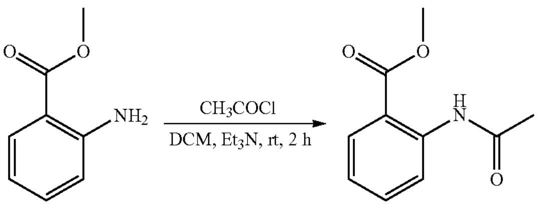

To a solution of methyl 2-aminobenzoate (1.00 g, 6.62 mmol) and $Et_3N$ (1.34 g, 13.3 mmol) in DCM (30 mL) at 0° C. was added acetyl chloride (1.05 g, 13.3 mmol). After being stirred at rt for 2 h, the mixture was concentrated. The resulting residue was diluted with water (50 mL) and extracted with EtOAc (2×50 mL). The combined organic phase was dried over $Na_2SO_4$, filtered and concentrated to give the title compound (1.20 g, crude) as brown oil, which was used directly in the next step. MS (ESI) m/z: 194.4 $[M+H]^+$.

Step 2. Synthesis of 2-acetamidobenzoic acid

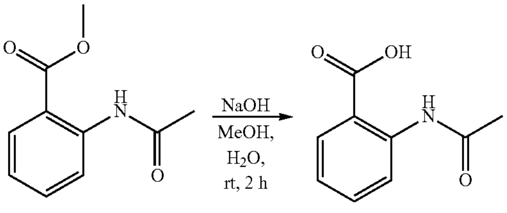

To a solution of methyl 2-acetamidobenzoate (1.20 g, crude) in MeOH (5 mL) was added a solution of NaOH (500 mg, 12.5 mmol) in $H_2O$ (3 mL). After being stirred at rt for 2 h, the mixture was diluted with water (50 mL). 1 N HCl was added to adjust pH to 3. The mixture was extracted with EtOAc (3×50 mL). The combined organic phase was dried over $Na_2SO_4$, filtered and concentrated to give the tide compound (1.00 g, 84.4% yield over two steps) as colorless oil.

Step 3. Synthesis of 2,5-dioxopyrrolidin-1-yl 2-acetamidobenzoate

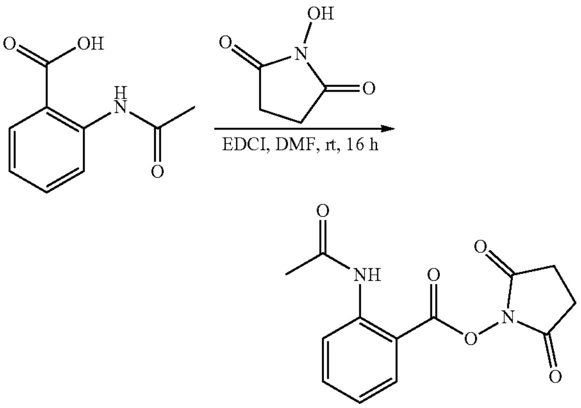

To a solution of 2-acetamidobenzoic acid (1.00 g, 5.55 mmol) in DMF (10.0 mL) were added 1-hydroxypyrrolidine-2,5-dione (765 mg, 6.65 mmol) and EDCI (3.30 g, 11.1 mmol). After being stirred at rt for 16 h, the mixture was diluted with water (50 mL) and extracted with EtOAc (2×50 mL). The combined organic phase was dried over $Na_2SO_4$, filtered and concentrated. The resulting residue was purified by silica gel column chromatography (petroleum ether: EtOAc=1:1) to give the title compound (600 mg, crude) as colorless oil.

Step 4. Synthesis of 2-acetamido-N-(5-nitrothiazol-2-yl)benzamide

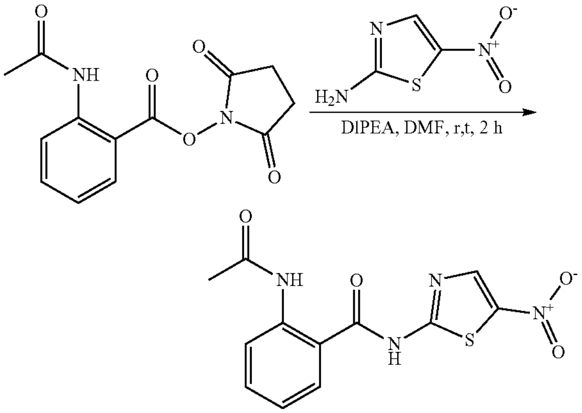

To a solution of 2,5-dioxopyrrolidin-1-yl 2-acetamidobenzoate (200 mg, crude) and 5-nitrothiazol-2-amine (126 mg, 0.84 mmol) in DMF (4 mL) was added DIPEA (187 mg, 1.45 mmol). After being stirred at it for 2 h, the reaction mixture was purified by prep-HPLC to give the title compound (40 mg, 18% yield over two steps) as yellow solid. $^1H$ NMR (400 MHz, DMSO-$d_6$): δ 13.47 (brs, 1H), 10.21 (brs, 1H), 8.68 (s, 1H), 7.71-7.65 (m, 2H), 7.58-7.54 (m, 1H), 7.26 (t, J=7.2 Hz, 1H), 2.01 (s, 3H). MS (ESI) m/z: 307.3 $[M+H]^+$.

Example 003. 2-Ethoxy-N-(5-nitrothiazol-2-yl)benzamide (B-7)

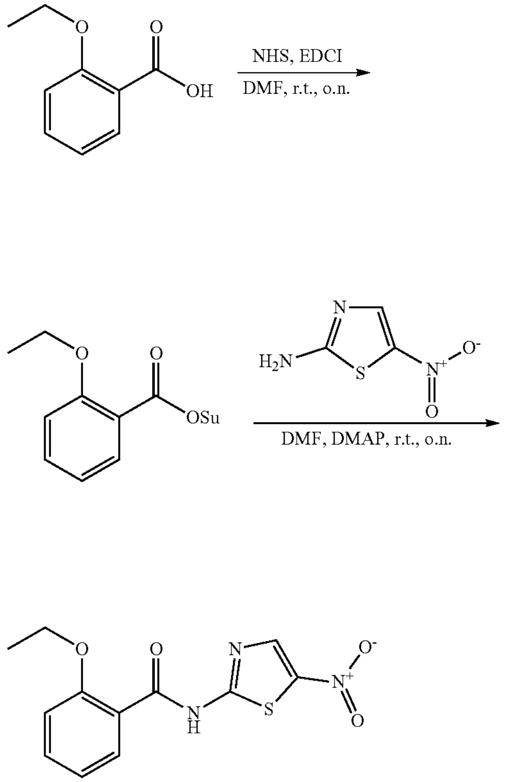

Step 1. Synthesis of 2,5-dioxopyrrolidin-1-yl 2-ethoxybenzoate

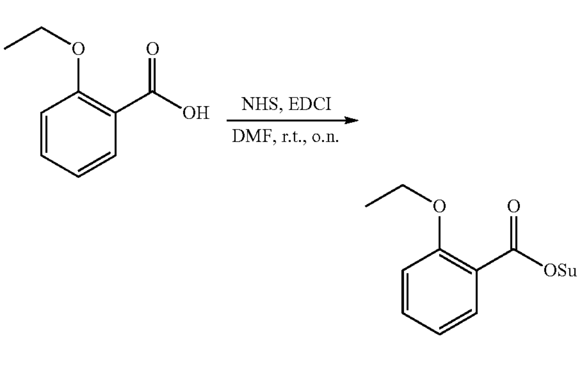

To a solution of 2-ethoxybenzoic acid (1.00 g, 6.02 mmol) in DMF (30 mL) were added 1-hydroxypyrrolidine-2,5-dione (900 mg, 7.82 mmol) and EDCI (2.31 mg, 12.0 mmol). After being stirred at rt overnight, the reaction mixture was diluted with EtOAc (50 mL), washed with brine, dried over $Na_2SO_4$, filtered and concentrated. The resulting residue, was purified by silica gel column chromatography (petroleum ether:EtOAc=1:1) to give the title compound (1.00 g, 63.1% yield) as white solid. MS (ESI) m/z: 286.3 $[M+Na]^+$.

Step 2. Synthesis of 2-ethoxy-N-(5-nitrothiazol-2-yl)benzamide

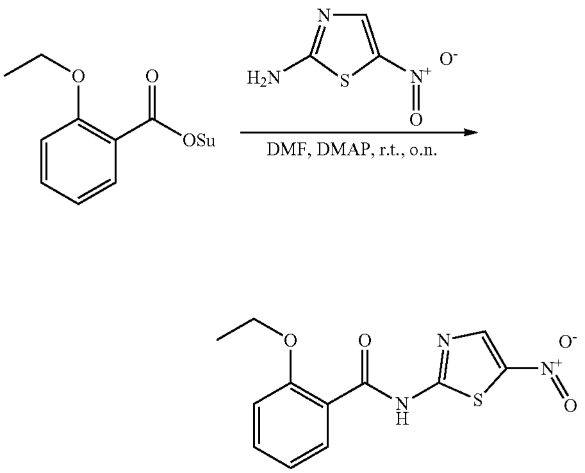

To a solution of 2,5-dioxopyrrolidin-1-yl 2-ethoxybenzoate (1.00 g, 1.14 mmol) in DMF (5 mL) were added 5-nitrothiazol-2-amine (182 mg, 1.25 mmol) and DMAP (209 mg, 1.71 mmol). After being stirred at rt overnight, the reaction mixture was purified by prep-HPLC to give the title compound (44.59 mg, 13.3% yield) as white solid. $^1H$ NMR (400 MHz, DMSO-$d_6$): δ 12.71 (s, 1H), 8.68 (s, 1H), 7.74-7.71 (m, 1H), 7.61-7.56 (m, 1H), 7.22-7.20 (m, 1H), 7.12-7.08 (m, 1H), 4.19 (q, J=7.2 Hz, 2H), 1.38 (t, J=6.8 Hz, 3H). MS (ESI) m/z: 294.3 $[M+H]^+$.

Example 004. 2-(Methyl(5-nitrothiazol-2-yl)carbamoyl)phenyl acetate (B-8)

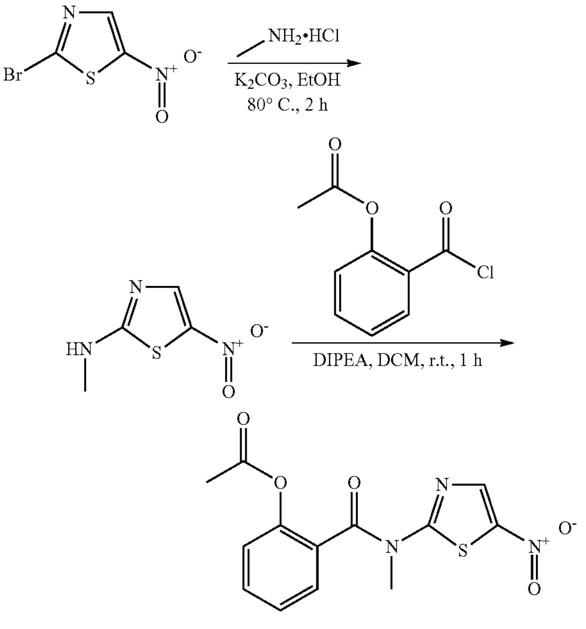

Step 1. Synthesis of N-methyl-5-nitrothiazol-2-amine

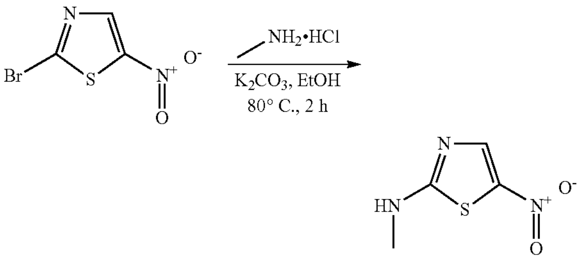

To a solution of 2-bromo-5-nitrothiazole (700 mg, 3.35 mmol) in EtOH (20 mL) were added methylamine hydrochloride (1.13 g, 16.7 mmol) and $K_2CO_3$ (2.32 g, 16.7 mmol). After being stirred at 80° C. for 2 h, the reaction mixture was concentrated. The resulting residue was purified by silica gel column chromatography (petroleum ether: EtOAc=1:1) to give the tide compound (300 mg, 56.3% yield) as yellow solid. MS (ESI) m/z: 160.1 $[M+H]^+$.

Step 2. Synthesis of 2-(methyl(5-nitrothiazol-2-yl)carbamoyl)phenyl acetate

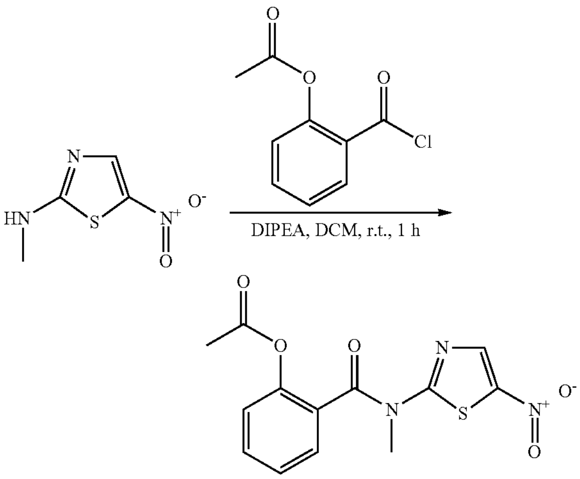

To a solution of N-methyl-5-nitrothiazol-2-amine (300 mg, 1.88 mmol) in DCM (20 mL) were added DIPEA (729 mg, 5.64 mmol) and 2-(chlorocarbonyl)phenyl acetate (449 mg, 2.26 mmol). After being stirred at rt for 1 h. the reaction mixture was diluted with DCM (50 mL), washed with 1 N HCl (30 mL), brine (2×30 mL), dried over $Na_2SO_4$, filtered and concentrated. The resulting residue was purified by silica gel column chromatography (petroleum ether: EtOAc=3:1) and recrystallized in EtOAc to give the title compound (123 mg, 20.4% yield) as off-yellow solid. $^1H$ NMR (400 MHz, DMSO-$d_6$): δ 8.77 (s, 1H), 7.74-7.72 (m, 1H), 7.67-7.65 (m, 1H), 7.49-7.46 (m, 1H), 7.40-7.37 (m, 1H), 3.50 (s, 3H), 2.18 (s, 3H). MS (ESI) m/z: 322.1 $[M+H]^+$.

Example 005. 2-(Methyl(5-nitrothiazol-2-yl)carbamoyl)phenyl acetate (B-10)

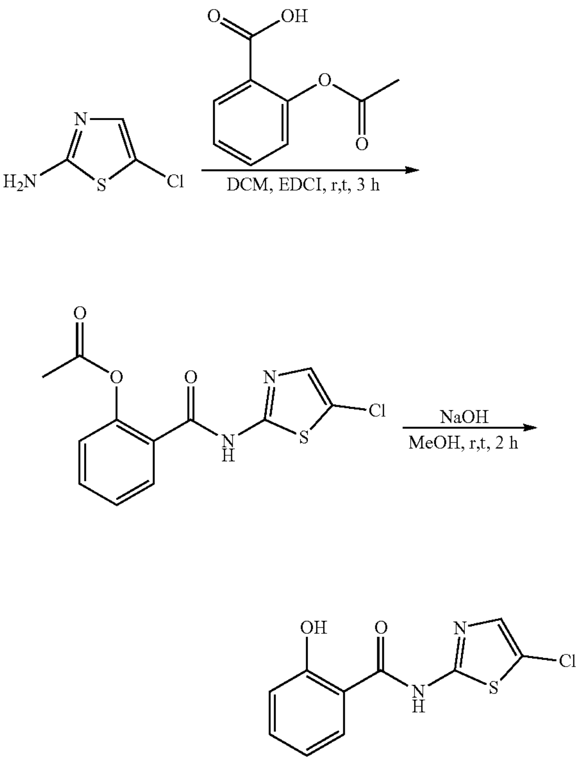

Step 1. Synthesis of 2-((5-chlorothiazol-2-yl)carbamoyl)phenyl acetate

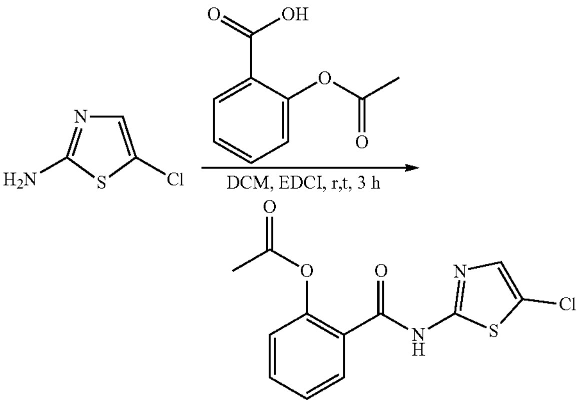

To a solution of 5-chlorothiazol-2-amine (350 mg, 2.61 mmol), 2-acetoxybenzoic acid (407 mg, 2.25 mmol) in DCM (30 mL) was added EDCI (784 mg, 4.10 mmol). After being stirred at it for 3 h, the mixture was concentrated. The resulting residue was purified by silica gel column chromatography (petroleum ether:EtOAc=1:1) to give the title compound (500 mg, crude) as yellow oil, which was used in the next step without further purification.

Step 2. Synthesis of 2-(methyl(5-nitrothiazol-2-yl)carbamoyl)phenyl acetate

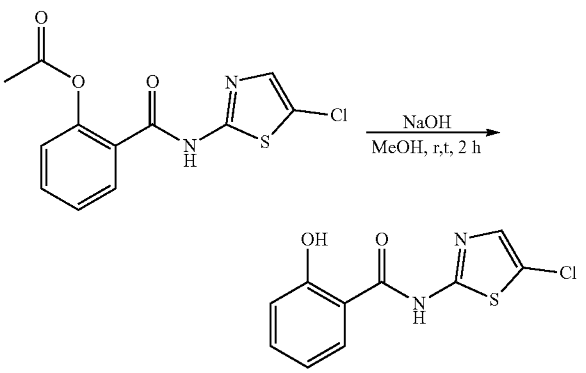

To a solution of 2-((5-chlorothiazol-2-yl)carbamoyl)phenyl acetate (200 mg, crude) in MeOH (5 mL) was added NaOH (1.00 g, 25.0 mmol). After being stirred at rt for 2 h, the reaction mixture was diluted with water (50 mL). After the pH value of the aqeuous phase was adjusted to 3 with 1 N HCl, the mixture was extracted with EtOAc (3x30 mL). The combined organic phase was dried over $Na_2SO_4$, filtered and concentrated. The resulting residue was recrystallized from MeOH to give the title compound (76.28 mg, 28.8% yield over two steps) as gray solid. $^1H$ NMR (400 MHz, DMSO-$d_6$): δ 12.24 (brs, 1H), 11.74 (brs, 1H), 7.96-7.93 (m, 1H), 7.61 (s, 1H), 7.50-7.46 (m, 1H), 7.05-6.98 (m, 2H). MS (ESI) m/z: 255.1 $[M+H]^+$.

Example 006. 2-(Methyl(5-nitrothiazol-2-yl)carbamoyl)phenyl acetate (B-6)

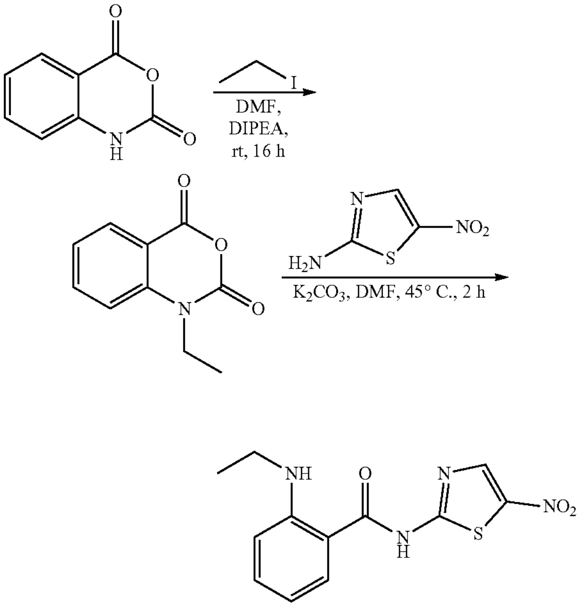

Step 1. Synthesis of 1-ethyl-2H-benzo[d][1,3]oxazine-2,4 (1H)-dione

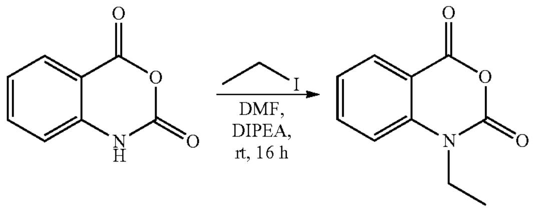

To a solution of 2H-benzo[d][1,3]oxazine-2,4 (1H)-dione (2.00 g, 12.2 mmol) and DIPEA (3.15 g, 24.4 mmol) in DMF (10 mL) was added iodoethane (3.00 g, 19.2 mmol). After being stirred at rt for 16 h, the mixture was concentrated. The resulting residue was purified by silica gel column chromatography (petroleum ether:EtOAc=2:1) to give the title compound (1.70 g, 34.9% yield) as white solid. MS (ESI) m/z: 192.2 $[M+H]^+$.

Step 2. Synthesis of 2-(methyl(5-nitrothiazol-2-yl)carbamoyl)phenyl acetate

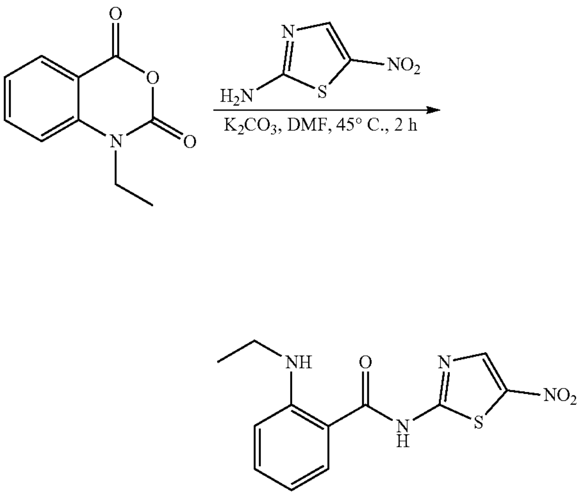

A solution of 1-ethyl-1H-benzo[d][1,3]oxazine-2,4-dione (400 mg, 2.09 mmol), 5-nitrothiazol-2-amine (334 mg, 2.30 mmol) and $K_2CO_3$ (865 mg, 6.27 mmol) in DMF (10 mL) was stirred at 45° C. for 2 h. After the mixture was cooled down to room, it was diluted with $H_2O$ (30 mL) and extracted with ethyl acetate (3x30 mL). The combined organic layer was washed with brine, dried over $Na_2SO_4$, filtered and concentrated. The resulting residue was purified by silica gel column chromatography (petroleum ether: EtOAc=1:1) to give the title compound (350 mg, 60% yield) as yellow solid. $^1H$ NMR (400 MHz, DMSO-$d_6$): δ 10.42 (s, 1H), 8.70 (s, 1H), 7.97 (dd, J=8.0, 1.4 Hz, 1H), 7.43-7.41 (m, 1H), 6.91 (d, J=8.4 Hz, 1H), 6.65-6.61 (m, 1H), 3.25 (q, J=3.24 Hz, 2H), 1.24 (t, J=7.2 Hz, 2H). MS (ESI) m/z: 293.1 $[M+H]^+$.

Example 007. 2-((4-Methyl-5-nitrothiazol-2-yl)carbamoyl)phenyl acetate (B-9)

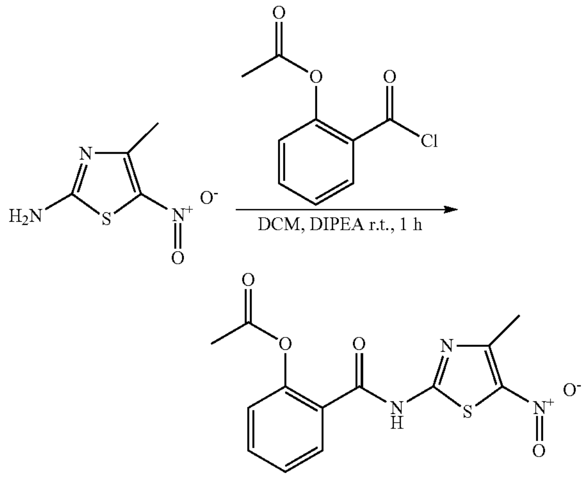

To a solution of 4-methyl-5-nitrothiazol-2-amine (250 mg, 1.57 mmol) in DCM (10 mL) were added DIPEA (609 mg, 4.71 mmol) and 2-(chlorocarbonyl)phenyl acetate (375 mg, 1.88 mmol). After being stirred at rt for 1 h, the mixture was diluted with DCM (50 mL), washed with 1 N HCl (50 mL) and brine (50 mL). The organic layer was dried over $Na_2SO_4$, filtered and concentrated. The resulting residue was purified by silica gel column chromatography (petroleum ether:EtOAc=3:1) and recrystallized from EtOAc (10 mL) to give the title compound (123 mg, 20.4% yield) as off-yellow solid. $^1H$ NMR (400 MHz, DMSO-$d_6$): δ 13.52 (s, 1H), 7.85-7.70 (m, 1H), 7.71-7.66 (m, 1H), 7.46-7.42 (m, 1H), 7.32-7.30 (m, 1H), 2.69 (s, 3H), 2.47 (s, 3H). MS (ESI) m/z: 322.3 $[M+H]^+$.

Example 008. $N^1$-Methyl-$N^2$-(5-nitrothiazol-2-yl) phthalamide (B-5)

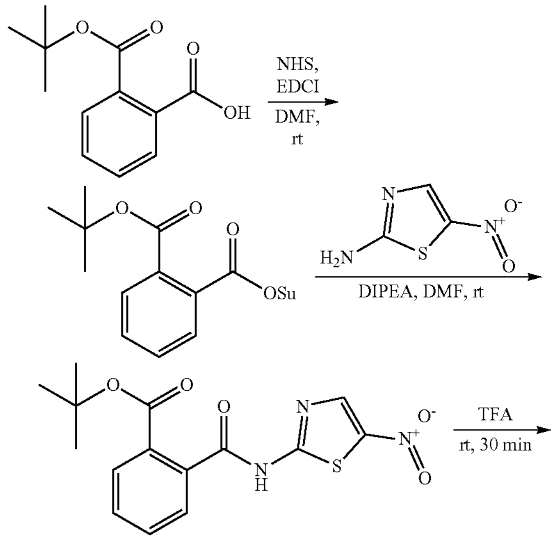

-continued

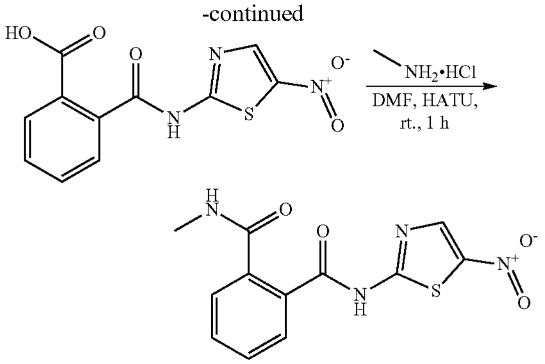

Step 1. Synthesis of tert-butyl (2,5-dioxopyrrolidin-1-yl) phthalate

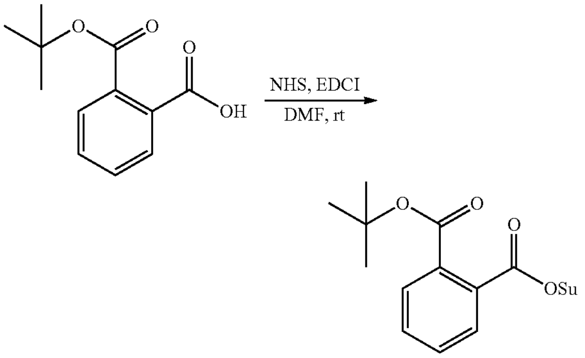

To a solution of 2-(tert-butoxycarbonyl)benzoic acid (2.00 g, 9.00 mmol) in DMF (20 mL) were added NHS (1.55 g, 13.5 mmol) and EDCI (3.45 g, 18.0 mmol). After being stirred at rt overnight, the reaction mixture was diluted with EtOAc (100 mL), washed with brine, dried over $Na_2SO_4$, filtered and concentrated. The resulting residue was purified by silica gel column chromatography (petroleum ether: EtOAc=1:1) to give the title compound (2.50 g, 87% yield) as white solid. MS (ESI) m/z: 264.1 $[M+H-56]^+$.

Step 2. Synthesis of tert-butyl 2-((5-nitrothiazol-2-yl)carbamoyl)benzoate

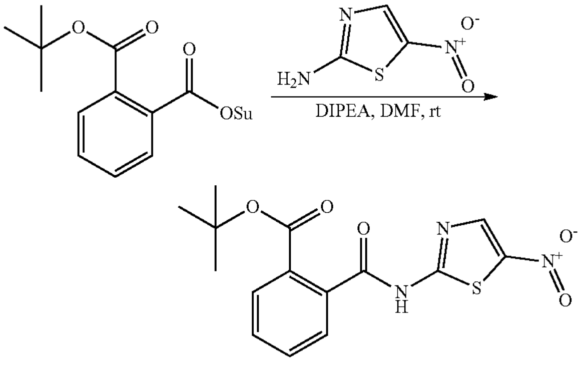

To a solution of tert-butyl (2,5-dioxopyrrolidin-1-yl) phthalate (2.50 g, 7.83 mmol) in DMF (20 mL) were added DMAP (4.78 g, 39.2 mmol) and 5-nitrothiazol-2-amine (3.41 g, 23.5 mmol). After being stirred at rt overnight, the reaction mixture was diluted with EtOAc (100 mL), washed with brine, dried over $Na_2SO_4$, filtered and concentrated. The resulting residue was purified by silica gel column chromatography (petroleum ether:EtOAc=1:1) to give the title compound (1.00 g, 36.6% yield) as off-yellow solid. MS (ESI) m/z: 348.2 $[M-H]^-$.

Step 3. Synthesis of 2-((5-nitrothiazol-2-yl)carbamoyl)benzoic acid

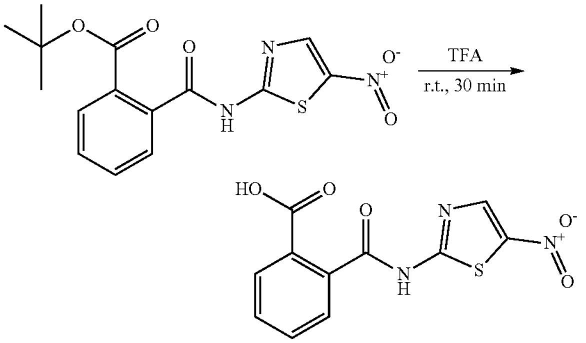

A solution of tert-butyl 2-((5-nitrothiazol-2-yl)carbamoyl)benzoate (1.00 g, 2.86 mmol) in TFA (2 mL) was stirred at rt for 30 min, before the reaction mixture was concentrated to give the title compound (900 mg, 100% crude yield) as white solid, which was used in the next step without further purification. MS (ESI) m/z: 294.2 $[M+H]^+$.

Step 4. Synthesis of $N^1$-methyl-$N^2$-(5-nitrothiazol-2-yl)phthalamide

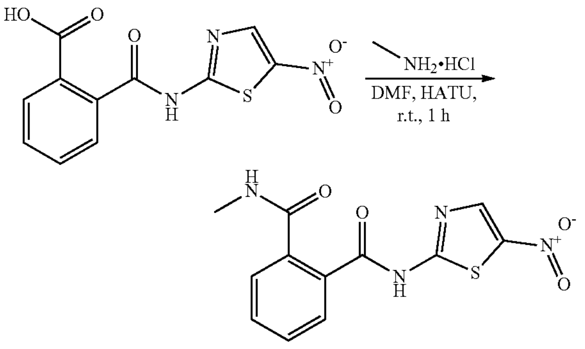

To a solution of 2-((5-nitrothiazol-2-yl)carbamoyl)benzoic acid (900 mg, crude) in DMF (5 mL) were added methylamine (3 mL, 2 M in THF) and HATU (2.17 g, 5.72 mmol). After being stirred at rt for 1 h, the pH value of the reaction mixture was adjusted to 7 with 1 N HCl. After the reaction mixture was extracted with EtOAc (3×50 mL), the combined organic layers were washed with brine, dried over $Na_2SO_4$, filtered and concentrated. The resulting residue was purified by silica gel column chromatography (100% EtOAc) and recrystallized from EtOAc to give the title compound (92.8 mg, 10.6% yield) as yellow solid. $^1H$ NMR (400 MHz, DMSO-$d_6$): δ 13.47 (s, 1H), 8.66 (s, 1H), 8.54-8.53 (m, 1H), 7.71-7.69 (m, 1H), 7.65-7.68 (m, 3H), 2.73 (d, J=4.4 Hz, 3H). MS (ESI) m/z: 305.2 $[M-H]^-$.

Example 009. 2-((5-Nitrothiazol-2-yl)carbamoyl)-5-(propylcarbamoyl)phenyl acetate (B-12)

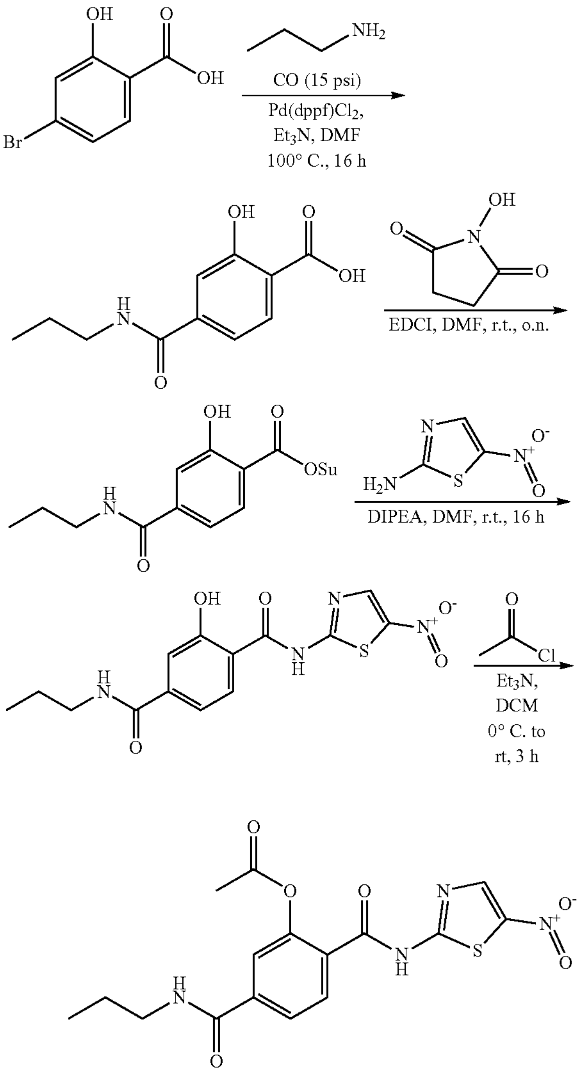

Step 1. Synthesis of 2-hydroxy-4-(propylcarbamoyl)benzoic acid

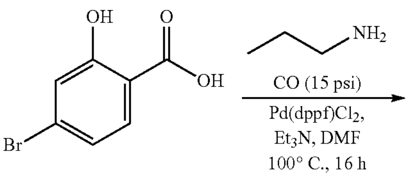

-continued

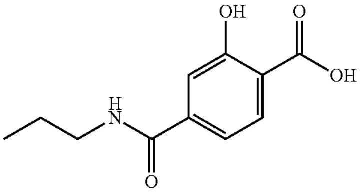

A solution of 4-bromo-2-hydroxybenzoic acid (3.00 g, 13.8 mmol), $Et_3N$ (4.18 g, 41.4 mmol), propan-1-amine (1.66 g, 27.6 mmol) and Pd(dppf)$Cl_2$ (1.01 g, 1.38 mmol) in DMF (100 mL) was stirred at 100° C. for 16 h under CO atmosphere (15 psi). At rt, the mixture was diluted with water (300 mL) and extracted with EtOAc (2×150 mL). The combined organic phase was dried over $Na_2SO_4$, filtered and concentrated to give the title compound (6.00 g, crude) as black oil, which was used in the next step without further purification. MS (ESI) m/z: 224.2 $[M+H]^+$.

Step 2. Synthesis of 2,5-dioxopyrrolidin-1-yl 2-hydroxy-4-(propylcarbamoyl)benzoate

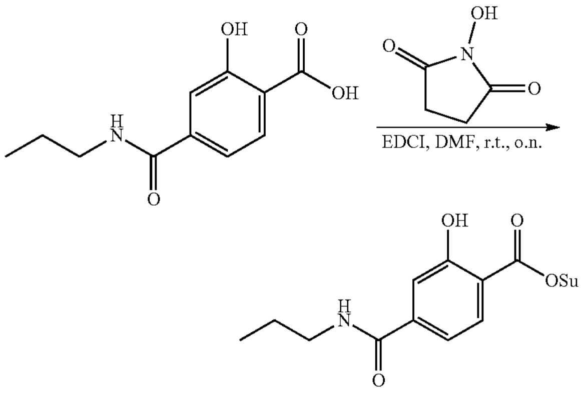

To a solution of 2-hydroxy-4-(propylcarbamoyl)benzoic acid (6.00 g, crude) in DMF (100 mL) were added 1-hydroxypyrrolidine-2,5-dione (1.90 g, 16.6 mmol) and EDCI (5.30 g, 27.6 mmol). After being stirred at it overnight, the mixture was diluted with water (300 mL) and extracted with EtOAc (3×300 mL). The combined organic phase was dried over $Na_2SO_4$, filtered and concentrated. The resulting residue was purified by silica gel column chromatography (petroleum ether:EtOAc=1:1) to give the title compound (1.90 g, 43.0% yield over two steps) as white solid. MS (ESI) m/z: 321.1 $[M+H]^-$.

Step 3. Synthesis of 2-hydroxy-$N^1$-(5-nitrothiazol-2-yl)-$N^1$-propylterephthalamide

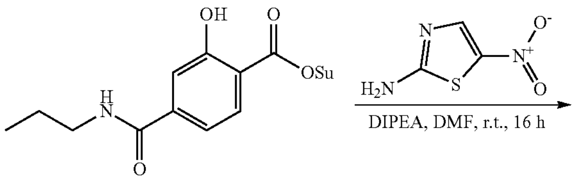

-continued

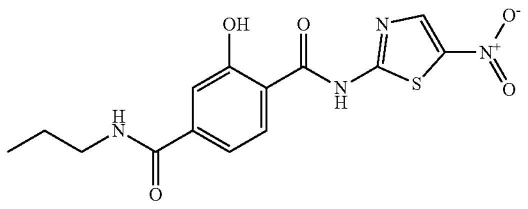

To a solution of 2,5-dioxopyrrolidin-1-yl 2-hydroxy-4-(propylcarbamoyl)benzoate (1.00 g, 3.12 mmol) and 5-nitrothiazol-2-amine in (907 mg, 6.24 mmol) in DMF (15 mL) was added DIPEA (806 mg, 6.25 mmol). After being stirred at rt for 16 h, the mixture was diluted with water (100 mL) and extracted with EtAOc (3×50 mL). The combined organic phase was dried over $Na_2SO_4$, filtered and concentrated. The resulting residue was purified by silica gel column chromatography (DCM:MeOH=1:1) to give the title compound (300 mg, 27.4% yield) as white solid. MS (ESI) m/z: 351.1 $[M+H]^+$.

Step 4. Synthesis of 2-((5-nitrothiazol-2-yl)carbamoyl)-5-(propylcarbamoyl)phenyl acetate

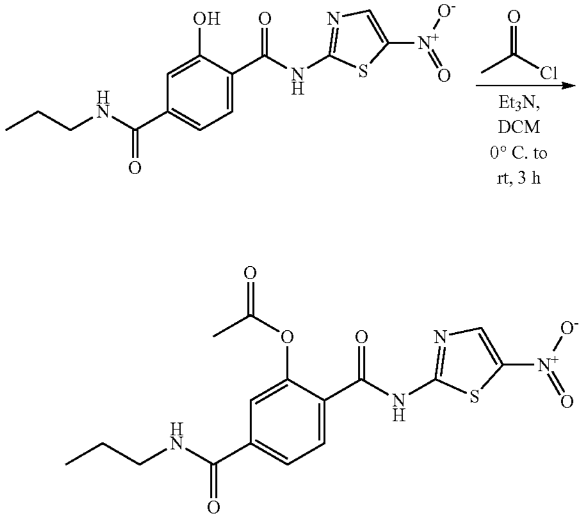

To a solution of 2-hydroxy-$N^1$-(5-nitrothiazol-2-yl)-N-propylterephthalamide (250 mg, 0.714 mmol) and $Et_3N$ (145 mg, 1.43 mmol) in DCM (10 mL) was added acetyl chloride (112 mg, 1.43 mmol) at 0° C. After being stirred at rt for 3 hours, the mixture was concentrated. The resulting residue was diluted with water (30 mL) and acidified with 1 N HCl to pH=3. The mixture was extracted with EtOAc (3×30 mL). The combined organic phase was dried over $Na_2SO_4$, filtered and concentrated. The resulting residue was purified by silica gel column chromatography (petroleum ether: EtOAc=1:1) to give the title compound (60.0 mg, 21.4% yield) as yellow solid. $^1H$ NMR (400 MHz, DMSO-$d_6$): δ 13.72 (brs, 1H), 8.71-8.65 (m, 2H), 7.95-7.93 (m, 1H), 7.89-7.86 (m, 1H), 7.74 (d, J=1.2 Hz, 1H), 3.26-3.21 (m, 2H), 2.27 (s, 3H), 1.56-1.54 (m, 2H), 0.90 (t, J=7.2 Hz, 3H). MS (ESI) m/z: 393.3 $[M+H]^+$.

Example 010. 4-Butyramido-2-((5-nitrothiazol-2-yl) carbamoyl)phenyl acetate (B-22)
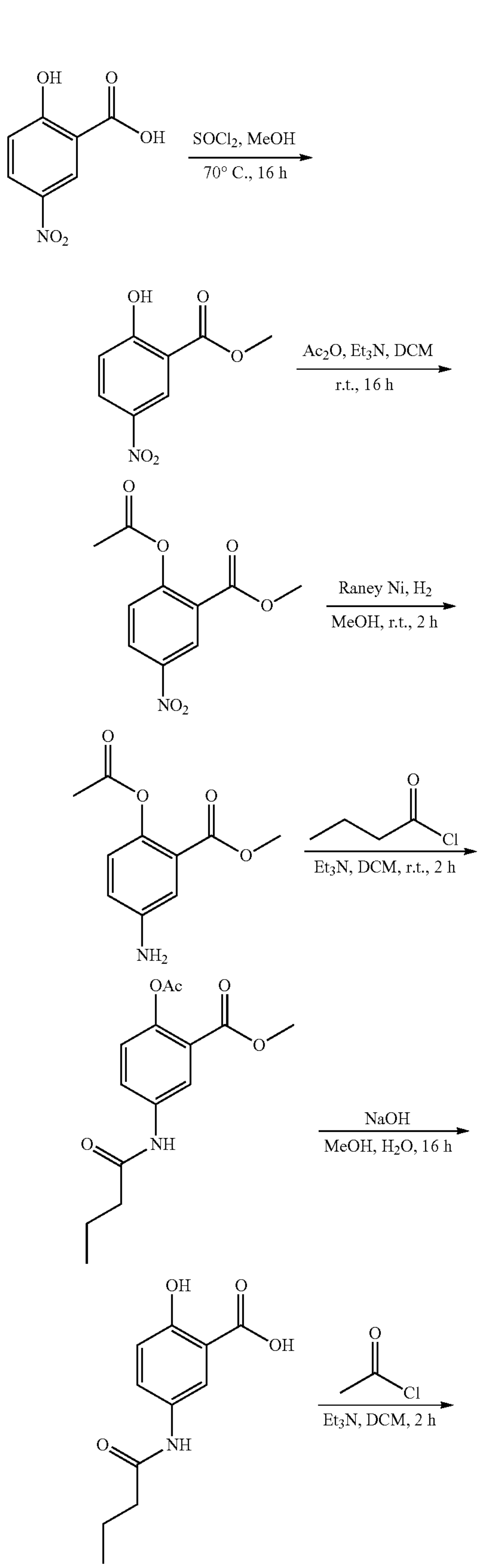
-continued
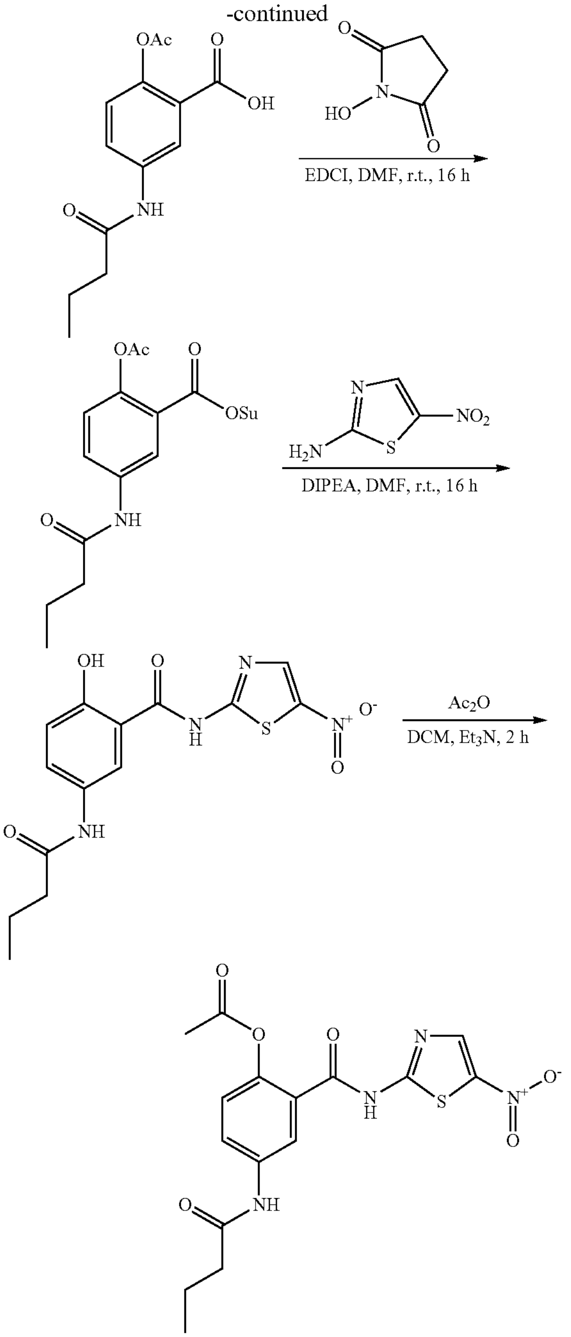
Step 1. Synthesis of methyl 2-hydroxy-5-nitrobenzoate
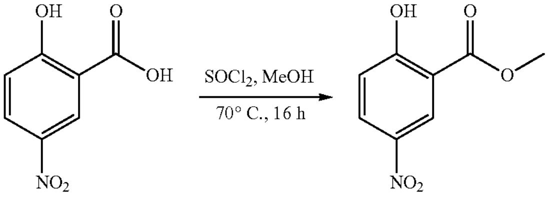

A solution of 2-hydroxy-5-nitrobenzoic acid (10.0 g, 54.6 mmol) and $SOCl_2$ (2 mL) in MeOH (100 mL) was stirred at 70° C. for 16 h, before the mixture was concentrated. The resulting residue was purified by silica gel column chromatography (petroleum ether:EtOAc=10:1) to give the title compound (10.0 g, 93.0% yield) as white solid.

Step 2. Synthesis of methyl 2-acetoxy-5-nitrobenzoate

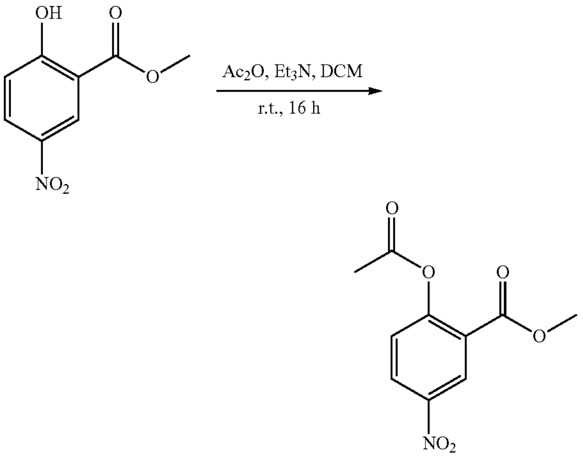

To a solution of methyl 2-hydroxy-5-nitrobenzoate (10.0 g, 50.7 mmol) and $Et_3N$ (12 mL) in DCM (200 mL) was added acetic anhydride (10.3 g, 101 mmol). After being stirred at rt for 16 h, the mixture was concentrated under vacuum. The resulting residue was purified by silica gel column chromatography (petroleum ether:EtOAc=10:1) to give the title compound (7.70 g, 64.0% yield) as white solid. $^1H$ NMR (400 MHz, DMSO-$d_6$): δ 8.66-8.65 (d, J=2.8 Hz, 1H), 8.52 (dd, J=8.8, 2.8 Hz, 1H), 7.58 (d, J=8.8 Hz, 1H), 3.88 (s, 3H), 2.34 (s, 3H).

Step 3. Synthesis of methyl 2-acetoxy-5-aminobenzoate

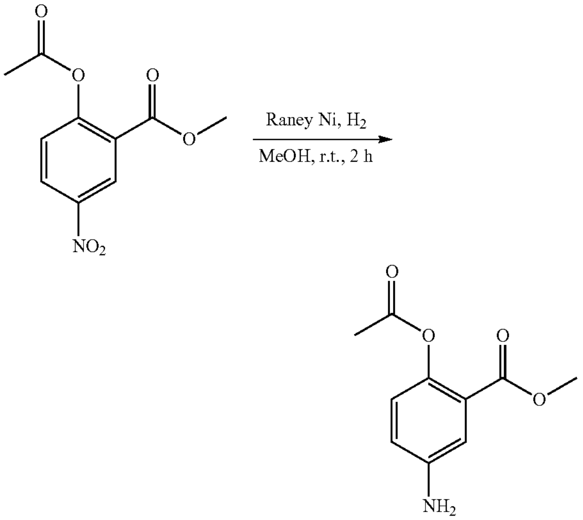

A solution of methyl 2-acetoxy-5-nitrobenzoate (7.70 g, 32.2 mmol) and Raney Ni (1.00 g) in MeOH (200 mL) was stirred at rt for 2 h under $H_2$ balloon. After the mixture was filtered, the filtrate was concentrated under vacuum to give the title compound (7.00 g, crude) as yellow solid, which was used in the next step without further purification. MS (ESI) m/z: 210.2 $[M+H]^+$.

Step 4. Synthesis of methyl 2-acetoxy-5-butyramidobenzoate

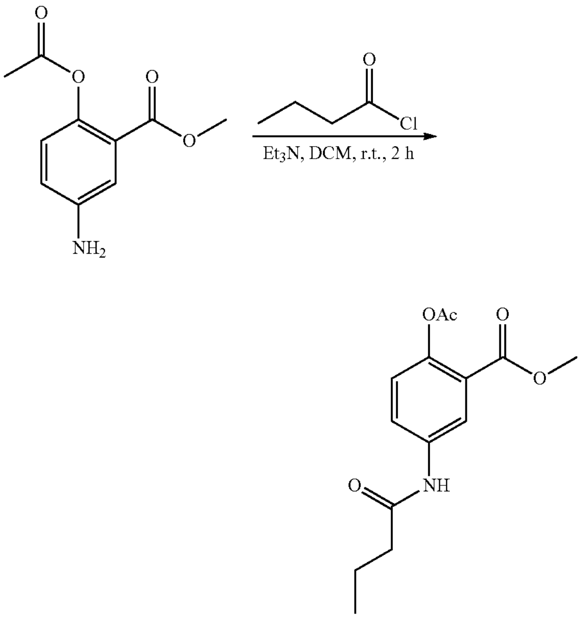

To a solution of methyl 2-acetoxy-5-aminobenzoate (2.50 g, crude) and $Et_3N$ (5 mL) in DCM (100 mL) was added butyryl chloride (1.25 mL) at 0° C. After being stirred at 0° C. for 2 h, the mixture was concentrated under vacuum. The resulting residue was purified by silica gel column chromatography (petroleum ether:EtOAc=2:1) to give the title compound (3.00 g, 93.4% yield over two steps) as yellow solid. MS (ESI) m/z: 280.1 $[M+H]^+$.

Step 5. Synthesis of 5-butyramido-2-hydroxybenzoic acid

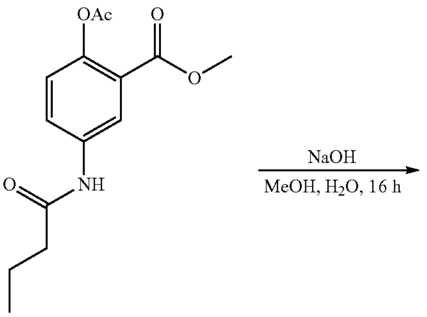

-continued

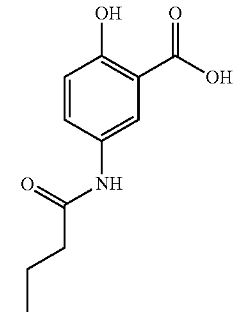

A solution of methyl 2-acetoxy-5-butyramidobenzoate (3.00 g, 10.7 mmol) and NaOH (2.50 g, 64.2 mmol) in $MeOH/H_2O$ (50 mL/20 mL) was stirred at rt for 16 h. After the pH value of the mixture was adjusted to 4 with 1 N aq. HCl, the mixture was extracted with EtOAc (3×30 mL). The combined organic phase was washed with brine (3×30 mL), dried over $Na_2SO_4$, filtered and concentrated under vacuum to give the title compound (2.40 g, crude) as yellow solid, which was used in the next step without further purification. MS (ESI) m/z: 224.2 $[M+H]^+$.

Step 6. Synthesis of 2-acetoxy-5-butyramidobenzoic acid

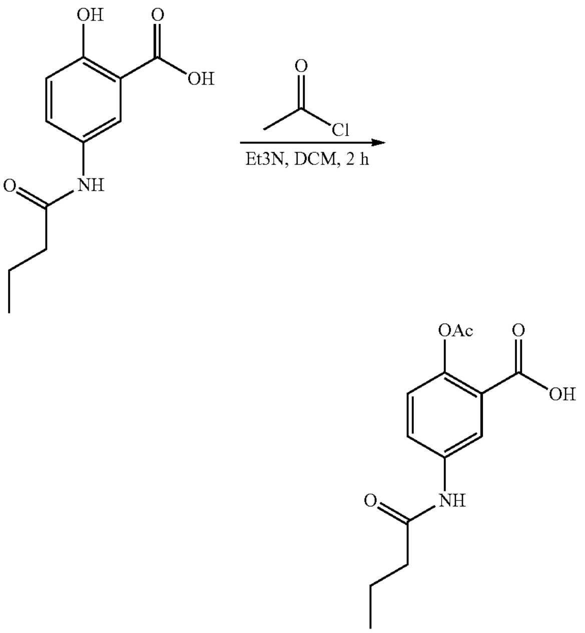

To a solution of 5-butyramido-2-hydroxybenzoic acid (1.30 g, crude) and $Et_3N$ (2 mL, 15.0 mmol) in DCM (60 mL) was added acetyl chloride (910 mg, 11.6 mmol) at 0° C. After being stirred at 0° C. for 2 h, the mixture was concentrated under vacuum. The resulting residue was purified by silica gel column chromatography (DCM: MeOH=10:1) to give the title compound (1.00 g, 61.8% yield over two steps) as yellow solid. MS (ESI) m/z: 264.2 $[M-H]^-$.

Step 7. Synthesis of 2,5-dioxopyrrolidin-1-yl 2-acetoxy-5-butyramidobenzoate

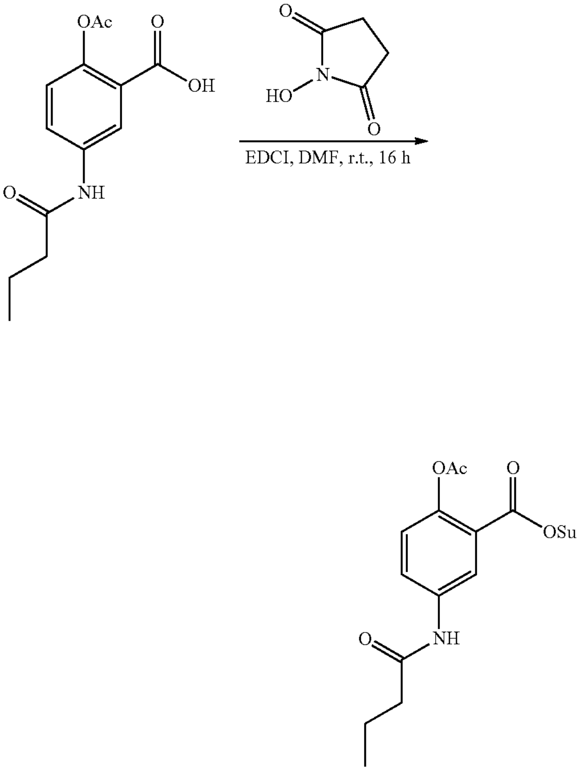

A solution of 2-acetoxy-5-butyramidobenzoic acid (1.00 g, 3.77 mmol), 1-hydroxypyrrolidine-2,5-dione (0.52 g, 4.53 mmol) and EDCI (1.08 g, 5.65 mmol) in DMF (20 mL) was stirred at rt for 16 h. After the mixture was diluted with $H_2O$ (30 mL), the mixture was extracted with EtOAc (3×30 mL). The combined organic layers were washed with brine (3×30 mL), dried over $Na_2SO_4$, filtered and concentrated under vacuum. The resulting residue was purified by silica gel column chromatography (petroleum ether:EtOAc=1:2) to give the title compound (0.90 g, 73.0% yield) as yellow solid. MS (ESI) m/z: 363.1 $[M+H]^+$.

Step 8. Synthesis of 5-butyramido-2-hydroxy-N-(5-nitrothiazol-2-yl)benzamide

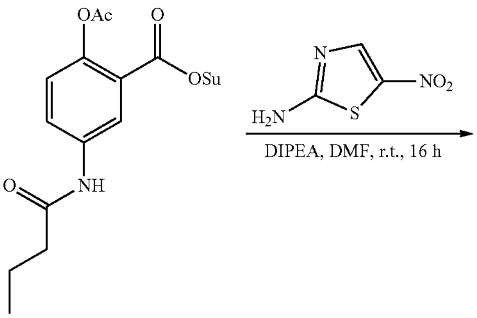

-continued

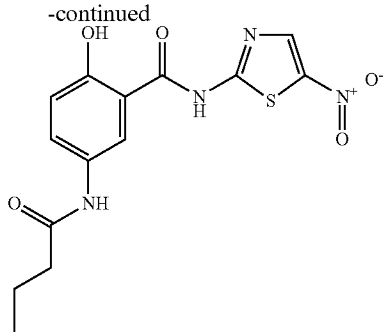

A solution of 2,5-dioxopyrrolidin-1-yl 2-acetoxy-5-butyramidobenzoate (0.70 g, 1.93 mmol), 5-nitrothiazol-2-amine (0.56 g, 3.87 mmol) and DIEA (1.5 mL) in DMF (10 mL) was stirred at rt for 16 h. After the mixture was diluted with $H_2O$ (30 mL), the mixture was extracted with EtOAc (3×30 mL). The combined organic layers were washed with brine (3×30 mL), dried over $Na_2SO_4$, filtered and concentrated under vacuum. The resulting residue was purified by silica gel column chromatography (DCM:MeOH=10:1) to give the title compound (0.42 g, 62.0% yield) as yellow solid. MS (ESI) m/z: 351.1 $[M+H]^+$.

Step 9. Synthesis of 4-butyramido-2-((5-nitrothiazol-2-yl)carbamoyl)phenyl acetate

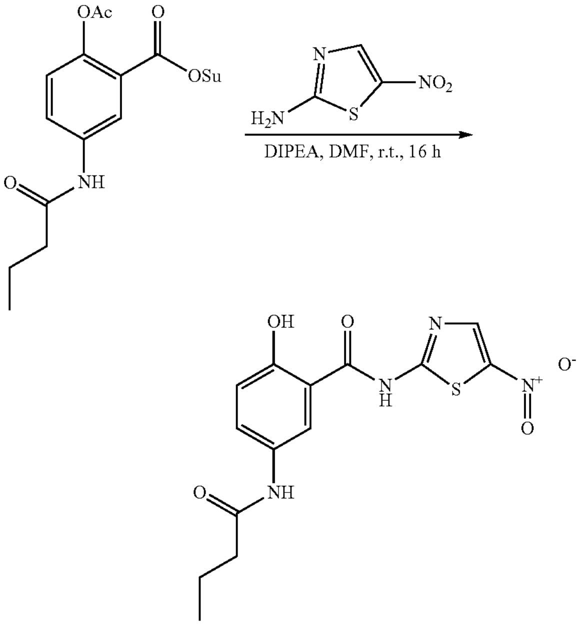

To a solution of 5-butyramido-2-hydroxy-N-(5-nitrothiazol-2-yl)benzamide (0.20 g, 0.57 mmol) and TEA (0.38 g, 3.76 mmol) in DCM (20 mL) was added acetyl chloride (0.55 g, 7.00 mmol) at 0° C. After being stirred at 0° C. for 2 h, the mixture was diluted with $MeOH/H_2O$ (20 mL/5 mL). After the pH of the mixture was adjusted to 5 with 2 N HCl at 0° C. the mixture was extracted with EtOAc (3×30 mL). The combined ethyl acetate layers were washed with $NaHCO_3$ (10% aqueous solution) and brine, dried over $Na_2SO_4$, filtered and concentrated under vacuum. The resulting residue was triturated with EtOAc (5 mL) to give the title compound (50.0 mg, 22.0% yield) as yellow solid. $^1H$ NMR (400 MHz, DMSO-$d_6$): δ 13.63 (s, 1H), 10.19 (s, 1H), 8.70 (s, 1H), 8.09 (d, J=2.4 Hz, 1H), 7.80 (dd, J=8.8, 2.5 Hz, 1H), 7.24 (d, J=8.8 Hz, 1H), 2.32 (t, J=7.2 Hz, 2H), 2.21 (s, 3H), 1.65-1.60 (m, 2H), 0.93 (t, J=7.4 Hz, 3H). MS (ESI) m/z: 393.1 $[M+H]^+$.

Example 011. 4-(Butylamino)-2-((5-nitrothiazol-2-yl)carbamoyl)phenyl acetate

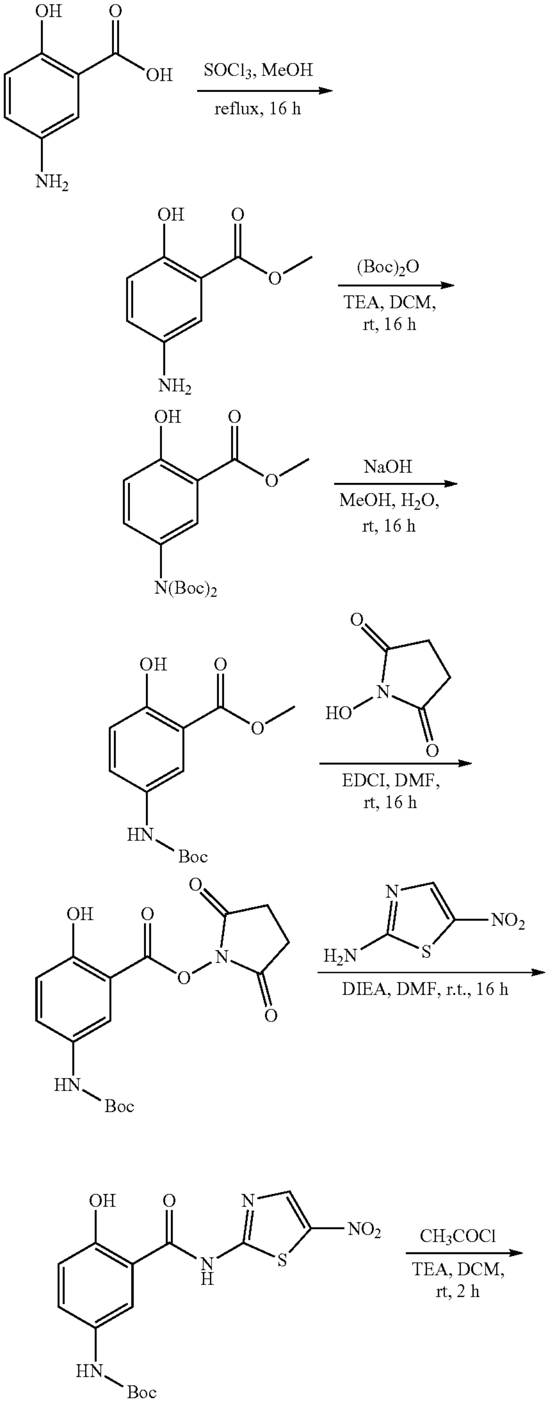

-continued

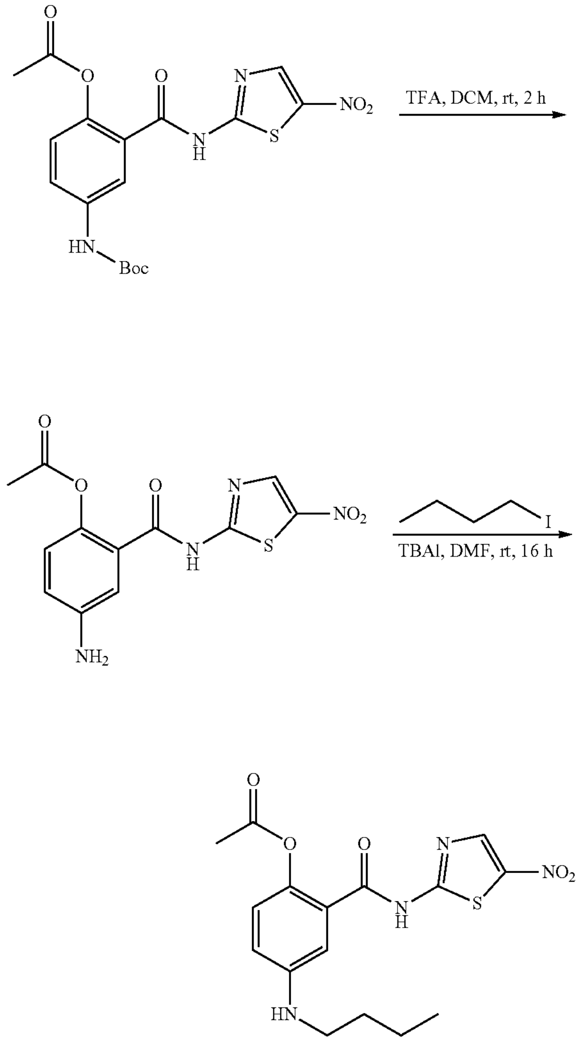

Step 1. Synthesis of methyl 5-amino-2-hydroxybenzoate

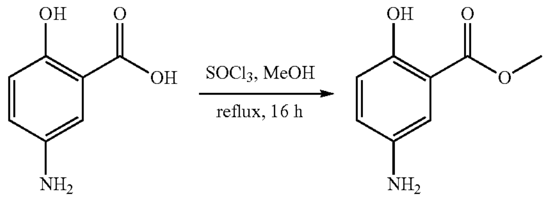

A solution of 5-amino-2-hydroxybenzoic acid (5.00 g, 32.6 mmol) and $H_2SO_4$ (2.00 mL) in MeOH (100 mL) was refluxed for 16 h. After the reaction mixture was cooled down to 0° C., the pH of the mixture was adjusted to 8~9 with 1 N NaOH. The resulting mixture was extracted with EtOAc (3x30 mL). The combined organic layers were washed with brine (3x30 mL), dried over $Na_2SO_4$, filtered and concentrated to give the title compound (10.0 g, 92.0% yield) as yellow solid. MS (ESI) m/z: 168.1 $[M+H]^+$.

Step 2. Synthesis of methyl 5,5'-((tert-butoxycarbonyl)amino)-2-hydroxybenzoate

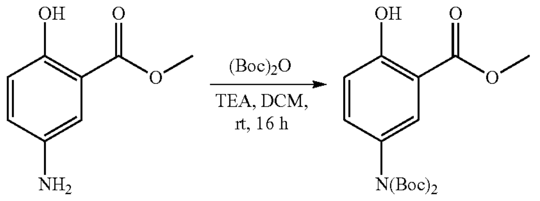

A solution of methyl 5-amino-2-hydroxybenzoate (4.00 g, 24.0 mmol), TEA (9.70 g, 96.0 mmol) and $(Boc)_2O$ (15.6 g, 71.8 mmol) in DCM (200 mL) was stirred at rt for 16 h. The reaction mixture was concentrated under reduced pressure and purified by silica gel column chromatography (petroleum ether:EtOAc=3:1) to give the title compounds (4.7 g, 53.0% yield yield) as white solid.

Step 3. Synthesis of methyl 5-((tert-butoxycarbonyl)amino)-2-hydroxybenzoate

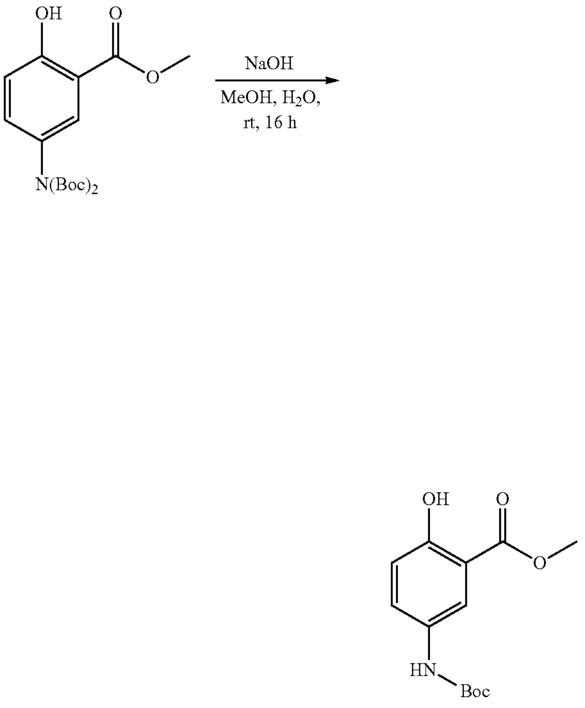

A solution of methyl 5,5'-((tert-butoxycarbonyl)amino)-2-hydroxybenzoate (4.70 g, 12.8 mmol) and NaOH (2.50 g, 64.0 mmol) in MeOH/$H_2O$ (100 mL/10 mL) was stirred at rt for 16 h. After the reaction mixture was cooled down to 0° C., the pH of the mixture was adjusted to 5 with 1 N HCl. The mixture was extracted with EtOAc (3x30 mL). The combined organic layers were washed with brine (3x30 mL), dried over $Na_2SO_4$, filtered and concentrated under reduced pressure to give the title compound (2.8 g, 87.5% yield) as yellow solid. MS (ESI) m/z: 252.2 $[M-H]^-$.

Step 4. Synthesis of 2,5-dioxopyrrolidin-1-yl 5-((tert-butoxycarbonyl)amino)-2-hydroxybenzoate

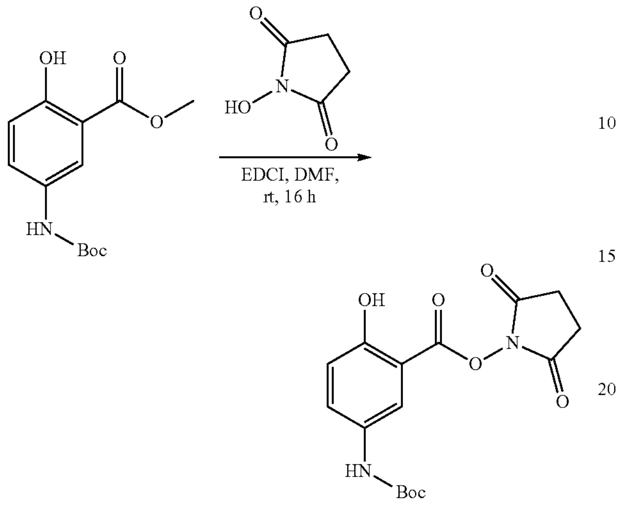

A solution of 5-((tert-butoxycarbonyl)amino)-2-hydroxybenzoic acid (1.20 g, 4.76 mmol), 1-hydroxypyrrolidine-2,5-dione (1.10 g, 9.52 mmol) and EDCI (1.80 g, 9.52 mmol) in DMF (20 mL) was stirred at rt for 16 h. After the mixture was diluted with $H_2O$ (30 mL), the mixture was extracted with EtOAc (3×30 mL). The combined organic layers were washed with brine (3×30 mL), dried over $Na_2SO_4$, filtered and concentrated under vacuum. The resulting residue was purified by silica gel column chromatography (petroleum ether:EtOAc=1:1) to give the title compound (1.00 g, 63.0% yield) as yellow solid. MS (ESI) m/z: 349.2 $[M-H]^-$.

Step 5. Synthesis of tert-butyl (4-hydroxy-3-((5-nitrothiazol-2-yl)carbamoyl)phenyl)carbamate

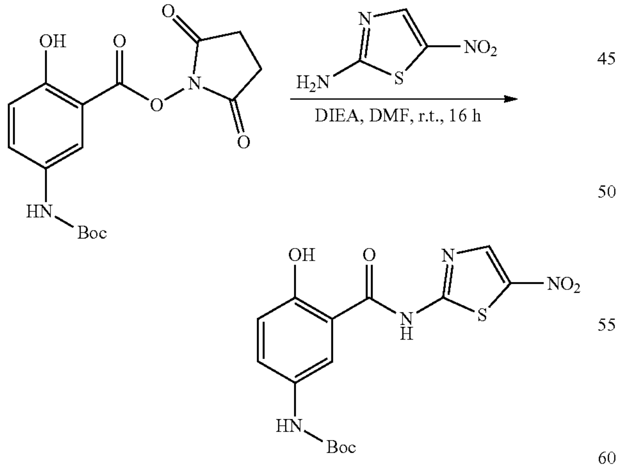

A solution of 2,5-dioxopyrrolidin-1-yl 5-((tert-butoxycarbonyl)amino)-2-hydroxybenzoate (1.00 g, 2.86 mmol), 5-nitrothiazol-2-amine (0.83 g, 5.71 mmol) and DIEA (2 mL) in DMF (10 mL) was stirred at rt for 16 h. After the mixture was diluted with $H_2O$ (30 mL), the mixture was extracted with EtOAc (3×30 mL). The combined organic layers were washed with brine (3×30 mL), dried over $Na_2SO_4$, filtered and concentrated under vacuum. The resulting residue was purified by silica gel column chromatography (DCM:MeOH=10:1) to give the title compound (1.00 g, 100% yield) as yellow solid. MS (ESI) m/z: 381.1 $[M+H]^+$.

Step 6. Synthesis of 4-((tert-butoxycarbonyl)amino)-2-((5-nitrothiazol-2-yl)carbamoyl)phenyl acetate

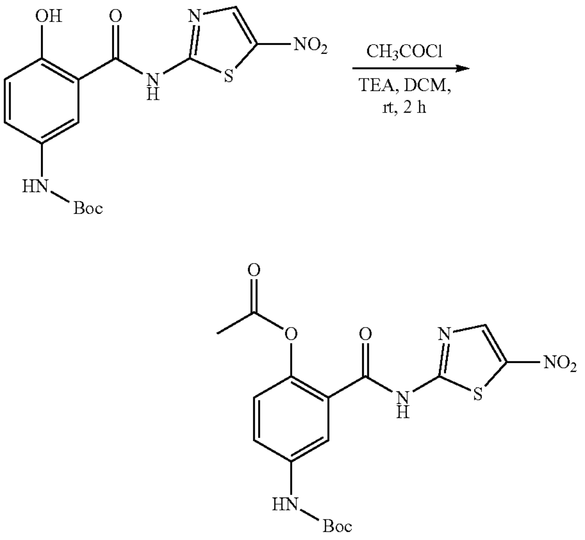

To a solution of tert-butyl (4-hydroxy-3-((5-nitrothiazol-2-yl)carbamoyl)phenyl)carbamate (1.00 g, 2.63 mmol) and TEA (1 mL, 7.50 mmol) in DCM (20 mL) was added acetyl chloride (1 mL) at 0° C. After being stirred at rt for 2 h. the mixture was concentrated under reduced pressure at rt. After the resulting residue was diluted with MeOH (20 mL) and $H_2O$ (5 mL) at 0° C., the mixture was acidified with 1 N HCl (pH=5). The mixture was extracted with EtOAc (3×50 mL). The combined EtOAc layers were washed with $NaHCO_3$ (10% aqueous solution) and brine, dried over $Na_2SO_4$, concentrated to give the title compound (0.90 g, 82.0% yield) as yellow solid.

Step 7. Synthesis of 4-amino-2-((5-nitrothiazol-2-yl)carbamoyl)phenyl acetate

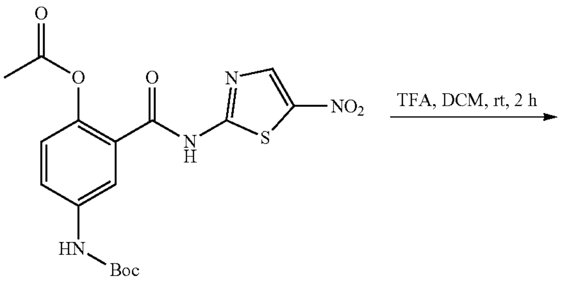

-continued

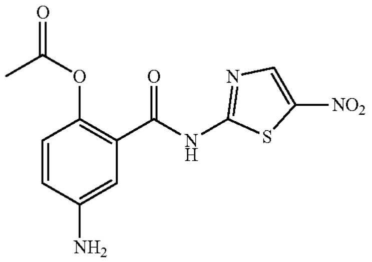

A solution of 4-((tert-butoxycarbonyl)amino)-2-((5-nitrothiazol-2-yl)carbamoyl)phenyl acetate (1.00 g, 2.36 mmol) and TFA (10 mL) in DCM (10 mL) was stirred at rt for 2 h. The mixture was washed with $NaHCO_3$ (10% aqueous solution) and water, dried over $Na_2SO_4$, filtered and concentrated under vacuum to give the title compound (460 mg, 61.0% yield) as yellow solid. MS (ESI) m/z: 323.1 $[M+H]^-$.

Step 8. Synthesis of 4-(butylamino)-2-((5-nitrothiazol-2-yl)carbamoyl)phenyl acetate

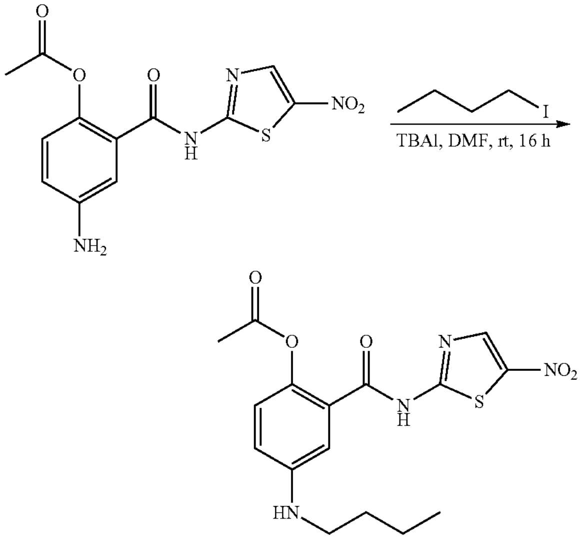

A solution of 4-amino-2-((5-nitrothiazol-2-yl)carbamoyl)phenyl acetate (0.20 g, 0.62 mmol), 5-nitrothiazol-2-amine (0.83 g, 5.71 mmol), 1-iodobutane (0.57 g, 3.10 mmol) and TBAI (0.46 g, 1.24 mmol) in DMF (5 mL) was stirred at it for 16 h. After the mixture was diluted with $H_2O$ (30 mL), the mixture was extracted with EtOAc (3x30 mL). The combined organic layers were washed with brine (3x30 mL), dried over $Na_2SO_4$, filtered and concentrated under vacuum. The resulting residue was purified by silica gel column chromatography (petroleum ether:EtOAc=2:1) to give the title compound (130 mg, 55.0% yield) as yellow solid. $^1$HNMR (400 MHz, DMSO-$d_6$): δ 13.44 (s, 1H), 8.68 (s, 1H), 6.97 (d, J=8.8 Hz, 1H), 6.88 (d, J=2.8 Hz, 1H), 6.78 (dd, J=8.8, 2.8 Hz, 1H), 5.92 (s, 1H), 3.07-3.03 (m, 2H), 2.17 (s, 3H), 1.57-1.51 (m, 2H), 1.42-1.37 (m, 2H), 0.92 (t, J=7.2 Hz, 3H). MS (ESI) m/z: 379.1 $[M+H]^+$.

Example 012. 5-Butyramido-2-((5-nitrothiazol-2-yl)carbamoyl)phenyl acetate (B-21)

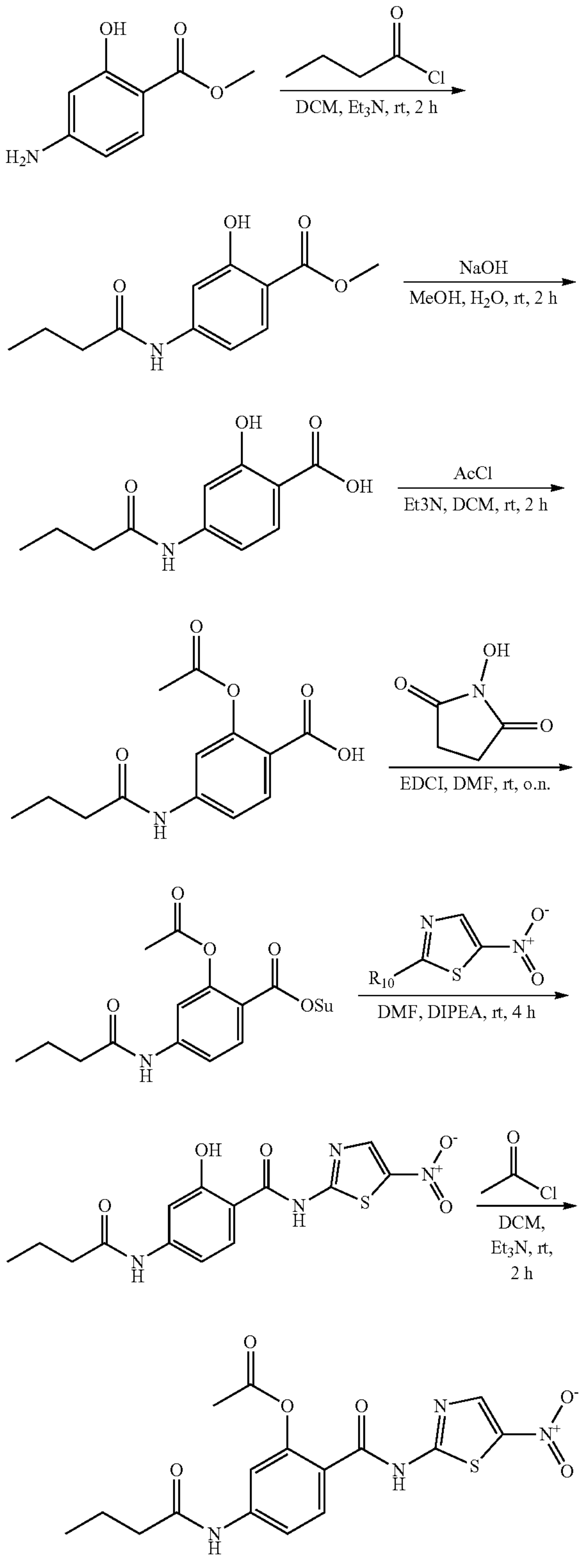

Step 1. Synthesis of methyl 4-butyramido-2-hydroxybenzoate

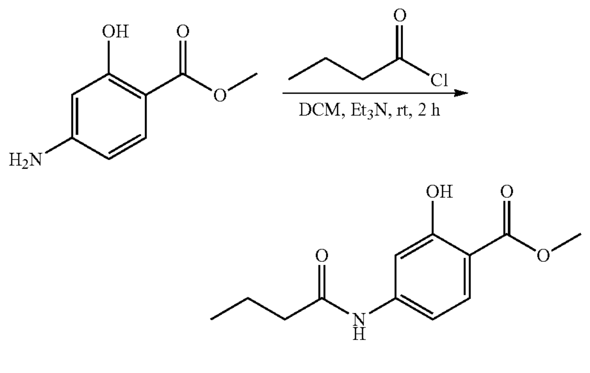

To a solution of methyl 4-amino-2-hydroxybenzoate (2.00 g, 12.0 mmol) and $Et_3N$ (3.64 g, 35.9 mmol) in DCM (60 mL) was added butyryl chloride (2.56 g, 24.0 mmol) dropwise at 0° C. After being stirred at rt for 2 h, the mixture was concentrated under vacuum. After the residue was diluted with water (100 mL), the pH of the mixture was adjusted to 4 with 1 N aq. HCl. The mixture was extracted with EtOAc (3×50 mL). The combined organic phase was dried over $Na_2SO_4$, filtered and concentrated under vacuum to give the crude title compound (3.50 g, crude) as colorless oil, which was used in the next step without further purification. MS (ESI) m/z: 238.2 $[M+H]^+$.

Step 2. Synthesis of 4-butyramido-2-hydroxybenzoic acid

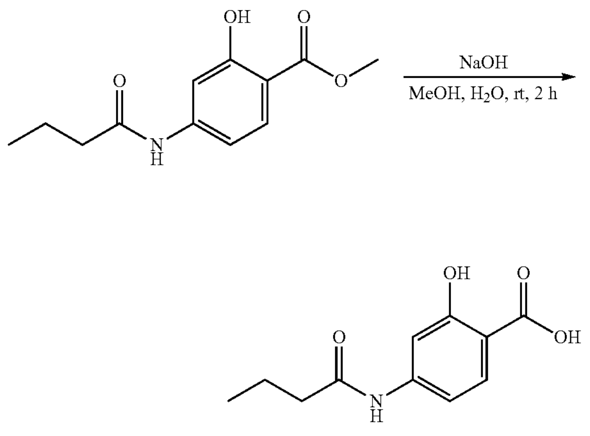

To a solution of methyl 4-butyramido-2-hydroxybenzoate (3.50 g, crude) in MeOH (15 mL) and $H_2O$ (15 mL) was added NaOH (10.0 g, 250 mmol). After being stirred at rt for 2 h, the mixture was diluted with water (50 mL). After the pH of the mixture was adjusted to 3 with 1 N aq. HCl, it was extracted with EtOAc (3×30 mL). The combined organic phase was dried over $Na_2SO_4$, filtered and concentrated under vacuum to give the title compound (1.70 g, 63.6% yield over two steps) as colorless oil. MS (ESI) m/z: 224.2 $[M+H]^+$.

Step 3. Synthesis of 2-acetoxy-4-butyramidobenzoic acid

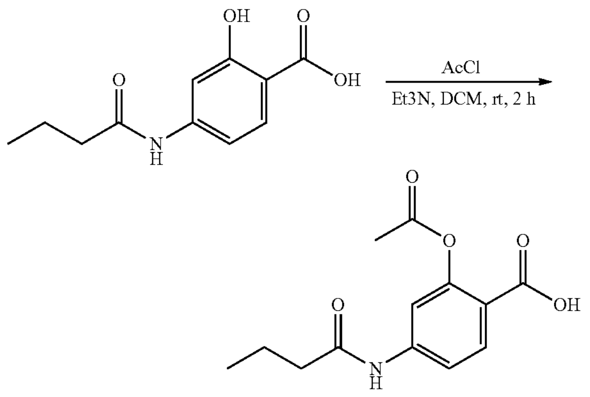

To a solution of 4-butyramido-2-hydroxybenzoic acid (1.00 g, 4.49 mmol) and $Et_3N$ (1.36 g, 13.4 mmol) in DCM (20 mL) was added acetyl chloride (705 mg, 8.98 mmol). After being stirred at rt for 2 h, the mixture was concentrated under vacuum and diluted with water (50 mL). After the pH of the mixture was adjusted to 4 with 1 N aq. HCl, the mixture was extracted with EtOAc (3×30 mL). The combined organic phase was dried over $Na_2SO_4$, filtered and concentrated under vacuum to give the crude title compound (1.00 g, crude) as colorless oil, which was used in the next step without further purification. MS (ESI) m/z: 266.3 $[M+]^+$.

Step 4. Synthesis of 2,5-dioxopyrrolidin-1-yl 2-acetoxy-4-butyramidobenzoate

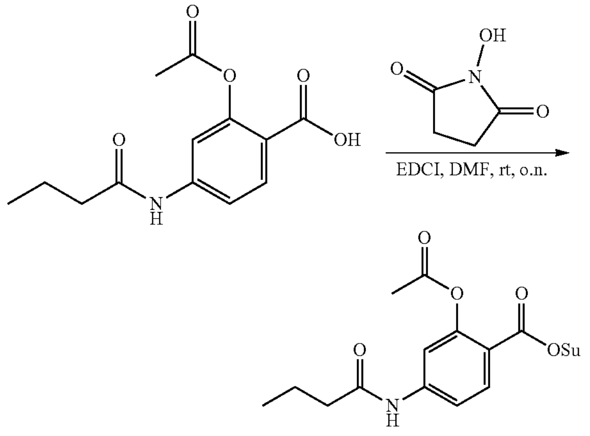

To a solution of 2-acetoxy-4-butyramidobenzoic acid (1.00 g, crude) in DMF (20 mL) were added 1-hydroxypyrrolidine-2,5-dione (868 mg, 7.55 mmol) and EDCI (1.81 g, 9.43 mmol). After being stirred at rt overnight, the mixture was diluted with water (200 mL) and extracted with EtOAc (3×100 mL). The combined organic phase was dried over $Na_2SO_4$, filtered and concentrated under vacuum. The resulting residue was purified by silica gel column chromatography (petroleum ether:EtOAc=5:1) to give the title compound (1.00 g, 61.5% yield) as white solid. MS (ESI) m/z: 361.2 $[M-H]^-$.

Step 5. Synthesis of 4-butyramido-2-hydroxy-N-(5-nitrothiazol-2-yl)benzamide

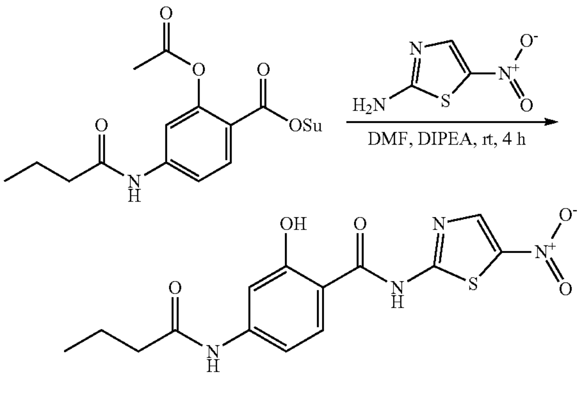

A solution of 2,5-dioxopyrrolidin-1-yl 2-acetoxy-4-butyramidobenzoate (1.00 g, 2.76 mmol), 5-nitrothiazol-2-amine in (784 mg, 5.52 mmol) and DIPEA (1.07 g, 8.28 mmol) in DMF (15 mL) was stirred at rt for 4 h, at which time the mixture was diluted with water (100 mL) and extracted with EtOAc (3×50 mL). The combined organic phase was dried over $Na_2SO_4$, filtered and concentrated under vacuum. The resulting residue was purified by silica gel column chromatography (DCM:MeOH=1:1) to give the title compound (190 mg, 19.7% yield) as yellow solid. MS (ESI) m/z: 351.1 $[M+H]^+$.

Step 6. Synthesis of 5-butyramido-2-((5-nitrothiazol-2-yl)carbamoyl)phenyl acetate

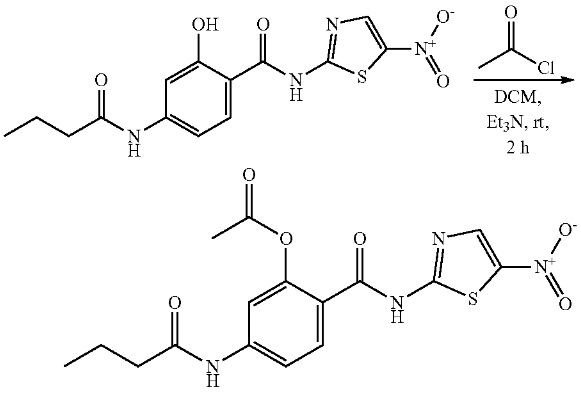

To a solution of 4-butyramido-2-hydroxy-N-(5-nitrothiazol-2-yl)benzamide (100 mg, 0.287 mmol) and $Et_3N$ (116 mg, 1.15 mmol) in DCM (20 mL) was added acetyl chloride (68 mg, 0.861 mmol) at 0° C. After being stirred at it for 2 h, the mixture was concentrated under vacuum. After the residue was diluted with water (20 mL), the pH of the mixture was adjusted to 3 with 1 N aq. HCl. The mixture was extracted with EtOAc (3×15 mL). The combined organic phase was dried over $Na_2SO_4$, filtered and concentrated under vacuum. The resulting residue was purified by silica gel column chromatography (petroleum ether:EtOAc=1:1) to give the title compound (22.0 mg, 19.6% yield) as white solid. $^1H$ NMR (400 MHz, DMSO-$d_6$): δ 13.44 (brs, 1H), 10.35 (s, 1H), 8.69 (s, 1H), 7.84 (d, J=8.4 Hz, 1H), 7.65 (d, J=2.0 Hz, 1H), 7.55-7.51 (m, 1H), 2.34 (t, J=7.2 Hz, 2H), 2.26 (s, 3H), 1.63-1.61 (m, 2H), 0.92 (t, J=7.2 Hz, 3H). MS (ESI) m/z: 393.3 $[M+H]^+$.

Example 013. 3-(Butylamino)-2-((5-nitrothiazol-2-yl)carbamoyl)phenyl acetate (B-19)

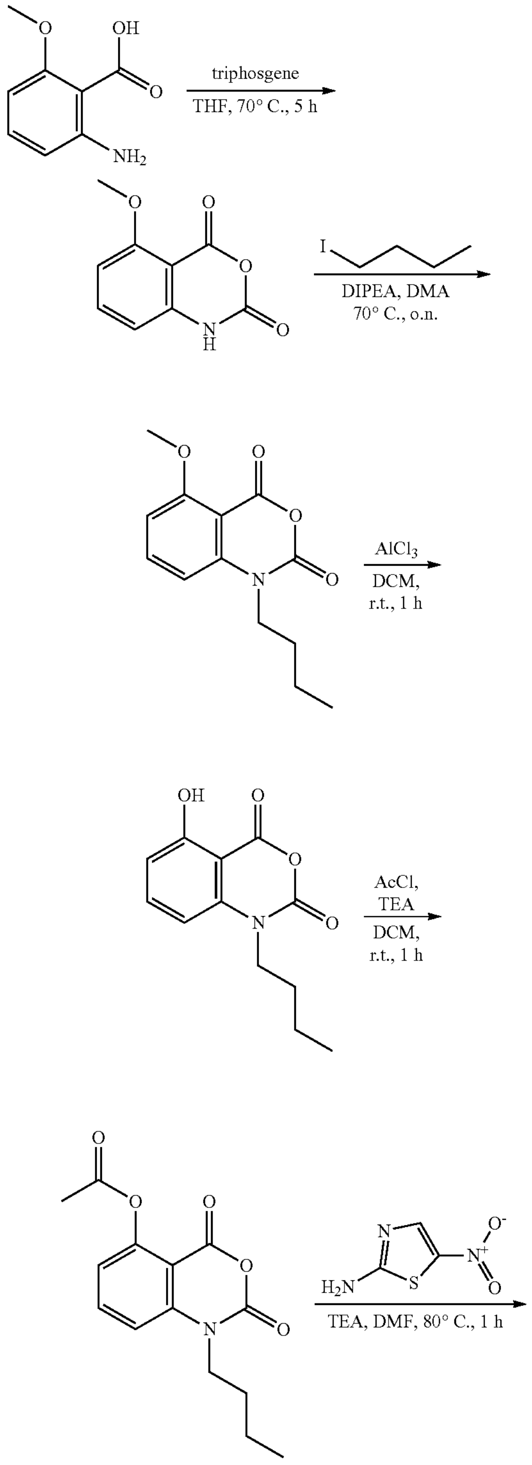

-continued

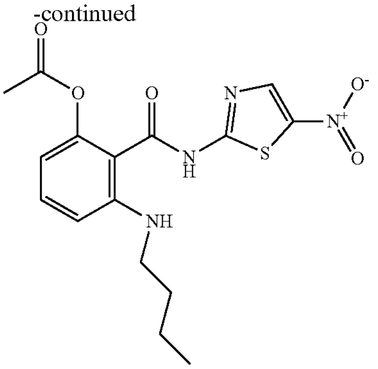

Step 1. Synthesis of 5-methoxy-2H-benzo[d][1,3]oxazine-2,4 (1H)-dione

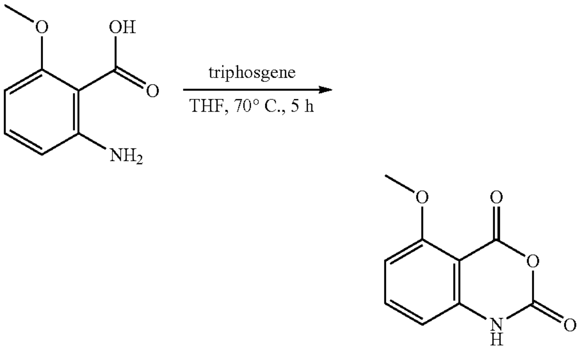

To a solution of 2-amino-6-methoxybenzoic acid (1.00 g, 6.00 mmol) in THF (20 mL) was added triphosgene (605 mg, 2.00 mmol). The reaction was stirred at 70° C. for 5 h. After the reaction mixture was cooled to rt, the solid was filtered and dried under vacuum to give the title compound (400 mg, 34.6% yield) as white solid. MS (ESI) m/z: 194.4 [M+H]+.

Step 2. Synthesis of 1-butyl-5-methoxy-2H-benzo[d][1,3]oxazine-2,4 (1H)-dione

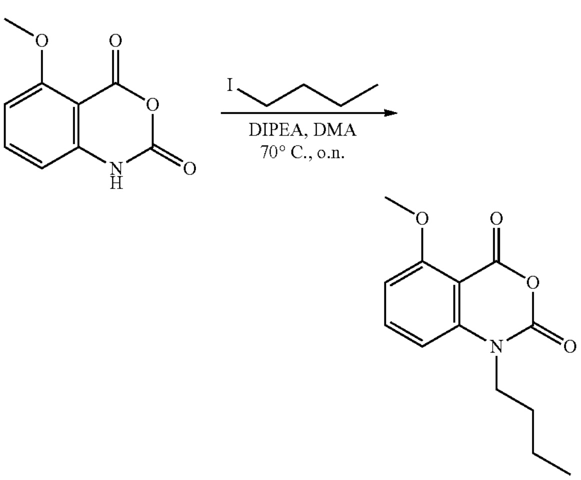

To a solution of 5-methoxy-2H-benzo[d][1,3]oxazine-2,4 (1H)-dione (400 mg, 2.07 mmol) in N,N-Dimethylacetamide (10 mL) were added DIPEA (802 mg, 6.21 mmol) and 1-iodobutane (762 mg, 4.14 mmol). After being stirred at 70° C. overnight, the mixture was cooled to rt, diluted with EtOAc (100 mL), washed with brine, dried over $Na_2SO_4$, filtered and concentrated. The resulting residue was purified by silica gel column chromatography (petroleum ether: EtOAc=3:1) to give the title compound (300 mg, 58.1% yield) as brown solid. MS (ESI) m/z: 250.4 [M+H]+.

Step 3. Synthesis of 1-butyl-5-hydroxy-2H-benzo[d][1,3]oxazine-2,4 (1H)-dione

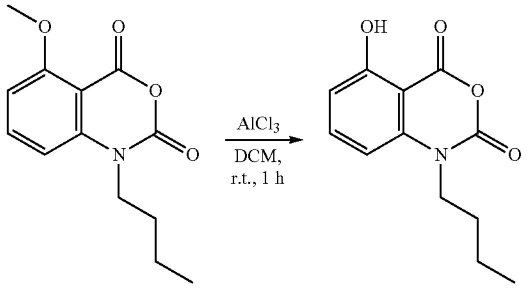

To a solution of 1-butyl-5-methoxy-2H-benzo[d][1,3]oxazine-2,4 (1H)-dione (300 mg, 1.20 mmol) in DCM (10 mL) was added $AlCl_3$ (320 mg, 2.40 mmol). After the resulting mixture was stirred at rt for 1 h, the reaction mixture was diluted with DCM (50 mL) and washed with brine. The organic layer was dried over $Na_2SO_4$, filtered and concentrated to give the title compound (300 mg, crude yield: 100% yield) as brown solid, which was used for next step without further purification. MS (ESI) m/z: 236.4 [M+H]+.

Step 4. Synthesis of 1-butyl-2,4-dioxo-1,4-dihydro-2H-benzo[d][1,3]oxazin-5-yl acetate

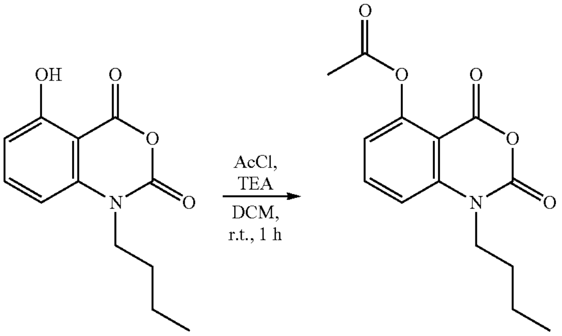 [SMILES: CCCCn1c(=O)oc(=O)c2c(O)cccc21 ; "AcCl,TEA" ; CCCCn1c(=O)oc(=O)c2c(OC(C)=O)cccc21]

To a solution of 1-butyl-5-hydroxy-2H-benzo[d][1,3]oxazine-2,4 (1H)-dione (300 mg, crude) in DCM (15 mL) were added TEA (243 mg, 2.40 mmol) and acetyl chloride (140 mg, 1.80 mmol). After the resulting mixture was stirred at rt for 1 h, the reaction mixture was concentrated under vacuum. The resulting residue was purified by silica gel column chromatography (petroleum ether:EtOAc=2:1) to give the title compound (30 mg, 9.0% yield over two steps) as white solid. MS (ESI) m/z: 278.3 [M+H]+.

Step 5. Synthesis of 3-(butylamino)-2-((5-nitrothiazol-2-yl)carbamoyl)phenyl acetate

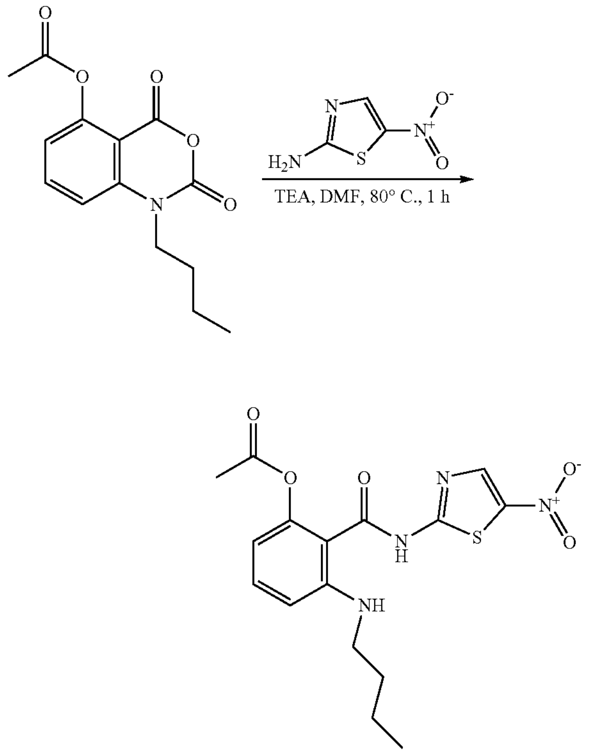 [SMILES: CCCCn1c(=O)oc(=O)c2c(OC(C)=O)cccc21 ; Nc1ncc([N+](=O)[O-])s1 ; CCCCNc1cccc(OC(C)=O)c1C(=O)Nc1ncc([N+](=O)[O-])s1]

To a solution of 1-butyl-2,4-dioxo-1,4-dihydro-2H-benzo[d][1,3]oxazin-5-yl acetate (30 mg, 0.108 mmol) in DMF (5 mL) were added DIPEA (30 mg, 0.216 mmol) and 5-nitrothiazol-2-amine (20 mg, 0.130 mmol). After the resulting mixture was stirred at 80° C. for 1 h, the reaction mixture was diluted with EtOAc (50 mL). The mixture was washed with brine, dried over $Na_2SO_4$, filtered and concentrated under vacuum. The resulting residue was purified by silica gel column chromatography (petroleum ether:EtOAc=2:1) to give the title compound (15.62 mg, 38.2% yield) as white solid. $^1$H NMR (400 MHz, DMSO-$d_6$): δ 9.61 (brs, 1H), 8.66 (s, 1H), 7.34 (t, J=8.4 Hz, 1H), 6.62 (d, J=8.4 Hz, 1H), 6.42 (d, J=8.0 Hz, 1H), 3.10 (t, J=7.0 Hz, 2H), 8.66 (s, 3H), 1.57-1.49 (m, 2H), 1.39-1.29 (m, 2H), 0.90 (t, J=7.2 Hz, 3H). MS (ESI) m/z: 379.2 $[M+H]^+$.

Example 014. 2-((5-Nitrothiazol-2-yl)carbamoyl)-3-(propylcarbamoyl)phenyl acetate (B-14)

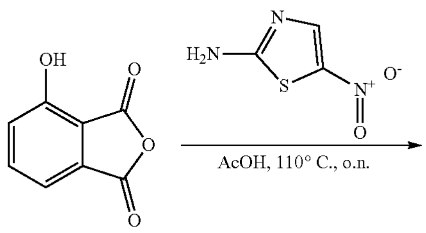

-continued

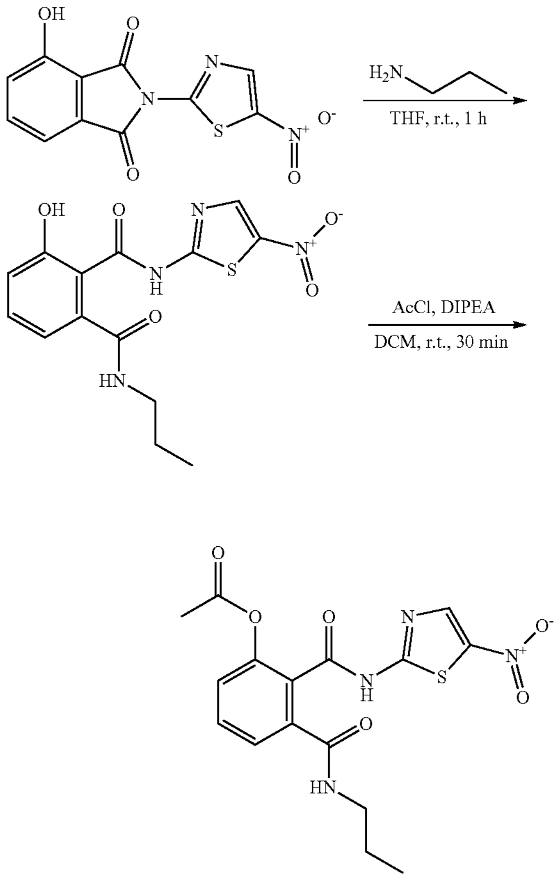

Step 1. Synthesis of 4-hydroxy-2-(5-nitrothiazol-2-yl)isoindoline-1,3-dione

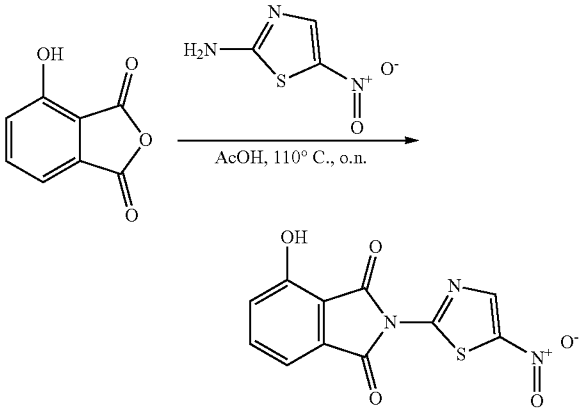

A solution of 4-hydroxyisobenzofuran-1,3-dione (1.50 g, 9.14 mmol) and 5-nitrothiazol-2-amine (1.46 g, 10.1 mmol) in AcOH (20 mL) was stirred at 110° C. overnight. After the reaction mixture was cooled to rt, the solid was collected after filtration and washed with EtOAc (50 mL) to give the title compound (800 mg, 30.1% yield) as brown solid. MS (ESI) m/z: 292.2 $[M+H]^+$.

Step 2. Synthesis of 3-hydroxy-N[2]-(5-nitrothiazol-2-yl)-N[1]-propylphthalamide

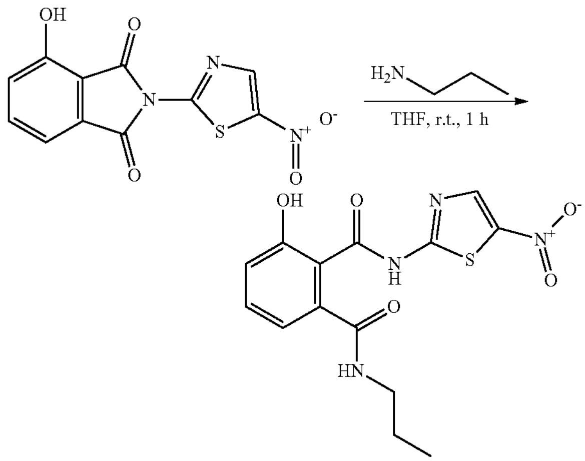

To a solution of 4-hydroxy-2-(5-nitrothiazol-2-yl)isoindoline-1,3-dione (500 mg, 1.71 mmol) in THF (20 mL) was added propan-1-amine (200 mg, 3.42 mmol). After being stirred at rt for 1 h, the mixture was concentrated under vacuum. The resulting residue was purified by silica gel column chromatography (DCM:MeOH=10:1) to give the title compound (400 mg, 66.8% yield) as yellow solid. MS (ESI) m/z: 351.3 $[M+H]^+$.

Step 3. Synthesis of 2-((5-nitrothiazol-2-yl)carbamoyl)-3-(propylcarbamoyl)phenyl acetate

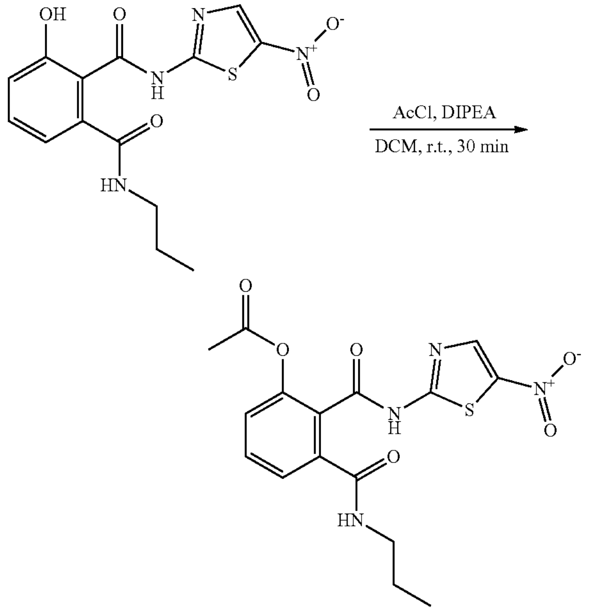

To a solution of 3-hydroxy-N[2]-(5-nitrothiazol-2-yl)-N[1]-propylphthalamide (300 mg, 0.85 mmol) and DIPEA (300 mg, 2.55 mmol) in DCM (10 mL) was added acetyl chloride (99 mg, 1.27 mmol) at 0° C. After being stirred at 0° C. for 30 min, the mixture was concentrated under vacuum. The resulting residue was purified by silica gel column chromatography (petroleum ether:EtOAc=10:1) to give the title compound (16.66 mg, 4.95% yield) as white solid. 1H NMR (400 MHz, DMSO-$d_6$): δ 13.45 (s, 1H), 8.70-8.67 (m, 1H), 8.64 (s, 1H), 7.73 (d, J=7.6 Hz, 1H), 7.65 (t, J=8.0 Hz, 1H), 7.46 (d, J=8.0 Hz, 1H), 3.16-3.11 (m, 2H), 2.13 (s, 1H), 1.52-1.43 (m, 2H), 0.86 (t, J=7.4 Hz, 3H). MS (ESI) m/z: 391.3 $[M+H]^+$.

Example 015. 5-(Butylamino)-2-((5-nitrothiazol-2-yl)carbamoyl)phenyl acetate (B-17)

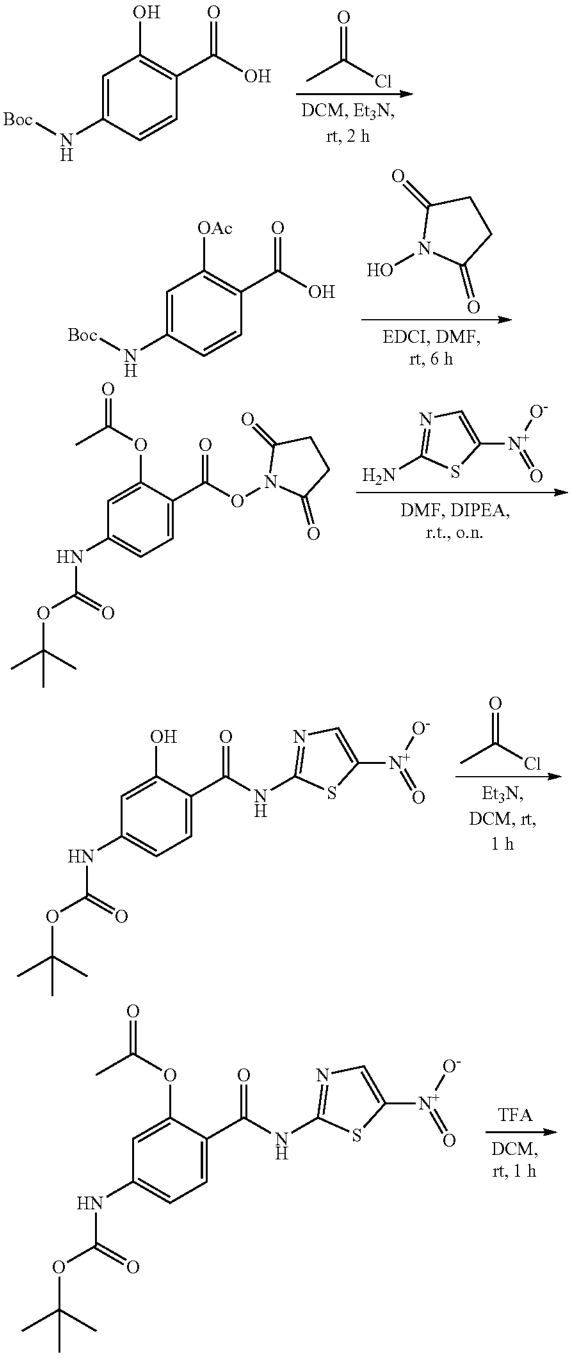

-continued

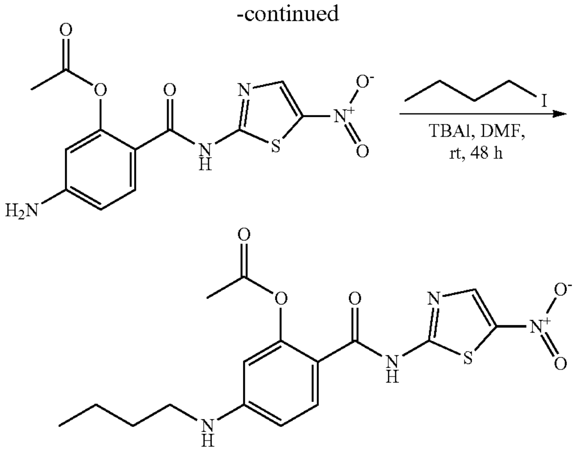

Step 1. Synthesis of 2-acetoxy-4-((tert-butoxycarbonyl)amino)benzoic acid

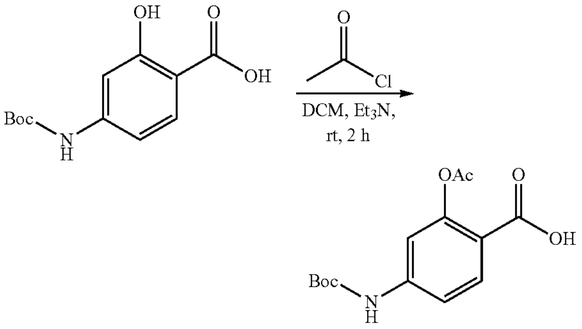

To a solution of 4-((tert-butoxycarbonyl)amino)-2-hydroxybenzoic acid (2.00 g, 79.0 mmol) and $Et_3N$ (3.20 g, 316 mmol) in DCM (100 mL) was added acetyl chloride (1.87 g, 237 mmol) dropwise at 0° C. After being stirred at rt for 2 h, the mixture was concentrated under vacuum to give a residue, which was diluted with $H_2O$ (300 mL) and acidified with 1 N HCl (pH=4). The mixture was extracted with EtOAc (3×50 mL). The combined organic phase was dried over $Na_2SO_4$, filtered and concentrated under vacuum to give the title compound (2.50 g, crude) as colorless oil, which was used in the next step without further purification. MS (ESI) m/z: 294.2 $[M-H]^-$.

Step 2. Synthesis of 2,5-dioxopyrrolidin-1-yl 2-acetoxy-4-((tert-butoxycarbonyl)amino)benzoate

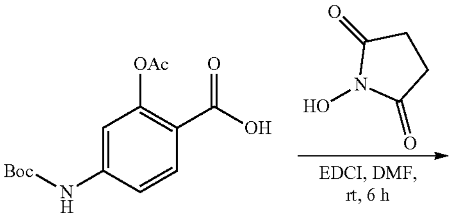

-continued

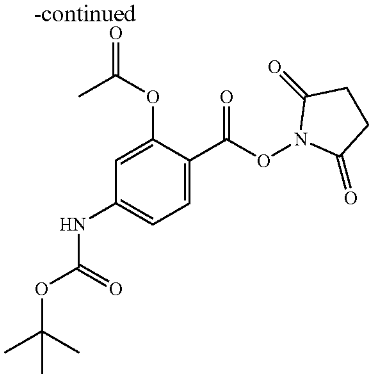

To a solution of 2-acetoxy-4-((tert-butoxycarbonyl)amino)benzoic acid (1.00 g, crude) in DMF (30 mL) were added 1-hydroxypyrrolidine-2,5-dione (780 mg, 6.78 mmol) and EDCI (1.60 g, 8.48 mmol). After the mixture was stirred at rt for 6 h. it was diluted with $H_2O$ (100 mL). The mixture was extracted with EtOAc (3×100 mL). The combined organic phase was dried over $Na_2SO_4$, filtered and concentrated under vacuum. The resulting residue was purified by silica gel column chromatography (petroleum ether: EtOAc=1:1) to give the title compound (1.00 g, 75.3% yield over two steps) as yellow oil. MS (ESI) m/z: 391.2 $[M-H]^-$.

Step 3. Synthesis of tert-butyl (3-hydroxy-4-((5-nitrothiazol-2-yl)carbamoyl)phenyl)carbamate

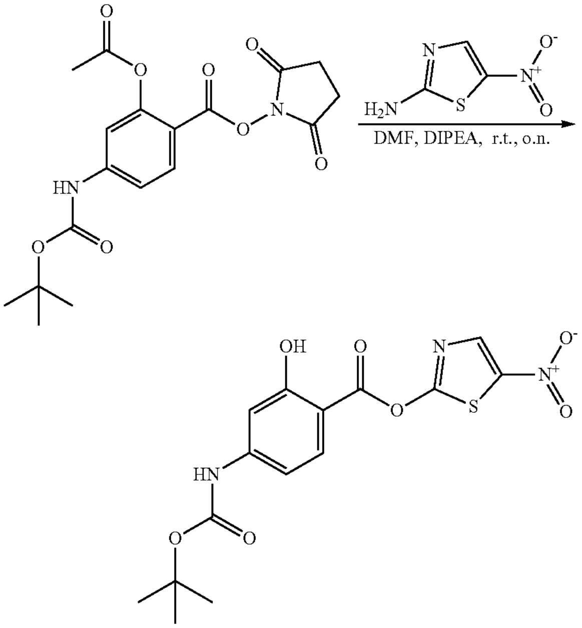

To a solution of 2,5-dioxopyrrolidin-1-yl 2-acetoxy-4-((tert-butoxycarbonyl)amino)benzoate (1.00 g, 2.55 mmol) and 5-nitrothiazol-2-amine in (725 mg, 5.10 mmol) in DMF (30 mL) was added DIEA (822 mg, 6.34 mmol). After being stirred at room temperature for 16 h, the mixture was diluted with $H_2O$ (100 mL) and extracted with EtOAc (3×50 mL). The combined organic phase was dried over $Na_2SO_4$, filtered and concentrated under vacuum. The resulting residue was purified by silica gel column chromatography (DCM:

MeOH=1:1) to give the title compound (700 mg, crude) as brown oil. MS (ESI) m/z: 381.3 $[M+H]^+$.

Step 4. Synthesis of 5-((tert-butoxycarbonyl)amino)-2-((5-nitrothiazol-2-yl)carbamoyl)phenyl acetate

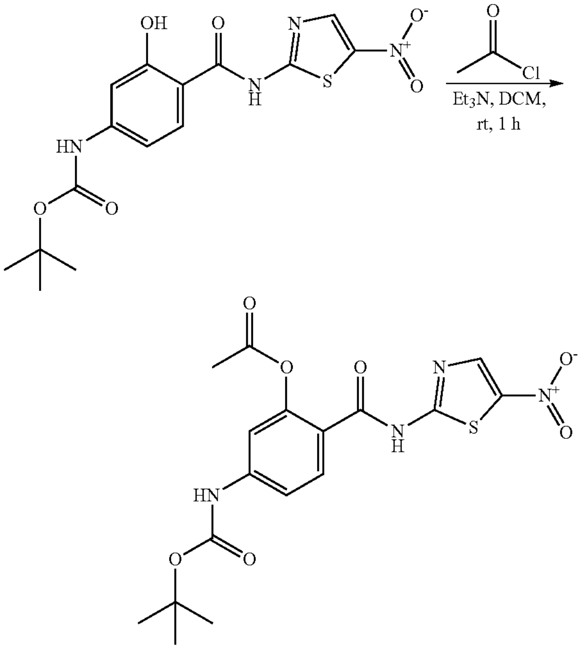

To a solution of tert-butyl (3-hydroxy-4-((5-nitrothiazol-2-yl)carbamoyl)phenyl)carbamate (700 mg, crude) and $Et_3N$ (560 mg, 5.52 mmol) in DCM (10 mL) was added acetyl chloride (290 mg, 3.69 mmol) at 0° C. After being stirred at rt for 1 h, the mixture was concentrated under vacuum. The resulting residue was diluted with $H_2O$ (50 mL), acidified with 1 N HCl to pH=3 and extracted with EtOAc (3×20 mL). The combined organic phase was dried over $Na_2SO_4$, filtered and concentrated under vacuum. The resulting residue was recrystallized from EtOAc to give the title compound (400 mg, 51.5% yield over two steps) as gray solid. MS (ESI) m/z: 423.1 $[M+H]^+$.

Step 5. Synthesis of 5-amino-2-((5-nitrothiazol-2-yl)carbamoyl)phenyl acetate

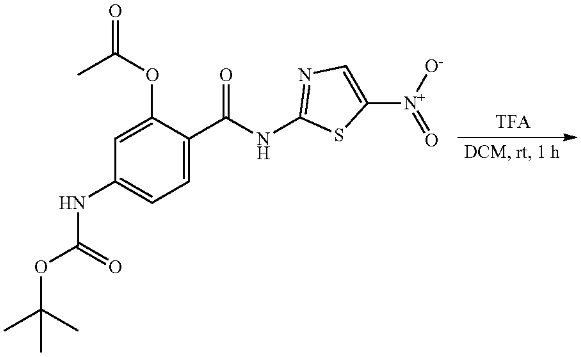

-continued

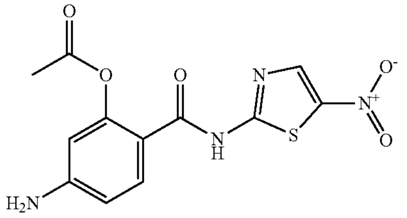

A solution of 5-((tert-butoxycarbonyl)amino)-2-((5-nitrothiazol-2-yl)carbamoyl)phenyl acetate (100 mg, 0.31 mmol) in DCM (5 mL) and TFA (5 mL) was stirred at rt for 1 h, before $Na_2SO_4$ (1.00 g) and $NaHCO_3$ (5.00 g) were added at 0° C. After the mixture was stirred at 0° C. for 30 min, it was filtered. The filtrate was washed with brine and extracted with EtOAc (3×5 mL). The combined organic layers were dried over $Na_2SO_4$, filtered and concentrated under vacuum to give the title product (150 mg, crude) as yellow solid. MS (ESI) m/z: 323.1 $[M+H]^+$.

Step 6. Synthesis of 5-(butylamino)-2-((5-nitrothiazol-2-yl)carbamoyl)phenyl acetate

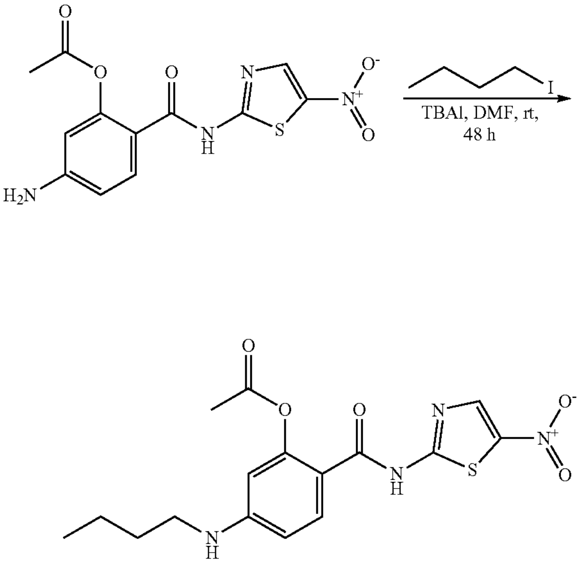

To a solution of 5-amino-2-((5-nitrothiazol-2-yl)carbamoyl)phenyl acetate (150 mg, crude) and TBAI (344 mg, 0.% mmol) in DMF (3 mL) was added 1-iodobutane (856 mg, 4.65 mmol). After the mixture was stirred at rt for 48 h, it was diluted with $H_2O$ (10 mL) and extracted with EtOAc (3×10 mL). The combined organic phase was dried over $Na_2SO_4$, filtered and concentrated under vacuum. The resulting residue was purified by silica gel column chromatography (petroleum ether:EtOAc=3:1) to give the title compound (13.0 mg, 7.40% yield over two steps) as yellow solid. $^1H$ NMR (400 MHz, DMSO-$d_6$): δ 12.97 (s, 1H), 8.65 (s, 1H), 7.74 (d, J=8.8 Hz, 1H), 6.84-6.82 (m, 1H), 6.53-6.50 (m, 1H), 6.34-6.33 (m, 1H), 3.09-3.06 (m, 2H), 2.24 (s, 3H), 1.55-1.51 (m, 2H), 1.40-1.35 (m, 2H), 0.91 (t, J=7.2 Hz, 3H). MS (ESI) m/z: 379.3 $[M+H]^-$.

Example 016. 2-((5-Nitrothiazol-2-yl)carbamoyl)-4-(propylcarbamoyl)phenyl acetate (B-13)

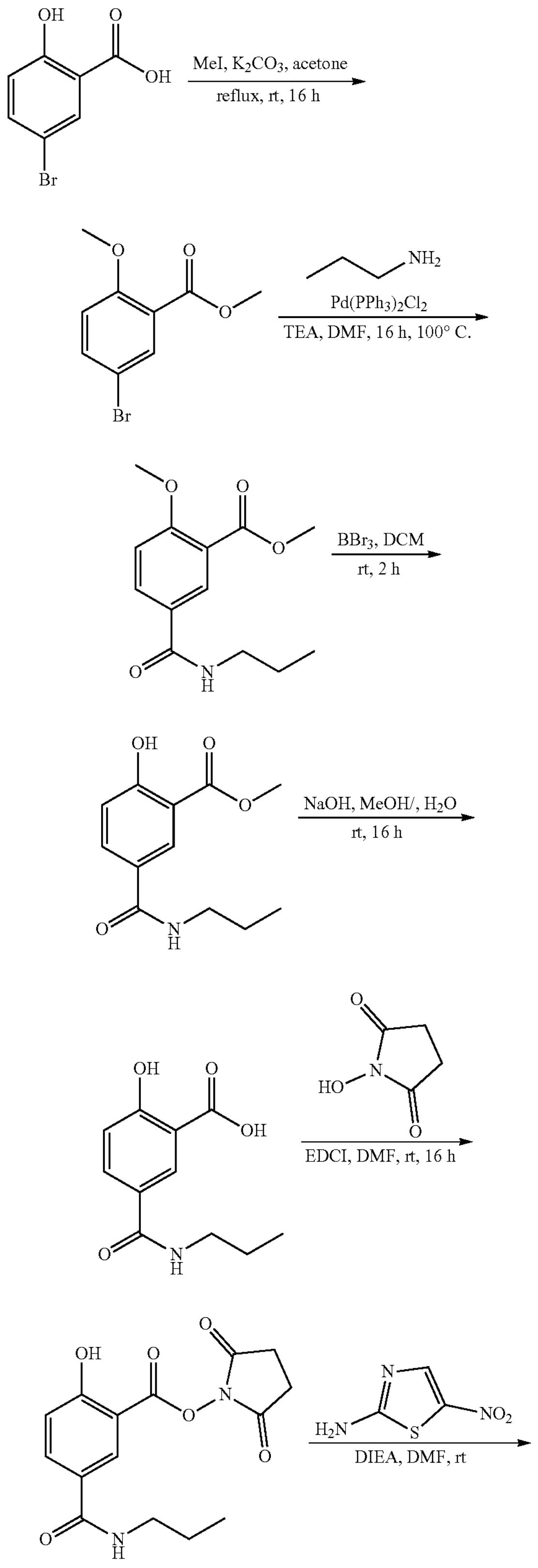

-continued

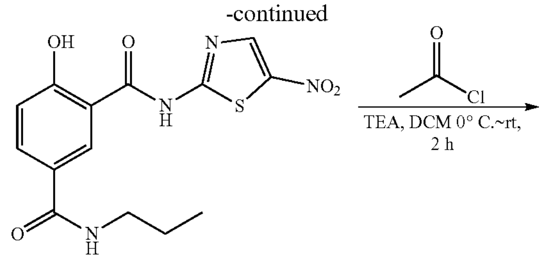

6

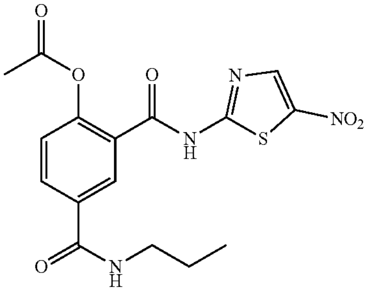

Step 1. Synthesis of methyl 5-bromo-2-methoxybenzoate

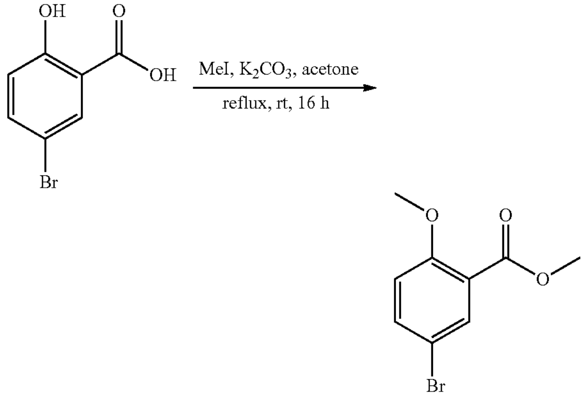

A solution of 5-bromo-2-hydroxybenzoic acid (10.0 g, 46.0 mmol), Mel (52.0 g, 368 mmol) and $K_2CO_3$ (25.0 g, 184 mmol) in acetone (200 mL) was refluxed for 16 h. The mixture was concentrated under vacuum. The resulting residue was purified by silica gel column chromatography (petroleum ether:EtOAc=10:1) to give the title compound (10.4 g, 93.0% yield) as yellow oil.

Step 2. Synthesis of methyl 2-methoxy-5-(propylcarbamoyl)benzoate

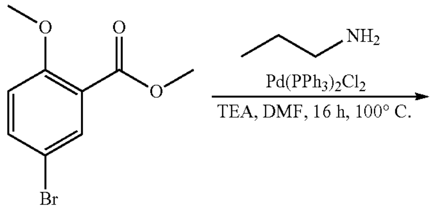

-continued

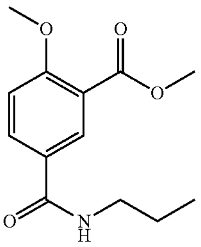

To a solution of methyl 5-bromo-2-methoxybenzoate (10.0 g, 40.8 mmol) in DMF (100 mL) were added $Pd(PPh_3)_2Cl_2$ (1.00 g, 1.40 mmol), propan-1-amine (14 mL, 237 mmol) and TEA (4 mL, 40.8 mmol). After degassed with CO for 3 times, the mixture was stirred at 100° C. for 16 h under CO atmosphere. After the mixture was cooled to rt, it was diluted with EtOAc (60 mL), washed with brine (3x30 mL), dried over $Na_2SO_4$, filtered and concentrated under vacuum. The resulting residue was purified by silica gel column chromatography (petroleum ether:EtOAc=2:1) to give the title compound (7.70 g, 64.0% yield) as yellow solid. MS (ESI) m/z: 252.5 $[M+H]^+$.

Step 3. Synthesis of methyl 2-hydroxy-5-(propylcarbamoyl)benzoate

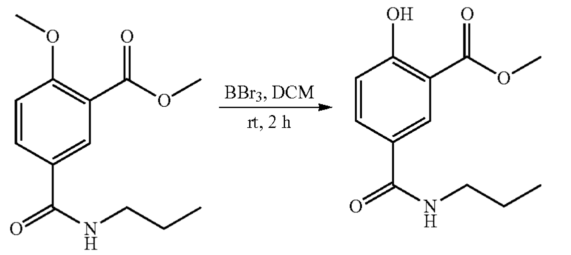

To a solution of methyl 2-methoxy-5-(propylcarbamoyl) benzoate (5.00 g, 21.0 mmol) in DCM (20 mL) was added $BBr_3$ (10 mL) slowly at 0° C. After being stirred at rt for 2 h, the mixture was diluted with dichloromethane (20 mL) and MeOH (10 mL) at 0° C. After 10 min, the reaction mixture was concentrated under vacuum at rt to give the title compound (crude 7.5 g) as yellow solid, which was used for the next step without further purification. MS (ESI) m/z: 238.2 $[M+H]^+$.

Step 4. Synthesis of 2-hydroxy-5-(propylcarbamoyl)benzoic acid

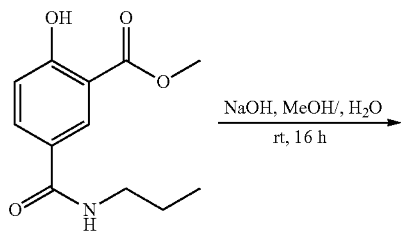

-continued

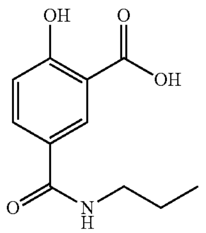

A solution of methyl 2-hydroxy-5-(propylcarbamoyl)benzoate (crude 7.5 g) and NaOH (10.0 g) in MeOH (200 mL) and $H_2O$ (20 mL) was stirred at rt for 16 h. After the reaction mixture was cooled down to 0° C., the pH of the mixture was adjusted to 3-4 with 1 N HCl. The mixture was extracted with EtOAc (3x30 mL). The combined organic layer was washed with brine (3x30 mL), dried over $Na_2SO_4$, filtered and concentrated under vacuum to give the title compound (3.1 g, 87.5% yield) as yellow solid. MS (ESI) m/z: 224.3 $[M-H]^-$.

Step 5. Synthesis of 2,5-dioxopyrrolidin-1-yl 2-hydroxy-5-(propylcarbamoyl)benzoate

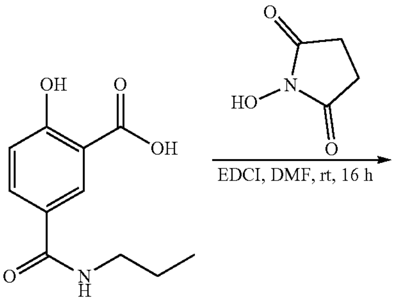

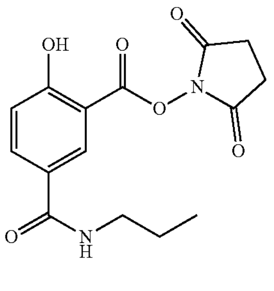

A solution of 2-hydroxy-5-(propylcarbamoyl)benzoic acid (3.10 g, 13.9 mmol), 1-hydroxypyrrolidine-2,5-dione (1.92 g, 16.7 mmol) and EDCI (4.00 g, 20.8 mmol) in DMF (40 mL) was stirred at rt for 16 h. After the mixture was diluted with $H_2O$ (30 mL), the mixture was extracted with ethyl acetate (3x30 mL). The organic layer was washed with brine, dried over $Na_2SO_4$, filtered and concentrated under vacuum, the mixture was purified by silica gel column chromatography (petroleum ether:EtOAc=1:1) to give the title compound (1.28 g, 30.0% yield) as yellow solid. MS (ESI) m/z: 321.2 $[M+H]^+$.

Step 6. Synthesis of 4-hydroxy-$N^3$-(5-nitrothiazol-2-yl)-$N^1$-propylisophthalamide

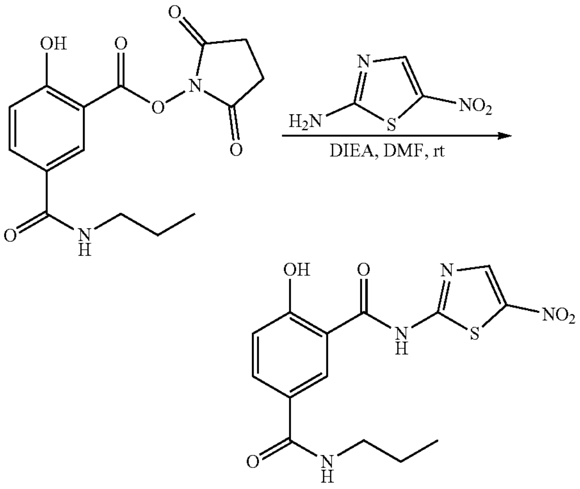

6

2,5-dioxopyrrolidin-1-yl 2-hydroxy-5-(propylcarbamoyl) benzoate (1.28 g, 4.00 mmol), 5-nitrothiazol-2-amine (1.14 g, 8.00 mmol) and DIPEA (4 mL) in DMF (20 mLl) was stirred at rt for 16 h. After the mixture was diluted with $H_2O$ (30 mL), the mixture was extracted with EtOAc (3×30 mL). The organic layer was washed with brine, dried over $Na_2SO_4$, filtered and concentrated under vacuum. The resulting residue was purified by silica gel column chromatography (petroleum ether:EtOAc=1:2) to give the title compound (0.6 g, 43.0% yield) as yellow solid. MS (ESI) m/z: 349.2 $[M+H]^+$.

Step 7. Synthesis of 2-((5-nitrothiazol-2-yl)carbamoyl)-4-(propylcarbamoyl)phenyl acetate

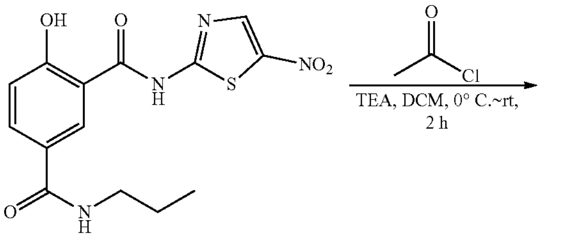

6

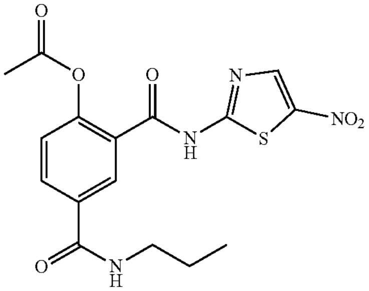

To a solution of 4-hydroxy-$N^3$-(5-nitrothiazol-2-yl)-$N^1$-propylisophthalamide (0.20 g, 0.57 mmol) and TEA (0.50 mL, 3.7 mmol) in DCM (20 mL) was added acetyl chloride (0.25 mL) at 0° C. After being stirred at rt for 2 h, the mixture was concentrated under vacuum. The resulting residue was purified by silica gel column chromatography (petroleum ether:EtOAc=1:1) to give the title compound (46.0 mg, 21.0% yield) as yellow solid. $^1H$ NMR (400 MHz, DMSO-$d_6$): δ 13.69 (s, 1H), 8.71 (s, 1H), 8.58-8.56 (m, 1H), 8.32 (s, 1H), 8.12 (dd, J=8.4, 2.0 Hz, 1H), 7.42 (d, J=8.4 Hz, 1H), 3.32-3.23 (m, 2H), 2.32 (s, 3H), 1.56-1.50 (m, 2H), 0.91 (t, J=7.2 Hz, 3H). MS (ESI) m/z: 393.1 $[M+H]^-$.

Example 017. 2-Butyramido-6-((5-nitrothiazol-2-yl) carbamoyl)phenyl butyrate (B-24)

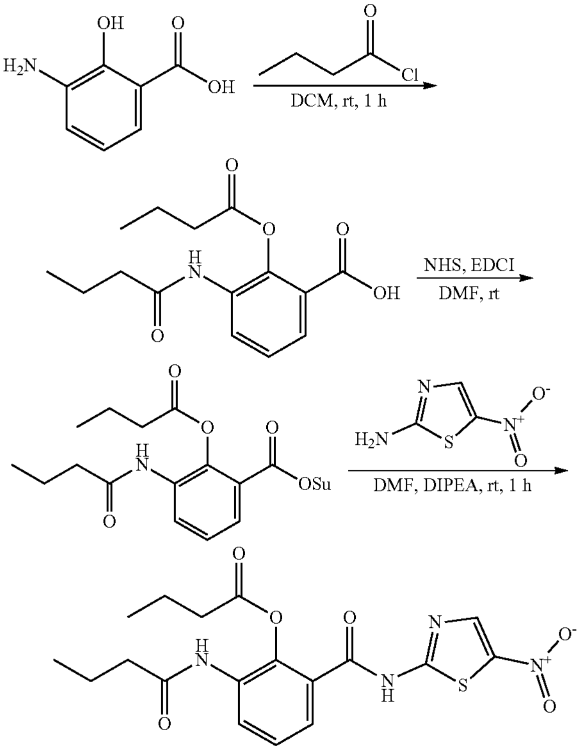

Step 1. Synthesis of 3-butyramido-2-(butyryloxy)benzoic acid

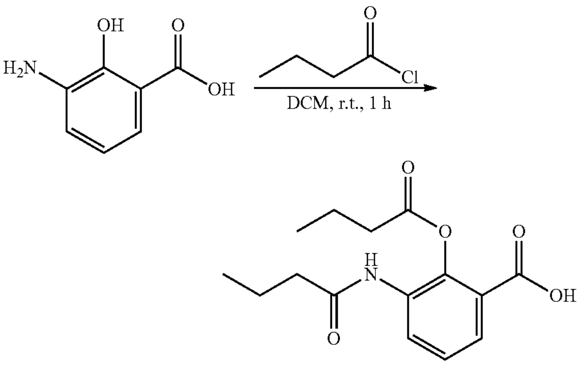

To a solution of 3-amino-2-hydroxybenzoic acid (400 mg, 2.61 mmol) and DIPEA (1.01 mg, 7.83 mmol) in DCM (10 mL) was added butyryl chloride (695 mg, 6.53 mmol) at 0° C. After being stirred at rt for 1 h, the pH of the mixture was adjusted to 6 with 1 N HCl. The mixture was extracted with DCM (3×30 mL). The organic phase was washed with brine, dried over $Na_2SO_4$, filtered and concentrated to give the title compound (600 mg, crude) as colorless oil, which was used in the next step without further purification. MS (ESI) m/z: 294.4 $[M+H]^+$.

Step 2. Synthesis of 2,5-dioxopyrrolidin-1-yl 3-butyramido-2-(butyryloxy)benzoate

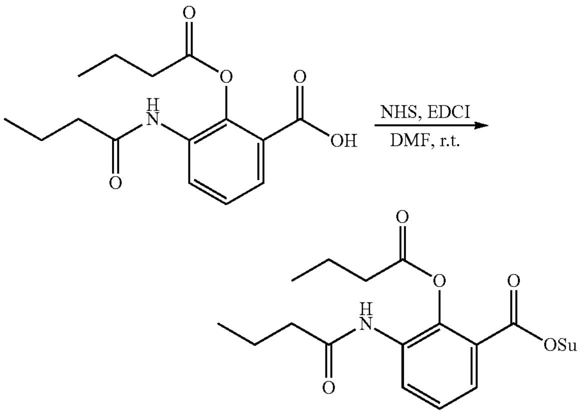

A solution of 3-butyramido-2-(butyryloxy)benzoic acid (600 mg, crude), N-Hydroxysuccinimide (600 mg, 5.22 mmol) and EDCI (1.00 g, 5.22 mmol) in DMF (20 mL) was stirred at rt overnight. Then, the mixture was diluted with water and extracted with EtOAc (3×30 mL), washed with brine, dried over $Na_2SO_4$, filtered and concentrated. The resulting residue was purified by silica gel column chromatography (petroleum ether:EtOAc=1:1) to give the title compound (600 mg, 59.0% yield over two steps) as white solid. MS (ESI) m/z: 391.2 $[M+H]^+$.

Step 3. Synthesis of 2-butyramido-6-((5-nitrothiazol-2-yl)carbamoyl)phenyl butyrate

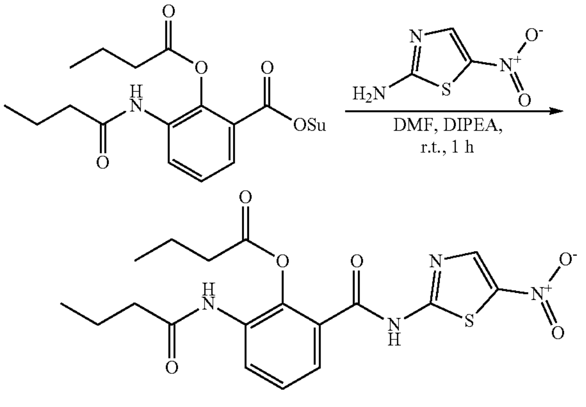

A solution of 2,5-dioxopyrrolidin-1-yl 3-butyramido-2-(butyryloxy)benzoate (600 mg, 1.54 mmol), DIPEA (398 mg, 3.08 mmol) and 5-nitrothiazol-2-amine (268 mg, 1.85 mmol) in DMF (20 mL) was stirred at rt for 1 h. After the mixture was diluted with EtOAc (30 mL) and washed with brine, the organic phase was dried over $Na_2SO_4$, filtered and concentrated. The resulting residue was purified by silica gel column chromatography (petroleum ether:EtOAc=1:1) to give the title compound (10.1 mg, 1.56% yield) as an off-yellow solid. $^1H$ NMR (400 MHz, DMSO-$d_6$): δ 13.79 (brs, 1H), 8.71 (s, 1H), 7.93 (d, J=7.6 Hz, 1H), 7.77-7.75 (m, 1H), 7.56 (t, J=7.8 Hz, 1H), 2.58-2.42 (m, 4H), 1.59-1.48 (m, 4H), 0.88-0.82 (m, 6H). MS (ESI) m/z: 421.3 $[M+H]^+$.

Example 019. 3-Butyramido-2-((5-nitrothiazol-2-yl)carbamoyl)phenyl butyrate (B-25)

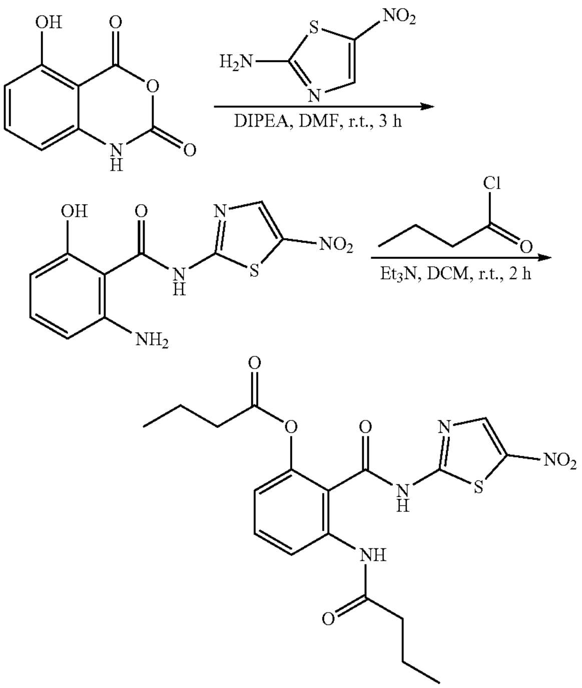

Step 1. Synthesis of 2-amino-6-hydroxy-N-(5-nitrothiazol-2-yl)benzamide

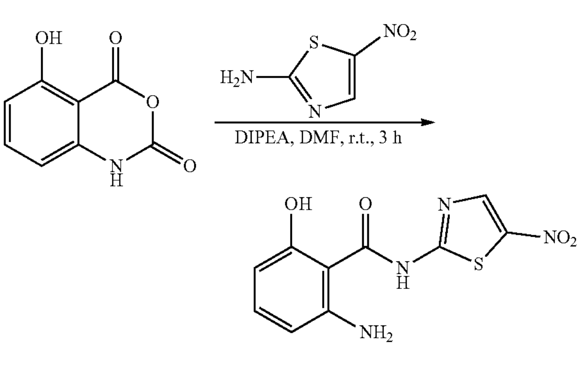

A mixture of 5-hydroxy-2H-benzo[d][1,3]oxazine-2,4(1H)-dione (100 mg, 0.559 mmol), 5-nitrothiazol-2-amine (160 mg, 1.12 mmol) and DIPEA (217 mg, 1.68 mmol) in DMF (5 mL) was stirred at rt for 3 h, at which time the reaction mixture was diluted with water (30 mL). The mixture was extracted with EtOAc (3×30 mL). The combined organic phase was washed with brine, dried over $Na_2SO_4$, filtered and concentrated under vacuum to give the title compound (250 mg, crude) as gray solid, which was used in the next step without further purification.

Step 2. Synthesis of 3-butyramido-2-((5-nitrothiazol-2-yl)carbamoyl)phenyl butyrat

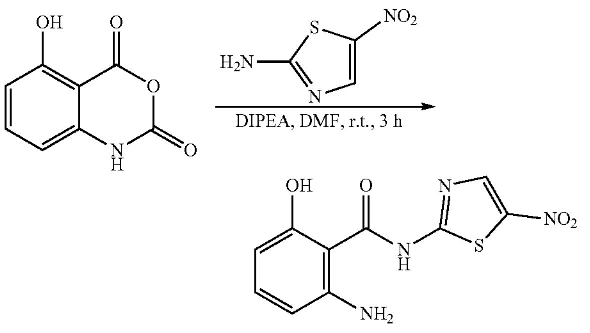

To a solution of 2-amino-6-hydroxy-N-(5-nitrothiazol-2-yl)benzamide (250 mg, crude) and $Et_3N$ (113 mg, 1.12 mmol) in DCM (5 mL) was added butyryl chloride (66.0 mg, 0.620 mmol) dropwise at 0° C. After being stirred at rt for 2 h, the mixture was concentrated under vacuum. The resulting residue was purified by silica gel column chromatography (petroleum ether:EtOAc=1:1) to give the title product (70 mg, 29.8% yield) as gray solid. $^1H$ NMR (400 MHz, DMSO-$d_6$): δ 13.51 (s, 1H), 9.94 (s, 1H), 8.65 (s, 1H), 7.54-7.52 (m, 1H), 7.40-7.37 (m 1H), 7.09-7.07 (m, 1H), 2.45-2.41 (m, 2H). 2.20 (t, J=7.6 Hz, 2H), 1.55-1.46 (m, 4H), 0.84-0.78 (m, 6H). MS (ESI) m/z: 421.3 $[M-H]^-$.

Example 020. N-(5-Nitrothiazol-2-yl)-2-phenoxybenzamide (B-76)

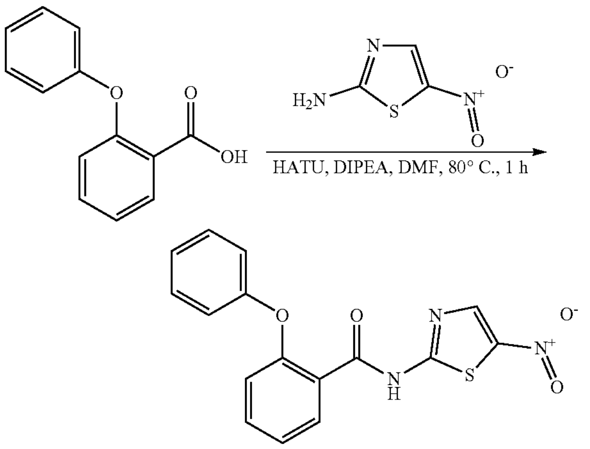

A solution of 2-phenoxybenzoic acid (100 mg, 0.467 mmol), HATU (177 mg, 0.467 mmol), 5-nitrothiazol-2-amine (66 mg, 0.467 mmol) and DIPEA (90 mg, 0.701 mmol) in DMF (2 mL) was stirred at 80° C. for 1 h. The mixture was cooled to rt, diluted with EtOAc (30 mL), washed with brine, dried over $Na_2SO_4$, filtered and concentrated under vacuum. The resulting residue was purified by pre-HPLC to provide the title compound (90 mg, 61.2% yield) as yellow solid. $^1H$ NMR (400 MHz, DMSO-$d_6$): δ 13.50 (s, 1H), 8.67 (s, 1H), 7.75 (d, J=7.6 Hz, 1H), 7.75-7.56 (m, 1H), 7.43-7.39 (m, 2H), 7.29 (t, J=7.2 Hz, 1H), 7.18 (t, J=7.6 Hz, 1H), 7.09 (d, J=7.6 Hz, 2H), 6.95 (d, J=8.4 Hz, 1H). MS (ESI) m/z: 342.0 $[M+H]^+$.

Example 021. 2-Fluoro-N-(5-nitrothiazol-2-yl)benzamide (B-91)

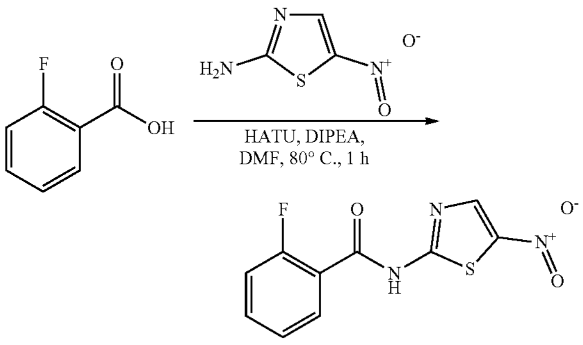

A solution of 2-fluorobenzoic acid (100 mg, 0.714 mmol), HATU (271 mg, 0.714 mmol), 5-nitrothiazol-2-amine (104 mg, 0.714 mmol) and DIPEA (138 mg, 1.071 mmol) in DMF (2 mL) was stirred at 80° C. for 1 h. The mixture was cooled to rt, diluted with EtOAc (30 mL), washed with brine, dried over $Na_2SO_4$, filtered and concentrated under vacuum. The resulting residue was purified by pre-HPLC to provide the title compound (90 mg, 47.19% yield) as yellow solid. $^1H$ NMR (400 MHz, DMSO-$d_6$): δ 13.60 (s, 1H), 8.71 (s, 1H), 7.83-7.79 (m, 1H), 7.73-7.67 (m, 1H), 7.44-7.37 (m, 2H). MS (ESI) m/z: 268.1 $[M+H]^+$.

Example 022. 2-chloro-N-(5-nitrothiazol-2-yl)benzamide (B-92)

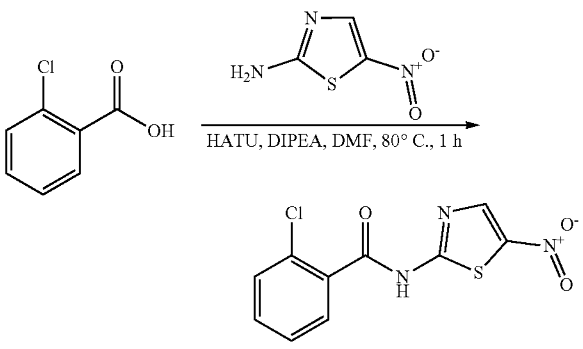

A solution of 2-chlorobenzoic acid (100 mg, 0.641 mmol), HATU (244 mg, 0.641 mmol) and 5-nitrothiazol-2-amine (93 mg, 0.641 mmol) in DMF (2 mL) was stirred at 80° C. DIPEA (124 mg, 0.962 mmol) was added at this temperature. After being stirred at 80° C. for another 1 h, the mixture was cooled to rt, diluted with EtOAc (30 mL), washed with brine, dried over $Na_2SO_4$, filtered and concentrated under vacuum. The resulting residue was purified by pre-HPLC to give the title compound (62 mg, 34.44% yield) as yellow solid. $^1$H NMR (400 MHz, DMSO-$d_6$): δ 13.74 (s, 1H), 8.70 (s, 1H), 7.74-7.72 (m, 1H), 7.64-7.58 (m, 2H), 7.53-7.49 (m, 1H). MS (ESI) m/z: 284.1 [M+H]$^+$.

Example 023. 2-Bromo-N-(5-nitrothiazol-2-yl)benzamide (B-93)

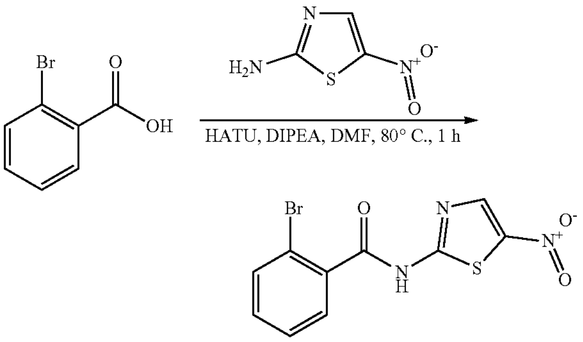

To a solution of 2-bromobenzoic acid (100 mg, 0.50 mmol), HATU (190 mg, 0.50 mmol) and 5-nitrothiazol-2-amine (73 mg, 0.50 mmol) in DMF (2 mL) was added DIPEA (97 mg, 0.75 mmol) at 80° C. After being stirred at 80° C. for 1 h, the mixture was cooled to rt and diluted with EtOAc (30 mL). The organic phase was washed with brine, dried over $Na_2SO_4$, filtered and concentrated under vacuum. The resulting residue was purified by pre-HPLC to give the title compound (50 mg, 34.67% yield) as yellow solid. $^1$H NMR (400 MHz, DMSO-$d_6$): δ 13.72 (s, 1H), 8.70 (s, 1H), 7.79-7.77 (m, 1H), 7.70-7.68 (m, 1H), 7.55-7.51 (m, 2H). MS (ESI) m/z: 328.0 [M+H]$^+$.

Example 024. N-(5-Nitrothiazol-2-yl)-[1,1'-biphenyl]-2-carboxamide (B-86)

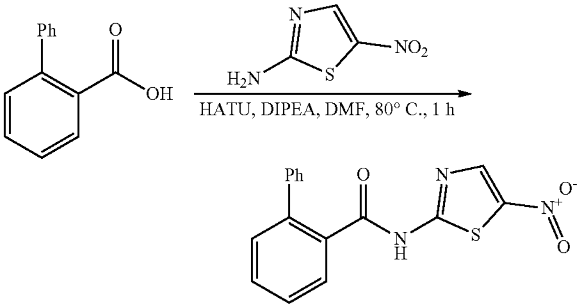

A solution of [1,1'-biphenyl]-2-carboxylic acid (200 mg, 1.01 mmol), 5-nitrothiazol-2-amine (182 mg, 1.05 mmol), HATU (478 mg, 1.26 mmol) and DIEA (0.35 mL) in DMF (5 mL) was stirred at 80° C. for 1 h. After the mixture was diluted with $H_2O$ (30 mL), the mixture was extracted with EtOAc (3x30 mL). The combined organic layers were washed with brine (3x30 mL), dried over $Na_2SO_4$, filtered and concentrated under vacuum. The resulting residue was purified by pre-HPLC to give the title compound (73.0 mg, 22.0% yield) as yellow solid. $^1$H NMR (400 MHz, DMSO-$d_6$): δ 13.47 (s, 1H), 8.62 (s, 1H), 7.72-7.67 (m, 2H), 7.54-7.52 (m, 2H), 7.40-7.32 (m, 5H). MS (ESI) m/z: 324.3 [M−H]$^-$.

Example 025. N-(5-Nitrothiazol-2-yl)-2-(trifluoromethyl)benzamide (B-89)

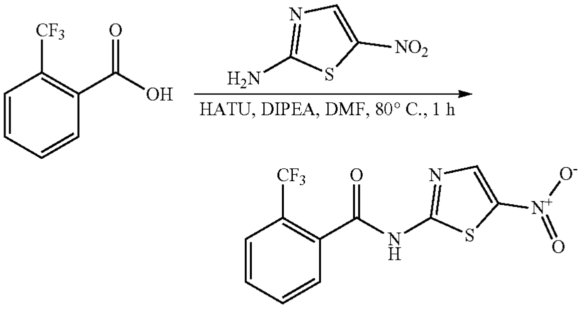

To a solution of 2-(trifluoromethyl)benzoic acid (200 mg, 1.05 mmol), 5-nitrothiazol-2-amine (182 mg, 1.05 mmol) and HATU (478 mg, 1.26 mmol) in DMF (5 mL) at 80° C. was added DIPEA (0.35 mL). After being stirred at 80° C. for 1 h, the mixture was cooled to rt, diluted with water (30 mL) and extracted with EtOAc (3x30 mL). The organic phase was washed with brine (3x30 mL), dried over $Na_2SO_4$, filtered and concentrated under vacuum and purified by pre-HPLC to give the title compound (140 mg, 42.0% yield) as yellow solid. $^1$H NMR (400 MHz, DMSO-$d_6$): δ 13.85 (s, 1H), 8.70 (s, 1H), 7.93 (d, J=7.6 Hz, 1H), 7.86-7.79 (m, 3H). MS (ESI) m/z: 316.1 [M−H]$^-$.

Example 026. 2-(dimethylamino)-N-(5-nitrothiazol-2-yl)benzamide (B-69)

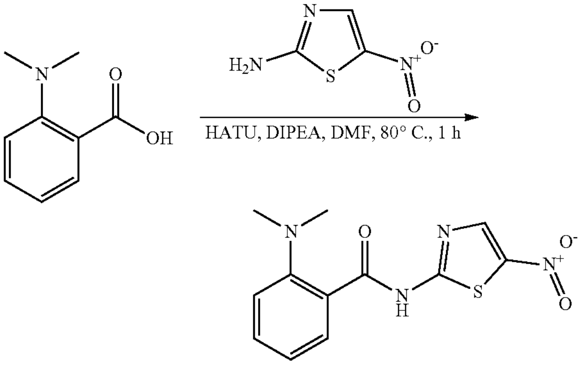

A solution of 2-(dimethylamino)benzoic acid (100 mg, 0.606 mmol), HATU (230 mg, 0.606 mmol), 5-nitrothiazol-2-amine (88 mg, 0.606 mmol) and DIPEA (117 mg, 0.909 mmol) in DMF (2 mL) was stirred at 80° C. for 1 h. The mixture was cooled to rt and diluted with EtOAc (30 mL), washed with brine, dried over $Na_2SO_4$, filtered and concentrated under vacuum. The resulting residue was purified by pre-HPLC (0.1% TFA) to give the title compound (60 mg, 33.9% yield) as yellow solid. $^1$H NMR (400 MHz, DMSO-$d_6$): δ 14.79 (brs, 1H), 8.68 (s, 1H), 7.87 (dd, J=8.0, 1.2 Hz, 1H), 7.64-7.60 (m, 1H), 7.47 (d, J=8.0 Hz, 1H), 7.25 (t, J=7.2 Hz, 1H), 2.83 (s, 3H). MS (ESI) m/z: 293.1 [M+H]$^+$.

Example 027. N-(5-nitrothiazol-2-yl)-2-(trifluoromethoxy)benzamide (B-77)

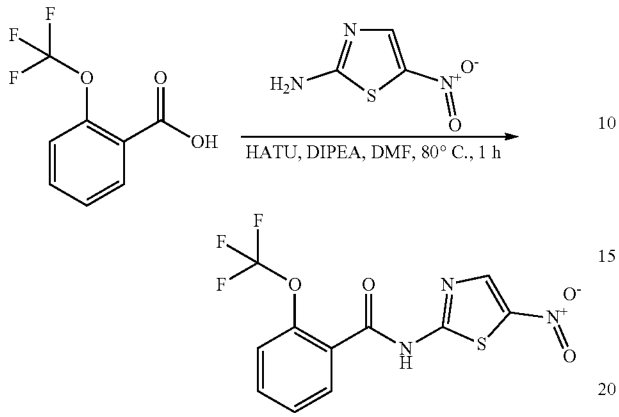

A solution of 2-(trifluoromethoxy)benzoic acid (100 mg, 0.485 mmol), HATU (184 mg, 0.485 mmol), 5-nitrothiazol-2-amine (70 mg, 0.485 mmol) and DIPEA (94 mg, 0.728 mmol) in DMF (2 mL) was stirred at 80° C. for 1 h. The mixture was cooled to rt and diluted with EtOAc (30 mL), washed with brine, dried over $Na_2SO_4$, filtered and concentrated under vacuum. The resulting residue was purified by pre-HPLC to give the title compound (75 mg, 46.53% yield) as yellow solid. $^1$H NMR (400 MHz, DMSO-$d_6$): δ 13.76 (s, 1H), 8.71 (s, 1H), 7.87-7.85 (m, 1H), 7.79-7.42 (m, 1H), 7.61-7.57 (m, 2H). MS (ESI) m/z: 334.1 $[M+H]^+$.

Example 028. 2-Isopropyl-N-(5-nitrothiazol-2-yl)benzamide (B-84)

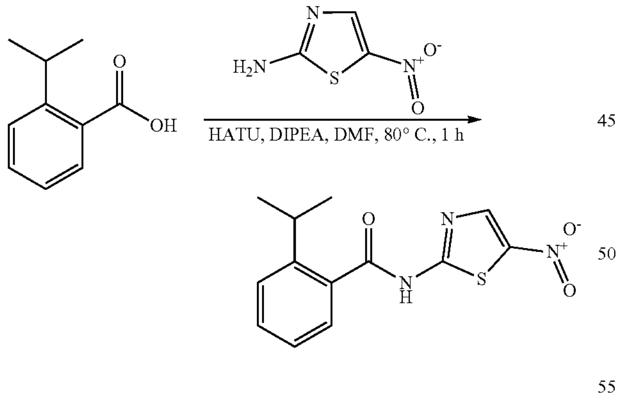

A solution of 2-isopropylbenzoic acid (100 mg, 0.606 mmol), HATU (230 mg, 0.606 mmol), 5-nitrothiazol-2-amine (88 mg, 606 mmol) and DIPEA (117 mg, 0.909 mmol) in DMF (2 mL) was stirred at 80° C. for 1 h. The mixture was cooled to rt, diluted with EtOAc (30 mL), washed with brine, dried over $Na_2SO_4$, filtered and concentrated under vacuum. The resulting residue was purified by pre-HPLC to provide the title compound (31 mg, 17.51% yield) as yellow solid. $^1$H NMR (400 MHz, DMSO-$d_6$): δ 13.57 (s, 1H), 8.69 (s, 1H), 7.57-7.48 (m, 3H), 7.36-7.32 (m, 1H), 3.23-3.16 (m, 1H), 1.21 (d, J=6.8 Hz, 6H). MS (ESI) m/z: 292.2 $[M+H]^+$.

Example 029. 2-Isobutyramido-N-(5-nitrothiazol-2-yl)benzamide (B-61)

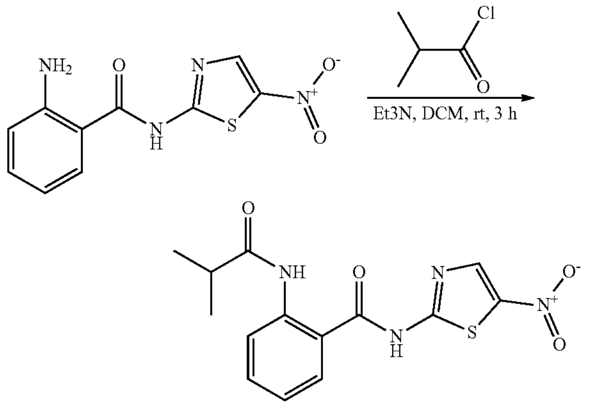

To a solution of 2-amino-N-(5-nitrothiazol-2-yl)benzamide (150 mg, 0.568 mmol) and $Et_3N$ (115 mg, 1.14 mmol) in DCM (5 mL) was added isobutyryl chloride (75.0 mg, 0.682 mmol) at 0° C. After the mixture was stirred at rt for 3 h, it was concentrated under vacuum. The resulting residue was purified by silica gel column chromatography (petroleum ether:EtOAc=10:1-3:1) to give the tide compound (105 mg, 55.15% yield) as white solid. $^1$H NMR (400 MHz, DMSO-$d_6$): δ 13.43 (brs, 1H), 10.23 (brs, 1H), 8.68 (s, 1H), 7.73-7.66 (m, 2H), 7.57 (t, J=7.6 Hz, 1H), 7.27 (t, J=7.6 Hz, 1H), 2.58-2.55 (m, 1H), 1.05 (d, J=6.8 Hz, 6H). MS (ESI) m/z: 333.2 $[M-H]^-$.

Example 030. 2-(Cyclopropanecarboxamido)-N-(5-nitrothiazol-2-yl)benzamide (B-62)

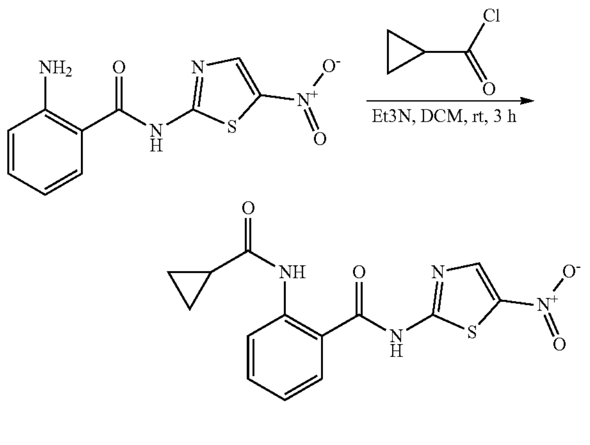

To a solution of 2-amino-N-(5-nitrothiazol-2-yl)benzamide (150 mg, 0.568 mmol) and $Et_3N$ (115 mg, 1.14 mmol) in DCM (5 mL) was added cyclopropanecarbonyl chloride (72.0 mg, 0.682 mmol) at 0° C. After the mixture was stirred at rt for 3 h, it was concentrated under vacuum. The resulting residue was purified by silica gel column chromatography (petroleum ether:EtOAc=10:1-3:1) and further purified by prep-HPLC to give the title compound (30.0 mg, 15.85% yield) as white solid. $^1$H NMR (400 MHz, DMSO-$d_6$): δ 13.43 (brs, 1H), 10.48 (brs, 1H), 8.68 (s, 1H), 7.71-7.60 (m, 2H), 7.56 (t, J=7.2 Hz, 1H), 7.24 (t, J=7.6 Hz, 1H), 1.78-1.75 (m, 1H), 0.79-0.69 (m, 4H). MS (ESI) m/z: 393.1 $[M+H]^+$.

Example 031. 2-(Methylamino)-N-(5-nitrothiazol-2-yl)benzamide (B-68)

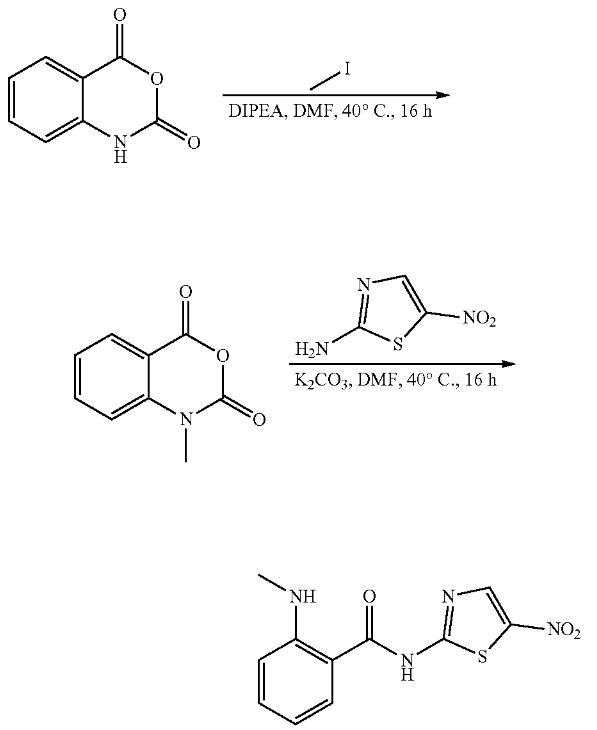

Step 1. Synthesis of 1-methyl-2H-benzo[d][1.3]oxazine-2,4 (1H)-dione

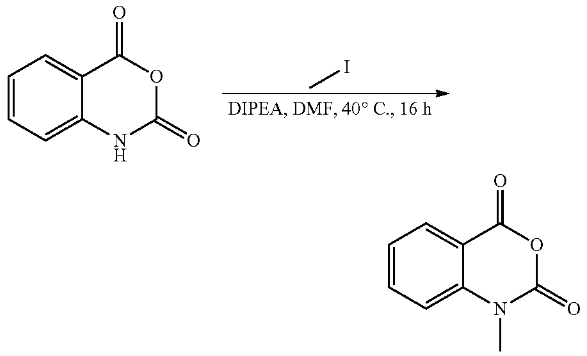

A solution of 1H-benzo[d][1,3]oxazine-2,4-dione (2.00 g, 12.2 mmol), iodomethane (3.00 g, 19.2 mmol) and DIPEA (5 mL) in DMF (10 mL) was stirred at 40° C. for 16 h. At rt, the mixture was concentrated under vacuum. The resulting residue was purified by silica gel column chromatography (petroleum ether:EtOAc=2:1) to give the title compound (1.40 g, 67.0% yield) as white solid.

Step 2. Synthesis of 2-(methylamino)-N-(5-nitrothiazol-2-yl)benzamide

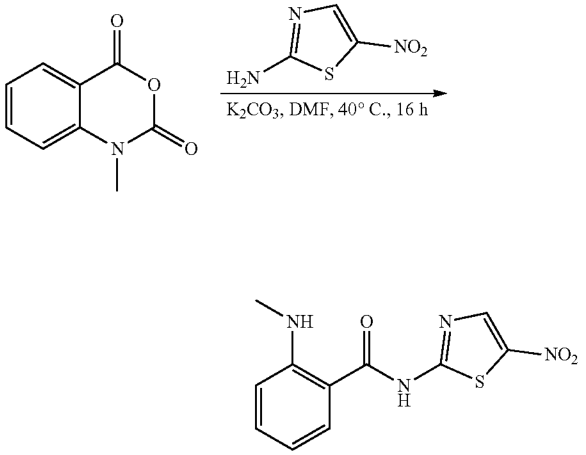

A solution of 1-methyl-1H-benzo[d][1,3]oxazine-2,4-dione (400 mg, 2.25 mmol) 5-nitrothiazol-2-amine (360 mg, 2.48 mmol) and $K_2CO_3$ (931 mg, 6.75 mmol) in DMF (10 mL) was stirred at 40° C. for 16 h. At it, the mixture was diluted with water (30 mL) and extracted with EtOAc (3x30 mL). The combined organic phase was washed with brine (3x30 mL), dried over $Na_2SO_4$, filtered and concentrated under vacuum. The resulting residue was purified by silica gel column chromatography (petroleum ether:EtOAc=3:1) to give the title compound (35.0 mg, 5.60% yield) as yellow solid. $^1H$ NMR (400 MHz, DMSO-$d_6$) δ 10.42 (brs, 2H), 8.70 (s, 1H), 7.96 (d, J=8.0 Hz, 1H), 7.46-7.43 (m, 1H), 6.77 (d, J=8.8 Hz, 1H), 6.64 (t, J=7.4 Hz, 1H), 2.87 (s, 3H). MS (ESI) m/z: 279.3 $[M+H]^+$.

Example 032. 2-(Isopropylamino)-N-(5-nitrothiazol-2-yl)benzamide (B-70)

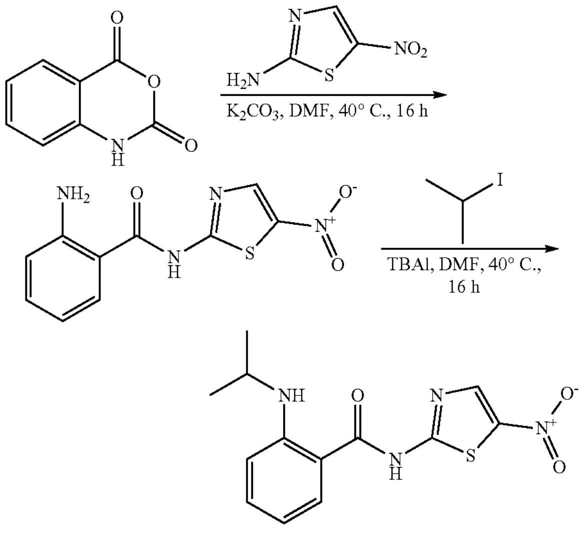

Step 1. Synthesis of 2-amino-N-(5-nitrothiazol-2-yl)benzamide

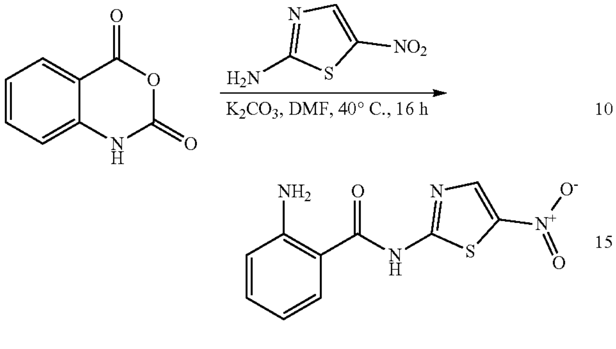

A solution of 1H-benzo[d][1,3]oxazine-2,4-dione (2.00 g, 12.2 mmol), 5-nitrothiazol-2-amine (1.96 g, 13.5 mmol) and $K_2CO_3$ (5.00 g, 36.7 mmol) in DMF (30 mL) was stirred at 40° C. for 16 h. At rt, the mixture was diluted with water (30 mL) and extracted with EtOAc (3×30 mL). The combined organic phase was washed with brine (3×30 mL), dried over $Na_2SO_4$, filtered and concentrated under vacuum. The resulting residue was purified by silica gel column chromatography (petroleum ether:EtOAc=3:1) to give the title compound (1.10 g, 34.0% yield) as yellow solid. MS (ESI) m/z: 265.1 $[M+H]^+$.

Step 2. Synthesis of 2-(isopropylamino)-N-(5-nitrothiazol-2-yl)benzamide

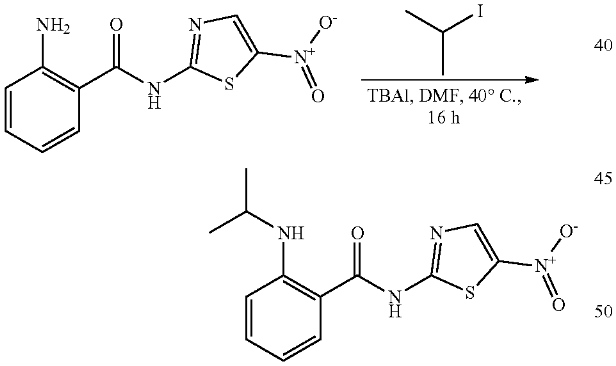

A solution of 2-amino-N-(5-nitrothiazol-2-yl)benzamide (200 mg, 0.757 mmol), 2-iodopropane (257 mg, 1.51 mmol) and TBAI (1.12 g, 3.02 mmol) in DMF (5 mL) was stirred at 40° C. for 16 h. At rt, the mixture was treated with water (30 mL) and extracted with EtOAc (3×30 mL). The combined organic phase was washed with brine (3×30 mL), dried over $Na_2SO_4$, filtered and concentrated under vacuum. The resulting residue was purified by prep-HPLC to give the title compound (5.50 mg, 2.00% yield) as yellow solid. 1H NMR (400 MHz, DMSO-$d_6$) δ 8.70 (s, 1H), 7.98 (d, J=8.0 Hz, 1H), 7.41 (t, J=7.8 Hz, 1H), 6.83 (d, J=8.4 Hz, 1H), 6.61 (t, J=7.6 Hz, 1H), 3.79-3.76 (m, 1H), 1.22 (d, J=6.0 Hz, 6H). MS (ESI) m/z: 307.4 $[M+H]^+$.

Example 033. N-(5-nitrothiazol-2-yl)-2-(phenylamino)benzamide (B-72)

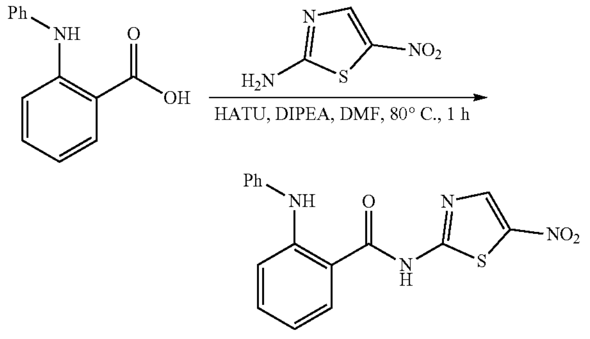

A solution of 2-(phenylamino)benzoic acid (200 mg, 0.76 mmol), 5-nitrothiazol-2-amine (182 mg, 1.05 mmol), HATU (400 mg, 1.26 mmol) and DIEA (0.40 mL) in DMF (5 mL) was stirred at 80° C. for 1 h. After the mixture was diluted with $H_2O$ (30 mL), it was extracted with EtOAc (3×30 mL). The combined organic layers were washed with brine (3×30 mL), dried over $Na_2SO_4$, filtered and concentrated under vacuum. The resulting residue was purified by pre-HPLC to give the title compound (53.0 mg, 15.0% yield) as yellow solid. $^1H$ NMR (400 MHz, DMSO-$d_6$): δ 13.42 (s, 1H), 9.12 (s, 1H), 8.71 (s, 1H), 7.92 (d, J=7.6 Hz, 1H), 7.44 (t, J=7.2 Hz, 1H), 7.35-7.28 (m, 3H), 7.21 (d, J=7.6 Hz, 2H), 7.02 (t, J=7.2 Hz, 1H), 6.91 (t, J=7.6 Hz, 1H). MS (ESI) m/z: 341.2 $[M+H]^+$.

Example 034. 2-Benzamido-N-(5-nitrothiazol-2-yl) benzamide (B-63)

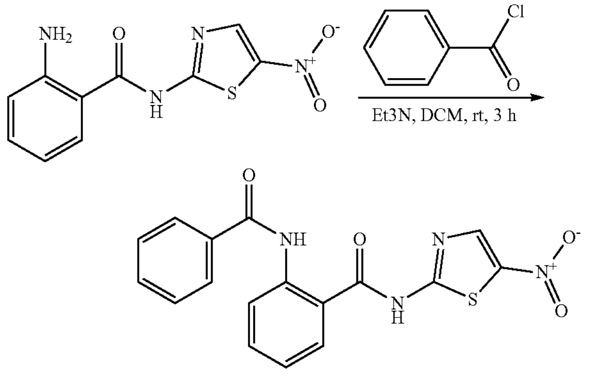

To a solution of 2-amino-N-(5-nitrothiazol-2-yl)benzamide (150 mg, 0.568 mmol) and $Et_3N$ (115 mg, 1.14 mmol) in DCM (5 mL) was added benzoyl chloride (168 mg, 0.682 mmol) at 0° C. After the mixture was stirred at rt for 3 h, it was concentrated under vacuum. The resulting residue was purified by prep-HPLC to give the title compound (50.0 mg, 23.8% yield) as white solid. $^1H$ NMR (400 MHz, DMSO-$d_h$): δ 13.59 (brs, 1H), 11.01 (brs, 1H), 8.68 (s, 1H), 8.06-7.89 (m, 4H), 7.65-7.54 (m, 4H), 7.31 (t, J=7.6 Hz, 1H). MS (ESI) m/z: 367.1 $[M-H]^-$.

Example 035. 2-Methyl-N-(5-nitrothiazol-2-yl)benzamide (B-83)

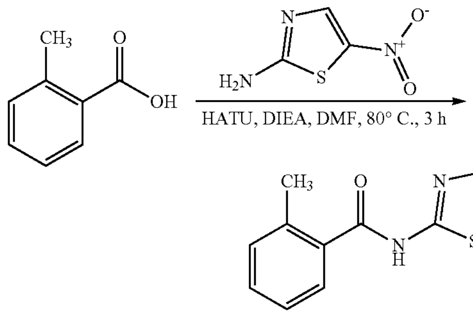

A solution of 2-methylbenzoic acid (200 mg, 1.47 mmol), 5-nitrothiazol-2-amine (257 mg, 1.77 mmol), HATU (559 mg, 1.47 mmol) and DIEA (380 mg, 2.94 mmol) in DMF (15 mL) was stirred at 80° C. for 3 h. The mixture was cooled to rt and purified by prep-HPLC to give the title compound (150 mg, 38.76% yield) as white solid. $^1H$ NMR (400 MHz, DMSO-$d_6$): δ 13.50 (s, 1H), 8.70 (s, 1H), 7.65-7.63 (m, 1H), 7.49-7.47 (m, 1H), 7.38-7.35 (m, 2H), 2.43 (s, 3H). MS (ESI) m/z: 264.0 $[M+H]^+$.

Example 036. 2-(3-(2-(2-(2-Aminoethoxy)ethoxy)ethoxy)propanamido)-N-(5-nitrothiazol-2-yl)benzamide (BL-3)

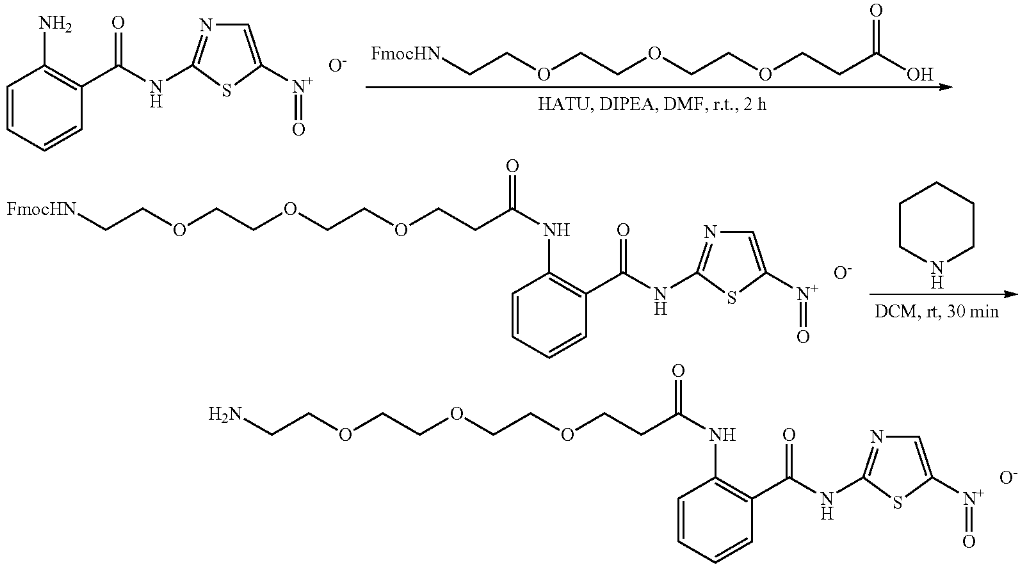

Step 1. Synthesis of (9H-fluoren-9-yl)methyl (2-(2-(2-(3-((2-((5-nitrothiazol-2-yl)carbamoyl)phenyl)amino)-3-oxopropoxy)ethoxy)ethoxy)ethyl)carbamate

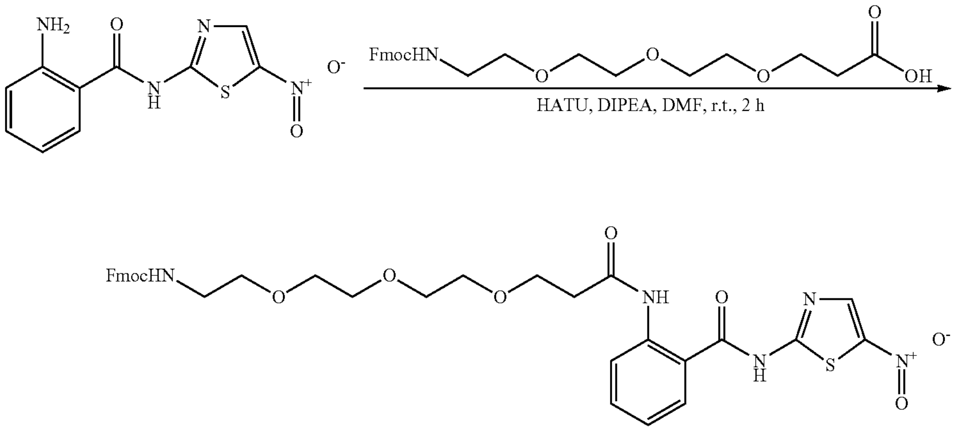

To a solution of 2-amino-N-(5-nitrothiazol-2-yl)benzamide (100 mg, 0.379 mmol), 1-(9H-fluoren-9-yl)-3-oxo-2,7,10,13-tetraoxa-4-azahexadecan-16-oic acid (151 mg, 0.341 mmol) and HATU (159 mg, 0.418 mmol) in DMF (5 mL) was added DIPEA (98 mg, 0.760 mmol). After being was stirred at rt for 2 h, the mixture was diluted with water (50 mL) and extracted with EtOAc (3×50 mL). The combined organic phase was dried over $Na_2SO_4$, filtered and concentrated under vacuum to give the crude title compound (250 mg, crude) as red oil, which was used in the next step without further purification. MS (ESI) m/z: 690.4 $[M+H]^+$.

Step 2. Synthesis of 2-(3-(2-(2-(2-aminoethoxy)ethoxy)ethoxy)propanamido)-N-(5-nitrothiazol-2-yl)benzamide

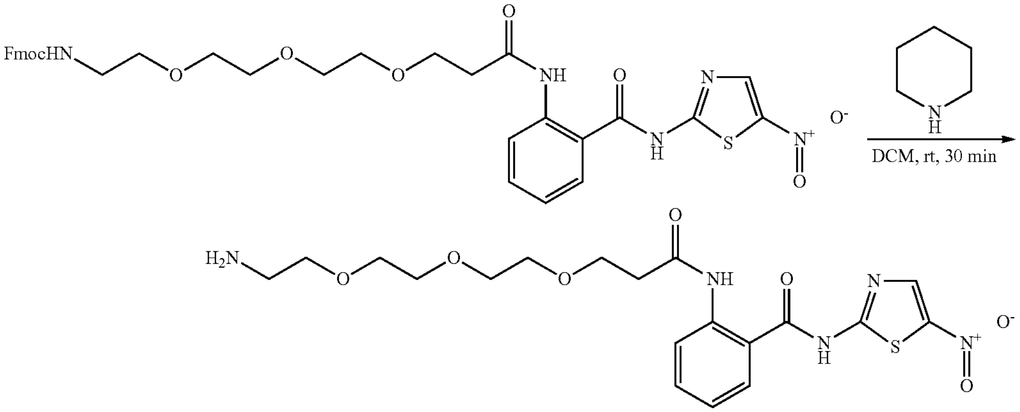

To a solution of (9H-fluoren-9-yl)methyl (2-(2-(2-(3-((2-((5-nitrothiazol-2-yl)carbamoyl)phenyl)amino)-3-oxopropoxy)ethoxy)ethoxy)ethyl)carbamate (250 mg, crude) in DCM (2 mL) was added piperidine (2.0 mL). After being stirred at rt for 30 min, the mixture was concentrated under vacuum. The resulting residue was purified by prep-HPLC to give the title product (46.1 mg, 28% yield over two steps) as white solid. $^1H$ NMR (400 MHz, DMSO-$d_6$): δ 13.78 (s, 1H), 8.60-8.58 (m, 1H), 8.55 (s, 1H), 8.21 (d, J=7.6 Hz, 1H), 7.67 (brs, 2H), 7.42 (t, J=7.2 Hz, 1H), 7.09 (t, J=7.2 Hz 1H), 3.83 (t, J=6.0 Hz, 2H), 3.55-3.48 (m, 10H), 2.92 (t, J=4.8 Hz, 2H), 2.66 (t, J=6.0 Hz, 2H). MS (ESI) m/z: 468.1 $[M+H]^+$.

Example 037. 2-Acetamido-N-(5-methylthiazol-2-yl)benzamide (B-42)

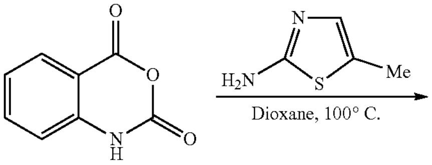

-continued

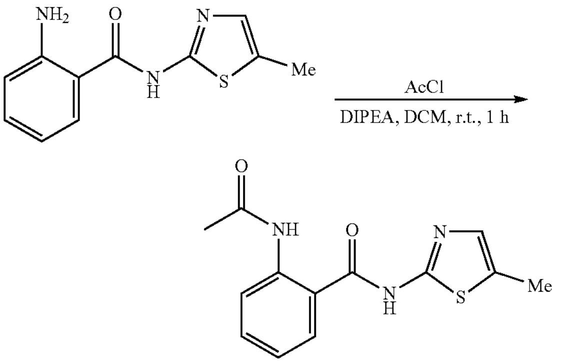

Step 1. Synthesis of 2-amino-N-(5-methylthiazol-2-yl)benzamide

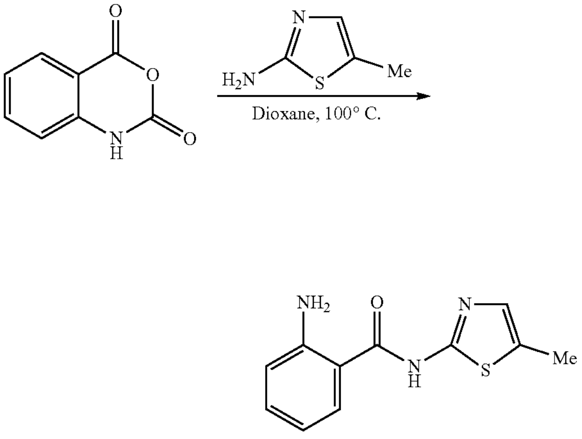

A solution of 2H-benzo[d][1,3]oxazine-2,4 (1H)-dione (200 mg, 1.22 mmol) in 1,4-dioxane (10 mL) was stirred at 100° C. overnight, before the reaction mixture was concentrated under vacuum. The resulting residue was purified by silica gel column chromatography (petroleum ether: EtOAc=2:1) to give the title compound (200 mg, 70.5% yield) as white solid. MS (ESI) m/z: 234.2 $[M+H]^+$.

Step 2. Synthesis of 2-acetamido-N-(5-methylthiazol-2-yl)benzamide

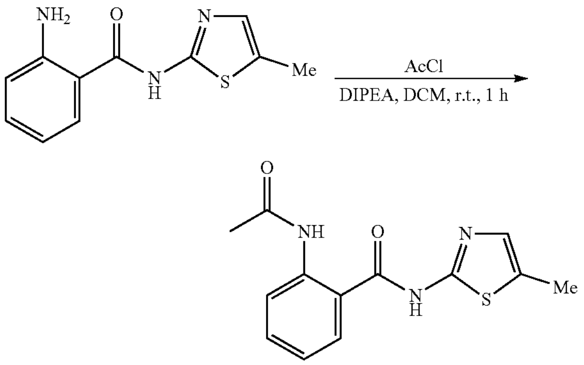

To a solution of 2-amino-N-(5-methylthiazol-2-yl)benzamide (200 mg, 0.857 mmol) and DIPEA (333 mg, 2.58 mmol) in DCM (10 mL) was added acetyl chloride (100 mg, 1.29 mmol). After being stirred at rt for 1 h, the reaction mixture was diluted with DCM (30 mL) and washed with brine. The organic phase was dried over $Na_2SO_4$, filtered and concentrated to give a residue, which was recrystallized from methanol to provide the title compound (50.3 mg, 21.3% yield) as white solid. $^1H$ NMR (400 MHz, DMSO-$d_6$): δ 12.49 (brs, 1H), 10.45 (brs, 1H), 8.06 (brs, 1H), 7.85 (brs, 1H), 7.50 (t, J=7.8 Hz, 1H), 7.23-7.16 (m, 2H), 2.36 (s, 3H), 2.08 (s, 3H). MS (ESI) m/z: 276.2 $[M+H]^+$.

Example 038. 2-Acetamido-N-(5-nitropyridin-2-yl)benzamide (B-53)

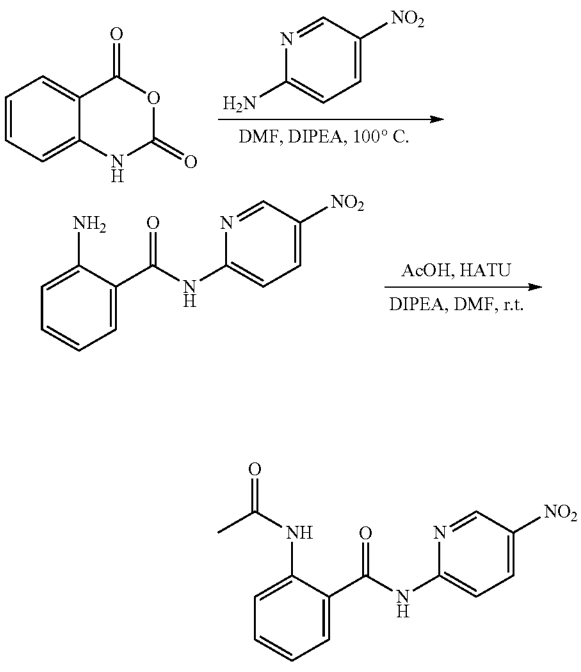

Step 1. Synthesis of 2-amino-N-(5-nitropyridin-2-yl)benzamide

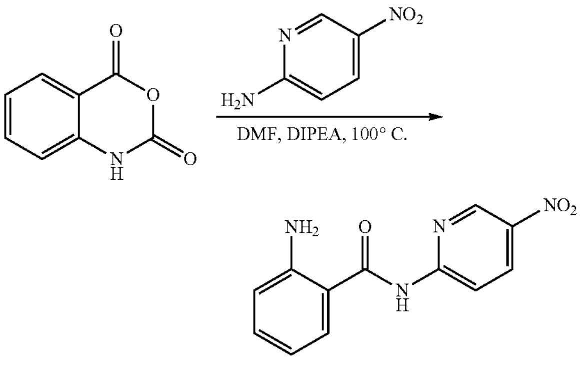

To a solution of 2H-benzo[d][1,3]oxazine-2,4 (1H)-dione (400 mg, 2.45 mmol) in DMF (10 mL) were added DIPEA (632 mg, 4.90 mmol) and 5-nitropyridin-2-amine (341 mg, 2.45 mmol). After being stirred at 100° C. overnight, the reaction mixture was cooled to rt and diluted with EtOAc (30 mL). The mixture was washed with brine (3×30 mL), dried over $Na_2SO_4$, filtered and concentrated under vacuum. The resulting residue was purified by silica gel column chromatography (petroleum ether:EtOAc=2:1) to give the title compound (60 mg, 9.5% yield) as yellow solid. MS (ESI) m/z: 259.2 $[M+H]^-$.

Step 2. Synthesis of 2-acetamido-N-(5-nitropyridin-2-yl)benzamide

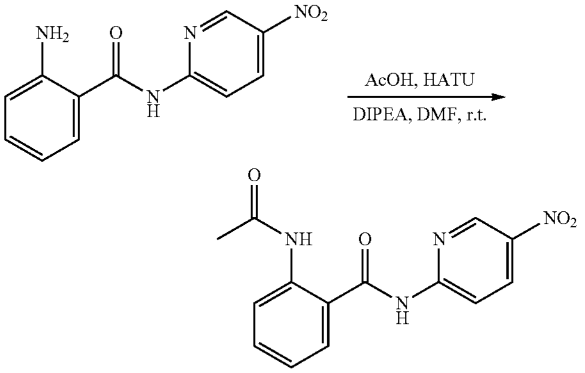

To a solution of 2-amino-N-(5-nitropyridin-2-yl)benzamide (60 mg, 0.232 mmol) in DMF (2 mL) were added acetic acid (27 mg, 0.464 mmol), HATU (175 mg, 0.464 mmol) and DIPEA (60 mg, 0.464 mmol). After being stirred at rt overnight, the reaction mixture was purified by prep-HPLC to give the title compound (12.0 mg, 17.2% yield) as yellow solid. $^1H$ NMR (400 MHz, DMSO-$d_6$): δ 11.49 (s, 1H), 10.09 (s, 1H), 9.21-9.20 (m, 1H), 8.66-8.63 (m, 1H), 8.36 (d, J=9.2 Hz, 1H), 7.75 (d, J=8.4 Hz, 1H), 7.69 (d, J=7.6 Hz, 1H), 7.52 (t, J=7.8 Hz, 1H), 7.22 (t, J=7.6 Hz, 1H), 2.00 (s, 3H). MS (ESI) m/z: 301.3 $[M+H]^+$.

Example 039. 2-Acetamido-N-(5-chloropyridin-2-yl)benzamide (B-54)

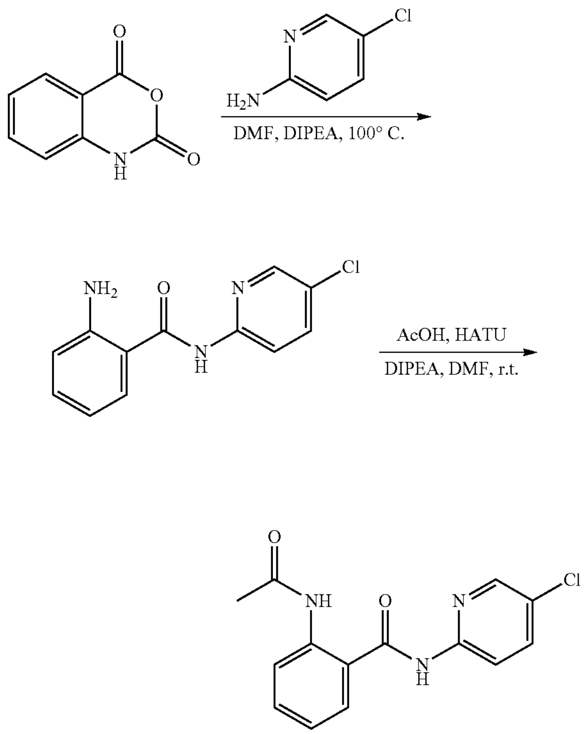

Step 1. Synthesis of 2-amino-N-(5-chloropyridin-2-yl)benzamide

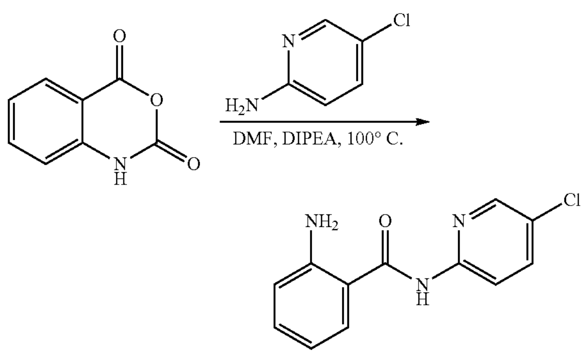

To a solution of 2H-benzo[d][1,3]oxazine-2,4 (1H)-dione (400 mg, 2.45 mmol) in DMF (10 mL) were added DIPEA (632 mg, 4.90 mmol) and 5-nitropyridin-2-amine (315 mg, 2.45 mmol). After being stirred at 100° C. overnight, the reaction mixture was cooled to room temperature and diluted with EtOAc (30 mL). The mixture was washed with brine (3×30 mL), dried over $Na_2SO_4$, filtered and concentrated under vacuum. The resulting residue was purified by silica gel column chromatography (petroleum ether: EtOAc=2:1) to give the title compound (40 mg, 6.60% yield) as white solid. MS (ESI) m/z: 248.2 $[M+H]^+$.

Step 2. Synthesis of 2-acetamido-N-(5-chloropyridin-2-yl)benzamide

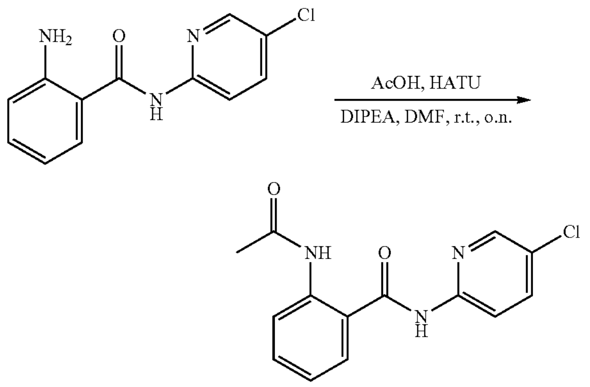

To a solution of 2-amino-N-(5-chloropyridin-2-yl)benzamide (40 mg, 0.161 mmol) in DMF (2 mL), were added acetic acid (19 mg, 0.322 mmol), HATU (122 mg, 0.322 mmol), DIPEA (41 mg, 0.322 mmol). After being stirred at it overnight, the reaction mixture was purified by prep-HPLC to give the title compound (10.5 mg, 22.5% yield) as yellow solid. 1H NMR (400 MHz, DMSO-$d_6$): δ 10.98 (s, 1H), 10.20 (s, 1H), 8.44-8.43 (m, 1H), 8.17-8.15 (m, 1H), 7.97-7.91 (m, 2H), 7.72 (d, J=8.0 Hz, 1H), 7.50 (t, J=8.0 Hz, 1H), 7.20 (t, J=7.6 Hz, 1H), 2.03 (s, 3H). MS (ESI) m/z: 290.4 $[M+H]^-$.

Example 040. 3-Butyramido-2-((5-nitrothiazol-2-yl) carbamoyl)phenyl acetate (B-23)

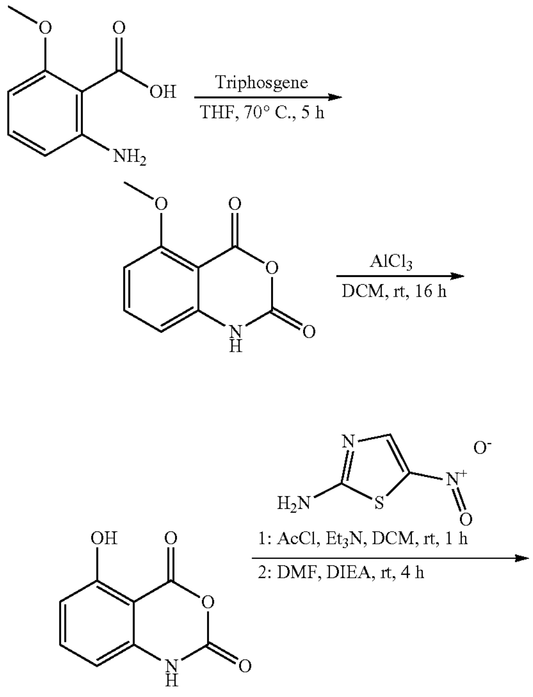

-continued

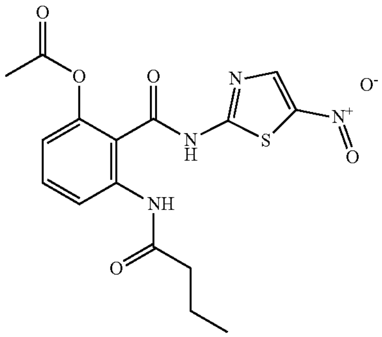

Step 1. Synthesis of 5-methoxy-2H-benzo[d][1,3]oxazine-2,4 (1H)-dione

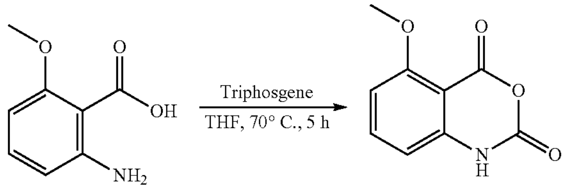

A solution of 2-amino-6-methoxybenzoic acid (2.00 g, 12.0 mmol) and triphosgene (1.30 g, 0.33 mmol) in THF (40 mL) was stirred at 70° C. for 5 h. At rt, the mixture was filtered and the filtered cake was dried under vacuum to give the title compound (1.90 g, 82.04% yield) as yellow solid. MS (ESI) m/z: 194.2 $[M+H]^+$.

Step 2. Synthesis of 5-hydroxy-2H-benzo[d][1,3]oxazine-2,4 (1H)-dione

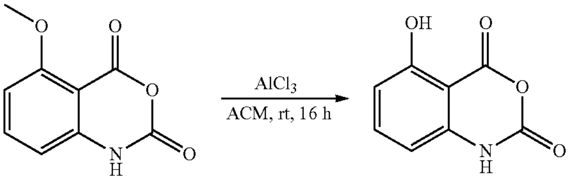

To a solution of 5-methoxy-1H-benzo[d][1,3]oxazine-2,4-dione (1.90 g, 9.83 mmol) in DCM (50 mL) was added $AlCl_3$ (2.80 g, 19.7 mmol). After being stirred at rt for 16 h, the mixture was quenched with brine (50 mL) and extracted with EtOAc (3×30 mL). The combined organic phase was dried over $Na_2SO_4$, filtered and concentrated under vacuum to give the title compound (1.70 g, 95.9% yield) as white solid. MS (ESI) m/z: 178.3 $[M-H]^-$.

Step 3. Synthesis of 3-butyramido-2-((5-nitrothiazol-2-yl)carbamoyl)phenyl acetate

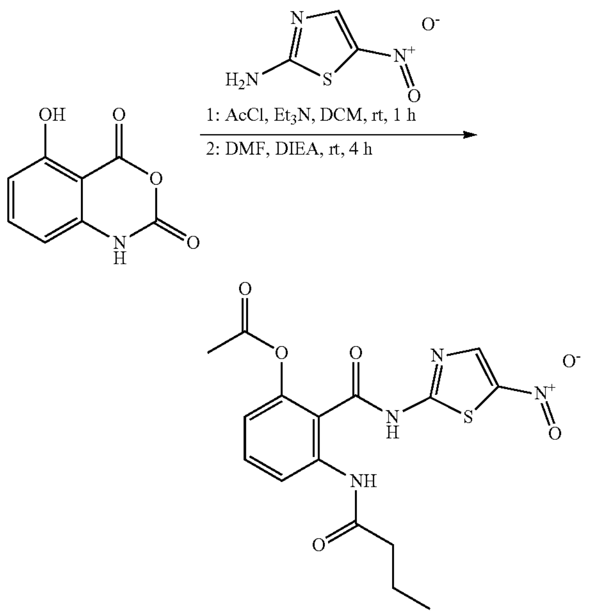

To a 5-hydroxy-1H-benzo[d][1,3]oxazine-2,4-dione (200 mg, 1.12 mmol) and $Et_3N$ (170 mg, 1.68 mmol) in DCM (5 mL) was added acetyl chloride (80 mg, 1.00 mmol). After the reaction was stirred at it for 1 h, a solution of 5-nitrothiazol-2-amine (320 mg, 2.24 mmol) in DMF (2 mL) was added. The resulting solution was stirred at rt for 4 h before butyryl chloride (0.3 mL) was added. After another 1 h, the reaction mixture was purified by prep-HPLC, and further purified by silica gel column chromatography (petroleum ether:EtOAc=5:1) to give the title compound (12.2 mg, 2.78% yield) as white solid. $^1H$ NMR (400 MHz, DMSO-$d_6$): δ 13.48 (s, 1H), 9.98 (s, 1H), 8.65 (s, 1H), 7.54 (t, J=7.2 Hz, 1H), 7.39 (brs, 1H), 7.09 (d, J=1.4 Hz, 1H), 2.20 (t, J=7.2 Hz, 2H), 2.14 (s, 3H), 1.49-1.48 (m, 2H), 0.82 (t, J=7.2 Hz, 3H). MS (ESI) m/z: 393.0 $[M+H]^+$.

Example 041. 2-(6-Aminohexanamido)-N-(4-methyl-5-nitrothiazol-2-yl)benzamide (BL-1)

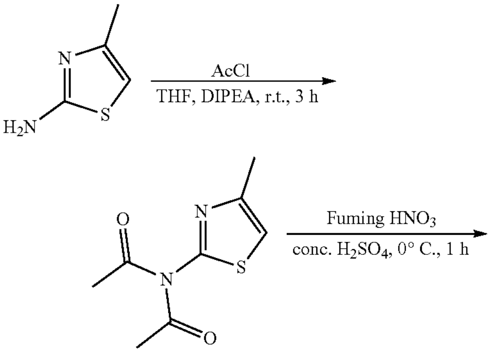

-continued

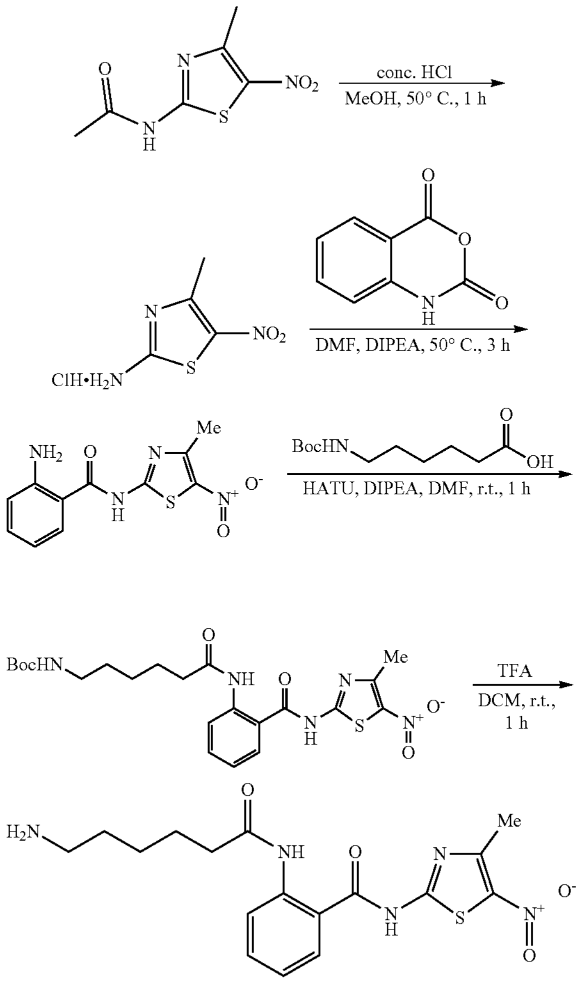

Step 1. Synthesis of N-acetyl-N-(4-methylthiazol-2-yl)acetamide

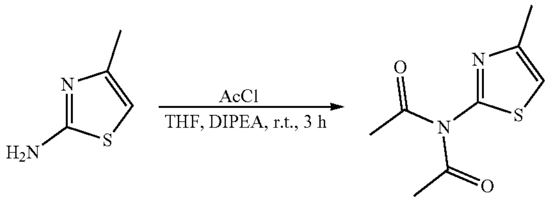

To a solution of 4-methylthiazol-2-amine (18.0 g, 157 mmol) and DIPEA (100 g, 785 mmol) in THF (300 mL) was added acetyl chloride (36.7 g, 471 mmol) at 0° C. After being stirred at rt for 3 h, the reaction mixture was acidified to pH=4.0 with 1 N HCl. The mixture was extracted with EtOAc (3x200 mL). The combined organic layer was washed with brine, dried over $Na_2SO_4$, filtered and concentrated under vacuum. The resulting residue was purified by silica gel column chromatography (petroleum ether: EtOAc=1:1) to give the title compound (10.0 g, 32.1% yield) as brown oil. MS (ESI) m/z: 199.1 $[M+H]^+$.

Step 2. Synthesis of N-(4-methyl-5-nitrothiazol-2-yl)acetamide

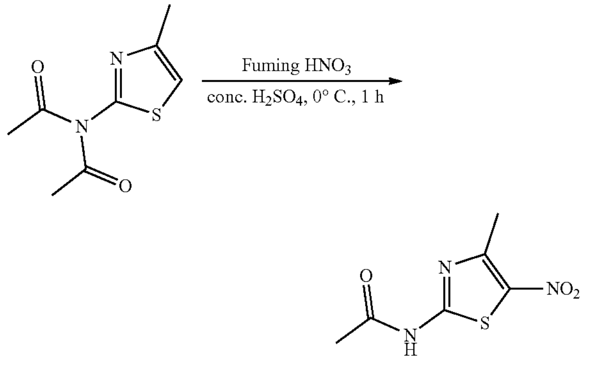

To a solution of N-acetyl-N-(4-methylthiazol-2-yl)acetamide (1.00 g, 5.04 mmol) in conc. $H_2SO_4$ (2 mL) was added fuming $HNO_3$ (1 mL) at 0° C. After being stirred at 0° C. for 1 h, the mixture was diluted with ice-water (20 mL) and pH was adjusted to 8 with aq. $NaHCO_3$. The mixture was extracted with EtOAc (3x30 mL). The combined organic layers were washed with brine, dried over $Na_2SO_4$, filtered and concentrated under vacuum. The resulting residue was purified by silica gel column chromatography (petroleum ether:EtOAc=1:1) to give the title compound (600 mg, 59.2% yield) as yellow solid. MS (ESI) m/z: 202.1 $[M+H]^+$.

Step 3. Synthesis of 4-methyl-5-nitrothiazol-2-amine hydrochloride

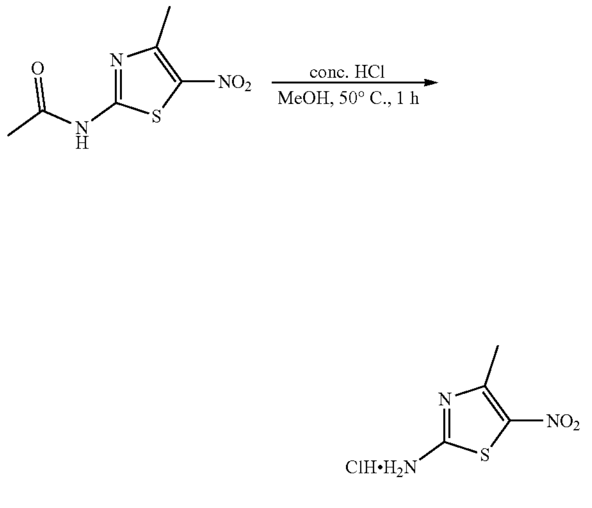

A solution of N-(4-methyl-5-nitrothiazol-2-yl)acetamide (600 mg, 2.98 mmol) in MeOH (5 mL) and conc. HCl (5 mL) was heated at 50° C. for 1 h, before the reaction mixture was concentrated under vacuum to give the title compound (400 mg, 68.6% yield) as yellow solid, which used in the next step without further purification. MS (ESI) m/z: 160.4 $[M+H]^+$.

Step 4. Synthesis of 2-amino-N-(4-methyl-5-nitrothiazol-2-yl)benzamide

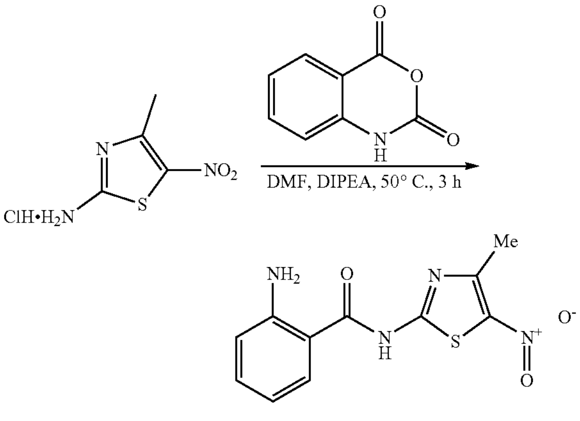

To a solution of 4-methyl-5-nitrothiazol-2-amine hydrochloride (400 mg, crude) in DMF (15 mL) were added DIPEA (791 mg, 6.12 mmol) and 2H-benzo[d][1,3]oxazine-2,4 (1H)-dione (665 mg, 4.08 mmol). After being stirred at 50° C. for 3 h, the reaction mixture was cooled to rt and diluted with EtOAc (50 mL). The mixture was washed with brine, dried over $Na_2SO_4$, filtered and concentrated under vacuum. The resulting residue was purified by silica gel column chromatography (petroleum ether:EtOAc=2:1) to give the title compound (450 mg, 79.2% yield) as yellow solid. MS (ESI) m/z: 279.3 $[M+H]^-$.

Step 5. Synthesis of tert-butyl (6-((2-((4-methyl-5-nitrothiazol-2-yl)carbamoyl)phenyl)amino)-6-oxohexyl)carbamate

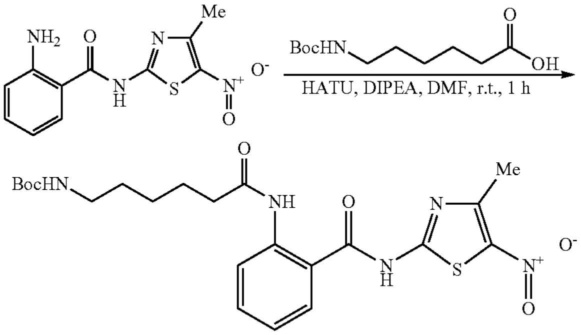

To a solution of 2-amino-N-(4-methyl-5-nitrothiazol-2-yl)benzamide (200 mg, 0.720 mmol) in DMF (10 mL) were added 6-((tert-butoxycarbonyl)amino)hexanoic acid (166 mg, 0.720 mmol), HATU (328 mg, 0.860 mmol) and DIPEA (186 mg, 1.44 mmol). After being stirred at rt for 1 h. the reaction mixture was diluted with EtOAc (40 mL), washed with brine, dried over $Na_2SO_4$, filtered and concentrated under vacuum. The resulting residue was purified by silica gel column chromatography (petroleum ether:EtOAc=1:1) to give the title compound (250 mg, 70.8% yield) as yellow solid. MS (ESI) m/z: 492.1 $[M+H]^+$.

Step 6. Synthesis of 2-(6-aminohexanamido)-N-(4-methyl-5-nitrothiazol-2-yl)benzamide

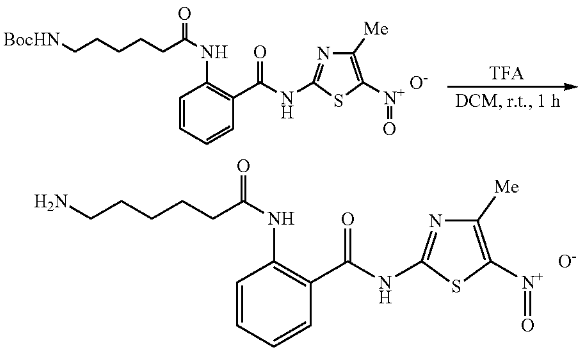

To a solution of tert-butyl (6-((2-((4-methyl-5-nitrothiazol-2-yl)carbamoyl)phenyl)amino)-6-oxohexyl)carbamate in DCM (3 mL) was added TFA (3 mL). After being stirred at rt for 1 h. the reaction mixture was concentrated under vacuum. The resulting residue was purified by prep-HPLC to give the title compound (210 mg, 81.5% yield) as yellow solid. $^1H$ NMR (400 MHz, DMSO-$d_6$): δ 13.41 (s, 1H), 10.43 (s, 1H), 7.76-7.64 (m, 4H), 7.56 (t, J=7.6 Hz, 1H), 7.24 (t, J=7.6 Hz, 1H), 2.80-2.72 (m, 2H), 2.70 (s, 3H), 2.31 (t, J=7.2 Hz, 2H), 1.60-1.49 (m, 4H), 1.36-1.31 (m, 2H). MS (ESI) m/z: 392.1 $[M+H]^+$.

Example 042. 2-Acetamido-N-(4-methyl-5-nitrothiazol-2-yl)benzamide (B-27)

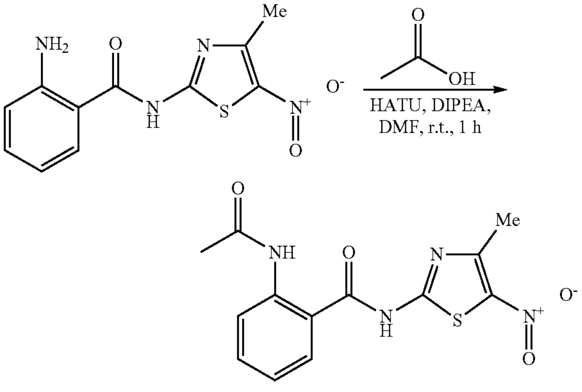

To a solution of 2-amino-N-(4-methyl-5-nitrothiazol-2-yl)benzamide (50 mg, 0.180 mmol) in DMF (2 mL) were added acetic acid (21 mg, 0.360 mmol), HATU (137 mg, 0.360 mmol) and DIPEA (70 mg, 0.540 mmol). After being stirred at rt for 1 h, the reaction mixture was purified by prep-HPLC to give the title compound (17.9 mg, 31.1% yield) as yellow solid. $^1H$ NMR (400 MHz, DMSO-$d_6$): δ 13.41 (s, 1H), 10.21 (s, 1H), 7.70-7.65 (m, 2H), 7.57 (t, J=7.6 Hz, 1H), 7.25 (t, J=7.6 Hz, 1H), 2.70 (s, 3H), 2.01 (s, 3H). MS (ESI) m/z: 321.0 $[M+H]^+$.

Example 043. 2-Acetamido-N-(5-chloro-4-methylthiazol-2-yl)benzamide (CLI-C049)

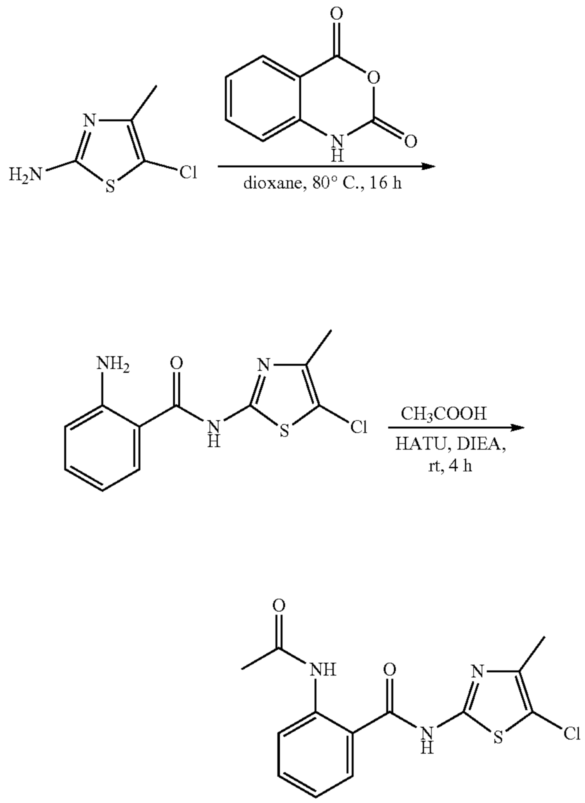

Step 1. Synthesis of 2-amino-N-(5-chloro-4-methylthiazol-2-yl)benzamide

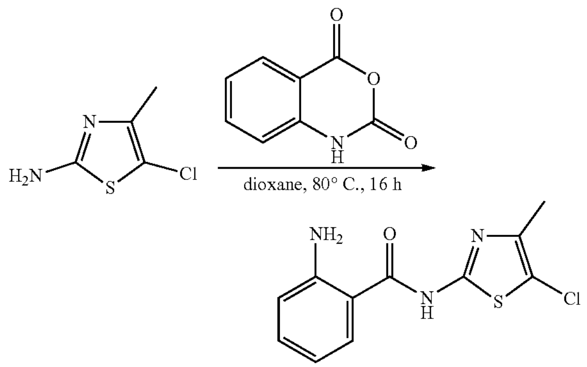

A solution of 1H-benzo[d][1,3]oxazine-2,4-dione (100 mg, 0.613 mmol) and 5-chloro-4-methylthiazol-2-amine (92.0 mg, 0.622 mmol) in dioxane (5.00 mL) was stirred at 80° C. for 16 h. The mixture was cooled to rt and concentrated. The resulting residue was purified by silica gel column chromatography (petroleum ether:EtOAc=10:1-1:1) to give the title compound (20 mg, 12.22% yield) as white solid. MS (ESI) m/z: 268.0 $[M+H]^+$.

Step 2. Synthesis of 2-acetamido-N-(5-chloro-4-methylthiazol-2-yl)benzamide

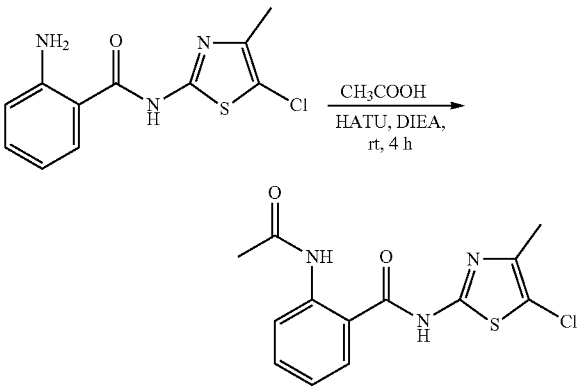

A solution of 2-amino-N-(5-chloro-4-methylthiazol-2-yl) benzamide (20.0 mg, 0.075 mmol), acetic acid (5.40 mg, 0.090 mmol), HATU (43.0 mg, 0.113 mmol) and DIEA (20.0 mg, 0.150 mmol) in DMF (2 mL) was stirred at it for 2 h. The mixture was purified by prep-HPLC to give the title compound (8.80 mg, 37.97% yield) as white solid. $^1$H NMR (400 MHz, DMSO-$d_6$): δ 12.75 (s, 1H), 10.14 (brs, 1H), 7.85 (brs, 1H), 7.73 (brs, 1H), 7.52 (t, J=6.4 Hz, 1H), 7.20 (t, J=6.4 Hz, 1H), 2.25 (s, 3H), 2.04 (s, 3H). MS (ESI) m/z: 310.3 $[M+H]^+$.

Example 044. 2-Acetamido-N-(thiazol-2-yl)benzamide (B-41)

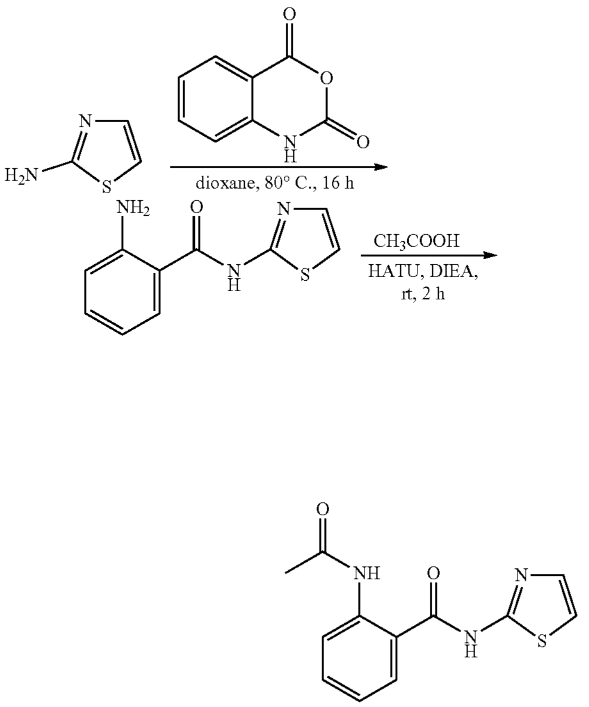

Step 1. Synthesis of 2-amino-N-(thiazol-2-yl)benzamide

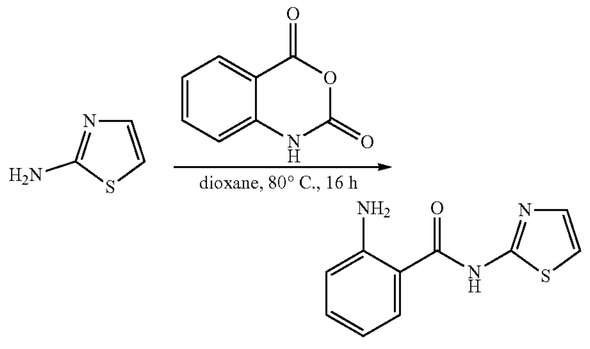

A solution of 1H-benzo[d][1,3]oxazine-2,4-dione (123 mg, 1.23 mmol) and thiazol-2-amine (200 mg, 1.23 mmol) in 1,4-dioxane (5 mL) was stirred at 80° C. for 16 h. The mixture was concentrated under vacuum. The resulting residue was purified by silica gel column chromatography (petroleum ether:EtOAc=3:1) to give the title compound (200 mg, 73.9% yield) as white solid. MS (ESI) m/z: 220.2 $[M+H]^+$.

Step 2. Synthesis of 2-acetamido-N-(thiazol-2-yl)benzamide

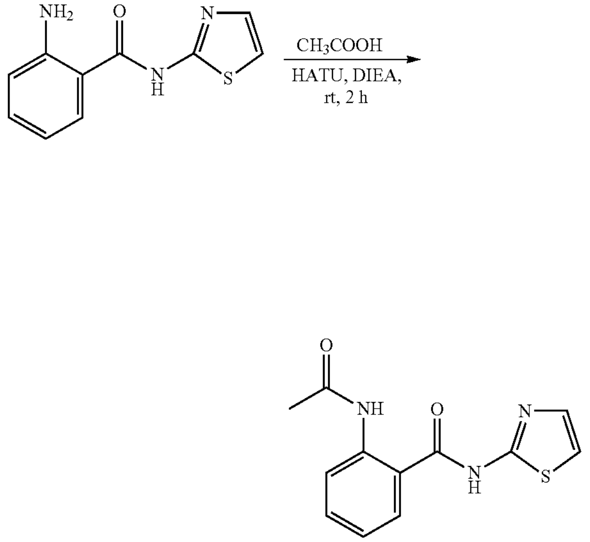

A solution of 2-amino-N-(thiazol-2-yl)benzamide (100 mg, 0.457 mmol), acetic acid (33.0 mg, 0.552 mmol), HATU (263 mg, 0.692 mmol) and DIEA (119 mg, 0.923 mmol) in DMF (5 mL) was stirred at rt for 2 h. The reaction mixture was purified by prep-HPLC to give title compound (48.0 mg, 40.24% yield) as white solid. $^1H$ NMR (400 MHz, DMSO-$d_6$): δ 12.65 (brs, 1H), 10.39 (brs, 1H), 8.13 (s, 0.3H, FA) 7.99 (s, 1H), 7.81 (s, 1H), 7.56-7.50 (m, 2H), 7.26 (d, J=3.6 Hz, 1H), 7.20 (t, J=7.6 Hz, 1H), 2.04 (s, 3H). MS (ESI) m/z: 262.4 $[M+H]^+$.

Example 045. 2-Acetamido-N-(5-bromopyridin-2-yl)benzamide (B-55)

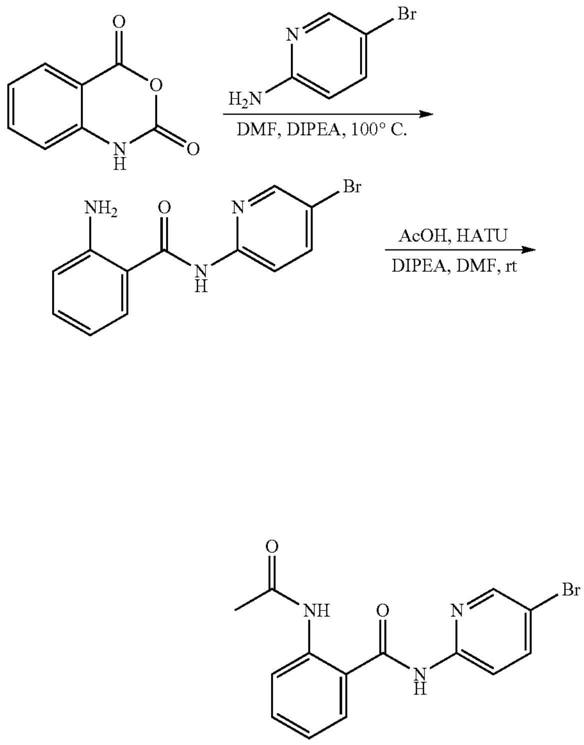

Step 1. Synthesis of 2-amino-N-(5-bromopyridin-2-yl)benzamide

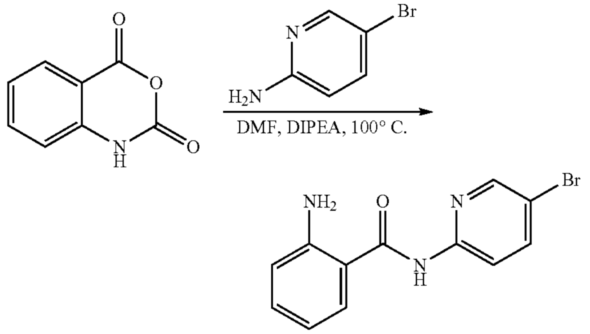

To a solution of 2H-benzo[d][1,3]oxazine-2,4 (1H)-dione (400 mg, 2.45 mmol) in DMF (10 mL) were added DIPEA (632 mg, 4.90 mmol) and 5-bromopyridin-2-amine (315 mg, 2.45 mmol). After being stirred at 100° C. overnight, the reaction mixture was cooled to rt and diluted with EtOAc (50 mL). The mixture was washed with brine (3×50 mL), dried over $Na_2SO_4$, filtered and concentrated under vacuum. The resulting residue was purified by silica gel column chromatography (petroleum ether:EtOAc=2:1) to give the title compound (40 mg, 5.71% yield) as white solid. MS (ESI) m/z: 292.2 $[M+H]^-$.

Step 2. Synthesis of 2-acetamido-N-(5-bromopyridin-2-yl)benzamide

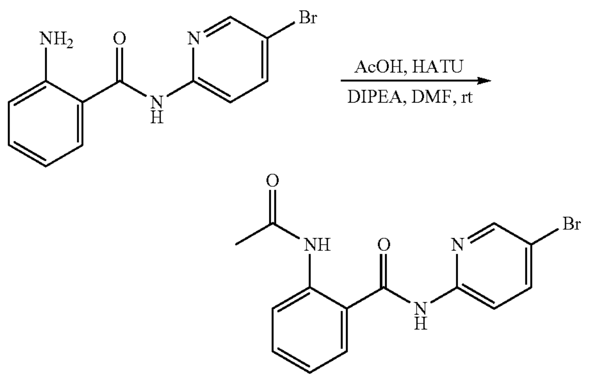

To a solution of 2-amino-N-(5-bromopyridin-2-yl)benzamide (40 mg, 0.140 mmol) in DMF (2 mL) were added acetic acid (17 mg, 0.280 mmol), HATU (107 mg, 0.280 mmol) and DIPEA (55 mg, 0.420 mmol). After being stirred at it overnight, the reaction mixture was purified by prep-HPLC to give the title compound (21.2 mg, 45.3% yield) as yellow solid. $^1$H NMR (400 MHz, DMSO-$d_6$): δ 10.97 (s, 1H), 10.19 (s, 1H), 8.51-8.50 (m, 1H), 8.13-8.05 (m, 2H), 7.92 (d, J=8.0 Hz, 1H), 7.72 (d, J=7.6 Hz, 1H), 7.50 (t, J=7.8 Hz, 1H), 7.20 (t, J=7.6 Hz, 1H), 2.03 (s, 3H). MS (ESI) m/z: 334.0 [M+H]$^+$.

Example 046. 2-(3-(2-(2-(2-Aminoethoxy)ethoxy)ethoxy)propanamido)-N-(4-methyl-5-nitrothiazol-2-yl)benzamide (BL-2)

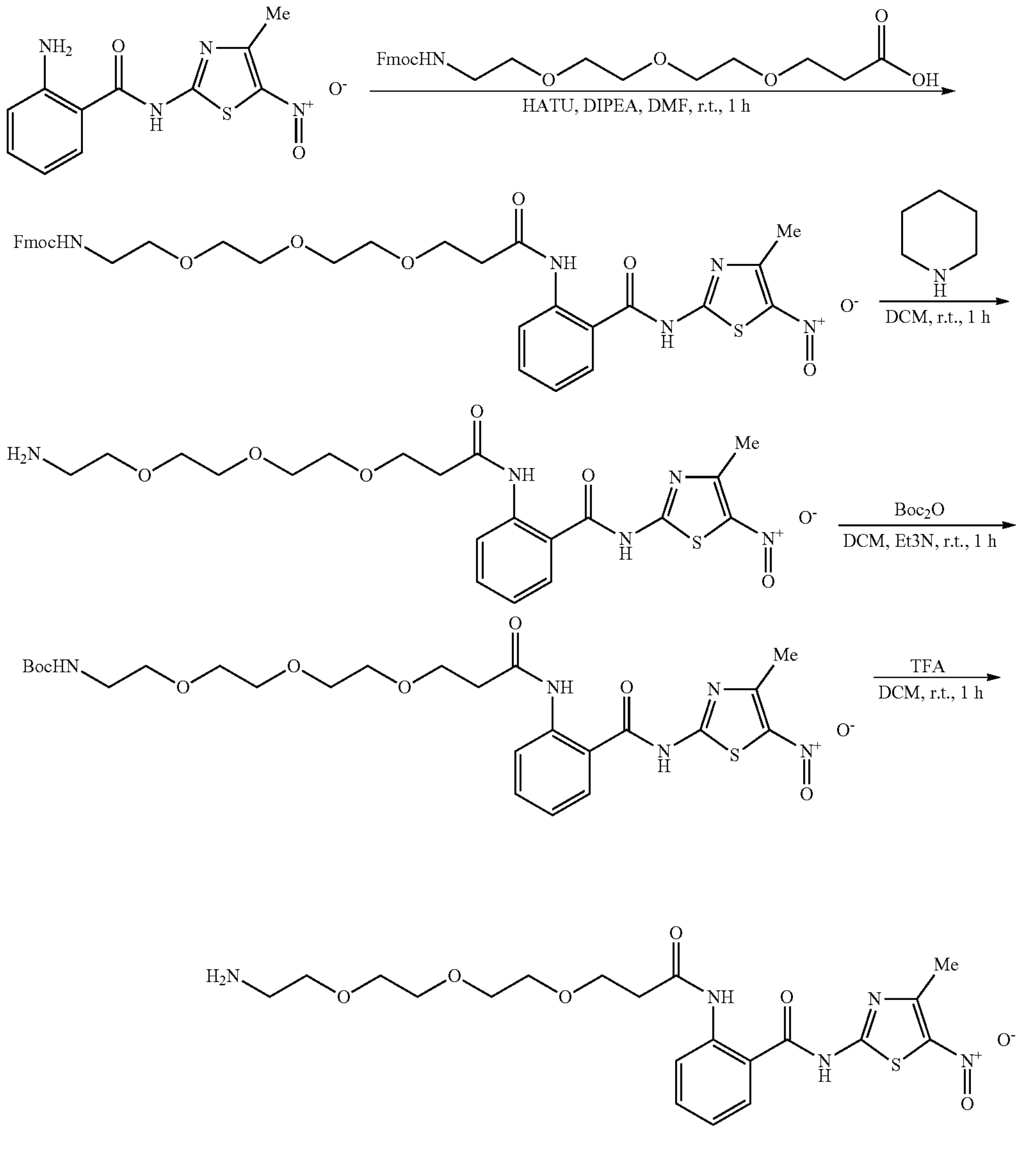

Step 1. Synthesis of (9H-fluoren-9-yl)methyl (2-(2-(2-(3-((2-((4-methyl-5-nitrothiazol-2-yl)carbamoyl)phenyl)amino)-3-oxopropoxy)ethoxy)ethoxy)ethyl)carbamate

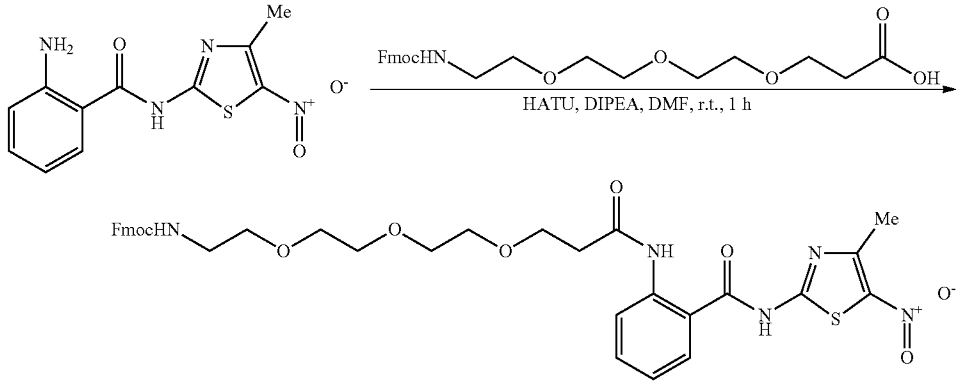

To a solution of 2-amino-N-(4-methyl-5-nitrothiazol-2-yl)benzamide (200 mg, 0.720 mmol) in DMF (10 mL) were added 1-(9H-fluoren-9-yl)-3-oxo-2,7,10,13-tetraoxa-4-aza-hexadecan-16-oic acid (319 mg, 0.720 mmol), HATU (328 mg, 0.860 mmol) and DIPEA (186 mg, 1.44 mmol). After being stirred at rt for 1 h, the reaction mixture was diluted with EtOAc (100 mL), washed with brine, dried over $Na_2SO_4$, filtered and concentrated under vacuum to give the title compound (500 mg, crude) as yellow solid, which was used in the next step without further purification. MS (ESI) m/z: 704.3 $[M+H]^+$.

Step 2. Synthesis of 2-(3-(2-(2-(2-aminoethoxy)ethoxy)ethoxy)propanamido)-N-(4-methyl-5-nitrothiazol-2-yl)benzamide

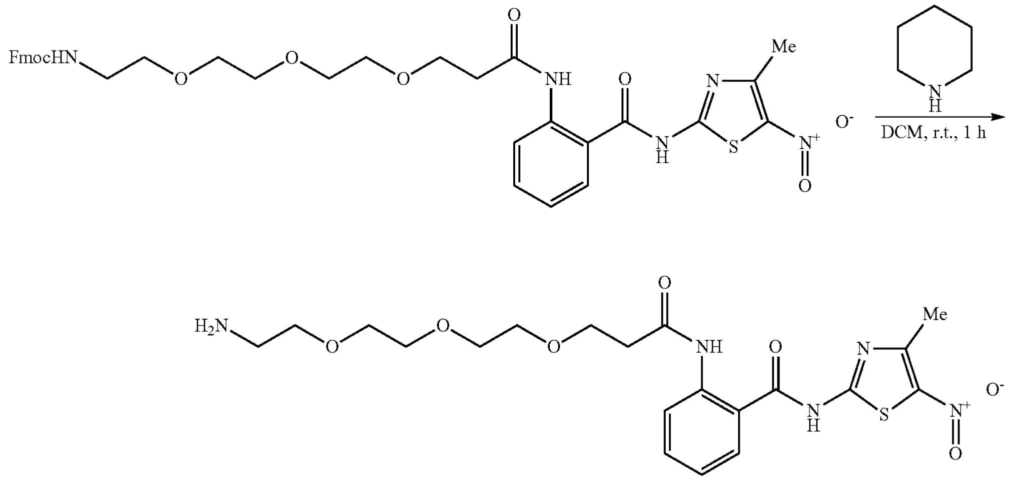

A solution of (9H-fluoren-9-yl)methyl (2-(2-(2-(3-((2-((4-methyl-5-nitrothiazol-2-yl)carbamoyl)phenyl)amino)-3-oxopropoxy)ethoxy)ethoxy)ethyl)carbamate in DCM (1 mL) and piperidine (1 mL) was stirred at rt for 1 h, before the reaction mixture was concentrated under vacuum to give the title product (600 mg, crude) as yellow oil, which was used in the next step without further purification. MS (ESI) m/z: 482.3 $[M+H]^+$.

Step 3. Synthesis of tert-butyl (2-(2-(2-(3-((2-((4-methyl-5-nitrothiazol-2-yl)carbamoyl)phenyl)amino)-3-oxopropoxy)ethoxy)ethoxy)ethyl)carbamate

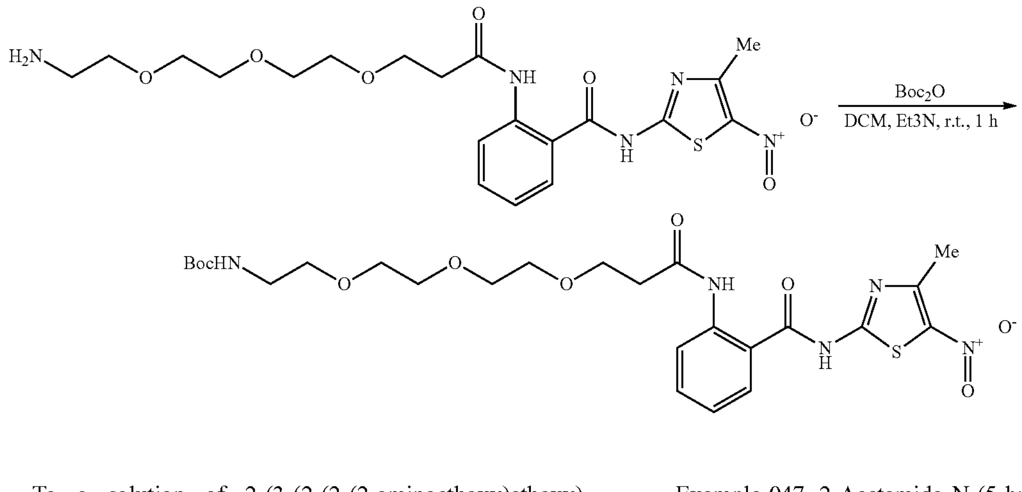

To a solution of 2-(3-(2-(2-(2-aminoethoxy)ethoxy)ethoxy)propanamido)-N-(4-methyl-5-nitrothiazol-2-yl)benzamide (600 mg, crude) in DCM (50 mL) were added TEA (730 mg, 7.20 mmol) and $Boc_2O$ (1.57 g, 7.20 mmol). After being stirred at rt for 1 h, the reaction mixture was washed with brine, dried over $Na_2SO_4$, filtered and concentrated under vacuum. The resulting residue was purified by silica gel column chromatography (DCM:MeOH=0:1) to give the title compound (500 mg, crude) as yellow solid, which was used in next step without further purification. MS (ESI) m/z: 582.3 $[M+H]^+$.

Step 4. Synthesis of 2-(3-(2-(2-(2-aminoethoxy)ethoxy)ethoxy)propanamido)-N-(4-methyl-5-nitrothiazol-2-yl)benzamide

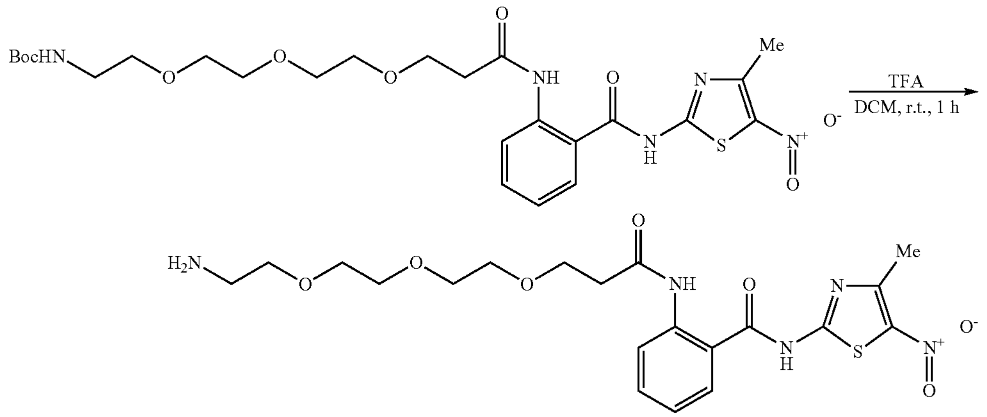

To a solution of tert-butyl (2-(2-(2-(3-((2-((4-methyl-5-nitrothiazol-2-yl)carbamoyl)phenyl)amino)-3-oxopropoxy)ethoxy)ethoxy)ethyl)carbamate (500 mg, crude) in DCM (1 mL) was added TFA (1 mL). After being stirred at rt 1 h, the reaction mixture was concentrated under vacuum. The resulting residue was purified by prep-HPLC to give the title compound (76.1 mg, 17.7% over four steps) as yellow solid. 1H NMR (400 MHz, DMSO-$d_6$+$D_2O$): 7.77-7.42 (m, 2H), 7.60 (t, J=7.8 Hz, 1H), 7.28 (t, J=7.6 Hz, 1H), 3.65 (t, J=6.2 Hz, 2H), 3.53-3.52 (m, 10H), 2.96-2.94 (m, 2H), 2.70 (s, 3H), 2.57-2.54 (m, 2H). MS (ESI) m/z: 482.4 $[M+H]^+$.

Example 047. 2-Acetamido-N-(5-bromothiazol-2-yl)benzamide (B-37)

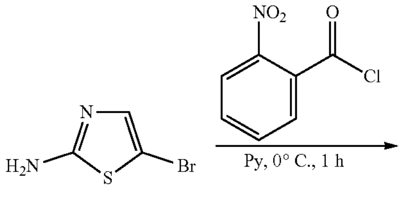

-continued

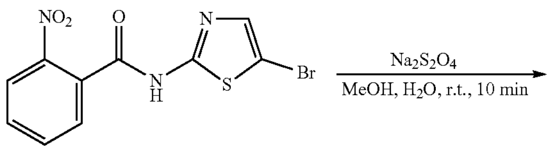

-continued

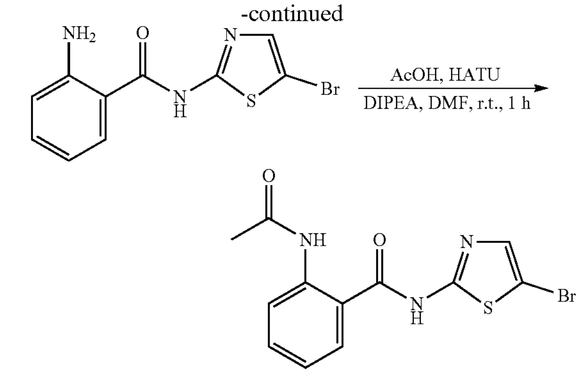

Step 1. Synthesis of N-(5-bromothiazol-2-yl)-2-nitrobenzamide

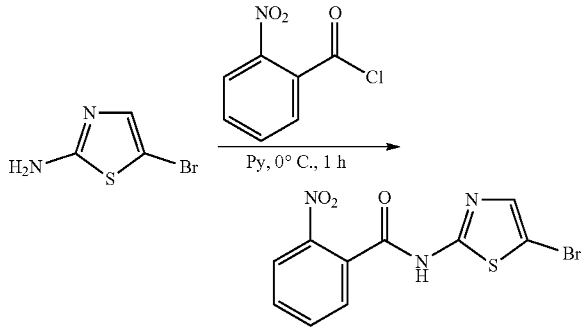

To a solution of 5-bromothiazol-2-amine hydrobromide (2.00 g, 7.69 mmol) in pyridine (100 mL) was added 2-nitrobenzoyl chloride (3.57 g, 19.2 mmol) dropwise at 0° C. After being stirred at 0° C. for 1 h, the reaction mixture was diluted with EtOAc (100 mL) and washed with water (10×50 mL). The organic layer was dried over $Na_2SO_4$, filtered and concentrated under vacuum to give the title compound (3.00 g, crude) as brown oil, which was used in the next step without further purification. MS (ESI) m/z: 328.0 $[M+H]^+$.

Step 2. Synthesis of 2-amino-N-(5-bromothiazol-2-yl)benzamide

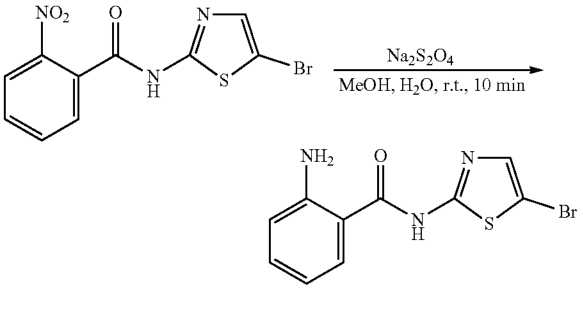

To a solution of N-(5-bromothiazol-2-yl)-2-nitrobenzamide (3.00 g, crude) in MeOH (50 mL) was added $Na_2S_2O_4$ (13.4 g, 76.9 mmol, in 50 mL water) at 0° C. After being stirred at 0° C. for 10 min, the mixture was diluted with aqueous $NaHCO_3$ (30 mL) and extracted with EtOAc (3×50 mL). The combined organic phase was washed with brine, dried over $Na_2SO_4$, filtered and concentrated under vacuum. The resulting residue was purified by silica gel column chromatography (petroleum ether:EtOAc=1:1) to give the title compound (400 mg, 15.2% yield over two steps) as white solid. MS (ESI) m/z: 298.0 $[M+H]^+$.

Step 3. Synthesis of 2-acetamido-N-(5-bromothiazol-2-yl)benzamide

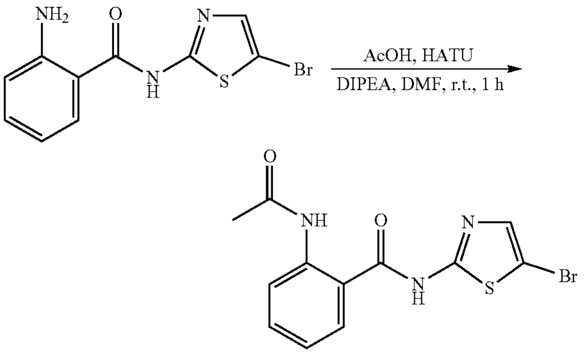

A solution of 2-amino-N-(5-bromothiazol-2-yl)benzamide (30 mg, 0.10 mmol), acetic acid (12 mg, 0.20 mmol), HATU (76 mg, 0.20 mmol) and DIPEA (38 mg, 0.300 mmol) in DMF (2 mL) was stirred at rt for 1 h, before the reaction mixture was purified by pre-HPLC to give the title compound (10.3 mg, 30.3% yield) as white solid. $^1H$ NMR (400 MHz, DMSO-$d_6$): δ 12.84 (brs, 1H), 10.62 (brs, 1H), 7.89 (d, J=7.6 Hz, 1H), 7.76 (d, J=7.6 Hz, 1H), 7.61 (s, 1H), 7.51 (t, J=7.4 Hz, 1H), 7.20 (t, J=7.6 Hz, 1H), 2.04 (s, 3H). MS (ESI) m/z: 341.9 $[M+H]^+$.

Example 048. 2-Acetamido-N-(4-chlorophenyl)benzamide (B-58)

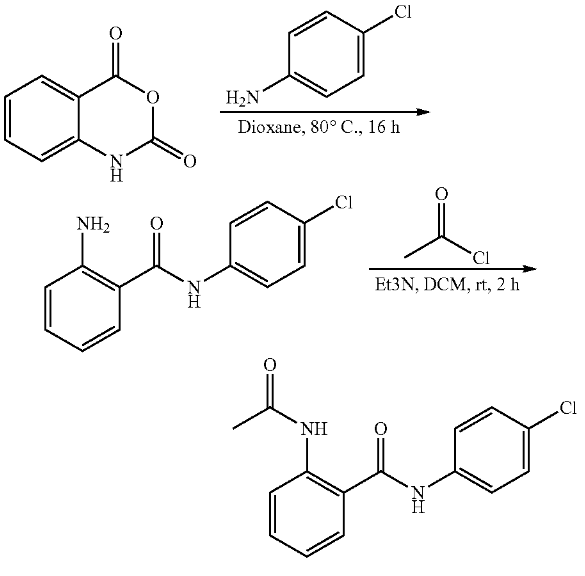

Step 1. Synthesis of 2-amino-N-(4-chlorophenyl)benzamide

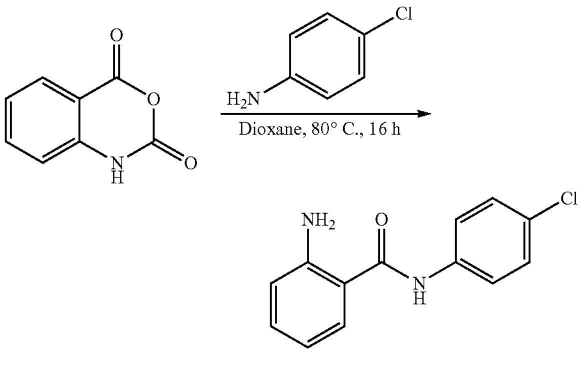

A solution of 1H-benzo[d][1,3]oxazine-2,4-dione (400 mg, 2.45 mmol) and 4-chloroaniline (620 mg, 4.90 mmol) in 1,4-dioxane (10 mL) was stirred at 80° C. for 16 h. At rt, the mixture was concentrated under vacuum. The resulting residue was purified by silica gel column chromatography (petroleum ether:EtOAc=3:1) to give the title compound (330 mg, 50.0% yield) as yellow solid. MS (ESI) m/z: 247.2 $[M+H]^+$.

Step 2. Synthesis of 2-acetamido-N-(4-chlorophenyl)benzamide

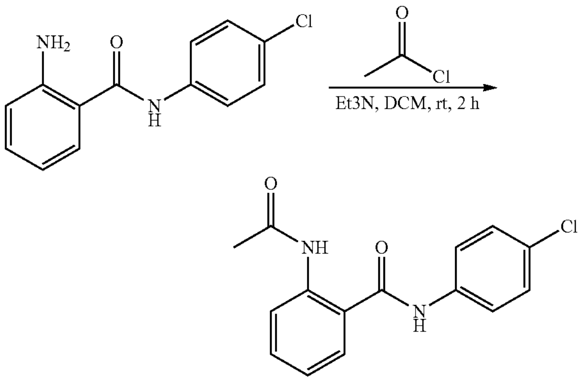

To a solution of 2-amino-N-(4-chlorophenyl)benzamide (130 mg, 0.57 mmol) and $Et_3N$ (2 mL) in DCM (20 mL) was added acetyl chloride (0.5 mL) at 0° C. After being stirred at rt for 2 h, the mixture was diluted with water (30 mL) and extracted with EtOAc (3×30 mL). The combined organic layers were washed with brine (3×30 mL), dried over $Na_2SO_4$, filtered and concentrated under vacuum. The resulting residue was purified by prep-HPLC to give the title compound (35.0 mg, 23.0% yield) as yellow solid. $^1H$ NMR (400 MHz, DMSO-$d_6$) δ 10.53 (s, 1H), 10.30 (s, 1H), 8.05 (d, J=8.0 Hz, 1H), 7.77-7.71 (m, 3H), 7.53-7.49 (m, 1H), 7.42 (d, J=8.8 Hz, 2H), 7.22 (t, J=7.4 Hz, 1H), 2.05 (s, 3H). MS (ESI) m/z: 289.3 $[M+H]^+$.

Example 049. 2-Acetamido-N-(4-bromophenyl)benzamide (B-59)

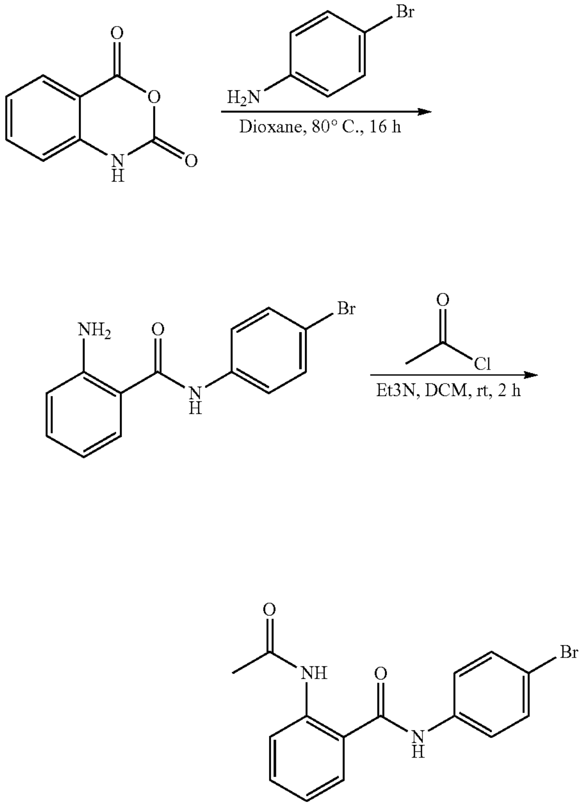

Step 1. Synthesis of 2-amino-N-(4-bromophenyl)benzamide

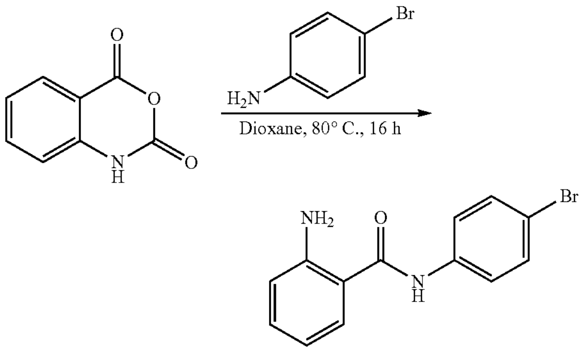

A solution of 1H-benzo[d][1,3]oxazine-2,4-dione (400 mg, 2.45 mmol) and 4-bromoaniline (840 mg, 4.90 mmol) in 1,4-dioxane (10 mL) was stirred at 80° C. for 16 h. At it, the mixture was concentrated under vacuum. The resulting residue was purified by silica gel column chromatography (petroleum ether:EtOAc=3:1) to give the title compound (800 mg, 90.0% yield) as yellow solid. MS (ESI) m/z: 291.3 $[M+H]^+$.

Step 2. Synthesis of 2-acetamido-N-(4-bromophenyl)benzamide

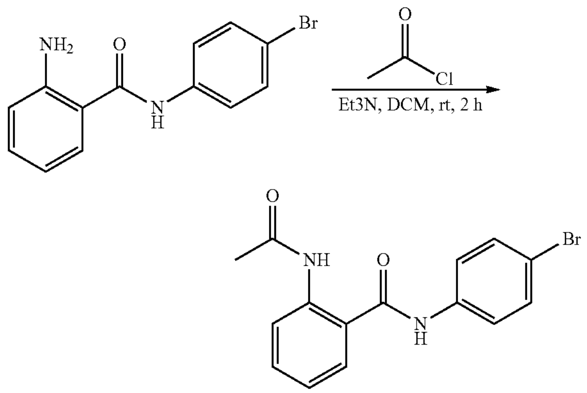

To a solution of 2-amino-N-(4-bromophenyl)benzamide (400 mg, 1.37 mmol) and $Et_3N$ (277 mg, 2.74 mmol) in DCM (20 mL) was added acetyl chloride (118 mg, 1.51 mmol) at 0° C. After being stirred at rt for 2 h, the mixture was treated with water (30 mL) and extracted with EtOAc (3x30 mL). The combined organic layers were washed with brine (3x30 mL), dried over $Na_2SO_4$, filtered and concentrated. The resulting residue was purified by prep-HPLC to give the title compound (160 mg, 35.0% yield) as yellow solid. $^1H$ NMR (400 MHz, DMSO-$d_6$) δ 10.52 (s, 1H), 10.29 (s, 1H), 8.05 (d, J=8.0 Hz, 1H), 7.73-7.69 (m, 3H), 7.55-7.49 (m, 3H), 7.22 (t, J=7.4 Hz, 1H), 2.05 (s, 3H). MS (ESI) m/z: 331.2 $[M+H]^+$.

Example 050. 2-Acetamido-N-(4-iodophenyl)benzamide (B-60)

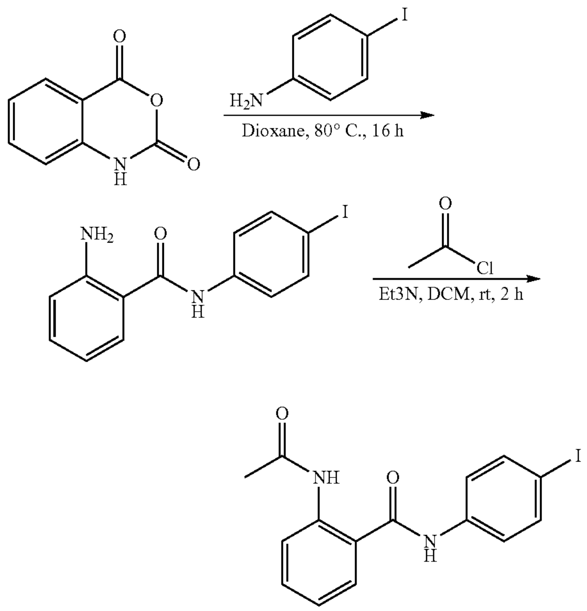

Step 1. Synthesis of 2-amino-N-(4-iodophenyl)benzamide

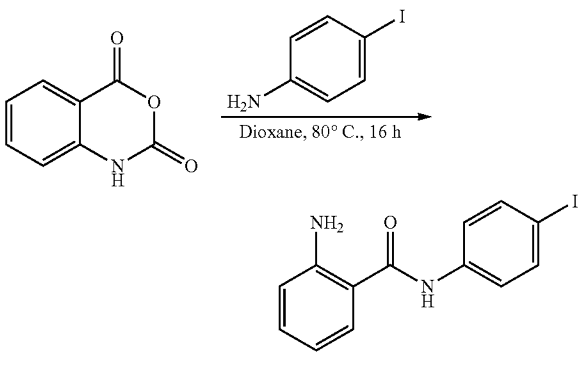

A solution of 1H-benzo[d][1,3]oxazine-2,4-dione (400 mg, 2.45 mmol) 4-iodoaniline (1.07 g, 4.90 mmol) in 1,4-dioxane (10 mL) was stirred at 80° C. for 16 h. The mixture was concentrated under vacuum. The resulting residue was purified by silica gel column chromatography (petroleum ether:EtOAc=3:1) to give the title compound (1.2 g, 100% yield) as yellow solid. MS (ESI) m/z: 339.3 $[M+H]^+$.

Step 2. Synthesis of 2-acetamido-N-(4-iodophenyl)benzamide

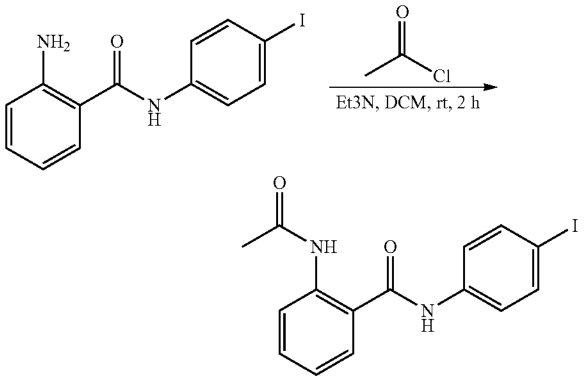

To a solution of 2-amino-N-(4-iodophenyl)benzamide (500 mg, 1.48 mmol) and $Et_3N$ (2 mL) in DCM (20 mL) was added acetyl chloride (0.5 mL) at 0° C. After being stirred at rt for 2 h, the reaction was quenched with water (30 mL) and extracted with EtOAc (3x30 mL). The combined organic layers were washed with brine (3x30 mL), dried over $Na_2SO_4$, filtered and concentrated under vacuum. The resulting residue was purified by prep-HPLC to give the title compound (170 mg, 60.0% yield over two steps) as yellow solid. $^1H$ NMR (400 MHz, DMSO-$d_6$): δ 10.48 (s, 1H), 10.29 (s, 1H), 8.05 (d, J=8.2 Hz, 1H), 7.72-7.69 (m, 3H), 7.58-7.49 (m, 3H), 7.22 (t, J=7.3 Hz, 1H), 2.04 (s, 3H). MS (ESI) m/z: 379.1 $[M-H]^-$.

Example 051. 2-(N-Methylacetamido)-N-(5-nitrothiazol-2-yl)benzamide (B-64)

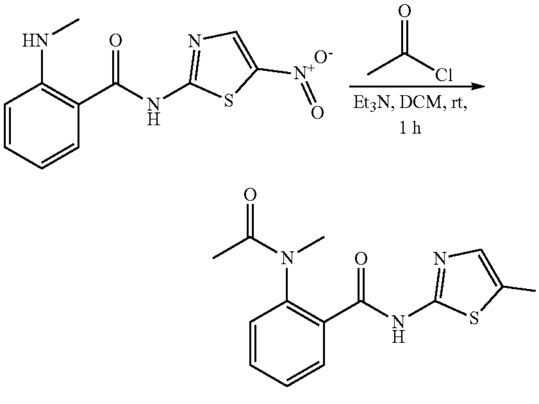

To a solution of 2-(methylamino)-N-(5-nitrothiazol-2-yl) benzamide (40.0 mg, 0.144 mmol) and $Et_3N$ (29.1 mg, 0.288 mmol) in DCM (5 mL) was added acetyl chloride (22.5 mg, 0.288 mmol) at 0° C. After the mixture was stirred at rt for 1 h, it was concentrated under vacuum. The resulting residue was purified by silica gel column chromatography (petroleum ether:EtOAc=10:1-1:1) to give the title compound (25.0 mg, 54.25% yield) as white solid. $^1H$ NMR (400 MHz, DMSO-$d_6$): δ 13.43 (brs, 1H), 8.68 (s, 1H), 7.81-7.48 (m, 4H), 3.40-3.39 (m, 1H), 3.16-3.07 (m, 2H), 2.08-1.71 (m, 3H). MS (ESI) m/z: 321.1 $[M+H]^+$.

Example 052. 2-Isopropoxy-N-(5-nitrothiazol-2-yl) benzamide (B-74)

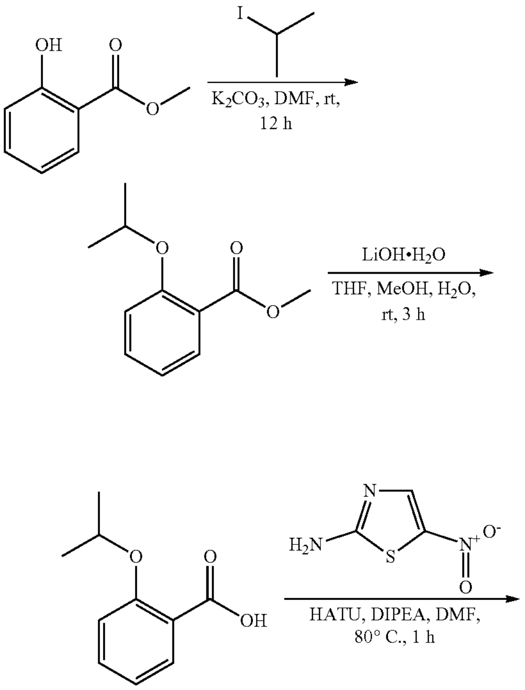

-continued

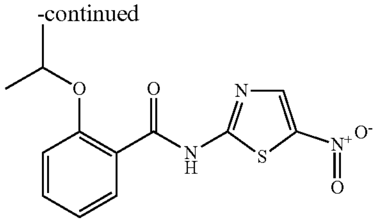

Step 1. Synthesis of methyl 2-isopropoxybenzoate

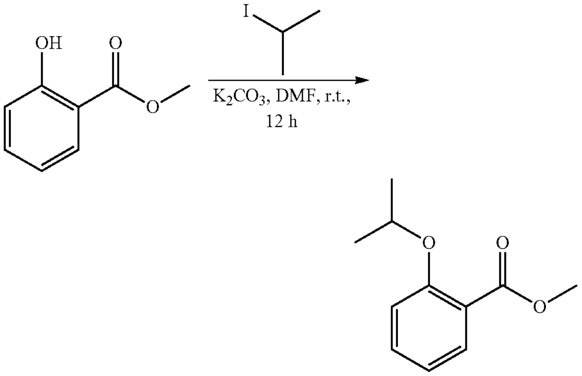

A solution of methyl 2-hydroxybenzoate (1.00 g, 6.56 mmol), 2-iodopropane (1.34 g, 7.89 mmol) and $K_2CO_3$ (2.72 g, 19.7 mmol) in DMF (10 mL) was stirred at rt for 12 h, at which time the mixture was poured into water (30 mL). The mixture was extracted with EtOAc (2×20 mL). The combined organic phase was washed with brine, dried over $Na_2SO_4$, concentrated under vacuum. The resulting residue was purified by silica gel column chromatography column (petroleum ether:EtOAc=10:1) to give the title compound (760 mg, 59.6% yield) as colorless oil. MS (ESI) m/z: 195.5 $[M+H]^+$.

Step 2. Synthesis of 2-isopropoxybenzoic acid

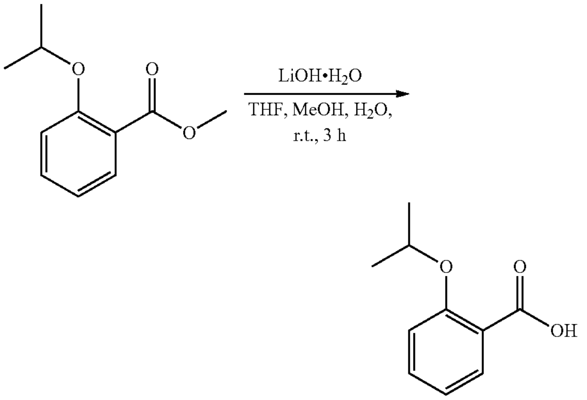

A mixture of methyl 2-isopropoxybenzoate (300 mg, 1.54 mmol) and LiOH $H_2O$ (340 mg, 7.69 mmol) in THF (4 mL), MeOH (4 mL) and $H_2O$ (1 mL) was stirred at rt for 3 h, at which time the pH of the reaction mixture was adjusted to 3 with 1 N aq. HCl. The mixture was extracted with EtOAc (3x30 mL). The combined organic phase was washed with brine, dried over $Na_2SO_4$, filtered and concentrated under vacuum to give the title compound (240 mg, crude) as white solid, which was used in the next step without further purification.

Step 3. Synthesis of 2-isopropoxy-N-(5-nitrothiazol-2-yl)benzamide

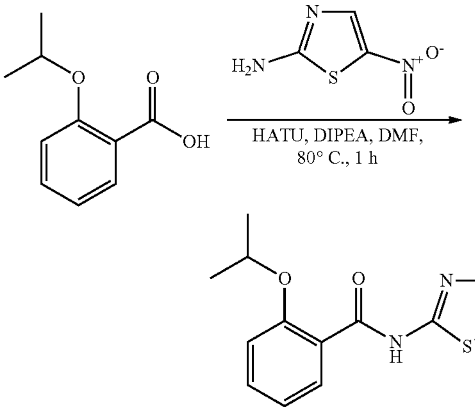

To a solution of 2-isopropoxybenzoic acid (140 mg, crude), HATU (445 mg, 1.17 mmol) and 5-nitrothiazol-2-amine (170 mg, 1.17 mmol) in DMF (2 mL) was added DIPEA (600 mg, 4.67 mmol). After being stirred at 80° C. for 1 h, the mixture was cooled to rt. The mixture was diluted with water (20 mL) and extracted with EtOAc (3x20 mL). The organic phase was washed with brine, dried over $Na_2SO_4$, filtered and concentrated under vacuum. The resulting residue was purified by pre-HPLC to get the title compound (8.10 mg, 3.67% yield over two steps) as yellow solid. $^1$H NMR (400 MHz, DMSO-$d_6$): δ 11.75 (s, 1H), 8.36 (s, 1H), 8.30-8.27 (m, 1H), 7.60-7.56 (m, 1H), 7.16 (t, J=7.6 Hz, 1H), 7.08 (d, J=8.4 Hz, 1H), 4.91-4.88 (m, 1H), 1.57 (d, J=6.4 Hz, 6H). MS (ESI) m/z: 308.3 $[M+H]^+$.

Example 053. 2-Acetamido-N-(4-chloro-5-nitrothiazol-2-yl)benzamide (B-29)

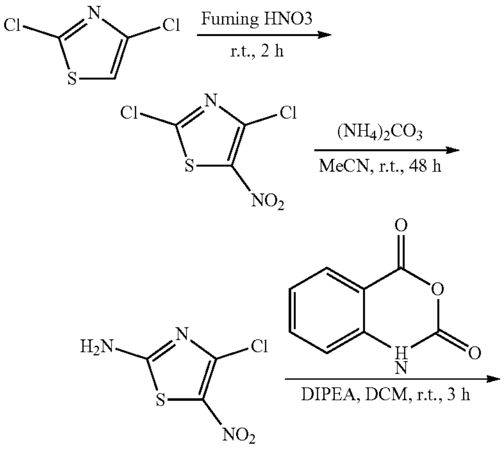

-continued

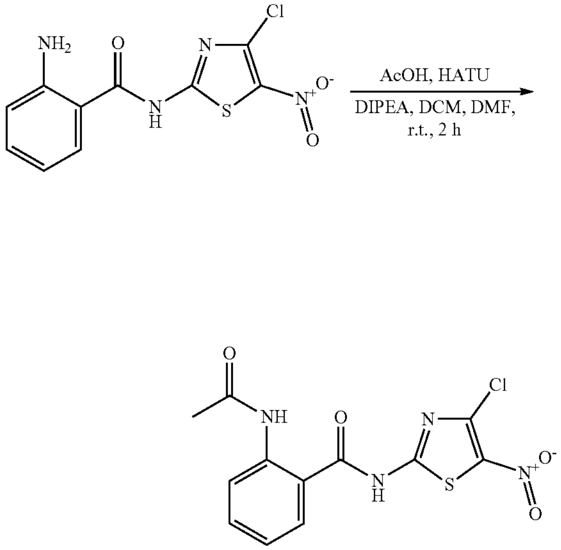

Step 1. Synthesis of 2,4-dichloro-5-nitrothiazole

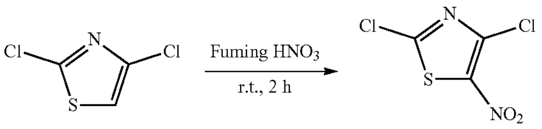 [SMILES: Clc1csc(Cl)n1 ; O=[N+]([O-])c1sc(Cl)nc1Cl]

A solution of 2,4-dichlorothiazole (1.00 g, 6.49 mmol) in fuming $HNO_3$ (2 mL) was stirred at rt for 2 h. Then, the mixture was poured into ice water (15 mL) and extracted with EtOAc (2x15 mL). The combined organic phase was washed with brine, dried over $Na_2SO_4$, filtered and concentrated under vacuum to give the title compound (700 mg, crude) as yellow solid, which was used in the next step without further purification.

Step 2. Synthesis of 4-chloro-5-nitrothiazol-2-amine

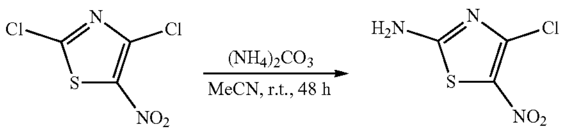 [SMILES: O=[N+]([O-])c1sc(Cl)nc1Cl ; "(NH4)2CO3" ; Nc1nc(Cl)c([N+](=O)[O-])s1]

A solution of 2,4-dichloro-5-nitrothiazole (700 mg, crude) and $(NH_4)_2CO_3$ (570 mg, 5.80 mmol) in acetonitrile (15 mL) was stirred at rt for 48 h. Then, the mixture was diluted with water (20 mL) and extracted with EtOAc (2x20 mL). The combined organic layers were washed with brine, dried over $Na_2SO_4$, filtered and concentrated. The resulting residue was purified by silica gel column chromatography (petroleum ether:EtOAc=3:1) to give the title compound (380 mg, 32.7% over two steps) as yellow solid. MS (ESI) m/z: 180.0 $[M+H]^+$.

Step 3. Synthesis of 2-amino-N-(4-chloro-5-nitrothiazol-2-yl)benzamide

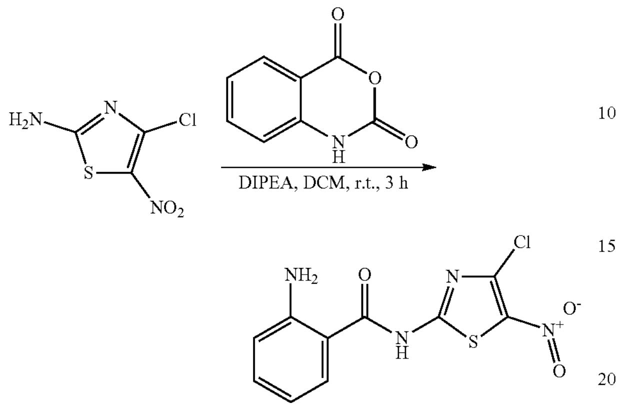

A solution of 4-chloro-5-nitrothiazol-2-amine (100 mg, 0.559 mmol), DIPEA (109 mg, 1.68 mmol) and 2H-benzo[d][1, 3]oxazine-2, 4 (1H)-dione (92 mg, 0.559 mmol) in DCM (2 mL) was stirred at rt for 3 h. Then the mixture was diluted with water (20 mL) and extracted with EtOAc (3×20 mL). The combined organic phase was dried over $Na_2SO_4$, filtered and concentrated. The resulting residue was purified by prep-TLC (petroleum ether:EtOAc=3:1) to give the title compound (46 mg, 27.6% yield) as yellow solid. MS (ESI) m/z: 298.9 $[M+H]^+$.

Step 4. Synthesis of 2-acetamido-N-(4-chloro-5-nitrothiazol-2-yl)benzamide

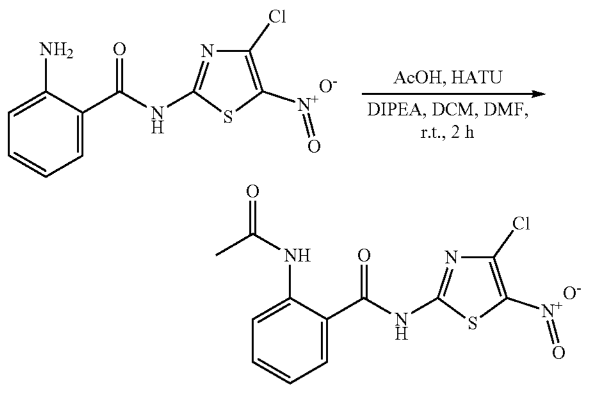

To a solution of 2-amino-N-(4-chloro-5-nitrothiazol-2-yl)benzamide (46 mg, 0.154 mmol) in DCM (2 mL)/DMF (one drop) were added acetic acid (10 mg, 0.160 mmol), HATU (88 mg, 0.231 mmol) and DIPEA (60 mg, 0.462 mmol). After being stirred at rt for 2 h, the mixture was concentrated under vacuum. The resulting residue was purified by prep-HPLC to give the title compound (6.10 mg, 11.6% yield) as yellow solid. $^1H$ NMR (400 MHz, DMSO-$d_6$): δ 11.02 (brs, 1H), 7.87-7.82 (m, 2H), 7.56-7.52 (m, 1H), 7.24-7.20 (m, 1H), 2.05 (s, 3H). MS (ESI) m/z: 341.1 $[M+H]^+$.

Example 054. 2-acetamido-N-(5-phenylthiazol-2-yl)benzamide (B-45)

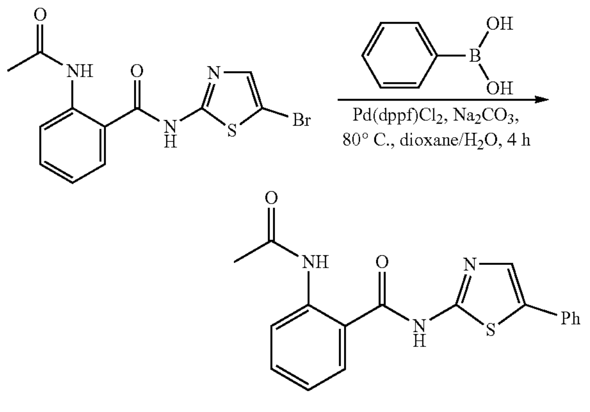

A solution of 2-acetamido-N-(5-bromothiazol-2-yl)benzamide (50.0 mg, 0.147 mmol), phenylboronic acid (37.0 mg, 0.303 mmol), $Pd(dppf)Cl_2$ (30.0 mg, 0.041 mmol) and $Na_2CO_3$ (30.0 mg, 0.303 mmol) in dioxane (2 mL) and $H_2O$ (1 mL) was stirred at 80° C. for 4 h under $N_2$. The mixture was purified by prep-HPLC to give the title compound (14.9 mg, 29.48% yield) as white solid. $^1H$ NMR (400 MHz, DMSO-$d_6$): δ 12.70 (brs, 1H), 10.39 (brs, 1H), 7.99-7.97 (m, 2H), 7.83 (brs, 1H), 7.66 (d, J=7.2 Hz, 2H), 7.53 (t, J=7.2 Hz, 1H), 7.45-7.41 (m, 2H), 7.34-7.32 (m, 1H), 7.23-7.21 (m, 1H), 2.08 (s, 3H). MS (ESI) m/z: 337.9 $[M+H]^+$.

Example 055. methyl (2-((5-nitrothiazol-2-yl)carbamoyl)phenyl)carbamate (B-65)

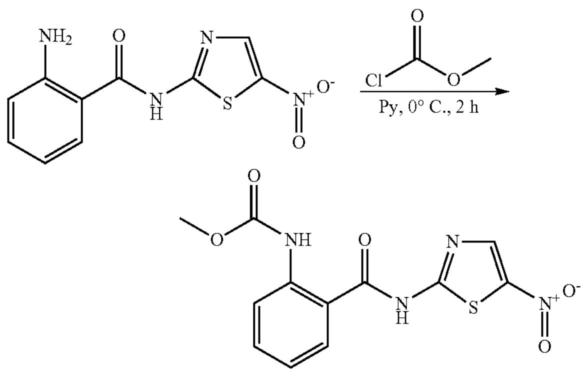

To a solution of 2-amino-N-(5-nitrothiazol-2-yl)benzamide (200 mg, 0.757 mmol) in pyridine (50 mL) was added methyl carbonochloridate (86 mg, 0.908 mmol) at 0° C. After being stirred at 0° C. for 2 h, the reaction mixture was diluted with EtOAc (200 mL) and washed with brine. The organic phase was dried over $Na_2SO_4$, concentrated in vacuum to give a residue, which was recrystallized with EtOAc to give the title compound (17.2 mg, 7.05% yield) as an off-yellow solid. $^1H$ NMR (400 MHz, DMSO-$d_6$): δ 13.57 (brs, 1H), 9.94 (brs, 1H), 8.71 (s, 1H), 7.81-7.78 (m, 2H), 7.58 (t, J=7.8 Hz, 1H), 7.22 (t, J=7.4 Hz, 1H), 3.63 (s, 3H). MS (ESI) m/z: 323.3 $[M+H]^+$.

Example 056. 2-(cyclopropylamino)-N-(5-nitrothiazol-2-yl)benzamide (B-71)

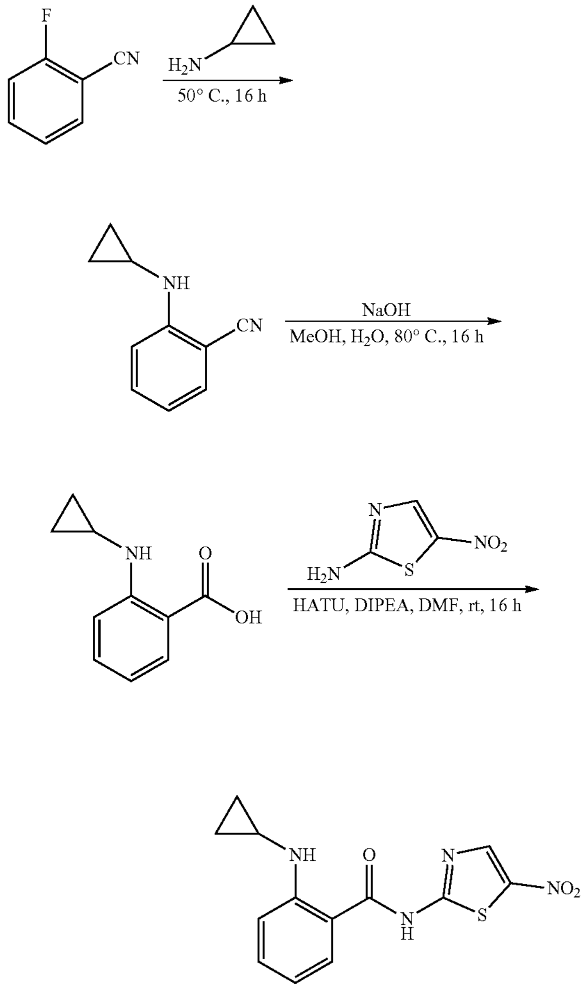

Step 1. Synthesis of 2-(cyclopropylamino)benzonitrile

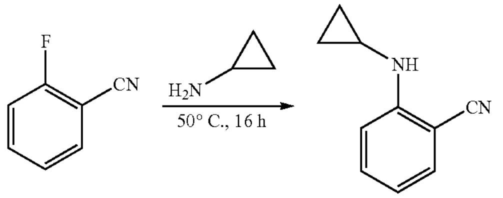

A solution of 2-fluorobenzonitrile (4.00 g, 12.2 mmol) in cyclopropanamine (14 mL) was stirred at 50° C. for 16 h. At rt, the mixture was concentrated under vacuum. The resulting residue was purified by silica gel column chromatography (petroleum ether:EtOAc=2:1) to give the title compound (3.20 g, 61.0% yield) as colorless oil. MS (ESI) m/z: 159.3 $[M+H]^+$.

Step 2. Synthesis of 2-(cyclopropylamino)benzoic acid

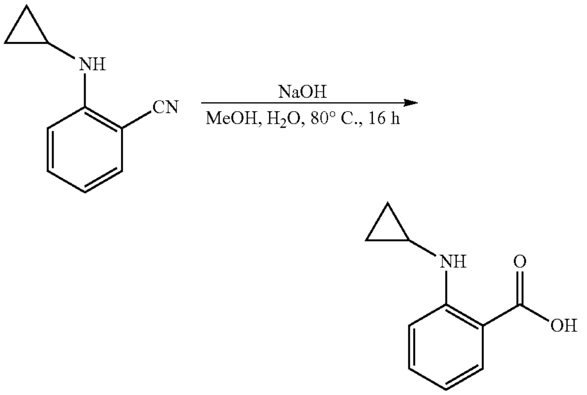

A solution of 2-(cyclopropylamino)benzonitrile (3.20 g, 0.76 mmol) and NaOH (8.10 g, 20.0 mmol) in MeOH (40 mL)/$H_2O$ (15 mL) was stirred at 80° C. for 16 h. At rt, the mixture was diluted with water (30 mL). After the pH of the mixture was adjusted to 4 with 1 N aq. HCl, it was extracted with EtOAc (3x30 mL). The combined organic phase was washed with brine (3x30 mL), dried over $Na_2SO_4$, filtered, concentrated under vacuum. The resulting residue was purified by pre-HPLC to give the title compound (200 mg, 10.0% yield) as white solid. MS (ESI) m/z: 178.5 $[M+H]^+$.

Step 3. Synthesis of 2-(cyclopropylamino)-N-(5-nitrothiazol-2-yl)benzamide

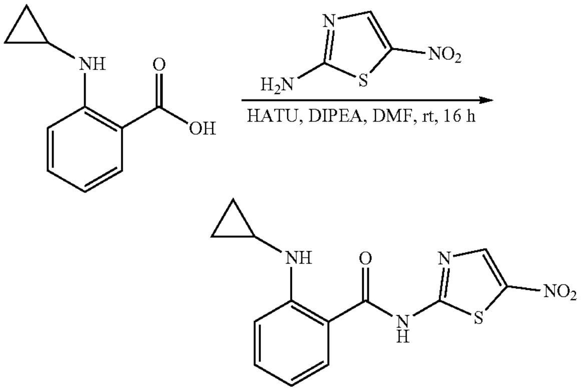

A solution of 2-(cyclopropylamino)benzoic acid (200 mg, 1.12 mmol) 5-nitrothiazol-2-amine (160 mg, 1.12 mmol), HATU (430 mg, 1.12 mmol) and DIPEA (1 mL) in DMF (10 mL) was stirred at rt for 16 h. Then, the mixture was diluted with EtOAc (3x30 mL), washed with brine (3x30 mL), dried over $Na_2SO_4$, filtered and concentrated under vacuum. The resulting residue was purified by silica gel column chromatography (petroleum ether:EtOAc=1:1) to give the title compound (100 mg, 30.0% yield) as yellow solid. $^1H$ NMR (400 MHz, DMSO-$d_6$): δ 8.71 (s, 1H), 7.98 (d, J=7.0 Hz, 1H), 7.48 (t, J=7.0 Hz, 1H), 7.18 (d, J=8.4 Hz, 1H), 6.71 (t, J=7.2 Hz, 1H), 2.52-2.51 (m, 1H), 0.83-0.81 (m, 2H), 0.52-0.50 (m, 2H). MS (ESI) m/z: 305.2 $[M+H]^+$.

Example 057. 2-methoxy-N-(5-nitrothiazol-2-yl) benzamide (B-73)

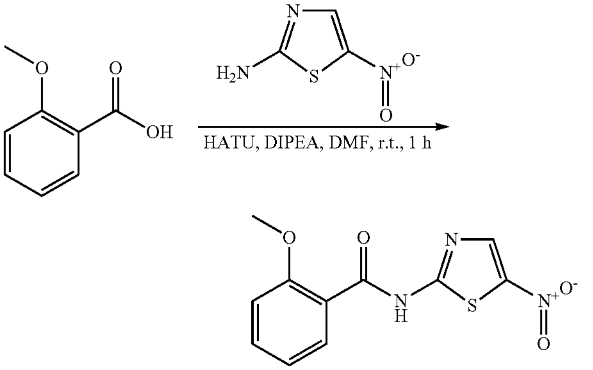

To a solution of 2-methoxybenzoic acid (300 mg, 1.97 mmol), HATU (1.12 g, 2.96 mmol) and 5-nitrothiazol-2-amine (286 mg, 1.97 mmol) in DMF (8 mL) was added DIPEA (764 mg, 5.91 mmol). After being heated at rt for 1 h, the reaction mixture was diluted with DCM (20 mL) water (20 mL), extracted with DCM (3×20 mL). The organic phase was washed with brine, dried over $Na_2SO_4$, filtered and concentrated in vacuum. The resulting residue was purified by pre-HPLC to give the title compound (9.20 mg, 1.67% yield) as yellow solid. $^1H$ NMR (400 MHz, DMSO-$d_6$): δ 12.69 (s, 1H), 8.48 (s, 1H), 7.49-7.47 (m, 1H), 7.43-7.39 (m, 1H), 7.04-7.02 (m, 1H), 6.92-6.89 (m, 1H), 3.70 (s, 3H). MS (ESI) m/z: 280.2 $[M+H]^+$.

Example 058. 2-cyclopropyl-N-(5-nitrothiazol-2-yl) benzamide (B-85)

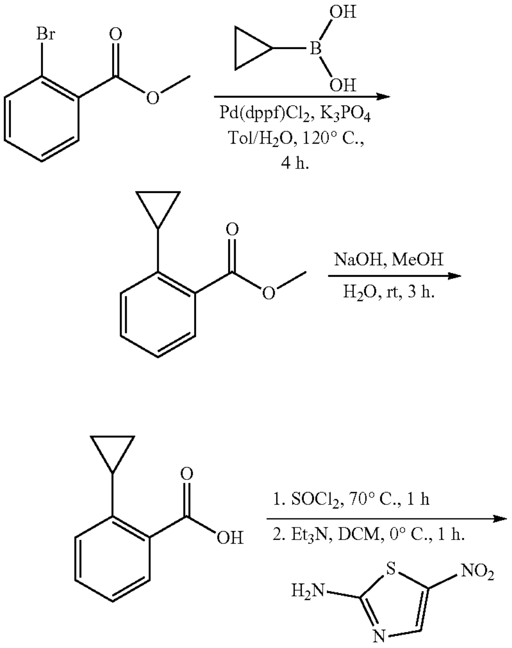

-continued

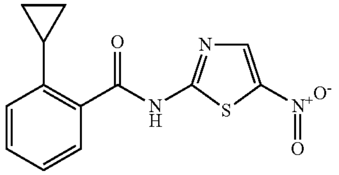

Step 1. Synthesis of methyl 2-cyclopropylbenzoate

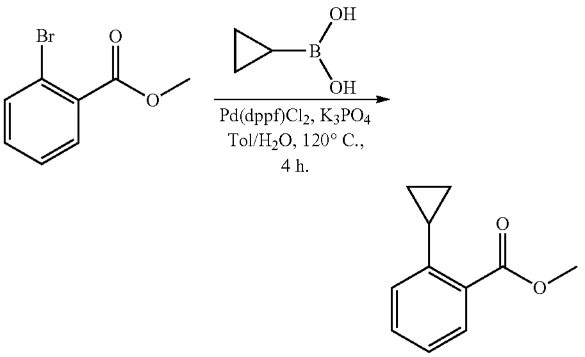

A solution of methyl 2-bromobenzoate (2.00 g, 8.69 mmol), $Pd(dppf)Cl_2$ (300 mg, 0.410 mmol), $K_3PO_4$ (5.65 g, 26.6 mmol) and cyclopropylboronic acid (1.39 g, 16.1 mmol) in toluene (30 mL) and $H_2O$ (1.5 mL) was stirred at 120° C. under argon for 4 h. At rt, the mixture was diluted with water (100 mL) and extracted with EtOAc (2×100 mL). The combined organic layers were washed with brine (2×100 mL), dried over $Na_2SO_4$, filtered and concentrated under vacuum. The resulting residue was purified by silica gel column chromatography (petroleum ether:EtOAc=1:1) to give the title compound (1.4 g, 91.5% yield) as colorless oil. MS (ESI) m/z: 177.2 $[M+H]^-$.

Step 2. Synthesis of 2-cyclopropylbenzoic acid

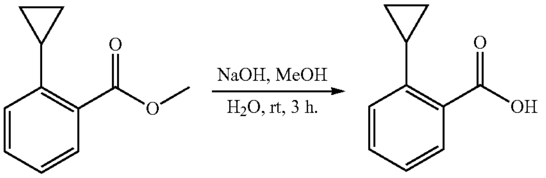

A solution of methyl 2-cyclopropylbenzoate (400 mg, 2.27 mmol) and NaOH (227 mg, 5.67 mmol) in $MeOH/H_2O$ (8 mL, v/v=1:1) was stirred at rt for 3 h. Then, the mixture was poured into ice-water (10 mL) and acidified by 1 N HCl to pH=2. The precipitation was filtered, washed with water (10 mL) and dried under vacuum to afford the title compound (270 mg, 74.0% yield) as white solid. MS (ESI) m/z: 163.3 $[M-H]^-$.

Step 3. Synthesis of 2-cyclopropyl-N-(5-nitrothiazol-2-yl)benzamide

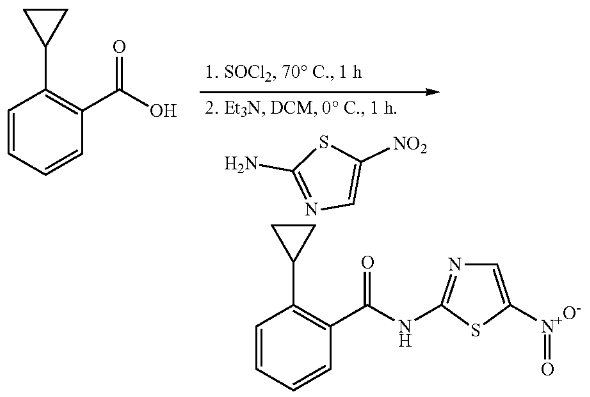

A solution of 2-cyclopropylbenzoic acid (50.0 mg, 0.308 mmol) in $SOCl_2$ (2 mL) was stirred at 70° C. for 1 h, before being concentrated under vacuum. The resulting residue was added to a solution of $Et_3N$ (60 mg, 0.594 mmol) and 5-nitrothiazol-2-amine (50 mg, 0.344 mmol) in DCM (4 mL) at 0° C. The resulting mixture was stirred at 0° C. for 1 h. Then the mixture was diluted with water (20 mL) and extracted with DCM (2×20 mL). The combined organic layers were washed with brine (2×20 mL), dried over $Na_2SO_4$, filtered and concentrated under vacuum. The resulting residue was purified by pre-HPLC to give the title compound 10.0 mg, 11.3% yield) as white solid. $^1H$ NMR (400 MHz, DMSO-$d_6$): δ 13.6 (brs, 1H), 8.69 (s, 1H), 7.55 (d, J=7.6 Hz, 1H), 7.47 (t, J=7.6 Hz, 1H), 7.30 (t, J=7.2 Hz, 1H), 7.07 (d, J=8.0 Hz, 1H), 2.26-2.19 (m, 1H), 0.96-0.90 (m, 2H), 0.71-0.67 (m, 2H). MS (ESI) m/z: 288.2 $[M-H]^-$.

Example 059. 2-acetamido-$N^4$-(2-(2-(2-(2-amino-ethoxy)ethoxy)ethoxy)ethyl)-$N^1$-(5-nitrothiazol-2-yl) terephthalamide (BL-6)

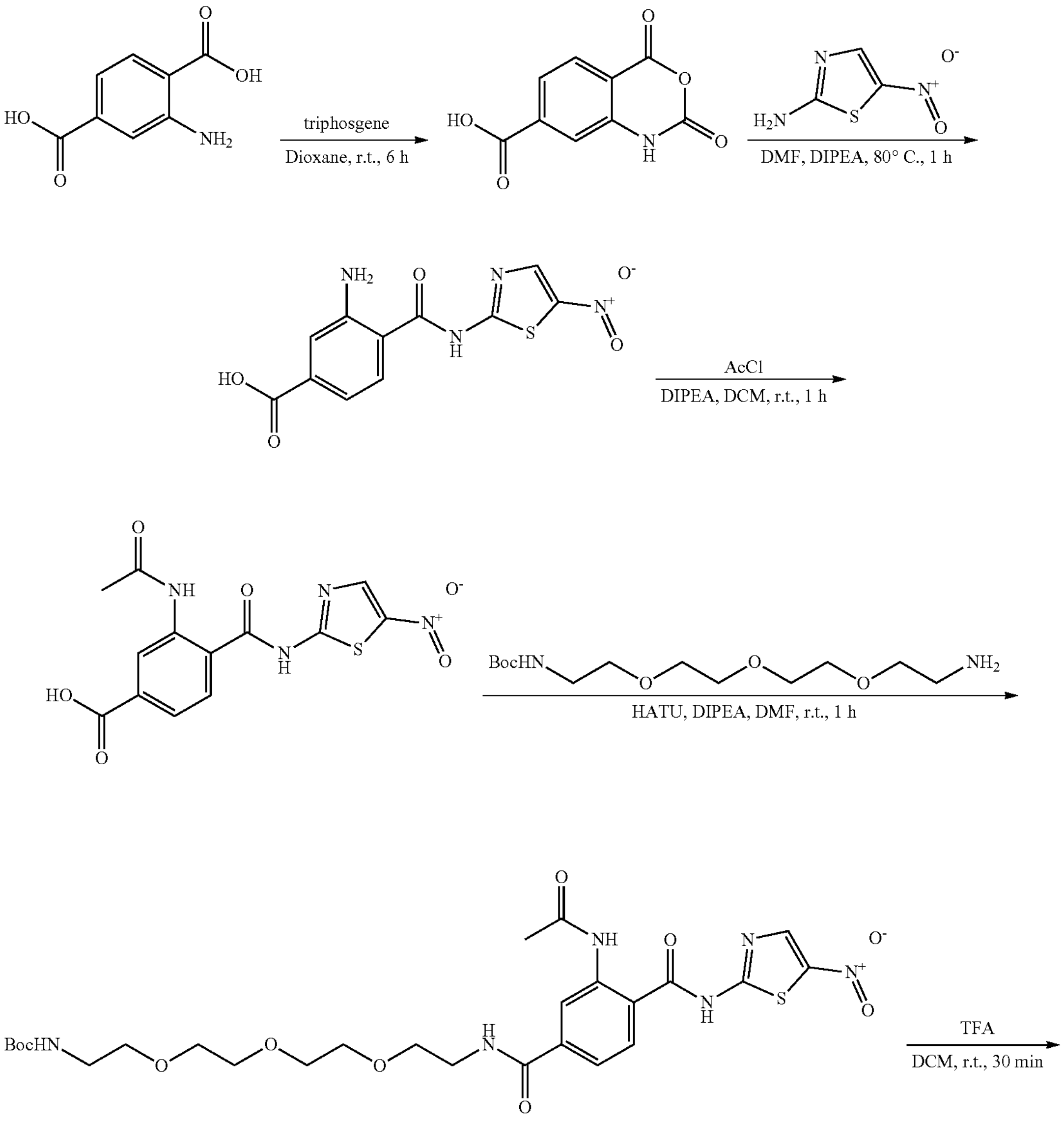

-continued

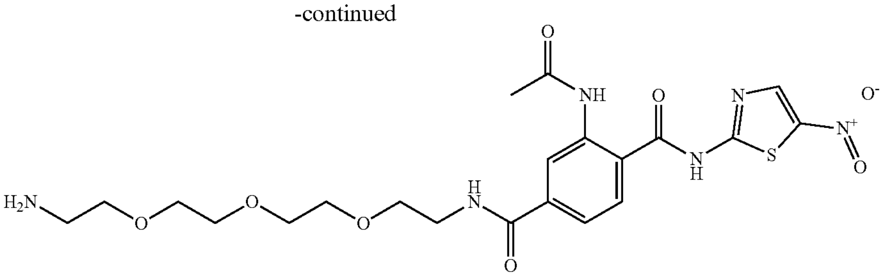

Step 1. Synthesis of 2,4-dioxo-1,4-dihydro-2H-benzo[d][1,3]oxazine-7-carboxylic acid

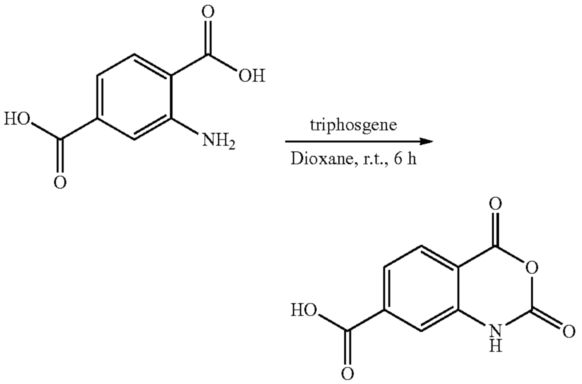

A solution of 2-aminoterephthalic acid (2.50 g, 13.8 mmol) and triphosgene (4.12 g, 13.8 mmol) in 1,4-dioxane (50 mL) was stirred at rt for 6 h. After completion, the reaction mixture was poured into water (50 mL) and extracted with EtOAc (3×50 mL). The organic phase was dried over $Na_2SO_4$, filtered and concentrated to give the title compound (2.20 g, 77.3% yield) as off-white solid. MS (ESI) m/z: 206.2 $[M-H]^-$.

Step 2. Synthesis of 3-amino-4-((5-nitrothiazol-2-yl)carbamoyl)benzoic acid

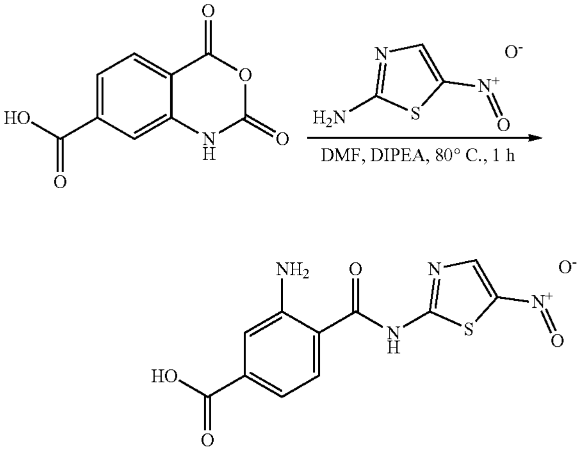

A solution of 2,4-dioxo-1,4-dihydro-2H-benzo[d][1,3]oxazine-7-carboxylic acid (500 mg, 2.42 mmol), DIPEA (940 mg, 7.26 mmol) and 5-nitrothiazol-2-amine (421 mg, 2.90 mmol) in DMF (20 mL) was heated at 80° C. for 1 h. At rt, the mixture was diluted with EtOAc (100 mL) and washed with brine, dried over $Na_2SO_4$, filtered and concentrated to give the title compound (600 mg, crude) as yellow solid, which was used in the next step without further purification. MS (ESI) m/z: 307.1 $[M-H]^-$.

Step 3. Synthesis of 3-acetamido-4-((5-nitrothiazol-2-yl)carbamoyl)benzoic acid

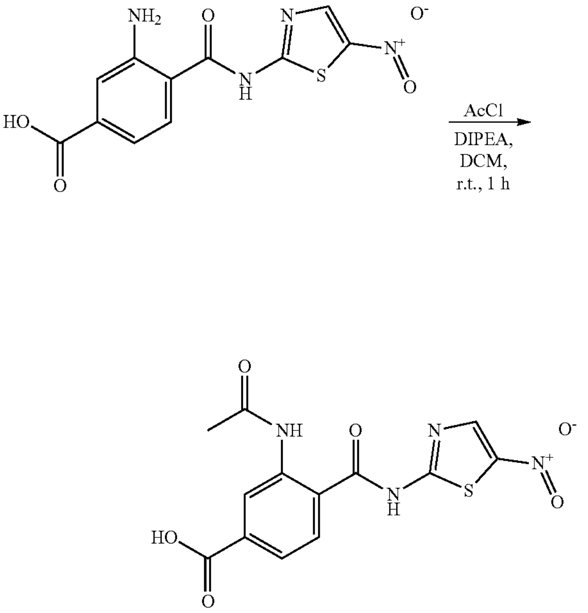

To a solution of 3-amino-4-((5-nitrothiazol-2-yl)carbamoyl)benzoic acid (600 mg, crude) and DIPEA (756 mg, 5.85 mmol) in DCM (5 mL) was added acetyl chloride (304 mg, 3.90 mmol) at 0° C. After being stirred at rt for 1 h, $K_2CO_3$ (807 mg, 5.85 mmol) was added. After being stirred for another 1 h, the mixture was diluted with water (50 mL). After the pH was adjusted to 4.0 with 1 N HCl, the mixture was extracted with DCM (3×50 mL). The combined organic phase was washed with brine, dried over $Na_2SO_4$, filtered and concentrated. The resulting residue was purified by pre-HPLC to give the title compound (100 mg, 14.6% yield over two steps) as yellow solid. MS (ESI) m/z: 348.9 $[M-H]^-$.

Step 4. Synthesis of tert-butyl (1-(3-acetamido-4-((5-nitrothiazol-2-yl)carbamoyl)phenyl)-1-oxo-5,8,11-trioxa-2-azatridecan-13-yl)carbamate

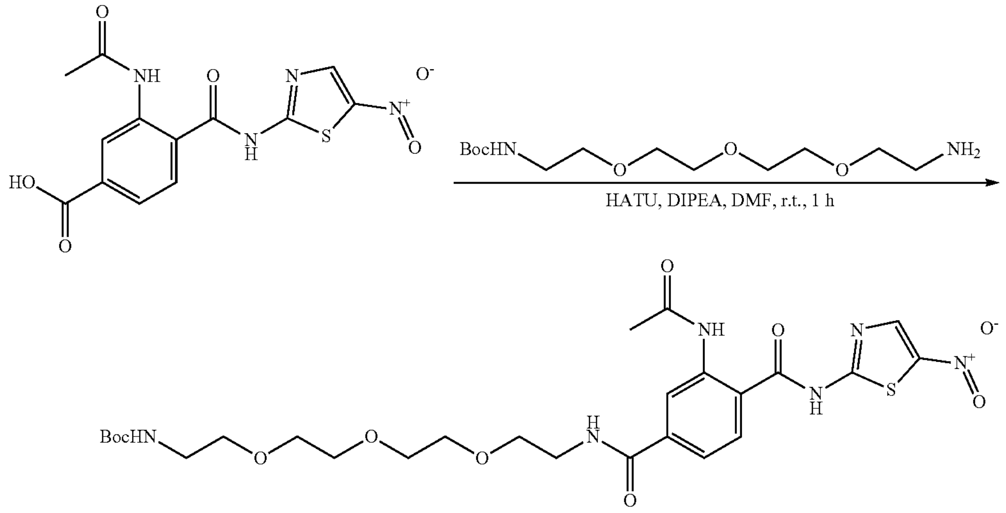

A solution of 3-acetamido-4-((5-nitrothiazol-2-yl)carbamoyl)benzoic acid (100 mg, 0.280 mmol), tert-butyl (2-(2-(2-(2-aminoethoxy)ethoxy)ethoxy)ethyl)carbamate (100 mg, 0.340 mmol), DIPEA (72 mg, 0.560 mmol) and HATU (130 mg, 0.340 mmol) in DMF (10 mL) was stirred at rt for 1 h. Then, the mixture was diluted with EtOAc (30 mL) and washed with brine, dried over $Na_2SO_4$, filtered and concentrated to give the title compound (200 mg, crude) as yellow solid, which was used in next step without further purification. MS (ESI) m/z: 625.3 $[M+H]^+$.

Step 5. Synthesis of 2-acetamido-$N^4$-(2-(2-(2-(2-aminoethoxy)ethoxy)ethoxy)ethyl)-$N^1$-(5-nitrothiazol-2-yl)terephthalamide

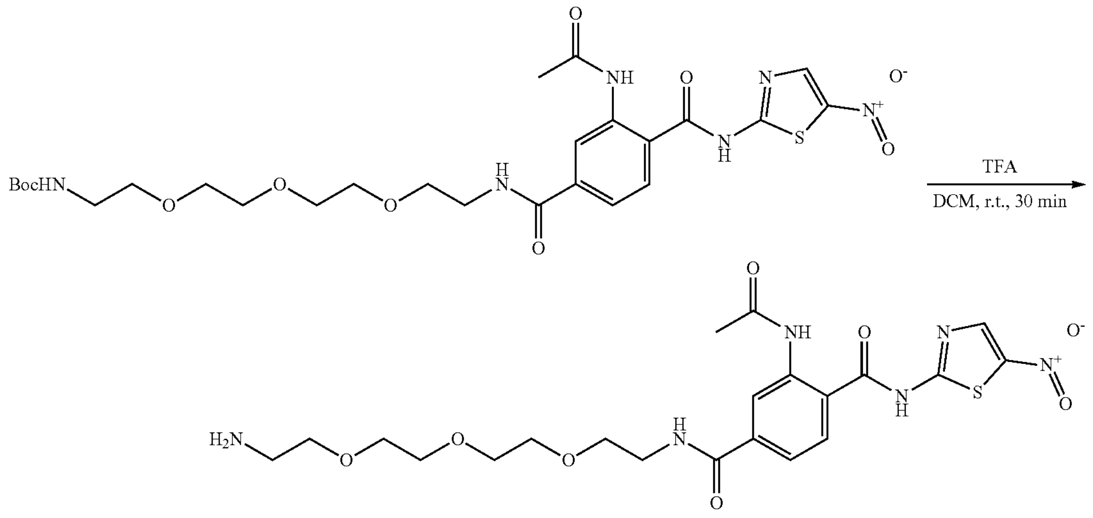

A solution of tert-butyl (1-(3-acetamido-4-((5-nitrothiazol-2-yl)carbamoyl)phenyl)-1-oxo-5,8,11-trioxa-2-azatridecan-13-yl)carbamate (200 mg, crude) in DCM (1 mL)/TFA (1 mL) was stirred at rt for 30 min. Then, the mixture was concentrated under vacuum. The resulting residue was purified by pre-HPLC to give the title compound (125 mg, 70.0% yield over two steps) as yellow solid. $^1H$ NMR (400 MHz, DMSO-$d_6$): δ 10.69 (brs, 1H), 8.70-8.68 (m, 1H), 8.16 (s, 1H), 7.83-7.81 (m, 4H), 7.66 (d, J=8.0 Hz, 1H), 3.72-3.42 (m, 14H), 2.97-2.96 (m, 2H), 2.04 (s, 1H). MS (ESI) m/z: 525.4 $[M+H]^+$.

Example 060. 2-acetamido-N-(5-(trifluoromethyl)thiazol-2-yl)benzamide (B-38)

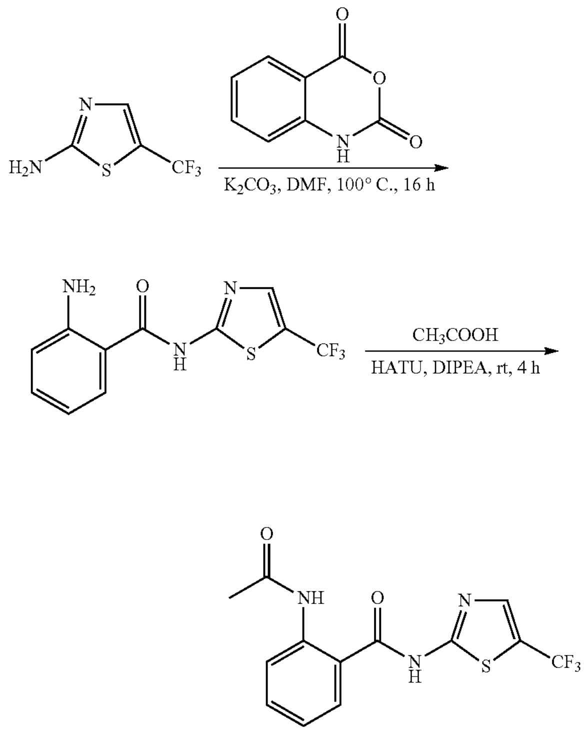

Step 1. Synthesis of 2-amino-N-(5-(trifluoromethyl)thiazol-2-yl)benzamide

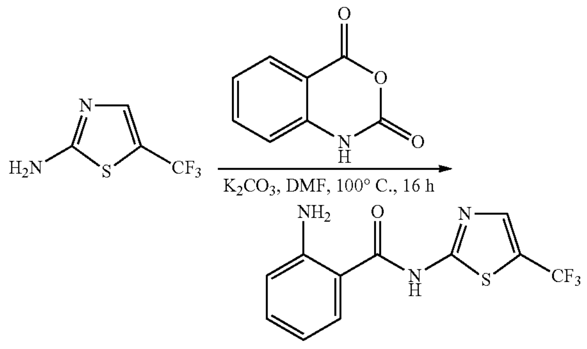

A solution of 1H-benzo[d][1,3]oxazine-2,4-dione (200 mg, 1.19 mmol), 5-(trifluoromethyl)thiazol-2-amine (200 mg, 1.23 mmol) and $K_2CO_3$ (500 mg, 3.62 mmol) in DMF (5.00 mL) was stirred at 100° C. for 16 h. The mixture was cooled to the rt, diluted with $H_2O$ (50 mL) and extracted with EtOAc (3×50 mL). The combined organic phase was dried over $Na_2SO_4$, filtered and concentrated under vacuum. The resulting residue was purified by silica gel column chromatography (petroleum ether:EtOAc=10:1-3:1) to give the title compound (150 mg, 43.6% yield) as white solid. MS (ESI) m/z: 288.0 $[M+H]^+$.

Step 2. Synthesis of 2-acetamido-N-(5-(trifluoromethyl)thiazol-2-yl)benzamide

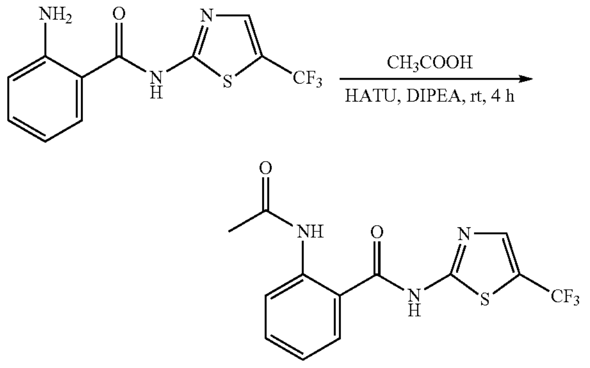

A solution of 2-amino-N-(5-(trifluoromethyl)thiazol-2-yl)benzamide (150 mg, 0.521 mmol), acetic acid (50.0 mg, 0.833 mmol), HATU (395 mg, 1.04 mmol) and DIEA (201 mg, 1.56 mmol) in DMF (3.00 mL) was stirred at rt for 4 h. The reaction mixture was purified by prep-HPLC to give title compound (9.48 mg, 5.54% yield) as white solid. $^1H$ NMR (400 MHz, DMSO-$d_6$): δ 13.14 (s, 1H), 10.09 (s, 1H), 8.17 (s, 1H), 7.71-7.70 (m, 2H), 7.57-7.53 (m, 1H), 7.26-7.22 (m, 1H), 2.01 (s, 3H). MS (ESI) m/z: 329.9 $[M+H]^+$.

Example 061. 2-acetamido-N-(5-cyanothiazol-2-yl)benzamide (B-39)

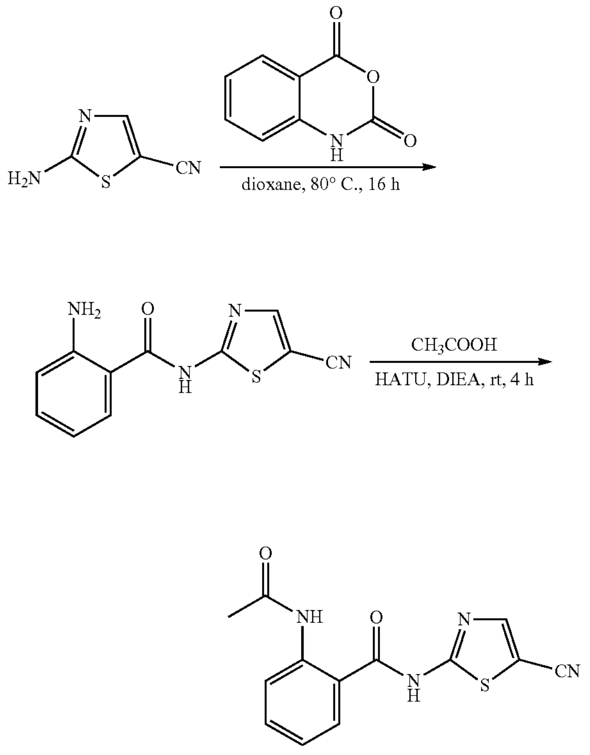

Step 1. Synthesis of 2-amino-N-(5-cyanothiazol-2-yl)benzamide

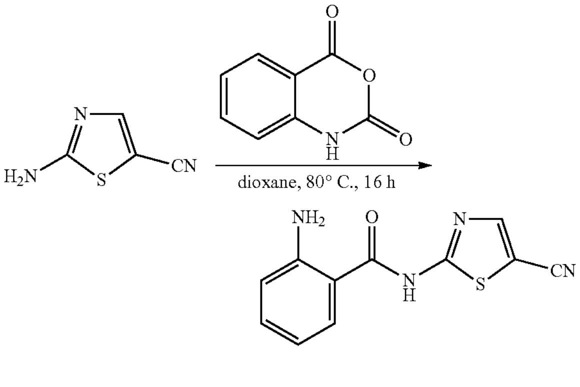

A solution of 1H-benzo[d][1,3]oxazine-2,4-dione (100 mg, 0.614 mmol) and 2-aminothiazole-5-carbonitrile (77.0 mg, 0.614 mmol) in dioxane (5.00 mL) was stirred at 80° C. for 16 h. The mixture was cooled to the rt and concentrated under vacuum. The resulting residue was purified by prep-HPLC to give title compound (45 mg, 30.04% yield) as white solid. MS (ESI) m/z: 245.3 $[M+H]^+$.

Step 2. Synthesis of 2-acetamido-N-(5-cyanothiazol-2-yl)benzamide

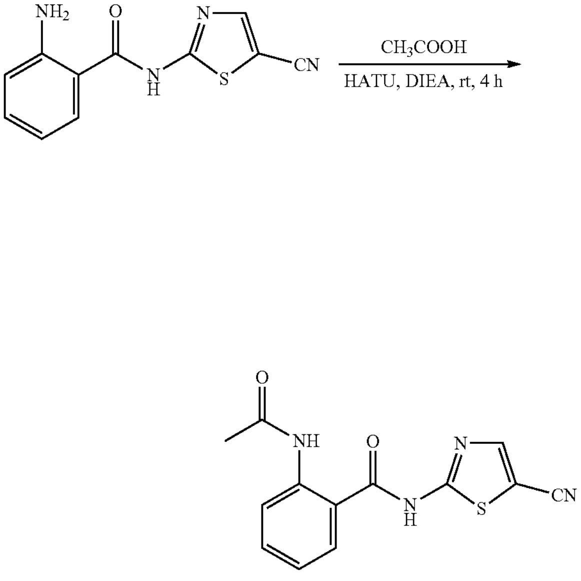 [SMILES: N#Cc1cnc(NC(=O)c2ccccc2N)s1 ; "CH3COOH" ; CC(=O)Nc1ccccc1C(=O)Nc1ncc(C#N)s1]

A solution of 2-amino-N-(5-cyanothiazol-2-yl)benzamide (30.0 mg, 0.105 mmol), acetic acid (20.0 mg, 0.126 mmol), HATU (60.0 mg, 0.158 mmol) and DIEA (27 mg, 0.21 mmol) in DMF (2.00 mL) was stirred at rt for 4 h. The reaction mixture was purified by prep-HPLC to give title compound (11.3 mg, 37.63% yield) as white solid. $^1H$ NMR (400 MHz, DMSO-$d_6$): δ 13.34 (s, 1H), 10.12 (s, 1H), 8.43 (s, 1H), 7.70-7.68 (m, 2H), 7.58 (t, J=8.4 Hz, 1H), 7.25 (t, J=8.4 Hz, 1H), 2.00 (s, 3H). MS (ESI) m/z: 287.1 $[M+H]^+$.

Example 062. 2-(N,N-dimethylsulfamoyl)-N-(5-nitrothiazol-2-yl)benzamide (B-82)

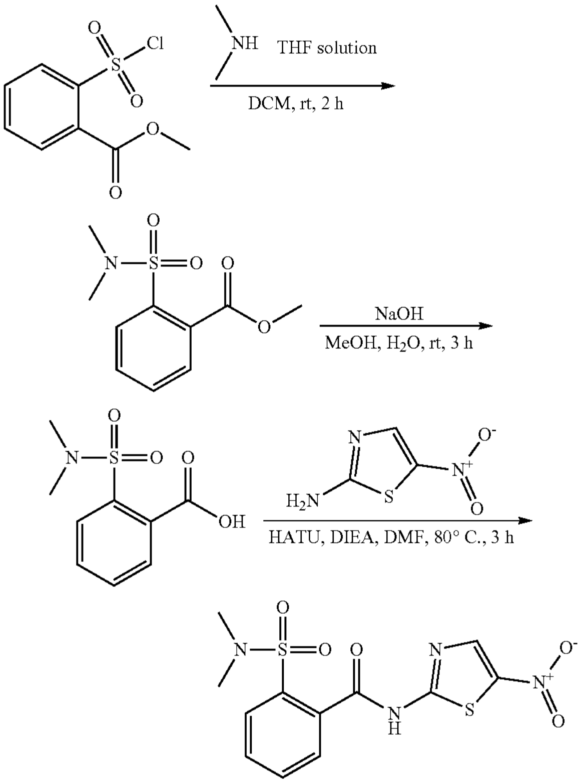

Step 1. Synthesis of methyl 2-(N,N-dimethylsulfamoyl)benzoate

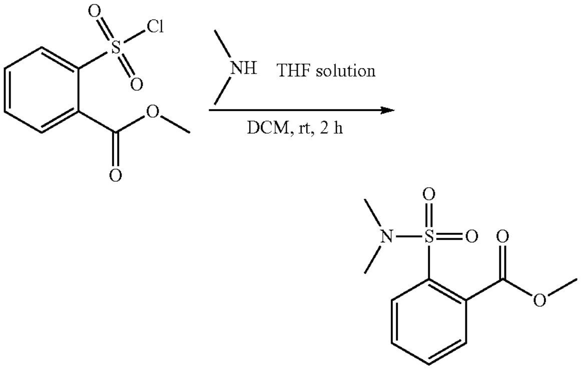

To a solution of methyl 2-(chlorosulfonyl)benzoate (200 mg, 0.855 mmol) and cyclopropanol (220 mg, 3.75 mmol) in DCM (2 mL) was added dimethylamine (2 mL, 2 N in THF). After being stirred at rt for 2 h, the mixture was concentrated under vacuum to give the title compound (250 mg, crude) as white solid, which was used in the next step without further purification. MS (ESI) m/z: 244.1 $[M+H]^+$.

Step 2. Synthesis of methyl 2-(N,N-dimethylsulfamoyl)benzoic acid

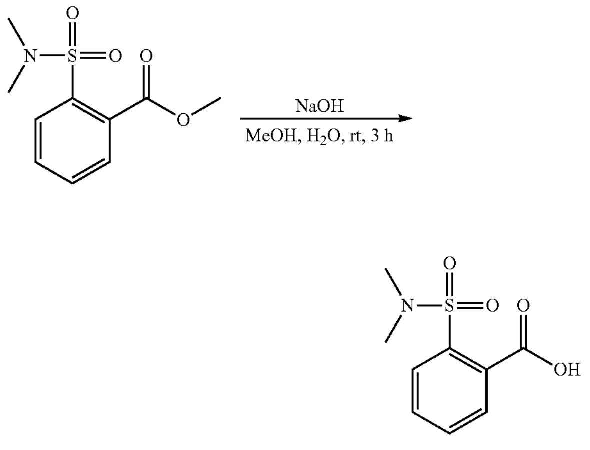

To a solution of methyl 2-(N,N-dimethylsulfamoyl)benzoate (250 mg, crude) in MeOH (5 mL) was added a solution of NaOH (2.00 g, 50.0 mmol) in $H_2O$ (3 mL). After being stirred at rt for 3 h, the mixture was diluted with $H_2O$ (20 mL), acidified with 1 N HCl to pH=3 and extracted with EtOAc (3×20 mL). The combined organic phase was dried over $Na_2SO_4$, filtered and concentrated under vacuum to give the title compound (250 mg, crude) as colorless oil. MS (ESI) m/z: 230.1 $[M+H]^-$.

Step 3. Synthesis of 2-(N,N-dimethylsulfamoyl)-N-(5-nitrothiazol-2-yl)benzamide

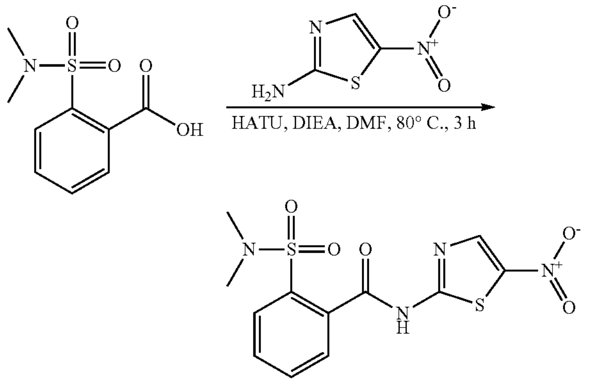

A solution of 2-(N,N-dimethylsulfamoyl)benzoic acid (250 mg, crude), 5-nitrothiazol-2-amine (152 mg, 1.05 mmol), HATU (670 mg, 1.74 mmol) and DIEA (225 mg, 1.74 mmol) in DMF (2 mL) was stirred at 80° C. for 3 h. The mixture was cooled to rt and purified by prep-HPLC to give the title compound (6.22 mg, 2.04% yield) as white solid. $^1H$ NMR (400 MHz, DMSO-$d_6$): δ 13.61 (s, 1H), 8.67 (s, 1H), 7.89-7.88 (m, 1H), 7.82-7.80 (m, 2H), 7.73-7.75 (m, 1H), 2.71 (s, 6H). MS (ESI) m/z: 357.1 $[M+H]^+$.

Example 063. 2-acetamido-$N^4$-(6-aminohexyl)-$N^1$-(4-methyl-5-nitrothiazol-2-yl)terephthalamide (BL-4)

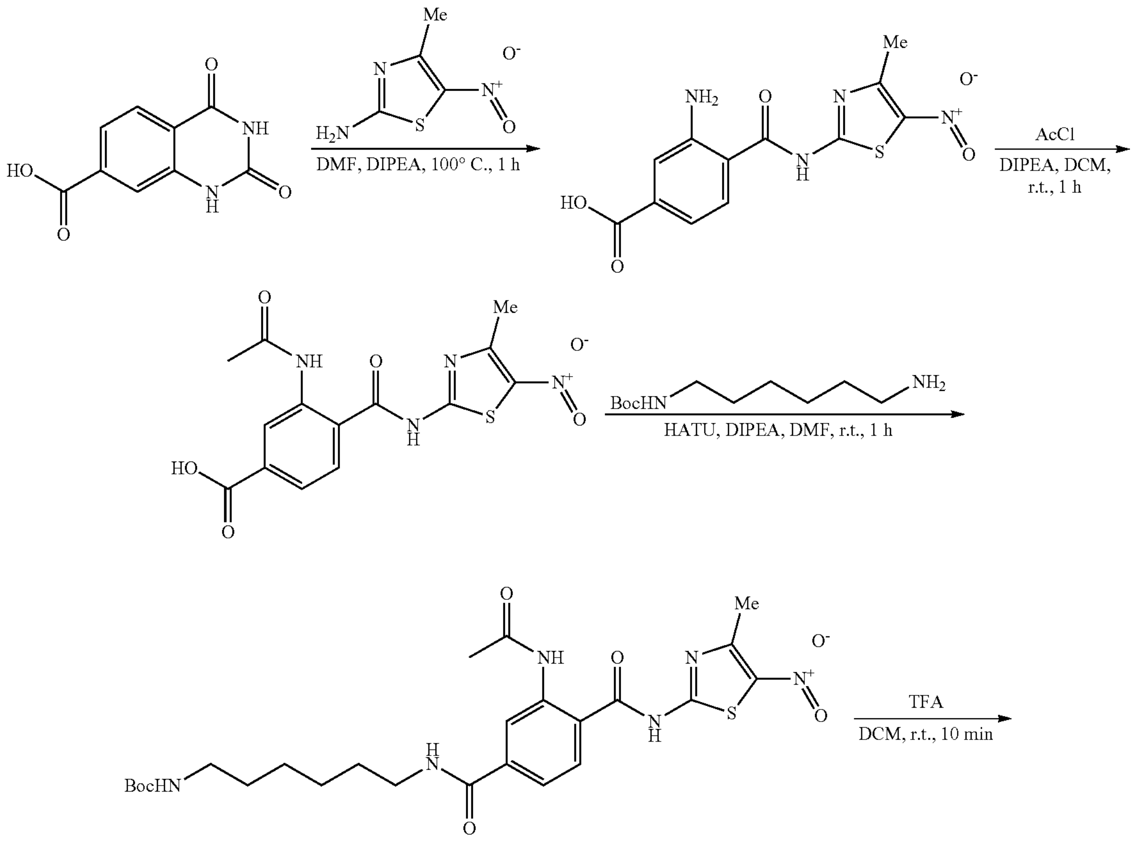

-continued

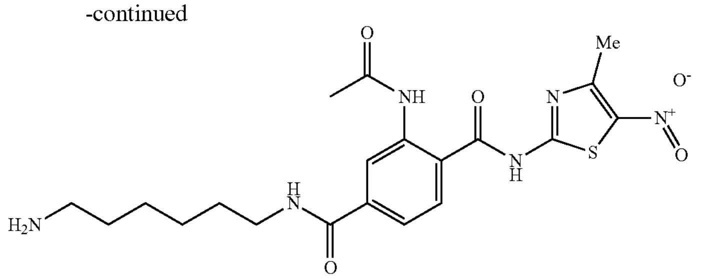

Step 1. Synthesis of methyl 3-amino-4-((4-methyl-5-nitrothiazol-2-yl)carbamoyl)benzoic acid

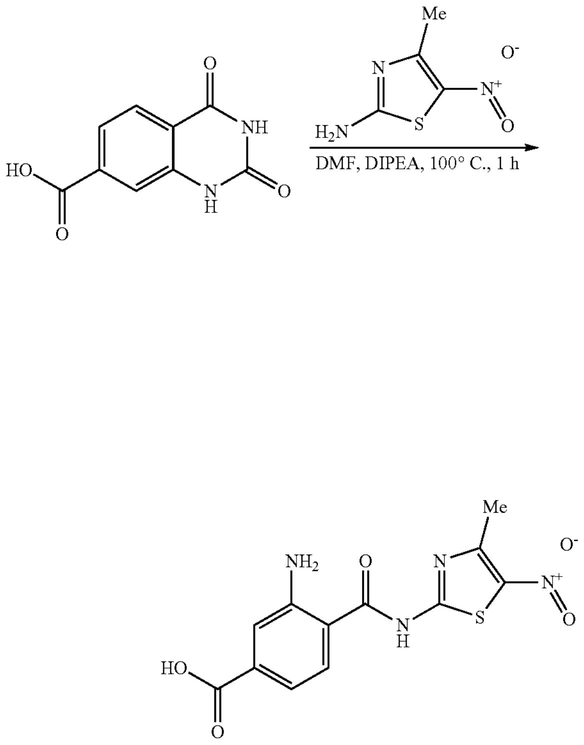

A solution of 2,4-dioxo-1,4-dihydro-2H-benzo[d][1,3]oxazine-7-carboxylic acid (900 mg, 3.11 mmol), DIPEA (1.21 mg, 9.33 mmol) and 4-methyl-5-nitrothiazol-2-amine hydrochloride (621 mg, 3.11 mmol) in DMF (50 mL) was stirred at 80° C. for 1 h. At rt, the reaction mixture was used in the next step without further purification. MS (ESI) m/z: 320.9 $[M-H]^-$.

Step 2. Synthesis of 3-acetamido-4-((4-methyl-5-nitrothiazol-2-yl)carbamoyl)benzoic acid

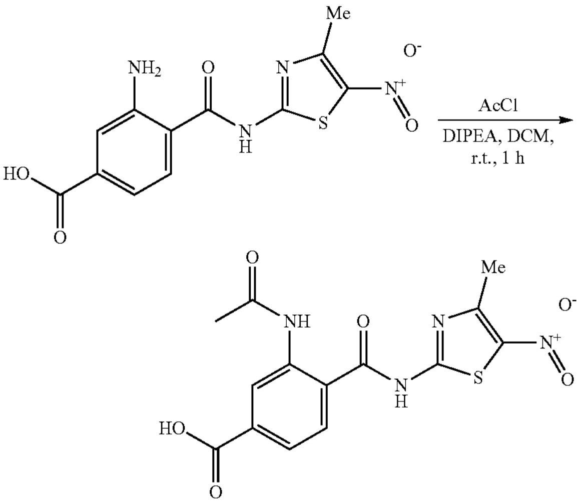

To a solution of 3-amino-4-((4-methyl-5-nitrothiazol-2-yl)carbamoyl)benzoic acid in DMF (50 mL) (from previous step) was added DIPEA (1.21 mg, 9.33 mmol) and acetyl chloride (486 mg, 6.22 mmol) at 0° C. After being stirred at it for 1 h, $K_2CO_3$ (2.15 mg, 15.6 mmol) was added. After being stirred for another 1 h, the mixture was diluted with water (50 mL). After the pH of the mixture was adjusted to 4 with 1 N HCl, it was extracted with EtOAc (2×50 mL). The combined organic phase was washed with brine, dried over $Na_2SO_4$, filtered and concentrated. The resulting residue was recrystallized from MeOH (20 mL) to give the title compound (900 mg, 79.4% yield over two steps) as yellow solid. MS (ESI) m/z: 365.0 $[M+H]^+$.

Step 3. Synthesis of tert-butyl (6-(3-acetamido-4-((4-methyl-5-nitrothiazol-2-yl)carbamoyl)benzamido)hexyl)carbamate

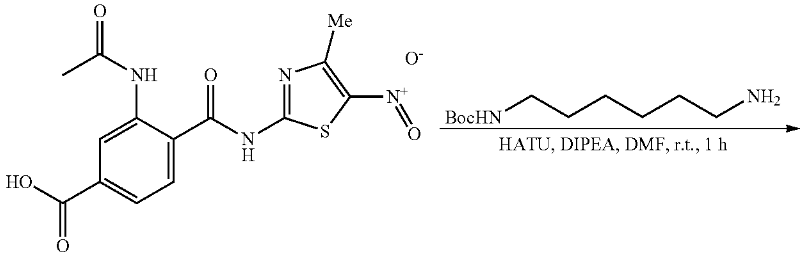

-continued

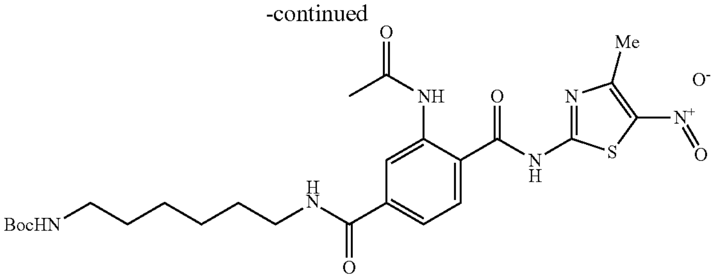

A solution of 3-acetamido-4-((4-methyl-5-nitrothiazol-2-yl)carbamoyl)benzoic acid (300 mg, 0.820 mmol), tert-butyl (6-aminohexyl)carbamate (177 mg, 0.820 mmol), DIPEA (212 mg, 1.64 mmol) and HATU (347 mg, 0.984 mmol) in DMF (10 mL) was stirred at rt for 1 h. Then, the mixture was diluted with EtOAc (30 mL) and washed with brine, dried over $Na_2SO_4$, filtered and concentrated to give the title compound (500 mg, crude) as yellow solid, which was used in the next step without further purification. MS (ESI) m/z: 563.4 $[M+H]^+$.

Step 4. Synthesis of 2-acetamido-$N^4$-(6-aminohexyl)-$N^1$-(4-methyl-5-nitrothiazol-2-yl)terephthalamide

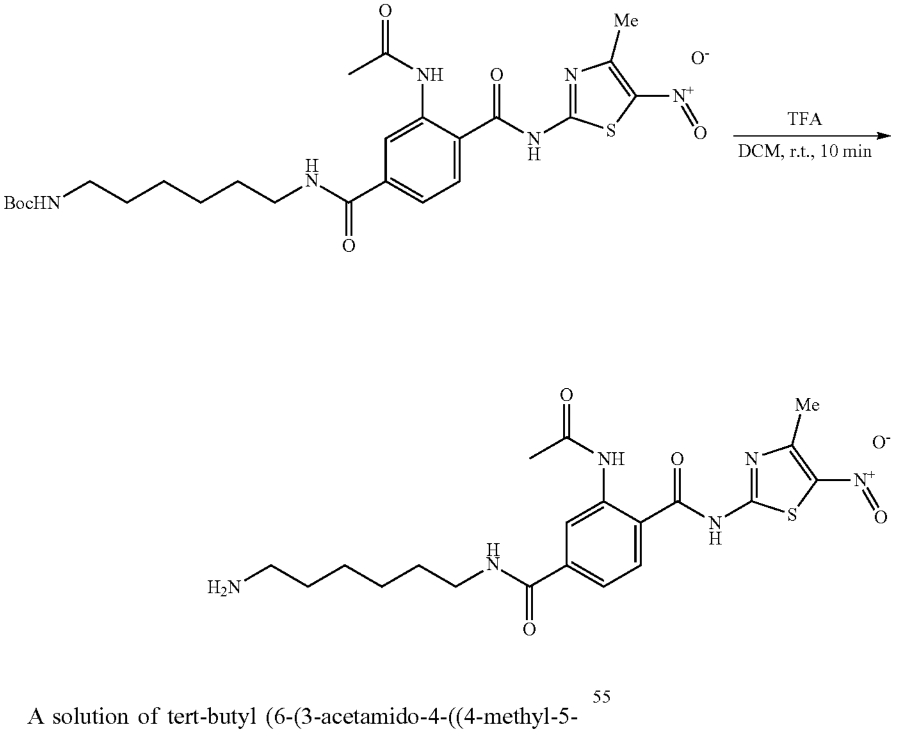

A solution of tert-butyl (6-(3-acetamido-4-((4-methyl-5-nitrothiazol-2-yl)carbamoyl)benzamido)hexyl)carbamate (500 mg, crude) in DCM (2 mL)/TFA (2 mL) was stirred at rt for 10 min. Then, the mixture was concentrated under vacuum. The resulting residue was purified by pre-HPLC to give the title compound (52.3 mg, 11.1% yield over two steps) as yellow solid. $^1H$ NMR (400 MHz, DMSO-$d_6$): δ 13.47 (brs, 1H), 10.34 (brs, 1H), 8.62-8.60 (m, 1H), 8.19-8.10 (m, 1H), 7.82-7.78 (m, 1H), 7.64-7.62 (m, 3H), 3.29-3.24 (m, 2H), 2.80-2.74 (m, 2H), 2.69 (s, 3H), 2.04 (s, 3H), 1.54-1.51 (m, 4H), 1.34-1.33 (m, 4H). MS (ESI) m/z: 463.1 $[M+H]^+$.

Example 064. 2-acetamido-$N^4$-(2-(2-(2-(2-aminoethoxy)ethoxy)ethoxy)ethyl)-$N^1$-(4-methyl-5-nitrothiazol-2-yl)terephthalamide (BL-5)
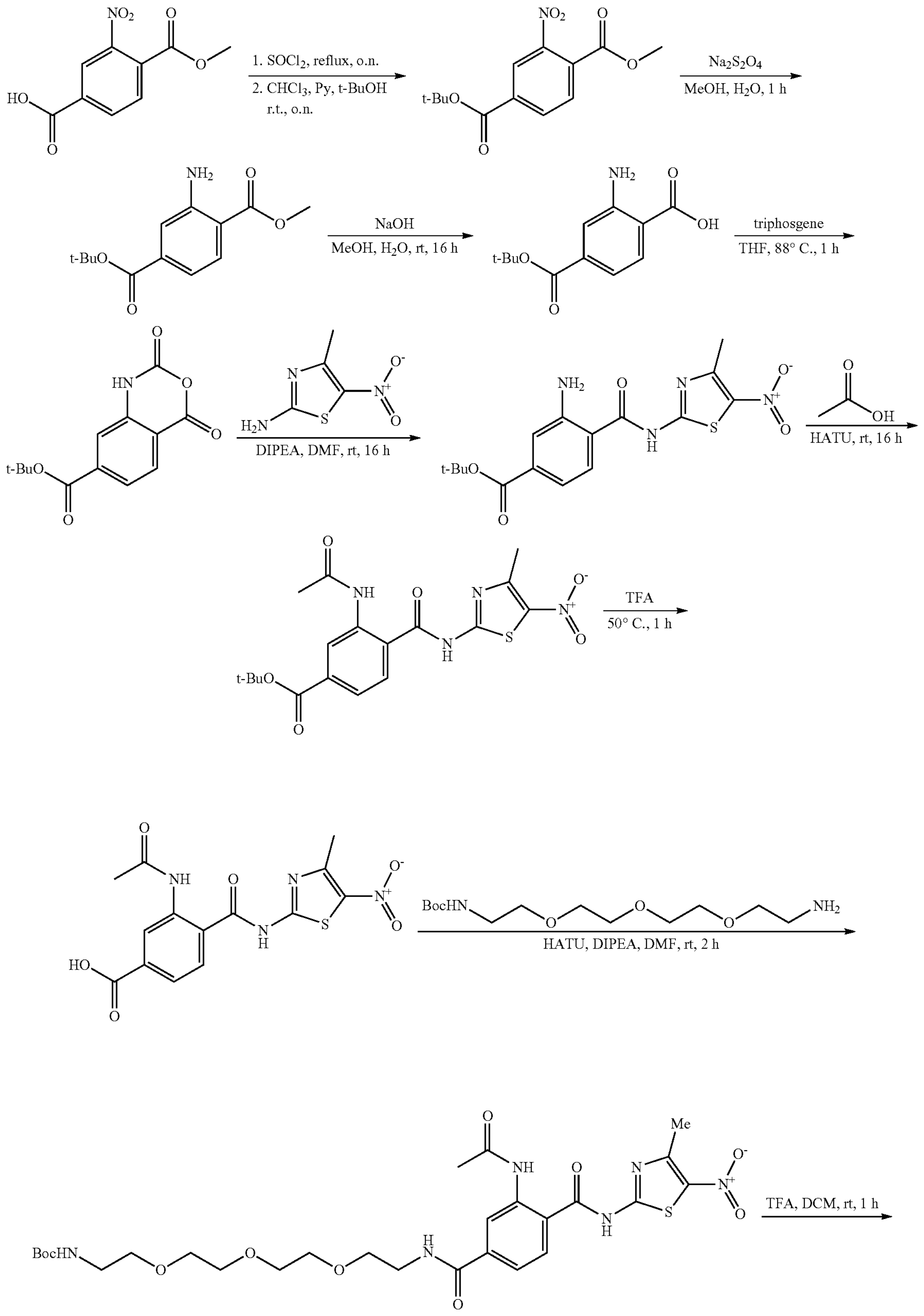

-continued

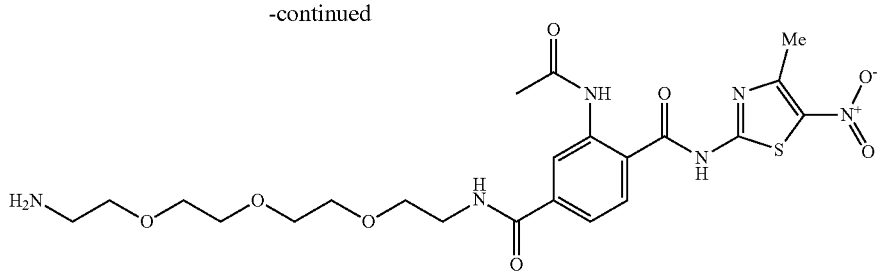

Step 1. Synthesis of 4-(tert-butyl) 1-methyl 2-nitroterephthalate

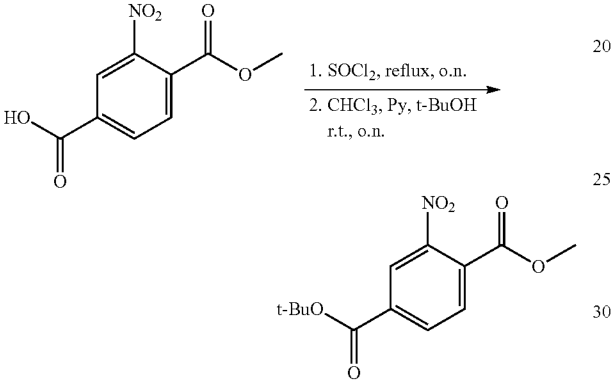

A solution of 4-(methoxycarbonyl)-3-nitrobenzoic acid (2.00 g, 8.89 mmol) in $SOCl_2$ (10 mL)/DMF (1 drop) was heated to reflux overnight. At rt, the mixture was concentrated under vacuum. The resulting residue was dissolved in $CHCl_3$ (10 mL)/pyridine (1 mL). And then tert-butanol (2 mL) was added at rt and stirred at rt overnight. Then, the mixture was concentrated under vacuum. The resulting residue was purified by silica gel column chromatography (petroleum ether:EtOAc=6:1) to give the title compound (800 mg, 32.0% yield) as yellow oil.

Step 2. Synthesis of 4-(tert-butyl) 1-methyl 2-aminoterephthalate

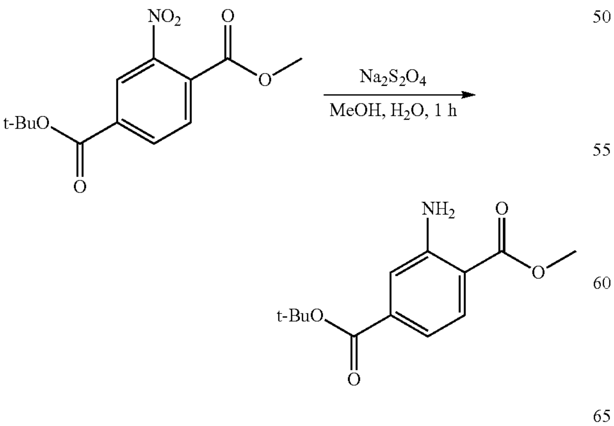

To a solution of 4-(tert-butyl) 1-methyl 2-nitroterephthalate (800 mg, 2.85 mmol) in MeOH (20 mL) was added $Na_2S_2O_4$ (2.00 g, 11.5 mmol) in $H_2O$ (5 mL). After being stirred at rt for 1 h, the mixture was diluted with EtOAc (50 mL) and washed with sat. $NaHCO_3$ (30 mL) and brine, dried over $Na_2SO_4$, filtered and concentrated under vacuum. The resulting residue was purified by silica gel column chromatography (petroleum ether:EtOAc=10:1) to give the title compound (550 mg, 77.0% yield) as yellow solid. MS (ESI) m/z: 463.1 $[M+H]^+$.

Step 3. Synthesis of 2-amino-4-(tert-butoxycarbonyl)benzoic acid

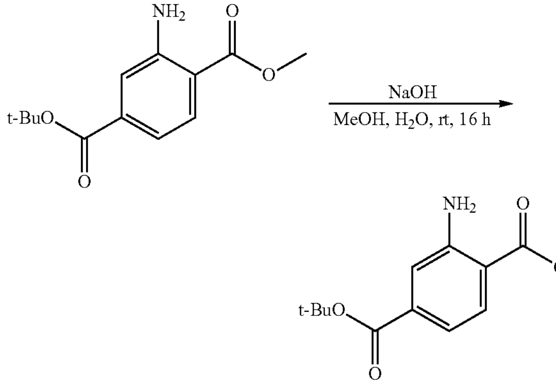

To a solution of 4-(tert-butyl) 1-methyl 2-aminoterephthalate (550 mg, 2.19 mmol) in MeOH (30 mL) was added NaOH (7 mL, 1 N). After being stirred at rt for 16 h, the mixture was diluted with water (30 mL). After the pH of the mixture was adjusted to 4 with 1 N HCl, it was extracted with EtOAc (3x30 mL). The combined organic layers were washed with brine (3x30 mL, dried over $Na_2SO_4$, filtered and concentrated under vacuum to give the title compound (290 mg, 56% yield) as yellow solid, which was used in the next step without further purification. MS (ESI) m/z: 238.4 $[M+H]^+$.

Step 4. Synthesis of tert-butyl 2,4-dioxo-1,4-dihydro-2H-benzo[d][1,3]oxazine-7-carboxylate

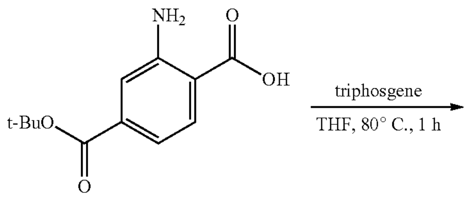

-continued

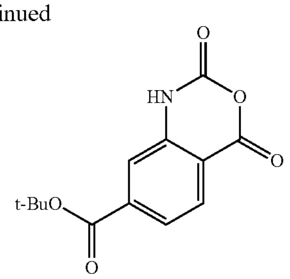

A solution of 2-amino-4-(tert-butoxycarbonyl)benzoic acid (290 mg, 1.22 mmol) and triphosgene (145 mg, 0.48 mmol) in THF (10 mL) was stirred at 80° C. for 1 h. After being was cooled down to rt, the mixture was filtered and the filtrate was dried under vacuum to give the title compound (335 mg, crude) as yellow solid. MS (ESI) m/z: 262.2 $[M-H]^-$.

Step 5. Synthesis of tert-butyl 3-amino-4-((4-methyl-5-nitrothiazol-2-yl)carbamoyl)benzoate

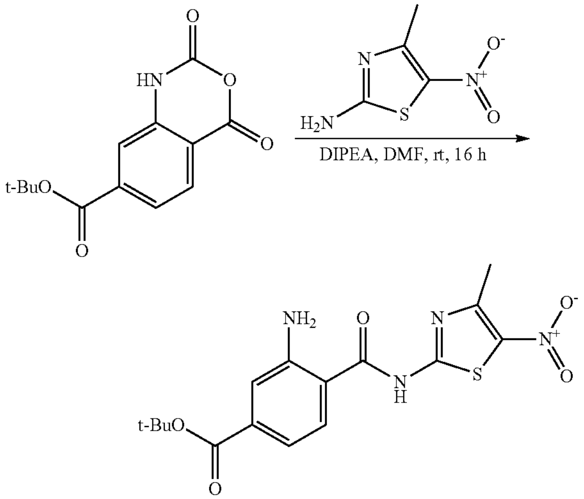

A solution of tert-butyl 2,4-dioxo-1,4-dihydro-2H-benzo[d][1,3]oxazine-7-carboxylate (335 mg, crude), 5-nitrothiazol-2-amine (249 mg, 1.27 mmol) and DIPEA (0.60 mL) in DMF (10 mL) was stirred at rt overnight. The mixture was used in the next step without further purification. MS (ESI) m/z: 379.2 $[M+H]^+$.

Step 6. Synthesis of tert-butyl 3-acetamido-4-((4-methyl-5-nitrothiazol-2-yl)carbamoyl)benzoate

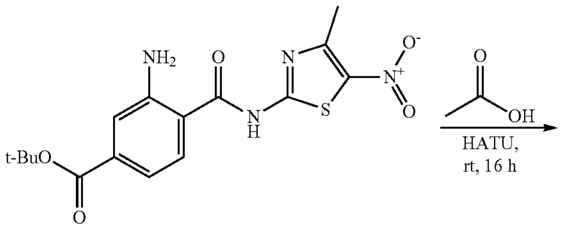

-continued

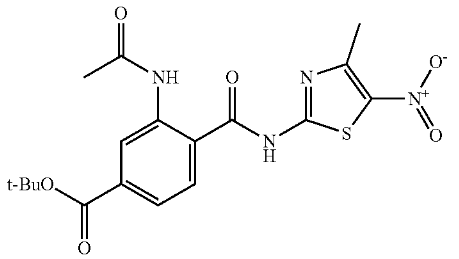

A solution of tert-butyl 3-amino-4-((4-methyl-5-nitrothiazol-2-yl)carbamoyl)benzoate (reaction solution), acetic acid (76 mg, 1.27 mmol) and HATU (482 mg, 1.27 mmol) in DMF (5 mL) was stirred at rt for 16 h. After the mixture was diluted with $H_2O$ (30 mL), the mixture was extracted with EtOAc (3x30 mL), washed with brine (3x30 mL), dried over $Na_2SO_4$, filtered and concentrated under vacuum and purified by silica gel column chromatography (DCM:MeOH=20:1) to give the title compound (500 mg, 72.0% yield) as yellow solid. MS (ESI) m/z: 421.2 $[M+H]^+$.

Step 7. Synthesis of 3-acetamido-4-((4-methyl-5-nitrothiazol-2-yl)carbamoyl)benzoic acid

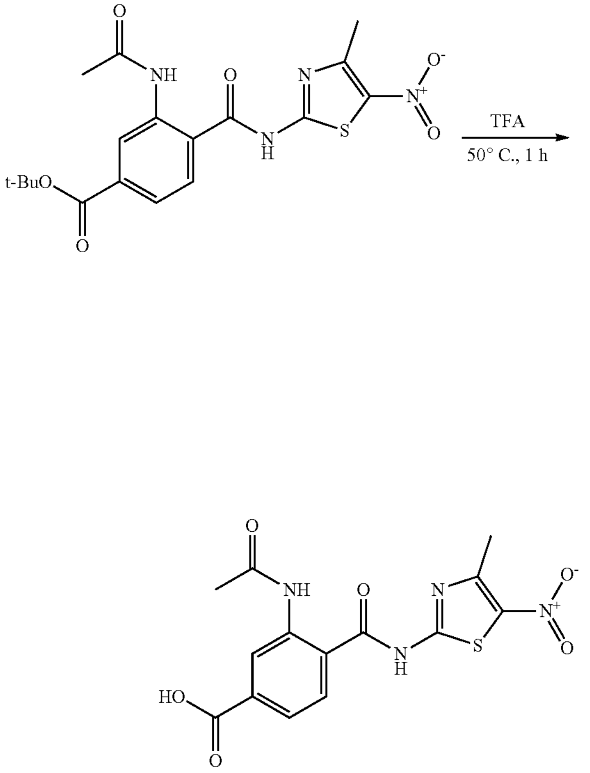

A solution of tert-butyl 3-acetamido-4-((4-methyl-5-nitrothiazol-2-yl)carbamoyl)benzoate (500 mg, 1.18 mmol) in TFA (15 mL) was stirred at 50° C. for 1 h. The mixture was concentrated under vacuum to give the title compound (750 mg, 100% yield) as yellow solid. MS (ESI) m/z: 364.9 $[M+H]^+$.

Step 8. Synthesis of tert-butyl (1-(3-acetamido-4-((4-methyl-5-nitrothiazol-2-yl)carbamoyl)phenyl)-1-oxo-5,8,11-trioxa-2-azatridecan-13-yl)carbamate

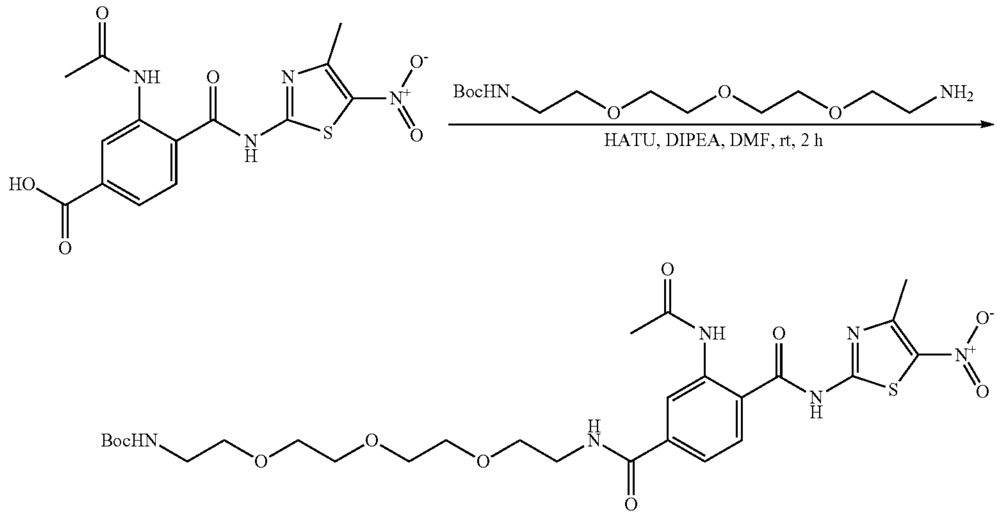

A solution of 3-acetamido-4-((4-methyl-5-nitrothiazol-2-yl)carbamoyl)benzoic acid (200 mg, 0.549 mmol), tert-butyl (2-(2-(2-(2-aminoethoxy)ethoxy)ethoxy)ethyl)carbamate (160 mg, 0.549 mmol), HATU (208 mg, 0.549 mmol) and DIEA (136 mg, 1.09 mmol) in DMF (5 mL) was stirred at rt for 2 h. After the mixture was diluted with $H_2O$ (30 mL), the mixture was extracted with EtOAc (3×30 mL), washed with brine (3×30 mL), dried over $Na_2SO_4$, filtered and concentrated under vacuum and purified by pre-HPLC to give the title compound (250 mg, 72.0% yield) as yellow solid. MS (ESI) m/z: 639.0 $[M+H]^-$.

Step 9. Synthesis of 2-acetamido-$N^4$-(2-(2-(2-(2-aminoethoxy)ethoxy)ethoxy)ethyl)-$N^1$-(4-methyl-5-nitrothiazol-2-yl)terephthalamide

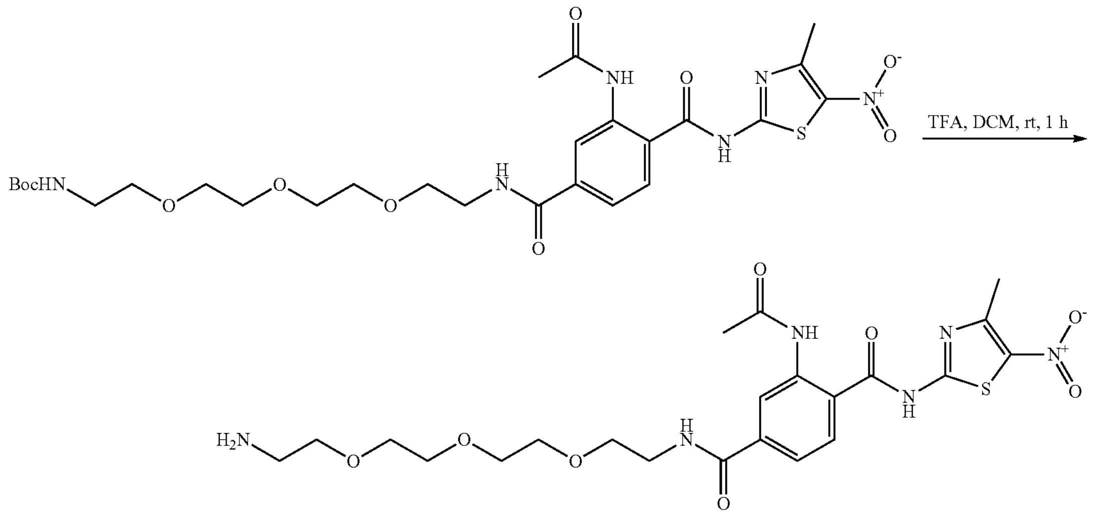 [SMILES: CC(=O)Nc1cc(C(=O)NCCOCCOCCOCCNC(=O)OC(C)(C)C)ccc1C(=O)Nc1nc(C)c([N+](=O)[O-])s1 ; CC(=O)Nc1cc(C(=O)NCCOCCOCCOCCN)ccc1C(=O)Nc1nc(C)c([N+](=O)[O-])s1]

A solution of tert-butyl (1-(3-acetamido-4-((4-methyl-5-nitrothiazol-2-yl)carbamoyl)phenyl)-1-oxo-5,8,1-trioxa-2-azatridecan-13-yl)carbamate (250 mg, 0.392 mmol) in TFA/DCM (15 mL, 6 mL) was stirred at rt for 1 h. The mixture was concentrated under vacuum and purified by pre-HPLC (0.1% $NH_3 \cdot H_2O$) to give the title compound (27.2 mg, 23.0% yield) as yellow solid. $^1$H NMR (400 MHz, DMSO-$d_6$): δ 13.67 (s, 1H), 8.95 (d, J=1.4 Hz, 1H), 8.53-8.51 (s, 1H), 8.26 (d, J=8.2 Hz, 1H), 7.48 (dd, J=8.2, 1.6 Hz, 1H), 3.56-3.41 (m, 14H), 2.94 (t, J=5.2 Hz, 2H), 2.64 (s, 3H), 2.19 (s, 3H). MS (ESI) m/z: 539.5 [M+H]$^+$.

Example 065. 2-acetamido-N-(4-phenylthiazol-2-yl) benzamide (B-46)

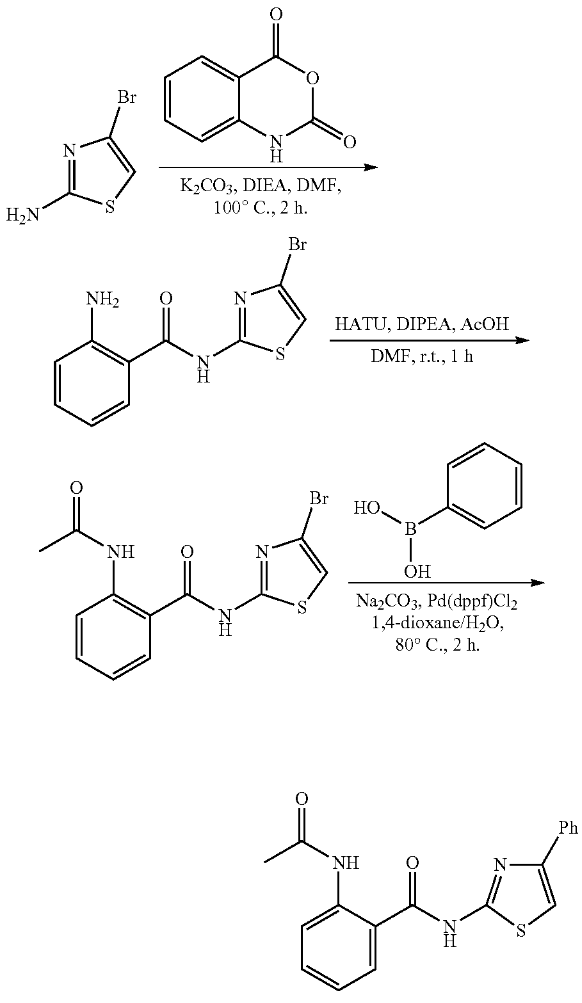

Step 1. Synthesis of 2-amino-N-(4-bromothiazol-2-yl)benzamide

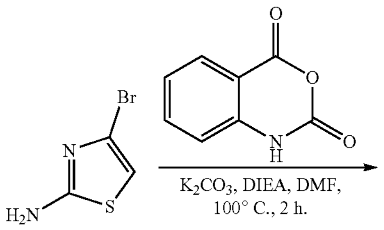

-continued

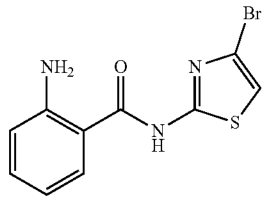

A solution of 4-bromothiazol-2-amine (200 mg, 1.12 mmol) 2H-benzo[d][1,3]oxazine-2,4 (1H)-dione (270 mg, 1.67 mmol) and $K_2CO_3$ (309 mg, 2.23 mmol) in DMF (8 mL) was stirred at 100° C. for 2 h. At rt, the mixture was poured into ice-water (100 mL) and extracted with EtOAc (3×50 mL). The combined organic phase was washed with brine (2×50 mL), dried over $Na_2SO_4$, filtered and concentrated under vacuum. The resulting residue was purified by silica gel column chromatography (petroleum ether: EtOAc=1:1) to give the title compound (120 mg, 36.0% yield) as white solid. MS (ESI) m/z: 300.1 [M+H]$^+$.

Step 2. Synthesis of 2-acetamido-N-(4-bromothiazol-2-yl)benzamide

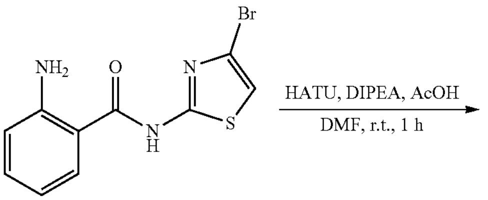

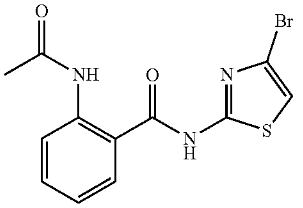

To a solution of 2-amino-N-(4-bromothiazol-2-yl)benzamide (100 mg, 0.335 mmol) in DMF (8 mL) were added HATU (255 mg, 0.671 mol), DIPEA (130 mg, 1.02 mmol) and acetic acid (40 mg, 0.671 mmol) at room temperature. After being stirred at rt for 1 h, the mixture was diluted with water (50 mL) and extracted with EtOAc (2×100 mL). The combined organic phase was washed with brine (2×50 mL), dried over $Na_2SO_4$, filtered and concentrated under vacuum to give the residue which was purified by silica gel column chromatography (petroleum ether:EtOAc=1:1) to give the title compound (100 mg, 88.5% yield) as white solid. MS (ESI) m/z: 339.9 [M+H]$^+$.

Step 3. Synthesis of 2-acetamido-N-(4-phenylthiazol-2-yl)benzamide

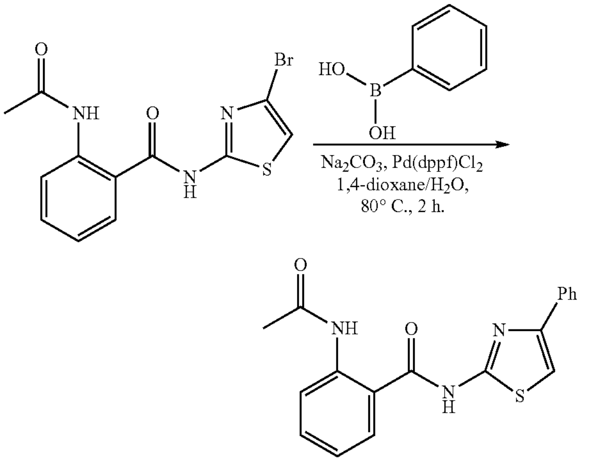

To a solution of 2-acetamido-N-(4-bromothiazol-2-yl) benzamide (50 mg, 0.150 mmol) in 1,4-dioxane/$H_2O$ (3 mL, v/v=20:1) were added phenylboronic acid (37 mg, 0.300 mmol), $Na_2CO_3$ (20 mg, 0.300 mmol) and Pd(dppf)$Cl_2$ (30 mg, 0.020 mmol). After degassed with argon for 3 times, the mixture was stirred at 80° C. for 2 h. Then, the mixture was cooled to rt and purified by prep-HPLC to give the tide compound (17.0 mg, 34.7% yield) as white solid. $^1H$ NMR (400 MHz, DMSO-$d_6$): δ 12.7 (brs, 1H), 10.2 (brs, 1H), 7.95-7.91 (m, 3H), 7.82-7.80 (m, 1H), 7.70 (s, 1H), 7.56-7.53 (m, 1H), 7.47-7.43 (m, 2H), 7.36-7.32 (m, 1H), 7.25-7.21 (m, 1H), 2.06 (s, 3H). MS (ESI) m/z: 338.0 $[M+H]^+$.

Example 066. 2-acetamido-N-(pyrimidin-4-yl)benzamide (B-57)

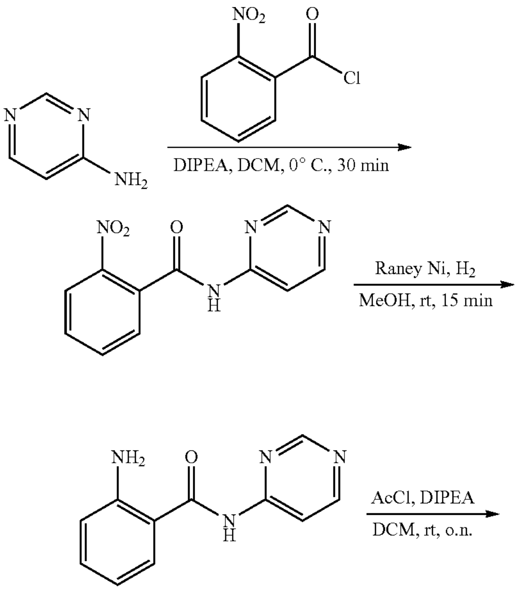

-continued

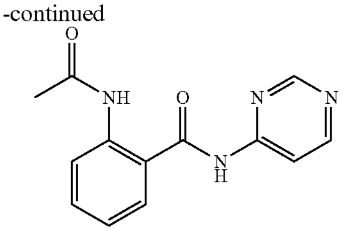

Step 1. Synthesis of 2-nitro-N-(pyrimidin-4-yl)benzamide

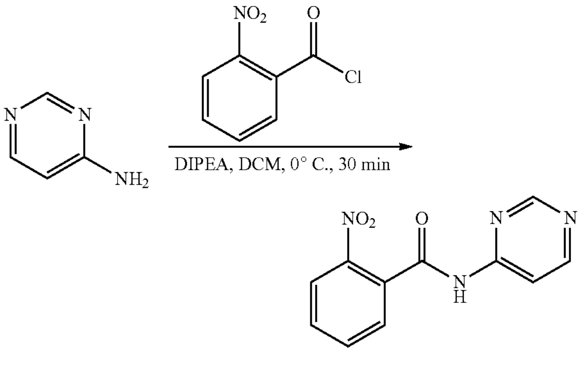

To a solution of pyrimidin-4-amine (200 mg, 2.10 mmol) and DIPEA (544 mg, 4.21 mmol) in DCM (5 mL) was added 2-nitrobenzoyl chloride (390 mg, 2.10 mmol) at 0° C. The reaction mixture was stirred at 0° C. for 30 min. Then, the mixture was diluted with water (20 mL) and extracted with DCM (2×20 mL). The combined organic layers were washed with brine (2×20 mL), dried over $Na_2SO_4$, filtered and concentrated under vacuum. The resulting residue was purified by silica gel column chromatography (petroleum ether:EtOAc=3:1) to give the title compound (60 mg, 12.0% yield) as white solid. MS (ESI) m/z: 338.0 $[M+H]^+$.

Step 2. Synthesis of 2-amino-N-(pyrimidin-4-yl)benzamide

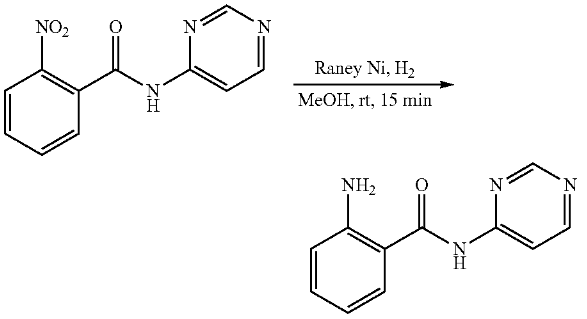

A solution of 2-nitro-N-(pyrimidin-4-yl)benzamide (60 mg, 0.246 mmol) and Raney Ni (10 mg) in MeOH (5 mL) was hydrogenated under 1 atm of hydrogen pressure for 15 min at rt. Then, the mixture was filtered and the filtrate was concentrated under vacuum to give the tide compound (28 mg, crude) as white solid, which was used in the next step without further purification. MS (ESI) m/z: 215.1 $[M+H]^+$.

Step 3. Synthesis of 2-acetamido-N-(pyrimidin-4-yl)benzamide

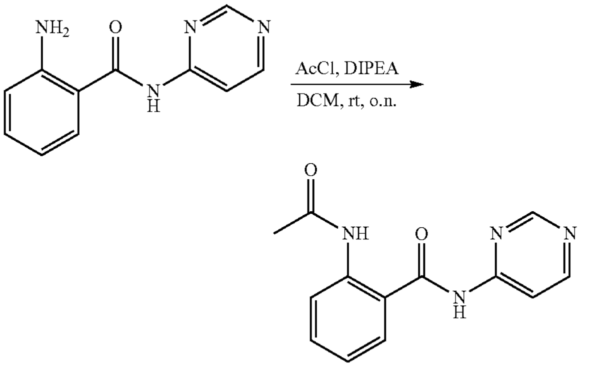

To a solution of 2-amino-N-(pyrimidin-4-yl)benzamide (12 mg, crude) and DIPEA (36 mg, 0.280 mmol) in DCM (3 mL) was added acetyl chloride (14 mg, 0.168 mmol) at 0° C. After being stirred at it overnight, the mixture was concentrated under vacuum. The resulting residue was purified by prep-HPLC to give the title compound (5.60 mg, 38.9% yield over two steps) as white solid. $^1H$ NMR (400 MHz, DMSO-$d_6$): δ 11.2 (brs, 1H), 10.1 (brs, 1H), 8.91 (s, 1H), 8.69 (d, J=6.0 Hz, 1H), 8.13 (dd, J=0.8, 5.8 Hz, 1H), 7.79 (d, J=8.0 Hz, 1H), 7.69 (d, J=7.2 Hz, 1H), 7.53-7.49 (m, 1H), 7.23-7.19 (m, 1H), 2.01 (s, 3H). MS (ESI) m/z: 257.4 $[M-H]^-$.

Example 067. 2-(3-methylureido)-N-(5-nitrothiazol-2-yl)benzamide (B-66)

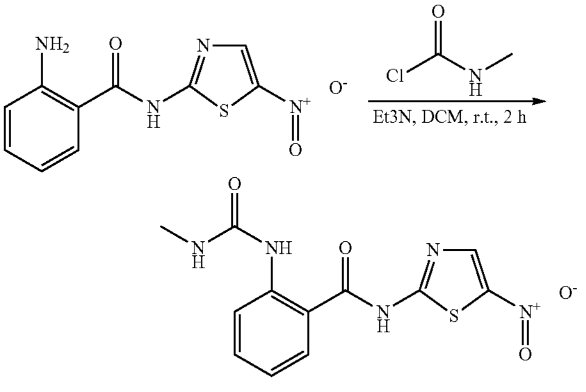

To a solution of 2-amino-N-(5-nitrothiazol-2-yl)benzamide (200 mg, 0.757 mmol) in DCM (4 mL) were added $Et_3N$ (121 mg, 1.20 mmol) and methylcarbamic chloride (71 mg, 0.757 mmol). After being stirred at rt for 2 h, the reaction mixture was diluted with water (20 mL), extracted with DCM (3×20 mL). The organic phase was washed with brine, dried over $Na_2SO_4$, concentrated in vacuum to give a residue, which was purified by pre-HPLC to give the title compound (9.60 mg, 3.95% yield) as yellow solid. $^1H$ NMR (400 MHz, DMSO-$d_6$): δ 13.53 (brs, 1H), 9.27 (brs, 1H), 8.72 (s, 1H), 8.10 (d, J=8.4 Hz, 1H), 7.84 (d, J=7.6 Hz, 1H), 7.53-7.49 (m, 1H), 7.08-7.03 (m, 2H), 2.62 (d, J=4.4 Hz, 3H). MS (ESI) m/z: 322.1 $[M+H]^+$.

Example 068. 2-(methylsulfonamido)-N-(5-nitrothiazol-2-yl)benzamide (B-67)

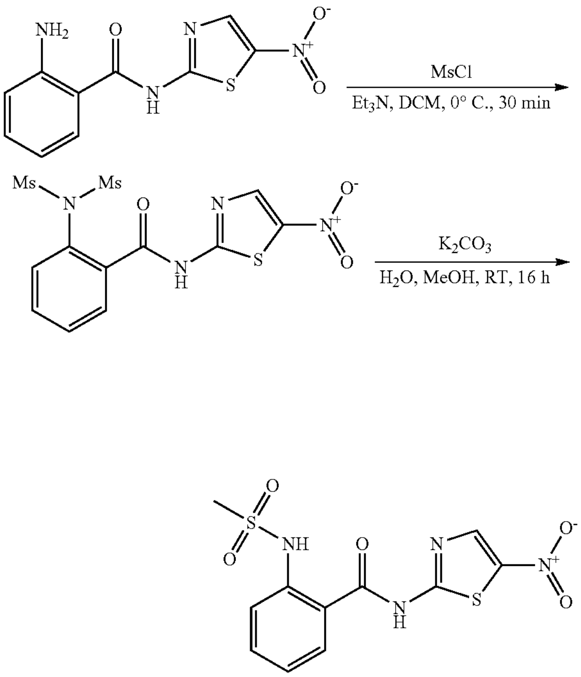

Step 1. Synthesis of 2-(N-(methylsulfonyl)methylsulfonamido)-N-(5-nitrothiazol-2-yl)benzamide

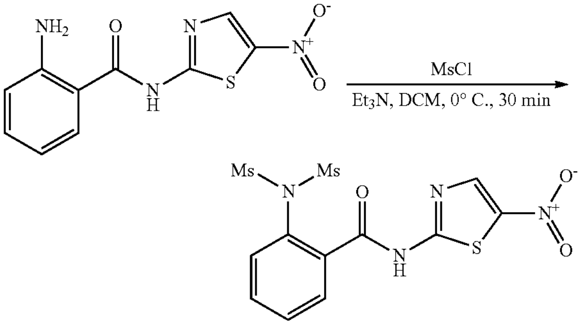

To a solution of 2-(methylamino)-N-(5-nitrothiazol-2-yl)benzamide (150 mg, 0.568 mmol) and $Et_3N$ (115 mg, 1.14 mmol) in DCM (5 mL) was added methanesulfonyl chloride (77.7 mg, 0.682 mmol) at 0° C. The mixture was stirred at 0° C. for 30 min. The mixture was concentrated under vacuum. The resulting residue was purified by silica gel column chromatography (petroleum ether:EtOAc=10:1-3:1) to give the title compound (50 mg, crude) as yellow solid. MS (ESI) m/z: 421.1 $[M+H]^+$.

Step 2. Synthesis of 2-(methylsulfonamido)-N-(5-nitrothiazol-2-yl)benzamide

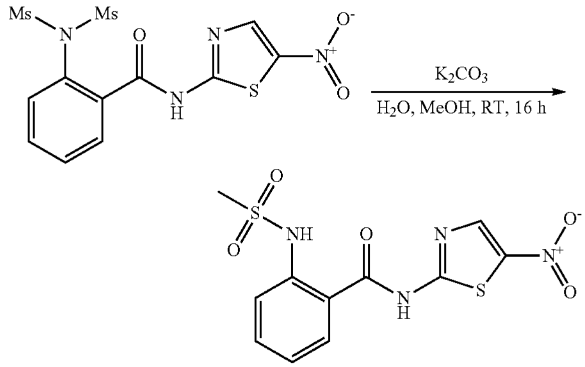

A solution of 2-(N-(methylsulfonyl)methylsulfonamido)-N-(5-nitrothiazol-2-yl)benzamide (50 mg, crude) and $K_2CO_3$ (30 mg, 0.217 mmol) in MeOH (2 mL) and $H_2O$ (2 mL) was stirred at rt for 16 h. After the mixture was diluted with $H_2O$ (30 mL), the mixture was acidified with 1 N HCl to pH=3, extracted with EtOAc (3×20 mL). The combined organic phase was dried over $Na_2SO_4$, filtered and concentrated under vacuum. The resulting residue was purified by prep-HPLC to give the title compound (12.3 mg, 29.9% yield) as white solid. 1H NMR (400 MHz, DMSO-$d_6$): δ 8.71 (s, 1H), 7.88 (d, J=7.2 Hz, 1H), 7.64-7.60 (m, 1H), 7.55-7.53 (m, 1H), 7.33-7.29 (m, 1H), 3.07 (s, 3H). MS (ESI) m/z: 343.1 $[M+H]^+$.

Example 069. 2-hydroxy-$N^1$-(5-nitrothiazol-2-yl)-$N^3$-propylisophthalamide (B-15)

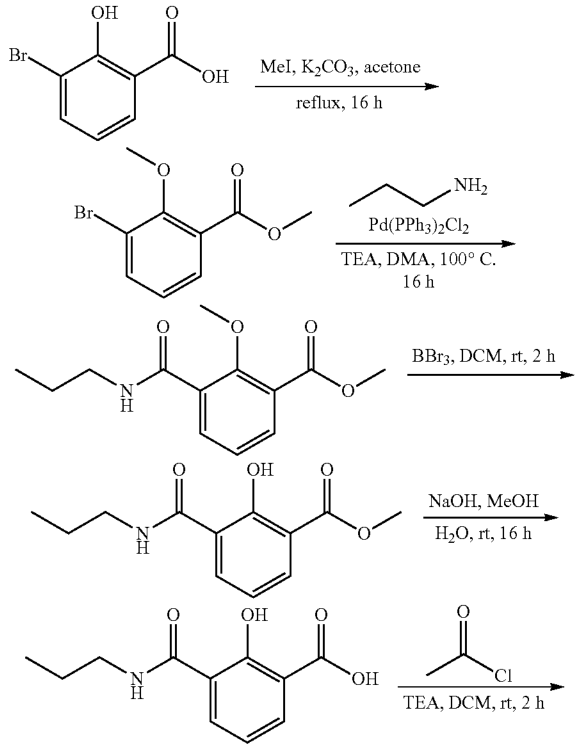

-continued

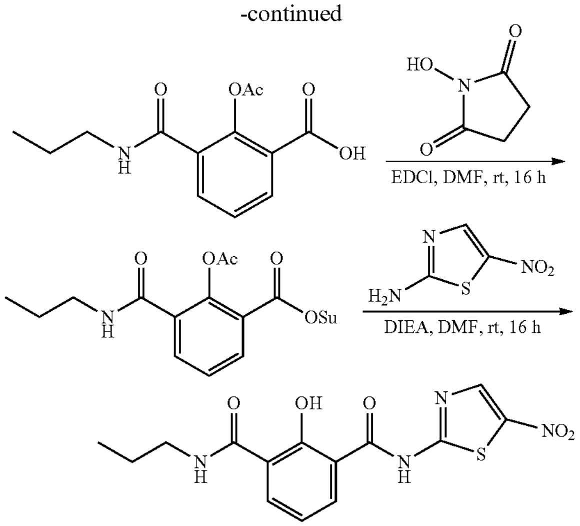

Step 1. Synthesis of methyl 3-bromo-2-methoxybenzoate

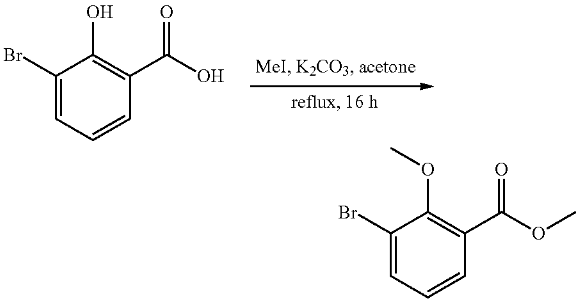

A solution of 3-bromo-2-hydroxybenzoic acid (10.0 g, 46.1 mmol), MeI (52.0 g, 366.2 mmol) and $K_2CO_3$ (25.0 g, 181.2 mmol) in acetone (200 mL) was refluxed overnight. The mixture was concentrated under vacuum. The resulting residue was purified by silica gel column chromatography (petroleum ether:EtOAc=10:1) to give the title compound (11.4 g, 97.0% yield) as yellow oil.

Step 2. Synthesis of methyl 2-methoxy-3-(propylcarbamoyl)benzoate

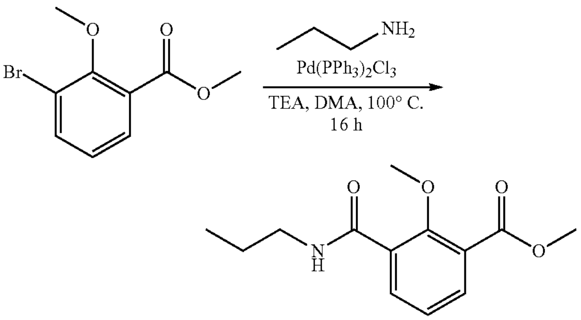

To a solution of methyl 3-bromo-2-methoxybenzoate (10.0 g, 44.9 mmol) in DMF (100 mL) were added $Pd(PPh_3)_2Cl_2$ (1.20 g, 4.50 mmol), propan-1-amine (16 mL, 359 mmol) and TEA (6 mL, 135 mmol). After degassed with CO for 3 times, the mixture was stirred at 100° C. for 16 h under CO. Then, the mixture was cooled to rt and diluted with EtOAc (60 mL). The mixture was washed with brine (3×30 mL), dried over $Na_2SO_4$, filtered and concentrated under vacuum. The resulting residue was purified by silica gel column chromatography (petroleum ether:EtOAc=2:1) to give the title compound (2.20 g, 24.0% yield) as yellow solid. MS (ESI) m/z: 252.5 $[M+H]^+$.

Step 3. Synthesis of methyl 2-hydroxy-3-(propylcarbamoyl)benzoate

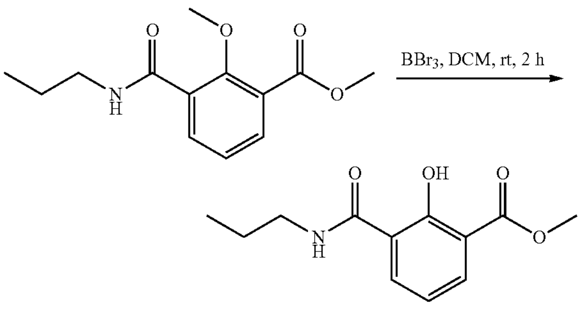

To a solution of methyl 2-methoxy-3-(propylcarbamoyl) benzoate (2.20 g, 8.76 mmol) in DCM (20 mL) was added $BBr_3$ (6 mL) slowly at 0° C. Then the mixture was warmed to rt and stirred for 2 h. The mixture was diluted with dichloromethane (20 mL) at 0° C. and then quenched with MeOH (10 mL) at 0° C. for 10 min. The resulting mixture was concentrated under vacuum at rt to give the title compound (crude 2.8 g) as yellow solid, which was used for the next step without further purification. MS (ESI) m/z: 238.2 $[M+H]^+$.

Step 4. Synthesis of 2-hydroxy-3-(propylcarbamoyl)benzoic acid

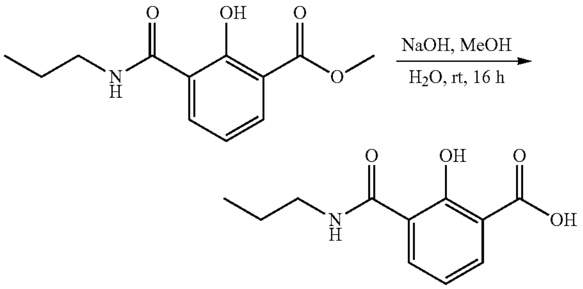

A solution of methyl 2-hydroxy-5-(propylcarbamoyl)benzoate (crude 2.8 g) and NaOH (10.0 g) in $MeOH/H_2O$ (50 mL, 10 mL) was stirred at it for 16 h. After the reaction mixture was cooled down to 0° C., the pH of the mixture was adjusted to 3-4 with 1 N HCl. The mixture was extracted with EtOAc (3×30 mL). The combined organic layer was washed with brine (3×30 mL), dried over $Na_2SO_4$, filtered and concentrated under vacuum to give the title compound (2.8 g, crude) as yellow solid.

Step 5. Synthesis of 2-acetoxy-3-(propylcarbamoyl)benzoic acid

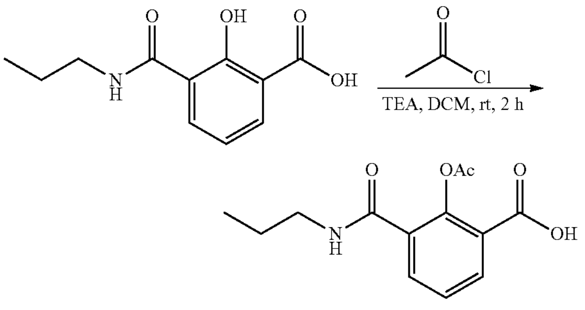

To a solution of 2-hydroxy-5-(propylcarbamoyl)benzoic acid (2.80 g, 12.6 mmol) and TEA (2 mL) in DCM (20 mL) was added acetyl chloride (1 mL) dropwise at 0° C. slowly. After being stirred at it for 2 h, the mixture was diluted with $H_2O$ (30 mL) and extracted with EtOAc (3×30 mL). The combined organic layer was washed with brine, dried over $Na_2SO_4$, filtered and concentrated under vacuum to give the title compound (1.76 g, crude) as yellow solid. MS (ESI) m/z: 264.3 $[M-H]^-$.

Step 6. Synthesis of 2,5-dioxopyrrolidin-1-yl 2-acetoxy-3-(propylcarbamoyl)benzoate

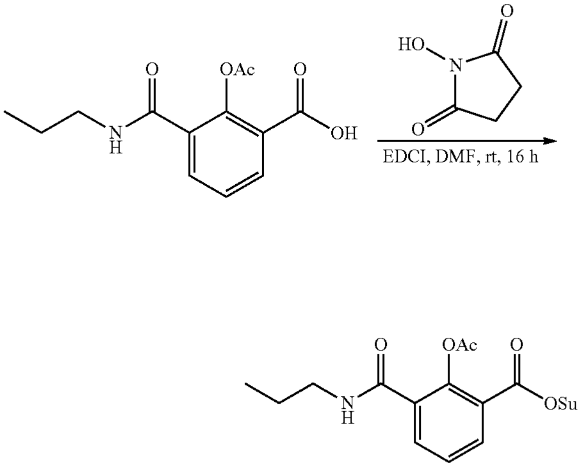

A solution of 2-acetoxy-3-(propylcarbamoyl)benzoic acid (1.76 g, 6.64 mmol), 1-hydroxypyrrolidine-2,5-dione (2.50 g, 13.3 mmol) and EDCI (1.50 g, 13.3 mmol) in DMF (50 mL) was stirred at rt for 16 h. After the mixture was diluted with $H_2O$ (30 mL), the mixture was extracted with EtOAc (3×30 mL). The organic layer was washed with brine, dried over $Na_2SO_4$, filtered and concentrated under vacuum to give the title compound (2.28 g. crude) as yellow solid. MS (ESI) m/z: 363.2 $[M+H]^+$.

Step 7. Synthesis of 2-hydroxy-$N^1$-(5-nitrothiazol-2-yl)-$N^3$-propylisophthalamide

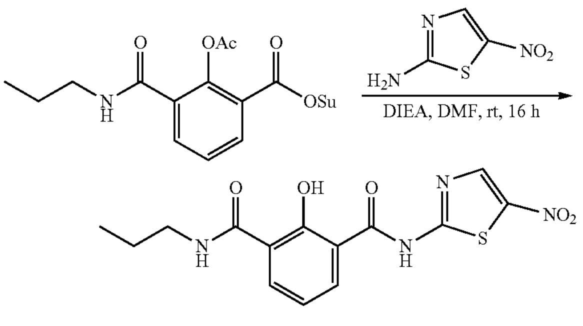

A solution of 2,5-dioxopyrrolidin-1-yl 2-acetoxy-3-(propylcarbamoyl)benzoate (2.28 g, 6.23 mmol), 5-nitrothiazol-2-amine (4.00 g, 27.58 mmol) and DIPEA (10 mL) in DMF (20 mLl) was stirred at rt for 16 h. After the mixture was diluted with $H_2O$ (30 mL), the mixture was extracted with EtOAc (3x30 mL). The organic layer was washed with brine, dried over $Na_2SO_4$, filtered and concentrated under vacuum. The resulting residue was purified by silica gel column chromatography (petroleum ether:EtOAc=1:2) to give the title compound (400 mg, 13.0% over 5 steps) as yellow solid. MS (ESI) m/z: 349.2 $[M-H]^-$.

Example 070. 2-acetamido-N-(4-bromo-5-nitrothiazol-2-yl)benzamide (B-30)

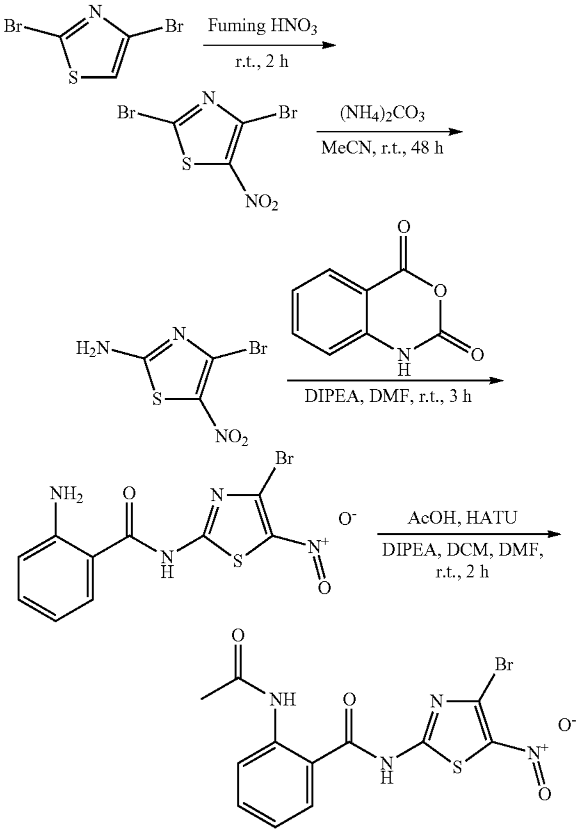

Step 1. Synthesis of 2,4-dibromo-5-nitrothiazole

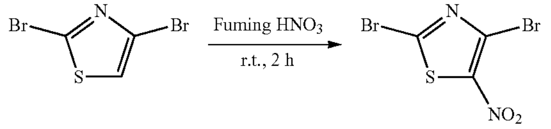 [SMILES: Brc1csc(Br)n1 ; O=[N+]([O-])c1sc(Br)nc1Br]

A solution of 2, 4-dibromothiazole (2.00 g, 8.23 mmol) in fuming $HNO_3$ (4 mL) was stirred at rt for 2 h. The reaction mixture was poured into ice water (30 mL). The solid was collected by filtration and dried under vacuum to give title compound (1.80 g, crude) as yellow solid, which was used in the next step without further purification.

Step 2. Synthesis of 4-bromo-5-nitrothiazol-2-amine

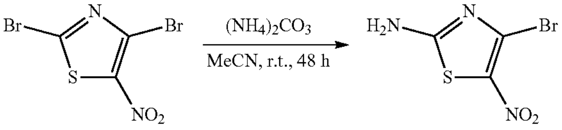

To a solution of 2,4-dibromo-5-nitrothiazole (1.80 g, crude) in acetonitrile (30 mL) was added $(NH_4)_2CO_3$ (900 mg, 9.36 mmol). After being stirred at rt for 48 h. the mixture was diluted with water (50 mL) and extracted with EtOAc (2x30 mL). The combined organic phase was dried over $Na_2SO_4$, filtered and concentrated under vacuum to give the title compound (1.48 g, crude) as yellow solid, which was used in the next step without further purification. MS (ESI) m/z: 224.1 $[M+H]^+$.

Step 3. Synthesis of 2-amino-N-(4-bromo-5-nitrothiazol-2-yl)benzamide

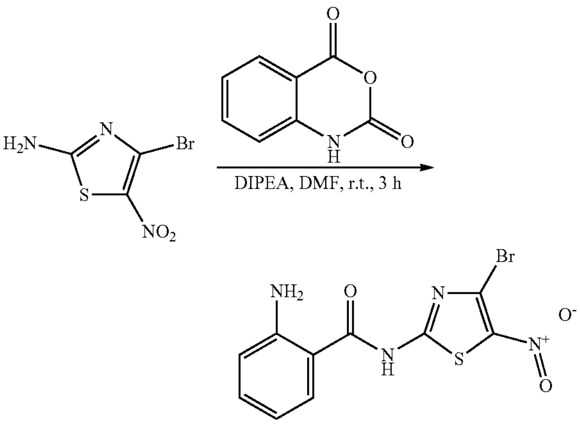

A solution of 4-bromo-5-nitrothiazol-2-amine (1.48 g, crude), DIPEA (1.31 g, 10.1 mmol) and 2H-benzo[d][1,3]oxazine-2,4 (1H)-dione (546 mg, 3.35 mmol) in DMF (10 mL) was stirred rt for 3 h, at which time the mixture was diluted with EtOAc (15 mL). The mixture was washed with water (15 mL), dried over $Na_2SO_4$, filtered and concentrated. The resulting residue was purified by silica gel column chromatography (petroleum ether:EtOAc=3:1) to give the title compound (72 mg, 2.54% yield over three steps) as yellow solid. MS (ESI) m/z: 342.9 $[M+H]^+$.

Step 4. Synthesis of 2-acetamido-N-(4-bromo-5-nitrothiazol-2-yl)benzamide

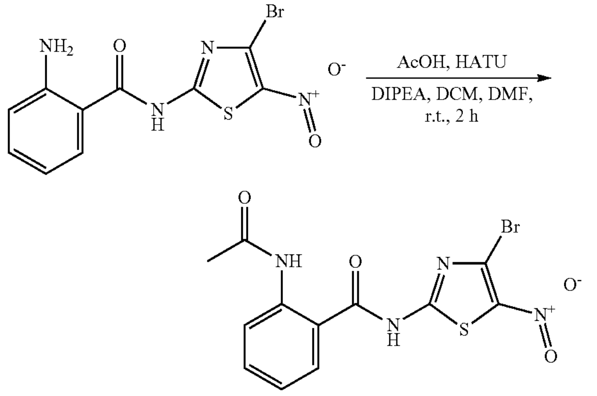

A solution of 2-amino-N-(4-bromo-5-nitrothiazol-2-yl) benzamide (30 mg, 0.0875 mmol), DIPEA (34 mg, 0.263 mmol), HATU (66 mg, 0.175 mmol) and acetate acid (10 mg, 0.175 mmol) in DCM (4 mL) and DMF (1 drop) was stirred at rt for 2 h, before the mixture was concentrated under vacuum. The resulting residue was purified by pre-HPLC (0.1% FA) to give the title compound (4.15 mg, 12.3% yield) as yellow solid. $^1H$ NMR (400 MHz, DMSO-$d_6$): δ 13.68 (s, 1H), 10.30 (s, 1H), 7.71-7.69 (m, 2H), 7.59-7.57 (m, 1H), 7.26 (t, J=7.8 Hz, 1H), 2.01 (s, 3H). MS (ESI) m/z: 383.1 $[M-H]^-$.

Example 071. 2-Acetamido-N-(4-cyclopropyl-5-nitrothiazol-2-yl)benzamide (B-32)

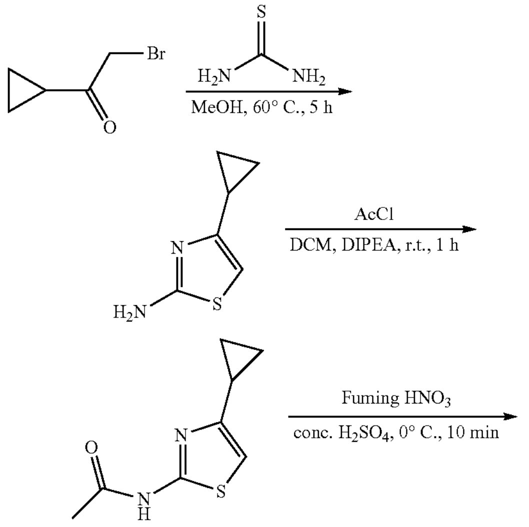

-continued

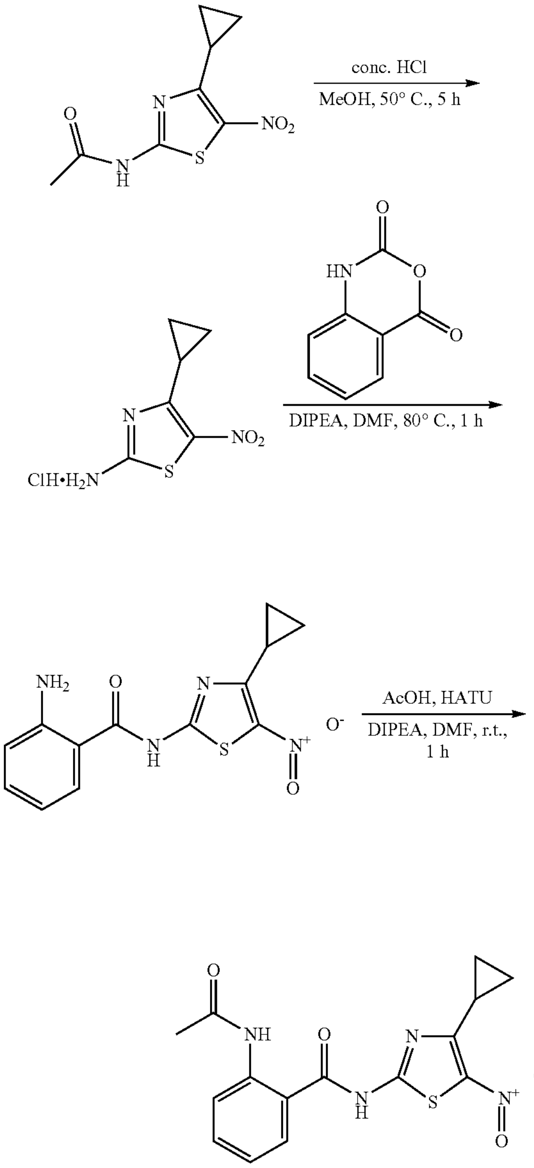

Step 1. Synthesis of 4-cyclopropylthiazol-2-amine

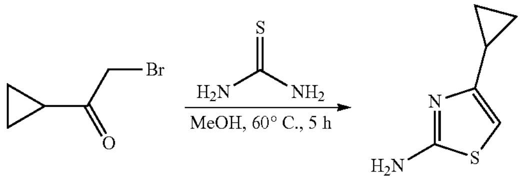

A solution of 2-bromo-1-cyclopropylethan-1-one (1.00 g, 6.13 mmol) and thiourea (466 mg, 6.13 mmol) in MeOH (20 mL) was heated at 60° C. for 5 h, before the reaction mixture was concentrated to give the title compound (1.20 g, crude) as white solid, which was used in the next step without further purification. MS (ESI) m/z: 141.4 $[M+H]^+$.

Step 2. Synthesis of N-(4-cyclopropylthiazol-2-yl)acetamide

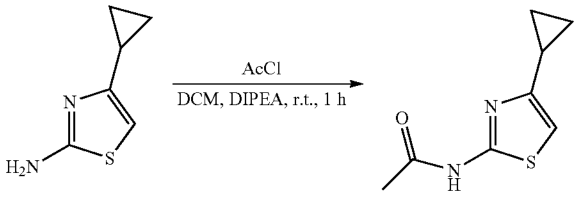

To a solution of 4-cyclopropylthiazol-2-amine (1.20 g, crude) and DIPEA (1.58 g, 12.3 mmol) in DCM (20 mL) was added acetyl chloride (718 mg, 9.20 mmol) at 0° C. After being stirred at rt for 1 h. the mixture was concentrated under vacuum. The resulting residue was purified by silica gel column chromatography (petroleum ether:EtOAc=1:1) to give the title compound (500 mg, 44.8% yield over two steps) as white solid. MS (ESI) m/z: 183.2 [M+H]$^+$.

Step 3. Synthesis of N-(4-cyclopropyl-5-nitrothiazol-2-yl)acetamide

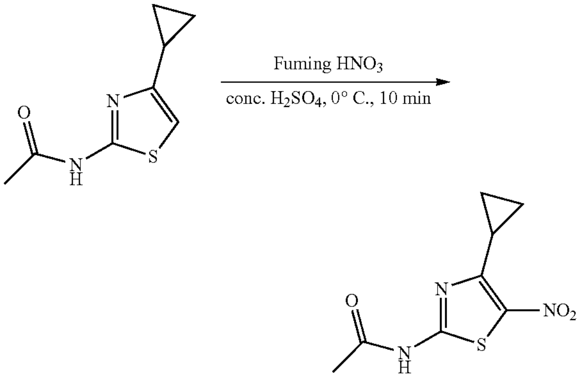

To a solution of N-(4-cyclopropylthiazol-2-yl)acetamide (500 mg, 2.74 mmol) in cone. $H_2SO_4$ (5 mL) was added fuming $HNO_3$ (2 mL) at 0° C. After being stirred at 0° C. for 10 min, the mixture was poured into ice-water (20 mL) and extracted with EtOAc (3×30 mL). The organic phase was washed with brine (5×30 mL), dried over $Na_2SO_4$, filtered and concentrated. The resulting residue was purified by silica gel column chromatography (petroleum ether: EtOAc=1:1) to give the title compound (300 mg, 48.2% yield) as yellow solid. MS (ESI) m/z: 228.2 [M+H]$^+$.

Step 4. Synthesis of 4-cyclopropyl-5-nitrothiazol-2-amine hydrochloride

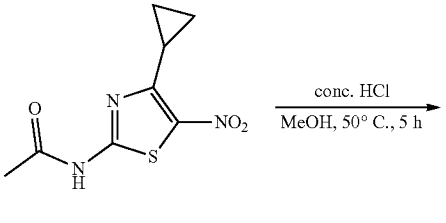

-continued

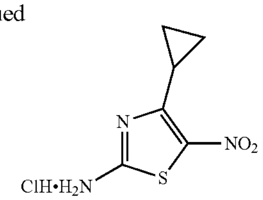

A solution of N-(4-cyclopropyl-5-nitrothiazol-2-yl)acetamide (300 mg, 1.32 mmol) and conc·HCl (5 mL) in MeOH (5 mL) was stirred at 50° C. for 5 h, before the mixture was concentrated under vacuum to give the title compound (230 mg, crude) as yellow solid, which was used in the next step without further purification. MS (ESI) m/z: 185.8 [M+H]$^+$.

Step 5. Synthesis of 2-amino-N-(4-cyclopropyl-5-nitrothiazol-2-yl)benzamide

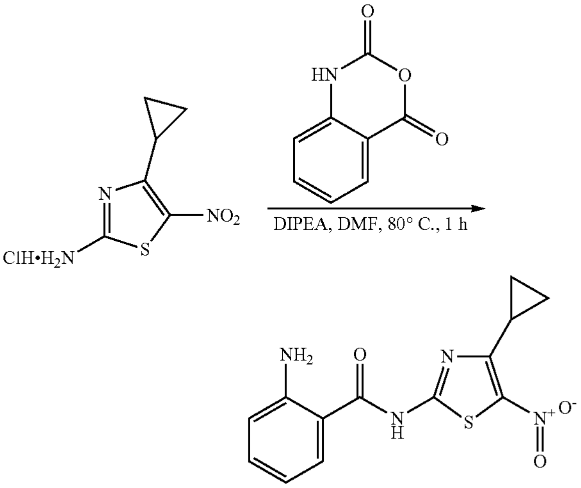

A solution of 4-cyclopropyl-5-nitrothiazol-2-amine hydrochloride (230 mg, crude mmol), DIPEA (507 mg, 3.96 mmol) and 2H-benzo[d][1,3]oxazine-2,4 (1H)-dione (215 mg, 1.32 mmol) in DMF (10 mL) was heated at 80° C. for 1 h. The mixture was diluted with EtOAc (30 mL) and washed with brine, dried over $Na_2SO_4$, filtered and concentrated. The resulting residue was purified by silica gel column chromatography (petroleum ether:EtOAc=1:1) to give the title compound (120 mg, 30.0% yield over two steps) as yellow solid. MS (ESI) m/z: 305.3 [M+H]$^+$.

Step 6. Synthesis of 2-acetamido-N-(4-cyclopropyl-5-nitrothiazol-2-yl)benzamide

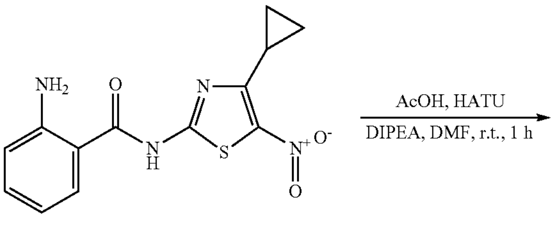

-continued

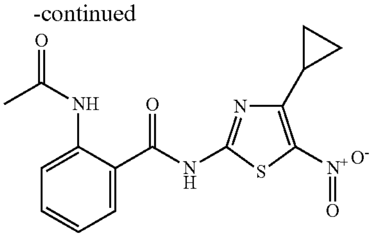

To a solution of 2-amino-N-(4-cyclopropyl-5-nitrothiazol-2-yl)benzamide (50 mg, 0.160 mmol), DIPEA (62 mg, 0.480 mmol) and AcOH (20 mg, 0.320 mmol) in DMF (5 mL) was added HATU (122 mg, 0.320 mmol) at 0° C. After being stirred at rt for 1 h, the mixture was purified by pre-HPLC to give the title compound (22.5 mg, 40.6% yield) as yellow solid. $^1H$ NMR (400 MHz, DMSO-$d_6$): δ 13.32 (s, 1H), 10.12 (s, 1H), 7.67-7.61 (m, 1H), 7.57-7.53 (m, 1H), 7.23 (t, J=7.6 Hz, 1H), 3.15-3.09 (m, 1H), 2.00 (s, 3H), 1.28-1.24 (m, 2H), 1.17-1.13 (m, 2H). MS (ESI) m/z: 347.3 $[M+H]^+$.

Example 072. 2-Acetamido-N-(5-chlorothiazol-2-yl) benzamide (B-35)

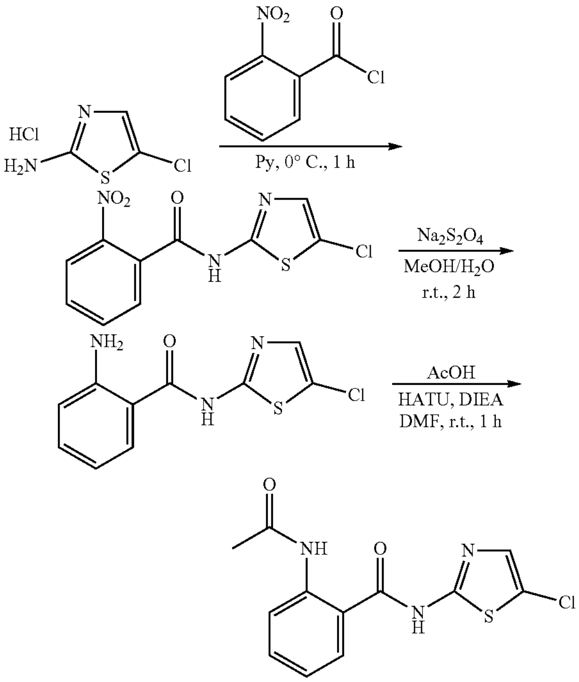

Step 1. Synthesis of N-(5-chlorothiazol-2-yl)-2-nitrobenzamide

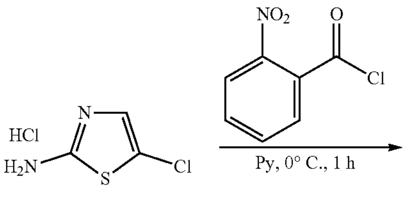

-continued

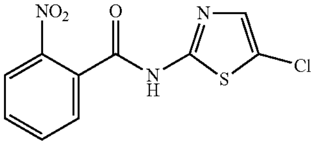

To a solution of 5-chlorothiazol-2-amine hydrochloride (200 mg, 1.23 mmol) in pyridine (5.00 mL) was added 2-nitrobenzoyl chloride (683 mg, 3.69 mmol) dropwise at 0° C. After being stirred at 0° C. for 1 h, the mixture was diluted with $H_2O$ (50 mL) and acidified with 1 N HCl to pH=3 and extracted with EtOAc (3×50 mL). The combined organic phase was dried over $Na_2SO_4$, filtered and concentrated under vacuum to give the crude title compound (300 mg, crude) as colorless oil, which was used in the next step without further purification.

Step 2. Synthesis of 2-amino-N-(5-chlorothiazol-2-yl)benzamide

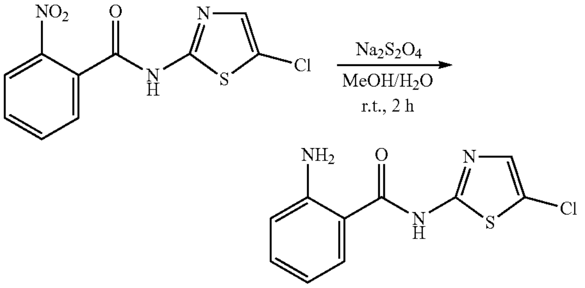

To a solution of N-(5-chlorothiazol-2-yl)-2-nitrobenzamide (200 mg, crude) in MeOH (15 mL) was added a solution of $Na_2S_2O_4$ (100 mg, 0.575 mmol) in $H_2O$ (15 mL). After being stirred at rt for 2 h, the mixture was diluted with $H_2O$ (50 mL) and extracted with EtOAc (3×30 mL). The combined organic phase was dried over $Na_2SO_4$, filtered and concentrated under vacuum. The resulting residue was purified by silica gel column chromatography (petroleum ether: EtOAc=3:1) to give the tide compound (40.0 mg, 19.3% yield over two steps) as white solid.

Step 3. Synthesis of 2-acetamido-N-(5-chlorothiazol-2-yl)benzamide

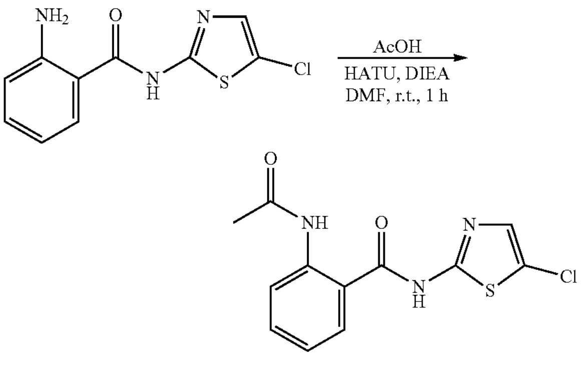

A solution of 2-amino-N-(5-chlorothiazol-2-yl)benzamide (40.0 mg, 0.158 mmol), acetic acid (14.3 mg, 0.237 mmol), HATU (90.0 mg, 0.237 mmol) and DIEA (41.0 mg, 0.316 mmol) in DMF (5 mL) was stirred at rt for 1 h. The reaction mixture was purified by prep-HPLC to give title compound (10.1 mg, 21.62% yield) as white solid. $^1$H NMR (400 MHz, DMSO-$d_6$): δ 12.78 (brs, 1H), 10.13 (brs, 1H), 7.79 (s, 1H), 7.71 (s, 1H) 7.59-7.52 (m, 2H), 7.22 (t, J=7.6 Hz, 1H), 2.04 (s, 3H). MS (ESI) m/z: 296.0 $[M+H]^+$.

Example 073. 2-Acetamido-N-(5-fluorothiazol-2-yl) benzamide (B-36)

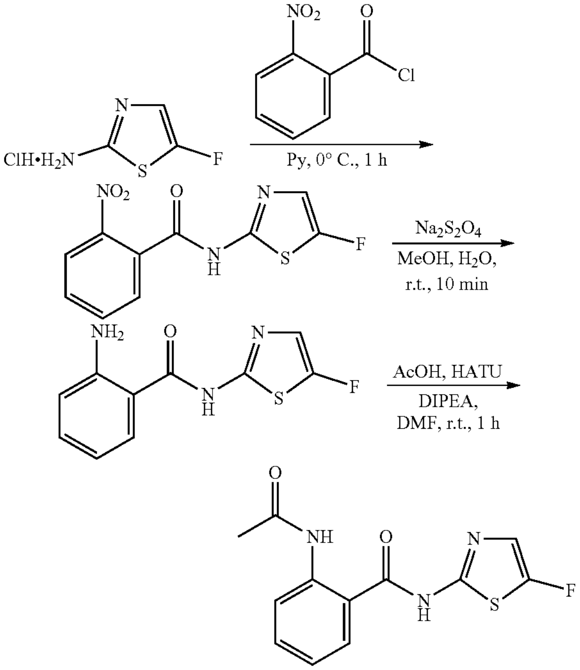

Step 1. Synthesis of N-(5-fluorothiazol-2-yl)-2-nitrobenzamide

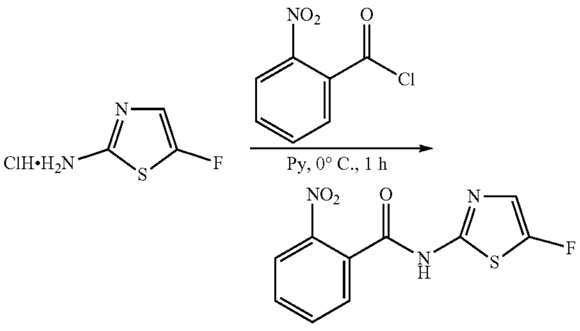

To a solution of 5-fluorothiazol-2-amine hydrochloride (250 mg, 1.62 mmol) in pyridine (5 mL) was added 2-nitrobenzoyl chloride (300 mg, 1.62 mmol) dropwise at 0° C. After being stirred at 0° C. for 1 h, the reaction mixture was diluted with EtOAc (50 mL) and washed with brine (3×50 mL). The organic layer was dried over $Na_2SO_4$, filtered and concentrated under vacuum to give the title compound (600 mg, crude) as brown oil, which was used in the next step without further purification. MS (ESI) m/z: 268.3 $[M+H]^+$.

Step 2. Synthesis of 2-amino-N-(5-fluorothiazol-2-yl)benzamide

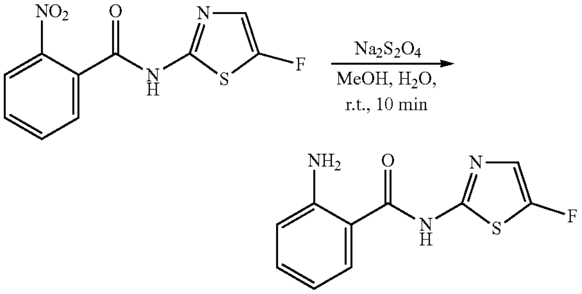

To a solution of N-(5-fluorothiazol-2-yl)-2-nitrobenzamide (600 mg, crude) in MeOH (10 mL) was added $Na_2S_2O_4$ (2.82 g, 16.2 mmol, in 10 mL water) at 0° C. After being stirred at 0° C. for 10 min, the mixture was diluted with EtOAc (20 mL) and wash with brine. The organic layer was dried over $Na_2SO_4$, filtered and concentrated under vacuum. The resulting residue was purified by silica gel column chromatography (petroleum ether:EtOAc=1:1) to give the title compound (20 mg, 5.20% yield over two steps) as white solid. MS (ESI) m/z: 237.8 $[M+H]^+$.

Step 3. Synthesis of 2-acetamido-N-(5-fluorothiazol-2-yl)benzamide

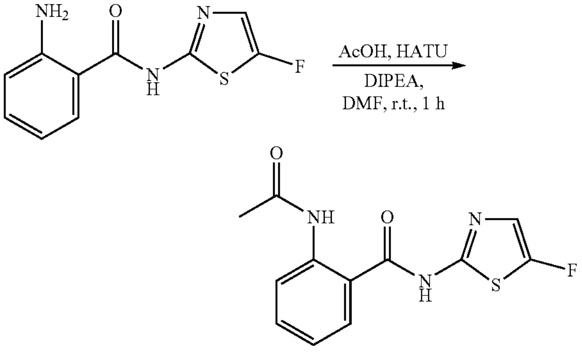

A solution of 2-amino-N-(5-fluorothiazol-2-yl)benzamide (20 mg, 0.0843 mmol), acetic acid (10 mg, 0.168 mmol), HATU (64 mg, 0.168 mmol), DIPEA (33 mg, 0.253 mmol) in DMF (1 mL) was stirred at rt for 1 h, before the reaction mixture was purified by pre-HPLC to give the title compound (5.10 mg, 21.6% yield) as white solid. $^1$H NMR (400 MHz, DMSO-$d_6$): δ 12.58 (s, 1H), 10.14 (s, 1H), 7.83-7.81 (m, 1H), 7.71-7.70 (m, 1H), 7.55-7.50 (m, 1H), 7.38 (s, 1H), 7.21 (t, J=7.6 Hz, 1H), 2.03 (s, 3H). MS (ESI) m/z: 280.3 $[M+H]^+$.

Example 074. 2-((5-Nitrothiazol-2-yl)carbamoyl)-6-(propylcarbamoyl)phenyl acetate (B-11)

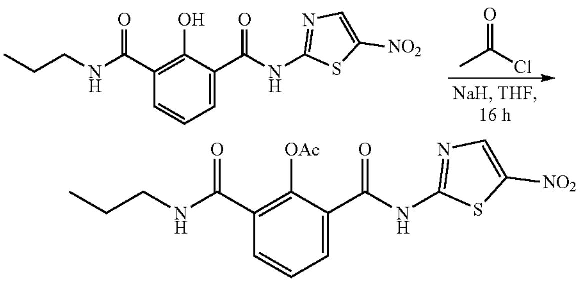

To a solution of 2-hydroxy-N[1]-(5-nitrothiazol-2-yl)-N[3]-propylisophthalamide (100 mg, 0.28 mmol) in THF (10 mL) was added NaH (0.114 g, 2.8 mmol) at 0° C. After being stirred at rt for 1 h, acetyl chloride (0.25 mL) was added at 0° C. The mixture was stirred at rt for 16 h before it was quenched with ice-$H_2O$ (50 mL). The resulting mixture was extracted with EtOAc (3x30 mL). The organic layers were washed with brine, dried over $Na_2SO_4$, filtered and concentrated under vacuum. The resulting residue was purified by pre-HPLC to give the tide compound (10 mg, 9.0% yield) as yellow solid. $^1H$ NMR (400 MHz, DMSO-$d_6$): δ 13.75 (s, 1H), 8.71 (s, 1H), 8.44 (t, J=5.6 Hz, 1H), 7.89 (dd, J=7.6, 1.6 Hz, 1H), 7.75 (dd, J=7.6, 1.6 Hz, 1H), 7.50 (t, J=7.6 Hz, 1H), 3.17 (dd, J=13.0, 6.6 Hz, 2H), 2.18 (s, 3H), 1.57-1.41 (m, 2H), 0.90 (t, J=7.6 Hz, 3H). MS (ESI) m/z: 349.2 $[M-H]^-$.

Example 075. 2-Acetamido-N-(5-nitro-4-(trifluoromethyl)thiazol-2-yl)benzamide (B-31)

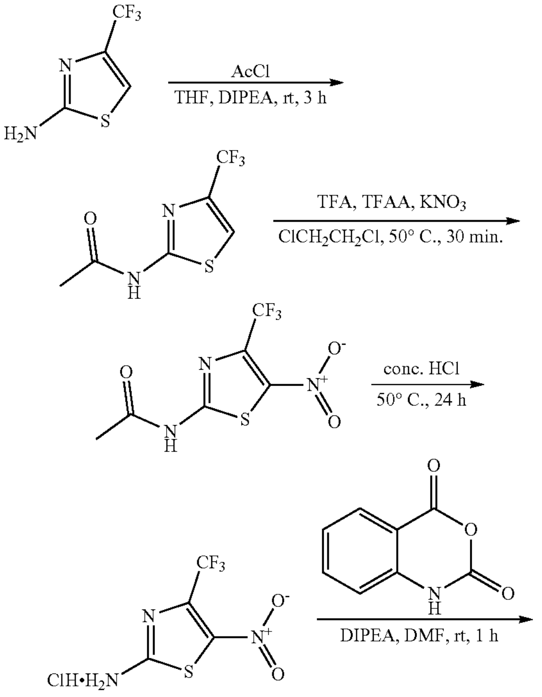

-continued

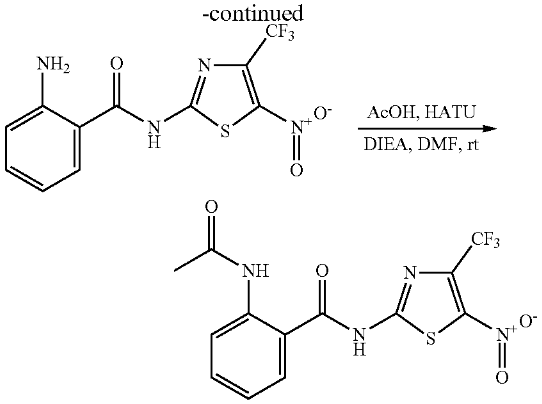

Step 1. Synthesis of N-(4-(trifluoromethyl)thiazol-2-yl)acetamide

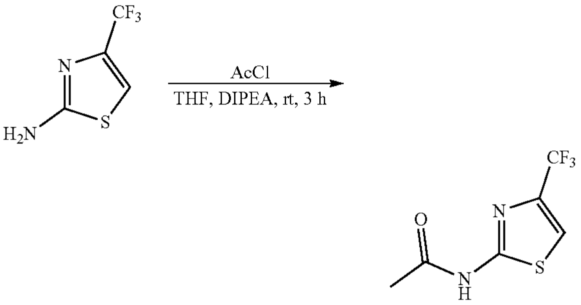

To a solution of 4-(trifluoromethyl)thiazol-2-amine (1.50 g, 8.91 mmol) and DIEA (5.70 g, 44.6 mmol) in THF (15 mL) was added acetyl chloride (3.10 g, 39.5 mmol) at 0° C. The mixture was stirred at rt for 3 h. The mixture was diluted with water (100 mL) and extracted with EtOAc (3x100 mL). The combined organic layers were washed with brine (2x100 mL), dried over $Na_2SO_4$, filtered and concentrated under vacuum. The resulting residue was purified by silica gel column chromatography (petroleum ether:EtOAc=3:1) to give the title compound (2.45 g, crude) as yellow solid. MS (ESI) m/z: 211.4 $[M+H]^+$.

Step 2. Synthesis of N-(5-nitro-4-(trifluoromethyl)thiazol-2-yl)acetamide

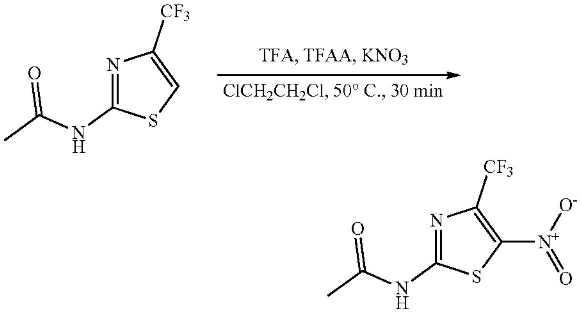

To a solution of $KNO_3$ (1.10 g, 10.9 mmol) in TFA (7.50 g, 65.8 mmol) and TFAA (2.50 g, 11.9 mmol) was added N-(4-(trifluoromethyl)thiazol-2-yl)acetamide (1.25 g, crude) in 1,2-dichloroethane (30 mL). The reaction mixture was stirred at it for 20 min and at 50° C. for 30 min. The mixture was poured into ice-water (100 mL) and extracted with EtOAc (3×100 mL). The combined organic phase was washed with brine (2×50 mL), dried over $Na_2SO_4$, filtered and concentrated under vacuum. The resulting residue was purified by silica gel column chromatography (petroleum ether:EtOAc=3:1) to give the title compound (800 mg, 52% yield over two steps) as yellow solid. MS (ESI) m/z: 254.1 $[M-H]^+$ Step 3. Synthesis of 5-nitro-4-(trifluoromethyl)thiazol-2-amine hydrochloride

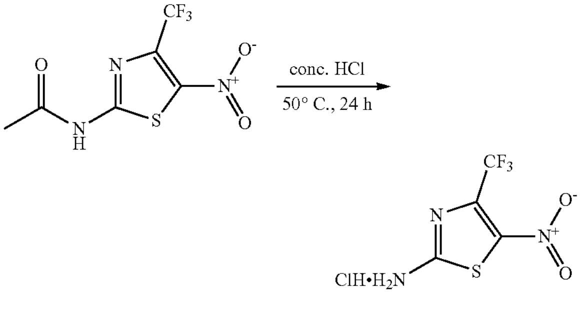

A solution of N-(5-nitro-4-(trifluoromethyl)thiazol-2-yl) acetamide (300 mg, 1.18 mmol) in conc·HCl (15 mL) was heated at 50° C. for 24 h, before the mixture was concentrated under vacuum to give the title compound (308 mg, crude) as yellow solid, which was used in the next step without further purification. MS (ESI) m/z: 212.1 $[M-H]^-$.

Step 4. Synthesis of 2-amino-N-(5-nitro-4-(trifluoromethyl)thiazol-2-yl)benzamide

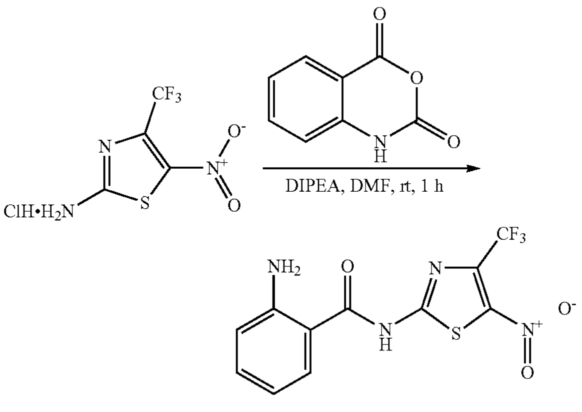

A solution of 5-nitro-4-(trifluoromethyl)thiazol-2-amine (250 mg, 1.15 mmol), 2H-benzo[d][1,3]oxazine-2,4 (1H)-dione (200 mg, 1.15 mmol) and DIPEA (400 mg, 2.75 mmol) in DMF (10 mL) was stirred at rt for 1 h. The mixture was poured into water (50 mL) and extracted with EtOAc (3×50 mL). The combined organic phase was washed with brine (2×50 mL), dried over $Na_2SO_4$, filtered and concentrated under vacuum. The resulting residue was purified by silica gel column chromatography (petroleum ether: EtOAc=3:1) to give the title compound (60 mg, 15.5% yield over two yield) as yellow solid. MS (ESI) m/z: 333.0 $[M+H]^+$.

Step 5. Synthesis of 2-acetamido-N-(5-nitro-4-(trifluoromethyl)thiazol-2-yl)benzamide

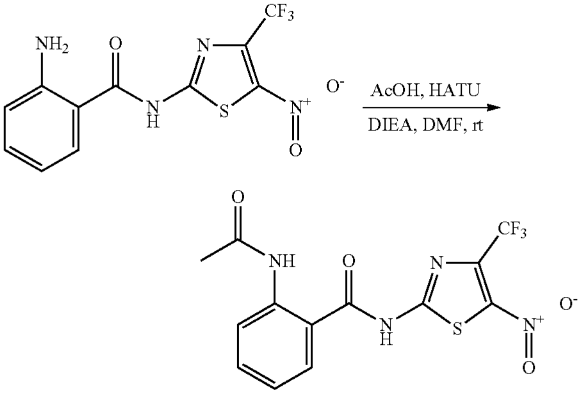

To a solution of 2-amino-N-(5-nitro-4-(trifluoromethyl) thiazol-2-yl)benzamide (60 mg, 0.180 mmol) in DMF (3 mL) were added HATU (137 mg, 0.360 mmol), acetic acid (22 mg, 0.540 mmol) and DIPEA (70 mg, 0.540 mmol). After the mixture was stirred at rt overnight, it was purified by prep-HPLC to give the title compound (25.6 mg, 38.2% yield) as white solid. $^1H$ NMR (400 MHz, DMSO-$d_6$): δ 13.9 (brs, 1H), 10.4 (brs, 1H), 7.73 (d, J=8.0 Hz, 1H), 7.66-7.67 (m, 1H), 7.60-7.55 (m, 1H), 7.26 (t, J=8.0 Hz, 1H), 2.02 (s, 3H). MS (ESI) m/z: 372.9 $[M-H]^-$.

Example 076. 2-Acetamido-N-(4-isopropyl-5-nitrothiazol-2-yl)benzamide (B-33)

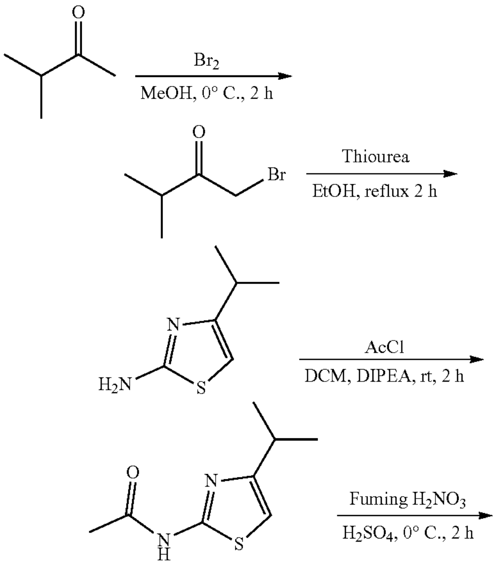

-continued

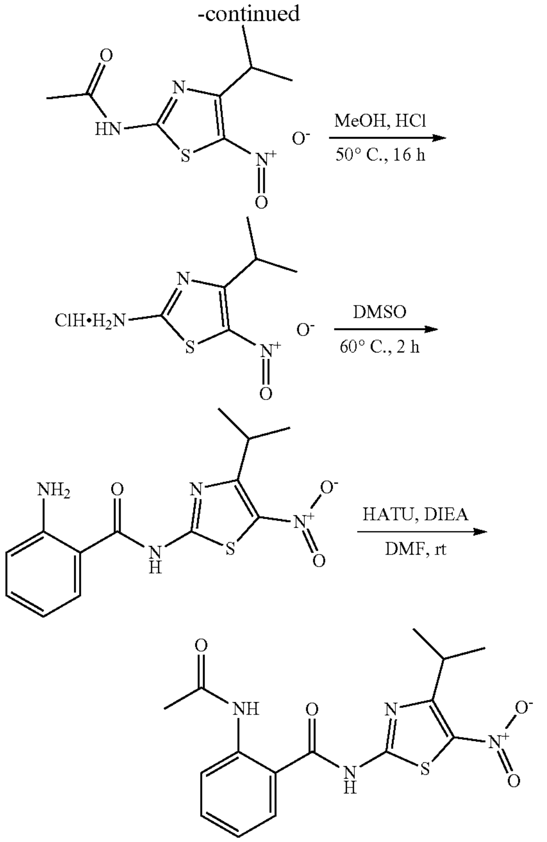

Step 1. Synthesis of 1-bromo-3-methylbutan-2-one

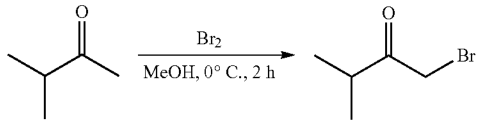

To a solution of 3-methylbutan-2-one (2.00 g, 23.6 mmol) in MeOH (100 mL) was added liquid bromine (6.40 g, 40.0 mmol) dropwise at 0° C. After being stirred at 0° C. for 2 h, the mixture was quenched by aq. $NH_4HCO$. (50 mL, 1 N) and extracted with diethyl ether (3×50 mL). The combined organic phase was dried over $Na_2SO_4$, filtered and concentrated under vacuum to give the crude title compound (3.50 g, crude) as yellow oil, which was used in the next step without further purification.

Step 2. Synthesis of 4-isopropylthiazol-2-amine

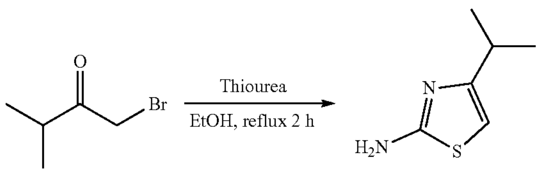

A solution of 1-bromo-3-methylbutan-2-one (3.50 g, crude) and thiourea (3.0 g, 39.5 mmol) in EtOH (100 mL) was refluxed for 2 h. At rt, the mixture was concentrated under vacuum. The resulting residue was diluted with water (100 mL) and extracted with EtOAc (3×100 mL). The combined organic phase was dried over $Na_2SO_4$, filtered and concentrated under vacuum to give the title compound (2.50 g, 74.6% yield over two steps) as white solid. MS (ESI) m/z: 143.2 $[M+H]^+$.

Step 3. Synthesis of N-(4-isopropylthiazol-2-yl)acetamide

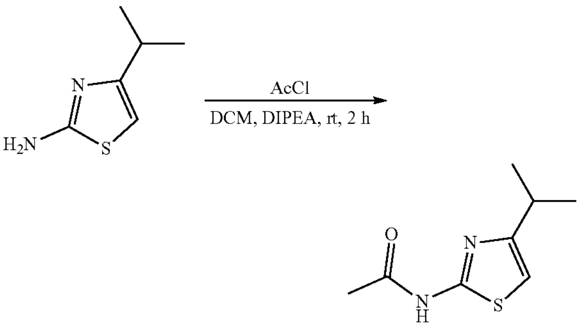

To a solution of 4-isopropylthiazol-2-amine (2.50 g, 17.6 mmol) and DIPEA (6.80 g, 52.8 mmol) in DCM (100 mL) was added acetyl chloride (4.20 g, 52.8 mmol) at 0° C. After being stirred at it for 2 h, the mixture was concentrated under vacuum. The resulting residue was diluted with $H_2O$ (100 mL), acidified with 1 N HCl to pH=4 and extracted with EtOAc (3×50 mL). The combined organic phase was dried over $Na_2SO_4$, filtered and concentrated under vacuum to give the crude title compound (3.50 g, crude) as colorless oil, which was used in the next step without further purification. MS (ESI) m/z: 185.1 $[M+H]^+$.

Step 3. Synthesis of N-(4-isopropyl-5-nitrothiazol-2-yl)acetamide

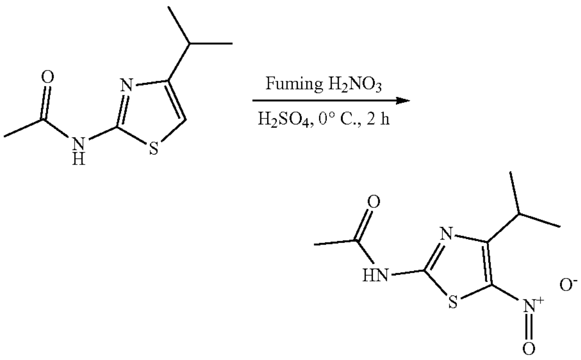

To a solution of N-(4-isopropylthiazol-2-yl)acetamide (1.00 g, crude) in $H_2SO_4$ (10 mL) was added fuming $HNO_3$ (10 mL) at 0° C. After being stirred at 0° C. for 3 h, the mixture was diluted with $H_2O$ (200 mL) and filtered. The solid was collected and dried to give the title compound (1.00 g, 86.8% yield over two steps) as yellow solid. MS (ESI) m/z: 230.1 $[M+H]^+$.

Step 4. Synthesis of 4-isopropyl-5-nitrothiazol-2-amine hydrochloride

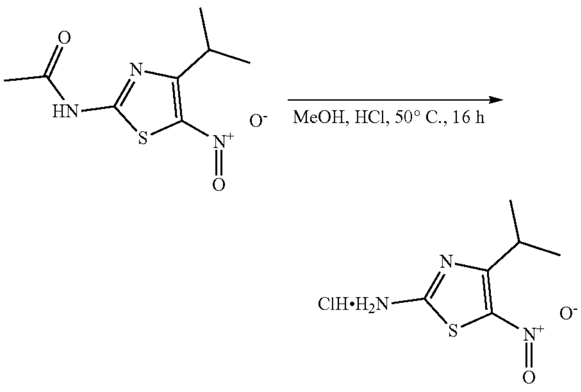

A solution of N-(4-isopropyl-5-nitrothiazol-2-yl)acetamide (1.00 g, 4.37 mmol) in HCl (10 mL, conc. aq.) and MeOH (50.0 mL) was stirred at 50° C. for 16 h. The mixture was concentrated under vacuum to give the title compound (700 mg, HCl salt) as yellow solid. MS (ESI) m/z: 188.1 $[M+H]^+$.

Step 5. Synthesis of 2-amino-N-(4-isopropyl-5-nitrothiazol-2-yl)benzamide

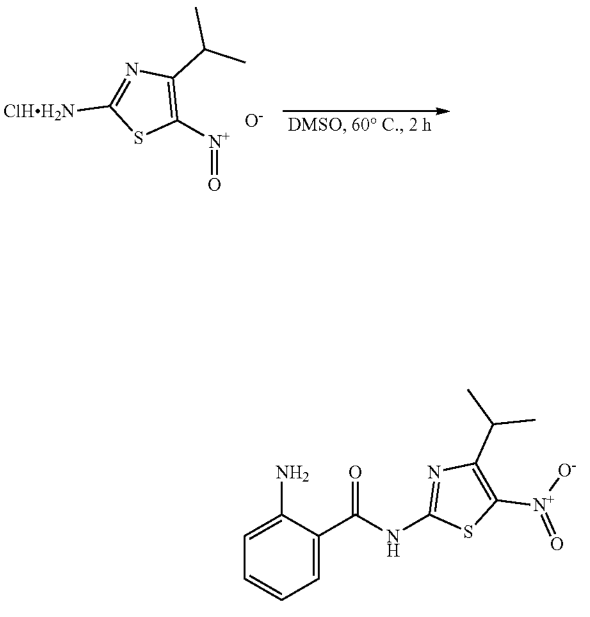

A solution of 1H-benzo[d][1,3]oxazine-2,4-dione (200 mg, 1.23 mmol), 4-isopropyl-5-nitrothiazol-2-amine hydrochloride (300 mg, 1.35 mmol) and DIPEA (476 mg, 3.69 mmol) in DMSO (5 mL) was stirred at 60° C. for 2 h. The mixture was diluted with $H_2O$ (100 mL) and filtered. The solid was collected and dried to give the title compound (200 mg, 53.2% yield over two steps) as yellow solid. MS (ESI) m/z: 307.1 $[M+H]^+$.

Step 6. Synthesis of 2-acetamido-N-(4-isopropyl-5-nitrothiazol-2-yl)benzamide

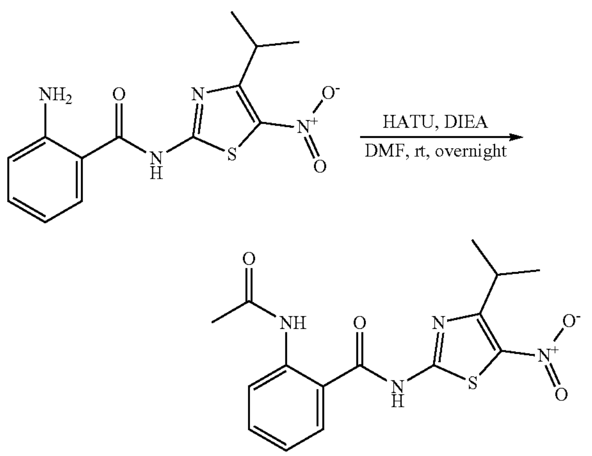

A solution of 2-amino-N-(4-isopropyl-5-nitrothiazol-2-yl)benzamide (100 mg, 0.327 mmol), acetic acid (40.0 mg, 0.654 mmol), HATU (186 mg, 0.490 mmol) and DIEA (127 mg, 0.981 mmol) in DMF (3 mL) was stirred at rt overnight. The mixture was purified by prep-HPLC to give title compound (50 mg, 43.9% yield) as white solid. $^1H$ NMR (400 MHz, DMSO-$d_6$): δ 13.43 (brs, 1H), 10.13 (s, 1H), 7.69 (d, J=7.2 Hz, 1H), 7.63-7.61 (d, J=7.6 Hz, 1H), 7.55 (t, J=8.0 Hz, 1H), 7.23 (t, J=8.0 Hz, 1H), 3.97-3.94 (m, 1H), 2.00 (s, 3H), 1.27 (d, J=6.8 Hz, 6H). MS (ESI) m/z: 349.1 $[M+H]^+$.

Example 077. 2-Acetamido-N-(5-isopropylthiazol-2-yl)benzamide (B-43)

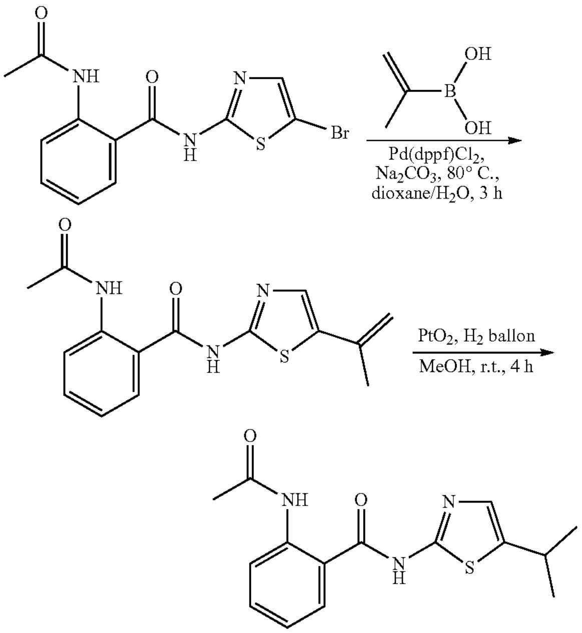

Step 1. Synthesis of 2-acetamido-N-(5-(prop-1-en-2-yl)thiazol-2-yl)benzamide

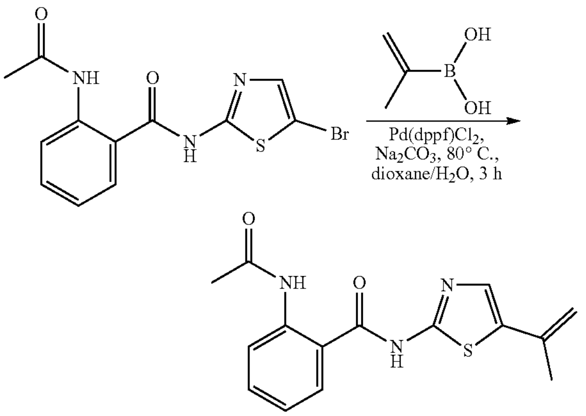

To a solution of 2-acetamido-N-(5-bromothiazol-2-yl) benzamide (160 mg, 0.471 mmol) in 1,4-dioxane (4 mL) and $H_2O$ (2 mL) were added prop-1-en-2-ylboronic acid (118 mg, 0.705 mmol), $Pd(dppf)Cl_2$ (69.0 mg, 0.094 mmol) and $Na_2CO_3$ (100 mg, 0.940 mmol). The reaction mixture was stirred at 80° C. for 3 h under $N_2$. After the mixture was cooled to the rt, it was diluted with $H_2O$ (50 mL) and extracted with EtOAc (3x30 mL). The combined organic phase was dried over $Na_2SO_4$, filtered and concentrated under vacuum to give the crude tide compound (200 mg crude) as black oil, which was used in the next step without further purification. MS (ESI) m/z: 302.2 $[M+H]^+$.

Step 2. Synthesis of 2-acetamido-N-(5-isopropylthiazol-2-yl)benzamide

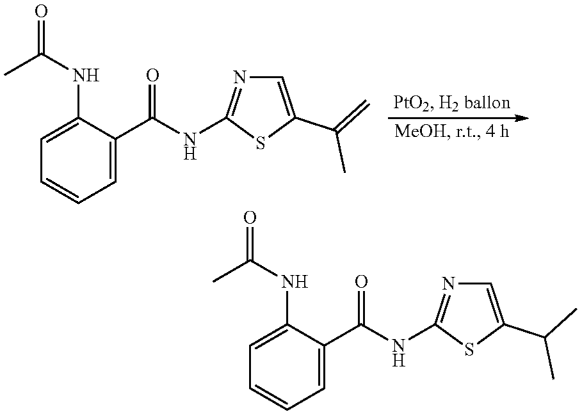

To a solution of 2-acetamido-N-(5-(prop-1-en-2-yl)thiazol-2-yl)benzamide (200 mg, crude) in MeOH (30.0 mL) was added $PtO_2$ (50 mg). After the reaction mixture was degassed with $H_2$ three times, it was stirred at rt for 4 h under $H_2$. The mixture was filtered and the filtrate was concentrated and purified by prep-HPLC to give title compound (6.50 mg, 4.56% yield) as white solid. $^1H$ NMR (400 MHz, DMSO-$d_6$): δ 12.50 (brs, 1H), 10.50 (brs, 0.5H), 8.07 (brs, 1H), 7.87 (brs, 1H), 7.51 (t, J=8.0 Hz, 1H), 7.25 (s, 1H), 7.18 (t, J=8.0 Hz, 1H), 3.15-3.15 (m, 1H), 2.09 (s, 3H), 1.29 (d, J=6.8 Hz, 6H). MS (ESI) m/z: 304.3 $[M+H]^+$.

Example 078. 2-Acetamido-N-(5-(methylsulfonyl) thiazol-2-yl)benzamide (B-47)

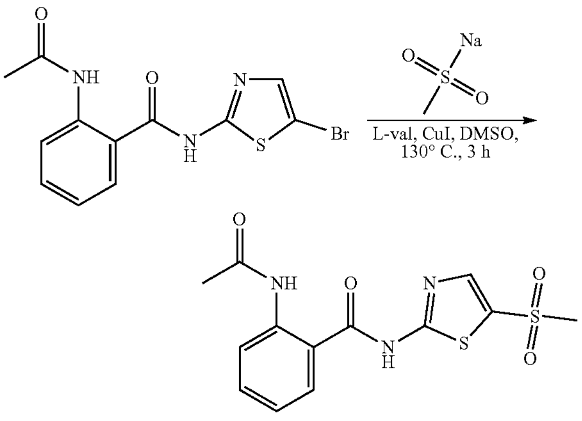

A solution of 2-acetamido-N-(5-bromothiazol-2-yl)benzamide (60.0 mg, 0.177 mmol), sodium methanesulfinate (230 mg, 1.77 mmol), L-val (20.7 mg, 0.177 mmol) and CuI (33.6 mg, 0.177 mmol) in DMSO (3 mL) was stirred at 130° C. for 3 h under $N_2$. The reaction mixture was purified by prep-HPLC to give crude tide compound (20 mg), which was further purified by silica gel column chromatography (petroleum ether:EtOAc=1:1-0:1) to give the title compound (9.20 mg, 15.33% yield) as white solid. $^1H$ NMR (400 MHz, DMSO-$d_6$): δ 13.20 (s, 1H), 10.14 (brs, 1H), 8.15 (s, 0.3H), 7.16 (s, 2H), 7.55 (d, J=7.2 Hz, 1H), 7.24 (t, J=7.6 Hz, 1H), 3.38 (s, 3H), 2.02 (s, 3H). MS (ESI) m/z: 340.0 $[M+H]^+$.

Example 079. 2-Acetamido-N-(4-(methylsulfonyl) thiazol-2-yl)benzamide (B-48)

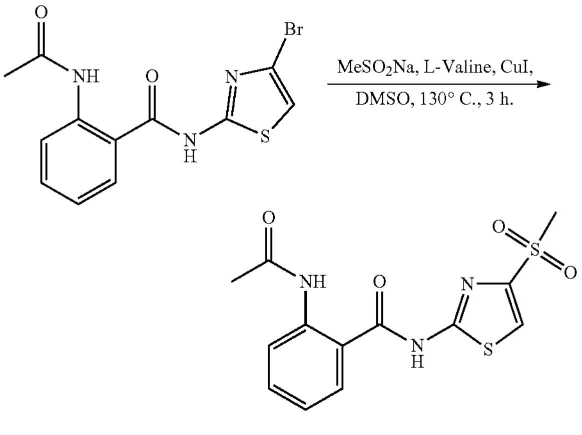

To a solution of 2-acetamido-N-(4-bromothiazol-2-yl) benzamide (30 mg, 0.088 mmol) in DMSO (3 mL) were added L-Valine (16 mg, 0.088 mmol), CuI (17 mg, 0.088 mmol) and sodium methanesulfinate (90 mg, 0.880 mmol). After the reaction mixture was degassed with argon for 3 times, it was stirred at 130° C. for 3 h. After the reaction was cooled to rt, it was purified by prep-HPLC to give the tide compound (10.0 mg, 33.0% yield) as white solid. $^1H$ NMR (400 MHz, DMSO-$d_6$): δ 13.1 (brs, 1H), 10.3 (brs, 1H), 8.04 (s, 1H), 7.84-7.75 (m, 2H), 7.54-7.51 (m, 1H), 7.23-7.20 (m, 1H), 3.19 (s, 3H), 2.04 (s, 3H). MS (ESI) m/z: 340.0 $[M+H]^+$.

Example 080. 2-(N-Methylsulfamoyl)-N-(5-nitrothiazol-2-yl)benzamide (B-81)

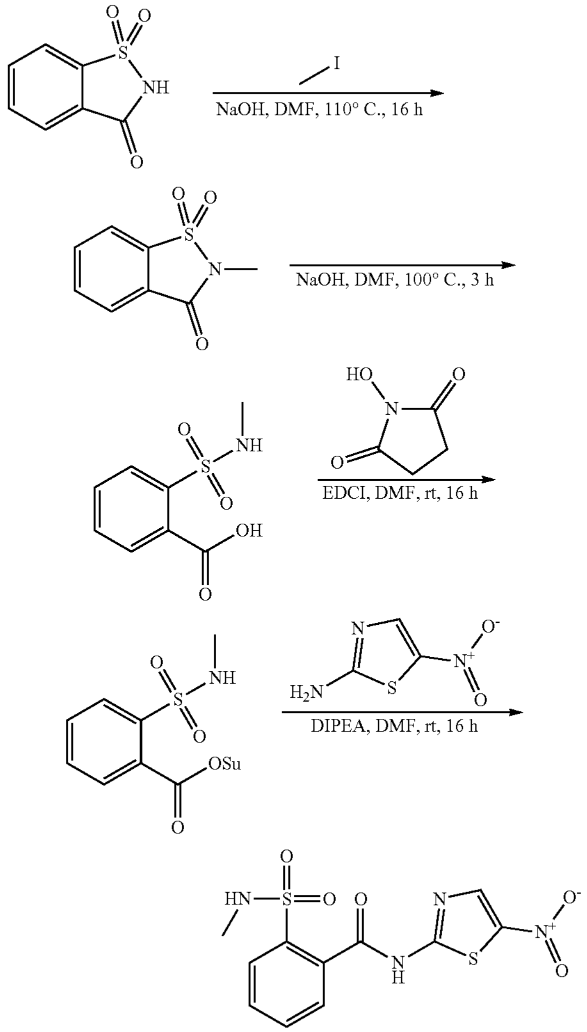

Step 1. Synthesis of 2-methylbenzo[d]isothiazol-3 (2H)-one 1,1-dioxide

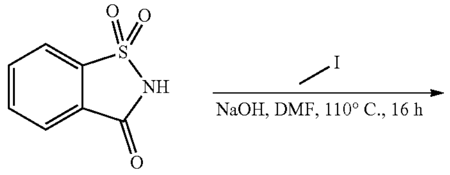

-continued

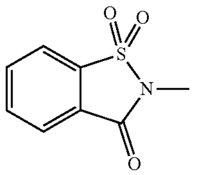

A mixture of benzo[d]isothiazol-3 (2H)-one 1,1-dioxide (1.00 g, 5.46 mmol), NaOH (218 mg, 5.47 mmol) and iodomethane (775 mg, 5.47 mmol) in DMF (15 mL) was stirred at 110° C. for 16 h. At rt, the mixture was poured into water (100 mL). After filtration, the solid was collected dried under vacuum to give the title product (700 mg, 64.9% yield) as white solid.

Step 2. Synthesis of 2-(N-methylsulfamoyl)benzoic acid

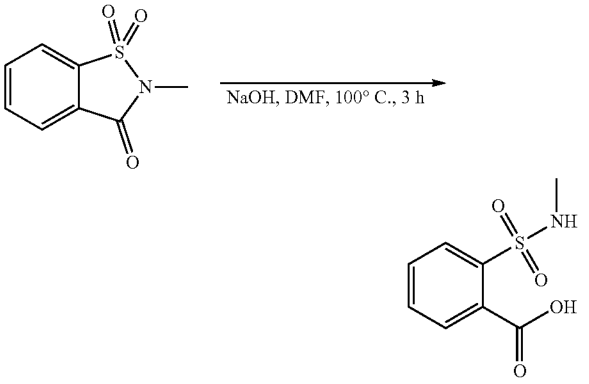

A solution of 2-methylbenzo[d]isothiazol-3 (2H)-one 1,1-dioxide (500 mg, 2.54 mmol) and NaOH (203 mg, 5.08 mmol) in DMF (5 mL) was stirred at 100° C. for 3 h. At rt, the mixture was diluted with water (50 mL). After the pH of the reaction mixture was adjusted to 3 with 1 N HCl, the mixture was extracted with EtOAc (3×30 mL). The combined organic phase was washed with brine, dried over $Na_2SO_4$, filtered and concentrated under vacuum to give the title compound (450 mg, 82.4% yield) as white solid. MS (ESI) m/z: 214.1 $[M-H]^-$.

Step 3. Synthesis of 2,5-dioxopyrrolidin-1-yl 2-(N-methylsulfamoyl)benzoate

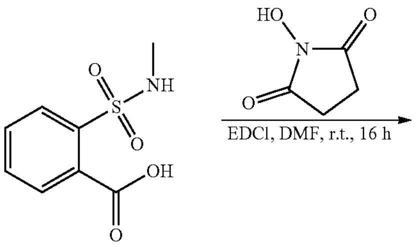

-continued

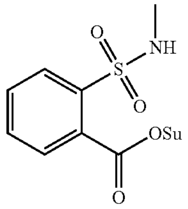

A solution of 2-(N-methylsulfamoyl)benzoic acid (400 mg, 1.86 mmol), 2-(N-methylsulfamoyl)benzoic acid (428 mg, 3.72 mmol) and EDCI (536 mg, 2.79 mmol) in DMF (20 mL) was stirred at rt for 16 h. The mixture was diluted with $H_2O$ (100 mL) and extracted with EtOAc (3x30 mL). The combined organic phase was washed with brine, dried over $Na_2SO_4$, filtered and concentrated under vacuum. The resulting residue was purified by Silica gel column chromatography (petroleum ether:EtOAc=1:1) to give the title product (300 mg, crude) as gray solid, which was used in the next step without further purification.

Step 4. Synthesis of 2-(N-methylsulfamoyl)-N-(5-nitrothiazol-2-yl)benzamide

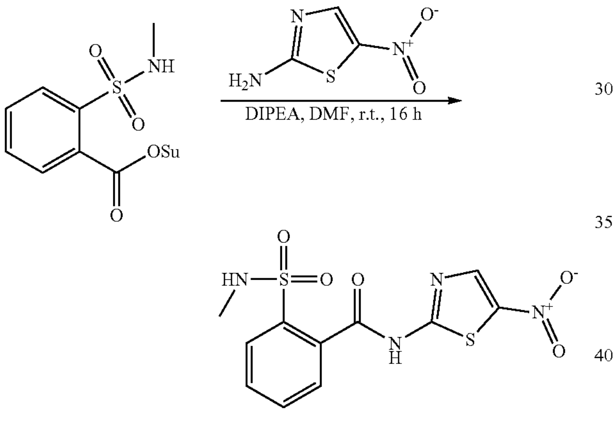

A mixture of 2,5-dioxopyrrolidin-1-yl 2-(N-methylsulfamoyl)benzoate (300 mg, crude), DIPEA (480 mg, 3.72 mmol) and 5-nitrothiazol-2-amine (405 mg, 2.79 mmol) in DMF (10 mL) was stirred at rt for 16 h, before the mixture was purified by pre-HPLC to give the crude product, which was recrystallized from EtOAc to give the title compound (12.0 mg, 1.89% yield over two steps) as white solid. $^1H$ NMR (400 MHz, DMSO-$d_6$): 8.44 (s, 1H), 8.03-8.01 (m, 1H), 7.80-7.70 (m, 3H), 2.73 (s, 3H). MS (ESI) m/z: 343.3 $[M+H]^+$.

Example 081. N-(5-Nitrothiazol-2-yl)-2-sulfamoylbenzamide (B-80)

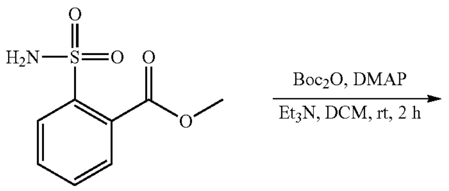

-continued

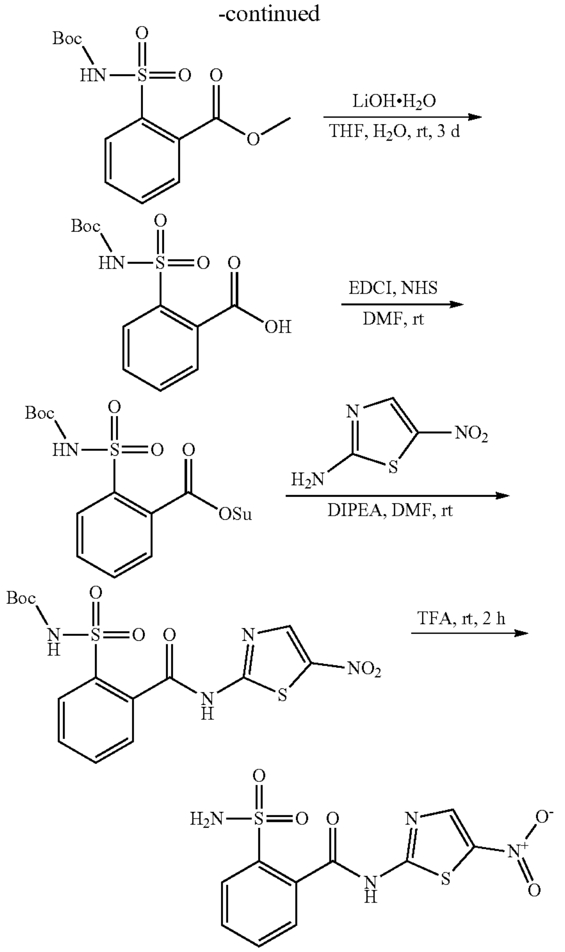

Step 1. Synthesis of methyl 2-(N-(tert-butoxycarbonyl)sulfamoyl)benzoate

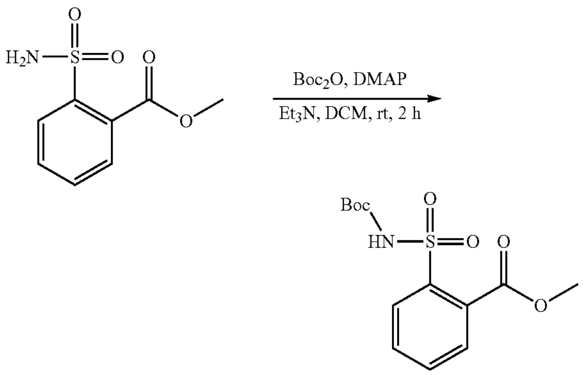

To a solution of methyl 2-sulfamoylbenzoate (500 mg, 2.32 mmol), DMAP (28.4 mg, 0.232 mmol) and $Et_3N$ (281 mg, 2.78 mmol) in DCM (10 mL) was added $(Boc)_2O$ (558 mg, 32.56 mmol) at rt. After being stirred at rt for 2 h, the mixture was diluted with water (50 mL) and extracted with EtOAc (3x50 mL). The combined organic layers were washed with brine (2x50 mL), dried over $Na_2SO_4$, filtered and concentrated under vacuum. The resulting residue was purified by silica gel column chromatography (petroleum ether:EtOAc=4:1) to give the title compound (200 mg, 27.2% yield) as white solid. $^1H$ NMR (400 MHz, DMSO-$d_6$): δ 8.28-8.26 (m, 1H), 7.92 (s, 1H), 7.84-7.83 (m, 1H), 7.70-7.68 (m, 2H), 4.00 (s, 3H), 1.40 (s, 9H).

Step 2. Synthesis of methyl 2-(N-(tert-butoxycarbonyl)sulfamoyl)benzoic acid

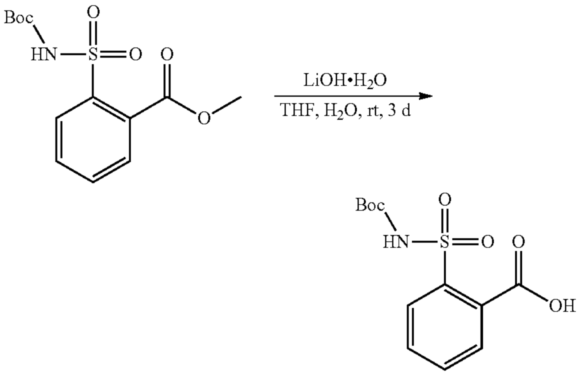

A solution of methyl 2-(N-(tert-butoxycarbonyl)sulfamoyl)benzoate (200 mg, 0.640 mmol) in THF (15 mL) was added $LiOH{\cdot}H_2O$ (240 mg, 5.72 mmol) in $H_2O$ (15 mL). After the reaction mixture was stirred at rt for 3 d, the mixture was poured into ice-water (50 mL) and acidified with 1 N HCl to pH=4. The mixture was extracted with EtOAc (3×50 mL). The combined organic phase was washed with brine (3×50 mL), dried over $Na_2SO_4$, filtered and concentrated under vacuum to give the title compound (200 mg, crude) as white solid, which was used in next step without further purification. MS (ESI) m/z: 323.9 $[M+Na]^+$.

Step 3. Synthesis of 2,5-dioxopyrrolidin-1-yl 2-(N-tert-butoxycarbonyl)sulfamoyl)benzoate

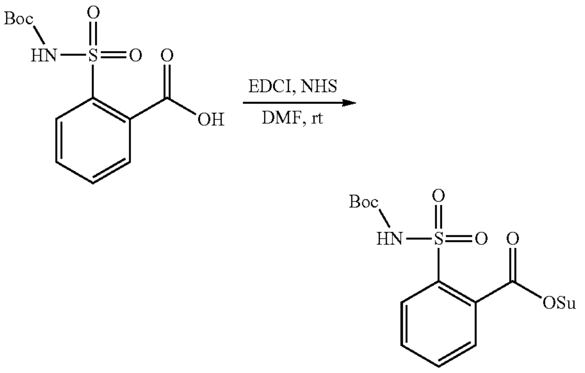

A solution of 2-(N-(tert-butoxycarbonyl)sulfamoyl)benzoic acid (190 mg, crude), EDCI (220 mg, 1.15 mmol) and NHS (133 mg, 1.15 mmol) in DMF (5 mL) was stirred at rt overnight. The mixture was diluted with water (50 mL) and extracted with EtOAc (2×50 mL). The combined organic layers were washed with brine (2×50 mL), dried over $Na_2SO_4$, filtered and concentrated under vacuum. The resulting residue was purified by silica gel column chromatography (petroleum ether:EtOAc=1:1) to give the title compound (158 mg, 69.3% yield over two steps) as white solid.

Step 4. Synthesis of tert-butyl ((2-((5-nitrothiazol-2-yl)carbamoyl)phenyl)sulfonyl)carbamate

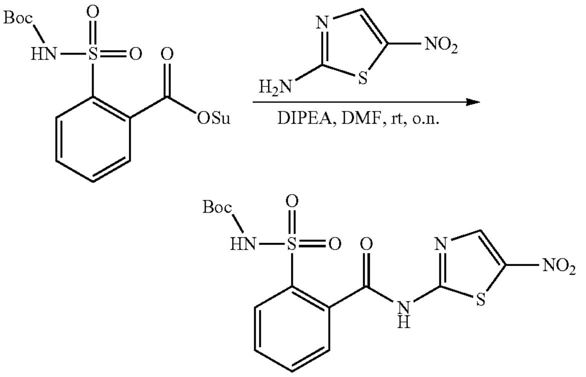

A solution of 2,5-dioxopyrrolidin-1-yl 2-(N-tert-butoxycarbonyl)sulfamoyl)benzoate (68 mg, 0.180 mmol), 5-nitrothiazol-2-amine (29.0 mg, 0.190 mmol) and DIPEA (46.0 mg, 0.356 mmol) in DMF (10 mL) was stirred at rt overnight, before the mixture was diluted with EtOAc (100 mL), washed with brine (2×50 mL), dried over $Na_2SO_4$, filtered and concentrated under vacuum to give the title compound (50 mg, crude) as brown oil, which was used in the next step without further purification. MS (ESI) m/z: 427.0 $[M-H]^-$.

Step 5. Synthesis of N-(5-nitrothiazol-2-yl)-2-sulfamoylbenzamide

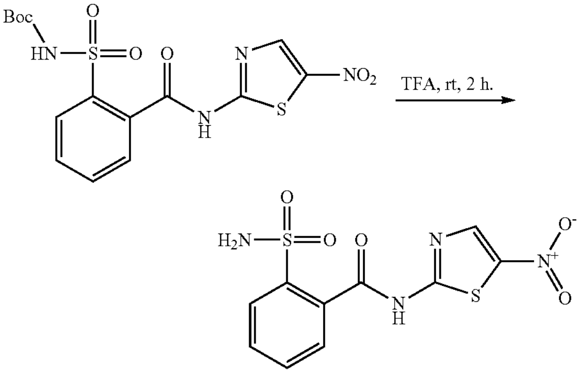

A solution of tert-butyl ((2-((5-nitrothiazol-2-yl)carbamoyl)phenyl)sulfonyl) carbamate (50 mg, crude) in TFA (2 mL) was stirred at rt for 2 h, before the reaction solution was concentrated under vacuum. The resulting residue was purified by pre-HPLC to give the title compound (11.6 mg, 19.9% yield over two steps) as white solid. $^1H$ NMR (400 MHz, DMSO-$d_6$): δ 13.7 (brs, 1H), 8.68 (s, 1H), 8.01-7.98 (m, 1H), 7.78-7.71 (m, 3H), 7.36-7.35 (m, 2H). MS (ESI) m/z: 329.0 $[M+H]^+$.

Example 082. 3-(2-((5-Nitrothiazol-2-yl)carbamoyl)phenyl)propanoic acid (B-88)

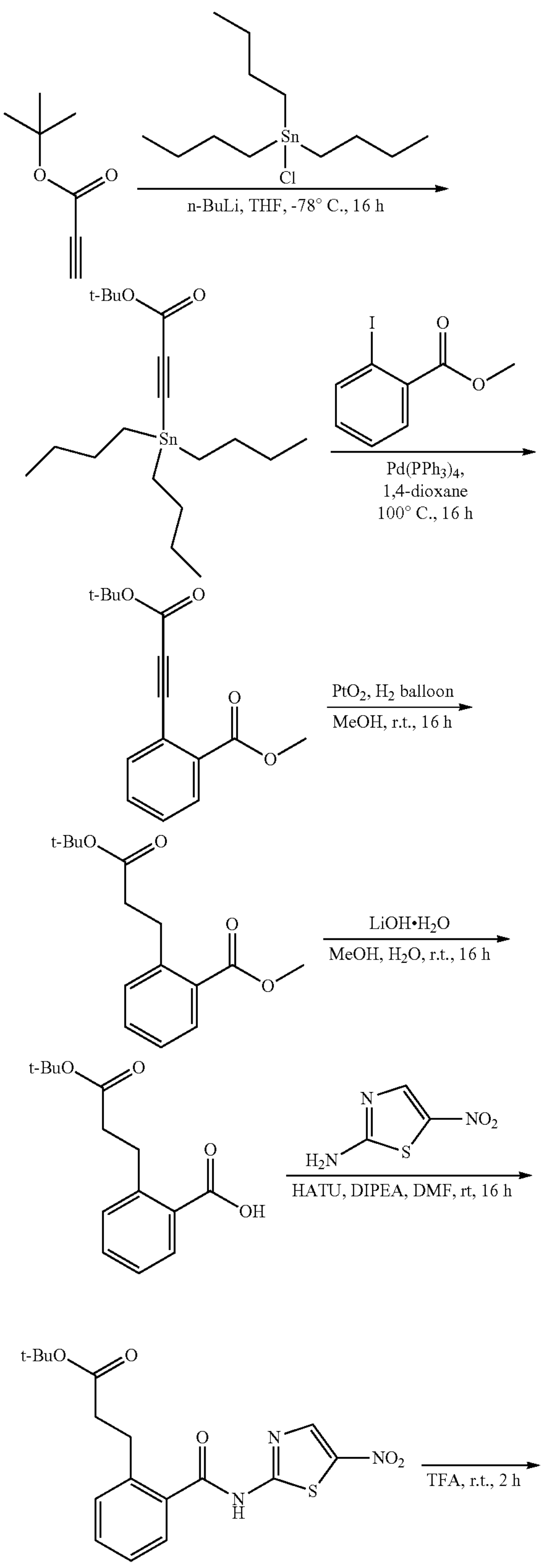

-continued

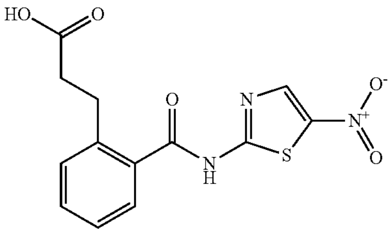

Step 1. Synthesis of tert-butyl 3-(tributylstannyl)propiolate

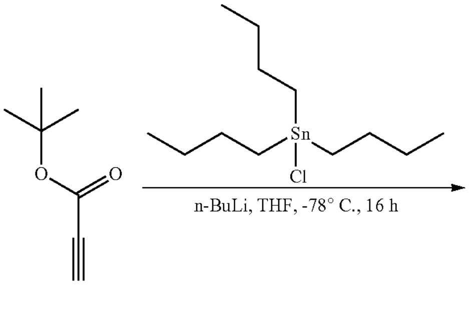

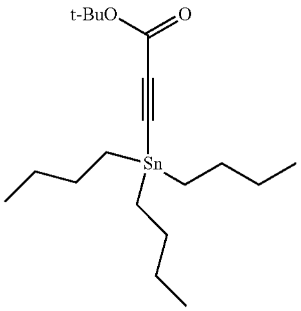

To a solution of tert-butyl propiolate (6.5 g, 51.6 mmol) in THF (300 mL) was added n-BuLi (32.5 mL, 51.6 mmol) at −78° C. for 30 min. The reaction was stirred at −78° C. for 1.5 h, before tributylchlorostannane (12.5 mL, 51.6 mmol) was added. The mixture was stirred at −78° C. for 1 h, and warmed up to rt for 16 h. The reaction mixture was quenched with $NH_4Cl$ (aq 10 mL) at −78° C., extracted with EtOAc (3×100 mL). The combined organic layers were washed with brine (3×30 mL), dried over $Na_2SO_4$, filtered and concentrated under vacuum. The resulting residue was purified by silica gel column chromatography (petroleum ether:EtOAc=1:1) to give the title compound (10.0 g, 50% yield) as yellow oil.

Step 2. Synthesis of methyl 2-(3-(tert-butoxy)-3-oxoprop-1-yn-1-yl)benzoate

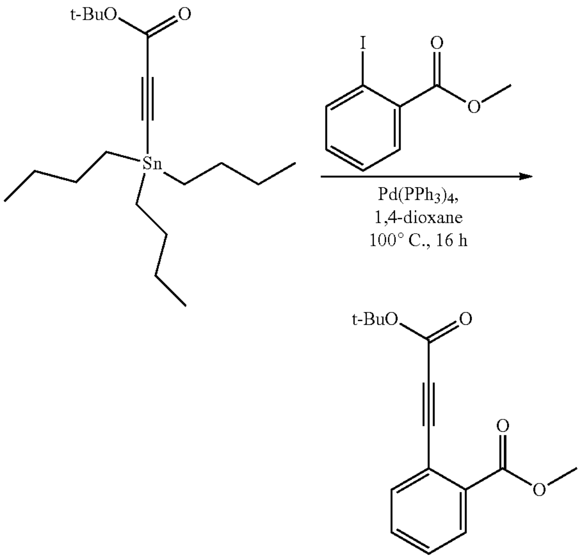

A solution of tert-butyl 3-(tributylstannyl)propiolate (10.0 g, 24.1 mmol), methyl 2-iodobenzoate (10.0 g, 38.2 mmol) and $Pd(PPh_3)_4$ (2.0 g, 0.48 mmol) in dioxane (400 mL) was stirred at 100° C. for 16 h under Ar. The mixture was cooled to rt, diluted with EtOAc (100 mL), washed with brine (3×30 mL), dried over $Na_2SO_4$, filtered and concentrated under vacuum. The resulting residue was purified by silica gel column chromatography (petroleum ether:EtOAc=2:1) to give the title compound (3.0 g, 33.0% yield) as yellow solid. MS (ESI) m/z: 278.4 $[M+H]^+$.

Step 3. Synthesis of methyl 2-(3-(tert-butoxy)-3-oxopropyl)benzoate

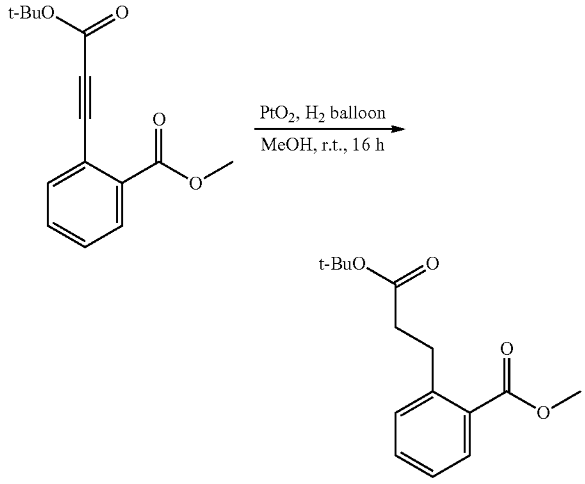 [SMILES: COC(=O)c1ccccc1C#CC(=O)OC(C)(C)C ; COC(=O)c1ccccc1CCC(=O)OC(C)(C)C]

A solution of methyl 2-(3-(tert-butoxy)-3-oxoprop-1-yn-1-yl)benzoate (2.20 g, 8.46 mmol) and $PtO_2$ (2.20 g, 0.85 mmol) in MeOH (200 mL) was stirred at rt under $H_2$ for 16 h. The mixture was filtered, and the filtrate was concentrated under vacuum to give the title compound (crude 1.7 g) as yellow oil, which was used for the next without further purification. MS (ESI) m/z: 209.2 $[M+H-56]^+$.

Step 4. Synthesis of 2-(3-(tert-butoxy)-3-oxopropyl)benzoic acid

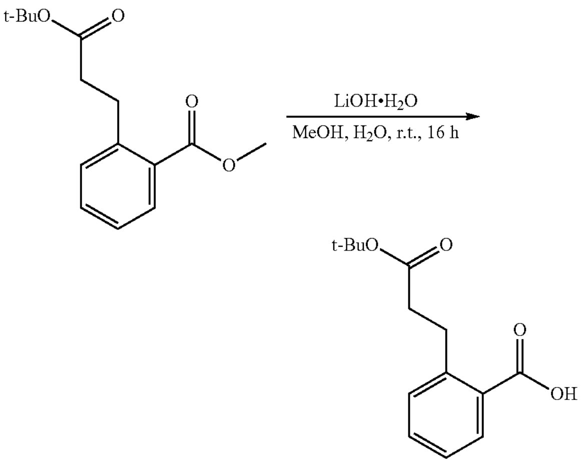

A solution of methyl 2-(3-(tert-butoxy)-3-oxopropyl)benzoate (0.85 g, 3.21 mmol) and $LiOH{\cdot}H_2O$ (0.54 g, 12.8 mmol) in $MeOH/H_2O$ (50 mL, 17 mL) was stirred at it for 16 h. After the reaction mixture was cooled down to 0° C., the pH of the mixture was adjusted to 5-6 with 1 N HCl. The mixture was extracted with EtOAc (3×30 mL). The combined organic layers were washed with brine (3×30 mL), dried over $Na_2SO_4$, filtered and concentrated under vacuum to give the title compound (0.62 mg, crude) as yellow solid, which was used for the next without further purification. MS (ESI) m/z: 249.2 $[M-H]^-$.

Step 5. Synthesis of tert-butyl 3-(2-((5-nitrothiazol-2-yl)carbamoyl)phenyl)propanoate

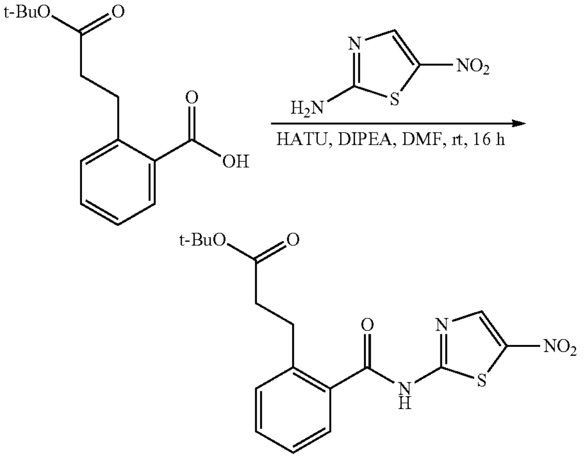

A solution of 2-(3-(tert-butoxy)-3-oxopropyl)benzoic acid (620 mg, 1.24 mmol), 5-nitrothiazol-2-amine (360 mg, 1.24 mmol), HATU (942 mg, 2.48 mmol) and DIEA (1 mL, 5.89 mmol) in DMF (10 mL) was stirred at rt for 16 h. After the reaction mixture was cooled down to 0° C. the pH of the mixture was adjusted to 5-6 with 1 N HCl. The mixture was extracted with EtOAc (3x30 mL). The combined organic layers were washed with brine (3x30 mL), dried over $Na_2SO_4$, filtered and concentrated under vacuum. The resulting residue was purified by silica gel column chromatography (petroleum ether:EtOAc=3:1) to give the title compound (200 mg, 53.0% yield) as yellow solid. MS (ESI) m/z: 377.9 $[M+H]^+$.

Step 6. Synthesis of 3-(2-((5-nitrothiazol-2-yl)carbamoyl)phenyl)propanoic acid

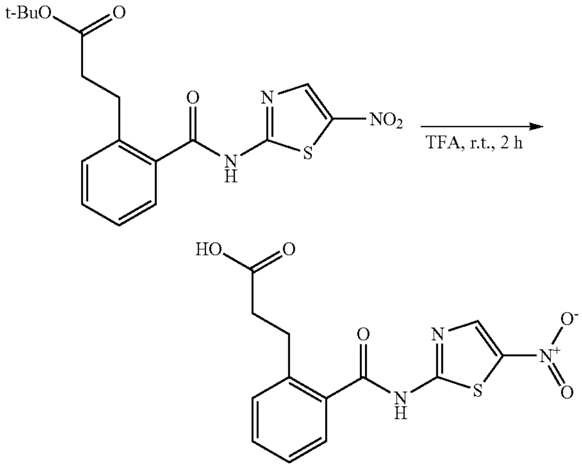 [SMILES: CC(C)(C)OC(=O)CCc1ccccc1C(=O)Nc1ncc([N+](=O)[O-])s1 ; O=C(O)CCc1ccccc1C(=O)Nc1ncc([N+](=O)[O-])s1]

A solution of tert-butyl 3-(2-((5-nitrothiazol-2-yl)carbamoyl)phenyl)propanoate (0.20 g, 0.53 mmol) in TFA (6 mL) was stirred at rt for 2 h. The mixture was concentrated under vacuum and purified by pre-HPLC to give the title compound (43.1 mg, 25.0% yield) as yellow solid. $^1H$ NMR (400 MHz, DMSO-$d_6$): δ 13.55 (s, 1H), 12.14 (s, 1H), 8.70 (s, 1H), 7.69-7.58 (m, 1H), 7.53 (td, J=7.6, 1.2 Hz, 1H), 7.49-7.29 (m, 2H), 2.99 (t, J=7.6 Hz, 2H), 2.55 (t, J=7.6 Hz, 2H). MS (ESI) m/z: 322.0 $[M+H]^+$.

Example 083. 2-Cyclopropoxy-N-(5-nitrothiazol-2-yl)benzamide (B-75)

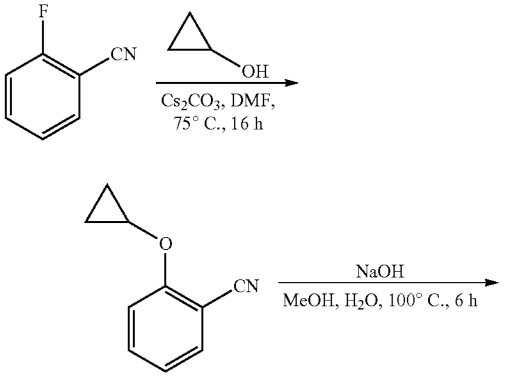

-continued

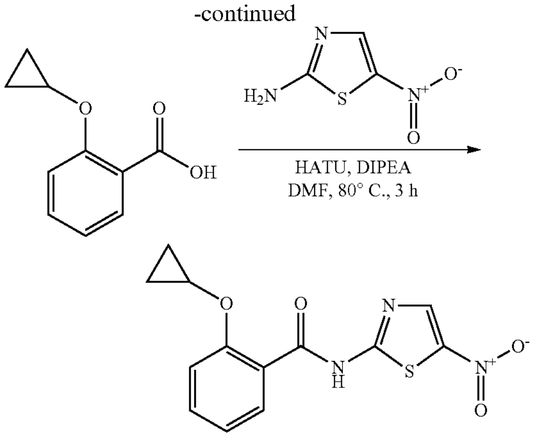

Step 1. Synthesis of 2-cyclopropoxybenzonitrile

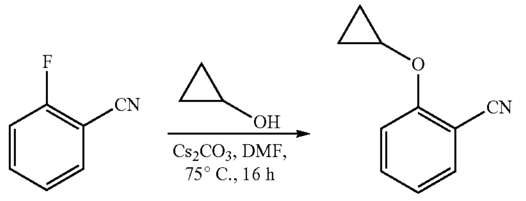

To a solution of 2-fluorobenzonitrile (300 mg, 2.50 mmol) and cyclopropanol (220 mg, 3.75 mmol) in DMF (3 mL) was added $Cs_2CO_3$ (1.20 mg, 3.75 mmol) under $N_2$ atmosphere. After the mixture was stirred at 75° C. for 16 h, it was cooled down to it. The mixture was diluted with $H_2O$ (50 mL) and extracted with EtOAc (3x50 mL). The combined organic phase was dried over $Na_2SO_4$, filtered and concentrated under vacuum to give the crude tide compound (300 mg, crude) as colorless oil, which was used in the next step without further purification.

Step 2. Synthesis of 2-cyclopropoxybenzoic acid

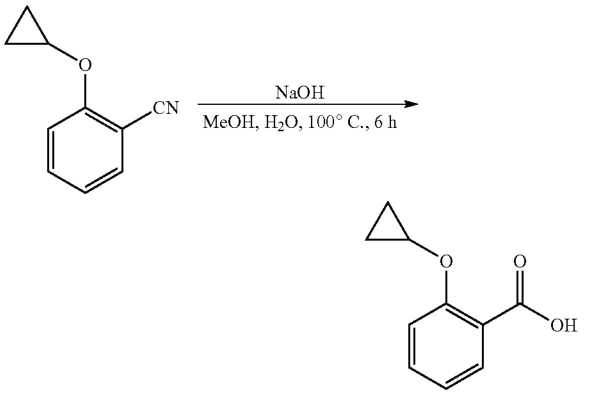

To a solution of 2-cyclopropoxybenzonitrile (100 mg, crude) in MeOH (2 mL) was added a solution of NaOH (126 mg, 3.15 mmol) in $H_2O$ (2 mL). After being stirred at 100° C. for 6 h, the mixture was cooled to the it and diluted with $H_2O$ (20 mL), acidified with 1 N HCl to pH=3, and extracted with EtOAc (3×20 mL). The combined organic phase was dried over $Na_2SO_4$, filtered and concentrated under vacuum. The resulting residue was purified by Pre-HPLC to give the title compound (50.0 mg, 11.24% yield) as white solid. MS (ESI) m/z: 179.1 $[M+H]^+$.

Step 3. Synthesis of 2-cyclopropoxy-N-(5-nitrothiazol-2-yl)benzamide

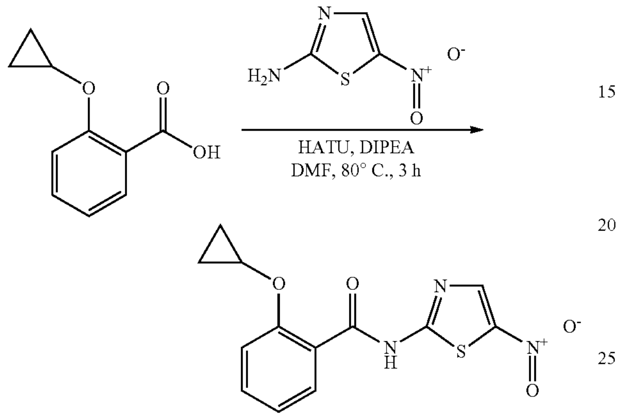

A solution of 2-cyclopropoxybenzoic acid (50.0 mg, 0.280 mmol), 5-nitrothiazol-2-amine (41.0 mg, 0.280 mmol), HATU (160 mg, 0.420 mmol) and DIEA (73.0 mg, 0.56 mmol) in DMSO (3.00 mL) was stirred at 80° C. for 3 h. The reaction mixture was purified by prep-HPLC to give title compound (12.5 mg, 14.64% yield) as white solid. $^1H$ NMR (400 MHz, DMSO-$d_6$): δ12.75 (s, 1H), 8.67 (s, 1H), 7.68-7.60 (m, 2H), 7.51-7.49 (m, 1H), 7.15-7.11 (m, 1H), 4.00-3.98 (m, 1H), 0.85-0.78 (m, 4H). MS (ESI) m/z: 306.0 $[M+H]^+$.

Example 084. 2-Acetamido-N-(5-nitro-4-phenylthiazol-2-yl)benzamide (CLI-C043)

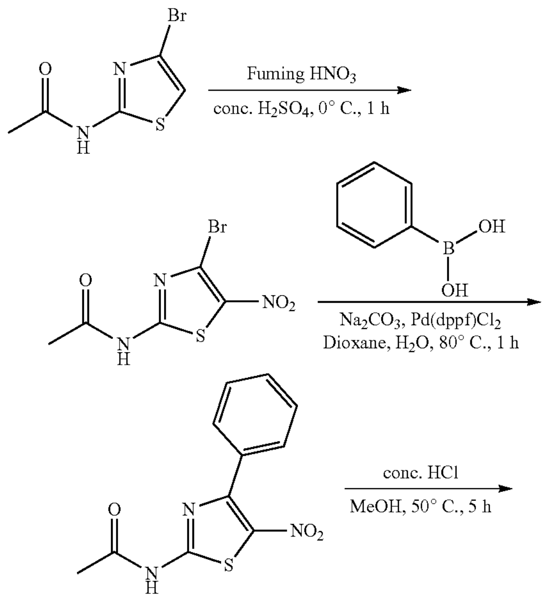

-continued

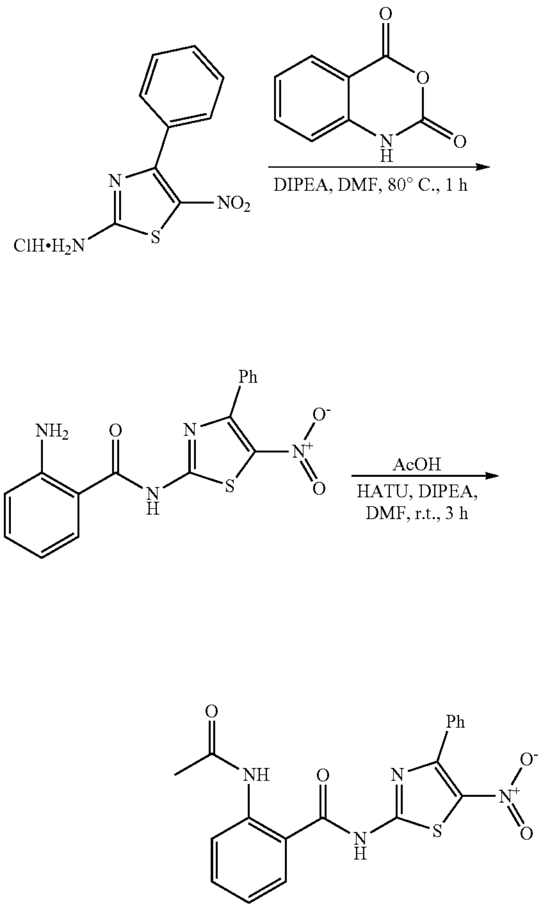

Step 1. Synthesis of N-(4-bromo-5-nitrothiazol-2-yl)acetamide

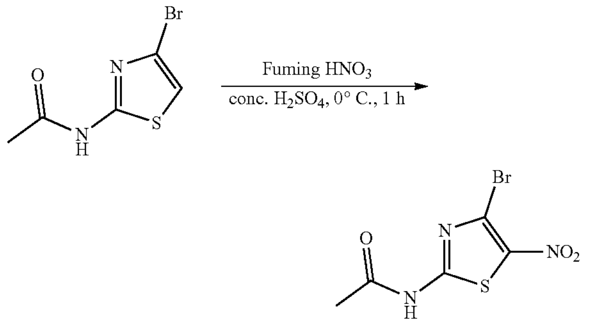

To a solution of N-(4-bromothiazol-2-yl) acetamide (270 mg, 1.22 mmol) in conc. $H_2SO_4$ (2 mL) was added fuming $HNO_3$ (0.2 mL) at 0° C. After being stirred at 0° C. for 1 h, the mixture was poured into ice 427ater (30 mL) and extracted with EtOAc (3×20 mL). The combined organic phase was washed with brine, dried over $Na_2SO_4$, filtered and concentrated to give the title compound (189 mg, crude) as yellow solid, which was used in the next step without further purification.

Step 2. Synthesis of N-(5-nitro-4-phenylthiazol-2-yl)acetamide

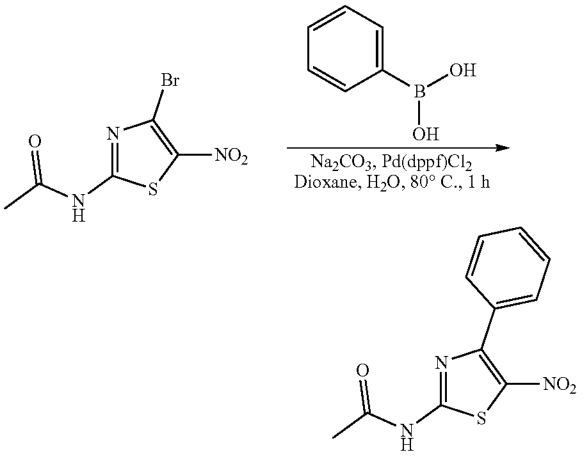

A solution of N-(4-bromo-5-nitrothiazol-2-yl)acetamide (300 mg, 1.13 mmol), $K_2CO_3$ (313 mg, 2.26 mmol), Pd(dppf)$Cl_2$ (83 mg, 0.113 mmol) and phenylboronic acid (276 mg, 2.26 mmol) in 1,4-dioxane (5 mL) and water (0.5 mL) was stirred at 80° C. for 1 h under Ar. At rt, the mixture was diluted with water (30 mL) and extracted with EtOAc (3×30 mL). The combined organic phase was washed with brine, dried over $Na_2SO_4$, filtered and concentrated. The resulting residue was purified by silica gel column chromatography (petroleum ether:EtOAc=4:1) to give the title compound (190 mg, 63.3%) as brown solid. MS (ESI) m/z: 263.9 $[M+H]^+$.

Step 3. Synthesis of 5-nitro-4-phenylthiazol-2-amine hydrochloride

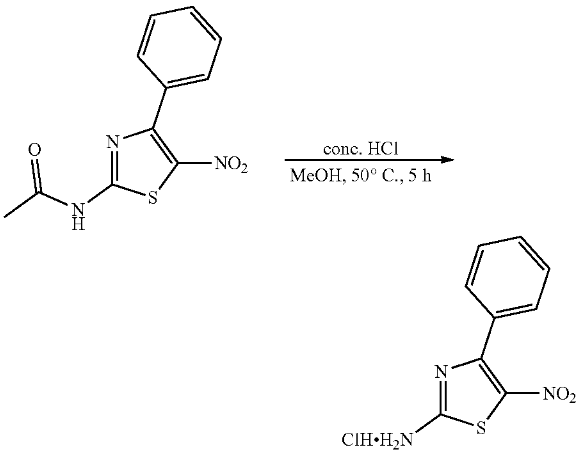

A solution of N-(5-nitro-4-phenylthiazol-2-yl)acetamide (140 mg, 0.532 mmol) in MeOH (4 mL) and conc. HCl (4 mL) was stirred at 50° C. for 5 h. The reaction mixture was concentrated under reduced pressure to give the title compound (82 mg, crude) as brown solid, which was used in the next step without further purification.

Step 4. Synthesis of 2-amino-N-(5-nitro-4-phenylthiazol-2-yl)benzamide

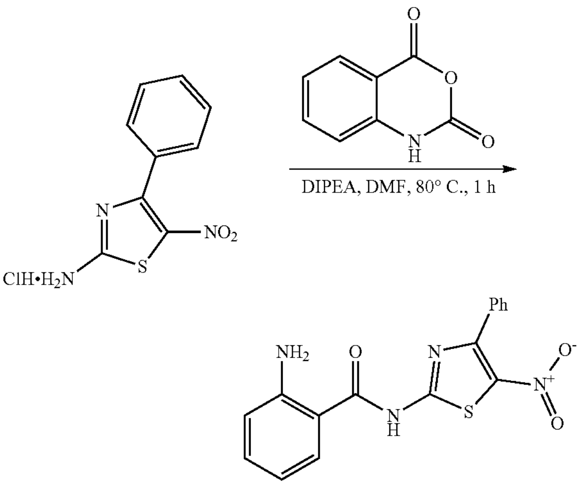

A mixture of 5-nitro-4-phenylthiazol-2-amine hydrochloride (80 mg, crude), DIPEA (72 mg, 4.14 mmol) and 2H-benzo[d][1,3]oxazine-2,4 (1H)-dione (65 mg, 3.04 mmol) in DMF (3 mL) was stirred at 80° C. for 1 h. At rt, the reaction mixture was diluted with water (10 mL) and extracted with EtOAc (2×20 mL). The combined organic phase was washed with brine, dried over $Na_2SO_4$, filtered and concentrated under vacuum. The resulting residue was purified by silica gel column chromatography (petroleum ether:EtOAc=2:1) to give the title compound (62 mg, 50.4% over two steps) as yellow solid. MS (ESI) m/z: 341.0 $[M+H]^+$.

Step 5. Synthesis of 2-acetamido-N-(5-nitro-4-phenylthiazol-2-yl)benzamide

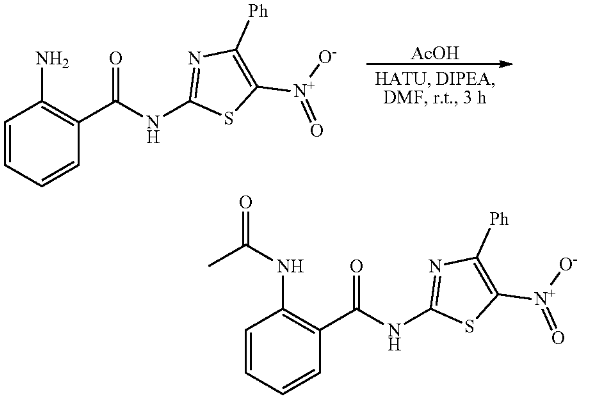

To a solution of 2-amino-N-(5-nitro-4-phenylthiazol-2-yl) benzamide (62 mg, 0.182 mmol), DIPEA (48 mg, 0.365 mmol) and acetic acid (22 mg, 0.365 mmol) in DMF (2 mL) was added HATU (138 mg, 0.365 mmol). After being stirred at rt for 3 h, the reaction mixture was purified by pre-HPLC to give the desired compound (54.8 mg, 78.7% yield) as yellow solid. $^1$H NMR (400 MHz, DMSO-$d_6$): δ 13.50 (s, 1H), 10.22 (s, 1H), 7.76-7.70 (m, 3H), 7.66-7.64 (m, 1H), 7.59-7.57 (m, 1H), 7.55-7.49 (m, 3H), 7.27-7.23 (m, 1H), 2.03 (s, 3H). MS (ESI) m/z: 405.0 [M+H]+.

Example 085. Methyl (2-((5-nitrothiazol-2-yl)carbamoyl)phenyl) carbonate (B-78)

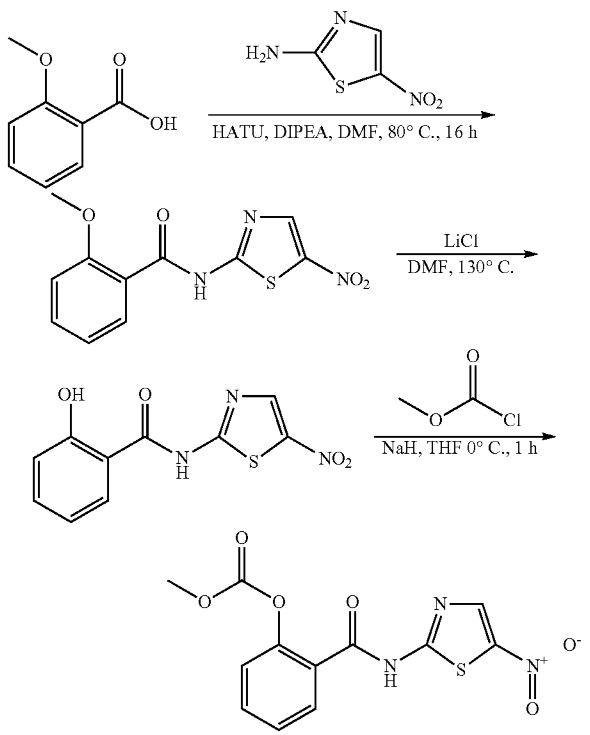

Step 1. Synthesis of 2-methoxy-N-(5-nitrothiazol-2-yl)benzamide

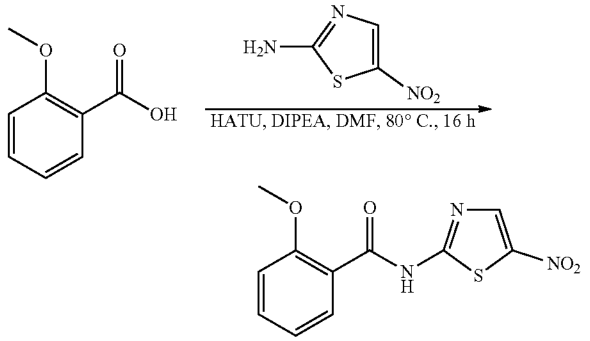

To a solution of 2-methoxybenzoic acid (2.00 g, 13.1 mmol), 5-nitrothiazol-2-amine (1.91 g, 13.1 mmol) and HATU (5.50 g, 13.1 mmol) in DMF (20 mL) was added DIPEA (5 mL, 29.4 mmol). After being stirred at 80° C. for 16 h, the mixture was cooled down to rt and poured into water (100 mL). The resulting solid was collected by filtration and dried to give the title compound (2.36 g, 65.0% yield) as yellow solid. MS (ESI) m/z: 279.9 [M+H]+.

Step 2. Synthesis of 2-hydroxy-N-(5-nitrothiazol-2-yl)benzamide

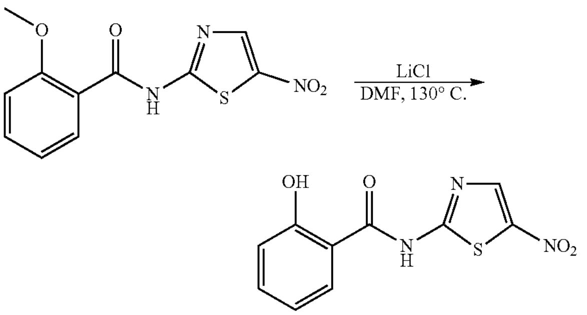

A solution of 2-methoxy-N-(5-nitrothiazol-2-yl)benzamide (1.50 g, 5.37 mmol) and LiCl (2.20 g, 53.7 mmol) in DMF (100 mL) was stirred at 130° C. for 3 h. At rt, the mixture was diluted with EtOAc (100 mL) and washed with brine (3×30 mL). The organic phase was dried over $Na_2SO_4$, filtered and concentrated under vacuum to give the title compound (600 mg, 43.0% yield) as yellow solid. MS (ESI) m/z: 264.0 [M−H]−.

Step 3. Synthesis of methyl (2-((5-nitrothiazol-2-yl)carbamoyl)phenyl) carbonate

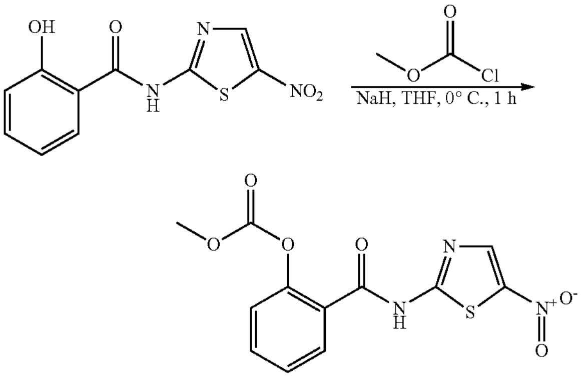

To a solution of 2-hydroxy-N-(5-nitrothiazol-2-yl)benzamide (300 mg, 1.13 mmol) in THF (10 mL) was added NaH (90 mg, 2.26 mmol, 60% in mineral oil) at 0° C. After being stirred at 0° C. for 1 h, methyl carbonochloridate (213 mg, 2.26 mmol) was added and stirred at rt for 2 h, at which time the mixture was poured into ice-water (30 mL). After the pH of the mixture was adjusted to 5 with 1 N aq. HCl, it was extracted with EtOAc (100 mL). The combined organic phase was washed with brine (3×30 mL), dried over $Na_2SO_4$, filtered and concentrated under vacuum. The resulting residue was purified by pre-HPLC to give the title compound (30 mg, 8.0% yield) as yellow solid. $^1H$ NMR (400 MHz, DMSO-$d_6$): δ 13.65 (brs, 1H), 8.70 (s, 1H), 7.89-7.86 (m, 1H), 7.72-7.68 (m, 1H), 7.48-7.43 (m, 2H), 3.81 (s, 3H). MS (ESI) m/z: 279.9 [M+H]+.

Example 086. 2-Acetamido-N-(5-nitrothiophen-2-yl)benzamide (B-51)

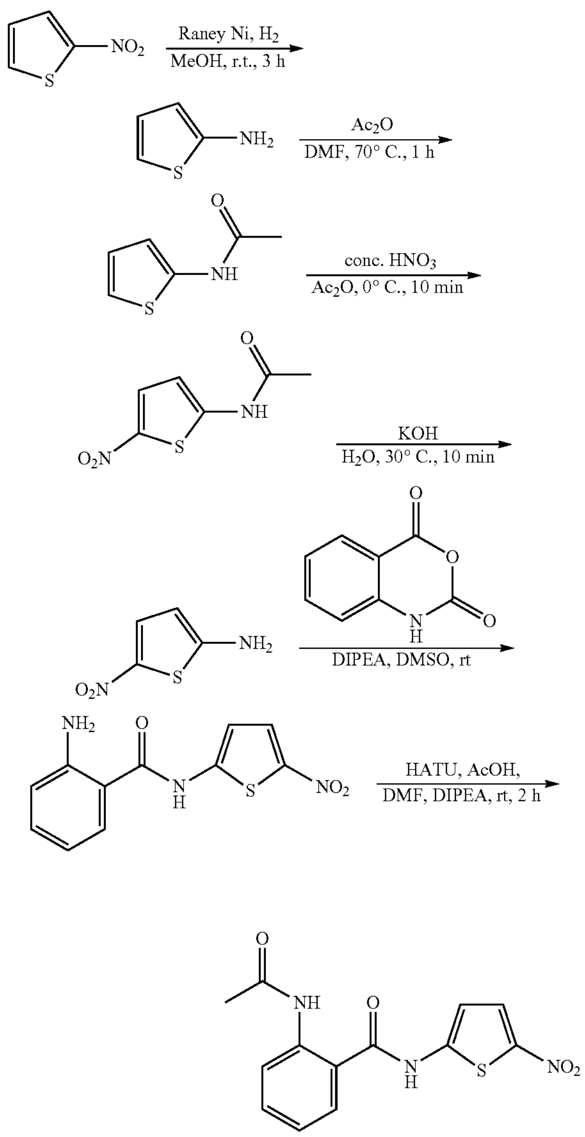

Step 1. Synthesis of thiophen-2-amine

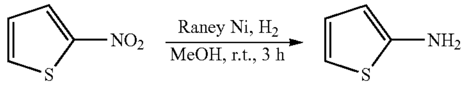

A solution of 2-nitrothiophene (2.00 g, 15.5 mmol) and Raney Ni (400 mg) in MeOH (10 mL) was hydrogenated under 1 atm of hydrogen pressure for 3 h at rt. The mixture was filtered and the filtrate was concentrated under vacuum to give the title compound (1.4 g, crude), which was used in the next step without further purification. MS (ESI) m/z: 100.2 $[M+H]^+$.

Step 2. Synthesis of N-(thiophen-2-yl)acetamide

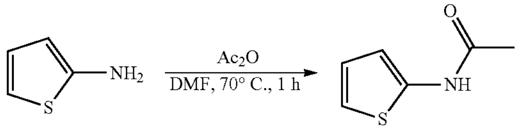

To a solution of thiophen-2-amine (1.40 g, crude) in DMF (10 mL) was added $Ac_2O$ (5.7 g, 56.6 mmol) at rt. After the reaction mixture was stirred at 70° C. for 1 h, the mixture was cooled to rt and concentrated under vacuum. The resulting residue was purified by silica gel column chromatography (petroleum ether:EtOAc=1:1) to give the title compound (1.00 g, crude) as yellow oil, which was used in the next step without further purification. MS (ESI) m/z: 142.0 $[M+H]^+$.

Step 3. Synthesis of N-(5-nitrothiophen-2-yl)acetamide

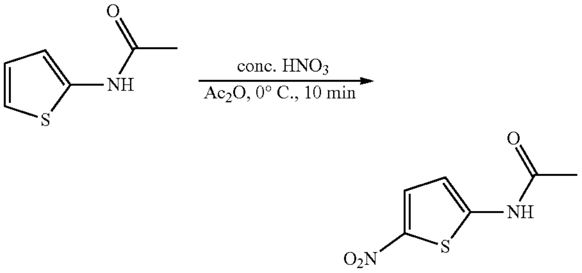

To a solution of conc. $HNO_3$ (1.4 mL) in $Ac_2O$ (20 mL) was added N-(thiophen-2-yl)acetamide (1.00 g, crude) at 0° C. The mixture was stirred at 0° C. for 10 min. Then, the mixture was diluted with water (50 mL) and neutralized with 1 N aq. $K_2CO_3$ to pH=7. The mixture was extracted with EtOAc (3x50 mL). The combined organic layers were washed with brine (2x50 mL), dried over $Na_2SO_4$, filtered and concentrated under vacuum. The resulting residue was purified by silica gel column chromatography (petroleum ether:EtOAc=1:1) to give the title compound (300 mg, 10.4% yield over three steps) as gray solid. MS (ESI) m/z: 187.1 $[M-H]^-$.

Step 4. Synthesis of 5-nitrothiophen-2-amine

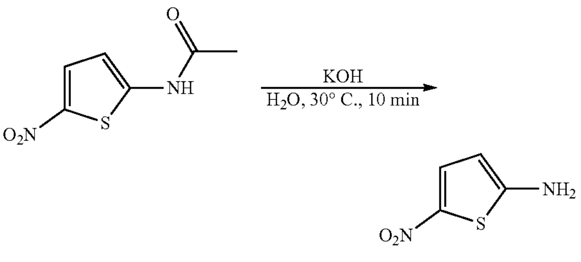

A solution of N-(5-nitrothiophen-2-yl)acetamide (230 mg, 1.24 mmol) and KOH (1.60 g, 28.5 mmol) in $H_2O$ (10 mL) was stirred at 30° C. for 10 min, before the mixture was diluted with water (20 mL) and acidified with 1 N HCl to pH=7. The mixture was extracted with EtOAc (2×50 mL). The combined organic phase was washed with brine (2×50 mL), dried over $Na_2SO_4$, filtered and concentrated under vacuum to give the title compound (100 mg, 56% yield) as gray solid. MS (ESI) m/z: 145.1 $[M+H]^+$.

Step 5. Synthesis of 2-acetamido-N-(5-nitrothiophen-2-yl)benzamide

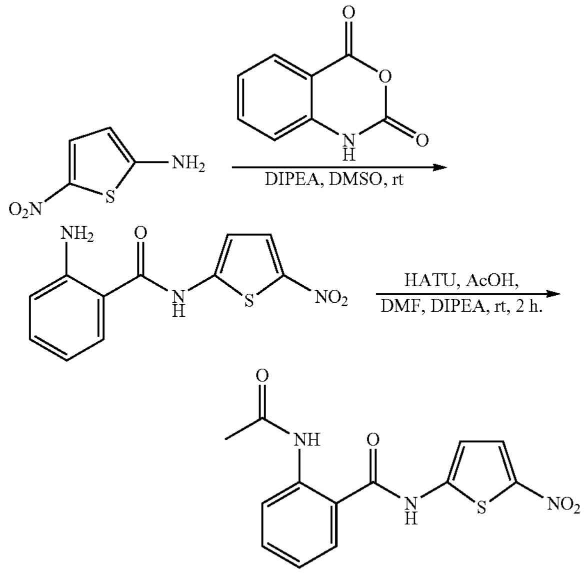

A solution of 5-nitrothiophen-2-amine (50.0 mg, 0.345 mmol), DIPEA (90.0 mg, 0.698 mmol) and 2H-benzo[d][1,3]oxazine-2,4 (1H)-dione (84.0 mg, 0.515 mmol) in DMSO (2 mL) was stirred at rt overnight. To the resulting reaction solution were added acetic acid (42 mg, 0.689 mmol), HATU (262 mg, 0.689 mmol) and DIPEA (41 mg, 0.318 mmol). After being stirred at rt for 2 h, the mixture was purified by prep-HPLC to give the title compound (26.6 mg, 25.3% yield) as white solid. $^1$H NMR (400 MHz, DMSO-$d_6$): δ 12.5 (s, 1H), 10.2 (s, 1H), 8.05 (d, J=4.8 Hz, 1H), 7.82 (d, J=8.0 Hz, 1H), 7.71 (d, J=6.8 Hz, 1H), 7.60-7.56 (m, 1H), 7.29 (t, J=7.2 Hz, 1H), 6.87 (d, J=4.8 Hz, 1H), 2.03 (s, 3H). MS (ESI) m/z: 304.0 $[M-H]^-$.

Example 087. 2-Acetamido-$N^1$-(5-nitrothiazol-2-yl)-$N^3$-propylisophthalamide (B-145)

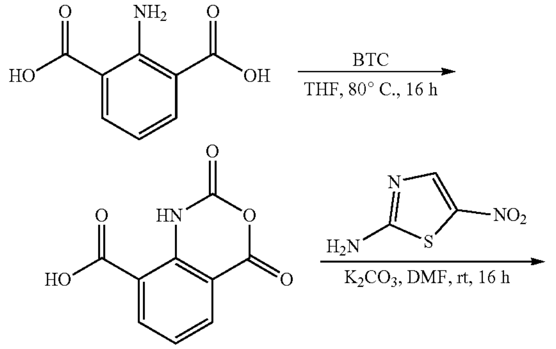

-continued

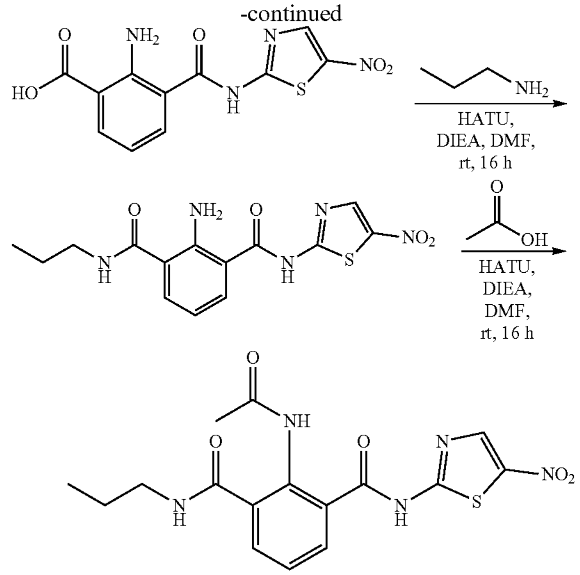

Step 1. Synthesis of 2,4-dioxo-1,4-dihydro-2H-benzo[d][1,3]oxazine-8-carboxylic acid

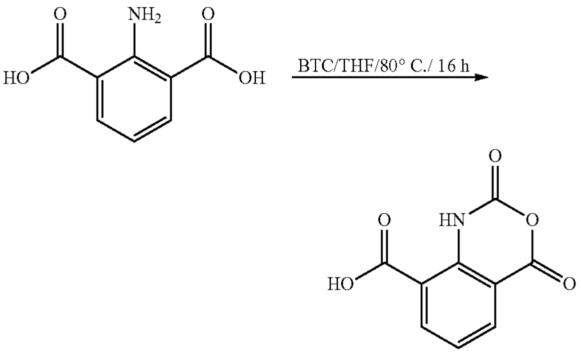

A solution of 2-aminoisophthalic acid (1.0 g, 5.52 mmol) and triphosgene (0.65 g, 2.20 mmol) in THF (50 mL) was stirred at 80° C. for 16 h. After the reaction was cooled down to rt, the precipitation was collected by filtration and dried under vacuum to give the title compound (1.30 g. crude) as yellow solid. MS (ESI) m/z: 206.1 $[M-H]^-$.

Step 2. Synthesis of 2-amino-3-((5-nitrothiazol-2-yl)carbamoyl)benzoic acid

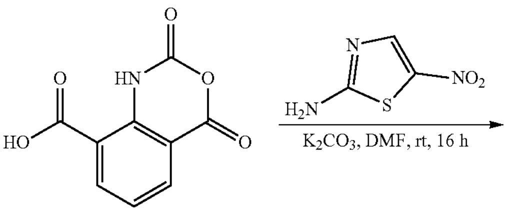

-continued

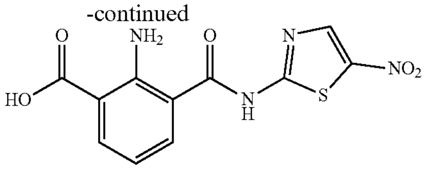

A solution of 2,4-dioxo-2,4-dihydro-1H-benzo[d][1,3]oxazine-8-carboxylic acid (1.30 g, 6.28 mmol), 5-nitrothiazol-2-amine (0.91 g, 6.28 mmol) and $K_2CO_3$ (1.70 g, 12.6 mmol) in DMF (50 mL) was stirred at rt for 16 h. The reaction solution was used in the next step without further purification. MS (ESI) m/z: 307.1 $[M-H]^-$.

Step 3. Synthesis of 2-amino-N[1]-(5-nitrothiazol-2-yl)-N[3]-propylisophthalamide

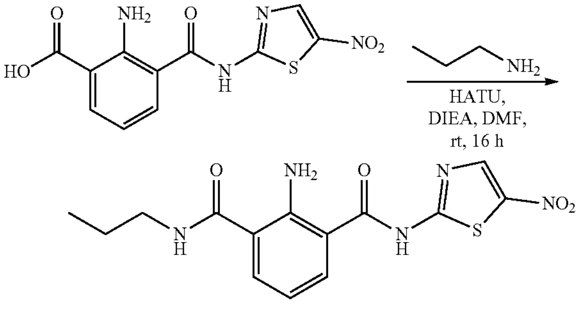

A solution of 2-amino-3-((5-nitrothiazol-2-yl)carbamoyl)benzoic acid (previous reaction solution) (6.28 mmol), propan-1-amine (0.74 g, 12.6 mmol), HATU (2.38 g, 6.28 mmol) and DIEA (1.60 g, 12.6 mmol) in DMF (50 mL) was stirred at rt for 16 h. After the mixture was diluted with $H_2O$ (30 mL), the pH was adjusted to 4 with 1 N HCL. The mixture was extracted with EtOAc (3×30 mL). The combined organic layers were washed with brine (3×30 mL), dried over $Na_2SO_4$, filtered and concentrated under vacuum. The resulting yellow residue was triturated with EtOAc (6 mL), filtered and dried to give the title compound (0.8 g, 38% yield) as yellow solid. MS (ESI) m/z: 350.0 $[M+H]^+$.

Step 4. Synthesis of 2-acetamido-N[1]-(5-nitrothiazol-2-yl)-N[3]-propylisophthalamide

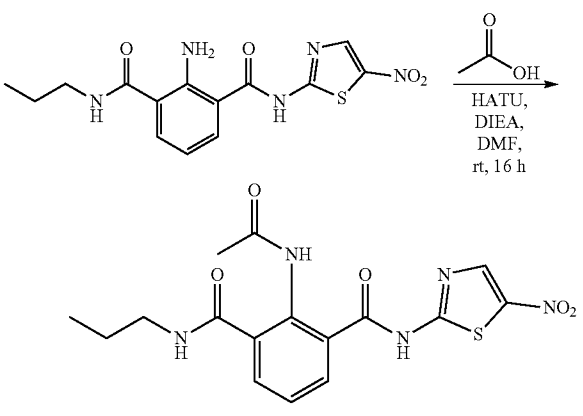

A solution of 2-amino-N[1]-(5-nitrothiazol-2-yl)-N[3]-propylisophthalamide (300 mg, 0.86 mmol mmol), AcOH (51 mg, 0.86 mmol), HATU (326 mg, 0.86 mmol) and DIEA (721 mg, 1.72 mmol) in DMF (50 mL) was stirred at rt for 16 h. The mixture was purified by pre-HPLC to give the title compound (74 mg, 22% yield) as yellow solid. $^1H$ NMR (400 MHz, DMSO-$d_6$): δ 13.45 (s, 1H), 10.29 (s, 1H), 8.66 (s, 1H), 8.59-8.57 (m, 1H) 7.74 (d, J=7.6 Hz, 1H), 7.70 (d, J=8.4 Hz, 1H), 7.38 (t, J=7.6 Hz, 1H), 3.22 (q, J=6.4 Hz, 2H), 1.95 (s, 3H), 1.60-1.47 (m, 2H), 0.91 (t, J=7.2 Hz, 3H). MS (ESI) m/z: 392.0 $[M+H]^+$.

Example 088. 2-Acetamido-3-butyramido-N-(5-nitrothiazol-2-yl)benzamide (B-146)

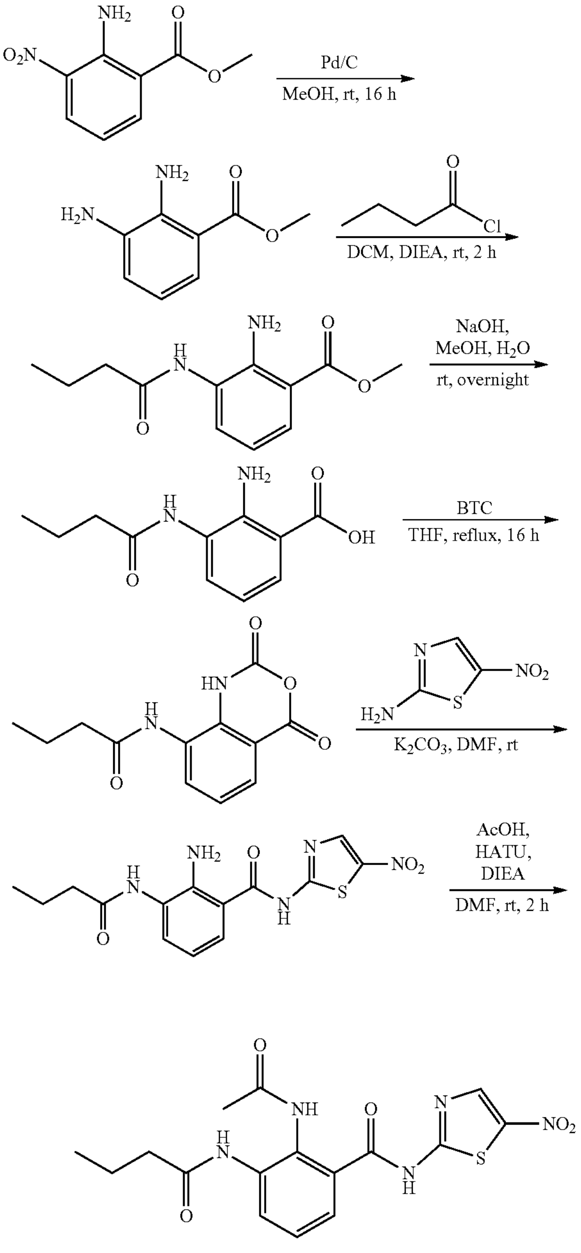

Step 1. Synthesis of methyl 2,3-diaminobenzoate

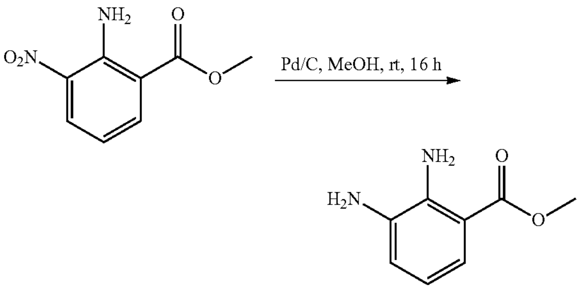

A solution of methyl 2-amino-3-nitrobenzoate (6.5 g, 33.2 mmol) and Pd/C (6.5 g, wet, 10% yield) in MeOH (200 mL) was stirred at rt for 16 h under $H_2$. The mixture was filtered, and the filtrate was concentrated under vacuum to give the title compound (5.4 g, 98.0% yield) as yellow oil. MS (ESI) m/z: 167.2 $[M+H]^+$.

Step 2. Synthesis of methyl 2-amino-3-butyramidobenzoate

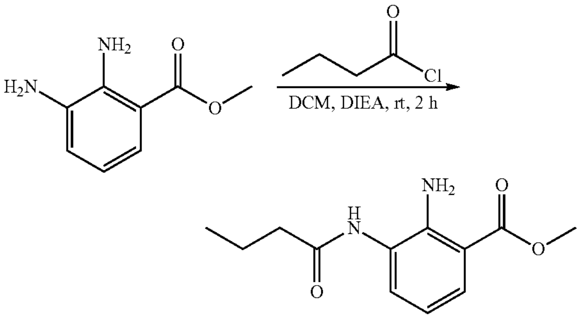

To a solution of methyl 2,3-diaminobenzoate (5.0 g, 30.1 mmol) and DIEA (7.77 g, 60.2 mmol) in DCM (100 mL) was added butyryl chloride (2.55 g, 24.1 mmol) at 0° C. After being stirred at rt for 2 h, the mixture was acidified (pH=3-4) with 1 N HCl at 0° C. The mixture was extracted with EtOAc (3x30 mL). The combined organic phase was washed with brine (3x30 mL), dried over $Na_2SO_4$, filtered and concentrated under vacuum to give the title compound (5.70 g, crude) as yellow solid, which was used in the next step without further purification. MS (ESI) m/z: 237.2 $[M+H]^+$.

Step 3. Synthesis of 2-amino-3-butyramidobenzoic acid

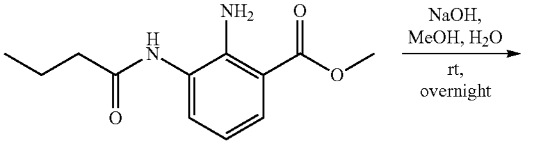

-continued

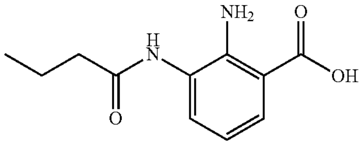

To a solution of methyl 2-amino-3-butyramidobenzoate (4.50 g, 19.06 mmol) in MeOH (100 mL) and $H_2O$ (10 mL) was added NaOH (3.05 g, 76.3 mmol). After being stirred at rt overnight, the mixture was acidified with 1 N HCl to pH=4. The mixture was extracted with EtOAc (3x30 mL). The combined organic layers were washed with brine (3x30 mL), dried over $Na_2SO_4$, filtered and concentrated under vacuum to give the title compound (4.10 g, 97% yield) as yellow solid, which was used in the next step without further purification. MS (ESI) m/z: 223.1 $[M+H]^+$.

Step 4. Synthesis of N-(2,4-dioxo-1,4-dihydro-2H-benzo[d][1,3]oxazin-8-yl)butyramide

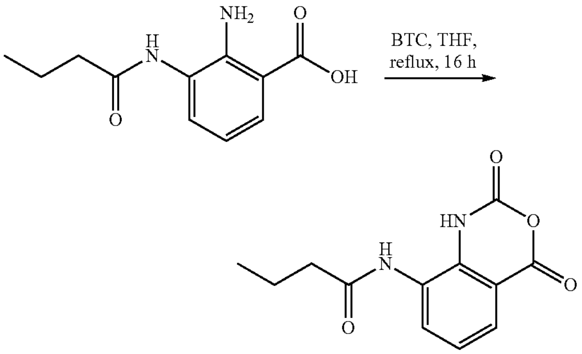

A solution of 2-amino-3-butyramidobenzoic acid (4.10 g, 18.46 mmol) and triphosgene (2.20 g, 7.38 mmol) in THF (100 mL) was stirred at 80° C. for 16 h. After the reaction was cooled down to rt, the precipitation was collected by filtration and dried under vacuum to give the title compound (2.30 g, crude) as yellow solid. MS (ESI) m/z: 249.0 $[M+H]^+$.

Step 5. Synthesis of 2-amino-3-butyramido-N-(5-nitrothiazol-2-yl)benzamide

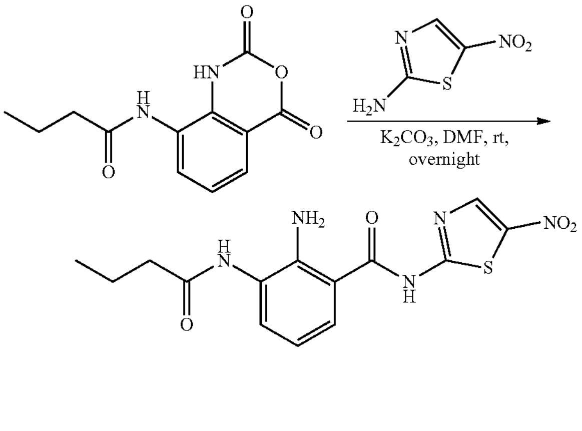

A solution of N-(2,4-dioxo-2,4-dihydro-1H-benzo[d][1,3]oxazin-8-yl)butyramide (2.30 g, 9.27 mmol), 5-nitrothiazol-2-amine (2.68 g, 18.6 mmol) and $K_2CO_3$ (2.55 g, 18.6 mmol) in DMF (20 mL) was stirred at rt overnight. The mixture was used in the next step without further purification. MS (ESI) m/z: 350.1 $[M+H]^+$.

Step 6. Synthesis of 2-acetamido-3-butyramido-N-(5-nitrothiazol-2-yl)benzamide

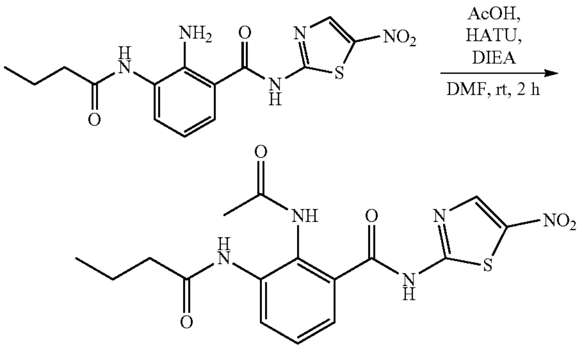

A solution of 2-amino-3-butyramido-N-(5-nitrothiazol-2-yl)benzamide (previous reaction solution), acetic acid (0.55 mg, 9.27 mmol), HATU (3.52 g, 9.27 mmol) and DIEA (2.39 g, 18.5 mmol) in DMF (20 mL) was stirred at rt for 2 h. After the mixture was diluted with $H_2O$ (30 mL), the pH was adjusted to 4 with 1 N HCL. The mixture was extracted with EtOAc (3×30 mL) and washed with brine (3×30 mL). The organic layer was dried over $Na_2SO_4$, filtered and concentrated under vacuum. The resulting residue was purified by pre-HPLC to give the title compound (30 mg, 0.8% over 3 steps) as yellow solid. $^1H$ NMR (400 MHz, DMSO-$d_6$): δ 13.47 (s, 1H), 9.48 (s, 1H), 9.42 (s, 1H), 8.67 (s, 1H), 7.85 (d, J=7.6 Hz, 1H), 7.41 (d, J=6.8 Hz, 1H), 7.35-7.31 (m, 1H), 2.37 (t, J=7.2 Hz, 2H), 1.96 (s, 3H), 1.80-1.50 (m, 2H), 0.94 (t, J=7.2 Hz, 3H). MS (ESI) m/z: 392.1 $[M+H]^+$.

Example 089. 2-Acetamido-4-((2-(2-(2-(2-aminoethoxy)ethoxy)ethoxy)ethyl)amino)-N-(5-nitrothiazol-2-yl)benzamide (BL-9)

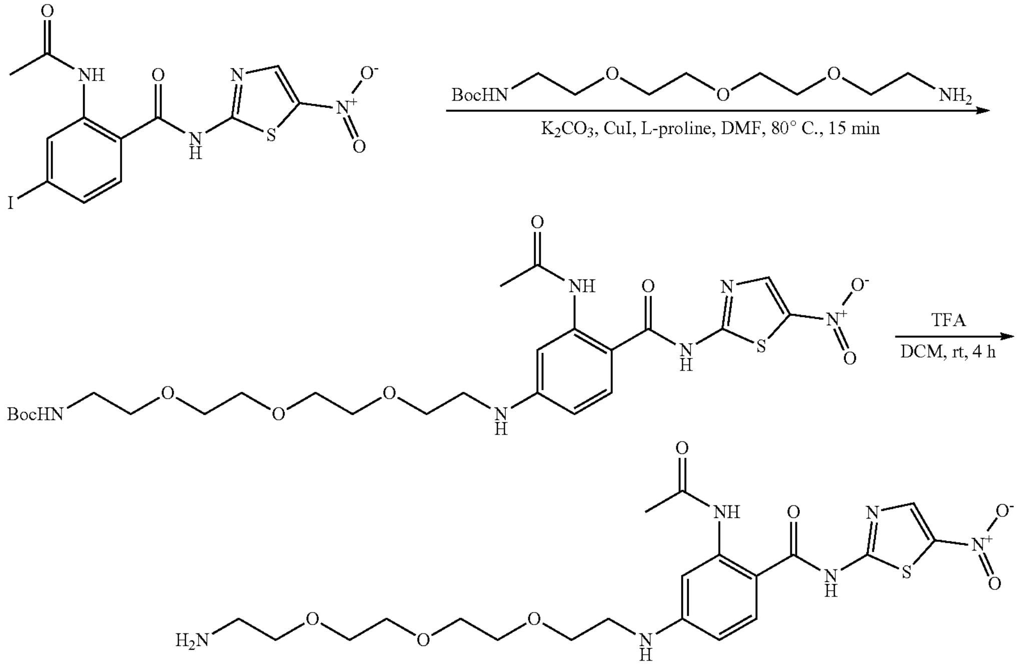

Step 1. Synthesis of tert-butyl (2-(2-(2-(2-((3-acetamido-4-((5-nitrothiazol-2-yl)carbamoyl)phenyl)amino)ethoxy)ethoxy)ethoxy)ethyl)carbamate

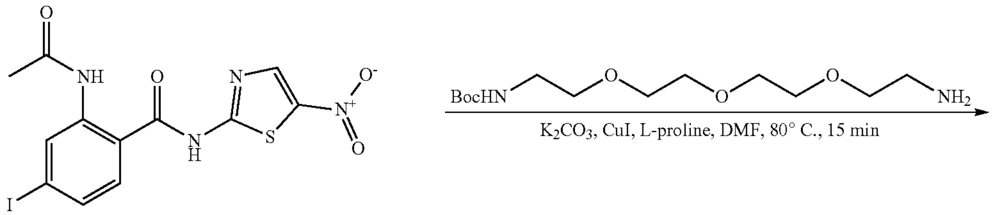

-continued

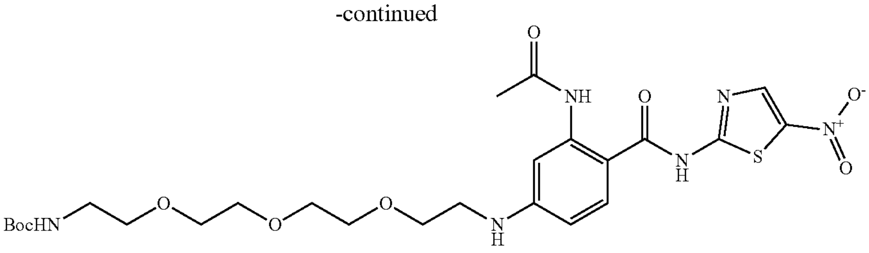

A solution of 2-acetamido-4-iodo-N-(5-nitrothiazol-2-yl) benzamide (200 mg, 0.449 mmol), tert-butyl (2-(2-(2-(2-aminoethoxy)ethoxy)ethoxy)ethyl)carbamate (263 mg, 0.898 mmol), L-proline (11 mg, 0.09 mmol), CuI (17 mg, 0.09 mmol) and $K_2CO_3$ (124 mg, 0.898 mmol) in DMF (3 mL) was stirred at 80° C. for 15 min under microwave in Ar. At rt, the mixture was poured into water (30 mL) and extracted with EtOAc (3×30 mL). The combined organic phase was washed with brine, dried over $Na_2SO_4$, filtered and concentrated under vacuum to give the crude title compound (300 mg, crude) as brown oil, which was used in the next step without further purification. MS (ESI) m/z: 597.0 $[M+H]^+$.

Step 2. Synthesis of 2-acetamido-4-((2-(2-(2-(2-aminoethoxy)ethoxy)ethoxy)ethyl)amino)-N-(5-nitrothiazol-2-yl)benzamide

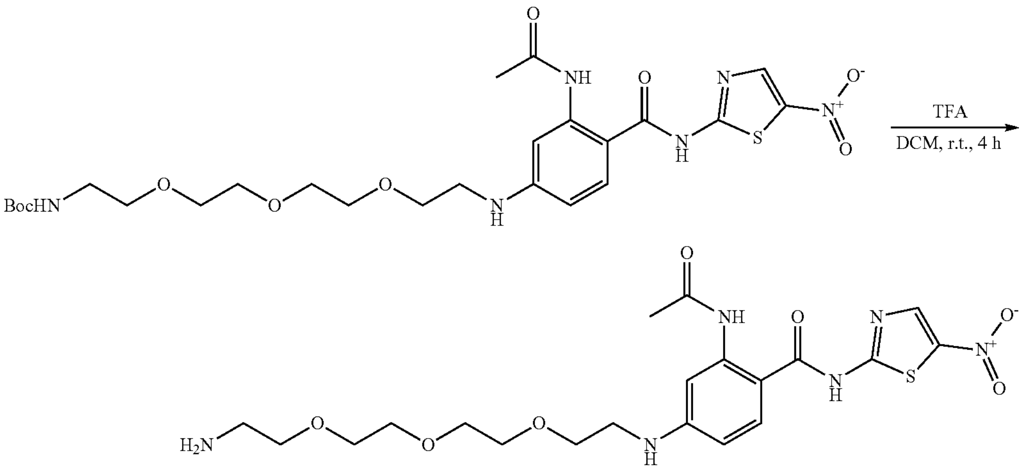

A solution of tert-butyl (2-(2-(2-(2-((3-acetamido-4-((5-nitrothiazol-2-yl)carbamoyl)phenyl)amino)ethoxy)ethoxy)ethoxy)ethyl)carbamate (300 mg, crude) in DCM (5 mL) and TFA (5 mL) was stirred at rt for 4 h. The mixture was concentrated under vacuum. The resulting residue was purified by pre-HPLC to give the title compound (10.2 mg, 4.58% yield) as red solid. $^1H$ NMR (400 MHz, $CD_3CN$): δ 8.45 (s, 1H), 8.10 (d, J=8.6 Hz, 1H), 7.98 (s, 1H), 6.47-6.45 (m, 1H), 3.67-3.64 (m, 4H), 3.61-3.59 (m, 8H), 3.37-3.34 (m, 2H), 3.10-3.07 (m, 2H), 1.99 (s, 3H). MS (ESI) m/z: 497.3 $[M+H]^+$.

Example 090. 1-(5-Nitrothiazol-2-yl)piperidin-2-one (B-99)

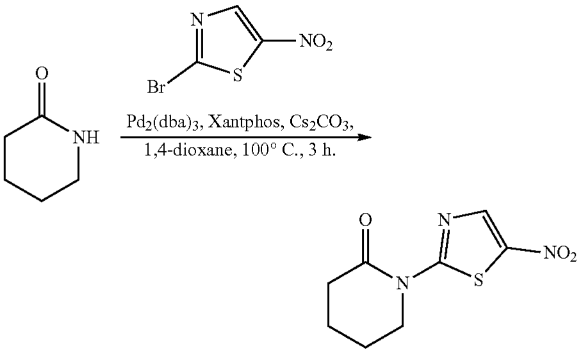

A solution of piperidin-2-one (47.6 mg, 0.481 mmol), 2-bromo-5-nitrothiazole (100 mg, 0.481 mmol), $Pd_2(dba)_3$ (22 mg, 0.024 mmol), Xantphos (14 mg, 0.024 mmol) and $Cs_2CO_3$ (314 mg, 0.962 mmol) in 1,4-dioxane (5 mL) was stirred at 100° C. for 3 h under argon atmosphere. At rt, the mixture was diluted with water (20 mL) and extracted with EtOAc (3×50 mL). The combined organic layers were washed with brine (2×50 mL), dried over $Na_2SO_4$, filtered and concentrated under vacuum. The resulting residue was purified by silica gel column chromatography (petroleum ether:EtOAc=4:1) to give the title compound (20.6 mg, 18.9% yield) as yellow solid. $^1H$ NMR (400 MHz, DMSO- $d_6$): δ 8.69 (s, 1H), 4.10 (t, J=6.0 Hz, 2H), 2.69 (t, J=6.8 Hz, 2H), 1.98-1.92 (m, 2H), 1.87-1.81 (m, 2H). MS (ESI) m/z: 228.1 $[M+H]^+$.

Example 091. 1-(5-Nitrothiazol-2-yl)azepan-2-one (B-100)

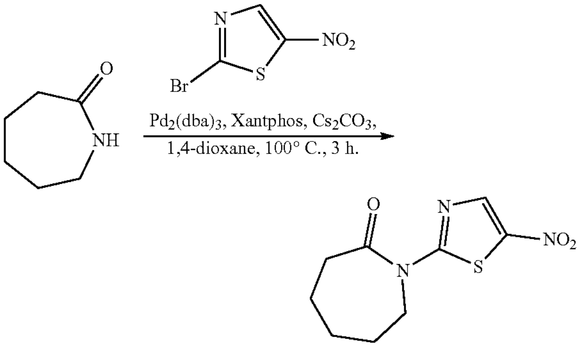

A solution of azepan-2-one (163 mg, 1.44 mmol), 2-bromo-5-nitrothiazole (300 mg, 1.44 mmol), $Pd_2(dba)_3$ (66 mg, 0.072 mmol), Xantphos (41.7 mg, 0.072 mmol) and $Cs_2CO_3$ (939 mg, 2.88 mmol) in 1,4-dioxane (15 mL) was stirred at 100° C. for 3 h under argon atmosphere. At rt, the mixture was diluted with water (20 mL) and extracted with EtOAc (3×50 mL). The combined organic layers were washed with brine (2×50 mL), dried over $Na_2SO_4$, filtered and concentrated under vacuum. The resulting residue was purified by silica gel column chromatography (petroleum ether:EtOAc=4:1) to give the title compound (48.9 mg, 14.1% yield) as yellow solid. $^1H$ NMR (400 MHz, DMSO-$d_6$): δ 8.66 (s, 1H), 4.49-4.48 (m, 2H), 2.91-2.89 (m, 2H), 1.75-1.73 (m, 6H). MS (ESI) m/z: 242.0 $[M+H]^+$.

Example 092. 2-Ethoxy-N-methyl-N-(5-nitrothiazol-2-yl)benzamide (B-102)

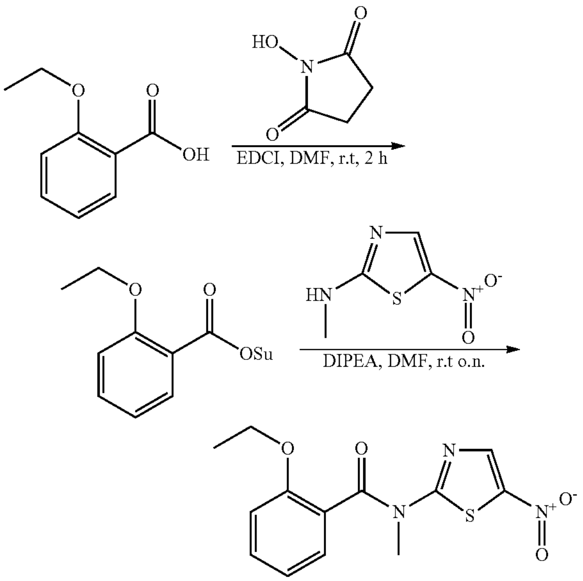

Step 1. Synthesis of 2,5-dioxopyrrolidin-1-yl 2-ethoxybenzoate

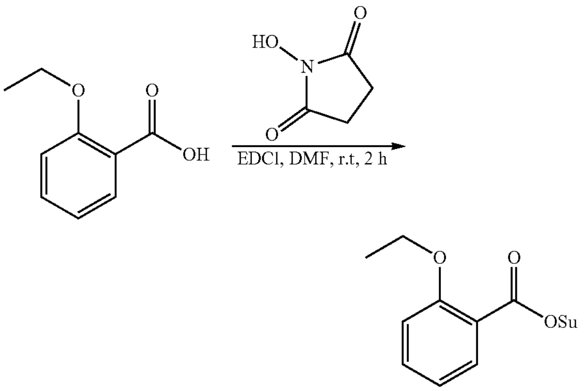

A solution of 2-ethoxybenzoic acid (1.00 g, 6.02 mmol), EDCI (2.30 g 12.0 mmol) and 1-hydroxypyrrolidine-2,5-dione (1.38 g 12.0 mmol) in DMF (20 mL) was stirred at rt 2 h. The reaction mixture was diluted with EtOAc (100 mL), washed with brine, dried over $Na_2SO_4$, filtered and concentrated under vacuum. The resulting residue was purified by silica gel column chromatography (petroleum ether: EtOAc=6:1) to give the title compound (750 mg, 47.3% yield) as white solid.

Step 2. Synthesis of 2-ethoxy-N-methyl-N-(5-nitrothiazol-2-yl)benzamide

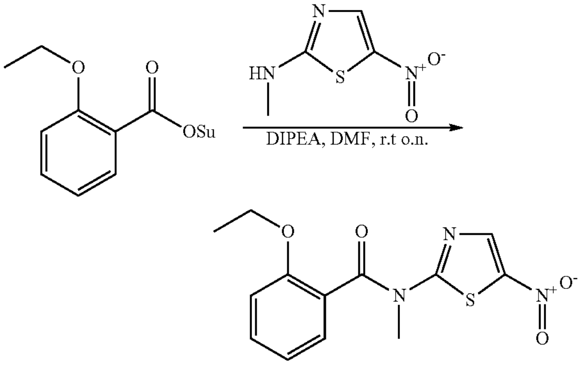

A solution of 2,5-dioxopyrrolidin-1-yl 2-ethoxybenzoate (100 mg, 0.380 mmol), DIPEA (0.2 mL) and N-methyl-5-nitrothiazol-2-amine (60 mg, 0.380 mmol) in DMF (5 mL) was stirred at rt overnight. The mixture was diluted with EtOAc (30 mL), washed with brine, dried over $Na_2SO_4$, filtered and concentrated under vacuum. The resulting residue was purified by silica gel column chromatography (petroleum ether:EtOAc=6:1) to give the title compound (55.0 mg, 47.1% yield) as white solid. $^1H$ NMR (400 MHz, DMSO-$d_6$): δ 8.75 (s, 1H), 7.56-7.53 (m, 1H), 7.47-7.45 (m, 1H), 7.21 (d, J=8.4 Hz, 1H), 7.10 (t, J=7.4 Hz, 1H), 4.15 (q, J=6.8 Hz, 3H), 3.46 (s, 3H), 1.25 (t, J=7.0 Hz, 3H). MS (ESI) m/z: 308.3 $[M+H]^+$.

Example 093. 2-Isobutoxy-N-methyl-N-(5-nitrothiazol-2-yl)benzamide (B-103)

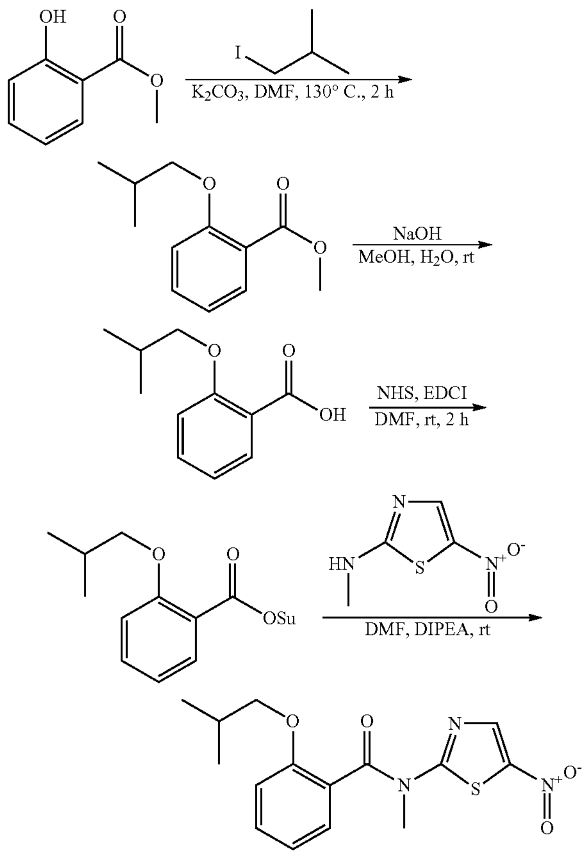

Step 1. Synthesis of methyl 2-isobutoxybenzoate

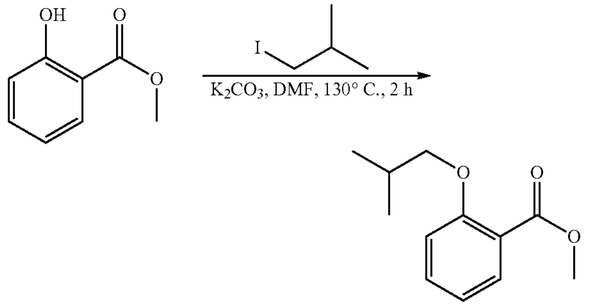

A solution of methyl 2-hydroxybenzoate (2.00 g, 13.2 mmol), 1-iodo-2-methylpropane (3.60 g 19.6 mmol) and $K_2CO_3$ (3.60 g, 26.1 mmol) in DMF (20 mL) was stirred at 130° C. for 2 h. At rt, the mixture was diluted with EtOAc (40 mL), washed with brine, dried over $Na_2SO_4$, filtered and concentrated. The resulting residue was purified by silica gel column chromatography (petroleum ether:EtOAc=6:1) to give the title compound (260 mg, 9.50% yield) as white solid. MS (ESI) m/z: 209.5 $[M+H]^+$.

Step 2. Synthesis of 2-isobutoxybenzoic acid

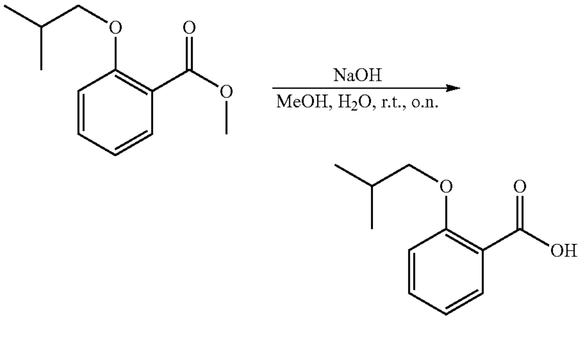

A solution of methyl 2-isobutoxybenzoate (260 mg, 1.25 mmol) and NaOH (500 mg, 12.5 mmol) in MeOH (5 mL)/water (1 mL) was stirred at rt overnight. After the pH of the reaction mixture was adjusted to 5 with aq. 1 N HCl, the mixture was extracted with EtOAc (3×20 mL). The combined organic layers were washed with brine, dried over $Na_2SO_4$, filtered and concentrated under vacuum to give the title compound (200 mg, crude) as gray solid, which was used in the next step without further purification.

Step 3. Synthesis of 2,5-dioxopyrrolidin-1-yl 2-isobutoxybenzoate

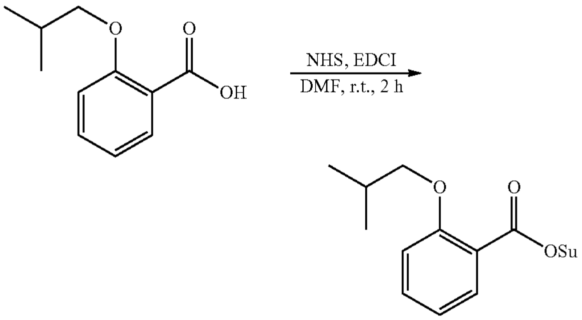

A solution of 2-isobutoxybenzoic acid (200 mg, crude), NHS (177 mg, 1.54 mmol) and EDCI (300 mg 0.0157 mmol) in DMF was stirred at rt for 2 h. The reaction mixture was diluted with EtOAc (30 mL), washed with brine, dried over $Na_2SO_4$, filtered and concentrated under vacuum. The resulting residue was purified by silica gel column chromatography (petroleum ether:EtOAc=6:1) to give the title compound (150 mg, 41.2%) as gray solid.

Step 4. Synthesis of 2-isobutoxy-N-methyl-N-(5-nitrothiazol-2-yl)benzamide

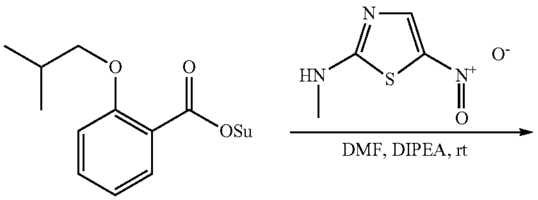

-continued

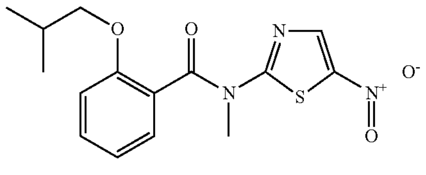

A solution of 2,5-dioxopyrrolidin-1-yl 2-isobutoxybenzoate (150 mg, 0.515 mmol), 2-(methyl-12-azanyl)-5-nitrothiazole (82.0 mg 0.515 mmol) and DIPEA (0.2 mL) in DMF (5 mL) was stirred at rt overnight. The reaction mixture was diluted with EtOAc (15 mL), washed with brine, dried over $Na_2SO_4$, filtered and concentrated under vacuum. The resulting residue was purified by silica gel column chromatography (petroleum ether:EtOAc=6:1) to give the title compound (80.0 mg, 46.3% yield) as yellow solid. $^1$H NMR (400 MHz, DMSO-$d_6$): δ 8.75 (s, 1H), 7.57-7.53 (m, 1H), 7.48-7.46 (m, 1H), 7.20 (d, J=8.4 Hz, 1H), 7.12 (t, J=7.4 Hz, 1H), 3.85 (d, J=6.4 Hz, 2H), 3.45 (s, 3H), 1.92-1.87 (m, 1H), 1.25 (d, J=6.8 Hz, 6H). MS (ESI) m/z: 336.4 $[M+H]^+$.

Example 094. N-Methyl-N-(5-nitrothiazol-2-yl)-2-propylbenzamide (B-104)

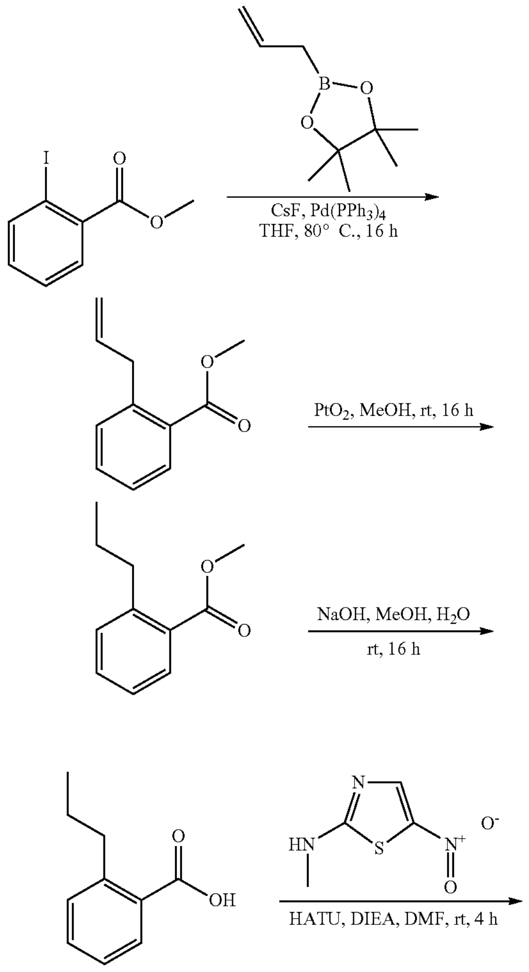

-continued

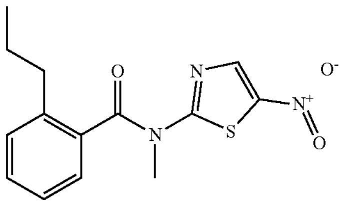

Step 1. Synthesis of methyl 2-allylbenzoate

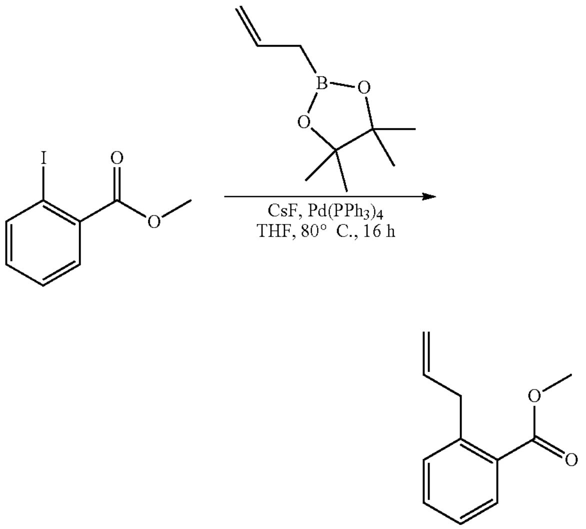

A solution of methyl 2-iodobenzoate (3.7 g, 14.1 mmol), 2-allyl-4,4,5,5-tetramethyl-1,3,2-dioxaborolane (2.37 g, 14.1 mmol), $Pd(PPh_3)_4$ (1.60 g, 1.41 mmol) and CsF (4.30 g, 28.2 mmol) in THF (100 mL) was stirred at 80° C. under Ar for 16 h. The mixture was concentrated under vacuum and purified by silica gel column chromatography (petroleum ether:EtOAc=10:1) to give the tide compound (2.80 g, crude) as yellow solid. MS (ESI) m/z: 177.2 $[M+H]^+$.

Step 2. Synthesis of methyl 2-propylbenzoate

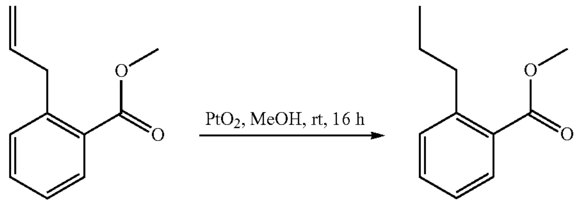

A solution of methyl 2-allylbenzoate (2.8 g, 15.9 mmol) and $PtO_2$ (0.36 g, 15.9 mmol) in MeOH (200 mL) was stirred at rt for 16 h. The mixture was filtered and the filtrate was concentrated under vacuum to give the title compound (2.0 g, 71.0% over two steps) as yellow solid.

Step 3. Synthesis of 2-propylbenzoic acid

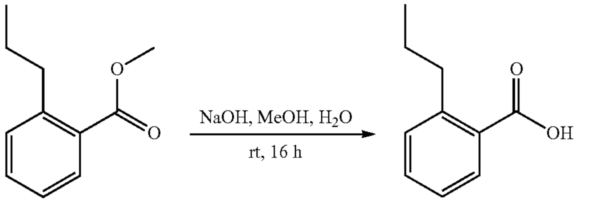

To a solution of methyl 2-propylbenzoate (2.0 g, 11.2 mmol) in MeOH (100 mL) and $H_2O$ (10 mL) was added NaOH (4.50 g, 112.4 mmol). After being stirred at rt for 16 h, the mixture was acidified (pH=4-5) with 1 N HCl. The mixture was extracted with EtOAc (3×30 mL). The combined organic layers were washed with brine (3×30 mL), dried over $Na_2SO_4$, filtered and concentrated under vacuum to give the title compound (4.10 g, 97% yield) as yellow solid, which was used in the next step without further purification. MS (ESI) m/z: 163.2 $[M-H]^-$.

Step 4. Synthesis of N-methyl-N-(5-nitrothiazol-2-yl)-2-propylbenzamide

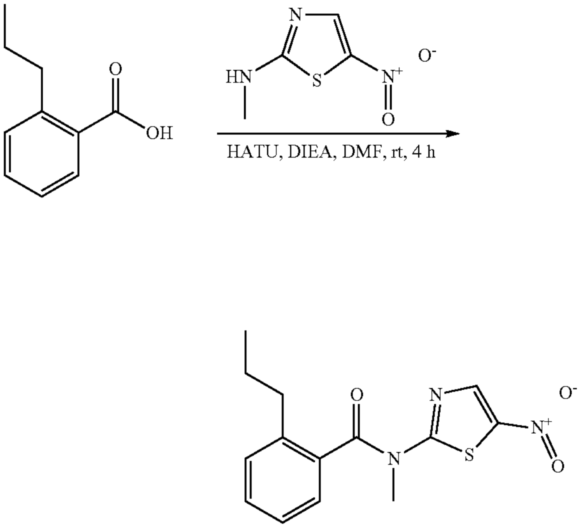

A solution of 2-propylbenzoic acid (200 mg, 1.22 mmol), N-methyl-5-nitrothiazol-2-amine (193 mg, 1.22 mmol), HATU (926 mg, 2.44 mmol) and DIEA (314 mg, 2.44 mmol) in DMF (10 mL) was stirred at rt for 4 h. After the mixture was diluted with $H_2O$ (30 mL), the mixture was extracted with EtOAc (3×30 mL). The combined organic layers were washed with brine (3×30 mL), dried over $Na_2SO_4$, filtered and concentrated under vacuum. The resulting residue was purified by silica gel column chromatography (petroleum ether:EtOAc=10:1) to give the title compound (120 mg, 32% yield) as yellow solid. $^1H$ NMR (400 MHz, DMSO-$d_6$): δ 8.78 (s, 1H), 7.53-7.36 (m, 4H), 3.43 (s, 3H), 2.52-2.50 (m, 2H), 1.58-1.52 (m, 2H), 0.84 (t, J=7.2 Hz, 3H). MS (ESI) m/z: 306.0 $[M+H]^+$.

Example 095. 2-Isobutyl-N-methyl-N-(5-nitrothiazol-2-yl)benzamide (B-106)

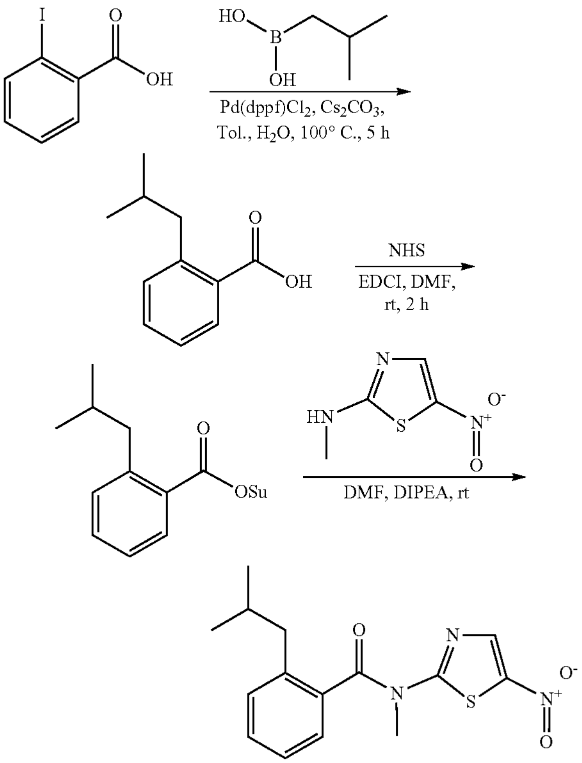

Step 1. Synthesis of 2-isobutylbenzoic acid

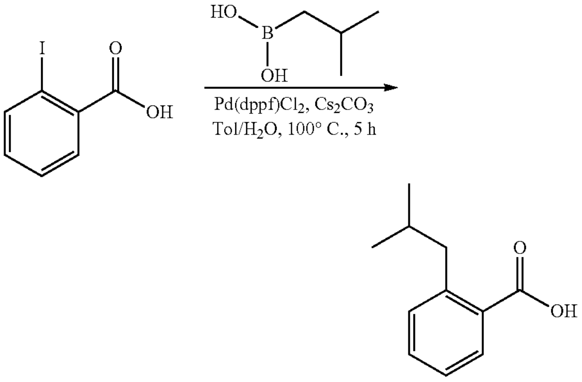

A solution of 2-iodobenzoic acid (2.0 g, 8.06 mmol), isobutylboronic acid (1.23 g, 12.1 mmol), Pd(dppf)$Cl_2$ (177 mg, 0.242 mmol) and $Cs_2CO_3$ (5.25 g, 16.1 mmol) in toluene/water (30 mL, v/v=10:1) was stirred at 100° C. for 5 h under argon atmosphere. At rt, the reaction mixture was diluted with EtOAc (50 mL), washed with brine, dried over $Na_2SO_4$, filtered and concentrated under vacuum. The resulting residue was purified by silica gel column chromatography (DCM:MeOH=10:1) to give the title compound (200 mg, 13.9% yield) as white solid. MS (ESI) m/z: 177.3 $[M-H]^-$.

Step 2. Synthesis of 2,5-dioxopyrrolidin-1-yl 2-isobutylbenzoate

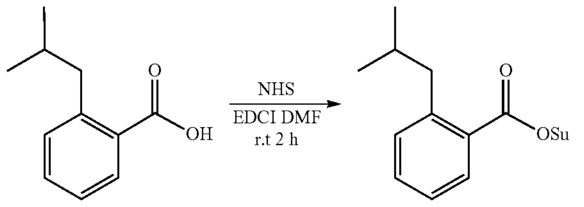

A solution of 2-isobutylbenzoic acid (100 mg, 0.561 mmol), EDCI (217 mg, 1.14 mmol) and NHS (130 mg, 1.13 mmol) in DMF (2 mL) was stirred at rt for 2 h. The reaction mixture was diluted with EtOAc (15 mL), washed with brine, dried over $Na_2SO_4$, filtered and concentrated. The resulting residue was purified by silica gel column chromatography (petroleum ether:EtOAc=1:1) to give the title compound (90 mg, 58.2% yield) as white solid.

Step 3. Synthesis of 2-isobutyl-N-methyl-N-(5-nitrothiazol-2-yl)benzamide

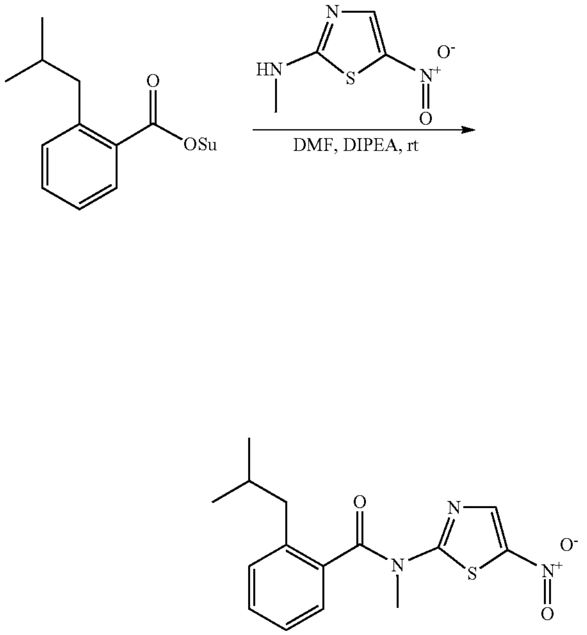

A solution of 2,5-dioxopyrrolidin-1-yl 2-isobutylbenzoate (90 mg, 0.327 mmol), N-methyl-5-nitrothiazol-2-amine (52 mg 0.327 mmol) and DIPEA (0.2 mL) in DMF (5 mL) was stirred at rt overnight. The reaction mixture was diluted with EtOAc (15 mL), washed with brine, dried over $Na_2SO_4$, filtered and concentrated. The resulting residue was purified by silica gel column chromatography (petroleum ether: EtOAc=1:1) to give the title compound (22.5 mg, 21.5% yield) as yellow solid. $^1H$ NMR (400 MHz, DMSO-$d_6$): δ 8.78 (s, 1H), 7.53-7.49 (m, 2H), 7.41-7.36 (m, 2H), 3.43 (s, 3H), 2.48-2.41 (m, 2H), 1.84-1.77 (m, 1H), 0.81 (d, J=6.4 Hz, 6H). MS (ESI) m/z: 320.1 [M+H]$^+$

Example 096. 5-(Butylamino)-N-(5-nitrothiazol-2-yl)-[1,1'-biphenyl]-2-carboxamide (B-110)

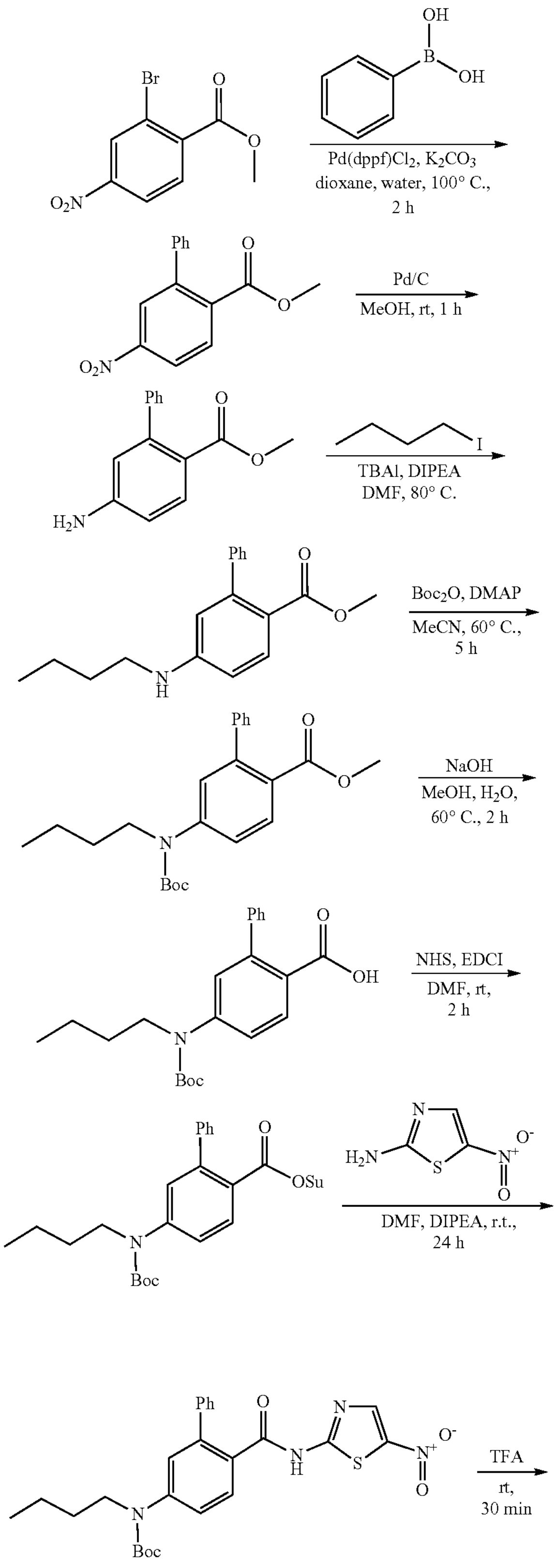

-continued

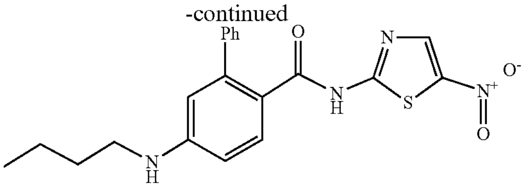

Step 1. Synthesis of methyl 5-nitro-[1,1'-biphenyl]-2-carboxylate

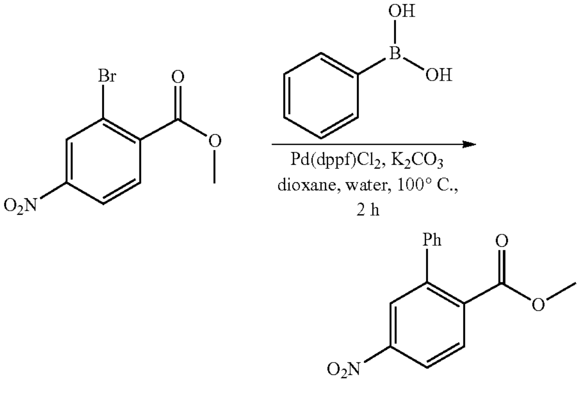

A solution of methyl 2-bromo-4-nitrobenzoate (2.00 g, 7.69 mmol), phenylboronic acid (1.41 g, 11.5 mmol), Pd(dppf)$Cl_2$ (281 mg, 0.385 mmol) and $K_2CO_3$ (2.12 g, 15.4 mmol) in 1,4-dioxane (30 mL) and $H_2O$ (3 mL) was heated at 100° C. for 2 h under argon atmosphere. At rt, the mixture was diluted with EtOAc (100 mL), washed with brine, dried over $Na_2SO_4$, filtered and concentrated. The resulting residue was purified by silica gel column chromatography (petroleum ether:EtOAc=10:1) to give the title compound (1.70 g, 85.9% yield) as white solid.

Step 2. Synthesis of methyl 5-amino-[1,1'-biphenyl]-2-carboxylate

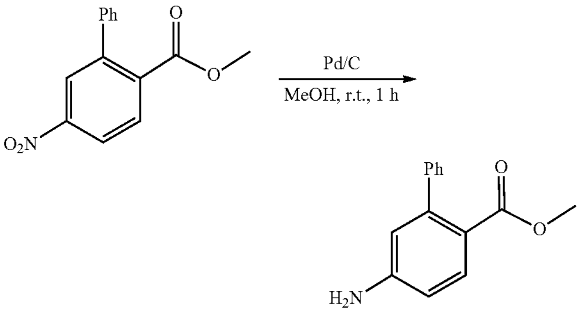

A solution of methyl 5-nitro-[1,1'-biphenyl]-2-carboxylate (1.70 g, 6.61 mmol) and wet 10% Pd/C (200 mg) in MeOH (20 mL) was stirred at rt for 1 h under $H_2$ atmosphere. The mixture was filtered and the filtrate was concentrated to give the title compound (1.50 g, crude) as white solid, which was used in the next step without further purification. MS (ESI) m/z: 228.2 $[M+H]^+$.

Step 3. Synthesis of methyl 5-(butylamino)-[1,1'-biphenyl]-2-carboxylate

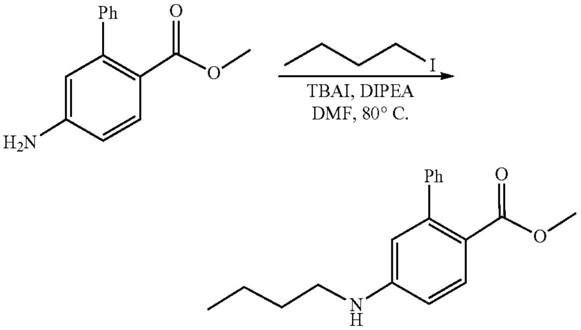

A solution of methyl 5-amino-[1,1'-biphenyl]-2-carboxylate (1.50 g, crude), DIPEA (2.56 g, 19.8 mmol), TBAI (2.44 g, 6.61 mmol) and 1-iodobutane (6.09 g, 33.1 mmol) in DMF (30 mL) was heated at 80° C. overnight. At rt, the mixture was diluted with EtOAc (50 mL) and washed with brine. The organic phase was dried over $Na_2SO_4$, filtered and concentrated under vacuum. The resulting residue was purified by silica gel column chromatography (petroleum ether:EtOAc=6:1) to give the title compound (1.20 g, 64.1% yield) as white solid. MS (ESI) m/z: 284.4 $[M+H]^+$.

Step 4. Synthesis of methyl 5-((tert-butoxycarbonyl)(butyl)amino)-[1,1'-biphenyl]-2-carboxylate

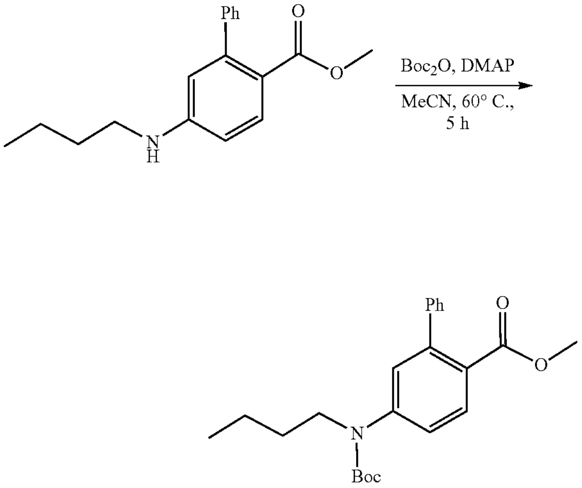

To a solution of 5-(butylamino)-[1,1'-biphenyl]-2-carboxylate (1.20 g, 4.23 mmol) and DMAP (517 mg, 4.23 mmol) in MeCN (20 mL) was added di-tert-butyl dicarbonate (4.62 g, 21.2 mmol) at 60° C. After being stirred at 60° C. for 2 h, the mixture was cooled to rt and diluted with EtOAc (50 mL). The organic phase was dried over $Na_2SO_4$, filtered and concentrated. The resulting residue was purified by silica gel column chromatography (petroleum ether: EtOAc=20:1) to give the title compound (1.20 g, 74.0% yield) as white solid. MS (ESI) m/z: 284.1 $[M+H-Boc]^+$.

Step 5. Synthesis of 5-((tert-butoxycarbonyl)(butyl) amino)-[1,1'-biphenyl]-2-carboxylic acid

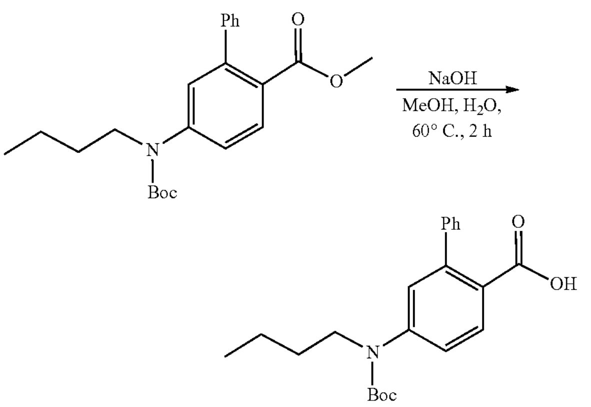

A solution of methyl 5-((tert-butoxycarbonyl)(butyl) amino)-[1,1'-biphenyl]-2-carboxylate (1.20 g, 3.13 mmol) and NaOH (628 mg, 15.7 mmol) in MeOH (10 mL) and $H_2O$ (10 mL) was heated at 60° C. for 2 h. At rt, the mixture was acidified (pH=5.0) with 1 N HCl. The mixture was extracted with EtOAc (2x30 mL). The combined organic phase was dried over $Na_2SO_4$, filtered and concentrated under vacuum to give the title compound (900 mg, 77.8% yield) as white solid. MS (ESI) m/z: 314.4 $[M+H]^+$.

Step 6. Synthesis of 2,5-dioxopyrrolidin-1-yl 5-((tert-butoxycarbonyl)(butyl)amino)-[1,1'-biphenyl]-2-carboxylate

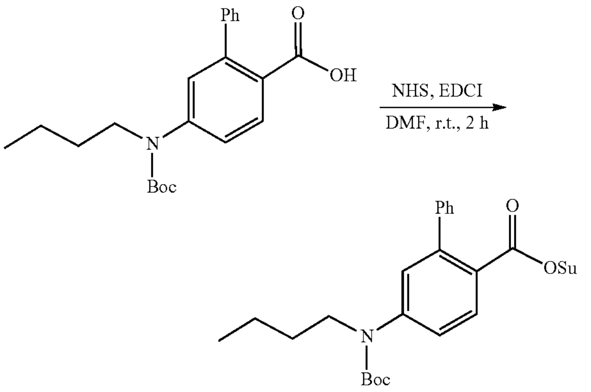

A solution of 5-((tert-butoxycarbonyl)(butyl)amino)-[1, 1'-biphenyl]-2-carboxylic acid, (300 mg, 0.812 mmol), EDCI (311 mg, 1.62 mmol) and N-hydroxysuccinimide (186 mg, 1.62 mmol) in DMF (10 mL) was stirred at rt for 2 h. Then, the mixture was diluted with EtOAc (30 mL) and washed with brine. The organic phase was dried over $Na_2SO_4$, filtered and concentrated under vacuum. The resulting residue was purified by silica gel column chromatography (petroleum ether:EtOAc=10:1) to give the title compound (300 mg, 79.2% yield) as white solid. MS (ESI) m/z: 489.5 $[M+H]^+$.

Step 7. Synthesis of tert-butyl butyl(6-((5-nitrothiazol-2-yl)carbamoyl)-[1,1'-biphenyl]-3-yl)carbamate

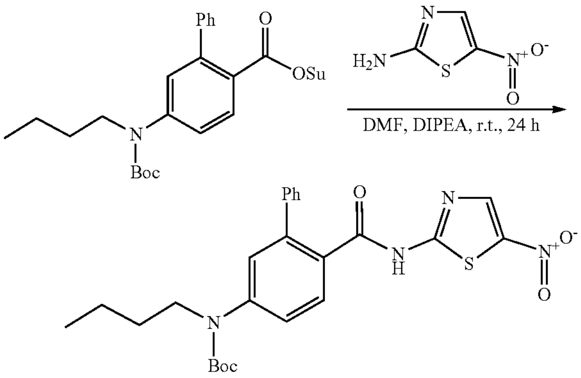

To a solution of 2,5-dioxopyrrolidin-1-yl 5-((tert-butoxycarbonyl)(butyl)amino)-[1,1'-biphenyl]-2-carboxylate (300 mg, 0.643 mmol), DIPEA (416 mg, 3.22 mmol) and 5-nitrothiazol-2-amine (467 mg, 3.22 mmol) in DMF (10 mL) was stirred at rt for 24 h. Then, the mixture was diluted with EtOAc (30 mL) and washed with brine. The organic phase was dried over $Na_2SO_4$, filtered and concentrated under vacuum. The resulting residue was purified by silica gel column chromatography (petroleum ether:EtOAc=10:1) to give the title compound (50 mg, 15.7% yield) as white solid. MS (ESI) m/z: 497.1 $[M+H]^+$.

Step 8. Synthesis of 5-(butylamino)-N-(5-nitrothiazol-2-yl)-[1,1'-biphenyl]-2-carboxamide

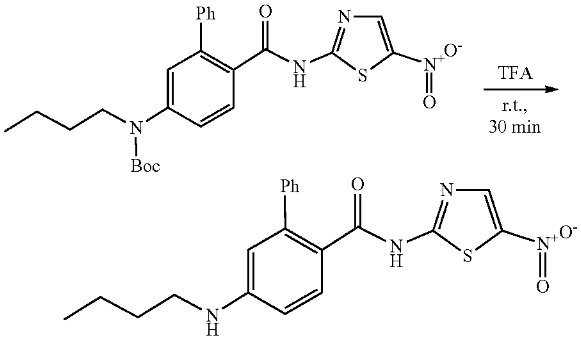

A solution of tert-butyl butyl(6-((5-nitrothiazol-2-yl)carbamoyl)-[1,1'-biphenyl]-3-yl)carbamate (50 mg, 0.100 mmol) in TFA (2 mL) was stirred at rt for 30 min. Then, the mixture was concentrated under vacuum. The resulting residue was purified by pre-HPLC to give the title compound (9.25 mg, 23.3% yield) as yellow solid. $^1H$ NMR (400 MHz, DMSO-$d_6$): δ 12.96 (s, 1H), 8.58 (s, 1H), 7.56 (d, J=8.4 Hz, 1H), 7.38-7.30 (m, 3H), 7.25-7.24 (m, 2H), 6.62-6.60 (m, 1H), 6.52-6.49 (m, 2H), 3.11-3.07 (m, 2H), 1.60-1.52 (m, 2H), 1.44-1.35 (m, 2H), 0.93-0.90 (m, 3H). MS (ESI) m/z: 397.5 $[M+H]^+$.

Example 097. 2-Acetamido-N-(pyridin-4-yl)benzamide (B-121)

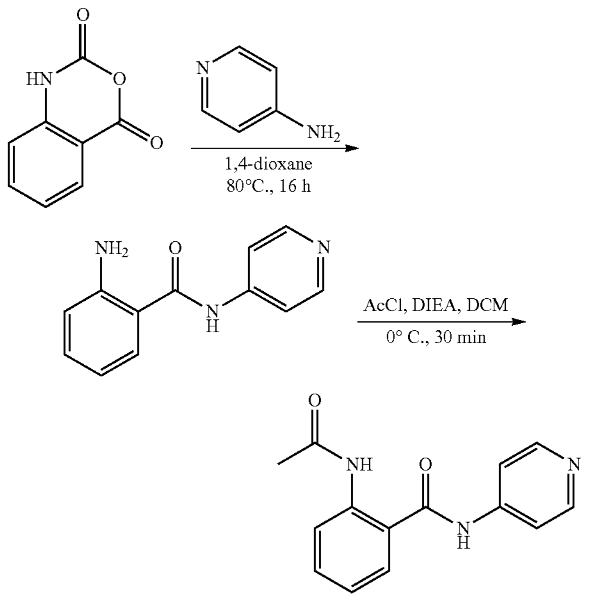

Step 1. Synthesis of 2-amino-N-(pyridin-4-yl)benzamide

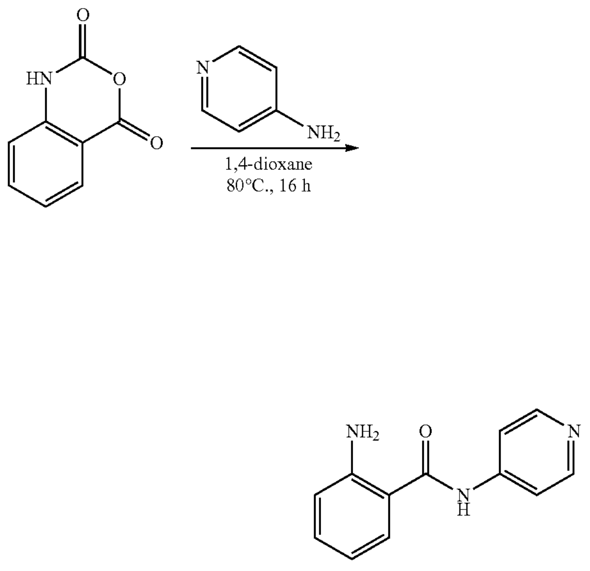

A solution of 1H-benzo[d][1,3]oxazine-2,4-dione (350 mg, 2.15 mmol) and pyridin-4-amine (400 mg, 4.29 mmol) in 1,4-dioxane (10 mL) was stirred at 80° C. for 16 h. At rt, the mixture was concentrated under vacuum. The resulting residue was purified by silica gel column chromatography (petroleum ether:EtOAc=1:1) to give the title compound (250 mg, 55.0% yield) as yellow solid. MS (ESI) m/z: 214.2 $[M+H]^+$.

Step 2. Synthesis of 2-acetamido-N-(pyridin-4-yl)benzamide

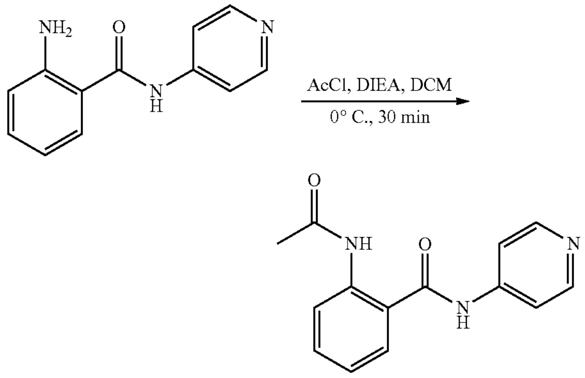

To a solution of 2-amino-N-(pyridin-4-yl)benzamide (250 mg, 1.17 mmol) and DIEA (301 mg, 2.33 mmol) in DCM (5 mL) was added acetyl chloride (181 mg, 2.33 mmol) at 0° C. After being stirred at 0° C. for 30 min, the mixture was diluted with $H_2O$ (30 mL) and EtOAc (3×30 mL), washed with brine (3×30 mL), dried over $Na_2SO_4$, filtered and concentrated under vacuum. The resulting residue was purified by pre-HPLC to give the title compound (150 mg, 50% yield) as yellow solid. $^1H$ NMR (400 MHz, DMSO-$d_6$): δ 11.07 (s, 1H), 10.18 (s, 1H), 8.56 (d, J=6.4 Hz, 2H), 7.90 (d, J=6.8 Hz, 2H), 7.82 (d, J=8.0 Hz, 1H), 7.70 (d, J=7.6 Hz, 1H), 7.54 (t, J=7.2 Hz, 1H), 7.26 (t, J=7.6 Hz, 1H), 2.02 (s, 3H). MS (ESI) m/z: 256.4 $[M+H]^+$.

Example 098. 5-(Butylamino)-N-(4-methyl-5-nitrothiazol-2-yl)-[1,1'-biphenyl]-2-carboxamide (B-111)

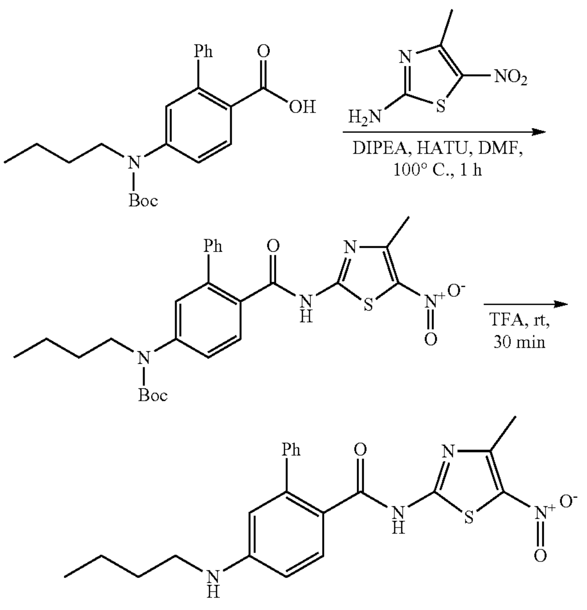

Step 1. Synthesis of tert-butyl butyl(6-((4-methyl-5-nitrothiazol-2-yl)carbamoyl)-[1,1'-biphenyl]-3-yl) carbamate

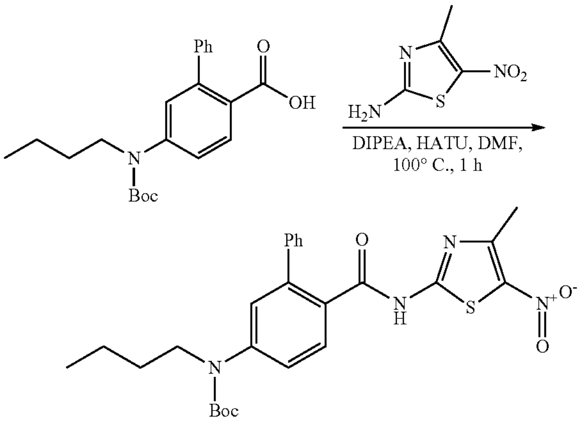

To a solution of 5-((tert-butoxycarbonyl)(butyl)amino)-[1,1'-biphenyl]-2-carboxylic acid (200 mg, 0.541 mmol), 4-methyl-5-nitrothiazol-2-amine (258 mg, 1.62 mmol), HATU (410 mg, 1.08 mmol) in DMF (10 mL) at 100° C. was added DIPEA (209 mg, 1.62 mmol). After being heated at 100° C. for 1 h, the mixture was cooled to rt and diluted with EtOAc (100 mL). The organic phase was washed with brine, dried over $Na_2SO_4$, filtered and concentrated under vacuum to give the title compound (400 mg, crude) as yellow oil, which was used in the next step without further purification. MS (ESI) m/z: 511.2 $[M+H]^+$.

Step 2. Synthesis of 5-(butylamino)-N-(4-methyl-5-nitrothiazol-2-yl)-[1,1'-biphenyl]-2-carboxamide

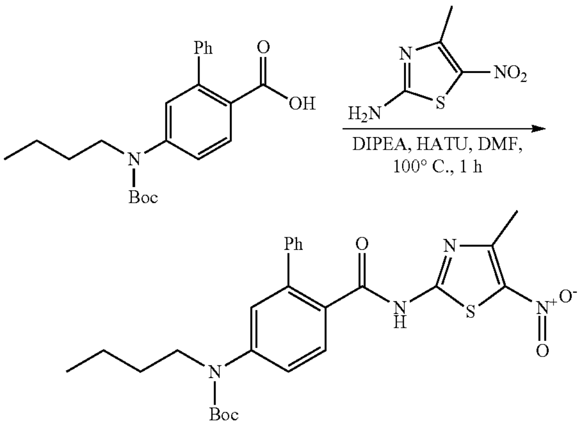

A solution of tert-butyl butyl(6-((4-methyl-5-nitrothiazol-2-yl)carbamoyl)-[1,1'-biphenyl]-3-yl)carbamate (400 mg, crude) in TFA (2 mL) was stirred at rt for 30 min. Then, the mixture was concentrated under vacuum. The resulting residue was purified by pre-HPLC to give the title compound (9.25 mg, 23.3% yield) as yellow solid. $^1H$ NMR (400 MHz, DMSO-$d_6$): δ 12.88 (s, 1H), 7.53 (d, J=8.8 Hz, 1H), 7.37-7.28 (m, 3H), 7.24-7.23 (m, 2H), 6.61-6.59 (m, 1H), 6.52-6.49 (m, 2H), 3.10 (t, J=6.8 Hz, 2H), 2.63 (s, 3H), 1.56-1.51 (m, 2H), 1.41-1.34 (m, 2H), 0.91 (t, J=7.2 Hz, 3H). MS (ESI) m/z: 411.4 $[M+H]^+$.

Example 099. 5-(Butylamino)-N-(5-chloro-4-methylthiazol-2-yl)-[1,1'-biphenyl]-2-carboxamide (B-116)

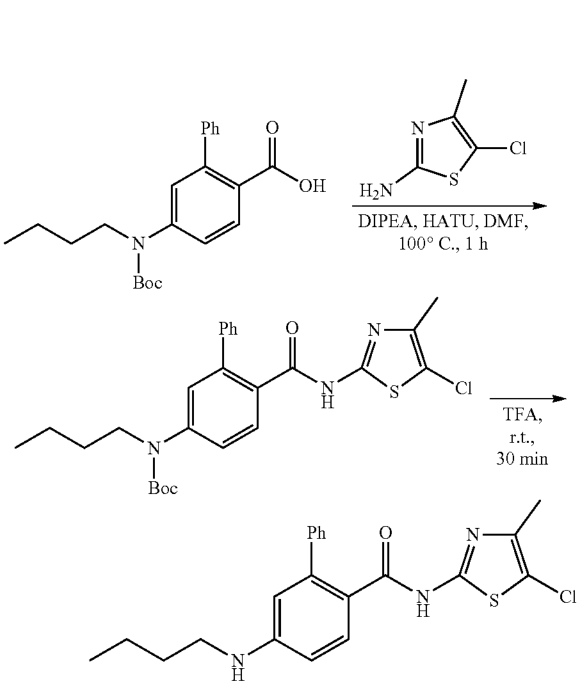

Step 1. Synthesis of tert-butyl butyl(6-((5-chloro-4-methylthiazol-2-yl)carbamoyl)-[1,1'-biphenyl]-3-yl) carbamate

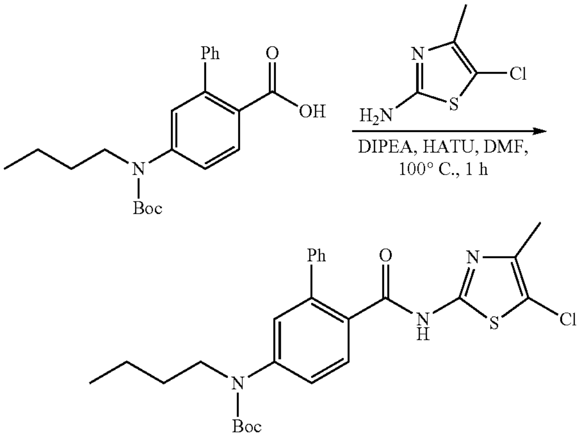

To a solution of 5-((tert-butoxycarbonyl)(butyl)amino)-[1,1'-biphenyl]-2-carboxylic acid (200 mg, 0.541 mmol), 5-chloro-4-methylthiazol-2-amine (81 mg, 0.541 mmol) and HATU (226 mg, 0.595 mmol) in DMF (10 mL) was added DIPEA (140 mg, 1.08 mmol) at 100° C. After being heated at 100° C. for 1 h, the mixture was cooled to rt and diluted with EtOAc (100 mL). The organic phase was washed with brine, dried over $Na_2SO_4$, filtered and concentrated under vacuum to give the title compound (300 mg, crude) as yellow oil, which was used in the next step without further purification. MS (ESI) m/z: 500.1 $[M+H]^+$.

Step 2. Synthesis of 5-(butylamino)-N-(5-chloro-4-methylthiazol-2-yl)-[1,1'-biphenyl]-2-carboxamide

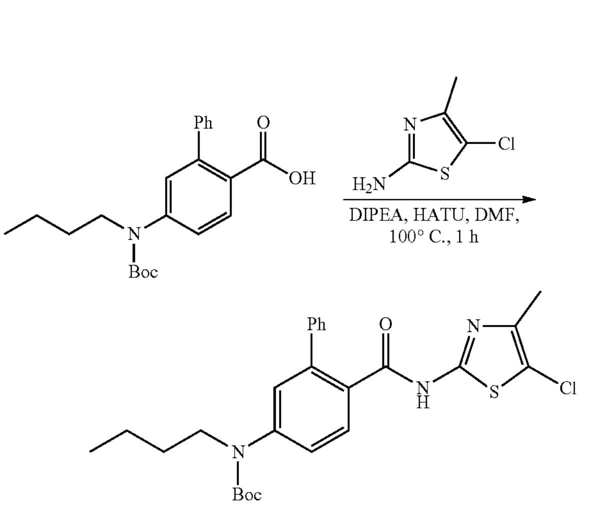

A solution of tert-butyl butyl(6-((5-chloro-4-methylthiazol-2-yl)carbamoyl)-[1,1'-biphenyl]-3-yl)carbamate (300 mg, crude) in TFA (2 mL) was stirred at rt for 30 min. Then, the mixture was concentrated under vacuum. The resulting residue was purified by pre-HPLC to give the title compound (10.1 mg, 3.63% yield) as off-white solid. $^1$H NMR (400 MHz, DMSO-$d_6$): δ 7.44-7.42 (m, 1H), 7.35-7.23 (m, 5H), 6.58-6.56 (m, 1H), 6.49 (d, J=1.6 Hz, 1H), 6.30-6.27 (m, 1H), 5.38 (brs, 1H), 3.10-3.06 (m, 2H), 2.17 (s, 3H), 1.56-1.51 (m, 2H), 1.41-1.36 (m, 2H), 0.91 (t, J=7.2 Hz, 3H). MS (ESI) m/z: 400.4 $[M+H]^-$.

Example 100. 5-(Butylamino)-N-(5-(trifluoromethyl)thiazol-2-yl)-[1,1'-biphenyl]-2-carboxamide (B-118)

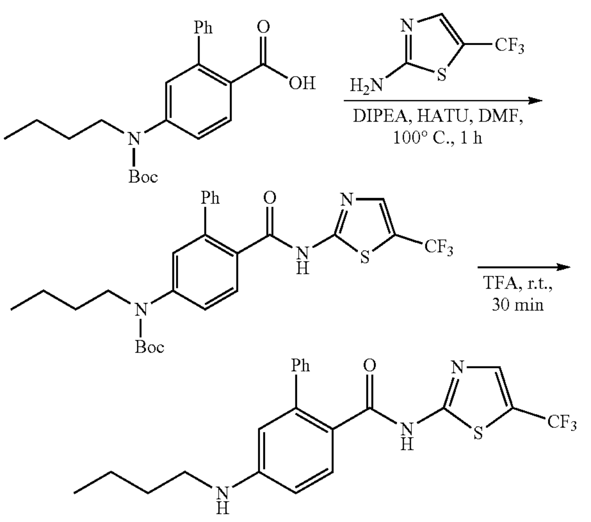

Step 1. Synthesis of tert-butyl butyl(6-((5-(trifluoromethyl)thiazol-2-yl)carbamoyl)-[1,1'-biphenyl]-3-yl)carbamate

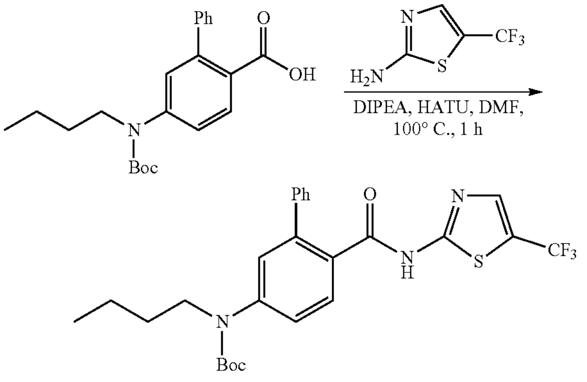

To a solution of 5-((tert-butoxycarbonyl)(butyl)amino)-[1,1'-biphenyl]-2-carboxylic acid (200 mg, 0.541 mmol), 5-(trifluoromethyl)thiazol-2-amine (91 mg, 0.541 mmol) and HATU (226 mg, 0.595 mmol) in DMF (10 mL) was added DIPEA (140 mg, 1.08 mmol) at 100° C. After being heated at 100° C. for 1 h, the mixture was cooled to rt and diluted with EtOAc (100 mL). The organic phase was washed with brine, dried over $Na_2SO_4$, filtered and concentrated under vacuum to give the title compound (300 mg, crude) as brown oil, which was used in the next step without further purification. MS (ESI) m/z: 520.2 $[M+H]^+$.

Step 2. Synthesis of 5-(butylamino)-N-(5-(trifluoromethyl)thiazol-2-yl)-[1,1'-biphenyl]-2-carboxamide

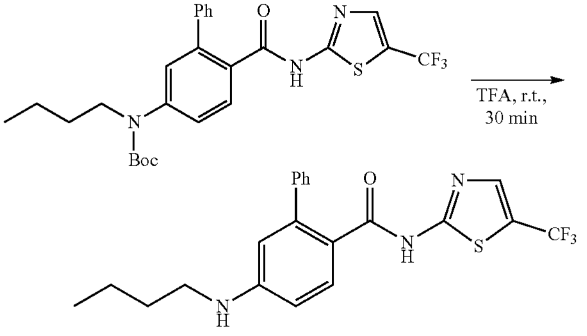

A solution of tert-butyl butyl(6-((5-(trifluoromethyl)thiazol-2-yl)carbamoyl)-[1,1'-biphenyl]-3-yl)carbamate (300 mg, crude) in TFA (2 mL) was stirred at rt for 30 min. Then the mixture was concentrated under vacuum. The resulting residue was purified by pre-HPLC to give the title compound (7.25 mg, 2.51% yield) as off-white solid. $^1$H NMR (400 MHz, DMSO-$d_6$): δ 10.91 (brs, 1H), 8.02 (s, 1H), 7.51 (d, J=8.4 Hz, 1H), 7.35-7.24 (m, 5H), 6.61-6.58 (m, 1H), 6.51 (s, 1H), 6.38 (t, J=4.8 Hz, 1H), 3.12-3.05 (m, 2H), 1.58-1.51 (m, 2H), 1.43-1.34 (m, 2H), 0.91 (t, J=7.2 Hz, 3H). MS (ESI) m/z: 420.4 $[M+H]^+$.

Example 101. 5-(Butylamino)-N-(5-cyanothiazol-2-yl)-[1,1'-biphenyl]-2-carboxamide (B-119)

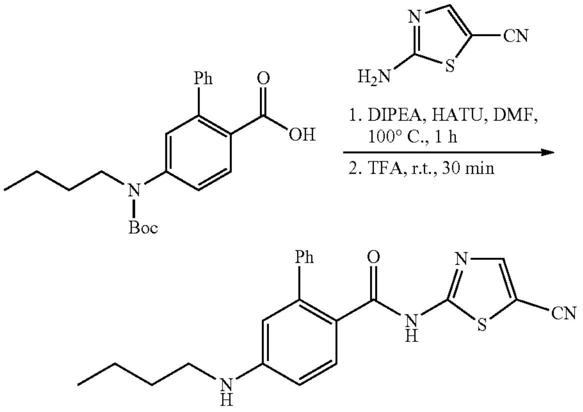

To a solution of 5-((tert-butoxycarbonyl)(butyl)amino)-[1,1'-biphenyl]-2-carboxylic acid (200 mg, 0.541 mmol), 2-aminothiazole-5-carbonitrile (68 mg, 0.541 mmol) and HATU (226 mg, 0.595 mmol) in DMF (3 mL) was added DIPEA (140 mg, 1.08 mmol) at 100° C. After the reaction was heated at 100° C. for 1 h, TFA (5 mL) was added. After being stirred at rt for 30 min, the mixture was concentrated under vacuum. The resulting residue was purified by pre-HPLC to give the title compound (14.0 mg, 5.28% yield) as off-white solid. $^1$H NMR (400 MHz, DMSO-$d_6$): δ 9.91 (brs, 1H), 8.24 (s, 1H), 7.55 (d, J=8.4 Hz, 1H), 7.34-7.22 (m, 5H), 6.59-6.57 (m, 1H), 6.49 (s, 1H), 6.33-6.31 (m, 1H), 3.11-3.07 (m, 2H), 1.58-1.51 (m, 2H), 1.43-1.34 (m, 2H), 0.91 (t, J=7.2 Hz, 3H). MS (ESI) m/z: 377.4 [M+H]$^+$.

Example 102. 2-Acetamido-N-(pyridin-2-yl)benzamide (B-123)

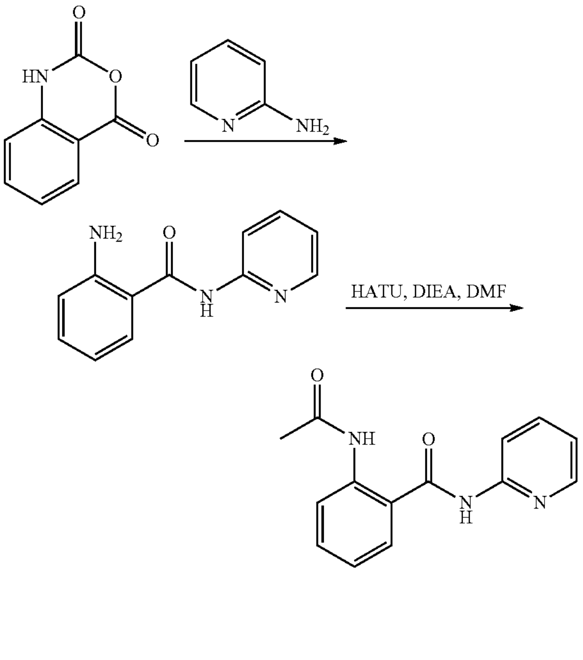

Step 1. Synthesis of 2-amino-N-(pyridin-2-yl)benzamide

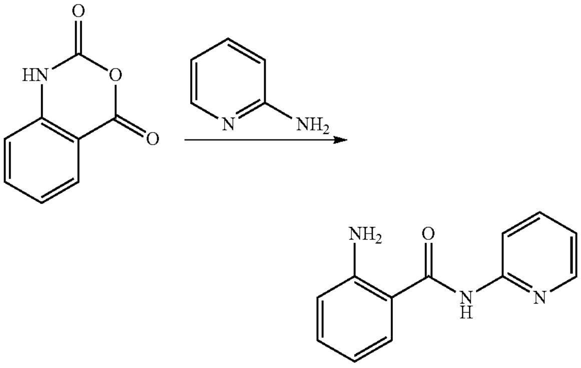

A solution of 1H-benzo[d][1,3]oxazine-2,4-dione (350 mg, 2.15 mmol) and pyridin-2-amine (400 mg, 4.29 mmol) in 1,4-dioxane (10 mL) was stirred at 80° C. for 16 h. At rt, the mixture was concentrated under vacuum. The resulting residue was purified by silica gel column chromatography (petroleum ether:EtOAc=1:1) to give the title compound (450 mg, 98.0% yield) as yellow solid. MS (ESI) m/z: 214.2 [M+H]$^+$.

Step 2. Synthesis of 2-acetamido-N-(pyridin-2-yl)benzamide

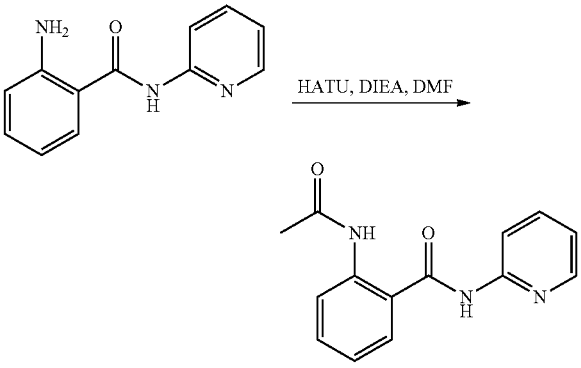

To a solution of 2-amino-N-(pyridin-2-yl)benzamide (100 mg, 0.47 mmol) AcOH (55 mg, 0.94 mmol) and HATU (355 mg, 0.94 mmol) in DMF (5 mL) was added DIEA (120 mg, 0.94 mmol) at 80° C. After being stirred at 80° C. for 30 min, the mixture was diluted with $H_2O$ (30 mL) and EtOAc (3×30 mL), washed with brine (3×30 mL), dried over $Na_2SO_4$, filtered and concentrated under vacuum. The resulting residue was purified by pre-HPLC to give the title compound (120 mg, 50% yield) as yellow solid. $^1$H NMR (400 MHz, DMSO-$d_6$): δ 8.38 (d, J=4.0 Hz, 1H), 8.12 (d, J=8.4 Hz, 1H), 8.01 (d, J=8.0 Hz, 1H), 7.91-7.71 (m, 2H), 7.50 (t, J=7.2 Hz, 1H), 7.28-7.10 (m, 2H), 6.03 (brs, 1H), 2.05 (s, 3H). MS (ESI) m/z: 256.2 [M+H]$^+$.

Example 103. 4-(Butylamino)-2-ethoxy-N-methyl-N-(5-nitrothiazol-2-yl)benzamide (B-107

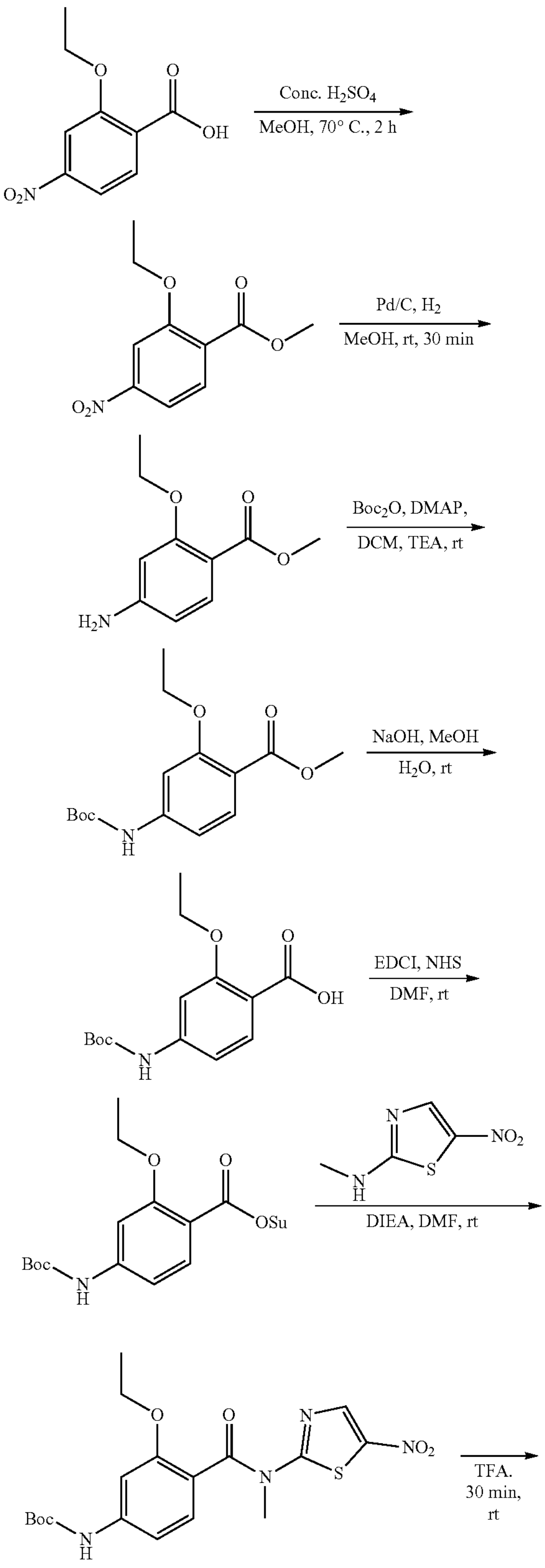

-continued

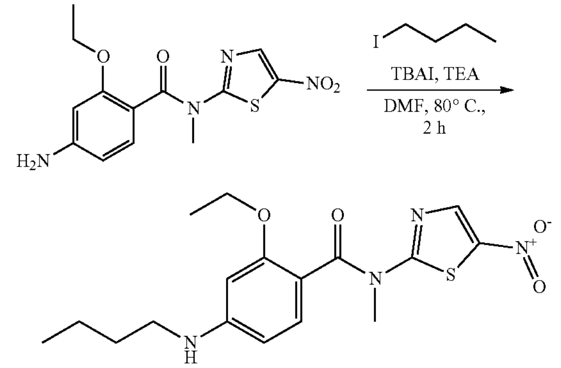

Step 1. Synthesis of methyl 2-ethoxy-4-nitrobenzoate

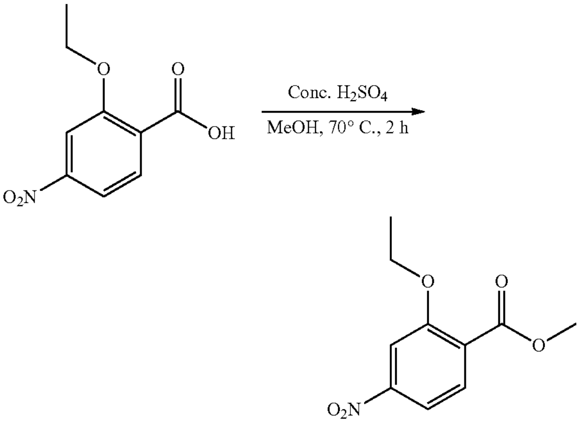

To a solution of 2-ethoxy-4-nitrobenzoic acid (1.50 g, 7.11 mmol) in MeOH (30 mL) was added conc. $H_2SO_4$ (3 mL) at rt. After being stirred at 70° C. for 2 h, the mixture was cooled to rt, diluted with water (100 mL) and extracted with EtOAc (2×100 mL). The combined organic phase was washed with brine (2×100 mL), dried over $Na_2SO_4$, filtered and concentrated under vacuum. The resulting residue was purified by silica gel column chromatography (petroleum ether:EtOAc=4:1) to give the title compound (1.50 g, 94.3% yield) as yellow solid. MS (ESI) m/z: 226.0 $[M+H]^+$.

Step 2. Synthesis of methyl 4-amino-2-ethoxybenzoate

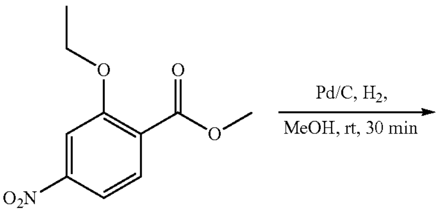

-continued

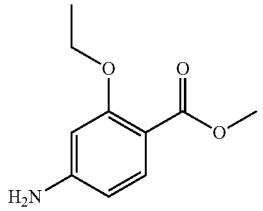

A mixture of methyl 2-ethoxy-4-nitrobenzoate (1.50 g, 6.67 mmol) and Pd/C (150 mg, 10% yield) in MeOH (30 mL) was stirred at rt for 30 min under $H_2$ atmosphere. The mixture was filtered and the filtrate was concentrated under vacuum to give the title compound (1.10 g, 84.6% yield) as gray solid. MS (ESI) m/z: 196.1 $[M+H]^+$.

Step 3. Synthesis of methyl 4-((tert-butoxycarbonyl)amino)-2-ethoxybenzoate

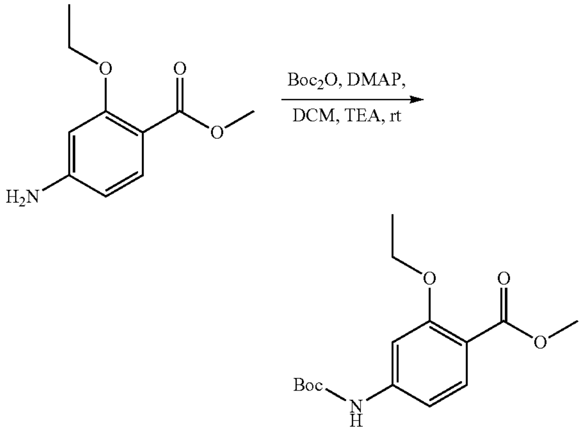

A solution of methyl 4-amino-2-ethoxybenzoate (1.00 g, 5.13 mmol), DMAP (621 mg, 5.13 mmol), $Et_3N$ (1.04 g, 10.26 mmol) and $Boc_2O$ (1.68 mg, 7.70 mmol) in MeOH (10 mL) was stirred at rt overnight. The mixture was diluted with water (50 mL) and extracted with DCM (2×50 mL). The combined organic phase was washed with brine (2×50 mL), dried over $Na_2SO_4$, filtered and concentrated under vacuum. The resulting residue was purified by silica gel column chromatography (petroleum ether:EtOAc=3:1) to give the title compound (1.10 g, 73.3% yield) as colorless oil. MS (ESI) m/z: 296.0 $[M+H]^+$.

Step 4. Synthesis of 4-((tert-butoxycarbonyl)amino)-2-ethoxybenzoic acid

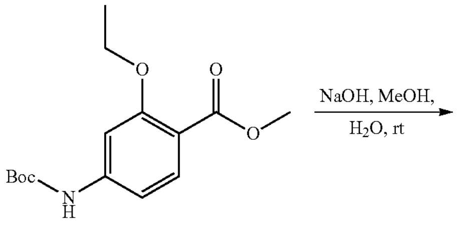

-continued

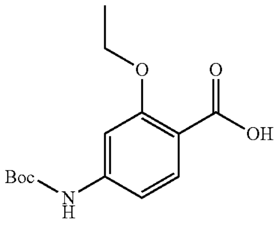

To a solution of methyl 4-((tert-butoxycarbonyl)amino)-2-ethoxybenzoate (900 mg, 3.05 mmol) in MeOH (30 mL) was added a solution of NaOH (183 mg, 4.58 mmol) in $H_2O$ (10 mL). After being stirred at rt overnight, the mixture was diluted with water (20 mL), acidified (pH=4) with 1 N HCl, extracted with EtOAc (2×50 mL). The combined organic layers were washed with brine (2×50 mL), dried over $Na_2SO_4$, filtered and concentrated under vacuum to give the title compound (850 mg, crude) as white solid, which was used in the next step without further purification. MS (ESI) m/z: 280.2 $[M-H]^-$.

Step 5. Synthesis of 2,5-dioxopyrrolidin-1-yl 4-((tert-butoxycarbonyl)amino)-2-ethoxybenzoate

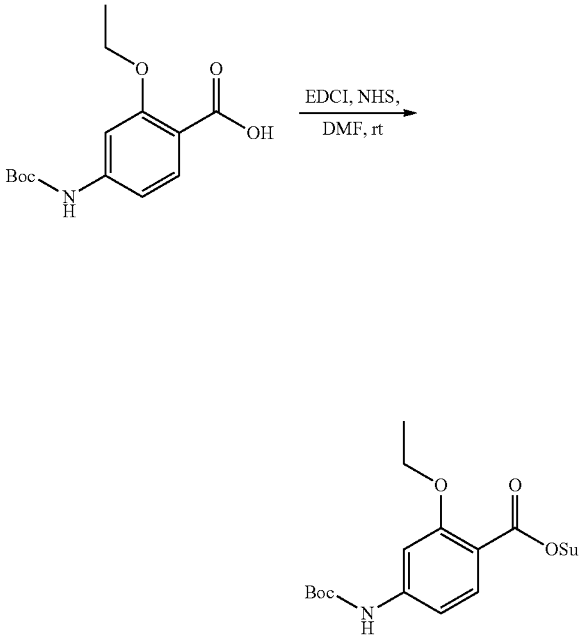

A solution of 4-((tert-butoxycarbonyl)amino)-2-ethoxybenzoic acid (850 mg, crude). EDCI (1.15 g, 6.02 mmol) and N-hydroxysuccinimide (700 mg, 6.02 mmol) in DMF (10 mL) was stirred at rt overnight. The mixture was diluted with water (50 mL) and extracted with EtOAc (2×50 mL). The combined organic phase was washed with brine (2×50 mL), dried over $Na_2SO_4$, filtered and concentrated. The resulting residue was purified by silica gel column chromatography (petroleum ether:EtOAc=3:1) to give the title compound (700 mg, 60.7% yield for two steps) as white solid. MS (ESI) m/z: 377.0 $[M-H]^-$.

Step 6. Synthesis of tert-butyl (3-ethoxy-4-(methyl (5-nitrothiazol-2-yl)carbamoyl)phenyl)carbamate

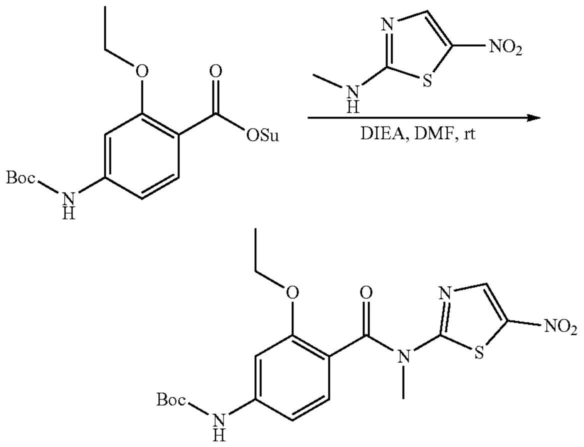

A solution of 2,5-dioxopyrrolidin-1-yl 4-((tert-butoxycarbonyl)amino)-2-ethoxybenzoate (400 mg, 1.06 mmol), N-methyl-5-nitrothiazol-2-amine (217 mg, 1.36 mmol) and DIEA (253 mg, 2.74 mmol) in DMF (5 mL) was stirred at it overnight. Then, the mixture was diluted with water (30 mL) and extracted with EtOAc (2×50 mL). The combined organic phase was washed with brine (2×50 mL), dried over $Na_2SO_4$, filtered and concentrated under vacuum. The resulting residue was purified by silica gel column chromatography (petroleum ether:EtOAc=2:1) to give the title compound (250 mg, 56.1% yield) as yellow solid. MS (ESI) m/z: 423.1 $[M+H]^+$.

Step 7. Synthesis of 4-amino-2-ethoxy-N-methyl-N-(5-nitrothiazol-2-yl)benzamide

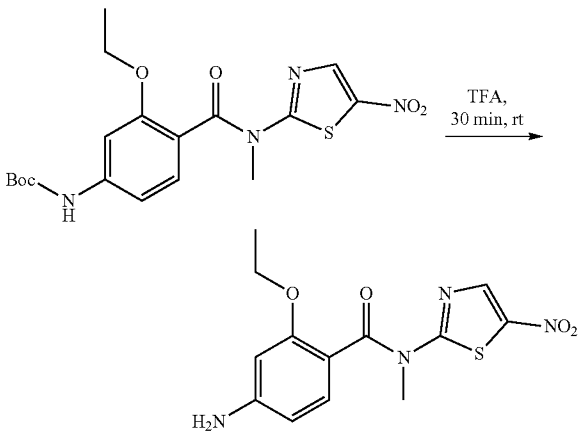

A solution of tert-butyl (3-ethoxy-4-(methyl(5-nitrothiazol-2-yl)carbamoyl)phenyl)carbamate (50.0 mg, 0.118 mmol) in TFA (2 mL) was stirred at it for 30 min. Then, the mixture was concentrated under vacuum to give the title compound (38 mg, crude), which was used directly next step. MS (ESI) m/z: 323.0 $[M+H]^+$.

Step 8. Synthesis of 4-(butylamino)-2-ethoxy-N-methyl-N-(5-nitrothiazol-2-yl)benzamide

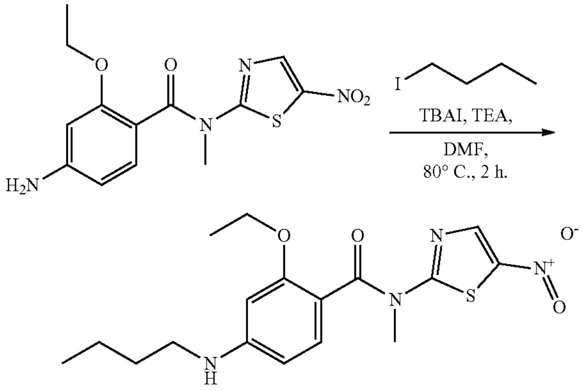

A solution of 4-amino-2-ethoxy-N-methyl-N-(5-nitrothiazol-2-yl)benzamide (38.0 mg, crude), 1-iodobutane (217 mg, 1.18 mmol), TBAI (87 mg, 0.240 mmol) and TEA (40 mg, 0.400 mmol) in DMF (5 mL) was stirred at 80° C. for 2 h. At it, the mixture was purified by pre-HPLC to give the title compound (12.0 mg, 26.8% yield for two steps) as yellow solid. $^1H$ NMR (400 MHz, DMSO-$d_6$): δ 8.72-8.71 (m, 1H), 7.19-7.16 (m, 1H), 6.40 (s, 1H), 6.28-6.24 (m, 2H), 4.08-4.06 (m, 2H), 3.51 (s, 3H), 3.09-3.07 (m, 2H), 1.57-1.54 (m, 2H), 1.41-1.38 (m, 2H), 1.28-1.35 (m, 3H), 0.95-0.91 (m, 3H). MS (ESI) m/z: 379.1 $[M+H]^+$.

Example 104. 2-Acetamido-N-(pyridin-3-yl)benzamide (B-122)

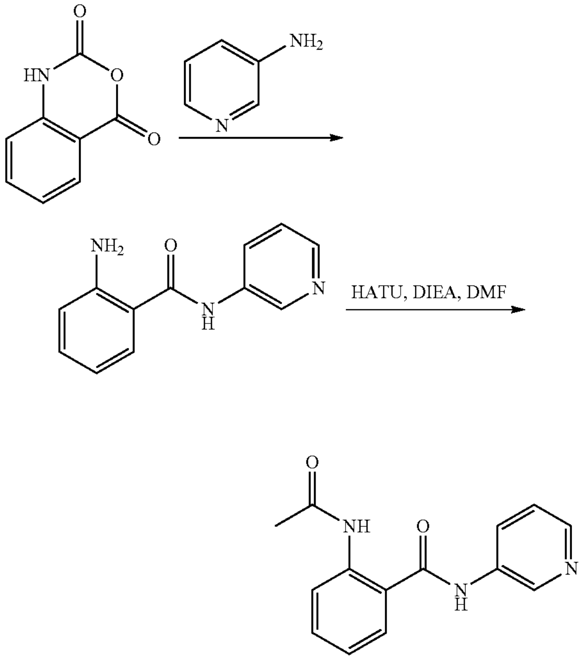

Step 1. Synthesis of 2-amino-N-(pyridin-3-yl)benzamide

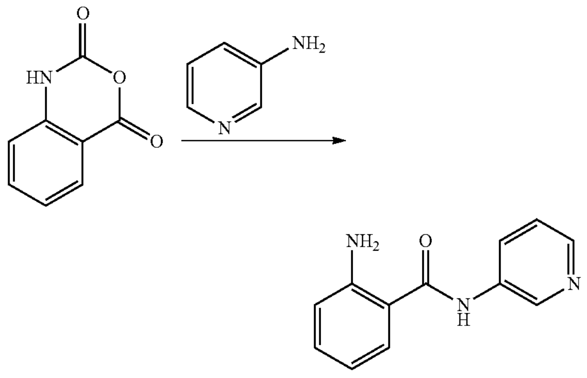

A solution of 1H-benzo[d][1,3]oxazine-2,4-dione (350 mg, 2.15 mmol) and pyridin-3-amine (400 mg, 4.29 mmol) in 1,4-dioxane (10 mL) was stirred at 80° C. for 16 h. At rt, the mixture was concentrated under vacuum. The resulting residue was purified by silica gel column chromatography (petroleum ether:EtOAc=1:1) to give the title compound (143 mg, 31.0% yield) as yellow solid. MS (ESI) m/z: 214.2 $[M+H]^+$.

Step 2. Synthesis of 2-acetamido-N-(pyridin-3-yl)benzamide

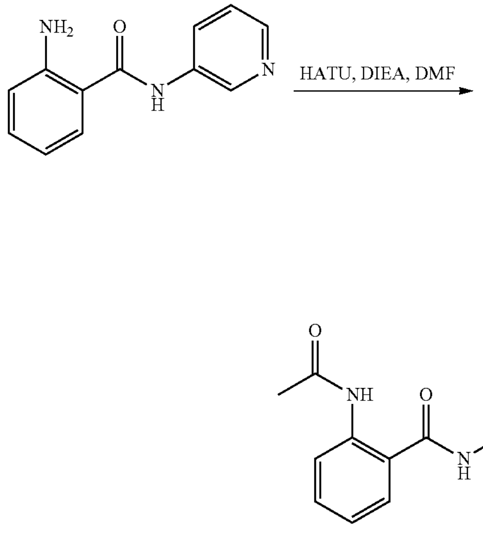

A solution of 2-acetamido-N-(pyridin-3-yl)benzamide (120 mg, 0.56 mmol) in $Ac_2O$ (4 mL) was stirred at rt for 16 h. The mixture was concentrated under vacuum and purified by pre-HPLC to give the title compound (90 mg, 63% yield) as yellow solid. $^1H$ NMR (400 MHz, DMSO-$d_6$): δ 8.87-8.86 (m, 1H), 8.32 (d, J=4.0 Hz, 1H), 8.14 (d, J=8.0 Hz, 1H), 8.05 (d, J=8.0 Hz, 1H), 7.76 (d, J=7.6 Hz, 1H), 7.53 (t, J=7.6 Hz, 1H), 7.41-7.38 (m, 1H), 7.24 (t, J=7.2 Hz, 1H), 6.05 (brs, 1H), 2.05 (s, 3H). MS (ESI) m/z: 256.2 $[M+H]^+$.

Example 105. 2-Acetamido-N-(5-isopropylthiophen-2-yl)benzamide (B-129)

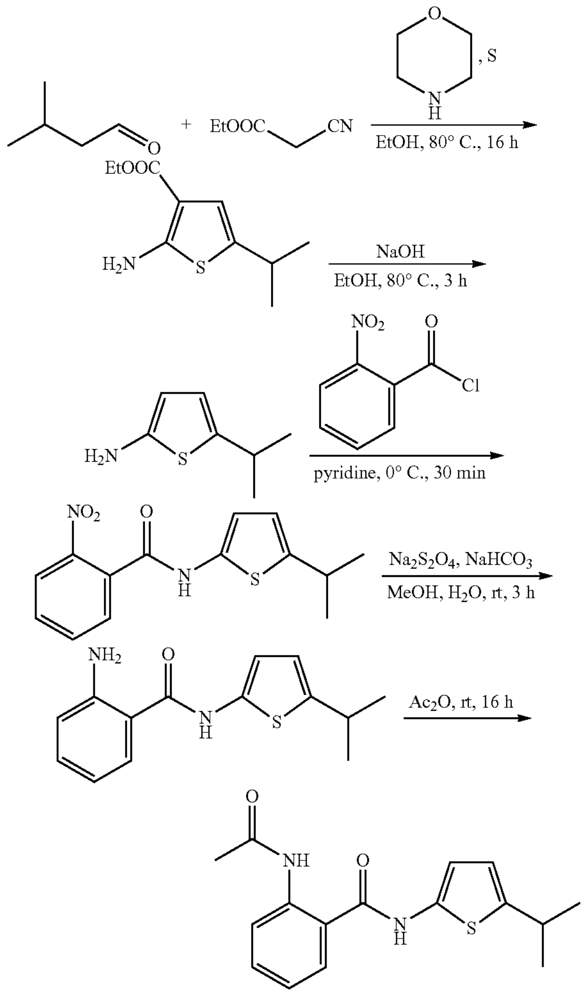

Step 1. Synthesis of ethyl 2-amino-5-isopropylthiophene-3-carboxylate

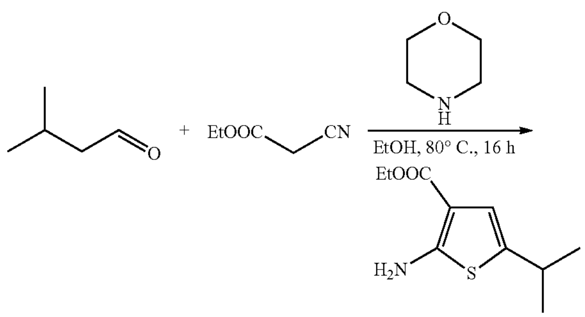

A solution of 3-methylbutanal (3.5 g, 40.69 mmol), ethyl 2-cyanoacetate (4.59 g, 40.69 mmol) and S (1.4 g, 44.76 mmol) in EtOH (70 mL) and morpholine (50 mL) was stirred at 80° C. for 16 h. At rt, the mixture was concentrated under vacuum to give the title compound (8.6 g, crude) as yellow oil. MS (ESI) m/z: 214.4 $[M+H]^+$.

Step 2. Synthesis of ethyl 5-isopropylthiophen-2-amine

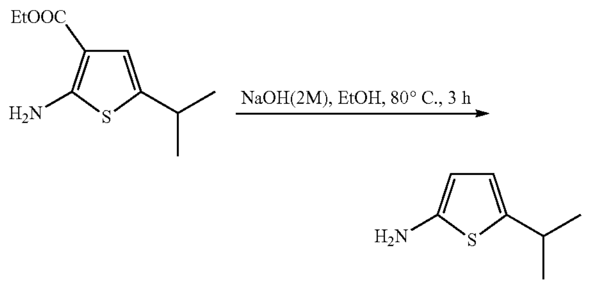

A solution of ethyl 2-amino-5-isopropylthiophene-3-carboxylate (8.6 g, 40.4 mmol) and NaOH (2 M, 80.7 mL) in EtOH (120 mL) was stirred at 80° C. for 3 h. After the reaction mixture was cooled down to 0° C., the pH of the mixture was adjusted to 4 with conc. $H_2SO_4$. The resulting mixture was warmed to 50° C. and stirred for 2 h. After the mixture was diluted with $H_2O$ (30 mL), the pH was adjusted to 10 with 8 N NaOH. The mixture was extracted with EtOAc (3×30 mL), and washed with brine (3×30 mL). The organic layer was dried over $Na_2SO_4$, filtered and concentrated under vacuum to give the title compound (2 g, 35%) as yellow solid. MS (ESI) m/z: 142.5 $[M+H]^+$.

Step 3. Synthesis of N-(5-isopropylthiophen-2-yl)-2-nitrobenzamide

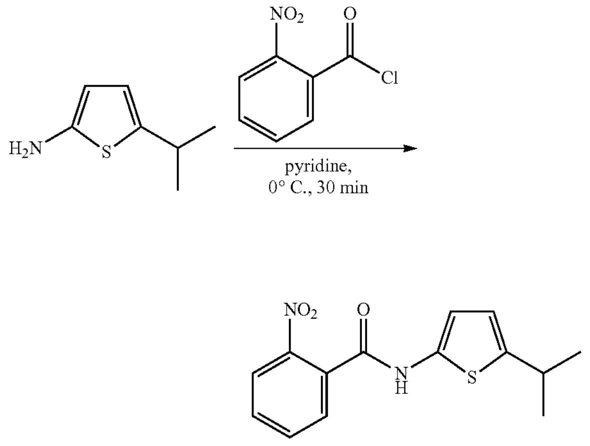

To a solution of 5-isopropylthiophen-2-amine (1.0 g, 7.09 mmol) in pyridine (10 mL) was added 2-nitrobenzoyl chloride (2.6 g, 14.2 mmol) at 0° C. After being stirred at 0° C. for 30 min, the mixture was diluted with $H_2O$ (30 mL) and EtOAc (3×30 mL), washed with brine (3×30 mL), dried over $Na_2SO_4$, filtered and concentrated under vacuum to give the title compound (1.5 g, 73%) as yellow solid. MS (ESI) m/z: 291.0 $[M+H]^+$.

Step 4. Synthesis of 2-amino-N-(5-isopropylthiophen-2-yl)benzamide

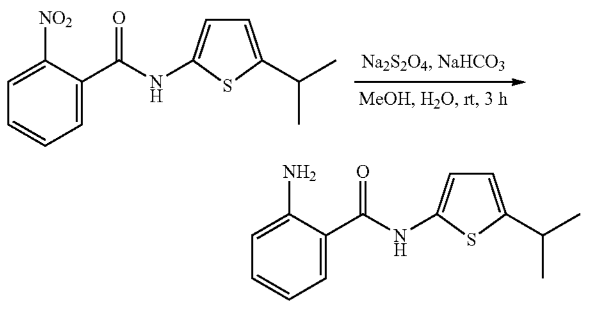

A solution of N-(5-isopropylthiophen-2-yl)-2-nitrobenzamide (1.5 g, 5.17 mmol), $Na_2S_2O_4$ (9.0 g, 51.7 mmol) and $NaHCO_3$ (5.5 g, 51.7 mmol) in MeOH (100 mL) and $H_2O$ (10 mL) was stirred at rt for 30 min. After the mixture was diluted with $H_2O$ (30 mL), the mixture was extracted with EtOAc (3×30 mL), washed with brine (3×30 mL), dried over $Na_2SO_4$, filtered and concentrated under vacuum. The resulting residue was purified by silica gel column chromatography (petroleum ether:EtOAc=3:1) to give the title compound (170 mg, 13.0% yield) as yellow solid. MS (ESI) m/z: 261.4 $[M+H]^+$.

Step 5. Synthesis of 2-acetamido-N-(5-isopropylthiophen-2-yl)benzamide

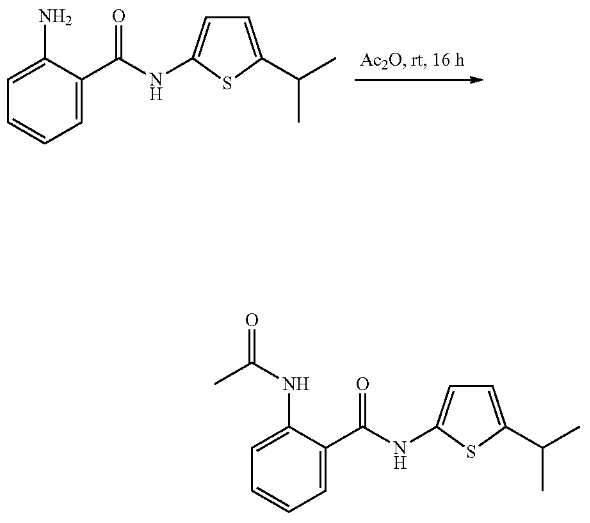

A solution of 2-amino-N-(5-isopropylthiophen-2-yl)benzamide (170 mg, 0.65 mmol) in $Ac_2O$ (10 mL) was stirred at rt for 16 h. The mixture was concentrated under vacuum and purified by pre-HPLC to give the title compound (30 mg, 15% yield) as yellow solid. $^1H$ NMR (400 MHz, DMSO-$d_6$): δ 11.49 (s, 1H), 10.50 (s, 1H), 8.17 (d, J=7.6 Hz, 1H), 7.75 (d, J=6.4 Hz, 1H), 7.55-7.51 (m, 1H), 7.23-7.22 (m, 1H), 6.70-6.61 (m, 2H), 3.10-3.06 (m, 1H), 2.08 (s, 3H), 1.28-1.26 (m, 6H). MS (ESI) m/z: 303.3 $[M+H]^+$.

Example 106. 2-Acetamido-N-(5-phenylthiophen-2-yl)benzamide (B-130)

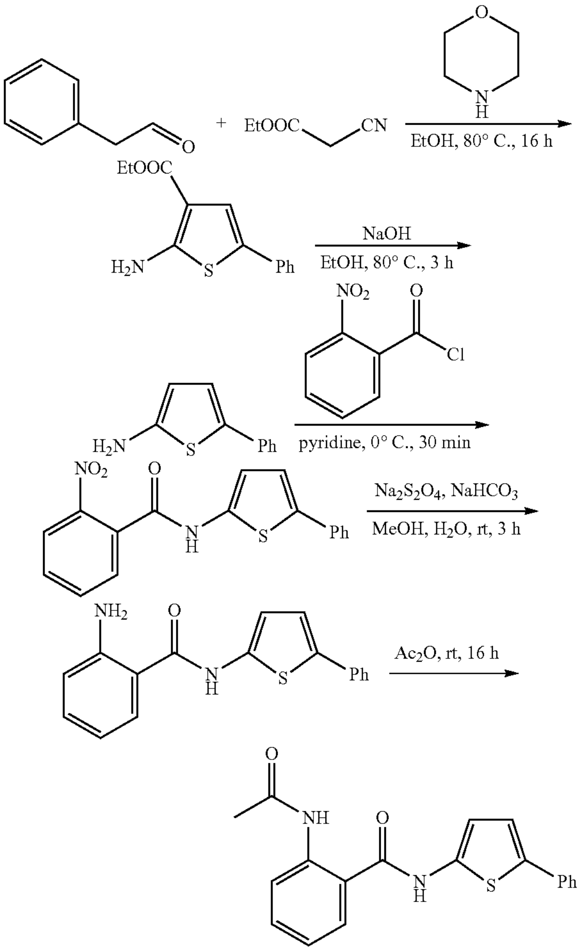

Step 1. Synthesis of ethyl 2-amino-5-phenylthiophene-3-carboxylate

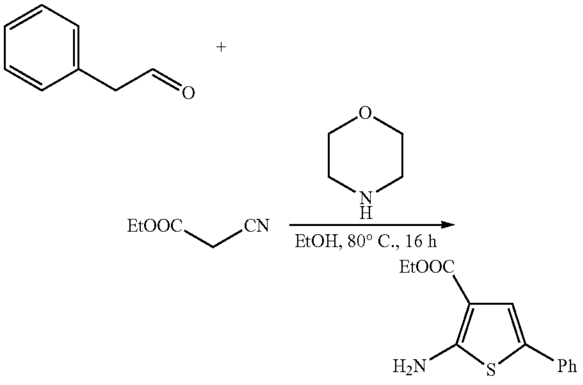

A solution of 2-phenylacetaldehyde (3.5 g, 29.2 mmol), ethyl 2-cyanoacetate (3.29 g, 29.2 mmol) and S (1.1 g, 32.1 mmol) in EtOH (70 mL) and morpholine (50 mL) was stirred at 80° C. for 16 h. At rt, the mixture was concentrated under vacuum to give the title compound (7.8 g, crude) as yellow oil. MS (ESI) m/z: 248.2 $[M+H]^+$.

Step 2. Synthesis of 5-phenylthiophen-2-amine

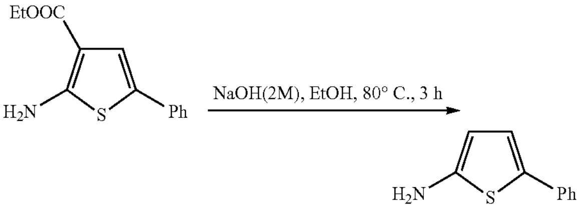

A solution of ethyl 2-amino-5-phenylthiophene-3-carboxylate (7.5 g, 30.4 mmol) and NaOH (2 N, 61 mL) in EtOH (120 mL) was stirred at 80° C. for 3 h. After the reaction mixture was cooled down to 0° C., the pH of the mixture was adjusted to 4 with conc. $H_2SO_4$. The reaction mixture was warmed to 50° C. and stirred for 2 h. After the mixture was diluted with $H_2O$ (30 mL), the reaction was basified (pH=10) with 8 N NaOH. The reaction mixture was extracted with EtOAc (3x30 mL), washed with brine (3x30 mL), dried over $Na_2SO_4$, filtered and concentrated under vacuum to give the tide compound (2.5 g, 47.0%) as yellow solid. MS (ESI) m/z: 176.4 $[M+H]^+$.

Step 3. Synthesis of 2-nitro-N-(5-phenylthiophen-2-yl)benzamide

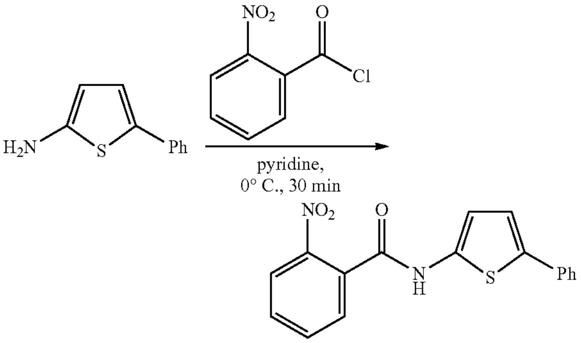

To a solution of 5-phenylthiophen-2-amine (1.0 g, 5.71 mmol) in pyridine (10 mL) was added 2-nitrobenzoyl chloride (2.1 g, 11.4 mmol) at 0° C. After being stirred at 0° C. for 30 min, the mixture was diluted with $H_2O$ (30 mL) and extracted with EtOAc (3x30 mL), washed with brine (3x30 mL), dried over $Na_2SO_4$, filtered and concentrated under vacuum to give the title compound (1.7 g, 99%) as yellow solid. MS (ESI) m/z: 325.0 $[M+H]^+$.

Step 4. Synthesis of 2-amino-N-(5-phenylthiophen-2-yl)benzamide

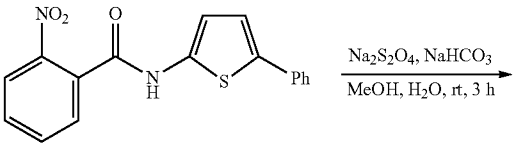

-continued

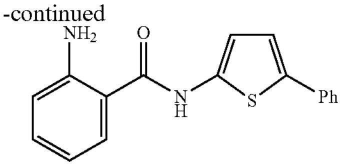

A solution of 2-nitro-N-(5-phenylthiophen-2-yl)benzamide (1.7 g, 5.24 mmol), $Na_2S_2O_4$ (9.1 g, 52.4 mmol) and $NaHCO_3$ (5.5 g, 52.4 mmol) in MeOH/$H_2O$ (100 mL/10 mL) was stirred at rt for 30 min. After the mixture was diluted with $H_2O$ (30 mL), the mixture was extracted with EtOAc (3×30 mL). The combined organic layers were washed with brine (3×30 mL), dried over $Na_2SO_4$, filtered and concentrated under vacuum. The resulting residue was purified by silica gel column chromatography (petroleum ether:EtOAc=3:1) to give the title compound (250 mg, 16.7% yield) as yellow solid. MS (ESI) m/z: 295.4 $[M+H]^+$.

Step 5. Synthesis of 2-acetamido-N-(5-phenylthiophen-2-yl)benzamide

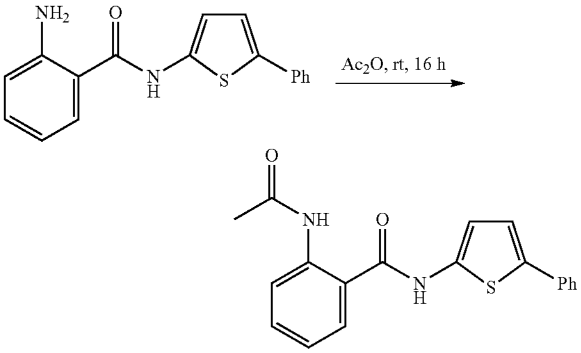

A solution of 2-amino-N-(5-phenylthiophen-2-yl)benzamide (250 mg, 0.85 mmol) in $Ac_2O$ (10 mL) was stirred at rt for 16 h. The mixture was concentrated under vacuum and purified by pre-HPLC to give the title compound (60 mg, 21% yield) as yellow solid. $^1H$ NMR (400 MHz, DMSO-$d_6$): δ 11.76 (s, 1H), 10.45 (s, 1H), 8.13 (d, J=8.0 Hz, 1H), 7.78 (d, J=6.4 Hz, 1H), 7.63-7.53 (m, 3H), 7.41-7.25 (m, 5H), 6.90 (d, J=3.6 Hz, 1H), 2.09 (s, 3H). MS (ESI) m/z: 335.2 $[M-H]^-$.

Example 107. 1-(5-Nitrothiazol-2-yl)azocan-2-one (B-101)

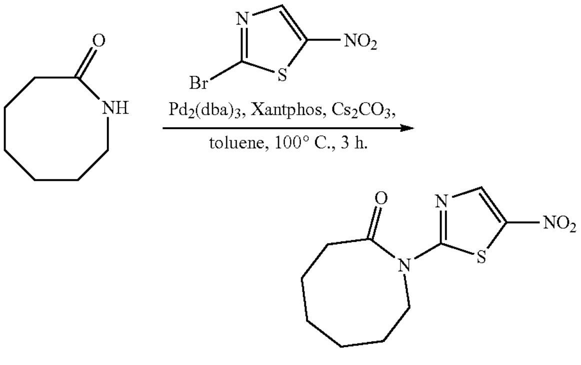

A solution of azocan-2-one (500 mg, 3.94 mmol), 2-bromo-5-nitrothiazole (818 mg, 3.94 mmol), $Pd_2(dba)_3$ (180 mg, 0.197 mmol), Xantphos (114 mg, 0.197 mmol) and $Cs_2CO_3$ (2.57 mg, 7.88 mmol) in toluene (15 mL) was stirred at 100° C. for 3 h under argon atmosphere. At rt, the mixture was diluted with water (100 mL) and extracted with EtOAc (3×100 mL). The combined organic layers were washed with brine (2×100 mL), dried over $Na_2SO_4$, filtered and concentrated under vacuum. The resulting residue was purified by silica gel column chromatography (petroleum ether:EtOAc=2:1) to give the title compound (399 mg, 39.7% yield) as yellow solid. $^1H$ NMR (400 MHz, DMSO-$d_6$): δ 8.69 (s, 1H), 4.46 (t, J=5.6 Hz, 2H), 2.88 (t, J=5.6 Hz, 2H), 1.79-1.77 (m, 4H), 1.55-1.54 (m, 2H), 1.37-1.35 (m, 2H). MS (ESI) m/z: 256.1 $[M+H]^+$.

Example 108. 5-(Butylamino)-N-(4-chloro-5-nitrothiazol-2-yl)-[1,1'-biphenyl]-2-carboxamide (B-112)

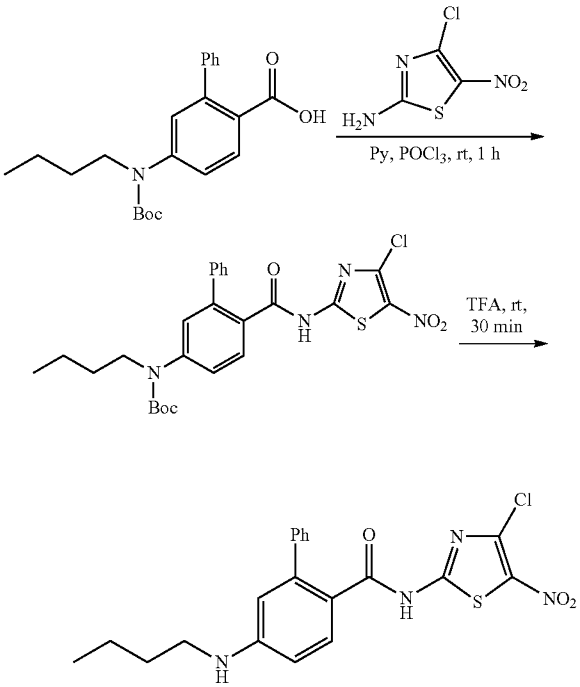

Step 1. Synthesis of tert-butyl butyl(6-((4-chloro-5-nitrothiazol-2-yl)carbamoyl)-[1,1'-biphenyl]-3-yl) carbamate

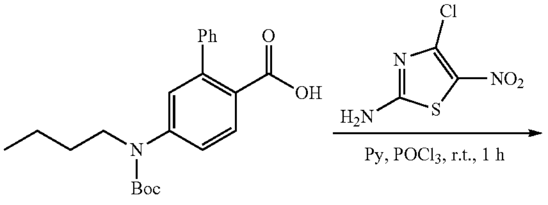

-continued

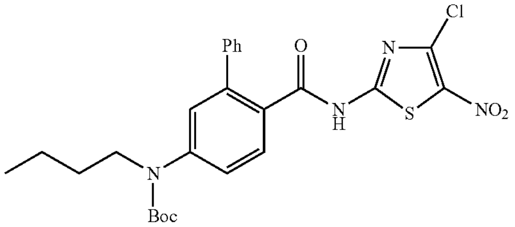

To a solution of 5-((tert-butoxycarbonyl)(butyl)amino)-[1,1'-biphenyl]-2-carboxylic acid (200 mg, 0.541 mmol) and 4-chloro-5-nitrothiazol-2-amine (97 mg, 0.541 mmol) in pyridine (10 mL) was added phosphorus oxychloride (166 mg, 1.08 mmol) at rt. After being stirred at rt for 1 h, the mixture was quenched with MeOH (5 mL) and concentrated under vacuum to give the title compound (400 mg, crude) as brown oil, which was used in the next step without further purification. MS (ESI) m/z: 531.5 $[M+H]^+$.

Step 2. Synthesis of 5-(butylamino)-N-(4-chloro-5-nitrothiazol-2-yl)-[1,1'-biphenyl]-2-carboxamide

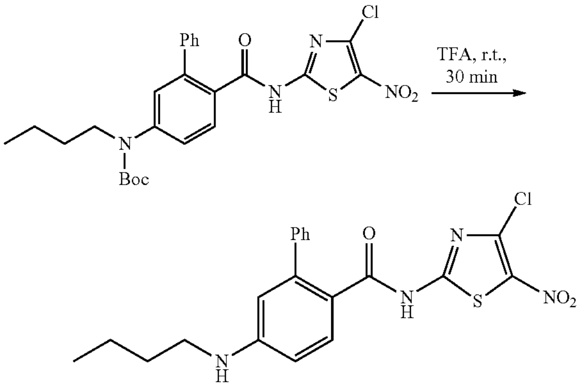 [SMILES: CCCCN(C(=O)OC(C)(C)C)c1ccc(C(=O)Nc2nc(Cl)c([N+](=O)[O-])s2)c(-c2ccccc2)c1 ; CCCCNc1ccc(C(=O)Nc2nc(Cl)c([N+](=O)[O-])s2)c(-c2ccccc2)c1]

A solution of tert-butyl butyl(6-((4-chloro-5-nitrothiazol-2-yl)carbamoyl)-[1,1'-biphenyl]-3-yl)carbamate (400 mg, crude) in TFA (5 mL) was stirred at rt for 30 min. Then the mixture was concentrated under vacuum. The resulting residue was purified by pre-HPLC to give the title compound (31.2 mg, 10.6% yield) as yellow solid. $^1$H NMR (400 MHz, DMSO-$d_6$): δ 13.22 (s, 1H), 7.57 (d, J=8.4 Hz, 1H), 7.56-7.31 (m, 3H), 7.24-7.23 (m, 2H), 6.62-6.59 (m, 2H), 6.52 (d, J=1.6 Hz, 1H), 3.11-3.10 (m, 2H), 1.58-1.49 (m, 2H), 1.43-1.36 (m, 2H), 0.91 (t, J=7.2 Hz, 3H). MS (ESI) m/z: 431.0 $[M+H]^+$.

Example 109. 5-(Butylamino)-N-(5-nitro-4-(trifluoromethyl)thiazol-2-yl)-[1,1'-biphenyl]-2-carboxamide (B-114)

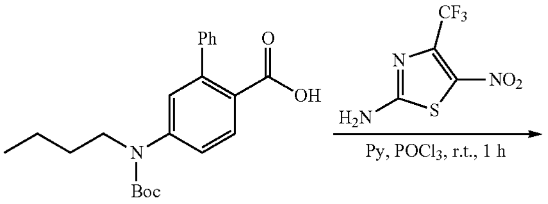

-continued

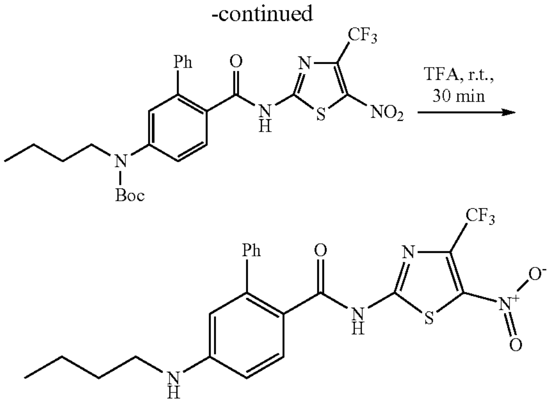

Step 1. Synthesis of tert-butyl butyl(6-((5-nitro-4-(trifluoromethyl)thiazol-2-yl)carbamoyl)-[1,1'-biphenyl]-3-yl)carbamate

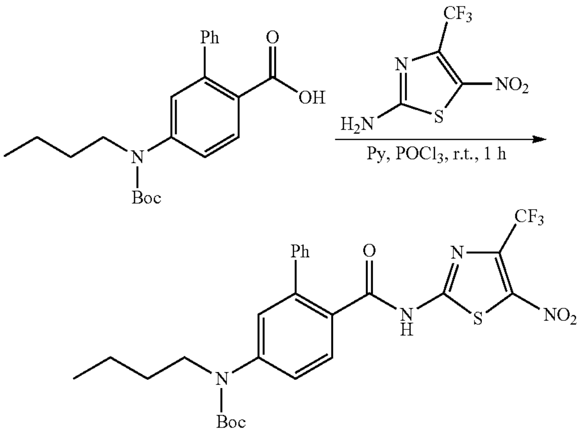

To a solution of 5-((tert-butoxycarbonyl)(butyl)amino)-[1,1'-biphenyl]-2-carboxylic acid (200 mg, 0.541 mmol), 5-nitro-4-(trifluoromethyl)thiazol-2-amine (115 mg, 0.541 mmol) in pyridine (10 mL) was added phosphorus oxychloride (166 mg, 1.08 mmol) at rt. After being stirred at rt for 1 h, the mixture was quenched with MeOH (5 mL) and concentrated under vacuum to give the title compound (400 mg, crude) as brown oil, which was used in the next step without further purification. MS (ESI) m/z: 563.3 $[M-H]^-$.

Step 2. Synthesis of 5-(butylamino)-N-(5-nitro-4-(trifluoromethyl)thiazol-2-yl)-[1,1'-biphenyl]-2-carboxamide

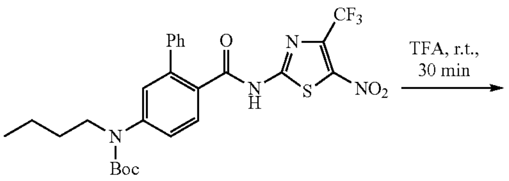

-continued

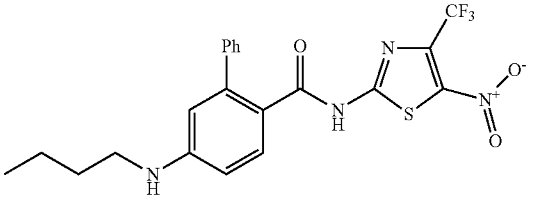

A solution of tert-butyl butyl(6-((5-nitro-4-(trifluoromethyl)thiazol-2-yl)carbamoyl)-[1,1'-biphenyl]-3-yl)carbamate (400 mg, crude) in TFA (5 mL) was stirred at rt for 30 min. Then the mixture was concentrated under vacuum. The resulting residue was purified by pre-HPLC to give the title compound (19.3 mg, 6.17% yield) as yellow solid. $^1$H NMR (400 MHz, DMSO-$d_6$): δ 13.41 (s, 1H), 7.60 (d, J=8.8 Hz, 1H), 7.37-7.29 (m, 3H), 7.25-7.23 (m, 2H), 6.63 (brs, 1H), 6.62-6.59 (m, 1H), 6.52 (d, J=1.6 Hz, 1H), 3.13-3.09 (m, 2H), 1.58-1.51 (m, 2H), 1.43-1.36 (m, 2H), 0.91 (t, J=7.2 Hz, 3H). MS (ESI) m/z: 465.0 [M+H]$^+$.

Example 110. 5-(Butylamino)-N-(5-phenylthiazol-2-yl)-[1,1'-biphenyl]-2-carboxamide (B-120)

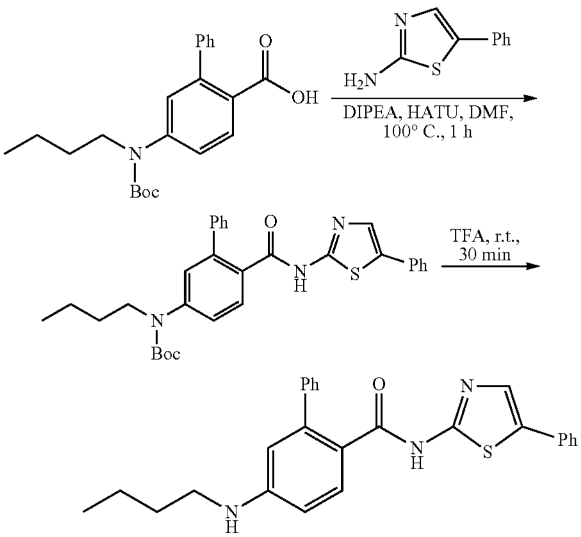

Step 1. Synthesis of tert-butyl butyl(6-((5-phenylthiazol-2-yl)carbamoyl)-[1,1'-biphenyl]-3-yl) carbamate

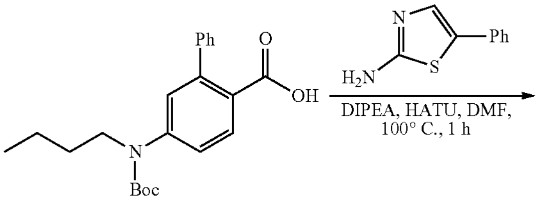

-continued

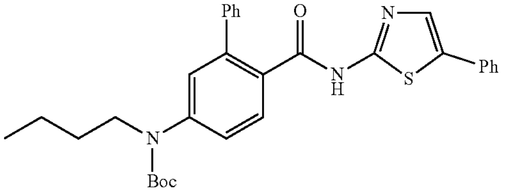

To a solution of 5-((tert-butoxycarbonyl)(butyl)amino)-[1,1'-biphenyl]-2-carboxylic acid (200 mg, 0.541 mmol), 5-(trifluoromethyl)thiazol-2-amine (106 mg, 0.541 mmol) and HATU (226 mg, 0.595 mmol) in DMF (10 mL) was added DIPEA (140 mg, 1.08 mmol) at 100° C. After being heated at 100° C. for 1 h, the mixture was cooled to rt and diluted with EtOAc (100 mL). The organic phase was washed with brine, dried over $Na_2SO_4$, filtered and concentrated under vacuum to give the title compound (300 mg, crude) as brown oil, which was used in the next step without further purification. MS (ESI) m/z: 528.6 [M+H]$^+$.

Step 2. Synthesis of 5-(butylamino)-N-(5-phenylthiazol-2-yl)-[1,1'-biphenyl]-2-carboxamide

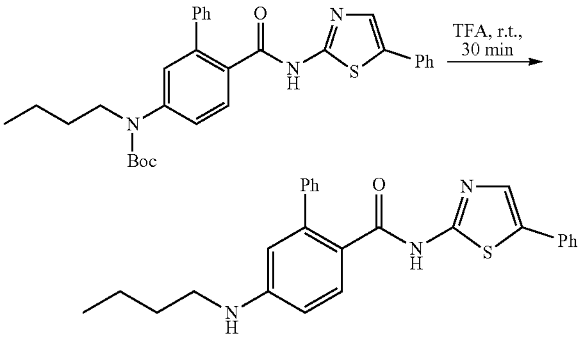

A solution of tert-butyl butyl(6-((5-(trifluoromethyl)thiazol-2-yl)carbamoyl)-[1,1'-biphenyl]-3-yl)carbamate (300 mg, crude) in TFA (2 mL) was stirred at rt for 30 min. Then the mixture was concentrated under vacuum. The resulting residue was purified by pre-HPLC to give the title compound (23.2 mg, 7.92% yield) as off-white solid. $^1$H NMR (400 MHz, DMSO-$d_6$): δ 12.01 (brs, 1H), 7.82 (s, 1H), 7.58 (d, J=7.2 Hz, 2H), 7.47 (d, J=8.4 Hz, 1H), 7.40-7.33 (m, 4H), 7.30-7.25 (m, 4H), 6.61-6.58 (m, 1H), 6.52 (d, J=1.2 Hz, 1H), 6.52 (t, J=4.4 Hz, 1H), 3.11-3.07 (m, 2H), 1.59-1.52 (m, 2H), 1.44-1.35 (m, 2H), 0.92 (t, J=7.2 Hz, 3H). MS (ESI) m/z: 428.2 [M+H]$^+$.

Example 111. 2-Acetamido-N-(5-cyanothiophen-2-yl)benzamide (B-128)

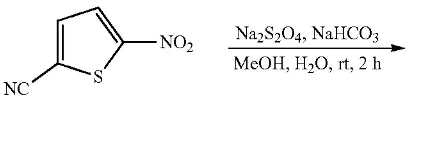

-continued

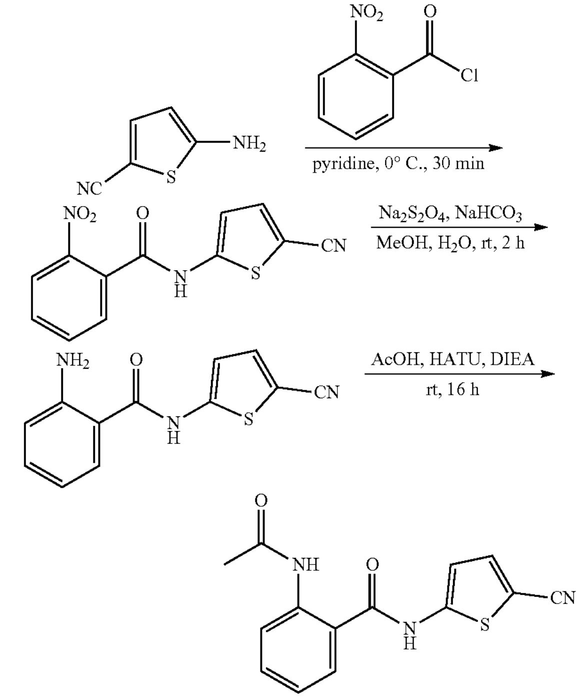

Step 1. Synthesis of 5-aminothiophene-2-carbonitrile

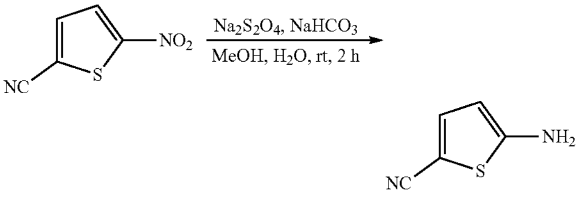

A solution of 5-nitrothiophene-2-carbonitrile (2.0 g, 12.9 mmol), $Na_2S_2O_4$ (4.5 g, 25.9 mmol) and $NaHCO_3$ (2.7 g, 25.9 mmol) in MeOH (100 mL) and $H_2O$ (10 mL) was stirred at rt for 2 h. After the mixture was diluted with $H_2O$ (30 mL), the mixture was extracted with EtOAc (3×30 mL), washed with brine (3×30 mL), dried over $Na_2SO_4$, filtered and concentrated under vacuum to give the tide compound (300 mg, 19.0% yield) as yellow solid. MS (ESI) m/z: 125.5 $[M+H]^+$.

Step 2. Synthesis of N-(5-cyanothiophen-2-yl)-2-nitrobenzamide

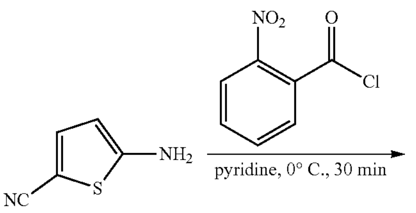

-continued

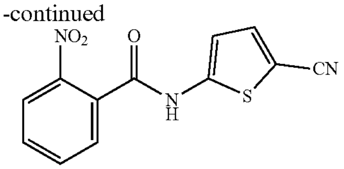

A solution of 5-aminothiophene-2-carbonitrile (0.3 g, 2.42 mmol) in pyridine (5 mL) was added 2-nitrobenzoyl chloride (0.89 g, 4.84 mmol) at 0° C. After being stirred at 0° C. for 30 min, the mixture was diluted with $H_2O$ (30 mL), extracted with EtOAc (3×30 mL), washed with brine (3×30 mL), dried over $Na_2SO_4$, filtered and concentrated under vacuum to give the title compound (0.4 g, 61%) as yellow solid. MS (ESI) m/z: 272.0 $[M-H]^-$.

Step 3. Synthesis of 2-amino-N-(5-cyanothiophen-2-yl)benzamide

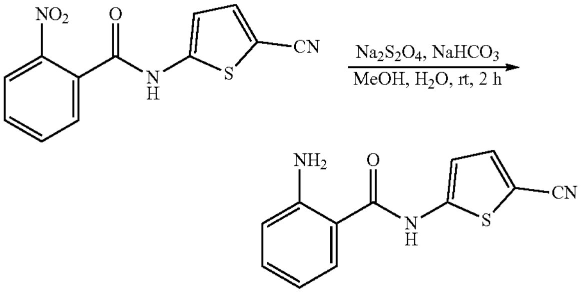

A solution of N-(5-cyanothiophen-2-yl)-2-nitrobenzamide (0.4 g, 1.46 mmol), $Na_2S_2O_4$ (0.51 g, 2.93 mmol) and $NaHCO_3$ (0.31 g, 2.93 mmol) in MeOH (20 mL) and $H_2O$ (2 mL) was stirred at rt for 2 h. After the mixture was diluted with $H_2O$ (30 mL), the mixture was extracted with EtOAc (3×30 mL), washed with brine (3×30 mL), dried over $Na_2SO_4$, filtered and concentrated under vacuum. The resulting residue was purified by silica gel column chromatography (petroleum ether:EtOAc=3:1) to give the title compound (110 mg, 31% yield) as yellow solid. MS (ESI) m/z: 244.0 $[M+H]^+$.

Step 4. Synthesis of 2-acetamido-N-(5-cyanothiophen-2-yl)benzamide

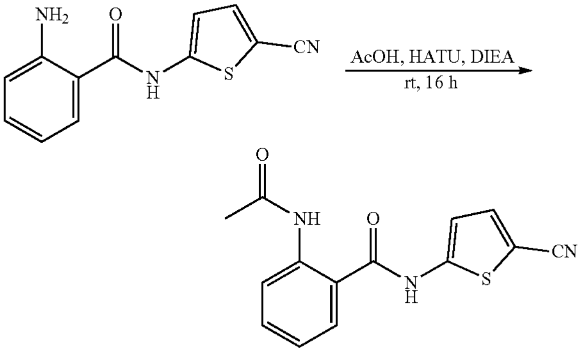

A solution of 2-amino-N-(5-cyanothiophen-2-yl)benzamide (110 mg, 0.45 mmol mmol), AcOH (27 mg, 0.45 mmol), HATU (171 mg, 0.45 mmol) and DIEA (116 mg, 0.90 mmol) in DMF (5 mL) was stirred at rt for 16 h. The mixture was purified by pre-HPLC to give the title compound (20 mg, 16% yield) as yellow solid. $^1$H NMR (400 MHz, DMSO-$d_6$): δ 12.36 (s, 1H), 10.21 (s, 1H), 7.90 (d, J=8.0 Hz, 1H), 7.78 (d, J=4.4 Hz, 1H), 7.72 (d, J=7.2 Hz, 1H), 7.56 (t, J=7.2 Hz, 1H), 7.27 (t, J=7.2 Hz, 1H), 6.92 (d, J=4.4 Hz, 1H), 2.04 (s, 3H). MS (ESI) m/z: 284.2 [M−H]$^-$.

Example 112. 5-(Butylamino)-N-(5-nitro-4-phenylthiazol-2-yl)-[1,1'-biphenyl]-2-carboxamide (B-131)

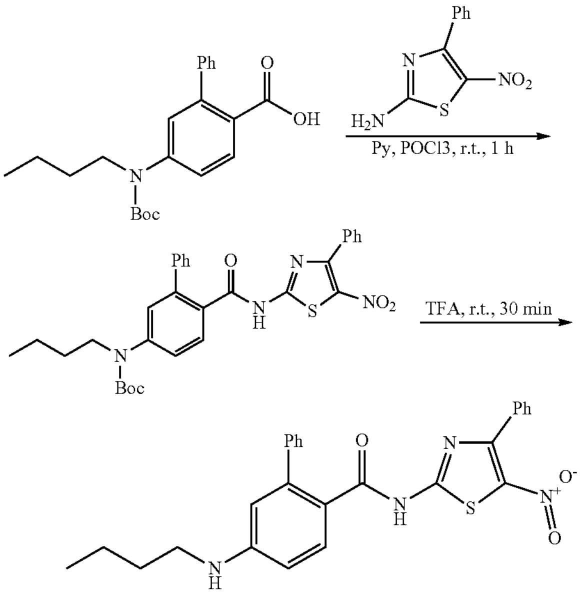

Step 1. Synthesis of tert-butyl butyl(6-((5-nitro-4-phenylthiazol-2-yl)carbamoyl)-[1,1'-biphenyl]-3-yl) carbamate

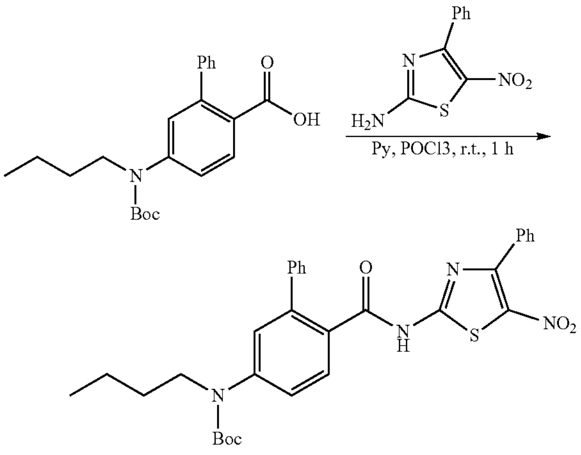

To a solution of 5-((tert-butoxycarbonyl)(butyl)amino)-[1,1'-biphenyl]-2-carboxylic acid (200 mg, 0.541 mmol), 5-nitro-4-(trifluoromethyl)thiazol-2-amine (115 mg, 0.541 mmol) in pyridine (10 mL) at it was added phosphorus oxychloride (166 mg, 1.08 mmol). After being stirred at rt for 1 h, the mixture was quenched with MeOH (5 mL) and concentrated under vacuum to give the title compound (400 mg, crude) as brown oil, which was used in the next step without further purification. MS (ESI) m/z: 573.3 [M+H]$^+$.

Step 2. Synthesis of 5-(butylamino)-N-(5-nitro-4-phenylthiazol-2-yl)-[1,1'-biphenyl]-2-carboxamide

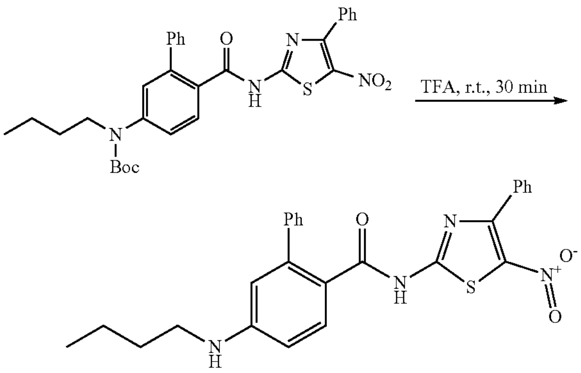

A solution of tert-butyl butyl(6-((5-nitro-4-(trifluoromethyl)thiazol-2-yl)carbamoyl)-[1,1'-biphenyl]-3-yl)carbamate (400 mg, crude) in TFA (5 mL) was stirred at it for 30 min. Then the mixture was concentrated under vacuum. The resulting residue was purified by pre-HPLC to give the title compound (18.4 mg, 5.79% yield) as yellow solid. $^1$H NMR (400 MHz, DMSO-$d_6$): δ 13.05 (s, 1H), 7.70 (d, J=5.6 Hz, 2H), 7.57 (d, J=8.4 Hz, 1H), 7.50-7.48 (m, 3H), 7.41-7.35 (m, 3H), 7.27-7.25 (m, 2H), 6.60 (d, J=8.4 Hz, 1H), 6.56-6.48 (m, 2H), 3.16-3.06 (m, 2H), 1.56-1.51 (m, 2H), 1.41-1.34 (m, 2H), 0.91 (t, J=7.2 Hz, 3H). MS (ESI) m/z: 473.1 [M+H]$^+$.

Example 113. 2-Ethoxy-N-(5-nitrothiazol-2-yl)-4-((tetrahydrofuran-3-yl)amino)benzamide (B-97)

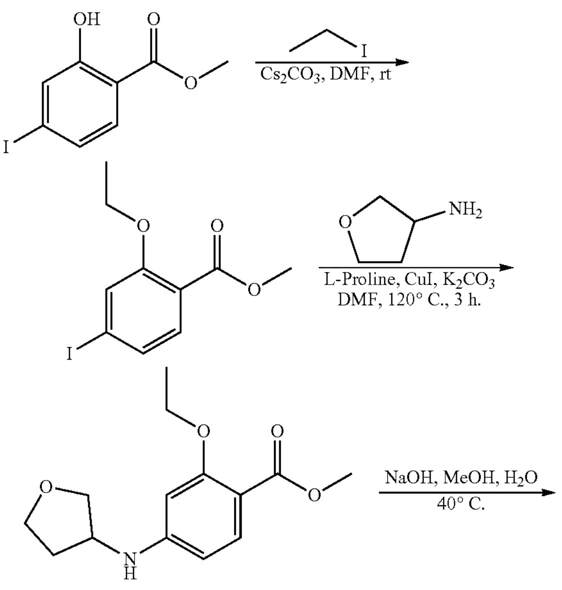

-continued

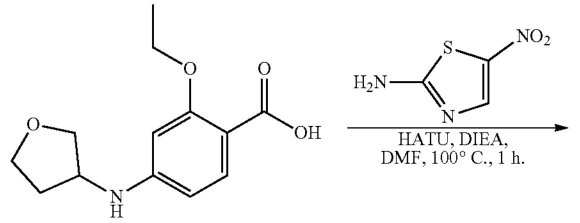

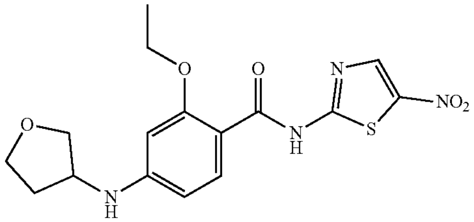

Step 1. Synthesis of methyl 2-ethoxy-4-iodobenzoate

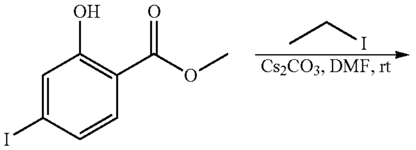

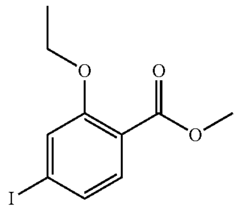

A mixture of methyl 2-hydroxy-4-iodobenzoate (5.00 g, 18.0 mmol), $Cs_2CO_3$ (11.7 g, 35.9 mmol) and iodoethane (2 mL) in DMF (30 mL) was stirred at rt overnight. Then, the mixture was diluted with water (200 mL) and extracted with EtOAc (3×200 mL). The combined organic phase was washed with brine (2×100 mL), dried over $Na_2SO_4$, filtered and concentrated under vacuum. The resulting residue was purified by silica gel column chromatography (petroleum ether:EtOAc=4:1) to give the title compound (5.5 g, 99.1% yield) as colorless oil. MS (ESI) m/z: 306.9 $[M+H]^+$.

Step 2. Synthesis of methyl 2-ethoxy-4-((tetrahydrofuran-3-yl)amino)benzoate

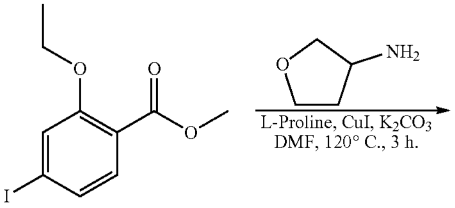

-continued

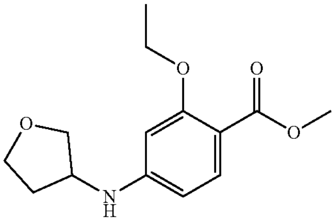

A solution of methyl 2-ethoxy-4-iodobenzoate (500 mg, 1.63 mmol), tetrahydrofuran-3-amine (284 mg, 3.26 mmol), L-Proline (187 mg, 1.63 mmol), CuI (310 mg, 1.63 mmol) and $K_2CO_3$ (450 mg, 3.26 mmol) in DMF (8 mL) was stirred at 120° C. for 3 h under argon atmosphere. At rt, the mixture was diluted with water (50 mL) and extracted with EtOAc (2×50 mL). The combined organic phase was washed with brine (2×50 mL), dried over $Na_2SO_4$, filtered and concentrated under vacuum. The resulting residue was purified by silica gel column chromatography (petroleum ether: EtOAc=1:1) to give the title compound (220 mg, 50.8% yield) as colorless oil. MS (ESI) m/z: 266.2 $[M+H]^+$.

Step 3. Synthesis of 2-ethoxy-4-((tetrahydrofuran-3-yl)amino)benzoic acid

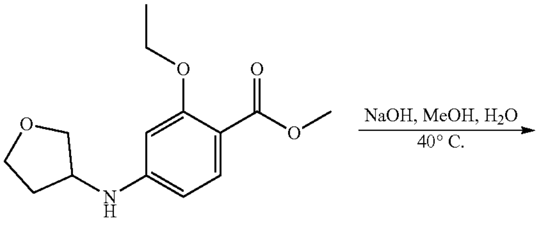

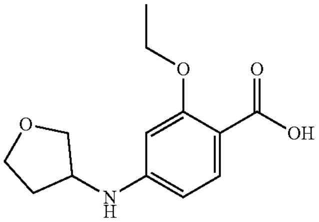

A solution of methyl 2-ethoxy-4-((tetrahydrofuran-3-yl)amino)benzoate (220 mg, 0.83 mmol) and NaOH (133 mg, 3.32 mmol) in MeOH (5 mL)/$H_2O$ (10 mL) was stirred at 40° C. overnight. Then, the mixture was diluted with water (20 mL), acidified (pH=4) with 1 N HCl and extracted with EtOAc (2×50 mL). The combined organic phase was washed with brine (2×50 mL), dried over $Na_2SO_4$, filtered and concentrated under vacuum to give the title compound (170 mg, 81.7% yield) as white solid. MS (ESI) m/z: 252.2 $[M+H]^+$.

Step 4. Synthesis of 2-ethoxy-N-(5-nitrothiazol-2-yl)-4-((tetrahydrofuran-3-yl)amino)benzamide

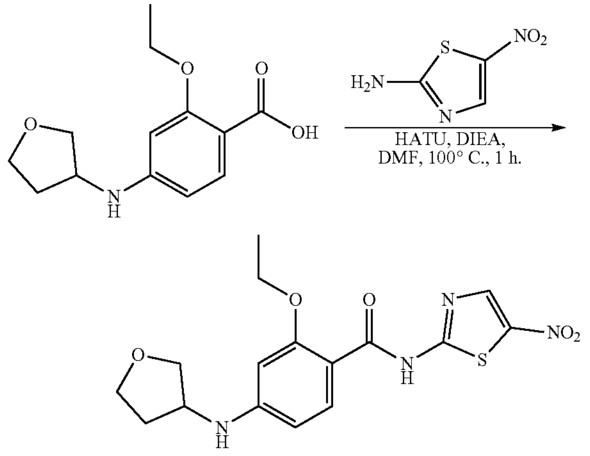

To a solution of 2-ethoxy-4-((tetrahydrofuran-3-yl) amino)benzoic acid (100 mg, 0.398 mmol), 5-nitrothiazol-2-amine (116 mg, 0.797 mmol) and HATU (302 mg, 0.797 mmol) in DMF (2 mL) was added DIEA (129 mg, 0.797 mmol) at 100° C. After being stirred at 100° C. for 1 h, the mixture was cooled to rt, concentrated and purified by pre-HPLC to give the title compound (29.0 mg, 19.3% yield) as yellow solid. $^1$H NMR (400 MHz, DMSO-$d_6$): δ 11.68 (s, 1H), 8.65 (s, 1H), 7.75 (d, J=8.8 Hz, 1H), 7.07 (d, J=6.0 Hz, 1H), 6.37 (d, J=8.8 Hz, 1H), 6.28 (s, 1H), 4.24 (q, J=6.8 Hz, 2H), 4.15 (s, 1H), 3.92-3.88 (m, 1H), 3.85-3.81 (m, 1H), 3.77-3.74 (m, 1H), 3.57-3.54 (m, 1H), 2.26-2.19 (m, 1H), 1.80-1.78 (m, 1H), 1.49 (t, J=6.8 Hz, 3H). MS (ESI) m/z: 379.1 [M+H]$^+$.

Example 114. 4-(Butylamino)-N-(5-nitrothiazol-2-yl)-2-(phenylamino)benzamide (B-108)

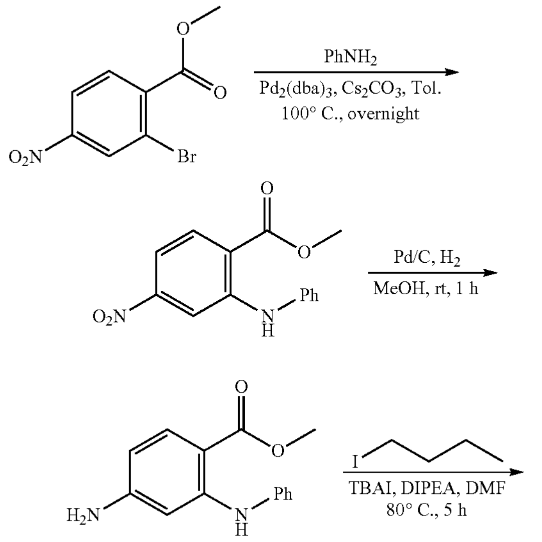

-continued

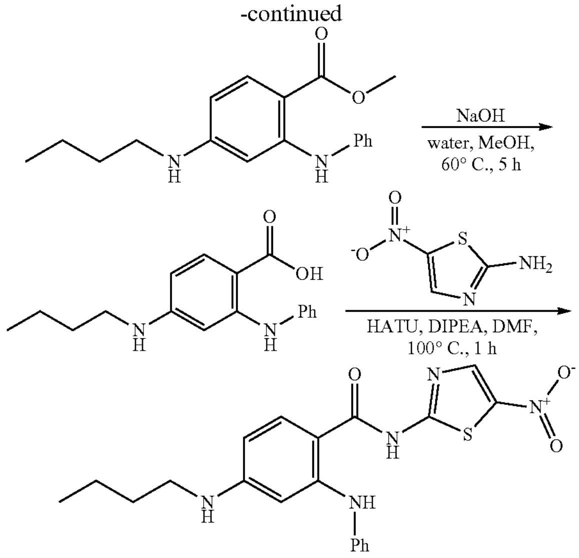

Step 1. Synthesis of methyl 4-nitro-2-(phenylamino)benzoate

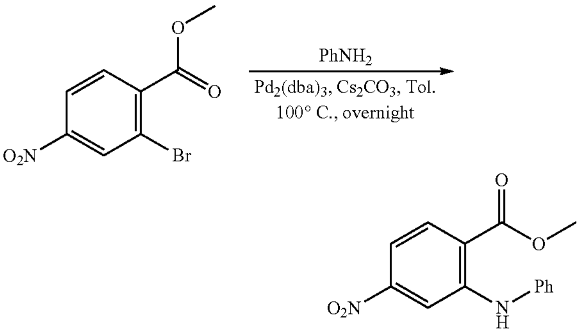

A solution of methyl 2-bromo-4-nitrobenzoate (5.00 g, 19.2 mmol), aniline (2.15 g, 23.0 mmol), $Cs_2CO_3$ (12.5 g, 38.4 mmol), $Pd_2(dba)_3$ (1.76 g, 1.92 mmol) and Xantphos (1.11 g, 1.92 mmol) in toluene (30 mL) was stirred at 100° C. overnight under argon atmosphere. At rt, the reaction mixture was diluted with water (100 mL) and extracted with EtOAc (3×50 mL). The combined organic phase was washed with brine, dried over $Na_2SO_4$, filtered and concentrated under vacuum. The resulting residue was purified by silica gel column chromatography (petroleum ether: EtOAc=1:1) to give the title compound (4.00 g, 76.5% yield) as yellow solid. MS (ESI) m/z: 273.4 [M+H]$^+$.

Step 2. Synthesis of methyl 4-amino-2-(phenylamino)benzoate

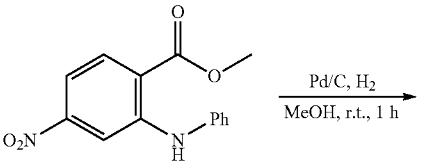

-continued

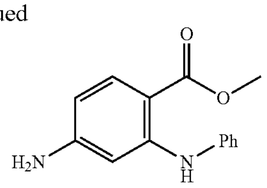

A solution of methyl 4-nitro-2-(phenylamino)benzoate (2.00 g, 7.35 mmol), Pd/C (200 mg, 10% palladium on activated carbon) in MeOH (20 mL) was stirred at rt for 1 h under hydrogen atmosphere. Then, the reaction mixture was filtered and the filtrate was concentrated under vacuum to give the title compound (2.00 g, crude) as off-white solid, which was used in the next step without further purification. MS (ESI) m/z: 243.4 [M+H]$^+$.

Step 3. Synthesis of methyl 4-(butylamino)-2-(phenylamino)benzoate

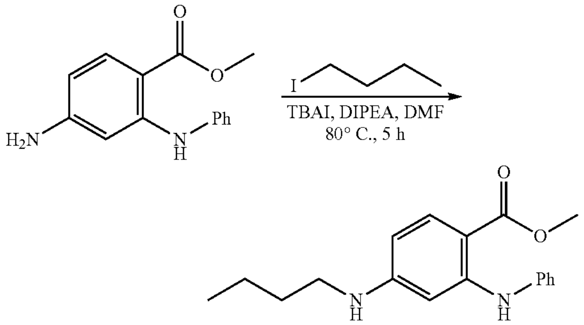

A solution of methyl 4-amino-2-(phenylamino)benzoate (2.00 g, crude), 1-iodobutane (6.76 g, 36.8 mmol), TBAI (2.71 g, 7.35 mmol) and DIPEA (2.82 g, 22.1 mmol) in DMF (30 mL) was stirred at 80° C. for 5 h. At rt, the mixture was diluted with EtOAc (50 mL) and washed with brine (3x30 mL). The organic phase was dried over $Na_2SO_4$, filtered and concentrated under vacuum. The resulting residue was purified by silica gel column chromatography (petroleum ether: EtOAc=5:1) to give the title compound (1.00 g, 45.6% yield) as white solid. MS (ESI) m/z: 299.5 [M+H]$^+$.

Step 4. Synthesis of 4-(butylamino)-2-(phenylamino)benzoic acid

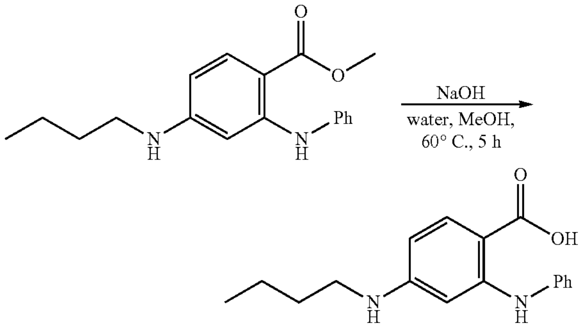

A solution of methyl 4-(butylamino)-2-(phenylamino) benzoate (1.0 g, 3.35 mmol), NaOH (670 mg, 16.8 mmol) in MeOH (5 mL) and $H_2O$ (2 mL) was heated at 60° C. for 5 h. At rt, the reaction mixture was diluted with water (50 mL). After the pH of the mixture was adjusted to 5 with 1 N HCl, the mixture was extracted with EtOAc (3x30 mL). The combined organic phase was dried over $Na_2SO_4$, filtered and concentrated under vacuum to give the tide compound (800 mg, 84.0% yield) as off-white solid. m/z: 285.2 [M+H]$^+$.

Step 5. Synthesis of 4-(butylamino)-N-(5-nitrothiazol-2-yl)-2-(phenylamino)benzamide

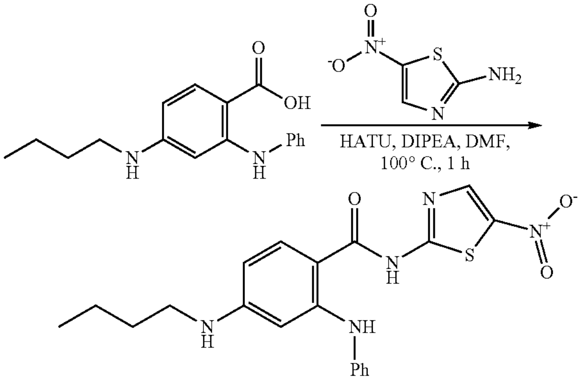

To a solution of 4-(butylamino)-2-(phenylamino)benzoic acid (200 mg, 0.703 mmol), 5-nitrothiazol-2-amine (153 mg, 1.06 mmol) and HATU (403 mg, 1.06 mmol) in DMF (3 mL) was added DIPEA (182 mg, 1.41 mmol) at 100° C. After being stirred at 100° C. for 1 h, the reaction mixture was cooled to rt and purified by pre-HPLC to give the title compound (6.85 mg, 1.86% yield) as yellow solid. $^1$H NMR (400 MHz, DMSO-$d_6$): δ 12.85 (brs, 1H), 9.73 (s, 1H), 8.66 (s, 1H), 7.88 (d, J=9.2, 1H), 7.38-7.34 (m, 2H), 7.27-7.25 (m, 2H), 7.07 (t, J=7.2 Hz, 1H), 6.67 (brs, 1H), 6.34 (s, 1H), 6.13-6.11 (m, 1H), 3.01-2.97 (m, 2H), 1.51-1.42 (m, 2H), 1.37-1.26 (m, 2H), 0.87 (t, J=7.2 Hz, 3H). MS (ESI) m/z: 412.2 [M+H]$^+$.

Example 115. 4-(Butylamino)-2-isopropyl-N-(5-nitrothiazol-2-yl)benzamide (B-109)

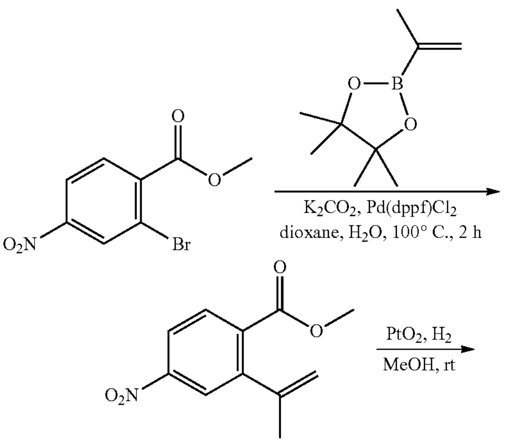

-continued

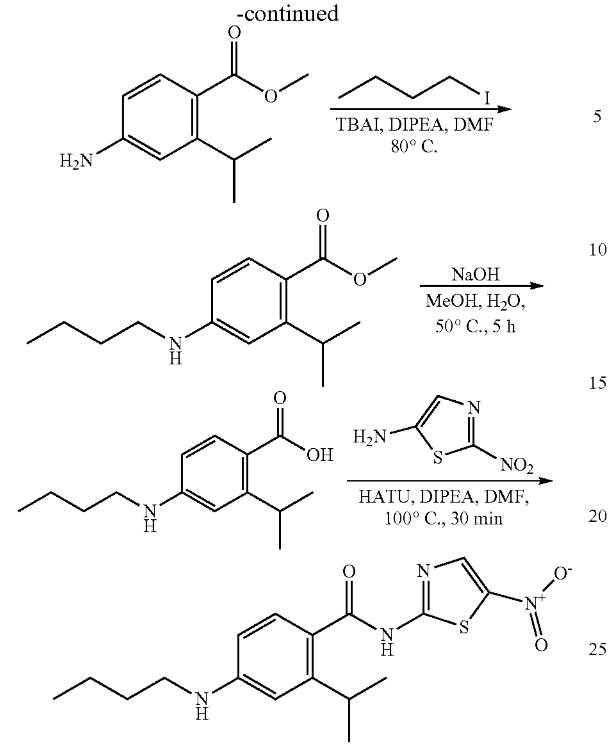

Step 1. Synthesis of methyl 4-nitro-2-(prop-1-en-2-yl)benzoate

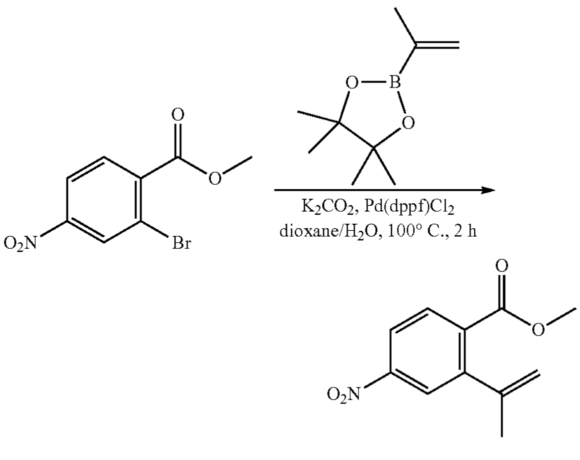

A solution of methyl 2-bromo-4-nitrobenzoate (1.28 g, 4.92 mmol), 4,4,5,5-tetramethyl-2-(prop-1-en-2-yl)-1,3,2-dioxaborolane (1.25 g, 7.44 mmol), $Pd(dppf)Cl_2$ (108 mg, 0.147 mmol) and $K_2CO_3$ (1.36 g, 9.85 mmol) in 1,4-dioxane/water (20 mL, v/v=10:1) was stirred at 100° C. for 2 h under argon atmosphere. At rt, the reaction mixture was diluted with EtOAc (40 mL), washed with brine, dried over $Na_2SO_4$, filtered and concentrated under vacuum. The resulting residue was purified by silica gel column chromatography (petroleum ether:EtOAc=10:1) to give the title compound (900 mg, yield 82.7% yield) as yellow solid MS (ESI) m/z: 222.2 $[M+H]^+$.

Step 2. Synthesis of methyl 4-amino-2-isopropylbenzoate

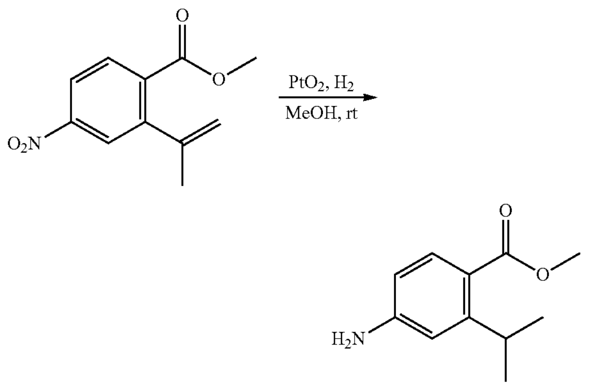

A solution of methyl 4-nitro-2-(prop-1-en-2-yl) benzoate (500 mg, 2.26 mmol) and $PtO_2$ (50 mg, 0.220 mmol) in MeOH (15 mL) was stirred at rt overnight under hydrogen atmosphere. Then, the mixture was filtered and concentrated to give the title compound (300 mg, crude) as brown solid. MS (ESI) m/z: 194.1 $[M+H]^+$.

Step 3. Synthesis of methyl 4-(butylamino)-2-isopropylbenzoate

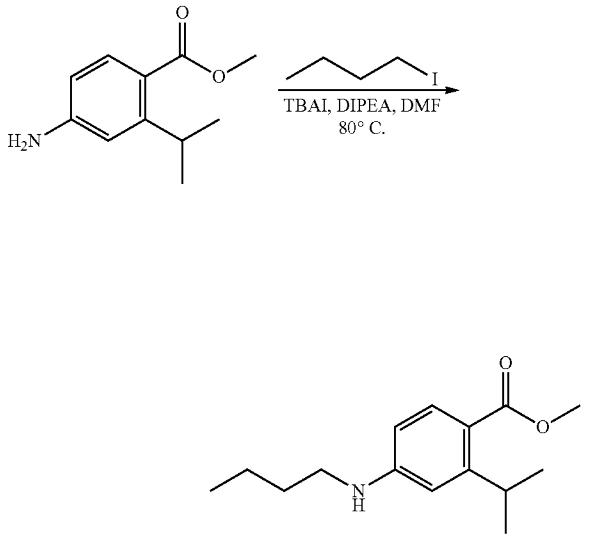

A solution of methyl 4-amino-2-isopropylbenzoate (300 mg, crude), 1-iodobutane (1.40 g, 7.65 mmol), TBAI (1.15 g, 3.11 mmol) and DIPEA (0.2 mL) in DMF (10 mL) were stirred at 80° C. overnight. At rt, the reaction mixture was diluted with EtOAc (30 mL), washed with brine, dried over $Na_2SO_4$, filtered and concentrated. The resulting residue was purified by silica gel column chromatography (petroleum ether:EtOAc=10:1) to give the title compound (150 mg, 26.6% yield over two steps) as white solid. MS (EST) m/z: 250.1 $[M+H]^+$.

Step 4. Synthesis of 4-(butylamino)-2-isopropylbenzoic acid

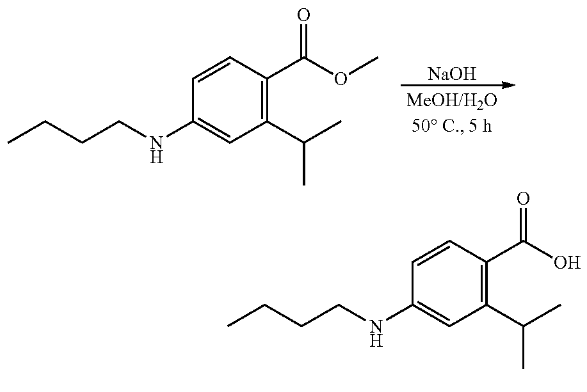

A solution of methyl 4-(butylamino)-2-isopropylbenzoate (150 mg, 0.602 mmol) and NaOH (500 mg, 12.5 mmol) in MeOH (5 mL) and water (1 mL) was stirred at 50° C. for 5 h. At rt, the mixture was acidified (pH=5) with aq. 1 N HCl. The mixture was extracted with EtOAc (3×20 mL). The combined organic phase was washed with brine, dried over $Na_2SO_4$, filtered and concentrated under vacuum to give the title compound (130 mg, crude) as white solid. MS (ESI) m/z: 236.5 $[M+H]^+$.

Step 5. Synthesis of 4-(butylamino)-2-isopropyl-N-(5-nitrothiazol-2-yl)benzamide

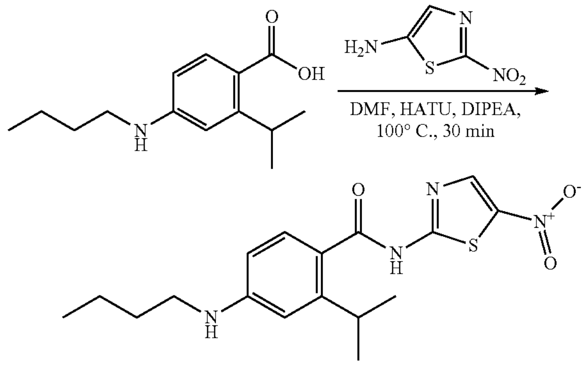

To a solution of 4-(butylamino)-2-isopropylbenzoic acid (130 mg, 0.553 mmol), 2-nitrothiazol-5-amine (180 mg 1.24 mmol) and HATU (480 mg, 1.26 mmol) in DMF (10 mL) was added DIPEA (0.5 mL) at 100° C. After being stirred at 100° C. for 30 min, the mixture was cooled tort and purified by pre-HPLC to give the title compound (23.8 mg, 8.3% yield over two steps) as yellow solid. $^1H$ NMR (400 MHz, DMSO-$d_6$): δ 13.06 (s, 1H), 8.65 (s, 1H), 7.45 (d, J=8.4 Hz, 1H), 6.63 (s, 1H), 6.44-6.36 (m, 2H), 3.59-3.50 (m, 1H), 3.09-3.05 (m, 2H), 1.55-1.50 (m, 2H), 1.41-1.36 (m, 2H), 1.17 (d, J=6.8 Hz, 6H), 0.92 (t, J=7.2 Hz, 3H). MS (ESI) m/z: 361.2 $[M+H]^+$.

Example 116. N-(5-Bromothiazol-2-yl)-5-(butylamino)-[1,1'-biphenyl]-2-carboxamide (B-117)

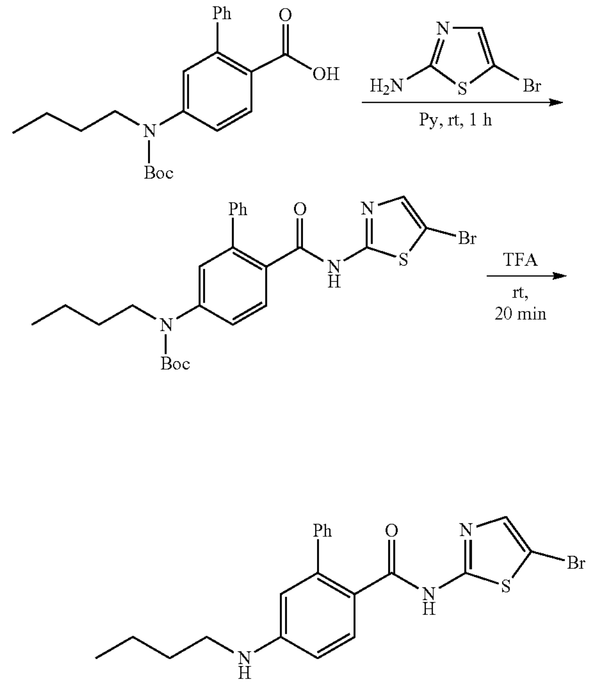

Step 1. Synthesis of tert-butyl (6-((5-bromothiazol-2-yl)carbamoyl)-[1,1'-biphenyl]-3-yl)(butyl)carbamate

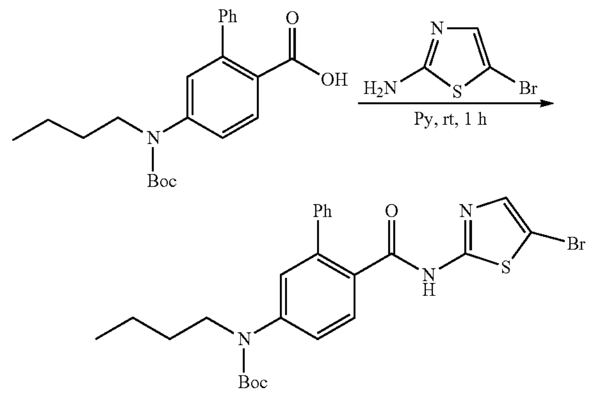

To a solution of 5-((tert-butoxycarbonyl)(butyl)amino)-[1,1'-biphenyl]-2-carboxylic acid (200 mg, 0.541 mmol) and 5-bromothiazol-2-amine hydrobromide (140 mg, 0.541 mmol) in pyridine (10 mL) at rt was added phosphorus oxychloride (166 mg, 1.08 mmol). After being stirred at rt for 1 h, the mixture was quenched with MeOH (5 mL) carefully and concentrated under vacuum to give the title compound (400 mg, crude) as brown oil, which was used in next step without further purification. MS (ESI) m/z: 530.0 $[M-H]^-$.

Step 2. Synthesis of N-(5-bromothiazol-2-yl)-5-(butylamino)-[1,1'-biphenyl]-2-carboxamide

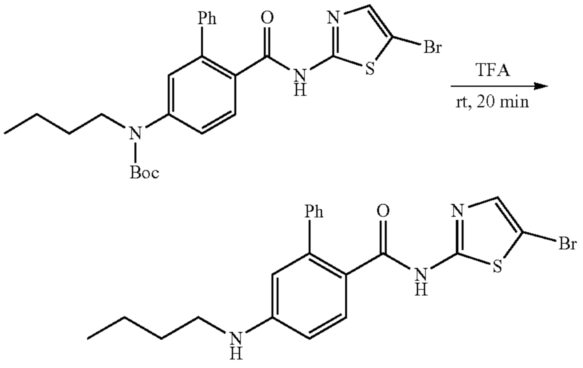

A solution of tert-butyl 6-((5-bromothiazol-2-yl)carbamoyl)-[1,1'-biphenyl]-3-yl)(butyl)carbamate (400 mg, crude) in TFA (5 mL) was stirred at rt for 20 min. The mixture was concentrated under vacuum and purified by pre-HPLC to give the title compound (7.10 mg, 2.41% yield over two steps) as yellow solid. $^1$H NMR (400 MHz, DMSO-$d_6$): δ 12.2 (s, 1H), 7.50 (s, 1H), 7.45 (d, J=8.4 Hz, 1H), 7.36-7.23 (m, 5H), 6.59 (d, J=6.8 Hz, 1H), 6.53-6.50 (m, 1H), 6.33 (brs, 1H), 3.10-3.07 (m, 2H), 1.58-1.51 (m, 2H), 1.41-1.34 (m, 2H), 0.91 (t, J=7.4 Hz, 3H). MS (ESI) m/z: 430.0 $[M+H]^+$.

Example 117. 2-Acetamido-N-(3-nitrophenyl)benzamide (B-124)

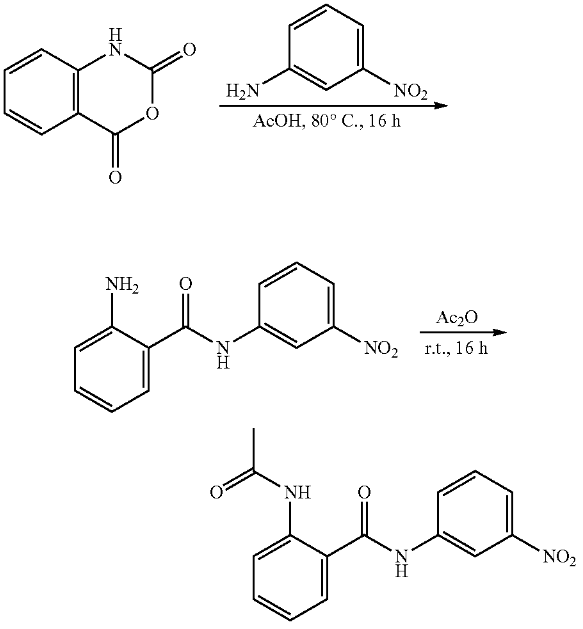

Step 1. Synthesis of 2-amino-N-(3-nitrophenyl)benzamide

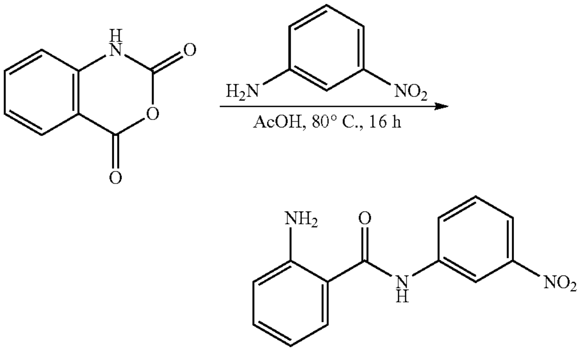

To a solution of 1H-benzo[d][1,3]oxazine-2,4-dione (500 mg, 3.06 mmol) in AcOH (10 mL) was added 3-nitroaniline (423 mg, 3.06 mmol). After being stirred at 80° C. for 16 h, the mixture was cooled to rt and concentrated under vacuum. The resulting residue was purified by silica gel column chromatography (petroleum ether:EtOAc=3:1) to give the title compound (270 mg, 34.0% yield) as yellow solid. MS (ESI) m/z: 258.0 $[M+H]^+$.

Step 2. Synthesis of 2-acetamido-N-(3-nitrophenyl)benzamide

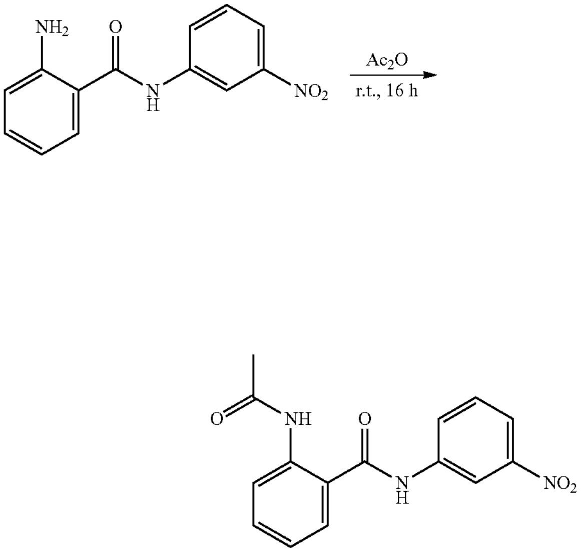

A solution of 2-amino-N-(3-nitrophenyl)benzamide (150 mg, 0.58 mmol) in $Ac_2O$ (10 mL) was stirred at rt for 16 h. The mixture was concentrated under vacuum and purified by pre-HPLC to give the title compound (85 mg, 48.8% yield) as yellow solid. $^1$H NMR (400 MHz, DMSO-$d_6$): δ 10.83 (s, 1H), 10.21 (s, 1H), 8.77 (s, 1H), 8.08 (d, J=7.6 Hz, 1H), 7.98 (d, J=6.4 Hz, 2H), 7.74 (d, J=7.6 Hz, 1H), 7.66 (t, J=8.0 Hz, 1H), 7.54 (t, J=7.6 Hz, 1H), 7.25 (t, J=7.6 Hz, 1H), 2.24-1.83 (s, 3H). MS (ESI) m/z: 300.1 $[M+H]^+$.

Example 118. 2-Acetamido-4-((4-aminobutyl)amino)-N-(5-nitrothiophen-2-yl)benzamide (BL-20)

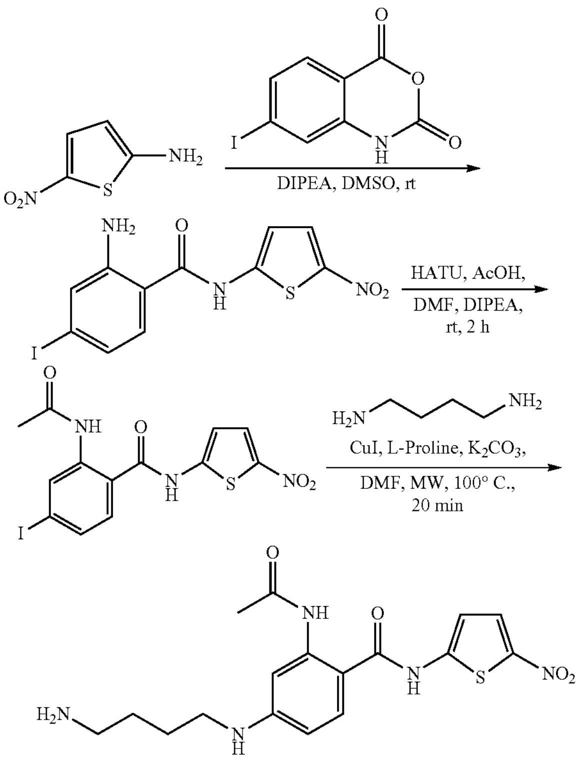

Step 1. Synthesis of 2-acetamido-4-iodo-N-(5-nitrothiophen-2-yl)benzamide

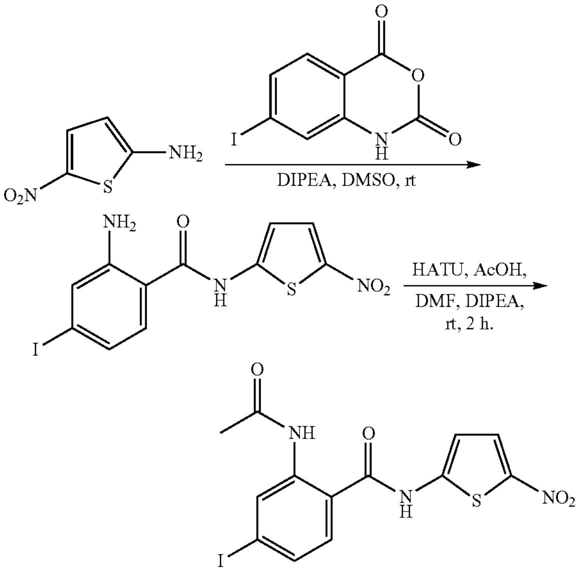

To a solution of 5-nitrothiophen-2-amine (170 mg, 1.18 mmol) and 7-iodo-2H-benzo[d][1,3]oxazine-2,4 (1H)-dione (511 mg, 1.77 mmol) in DMSO (6 mL) was added DIEA (305 mg, 2.36 mmol) at rt. After the reaction mixture was stirred at rt overnight, HATU (918 mg, 2.41 mmol), AcOH (212 mg, 3.54 mmol) and DIEA (305 mg, 2.36 mmol) were added. The resulting mixture was stirred at rt for another 2 h. Then, the mixture was diluted with water (100 mL) and extracted with EtOAc (3×100 mL). The combined organic phase was washed with brine (2×100 mL), dried over $Na_2SO_4$, filtered and concentrated under vacuum. The resulting residue was purified by silica gel column chromatography (petroleum ether:EtOAc=1:1) to give the title compound (270 mg, 53.1% yield) as a red solid. MS (ESI) m/z: 430.0 $[M-H]^-$.

Step 2. Synthesis of 2-acetamido-4-((4-aminobutyl)amino)-N-(5-nitrothiophen-2-yl)benzamide

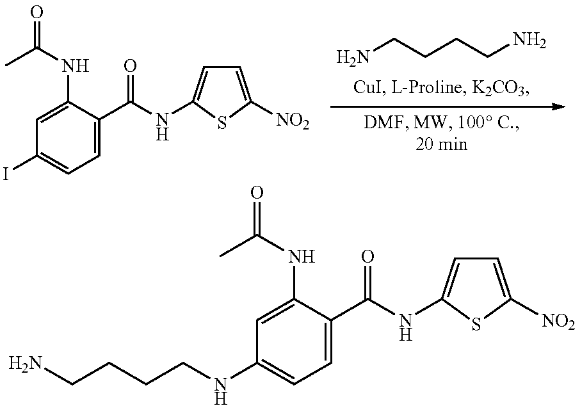

A solution of 2-acetamido-4-iodo-N-(5-nitrothiophen-2-yl)benzamide (250 mg, 0.58 mmol), butane-1,4-diamine (255 mg, 2.90 mmol), L-Proline (13.4 mg, 0.116 mmol), CuI (22.1 mg, 0.116 mmol) and $K_2C03$ (240 mg, 1.74 mmol) in DMF (3 mL) was stirred at 100° C. for 20 min under microwave under argon atmosphere. At rt, the mixture was concentrated and purified by pre-HPLC to give the title compound (48.8 mg, 16.7% yield) as a red solid. 1H NMR (400 MHz, DMSO-d6): δ 13.50 (s, 1H), 7.95 (d, J=8.8 Hz, 1H), 7.87 (d, J=4.8 Hz, 1H), 7.84 (s, 1H), 7.59 (brs, 3H), 6.47 (d, J=4.8 Hz, 1H), 6.30-6.26 (m, 2H), 3.08-3.07 (m, 2H), 2.83-2.81 (m, 2H), 2.14 (s, 3H), 1.61-1.59 (m, 4H). MS (ESI) m/z: 392.1 $[M+H]^+$.

Example 119. N-(4-Bromo-5-nitrothiazol-2-yl)-5-(butylamino)-[1,1'-biphenyl]-2-carboxamide (B-113)

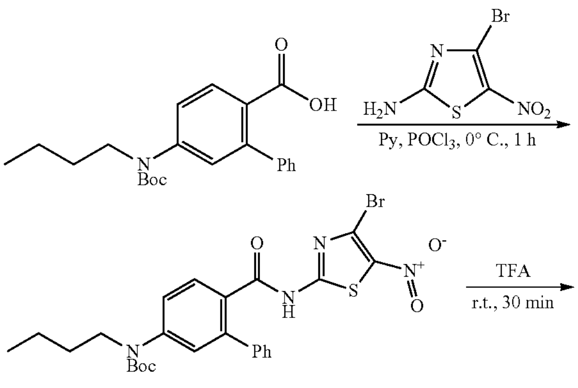

-continued

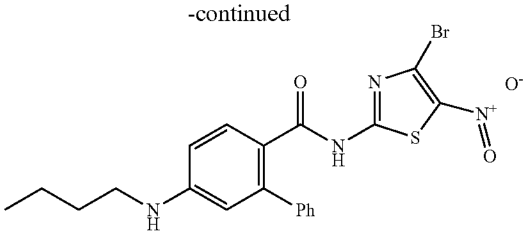

Step 1. Synthesis of tert-butyl (6-((4-bromo-5-nitrothiazol-2-yl)carbamoyl)-[1,1'-biphenyl]-3-yl)(butyl)carbamate

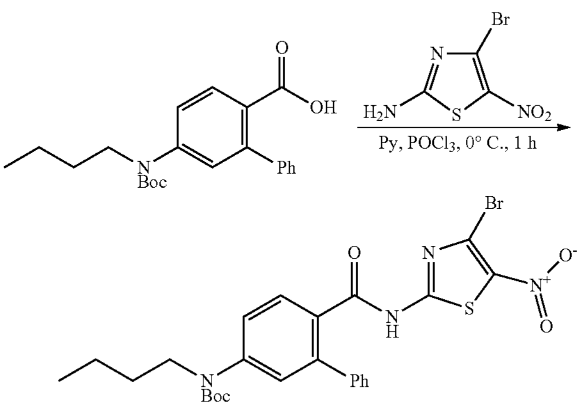

To a solution of 5-((tert-butoxycarbonyl)(butyl)amino)-[1,1'-biphenyl]-2-carboxylic acid (200 mg, 0.541 mmol) and 4-bromo-5-nitrothiazol-2-amine (121 mg, 0.541 mmol) in pyridine (10 mL) was added phosphorus oxychloride (166 mg, 1.08 mmol) at 0° C. After being stirred at 0° C. for 1 h, the mixture was quenched with MeOH (5 mL) at 0° C. and concentrated under vacuum to give the title compound (400 mg, crude) as brown oil, which was used in the next step without further purification. MS (ESI) m/z: 575.0 $[M+H]^+$.

Step 2. Synthesis of N-(4-bromo-5-nitrothiazol-2-yl)-5-(butylamino)-[1,1'-biphenyl]-2-carboxamide

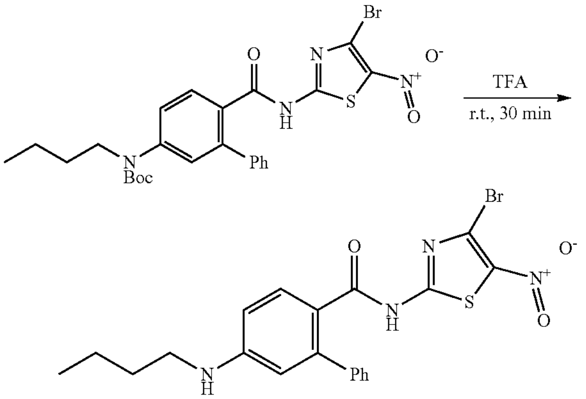

A solution of tert-butyl (6-((4-bromo-5-nitrothiazol-2-yl)carbamoyl)-[1,1'-biphenyl]-3-yl)(butyl)carbamate (400 mg, crude) in TFA (5 mL) was stirred at rt for 30 min. Then the mixture was concentrated under vacuum. The resulting residue was purified by pre-HPLC to give the title compound (10.1 mg, 3.17% yield over two steps) as yellow solid. $^1H$ NMR (400 MHz, DMSO-$d_6$): δ 13.2 (brs, 1H), 7.57 (d, J=8.8 Hz, 1H), 7.39-7.31 (m, 3H), 7.34 (d, J=6.8 Hz, 2H), 6.64-6.59 (m, 2H), 6.52 (brs, 1H), 3.16-3.06 (m, 2H), 1.58-1.53 (m, 2H), 1.41-1.36 (m, 2H), 0.91 (t, J=7.2 Hz, 3H). MS (ESI) m/z: 473.0 $[M-H]^-$.

Example 120. 5-(Butylamino)-N-(4-cyclopropyl-5-nitrothiazol-2-yl)-[1,1'-biphenyl]-2-carboxamide (B-115)

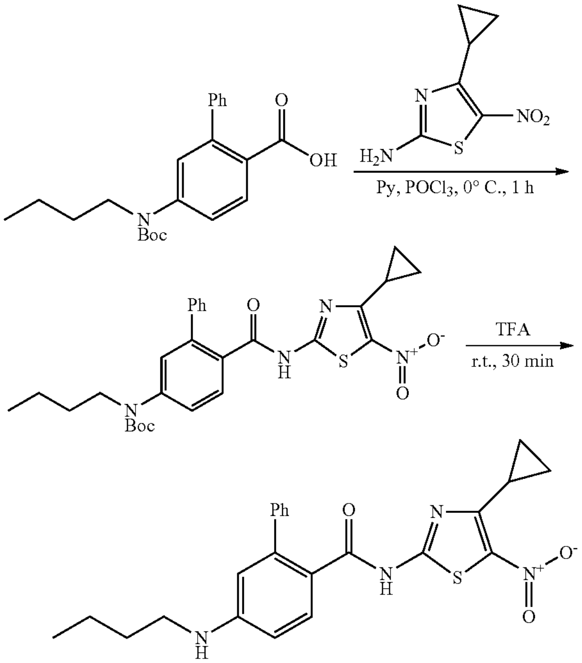

Step 1. Synthesis of tert-butyl butyl(6-((4-cyclopropyl-5-nitrothiazol-2-yl)carbamoyl)-[1,1'-biphenyl]-3-yl)carbamate

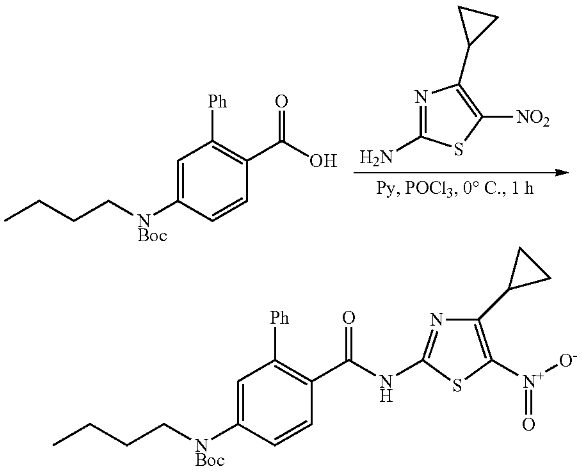

To a solution of 5-((tert-butoxycarbonyl)(butyl)amino)-[1,1'-biphenyl]-2-carboxylic acid (200 mg, 0.541 mmol) and 4-cyclopropyl-5-nitrothiazol-2-amine (100 mg, 0.541 mmol) in pyridine (10 mL) was added phosphorus oxychloride (166 mg, 1.08 mmol) at 0° C. After being stirred at 0° C. for 1 h, the mixture was quenched with MeOH (5 mL) at 0° C. and concentrated under vacuum to give the title compound (400 mg, crude) as brown oil, which was used in the next step without further purification. MS (ESI) m/z: 537.1 [M+H]$^+$.

Step 1. Synthesis of 5-(butylamino)-N-(4-cyclopropyl-5-nitrothiazol-2-yl)-[1,1'-biphenyl]-2-carboxamide

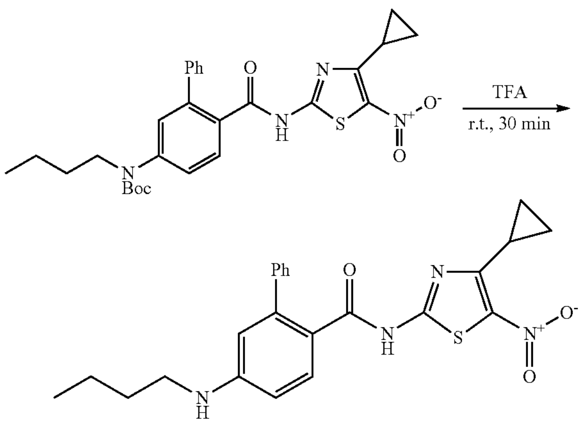

A solution of tert-butyl butyl(6-((4-cyclopropyl-5-nitrothiazol-2-yl)carbamoyl)-[1,1'-biphenyl]-3-yl)carbamate (400 mg, crude) in TFA (5 mL) was stirred at rt for 30 min. Then the mixture was concentrated under vacuum. The resulting residue was purified by pre-HPLC to give the title compound (17.8 mg, 5.98% yield over two steps) as yellow solid. $^1$H NMR (400 MHz, DMSO-d$_6$): δ 12.8 (s, 1H), 7.52 (d, J=8.4 Hz, 1H), 7.39-7.28 (m, 3H), 7.23-7.21 (m, 2H), 6.58-6.56 (m, 1H), 6.51-6.49 (m, 1H), 5.39 (brs, 1H), 3.11-3.04 (m, 3H), 1.58-1.51 (m, 2H), 1.43-1.34 (m, 2H), 1.22-1.20 (m, 2H), 1.11-1.07 (m, 2H), 0.91 (t, J=7.4 Hz, 3H). MS (ESI) m/z: 437.1 [M+H]$^+$.

Example 121. 2-Acetamido-N-(4-nitrophenyl)benzamide (B-125)

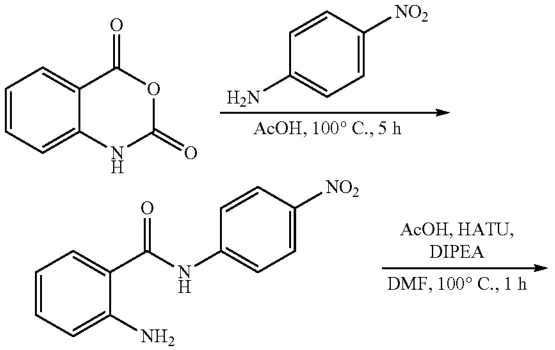

-continued

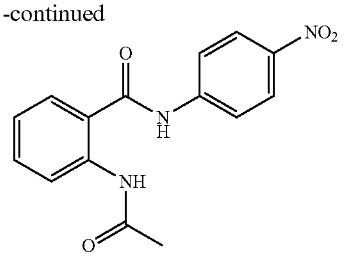

Step 1. Synthesis of 2-amino-N-(4-nitrophenyl)benzamide

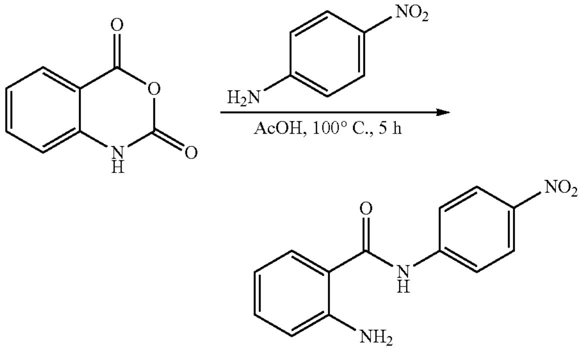

A solution of 1H-benzo[d][1.3]oxazine-2,4-dione (2.00 g, 12.3 mmol) and 4-nitroaniline (1.70 g, 12.3 mmol) in AcOH (50 mL) was stirred at 100° C. for 5 h. At it, the mixture was concentrated under vacuum. The resulting residue was purified by silica gel column chromatography (petroleum ether: EtOAc=3:1) to give the title compound (100 mg, 3.16% yield) as yellow solid. MS (EST) m/z: 258.1 [M+H]$^+$.

Step 2. Synthesis of 2-acetamido-N-(4-nitrophenyl)benzamide

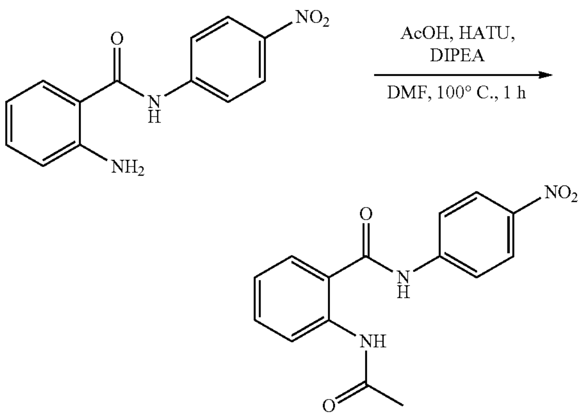

To a solution of 2-amino-N-(4-nitrophenyl)benzamide (100 mg, 0.390 mmol), HATU (222 mg, 0.585 mmol) and AcOH (35 mg, 0.585 mmol) in DMF (5 mL) was added DIPEA (151 mg, 1.17 mmol) at 100° C. After being stirred at 100° C. for 1 h. the mixture was cooled to rt and purified by pre-HPLC to give the title compound (18.1 mg, 15.5% yield) as yellow solid. $^1$H NMR (400 MHz, DMSO-$d_6$): δ 10.92 (s, 1H), 10.12 (s, 1H), 8.26 (d, J=9.2 Hz, 2H), 7.98 (d, J=9.2 Hz, 2H), 7.88 (d, J=8.0 Hz, 1H), 7.70 (d, J=7.6 Hz, 1H), 7.53 (t, J=7.6 Hz, 1H), 7.25 (t, J=7.2 Hz, 1H), 2.02 (s, 3H). MS (ESI) m/z: 298.2 [M−H]$^-$ Example 122. 5-(Butylamino)-N-(5-nitrothiophen-2-yl)-[1,1'-biphenyl]-2-carboxamide (B-135)

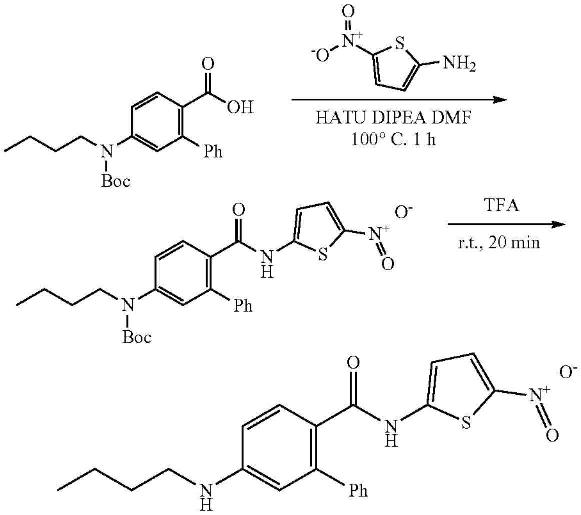

Step 1. Synthesis of tert-butyl butyl(6-((5-nitrothiophen-2-yl)carbamoyl)-[1,1'-biphenyl]-3-yl)carbamate

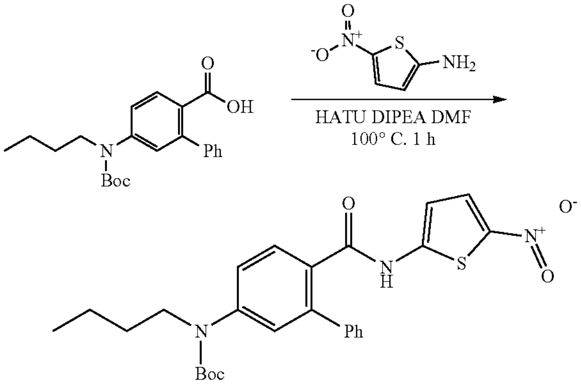

A solution of 5-((tert-butoxycarbonyl)(butyl)amino)-[1,1'-biphenyl]-2-carboxylic acid (100 mg, 0.271 mmol), 5-nitrothiophen-2-amine (78 mg, 0.542 mmol), HATU (206 mg, 0.542 mmol) and DIPEA (10 mg, 0.542 mmol) in DMF (10 mL) was stirred at 100° C. for 1 h. At rt, the reaction mixture was diluted with EtOAc (40 mL), washed with brine, dried over $Na_2SO_4$, filtered and concentrated under vacuum to give the title compound (100 mg, crude) as yellow solid, which was used in the next step without further purification.

Step 2. Synthesis of 5-(butylamino)-N-(5-nitrothiophen-2-yl)-[1,1'-biphenyl]-2-carboxamide

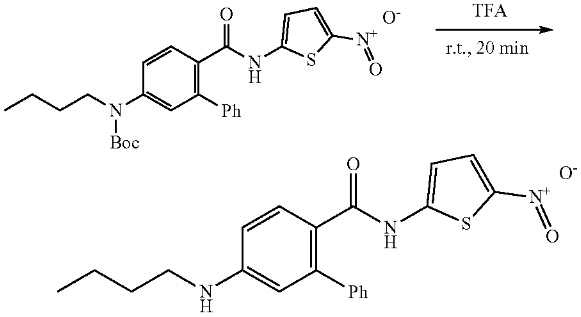

A solution of tert-butyl butyl(6-((5-nitrothiophen-2-yl)carbamoyl)-[1,1'-biphenyl]-3-yl)carbamate (100 mg, crude), and TFA (3 mL) in DCM (3 mL) was stirred at rt for 20 minutes. Then, the mixture was concentrated under reduced pressure. The resulting residue was purified by pre-HPLC to give the title compound (17.6 mg, 16.4% yield over two steps) as yellow solid. $^1$H NMR (400 MHz, DMSO-$d_6$): δ 12.08 (s, 1H), 7.96 (d, J=4.8 Hz, 1H), 7.49 (d, J=8.4 Hz, 1H), 7.36-7.24 (m, 5H), 6.65-6.55 (m, 2H), 6.55 (s, 1H), 3.12-3.09 (m, 2H), 1.57-1.53 (m, 2H), 1.41-1.36 (m, 2H), 0.93-0.90 (t, J=7.2 Hz, 3H). LC-MS (ESI) m/z: 396.4 [M+H]$^+$.

Example 123. 2-((5-Nitrothiazol-2-yl)carbamoyl)-5-((tetrahydro-2H-pyran-4-yl)amino)phenyl acetate (B-96)

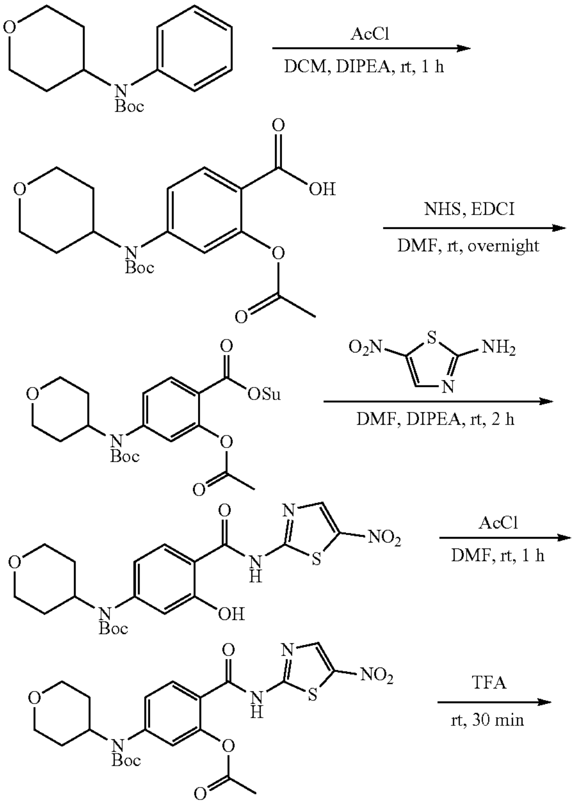

-continued

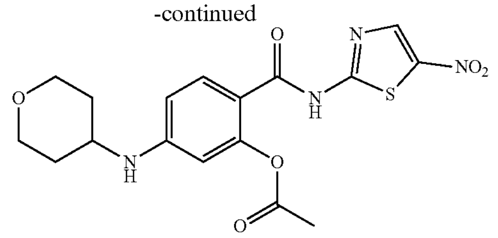

Step 1. Synthesis of 2-acetoxy-4-((tert-butoxycarbonyl)(tetrahydro-2H-pyran-4-yl)amino)benzoic acid

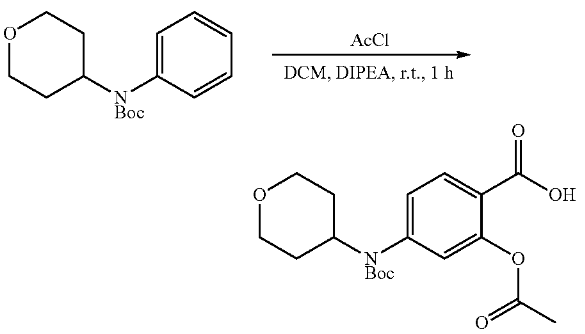

To a solution of 4-((tert-butoxycarbonyl)(tetrahydro-2H-pyran-4-yl)amino)-2-hydroxybenzoic acid (500 mg, 1.48 mmol) and DIPEA (574 mg, 4.45 mmol) in DCM (20 mL) was added acetyl chloride (231 mg, 2.96 mmol). After being stirred at rt for 1 h, the mixture was diluted with DCM (30 mL) and washed with aq. HCl (20 mL, 1 N). The organic layer was washed with brine, dried over $Na_2SO_4$, filtered and concentrated under vacuum to give the title compound (200 mg, crude) as yellow solid, which was used in next step without further purification. MS (ESI) m/z: 323.9 $[M+H-56]^+$.

Step 2. Synthesis of 2,5-dioxopyrrolidin-1-yl 2-acetoxy-4-((tert-butoxycarbonyl)(tetrahydro-2H-pyran-4-yl)amino)benzoate

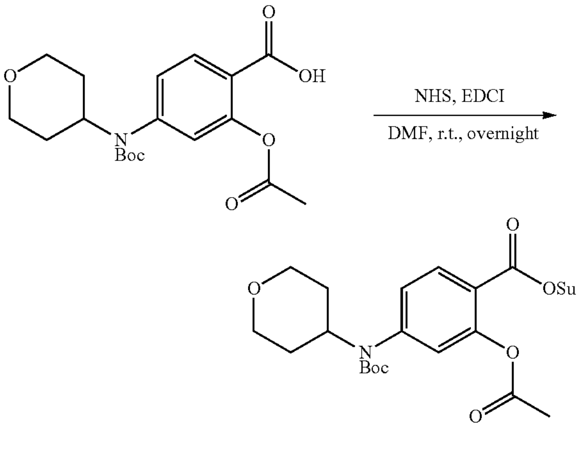

A solution of 2-acetoxy-4-((tert-butoxycarbonyl)(tetrahydro-2H-pyran-4-yl)amino)benzoic acid (200 mg, crude), NHS (120 mg, 1.05 mmol) and EDCI (200 mg, 1.05 mmol) in DMF (10 mL) was stirred at rt overnight. Then, the mixture was poured into water (50 mL) and extracted with EtOAc (3×50 mL). The combined organic phase was washed with brine, dried over $Na_2SO_4$, filtered and concentrated under vacuum. The resulting residue was purified by silica gel column chromatography (petroleum ether: EtOAc=0:1) to give the title compound (50 mg, 7.43% yield over two steps) as yellow solid.

Step 3. Synthesis of tert-butyl (3-hydroxy-4-((5-nitrothiazol-2-yl)carbamoyl)phenyl)(tetrahydro-2H-pyran-4-yl)carbamate

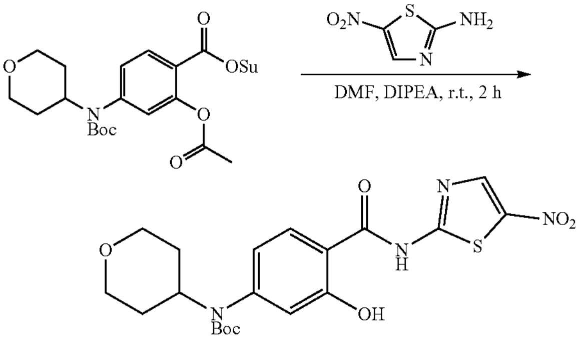

A solution of 2,5-dioxopyrrolidin-1-yl 2-acetoxy-4-((tert-butoxycarbonyl)(tetrahydro-2H-pyran-4-yl)amino)benzoate (50 mg, 0.11 mmol), DIPEA (57 mg, 0.44 mmol) and 5-nitrothiazol-2-amine (32 mg, 0.22 mmol) in DMF (5 mL) was stirred at rt for 2 h. The mixture was used in the next step without further purification. MS (ESI) m/z: 463.1 $[M-H]^-$.

Step 4. Synthesis of 5-((tert-butoxycarbonyl)(tetrahydro-2H-pyran-4-yl)amino)-2-((5-nitrothiazol-2-yl)carbamoyl)phenyl acetate

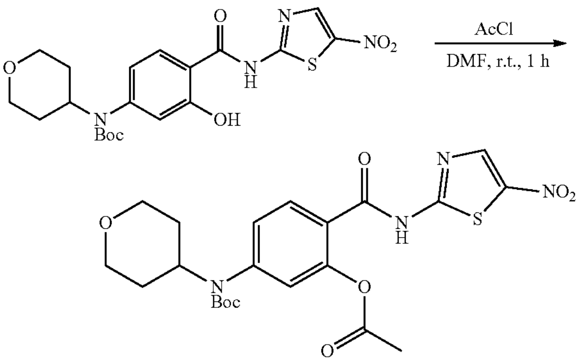

To a solution of tert-butyl (3-hydroxy-4-((5-nitrothiazol-2-yl)carbamoyl)phenyl)-(tetrahydro-2H-pyran-4-yl)carbamate (5 mL reaction mixture from previous step) was added acetyl chloride (17 mg, 0.22 mmol). After being stirred at rt for 1 h, the mixture was diluted with EtOAc (50 mL), washed with aq. HCl (10 mL, 1 N), washed with brine, dried over $Na_2SO_4$, filtered and concentrated under vacuum to give the title compound (60 mg, crude) as yellow solid, which was used in the next step without further purification. MS (ESI) m/z: 505.1 [M−H]⁻.

Step 5. Synthesis of 2-((5-nitrothiazol-2-yl)carbamoyl)-5-((tetrahydro-2H-pyran-4-yl)amino)phenyl acetate

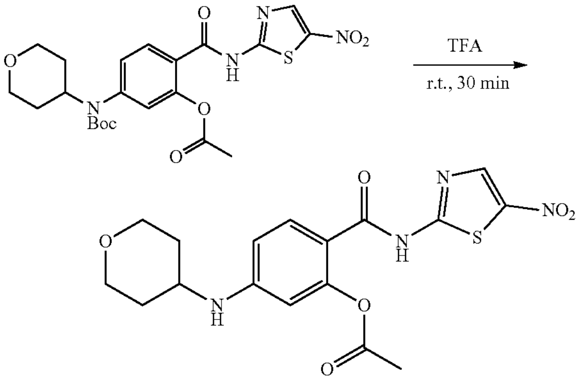

A solution of 5-((tert-butoxycarbonyl)(tetrahydro-2H-pyran-4-yl)amino)-2-((5-nitrothiazol-2-yl)carbamoyl)phenyl acetate (60 mg, crude) in TFA (2 mL) was stirred at rt 30 min. Then, the mixture was concentrated and purified by pre-HPLC to give the title compound (9.16 mg, 20.4% yield over two steps) as yellow solid. $^1$H NMR (400 MHz, DMSO-$d_6$): δ 13.00 (s, 1H), 8.66 (s, 1H), 7.74 (d, J=8.8 Hz, 1H), 6.80 (d, J=8.0 Hz, 1H), 6.58-6.55 (m, 1H), 6.41 (d, J=2.0 Hz, 1H), 3.88-3.85 (m, 2H), 3.61-3.53 (m, 1H), 3.45-3.40 (m, 2H), 2.24 (s, 3H), 1.88-1.84 (m, 2H), 1.45-1.35 (m, 2H). MS (ESI) m/z: 407.1 [M+H]$^+$.

Example 124. 2-Ethoxy-N-(5-nitrothiazol-2-yl)-4-((tetrahydro-2H-pyran-4-yl)amino)benzamide (B-98)

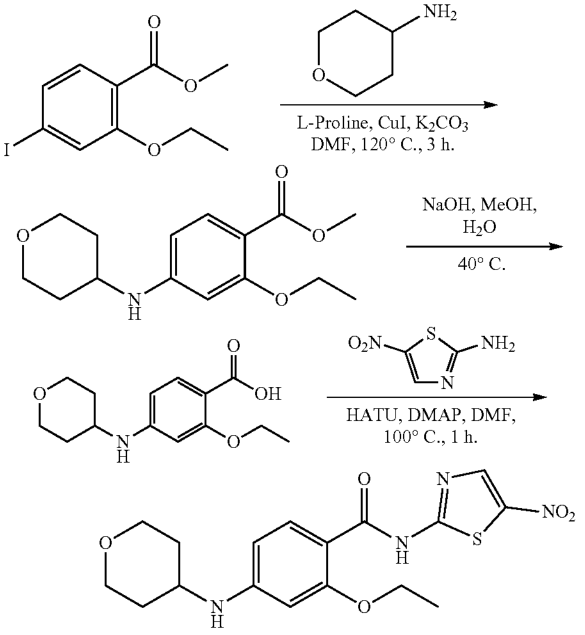

Step 1. Synthesis of methyl 2-ethoxy-4-((tetrahydro-2H-pyran-4-yl)amino)benzoate

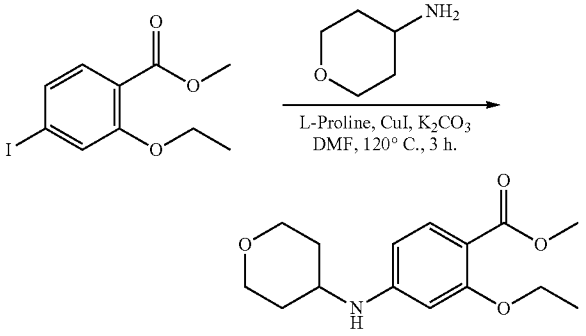

A solution of methyl 2-ethoxy-4-iodobenzoate (500 mg, 1.63 mmol), tetrahydro-2H-pyran-4-amine (333 mg, 3.26 mmol), L-Proline (187 mg, 1.63 mmol), CuI (310 mg, 1.63 mmol) and $K_2CO_3$ (450 mg, 3.26 mmol) in DMF (8 mL) was stirred at 120° C. for 3 h under argon atmosphere. At it, the mixture was diluted with water (50 mL) and extracted with EtOAc (2×50 mL). The combined organic phase was washed with brine (2×50 mL), dried over $Na_2SO_4$, filtered and concentrated under vacuum. The resulting residue was purified by silica gel column chromatography (petroleum ether:EtOAc=1:1) to give the title compound (200 mg, 43.9% yield) as colorless oil. MS (ESI) m/z: 280.1 [M+H]$^+$.

Step 2. Synthesis of methyl 2-ethoxy-4-((tetrahydro-2H-pyran-4-yl)amino)benzoic acid

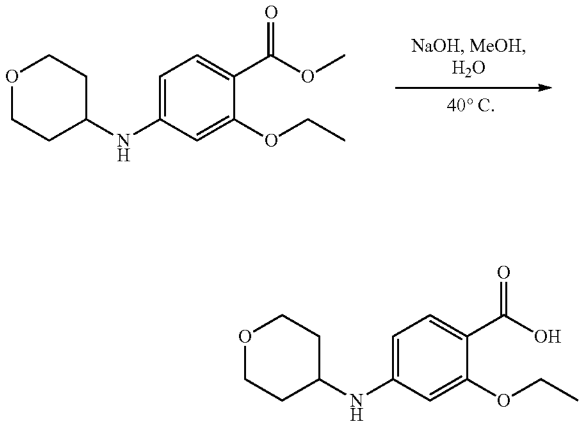

A solution of methyl 2-ethoxy-4-((tetrahydro-2H-pyran-4-yl)amino)benzoate (200 mg, 0.72 mmol) and NaOH (115 mg, 2.87 mmol) in MeOH (5 mL) and $H_2O$ (10 mL) was stirred at 40° C. overnight. Then, the mixture was diluted with water (20 mL) and acidified (pH=4) with 1 N HCl. The mixture was extracted with EtOAc (2×50 mL). The combined organic phase was washed with brine (2×50 mL), dried over $Na_2SO_4$, filtered and concentrated under vacuum to give the title compound (170 mg, 89.5% yield) as white solid. MS (ESI) m/z: 266.2 [M+H]$^+$.

Step 3. Synthesis of 2-ethoxy-N-(5-nitrothiazol-2-yl)-4-((tetrahydro-2H-pyran-4-yl)amino)benzamide

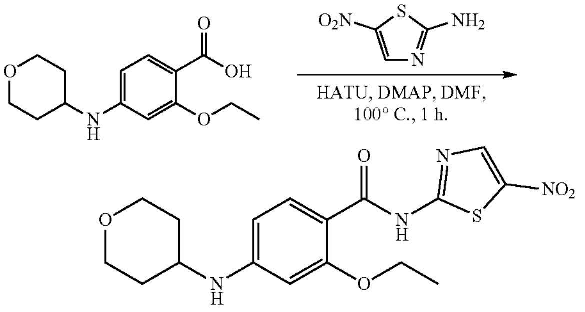

To a solution of 2-ethoxy-4-((tetrahydro-2H-pyran-4-yl)amino)benzoic acid (100 mg, 0.377 mmol), 5-nitrothiazol-2-amine (109 mg, 0.755 mmol) and HATU (287 mg, 0.755 mmol) in DMF (2 mL) at 100° C. was added DMAP (138 mg, 1.13 mmol). After being stirred at 100° C. for 1 h. the mixture was cooled to rt and purified by pre-HPLC (0.1% TFA) to give the title compound (10.0 mg, 6.75% yield) as yellow solid. $^1$H NMR (400 MHz, DMSO-$d_6$): δ 11.69 (s, 1H), 8.65 (s, 1H), 7.74 (d, J=8.8 Hz, 1H), 6.82 (d, J=7.6 Hz, 1H), 6.41-6.38 (m, 1H), 6.31 (s, 1H), 4.24 (q, J=6.8 Hz, 2H), 3.88-3.86 (m, 2H), 3.64 (s, 1H), 3.47-3.41 (m, 2H), 1.89-1.86 (m, 2H), 1.49 (t, J=6.8 Hz, 3H), 1.47-1.40 (m, 2H). MS (ESI) m/z: 393.1 $[M+H]^+$.

Example 125. N-Methyl-N-(5-nitrothiazol-2-yl)-2-(3,3,3-trifluoropropyl)benzamide (B-105)

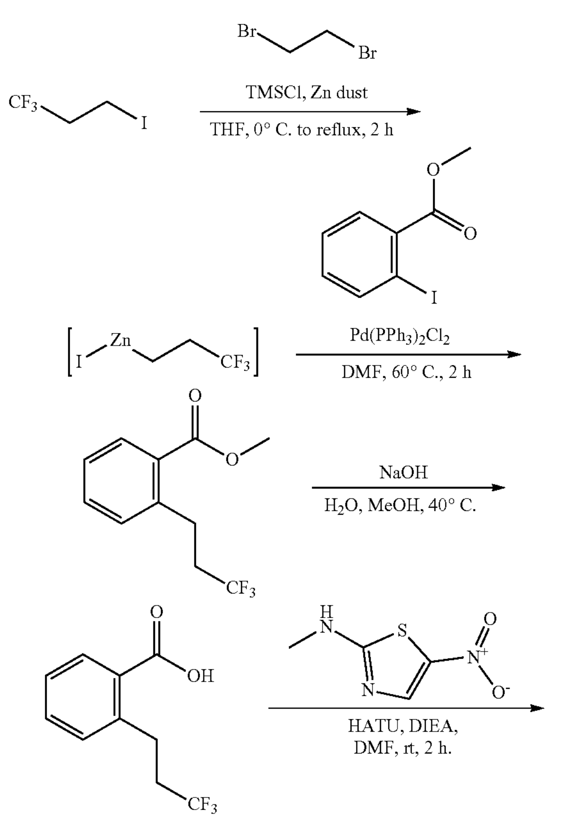

-continued

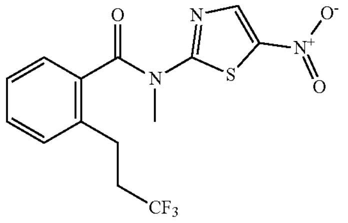

Step 1. Synthesis of methyl 2-(3,3,3-trifluoropropyl)benzoate

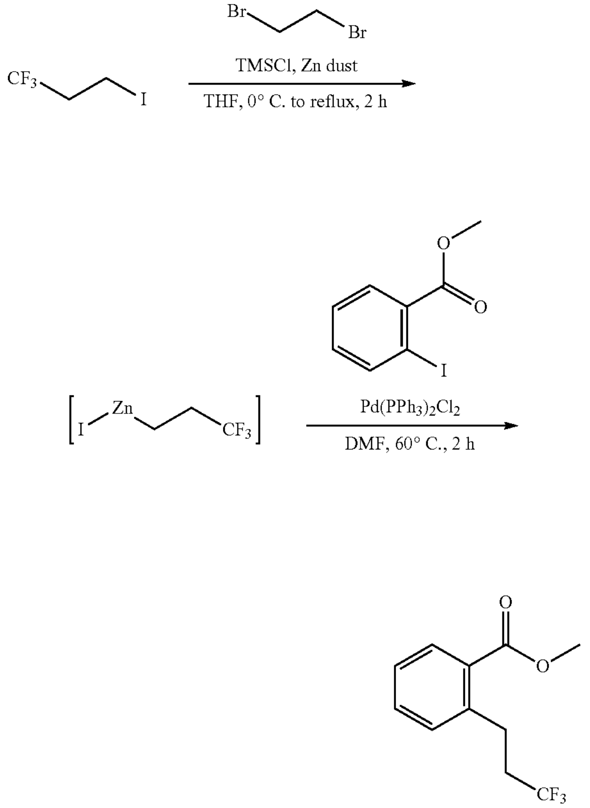

To a solution of Zn dust (1.30 g, 20.1 mmol) in dry THF (10 mL) was added 1,2-dibromoethane (1.00 g, 5.36 mmol). The mixture was heated to reflux for 2 h, before it was cooled to 0° C. TMSCl (582 mg, 5.36 mmol) was slowly added. The resulting mixture was stirred for 15 min at 0° C. To the mixture was added a solution of methyl 2-iodobenzoate (1.16 g, 4.42 mmol) and $Pd(PPh_3)_2Cl_2$ (1.88 g, 2.68 mmol) in dry DMF (10 mL). After being stirred at 60° C. for 2 h, the mixture was diluted with water (100 mL) and extracted with EtOAc (3×100 mL). The combined organic phase was washed with brine (2×100 mL), dried over $Na_2SO_4$, filtered and concentrated under vacuum. The resulting residue was purified by silica gel column chromatography (petroleum ether:EtOAc=4:1) to give the title compound (900 mg, 87.8% yield) as colorless oil. MS (ESI) m/z: 232.9 $[M+H]^+$.

Step 2. Synthesis of 2-(3,3,3-trifluoropropyl)benzoic acid

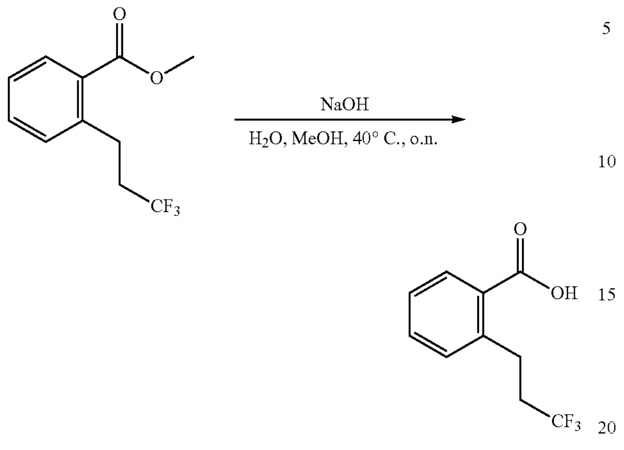

A solution of methyl 2-(3,3,3-trifluoropropyl)benzoate (400 mg, 1.72 mmol) and NaOH (206 mg, 5.15 mmol) in MeOH (10 mL) and $H_2O$ (10 mL) was stirred at 40° C. overnight. Then, the mixture was diluted with water (20 mL) and acidified (pH=2) with 1 N HCl. The mixture was extracted with EtOAc (2×50 mL). The combined organic phase was washed with brine (2×50 mL), dried over $Na_2SO_4$, filtered and concentrated under vacuum to give the title compound (300 mg, 79.8% yield) as white solid. MS (ESI) m/z: 216.9 $[M-H]^-$.

Step 3. Synthesis of N-methyl-N-(5-nitrothiazol-2-yl)-2-(3,3,3-trifluoropropyl)benzamide

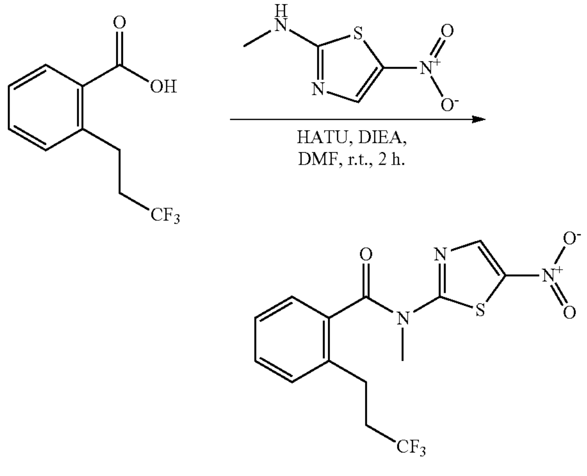

To a solution of 2-(3,3,3-trifluoropropyl)benzoic acid (100 mg, 0.398 mmol), N-methyl-5-nitrothiazol-2-amine (109 mg, 0.688 mmol) and HATU (349 mg, 0.917 mmol) in DMF (2 mL) at rt was added DIEA (177 mg, 1.38 mmol). After being stirred at rt for 2 h, the mixture was purified by pre-HPLC to give the title compound (56.0 mg, 26.6% yield) as yellow solid. $^1H$ NMR (400 MHz, DMSO-$d_6$): δ 8.79 (s, 1H), 7.60-7.55 (m, 3H), 7.46-7.42 (m, 1H), 3.46 (s, 3H), 2.84-2.80 (m, 2H), 2.63-2.56 (m, 2H). MS (ESI) m/z: 359.9 $[M+H]^+$.

Example 126. 4-(Butylamino)-2-isopropyl-N-(5-nitrothiophen-2-yl)benzamide (B-134)

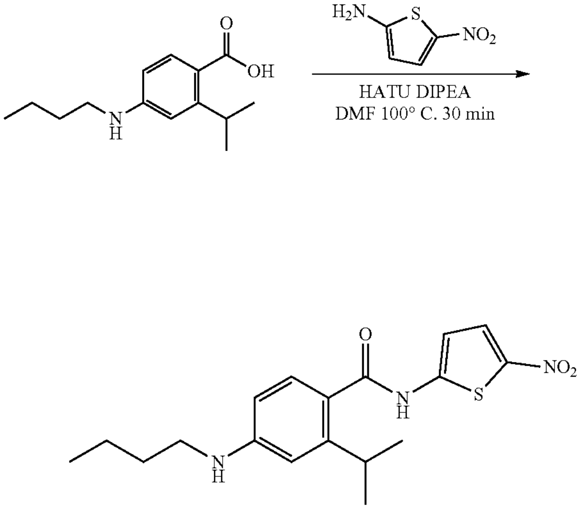 [SMILES: CCCCNc1ccc(C(=O)O)c(C(C)C)c1 ; Nc1ccc([N+](=O)[O-])s1 ; CCCCNc1ccc(C(=O)Nc2ccc([N+](=O)[O-])s2)c(C(C)C)c1]

To a solution of 4-(butylamino)-2-isopropylbenzoic acid (100 mg, 0.425 mmol), 5-nitrothiophen-2-amine (120 mg, 0.833 mmol) and HATU (330 mg, 0.868 mmol) in DMF (10 mL) at 100° C. was added DIPEA (0.5 mL). After being stirred at 100° C. for 30 min, the mixture was cooled to rt and purified by pre-HPLC to give the title compound (6.92 mg, 3.42% yield) as yellow solid. $^1H$ NMR (400 MHz, DMSO-$d_6$): δ 12.15 (s, 1H), 8.02 (d, J=4.8 Hz, 1H), 7.38 (d, J=8.4 Hz, 1H), 6.80 (d, J=4.8 Hz, 1H), 6.63 (d, J=2.0 Hz, 1H), 6.47-6.44 (m, 1H), 3.55-3.46 (m, 1H), 3.9-3.05 (m, 2H), 1.55-1.52 (m, 2H), 1.41-1.36 (m, 2H), 1.17-1.12 (m, 6H), 0.93-0.90 (m, 1H). MS (ESI) m/z: 362.4 $[M+H]^+$.

Example 127. 2-Acetamido-4-((7-aminoheptyl) amino)-N-(4-methyl-5-nitrothiazol-2-yl)benzamide (BL-7)

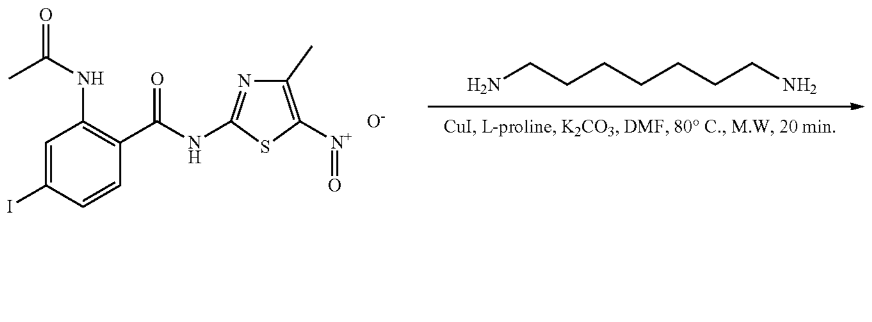

-continued

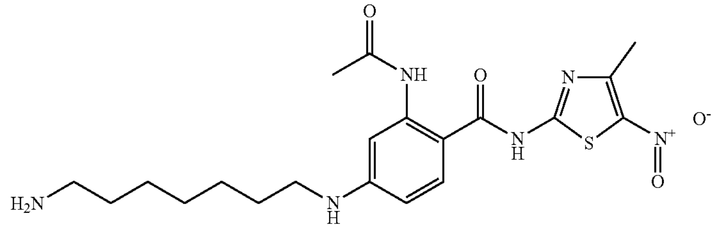

To a solution of 2-acetamido-4-iodo-N-(4-methyl-5-nitrothiazol-2-yl)benzamide (180 mg, 0.404 mmol) and heptane-1,7-diamine (263 mg, 2.02 mmol) in DMF (5 mL) were added CuI (15.4 mg, 0.081 mmol), K2CO3 (112 mg, 0.807 mmol) and L-proline (9.32 mg, 0.081 mmol). The mixture was irradiated at 80° C. for 20 min under N2 in microwave reactor. The mixture was purified by pre-HPLC to give title compound (13.6 mg, 6.18% yield) as yellow solid. 1H NMR (400 MHz, DMSO-d6): δ 13.00 (brs, 1H), 11.09 (brs, 1H), 7.90-7.88 (m, 1H), 7.74 (s, 1H), 7.64 (brs, 3H), 6.91 (s, 1H), 6.34-6.36 (m, 1H), 3.10-3.05 (m, 2H), 2.80-2.78 (m, 2H), 2.69 (s, 3H), 2.13 (s, 3H), 1.55-1.52 (m, 4H), 1.33-1.31 (m, 6H). MS (ESI) m/z: 449.2 $[M+H]^+$.

Example 128. 2-Acetamido-4-((2-(2-(2-(2-aminoethoxy)ethoxy)ethoxy)ethyl)amino)-N-(4-methyl-5-nitrothiazol-2-yl)benzamide (BL-8)

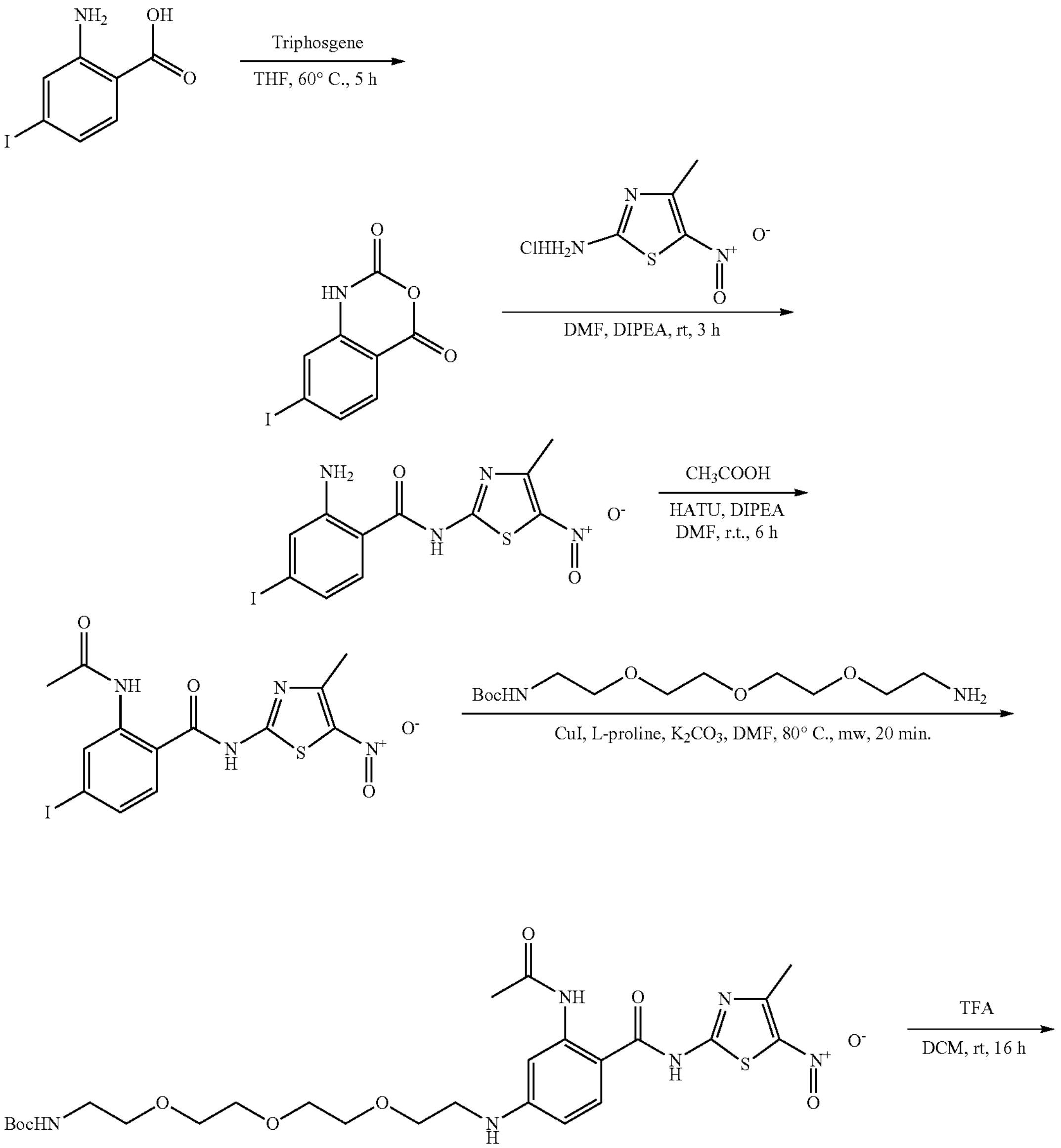

-continued

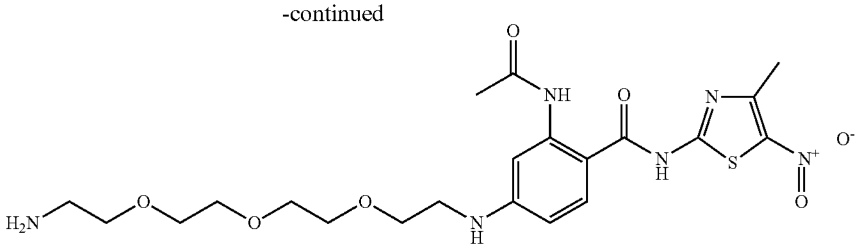

Step 1. Synthesis of 7-iodo-2H-benzo[d][1,3]oxazine-2,4 (1H)-dione

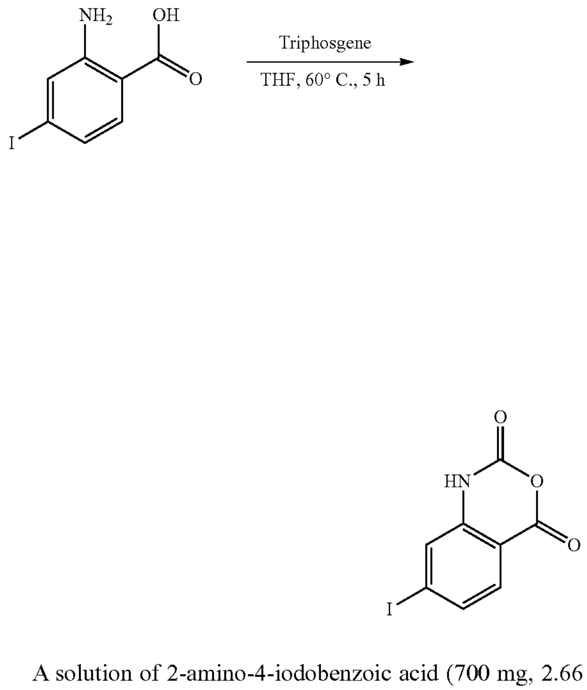

A solution of 2-amino-4-iodobenzoic acid (700 mg, 2.66 mmol) and triphosgene (452 mg, 4.52 mmol) in THF (30 mL) was stirred at 60° C. for 5 h. before the reaction mixture was concentrated under vacuum. The resulting residue was diluted with $H_2O$ (150 mL) and extracted with EtOAc (3×50 mL). The combined organic phase was dried over $Na_2SO_4$, filtered and concentrated under vacuum to give the title compound (750 mg, 68.29% yield) as yellow solid.

Step 2. Synthesis of 2-amino-4-iodo-N-(4-methyl-5-nitrothiazol-2-yl)benzamide

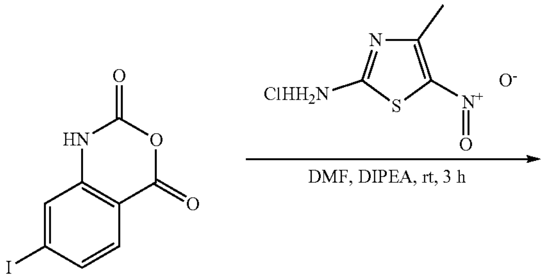

-continued

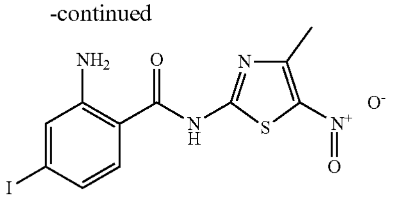

To a solution of 7-iodo-2H-benzo[d][1,3]oxazine-2,4 (1H)-dione (200 mg, 0.692 mmol) and 4-methyl-5-nitrothiazol-2-amine hydrochloride (163 mg, 0.830 mmol)) in DMF (5 mL) was added DIPEA (268 mg, 2.08 mmol). The solution was stirred at it for 3 h. The reaction mixture was used in the next step without further purification. MS (ESI) m/z: 404.9 $[M+H]^+$.

Step 3. Synthesis of 2-acetamido-4-iodo-N-(4-methyl-5-nitrothiazol-2-yl)benzamide

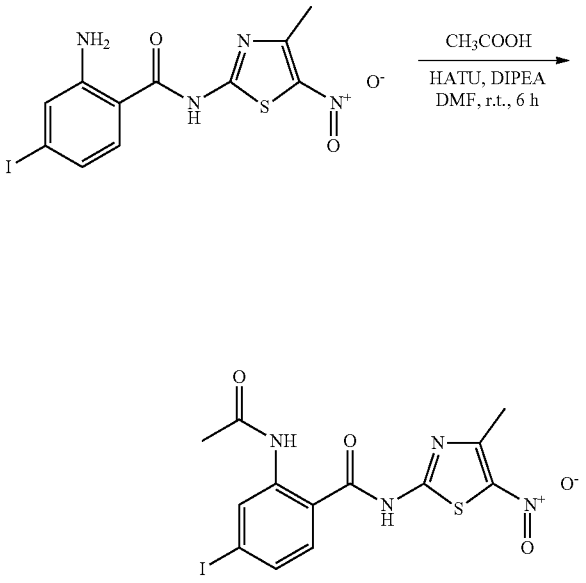

To a solution of 2-amino-4-iodo-N-(4-methyl-5-nitrothiazol-2-yl)benzamide (280 mg, crude) in DMF (5 mL) were added acetic acid (166 mg, 1.04 mmol). HATU (526 mg, 1.38 mmol) and DIEA (260 mg, 2.06 mmol). The mixture was stirred at rt for 6 h and diluted with $H_2O$ (100 mL). The precipitate was collected by filtration to give the title compound (180 mg, 58.23% yield) as white solid. MS (ESI) m/z: 446.8 $[M+H]^+$.

Step 4. Synthesis of tert-butyl (2-(2-(2-(2-((3-acetamido-4-((4-methyl-5-nitrothiazol-2-yl)carbamoyl)phenyl)amino)ethoxy)ethoxy)ethoxy)ethyl)carbamate

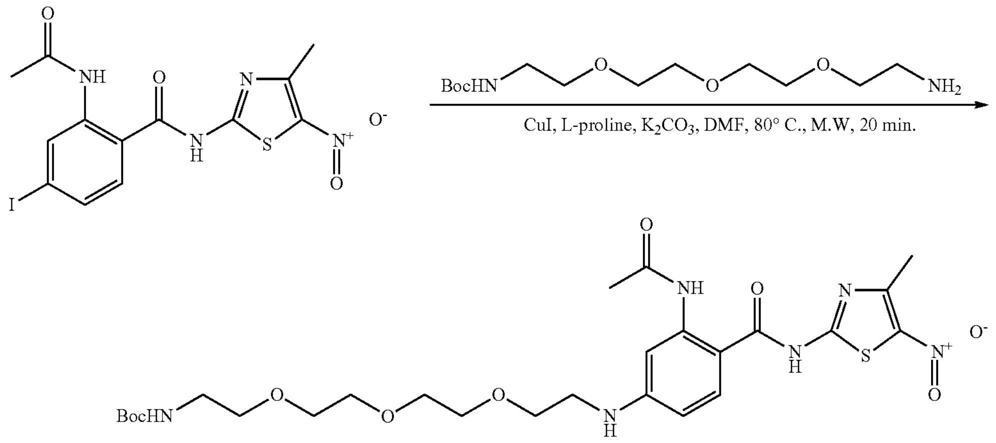

To a solution of 2-acetamido-4-iodo-N-(4-methyl-5-nitrothiazol-2-yl)benzamide (180 mg, 0.404 mmol) and tert-butyl (2-(2-(2-(2-aminoethoxy)ethoxy)ethoxy)ethyl)carbamate (236 mg, 0.807 mmol) in DMF (3 mL) were added CuI (15.4 mg, 0.081 mmol), $K_2CO_3$ (112 mg, 0.807 mmol) and L-priline (9.32 mg, 0.081 mmol). The mixture was irradiated at 80° C. for 20 min under $N_2$ in microwave reactor. The mixture was diluted with $H_2O$ (30 mL) and extracted with EtOAc (3×30 mL). The combined organic phase was dried over $Na_2SO_4$, filtered and concentrated under vacuum to give the crude title compound (300 mg, crude) as brown oil, which was used in the next step without further purification. MS (ESI) m/z: 611.2 $[M+H]^+$.

Step 5. Synthesis of 2-acetamido-4-((2-(2-(2-(2-aminoethoxy)ethoxy)ethoxy)ethyl)amino)-N-(4-methyl-5-nitrothiazol-2-yl)benzamide

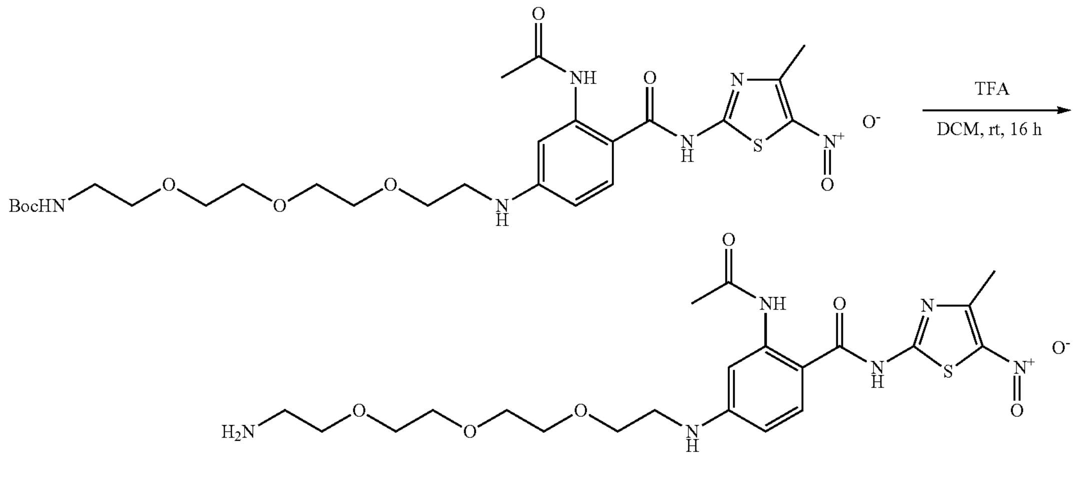

To a solution of (tert-butyl (2-(2-(2-(2-((3-acetamido-4-((4-methyl-5-nitrothiazol-2-yl)carbamoyl)phenyl)amino)ethoxy)ethoxy)ethoxy)ethyl)carbamate (300 mg crude) in DCM (10 mL) was added TFA (10 mL). After being stirred at rt for 16 h, the reaction mixture was concentrated under vacuum. The resulting residue was purified by prep-HPLC to give title compound (30.0 mg, 14.6% yield over 2 steps) as yellow solid. $^1H$ NMR (400 MHz, DMSO-$d_6$): δ 13.00 (brs, 1H), 11.04 (brs, 1H), 7.90-7.88 (m, 1H), 7.74-7.73 (m, 4H), 6.93 (s, 1H), 6.36-6.34 (m, 1H), 3.58-3.55 (m, 12H), 3.29-3.26 (m, 2H), 2.98-2.93 (m, 2H), 2.69 (s, 3H), 2.13 (s, 3H). MS (ESI) m/z: 511.1 $[M+H]^+$.

Example 129. 2-Acetamido-4-((2-aminoethyl)amino)-N-(4-methyl-5-nitrothiazol-2-yl)benzamide (BL-10)

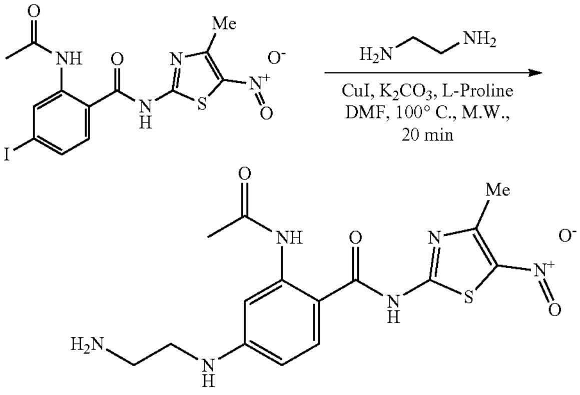

A solution of 2-acetamido-4-iodo-N-(4-methyl-5-nitrothiazol-2-yl)benzamide (200 mg, 0.448 mmol), $K_2CO_3$ (124 mg, 0.896 mmol), L-proline (10 mg, 0.090 mmol), CuI (17 mg, 0.090 mmol) and ethane-1,2-diamine (135 mg, 2.24 mmol) in DMF (4 mL) was irradiated at 100° C. for 20 min under microwave under argon atmosphere. The mixture was purified by pre-HPLC (0.1% TFA) to give the title compound (65.8 mg, yield 29.7% yield) as yellow solid. $^1H$ NMR (400 MHz, DMSO-$d_6$): δ 13.09 (brs, 1H), 11.06 (brs, 1H), 7.93 (d, J=8.4 Hz, 1H), 7.82 (s, 2H), 7.75 (d, J=2.0 Hz, 1H), 6.88 (s, 1H), 6.40 (d, J=8.4 Hz, 1H), 3.38-3.35 (m, 2H), 3.00 (d, J=5.2 Hz, 2H), 2.70 (s, 3H), 2.13 (s, 3H). MS (ESI) m/z: 379.0 $[M+H]^+$.

Example 130. 2-Acetamido-4-((4-aminobutyl)amino)-N-(4-methyl-5-nitrothiazol-2-yl)benzamide (BL-11)

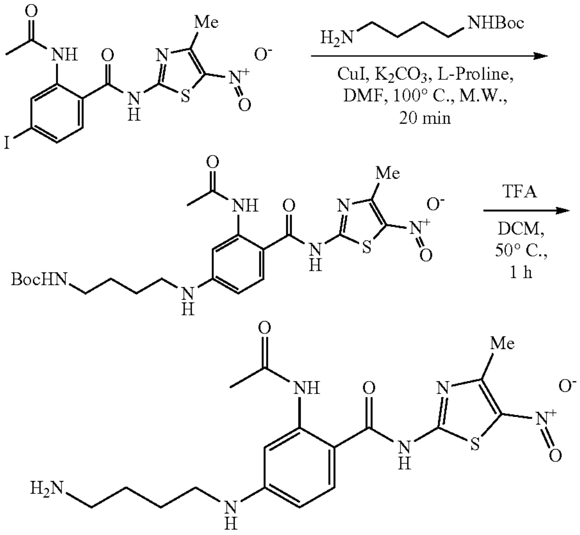

Step 1. Synthesis of tert-butyl (4-((3-acetamido-4-((4-methyl-5-nitrothiazol-2-yl)carbamoyl)phenyl)amino)butyl)carbamate

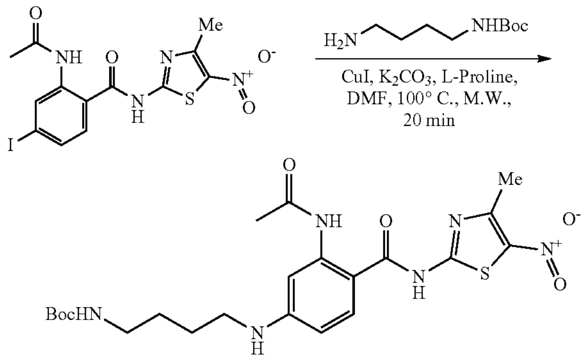

A solution of 2-acetamido-4-iodo-N-(4-methyl-5-nitrothiazol-2-yl)benzamide (300 mg, 0.448 mmol), $K_2CO_3$ (124 mg, 0.896 mmol), L-proline (10 mg, 0.090 mmol), CuI (17 mg, 0.09 mmol) and tert-butyl (4-aminobutyl) carbamate (423 mg, 2.24 mmol) in DMF (3.5 mL) was irradiated at 100° C. for 20 min under microwave under argon atmosphere. The mixture was diluted with water (30 mL) and extracted with EtOAc (3×30 mL). The organic phase was washed with brine, dried over $Na_2SO_4$, filtered and concentrated under vacuum to give the title compound (298 mg, crude) as yellow solid, which was used in the next step without further purification.

Step 2. Synthesis of 2-acetamido-4-((4-aminobutyl)amino)-N-(4-methyl-5-nitrothiazol-2-yl)benzamide

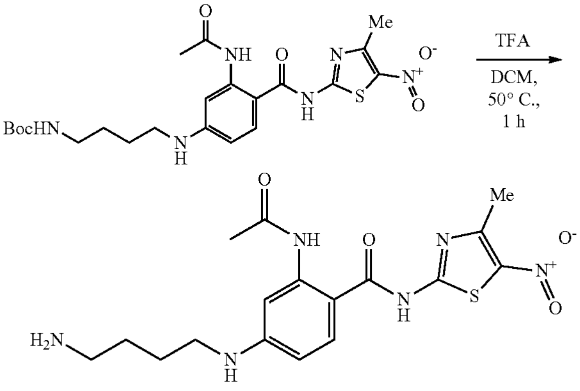

A solution of tert-butyl (4-((3-acetamido-4-((4-methyl-5-nitrothiazol-2-yl)carbamoyl)phenyl)amino)butyl)carbamate (298 mg, crude) in DCM (3 mL) and TFA (1 mL) was stirred at 50° C. under $N_2$ for 1 h. The mixture was concentrated under vacuum and purified by pre-HPLC to give the title compound (65.6 mg, 28.1% over two steps) as yellow solid. $^1H$ NMR (400 MHz, DMSO-$d_6$): δ 12.99 (s, 1H), 11.09 (s, 1H), 7.91 (d, J=8.9 Hz, 1H), 7.75 (d, J=2.0 Hz, 1H), 7.68 (s, 2H), 6.95 (s, 1H), 6.34 (dd, J=9.0, 2.4 Hz, 1H), 3.12-3.10 (m, 2H), 2.82 (d, J=6.0 Hz, 2H), 2.70 (s, 3H), 2.13 (s, 3H), 1.60 (d, J=3.4 Hz, 4H). MS (EST) m/z: 407.1 $[M+H]^+$.

Example 131. 2-Acetamido-4-((6-aminohexyl)amino)-N-(4-methyl-5-nitrothiazol-2-yl)benzamide (BL-12)

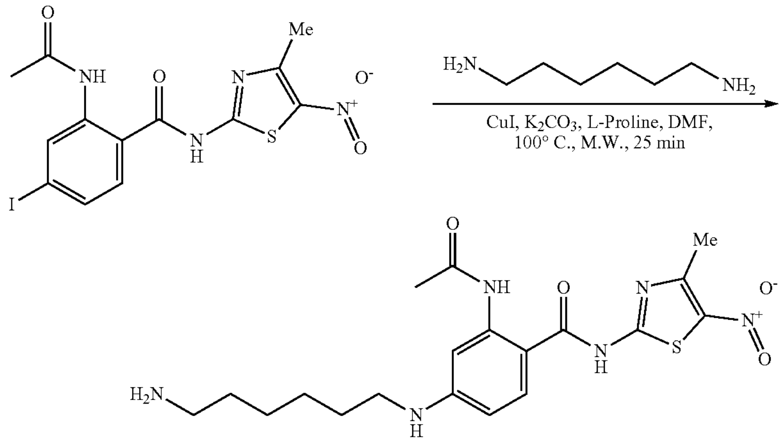

A solution of 2-acetamido-4-iodo-N-(4-methyl-5-nitrothiazol-2-yl)benzamide (300 mg, 0.673 mmol), hexane-1,6-diamine (390 mg, 3.37 mmol), L-proline (16 mg, 0.135 mmol), CuI (26 mg, 0.135 mmol) and $K_2CO_3$ (186 mg, 1.35 mmol) in DMF (5 mL) was irradiated at 100° C. for 25 min under microwave under argon atmosphere. The mixture was purified by pre-HPLC to give the title compound (65 mg, 4.58% yield) as yellow solid. $^1$H NMR (400 MHz, DMSO-$d_6$): 12.95 (brs, 1H), 11.08 (brs, 1H), 7.89 (d, J=9.2 Hz, 1H), 7.89 (d, J=2.0 Hz, 1H), 7.59 (brs, 3H), 6.90-6.89 (m, 1H), 6.34-6.31 (m, 1H), 3.10-3.06 (m, 2H), 2.81-2.76 (m, 2H), 2.69 (s, 3H), 2.13 (s, 3H), 1.55-1.51 (m, 4H), 1.36-1.34 (m, 4H). MS (ESI) m/z: 435.4 [M+H]$^+$.

Example 132. 2-Acetamido-4-((8-aminooctyl)amino)-N-(4-methyl-5-nitrothiazol-2-yl)benzamide (BL-13)

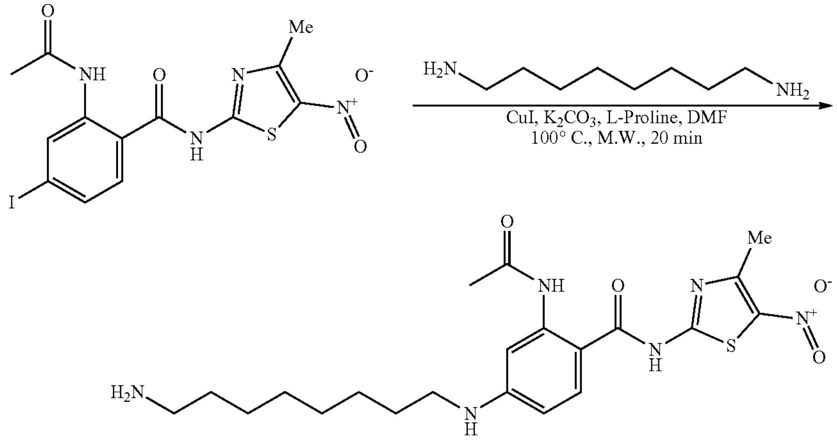

A solution of 2-acetamido-4-iodo-N-(4-methyl-5-nitrothiazol-2-yl)benzamide (200 mg, 0.450 mmol), $K_2CO_3$ (124 mg, 0.900 mmol), L-proline (10 mg, 0.09 mmol), CuI (17 mg, 0.09 mmol) and octane-1,8-diamine (324 mg, 2.25 mmol) in DMF (4 mL) was irradiated 100° C. for 20 min under microwave under argon. The mixture was purified by pre-HPLC (0.1% TFA) to give the title compound (46.8 mg, 18.0% yield) as yellow solid. $^1$H NMR (400 MHz, DMSO-$d_6$): δ 12.96 (brs, 1H), 11.05 (brs, 1H), 7.88 (d, J=8.8 Hz, 1H), 7.73 (d, J=2.0 Hz, 1H), 7.60 (brs, 2H), 6.90 (s, 1H), 6.32 (dd, J=8.8 Hz, 2.4 Hz, 1H), 3.07 (s, 2H), 2.79-2.74 (m, 2H), 2.69 (s, 3H), 2.12 (s, 3H), 1.57-1.49 (m, 4H), 1.35-1.29 (m, 8H). MS (ESI) m/z: 463.1 [M+H]$^+$.

Example 133. 2-Acetamido-4-((10-aminodecyl)amino)-N-(4-methyl-5-nitrothiazol-2-yl)benzamide (BL-14)

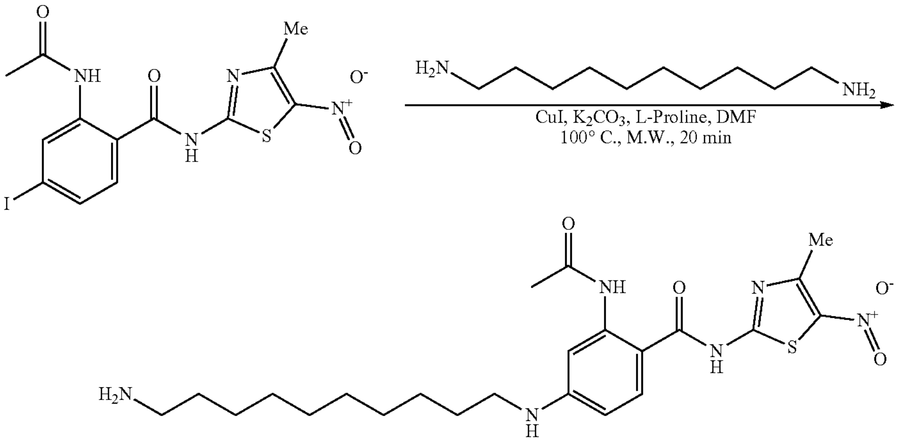

A solution of 2-acetamido-4-iodo-N-(4-methyl-5-nitrothiazol-2-yl)benzamide (200 mg, 0.450 mmol), $K_2CO_3$ (124 mg, 0.900 mmol), L-proline (10 mg, 0.09 mmol), CuI (17 mg, 0.09 mmol) and decane-1,10-diamine (388 mg, 2.25 mmol) in DMF (4 mL) was irradiated at 100° C. for 20 min under microwave under argon. The mixture was purified by pre-HPLC (0.1% TFA) to give the title compound (42.6 mg, 15.6% yield) as yellow solid. $^1$H NMR (400 MHz, DMSO-$d_6$): δ 12.96 (brs, 1H), 11.10 (brs, 1H), 7.88 (d, J=8.8 Hz, 1H), 7.72 (s, 1H), 7.59 (s, 2H), 6.89-6.88 (m, 1H), 6.32 (d, J=9.2 Hz, 1H), 3.11-3.06 (m, 2H), 2.79-2.74 (m, 2H), 2.69 (s, 3H), 2.12 (s, 3H), 1.54-1.47 (m, 4H), 1.30-1.21 (m, 12H). MS (ESI) m/z: 491.2 $[M+H]^+$.

Example 134. 2-Acetamido-4-((2-(2-aminoethoxy)ethyl)amino)-N-(4-methyl-5-nitrothiazol-2-yl)benzamide (BL-15)

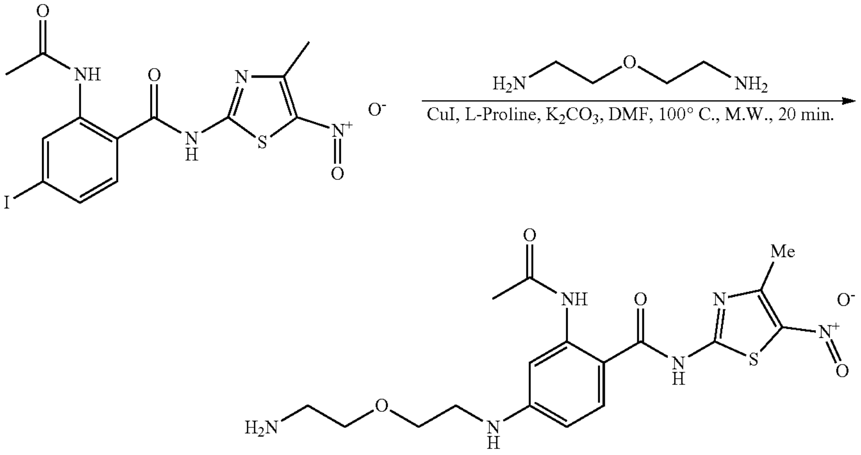

A solution of 2-acetamido-4-iodo-N-(4-methyl-5-nitrothiazol-2-yl)benzamide (300 mg, 0.672 mmol), 2,2'-oxybis(ethan-1-amine) (350 mg, 3.36 mmol), CuI (26 mg, 0.134 mmol), $K_2CO_3$ (186 mg, 1.34 mmol) and L-proline (15 mg, 0.134 mmol) was irradiated at 100° C. for 20 min under microwave under argon atmosphere. The mixture was purified by pre-HPLC to give title compound (76.7 mg, 21.3% yield) as yellow solid. $^1$H NMR (400 MHz, DMSO-$d_6$): δ 13.01 (brs, 1H), 11.05 (brs, 1H), 7.91 (d, J=9.2 Hz, 1H), 7.77-7.76 (m, 3H), 6.82 (brs, 1H), 6.39-6.36 (m, 1H), 3.62-3.60 (m, 4H), 3.31 (brs, 2H), 3.03-2.99 (m, 2H), 2.69 (s, 3H), 2.13 (s, 3H). MS (ESI) m/z: 423.4 $[M+H]^+$.

Example 135. 2-Acetamido-4-((2-(2-(2-aminoethoxy)ethoxy)ethyl)amino)-N-(4-methyl-5-nitrothiazol-2-yl)benzamide (BL-16)

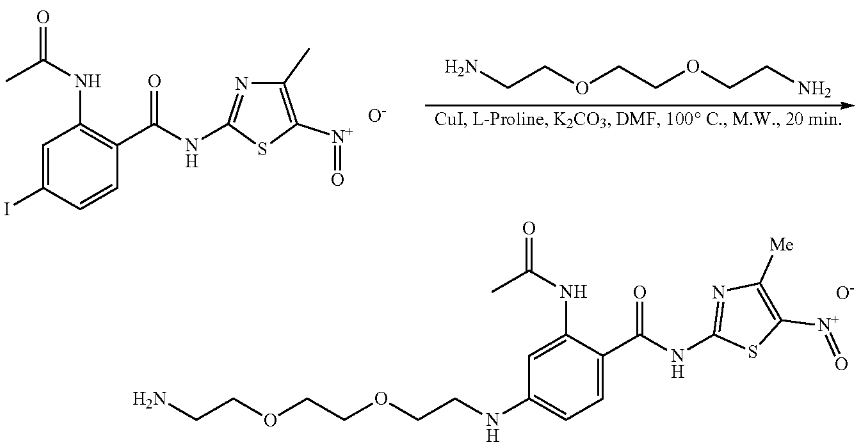

A solution of 2-acetamido-4-iodo-N-(4-methyl-5-nitrothiazol-2-yl)benzamide (300 mg, 0.672 mmol), 2,2'-(ethane-1,2-diylbis(oxy))bis(ethan-1-amine) (500 mg, 3.36 mmol), CuI (26 mg, 0.134 mmol), $K_2CO_3$ (186 mg, 1.34 mmol) and L-proline (15 mg, 0.134 mmol) in DMF (3 mL) was irradiated at 100° C. for 20 min under microwave under argon atmosphere. The mixture was purified by pre-HPLC to give title compound (76.7 mg, 40.2% yield) as yellow solid. $^1H$ NMR (400 MHz, DMSO-$d_6$): δ 13.01 (brs, 1H), 11.10 (brs, 1H), 7.91 (d, J=8.8 Hz, 1H), 7.75-7.74 (m, 3H), 6.89 (brs, 1H), 6.38-6.36 (m, 1H), 3.59-3.56 (m, 8H), 3.30-3.26 (m, 2H), 2.98-2.95 (m, 2H), 2.69 (s, 3H), 2.13 (s, 3H). MS (ESI) m/z: 467.4 $[M+H]^+$.

Example 136. 2-Acetamido-4-((14-amino-3,6,9,12-tetraoxatetradecyl)amino)-N-(4-methyl-5-nitrothiazol-2-yl)benzamide (BL-17)

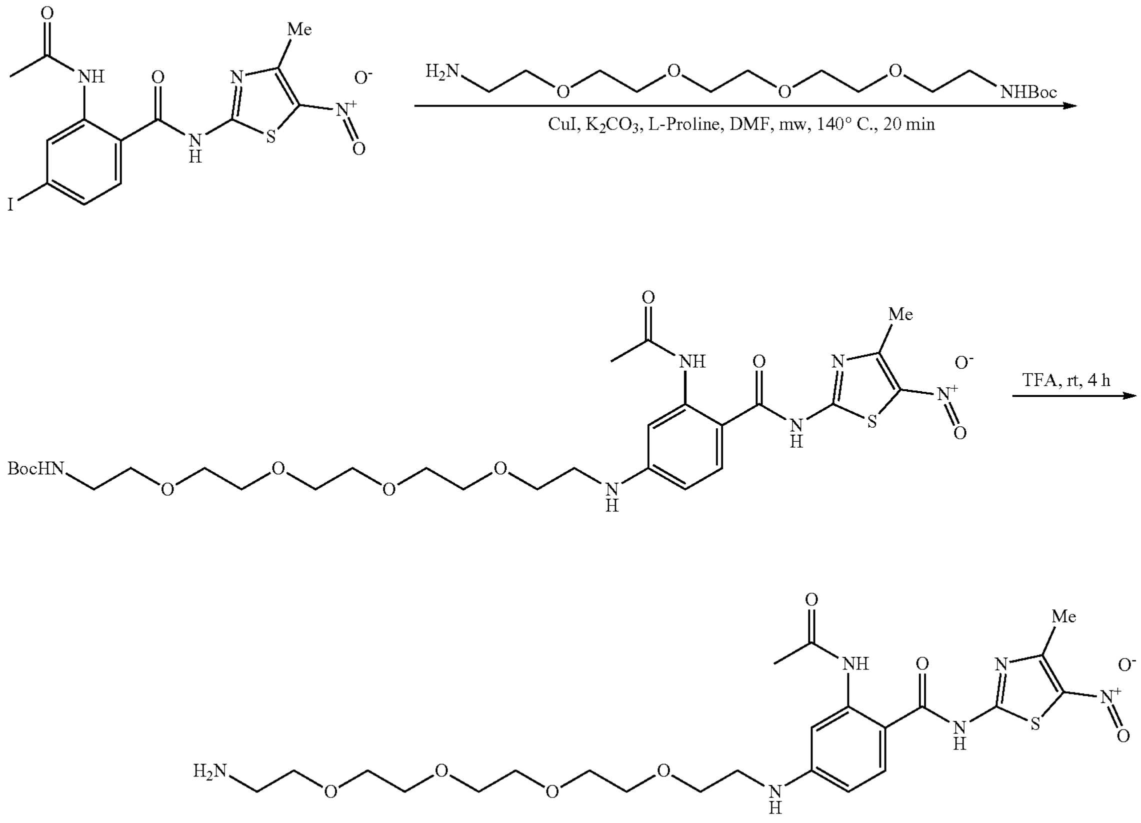

Step 1. Synthesis of tert-butyl (14-((3-acetamido-4-((4-methyl-5-nitrothiazol-2-yl)carbamoyl)phenyl) amino)-3,6,9,12-tetraoxatetradecyl)carbamate

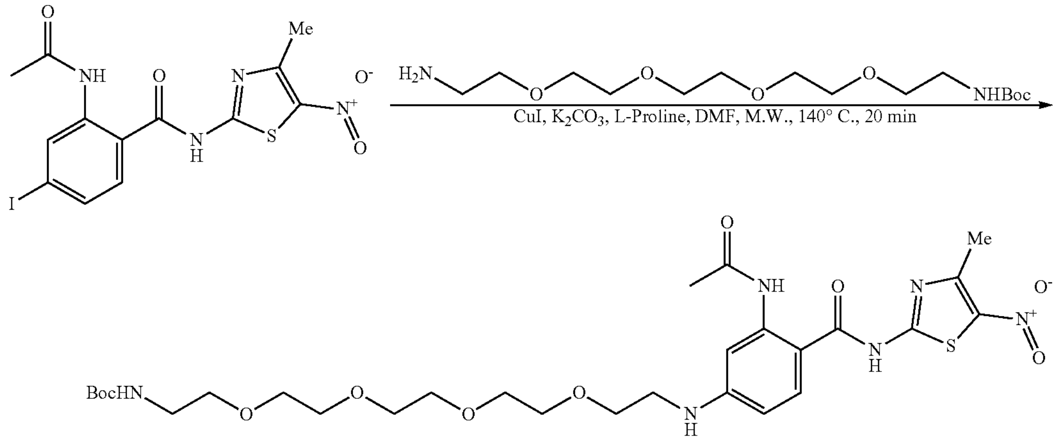

A solution of 2-acetamido-4-iodo-N-(4-methyl-5-nitrothiazol-2-yl)benzamide (300 mg, 0.673 mmol), tert-butyl (14-amino-3,6,9,12-tetraoxatetradecyl)carbamate (249 mg, 0.740 mmol), L-proline (16 mg, 0.135 mmol), CuI (26 mg, 0.135 mmol) and $K_2CO_3$ (186 mg, 1.35 mmol) in DMF (5 mL) was irradiated at 140° C. under microwave for 20 min under argon atmosphere. The mixture was poured into water (30 mL) and extracted with EtOAc (3×30 mL). The combined organic phase was washed with brine, dried over $Na_2SO_4$, filtered and concentrated under vacuum to give the crude title compound (400 mg, crude) as brown oil, which was used in the next step without further purification. MS (ESI) m/z: 655.2 $[M+H]^+$.

Step 2. Synthesis of 2-acetamido-4-((14-amino-3,6,9,12-tetraoxatetradecyl)amino)-N-(4-methyl-5-nitrothiazol-2-yl)benzamide

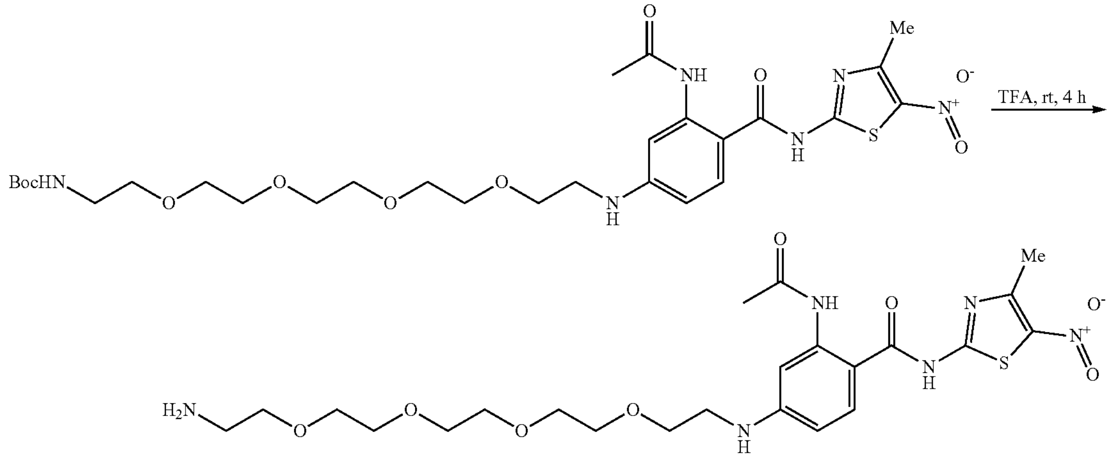

A solution of tert-butyl (14-((3-acetamido-4-((4-methyl-5-nitrothiazol-2-yl)carbamoyl)phenyl)amino)-3,6,9,12-tetraoxatetradecyl)carbamate (400 mg, crude) in TFA (10 mL) was stirred at rt for 4 h. Then the mixture was concentrated under vacuum. The resulting residue was purified by pre-HPLC to give the title compound (80.6 mg, 17.4% yield) as yellow solid. $^1$H NMR (400 MHz, DMSO-$d_6$): 13.04 (brs, 1H), 11.05 (brs, 1H), 7.89 (d, J=8.8 Hz, 1H), 7.81-7.73 (m, 3H), 6.89 (s, 1H), 6.38-6.36 (m, 1H), 3.59-3.52 (m, 16H), 3.27-3.26 (m, 2H), 2.99-2.95 (m, 2H), 2.69 (s, 3H), 2.12 (s, 3H). MS (ESI) m/z: 555.2 $[M+H]^+$.

Example 137. 2-Acetamido-4-((17-amino-3,6,9,12,15-pentaoxaheptadecyl)amino)-N-(4-methyl-5-nitrothiazol-2-yl)benzamide (BL-18)

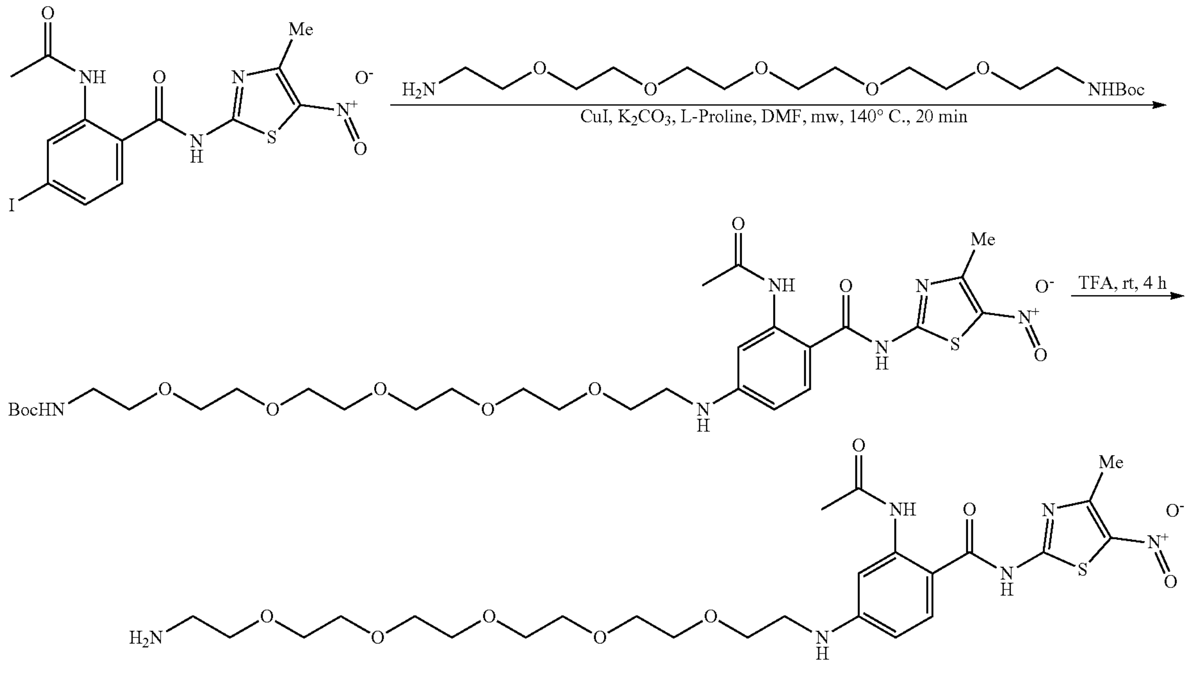

Step 1. Synthesis of tert-butyl (17-((3-acetamido-4-((4-methyl-5-nitrothiazol-2-yl)carbamoyl)phenyl)amino)-3,6,9,12,15-pentaoxaheptadecyl)carbamate

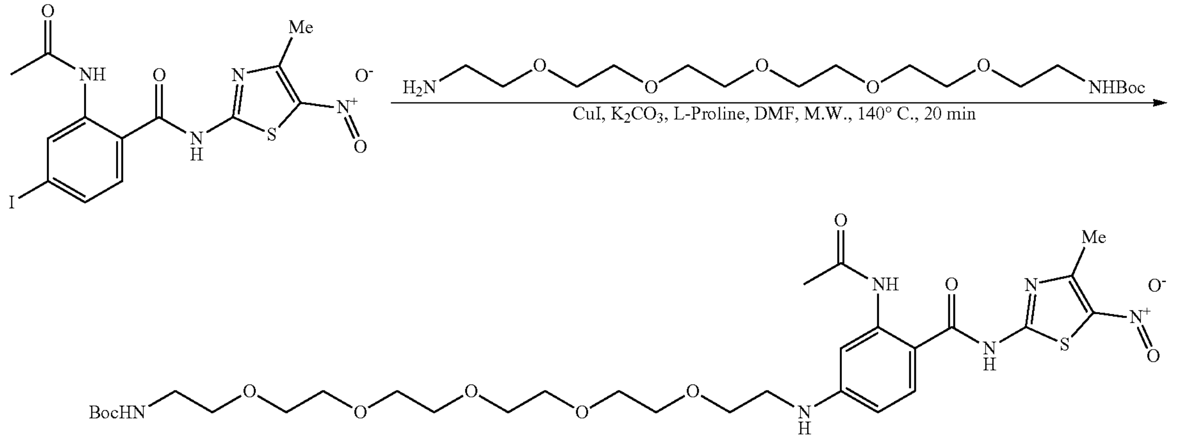

A solution of 2-acetamido-4-iodo-N-(4-methyl-5-nitrothiazol-2-yl)benzamide (300 mg, 0.673 mmol), tert-butyl (17-amino-3,6,9,12,15-pentaoxaheptadecyl)carbamate (281 mg, 0.740 mmol), L-proline (16 mg, 0.135 mmol), CuI (26 mg, 0.135 mmol) and $K_2CO_3$ (186 mg, 1.35 mmol) in DMF (5 mL) was irradiated at 140° C. for 20 min under microwave under argon atmosphere. The mixture was poured into water (30 mL) and extracted with EtOAc (3×30 mL). The combined organic phase was washed with brine, dried over $Na_2SO_4$, filtered and concentrated under vacuum to give the crude title compound (400 mg, crude) as brown oil, which was used in the next step without further purification. MS (ESI) m/z: 699.2 $[M+H]^+$.

Step 2. Synthesis of 2-acetamido-4-((17-amino-3,6,9,12,15-pentaoxaheptadecyl)amino)-N-(4-methyl-5-nitrothiazol-2-yl)benzamide

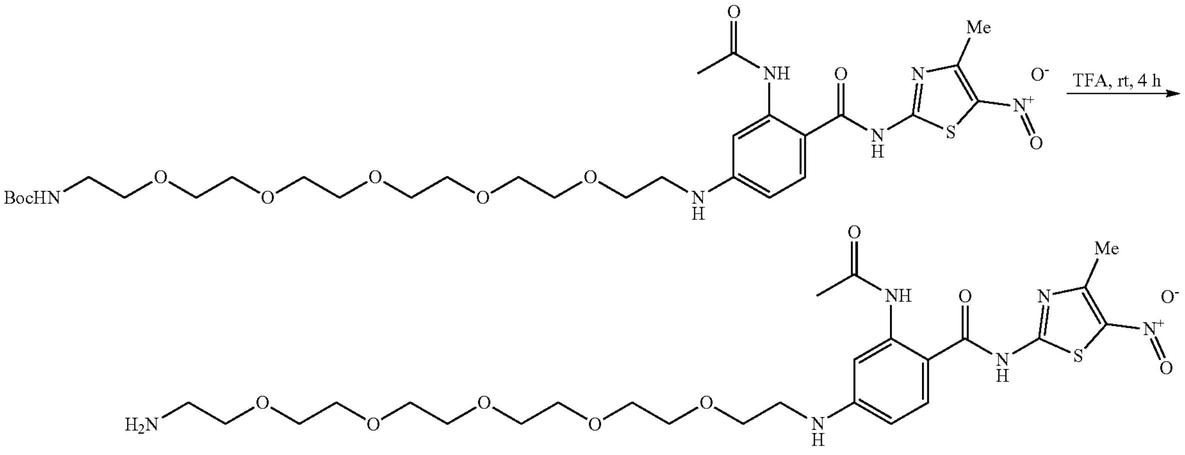

A solution of tert-butyl (17-((3-acetamido-4-((4-methyl-5-nitrothiazol-2-yl)carbamoyl)phenyl)amino)-3,6,9,12,15-pentaoxaheptadecyl)carbamate (400 mg, crude) in TFA (10 mL) was stirred at rt for 4 h. Then the mixture was concentrated under vacuum. The resulting residue was purified by pre-HPLC to give the title compound (53.7 mg, 10.8% over two steps) as yellow solid. $^1H$ NMR (400 MHz, DMSO-$d_6$): 13.04 (brs, 1H), 11.05 (brs, 1H), 7.89 (d, J=8.8 Hz, 1H), 7.80 (brs, 3H), 7.73-7.72 (m, 1H), 6.93 (brs, 1H), 6.38-6.36 (m, 1H), 3.59-3.51 (m, 12H), 3.48-3.41 (m, 8H), 3.28-3.25 (m, 2H), 2.98-2.96 (m, 2H), 2.68 (s, 3H), 2.12 (s, 3H). MS (ESI) m/z: 599.2 $[M+H]^+$.

Example 138. 2-Acetamido-4-((20-amino-3,6,9,12,15,18-hexaoxaicosyl)amino)-N-(4-methyl-5-nitrothiazol-2-yl)benzamide (BL-19)

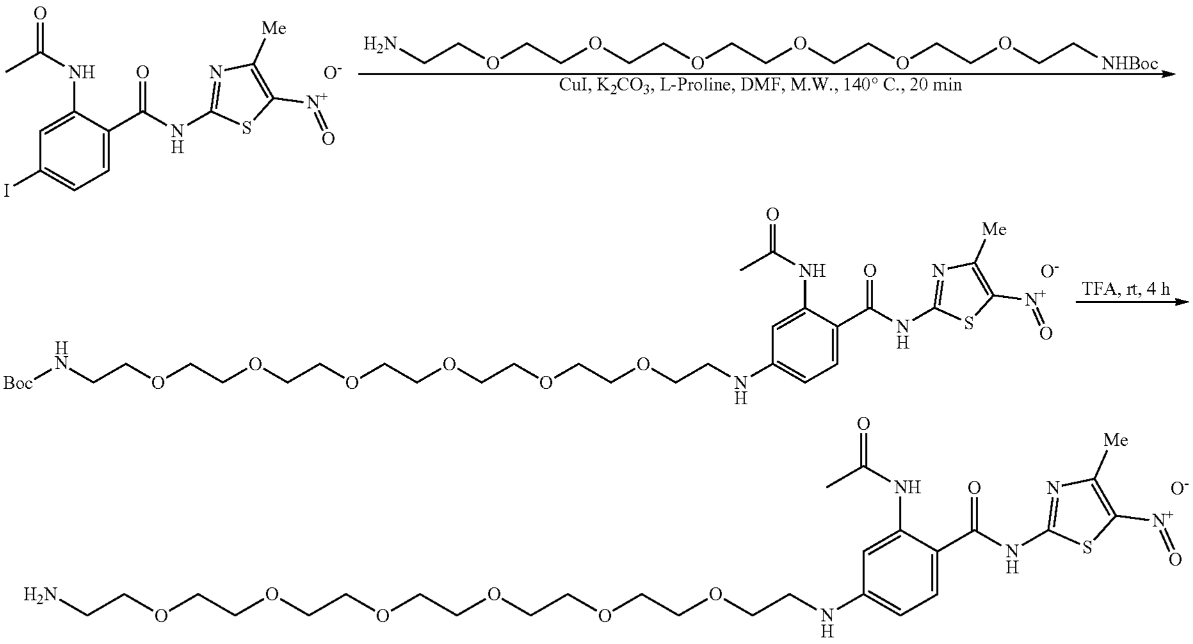

Step 1. Synthesis of tert-butyl (20-((3-acetamido-4-((4-methyl-5-nitrothiazol-2-yl)carbamoyl)phenyl)amino)-3,6,9,12,15,18-hexaoxaicosyl)carbamate

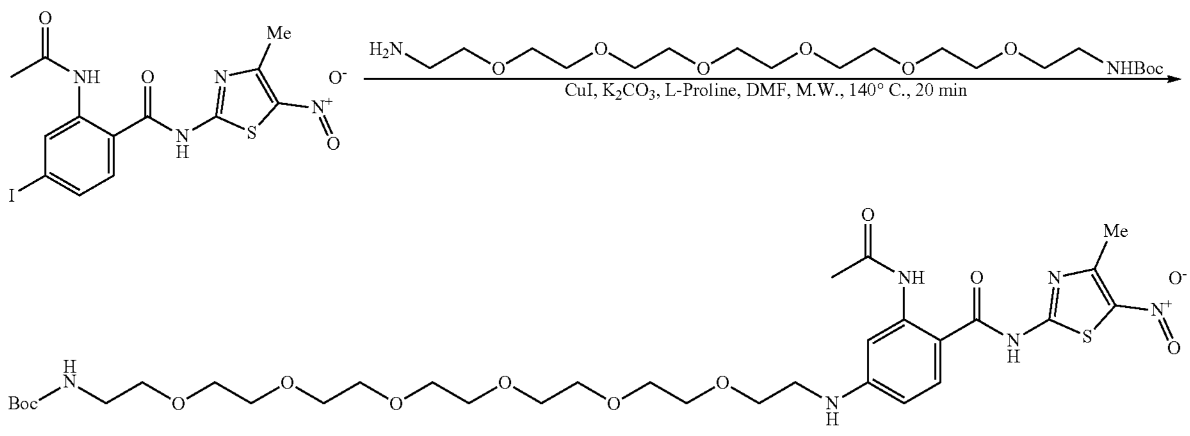

A solution of 2-acetamido-4-iodo-N-(4-methyl-5-nitrothiazol-2-yl)benzamide (300 mg, 0.673 mmol), tert-butyl (20-amino-3,6,9,12,15,18-hexaoxaicosyl)carbamate (311 mg, 0.740 mmol), L-proline (16 mg, 0.135 mmol), CuI (26.0 mg, 0.135 mmol) and $K_2CO_3$ (186 mg, 1.35 mmol) in DMF (5 mL) was irradiated at 140° C. for 20 min under microwave under argon atmosphere. The mixture was poured into water (30 mL) and extracted with EtOAc (3x30 mL). The combined organic phase was washed with brine, dried over $Na_2SO_4$, filtered and concentrated under vacuum to give the title compound (400 mg, crude) as brown oil, which was used in the next step without further purification. MS (ESI) m/z: 743.2 $[M+H]^+$.

Step 2. Synthesis of 2-acetamido-4-((20-amino-3,6,9,12,15,18-hexaoxaicosyl)amino)-N-(4-methyl-5-nitrothiazol-2-yl)benzamide

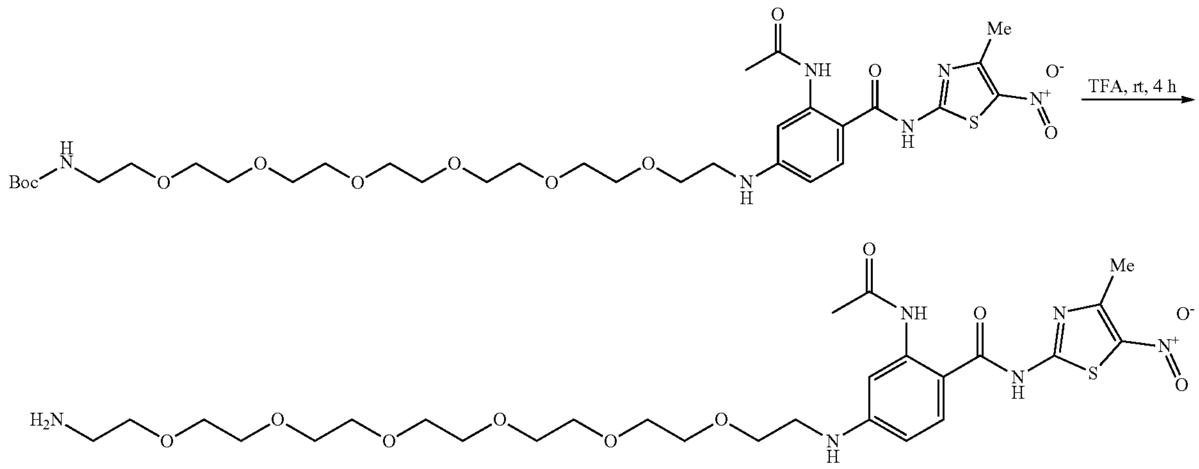

A solution of tert-butyl (1-((3-acetamido-4-((4-methyl-5-nitrothiazol-2-yl)carbamoyl)phenyl)amino)-3,6,9,12,18-pentaoxaicosan-20-yl)carbamate (400 mg, crude) in TFA (10 mL) was stirred at rt for 4 h. Then the mixture was concentrated under vacuum. The resulting residue was purified by pre-HPLC to give the title compound (75.4 mg, 14.8% yield) as yellow solid. $^1H$ NMR (400 MHz, DMSO-$d_6$): 13.02 (brs, 1H), 11.03 (brs, 1H), 7.89 (d, J=8.8 Hz, 1H), 7.75-7.71 (m, 4H), 6.95 (brs, 1H), 6.38-6.36 (m, 1H), 3.59-3.54 (m, 12H), 3.49-3.50 (m, 12H), 3.28-3.25 (m, 2H), 2.99-2.95 (m, 2H), 2.69 (s, 3H), 2.12 (s, 3H). MS (ESI) m/z: 643.2 $[M+H]^+$.

Example 139. 2-Acetamido-4-((3-aminopropyl)amino)-N-(4-methyl-5-nitrothiazol-2-yl)benzamide (BL-21)

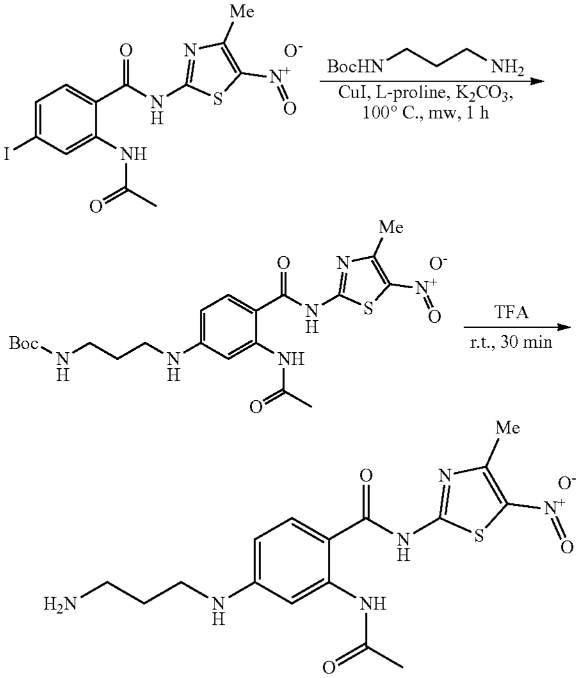

Step 1. Synthesis of tert-butyl (3-((3-acetamido-4-((4-methyl-5-nitrothiazol-2-yl)carbamoyl)phenyl)amino)propyl)carbamate

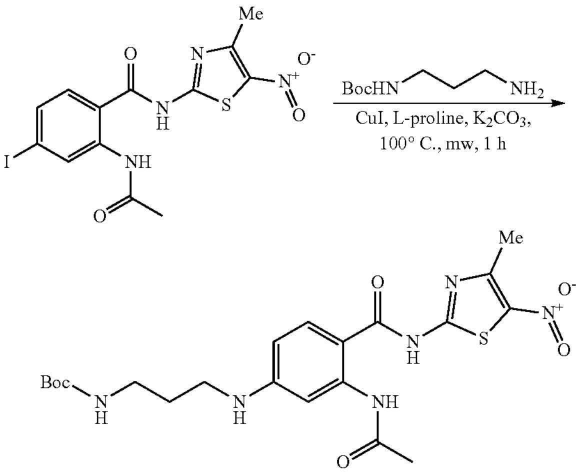

A solution of 2-acetamido-4-iodo-N-(4-methyl-5-nitrothiazol-2-yl)benzamide (1.0 g, 2.24 mmol), tert-butyl (3-aminopropyl)carbamate (468 mg, 2.68 mmol), L-proline (257 mg, 2.24 mmol), CuI (425 mg, 2.24 mmol) and $K_2CO_3$ (618 mg, 4.48 mmol) in DMF (15 mL) were irradiated at 100° C. in microwave reactor for 1 h under argon atmosphere, before the mixture was poured into water (50 mL) and extracted with EtOAc (3×50 mL). The combined organic phase was washed with brine, dried over $Na_2SO_4$, filtered and concentrated under vacuum. The resulting residue was purified by silica gel column chromatography (petroleum ether: EtOAc=0:1) to give the title compound (550 mg, 49.8% yield) as yellow solid.

Step 2. Synthesis of 2-acetamido-4-((3-aminopropyl)amino)-N-(4-methyl-5-nitrothiazol-2-yl)benzamide

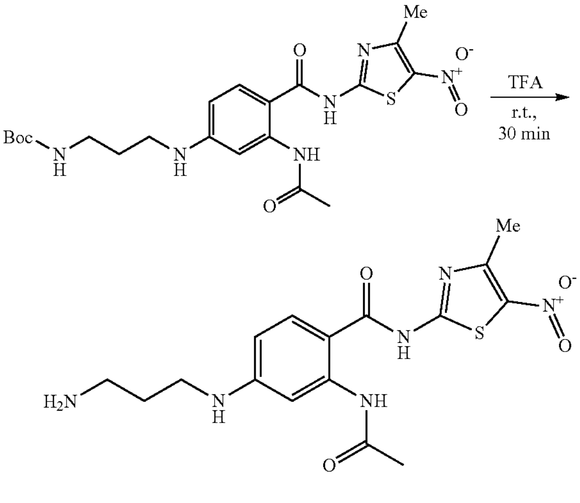

A solution of tert-butyl (3-((3-acetamido-4-((4-methyl-5-nitrothiazol-2-yl)carbamoyl)phenyl)amino)propyl)carbamate (550 mg, 1.12 mmol) in TFA (5 mL) was stirred at rt 30 min. Then, the mixture was concentrated and lyophilized to give the title compound (480 mg, 84.7% yield) as yellow solid. $^1H$ NMR (400 MHz, DMSO-$d_6$): δ 13.03 (s, 1H), 11.03 (s, 1H), 7.95-7.91 (m, 1H), 7.80-7.71 (m, 4H), 6.95 (brs, 1H), 6.37-6.34 (m, 1H), 3.19-3.16 (m, 2H), 2.91-2.86 (m, 2H), 2.69 (s, 3H), 2.13 (s, 3H), 1.86-1.78 (m, 2H). MS (ESI) m/z: 393.1 $[M+H]^+$.

Example 140. 2-Acetamido-4-((5-aminopentyl)amino)-N-(4-methyl-5-nitrothiazol-2-yl)benzamide (BL-22)

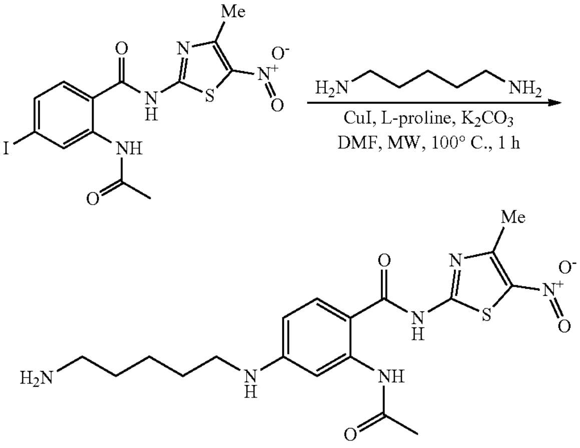

A solution of 2-acetamido-4-iodo-N-(4-methyl-5-nitrothiazol-2-yl)benzamide (1.0 g, 2.24 mmol), pentane-1,5-diamine (1.0 g, 9.80 mmol), CuI (300 mg, 1.57 mmol), $K_2CO_3$ (618 mg, 4.47 mmol) and L-proline (200 mg, 1.74 mmol) in NMP (15 mL) was irradiated at 100° C. for 1 h in microwave reactor under argon atmosphere, before the mixture was purified by prep-HPLC to give title compound (254 mg, 26.9% yield) as yellow solid. $^1H$ NMR (400 MHz, DMSO-$d_6$): δ 13.03 (s, 1H), 11.06 (s, 1H), 7.89 (d, J=9.2 Hz, 1H), 7.73-7.66 (m, 3H), 6.63 (s, 1H), 6.34-6.31 (m, 1H), 3.10-3.06 (m, 2H), 2.79-2.76 (m, 2H), 2.69 (s, 3H), 2.13 (s, 3H), 1.59-1.55 (m, 4H), 1.43-1.35 (m, 2H). MS (ESI) m/z: 421.1 $[M+H]^+$.

Example 141. 2-Acetamido-4-((11-aminoundecyl)amino)-N-(4-methyl-5-nitrothiazol-2-yl)benzamide (BL-23)

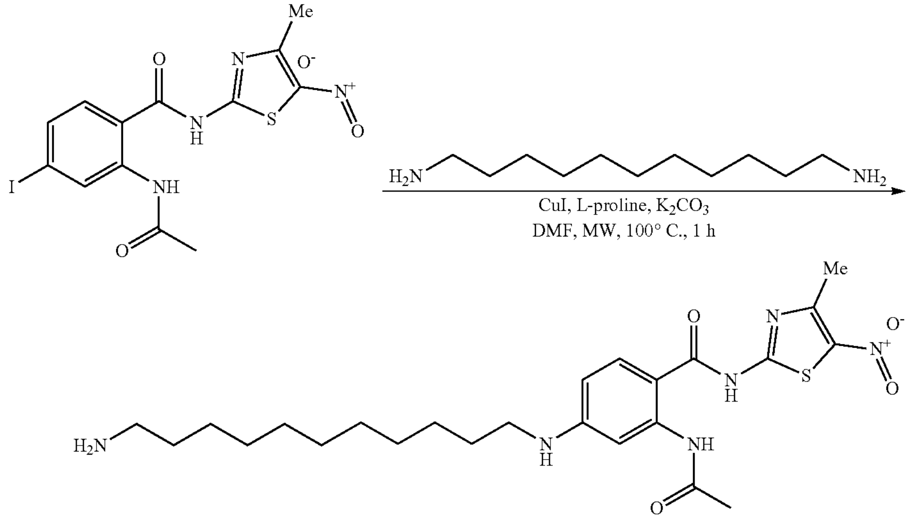

A solution of 2-acetamido-4-iodo-N-(4-methyl-5-nitrothiazol-2-yl)benzamide (1.0 g, 2.24 mmol), undecane-1,11-diamine (2.1 g, 11.2 mmol), CuI (300 mg, 1.57 mmol), $K_2CO_3$ (618 mg, 4.47 mmol) and L-proline (200 mg, 1.74 mmol) in DMF (15 mL) was irradiated at 100° C. for 1 h under microwave under argon atmosphere, before the mixture was purified by RP-HPLC to give tide compound (274 mg, 24.2% yield) as yellow solid. $^1H$ NMR (400 MHz, DMSO-$d_6$): δ 11.07 (s, 1H), 7.89-7.87 (m, 1H), 7.72-7.71 (m, 3H), 6.63 (s, 1H), 6.33-6.30 (m, 1H), 3.08-3.04 (m, 2H), 2.78-2.74 (m, 2H), 2.69 (s, 3H), 2.12 (s, 3H), 1.56-1.51 (m, 4H), 1.33-1.26 (m, 14H). MS (ESI) m/z: 505.2 $[M+H]^+$.

Example 142. 3-((3-Acetamido-4-((4-methyl-5-nitrothiazol-2-yl)carbamoyl)phenyl)amino)propanoic acid (BL-24)

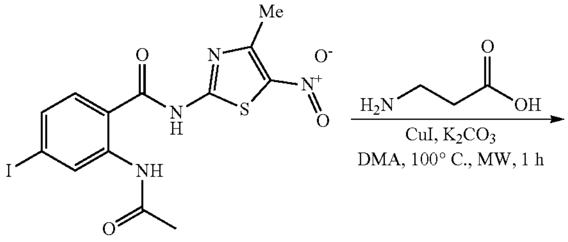

-continued

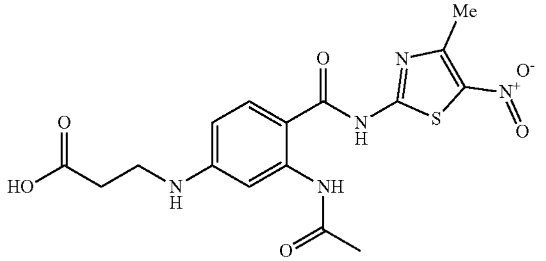

A solution of 2-acetamido-4-iodo-N-(4-methyl-5-nitrothiazol-2-yl)benzamide (1.0 g, 2.24 mmol), 3-aminopropanoic acid (998 mg, 11.2 mmol), L-proline (257 mg, 2.24 mmol), CuI (425 mg, 2.24 mmol) and $K_2CO_3$ (1.85 g, 13.4 mmol) in DMF (15 mL) was irradiated at 100° C. under microwave for 1 h under argon atmosphere, before the mixture was purified by reversed phase column chromatography to give the title compound (300 mg, 32.9% yield) as yellow solid. $^1H$ NMR (400 MHz, DMSO-$d_6$): δ 13.01 (brs, 1H), 12.30 (brs, 1H), 11.03 (brs, 1H), 7.89 (d, J=8.8 Hz, 1H), 7.70 (brs, 1H), 6.95 (brs, 1H), 6.36-6.33 (m, 1H), 3.33-3.27 (m, 2H), 2.69 (s, 3H), 2.54-2.53 (m, 2H), 2.12 (s, 3H). MS (ESI) m/z: 408.1 $[M+H]^+$.

Example 143. 7-((3-Acetamido-4-((4-methyl-5-nitrothiazol-2-yl)carbamoyl)phenyl)amino)heptanoic acid (BL-25)

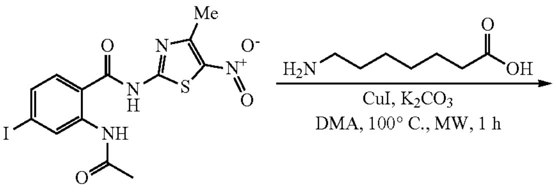

-continued

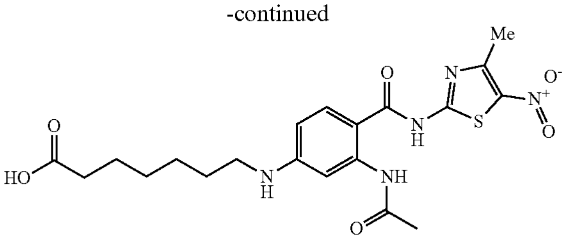

A solution of 2-acetamido-4-iodo-N-(4-methyl-5-nitrothiazol-2-yl)benzamide (1.0 g, 2.24 mmol), 7-aminoheptanoic acid (1.63 g, 11.2 mmol), L-proline (257 mg, 2.24 mmol), CuI (425 mg, 2.24 mmol) and $K_2CO_3$ (1.85 g, 13.4 mmol) in DMF (15 mL) was irradiated at 100° C. under microwave for 1 h under argon atmosphere. At rt, the mixture was purified by reversed phase column chromatography to give the title compound (280 mg, 26.7% yield) as yellow solid. $^1$H NMR (400 MHz, DMSO-$d_6$): δ 12.97 (brs, 1H), 11.98 (brs, 1H), 11.09 (brs, 1H), 7.88 (d, J=8.8 Hz, 1H), 7.72 (s, 1H), 6.89 (d, J=4.8 Hz, 1H), 6.32-6.30 (m, 1H), 3.08-3.04 (m, 2H), 2.69 (s, 3H), 2.20-2.12 (m, 2H), 2.12 (s, 3H), 1.57-1.38 (m, 4H), 1.32-1.26 (m, 4H). MS (ESI) m/z: 464.1 $[M+H]^+$ Example 144. 3-(2-(2-(2-((3-acetamido-4-((4-methyl-5-nitrothiazol-2-yl)carbamoyl)phenyl)amino)ethoxy)ethoxy)ethoxy)propanoic acid (BL-26)

Step 1. Synthesis of tert-butyl 3-(2-(2-(2-((3-acetamido-4-((4-methyl-5-nitrothiazol-2-yl)carbamoyl)phenyl)amino)ethoxy)ethoxy)ethoxy)propanoate

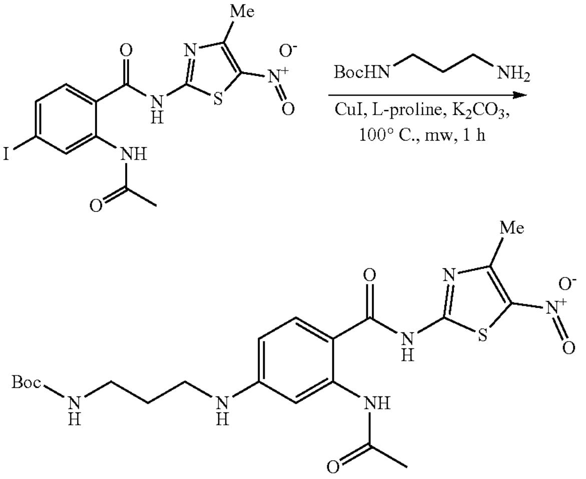

A solution of 2-acetamido-4-iodo-N-(4-methyl-5-nitrothiazol-2-yl)benzamide (1.0 g, 2.24 mmol), tert-butyl 3-(2-(2-(2-aminoethoxy)ethoxy)ethoxy)propanoate (661 mg, 2.91 mmol), L-proline (257 mg, 2.24 mmol), CuI (428 mg, 2.24 mmol) and $K_2CO_3$ (927 mg, 6.72 mmol) in DMF (8 mL) was irradiated at 100° C. under microwave for 2 h under argon atmosphere. At rt, the mixture was poured into water (50 mL) and extracted with EtOAc (3×50 mL). The combined organic phase was washed with brine, dried over $Na_2SO_4$, filtered and concentrated under vacuum to give the crude, which was used directly for next step. MS (ESI) m/z: 596.2 $[M+H]^+$.

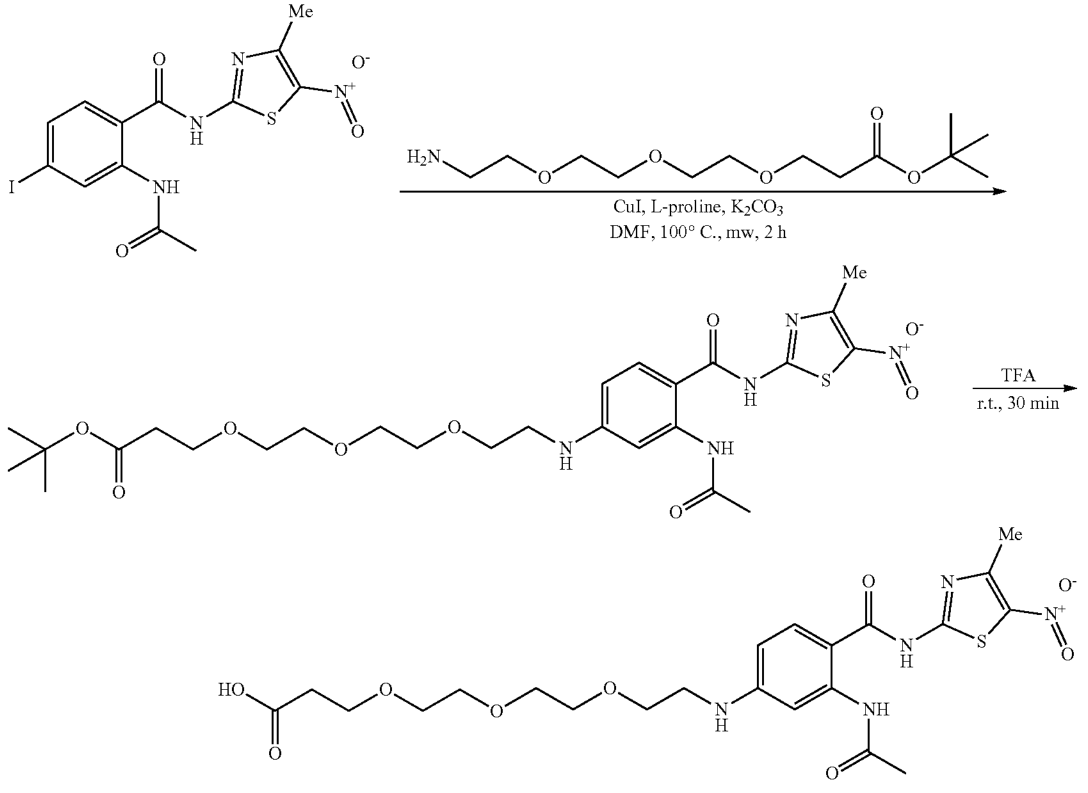

Step 2. Synthesis of 3-(2-(2-(2-((3-acetamido-4-((4-methyl-5-nitrothiazol-2-yl)carbamoyl)phenyl)amino)ethoxy)ethoxy)ethoxy)propanoic acid

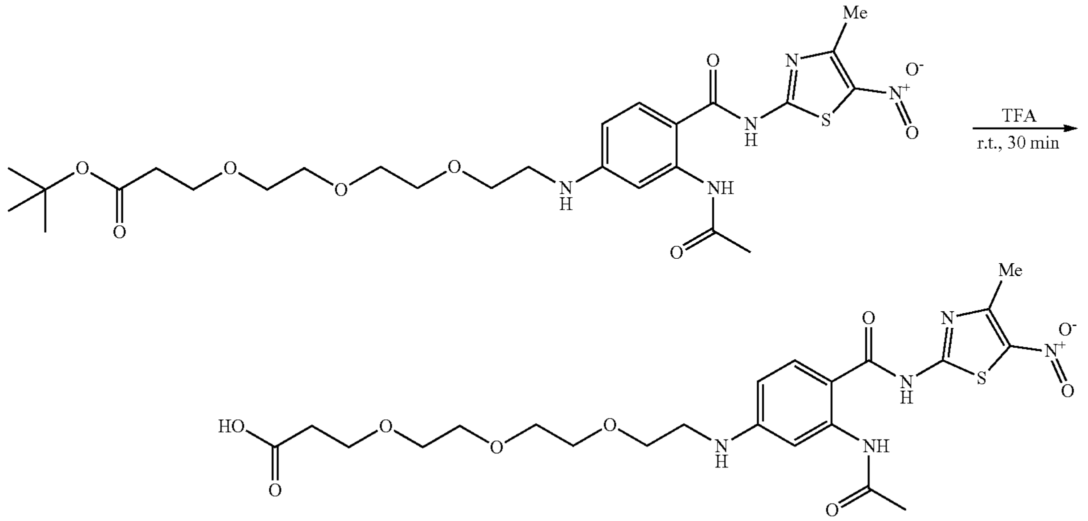

A solution of tert-butyl 3-(2-(2-(2-((3-acetamido-4-((4-methyl-5-nitrothiazol-2-yl)carbamoyl)phenyl)amino)ethoxy)ethoxy)ethoxy)propanoate (crude) in TFA (5 mL) was stirred at rt 30 min. Then, the mixture was purified by prep-HPLC to give title compound (570 mg, 39.8% yield over two steps) as yellow solid. $^1$H NMR (400 MHz, DMSO-$d_6$): δ 12.98 (brs, 1H), 11.02 (s, 1H), 7.88 (d, J=8.8 Hz, 1H), 7.73 (s, 1H), 6.96 (brs, 1H), 6.37 (d, J=9.2 Hz, 1H), 3.61-3.49 (m, 12H), 3.27-3.26 (m, 2H), 2.69 (s, 3H), 2.43 (t, J=6.4 Hz, 2H), 2.14 (s, 3H). MS (ESI) m/z: 540.0 [M+H]$^+$.

Example 145. (3-Acetamido-4-((4-methyl-5-nitrothiazol-2-yl)carbamoyl)phenyl)glycine (BL-27)

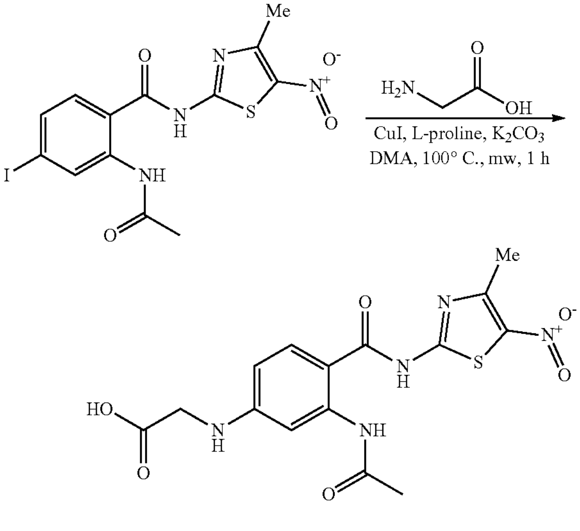

A solution of 2-acetamido-4-iodo-N-(4-methyl-5-nitrothiazol-2-yl)benzamide (1.0 g, 2.24 mmol), glycine (840 mg, 11.2 mmol), L-proline (257 mg, 2.24 mmol), CuI (425 mg, 2.24 mmol) and $K_2CO_3$ (1.85 g, 13.4 mmol) in DMF (15 mL) were irradiated at 100° C. under microwave for 1 h under argon atmosphere, before the mixture was purified by pre-HPLC to give the title compound (200 mg, 22.7% yield) as yellow solid. $^1$H NMR (400 MHz, DMSO-$d_6$): δ 13.67 (brs, 1H), 8.63 (brs, 1H), 7.97 (d, J=8.2 Hz, 1H), 7.78 (brs, 1H), 6.26-6.24 (m, 1H), 6.00 (brs, 1H), 3.63 (brs, 2H), 2.62 (s, 3H), 2.13 (s, 3H). MS (EST) m/z: 394.1 [M+H]$^+$.

Example 146. 6-((3-Acetamido-4-((4-methyl-5-nitrothiazol-2-yl)carbamoyl)phenyl)amino)hexanoic acid (BL-28)

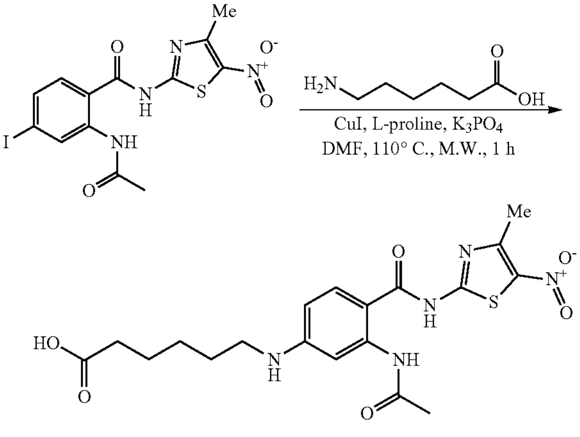

A solution of 2-acetamido-4-iodo-N-(4-methyl-5-nitrothiazol-2-yl)benzamide (1.0 g, 2.24 mmol), 6-aminohexanoic acid (1.47 g, 11.2 mmol), L-proline (257 mg, 2.24 mmol), CuI (425 mg, 2.24 mmol) and $K_3PO_4$ (2.84 g, 13.4 mmol) in DMF (15 mL) were irradiated at 110° C. under microwave for 1 h under argon atmosphere, before the mixture was purified by pre-HPLC to give the title compound (420 mg, 41.7% yield) as yellow solid. $^1$H NMR (400 MHz, DMSO-$d_6$): δ 12.98 (brs, 1H), 12.00 (brs, 1H), 11.09 (brs, 1H), 7.88 (d, J=8.8 Hz, 1H), 7.72 (d, J=1.6 Hz, 1H), 6.92-6.89 (m, 1H), 6.33-6.30 (m, 1H), 3.09-3.04 (m, 2H), 2.69 (s, 3H), 2.23-2.19 (m, 2H), 2.12 (s, 3H), 1.59-1.49 (m, 4H), 1.39-1.33 (m, 2H). MS (ESI) m/z: 450.1 [M+H]$^+$.

Example 147. 10-((3-Acetamido-4-((4-methyl-5-nitrothiazol-2-yl)carbamoyl)phenyl)amino)decanoic acid (BL-29)

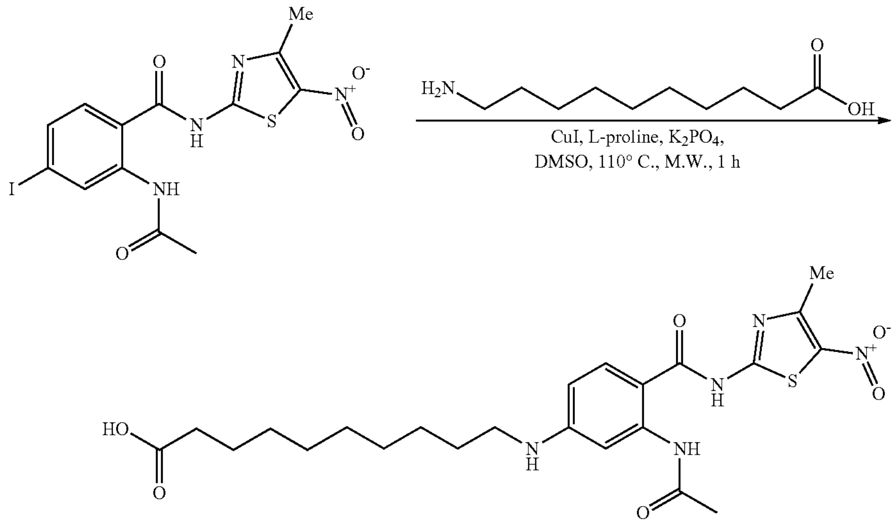

A solution of 2-acetamido-4-iodo-N-(4-methyl-5-nitrothiazol-2-yl)benzamide (1.0 g, 2.24 mmol), 10-aminodecanoic acid (2.1 g, 11.2 mmol), CuI (425 mg, 2.24 mmol), $K_2PO_4$ (2.84 g, 13.4 mmol) and L-proline (257 mg, 2.24 mmol) in DMSO (15 mL) was irradiated at 110° C. for 1 h under microwave under argon atmosphere, before the mixture was purified by pre-HPLC to give title compound (280 mg, 24.7% yield) as yellow solid. $^1$H NMR (400 MHz, DMSO-$d_6$): δ 12.92 (brs, 1H), 12.02 (brs, 1H), 11.10 (brs, 1H), 7.88 (d, J=9.2 Hz, 1H), 7.42 (d, J=1.6 Hz, 1H), 6.89-6.88 (m, 1H), 6.32-6.30 (m, 1H), 3.08-3.04 (m, 2H), 2.68 (s, 3H), 2.20-2.16 (m, 2H), 2.12 (s, 3H), 1.55-1.46 (m, 4H), 1.33-1.26 (m, 10H). MS (ESI) m/z: 506.2 $[M+H]^+$.

Example 148. 11-((3-Acetamido-4-((4-methyl-5-nitrothiazol-2-yl)carbamoyl)phenyl)amino)undecanoic acid (BL-30)

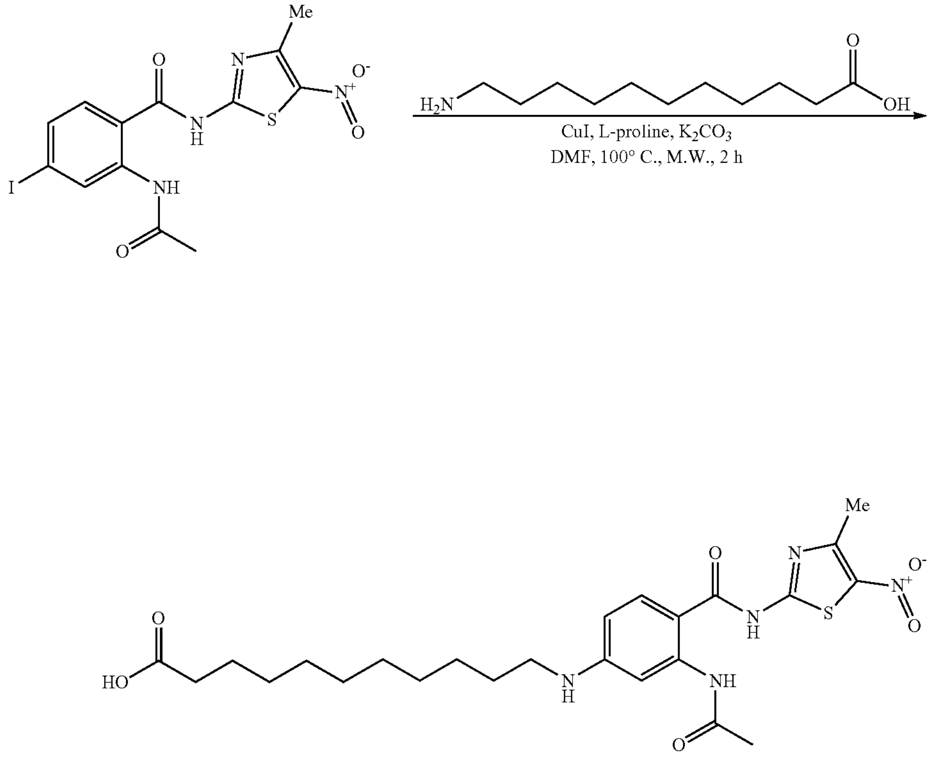

A solution of 2-acetamido-4-iodo-N-(4-methyl-5-nitrothiazol-2-yl)benzamide (1.0 g, 2.24 mmol), 11-aminoundecanoic acid (2.25 g, 11.2 mmol), CuI (425 mg, 2.24 mmol), $K_2CO_3$ (618 mg, 4.47 mmol) and L-proline (257 mg, 2.24 mmol) in DMF (15 mL) was irradiated at 100° C. for 2 h under microwave under argon atmosphere, before the mixture was purified by pre-HPLC to give title compound (218 mg, 18.7% yield) as yellow solid. $^1$H NMR (400 MHz, DMSO-$d_6$): δ 12.96 (brs, 1H), 12.08 (brs, 1H), 11.10 (brs, 1H), 7.88 (d, J=8.8 Hz, 1H), 7.72 (s, 1H), 6.89 (s, 1H), 6.31 (d, J=7.6 Hz, 1H), 3.08-3.01 (m, 2H), 2.68 (s, 3H), 2.19-2.16 (m, 2H), 2.12 (s, 3H), 1.55-1.46 (m, 4H), 1.33-1.25 (m, 12H). MS (ESI) m/z: 520.2 [M+H]$^+$.

Example 149. 3-(2-(2-((3-Acetamido-4-((4-methyl-5-nitrothiazol-2-yl)carbamoyl)phenyl)amino)ethoxy)ethoxy)propanoic acid (BL-31)

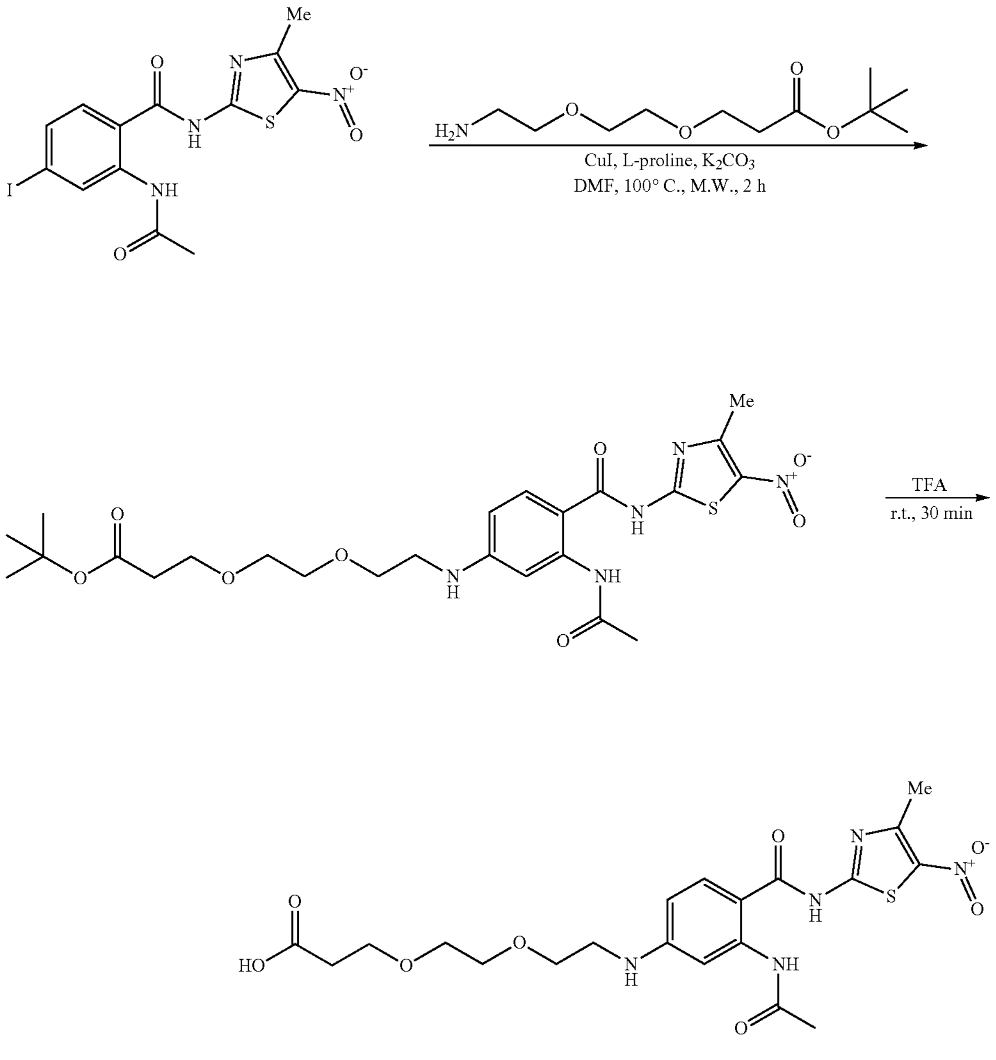

Step 1. Synthesis of tert-butyl 3-(2-(2-((3-acetamido-4-((4-methyl-5-nitrothiazol-2-yl)carbamoyl)phenyl)amino)ethoxy)ethoxy)propanoate

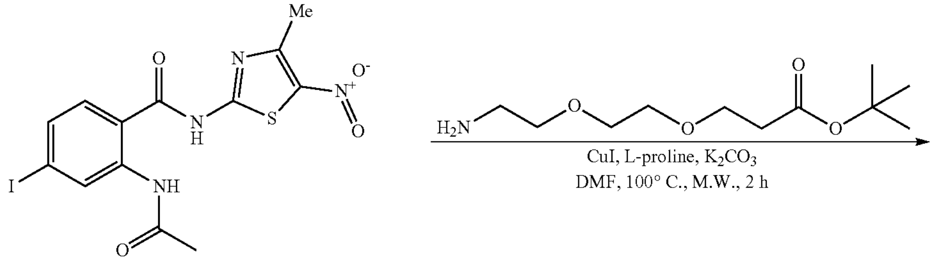

-continued

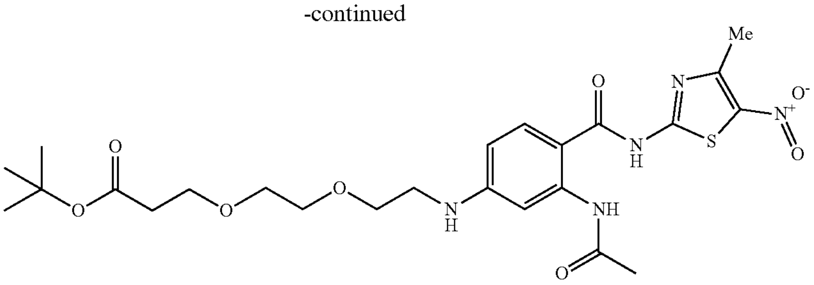

A solution of 2-acetamido-4-iodo-N-(4-methyl-5-nitrothiazol-2-yl)benzamide (1.0 g, 2.24 mmol), tert-butyl 3-(2-(2-aminoethoxy)ethoxy)propanoate (679 mg, 2.91 mmol), L-proline (257 mg, 2.24 mmol), CuI (428 mg, 2.24 mmol) and $K_2CO_3$ (927 mg, 6.72 mmol) in DMF (8 mL) were irradiated at 100° C. under microwave for 2 h under argon atmosphere, before the mixture was poured into water (50 mL) and extracted with EtOAc (3×50 mL). The combined organic phase was washed with brine, dried over $Na_2SO_4$, filtered and concentrated under vacuum to give the crude, which was used directly for next step. MS (ESI) m/z: 552.2 $[M+H]^+$ Step 2. Synthesis of 3-(2-(2-((3-acetamido-4-((4-methyl-5-nitrothiazol-2-yl)carbamoyl)phenyl)amino)ethoxy)ethoxy)propanoic acid

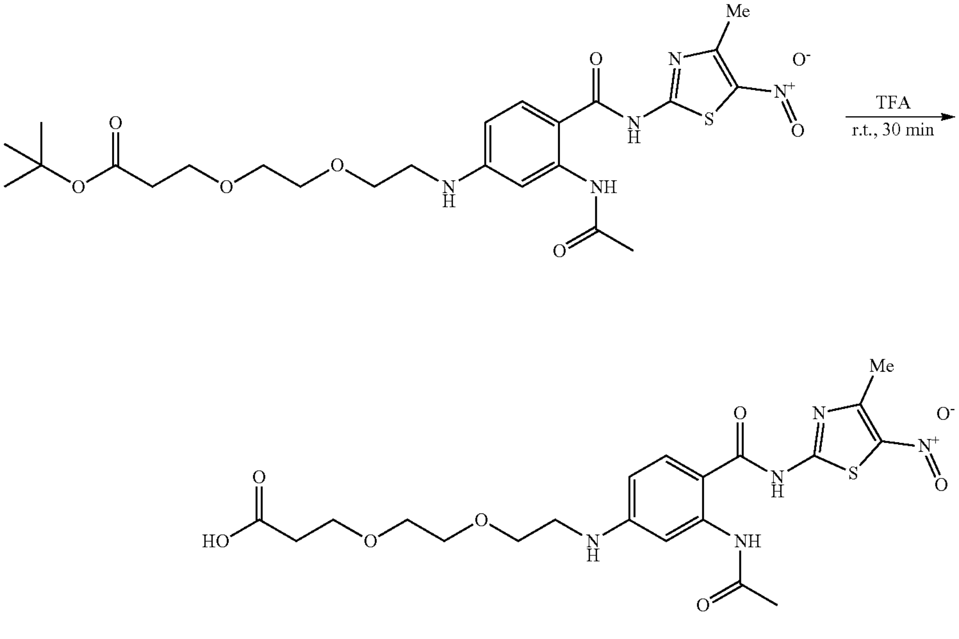

A solution of tert-butyl 3-(2-(2-((3-acetamido-4-((4-methyl-5-nitrothiazol-2-yl)carbamoyl)phenyl)amino)ethoxy)ethoxy)propanoate (crude) in TFA (10 mL) was stirred at rt for 30 min. Then, the mixture was concentrated to give a residue, which was purified by pre-HPLC to give title compound (144 mg, 13.0% over two steps) as yellow solid. $^1H$ NMR (400 MHz, DMSO-$d_6$): δ 13.67 (brs, 1H), 8.20 (brs, 3H), 7.97 (d, J=8.8 Hz, 1H), 7.85 (d, J=2.0 Hz, 1H), 6.30-6.27 (m, 1H), 6.25 (t, J=5.4 Hz, 1H), 3.62-3.50 (m, 8H), 3.23-3.20 (m, 2H), 2.59 (s, 3H), 2.43 (t, J=6.4 Hz, 2H), 2.14 (s, 3H). MS (EST) m/z: 496.0 $[M+H]^+$.

Example 150. 2-Acetamido-4-((9-aminononyl)amino)-N-(4-methyl-5-nitrothiazol-2-yl)benzamide (BL-32)

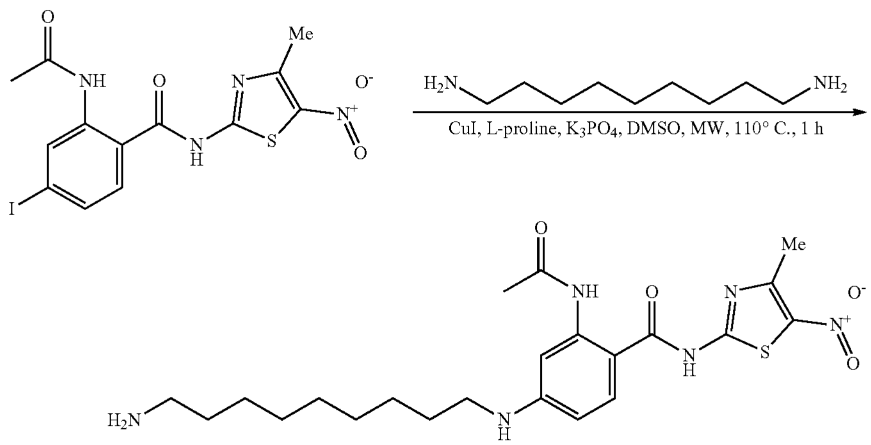

A solution of 2-acetamido-4-iodo-N-(4-methyl-5-nitrothiazol-2-yl)benzamide (1.0 g, 2.24 mmol), nonane-1,9-diamine (1.42 g, 8.97 mmol), L-proline (257 mg, 2.24 mmol), CuI (428 mg, 2.24 mmol) and $K_3PO_4$ (1.42 g, 6.72 mmol) in DMSO (10 mL) was irradiated at 110° C. under microwave for 1 h under argon atmosphere, before the mixture was purified by prep-HPLC to give title compound (404 mg, 30.6% yield) as yellow solid. $^1$H NMR (400 MHz, DMSO-$d_6$): δ 13.03 (brs, 1H), 11.06 (s, 1H), 7.88 (d, J=8.8 Hz, 1H), 7.73-7.69 (m, 4H), 6.33-6.30 (m, 1H), 3.07 (t, J=7.2 Hz, 2H), 2.79-2.74 (m, 2H), 2.69 (s, 3H), 2.13 (s, 3H), 1.57-1.50 (m, 4H), 1.34-1.28 (m, 10H). MS (EST) m/z: 477.6 $[M+H]^+$.

Example 151. 4-((3-Acetamido-4-((4-methyl-5-nitrothiazol-2-yl)carbamoyl)phenyl)amino)butanoic acid (BL-33)

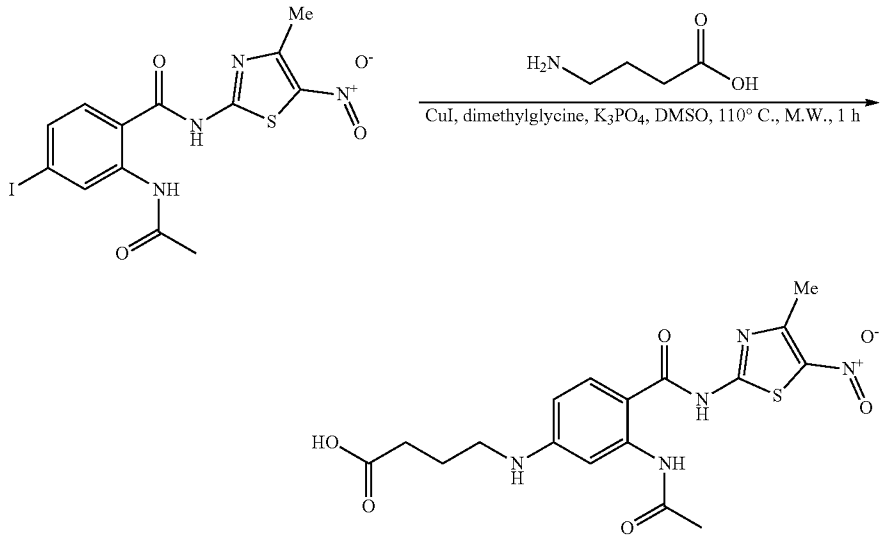

A solution of 2-acetamido-4-iodo-N-(4-methyl-5-nitrothiazol-2-yl)benzamide (1.0 g, 2.24 mmol), 4-aminobutanoic acid (1.15 g, 11.2 mmol), dimethylglycine (231 mg, 2.24 mmol), CuI (425 mg, 2.24 mmol) and $K_3PO_4$ (2.84 g, 13.4 mmol) in DMSO (15 mL) was irradiated at 110° C. under microwave for 1 h under argon atmosphere, before the mixture was purified by prep-HPLC to give the title compound (800 mg, 84.8% yield) as yellow solid. $^1$H NMR (400

MHz, DMSO-$d_6$): δ 13.67 (brs, 1H), 10.02 (brs, 1H), 7.97 (d, J=8.8 Hz, 1H), 7.82 (d, J=2.4 Hz, 1H), 6.32-6.29 (m, 1H), 6.27-6.24 (m, 1H), 3.31 (brs, 1H), 3.06-3.32 (m, 2H), 2.59 (s, 3H), 2.34-2.13 (m, 2H), 2.13 (s, 3H), 1.80-1.73 (m, 4H). MS (ESI) m/z: 422.1 $[M+H]^+$ Example 152. 5-((3-Acetamido-4-((4-methyl-5-nitrothiazol-2-yl)carbamoyl)phenyl)amino)pentanoic acid (BL-34)

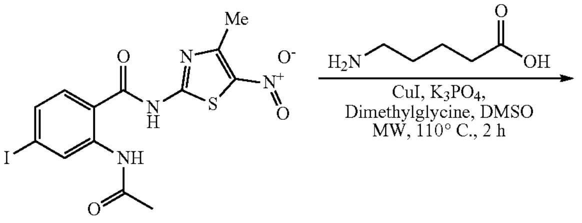

-continued

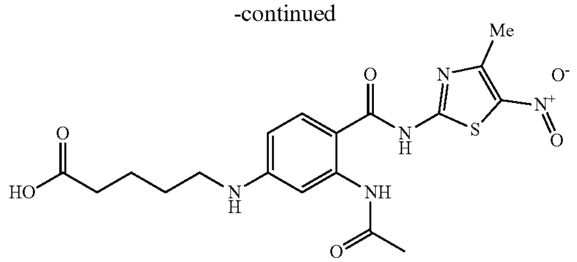

A solution of 2-acetamido-4-iodo-N-(4-methyl-5-nitrothiazol-2-yl)benzamide (1.0 g, 2.24 mmol), 5-aminopentanoic acid (1.31 g, 11.2 mmol), CuI (427 mg, 2.24 mmol), $K_2PO_4$ (2.84 g, 13.4 mmol) and dimethylglycine (231 mg, 2.24 mmol) in DMSO (15 mL) was irradiated at 110° C. for 2 h under microwave under argon atmosphere, before the mixture was purified by prep-HPLC to give title compound (280 mg, 28.7% yield) as yellow solid. $^1H$ NMR (400 MHz, DMSO-$d_6$): δ 12.98 (brs, 1H), 12.08 (brs, 1H), 11.10 (brs, 1H), 7.89 (d, J=8.8 Hz, 1H), 7.73 (s, 1H), 6.93-6.92 (m, 1H), 6.33-6.31 (m, 1H), 3.09-3.07 (m, 2H), 2.68 (s, 3H), 2.26-2.23 (m, 2H), 2.10 (s, 3H), 1.58-1.56 (m, 4H). MS (ESI) m/z: 436.0 $[M+H]^+$.

Example 153. 3-(2-((3-Acetamido-4-((4-methyl-5-nitrothiazol-2-yl)carbamoyl)phenyl)amino)ethoxy)propanoic acid (BL-35)

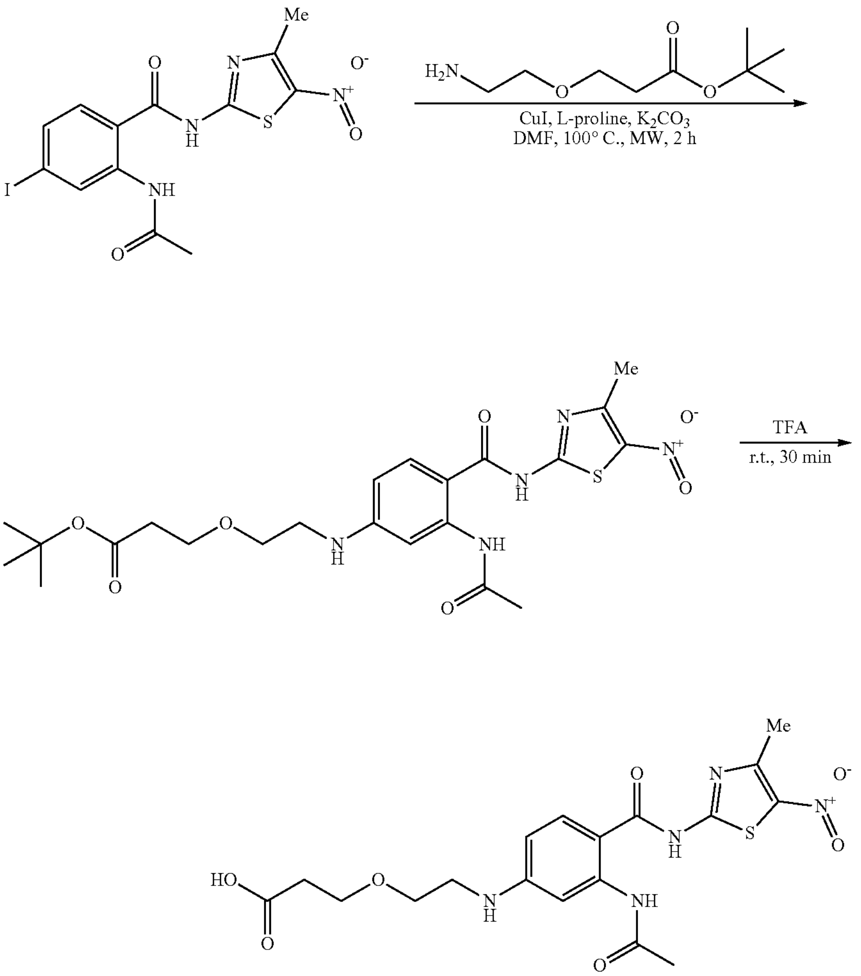

Step 1. Synthesis of tert-butyl 3-(2-((3-acetamido-4-((4-methyl-5-nitrothiazol-2-yl)carbamoyl)phenyl)amino)ethoxy)propanoate

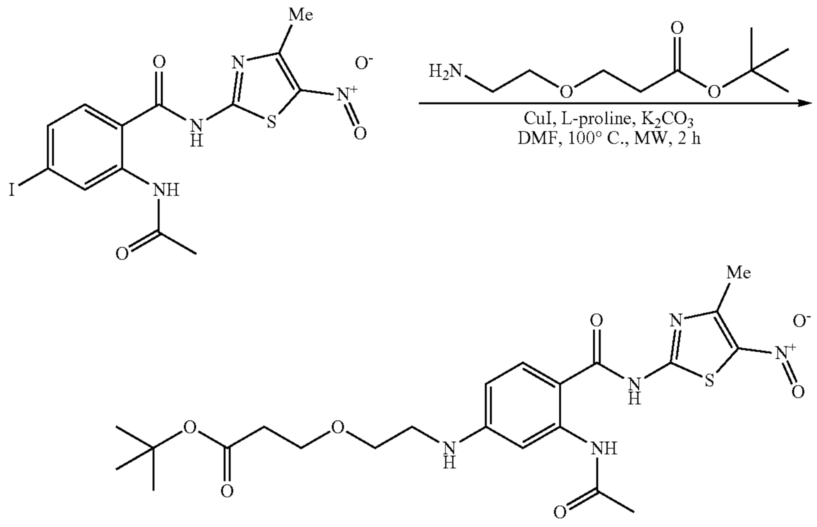

A solution of 2-acetamido-4-iodo-N-(4-methyl-5-nitrothiazol-2-yl)benzamide (1.0 g, 2.24 mmol), tert-butyl 3-(2-aminoethoxy)propanoate (550 mg, 2.91 mmol), L-proline (257 mg, 2.24 mmol), CuI (428 mg, 2.24 mmol) and $K_2CO_3$ (927 mg, 6.72 mmol) in DMF (8 mL) was irradiated at 100° C. under microwave for 2 h under argon atmosphere, before the mixture was the mixture was purified by prep-HPLC to give the title compound (500 mg, 44.1% yield) as yellow oil. MS (ESI) m/z: 508.1 $[M+H]^+$.

Step 2. Synthesis of 3-(2-((3-acetamido-4-((4-methyl-5-nitrothiazol-2-yl)carbamoyl)phenyl)amino)ethoxy)propanoic acid

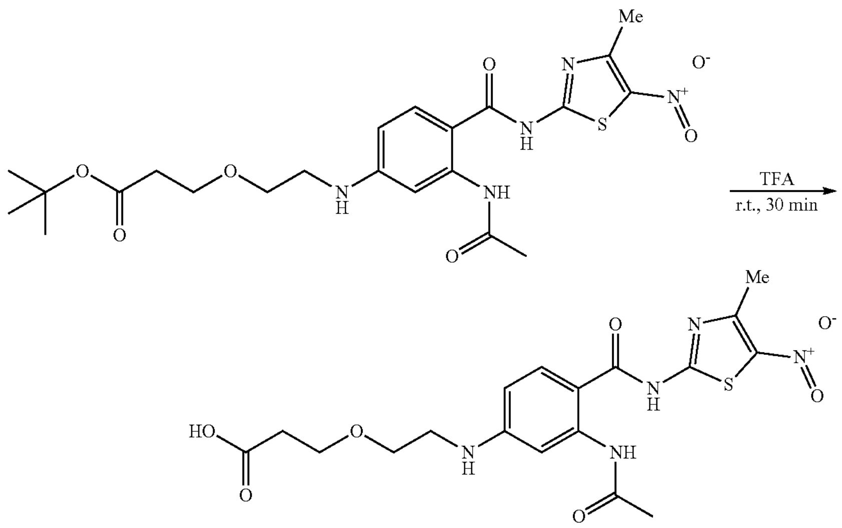

A solution of tert-butyl 3-(2-((3-acetamido-4-((4-methyl-5-nitrothiazol-2-yl)carbamoyl)phenyl)amino)ethoxy)propanoate (500 mg, 0.99 mmol) in TFA (10 mL) was stirred at rt for 30 min. Then, the mixture was concentrated to give title compound (426 mg, 95.7% yield) as yellow solid. $^1H$ NMR (400 MHz, DMSO-$d_6$): δ 13.00 (brs, 1H), 11.01 (s, 1H), 7.88 (d, J=8.8 Hz, 1H), 7.72 (d, J=2.0 Hz, 1H), 6.98 (brs, 1H), 6.38-6.35 (m, 1H), 3.64 (t, J=6.2 Hz, 2H), 3.55 (t, J=5.6 Hz, 2H), 3.25 (t, J=5.6 Hz, 2H), 2.69 (s, 3H), 2.48 (t, J=6.4 Hz, 2H), 2.12 (s, 3H). MS (ESI) m/z: 452.0 $[M+H]^+$.

Example 154. 1-((3-Acetamido-4-((4-methyl-5-nitrothiazol-2-yl)carbamoyl)phenyl)amino)-3,6,9,12-tetraoxapentadecan-15-oic acid (BL-36)

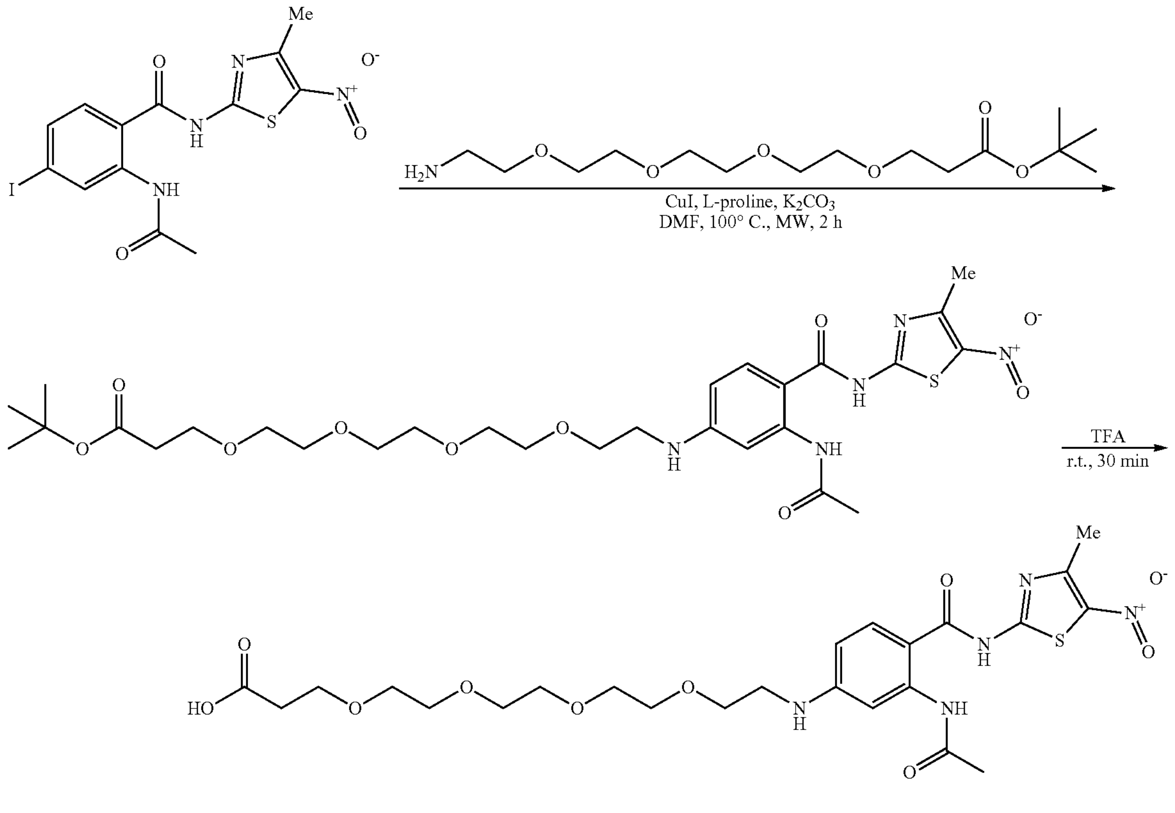

Step 1. Synthesis of tert-butyl 1-((3-acetamido-4-((4-methyl-5-nitrothiazol-2-yl)carbamoyl)phenyl)amino)-3,6,9,12-tetraoxapentadecan-15-oate

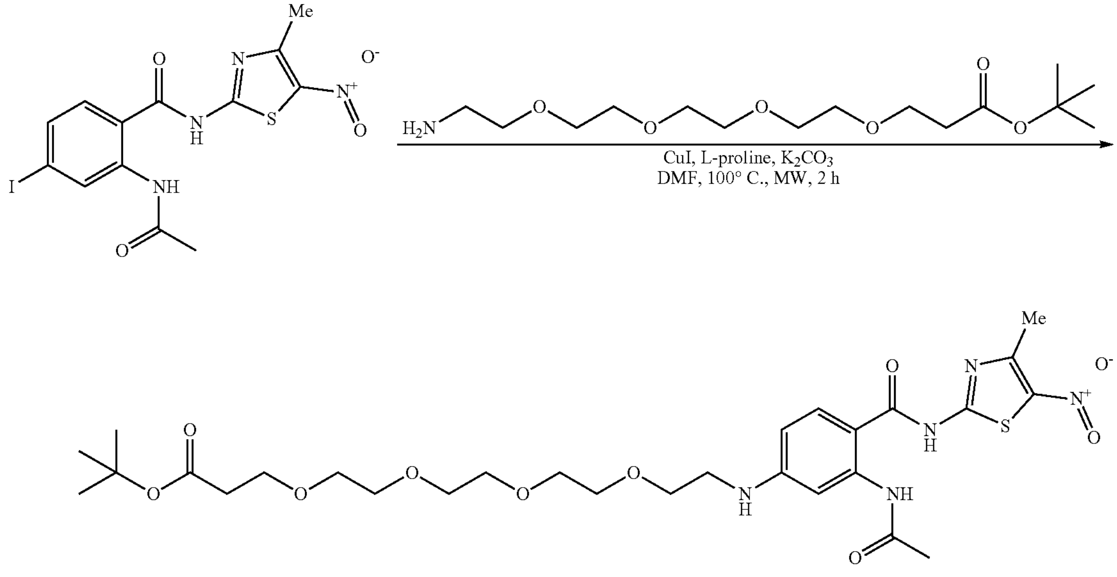

A solution of 2-acetamido-4-iodo-N-(4-methyl-5-nitrothiazol-2-yl)benzamide (500 mg, 1.12 mmol), tert-butyl 1-amino-3,6,9,12-tetraoxapentadecan-15-oate (468 mg, 1.46 mmol), L-proline (128 mg, 1.12 mmol), CuI (214 mg, 1.12 mmol) and $K_2CO_3$ (463 mg, 3.36 mmol) in DMF (5 mL) was irradiated at 100° C. under microwave for 2 h under argon atmosphere, before the mixture was purified by prep-HPLC to give the title compound (130 mg, 18.2% yield) as yellow oil. MS (ESI) m/z: 640.2 $[M+H]^+$ Step 2. Synthesis of 1-((3-acetamido-4-((4-methyl-5-nitrothiazol-2-yl)carbamoyl)phenyl)amino)-3,6,9,12-tetraoxapentadecan-15-oic acid

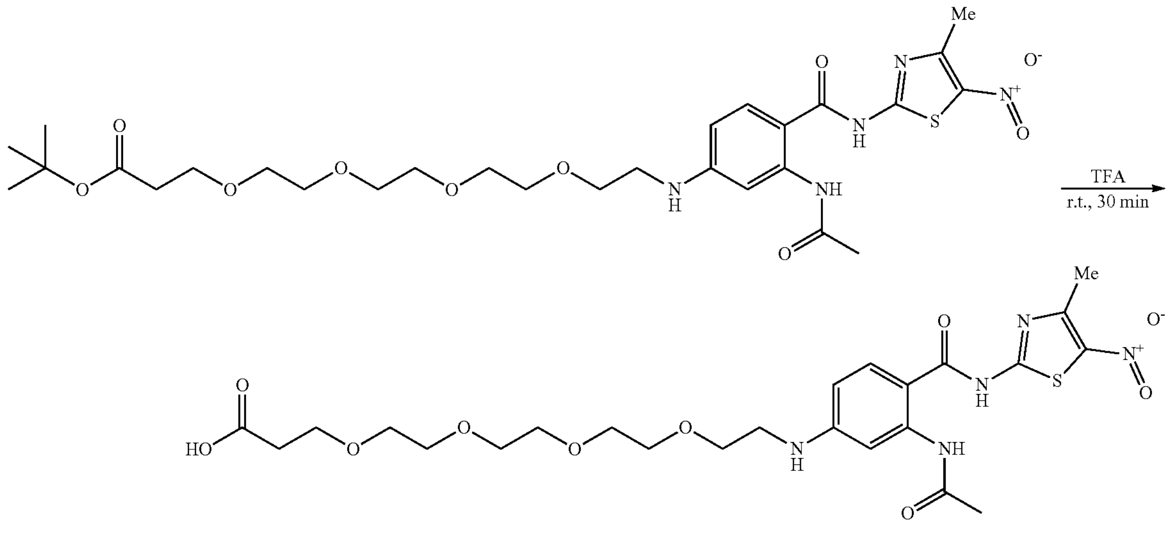

A solution of tert-butyl 1-((3-acetamido-4-((4-methyl-5-nitrothiazol-2-yl)carbamoyl)phenyl)amino)-3,6,9,12-tetraoxapentadecan-15-oate (130 mg, 0.203 mmol) in TFA (10 mL) was stirred at rt for 30 min. Then, the mixture was concentrated to give title compound (118 mg, 83.7% yield) as yellow solid. $^1$H NMR (400 MHz, DMSO-$d_6$): δ 12.89 (brs, 1H), 11.02 (s, 1H), 7.88 (d, J=8.8 Hz, 1H), 7.72 (d, J=2.0 Hz, 1H), 6.97 (brs, 1H), 6.38-6.36 (m, 1H), 3.60-3.48 (m, 16H), 3.27 (t, J=5.4 Hz, 2H), 2.69 (s, 3H), 2.43 (t, J=6.4 Hz, 2H), 2.12 (s, 3H). MS (ESI) m/z: 584.5 $[M+H]^+$.

Example 155. 1-((3-Acetamido-4-((4-methyl-5-nitrothiazol-2-yl)carbamoyl)phenyl)amino)-3,6,9,12,15-pentaoxaoctadecan-18-oic acid (BL-37)

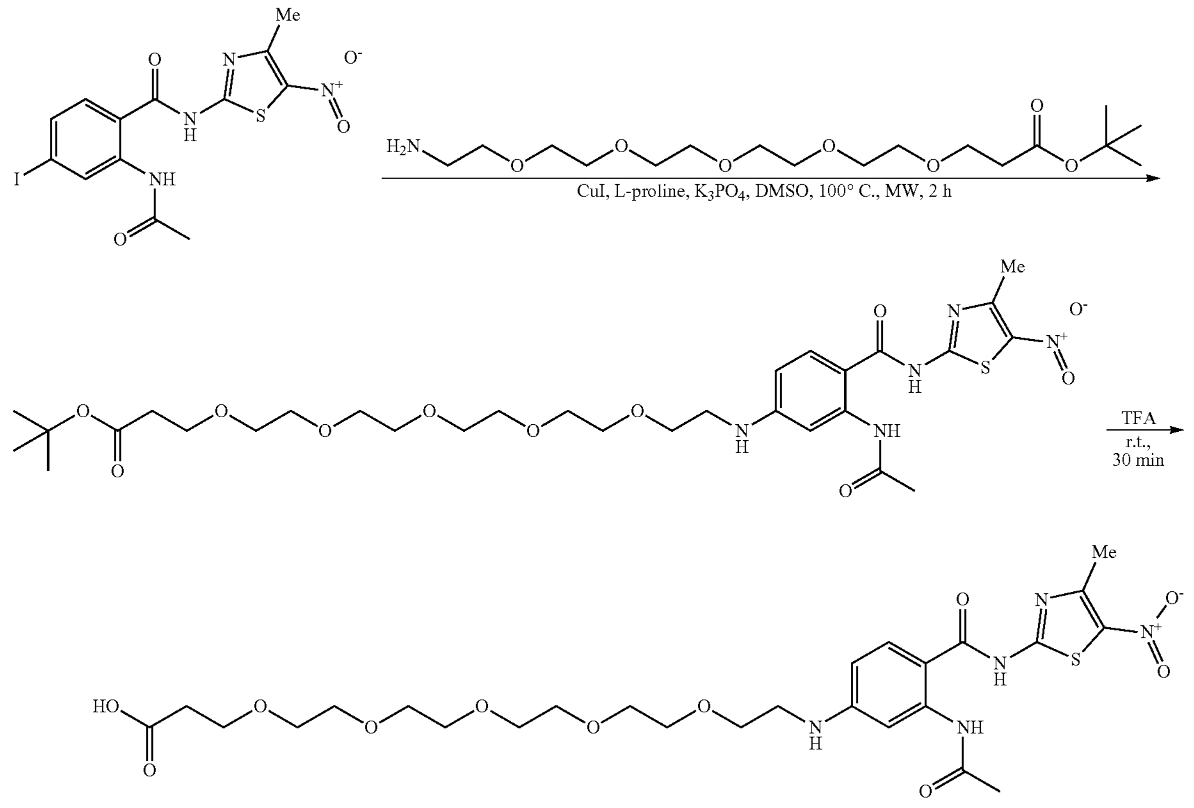

Step 1. Synthesis of tert-butyl 1-((3-acetamido-4-((4-methyl-5-nitrothiazol-2-yl)carbamoyl)phenyl)amino)-3,6,9,12,15-pentaoxaoctadecan-18-oate

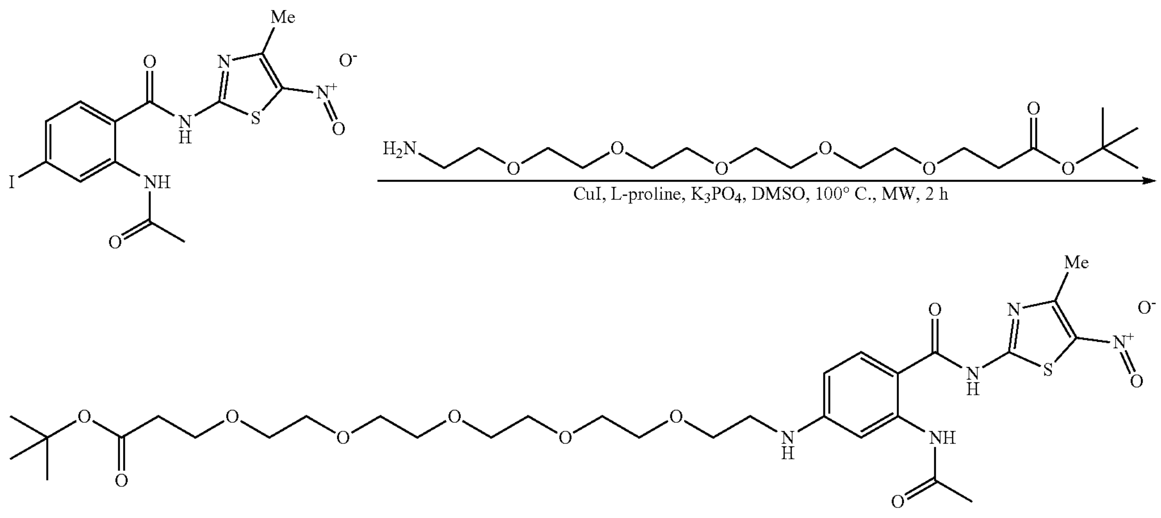

A solution of 2-acetamido-4-iodo-N-(4-methyl-5-nitrothiazol-2-yl)benzamide (1 g, 2.24 mmol), tert-butyl 1-amino-3,6,9,12,15-pentaoxaoctadecan-18-oate (1.06 g, 2.91 mmol), L-proline (258 mg, 2.24 mmol), CuI (428 mg, 2.24 mmol) and $K_3PO_4$ (1.42 g, 6.72 mmol) in DMSO (15 mL) was irradiated at 100° C. under microwave for 2 h under argon atmosphere, before the mixture was purified by prep-HPLC to give the title compound (480 mg, 31.4% yield) as yellow oil. MS (ESI) m/z: 684.6 $[M+H]^+$.

Step 2. Synthesis of 1-((3-acetamido-4-((4-methyl-5-nitrothiazol-2-yl)carbamoyl)phenyl)amino)-3,6,9,12,15-pentaoxaoctadecan-18-oic acid

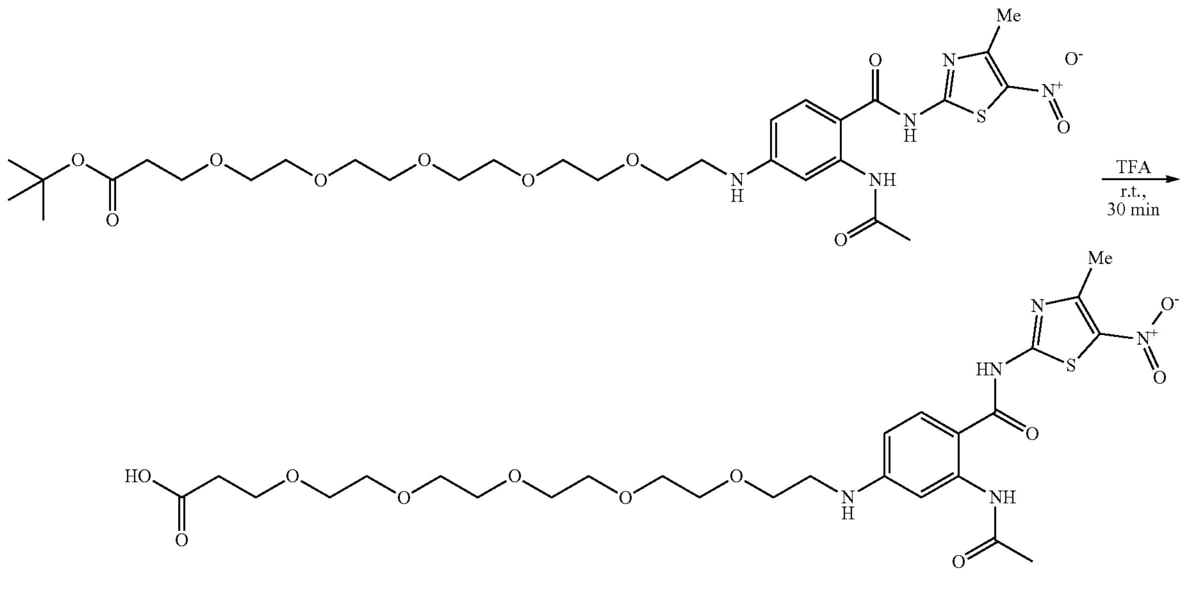

A solution of tert-butyl 1-((3-acetamido-4-((4-methyl-5-nitrothiazol-2-yl)carbamoyl)phenyl)amino)-3,6,9,12,15-pentaoxaoctadecan-18-oate (480 mg, 0.702 mmol) in TFA (10 mL) was stirred at rt for 30 min. Then, the mixture was concentrated to give title compound (485 mg, 93.3% yield) as yellow solid. $^1H$ NMR (400 MHz, DMSO-$d_6$): δ 13.00

(brs, 1H), 11.02 (s, 1H), 7.88 (d, J=8.8 Hz, 1H), 7.72 (d, J=2.0 Hz, 1H), 6.97 (brs, 1H), 6.38-6.36 (m, 1H), 3.60-3.48 (m, 20H), 3.27 (t, J=5.6 Hz, 2H), 2.69 (s, 3H), 2.43 (t, J=6.2 Hz, 2H), 2.12 (s, 3H). MS (ESI) m/z: 628.6 [M+H]$^+$.

Example 156. 8-((3-Acetamido-4-((4-methyl-5-nitrothiazol-2-yl)carbamoyl)phenyl)amino)octanoic acid (BL-38)

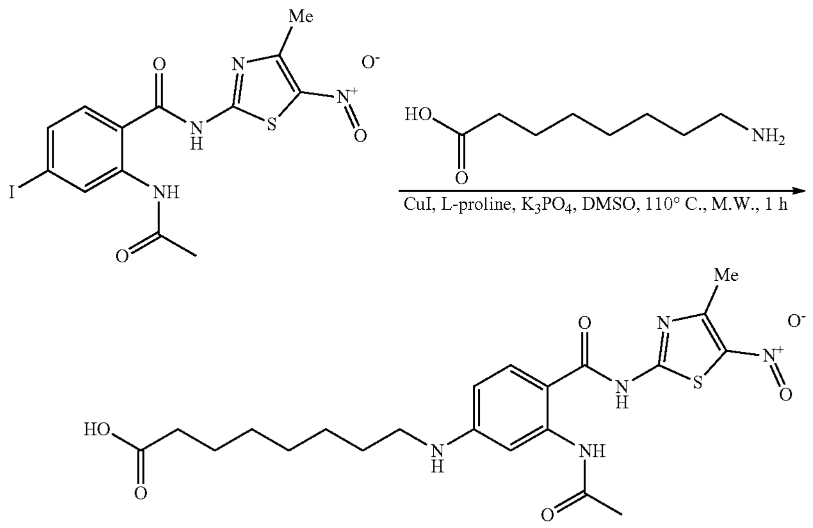

A solution of 2-acetamido-4-iodo-N-(4-methyl-5-nitrothiazol-2-yl)benzamide (1.00 g, 2.24 mmol), 8-aminooctanoic acid (1.07 g, 6.72 mmol), L-proline (258 mg, 2.24 mmol), CuI (428 mg, 2.24 mmol) and $K_3PO_4$ (2.37 g, 11.2 mmol) in DMSO (15 mL) was irradiated at 110° C. under microwave for 1 h under argon atmosphere, before the mixture was purified by prep-HPLC to give the title compound (370 mg, 34.6% yield) as yellow solid. $^1$H NMR (400 MHz, DMSO-$d_6$): δ 13.00 (brs, 1H), 11.98 (s, 1H), 11.18 (s, 1H), 7.88 (d, J=9.2 Hz, 1H), 7.72 (d, J=2.4 Hz, 1H), 6.88 (t, J=4.4 Hz, 1H), 6.32-6.30 (m, 1H), 3.08-3.05 (m, 2H), 2.68 (s, 3H), 2.19 (t, J=7.2 Hz, 2H), 2.12 (s, 3H), 1.56-1.48 (m, 4H), 1.35-1.23 (m, 6H). MS (ESI) m/z: 478.2 [M+H]$^+$.

Example 157. 9-((3-Acetamido-4-((4-methyl-5-nitrothiazol-2-yl)carbamoyl)phenyl)amino)nonanoic acid (BL-39)

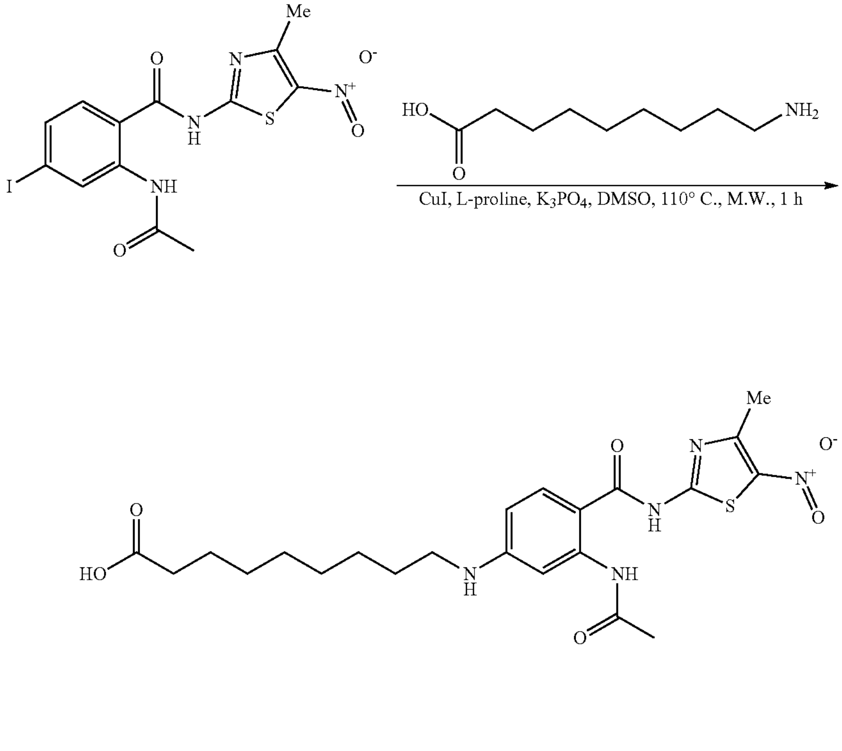

A solution of 2-acetamido-4-iodo-N-(4-methyl-5-nitrothiazol-2-yl)benzamide (1.00 g, 2.24 mmol), 9-aminononanoic acid (1.16 g, 6.72 mmol), L-proline (258 mg, 2.24 mmol), CuI (428 mg, 2.24 mmol) and $K_3PO_4$ (2.37 g, 11.2 mmol) in DMSO (15 mL) was irradiated at 110° C. under microwave for 1 h under argon atmosphere, before the mixture was purified by prep-HPLC to give the title compound (430 mg, 39.1% yield) as yellow solid. $^1$H NMR (400 MHz, DMSO-$d_6$): δ 12.95 (brs, 1H), 11.99 (s, 1H), 11.28 (s, 1H), 7.88 (d, J=9.2 Hz, 1H), 7.73 (d, J=1.6 Hz, 1H), 6.85 (t, J=5.6 Hz, 1H), 6.32-6.29 (m, 1H), 3.08-3.03 (m, 2H), 2.68 (s, 3H), 2.19 (t, J=7.2 Hz, 2H), 2.12 (s, 3H), 1.56-1.47 (m, 4H), 1.35-1.21 (m, 8H). MS (ESI) m/z: 492.1 $[M+H]^+$.

Example 158. (S)-2-Acetamido-4-((2-(2-(4-(4-chlorophenyl)-2,3,9-trimethyl-6H-thieno[3,2-f][1,2,4]triazolo[4,3-a][1,4]diazepin-6-yl)acetamido)ethyl)amino)-N-(4-methyl-5-nitrothiazol-2-yl)benzamide (D-26)

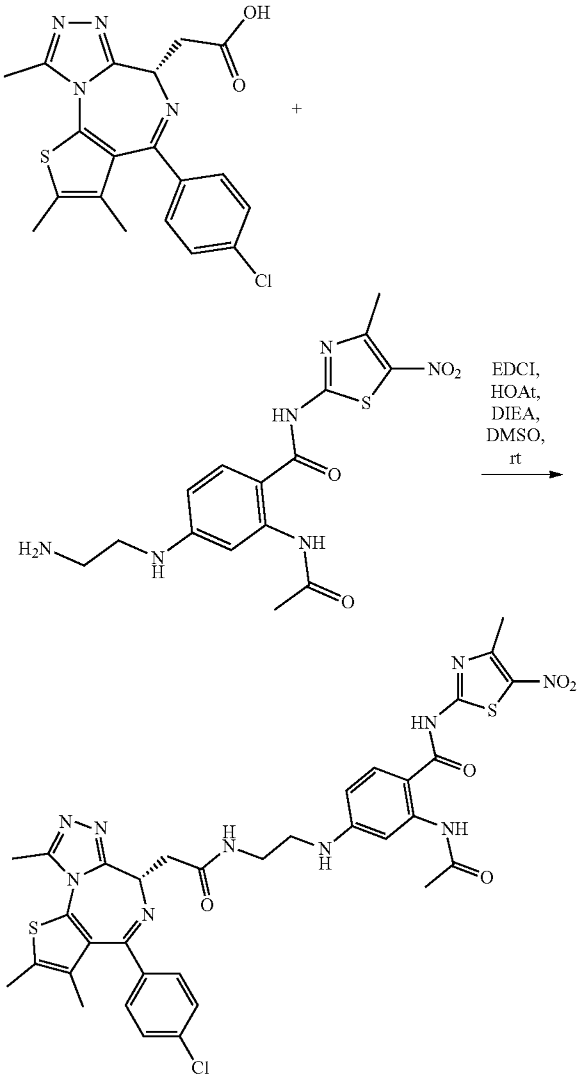

A solution of (S)-2-(4-(4-chlorophenyl)-2,3,9-trimethyl-6H-thieno[3,2-f][1,2,4]triazolo[4,3-a][1,4]diazepin-6-yl) acetic acid (5 mg, 0.0125 mmol), 2-acetamido-4-((2-aminoethyl)amino)-N-(4-methyl-5-nitrothiazol-2-yl)benzamide (4.72 mg, 0.0125 mmol), HOAt (8.5 mg, 0.0625 mmol), EDCI (12 mg, 0.0625) and DIEA (16 mg, 0.125 mmol) in DMSO (1 mL) was stirred at rt overnight. The reaction solution was purified with reverse phase chromatography to give the title compound (1.54 mg, 16.2% yield) as yellow solid. MS (ESI) m/z: 761.5 $[M+H]^+$.

Example 159. (S)-2-Acetamido-4-((4-(2-(4-(4-chlorophenyl)-2,3,9-trimethyl-6H-thieno[3,2-f][1,2,4]triazolo[4,3-a][1,4]diazepin-6-yl)acetamido)butyl)amino)-N-(4-methyl-5-nitrothiazol-2-yl)benzamide (D-27)

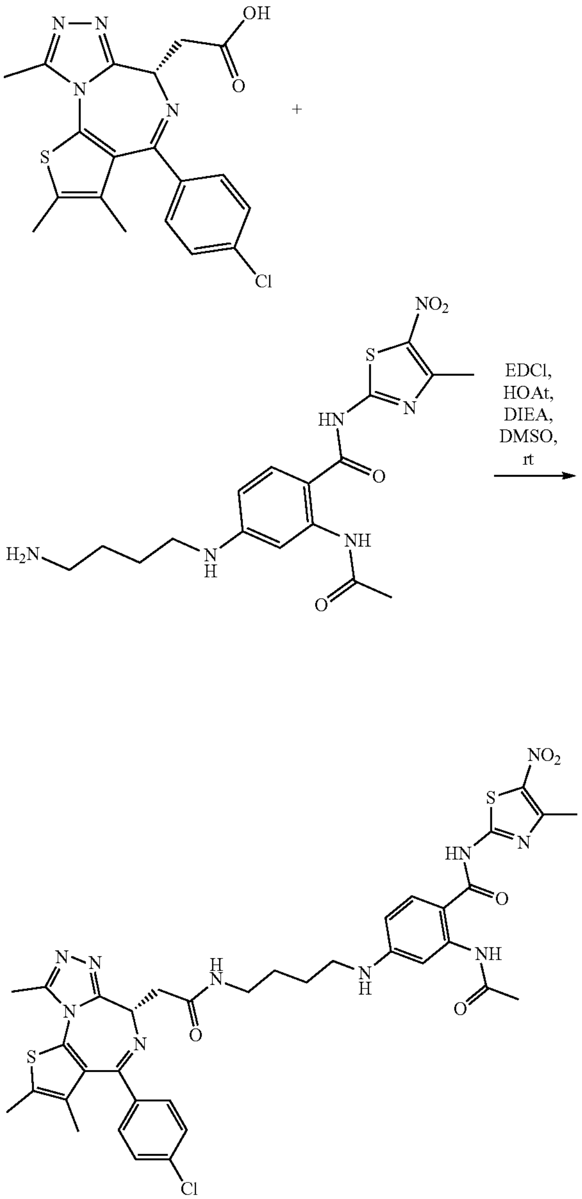

D-27 was synthesized following the standard procedure for preparing D-26 (4.96 mg, 50.3% yield). MS (EST) m/z: 789.6 $[M+H]^+$.

Example 160. (S)-2-Acetamido-4-((6-(2-(4-(4-chlorophenyl)-2,3,9-trimethyl-6H-thieno[3,2-f][1,2,4]triazolo[4,3-a][1,4]diazepin-6-yl)acetamido)hexyl)amino)-N-(4-methyl-5-nitrothiazol-2-yl)benzamide (D-28)
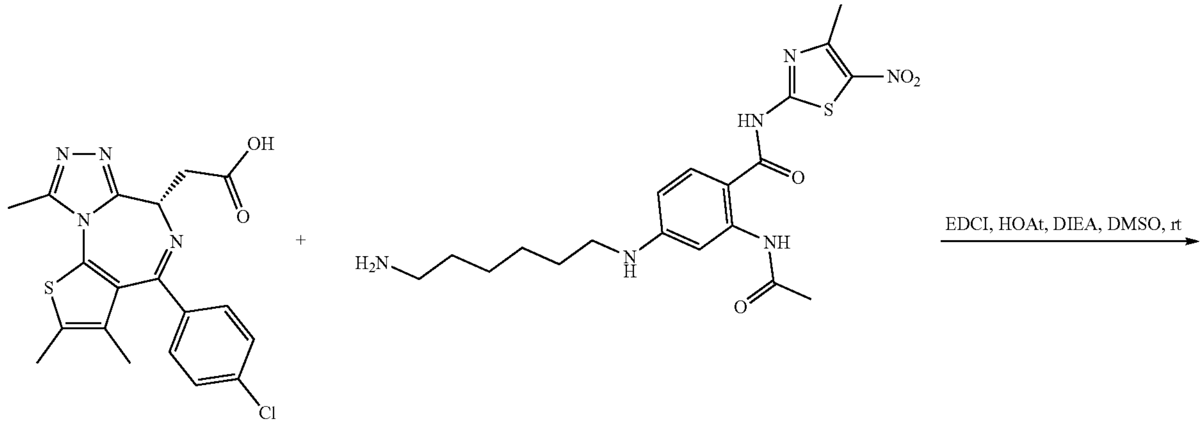
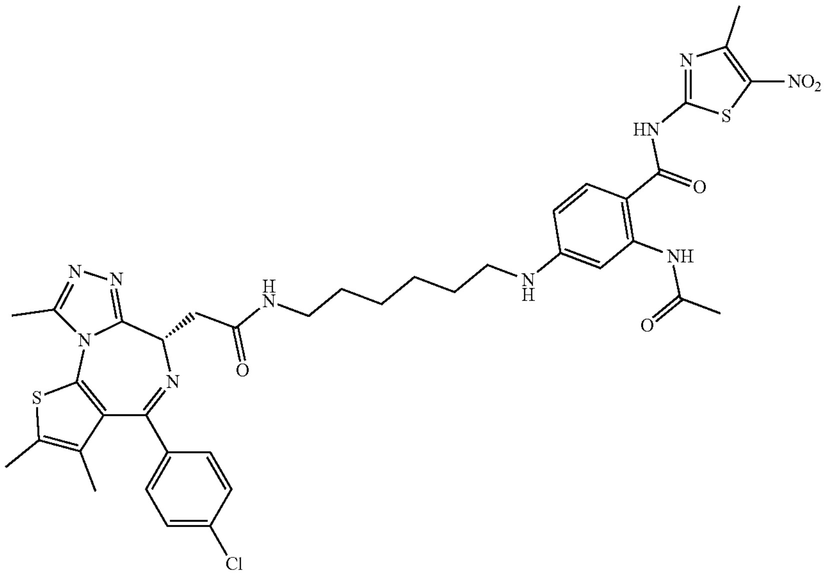
D-28 was synthesized following the standard procedure for preparing D-26 (3.44 mg, 33.6% yield). MS (EST) m/z: 817.6 $[M+H]^+$.

Example 161. (S)-2-Acetamido-4-((7-(2-(4-(4-chlorophenyl)-2,3,9-trimethyl-6H-thieno[3,2-f][1,2,4]triazolo[4,3-a][1,4]diazepin-6-yl)acetamido)heptyl)amino)-N-(4-methyl-5-nitrothiazol-2-yl)benzamide (D-29)
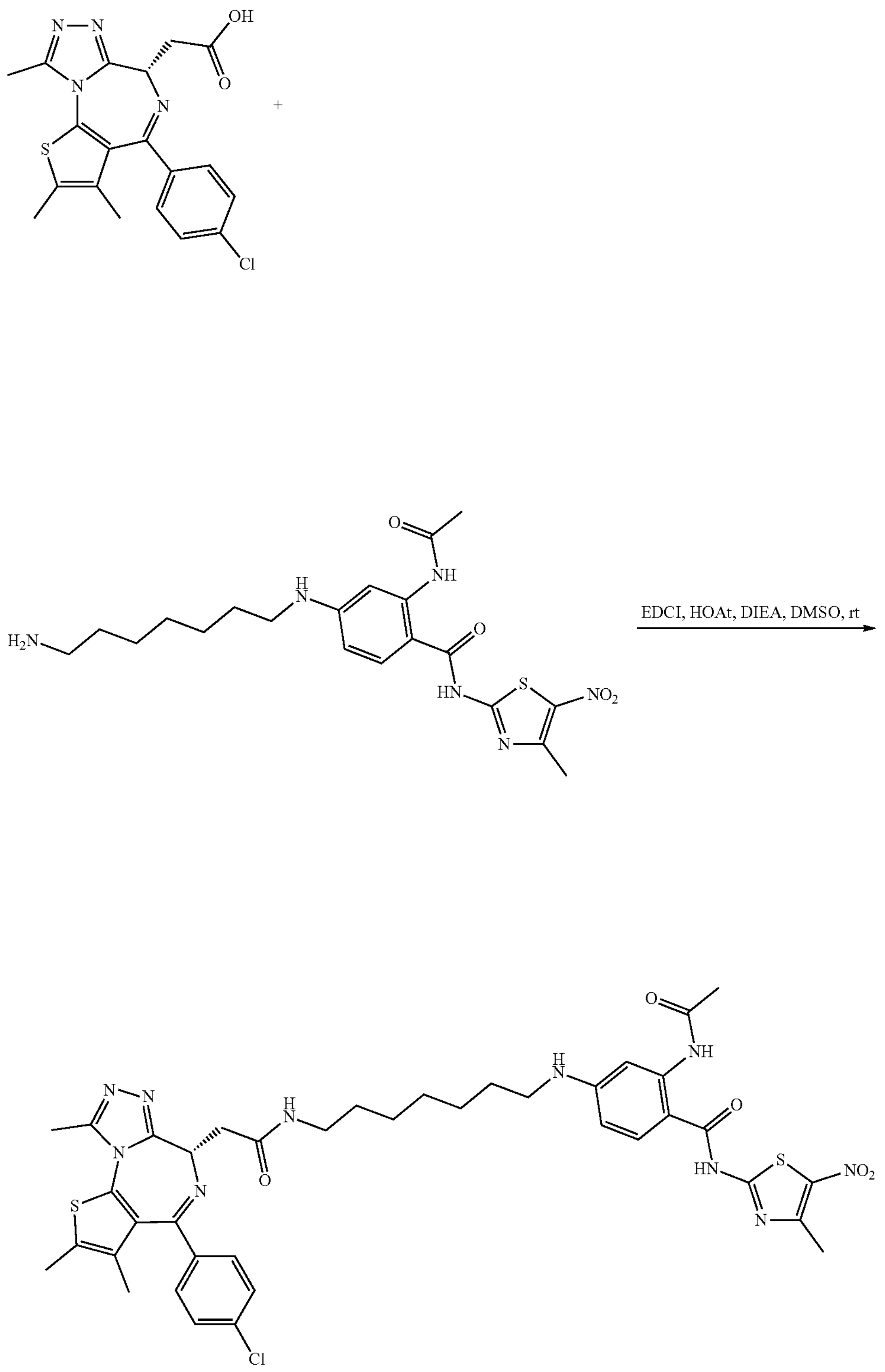
D-29 was synthesized following the standard procedure for preparing D-26 (3.59 mg, 34.5% yield). MS (EST) m/z: 831.7 $[M+H]^+$.

Example 162. (S)-2-Acetamido-4-((8-(2-(4-(4-chlorophenyl)-2,3,9-trimethyl-6H-thieno[3,2-f][1,2,4]triazolo[4,3-a][1,4]diazepin-6-yl)acetamido)octyl)amino)-N-(4-methyl-5-nitrothiazol-2-yl)benzamide (D-30)
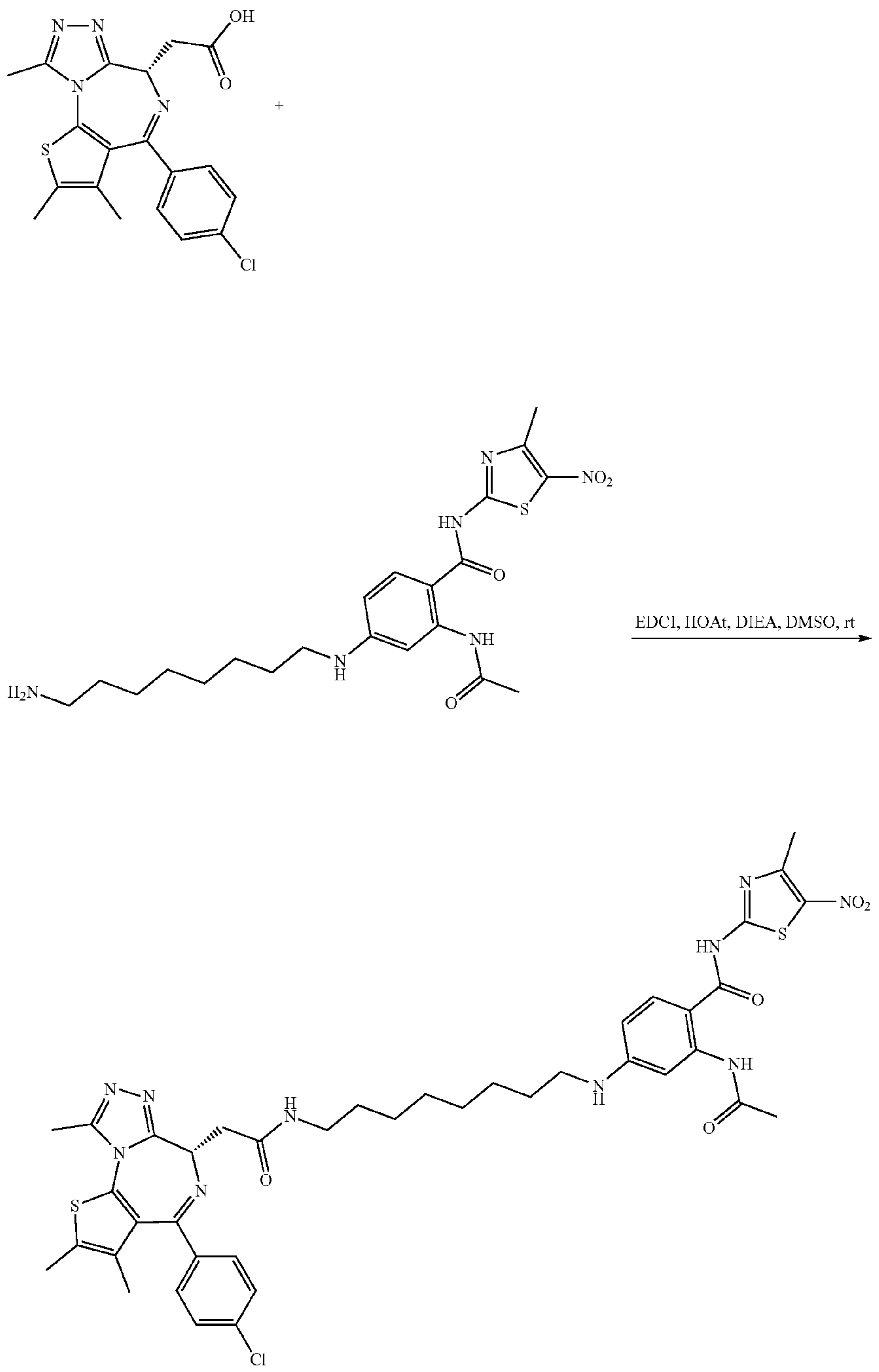
D-30 was synthesized following the standard procedure for preparing D-26 (4.96 mg, 46.9% yield). MS (EST) m/z: 845.7 [M+H]$^+$.

Example 163. (S)-2-Acetamido-4-((10-(2-(4-(4-chlorophenyl)-2,3,9-trimethyl-6H-thieno[3,2-f][1,2,4]triazolo[4,3-a][1,4]diazepin-6-yl)acetamido)decyl)amino)-N-(4-methyl-5-nitrothiazol-2-yl)benzamide (D-31)
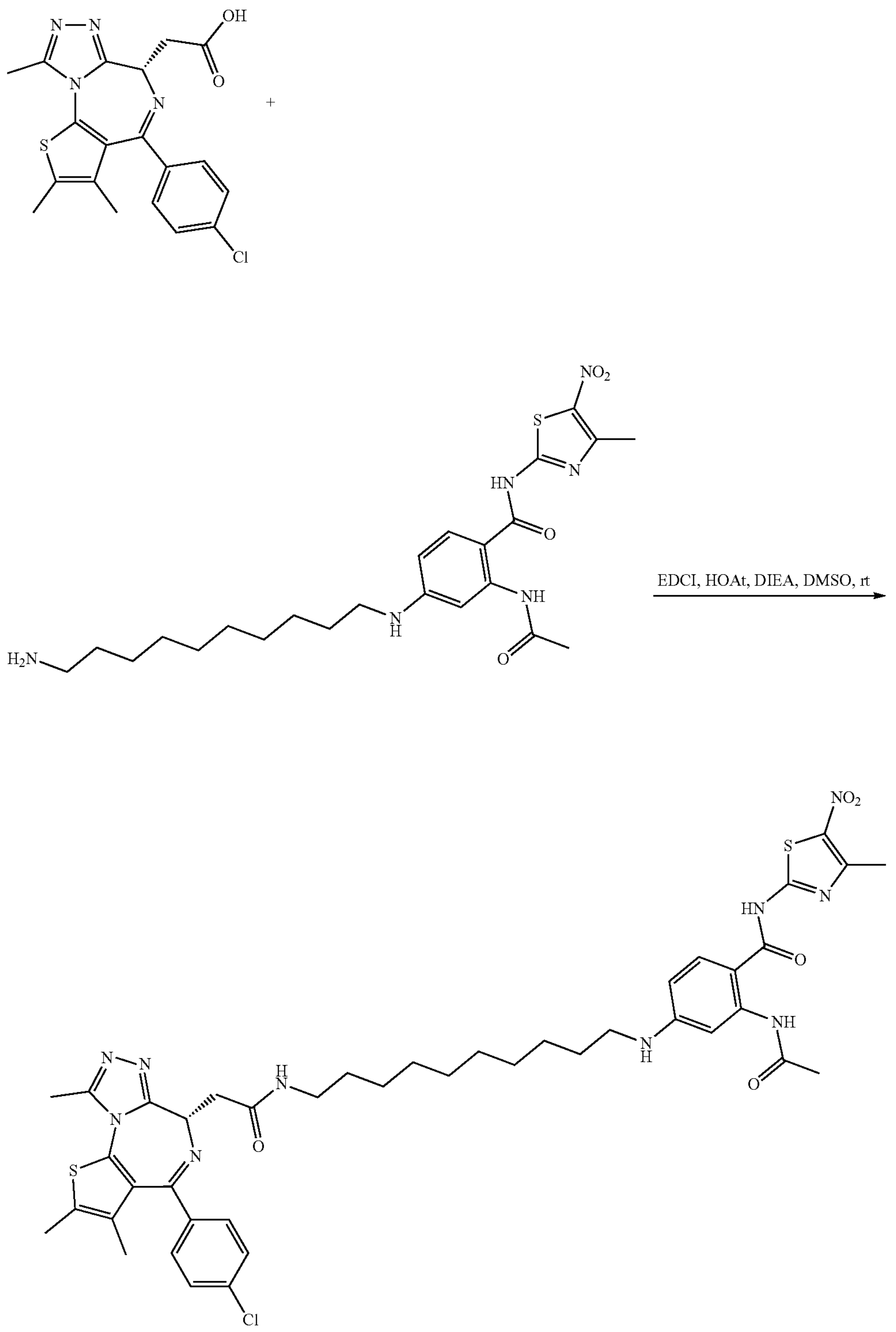
D-31 was synthesized following the standard procedure for preparing D-26 (4.08 mg, 37.3% yield). MS (EST) m/z: 873.7 $[M+H]^+$.

Example 164. (S)-2-Acetamido-4-((2-(2-(2-(4-(4-chlorophenyl)-2,3,9-trimethyl-6H-thieno[3,2-f][1,2,4]triazolo[4,3-a][1,4]diazepin-6-yl)acetamido)ethoxy)ethyl)amino)-N-(4-methyl-5-nitrothiazol-2-yl)benzamide (D-32)

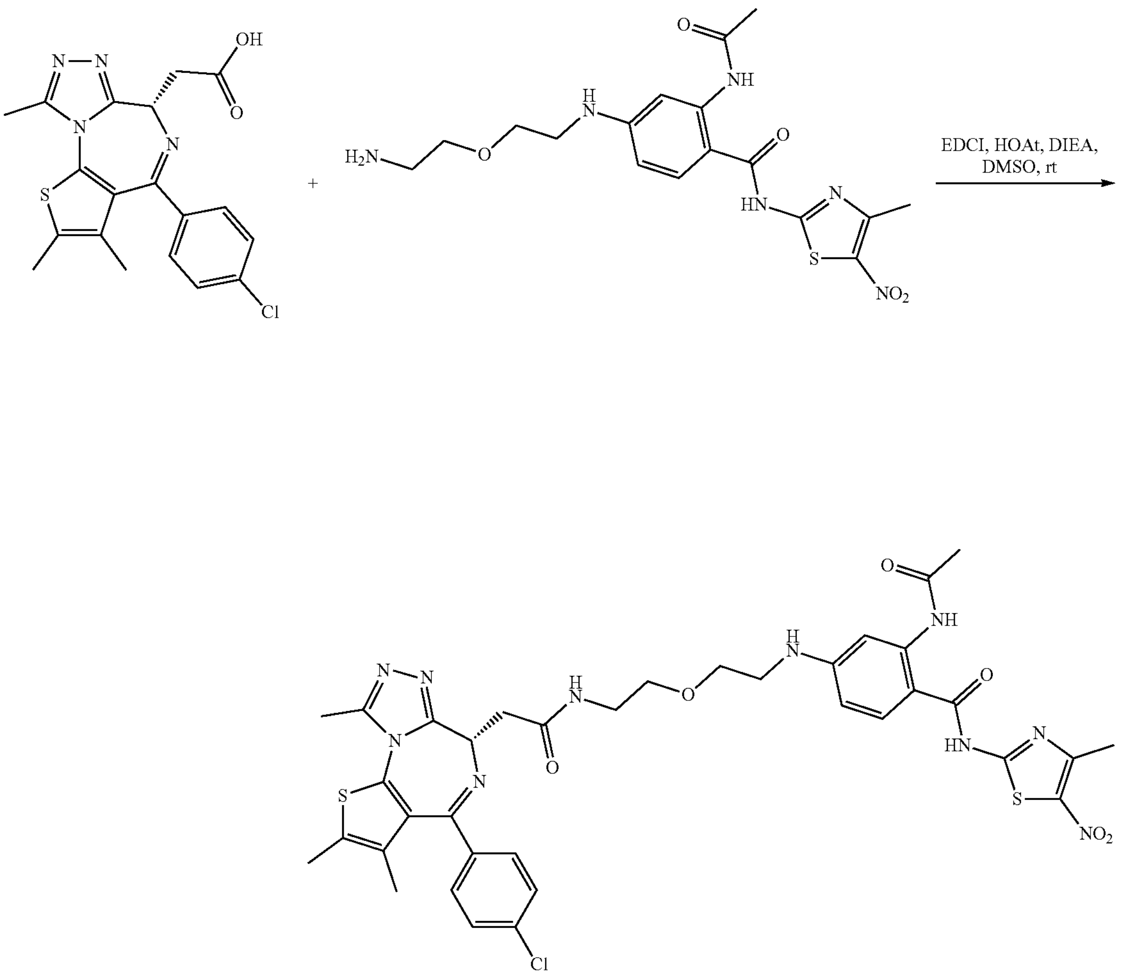

D-32 was synthesized following the standard procedure for preparing D-26 (4.87 mg, 48.4% yield). MS (ESI) m/z: 805.6 $[M+H]^+$.

Example 165. (S)-2-Acetamido-4-((2-(2-(2-(2-(4-(4-chlorophenyl)-2,3,9-trimethyl-6H-thieno[3,2-f][1,2,4]triazolo[4,3-a][1,4]diazepin-6-yl)acetamido)ethoxy)ethoxy)ethyl)amino)-N-(4-methyl-5-nitrothiazol-2-yl)benzamide (D-33)

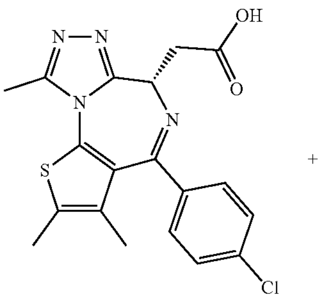

-continued
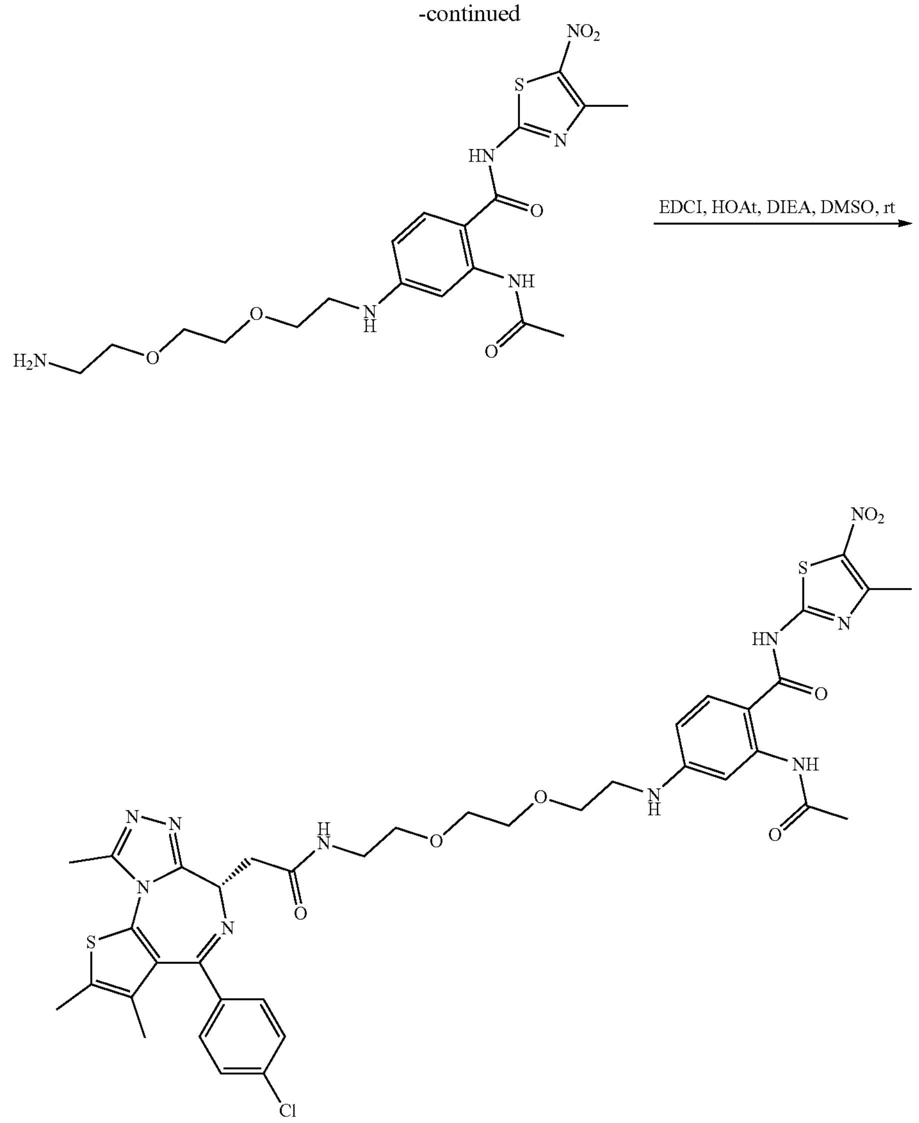
D-33 was synthesized following the standard procedure for preparing D-26 (7.87 mg, 74.1% yield). MS (EST) m/z: 849.6 $[M+H]^+$.
Example 166. (S)-2-Acetamido-4-((1-(4-(4-chlorophenyl)-2,3,9-trimethyl-6H-thieno[3,2-f][1,2,4]triazolo[4,3-a][1,4]diazepin-6-yl)-2-oxo-6,9,12-trioxa-3-azatetradecan-14-yl)amino)-N-(4-methyl-5-nitrothiazol-2-yl)benzamide (D-34)
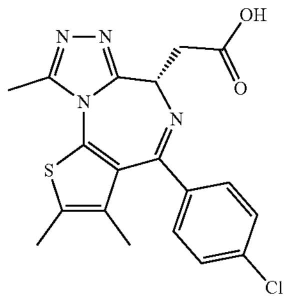
+

-continued
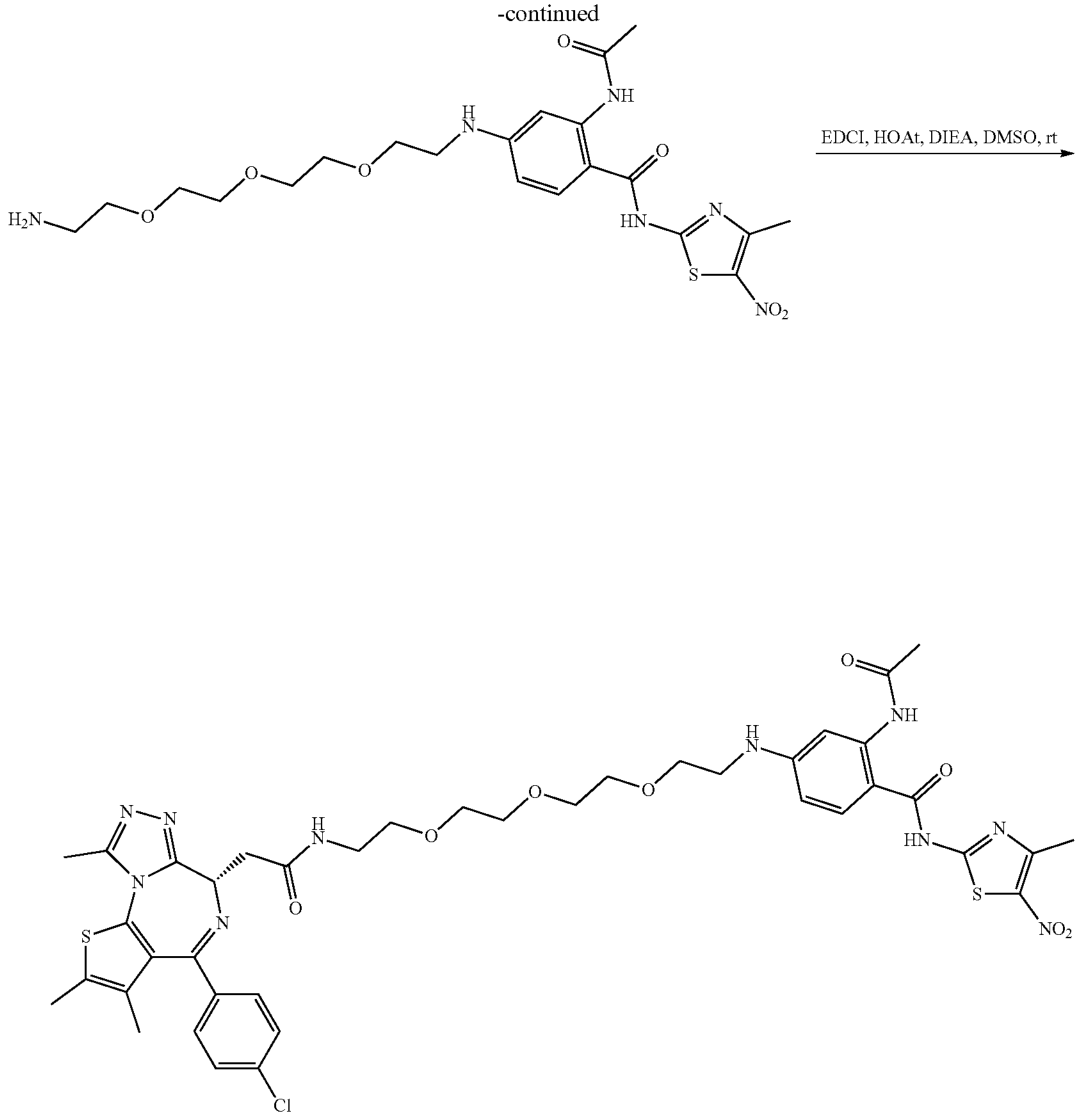
D-34 was synthesized following the standard procedure for preparing D-26 (3.44 mg, 30.8% yield). MS (EST) m/z: 893.7 [M+H]$^+$.
Example 167. (S)-2-Acetamido-4-((1-(4-(4-chlorophenyl)-2,3,9-trimethyl-6H-thieno[3,2-f][1,2,4]triazolo[4,3-a][1,4]diazepin-6-yl)-2-oxo-6,9,12,15-tetraoxa-3-azaheptadecan-17-yl)amino)-N-(4-methyl-5-nitrothiazol-2-yl)benzamide (D-35)
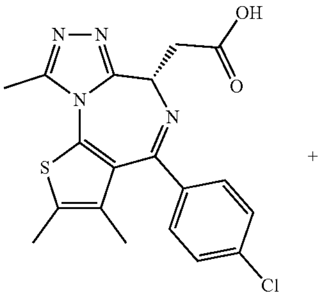

-continued
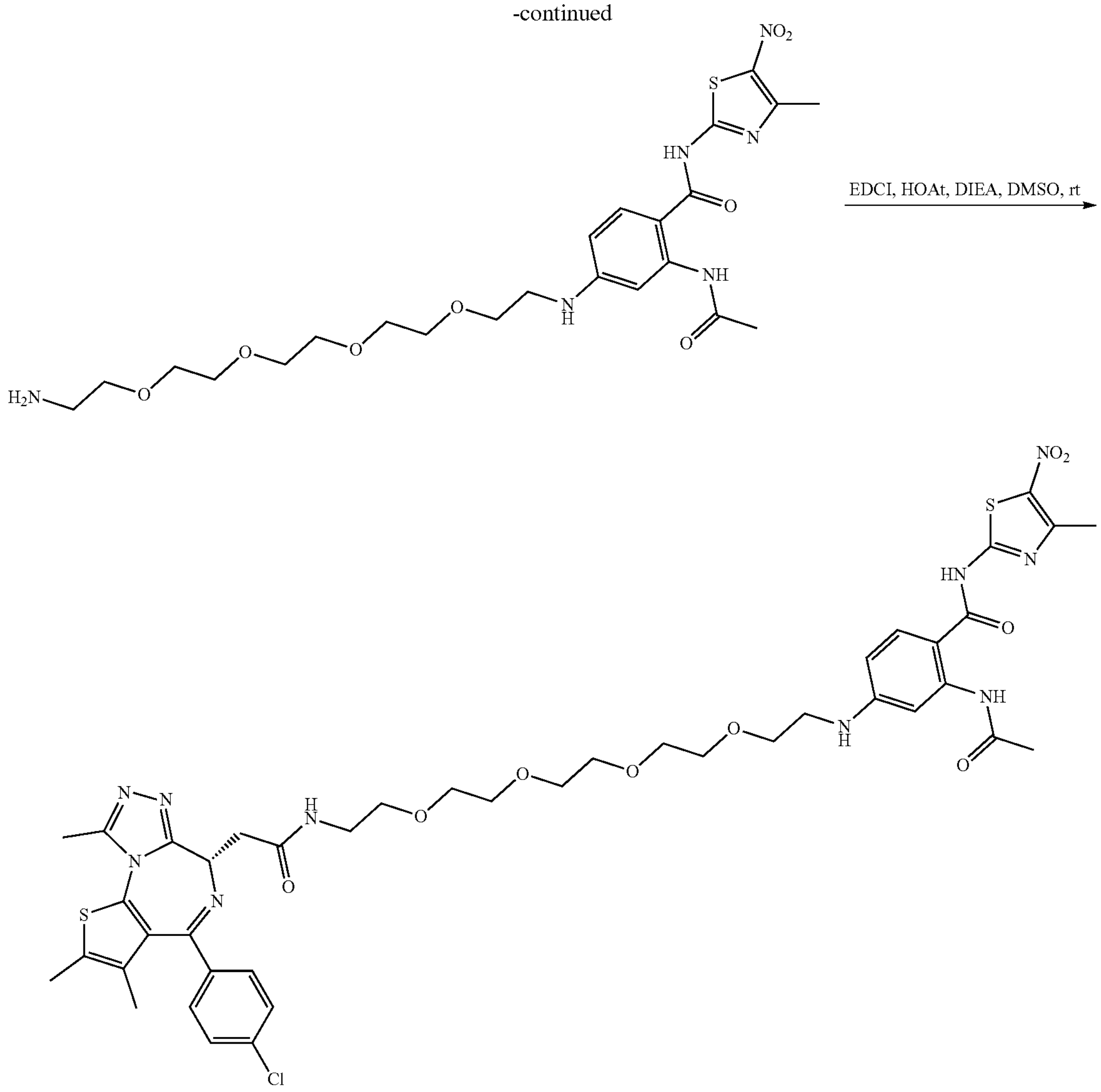
D-35 was synthesized following the standard procedure for preparing D-26 (6.98 mg, 59.5% yield). MS (EST) m/z: 937.6 [M+H]$^+$.
Example 168. (S)-2-Acetamido-4-((1-(4-(4-chlorophenyl)-2,3,9-trimethyl-6H-thieno[3,2-f][1,2,4]triazolo[4,3-a][1,4]diazepin-6-yl)-2-oxo-6,9,12,15,18-pentaoxa-3-azaicosan-20-yl)amino)-N-(4-methyl-5-nitrothiazol-2-yl)benzamide (D-36)
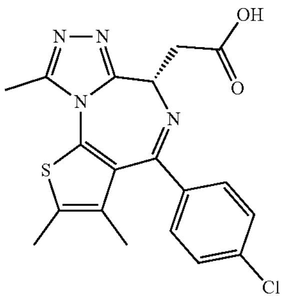
+

-continued
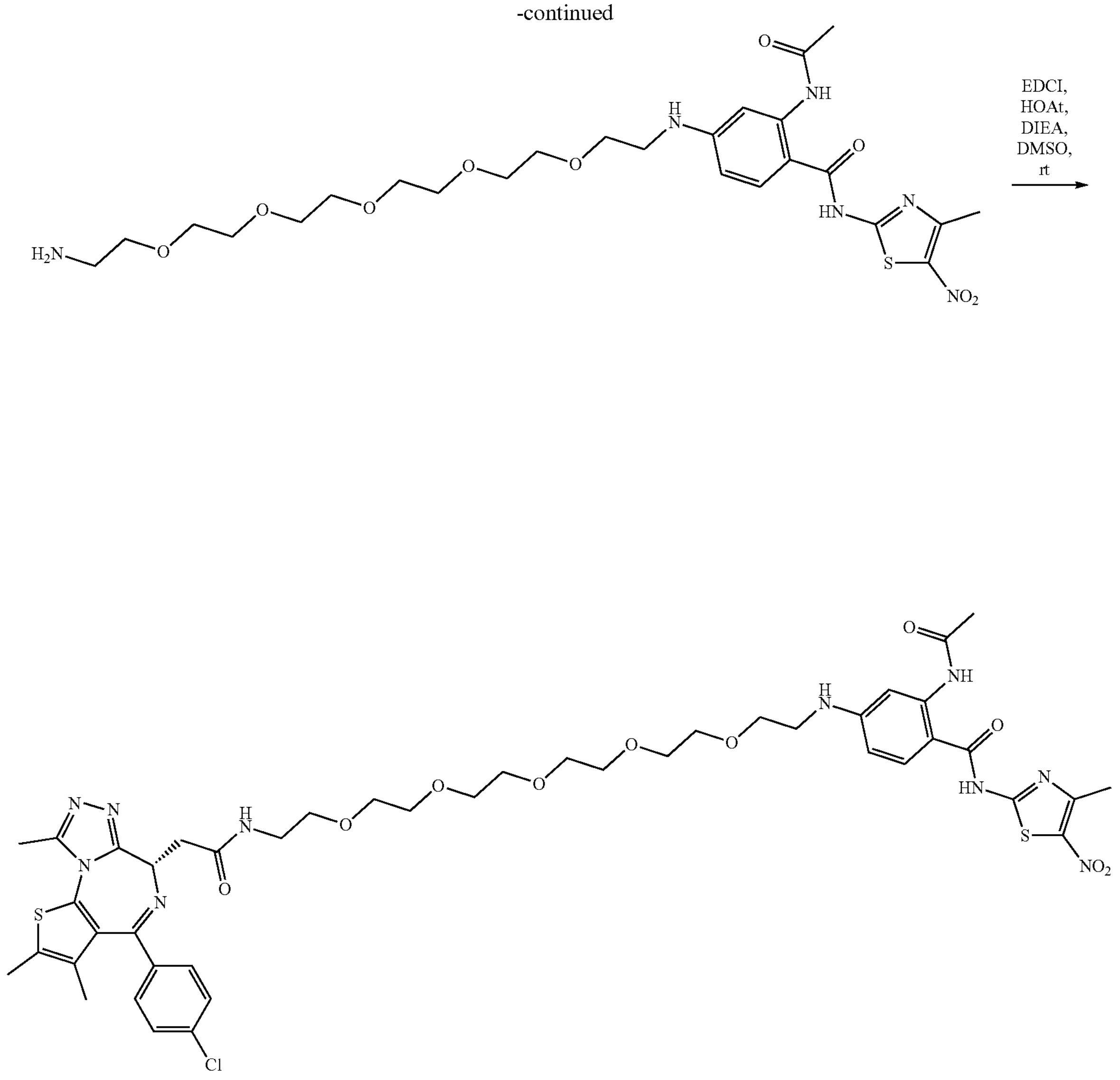
D-36 was synthesized following the standard procedure for preparing D-26 (5.96 mg, 48.6% yield). MS (EST) m/z: 981.8 $[M+H]^+$.
Example 169. (S)-2-Acetamido-4-((1-(4-(4-chlorophenyl)-2,3,9-trimethyl-6H-thieno[3,2-f][1,2,4]triazolo[4,3-a][1,4]diazepin-6-yl)-2-oxo-6,9,12,15,18,21-hexaoxa-3-azatricosan-23-yl)amino)-N-(4-methyl-5-nitrothiazol-2-yl)benzamide (D-37)
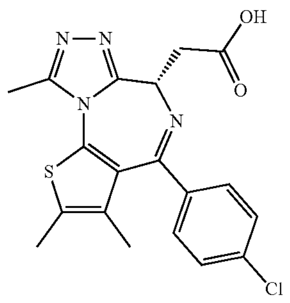
+

-continued
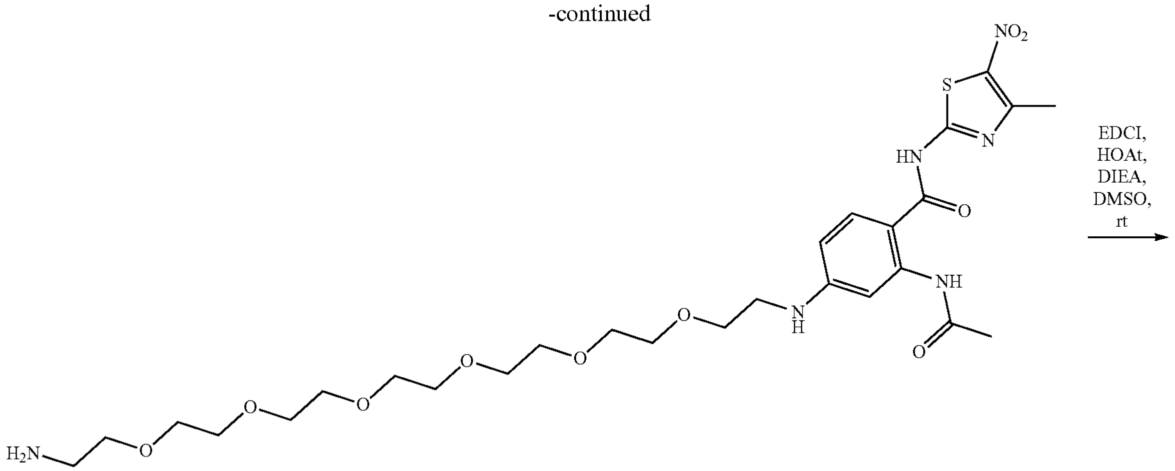
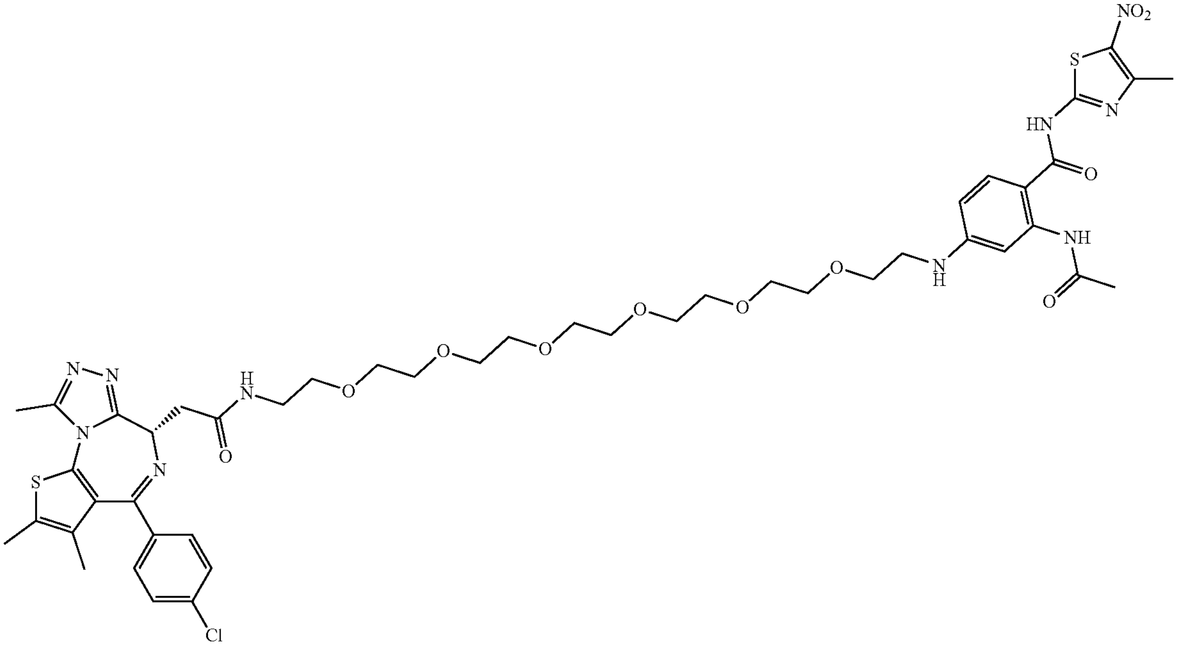
D-33 was synthesized following the standard procedure for preparing D-26 (7.29 mg, 56.8% yield). MS (EST) m/z: 1025.8 $[M+H]^+$.
Example 170. 2-Acetamido-4-((4-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)butyl)amino)-N-(4-methyl-5-nitrothiazol-2-yl)benzamide (D-2)
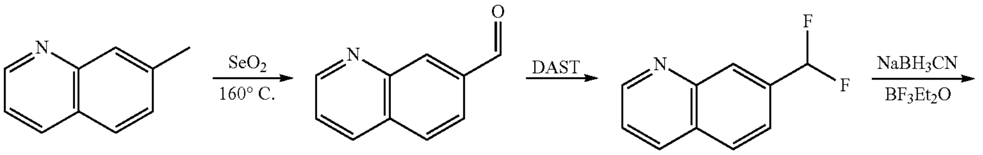

-continued
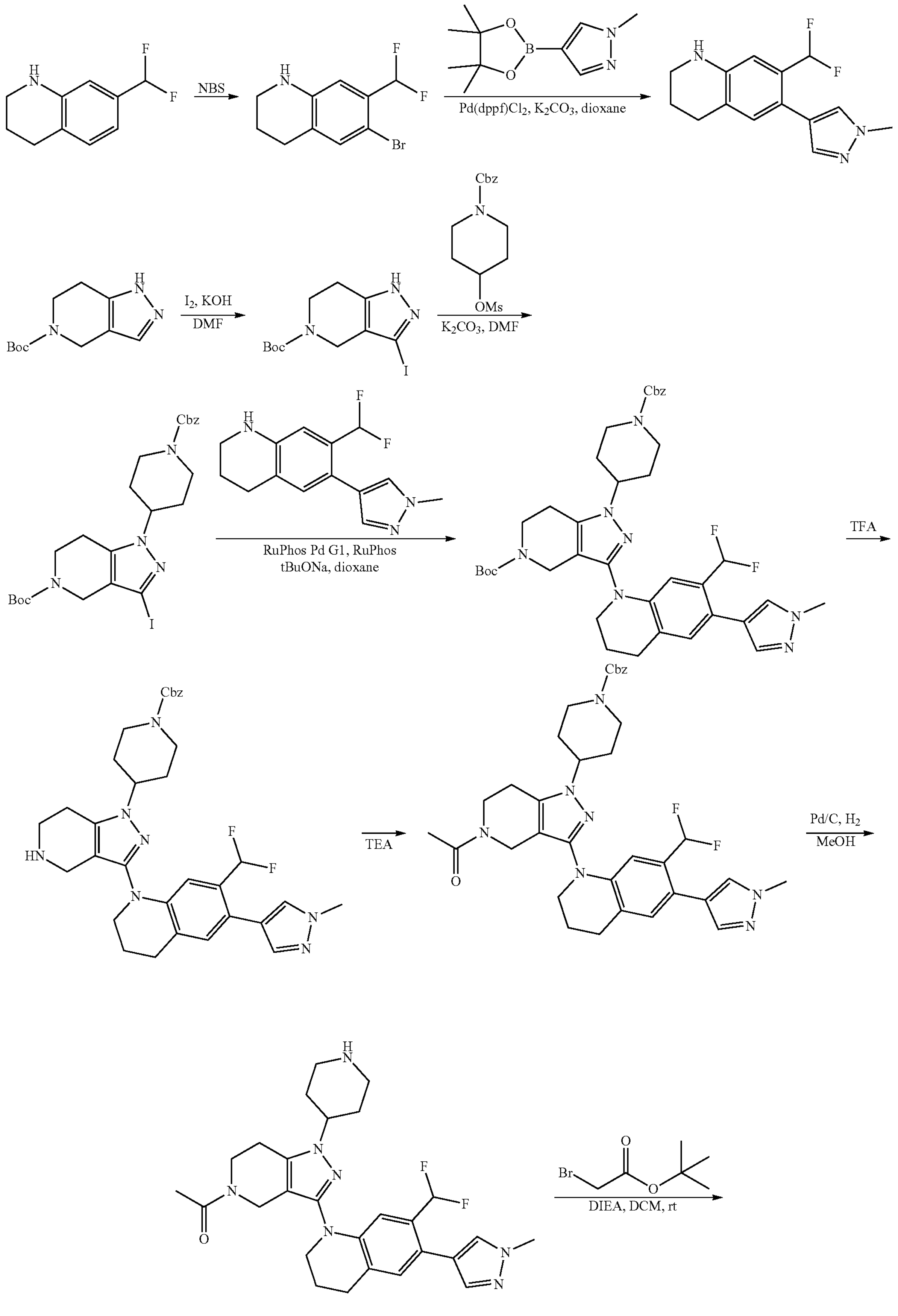

-continued
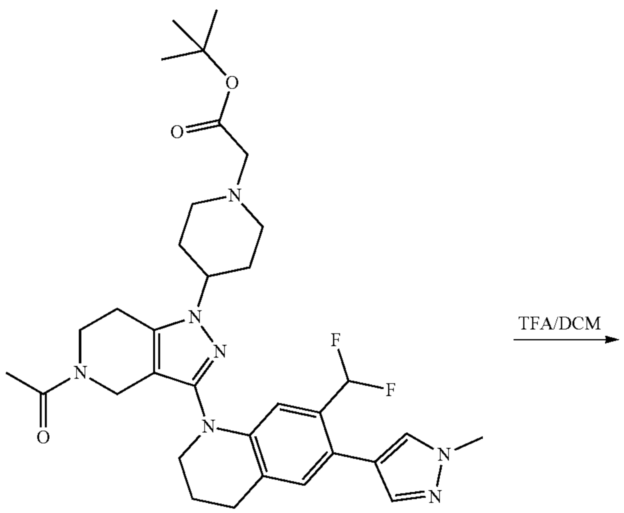
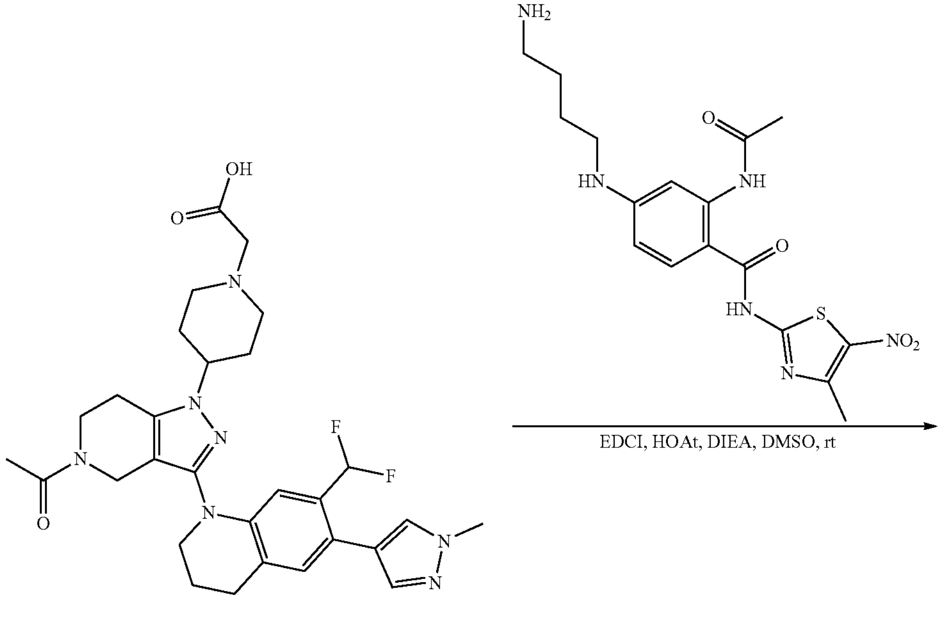

-continued

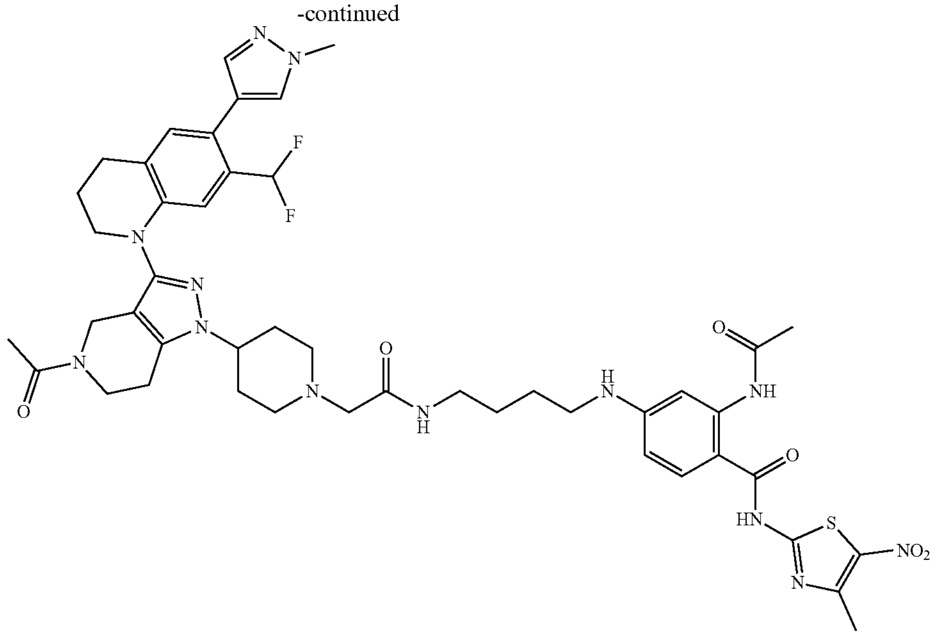

Step 1. Synthesis of quinoline-7-carbaldehyde

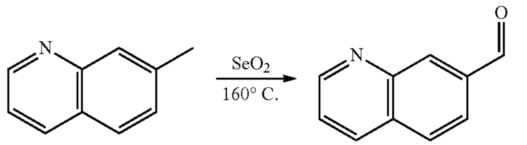

To a solution of 7-methylquinoline (235.0 g, 1.643 mol) at 160° C. was added $SeO_2$ (220 g, 1.97 mol) portionwise over 25 min. The mixture was stirred at 160° C. for 8 h. After the reaction was cooled to rt. DCM (2000 mL) was added and the mixture was filtered through a pad of Celite. The filtrate was concentrated and the resulting crude residue was purified by silica gel column chromatography (petroleum ether:EtOAc=10:1) to give quinoline-7-carbaldehyde (100 g, 38% yield) as yellow solid.

Step 2. Synthesis of 7-(difluoromethyl)quinoline

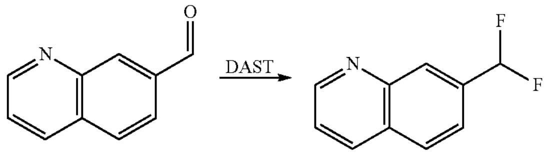

To a cooled (0° C.) solution of quinoline-7-carbaldehyde (35.0 g, 223 mmol) in DCM (400 mL) was added diethylaminosulfurtrifluoride (162.0 g, 1150 mmol) dropwise over 30 min. The mixture was stirred at rt for 16 h, before it was poured into sat. aq $NaHCO_3$ (2 L) at 0° C. and extracted with DCM (2×400 mL). The combined organic layers were dried over anhydrous $Na_2SO_4$, filtered, and concentrated in vacuo. The crude residue was purified by silica gel column chromatography (petroleum ether:EtOAc=5:1) to give 7-(difluoromethyl)quinolone (26.0 g, 65% yield) as yellow oil.

Step 3. Synthesis of 7-(difluoromethyl)-1,2,3,4-tetrahydroquinoline

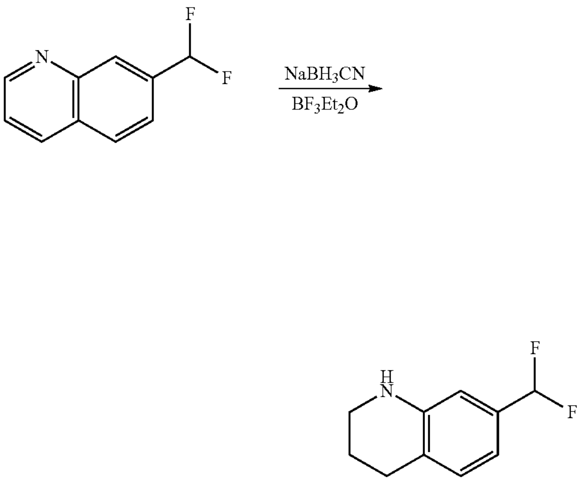

To a cooled (0° C.) solution of 7-(difluoromethyl)quinolone (26.0 g, 72.6 mmol) and $NaBH_3CN$ (46.1 g, 726 mmol) in MeOH (300 mL) was added boron trifluoride diethyl etherate (41.2, 290 mmol) dropwise over 20 min. The mixture was heated to 90° C. for 24 h. After the reaction was cooled to rt, the mixture was poured into sat. aq. $NaHCO_3$ (2 L) at 0° C. and extracted with DCM (2×500 mL). The combined organic layers were dried over $Na_2SO_4$, filtered, and concentrated in vacuo. The crude residue was purified by silica gel column chromatography (petroleum ether:EtOAc=20:1) to give 7-(difluoromethyl)-1,2,3,4-tetrahydroquinoline (13.0 g, 49% yield) as brown oil.

Step 4. Synthesis of 6-bromo-7-(difluoromethyl)-1,2,3,4-tetrahydroquinoline

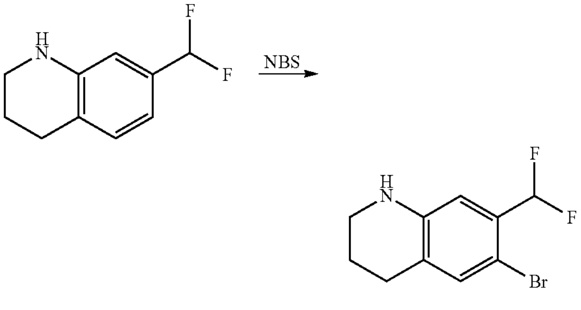

To a solution of 7-(difluoromethyl)-1,2,3,4-tetrahydroquinoline (29.0 g, 158.5 mmol) in DCM (600 mL) at 0° C. was added N-bromosuccinimide (6.90 g, 38.3 mmol) portion-wise over 20 min. The mixture was stirred at rt for 16 h, before it was poured into water (100 mL) and extracted with DCM (2×400 mL). The combined organic layers were dried over $Na_2SO_4$, filtered, and concentrated in vacuo. The crude residue was purified by silica gel column chromatography (petroleum ether:EtOAc=300:1) to give 6-bromo-7-(difluoromethyl)-1,2,3,4-tetrahydroquinoline (22.0 g, 52.8% yield) as white solid. $^1$HNMR (400 MHz, $CDCl_3$) δ 7.12 (s, 1H), 6.77 (t, J=55.2 Hz, 1H), 6.77 (s, 1H), 4.01 (s, 1H), 3.30 (t, J=6.4 Hz, 2H), 2.74 (t, J=6.0 Hz, 2H), 1.94-1.88 (m, 2H).

Step 5. Synthesis of 7-(difluoromethyl)-6-(1-methyl-1H-pyrazol-4-yl)-1,2,3,4-tetrahydroquinoline

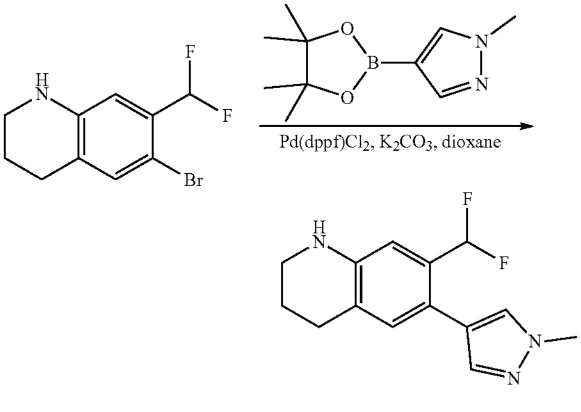

To a solution of 6-bromo-7-(difluoromethyl)-1,2,3,4-tetrahydroquinoline (2 g, 7.66 mmol) and 1-methyl-4-(4,4,5,5-tetramethyl-1,3,2-dioxaborolan-2-yl)-1H-pyrazole (1.59 g, 7.66 mmol) in 1,4-dixoane (50 mL) were added Pd(dppf)$Cl_2$ (1.6 g, 2.3 mmol), $K_2CO_3$ (2.11 g, 15.32 mmol). The reaction mixture was heated to 95° C. overnight, before it was diluted with EtOAc, and washed with water and brine. The organic layer was concentrated in vacuo and the residue was purified by silica gel column (petroleum ether: EtOAc=5:1) to afforded 7-(difluoromethyl)-6-(1-methyl-1H-pyrazol-4-yl)-1,2,3,4-tetrahydroquinoline (1.4 g, 69% yield) as an white solid. MS (ESI) m/z: 264.4 $[M+H]^+$.

Step 6. Synthesis of tert-butyl 3-iodo-1,4,6,7-tetrahydro-5H-pyrazolo[4,3-c]pyridine-5-carboxylate

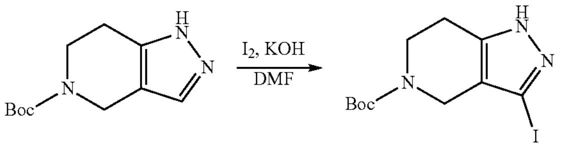

To a solution of tert-butyl 1,4,6,7-tetrahydro-5H-pyrazolo[4,3-c]pyridine-5-carboxylate (10 g, 44.84 mmol) in DMF (100 mL) were added $I_2$ (22.76 g, 89.68 mmol) and KOH (10.04 g, 179.36 mmol). The resulting mixture was stirred at 50° C. overnight. The reaction was quenched with aq. $Na_2SO_3$ and extracted with EtOAc. The organic layer was dried over $Na_2SO_4$, filtered and concentrated. The resulting residue was purified by silica gel column chromatography (petroleum ether:EtOAc=3:1) to give desired product (8.0 g, 51% yield) as a colorless oil. MS (ESI) m/z: 350.2 $[M+H]^+$.

Step 7. Synthesis of tert-butyl 1-(1-((benzyloxy)carbonyl)piperidin-4-yl)-3-iodo-1,4,6,7-tetrahydro-5H-pyrazolo[4,3-c]pyridine-5-carboxylate

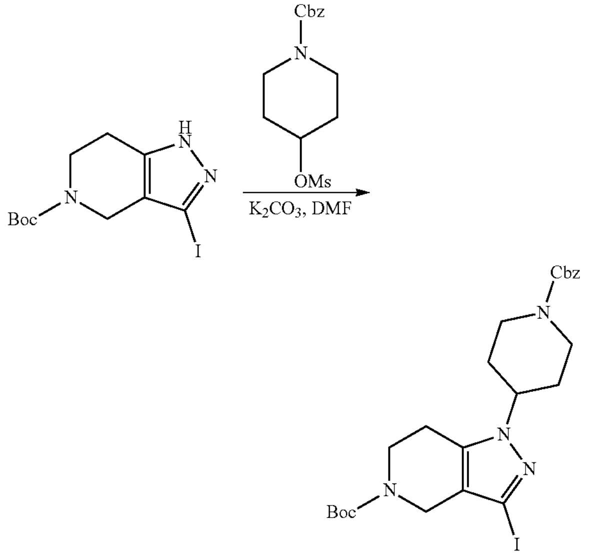

To a solution of tert-butyl 3-iodo-1,4,6,7-tetrahydro-5H-pyrazolo[4,3-c]pyridine-5-carboxylate (6 g, 17.19 mmol) in DMF (50 mL) were added benzyl 4-((methylsulfonyl)oxy)piperidine-1-carboxylate (8.07 g, 25.79 mmol) and $K_2CO_3$ (4.74 g, 34.38 mmol). The resulting mixture was stirred at 100° C. overnight. After the reaction was cooled to rt, the mixture was diluted with water, extracted with EtOAc. The combined organic phase was washed with brine, dried over $Na_2SO_4$, filtered and concentrated. The resulting residue was purified by silica gel column chromatography (petroleum ether:EtOAc=1:1) to give desired product (4.0 g, 41% yield) as white solid. MS (ESI) m/z: 567.4 $[M+H]^+$.

Step 8. Synthesis of tert-butyl 1-(1-((benzyloxy)carbonyl)piperidin-4-yl)-3-(7-(difluoromethyl)-6-(1-methyl-1H-pyrazol-4-yl)-3,4-dihydroquinolin-1(2H)-yl)-1,4,6,7-tetrahydro-5H-pyrazolo[4,3-c]pyridine-5-carboxylate

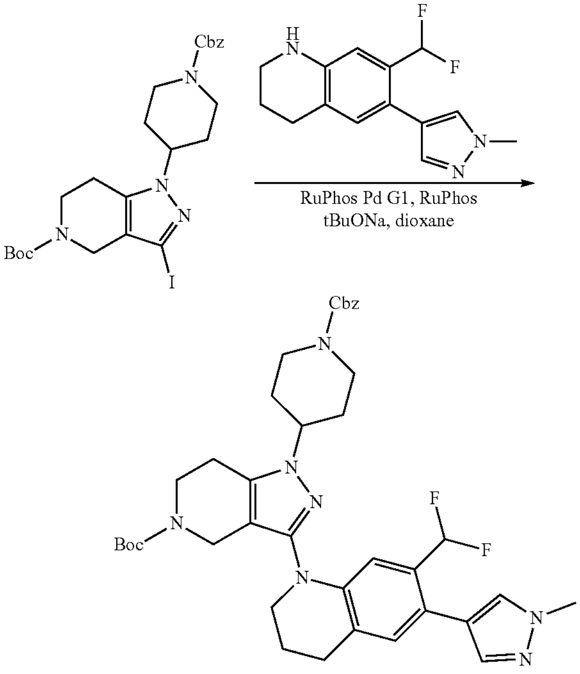

To a solution of tert-butyl 1-(1-((benzyloxy)carbonyl)piperidin-4-yl)-3-iodo-1,4,6,7-tetrahydro-5H-pyrazolo[4,3-c]pyridine-5-carboxylate (132 mg, 0.233 mmol) and 7-(difluoromethyl)-6-(1-methyl-1H-pyrazol-4-yl)-1,2,3,4-tetrahydroquinoline (74 mg, 0.280 mmol) in dioxane (3 mL) were added RuPhos Pd GI (22.8 mg, 0.028 mmol), RuPhos (13.0 mg, 0.028 mmol) and $^{t}$BuONa (78.3 mg, 0.816 mmol). The resulting mixture was stirred at reflux overnight. The reaction mixture was purified by reverse phase flash chromatography to give desired product (80 mg, 49% yield) as white solid. MS (ESI) m/z: 703.1 [M+H]$^+$.

Step 9. Synthesis of benzyl 4-(3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidine-1-carboxylate

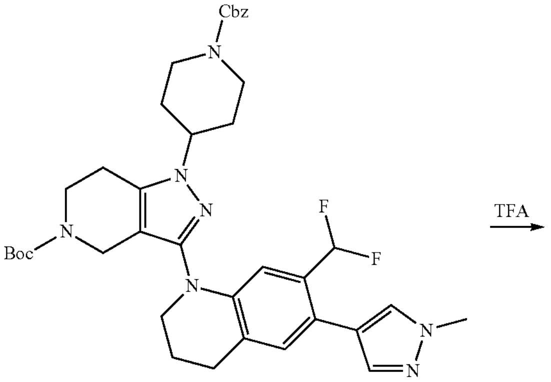

-continued

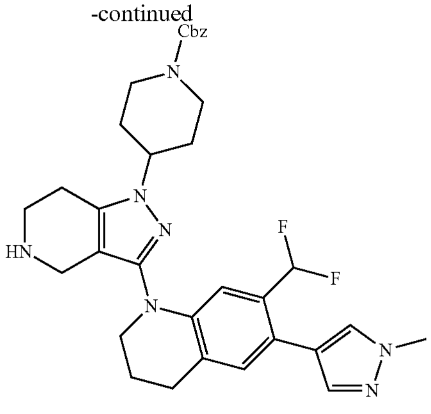

The mixture of tert-butyl 1-(1-((benzyloxy)carbonyl)piperidin-4-yl)-3-(7-(difluoromethyl)-6-(1-methyl-1H-pyrazol-4-yl)-3,4-dihydroquinolin-1(2H)-yl)-1,4,6,7-tetrahydro-5H-pyrazolo[4,3-c]pyridine-5-carboxylate (189 mg, 0.27 mmol) in DCM and TFA (10 ml, v/v=1:1) was stirred at it for 3 h, before it was concentrated. The resulting residue was used in the next step without further purification.

Step 10. Synthesis of benzyl 4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidine-1-carboxylate

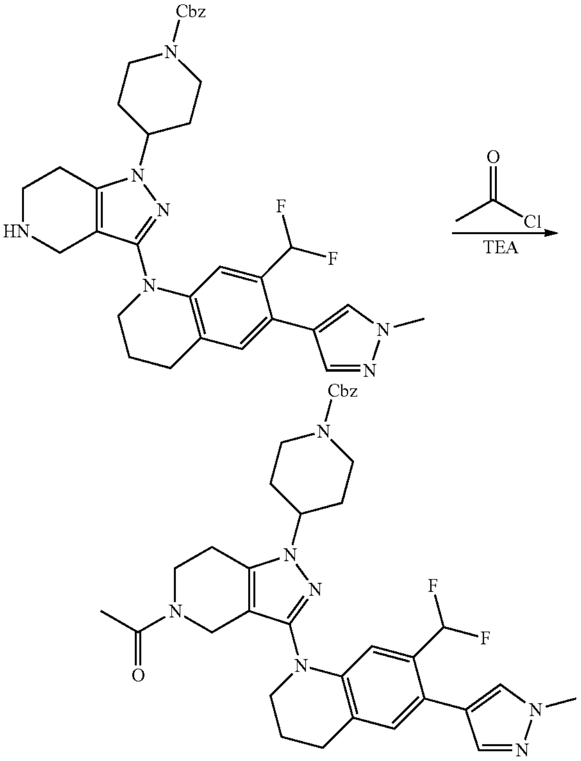

To a mixture of benzyl 4-(3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidine-1-carboxylate (77 mg, 0.13 mmol) and TEA (39 mg, 0.38 mmol) in DCM (3 mL) was added a solution of acetyl chloride (15 mg, 0.19 mmol) in DCM (1 mL) dropwise at 0° C. The reaction mixture was stirred at 0° C. for 1.5 h, before it was concentrated. The residue was purified by prep-HPLC to give the desired product (51 mg, yield 62% yield). MS (ESI) m/z: 645.2 [M+H]+.

Step 11. Synthesis of 1-(3-(7-(difluoromethyl)-6-(1-methyl-1H-pyrazol-4-yl)-3,4-dihydroquinolin-1(2H)-yl)-1-(piperidin-4-yl)-1,4,6,7-tetrahydro-5H-pyrazolo[4,3-c]pyridin-5-yl)ethan-1-one

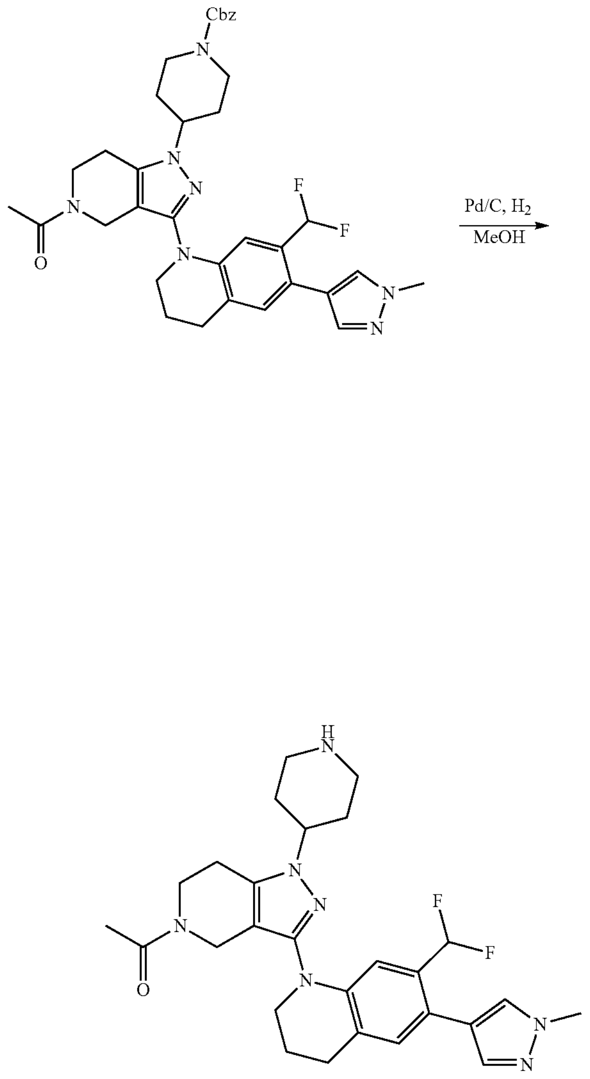

A mixture of benzyl 4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidine-1-carboxylate (2.5 g, 3.88 mmol), Pd/C (231 mg) and TFA (one drop) in MeOH (24 mL) was stirred at 30° C. for 4 h, before the reaction mixture was filtered. After the filtrate was concentrated, the resulting residue was diluted with aq. $NaHCO_3$ and extracted with EtOAc. The combined organic layers were dried over $Na_2SO_4$, filtered and concentrated to give the desired product (1.8 g, 91% yield). MS (ESI) m/z: 511.0 [M+H]+.

Step 12. Synthesis of tert-butyl 2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetate

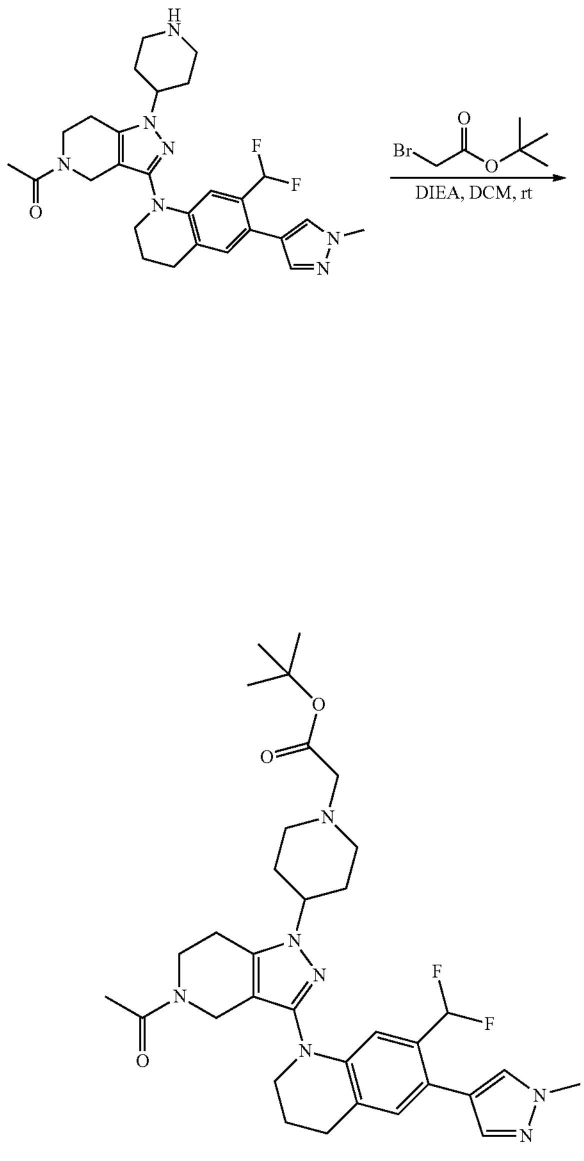

To a solution of 1-(3-(7-(difluoromethyl)-6-(1-methyl-1H-pyrazol-4-yl)-3,4-dihydroquinolin-1(2H)-yl)-1-(piperidin-4-yl)-1,4,6,7-tetrahydro-5H-pyrazolo[4,3-c]pyridin-5-yl)ethan-1-one (150 mg, 0.294 mmol), DIEA (190 mg, 1.47 mmol) in DCM (5 mL) was added tert-butyl 2-bromoacetate (68 mg, 0.352 mmol) at 0° C. Then the reaction solution was stirred at rt for 1 h, before it was diluted with DCM (50 mL), washed with brine, dried over $Na_2SO_4$, filtered, and concentrated. The resulting residue was purified by silica gel column (DCM:MeOH=1:0 to 10:1) to give tert-butyl 2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetate (200 mg, 99% yield) as white solid. MS (ESI) m/z: 624.5 [M+H]+.

Step 13. Synthesis of 2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetic acid

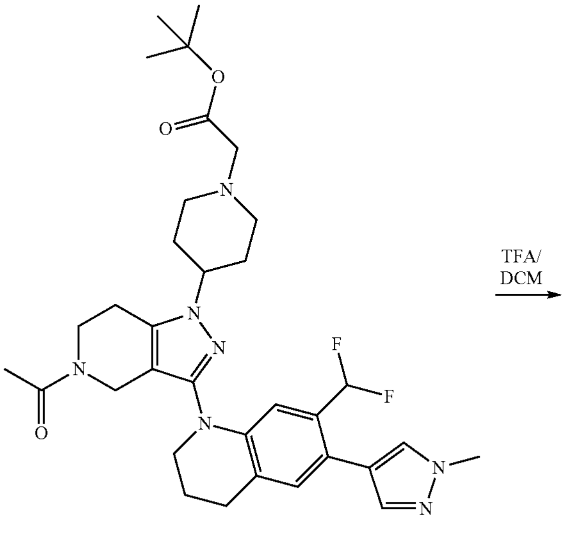

-continued

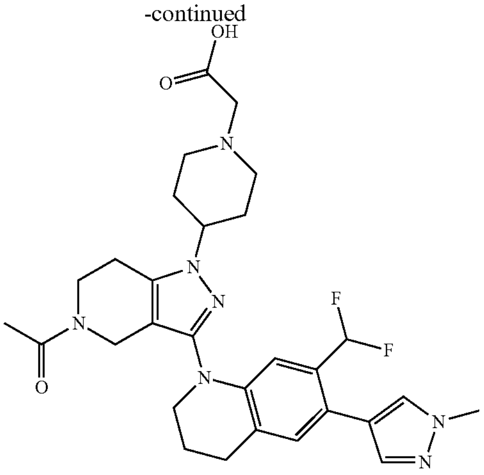

A solution of tert-butyl 2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetate (200 mg, 0.321 mmol) in TFA (2 ml) and DCM (2 ml) was stirred at rt overnight. The reaction solution was concentrated and purified with C18 flash column to give 2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetic acid (160 mg, 87.9% yield) as white solid. MS (ESI) m/z: 568.6 [M+H]+.

Step 14. Synthesis of 2-acetamido-4-((4-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)butyl)amino)-N-(4-methyl-5-nitrothiazol-2-yl)benzamide

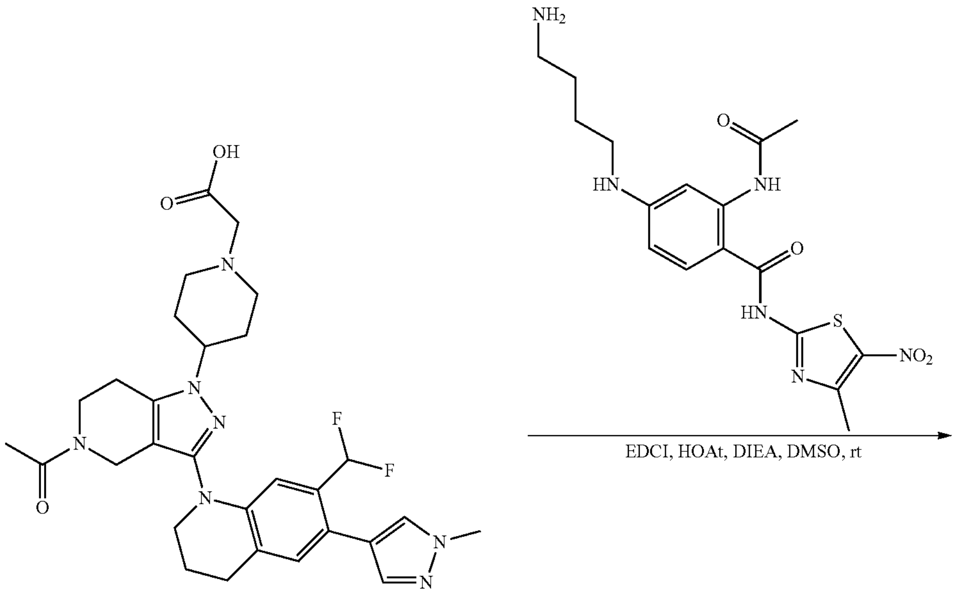

-continued

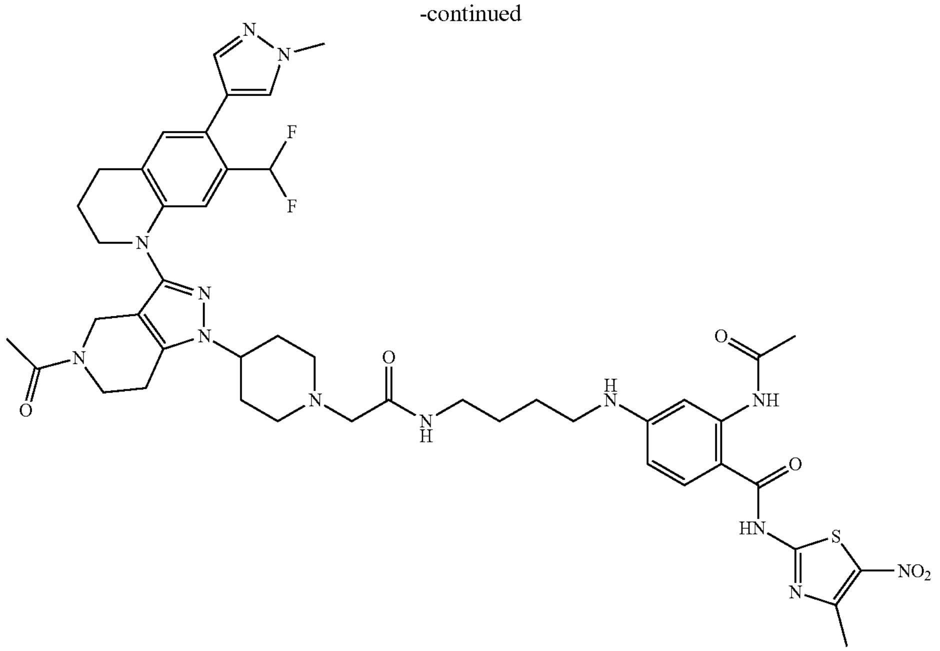

A solution of 2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetic acid (5 mg, 0.008 mmol), HOAt (6 mg, 0.044 mmol), EDCI (7.64 mg, 0.044 mmol), DIEA (10 mg, 0.08 mmol) and 2-acetamido-4-((4-aminobutyl)amino)-N-(4-methyl-5-nitrothiazol-2-yl)benzamide (3 mg, 0.008 mmol) in DMSO (1 ml) was stirred at rt overnight. Then the reaction solution was purified by C18 flash column to give desired product (3 mg, 40.2% yield) as yellow solid. MS (ESI) m/z: 956.8 $[M+H]^+$ Example 171. 2-Acetamido-4-((6-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)hexyl)amino)-N-(4-methyl-5-nitrothiazol-2-yl)benzamide (D-3)

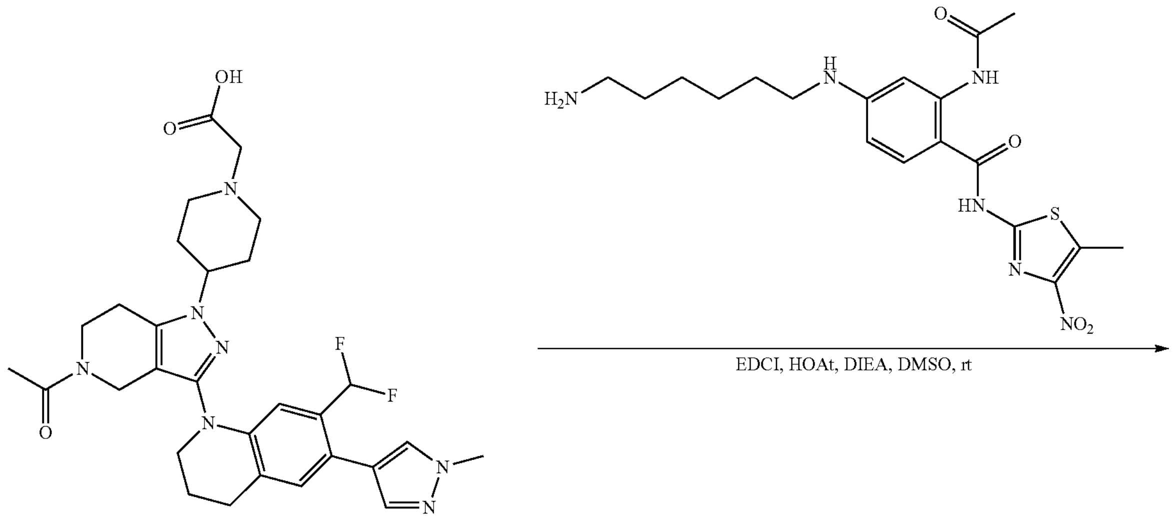

-continued
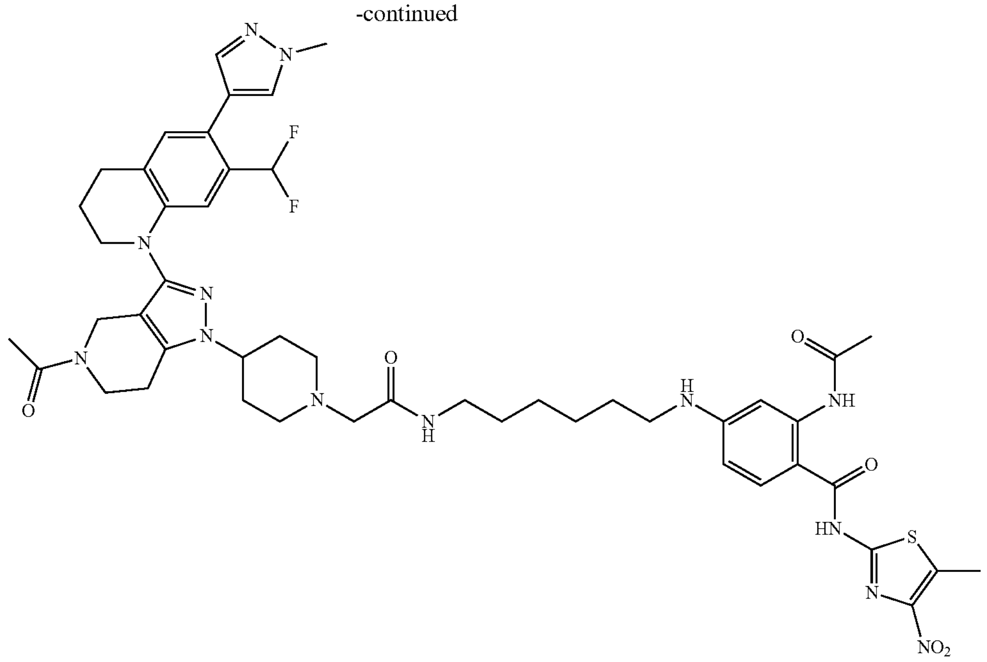
D-3 was synthesized following the standard procedure for preparing D-2 (3 mg, 38% yield). MS (ESI) m/z: 984.8 $[M+H]^+$.
Example 172. 2-Acetamido-4-((10-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)decyl)amino)-N-(4-methyl-5-nitrothiazol-2-yl)benzamide (D-6)

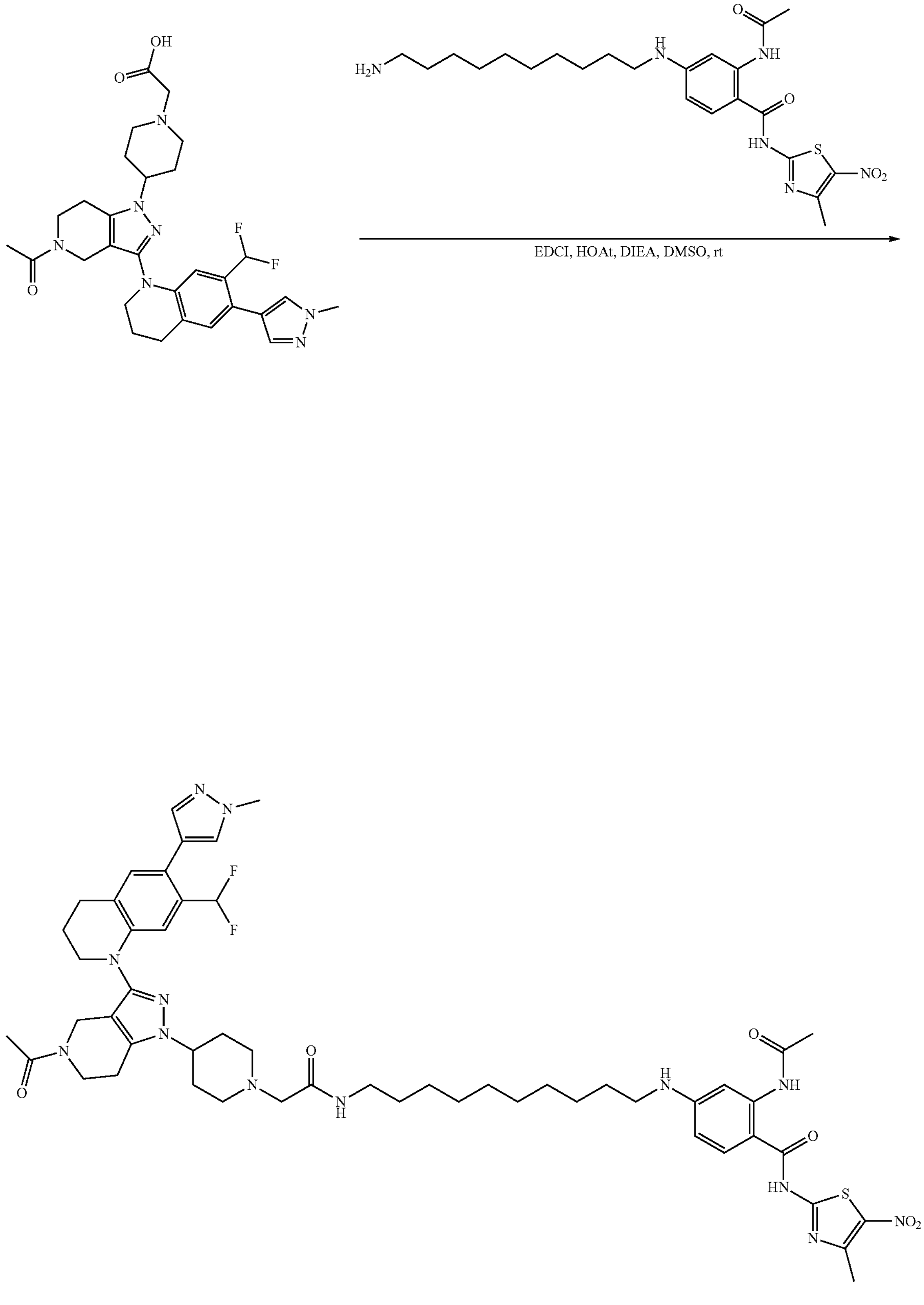
D-6 was synthesized following the standard procedure for preparing D-2 (3 mg, 36% yield). MS (ESI) m/z: 1041.0 $[M+H]^+$.

Example 173. 2-Acetamido-4-((2-(2-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl) acetamido)ethoxy)ethyl)amino)-N-(4-methyl-5-nitrothiazol-2-yl)benzamide (D-7)
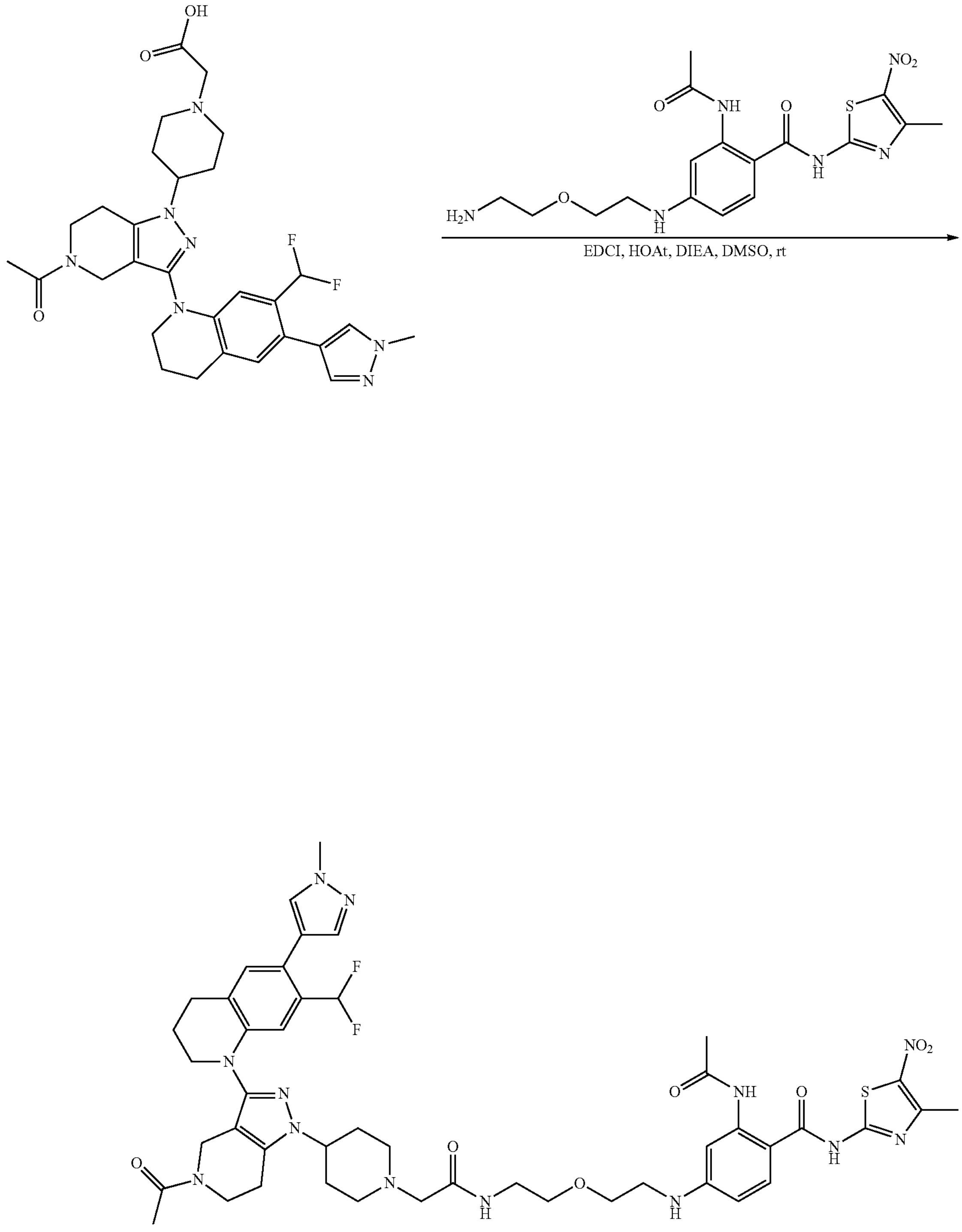
D-7 was synthesized following the standard procedure for preparing D-2 (3 mg, 39% yield). MS (ESI) m/z: 972.8 $[M+H]^+$ Example 174. 2-Acetamido-4-((2-(2-(2-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)ethoxy)ethoxy)ethyl)amino)-N-(4-methyl-5-nitrothiazol-2-yl)benzamide (D-8)
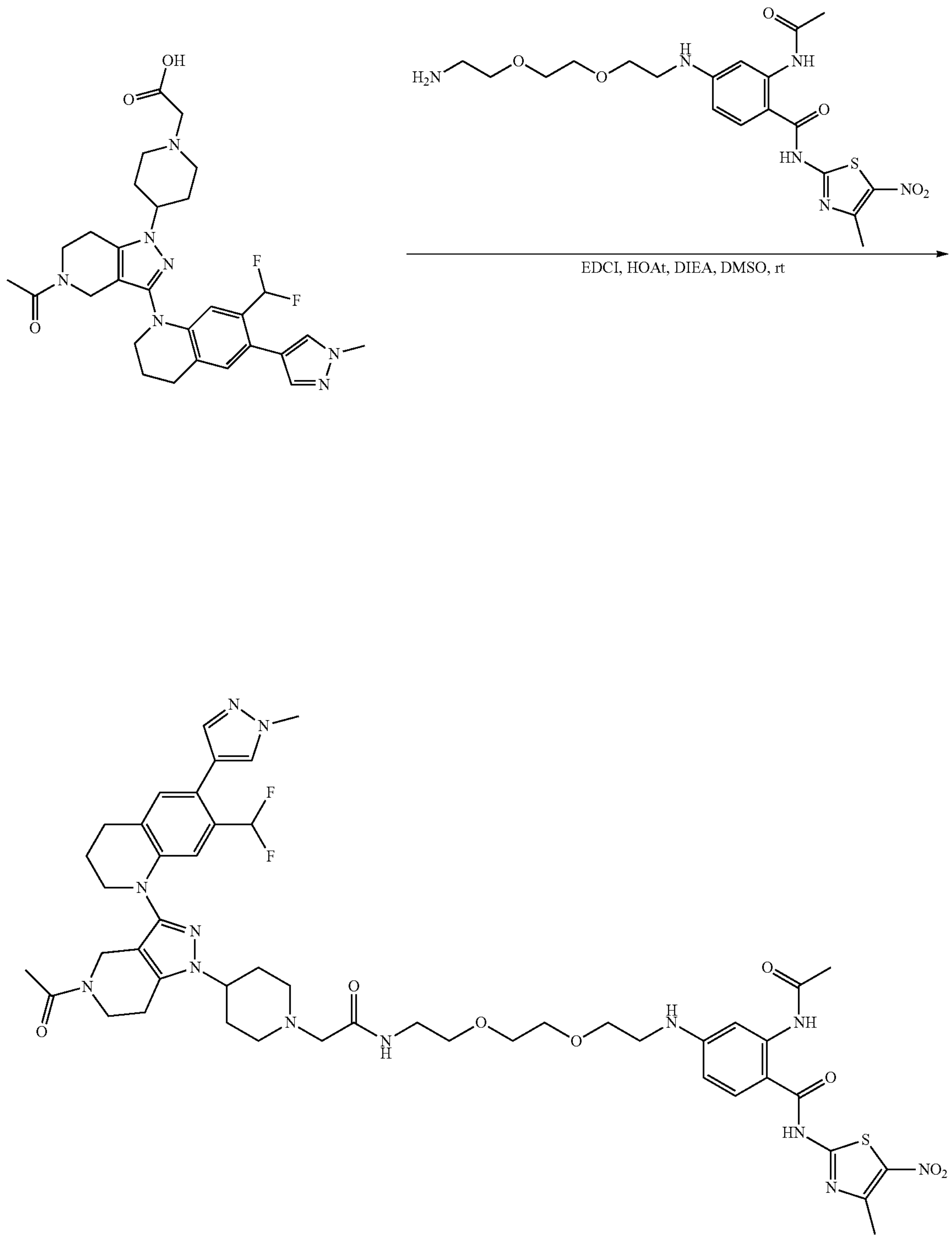
D-8 was synthesized following the standard procedure for preparing D-2 (3 mg, 37% yield). MS (ESI) m/z: 1012.9 $[M+H]^+$.

Example 175. 2-Acetamido-4-((1-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)-2-oxo-6,9,12-trioxa-3-azatetradecan-14-yl)amino)-N-(4-methyl-5-nitrothiazol-2-yl)benzamide (D-9)
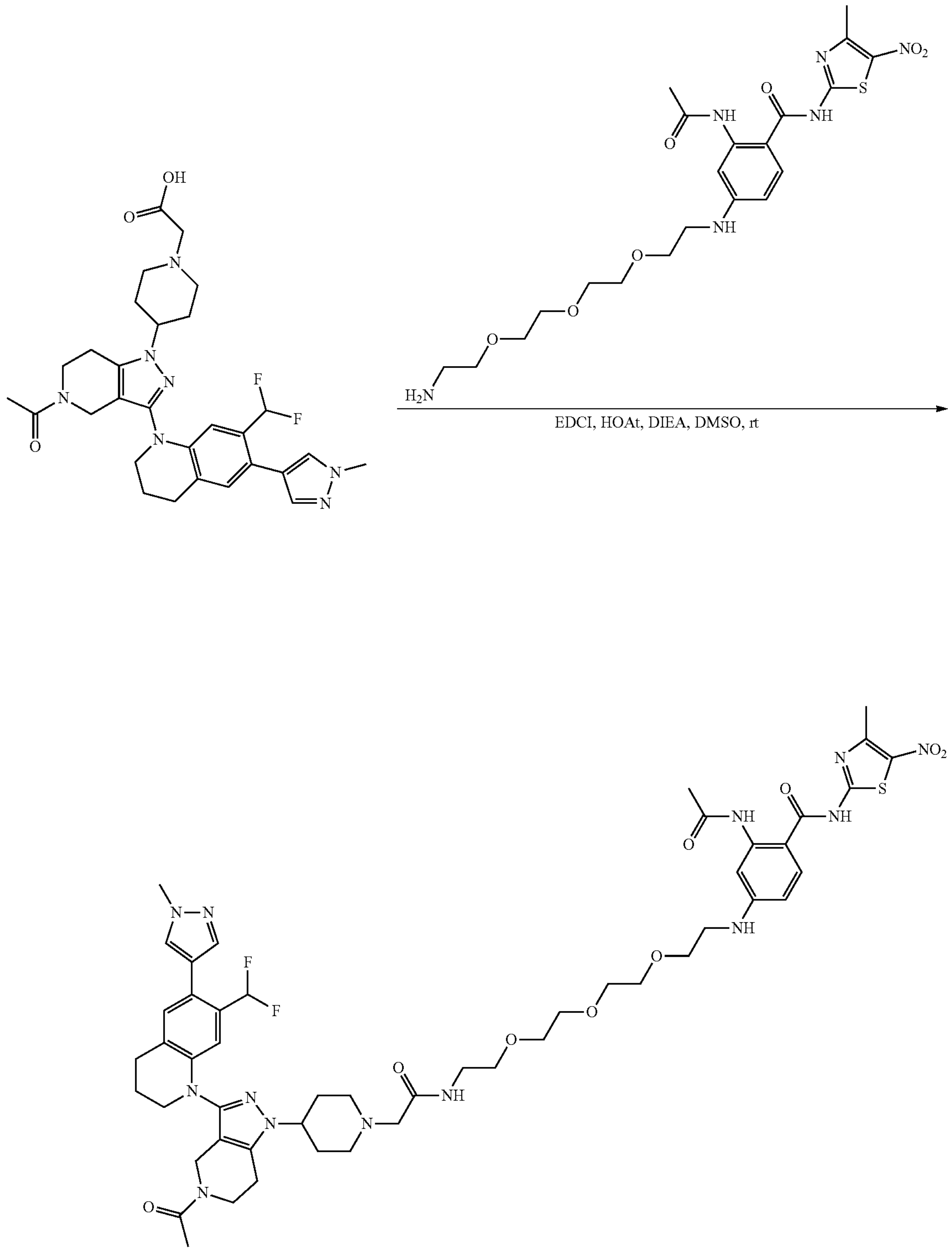
D-9 was synthesized following the standard procedure for preparing D-2 (3 mg, 35% yield). MS (ESI) m/z: 1061.0 $[M+H]^+$.

Example 176. 2-Acetamido-4-((1-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)-2-oxo-6,9,12,15-tetraoxa-3-azaheptadecan-17-yl)amino)-N-(4-methyl-5-nitrothiazol-2-yl)benzamide (D-10)

Example 177. 2-Acetamido-4-((1-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)-2-oxo-6,9,12,15,18-pentaoxa-3-azaicosan-20-yl)amino)-N-(4-methyl-5-nitrothiazol-2-yl)benzamide (D-11)

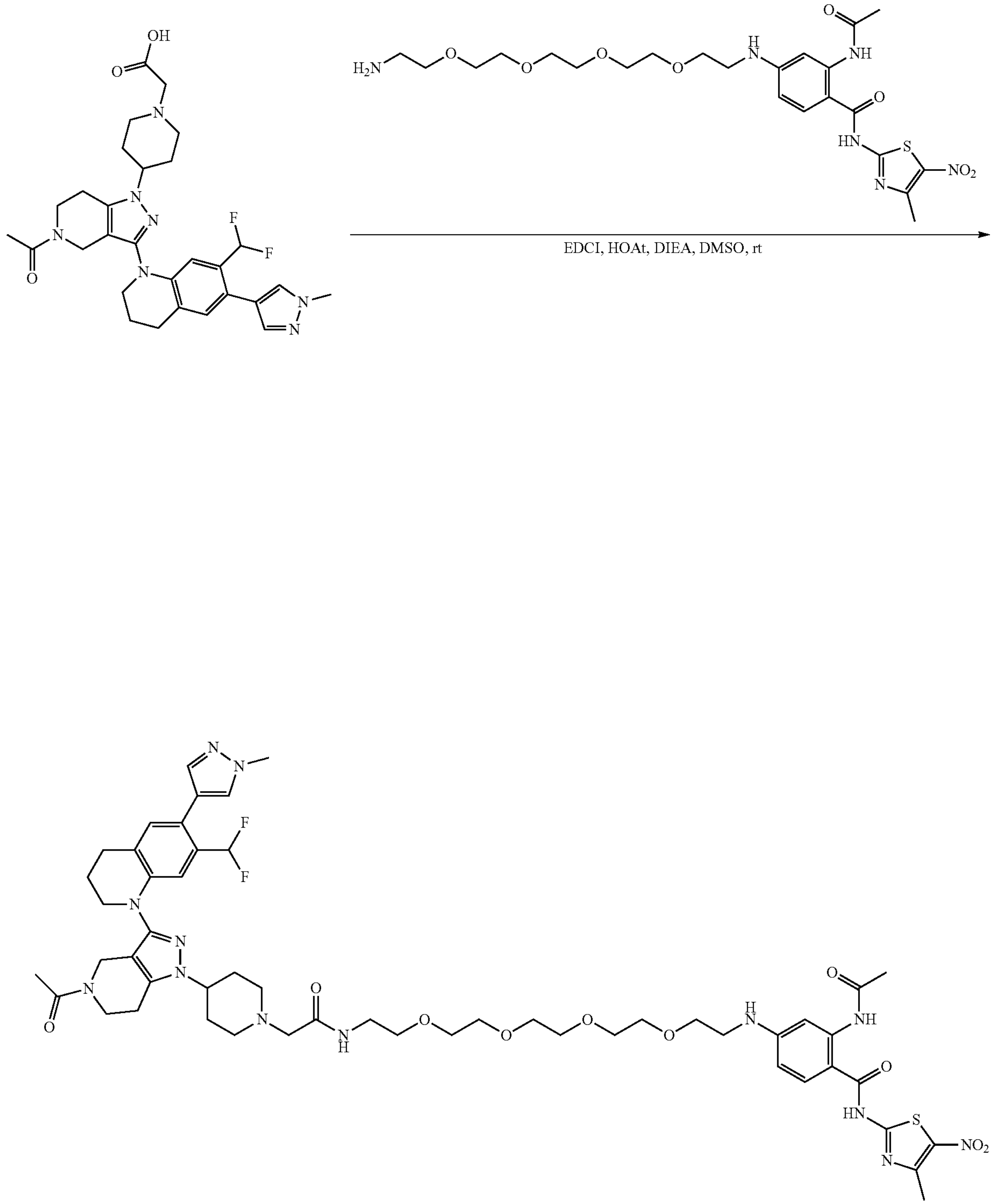

D-10 was synthesized following the standard procedure for preparing D-2 (3 mg, 34% yield). MS (ESI) m/z: 1105.0 $[M+H]^+$.

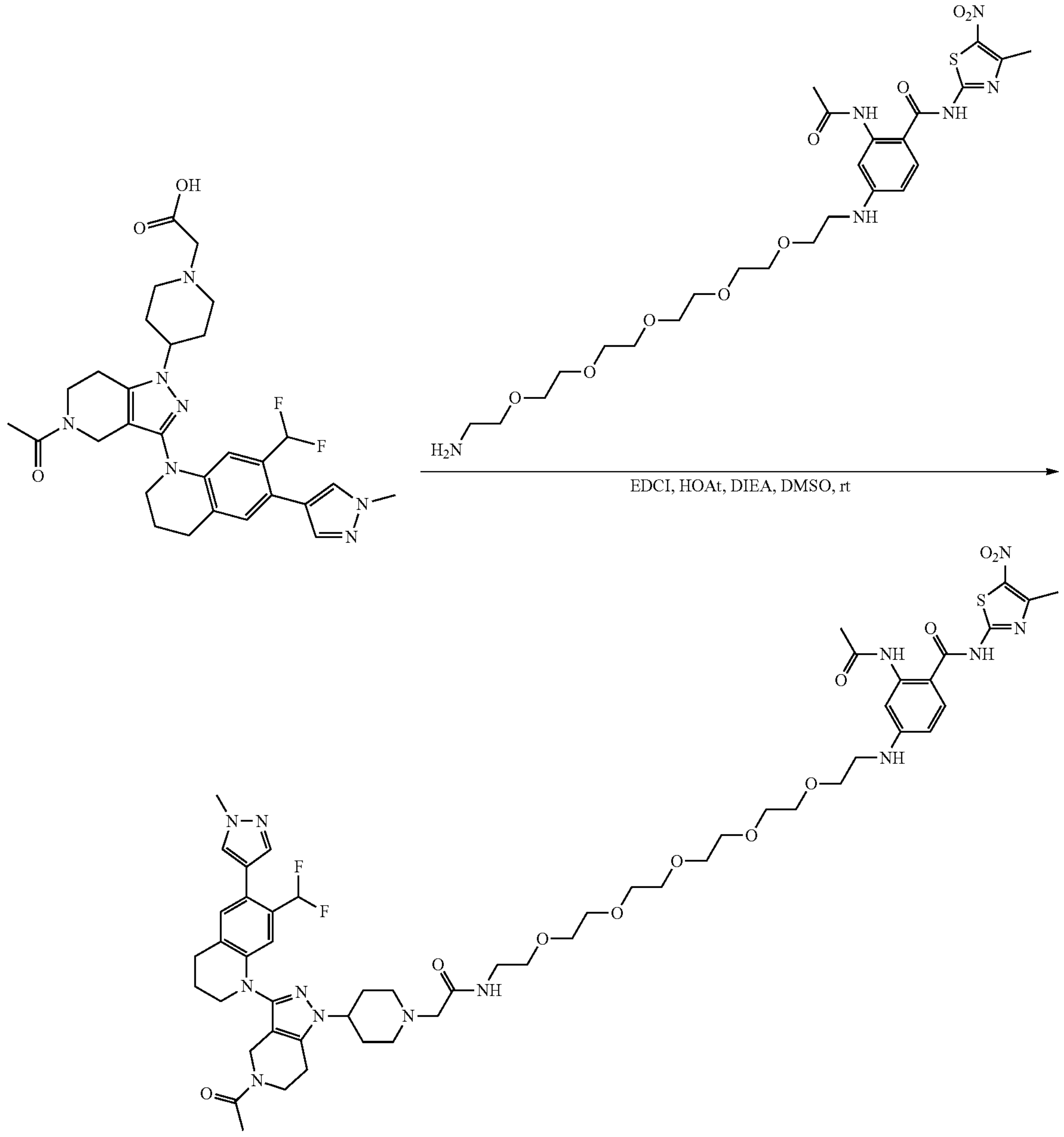
D-11 was synthesized following the standard procedure for preparing D-2 (3 mg, 33% yield). MS (ESI) m/z: 1149.0 $[M+H]^+$.
Example 178. 2-Acetamido-4-((1-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)-2-oxo-6,9,12,15,18,21-hexaoxa-3-azatricosan-23-yl)amino)-N-(4-methyl-5-nitrothiazol-2-yl)benzamide (D-12)

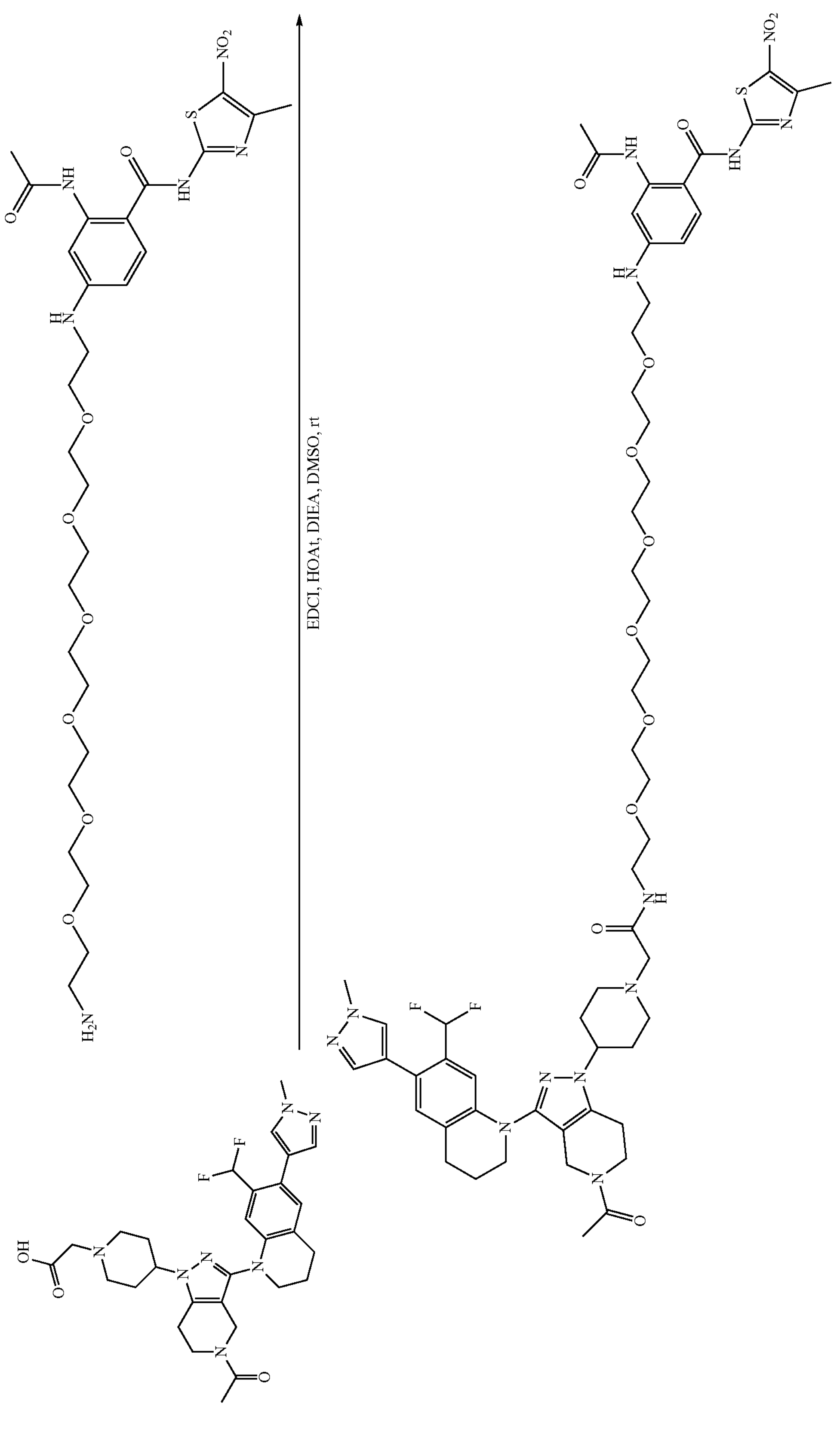
EDCI, HOAt, DIEA, DMSO, rt

D-12 was synthesized following the standard procedure for preparing D-2 (3 mg, 31% yield). MS (ESI) m/z: 1193.2 $[M+H]^+$.

Example 179. 2-Acetamido-4-((2-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)ethyl)amino)-N-(4-methyl-5-nitrothiazol-2-yl)benzamide (D-1)

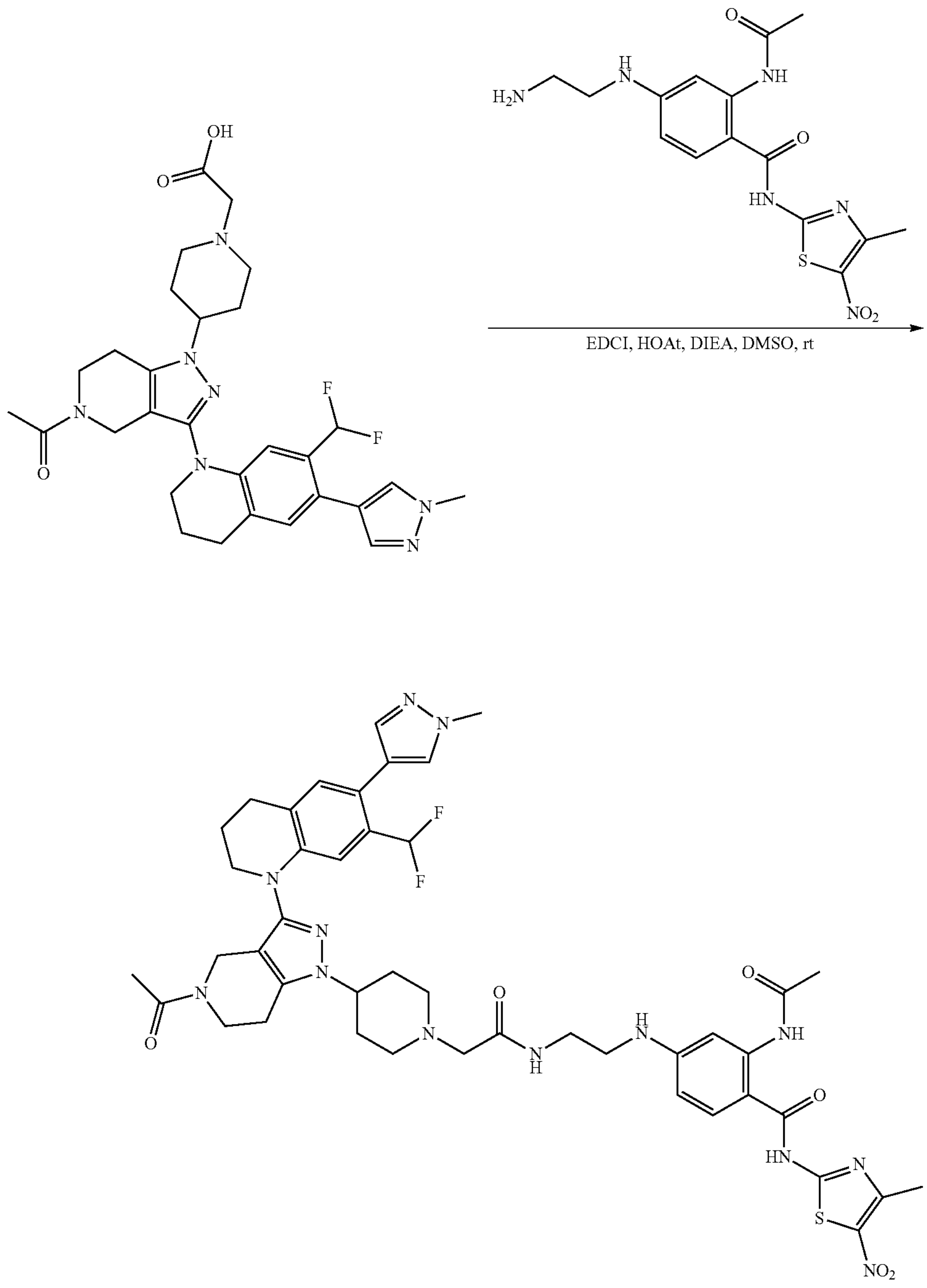

D-1 was synthesized following the standard procedure for preparing D-2 (1 mg, 13.5% yield). MS (ESI) m/z: 928.7 $[M+H]^+$.

Example 180. 2-Acetamido-4-((7-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)heptyl)amino)-N-(4-methyl-5-nitrothiazol-2-yl)benzamide (D-4)
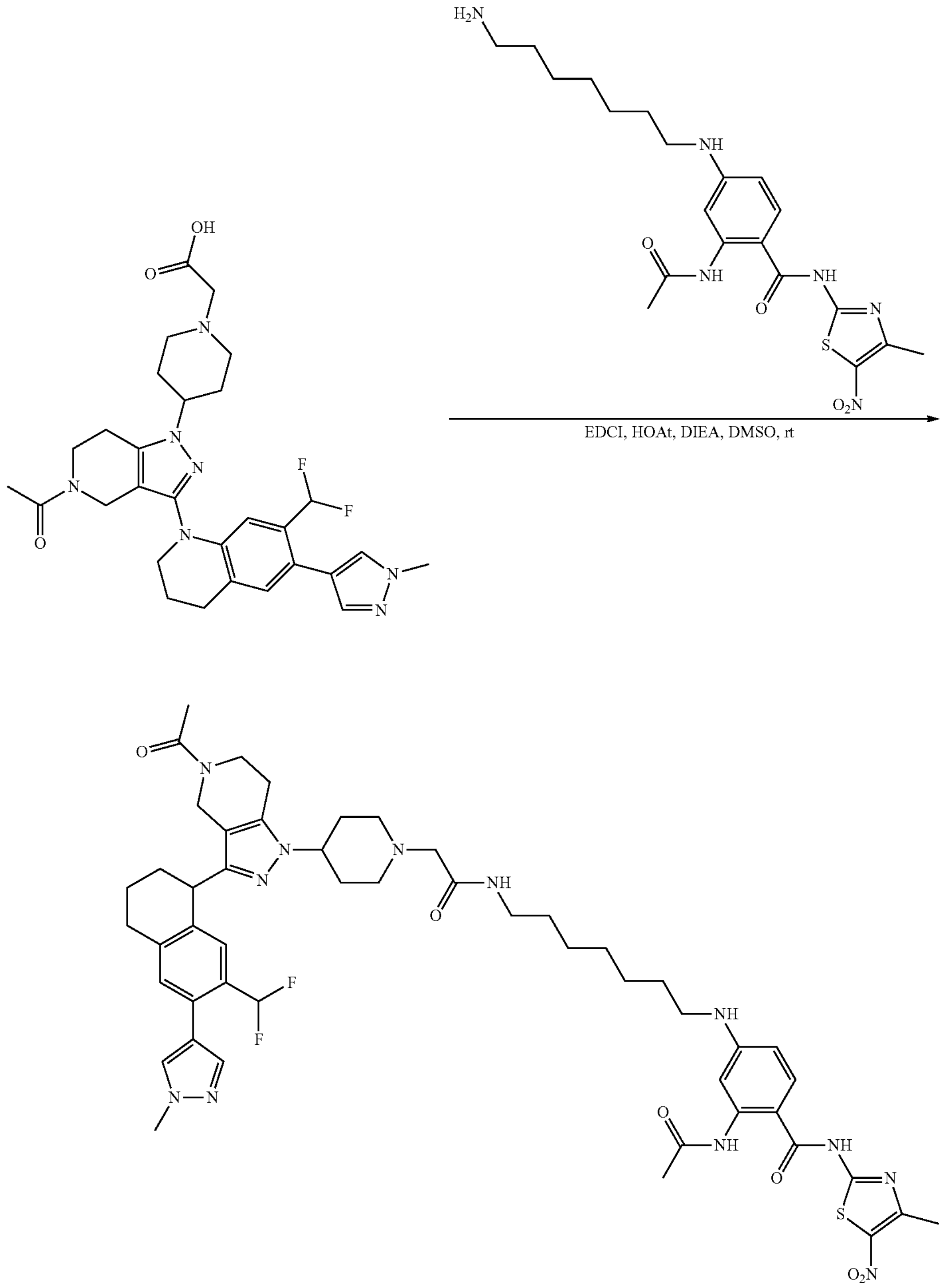
D-4 was synthesized following the standard procedure for preparing D-2 (1 mg, 12.5% yield). MS (ESI) m/z: 998.8 $[M+H]^+$.

Example 181. 2-Acetamido-4-((8-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)octyl)amino)-N-(4-methyl-5-nitrothiazol-2-yl)benzamide (D-5)
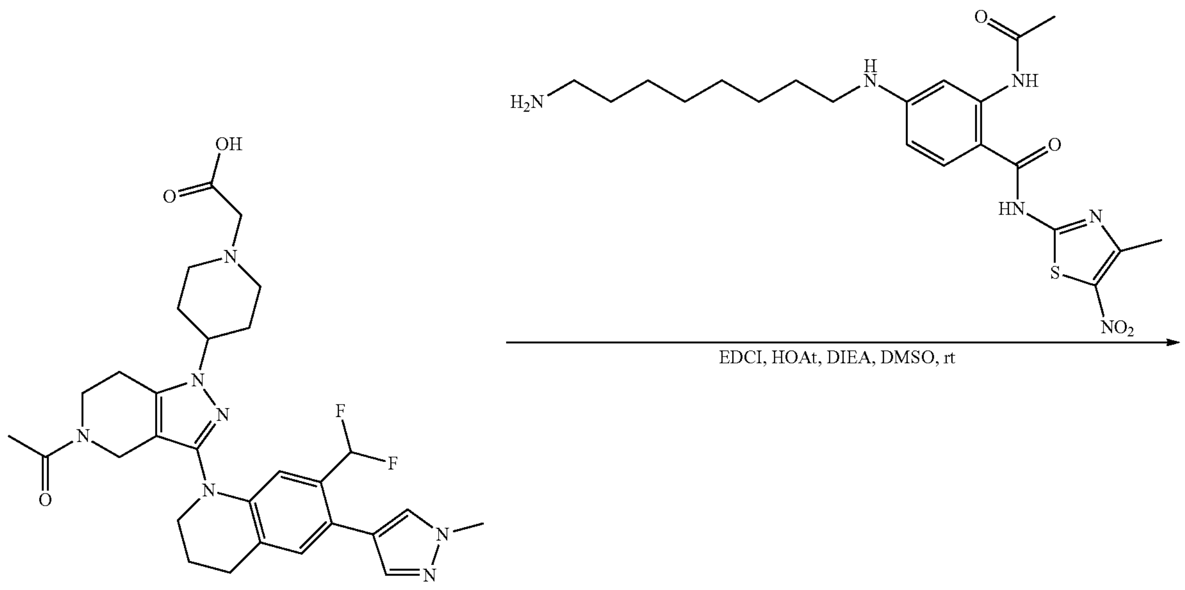
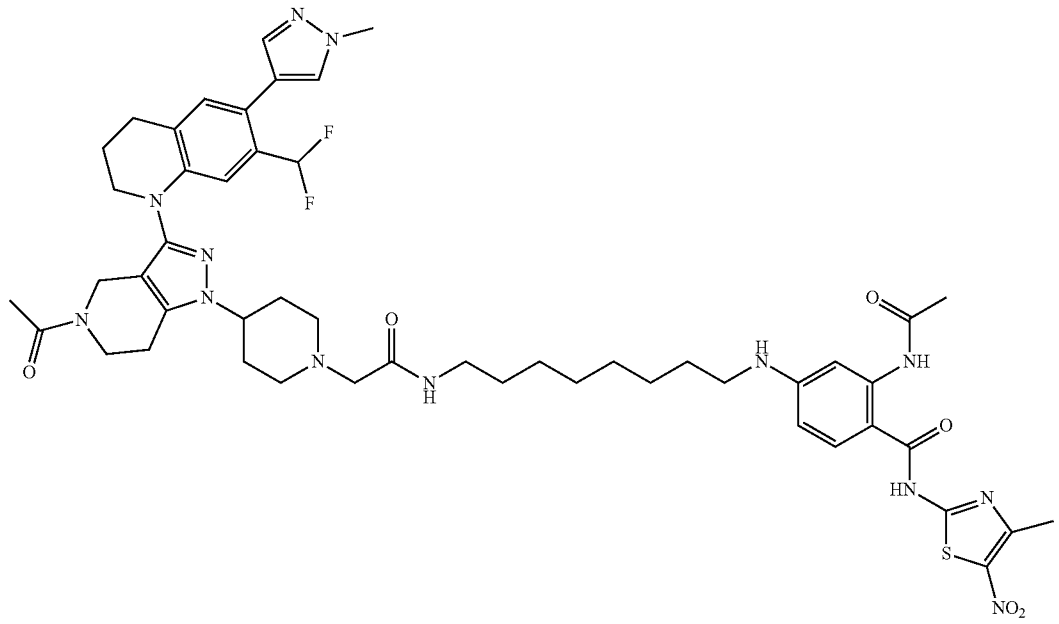
D-5 was synthesized following the standard procedure for preparing D-2 (2 mg, 25% yield). MS (ESI) m/z: 1012.9 $[M+H]^+$.

Example 182. 2-Acetamido-4-((4-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)butyl)amino)-N-(5-nitrothiophen-2-yl)benzamide (D-13)
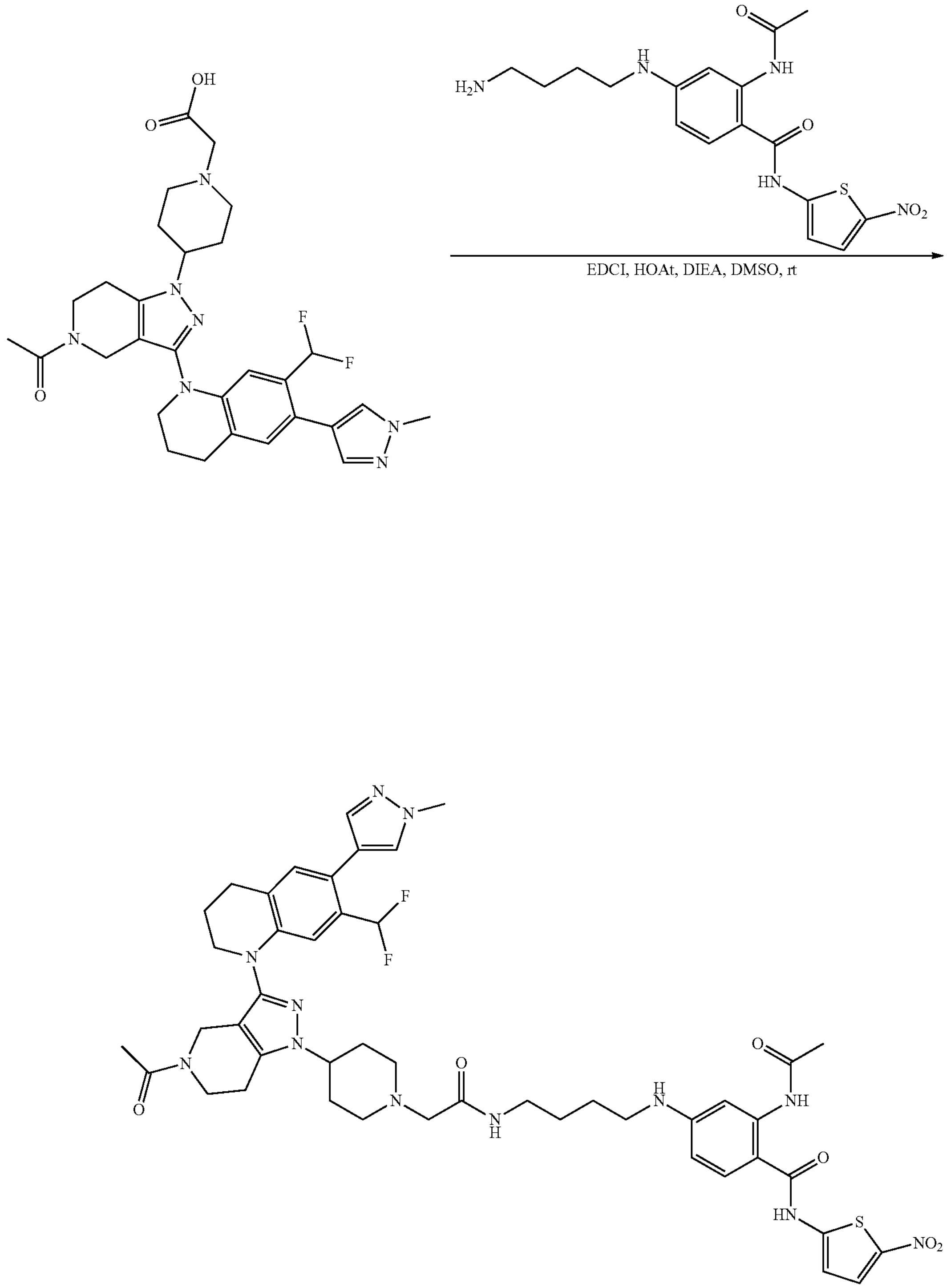
D-13 was synthesized following the standard procedure for preparing D-2 (4.4 mg, 26% yield). MS (EST) m/z: 941.5 $[M+H]^+$ Example 183. 2-Acetamido-4-((2-(2-(2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)acetamido)ethoxy)ethyl)amino)-N-(4-methyl-5-nitrothiazol-2-yl)benzamide (D-44)
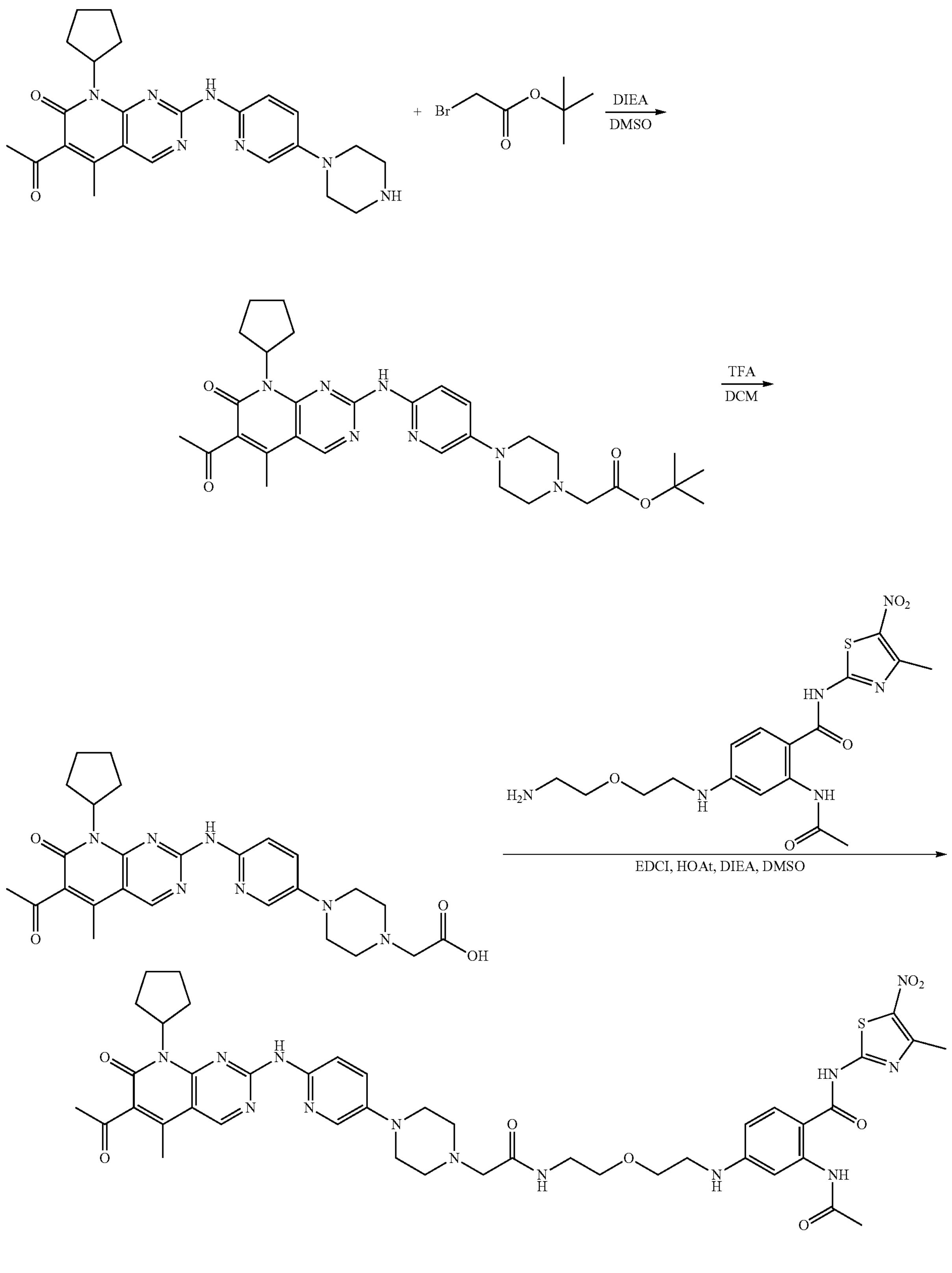

Step 1. Synthesis of tert-butyl 2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl) acetate

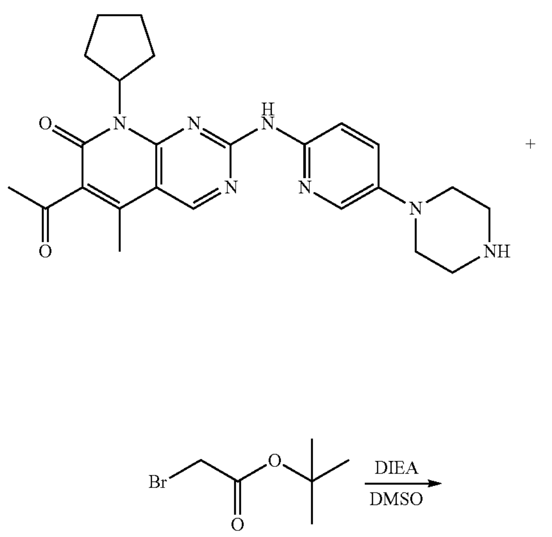

-continued

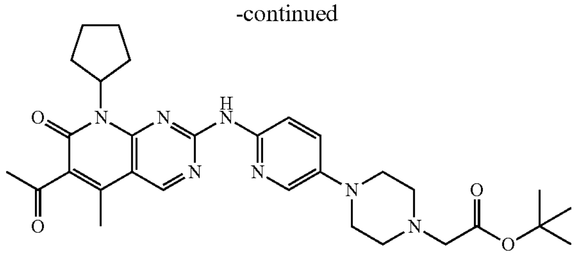

A mixture of 6-acetyl-8-cyclopentyl-5-methyl-2-((5-(piperazin-1-yl)pyridin-2-yl)amino)pyrido[2,3-d]pyrimidin-7(8H)-one (200 mg, 0.45 mmol) and DIEA (284 mg, 1.8 mmol) in DMSO (20 mL) was added tert-butyl 2-bromoacetate (88 mg, 0.45 mmol), the resulting mixture was stirred at 25° C. for 16 h. The mixture was treated with water and extracted with DCM (3×30 mL). The combined organic layers were combined and washed with brine (2×40 mL), dried over $Na_2SO_4$ and concentrated under vacuum to give tert-butyl 2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetate (230 mg, 91.6% yield) as yellow solid. MS (ESI) m/z: 562.6 $[M+H]^+$.

Step 2. Synthesis of 2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetic acid

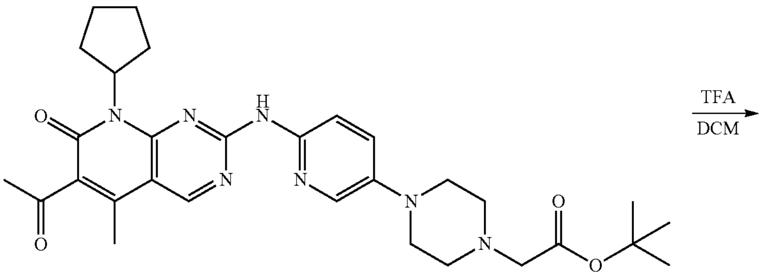

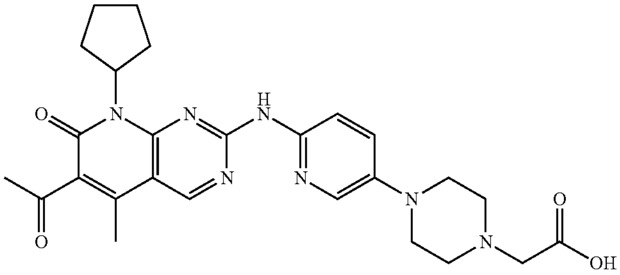

To a mixture of tert-butyl 2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetate (230 mg, 0.41 mmol) in DCM (10 mL) was added TFA (10 mL). The resulting mixture was stirred at 25° C. for 16 h. The solvent was removed and the residue was purified by reverse-phase chromatography to give 2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetic acid (180 mg, 86.7% yield) as yellow solid. MS (ESI) m/z: 506.6 $[M+H]^+$.

Step 3. Synthesis of 2-acetamido-4-((2-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)ethoxy)ethyl)amino)-N-(4-methyl-5-nitrothiazol-2-yl)benzamide

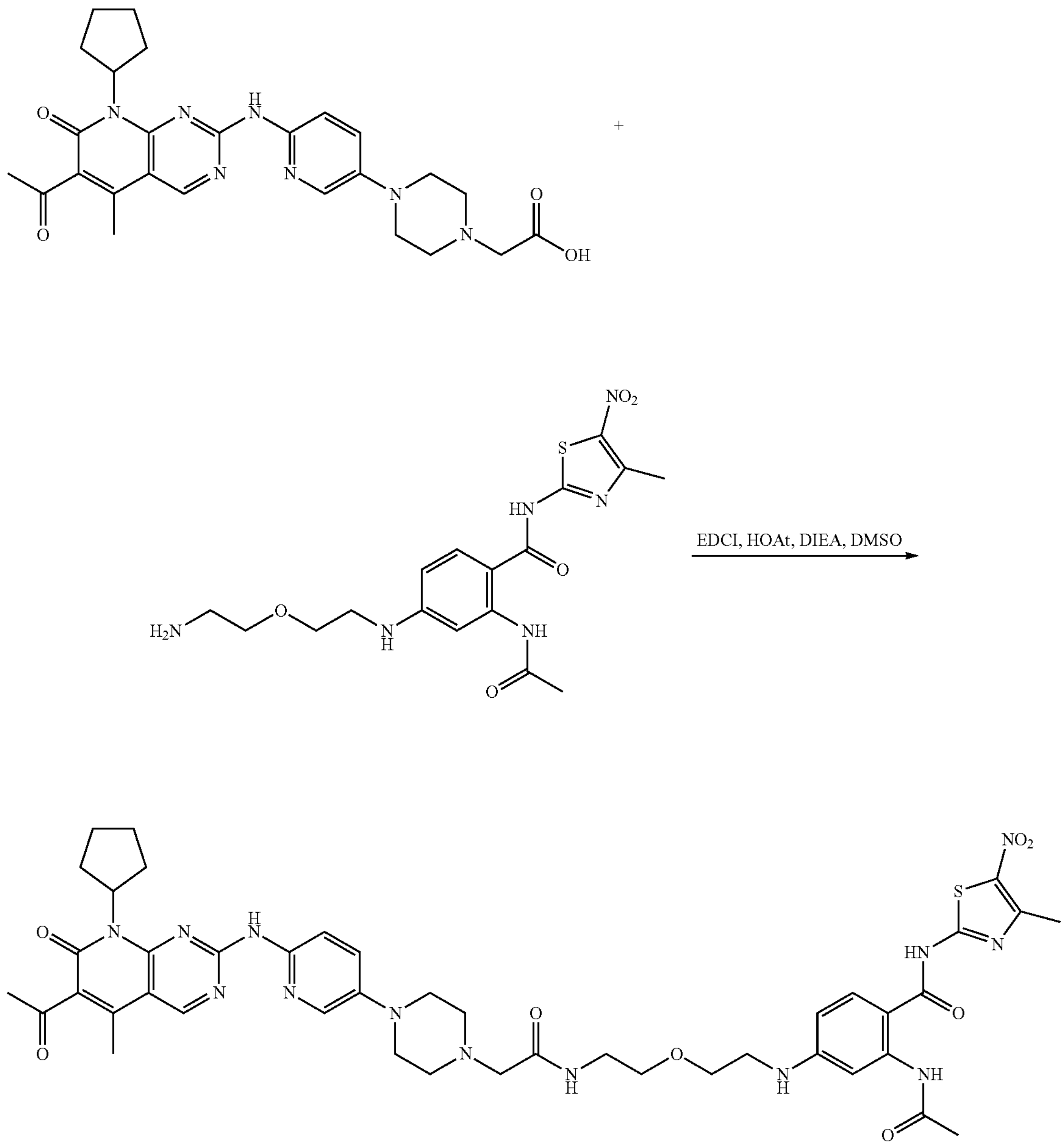

To a mixture of 2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetic acid (5 mg, 0.01 mmol) and HOAt (2.7 mg, 0.02 mmol), EDCI (3.8 mg, 0.02 mmol) in DMSO (1 mL) were added DIEA (5 mg, 0.05 mmol) and 2-acetamido-4-((2-(2-aminoethoxy)ethyl)amino)-N-(4-methyl-5-nitrothiazol-2-yl)benzamide (4.2 mg, 0.01 mmol). The mixture was stirred at 25° C. for 16 h. The mixture was purified by reverse-phase chromatography to give tert-butyl (1-(2-(2,6-dioxopiperidin-3-yl)-1,3-dioxoisoindolin-5-yl)azetidin-3-yl)carbamate (1.05 mg, 11.7% yield) as yellow solid. MS (ESI) m/z: 910.6 $[M+H]^+$.

Example 184. 2-Acetamido-4-((2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)ethyl)amino)-N-(4-methyl-5-nitrothiazol-2-yl)benzamide (D-38)

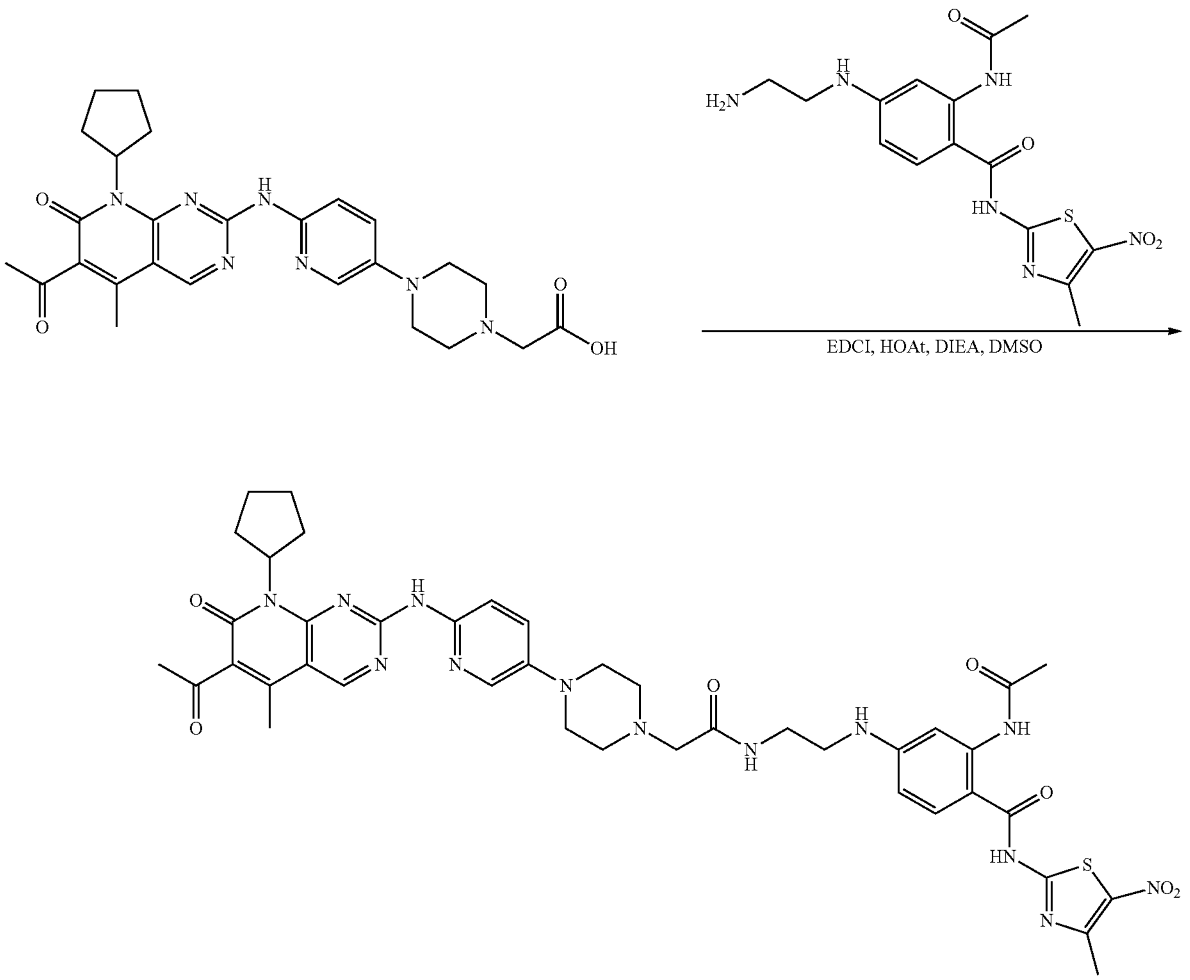

D-38 was synthesized following the standard procedure for preparing D-44 (1.08 mg, 12.6% yield). MS (ESI) m/z: 866.0 $[M+H]^+$.

Example 185. 2-Acetamido-4-((4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)butyl)amino)-N-(4-methyl-5-nitrothiazol-2-yl)benzamide (D-39)

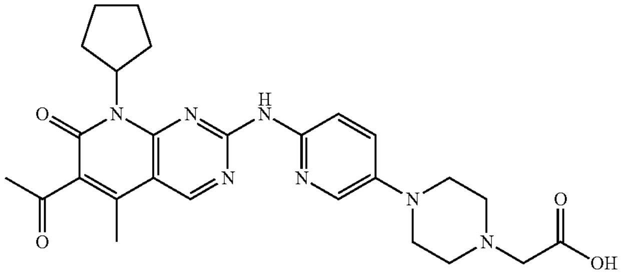

+

-continued
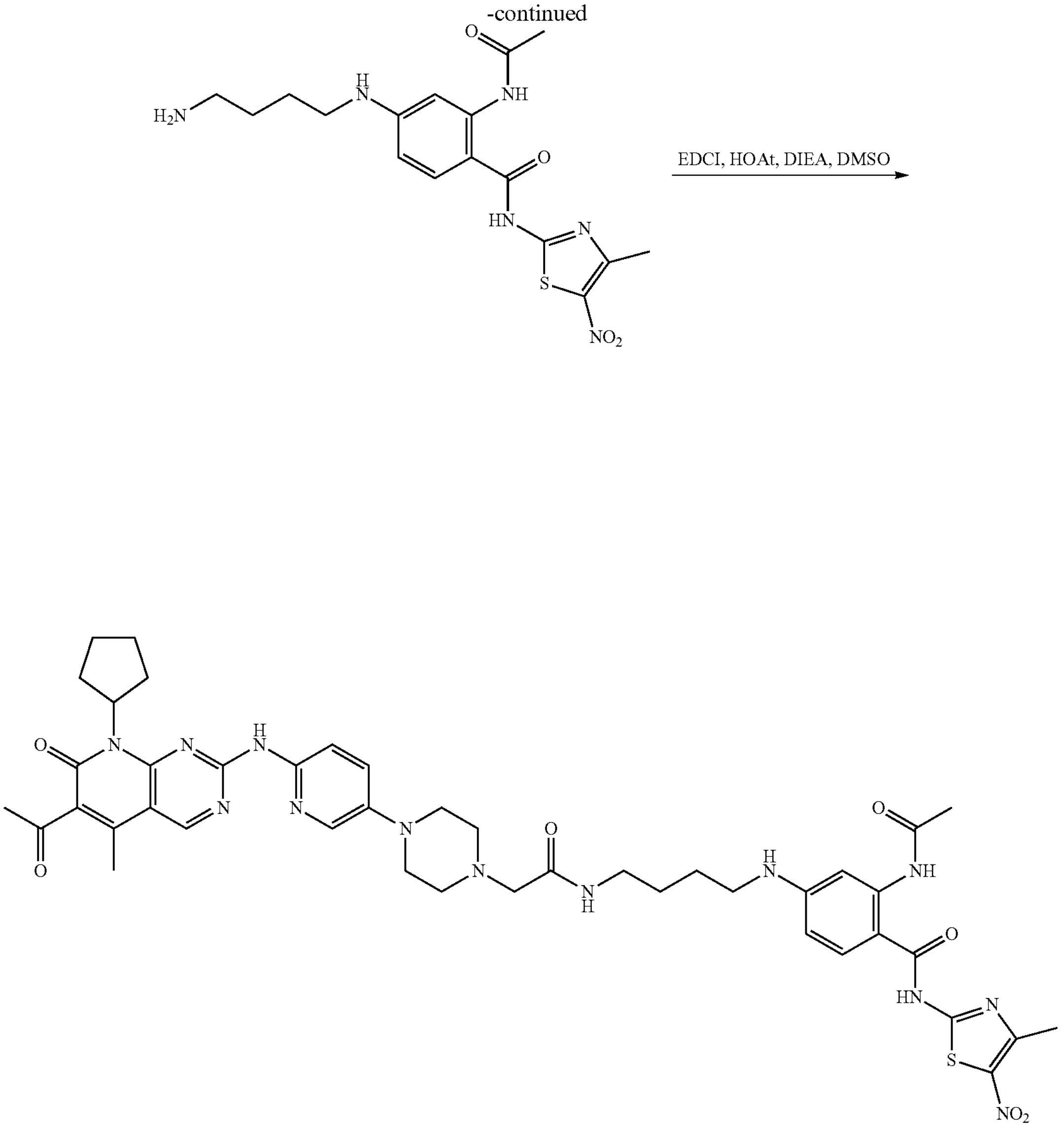
D-39 was synthesized following the standard procedure for preparing D-44 (1.68 mg, 19.0% yield). MS (EST) m/z: 894.5 $[M+H]^+$.
Example 186. 2-Acetamido-4-((6-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)hexyl)amino)-N-(4-methyl-5-nitrothiazol-2-yl)benzamide (D-40)
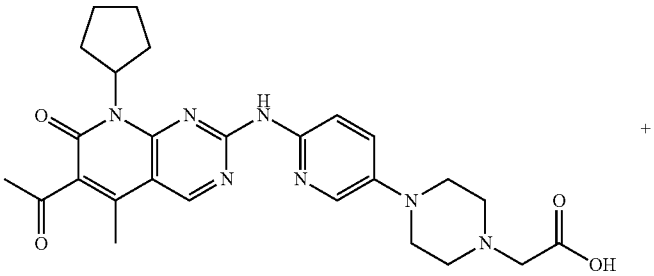

-continued
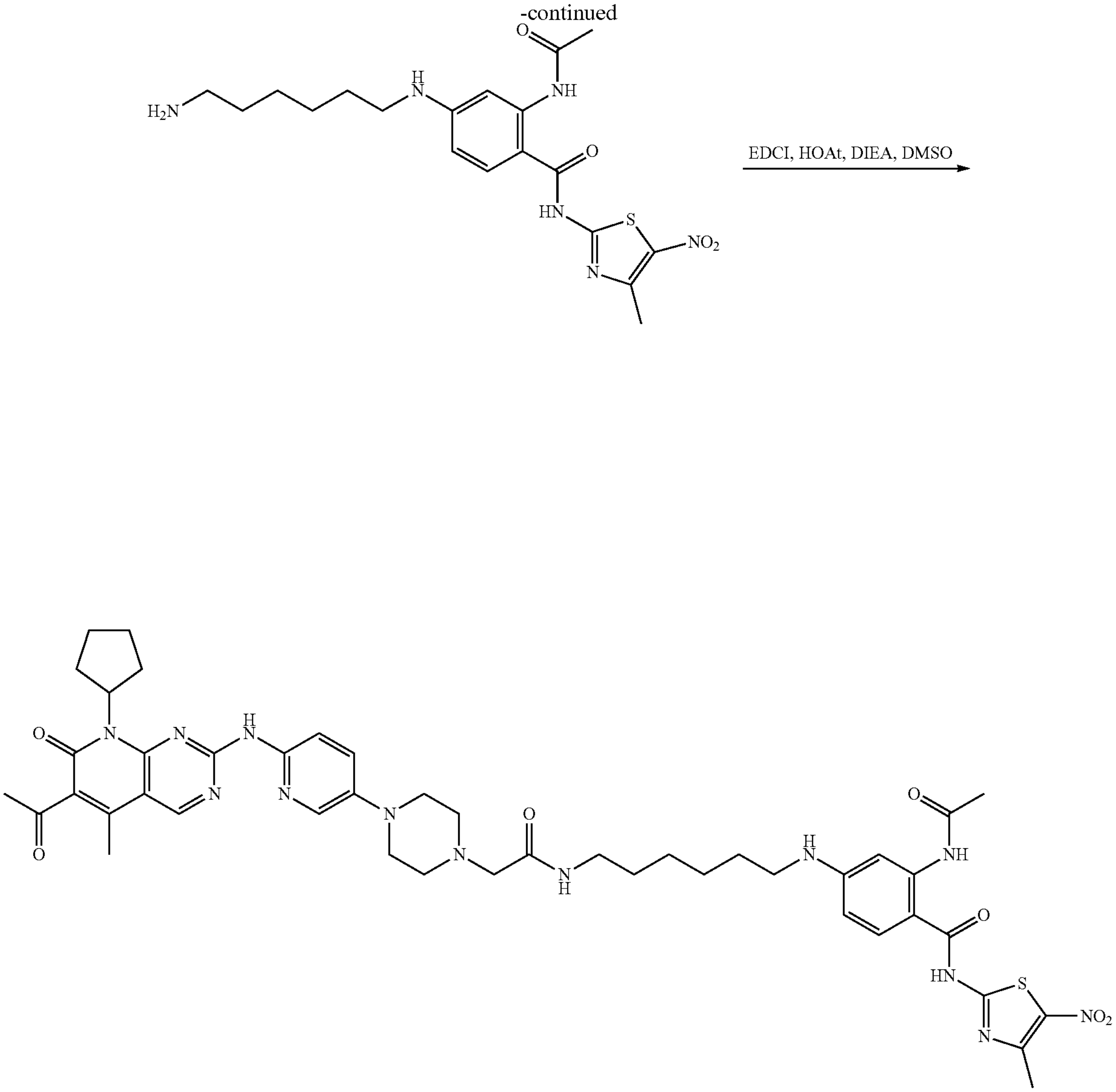
D-40 was synthesized following the standard procedure for preparing D-44 (2.80 mg, 30.7% yield). MS (EST) m/z: 922.5 $[M+H]^+$.
Example 187. 2-Acetamido-4-((7-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)heptyl)amino)-N-(4-methyl-5-nitrothiazol-2-yl)benzamide (D-41)
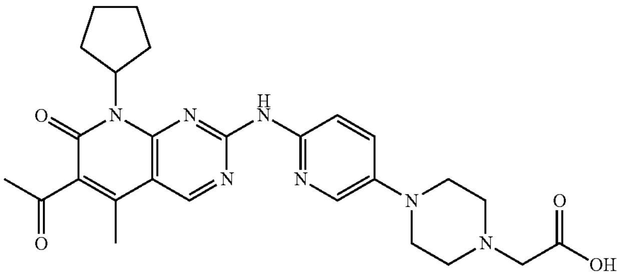
+

-continued
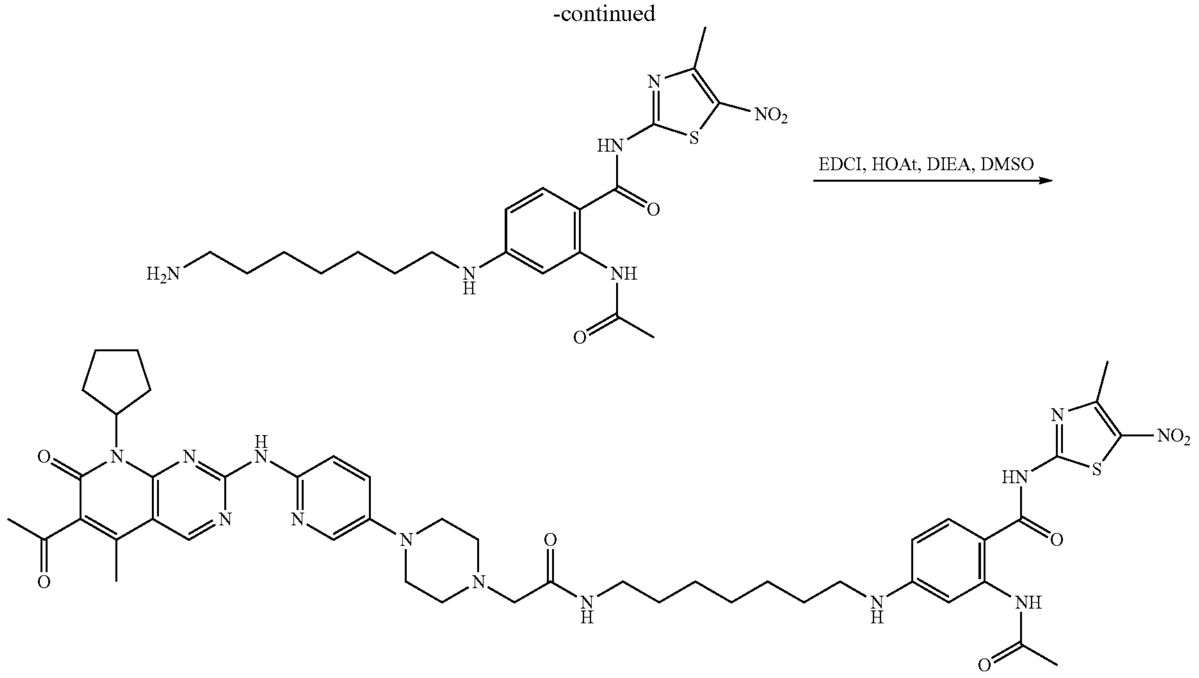
D-41 was synthesized following the standard procedure for preparing D-44 (0.88 mg, 9.5% yield). MS (EST) m/z: 936.5 [M+H]$^+$.
Example 188. 2-Acetamido-4-((8-(2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)acetamido)octyl)amino)-N-(4-methyl-5-nitrothiazol-2-yl)benzamide (D-42)
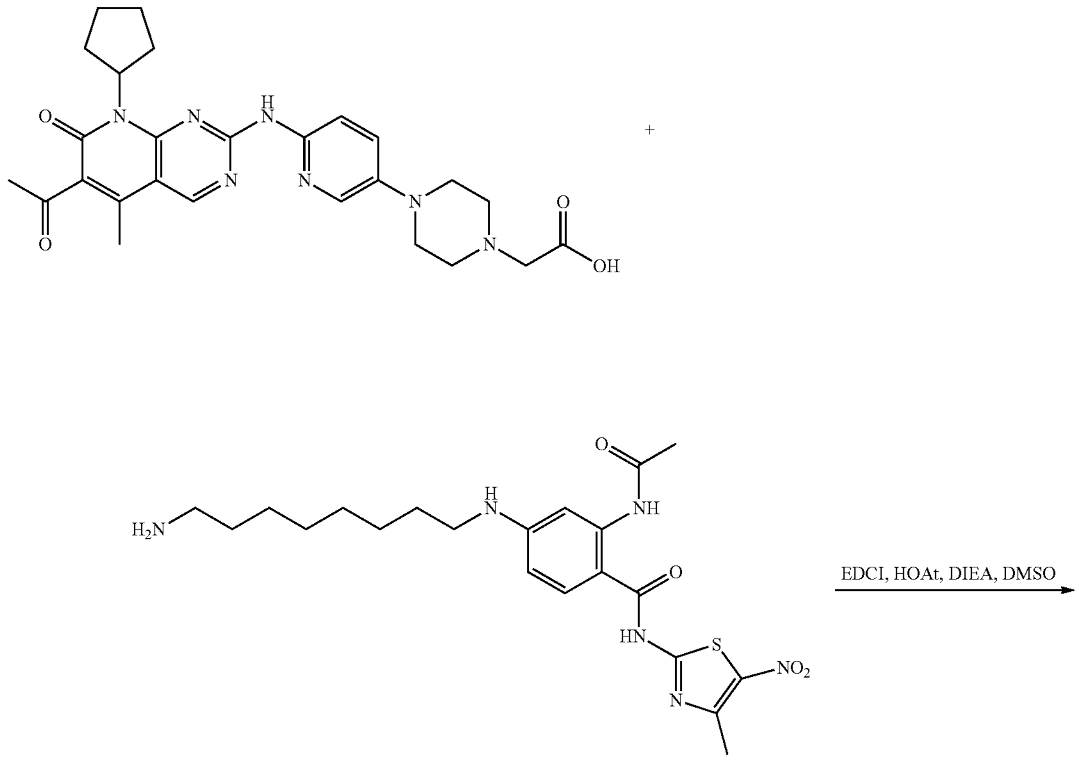

-continued
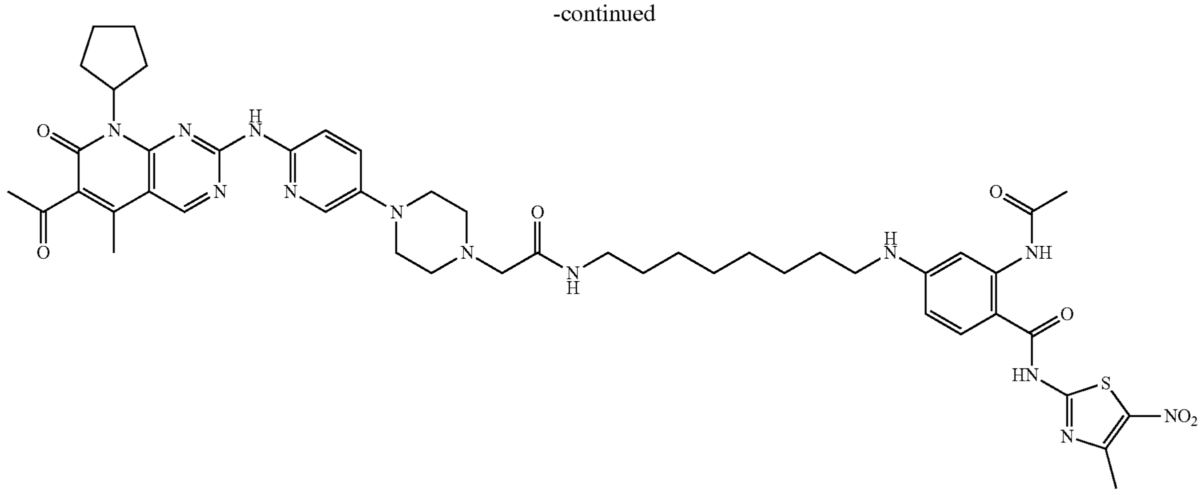
D-42 was synthesized following the standard procedure for preparing D-44 (2.39 mg, 25.5% yield). MS (EST) m/z: 950.5 $[M+H]^+$
Example 189. 2-Acetamido-4-((10-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)decyl)amino)-N-(4-methyl-5-nitrothiazol-2-yl)benzamide (D-43)
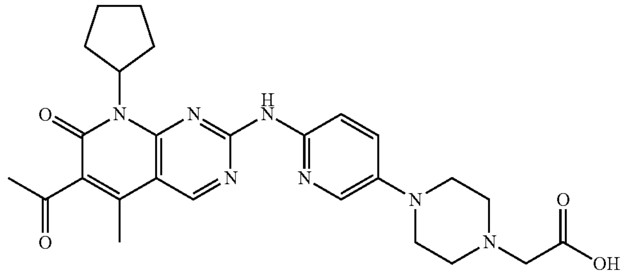
+
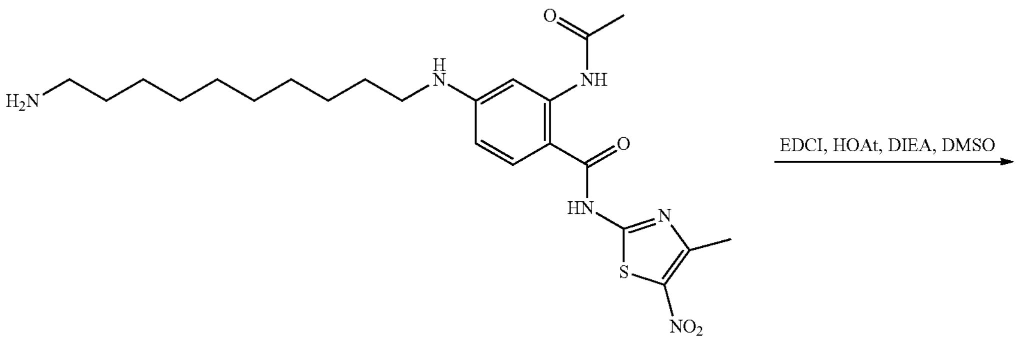

-continued
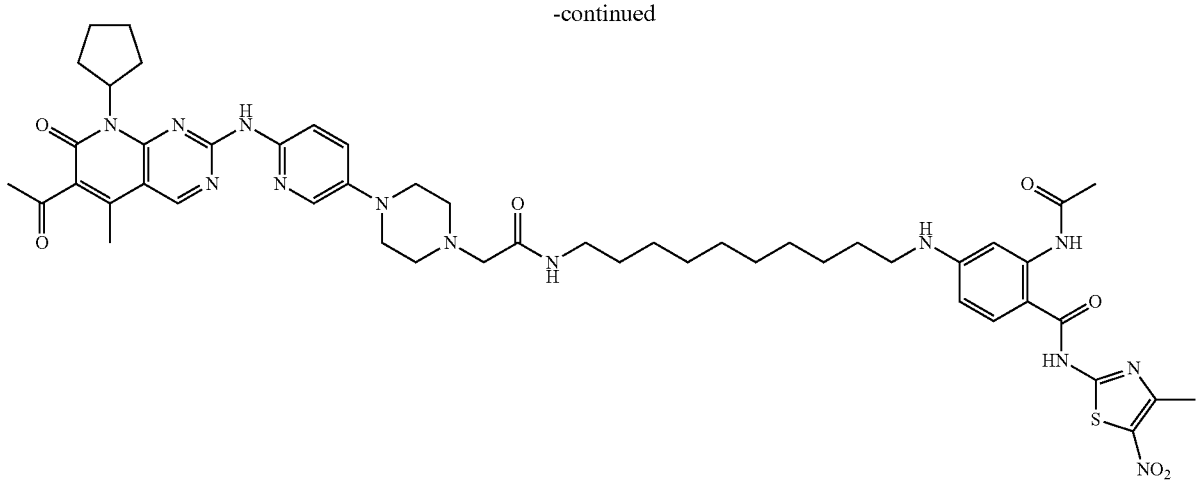
D-43 was synthesized following the standard procedure for preparing D-44 (2.32 mg, 24% yield). MS (EST) m/z: 978.6 $[M+H]^+$.
Example 190. 2-Acetamido-4-((2-(2-(2-(2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)acetamido)ethoxy)ethoxy)ethyl)amino)-N-(4-methyl-5-nitrothiazol-2-yl)benzamide (D-45)
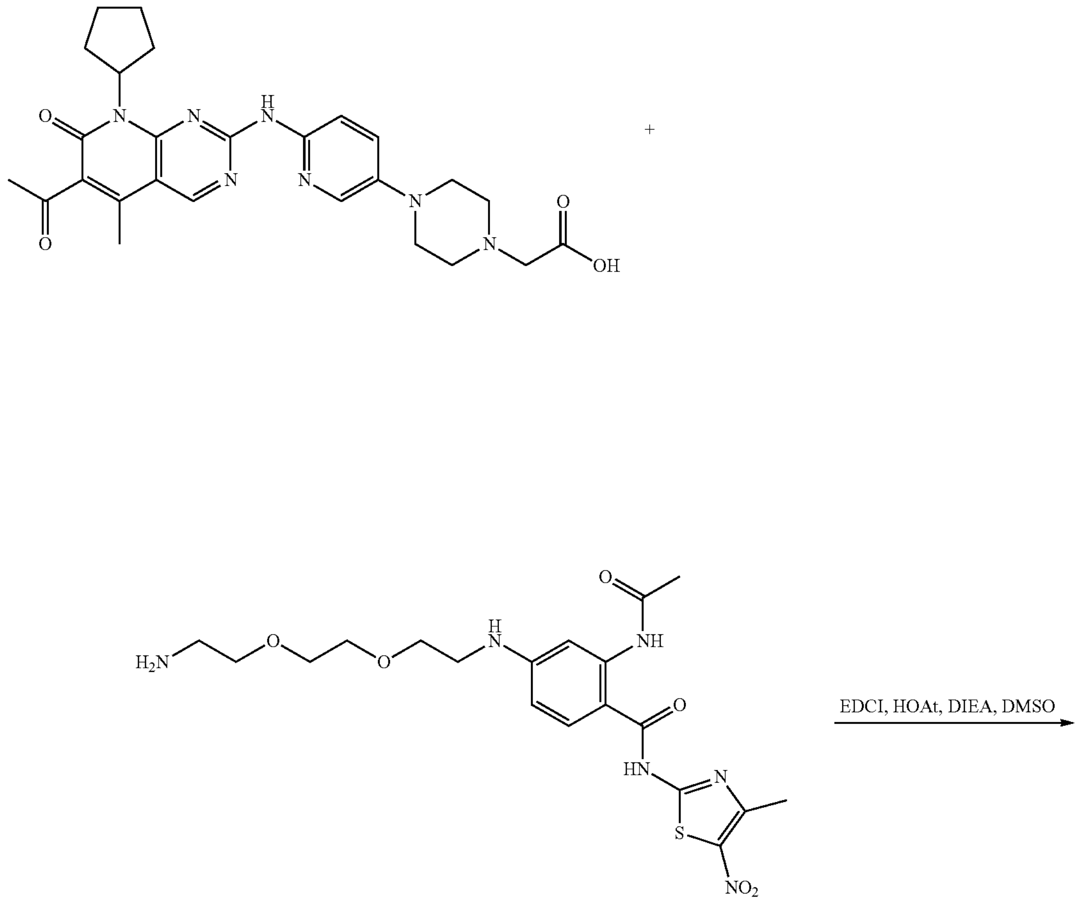

-continued
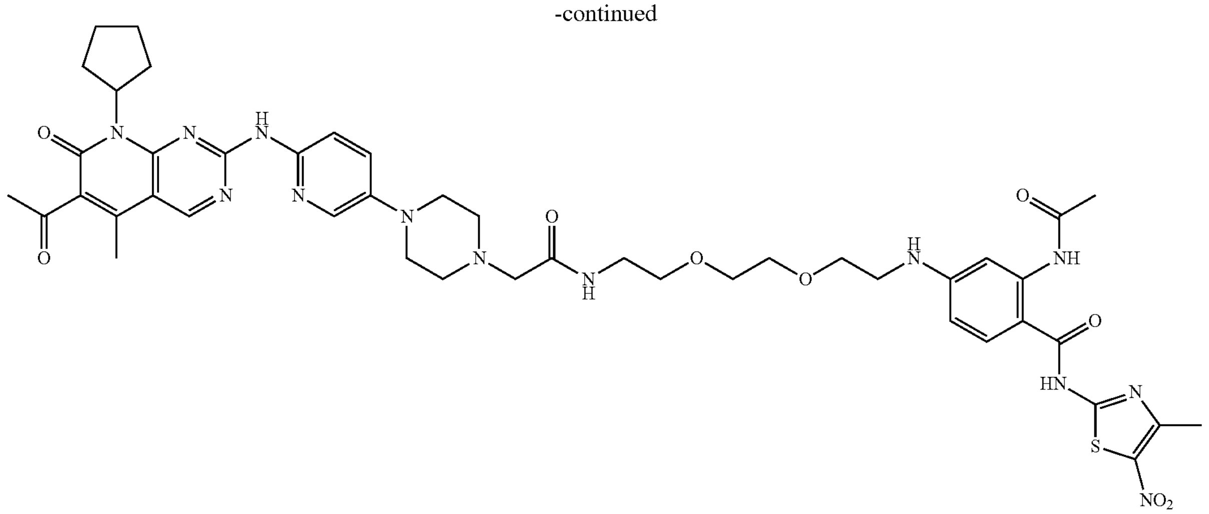
D-45 was synthesized following the standard procedure for preparing D-44 (3.36 mg, 35.5% yield). MS (ESI) m/z: 954.6 $[M+H]^+$.
Example 191. 2-Acetamido-4-((1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12-trioxa-3-azatetradecan-14-yl)amino)-N-(4-methyl-5-nitrothiazol-2-yl)benzamide (D-46)
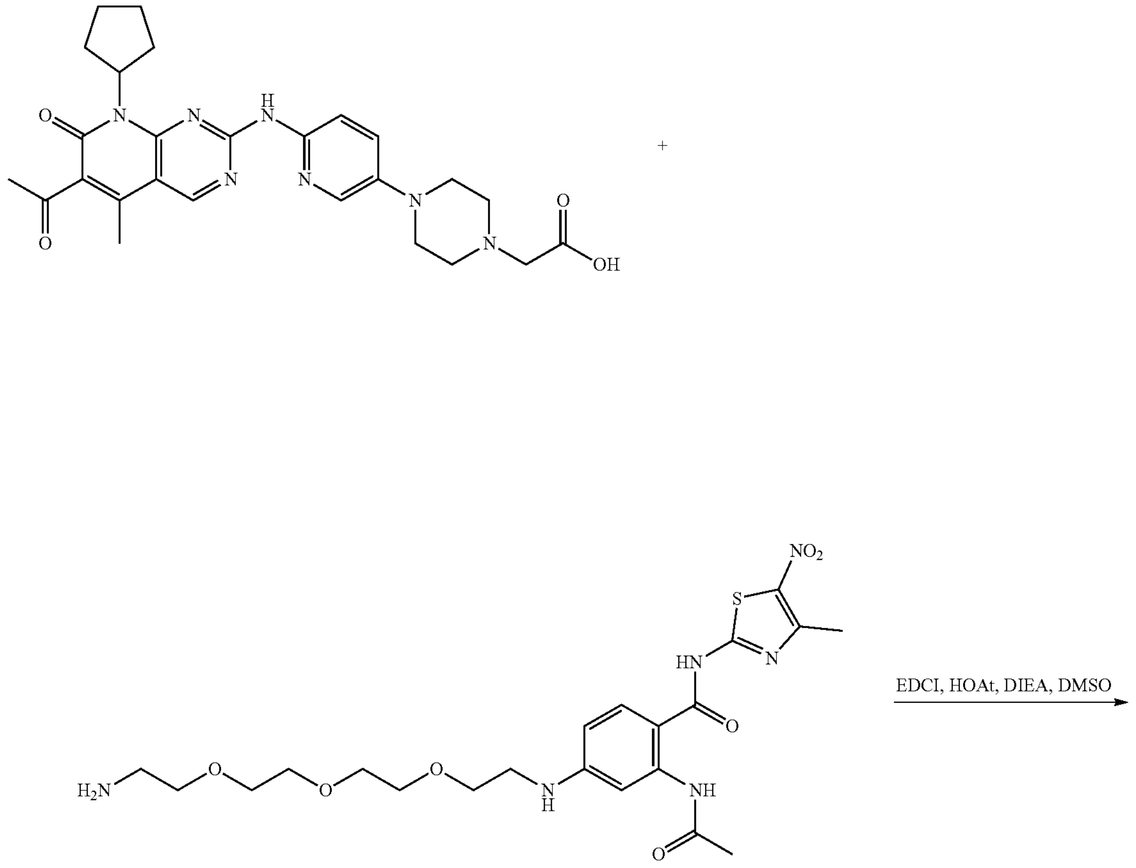

-continued
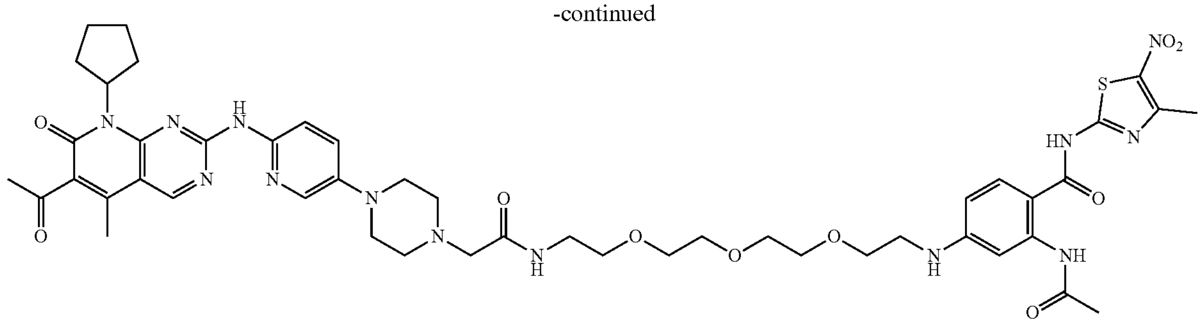
D-46 was synthesized following the standard procedure for preparing D-44 (1.16 mg, 11.7% yield). MS (ESI) m/z: 998.5 $[M+H]^+$.
Example 192. 2-Acetamido-4-((1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15-tetraoxa-3-azaheptadecan-17-yl)amino)-N-(4-methyl-5-nitrothiazol-2-yl)benzamide (D-47)
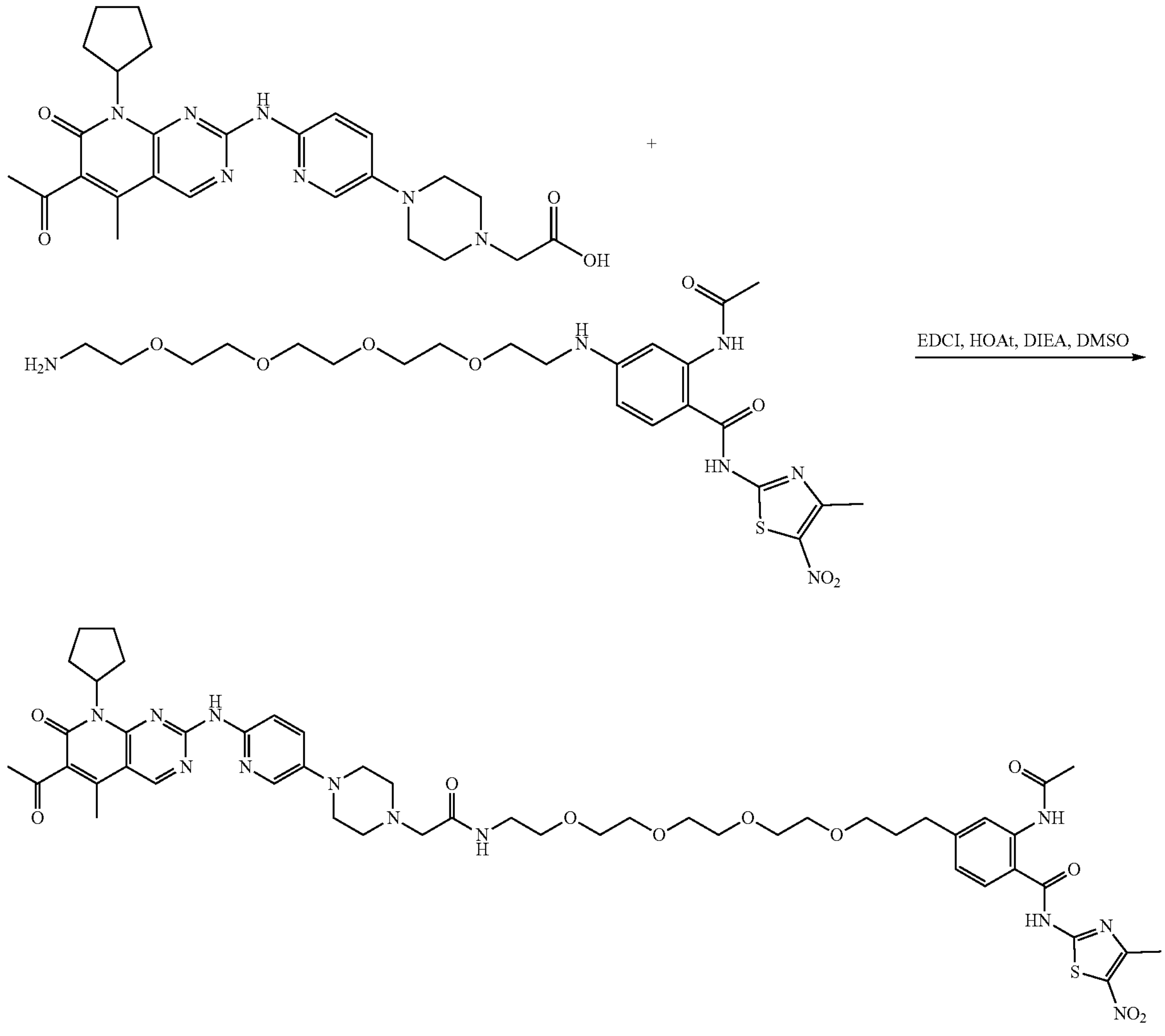

D-47 was synthesized following the standard procedure for preparing D-44 (4.08 mg, 39.6% yield). MS (EST) m/z: 1042.6 $[M+H]^+$ Example 193. 2-Acetamido-4-((1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15,18-pentaoxa-3-azaicosan-20-yl)amino)-N-(4-methyl-5-nitrothiazol-2-yl)benzamide (D-48

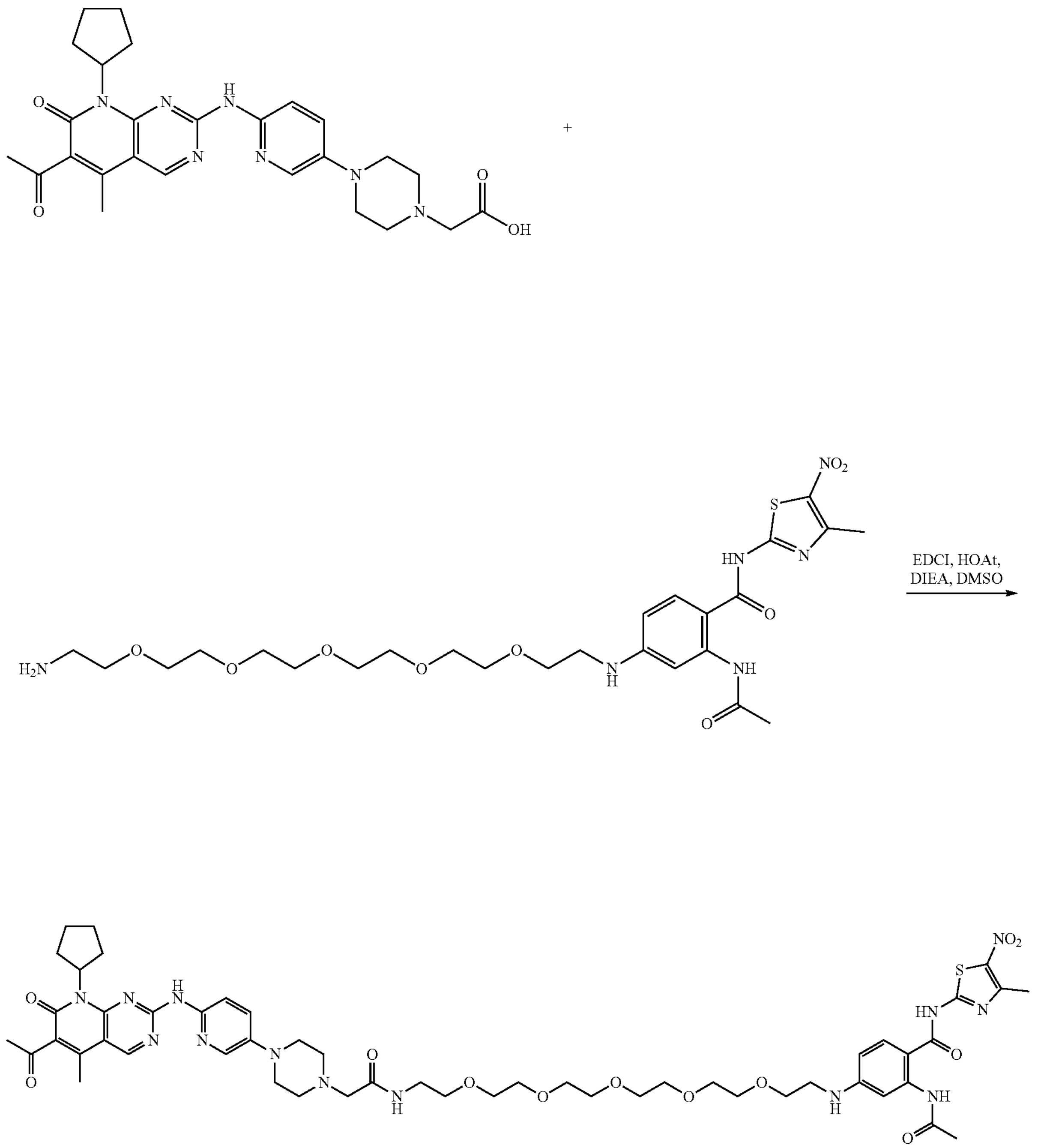

D-48 was synthesized following the standard procedure for preparing D-44 (3.84 mg, 35.7% yield). MS (EST) m/z: 1086.6 $[M+H]^+$.

Example 194. 2-Acetamido-4-((1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15,18,21-hexaoxa-3-azatricosan-23-yl)amino)-N-(4-methyl-5-nitrothiazol-2-yl)benzamide (D-49)

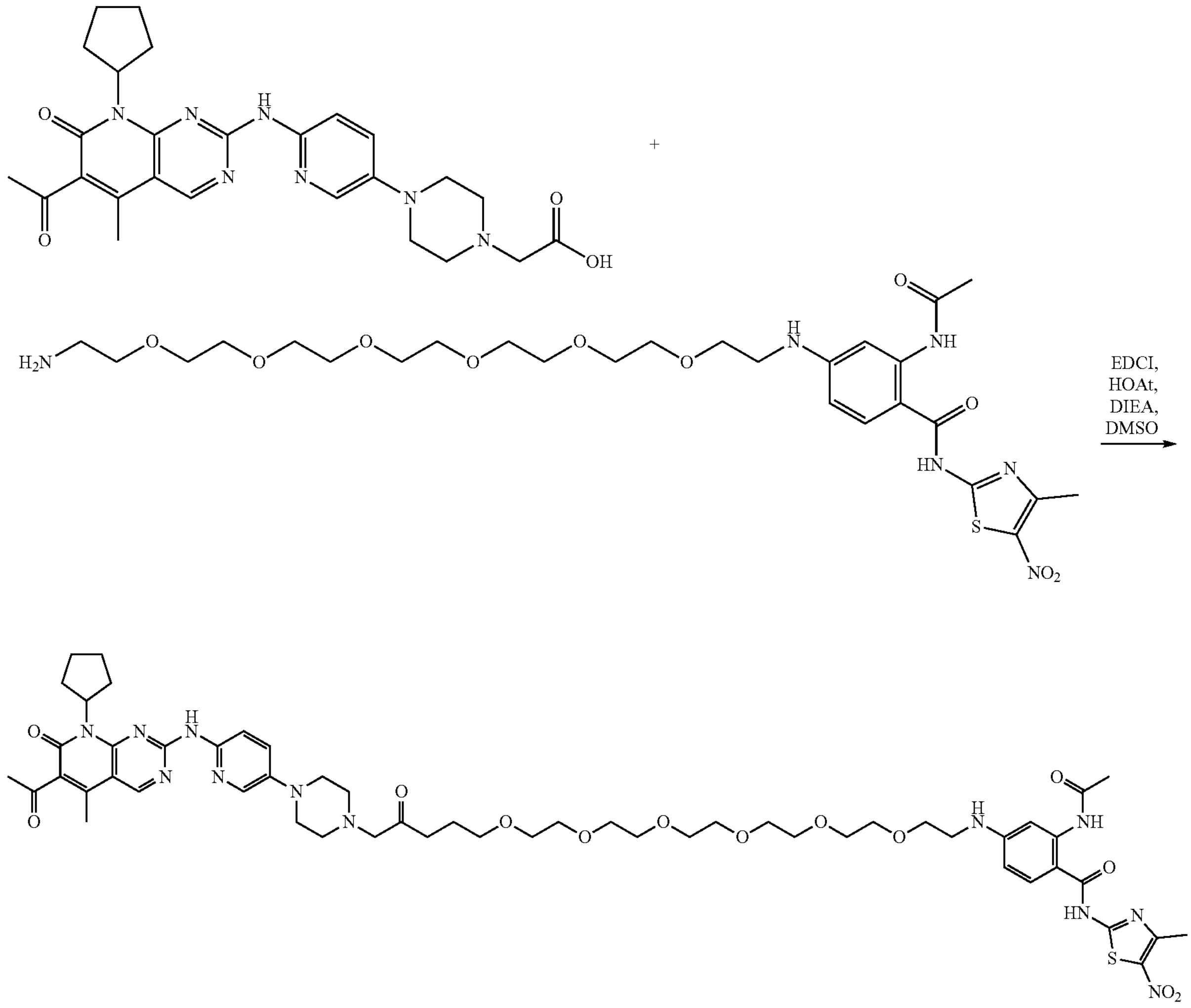

D-49 was synthesized following the standard procedure for preparing D-44 (4.11 mg, 36.8% yield). MS (EST) m/z: 1130.6 $[M+H]^+$.

Example 195. (R)-2-Acetamido-4-((2-(2-(4-(6-(6-(2-(3-fluorophenyl)pyrrolidin-1-yl)imidazo[1,2-b]pyridazin-3-yl)pyridin-2-yl)piperazin-1-yl)acetamido)ethyl)amino)-N-(4-methyl-5-nitrothiazol-2-yl)benzamide (D-14)

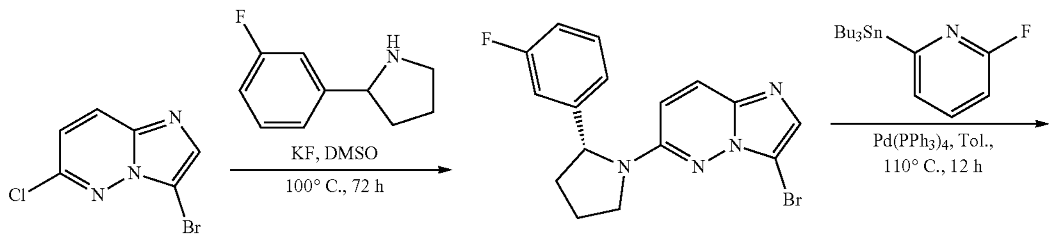

-continued
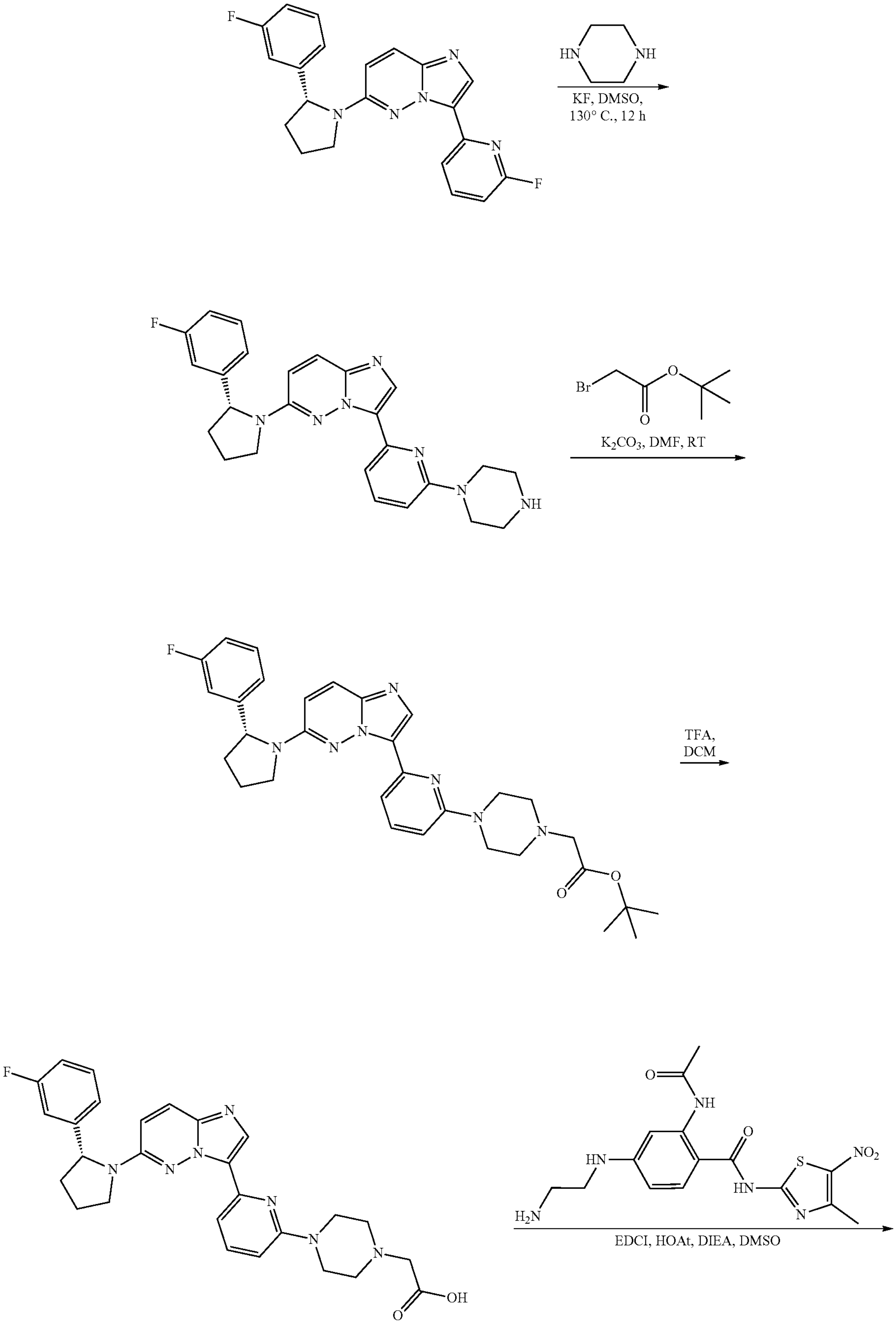

-continued

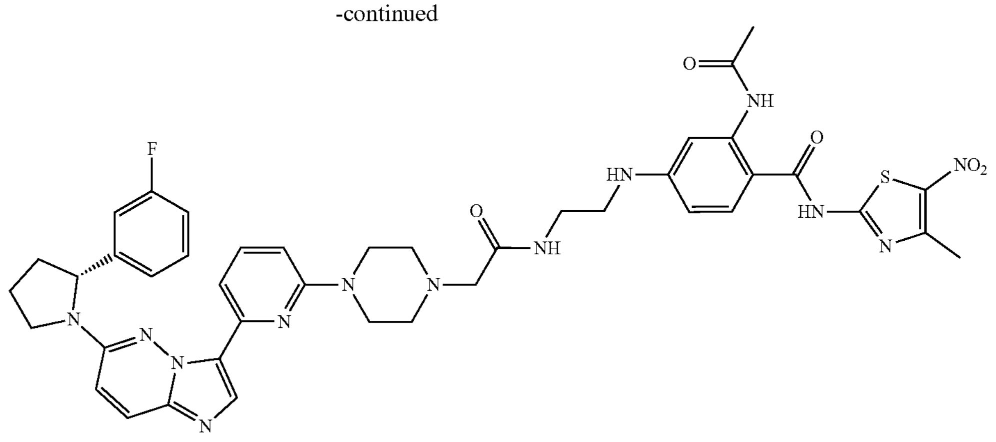

Step 1. Synthesis of (R)-3-bromo-6-(2-(3-fluorophenyl)pyrrolidin-1-yl)imidazo[1,2-b]pyridazine

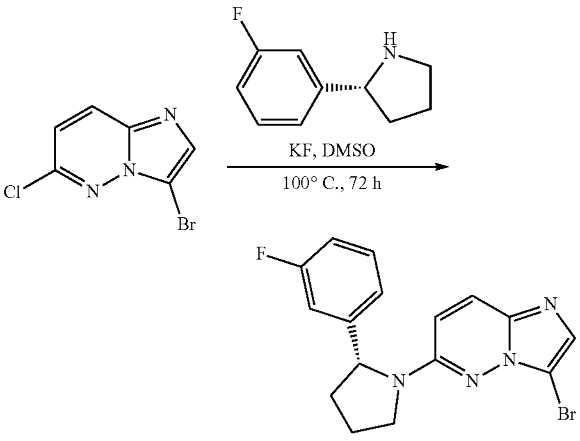

To a solution of 3-bromo-6-chloroimidazo[1,2-b]pyridazine (4.6 g, 20.0 mmol) in dimethylsuphoxide (40 mL) were added potassium fluoride (20 g, 362 mmol) and (R)-2-(3-fluorophenyl)pyrrolidine (3 g, 18.2 mmol). The resulting mixture was stirred at 100° C. for 12 h. The mixture was diluted with EtOAc, and washed with water. The organic layer was concentrated and the residue was purified by column chromatography (100% EtOAc) to give (R)-3-bromo-6-(2-(3-fluorophenyl)pyrrolidin-1-yl)imidazo[1,2-b]pyridazine (1.8 g, 28% yield) as yellow solid. MS (ESI) m/z: 360.9 $[M+H]^+$.

Step 2. Synthesis of (R)-6-(2-(3-fluorophenyl)pyrrolidin-1-yl)-3-(6-fluoropyridin-2-yl)imidazo[1,2-b]pyridazine

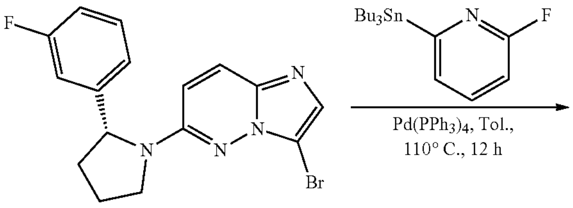

-continued

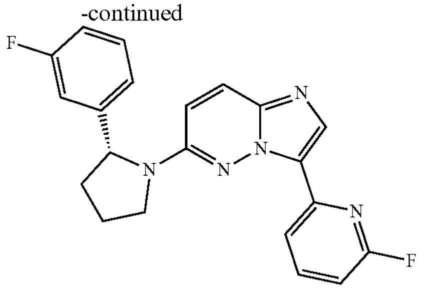

To a solution of (R)-3-bromo-6-(2-(3-fluorophenyl)pyrrolidin-1-yl)imidazo[1,2-b]pyridazine (2.17 g, 6.03 mmol) in toluene (50 mL) were added 2-fluoro-6-(tributylstannyl)pyridine (3.5 g, 9.04 mmol) and tetrakis(triphenylphosphine)palladium (566 mg, 0.49 mmol). The resulting mixture was stirred at 110° C. for 12 h under nitrogen atmosphere, before it was poured into EtOAc and sat. potassium fluoride. After being stirred at rt for 2 h, the mixture was extracted with EtOAc. The combined organic layers were concentrated and purified by column chromatography (hexanes:EtOAc=1:1 to 0:1) to give (R)-6-(2-(3-fluorophenyl)pyrrolidin-1-yl)-3-(6-fluoropyridin-2-yl)imidazo[1,2-b]pyridazine (2.2 g, 97% yield) as yellow oil. MS (ESI) m/z 378.0 $[M+H]^+$.

Step 3. Synthesis of (R)-6-(2-(3-fluorophenyl)pyrrolidin-1-yl)-3-(6-(piperazin-1-yl)pyridin-2-yl)imidazo[1,2-b]pyridazine

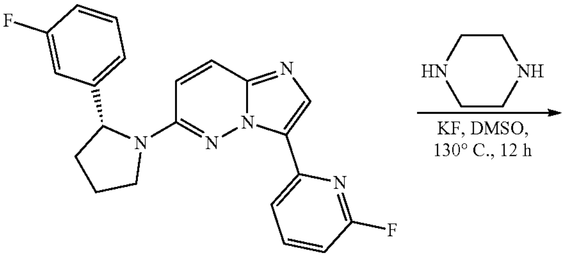

-continued

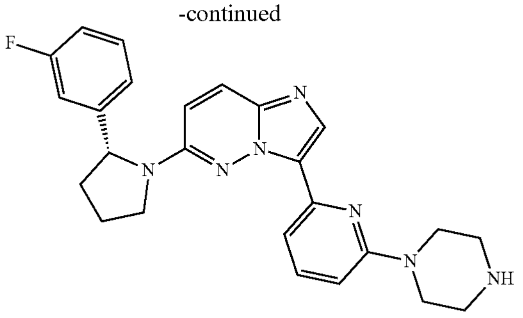

To a solution of (R)-6-(2-(3-fluorophenyl)pyrrolidin-1-yl)-3-(6-fluoropyridin-2-yl)imidazo [1,2-b]pyridazine (5, 1.4 g, 3.7 mmol) in dimethylsuphoxide (40 mL) was added piperazine (6.4 g, 74 mmol), followed by potassium fluoride (8.6 g, 148 mmol). The resulting mixture was stirred at 130° C. for 12 h, before it was poured into water and extracted with EtOAc. The combined organic layers were washed with water, concentrated and purified by column chromatography (DCM:MeOH=10:1 to 5:1) to give desired product as yellow oil, which was dissolved in hydrochloric acid in EtOAc (4 M), and stirred for 1 h. The mixture was concentrated to give (R)-6-(2-(3-fluorophenyl)pyrrolidin-1-yl)-3-(6-(piperazin-1-yl)pyridin-2-yl)imidazo[1,2-b]pyridazine (1.168 g, 66% yield) as yellow solid. $^1$H NMR (400 MHz, DMSO-$d_6$): δ 9.62 (s, 2H), 8.63 (s, 1H), 8.21 (s, 1H), 7.62-7.19 (m, 6H), 7.06-7.01 (m, 2H), 5.26-5.25 (m, 1H), 4.07-4.02 (m, 1H), 3.86-3.85 (m, 4H), 3.74-3.72 (m, 1H), 3.16-3.15 (m, 4H), 2.08-2.07 (m, 2H), 1.92-1.91 (m, 2H). MS (ESI) m/z: 444.2 [M+H]$^+$.

Step 4. Synthesis of tert-butyl (R)-2-(4-(6-(6-(2-(3-fluorophenyl)pyrrolidin-1-yl)imidazo[1,2-b]pyridazin-3-yl)pyridin-2-yl)piperazin-1-yl)acetate

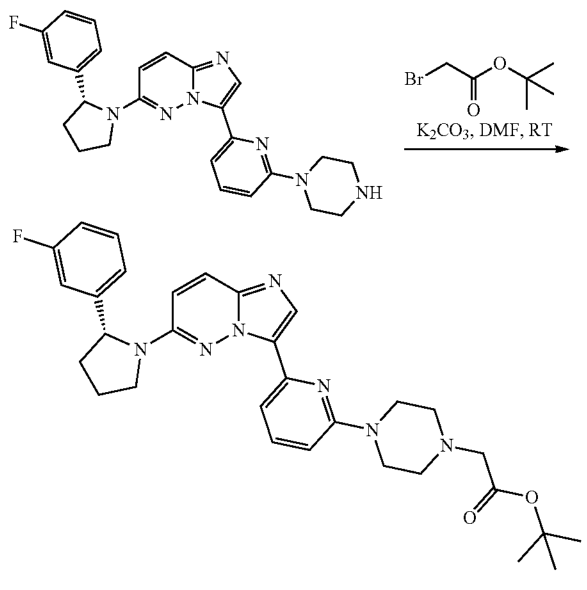

To a solution of (R)-6-(2-(3-fluorophenyl)pyrrolidin-1-yl)-3-(6-(piperazin-1-yl)pyridine-2-yl)imidazo[1,2-b] pyridazine (1 g, 2.25 mmol) in DMF (40 ml) were added $K_2CO_3$ (621 mg, 4.50 mmol) and tert-butyl 2-bromoacetate (510 mg, 2.60 mmol). The resulting mixture was stirred at rt for 3 h, at which time the reaction was poured into water (300 mL) and extracted with EtOAc (3x50 mL). The combined organic layers were washed with saturated brine (100 mL) and dried over anhydrous sodium sulfate. After filtration, the filtrate was concentrated under reduced pressure. The resulting residue was purified by silica gel column chromatography to give tert-butyl (R)-2-(4-(6-(6-(2-(3-fluoro phenyl)pyrrolidin-1-yl) imidazo[1,2-b]pyridazin-3-yl)pyridin-2-yl)piperazin-1-yl)acetate (1.05 g, 84% yield) as a light yellow solid. MS (ESI) m/z: 558.7 [M+H]$^+$.

Step 5. Synthesis of (R)-2-(4-(6-(6-(2-(3-fluorophenyl)pyrrolidin-1-yl)imidazo[1,2-b]pyridazin-3-yl) pyridin-2-yl)piperazin-1-yl)acetic acid

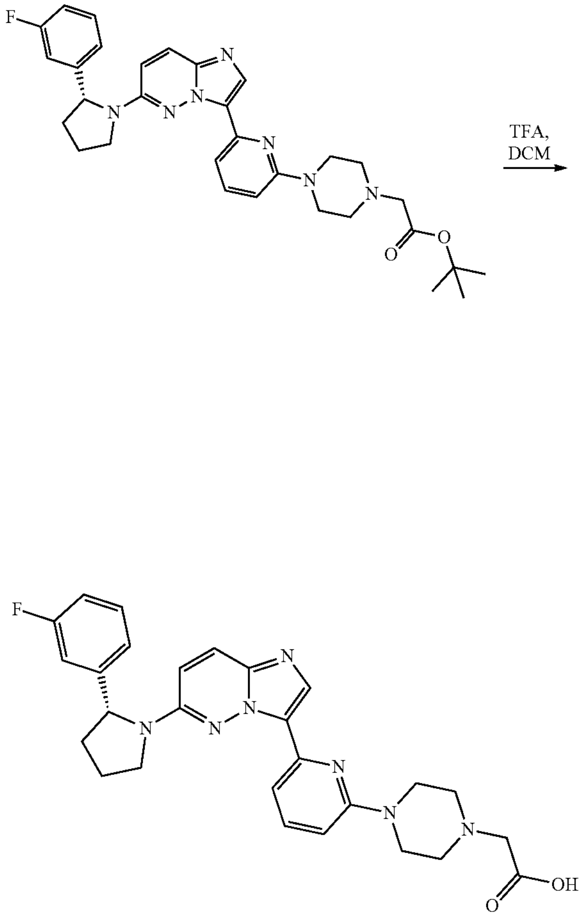

To a solution of tert-butyl (R)-2-(4-(6-(6-(2-(3-fluorophenyl)pyrrolidin-1-yl)imidazo[1,2-b]pyridazin-3-yl)pyridin-2-yl)piperazin-1-yl)acetate (1 g, 1.79 mmol) in dichloromethane (20 ml) was added trifluoroacetic acid (20 mL). The resulting mixture was stirred at rt for 3 h. After the starting material was totally consumed, the reaction was evaporated under reduced pressure. The resulting residue was purified by reverse-phase chromatography to give (R)-2-(4-(6-(6-(2-(3-fluorophenyl)pyrrolidin-1-yl)imidazo[1,2-b] pyridazin-3-yl)pyridin-2-yl)piperazin-1-yl)acetic acid (860 mg, 96% yield) as a light yellow solid. MS (ESI) m/z: 502.6 [M+H]$^+$.

Step 6. Synthesis of (R)-2-acetamido-4-((2-(2-(4-(6-(6-(2-(3-fluorophenyl)pyrrolidin-1-yl)imidazo[1,2-b]pyridazin-3-yl)pyridin-2-yl)piperazin-1-yl)acetamido)ethyl)amino)-N-(4-methyl-5-nitrothiazol-2-yl)benzamide

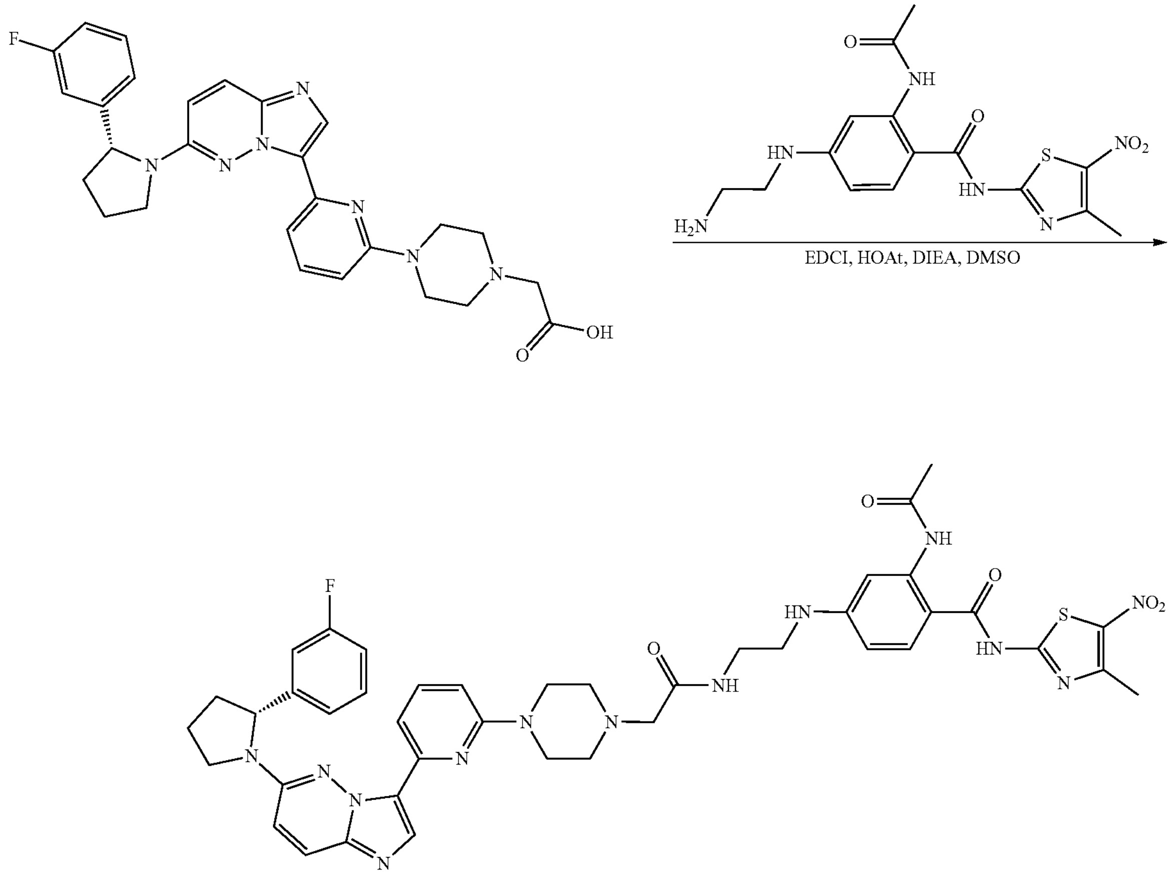 [SMILES: O=C(O)CN1CCN(c2cccc(-c3cnc4ccc(N5CCC[C@@H]5c5cccc(F)c5)nn34)n2)CC1 ; CC(=O)Nc1cc(NCCN)ccc1C(=O)Nc1nc(C)c([N+](=O)[O-])s1 ; CC(=O)Nc1cc(NCCNC(=O)CN2CCN(c3cccc(-c4cnc5ccc(N6CCC[C@@H]6c6cccc(F)c6)nn45)n3)CC2)ccc1C(=O)Nc1nc(C)c([N+](=O)[O-])s1]

A solution of (R)-2-(4-(6-(6-(2-(3-fluorophenyl)pyrrolidin-1-yl)imidazo[1,2-b]pyridazin-3-yl)pyridin-2-yl)piperazin-1-yl)acetic acid (4 mg, 0.0079 mmol), HOAt (5 mg, 0.039 mmol), EDCI (7.6 mg, 0.039 mmol), DIEA (10 mg, 0.08 mmol) and 2-acetamido-4-((2-aminoethyl)amino)-N-(4-methyl-5-nitrothiazol-2-yl)benzamide (3 mg, 0.008 mmol) in DMSO (1 ml) was stirred at rt overnight. Then the reaction solution was purified with reverse phase chromatography to give (R)-2-acetamido-4-((2-(2-(4-(6-(6-(2-(3-fluorophenyl)pyrrolidin-1-yl)imidazo[1,2-b]pyridazin-3-yl)pyridin-2-yl)piperazin-1-yl)acetamido)ethyl)amino)-N-(4-methyl-5-nitrothiazol-2-yl)benzamide (2 mg, 29.4% yield) as yellow solid. MS (ESI) m/z: 862.5 $[M+H]^+$.

Example 196. (R)-2-Acetamido-4-((4-(2-(4-(6-(6-(2-(3-fluorophenyl)pyrrolidin-1-yl)imidazo[1,2-b]pyridazin-3-yl)pyridin-2-yl)piperazin-1-yl)acetamido)butyl)amino)-N-(4-methyl-5-nitrothiazol-2-yl)benzamide (D-15)

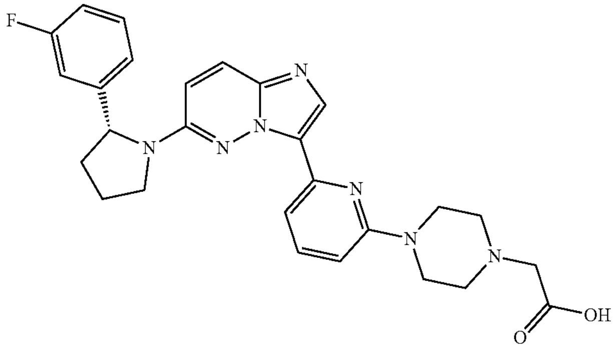

+

-continued
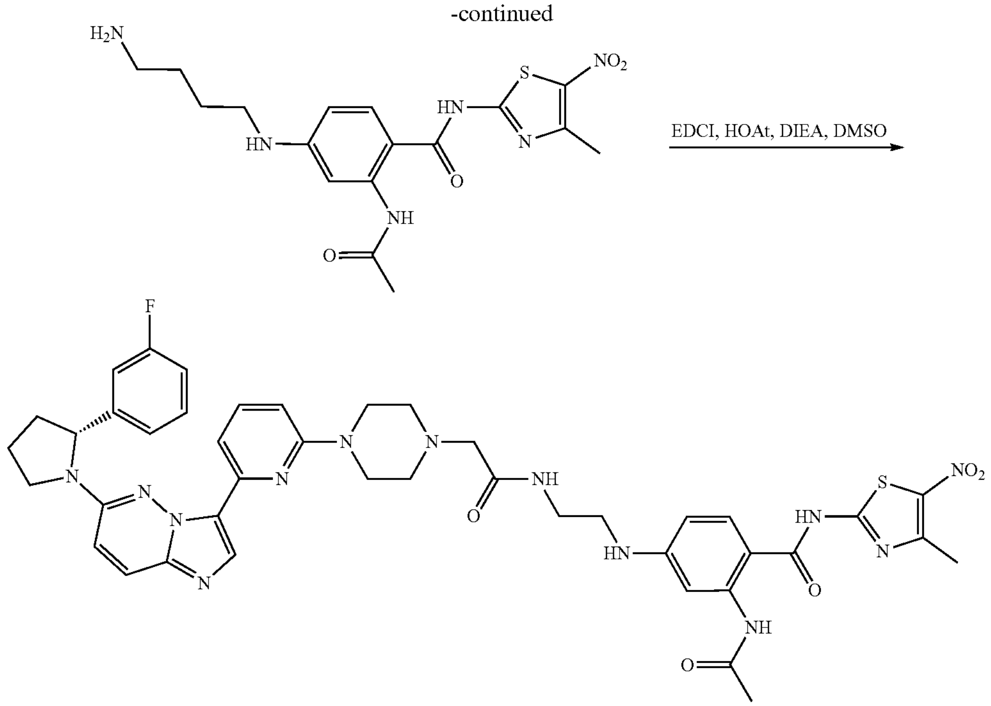
D-15 was synthesized following the standard procedure for preparing D-14 (4.4 mg, 62.5% yield). MS (EST) m/z: 890.5 $[M+H]^+$.
Example 197. (R)-2-Acetamido-4-((6-(2-(4-(6-(6-(2-(3-fluorophenyl)pyrrolidin-1-yl)imidazo[1,2-b]pyridazin-3-yl)pyridin-2-yl)piperazin-1-yl)acetamido)hexyl)amino)-N-(4-methyl-5-nitrothiazol-2-yl)benzamide (D-16)
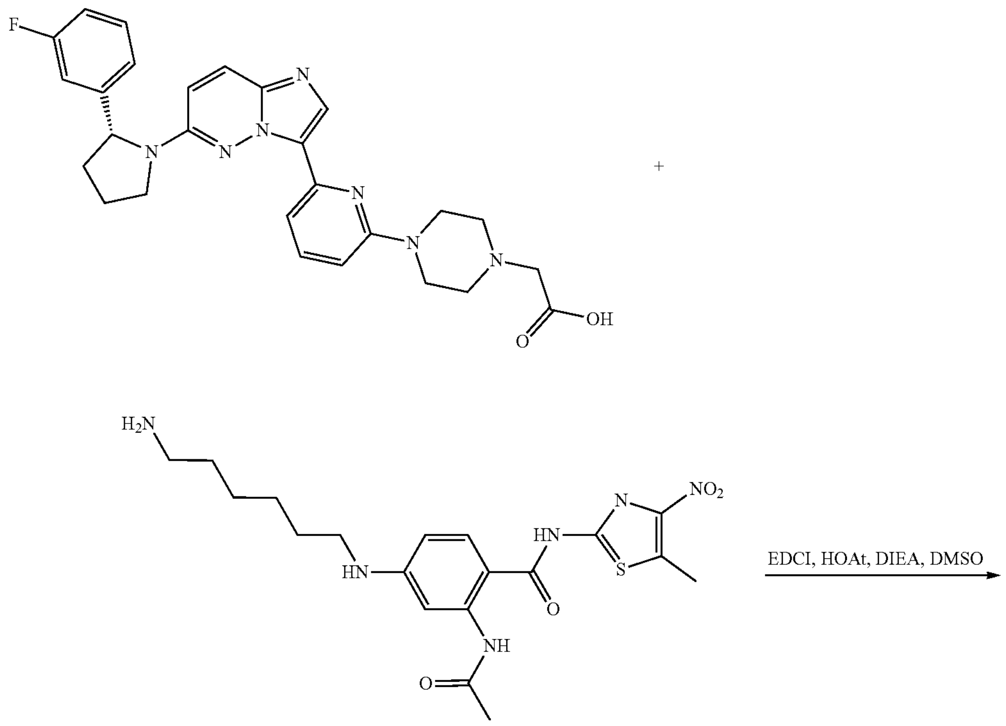

-continued
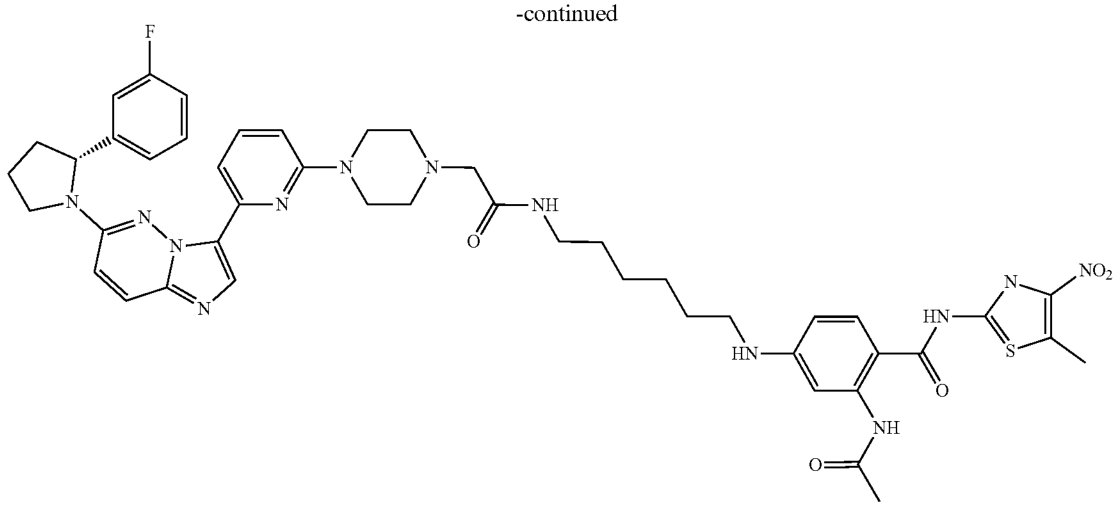
D-16 was synthesized following the standard procedure for preparing D-14 (3 mg, 41.3% yield). MS (EST) m/z: 918.6 [M+H]+.
Example 198. (R)-2-Acetamido-4-((7-(2-(4-(6-(6-(2-(3-fluorophenyl)pyrrolidin-1-yl)imidazo[1,2-b]pyridazin-3-yl)pyridin-2-yl)piperazin-1-yl)acetamido)heptyl)amino)-N-(4-methyl-5-nitrothiazol-2-yl)benzamide (D-17)
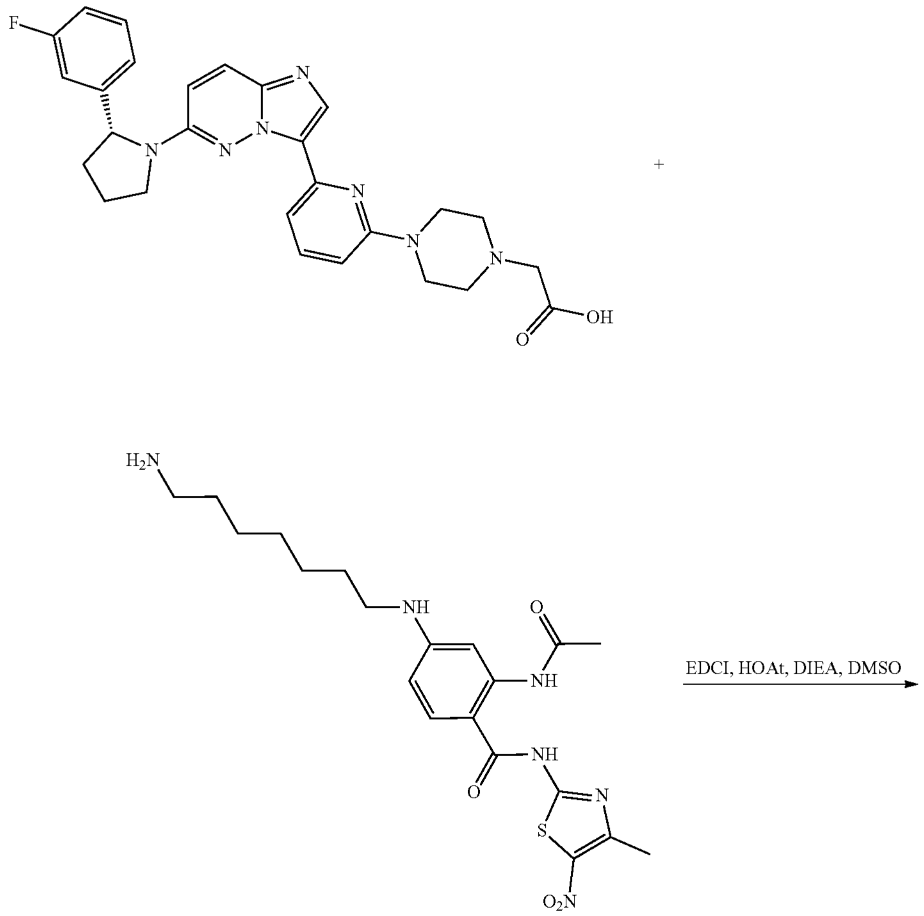

-continued
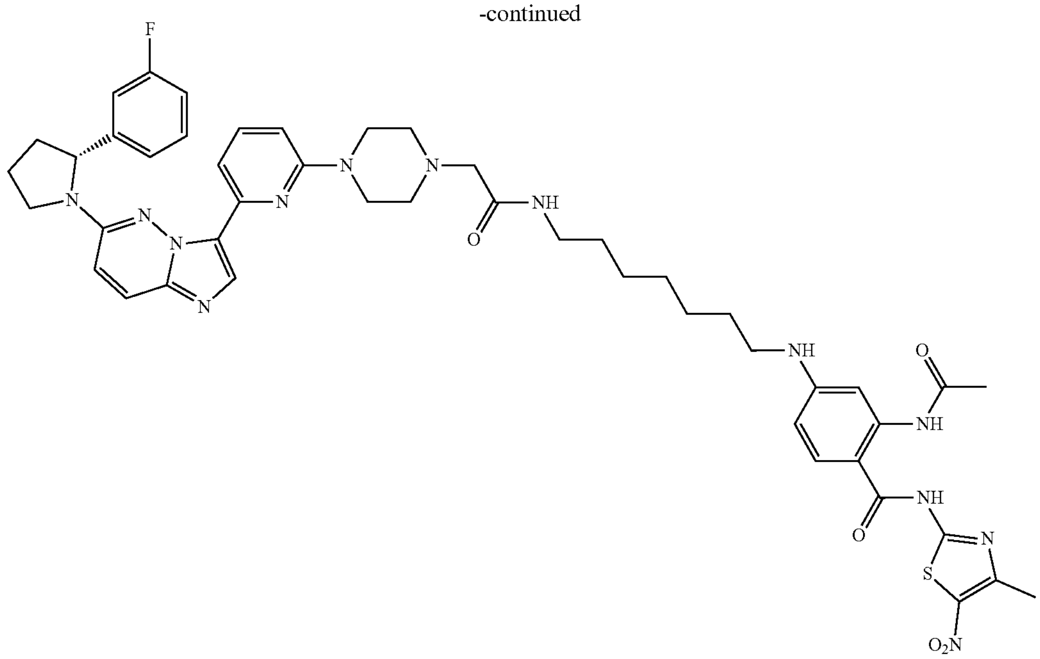
D-17 was synthesized following the standard procedure for preparing D-14 (3.6 mg, 48.8% yield). MS (EST) m/z: 932.7 $[M+H]^+$.
Example 199. (R)-2-Acetamido-4-((8-(2-(4-(6-(6-(2-(3-fluorophenyl)pyrrolidin-1-yl)imidazo[1,2-b]pyridazin-3-yl)pyridin-2-yl)piperazin-1-yl)acetamido)octyl)amino)-N-(4-methyl-5-nitrothiazol-2-yl)benzamide (D-18)
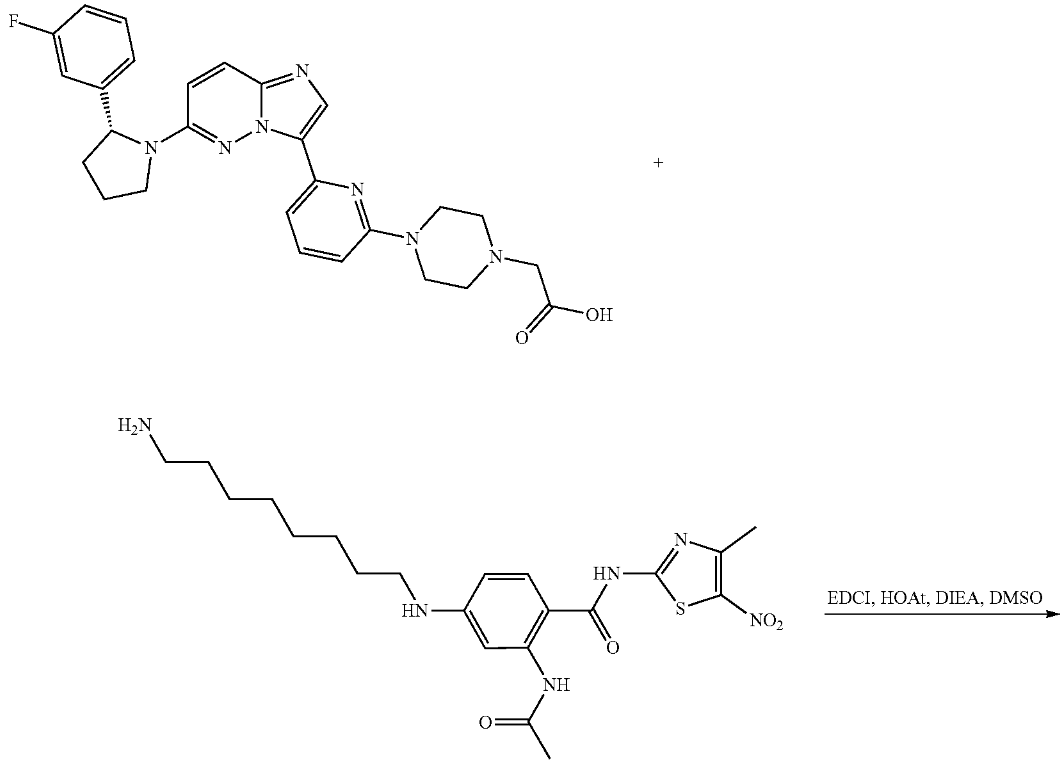

-continued
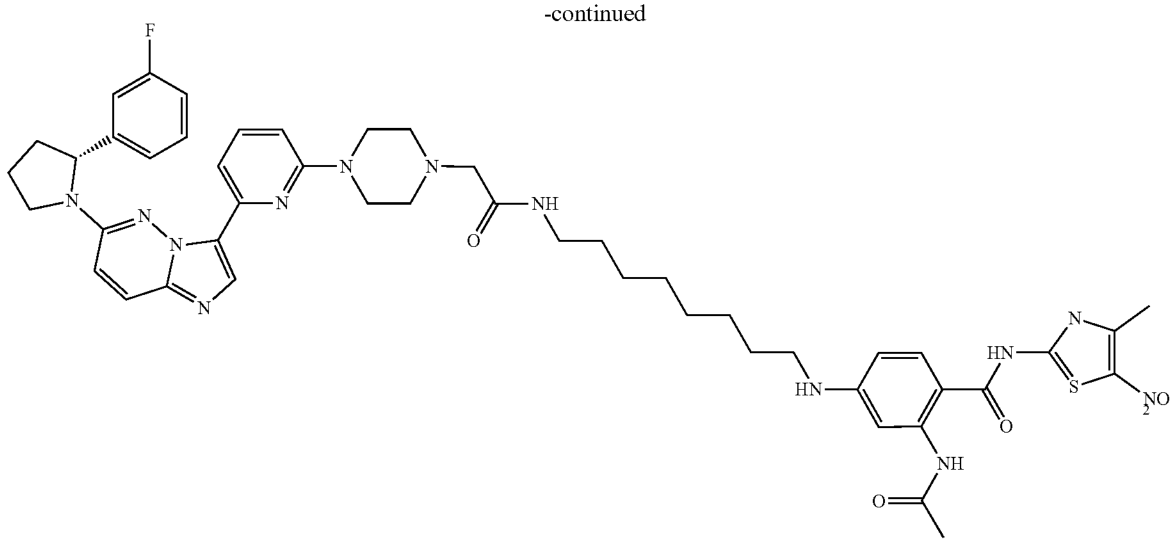
D-18 was synthesized following the standard procedure for preparing D-14 (3 mg, 40.1% yield). MS (EST) m/z: 946.6 [M+H]+
Example 200. (R)-2-Acetamido-4-((10-(2-(4-(6-(6-(2-(3-fluorophenyl)pyrrolidin-1-yl)imidazo[1,2-b]pyridazin-3-yl)pyridin-2-yl)piperazin-1-yl)acetamido)decyl)amino)-N-(4-methyl-5-nitrothiazol-2-yl)benzamide (D-19)
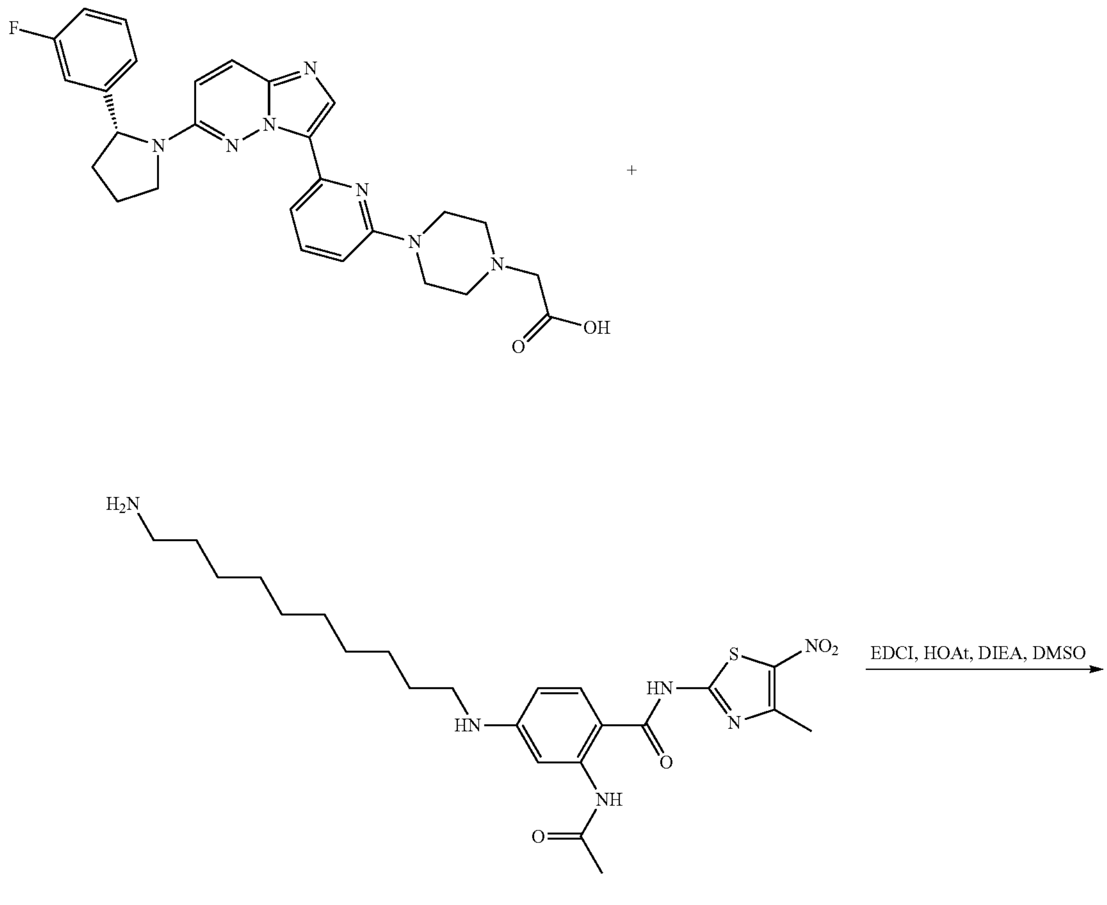

-continued
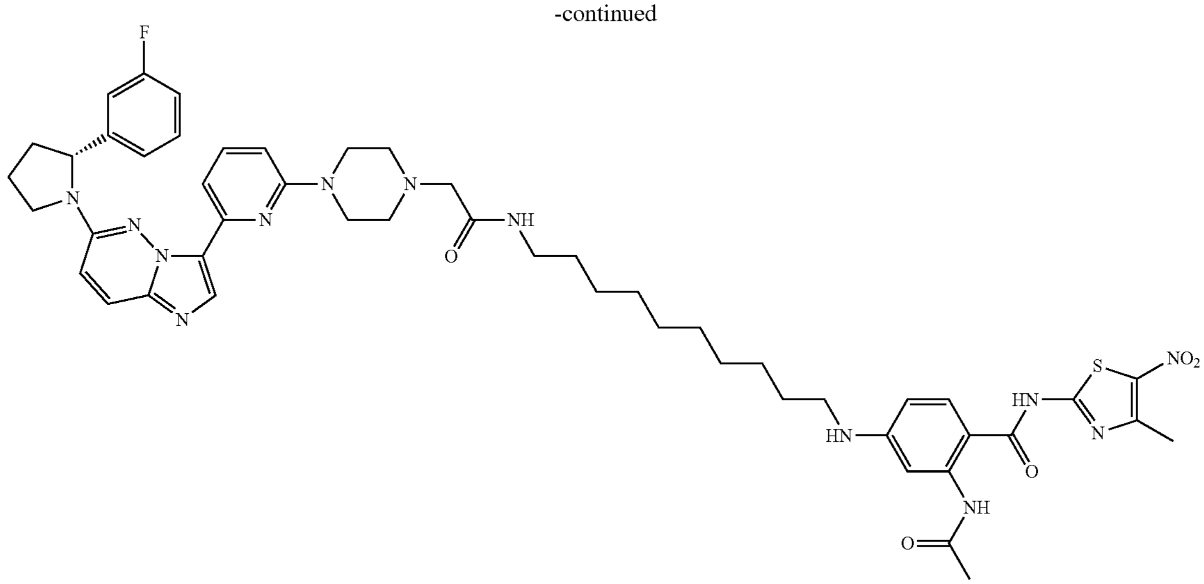
D-19 was synthesized following the standard procedure for preparing D-14 (3 mg, 38.9% yield). MS (EST) m/z: 974.7 $[M+H]^+$.
Example 201. (R)-2-Acetamido-4-((2-(2-(2-(4-(6-(6-(2-(3-fluorophenyl)pyrrolidin-1-yl)imidazo[1,2-b]pyridazin-3-yl)pyridin-2-yl)piperazin-1-yl)acetamido)ethoxy)ethyl)amino)-N-(4-methyl-5-nitrothiazol-2-yl)benzamide (D-20)
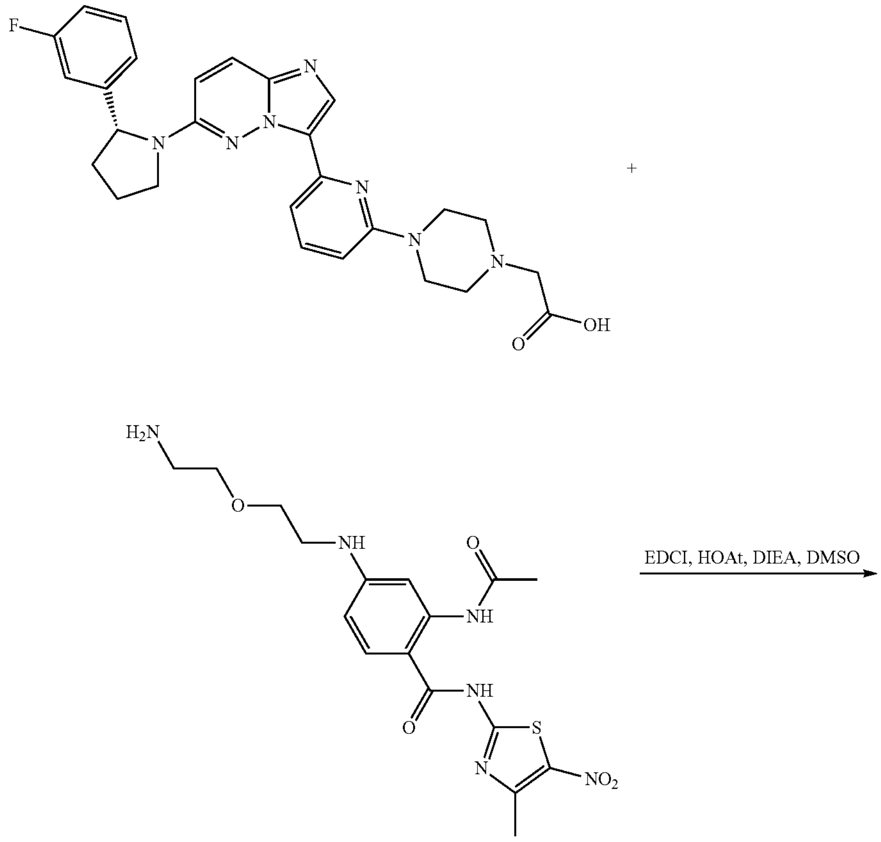

-continued
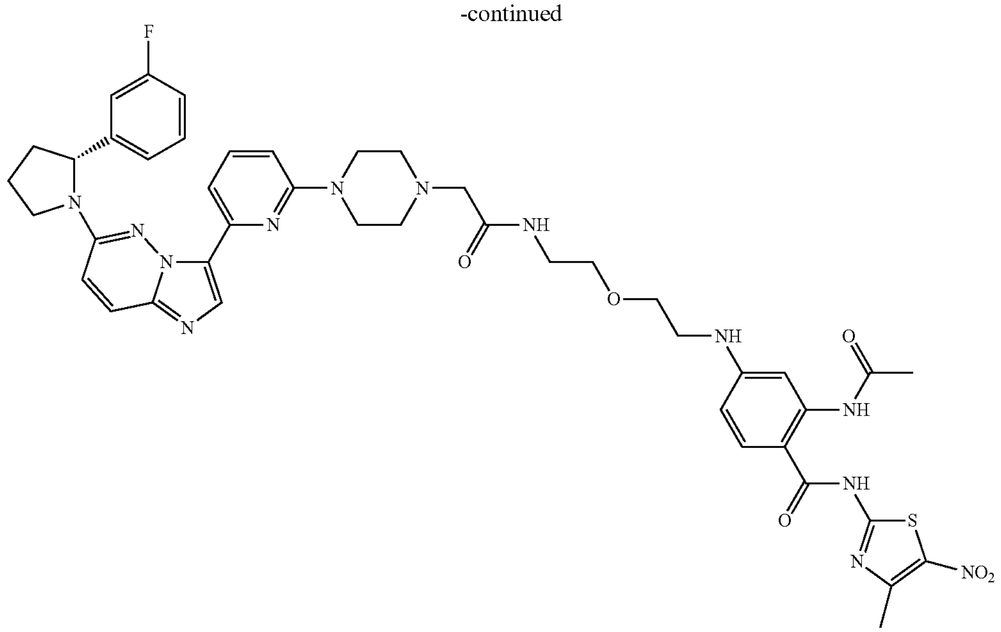
D-20 was synthesized following the standard procedure for preparing D-14 (5.5 mg, 76.8% yield). MS (EST) m/z: 906.5 $[M+H]^+$.
Example 202. (R)-2-Acetamido-4-((2-(2-(2-(2-(4-(6-(6-(2-(3-fluorophenyl)pyrrolidin-1-yl)imidazo[1,2-b]pyridazin-3-yl)pyridin-2-yl)piperazin-1-yl)acetamido)ethoxy)ethoxy)ethyl)amino)-N-(4-methyl-5-nitrothiazol-2-yl)benzamide (D-21)
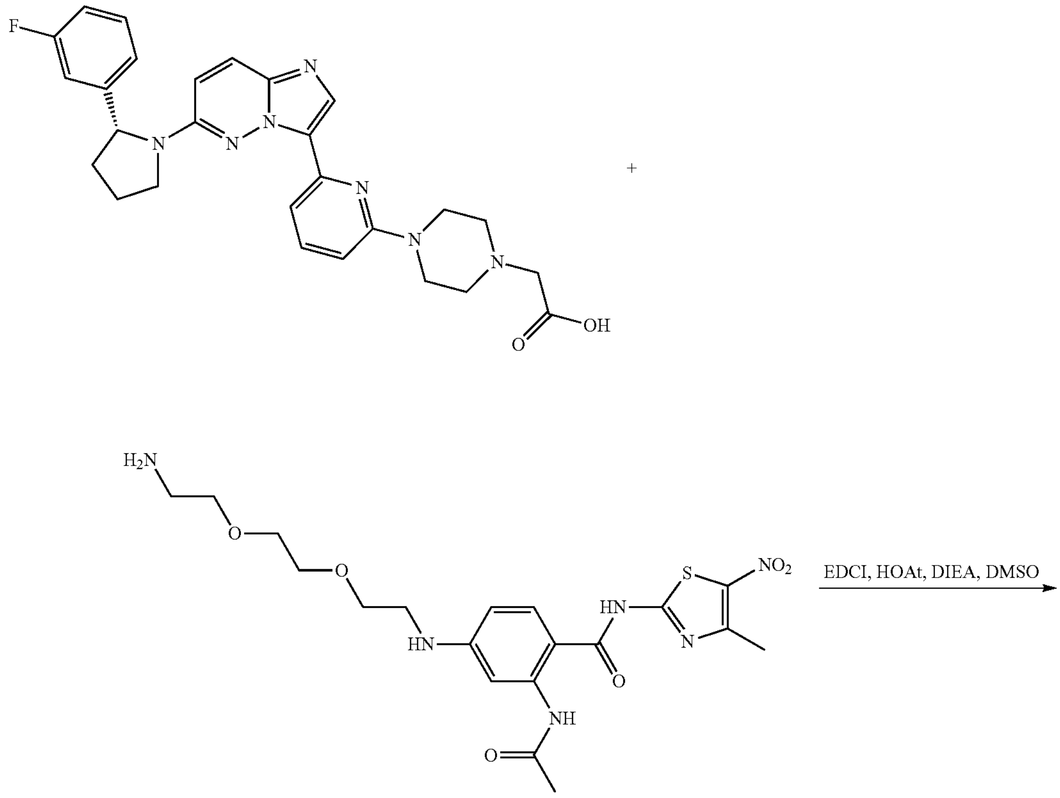

-continued
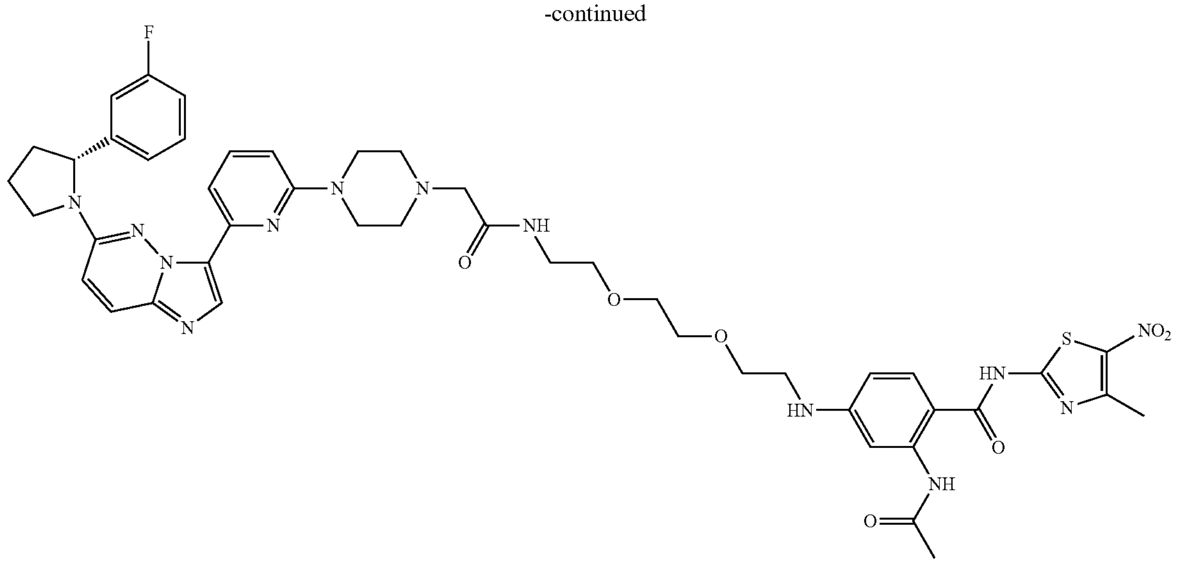
D-21 was synthesized following the standard procedure for preparing D-14 (3 mg, 39.9% yield). MS (ESI) m/z: 950.5 $[M+H]^+$.
Example 203. (R)-2-Acetamido-4-((1-(4-(6-(6-(2-(3-fluorophenyl)pyrrolidin-1-yl)imidazo[1,2-b]pyridazin-3-yl)pyridin-2-yl)piperazin-1-yl)-2-oxo-6,9,12-trioxa-3-azatetradecan-14-yl)amino)-N-(4-methyl-5-nitrothiazol-2-yl)benzamide (D-22)
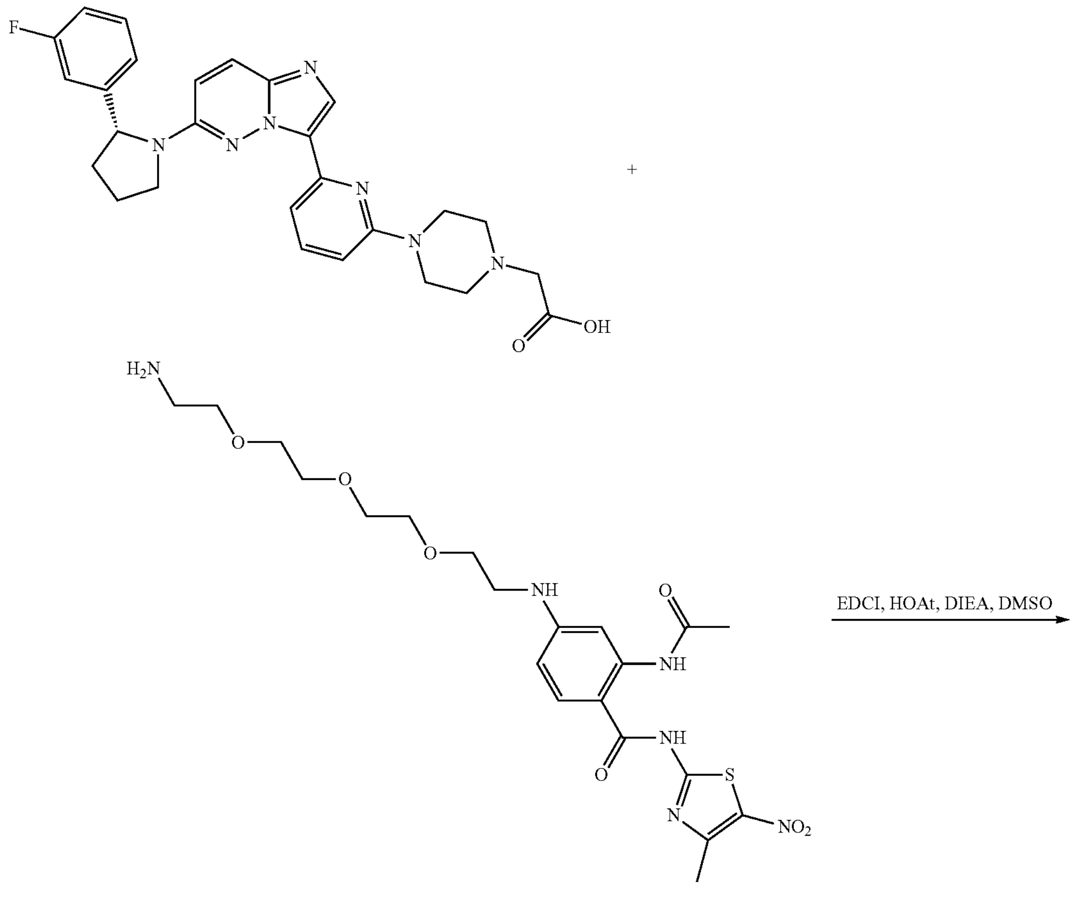

-continued
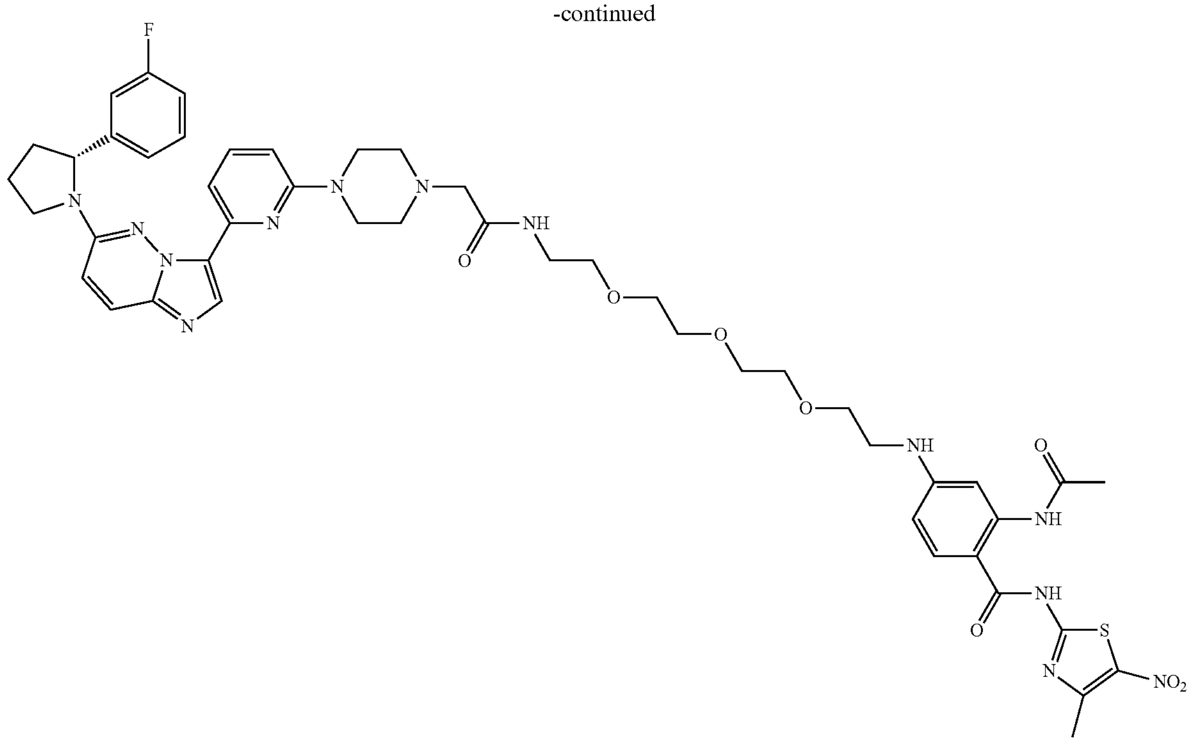
D-22 was synthesized following the standard procedure for preparing D-14 (3.5 mg, 44.5% yield). MS (EST) m/z: 994.6 [M+H]+.
Example 204. (R)-2-Acetamido-4-((1-(4-(6-(6-(2-(3-fluorophenyl)pyrrolidin-1-yl)imidazo[1,2-b]pyridazin-3-yl)pyridin-2-yl)piperazin-1-yl)-2-oxo-6,9,12,15-tetraoxa-3-azaheptadecan-17-yl)amino)-N-(4-methyl-5-nitrothiazol-2-yl)benzamide (D-23)
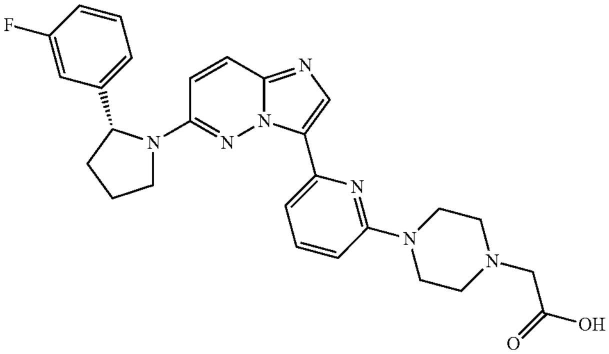
+

-continued
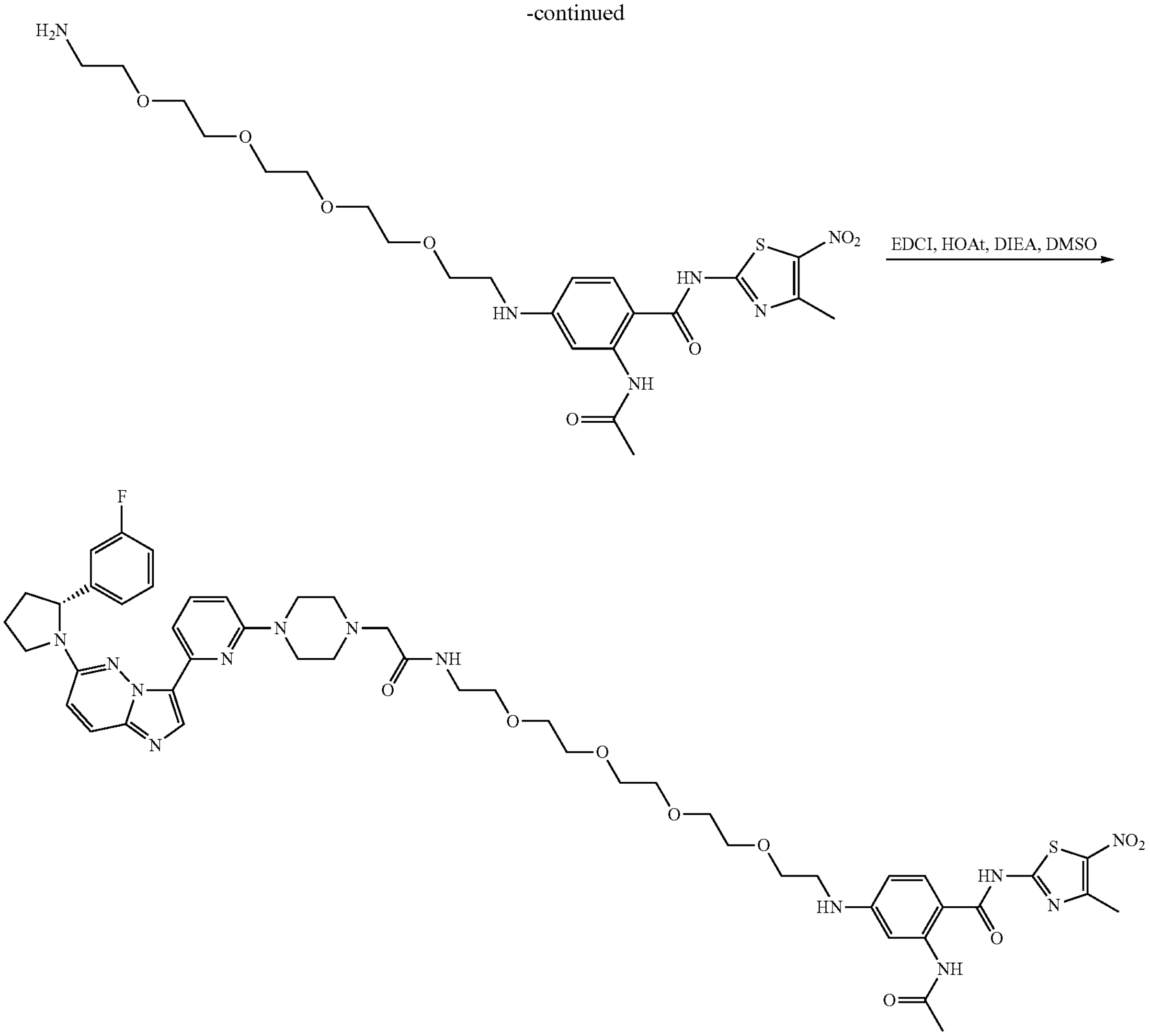
D-23 was synthesized following the standard procedure for preparing D-14 (3 mg, 36.5% yield). MS (EST) m/z: 1038.6 $[M+H]^+$.
Example 205. (R)-2-Acetamido-4-((1-(4-(6-(6-(2-(3-fluorophenyl)pyrrolidin-1-yl)imidazo[1,2-b]pyridazin-3-yl)pyridin-2-yl)piperazin-1-yl)-2-oxo-6,9,12,15,18-pentaoxa-3-azaicosan-20-yl)amino)-N-(4-methyl-5-nitrothiazol-2-yl)benzamide (D-24)
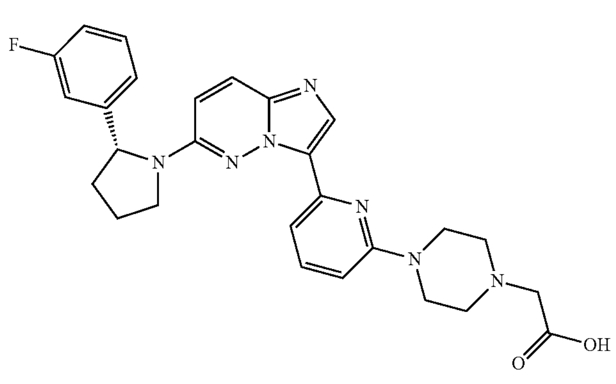
+

-continued
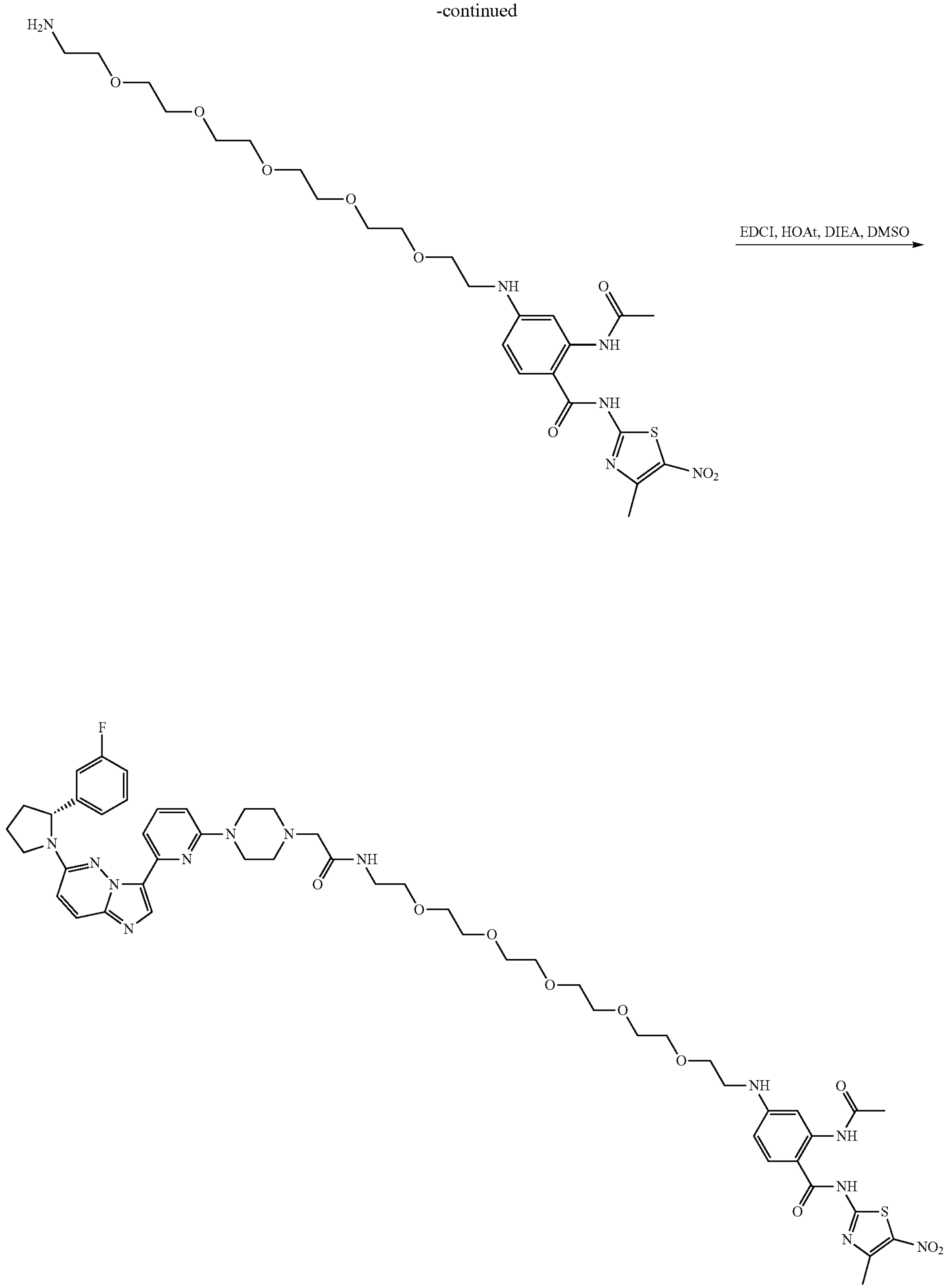
D-24 was synthesized following the standard procedure for preparing D-14 (3 mg, 35.1% yield). MS (EST) m/z: 1082.6 $[M+H]^+$.

Example 206. (R)-2-Acetamido-4-((1-(4-(6-(6-(2-(3-fluorophenyl)pyrrolidin-1-yl)imidazo[1,2-b]pyridazin-3-yl)pyridin-2-yl)piperazin-1-yl)-2-oxo-6,9,12,15,18,21-hexaoxa-3-azatricosan-23-yl)amino)-N-(4-methyl-5-nitrothiazol-2-yl)benzamide (D-25)
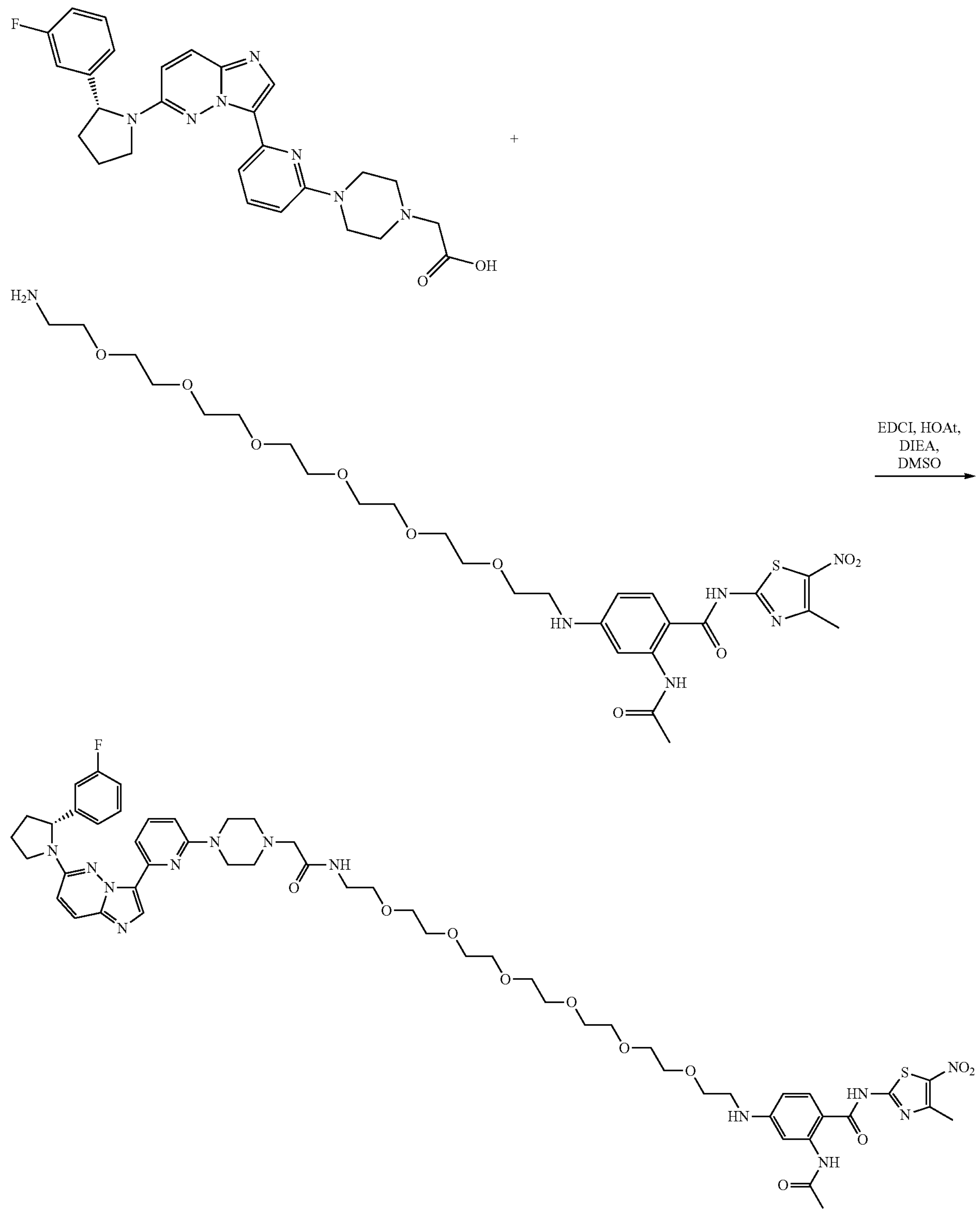
D-25 was synthesized following the standard procedure for preparing D-14 (3 mg, 33.7% yield). MS (EST) m/z: 1126.7 [M+H]$^+$.

Example 207. 2-Acetamido-4-((2-(2-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)ethoxy)ethyl)amino)-N-(4-methyl-5-nitrothiazol-2-yl)benzamide (D-56)
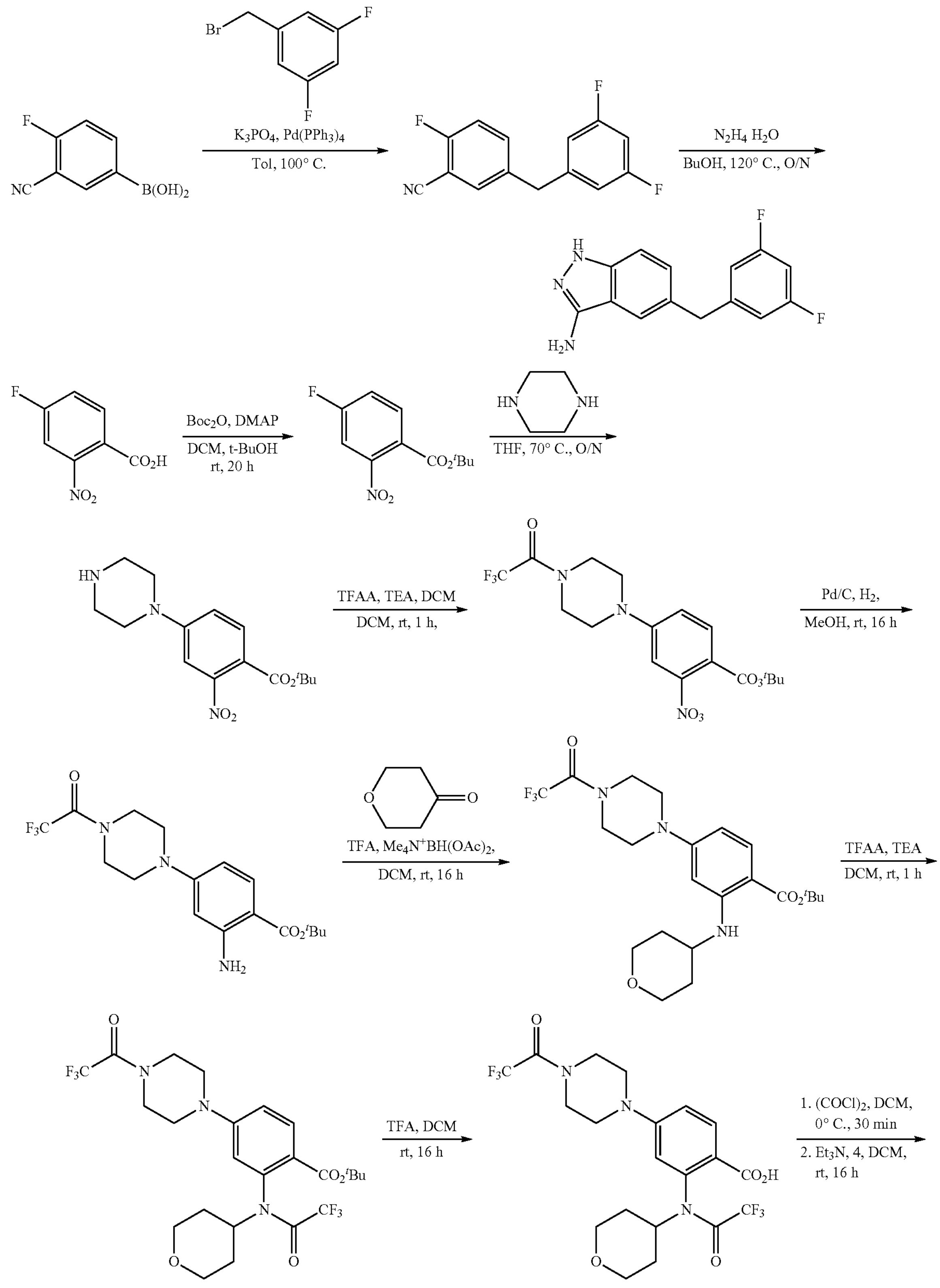

-continued
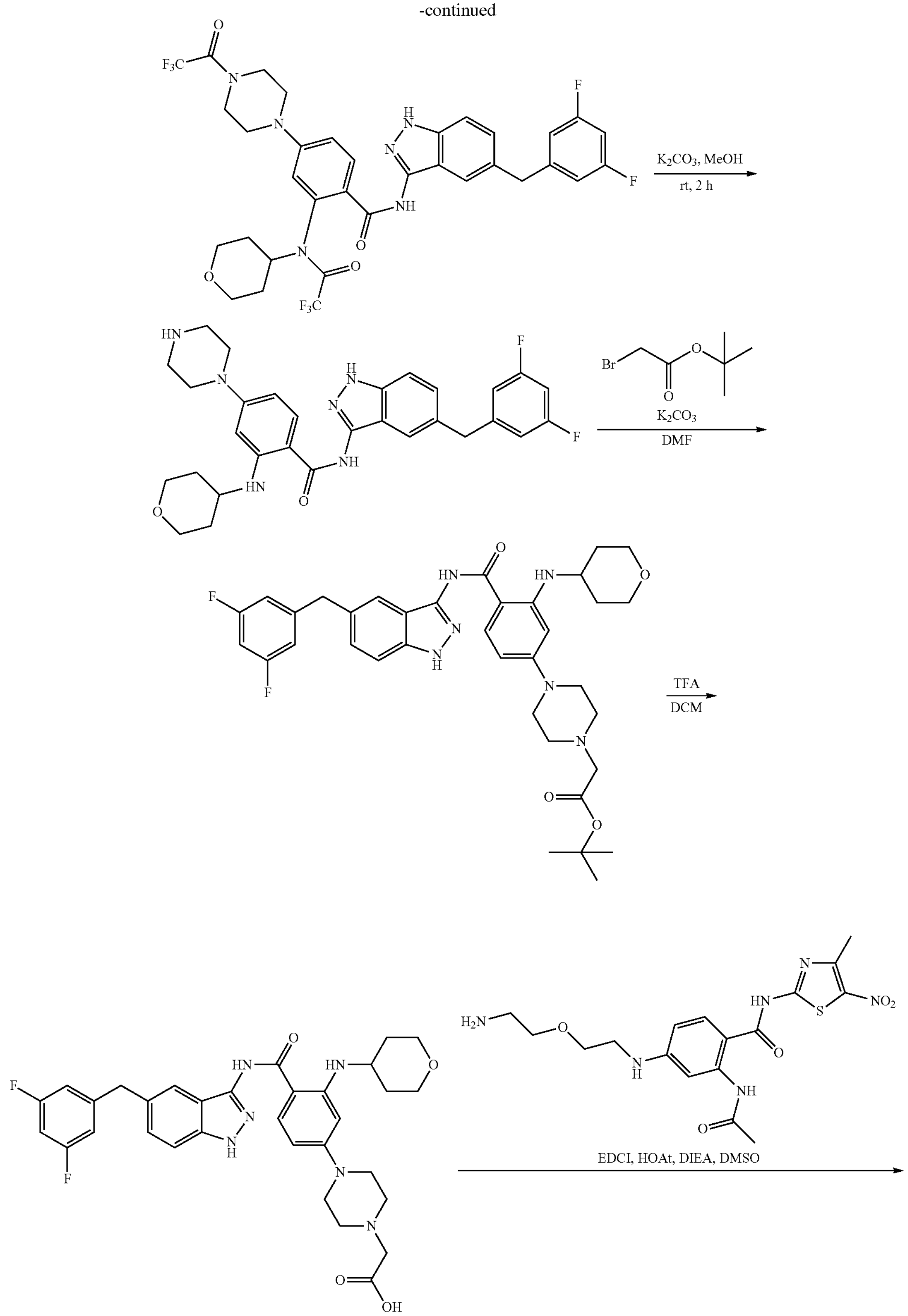

-continued

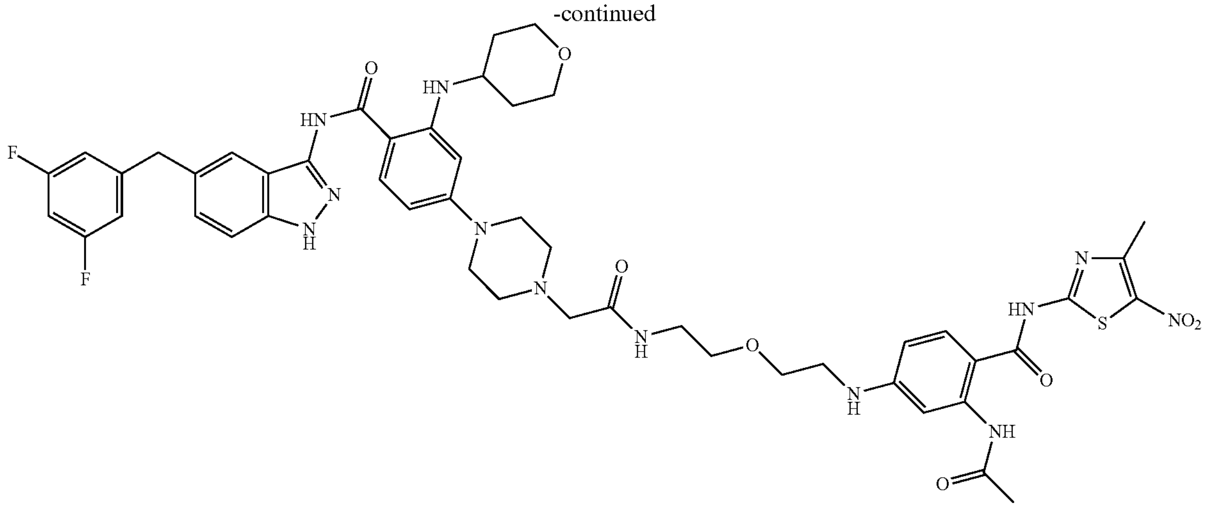

Step 1. Synthesis of 5-(3,5-difluorobenzyl)-2-fluorobenzonitrile

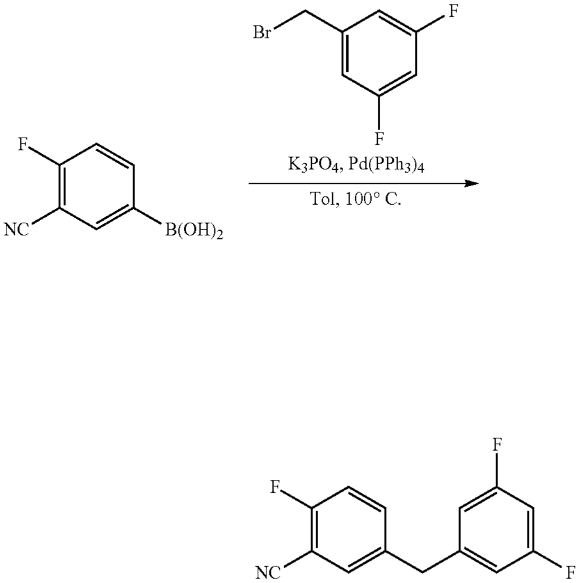

To a solution of 3-cyano-4-fluorophenylboronic acid (3.3 g, 20 mmol) in toluene (30 mL) were added potassium phosphate (8.5 g, 40 mmol) and tetrakis(triphenylphosphine)palladium (462 mg, 0.4 mmol), followed by 3,5-difluorobenzyl bromide (4.2 g, 10 mmol). The reaction mixture was heated to 100° C. for 2 h. After the reaction was completion, the resulting black mixture was diluted with ether (200 mL), washed with saturated aqueous ammonium chloride (2×50 mL), brine (3×50 mL), dried over sodium sulphate, evaporated and purified by silica gel flash chromatography (n-hexane:EtOAc=95:5) to yield 5-(3,5-difluorobenzyl)-2-fluorobenzonitrile (2.9 g, 59% yield) as white solid. $^1$H NMR (400 MHz, DMSO-$d_6$) 7.90 (dd, J=6.0 Hz, 2.0 Hz, 1H), 7.73-7.69 (m, 1H), 7.46 (t, J=8.8 Hz, 1H), 7.09-7.04 (m, 3H), 4.01 (s, 2H). MS (EST) m/z: 248.2 $[M+H]^+$.

Step 2. Synthesis of 5-(3,5-difluorobenzyl)-1H-indazol-3-amine

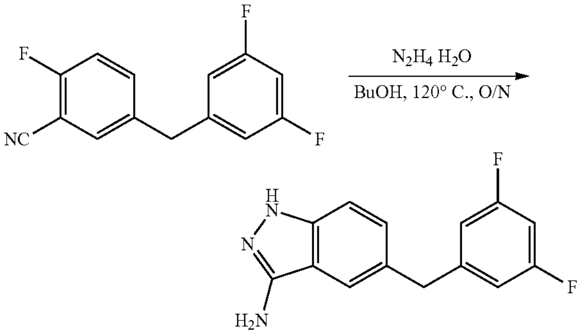

A mixture of 5-(3,5-difluoro-benzyl)-2-fluoro-benzonitrile (2.9 g, 11.74 mmol) and hydrazine hydrate (1.76 mL, 35.22 mmol) in n-butanol (200 mL) was heated at 120° C. overnight. The reaction mixture was diluted with water and EtOAc. The organic phase was washed with brine (2×), dried and concentrated. The resulting residue was purified by silica gel column chromatography (DCM:MeOH=95:5) to afforded 5-(3,5-difluorobenzyl)-1H-indazol-3-amine (2.7 g, 89% yield) as white solid. $^1$H NMR (400 MHz, DMSO-$d_6$) δ 11.32 (s, 1H), 7.52 (s, 1H), 7.18-7.11 (m, 2H), 7.04 (t, J=9.6 Hz, 1H), 6.95-6.93 (m, 2H), 5.26 (s, 2H), 4.00 (s, 2H). MS (ESI) m/z: 260.0 $[M+H]^+$.

Step 3. Synthesis of tert-butyl 4-fluoro-2-nitrobenzoate

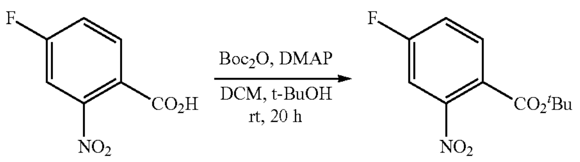 [SMILES: O=C(O)c1ccc(F)cc1[N+](=O)[O-] ; CC(C)(C)OC(=O)c1ccc(F)cc1[N+](=O)[O-]]

A solution of 4-fluoro-2-nitro-benzoic acid (10 g, 54 mmol), di-tert-butyl-dicarbonate (23.6 g, 108 mmol) and 4-dimethylaminopyridine (1.98 g, 16.2 mmol) in tert-butanol (100 mL) and dichloromethane (100 mL) was stirred at rt overnight. The reaction mixture was then diluted with EtOAc (500 mL), washed with 1 N hydrochloric acid (500 mL), water (500 mL), and brine (500 mL), dried over sodium sulfate, concentrated and purified by silica gel column chromatography (DCM:MeOH=20:1) to afford tert-butyl 4-fluoro-2-nitrobenzoate as yellow solid (10.7 g, 82% yield). $^1H$ NMR (400 MHz, DMSO-$d_6$): δ 8.04 (dd, J=8.4 Hz, 2.8 Hz, 1H), 7.94 (dd, J=8.8 Hz, 1.6 Hz, 1H), 7.71 (dd, J=8.4 Hz, 2.4 Hz, 1H), 1.50 (s, 9H). MS (ESI) m/z 242.2 $[M+H]^+$.

Step 4. Synthesis of tert-butyl 2-nitro-4-(piperazin-1-yl)benzoate

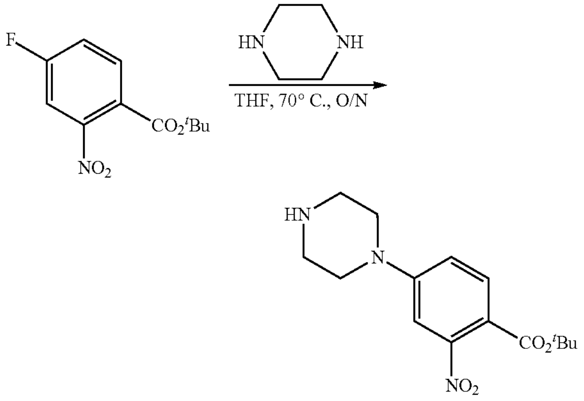

To a solution of piperazine (13.7 g, 159.75 mmol) in tetrahydrofuran (150 mL) was added tert-butyl 4-fluoro-2-nitrobenzoate (7.7 g, 31.95 mmol). The mixture was stirred at 70° C. for 16 h, before it was poured into water and extracted with EtOAc (3×100 mL). The combined organic layers were washed with water, brine, dried over sodium sulfate and evaporated to give crude tert-butyl 2-nitro-4-(piperazin-1-yl)benzoate (9.7 g, 99% yield) as yellow oil, which was used in the next step without further purification. MS (ESI) m/z: 308.1 $[M+H]^+$.

Step 5. Synthesis of tert-butyl 2-nitro-4-(4-(2,2,2-trifluoroacetyl)piperazin-1-yl)benzoate

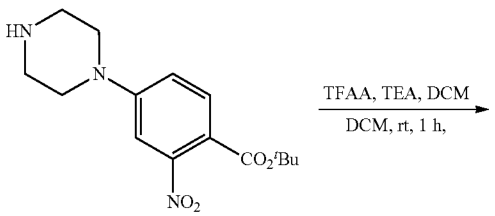

-continued

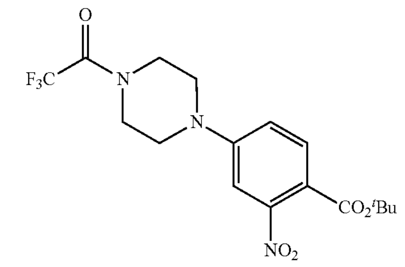

To a solution of 2-nitro-4-piperazin-1-yl-benzoic acid tert-butyl ester (13.5 g, 44.12 mmol) in dichloromethane (200 mL) were added triethylamine (13.4 g, 132.35 mmol) and trifluoroacetic anhydride (18.5 g, 88.24 mmol) at 0° C. The mixture was stirred at rt for 1 h. The solvent was evaporated to give a residue, which was purified by silica gel flash chromatography (petroleum ether:EtOAc=1:1) to give tert-butyl 2-nitro-4-(4-(2,2,2-trifluoroacetyl)piperazin-1-yl) benzoate (16.5 g, 93% yield) as yellow solid. $^1H$ NMR (400 MHz, DMSO-$d_6$): δ 7.72 (d, J=9.2 Hz, 1H), 7.32 (d, J=2.8 Hz, 1H), 7.16 (dd, J=2.8, 9.2 Hz, 1H), 3.72-3.70 (m, 4H), 3.56-3.52 (m, 4H), 1.45 (s, 9H). MS (ESI) m/z: 404.3 $[M+H]^+$.

Step 6. Synthesis of tert-butyl 2-amino-4-(4-(2,2,2-trifluoroacetyl)piperazin-1-yl)benzoate

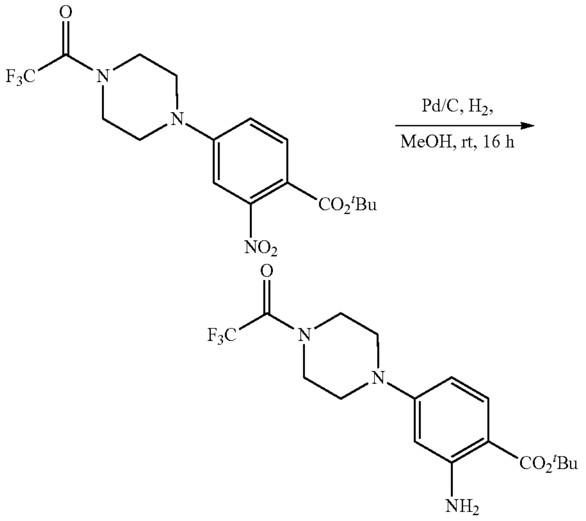

tert-Butyl 2-nitro-4-(4-(2,2,2-trifluoroacetyl)piperazin-1-yl)benzoate (8.0 g, 19.85 mmol) was dissolved in methanol (150 ml). To the solution was added Pd/C (1.0 g). After the mixture was purged with $H_2$ 3 times, it was stirred under hydrogen atmosphere for 16 h. The mixture was filtered over a pad of celite and washed with methanol. Solvent was removed under vacuum to afford tert-butyl 2-amino-4-(4-(2,2,2-trifluoroacetyl)piperazin-1-yl)benzoate (6.3 g, 85% yield) as yellow solid. $^1H$ NMR (400 MHz, DMSO-$d_6$): δ 7.51 (d, J=9.2 Hz, 1H), 6.47 (br, 2H), 6.20 (dd, J=2.8, 9.2 Hz, 1H), 6.13 (d, J=2.8 Hz, 1H), 3.71-3.69 (m, 4H), 3.31-3.29 (m, 4H), 1.50 (s, 9H). MS (ESI) m/z: 374.0 $[M+H]^+$.

Step 7. Synthesis of tert-butyl 2-((tetrahydro-2H-pyran-4-yl)amino)-4-(4-(2,2,2-trifluoroacetyl)piperazin-1-yl)benzoate

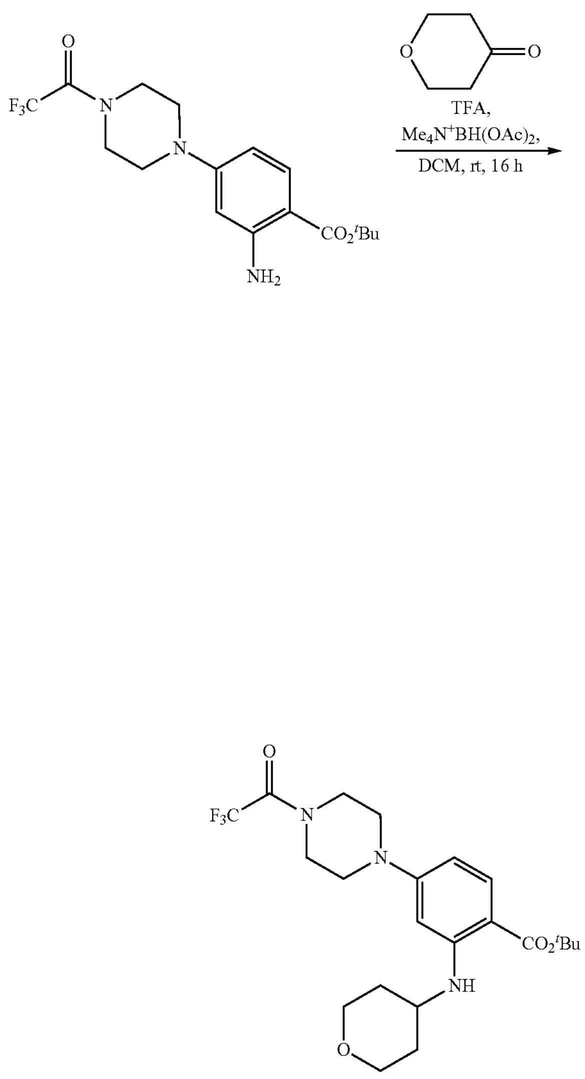

To a solution of tert-butyl 2-amino-4-(4-(2,2,2-trifluoroacetyl)piperazin-1-yl)benzoate (6.3 g, 16.89 mmol) in dichloromethane (150 mL) were added tetrahydro-pyran-4-one (2.1 g, 21.11 mmol), trifluoroacetic acid (3.5 mL) and tetramethylammonium triacetoxyborohydride (6.7 g, 25.34 mmol). The mixture was stirred at rt for 16 h, before it was washed with 0.5 N hydrochloric acid, with 0.5 N sodium hydroxide and with a saturated solution of sodium bicarbonate. The organic layer was dried over sodium sulfate and evaporated to dryness to afford tert-butyl 2-((tetrahydro-2H-pyran-4-yl)amino)-4-(4-(2,2,2-trifluoroacetyl)piperazin-1-yl)benzoate (3.5 g, 50% yield) as a pale yellow solid. $^1$HNMR (400 MHz, DMSO-$d_6$): δ 7.72 (d, J=7.6 Hz, 1H), 7.60 (d, J=9.2 Hz, 1H), 6.20 (dd, J=2.4, 9.2 Hz, 1H), 6.09 (d, J=2.0 Hz, 1H), 3.86-3.82 (m, 2H), 3.70-3.69 (m, 5H), 3.52-3.46 (m, 2H), 3.39-3.38 (m, 4H), 1.97-1.94 (m, 2H), 1.50 (s, 9H), 1.43-1.34 (m, 2H). MS (ESI) m/z: 458.1 $[M+H]^+$.

Step 8. Synthesis of tert-butyl 2-(2,2,2-trifluoro-N-(tetrahydro-2H-pyran-4-yl)acetamido)-4-(4-(2,2,2-trifluoroacetyl)piperazin-1-yl)benzoate

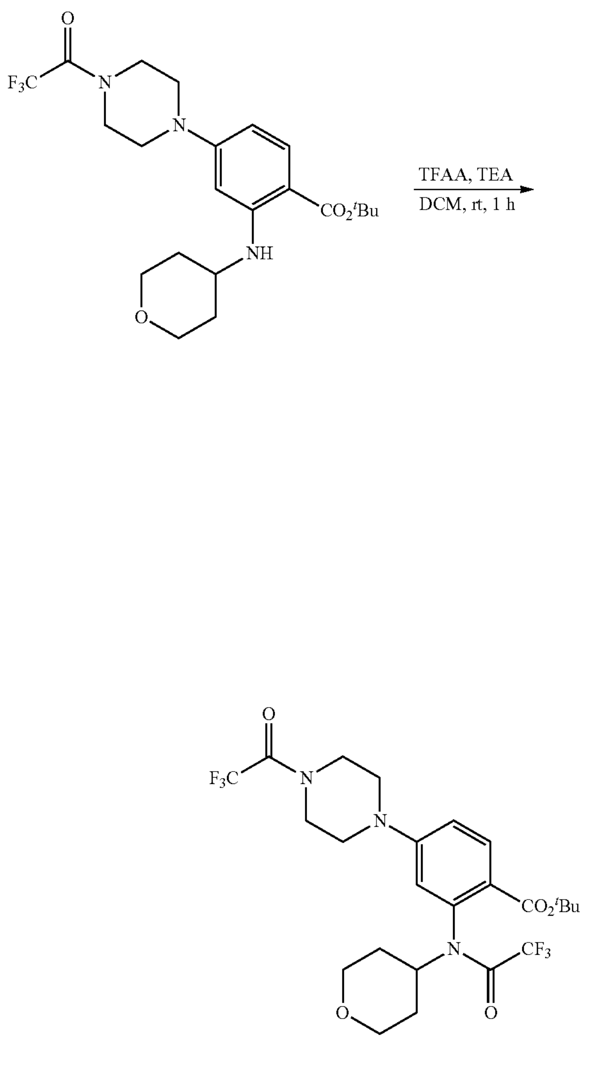

Under nitrogen atmosphere tert-butyl 2-((tetrahydro-2H-pyran-4-yl)amino)-4-(4-(2,2,2-trifluoroacetyl) piperazin-1-yl)benzoate (3.8 g, 8.32 mmol) was dissolved in dichloromethane (100 ml) and cooled to 0° C. Then triethylamine (1.3 g, 12.47 mmol) was added followed by a slow addition of trifluoroacetic anhydride (2.3 g, 10.81 mmol). Reaction was quenched after 1 h with water, diluted with DCM, washed with a saturated solution of aqueous sodium bicarbonate, brine, dried over sodium sulfate, filtered, evaporated and purified by silica gel column chromatography (petroleum ether:EtOAc=2:1) to give tert-butyl 2-(2,2,2-trifluoro-N-(tetrahydro-2H-pyran-4-yl)acetamido)-4-(4-(2,2,2-trifluoroacetyl)piperazin-1-yl)benzoate (4.2 g, 91% yield) as yellow solid. $^1$HNMR (400 MHz, DMSO-$d_6$): δ 7.85 (d, J=8.8 Hz, 1H), 7.08 (dd, J=2.4, 8.8 Hz, 1H), 6.85 (d, J=2.4 Hz, 1H), 4.52-4.44 (m, 1H), 3.89-3.77 (m, 2H), 3.75-3.72 (m, 4H), 3.55-3.49 (m, 4H), 345-3.32 (m, 2H), 1.99-1.97 (m, 1H), 1.65-1.53 (m, 1H), 1.48-1.45 (m, 1H), 1.45 (s, 9H), 1.08-0.96 (m, 1H). MS (ESI) m/z: 554.1 $[M+H]^+$.

Step 9. Synthesis of 2-(2,2,2-trifluoro-N-(tetrahydro-2H-pyran-4-yl)acetamido)-4-(4-(2,2,2-trifluoroacetyl)piperazin-1-yl)benzoic acid

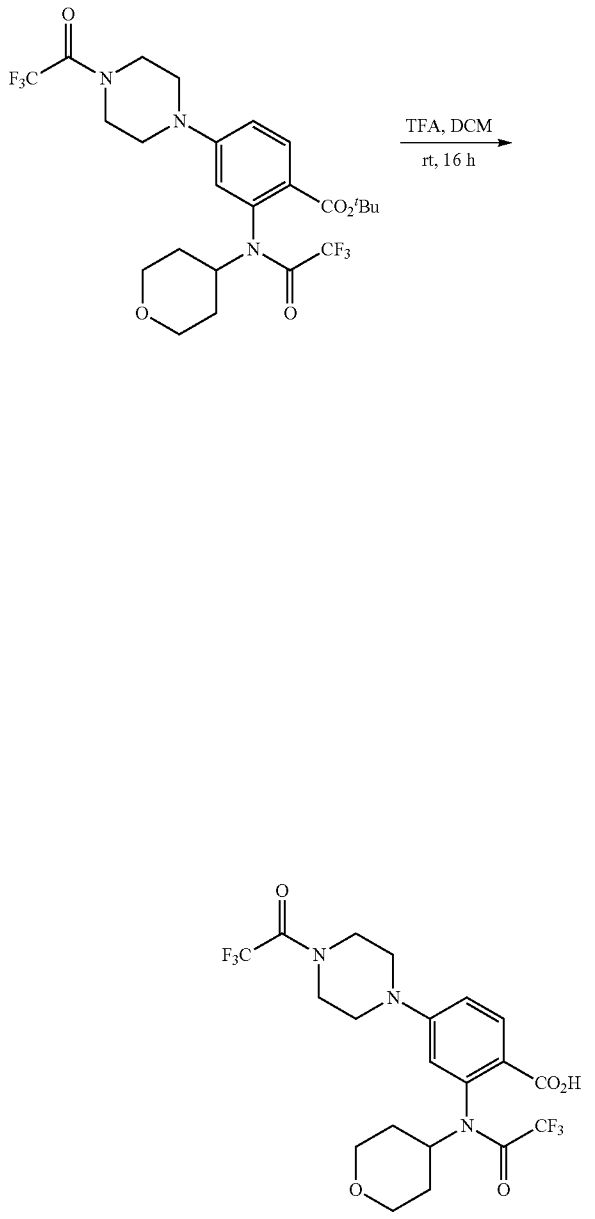

To a solution of tert-butyl 2-(2,2,2-trifluoro-N-(tetrahydro-2H-pyran-4-yl)acetamido)-4-(4-(2,2,2-trifluoroacetyl)piperazin-1-yl)benzoate (4.2 g, 7.59 mmol) in DCM (50 ml) was added TFA (50 ml) at 0° C. The reaction was stirred at rt for 16 h before the solvent was removed under vacuum. The residue was washed with diethyl ether to give 2-(2,2,2-trifluoro-N-(tetrahydro-2H-pyran-4-yl)acetamido)-4-(4-(2,2,2-trifluoroacetyl)piperazin-1-yl)benzoic acid (3.5 g, 93% yield) as white solid. $^1$H NMR (400 MHz, DMSO-$d_6$) δ 12.70 (s, 1H), 7.90 (d, J=8.8 Hz, 1H), 7.06 (dd, J=2.8, 9.2 Hz, 1H), 6.86 (d, J=2.0 Hz, 1H), 4.51-4.43 (m, 1H), 3.88-3.79 (m, 2H), 3.75-3.72 (m, 4H), 3.55-3.41 (m, 6H), 1.97-1.94 (m, 1H), 1.64-1.49 (m, 2H), 1.12-1.02 (m, 1H). MS (ESI) m/z 498.0 $[M+H]^+$.

Step 10. Synthesis of N-(5-(3,5-difluorobenzyl)-1H-indazol-3-yl)-2-(2,2,2-trifluoro-N-(tetrahydro-2H-pyran-4-yl)acetamido)-4-(4-(2,2,2-trifluoroacetyl) piperazin-1-yl)benzamide

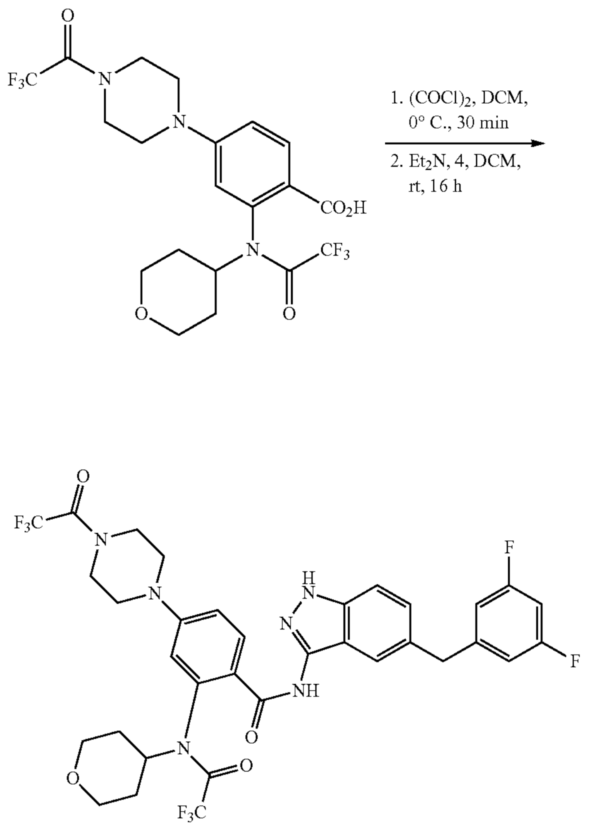

To a suspension of 2-(2,2,2-trifluoro-N-(tetrahydro-2H-pyran-4-yl)acetamido)-4-(4-(2,2,2-trifluoroacetyl) piperazin-1-yl)benzoic acid (3.5 g, 7.04 mmol) in dry dichloromethane (150 mL) were added catalytic amount of N,N-dimethylformamide, oxalyl chloride (2.7 g, 21.13 mmol) at 0° C. After the mixture was stirred for 1.5 h, the solvent was evaporated. The resulting residue was azeotroped twice with dry dichloromethane. The acyl chloride was dissolved in dry dichloromethane (50 mL). And the resulting solution was added gradually to a solution of 5-(3,5-difluoro-benzyl)-1H-indazol-3-ylamine (1.86 g, 7.04 mol) and triethylamine (2.2 g, 21.13 mmol) in dry tetrahydrofuran (100 mL) at −20° C. The mixture was stirred at rt for 16 h before the solvent was evaporated. The resulting residue was purified by silica gel column chromatography (petroleum ether:EtOAc=1:1) to give N-(5-(3,5-difluorobenzyl)-1H-indazol-3-yl)-2-(2,2,2-trifluoro-N-(tetrahydro-2H-pyran-4-yl)acetamido)-4-(4-(2,2,2-trifluoroacetyl)piperazin-1-yl)benzamide (4.0 g, 77% yield) as yellow solid. $^1$H NMR (400 MHz, DMSO-$d_6$) δ 12.70 (s, 1H), 10.58 (s, 1H), 7.86 (d, J=8.4 Hz, 1H), 7.43-7.41 (m, 2H), 7.27 (d, J=9.2 Hz, 1H), 7.18-7.11 (m, 1H), 7.04-6.99 (m, 1H), 6.95-6.93 (m, 3H), 4.47-4.41 (m, 1H), 4.01 (s, 2H), 3.80-3.72 (m, 4H), 3.22-3.17 (m, 4H), 3.51-3.47 (m, 4H), 1.93-1.90 (m, 1H), 1.67-1.64 (m, 1H), 1.60-1.50 (m, 1H), 1.37-1.26 (m, 1H). MS (ESI) m/z: 739.0 $[M+H]^+$.

Step 11. Synthesis of N-(5-(3,5-difluorobenzyl)-1H-indazol-3-yl)-4-(piperazin-1-yl)-2-((tetrahydro-2H-pyran-4-yl)amino)benzamide

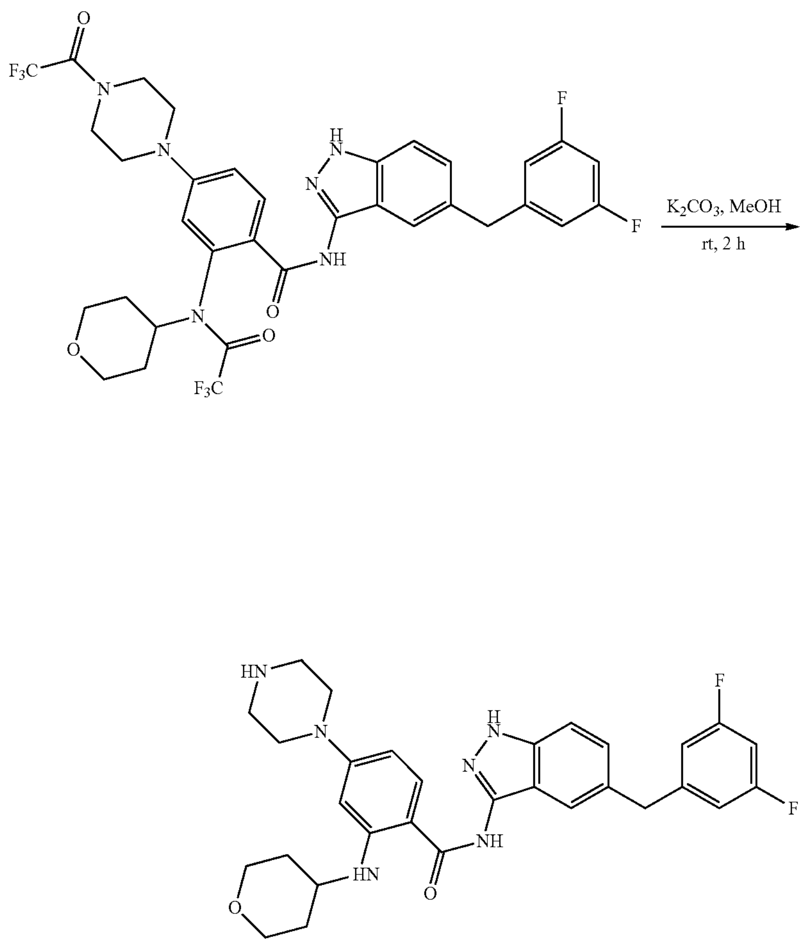 [SMILES: O=C(Nc1n[nH]c2ccc(Cc3cc(F)cc(F)c3)cc12)c1ccc(N2CCN(C(=O)C(F)(F)F)CC2)cc1N(C(=O)C(F)(F)F)C1CCOCC1 ; O=C(Nc1n[nH]c2ccc(Cc3cc(F)cc(F)c3)cc12)c1ccc(N2CCNCC2)cc1NC1CCOCC1]

To a solution of N-(5-(3,5-difluorobenzyl)-1H-indazol-3-yl)-2-(2,2,2-trifluoro-N-(tetrahydro-2H-pyran-4-yl)acetamido)-4-(4-(2,2,2-trifluoroacetyl)piperazin-1-yl)benzamide (4.0 g, 5.42 mmol) in methanol (100 mL) was added potassium carbonate (3.7 g, 27.1 mmol). The mixture was stirred at rt for 2 h before it was filtered. The filtrate was evaporated and the residue was purified by silica gel chromatography (DCM:MeOH=10:1) to give N-(5-(3,5-difluorobenzyl)-1H-indazol-3-yl)-4-(piperazin-1-yl)-2-((tetrahydro-2H-pyran-4-yl)amino)benzamide (1.9 g, 64% yield) as a blue solid. $^1$H NMR (400 MHz, DMSO-$d_6$) δ 12.68 (s, 1H), 10.12 (s, 1H), 8.31 (d, J=6.8 Hz, 1H), 7.81 (d, J=8.4 Hz, 1H), 7.50 (s, 1H), 7.41 (d, J=8.4 Hz, 1H), 7.26 (d, J=8.4 Hz, 1H), 7.03-6.98 (m, 3H), 6.23 (d, J=8.4 Hz, 11H), 6.13 (s, 1H), 4.04 (s, 2H), 3.83-3.80 (m, 2H), 3.68-3.62 (m, 1H), 3.52-3.47 (m, 2H), 3.22-3.17 (m, 4H), 2.87-2.80 (m, 4H), 1.95-1.92 (m, 2H), 1.36-1.34 (m, 2H). MS (ESI) m/z: 547.2 $[M+H]^+$.

Step 12. Synthesis of tert-butyl 2-(4-(4-((5-(3,5-difluorobenzyl)-1H-indazol-3-yl)carbamoyl)-3-((tetrahydro-2H-pyran-4-yl)amino)phenyl)piperazin-1-yl)acetate

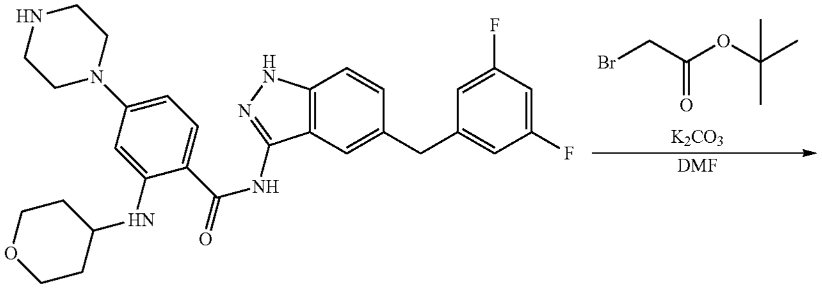

-continued

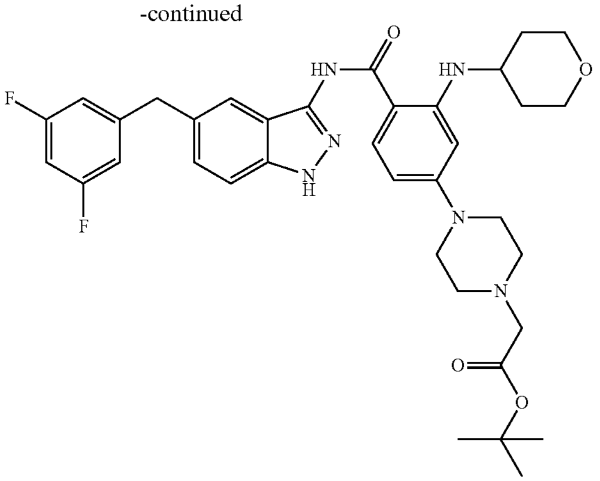

To a solution of N-(5-(3,5-difluorobenzyl)-1H-indazol-3-yl)-4-(piperazin-1-yl)-2-((tetra hydro-2H-pyran-4-yl)amino)benzamide (1.0 g, 1.83 mmol) in DMF (40 ml) were added $K_2CO_3$ (505 mg, 3.66 mmol) and tert-butyl 2-bromo-acetate (357 mg, 1.83 mmol). The resulting mixture was stirred at rt for 3 h. After the amine was totally consumed, the reaction was poured into water (300 mL) and extracted with EtOAc (3×50 mL). The combined organic layers were washed with saturated brine (100 mL) and dried over anhydrous sodium sulfate. After filtration, the filtrate was concentrated under reduced pressure. The resulting residue was purified by silica gel column chromatography to give tert-butyl 2-(4-(4-((5-(3,5-difluorobenzyl)-1H-indazol-3-yl)carbamoyl)-3-((tetrahydro-2H-pyran-4-yl)amino)phenyl)piperazin-1-yl)acetate (1.03 g, 85% yield) as a light yellow solid. MS (ESI) m/z: 661.3 $[M+H]^+$.

Step 13. Synthesis of 2-(4-(4-((5-(3,5-difluorobenzyl)-1H-indazol-3-yl)carbamoyl)-3-((tetrahydro-2H-pyran-4-yl)amino)phenyl)piperazin-1-yl)acetic acid

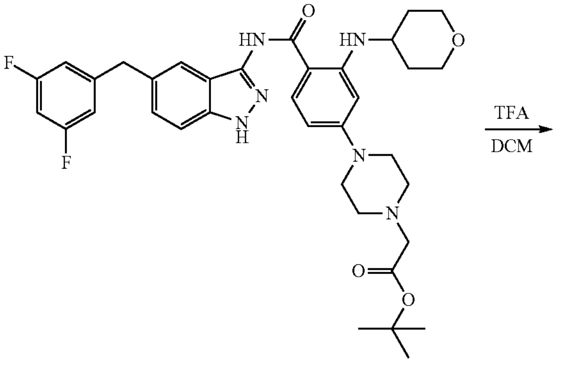

-continued

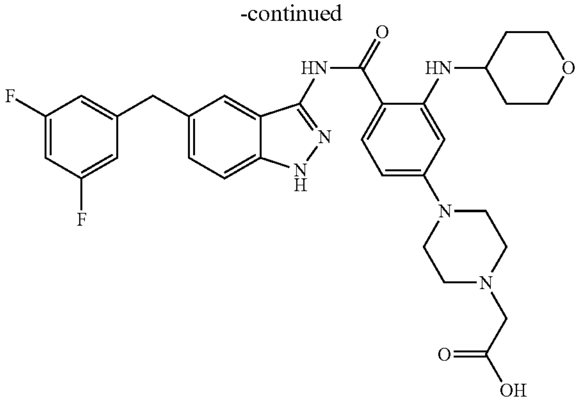

To a solution of tert-butyl 2-(4-(4-((5-(3,5-difluorobenzyl)-1H-indazol-3-yl)carbamoyl)-3-((tetrahydro-2H-pyran-4-yl)amino)phenyl)piperazin-1-yl)acetate (1 g, 1.51 mmol) in dichloromethane (20 ml) was added trifluoroacetic acid (20 mL). The resulting mixture was stirred at rt for 3 h. After the starting material was totally consumed, the solvent was evaporated under reduced pressure. The resulting residue was purified by reverse-phase chromatography to give 2-(4-(4-((5-(3,5-difluorobenzyl)-1H-indazol-3-yl)carbamoyl)-3-((tetrahydro-2H-pyran-4-yl)amino)phenyl)piperazin-1-yl)acetic acid (790 mg, 73% yield) as a light yellow solid. MS (ESI) m/z: 605.3 $[M+H]^+$.

Step 14. Synthesis of 2-acetamido-4-((2-(2-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)ethoxy)ethyl)amino)-N-(4-methyl-5-nitrothiazol-2-yl)benzamide

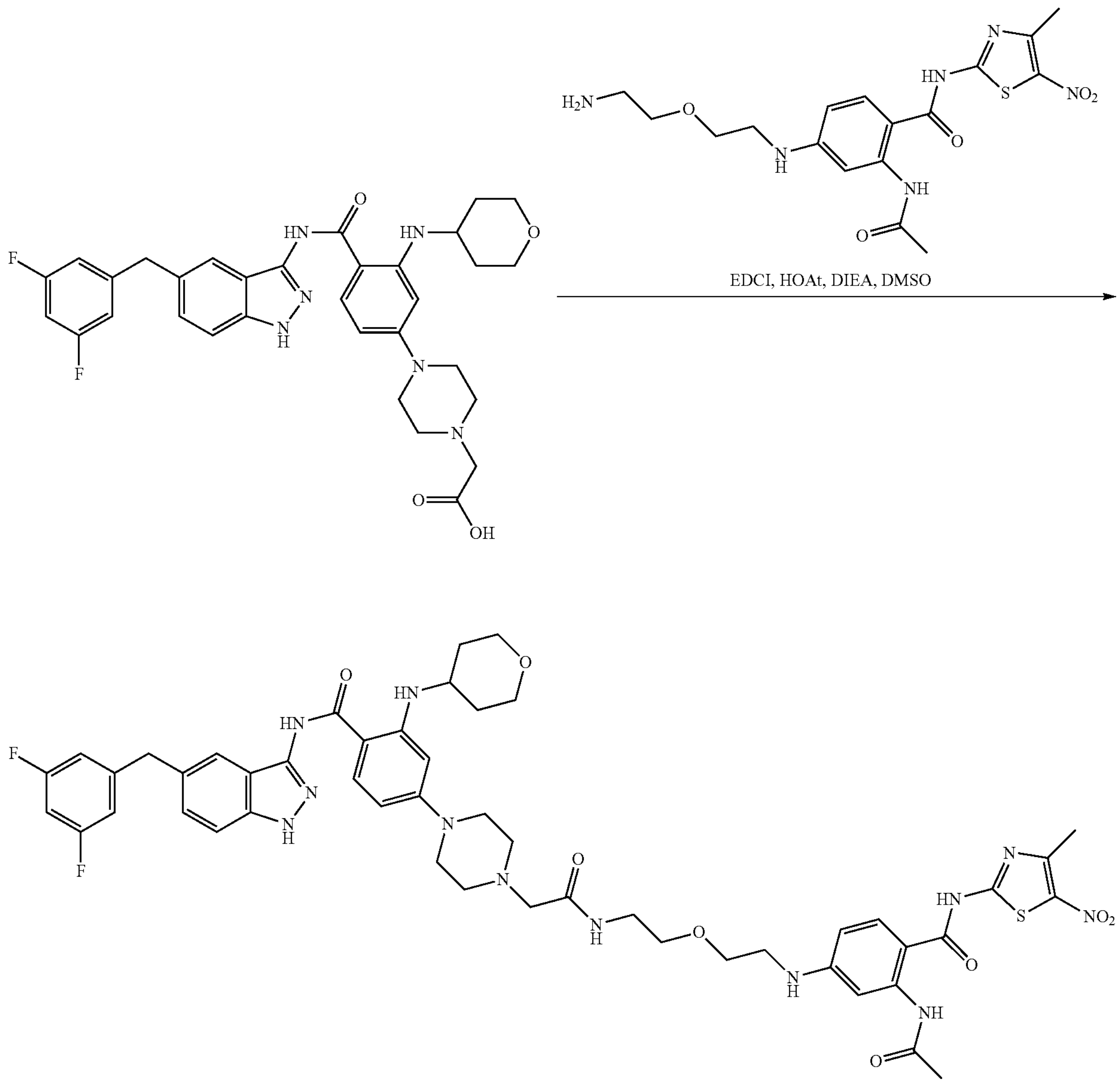 [SMILES: O=C(O)CN1CCN(c2ccc(C(=O)Nc3n[nH]c4ccc(Cc5cc(F)cc(F)c5)cc34)c(NC3CCOCC3)c2)CC1 ; CC(=O)Nc1cc(NCCOCCN)ccc1C(=O)Nc1nc(C)c([N+](=O)[O-])s1 ; CC(=O)Nc1cc(NCCOCCNC(=O)CN2CCN(c3ccc(C(=O)Nc4n[nH]c5ccc(Cc6cc(F)cc(F)c6)cc45)c(NC4CCOCC4)c3)CC2)ccc1C(=O)Nc1nc(C)c([N+](=O)[O-])s1]

To a mixture of 2-(4-(4-((5-(3,5-difluorobenzyl)-1H-indazol-3-yl)carbamoyl)-3-((tetrahydro-2H-pyran-4-yl)amino)phenyl)piperazin-1-yl)acetic acid (6 mg, 0.01 mmol) and HOAt (2.7 mg, 0.02 mmol), EDCI (3.8 mg, 0.02 mmol) in DMSO (1 mL) were added DIEA (5 mg, 0.05 mmol) and 2-acetamido-4-((2-(2-aminoethoxy)ethyl)amino)-N-(4-methyl-5-nitrothiazol-2-yl)benzamide (4.2 mg, 0.01 mmol). After the mixture was stirred at 25° C. for 16 h, it was purified by reverse-phase chromatography to give 2-acetamido-4-((2-(2-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)ethoxy)ethyl)amino)-N-(4-methyl-5-nitrothiazol-2-yl)benzamide (2.67 mg, 26.6% yield) as yellow solid. MS (ESI) m/z: 1009.5 $[M+H]^+$.

Example 208. 2-Acetamido-4-((2-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)ethyl)amino)-N-(4-methyl-5-nitrothiazol-2-yl)benzamide (D-50)
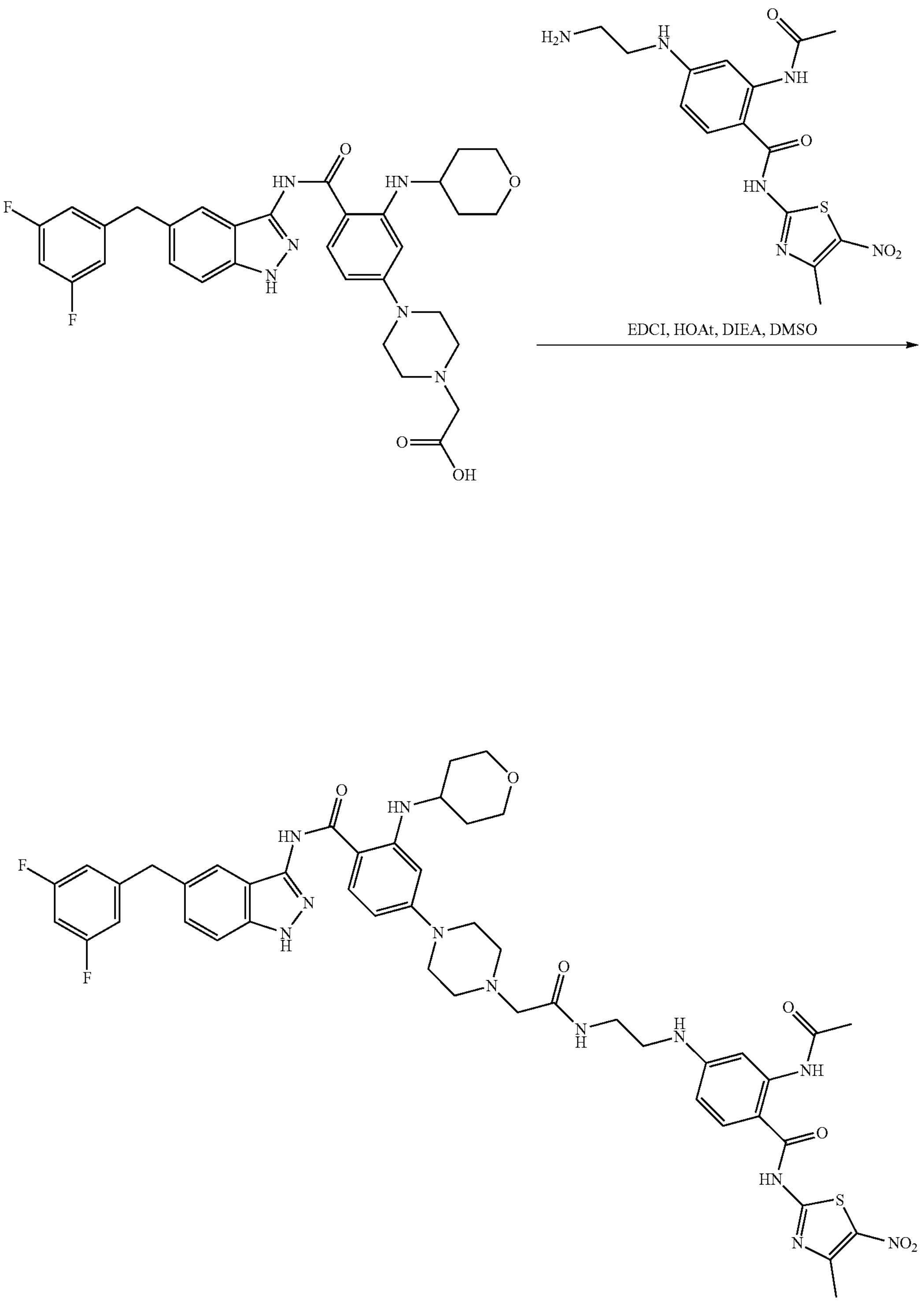
D-50 was synthesized following the standard procedure for preparing D-56 (1.56 mg, 16.3% yield). MS (EST) m/z: 965.5 $[M+H]^+$.

Example 209. 2-Acetamido-4-((4-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)butyl)amino)-N-(4-methyl-5-nitrothiazol-2-yl)benzamide (D-51)
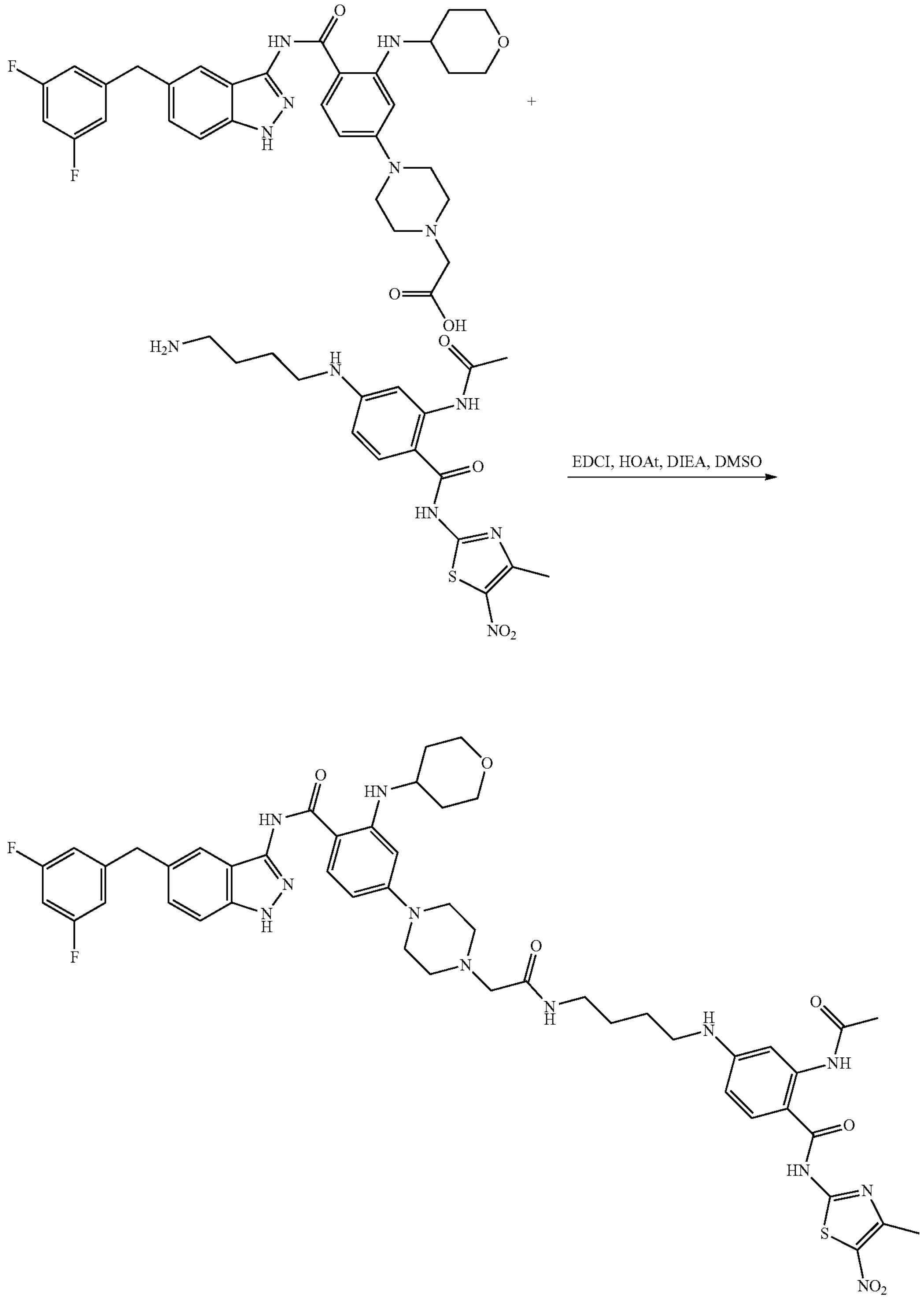
D-51 was synthesized following the standard procedure for preparing D-56 (2.73 mg, 27.7% yield). MS (EST) m/z: 993.5 $[M+H]^+$.

Example 210. 2-Acetamido-4-((6-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)hexyl)amino)-N-(4-methyl-5-nitrothiazol-2-yl)benzamide (D-52)
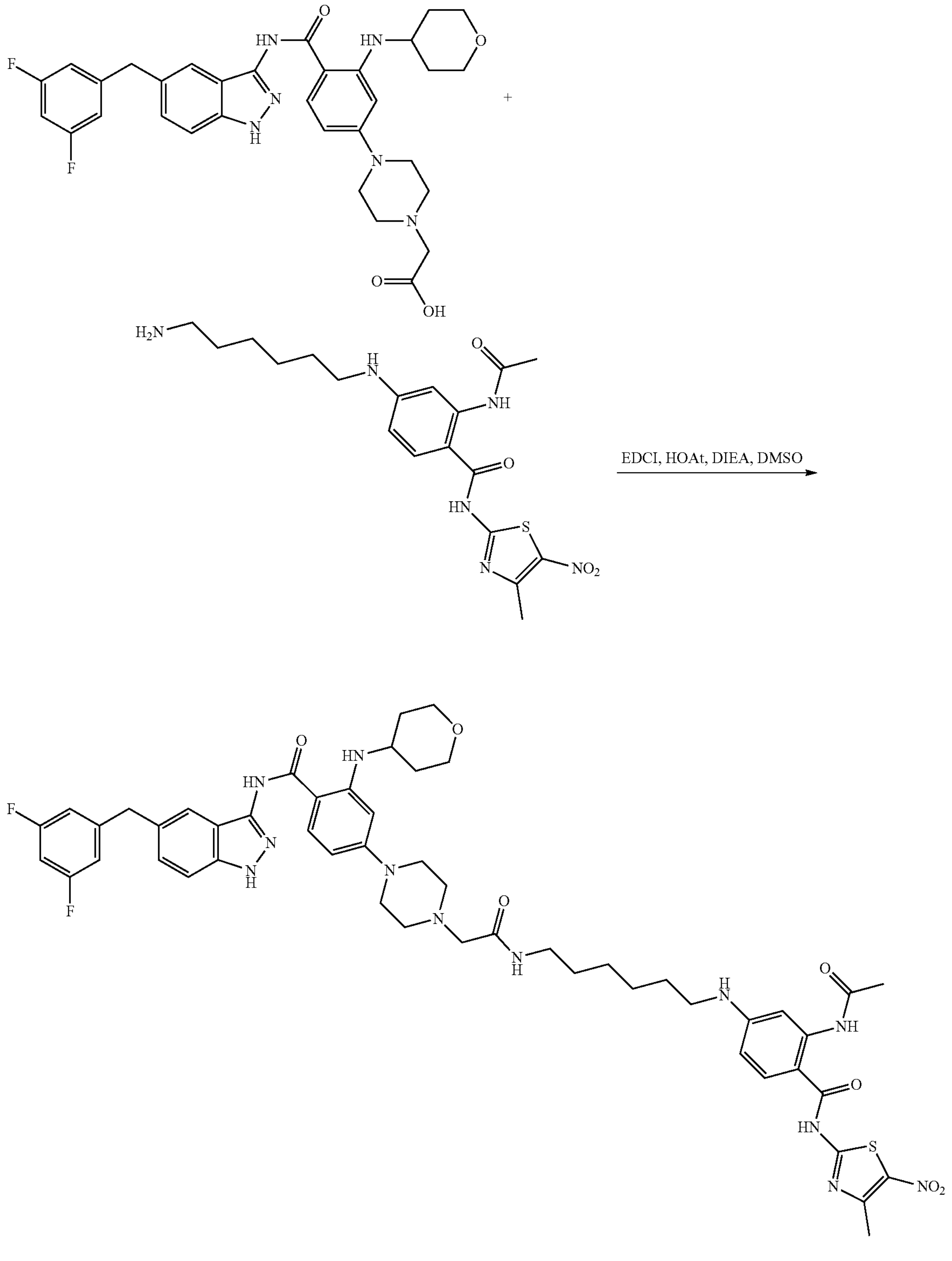
D-52 was synthesized following the standard procedure for preparing D-56 (4.41 mg, 43.5% yield). MS (EST) m/z: 1021.6 $[M+H]^+$.

Example 211. 2-Acetamido-4-((7-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)heptyl)amino)-N-(4-methyl-5-nitrothiazol-2-yl)benzamide (D-53)
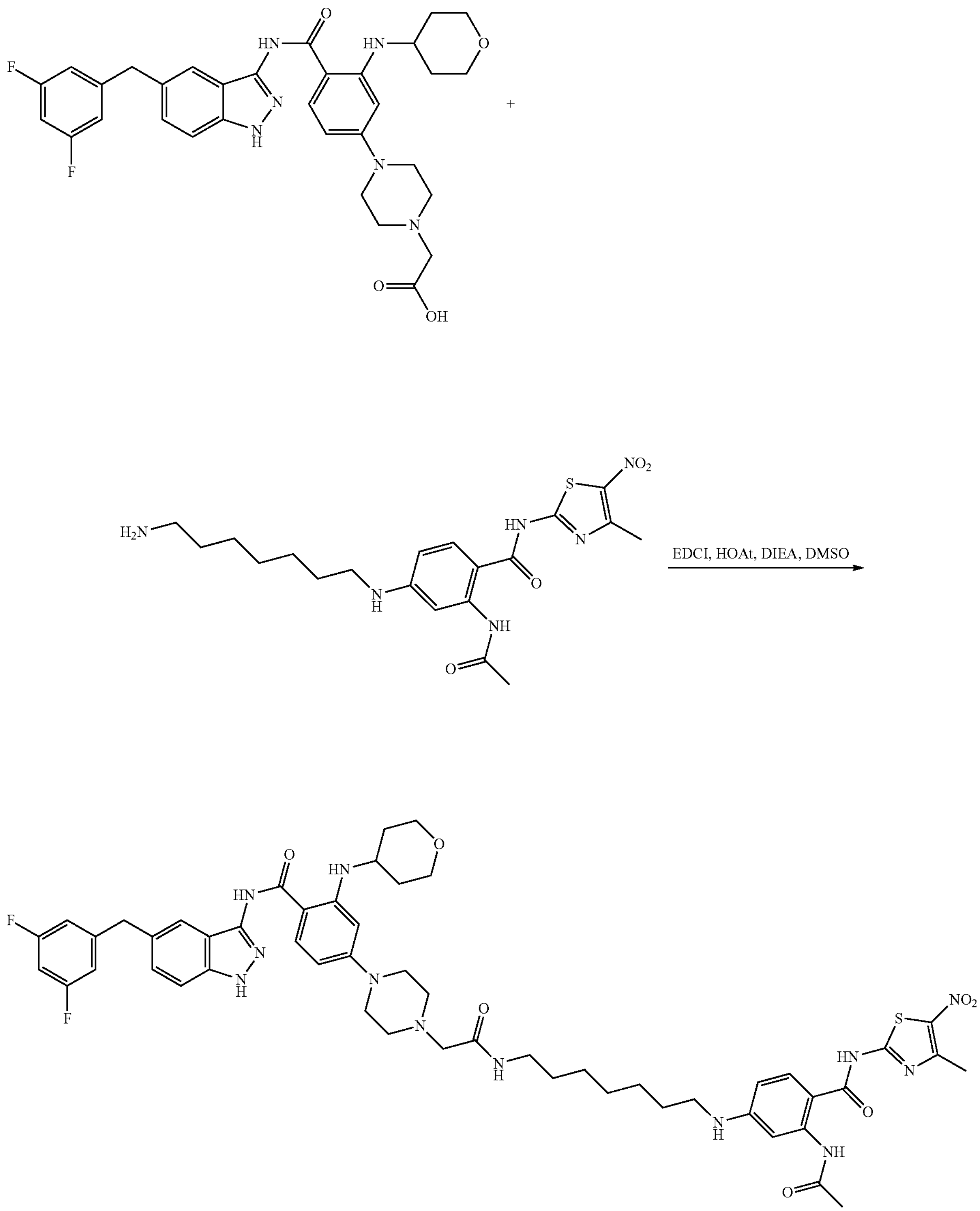
D-53 was synthesized following the standard procedure for preparing D-56 (3.15 mg, 30.7% yield). MS (EST) m/z: 1035.6 [M+H]$^+$.

Example 212. 2-Acetamido-4-((8-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)octyl)amino)-N-(4-methyl-5-nitrothiazol-2-yl)benzamide (D-54)
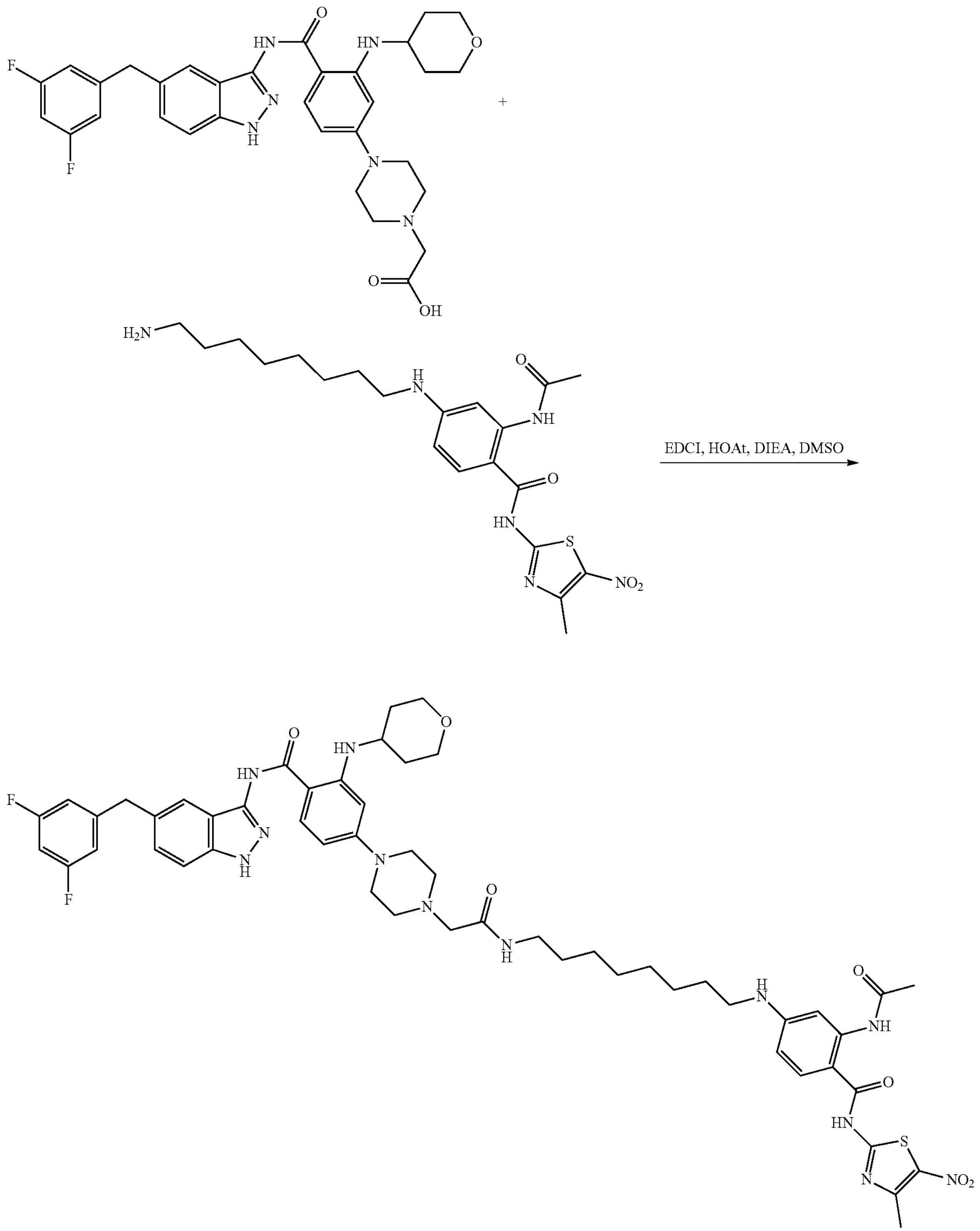
D-54 was synthesized following the standard procedure for preparing D-56 (4.49 mg, 43.1% yield). MS (EST) m/z: 1049.6 $[M+H]^+$.

Example 213. 2-Acetamido-4-((10-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)decyl)amino)-N-(4-methyl-5-nitrothiazol-2-yl)benzamide (D-55)
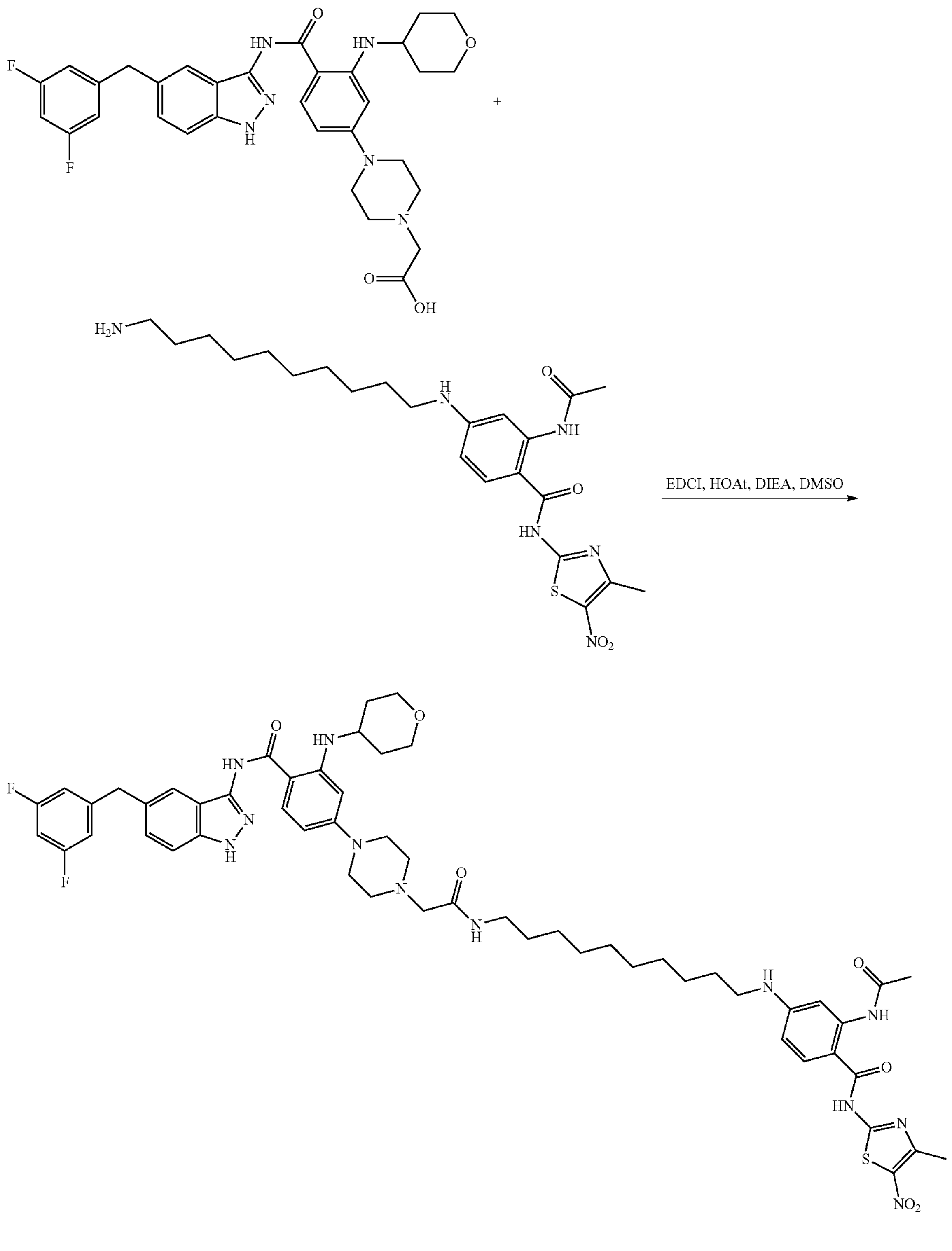
D-55 was synthesized following the standard procedure for preparing D-56 (3.08 mg, 28.8% yield). MS (EST) m/z: 1077.7 $[M+H]^+$.

Example 214. 2-Acetamido-4-((2-(2-(2-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)ethoxy)ethoxy)ethyl)amino)-N-(4-methyl-5-nitrothiazol-2-yl)benzamide (D-57)
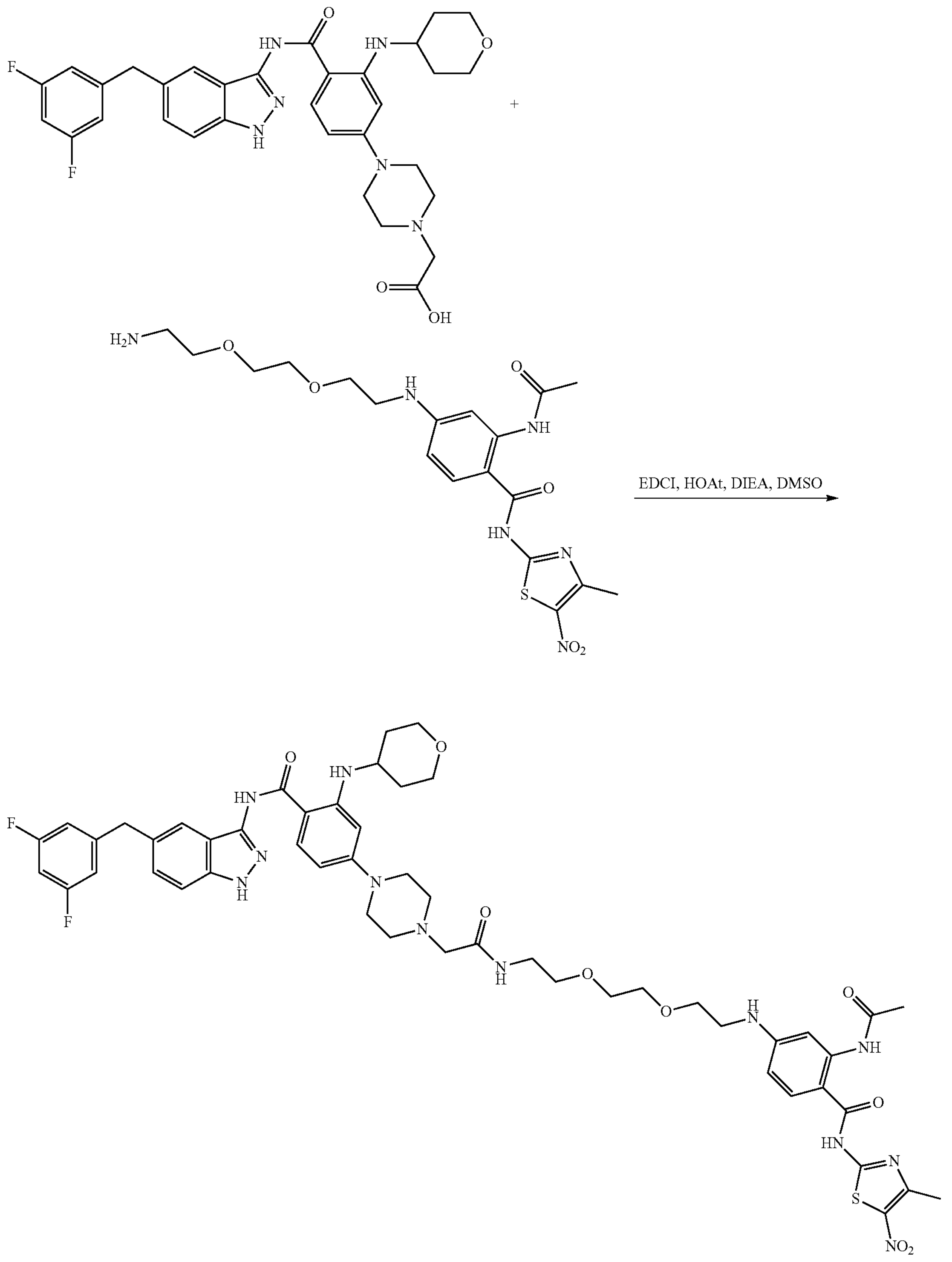
D-57 was synthesized following the standard procedure for preparing D-56 (1.49 mg, 14.3% yield). MS (EST) m/z: 1053.6 [M+H]$^+$.

Example 215. 2-Acetamido-4-((1-(4-(4-((5-(3,5-difluorobenzyl)-1H-indazol-3-yl)carbamoyl)-3-((tetrahydro-2H-pyran-4-yl)amino)phenyl)piperazin-1-yl)-2-oxo-6,9,12-trioxa-3-azatetradecan-14-yl)amino)-N-(4-methyl-5-nitrothiazol-2-yl)benzamide (D-58)
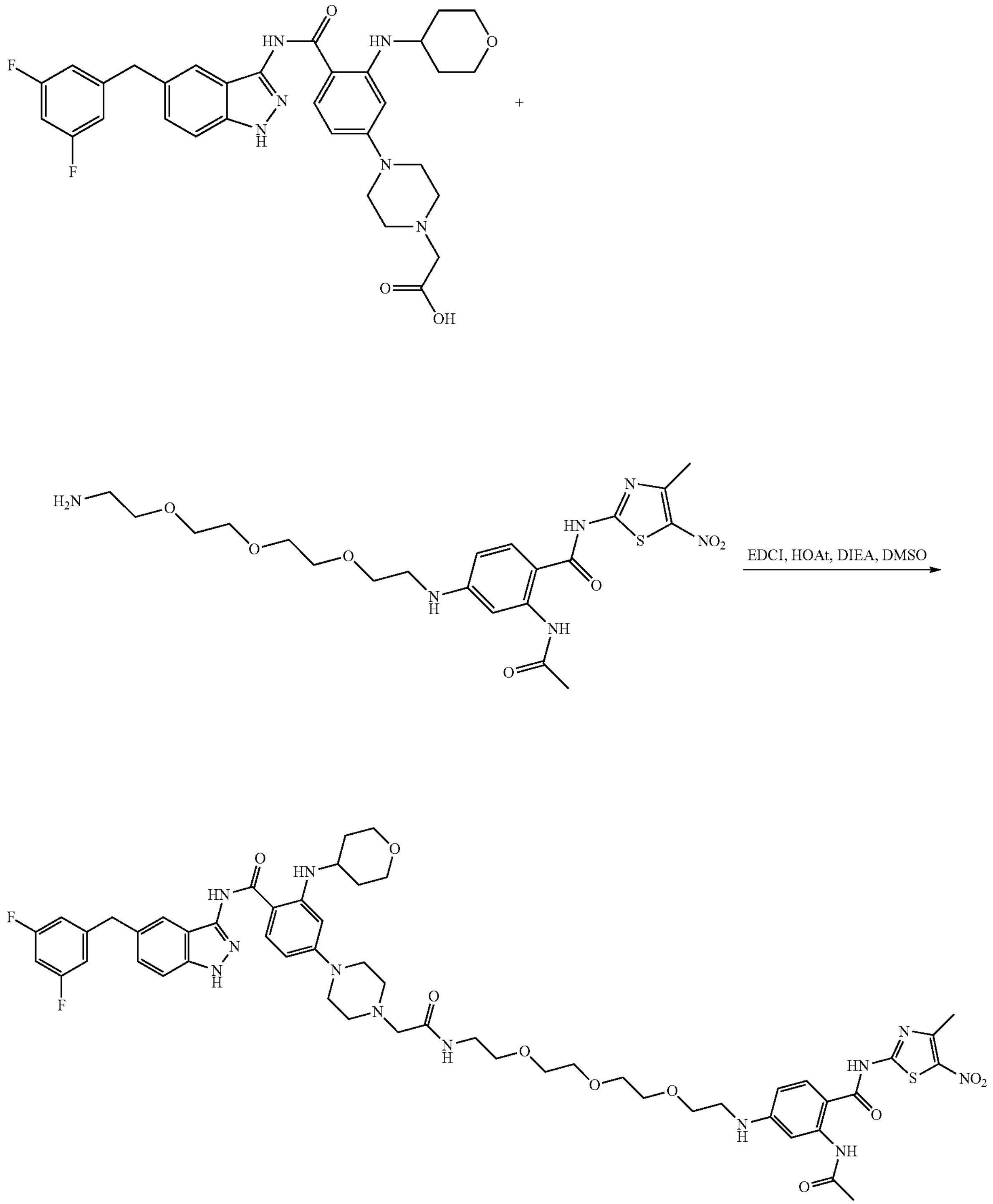
D-58 was synthesized following the standard procedure for preparing D-56 (2.41 mg, 22.2% yield). MS (EST) m/z: 1097.6 $[M+H]^+$.

Example 216. 2-Acetamido-4-((1-(4-(4-((5-(3,5-difluorobenzyl)-1H-indazol-3-yl)carbamoyl)-3-((tetrahydro-2H-pyran-4-yl)amino)phenyl)piperazin-1-yl)-2-oxo-6,9,12,15-tetraoxa-3-azaheptadecan-17-yl)amino)-N-(4-methyl-5-nitrothiazol-2-yl)benzamide (D-59)
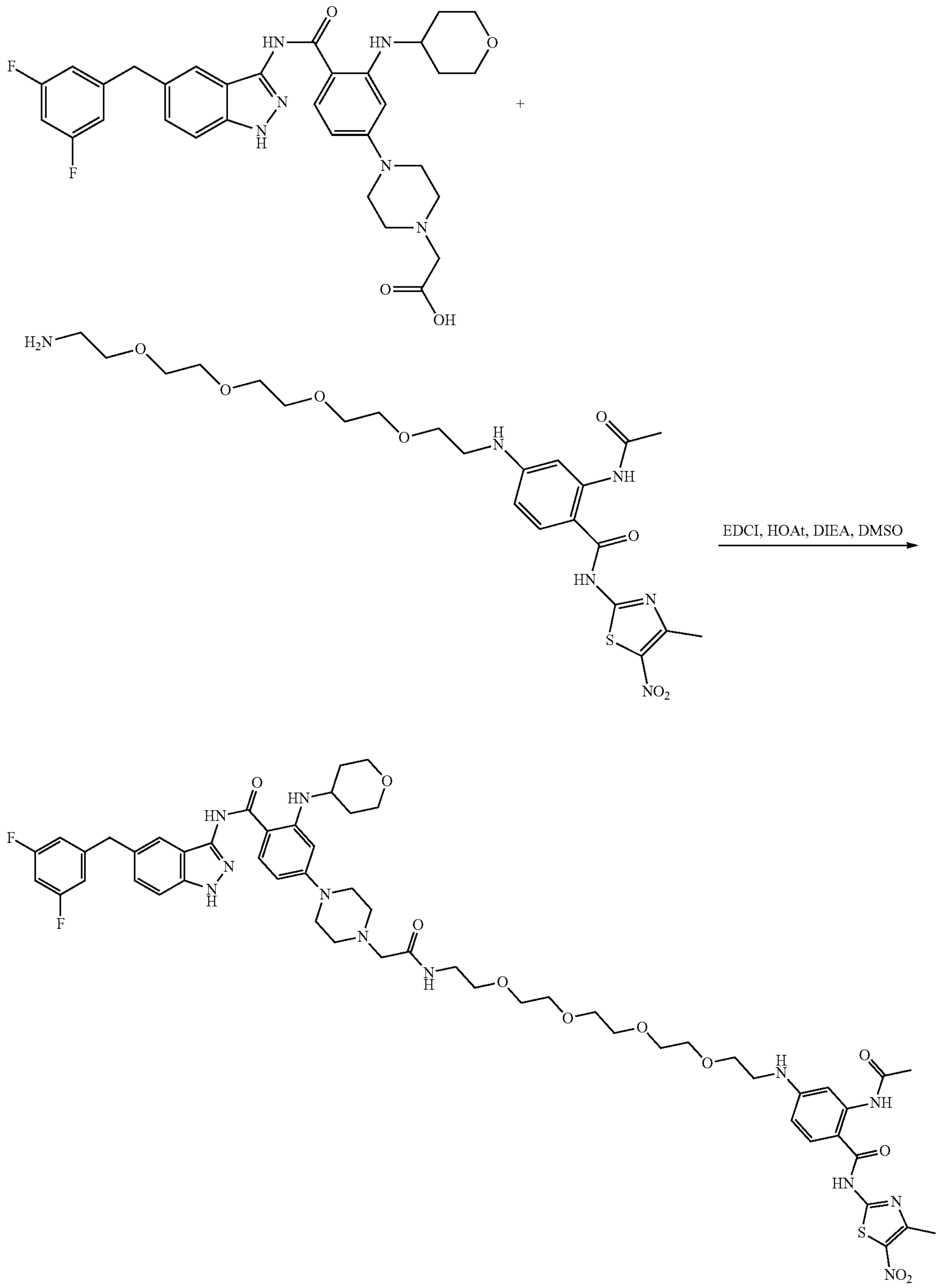

D-59 was synthesized following the standard procedure for preparing D-56 (3.15 mg, 27.8% yield). MS (EST) m/z: 1141.6 $[M+H]^+$.

Example 217. 2-Acetamido-4-((1-(4-(4-((5-(3,5-difluorobenzyl)-1H-indazol-3-yl)carbamoyl)-3-((tetrahydro-2H-pyran-4-yl)amino)phenyl)piperazin-1-yl)-2-oxo-6,9,12,15,18-pentaoxa-3-azaicosan-20-yl)amino)-N-(4-methyl-5-nitrothiazol-2-yl)benzamide (D-60)

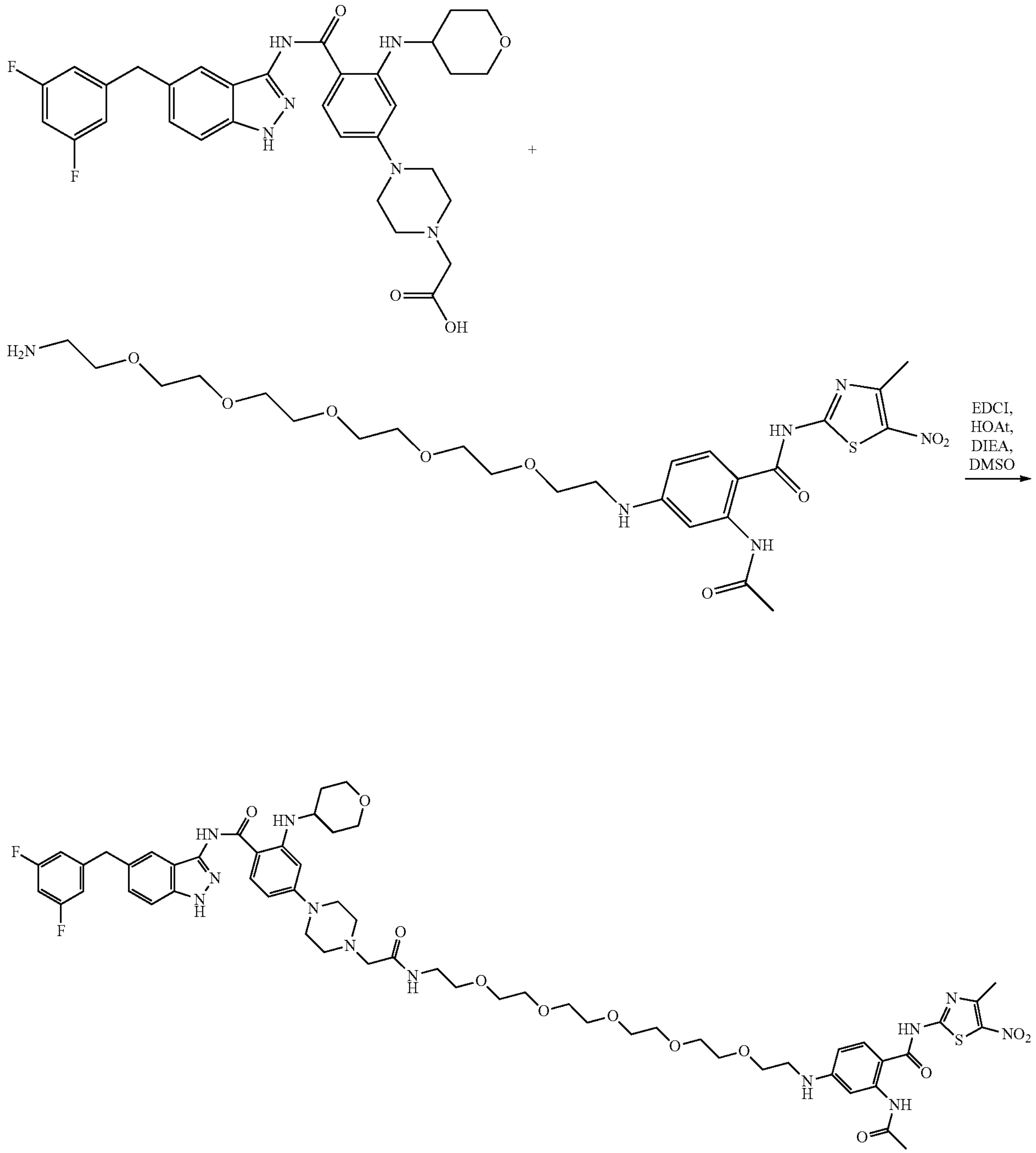

D-60 was synthesized following the standard procedure for preparing D-56 (2.43 mg, 20.7% yield). MS (EST) m/z: 1185.6 $[M+H]^+$.

Example 218. 2-Acetamido-4-((1-(4-(4-((5-(3,5-difluorobenzyl)-1H-indazol-3-yl)carbamoyl)-3-((tetrahydro-2H-pyran-4-yl)amino)phenyl)piperazin-1-yl)-2-oxo-6,9,12,15,18,21-hexaoxa-3-azatricosan-23-yl)amino)-N-(4-methyl-5-nitrothiazol-2-yl) benzamide (D-61)
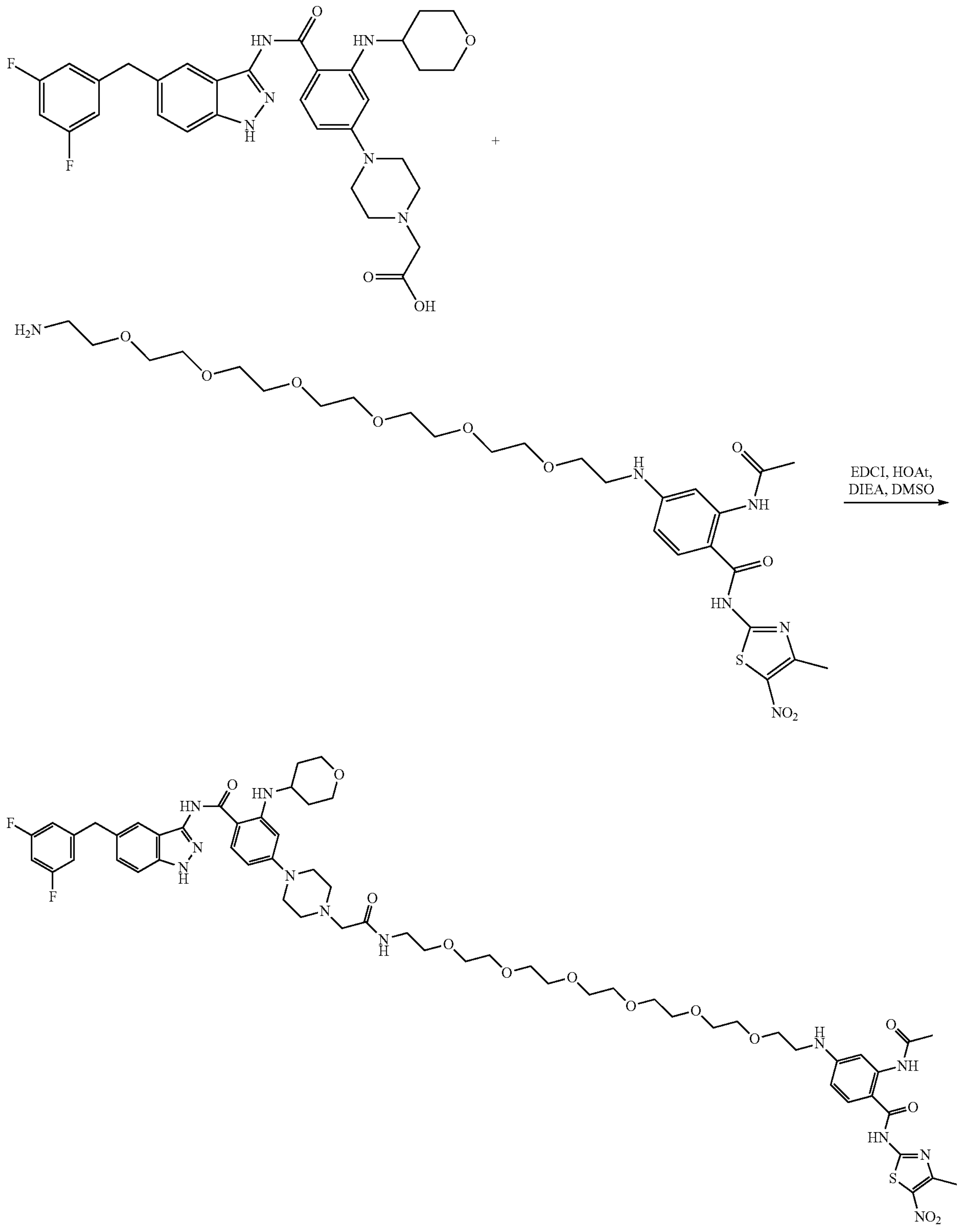

D-61 was synthesized following the standard procedure for preparing D-56 (3.41 mg, 27.9% yield). MS (EST) m/z: 1229.6 $[M+H]^+$
Example 219. N-(3-((2-((3-Acetamido-4-((4-methyl-5-nitrothiazol-2-yl)carbamoyl)phenyl)amino)ethyl)amino)propoxy)-3,4-difluoro-2-((2-fluoro-4-iodophenyl)amino)benzamide (D-72)
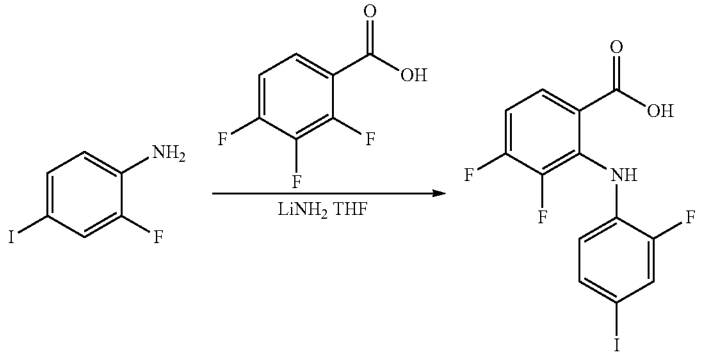 [SMILES: Nc1ccc(I)cc1F ; O=C(O)c1ccc(F)c(F)c1F ; O=C(O)c1ccc(F)c(F)c1Nc1ccc(I)cc1F ; "LiNH2 THF"]
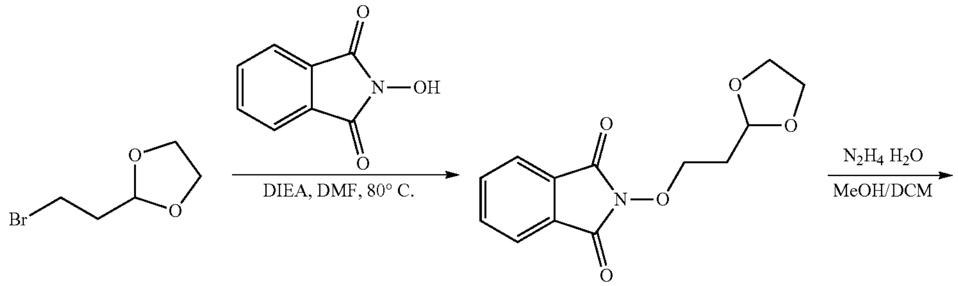
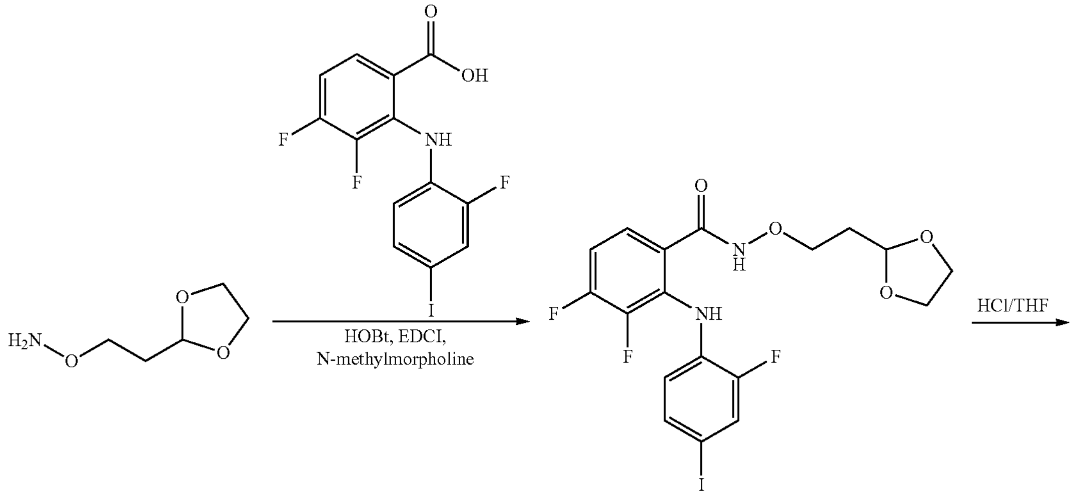

-continued
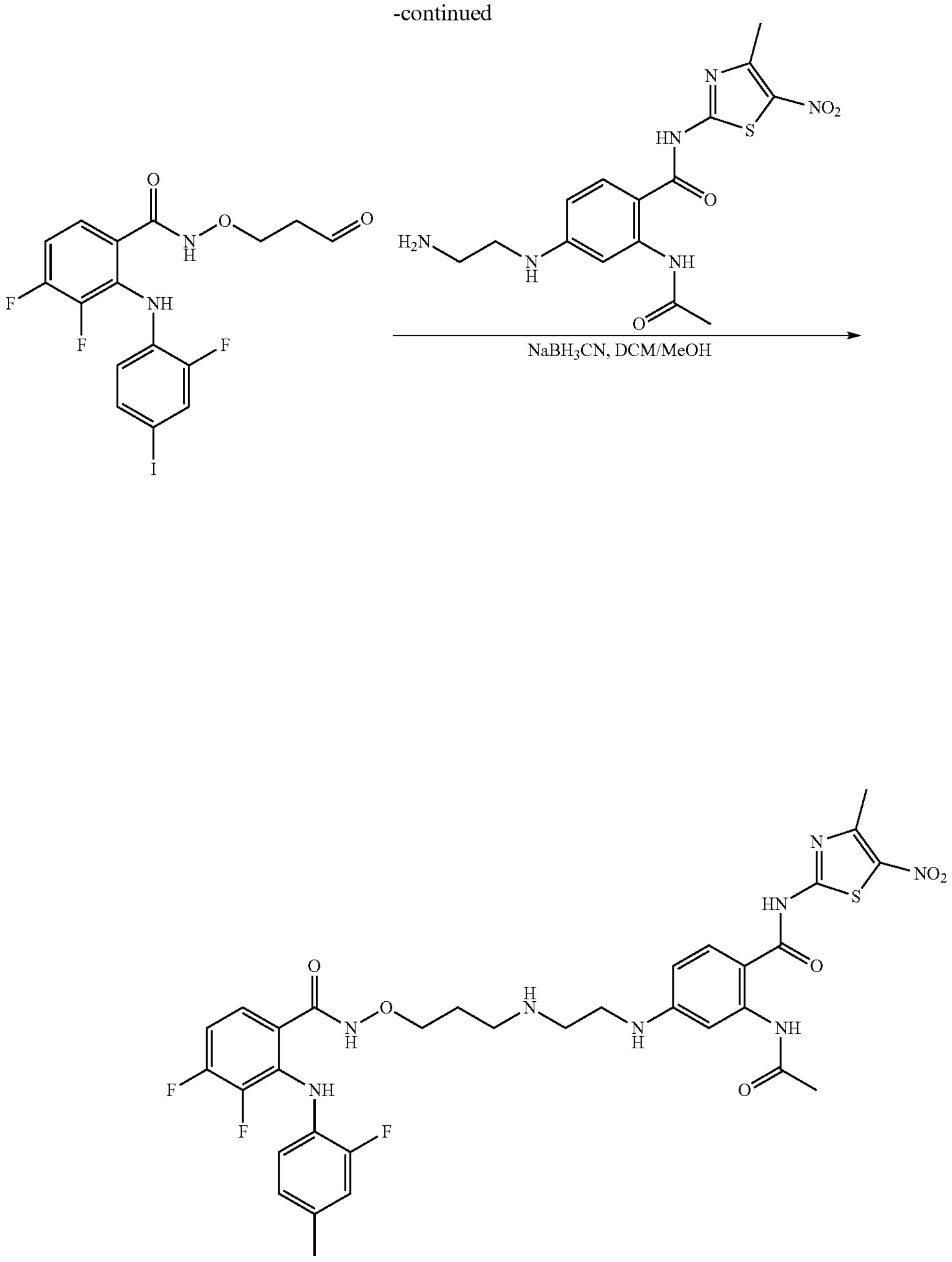
Step 1. Synthesis of 3,4-difluoro-2-((2-fluoro-4-iodophenyl)amino)benzoic acid
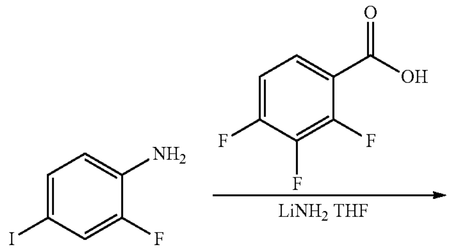
-continued
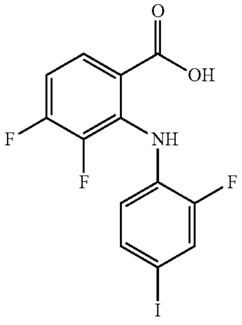

To a solution of $LiNH_2$ (1.02 g, 44.29 mmol) in THF (8 mL) was added a solution of 2-fluoro-4-iodoaniline (3.28 g, 13.84 mmol) and 2,3,4-trifluorobenzoic acid (2.4 g, 13.64 mmol) in THF (8 mL) at 55° C. The resulting reaction mixture was stirred for 2 h, before it was poured into HCl (6N) and extracted with EtOAc twice. The combined organic layers were dried over $Na_2SO_4$, filtered and concentrated to give crude product. It was purified by silica gel column chromatography (petroleum ether:EtOAc=1:0 to 1:1) to give 3,4-difluoro-2-((2-fluoro-4-iodophenyl)amino) benzoic acid (5.04 g, 92.6% yield) as orange solid. MS (ESI) m/z: 394 $[M+H]^+$.

Step 2. Synthesis of 2-(2-(1,3-dioxolan-2-yl)ethoxy) isoindoline-1,3-dione

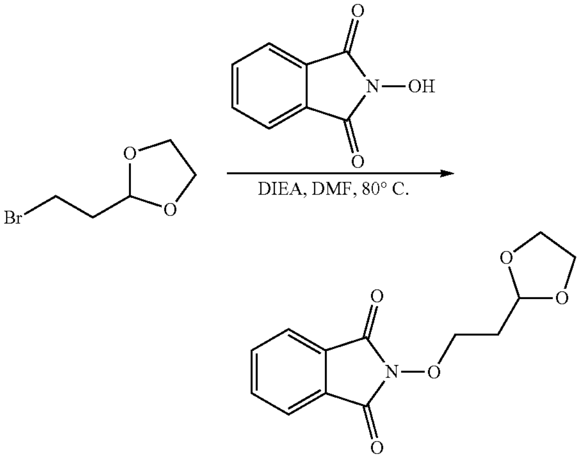

To a solution of 2-(2-bromoethyl)-1,3-dioxolane (5 g, 27.62 mmol) in DMF (50 mL) were added 2-hydroxyisoindoline-1,3-dione (4.5 g, 27.62 mmol) and DIEA (7.12 g, 55.24 mmol) at 0° C. After the reaction mixture was heated to 80° C. for overnight, it was concentrated. The resulting residue was purified by silica gel column chromatography (petroleum ether:EtOAc=1:0 to 1:1) to give 2-(2-(1,3-dioxolan-2-yl)ethoxy)isoindoline-1,3-dione (6.58 g, 90.6% yield) as white solid. MS (ESI) m/z: 264 $[M+H]^+$.

Step 3. Synthesis of O-(2-(1,3-dioxolan-2-yl)ethyl)hydroxylamine

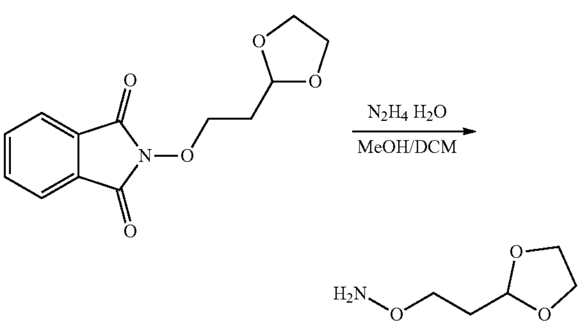

To a solution of 2-(2-(1,3-dioxolan-2-yl)ethoxy)isoindoline-1,3-dione (6.58 g, 25.02 mmol) in MeOH (22 mL) and DCM (11 mL) at 0° C. was added $N_2H_4{\cdot}H_2O$ (2.45 mL, 50.04 mmol). After the reaction mixture was stirred at rt for 2 h, it was filtered and the filtrate was concentrated. The resulting residue was purified by silica gel column chromatography (DCM:MeOH=1:0 to 20:1) to give the 0-(2-(1,3-dioxolan-2-yl)ethyl)hydroxylamine (3.11 g, 93.4% yield) as yellow oil. MS (EST) m/z: 134 $[M+H]^+$.

Step 4. Synthesis of N-(2-(1,3-dioxolan-2-yl) ethoxy)-3,4-difluoro-2-((2-fluoro-4-iodophenyl) amino)benzamide

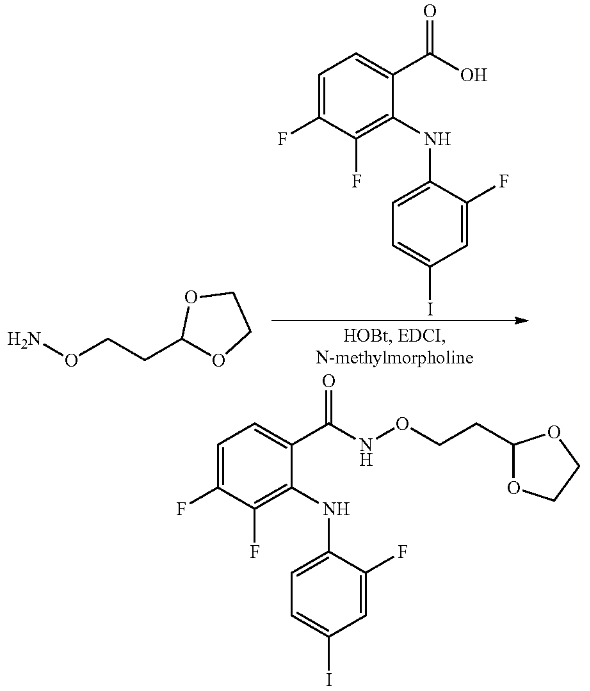

To a solution of O-(2-(1,3-dioxolan-2-yl)ethyl)hydroxylamine (I g, 7.519 mmol) in DMSO (50 mL) at 0° C. were added 3,4-difluoro-2-((2-fluoro-4-iodophenyl)amino)benzoic acid (3.13 g, 7.97 mmol), HOBt (1.22 g, 9.023 mmol), EDCI (1.73 g, 9.023 mmol) and N-methylmorpholine (2.28 g, 22.56 mmol). After the reaction mixture was stirred at rt for overnight, it was poured into water and extracted with EtOAc twice. The combined organic layers were dried over $Na_2SO_4$, filtered and concentrated. The resulting residue was purified with silica gel column chromatography (DCM: MeOH=50:1 to 20:1) to give the N-(2-(1,3-dioxolan-2-yl) ethoxy)-3,4-difluoro-2-((2-fluoro-4-iodophenyl)amino)benzamide (2.4 g, 65% yield) as pink solid. MS (ESI) m/z: 509 $[M+H]^+$. $^1H$ NMR (400 MHz, DMSO-$d_6$) δ 11.80 (s, 1H), 8.68 (s, 1H), 7.58 (d, J=10.8 Hz, 1H), 7.41-7.36 (m, 2H), 7.24-7.18 (m, 1H), 6.70-6.64 (m, 1H), 4.92 (t, J=4.4 Hz, 1H), 3.91-3.86 (m, 4H), 3.77-3.74 (m, 2H), 1.90-1.85 (m, 2H).

Step 5. Synthesis of 3,4-difluoro-2-((2-fluoro-4-iodophenyl)amino)-N-(3-oxopropoxy)benzamide

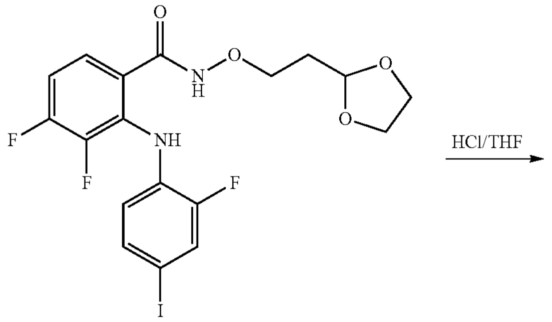

-continued

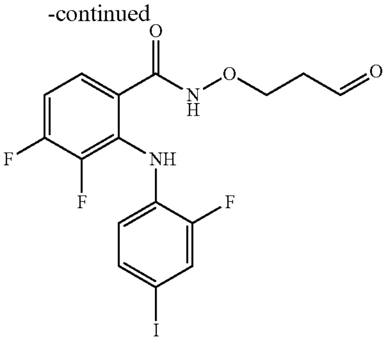

A solution of N-(2-(1,3-dioxolan-2-yl)ethoxy)-3,4-difluoro-2-((2-fluoro-4-iodophenyl)amino)benzamide (600 mg, 1.18 mmol) in a HCl solution in THF (20 mL, 3N) was stirred at rt for 6 h. before the reaction solution was poured into saturated $NaHCO_3$ solution (100 mL), extracted with EtOAc (2×50 mL). The combined organic layers were washed with brine, dried over $Na_2SO_4$, filtered, and concentrated. The resulting residue was purified with silica gel (petroleum ether:EtOAc=1:0 to 2:1) to give the title compound (300 mg, 54.7% yield) as brown solid. MS (ESI) m/z: 465.0 $[M+H]^+$.

Step 5. Synthesis of N-(3-((2-((3-acetamido-4-((4-methyl-5-nitrothiazol-2-yl)carbamoyl)phenyl)amino)ethyl)amino)propoxy)-3,4-difluoro-2-((2-fluoro-4-iodophenyl)amino)benzamide

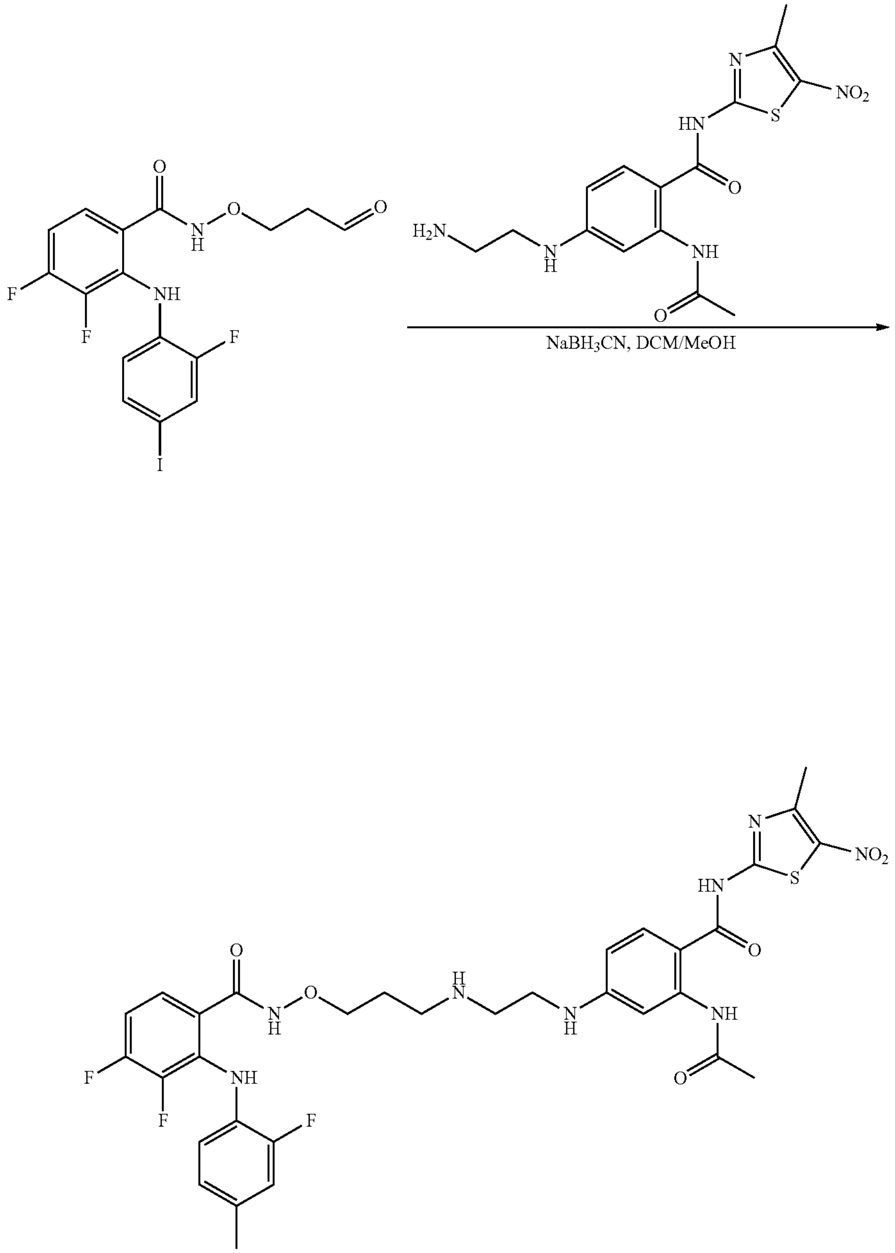

A solution of 3,4-difluoro-2-((2-fluoro-4-iodophenyl)amino)-N-(3-oxopropoxy)benzamide (7 mg, 0.015 mmol) and 2-acetamido-4-((2-aminoethyl)amino)-N-(4-methyl-5-nitrothiazol-2-yl)benzamide (5 mg, 0.015 mmol) in DCM and MeOH (1 mL, v/v=2:1) was stirred at rt for 0.5 h. Then $NaBH_3CN$ (9 mg, 0.15 mmol) was added at it. The resulting mixture was stirred at rt for 1 h, at which time the reaction was quenched with saturated $NaHCO_3$ (5 ml). And the mixture was extracted with EtOAc (2×3 mL). The combined organic layers were washed with brine, dried over $Na_2SO_4$, filtered, and concentrated. The crude product was purified by prep-HPLC to give the title compound (1 mg, 8% yield) as yellow solid. MS (ESI) m/z: 827.3 $[M+H]^+$.

Example 220. N-(3-((4-((3-Acetamido-4-((4-methyl-5-nitrothiazol-2-yl)carbamoyl)phenyl)amino)butyl)amino)propoxy)-3,4-difluoro-2-((2-fluoro-4-iodophenyl)amino)benzamide (D-62)

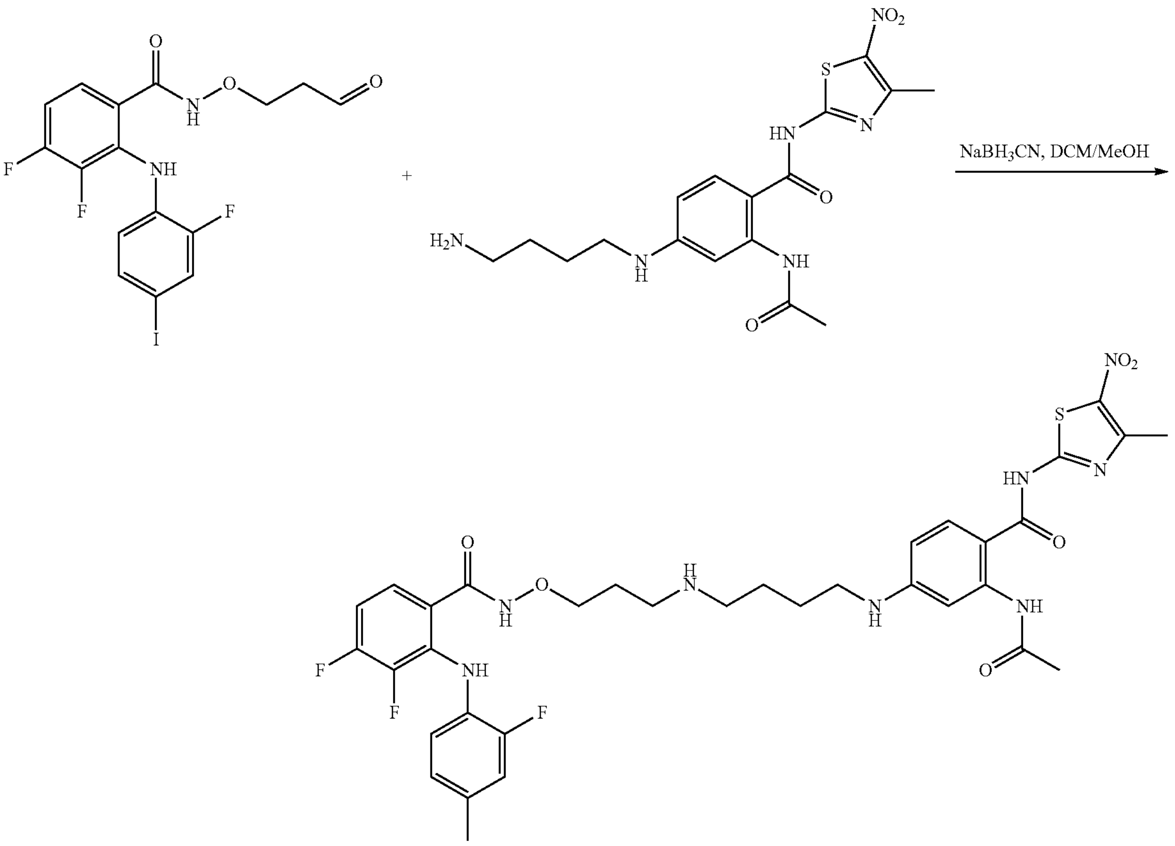

D-62 was synthesized following the standard procedure for preparing D-72 (3 mg, 23.4% yield). MS (EST) m/z: 855.3 $[M+H]^+$.

Example 221. N-(3-((6-((3-Acetamido-4-((4-methyl-5-nitrothiazol-2-yl)carbamoyl)phenyl)amino)hexyl)amino)propoxy)-3,4-difluoro-2-((2-fluoro-4-iodophenyl)amino)benzamide (D-63)

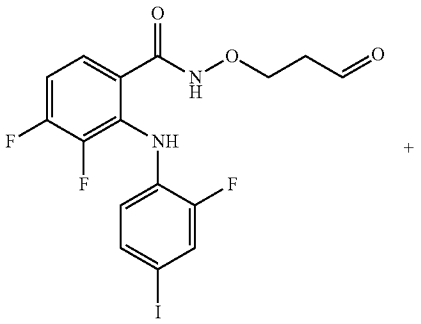

-continued
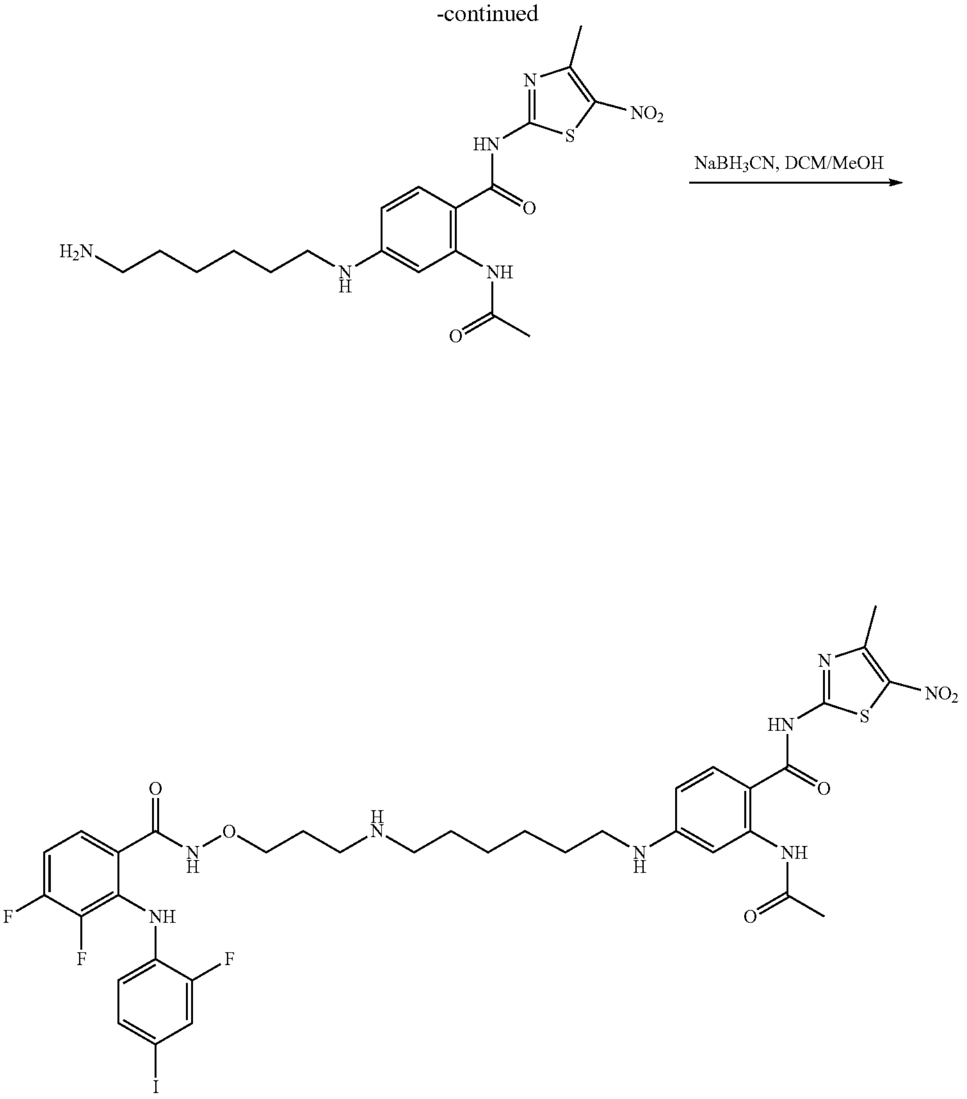
D-63 was synthesized following the standard procedure for preparing D-72 (2 mg, 15.1% yield). MS (EST) m/z: 883.3 $[M+H]^+$.
Example 222. N-(3-((7-((3-Acetamido-4-((4-methyl-5-nitrothiazol-2-yl)carbamoyl)phenyl)amino) heptyl)amino)propoxy)-3,4-difluoro-2-((2-fluoro-4-iodophenyl)amino)benzamide (D-64)
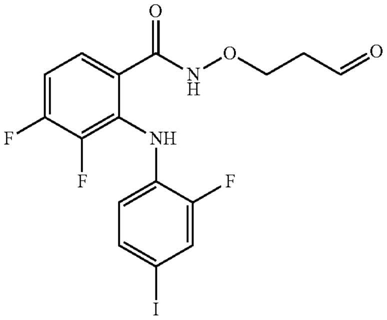
+

-continued
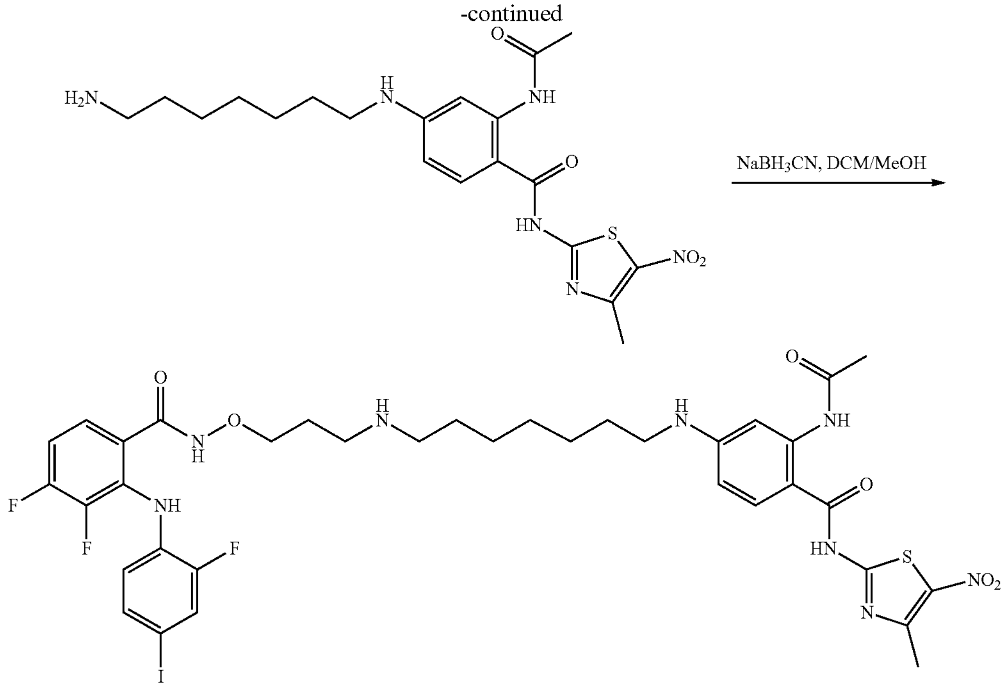
D-64 was synthesized following the standard procedure for preparing D-72 (1 mg, 7.4% yield). MS (EST) m/z: 897.4 $[M+H]^+$.
Example 223. N-(3-((10-((3-Acetamido-4-((4-methyl-5-nitrothiazol-2-yl)carbamoyl)phenyl)amino)decyl)amino)propoxy)-3,4-difluoro-2-((2-fluoro-4-iodophenyl)amino)benzamide (D-65)
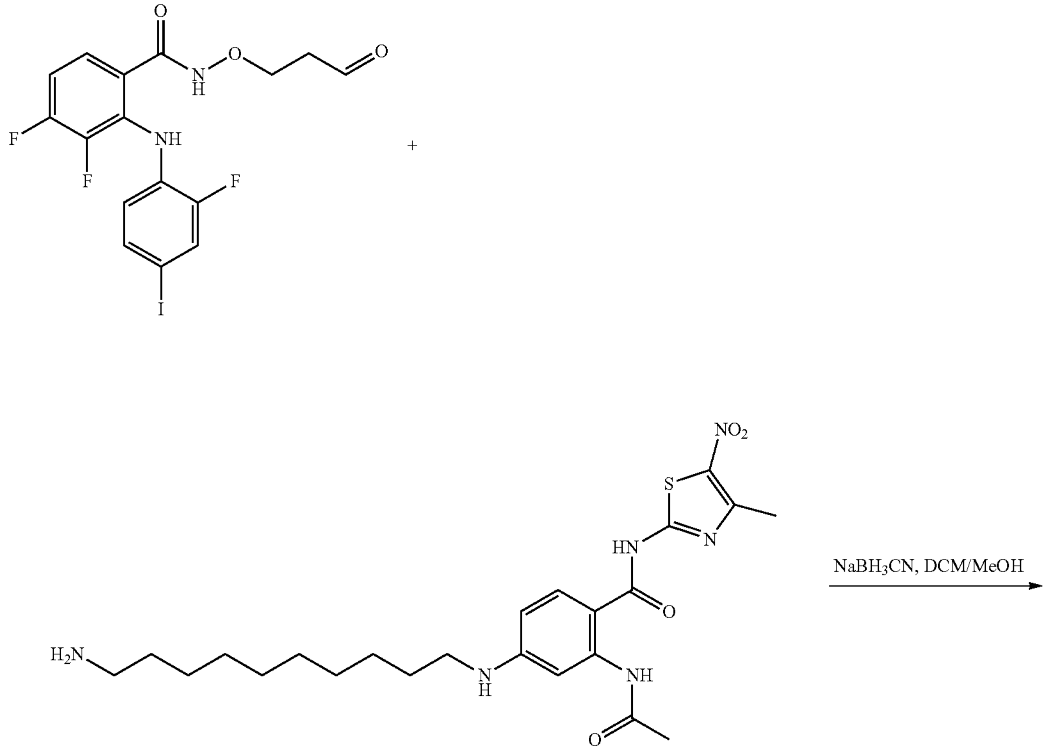

-continued
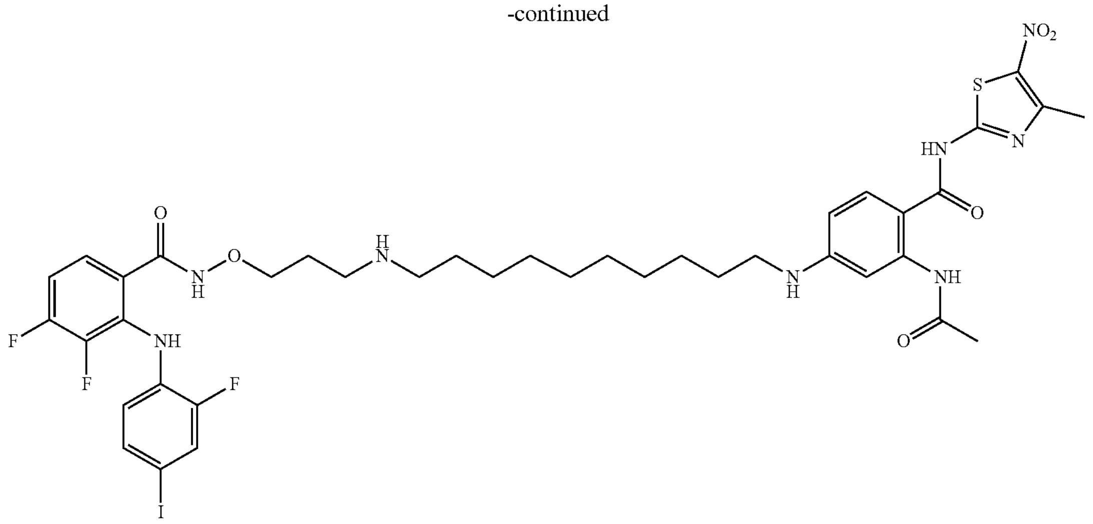
D-65 was synthesized following the standard procedure for preparing D-72 (2 mg, 14.2% yield). MS (EST) m/z: 939.4 $[M+H]^+$.
Example 224. N-(3-((2-(2-((3-Acetamido-4-((4-methyl-5-nitrothiazol-2-yl)carbamoyl)phenyl)amino)ethoxy)ethyl)amino)propoxy)-3,4-difluoro-2-((2-fluoro-4-iodophenyl)amino)benzamide (D-66)
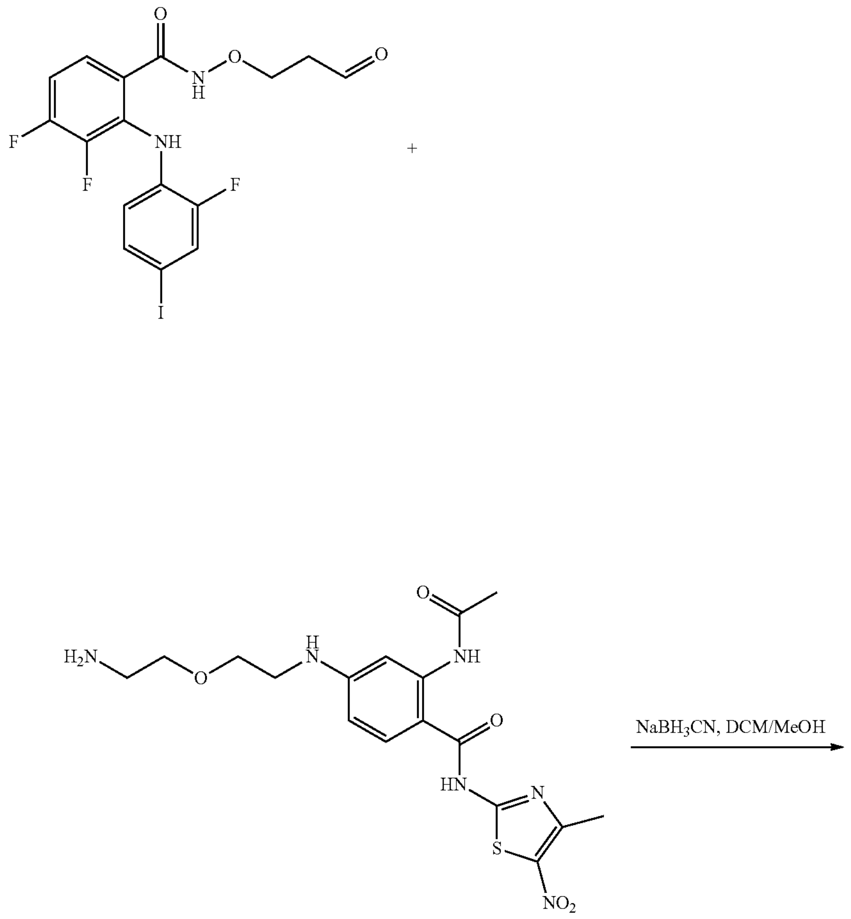

-continued
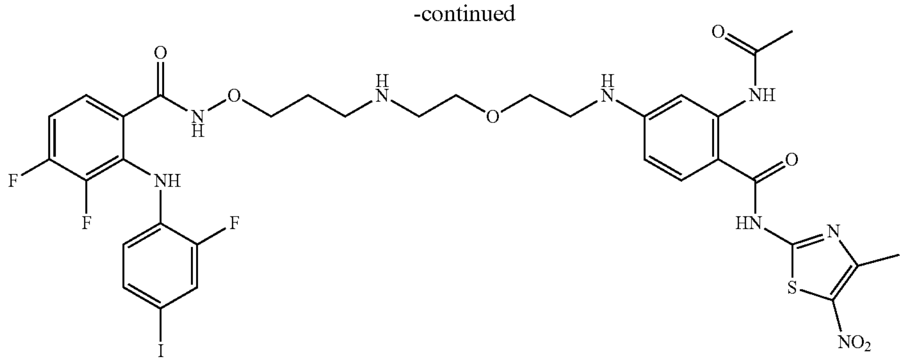
D-66 was synthesized following the standard procedure for preparing D-72 (3 mg, 22.9% yield). MS (EST) m/z: 871.3 $[M+H]^+$.
Example 225. N-(3-((2-(2-(2-((3-Acetamido-4-((4-methyl-5-nitrothiazol-2-yl)carbamoyl)phenyl)amino)ethoxy)ethoxy)ethyl)amino)propoxy)-3,4-difluoro-2-((2-fluoro-4-iodophenyl)amino)benzamide (D-67)
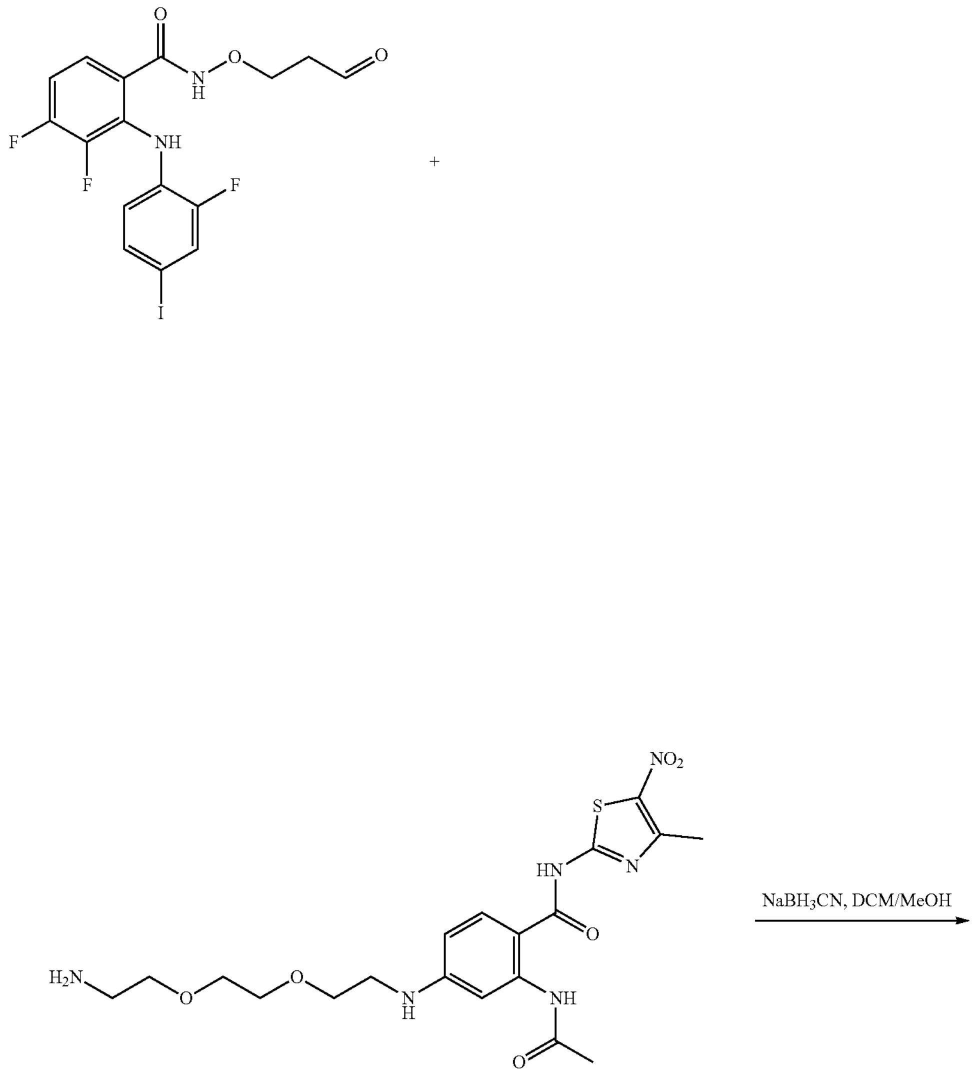

-continued
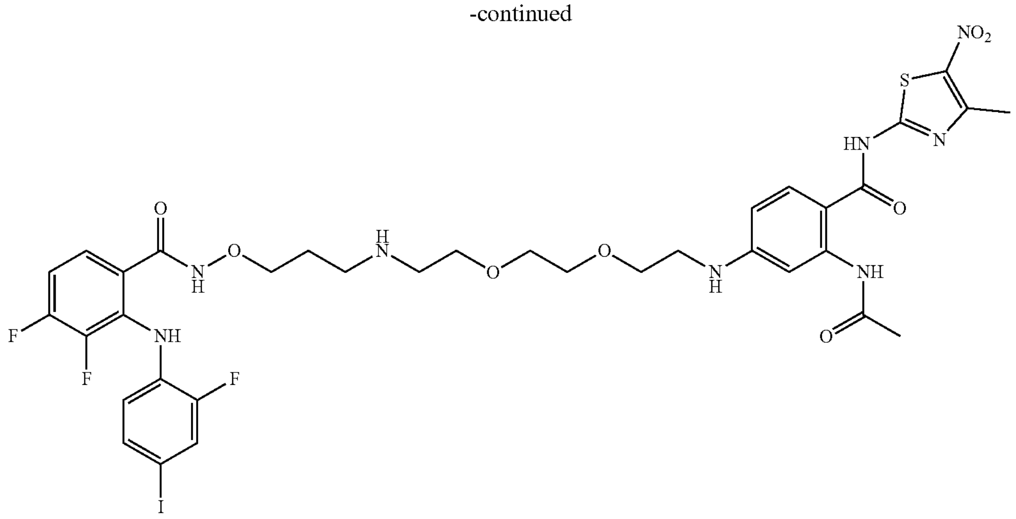
D-67 was synthesized following the standard procedure for preparing D-72 (1 mg, 7.3% yield). MS (EST) m/z: 915.4 $[M+H]^+$.
Example 226. N-(3-((8-((3-Acetamido-4-((4-methyl-5-nitrothiazol-2-yl)carbamoyl)phenyl)amino)octyl)amino)propoxy)-3,4-difluoro-2-((2-fluoro-4-iodophenyl)amino)benzamide (D-68)
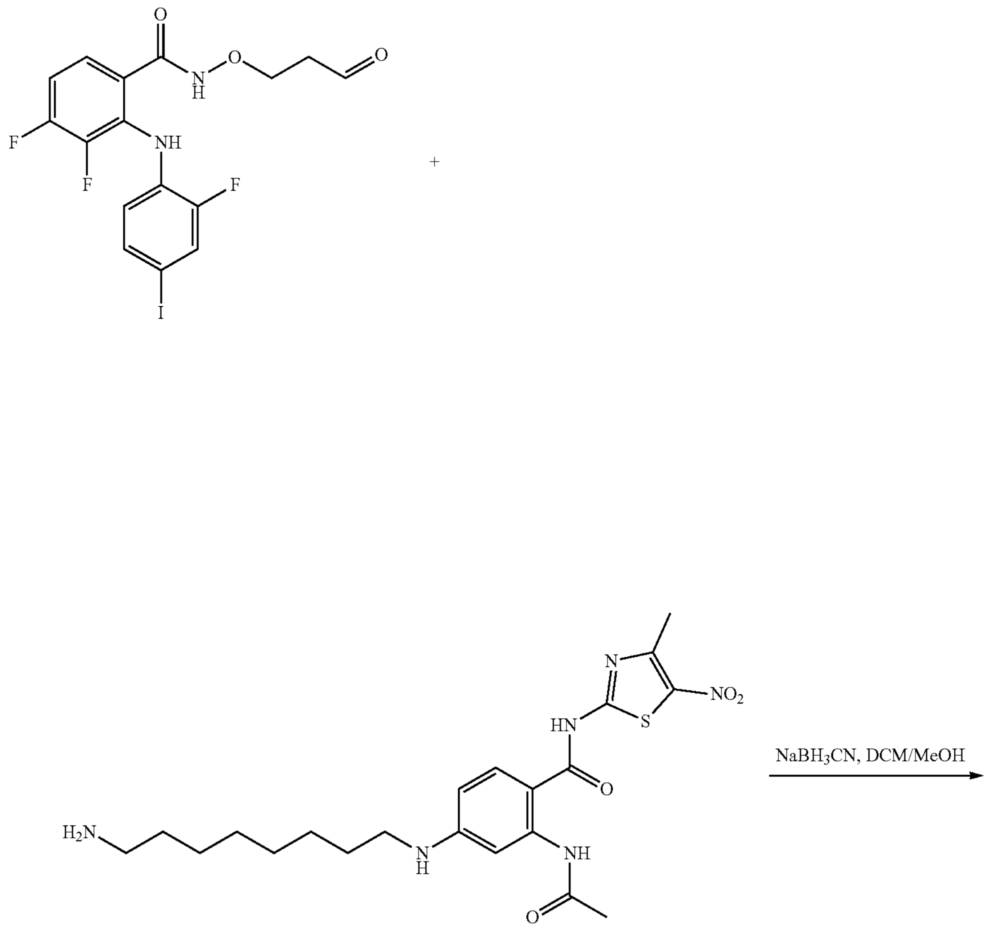

-continued
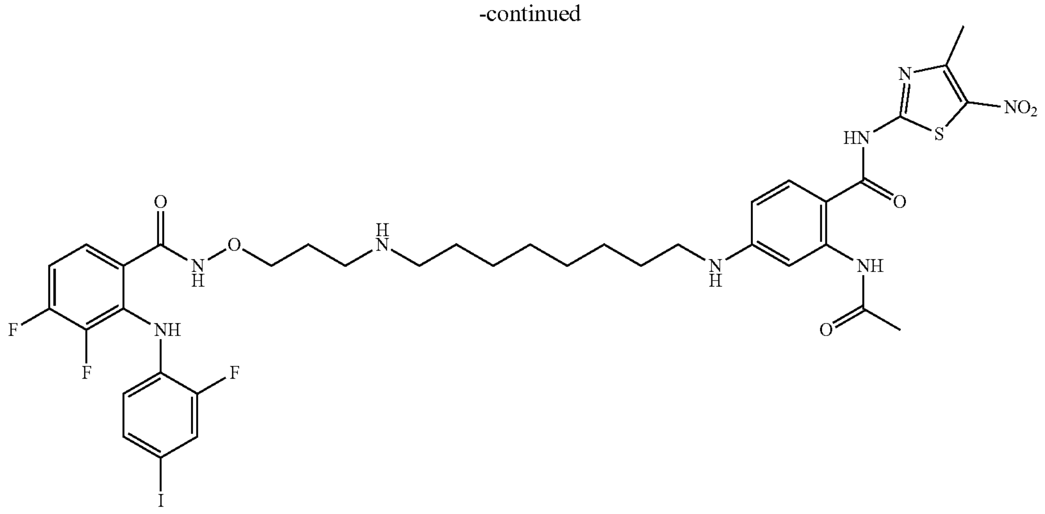
D-68 was synthesized following the standard procedure for preparing D-72 (1 mg, 7.3% yield). MS (EST) m/z: 911.3 $[M+H]^+$.
Example 227. N-(3-((9-((3-Acetamido-4-((4-methyl-5-nitrothiazol-2-yl)carbamoyl)phenyl)amino)nonyl)amino)propoxy)-3,4-difluoro-2-((2-fluoro-4-iodophenyl)amino)benzamide (D-69)
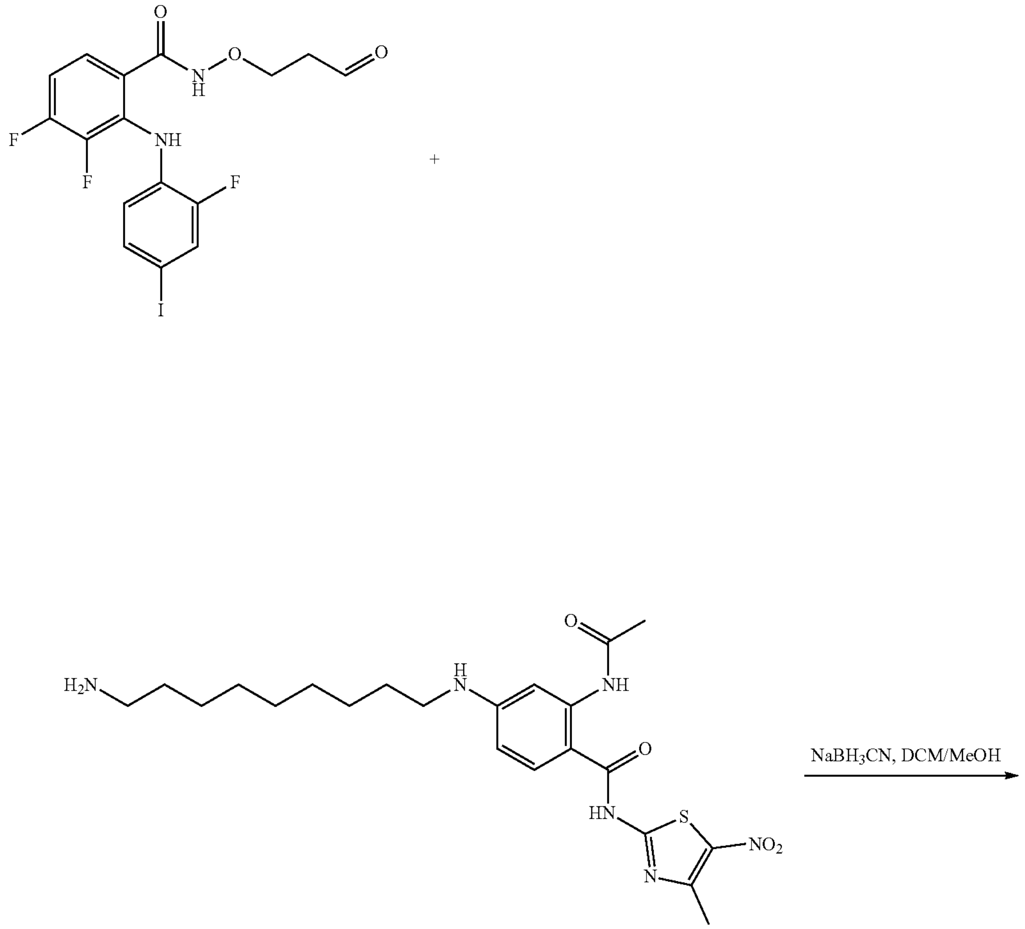

-continued
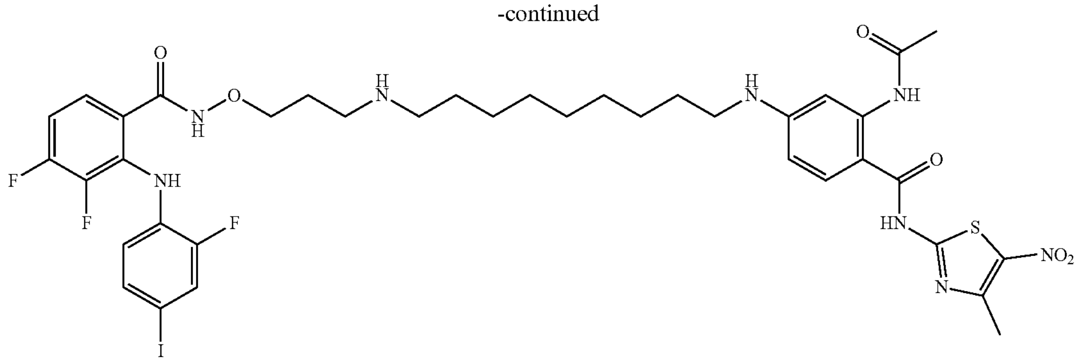
D-69 was synthesized following the standard procedure for preparing D-72 (2 mg, 14.4% yield). MS (EST) m/z: 925.5 [M+H]+.
Example 228. N-(3-((11-((3-Acetamido-4-((4-methyl-5-nitrothiazol-2-yl)carbamoyl)phenyl)amino)undecyl)amino)propoxy)-3,4-difluoro-2-((2-fluoro-4-iodophenyl)amino)benzamide (D-70)
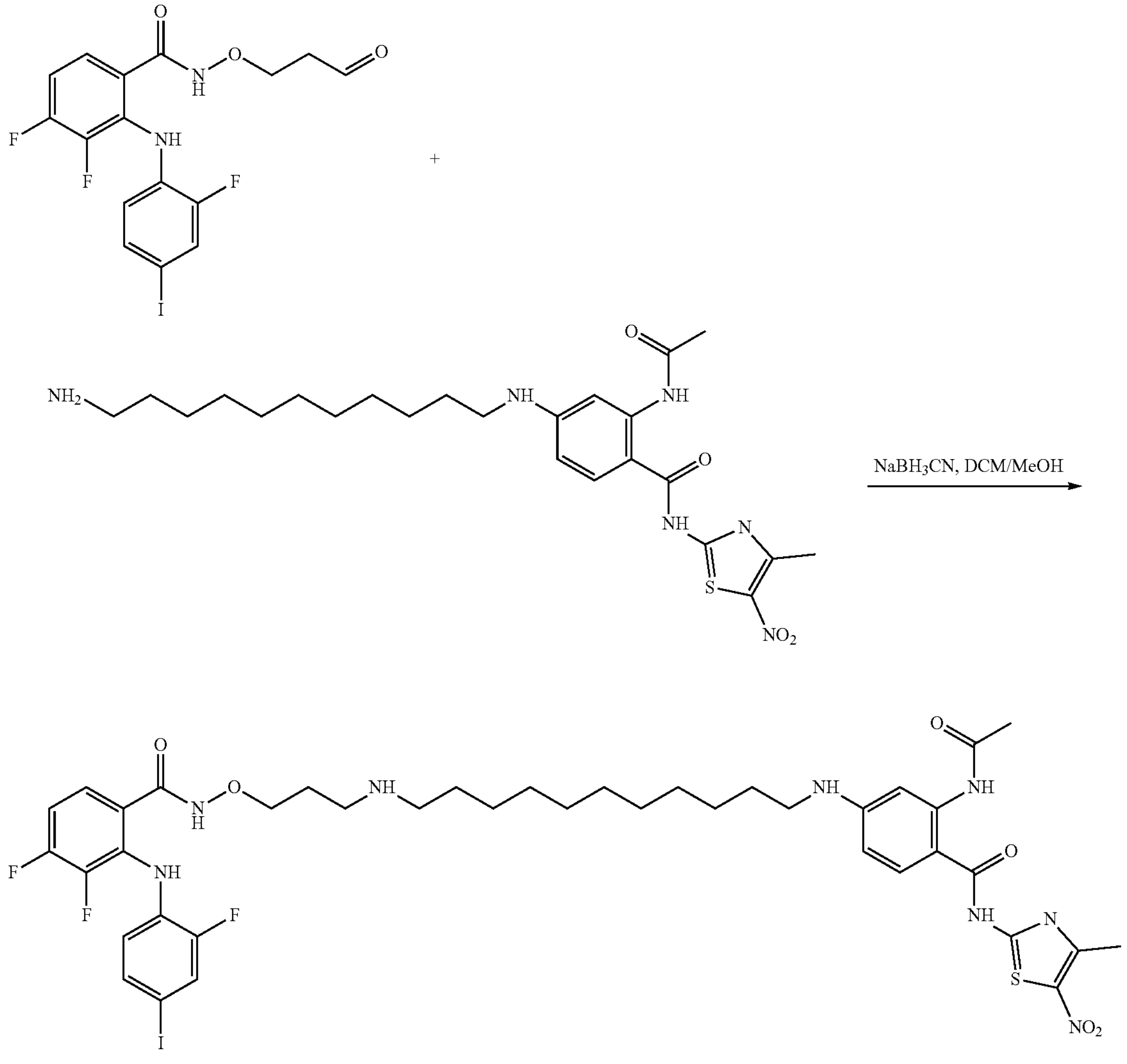

D-70 was synthesized following the standard procedure for preparing D-72 (3 mg, 21% yield). MS (EST) m/z: 953.6 $[M+H]^+$.
Example 229. N-((1-((3-Acetamido-4-((4-methyl-5-nitrothiazol-2-yl)carbamoyl)phenyl)amino)-3,6,9-trioxa-12-azapentadecan-15-yl)oxy)-3,4-difluoro-2-((2-fluoro-4-iodophenyl)amino)benzamide (D-71)
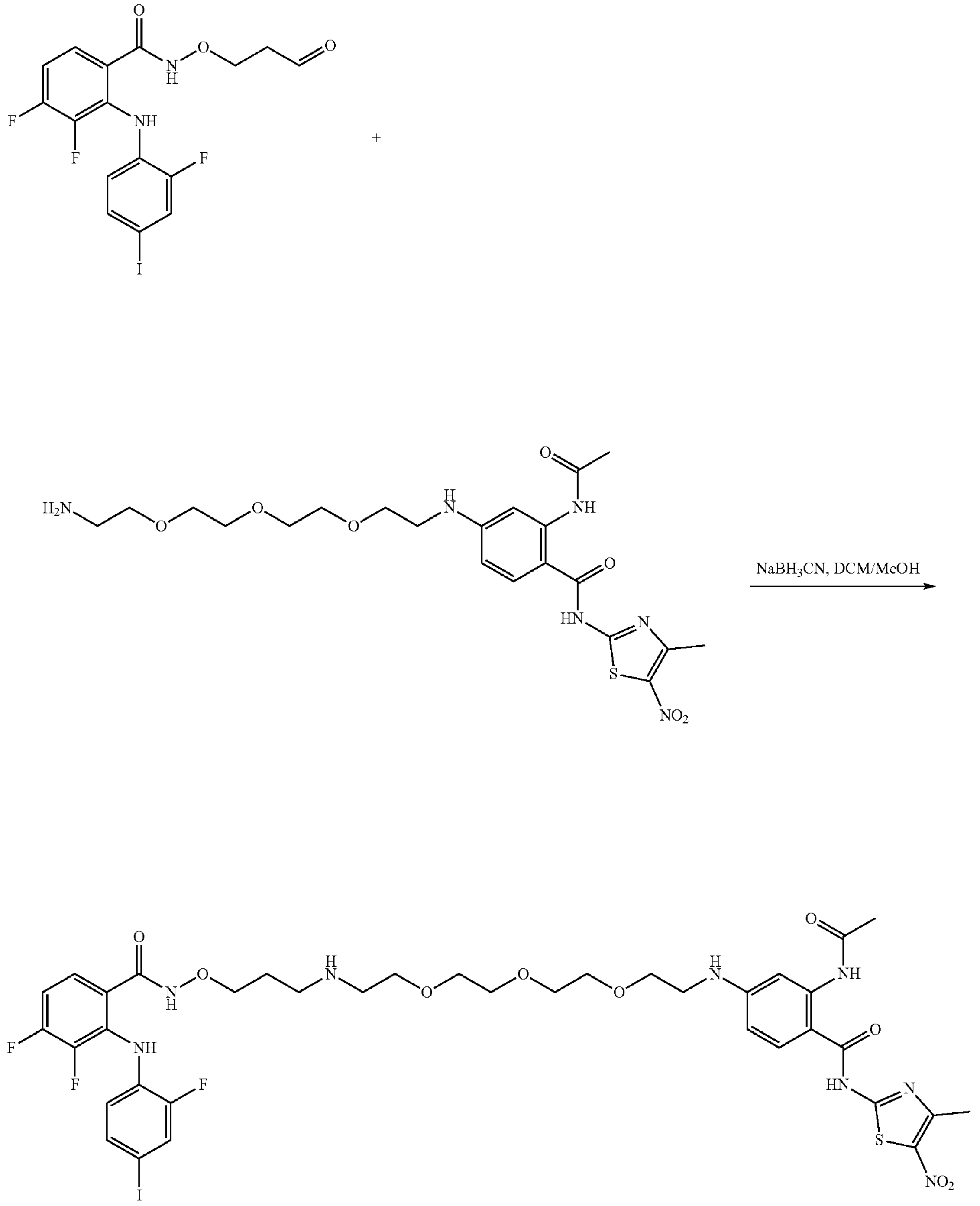
D-71 was synthesized following the standard procedure for preparing D-72 (1 mg, 6.9% yield). MS (EST) m/z: 959.5 $[M+H]^+$.

Example 230. N-(3-((3-((3-Acetamido-4-((4-methyl-5-nitrothiazol-2-yl)carbamoyl)phenyl)amino)propyl)amino)propoxy)-3,4-difluoro-2-((2-fluoro-4-iodophenyl)amino)benzamide (D-73)

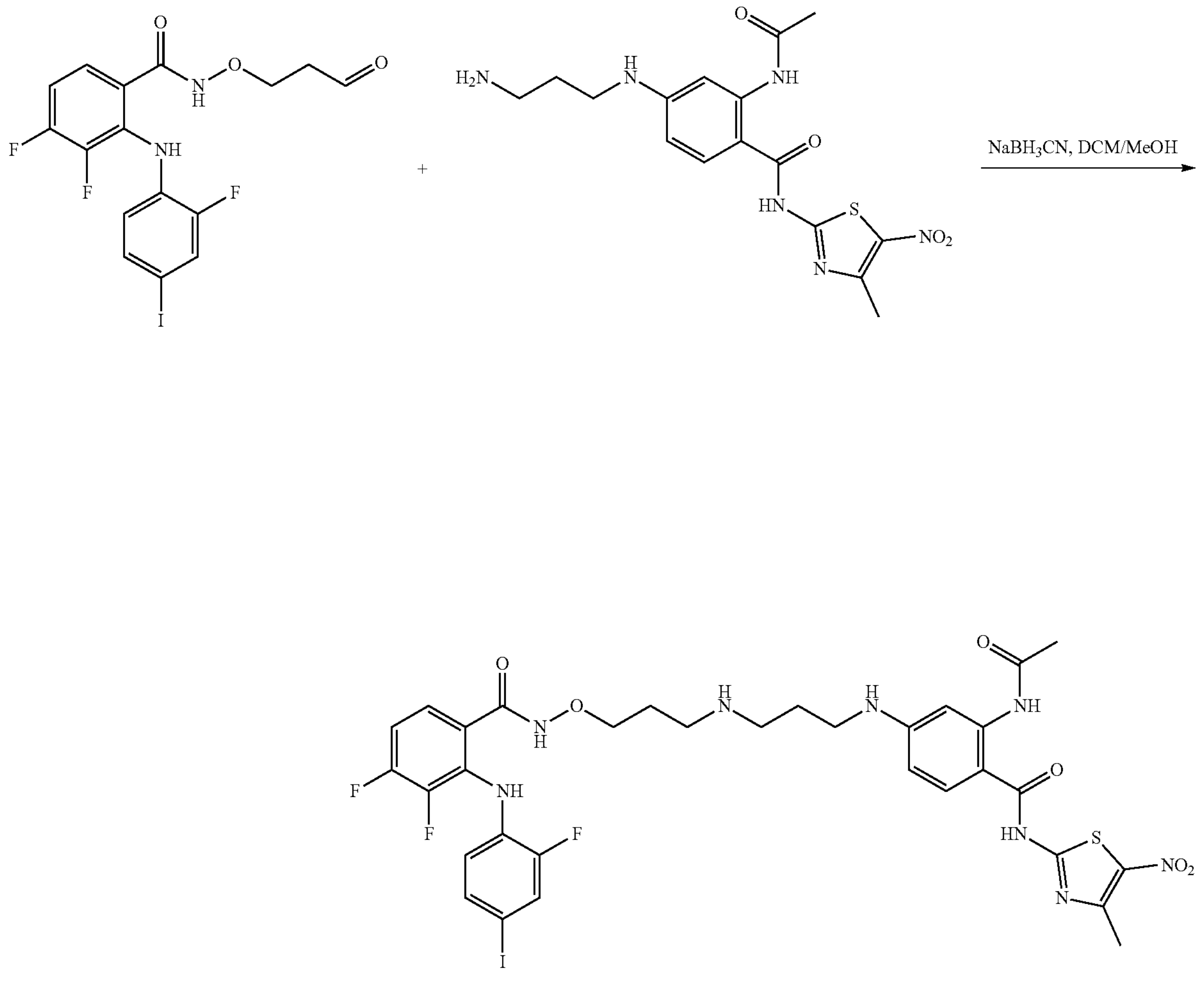

D-73 was synthesized following the standard procedure for preparing D-72 (1.67 mg, 13.3% yield). MS (EST) m/z: 841.3 $[M+H]^+$.

Example 231. N-(3-((5-((3-Acetamido-4-((4-methyl-5-nitrothiazol-2-yl)carbamoyl)phenyl)amino)pentyl)amino)propoxy)-3,4-difluoro-2-((2-fluoro-4-iodophenyl)amino)benzamide (D-74)

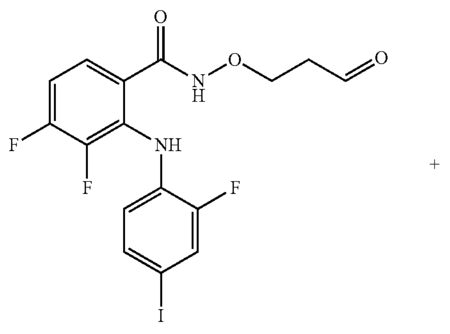

-continued
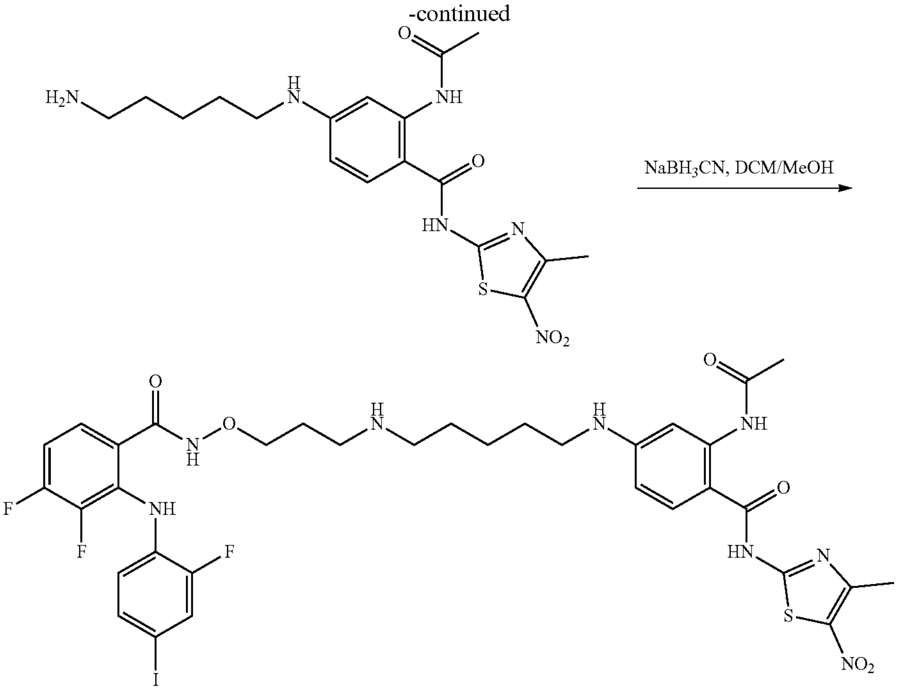
D-74 was synthesized following the standard procedure for preparing D-72 (1.75 mg, 13.4% yield). MS (EST) m/z: 869.3 $[M+H]^+$.
Example 232. N-((1-((3-Acetamido-4-((4-methyl-5-nitrothiazol-2-yl)carbamoyl)phenyl)amino)-3,6,9,12-tetraoxa-15-azaoctadecan-18-yl)oxy)-3,4-difluoro-2-((2-fluoro-4-iodophenyl)amino)benzamide (D-75)
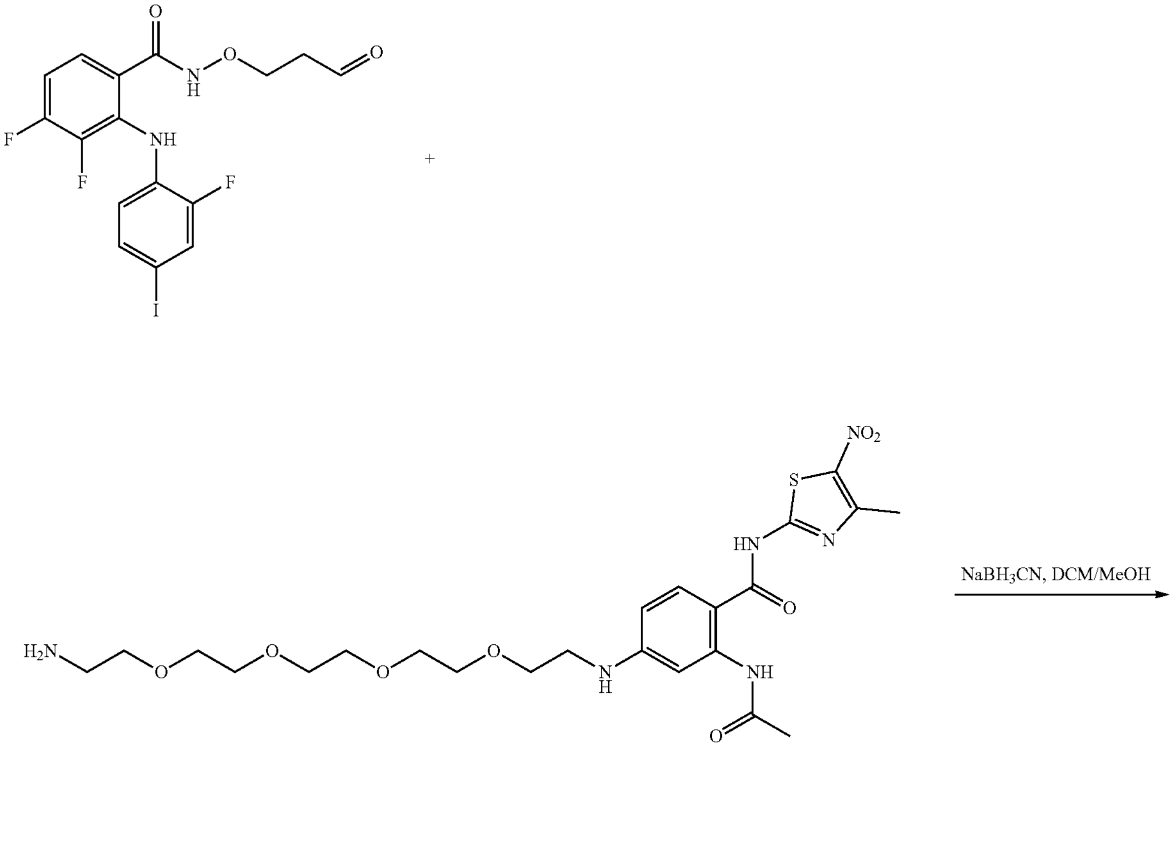

-continued
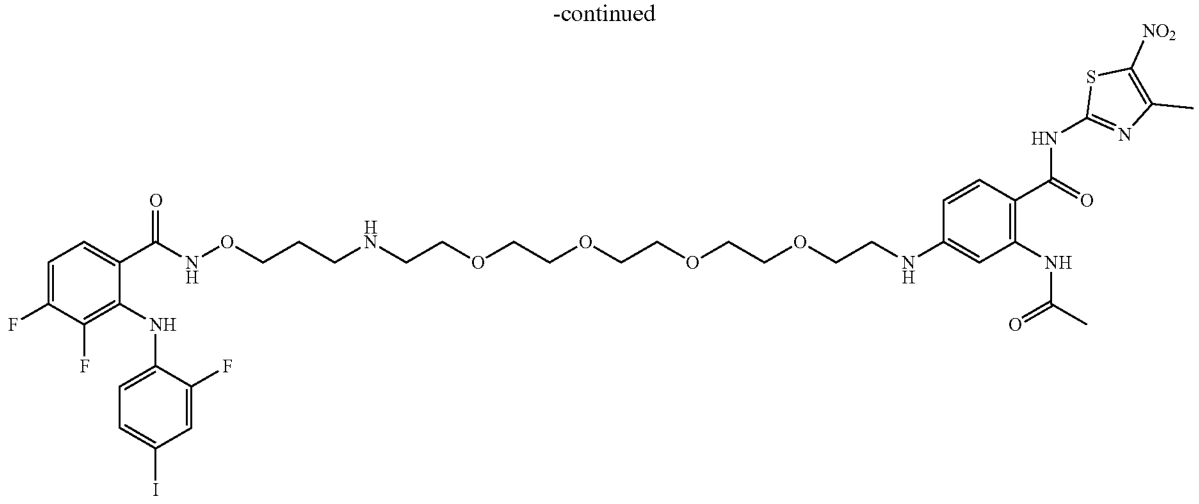
D-75 was synthesized following the standard procedure for preparing D-72 (1.75 mg, 11.6% yield). MS (EST) m/z: 1003.4 $[M+H]^+$.
Example 233. N-((1-((3-Acetamido-4-((4-methyl-5-nitrothiazol-2-yl)carbamoyl)phenyl)amino)-3,6,9,12,15-pentaoxa-18-azahenicosan-21-yl)oxy)-3,4-difluoro-2-((2-fluoro-4-iodophenyl)amino)benzamide (D-76)
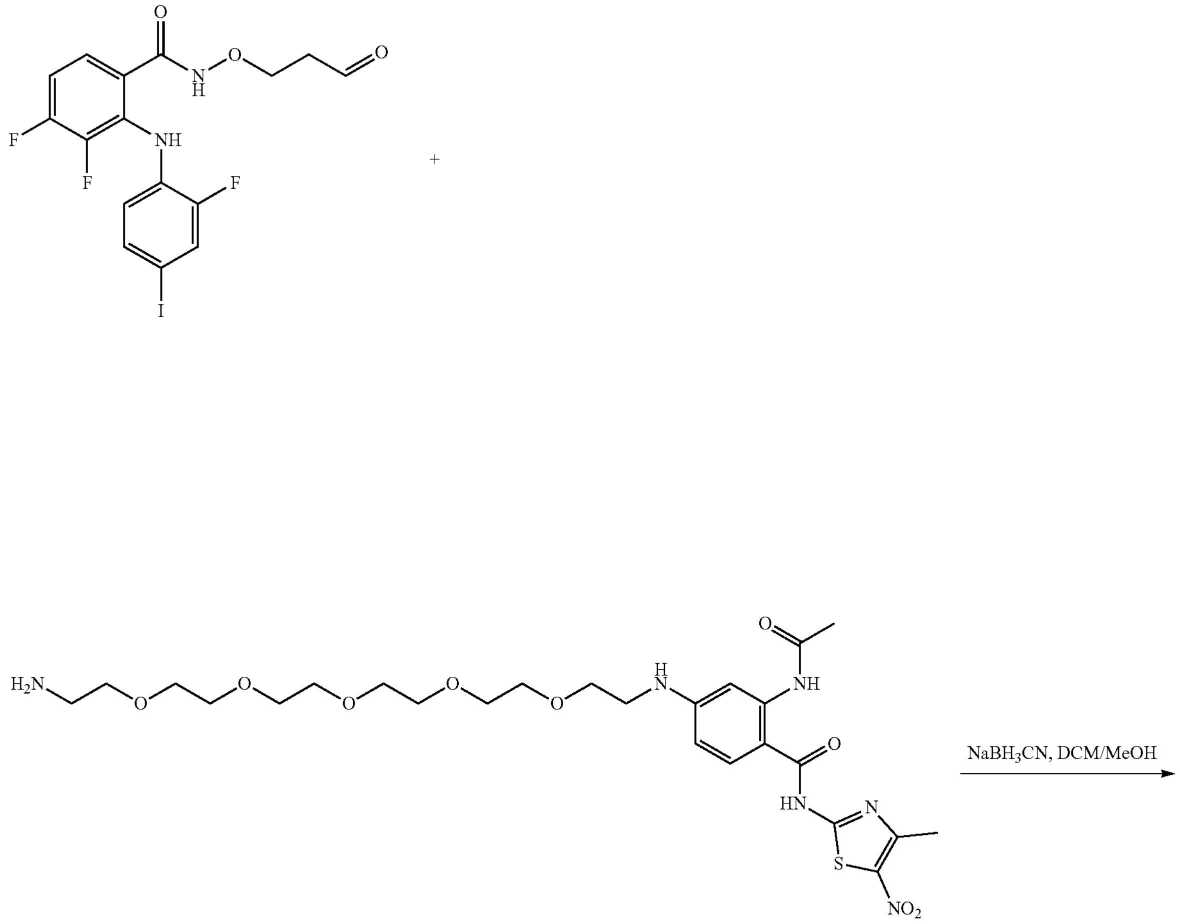

-continued
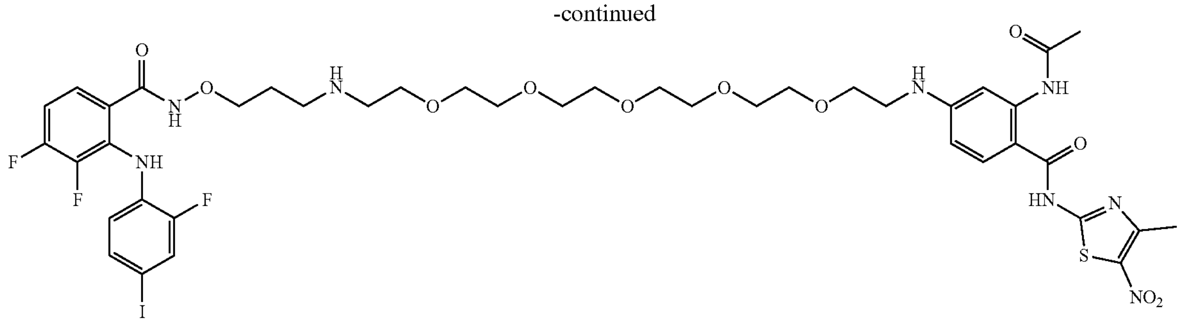
D-76 was synthesized following the standard procedure for preparing D-72 (1.54 mg, 9.8% yield). MS (EST) m/z: 1047.5 $[M+H]^+$.
Example 234. N-((1-((3-Acetamido-4-((4-methyl-5-nitrothiazol-2-yl)carbamoyl)phenyl)amino)-3,6,9,12,15,18-hexaoxa-21-azatetracosan-24-yl)oxy)-3,4-difluoro-2-((2-fluoro-4-iodophenyl)amino)benzamide (D-77)
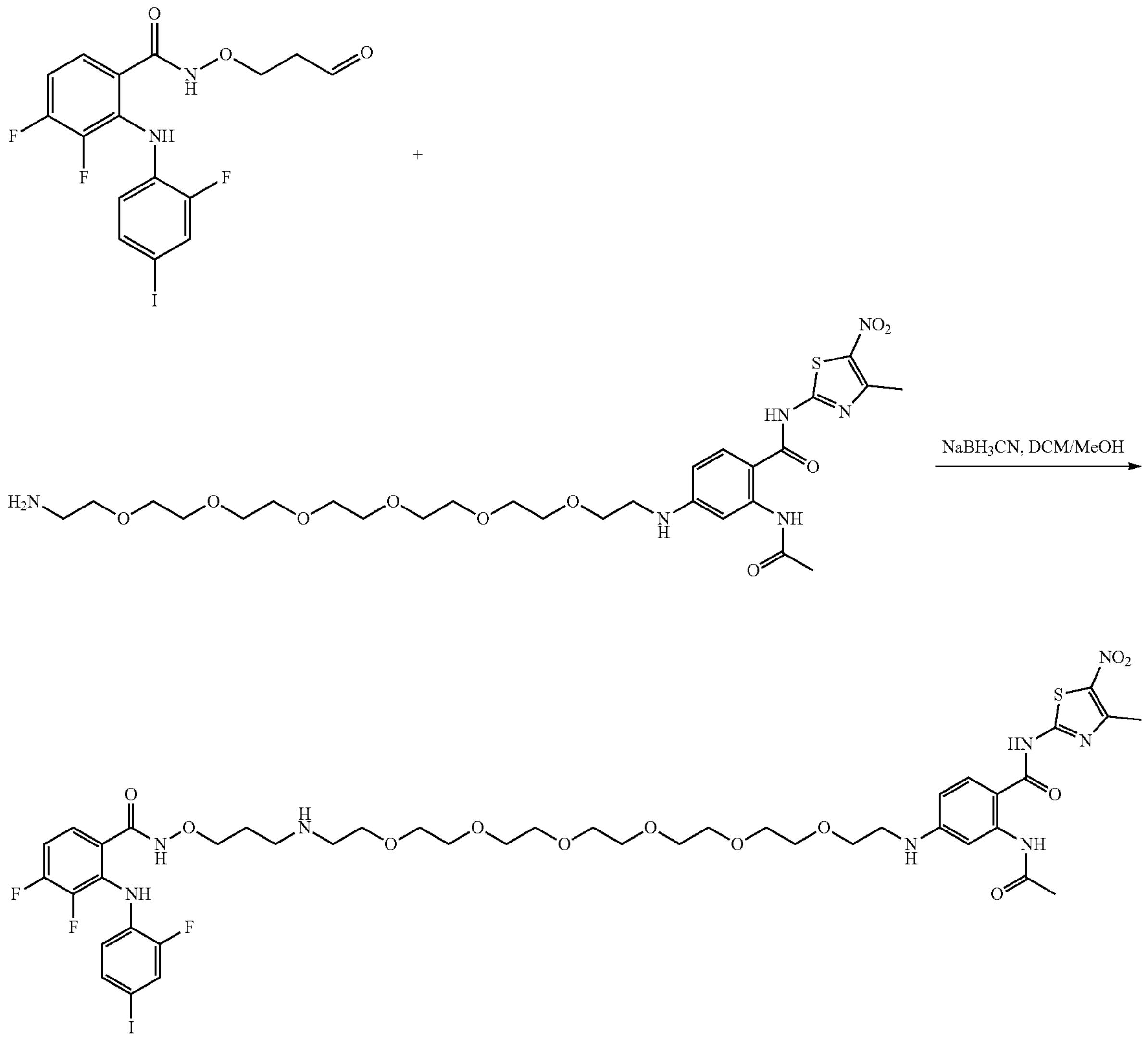

D-77 was synthesized following the standard procedure for preparing D-72 (2 mg, 12.2% yield). MS (EST) m/z: 1091.6 $[M+H]^+$.

Example 235. 6-Methylheptyl 3-((4-(methylamino)-4-oxobutyl)carbamoyl)-6,7-dihydro-[1,2,3]triazolo[1,5-a]pyrazine-5 (4H)-carboxylate (B-144)

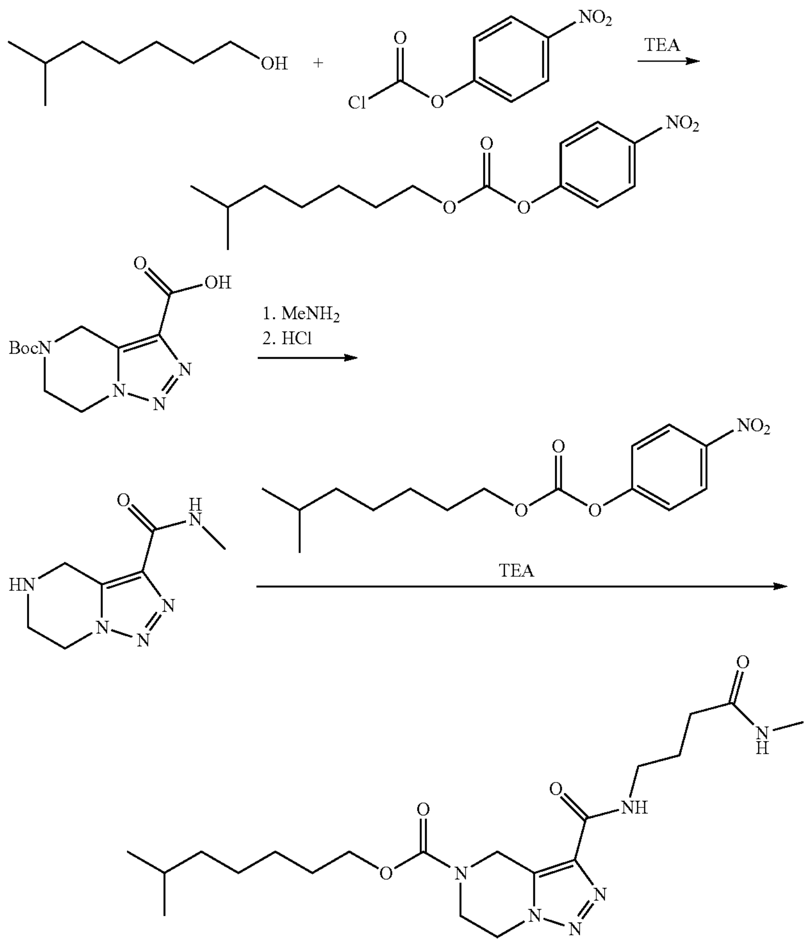

Step 1. Synthesis of 6-methylheptyl (4-nitrophenyl) carbonate

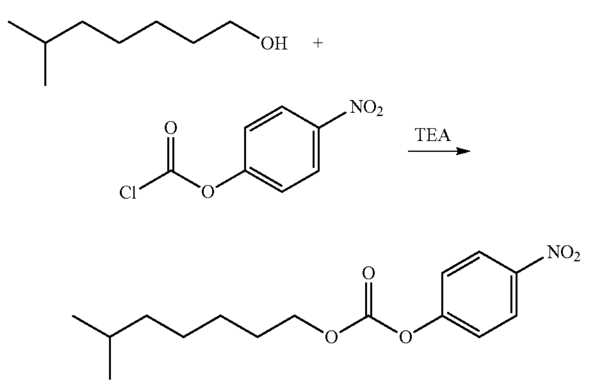

To a solution of 6-methylheptan-1-ol (0.5 g, 3.85 mmol) in DCM (5 mL) was added 4-nitrophenyl carbonochloridate (734 mg, 3.65 mmol) followed by TEA (855 mg, 8.47 mmol) at 0° C. The reaction was allowed to stir at rt for 1 h before it was quenched with water (50 mL). The aqueous phase was extracted with DCM (2×50 mL). The combined organic layers were washed with HCl (100 mL, 1N), brine (100 mL), dried over $Na_2SO_4$, filtered, and concentrated to afford the title compound as white solid (1.1 g, 99% yield), which was used directly in the next step without further purification.

Step 2. Synthesis of N-methyl-4,5,6,7-tetrahydro-[1,2,3]triazolo[1,5-a]pyrazine-3-carboxamide

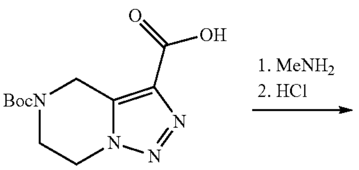

-continued

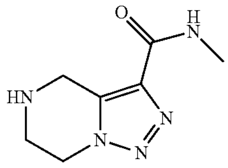

To a solution of 5-(tert-butoxycarbonyl)-4,5,6,7-tetrahydro-[1,2,3]triazolo[1,5-a]pyrazine-3-carboxylic acid (150 mg, 0.56 mmol) in DMF (5 mL) were added $MeNH_2$ (17.4 mg, 0.56 mmol), EDCI (129 mg, 0.67 mmol) and HOBt (91 mg, 0.67 mmol) followed by DIEA (145 mg, 1.12 mmol). The reaction was stirred at rt overnight before it was quenched with water (50 mL). The resulting mixture were extracted with DCM (3×50 mL). The combined organic layers were washed with brine (100 mL), dried over $Na_2SO_4$, filtered, and concentrated. The resulting residue was purified by flash chromatography to afford the Boc protected intermediate. The purified intermediate was treated with HCl/dioxane (5 mL, 4 N) for 2 h. The reaction mixture was concentrated to afford the title compound, which was used in the nest step without further purification.

Step 3. Synthesis of 6-methylheptyl 3-((4-(methylamino)-4-oxobutyl)carbamoyl)-6,7-dihydro-[1,2,3]triazolo[1,5-a]pyrazine-5 (4H)-carboxylate

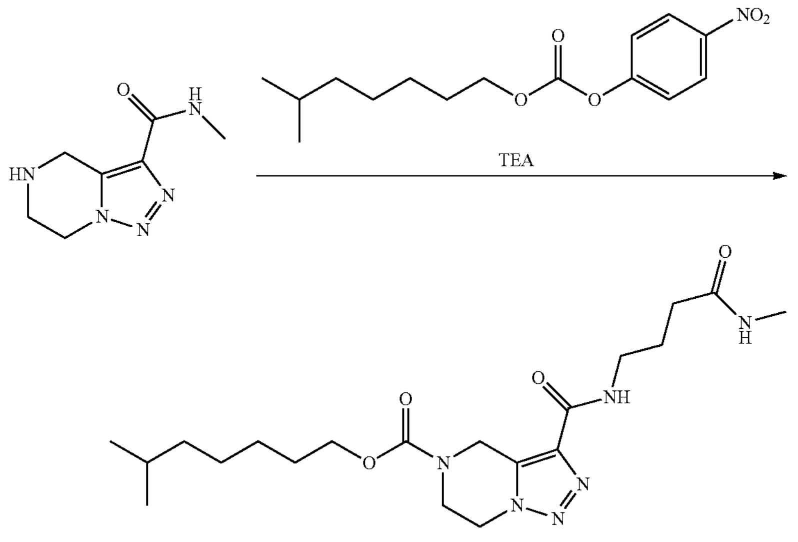

To a solution of N-methyl-4,5,6,7-tetrahydro-[1,2,3]triazolo[1,5-a]pyrazine-3-carboxamide (72.4 mg, 0.4 mmol) in DMF (3 mL) was added 6-methylheptyl (4-nitrophenyl) carbonate (118 mg, 0.4 mol) followed by TEA (121 mg, 1.2 mmol). The reaction was stirred at rt until the materials was consumed. The reaction was quenched with water (50 mL) and the reaction mixture was extracted with EtOAc (3×50 mL). The combined organic layers were washed with brine (100 mL), dried over $Na_2SO_4$, filtered, and concentrated. The resulting residue was purified by prep-HPLC to afford the title compound (67 mg, 39.7% yield) as an oil. $^1$HNMR (400 MHz, $CDCl_3$): δ 7.32 (s, 1H), 6.08 (brs, 1H), 5.04 (s, 2H), 4.46 (t, J=5.2 Hz, 2H), 4.16 (t, J=6.8 Hz, 2H), 3.98 (t, J=4.8 Hz, 2H), 3.50 (q, J=6.4 Hz, 2H), 2.83 (d, J=4.8 Hz, 3H), 2.26 (t, J=6.8 Hz, 2H), 1.97 (t, J=6.8 Hz, 2H), 1.64-1.69 (m, 2H), 1.50-1.54 (m, 1H), 1.16-1.34 (m, 6H), 0.87 (d, J=6.8 Hz, 6H). MS (ESI) m/z: 423.0 [M+H]$^+$.

Example 236. 2-((Cyclopropylmethyl)amino)-6-(3-hydroxyphenyl)-N-methylnicotinamide (B-143)

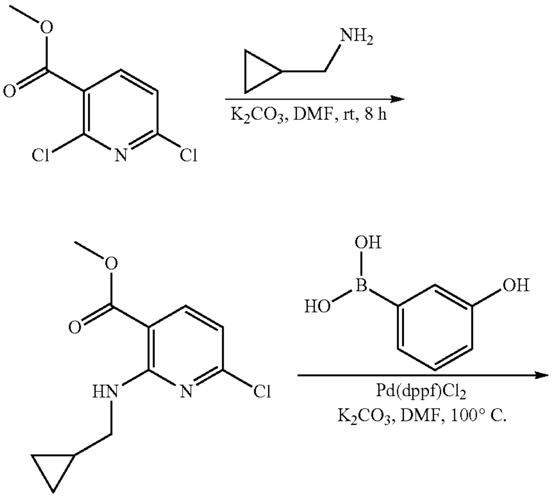

-continued

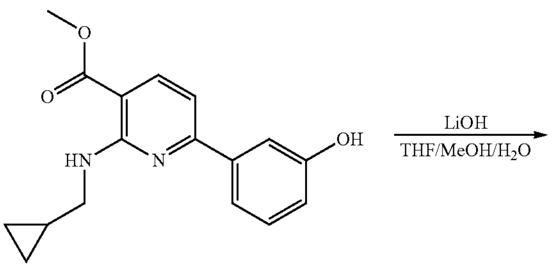

-continued

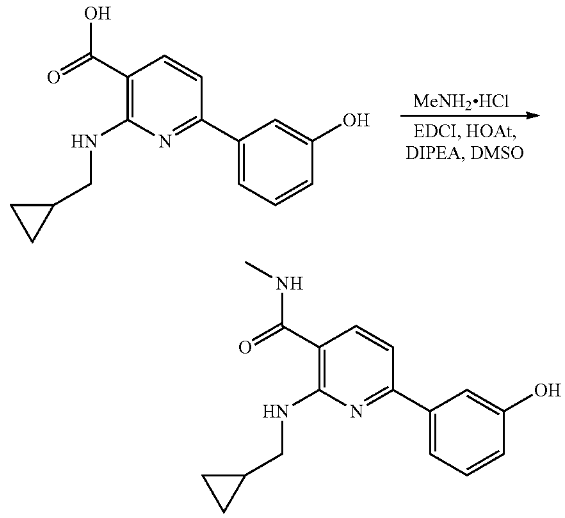

Step 1. Synthesis of methyl 6-chloro-2-((cyclopropylmethyl)amino)nicotinate

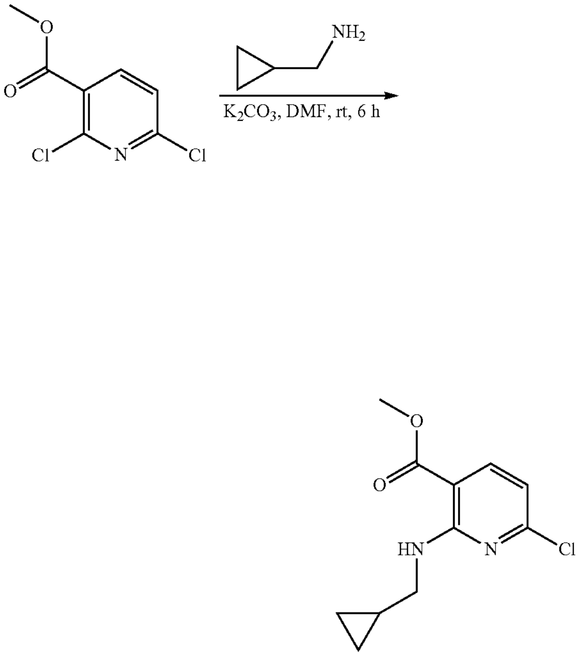

A mixture of methyl 2,6-dichloronicotinate (200 mg, 0.98 mol), cyclopropylmethanamine (69 mg, 0.98 mmol), and $K_2CO_3$ (270 mg, 1.96 mmol) in DMF (5 mL) was stirred at rt for 16 h. The reaction was poured into water (50 mL) and extracted with EtOAc (3×20 mL). The combined organic layers were washed with saturated brine (50 mL), dried over anhydrous $Na_2SO_4$, filtered and evaporated under reduced pressure. The resulting residue was purified by silica gel column chromatography to give the desired product (120 mg, 51.1% yield) as a light yellow solid. MS (ESI) m/z: 241.1 $[M+H]^+$.

Step 2. Synthesis of methyl 2-((cyclopropylmethyl) amino)-6-(3-hydroxyphenyl)nicotinate

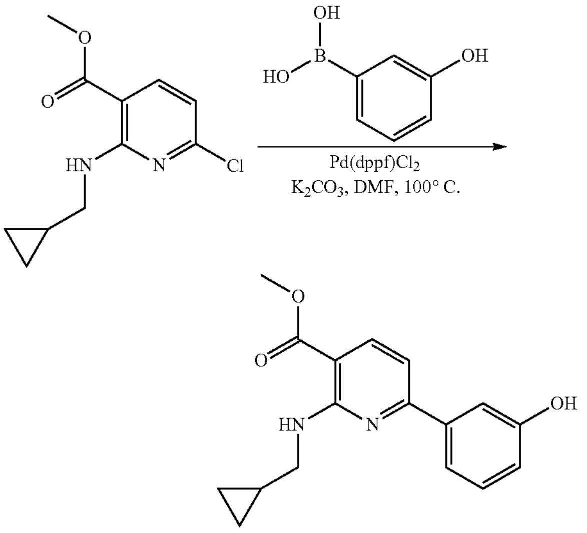

A mixture of methyl 6-chloro-2-((cyclopropylmethyl) amino)nicotinate (90 mg, 0.38 mmol), (3-hydroxyphenyl) boronic acid (58 mg, 0.42 mmol), $Pd(dppf)Cl_2$ (41 mg, 0.057 mmol), and $K_2CO_3$ (105 mg, 0.76 mmol) in DMF (3 mL) was stirred at 100° C. for 16 h. The reaction was poured into water (50 mL) and extracted with EtOAc (3×20 mL). The combined organic layers were washed with saturated brine (50 mL), dried over anhydrous $Na_2SO_4$, filtered and evaporated under reduced pressure. The resulting residue was purified by silica gel column chromatography to give the desired product (95 mg, 83.3% yield) as a light yellow solid. MS (EST) m/z: 299.1 $[M+H]^+$.

Step 3. Synthesis of 2-((cyclopropylmethyl)amino)-6-(3-hydroxyphenyl)nicotinic acid

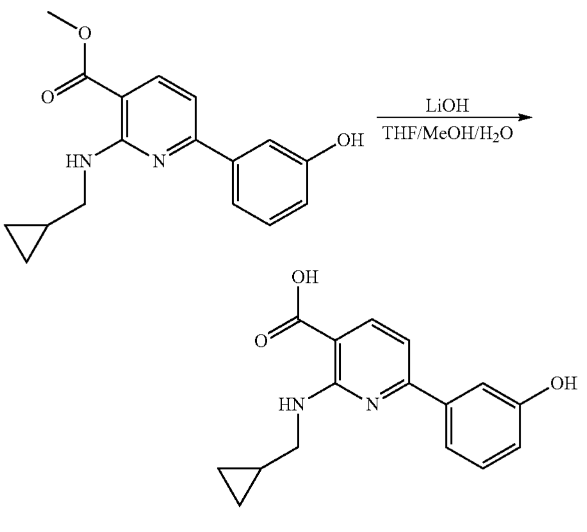

A mixture of methyl 2-((cyclopropylmethyl)amino)-6-(3-hydroxyphenyl)nicotinate (90 mg, 0.30 mmol), LiOH (72 mg, 3.00 mmol) in THF (2 mL), MeOH (2 mL), and $H_2O$ (1 mL) was stirred at rt for 3 h. The reaction was poured into water (50 mL). After the pH of the mixture was adjusted to 1, it was extracted with DCM (3×20 mL). The combined organic layers were washed with saturated brine (50 mL), dried over anhydrous $Na_2SO_4$, filtered and evaporated under reduced pressure. The resulting residue was purified by reverse-phase chromatography to give the desired product (78 mg, 91.2% yield) as a light yellow solid. MS (ESI) m/z: 283.1 $[M-H]^-$.

Step 4. Synthesis of 2-((cyclopropylmethyl)amino)-6-(3-hydroxyphenyl)-N-methylnicotinamide

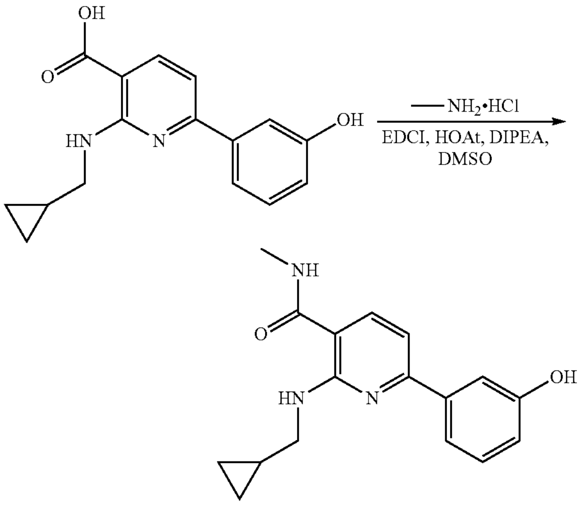

A mixture of 2-((cyclopropylmethyl)amino)-6-(3-hydroxyphenyl)nicotinic acid (50 mg, 0.18 mmol), methylamine hydrochloride (16 mg, 0.23 mmol), EDCI (51 mg, 0.26 mmol), HOAt (36 mg, 0.26 mmol), and DIPEA (116 mg, 0.90 mmol) in DMSO (3 mL) was stirred at rt for 16 h. The reaction was poured into water (50 mL) and extracted with EtOAc (3×20 mL). The combined organic layers were washed with saturated brine (50 mL), dried over anhydrous $Na_2SO_4$, filtered and evaporated under reduced pressure. The resulting residue was purified by reverse-phase chromatography to give the desired product (39 mg, 72.9% yield) as a light yellow solid. MS (ESI) m/z: 298.1 $[M+H]^+$.

Example 237. 4-(Piperidin-2-yl)-N-(pyrimidin-5-yl)pyrimidin-2-amine (B-137)

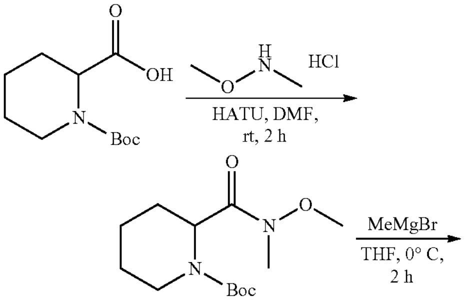

-continued

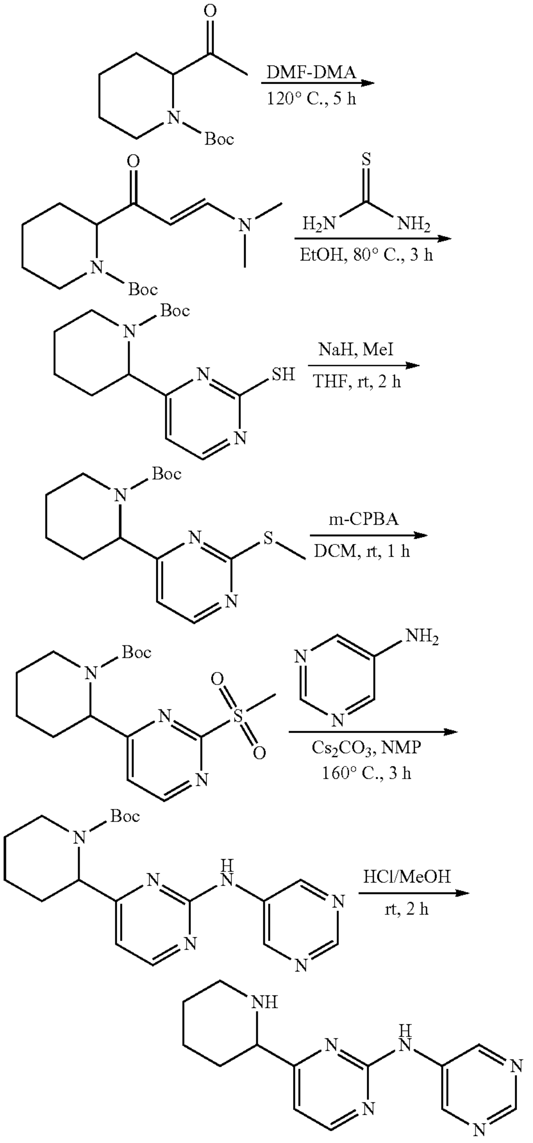

Step 1. Synthesis of tert-butyl 2-(methoxy(methyl)carbamoyl)piperidine-1-carboxylate

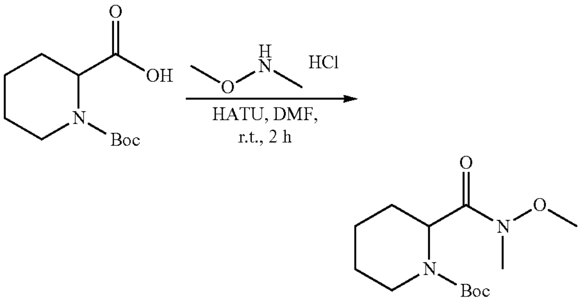

To a solution of 1-tert-butoxycarbonyl)piperidine-2-carboxylic acid (3.00 g, 13.10 mmol), HATU (7.40 g, 19.60 mmol) and DIPEA (5.07 g, 39.30 mol) in DMF (25 mL) was added N,O-dimethylhydroxylamine hydrochloride (1.90 g, 19.6 mmol) at rt. The mixture was stirred at it for 2 h. The mixture was quenched with water (3x50 mL) and extracted with ethyl acetate (3x50 mL). The combined organic phase was dried over $Na_2SO_4$, filtered and concentrated to give a residue, which was purified by silica gel column chromatography (petroleum ether:EtOAc=50:1 to 10:1) to give the title compound (2.8 g, yield: 80%) as colorless oil.

Step 2. Synthesis of tert-butyl 2-acetylpiperidine-1-carboxylate

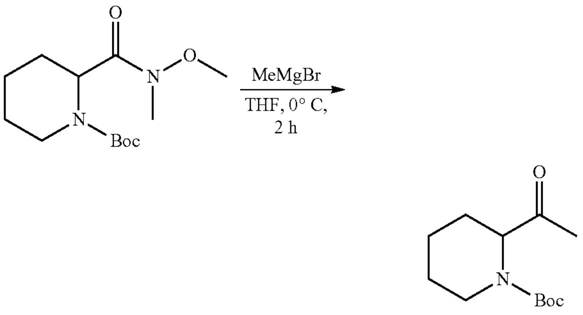 [SMILES: "MeMgBr" ; CON(C)C(=O)C1CCCCN1C(=O)OC(C)(C)C ; CC(=O)C1CCCCN1C(=O)OC(C)(C)C]

To a solution of tert-butyl 2-(methoxy(methyl)carbamoyl) piperidine-1-carboxylate (1.85 g, 6.80 mol) in THF (20 mL) was added MeMgBr (2.7 mL, 3N THF solution, 8.16 mmol) at 0° C. The reaction solution was stirred for 2 h at 0° C. The mixture was quenched with HCl (1N) (pH=5-6) and extracted with ethyl acetate (3x50 mL). The combined organic phase was dried over $Na_2SO_4$, filtered and concentrated to give a residue, which was purified by silica gel column chromatography (petroleum ether:EtOAc=50:1 to 10:1) to give the tide compound (1.54 g, yield: 97%) as colorless oil.

Step 3. Synthesis of tert-butyl (E)-2-(3-(dimethylamino)acryloyl)piperidine-1-carboxylate

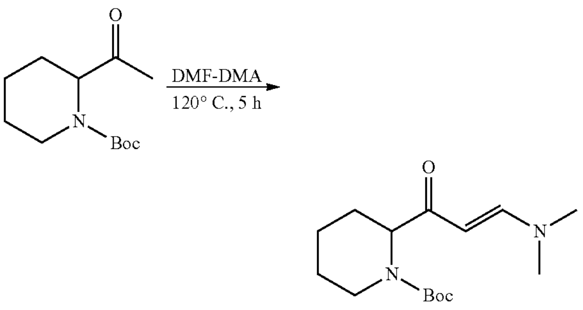

To a solution of tert-butyl 2-acetylpiperidine-1-carboxylate (1.54 g, 6.78 mmol) in DMF (5 mL) and D MA (5 mL) was heated to 120° C. for 5 h. The reaction was cooled to rt and diluted with n-hexane (50 mL). The precipitate was collected by filtration and dried to give the title compound (1.20 g, yield: 63%) as brown solid.

Step 4. Synthesis of tert-butyl 2-(2-mercaptopyrimidin-4-yl)piperidine-1-carboxylate

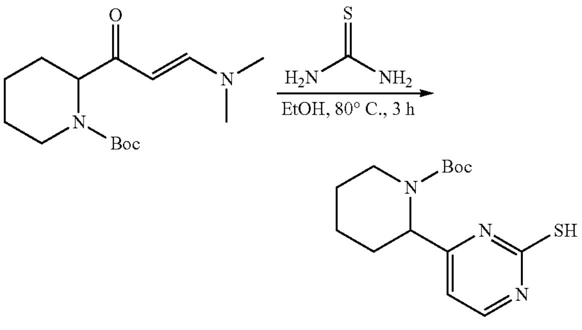

To a solution of tert-butyl (E)-2-(3-(dimethylamino)acryloyl)piperidine-1-carboxylate (1.20 g, 4.25 mmol) in EtOH (10 mL) were added thiourea (485 mg, 6.38 mmol) and KOH (357 mg, 12.76 mmol). The mixture was heated to 80° C. for 3 h. The mixture was pour into saturated aqueous solution of $NH_4Cl$ (50 mL) and extracted with EtOAc (3x35 mL). The combine organic layer was washed with brine (30 mL), dried over $Na_2SO_4$, filtered and concentrated in vacuo. The residue was purified by silica gel column chromatography (petroleum ether:EtOAc=20:1 to 5:1) to give the title compound (1.0 g, yield: 80%) as yellow oil. MS (ESI) m/z: 296.0 $[M+H]^+$.

Step 5. Synthesis of tert-butyl 2-(2-(methylthio) pyrimidin-4-yl)piperidine-1-carboxylate

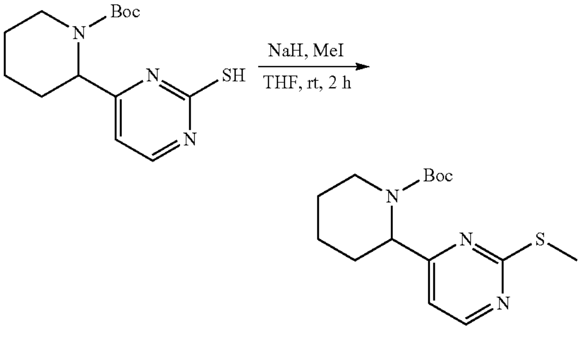 [SMILES: CC(C)(C)OC(=O)N1CCCCC1c1ccnc(S)n1 ; CSc1nccc(C2CCCCN2C(=O)OC(C)(C)C)n1]

To a solution of tert-butyl 2-(2-mercaptopyrimidin-4-yl) piperidine-1-carboxylate (1.00 g, 4.06 mmol) in THF (10 mL) was added NaH (179 mg, 4.47 mmol). The mixture was stirred at rt for 1 h. MeI (635 mg, 4.47 mmol) was added to the reaction solution. Then the reaction solution was stirred for 2 h at rt. The reaction was quenched by water (10 mL) and extracted with EtOAc (3x15 mL), The combines organic layer was washed with brine (30 mL), dried over $Na_2SO_4$, filtered and concentrated. The residue was purified by silica gel column chromatography (petroleum ether:EtOAc=20:1) to give the title compound (800 mg, yield: 75%) as a yellow oil.

Step 6. Synthesis of tert-butyl 2-(2-(methylsulfonyl)pyrimidin-4-yl)piperidine-1-carboxylate

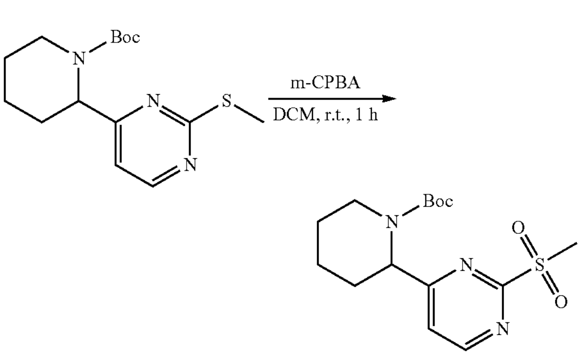

To a solution of tert-butyl 2-(2-(methylthio)pyrimidin-4-yl)piperidine-1-carboxylate (300 mg, 0.97 mmol) in DCM (3 mL) was added m-CPBA (335 mg, 1.94 mmol). The mixture was stirred at rt for 1 h. The mixture was poured into water (10 mL) and extracted with DCM (3×10 mL). The combined organic phase was concentrated in vacuum to give a residue, which was purified by silica gel column chromatography (petroleum ether:EtOAc=5:1) to give the title compound (280 mg, 82% yield) as a yellow solid. MS (ESI) m/z: 242.1 $[M-100+H]^+$.

Step 7. Synthesis of tert-butyl 2-(2-(pyrimidin-5-ylamino)pyrimidin-4-yl)piperidine-1-carboxylate

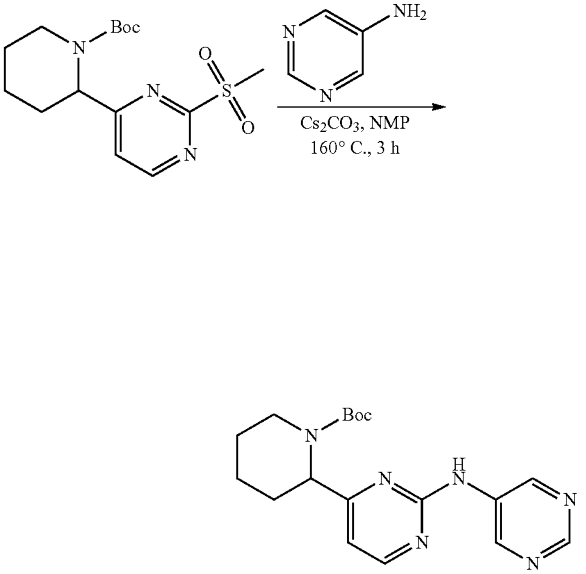

A solution of tert-butyl 2-(2-(methylsulfonyl)pyrimidin-4-yl)piperidine-1-carboxylate (280 mg, 0.83 mmol), pyrimidin-5-amine (234 mg, 2.74 mmol) and $Cs_2CO_3$ (541.2 mg, 1.66 mmol) in NMP (5 mL) was heated to 160° C. for 3 h. The reaction was purified by prep-HPLC to give the title compound (80 mg, 39% yield) as yellow solid. MS (ESI) m/z: 357.1 $[M+H]^+$.

Step 8. Synthesis of 4-(piperidin-2-yl)-N-(pyrimidin-5-yl)pyrimidin-2-amine

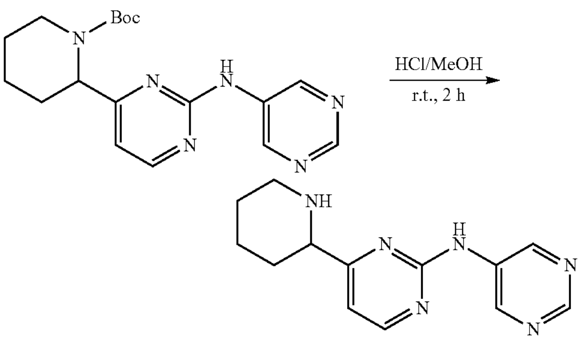

To a solution of tert-butyl 2-(2-(pyrimidin-5-ylamino)pyrimidin-4-yl)piperidine-1-carboxylate (80 mg, 0.23 mmol) in MeOH (1 mL) was added a solution of HCl in MeOH (5 mL, 3N) at rt. The mixture was stirred at rt for 2 h before the reaction mixture was concentrated and purified by prep-HPLC (0.1% $NH_4$·OH) to give the compound (40 mg, 70.0% yield) as a white solid. $^1$H NMR (400 MHz, DMSO-$d_6$): δ 10.00 (s, 1H), 9.18 (s, 2H), 8.78 (s, 1H), 8.53 (d, J=5.2 Hz, 1H), 7.03 (d, J=5.2 Hz, 1H), 3.78-3.76 (m, 1H), 3.17-3.14 (d, J=12 Hz, 1H), 2.78-2.69 (m, 1H), 2.00-1.97 (m, 1H), 1.86-1.84 (m, 1H), 1.65-1.62 (m, 1H), 1.55-1.41 (m, 3H). MS (ESI) m/z: 257.1 $[M+H]^+$.

Example 238. 5-(1-((2-(Furan-2-yl)-6,7,8,9-tetrahydro-5H-pyrimido[4,5-d]azepin-4-yl)amino)ethyl)-1,3,4-thiadiazol-2-amine (B-138)

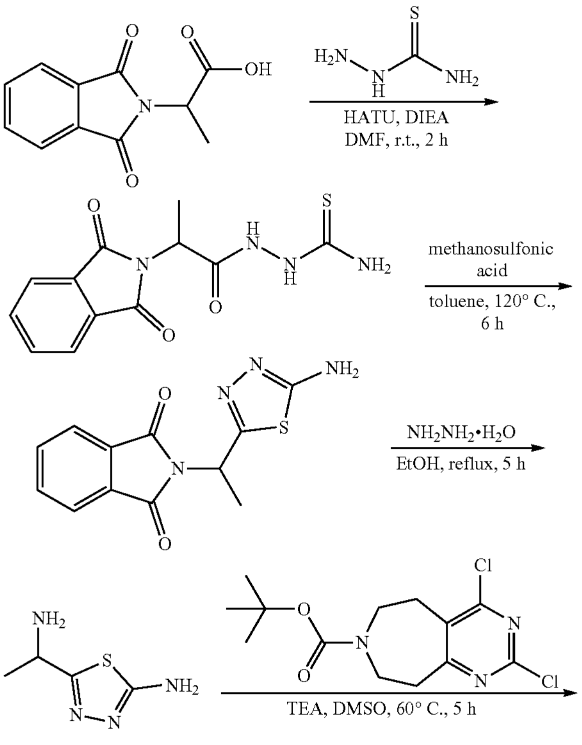

-continued

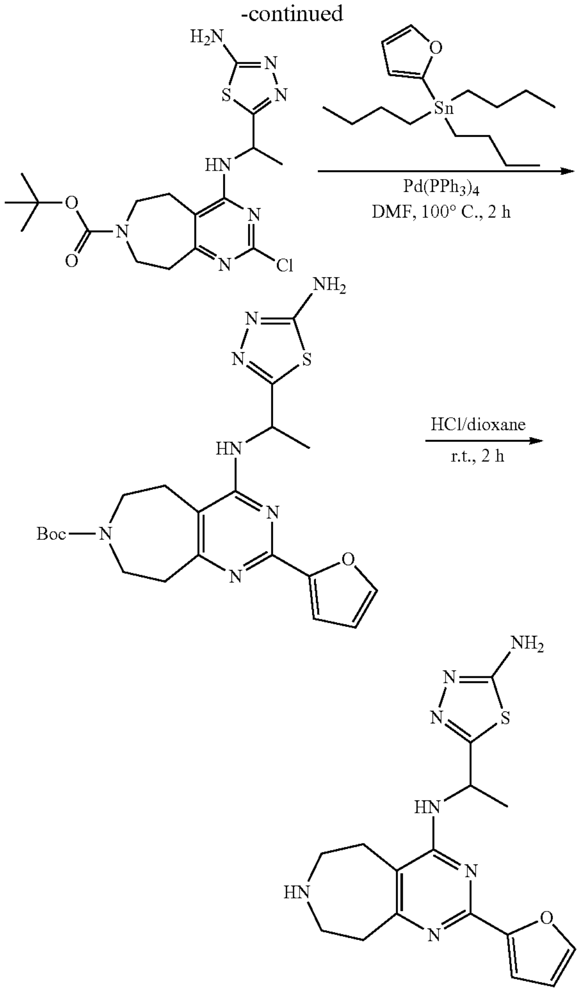

Step 1. Synthesis of 2-(2-(1,3-dioxoisoindolin-2-yl)propanoyl)hydrazine-1-carbothioamide

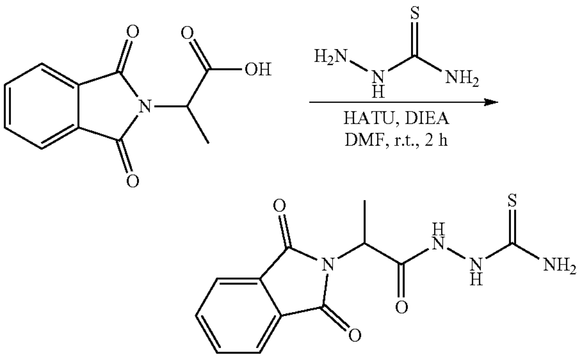

To a solution of 2-(1,3-dioxoisoindolin-2-yl)propanoic acid (2.00 g, 9.13 mmol) in DMF (10.0 mL) were added HATU (4.16 g, 10.90 mmol), DIEA (3.53 g, 27.40 mmol) and hydrazinecarbothioamide (831 mg, 9.13 mmol) at rt. The mixture was stirred at rt for 2 h, before the mixture was poured into water (10 mL) and extracted with EtOAc (3×20 mL). The combined organic layers was washed with brine, dried over $Na_2SO_4$, filtered and concentrated to give the crude product (6.9 g, crude) as yellow oil.

Step 2. Synthesis of 2-(1-(5-amino-1,3,4-thiadiazol-2-yl)ethyl)isoindoline-1,3-dione

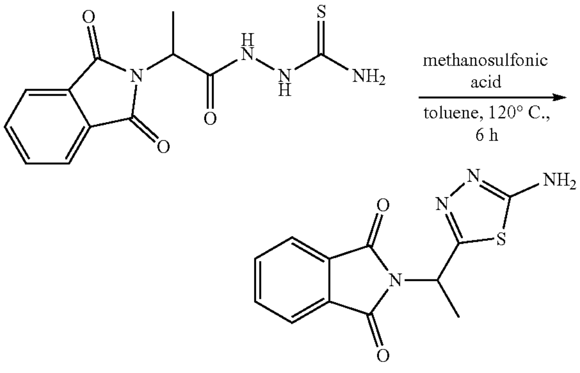

To a solution of 2-(2-(1,3-dioxoisoindolin-2-yl)propanoyl)hydrazine-1-carbothioamide (6.90 g, 23.6 mol) in toluene (20.0 mL) was added methanesulfonic acid (2.23 g, 23.6 mmol) at rt. The reaction mixture was heated to 120° C. for 6 h. After being cooled to rt, the mixture was poured into water (50 mL) and extracted with EtOAc (3×50 mL). The combined organic layers were washed with brine, dried over $Na_2SO_4$, filtered and concentrated to give a residue, which was purified by silica gel column chromatography (DCM:MeOH=100:1 to 50:1) to give the title compound (800 mg, 11.5% yield over two steps) as yellow solid. MS (ESI) m/z: 275.0 $[M+H]^+$.

Step 3. Synthesis of 5-(1-aminoethyl)-1,3,4-thiadiazol-2-amine

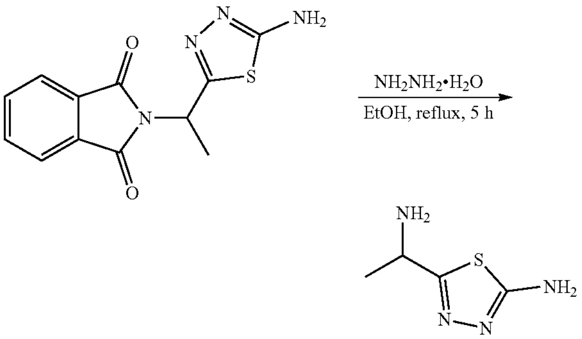

To a solution of 2-(1-(5-amino-1,3,4-thiadiazol-2-yl)ethyl)isoindoline-1,3-dione (800 mg, 2.92 mmol) in EtOH (10 mL) was added hydrazine hydrate (233.60 mg, 5.83 mmol) at it. The mixture was heated to reflux for 5 h, before the mixture was filtered and the filtrate was concentrated under vacuum to get a crude compound (200 mg, 47.5% yield) as white solid. MS (ESI) m/z: 145.1 $[M+H]^+$.

Step 4. Synthesis of tert-butyl 4-((1-(5-amino-1,3,4-thiadiazol-2-yl)ethyl)amino)-2-chloro-5,6,8,9-tetrahydro-7H-pyrimido[4,5-d]azepine-7-carboxylate

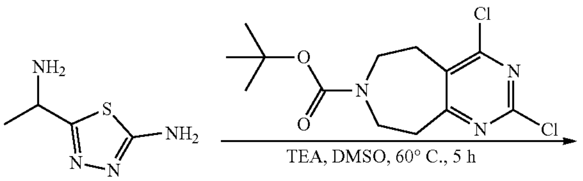

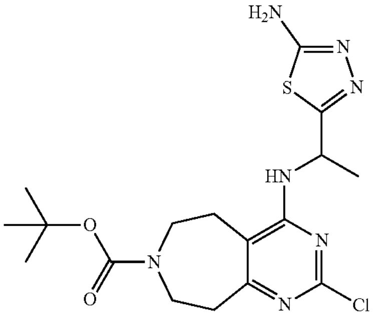

To a solution of 5-(1-aminoethyl)-1,3,4-thiadiazol-2-amine (350 mg, 2.43 mmol) in DMSO (10 mL) were added tert-butyl 2,4-dichloro-5,6,8,9-tetrahydro-7H-pyrimido[4,5-d]azepine-7-carboxylate (772.90 mg, 2.43 mmol) and TEA (736.40 mg, 7.29 mmol) at rt. The mixture was heated at 60° C. for 5 h. The mixture was poured into water (20 mL) and extracted with EtOAc (3×20 mL). The organic layer was dried over $Na_2SO_4$, filtered and concentrated to give a residue, which was purified by prep-HPLC to provide the title compound (100 mg, 9.68% yield) as a white solid. MS (ESI) m/z: 426.0 $[M+H]^+$.

Step 5. Synthesis of tert-butyl 4-((1-(5-amino-1,3,4-thiadiazol-2-yl)ethyl)amino)-2-(furan-2-yl)-5,6,8,9-tetrahydro-7H-pyrimido[4,5-d]azepine-7-carboxylate

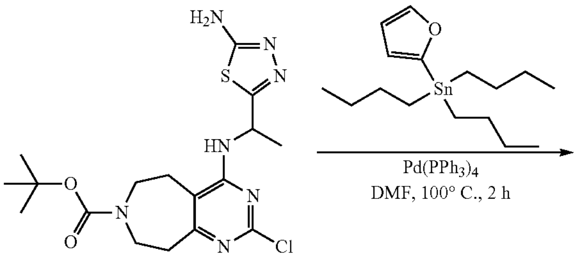

-continued

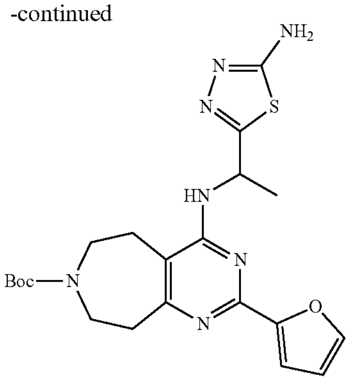

To a solution of tert-butyl 4-((1-(5-amino-1,3,4-thiadiazol-2-yl)ethyl)amino)-2-chloro-5,6,8,9-tetrahydro-7H-pyrimido[4,5<d]azepine-7-carboxylate (425 mg, 1.0 mmol) and tributyl(furan-2-yl)stannane (429.6 mg, 1.2 mmol) in DMF (10 mL) was added $Pd(PPh_3)_4$ (20 mg). The reaction was irradiated for 2 h at 100° C. under microwave. The reaction was purified by prep-HPLC to give the title compound (100 mg, 21.9% yield) as a white solid. MS (ESI) m/z: 458.0 $[M+H]^+$.

Step 6. Synthesis of 5-(1-((2-(furan-2-yl)-6,7,8,9-tetrahydro-5H-pyrimido[4,5-d]azepin-4-yl)amino)ethyl)-1,3,4-thiadiazol-2-amine

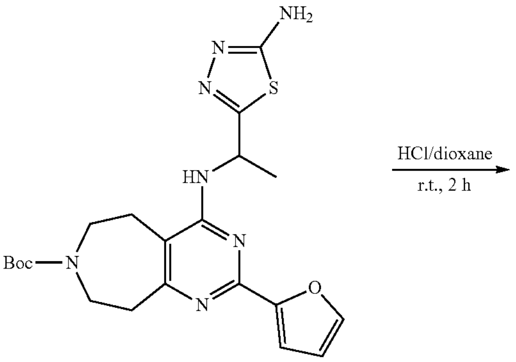

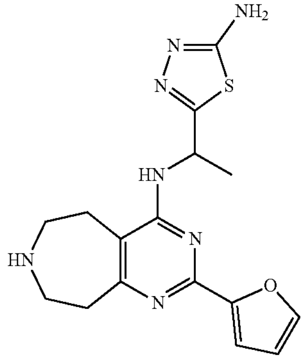

To a solution of tert-butyl 4-((1-(5-amino-1,3,4-thiadiazol-2-yl)ethyl)amino)-2-(furan-2-yl)-8,9-dihydro-5H-pyrimido[4,5-d]azepine-7 (6H)-carboxylate (100 mg, 0.218 mmol) in MeOH (1 mL) was added HCl/MeOH (10 mL, 4N) at rt. The mixture was stirred at rt for 2 h, before the reaction mixture was purified by prep-HPLC to give the title compound (25 mg, 32.0% yield) as white solid. $^1$H NMR (400 MHz, DMSO-$d_6$): δ 7.78 (d, J=0.8 Hz, 1H), 7.28 (d, J=7.6 Hz, 1H), 7.08-7.07 (m, 1H), 6.93 (s, 2H), 6.60-6.59 (m, 1H), 5.57-5.50 (m, 1H), 2.88-2.66 (m, 8H), 1.62 (d, J=6.8 Hz, 3H). MS (ESI) m/z: 358.0 $[M+H]^+$.

Example 239. N-(3-(2-oxooxazolidin-3-yl)phenyl)-2-(pyrrolidin-2-yl)benzamide (B-140)

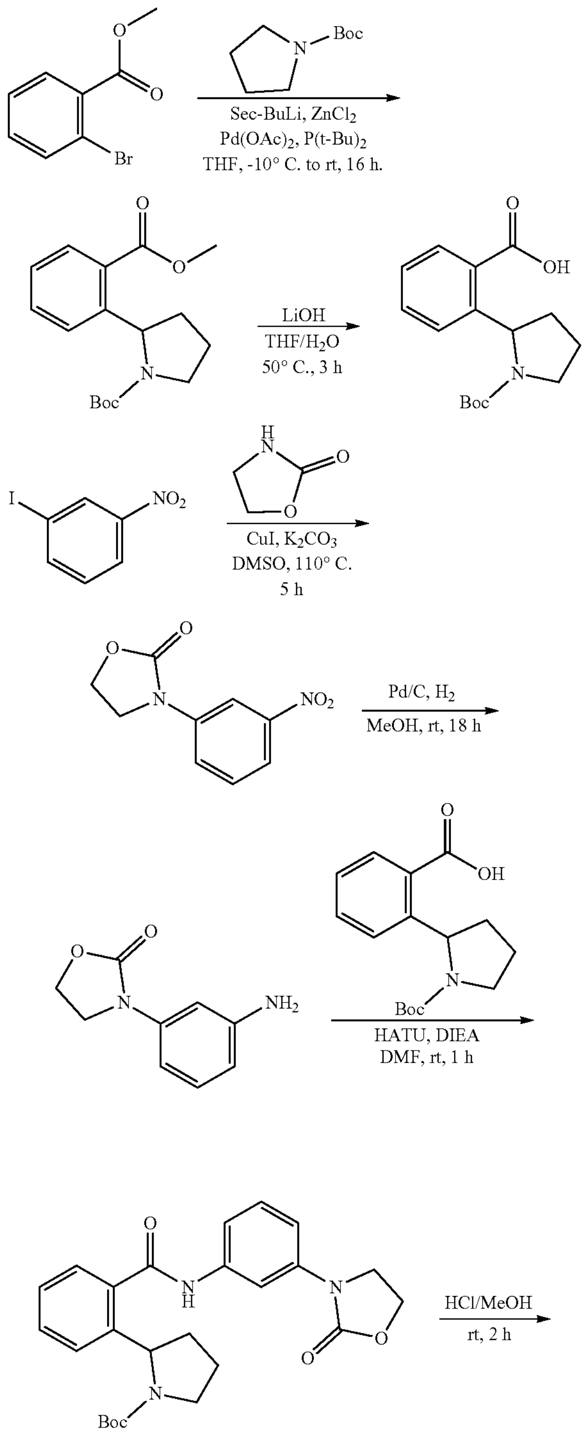

-continued

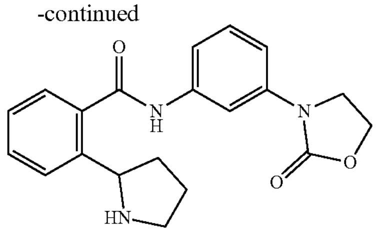

Step 1. Synthesis of tert-butyl 2-(2-(methoxycarbonyl)phenyl)pyrrolidine-1-carboxylate

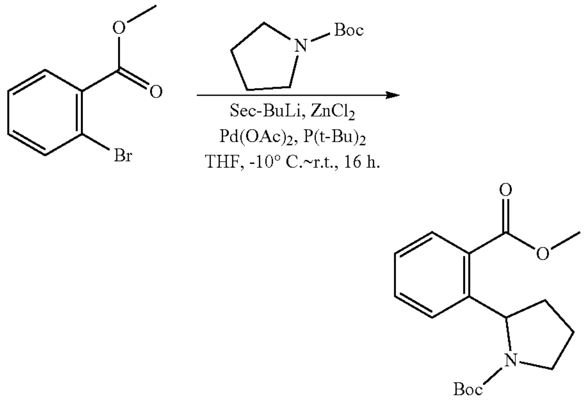

To a solution of methyl 2-bromobenzoate (2.50 g, 11.6 mmol) in THF (5.00 mL) were added tert-butyl pyrrolidine-1-carboxylate (2.38 g, 13.95 mmol), $ZnCl_2$ (1.90 g, 13.95 mmol), $P(t\text{-}Bu)_3$ (500 mg, 0.15 mmol), Pd $(OAc)_3$ (300 mg, 0.012 mmol) and Sec-BuLi (15 mL, 15.1 mmol) at −10° C. The mixture was stirred at r.t for 16 h, before it was quenched with water and extracted with EtOAc (3×10 mL). The combined organic layers were dried over $Na_2SO_4$, filtered and concentrated to give a residue, which was purified by silica gel column chromatography (petroleum ether:EtOAc=100:1 to 10:1) to give the title compound (500 mg, yield: 14.0%) as yellow oil.

Step 2. Synthesis of 2-(1-(tert-butoxycarbonyl)pyrrolidin-2-yl)benzoic acid

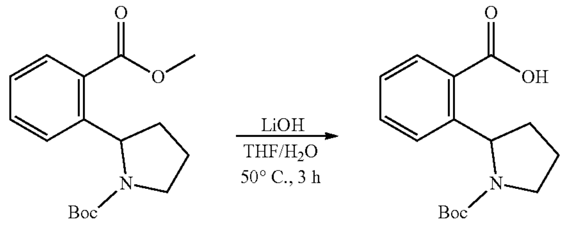 [SMILES: COC(=O)c1ccccc1C1CCCN1C(=O)OC(C)(C)C ; "LiOH" ; CC(C)(C)OC(=O)N1CCCC1c1ccccc1C(=O)O]

To a solution of tert-butyl 2-(2-(methoxycarbonyl)phenyl) pyrrolidine-1-carboxylate (500 mg, 1.63 mol) in THF (10 mL) and $H_2O$ (2 mL) was added LiOH·$H_2O$ (69 mg, 16.3.0 mmol). After being stirred at 50° C. for 3 h, the mixture was acidified with HCl (2N) to pH=6 and extracted with EtOAc (3×20 mL). The combined organic layers were concentrated to give a residue, which was purified by silica gel column chromatography (MeOH:DCM=100:1 to 10:1) to give the title compound (340 mg, 71.2% yield) as white solid. MS (ESI) m/z: 292.2 [M+H]+.

Step 3. Synthesis of 3-(3-nitrophenyl)oxazolidin-2-one

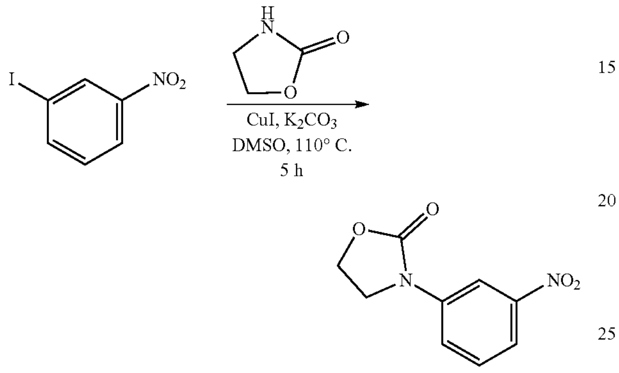

To a solution of 1-iodo-3-nitrobenzene (2.00 g, 8.03 mmol) in DMSO (20 mL) were added oxazolidin-2-one (1.05 g, 12.04 mmol), $K_2CO_3$ (2.20 g, 16.06 mmol) and CuI (200 mg, 0.803 mmol) at rt. The mixture was heated to 110° C. and stirred at 110° C. for 5 h, before the mixture was poured into water (50 mL) and extracted with EtOAc (3×50 mL). The combined organic phase was wash with brine, dried over $Na_2SO_4$, filtered and concentrated. The resulting residue was purified by silica gel column chromatography (petroleum ether:EtOAc=50:1 to 10:1) to give the title compound (950 mg, yield: 56.8%) as a yellow solid. MS (ESI) m/z: 250.1 [M+H+41]+.

Step 4. Synthesis of 3-(3-aminophenyl)oxazolidin-2-one

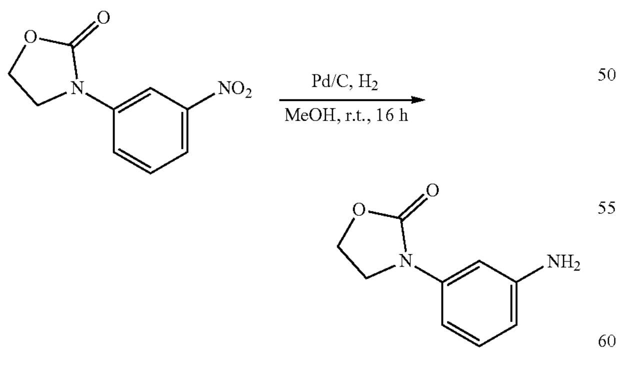

A mixture of 3-(3-nitrophenyl)oxazolidin-2-one (300 mg, 1.44 mmol) and Pd/C (30 mg) in MeOH (20 mL) was stirred at rt 16 h. The mixture was filtered and the filtrate was concentrated to give the title compound (200 mg, crude) as yellow solid. MS (ESI) m/z: 179.1 [M+H]+.

Step 5. Synthesis of tert-butyl 2-(2-((3-(2-oxooxazolidin-3-yl)phenyl)carbamoyl)phenyl)pyrrolidine-1-carboxylate

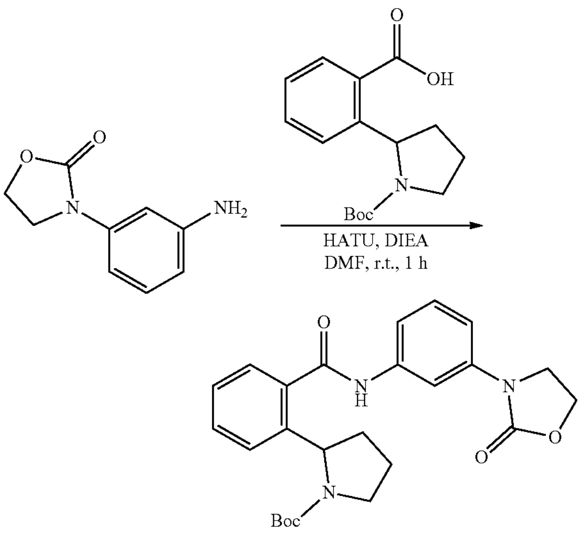

To a solution of 2-(1-(tert-butoxycarbonyl)pyrrolidin-2-yl)benzoic acid (340 mg, 1.16 mmol) in DMF (5 mL) were added HATU (666 mg, 1.75 mmol), DIEA (452.2 mg, 3.51 mmol) and 3-(3-aminophenyl)oxazolidin-2-one (208 mg, 1.16 mmol). The mixture was stirred at rt for 1 h, before it was poured into water (10 mL) and extracted with EtOAc (3×10 mL). The combined organic layers were concentrated to give a residue, which was purified by silica gel column chromatography (petroleum ether:EtOAc=10:1) to give the title compound (290 mg, 85.2% yield) as a yellow solid. MS (ESI) m/z: 452.1 [M+H]+.

Step 6. Synthesis of N-(3-(2-oxooxazolidin-3-yl)phenyl)-2-(pyrrolidin-2-yl)benzamide

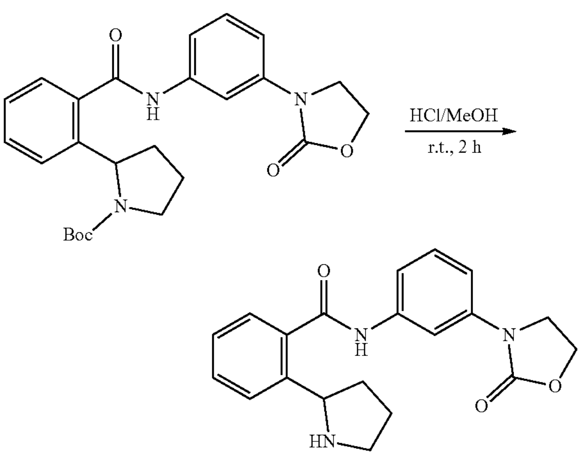

To a solution of tert-butyl 2-(2-((3-(2-oxooxazolidin-3-yl)phenyl)carbamoyl)phenyl)pyrrolidine-1-carboxylate (290 mg, 0.65 mmol) in MeOH (1 mL) was added a solution of HCl in MeOH (10 mL, 3N) at it. The mixture was stirred at rt for 2 h, before it was concentrated under vacuum to provide a residue, which was purified by prep-HPLC to give the title compound (49.0 mg, 16.8% yield) as a white solid. $^1H$ NMR (400 MHz, DMSO-$d_6$): δ 10.76 (s, 1H), 9.28 (brs, 1H), 8.84 (brs, 1H), 8.04 (t, J=1.6 Hz, 1H), 7.74-7.70 (m, 2H), 7.70-7.63 (m, 1H), 7.59-7.55 (m, 1H), 7.38 (t, J=8.0 Hz, 1H), 7.31-7.29 (m, 1H), 4.86-4.79 (m, 1H), 4.45 (t, J=7.6 Hz, 2H), 4.05 (t, J=7.6 Hz, 2H), 3.37-3.30 (m, 2H), 2.37-2.33 (m, 1H), 2.12-1.98 (m, 3H). MS (ESI) m/z: 352.1 $[M+H]^+$.

Example 240. N-((5-Ethyl-1,3,4-thiadiazol-2-yl)methyl)-2-(pyrrolidin-3-yl)benzamide (B-141)

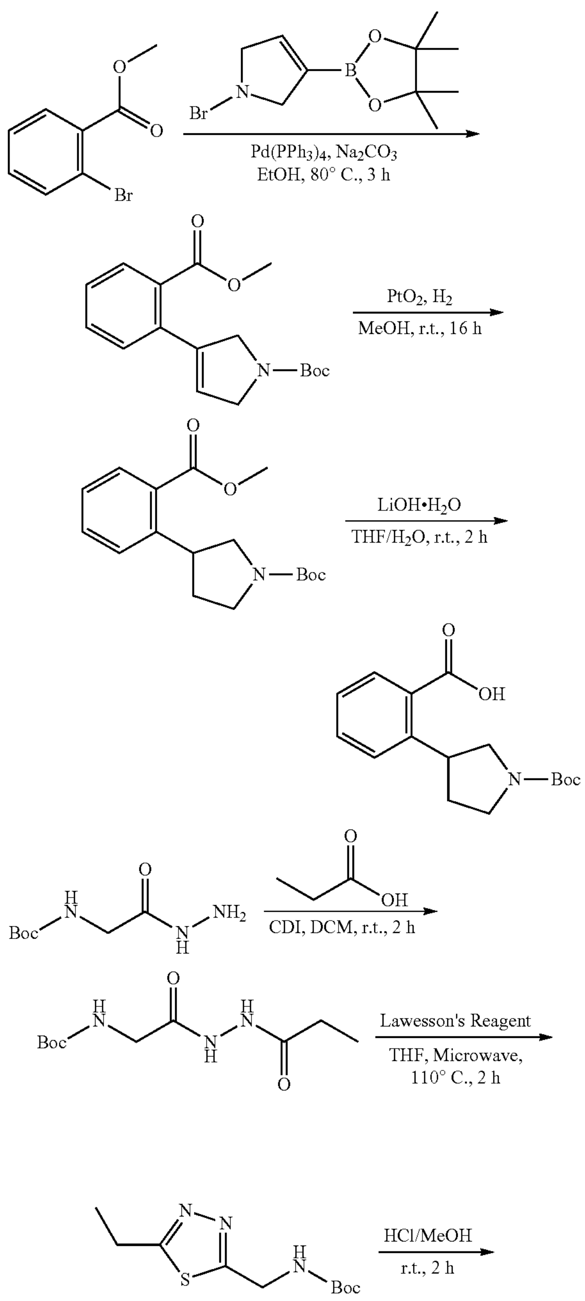

-continued

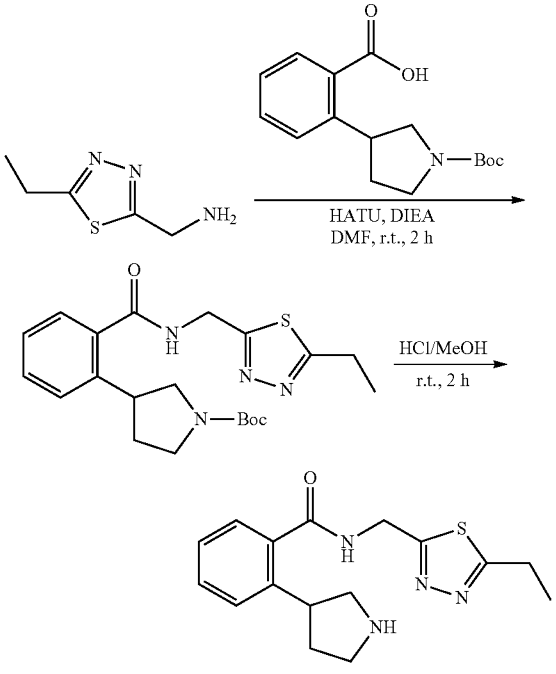

Step 1. Synthesis of tert-butyl 3-(2-(methoxycarbonyl)phenyl)-2,5-dihydro-1H-pyrrole-1-carboxylate

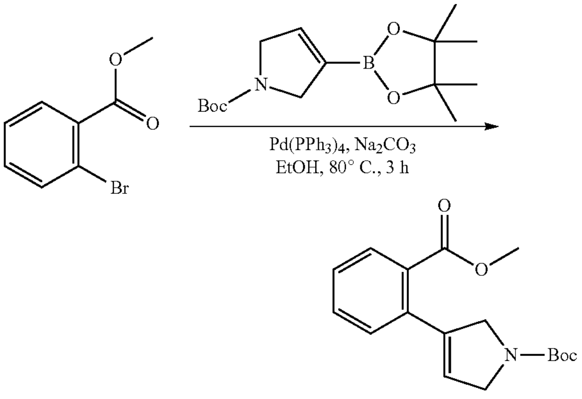

To a solution of methyl 2-bromobenzoate (4.0 g, 1.86 mmol) in EtOH (10 mL) and water (1 mL) were added tert-butyl 3-(4,4,5,5-tetramethyl-1,3,2-dioxaborolan-2-yl)-2,5-dihydro-1H-pyrrole-1-carboxylate (548 mg, 1.86 mmol), $Pd(PPh_3)_4$ (50 mg) and $Na_2CO_3$ (394 mg, 37.2 mmol) at rt. The mixture was heated to 80° C. for 3 h. The reaction mixture was poured into waters (20 mL) and extracted with EtOAc (3×20 mL). The organic layers was washed with brine, dried over $Na_2SO_4$, filtered and concentrated in vacuo to give a residue, which was purified by column silica gel column chromatography (petroleum ether: EtOAc=100:1 to 10:1) to give the title compound (300 mg, yield: 53.2%) as colorless oil. MS (ESI) m/z: 204.2 $[M-100+H]^+$.

Step 2. Synthesis of tert-butyl 3-(2-(methoxycarbonyl)phenyl)pyrrolidine-1-carboxylate

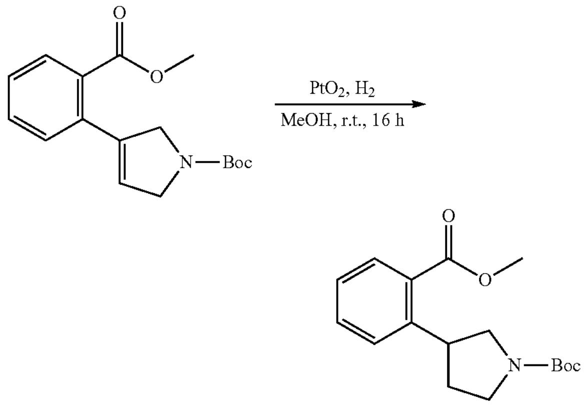 [SMILES: COC(=O)c1ccccc1C1=CCN(C(=O)OC(C)(C)C)C1 ; COC(=O)c1ccccc1C1CCN(C(=O)OC(C)(C)C)C1]

A mixture of tert-butyl 3-(2-(methoxycarbonyl)phenyl)-2,5-dihydro-1H-pyrrole-1-carboxylate (300 mg, 1.86 mol) and $PtO_2$ (300 mg, 0.10 mmol) in MeOH (5 mL) was stirred at rt for 16 h under $H_2$ atmosphere. The mixture was filtered and the filtrate was concentrated to give the crude title compound (280 mg, crude) as a white solid which was used directly in the next step.

Step 3. Synthesis of 24 (1-(tert-butoxycarbonyl)pyrrolidin-3-yl)benzoic acid

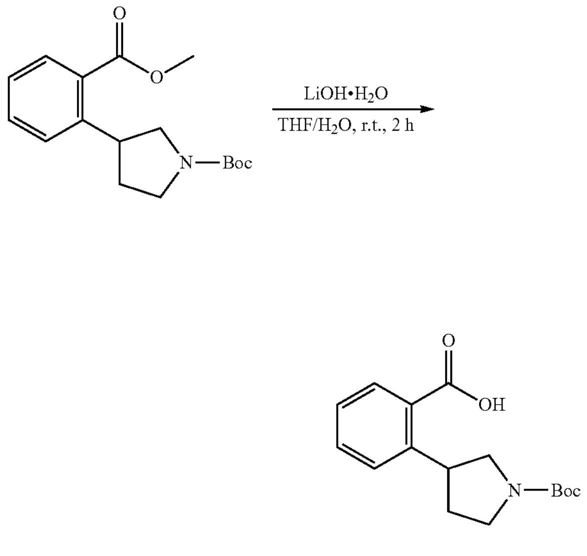

To a solution of tert-butyl 3-(2-(methoxycarbonyl)phenyl) pyrrolidine-1-carboxylate (280 mg, 0.918 mmol) in THF (6 mL) $H_2O$ (1 mL) was added LiOH·$H_2O$ (200 mg, 3.67 mmol) at 0° C. The mixture was stirred at rt for 2 h, before it was acidified with HCl (1N) to pH=4 and extracted with EtOAc (3×15 mL). The combined organic phase was dried over $Na_2SO_4$, filtered and concentrated to give the title compound (150 mg, yield: 56.1%) as yellow oil. MS (ESI) m/z: 192.1 $[M-100+H]^+$.

Step 4. Synthesis of tert-butyl (2-oxo-2-(2-propionylhydrazinyl)ethyl)carbamate

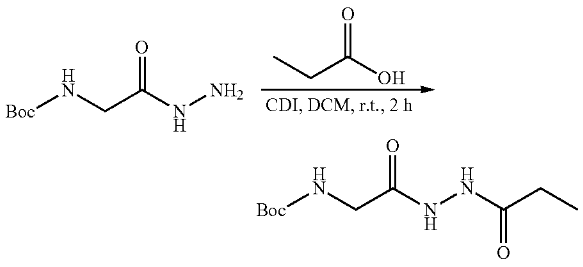

To a solution of propionic acid (2.0 g, 10.5 mmol) in DCM (20.0 mL) was added CDI (2.0 g, 12.6 mmol). After the reaction was stirred for 1 h at rt, tert-butyl (2-hydrazinyl-2-oxoethyl)carbamate (939 mg, 12.69 mmol) was added. After being stirred at r.t for 2 h, the mixture was poured into water (30 mL) and extracted with DCM (3×30 mL). The combined organic layers were dried over $Na_2SO_4$, filtered and concentrated to give the title compound (500 mg, crude) as yellow oil which was used directly in the next step.

Step 5. Synthesis of tert-butyl ((5-ethyl-1,3,4-thiadiazol-2-yl)methyl)carbamate

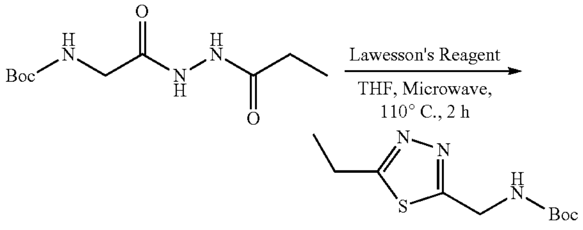

To a solution of tert-butyl (2-oxo-2-(2-propionylhydrazinyl)ethyl)carbamate (300 mg, 1.22 mmol) in THF (2.0 mL) was added Lawesson's Reagent (270 mg, 1.22 mmol) at rt. The mixture was irradiated at 110° C. for 2 h under microwave. The mixture was concentrated to give a residue, which was purified by prep-HPLC to give the title compound (78 mg, 26.5% yield) as a yellow solid. MS (ESI) m/z: 244.1 $[M+H]^+$.

Step 6. Synthesis of (5-ethyl-1,3,4-thiadiazol-2-yl)methanamine

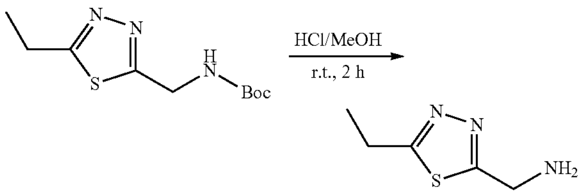

To a solution of tert-butyl ((5-ethyl-1,3,4-thiadiazol-2-yl) methyl)carbamate (78 mg, 0.32 mmol) in HCl/MeOH (5 mL, 3M) was stirred at rt for 2 h. The mixture was concentrated to give a crude compound (46 mg, crude) as white solid which was used directly in the next step. MS (ESI) m/z: 144.1 $[M+H]^+$.

Step 7. Synthesis of tert-butyl 3-(2-(((5-ethyl-1,3,4-thiadiazol-2-yl)methyl)carbamoyl)phenyl)pyrrolidine-1-carboxylate

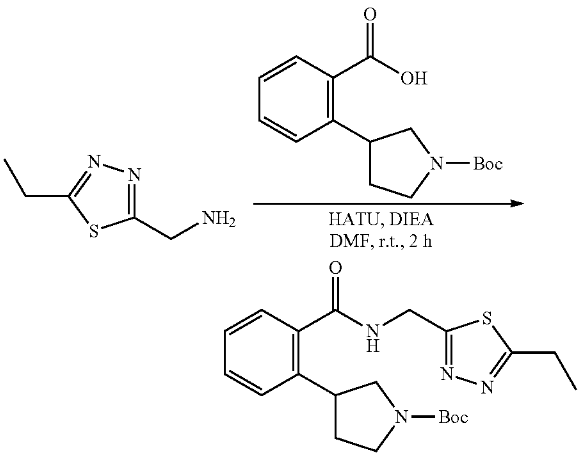

To a solution of 2-(1-tert-butoxycarbonyl)pyrrolidin-3-yl) benzoic acid (180 mg, 0.17 mmol) in DMF (3.0 mL) were added HATU (352.5 mg, 0.257 mmol) and DIEA (240 mg, 0.515 mmol), followed by (5-ethyl-1,3,4-thiadiazol-2-yl) methanamine (122 mg, 0.189 mmol). The resulting reaction was stirred at rt for 2 h, before it was purified by prep-HPLC to give the title compound (205 mg, 80.0% yield) as a white solid. MS (ESI) m/z: 417.1 $[M+H]^+$.

Step 8. Synthesis of N-((5-ethyl-1,3,4-thiadiazol-2-yl)methyl)-2-(pyrrolidin-3-yl)benzamide

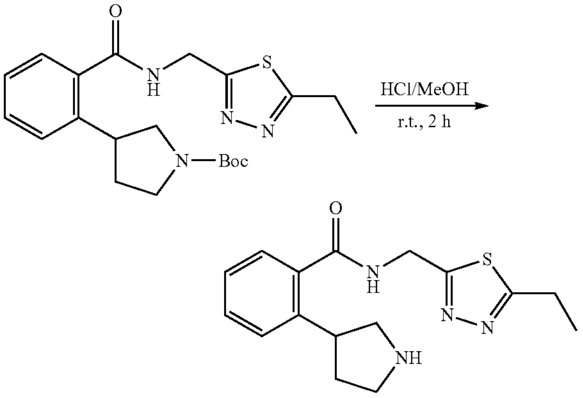

To a solution of tert-butyl 3-(2-(((5-ethyl-1,3,4-thiadiazol-2-yl)methyl)carbamoyl)phenyl)pyrrolidine-1-carboxylate (205 mg, 0.495 mmol) in HCl/MeOH (10 mL, 3N) was stirred at rt for 2 h. The reaction mixture was purified by prep-HPLC to give the title compound (19 mg, 12.2%) as a white solid. $^1H$ NMR (400 MHz, MeOD-$d_4$): δ 7.52 (d, J=4.0 Hz, 2H), 7.47 (d, J=7.6 Hz, 1H), 7.40-7.36 (m, 1H), 4.91 (s, 2H), 3.97-3.88 (m, 1H), 3.78-3.74 (m, 1H), 3.61-3.55 (m, 1H), 3.39-3.31 (m, 1H), 3.24-3.11 (m, 3H), 2.47-2.43 (m, 1H), 2.20-2.15 (m, 1H), 1.41 (t, J=7.6 Hz, 3H). MS (ESI) m/z: 317.0 $[M+H]^+$.

Example 241. 2-Morpholino-7-(quinolin-8-ylmethyl)-5,6,7,8-tetrahydropyrido[3,4-d]pyrimidin-4-amine (B-136)

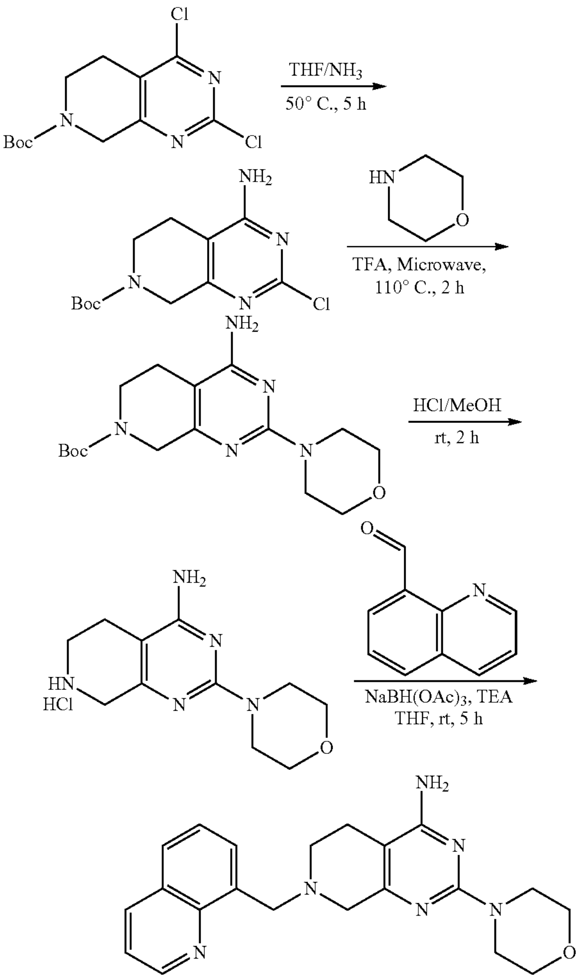

Step 1. Synthesis of tert-butyl 4-amino-2-chloro-5,8-dihydropyrido[3,4-d]pyrimidine-7 (6H)-carboxylate

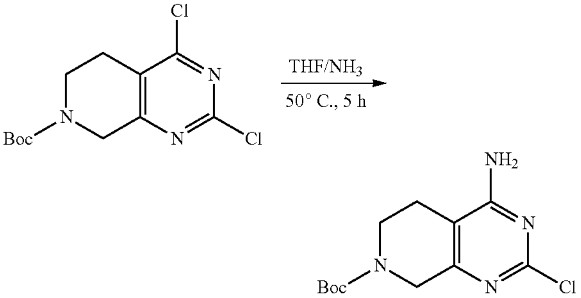

A solution of tert-butyl 2,4-dichloro-5,6-dihydropyrido[3,4-d]pyrimidine-7 (8H)-carboxylate (3.0 g, 9.80 mmol) in THF (30.0 mL) was saturated with $NH_3$. The resulting mixture was stirred at 50° C. for 5 h in 100 mL of autoclave. The mixture was concentrated to give a residue, which was purified by silica gel column chromatography (DCM: MeOH=50:1 to 20:1) to give the title compound (1.0 g, yield: 35.6%) as yellow solid. MS (ESI) m/z: 285.0 $[M+H]^+$.

Step 2. Synthesis of tert-butyl 4-amino-2-morpholino-5,8-dihydropyrido[3,4-d]pyrimidine-7 (6H)-carboxylate

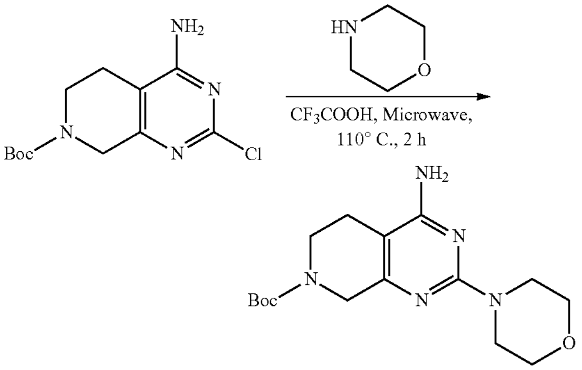

To a solution of tert-butyl 4-amino-2-chloro-5,6-dihydropyrido[3,4-d]pyrimidine-7 (8H)-carboxylate (1.00 g, 3.52 mmol) in morpholine (10.0 mL) was added TFA (three drops) at rt. Then the reaction mixture was irradiated at 110° C. for 2 h under microwave. After being cooled to rt, the mixture was poured into water (20.0 mL) and extracted with EtOAc (3×20 mL). The combined organic layers were concentrated to give a residue, which was purified by silica gel column chromatography (petroleum ether:EtOAc=10:1 to 1:1) to give the title compound (950 mg, 80% yield) as yellow solid. MS (ESI) m/z: 336.1 $[M+H]^+$.

Step 3. Synthesis of 2-morpholino-5,6,7,8-tetrahydropyrido[3,4-d]pyrimidin-4-amine hydrochloride

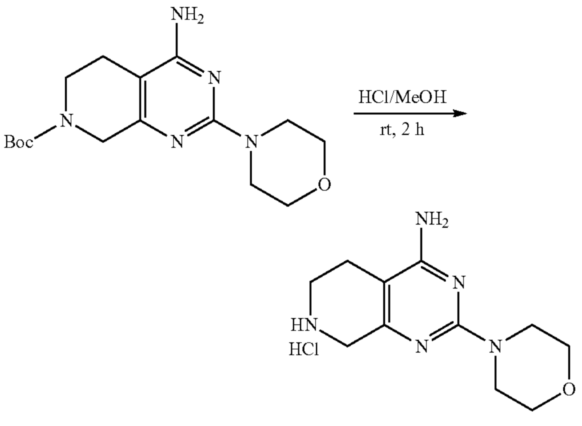

A solution of tert-butyl 4-amino-2-morpholino-5,6-dihydropyrido[3,4-d]pyrimidine-7 (8H)-carboxylate (950 mg, 2.83 mmol) in HCl/MeOH (10.0 mL, 3N) was stirred at rt for 2 h. The mixture was concentrated under vacuum to give the title compound (850 mg, crude) as yellow solid. MS (ESI) m/z: 236.1 $[M+H]^+$.

Step 4. Synthesis of 2-morpholino-7-(quinolin-8-ylmethyl)-5,6,7,8-tetrahydropyrido[3,4-d]pyrimidin-4-amine

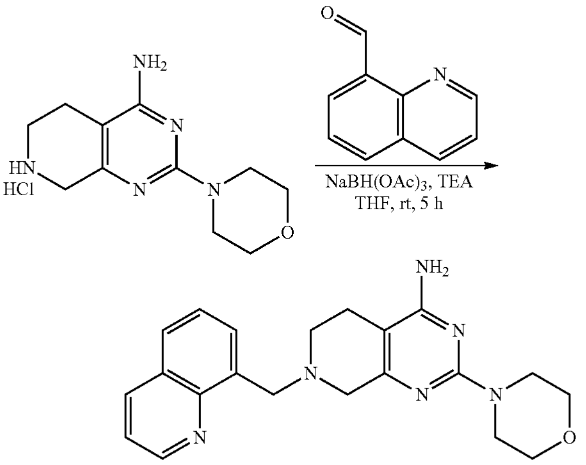

To a solution of 2-morpholino-5,6,7,8-tetrahydropyrido[3,4-d]pyrimidin-4-amine hydrochloride (300 mg, 1.11 mmol) in THF (5.0 mL) were added quinoline-8-carbaldehyde (190.8 mg, 1.22 mmol) and TEA (122.70 mg, 1.215 mmol), followed by $NaBH(OAc)_3$ (351 mg, 1.66 mmol) at rt. The mixture was stirred at rt for 5 h, before it was quenched with aq. $NaHCO_3$ (20 mL) and extracted with EtOAc (3×20 mL). The combined organic layers were washed with brine, dried over $Na_2SO_4$, filtered and concentrated to give a residue, which was purified by silica gel column chromatography (DCM:MeOH=100:1 to 10:1) to give the tide compound (64 mg, 15.4% yield over 2 steps) as a white solid. $^1H$ NMR (400 MHz, DMSO-$d_6$): δ 8.93 (dd, J=4.0 Hz, 1.2 Hz 1H), 8.39-8.37 (m, 1H), 7.70 (dd, J=15.2 Hz, 8.4 Hz, 2H), 7.62 (t, J=15.6 Hz, 1H), 7.56 (dd, J=8.4 Hz, 4.0 Hz 1H), 6.26 (s, 2H), 4.31 (s, 2H), 3.55-3.49 (m, 8H), 3.30 (s, 2H), 2.78 (t, J=6.0 Hz, 2H), 2.36 (t, J=5.6 Hz, 2H). MS (ESI) m/z: 377.1 $[M+H]^+$.

Example 242. 3-(1H-Benzo[d]imidazol-2-yl)-1-(3-(methyl(phenethyl)amino)piperidin-1-yl)propan-1-one (B-139)

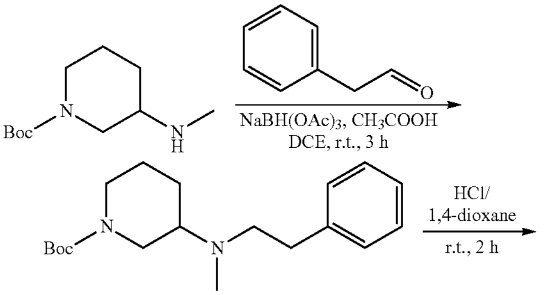

-continued

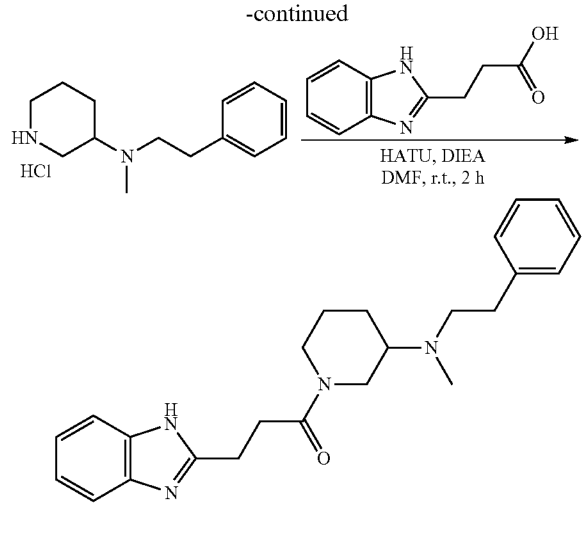

Step 1. Synthesis of tert-butyl 3-(methyl(phenethyl)amino)piperidine-1-carboxylate

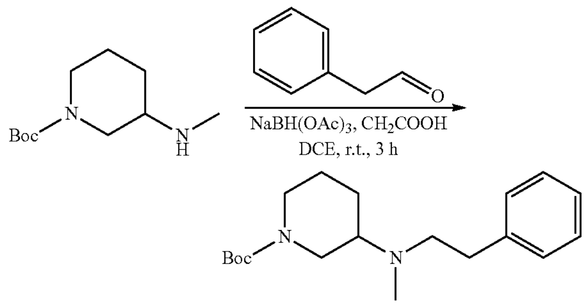

To a solution of tert-butyl 3-(methylamino)piperidine-1-carboxylate (1.30 g, 6.07 mmol) in DCE (10 mL) were added 2-phenylacetaldehyde (1.45 g, 12.1 mmol) and TFA (four drops). The reaction was stirred at rt for 1 h, before $NaBH(OAc)_3$ (2.57 g, 12.4 mmol) was added. After the mixture was stirred at rt for 3 h, it was concentrated to give a residue, which was purified by silica gel column chromatography (petroleum ether:EtOAc=20:1 to 3:1) to give the title compound (145 mg, yield: 7.5%) as yellow solid. MS (ESI) m/z: 319.2 $[M+H]^+$.

Step 2. Synthesis of N-methyl-N-phenethylpiperidin-3-amine hydrochloride

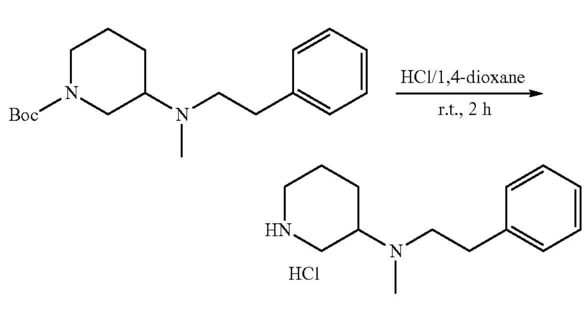

A solution of tert-butyl 3-(methyl(phenethyl)amino)piperidine-1-carboxylate (145 mg, 0.445 mmol) in HCl/dioxane (10.0 mL, 4N) was stirred at rt for 2 h. The mixture was concentrated to give the title compound (120 mg, crude yield: 100%) as a white solid. MS (EST) m/z: 219.5 $[M+H]^+$.

Step 3. Synthesis of 3-(1H-benzo[d]imidazol-2-yl)-1-(3-(methyl(phenethyl)amino)piperidin-1-yl)propan-1-one

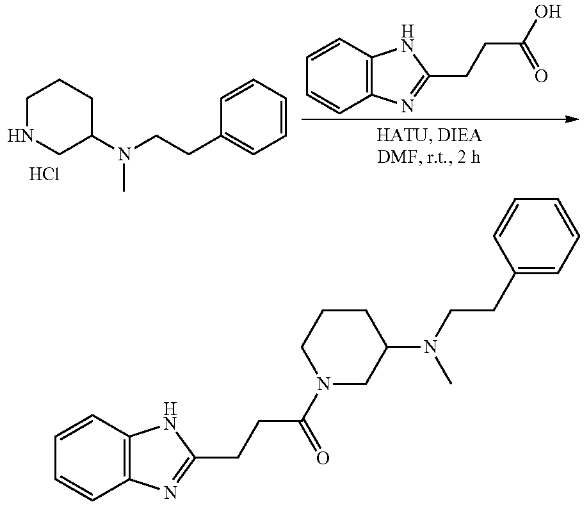

A solution of 3-(1H-benzo[d]imidazol-2-yl)propanoic acid (88.8 mg, 0.468 mmol), HATU (222.16 mg, 0.584 mmol), DIEA (150.80 mg, 1.169 mmol) and N-methyl-N-phenethylpiperidin-3-amine (99.00 mg, 0.389 mmol) in DMF (3 mL) was stirred at rt for 2 h. The mixture was purified by prep-HPLC. The product fractions were concentrated. The resulting residue was dissolved in EtOAc, washed with aq. $NaHCO_3$ and extracted with EtOAc (3×20 mL), dried over $Na_2SO_4$, filtered and concentrated to give the title compound (44.0 mg, yield: 44.4%) as yellow solid. $^1H$ NMR (400 MHz, MeOD-$d_4$): δ 7.48 (s, 2H), 7.25-7.16 (m, 7H), 4.61-4.40 (m, 1H), 3.98-3.86 (m, 1H), 3.17 (t, J=7.2 Hz, 2H), 3.00-2.89 (m, 3H), 2.78-2.71 (m, 4H), 2.50-2.41 (m, 1H), 2.40 (s, 3H), 1.96-1.93 (m, 1H), 1.81-1.77 (m, 1H), 1.55-1.28 (m, 3H). MS (ESI) m/z: 391.2 $[M+H]^+$ Example 243. N-(2-(5-((1H-Indol-4-yl)methyl)-4,5,6,7-tetrahydropyrazolo[1,5-a]pyrazin-7-yl)ethyl) isobutyramide (B-142)

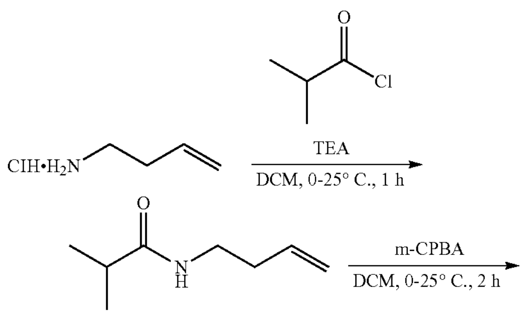

-continued

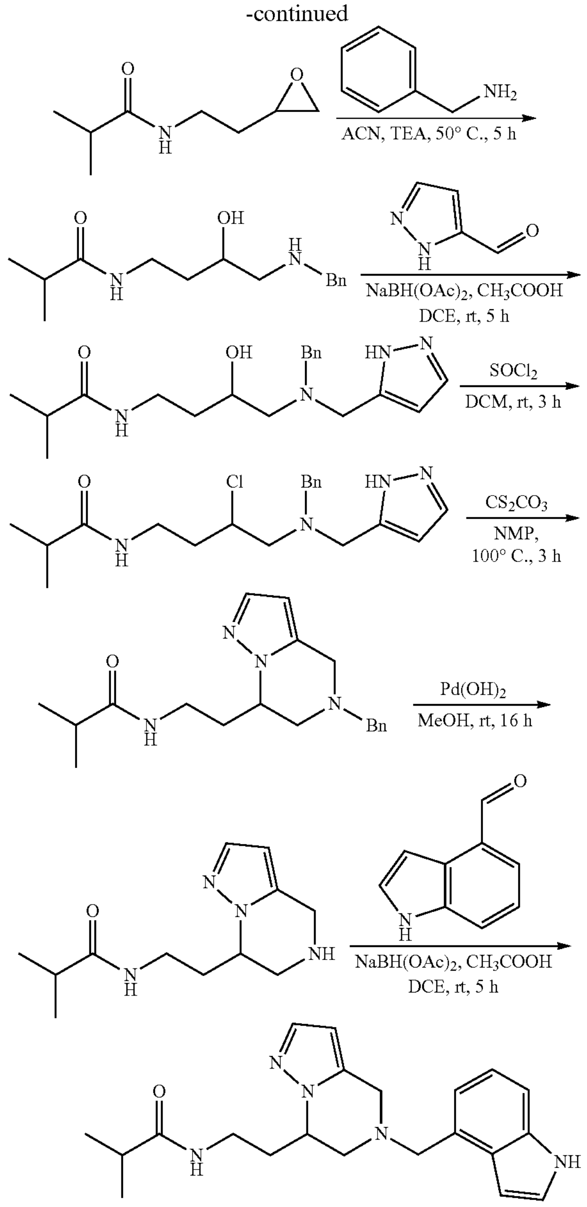

Step 1. Synthesis of N-(but-3-en-1-yl)isobutyramide

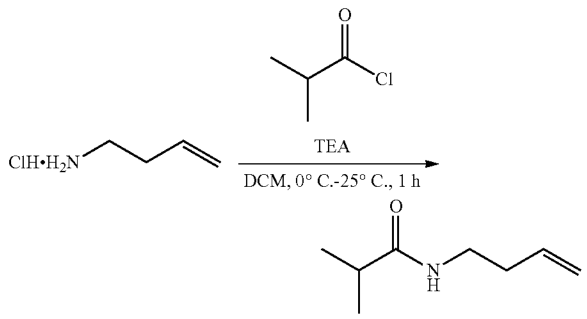

To a solution of but-3-en-1-amine hydrochloride (4.00 g, 37.38 mmol) and TEA (7.92 g, 78.50 mmol) in DCM (40.00 mL) was added isobutyryl chloride (4.1 g, 39.25 mmol) at 0° C. The mixture was stirred at rt for 1 h, before it was quenched with water (250 mL) and extracted with DCM (3×250 mL). The combined organic layers were washed with brine, dried over $Na_2SO_4$, filtered and concentrated to give a residue, which was purified by silica gel column chromatography (petroleum ether:EtOAc=3:1) to give the title compound (5.2 g, yield: 87%) as yellow oil.

Step 2. Synthesis of N-(2-(oxiran-2-yl)ethyl)isobutyramide

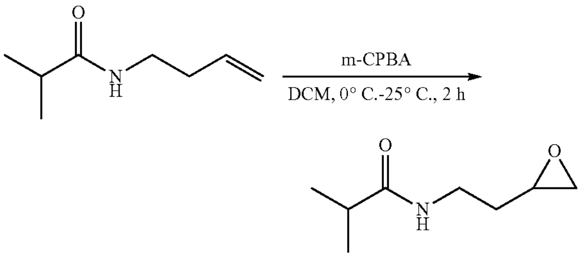

To a solution of N-(but-3-en-1-yl)isobutyramide (5.20 g, 36.80 mmol) in DCM (50.00 mL) was added m-CPBA (6.38 g, 36.80 mmol) at 0° C. The resulting mixture was stirred at rt for 2 h, before it was quenched with water (30 mL) and extracted with DCM (3×30.0 mL). The combined organic layers were washed with brine, dried over $Na_2SO_4$, filtered and concentrated to give a residue, which was purified by silica gel column chromatography (petroleum ether: EtOAc=3:1) to give the title compound (5.2 g, crude) as yellow oil. MS (ESI) m/z: 158.2 $[M+H]^+$.

Step 3. Synthesis of N-(4-(benzylamino)-3-hydroxybutyl)isobutyramide

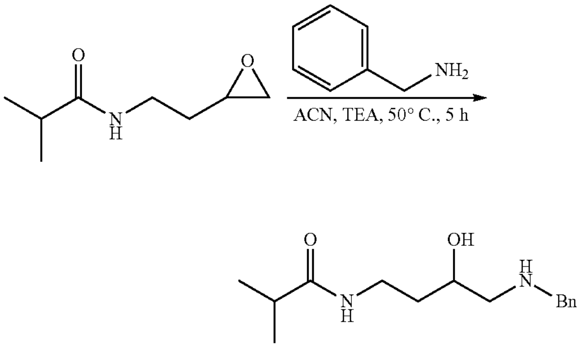

To a solution of N-(2-(oxiran-2-yl)ethyl)isobutyramide (5.20 g, crude) in $CH_3CN$ (50 mL) were added phenylmethanamine (3.54 g, 33.1 mmol) and TEA (10.00 g, 99.3 mmol). The resulting mixture wash heated to 50° C. for 5 h, before it was concentrated to give a residue, which was purified by silica gel column chromatography (DCM:MeOH=30:1) to give the title compound (1.9 g, 36.5% yield over two steps) as yellow solid. MS (ESI) m/z: 265.0 $[M+H]^+$.

Step 4. Synthesis of N-(4-(((1H-pyrazol-5-yl)methyl)(benzyl)amino)-3-hydroxybutyl)isobutyramide

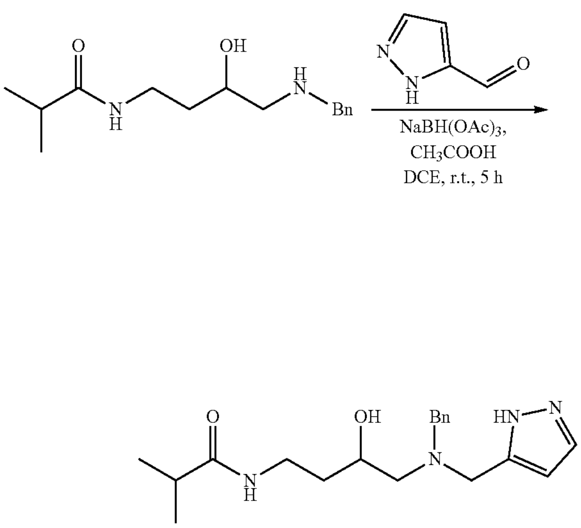

A solution of N-(4-(benzylamino)-3-hydroxybutyl)isobutyramide (1.00 g, 3.79 mmol), AcOH (227.00 mg, 3.79 mmol) and 1H-pyrazole-5-carbaldehyde (472 mg, 4.93 mmol) in DCE (10.00 mL) was stirred at rt for 0.5 h, before $NaBH(OAc)_3$ (1.61 g, 7.57 mmol) was added. After the resulting mixture was stirred at rt for 5 h, it was quenched with aq $NaHCO_3$ solution (150 mL) and extracted with DCM (3×150 mL). The combined organic layers were washed with brine, dried over $Na_2SO_4$, filtered and concentrated to give a residue, which was purified by silica gel column chromatography (DCM:MeOH=30:1) to give the title compound (900 mg, 60.1% yield) as yellow solid. MS (ESI) m/z: 345.3 $[M+H]^+$.

Step 5. Synthesis of N-(4-(((1H-pyrazol-5-yl)methyl)(benzyl)amino)-3-chlorobutyl)isobutyramide

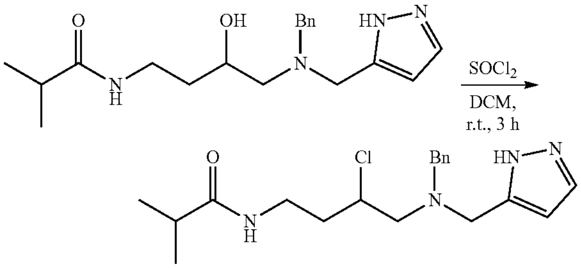

To a solution of N-(4-(((1H-pyrazol-5-yl)methyl)(benzyl)amino)-3-hydroxybutyl)isobutyramide (800 mg, 2.30 mmol) in DCM (5.00 mL) was added $SOCl_2$ (1.37 g, 11.62 mmol). The mixture was stirred at rt for 3 h. The mixture was concentrated to give the title compound (840 mg, crude), which was used directly for the next step without purification.

Step 6. Synthesis of N-(2-(5-benzyl-4,5,6,7-tetrahydropyrazolo[1,5-a]pyrazin-7-yl)ethyl)isobutyramide

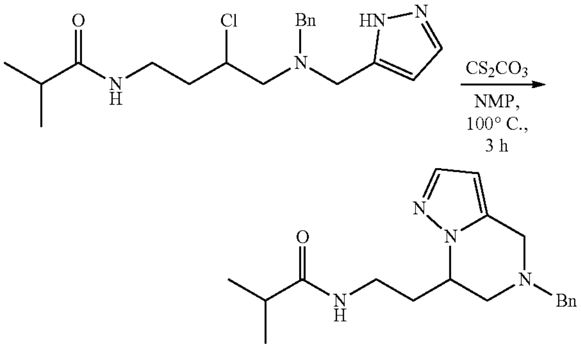

A solution of N-(4-(((1H-pyrazol-5-yl)methyl)(benzyl)amino)-3-chlorobutyl)isobutyramide (840 mg, crude) and $CS_2CO_3$ (3.79 g, 11.62 mmol) in NMP (10 mL) was stirred at 100° C. for 3 h. The reaction mixture was quenched with water (50 mL) and extracted with EtOAc (3×50 mL). The combines organic layers was washed with brine, dried over $Na_2SO_4$, filtered and concentrated to give a residue, which was purified by silica gel column chromatography (DCM:MeOH=50:1) to give the title compound (120 mg, 15.8% yield over two steps) as yellow solid. MS (ESI) m/z: 327.1 $[M+H]^+$.

Step 7. Synthesis of N-(2-(4,5,6,7-tetrahydropyrazolo[1,5-a]pyrazin-7-yl)ethyl)isobutyramide

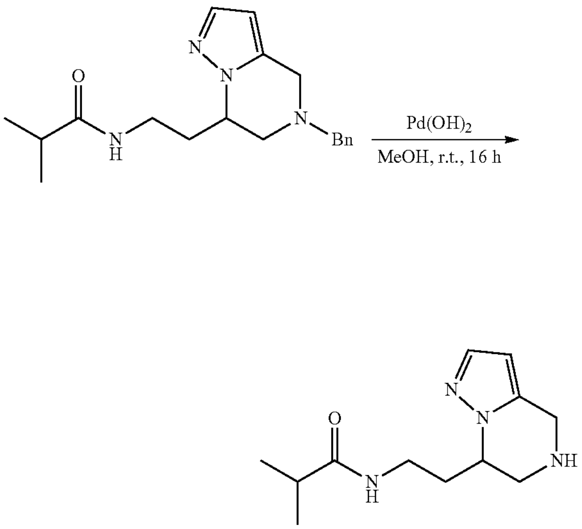

To a solution of N-(2-(5-benzyl-4,5,6,7-tetrahydropyrazolo[1,5-a]pyrazin-7-yl)ethyl)isobutyramide (120 mg, 0.37 mmol) in MeOH (5 mL) was added $Pd(OH)_2$ (12 mg). The mixture was stirred at rt for 16 h under $H_2$ atmosphere. The reaction mixture was filtered and the filtrate was concentrated to give the title compound (68 mg, 78% yield) as white solid. MS (ESI) m/z: 237.1 $[M+H]^+$.

Step 8. Synthesis of N-(2-(5-((1H-indol-4-yl)methyl)-4,5,6,7-tetrahydropyrazolo[1,5-a]pyrazin-7-yl)ethyl)isobutyramide

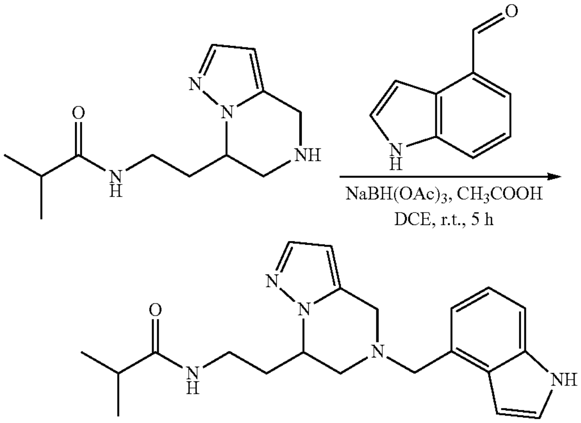

A solution of N-(2-(5-benzyl-4,5,6,7-tetrahydropyrazolo[1,5-a]pyrazin-7-yl)ethyl)isobutyramide (68.00 mg, 0.288 mmol), 1H-indole-4-carbaldehyde (62.67 mg, 0.43 mmol) and AcOH (20.70 mg, 0.35 mmol) in DCE (5 mL) was stirred at rt for 30 min, before NaBH(OAc). (122 mg, 0.58 mmol) was added. After the resulting mixture was stirred at rt for 5 h, it was quenched with water (30 mL) and extracted with DCM (3×30.0 mL). The combined organic layers were washed with brine, dried over $Na_2SO_4$, filtered and concentrated to give a residue, which was purified by prep-HPLC to give the title compound (36 mg, 31% yield) as white solid. $^1$H NMR (400 MHz, DMSO-$d_6$): δ 11.35 (s, 1H), 7.58-7.50 (m, 2H), 7.50 (s, 1H), 7.23 (d, J=4.0 Hz, 2H), 6.77 (s, 1H), 6.23 (s, 1H), 4.73-4.66 (m, 2H), 4.46-4.35 (m, 3H), 3.63 (t, J=10.8 Hz, 1H), 3.29-3.13 (m, 2H), 2.34-2.31 (m, 2H), 1.99-1.94 (m, 1H), 1.00-0.99 (m, 6H). MS (ESI) m/z: 366.1 $[M+H]^+$.

Example 244. 2-Acetamido-4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)amino)-N-(4-methyl-5-nitrothiazol-2-yl)benzamide (D-78)

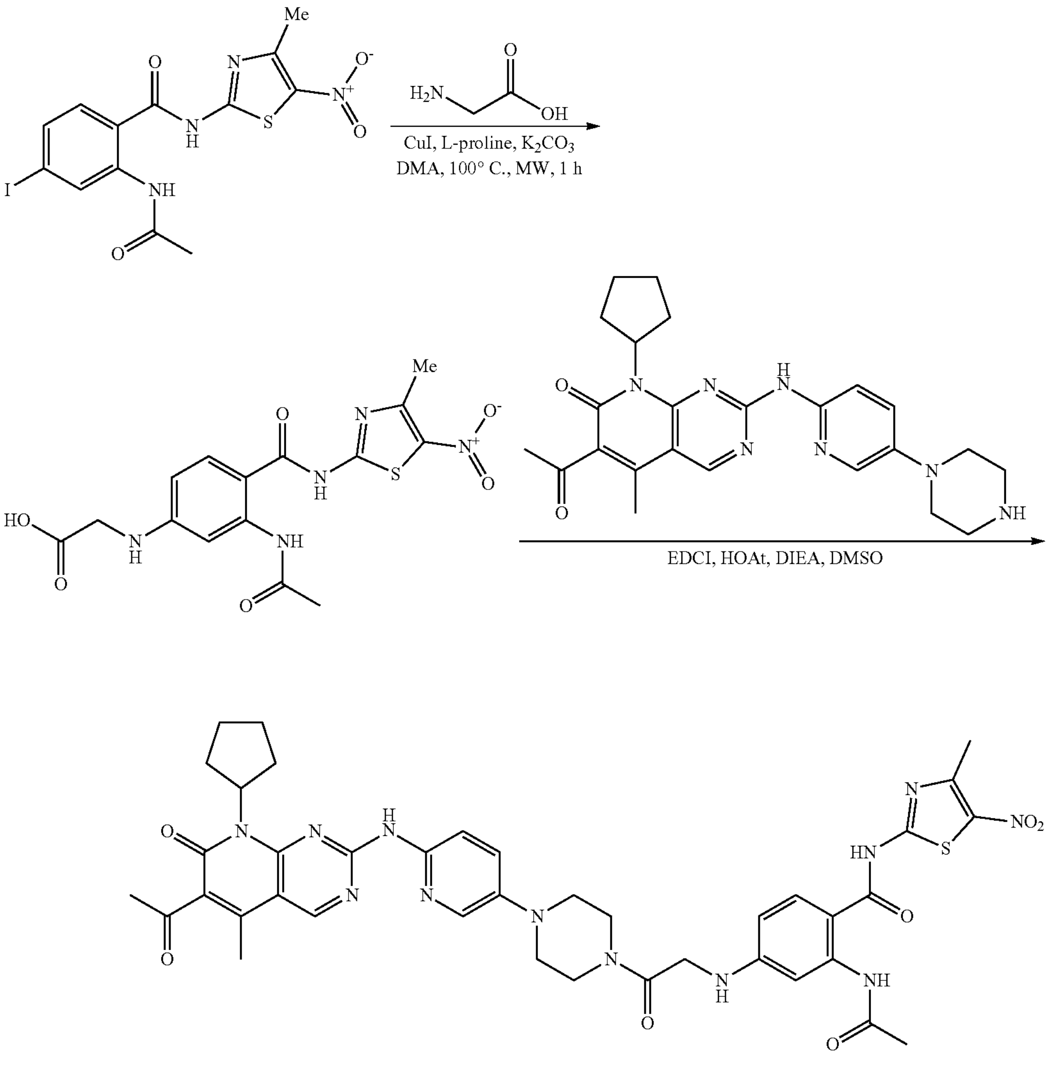

Step 1. Synthesis of (3-acetamido-4-((4-methyl-5-nitrothiazol-2-yl)carbamoyl)phenyl)glycine

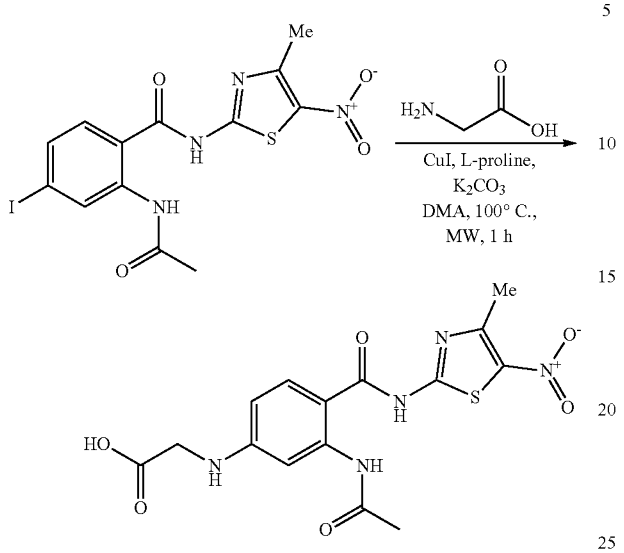

A solution of 2-acetamido-4-iodo-N-(4-methyl-5-nitrothiazol-2-yl)benzamide (1.0 g, 2.24 mmol), glycine (840 mg, 11.2 mmol), L-proline (257 mg, 2.24 mmol), CuI (425 mg, 2.24 mmol) and $K_2CO_3$ (1.85 g, 13.4 mmol) in DMF (15 mL) was heated at 100° C. with microwave for 1 h under argon atmosphere. After being cooled to room temperature, the mixture was purified by prep-HPLC (0.1% $NH_3 \cdot H_2O$) to give the title compound (200 mg, yield: 22.7%) as a yellow solid. $^1H$ NMR (400 MHz, DMSO-$d_6$): δ 13.67 (br s, 1H), 8.63 (br s, 1H), 7.97 (d, J=8.2 Hz, 1H), 7.78 (brs, 1H), 6.26-6.24 (m, 1H), 6.00 (brs, 1H), 3.63 (brs, 2H), 2.62 (s, 3H), 2.13 (s, 3H). MS (ESI) m/z: 394.1 $[M+H]^+$.

Step 2. Synthesis of 2-acetamido-4-((2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxoethyl)amino)-N-(4-methyl-5-nitrothiazol-2-yl)benzamide

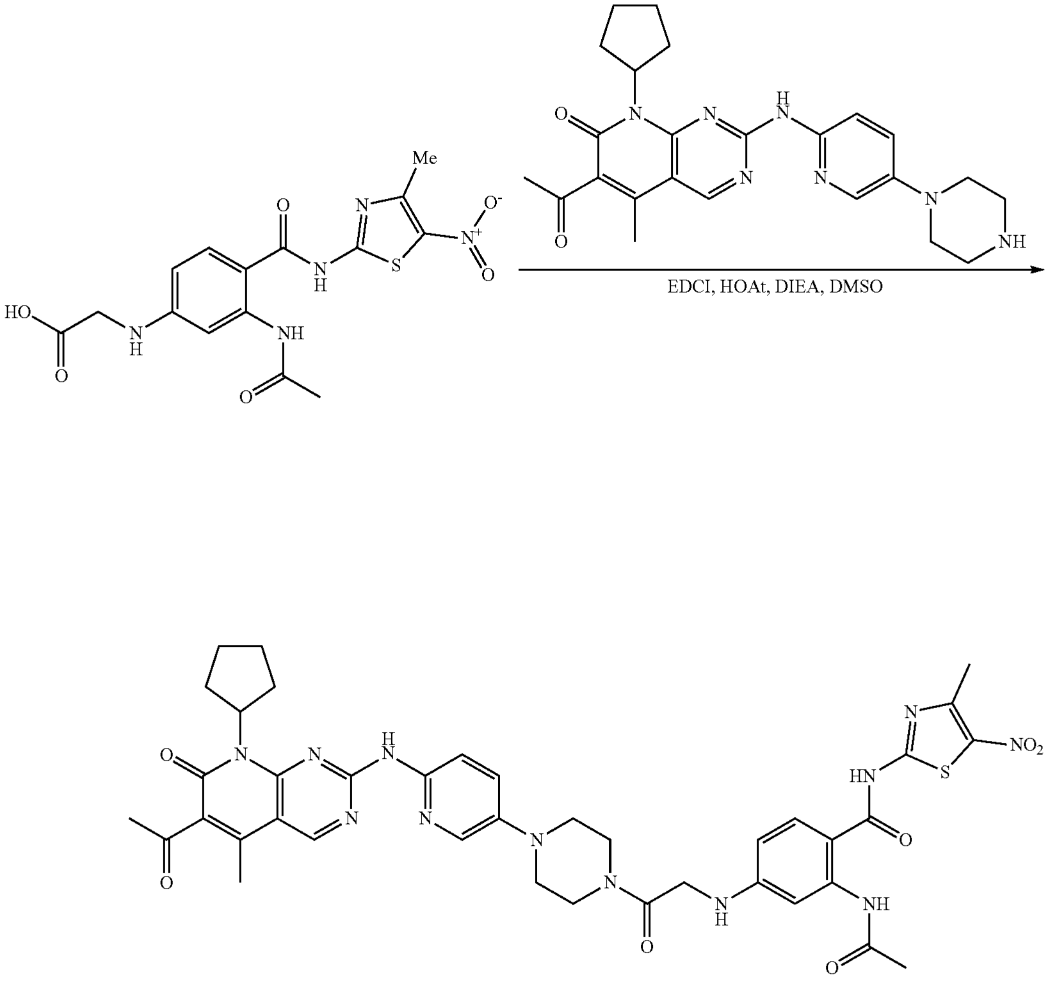

To a mixture of 6-acetyl-8-cyclopentyl-5-methyl-2-((5-(piperazin-1-yl)pyridin-2-yl)amino)pyrido[2,3-d]pyrimidin-7 (8H)-one (10 mg, 0.022 mmol) and HOAt (6 mg, 0.044 mmol), EDCI (8.4 mg, 0.044 mmol) in DMSO (1 mL) were added DIEA (10 mg, 0.11 mmol) and (3-acetamido-4-((4-methyl-5-nitrothiazol-2-yl)carbamoyl)phenyl)glycine (8.6 mg, 0.022 mmol). The resulting mixture was stirred at 25° C. for 16 h. The mixture was purified by reverse-phase chromatography to give the title compound (3.24 mg, yield: 17.9%) as a yellow solid. MS (EST) m/z: 823.5 $[M+H]^+$.

Example 245. 2-Acetamido-4-((3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropyl)amino)-N-(4-methyl-5-nitrothiazol-2-yl)benzamide (D-79)

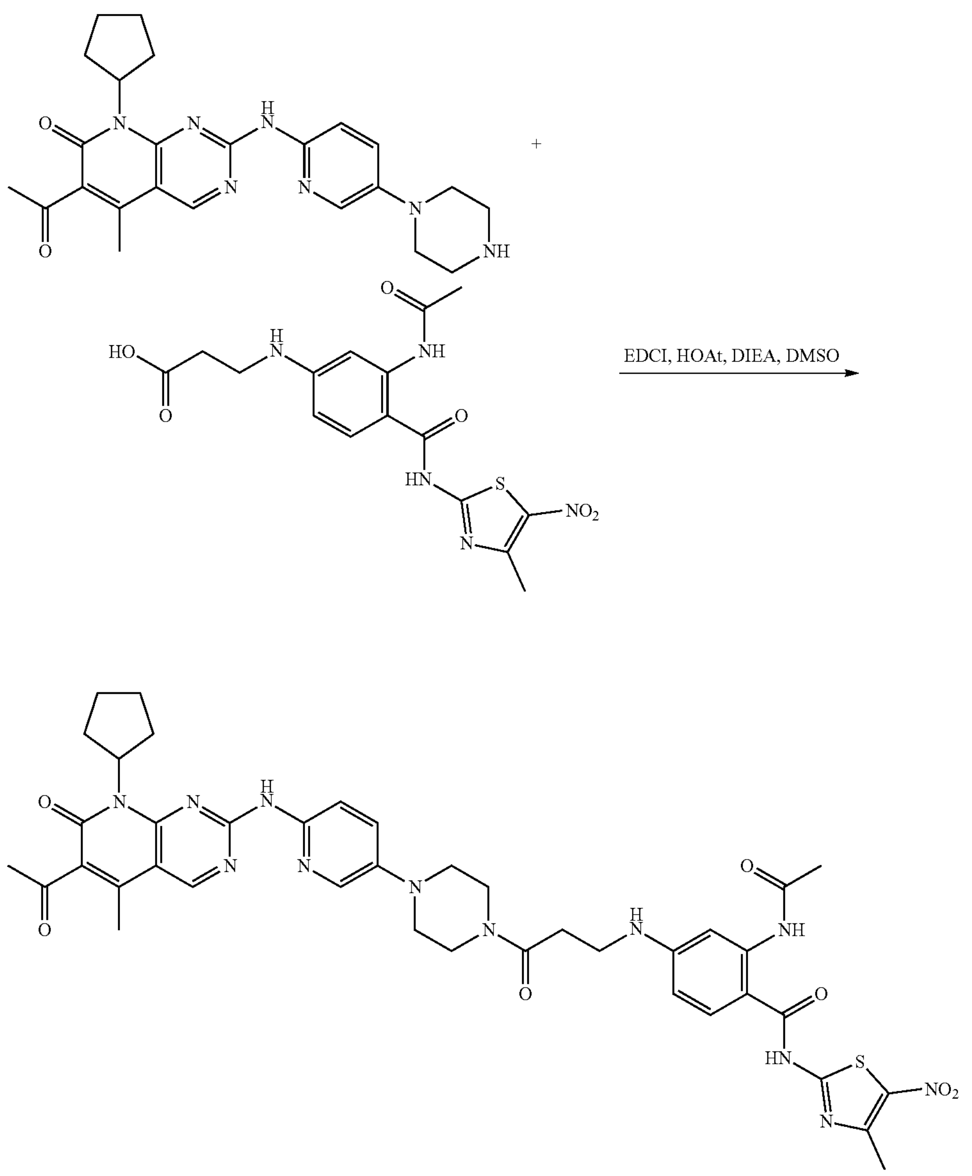

D-79 was synthesized following the same procedure as D-78. (3.16 mg, yield: 17.2%). MS (ESI) m/z: 837.7 $[M+H]^+$.

Example 246. 2-Acetamido-4-((4-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-4-oxobutyl)amino)-N-(4-methyl-5-nitrothiazol-2-yl)benzamide (D-80)

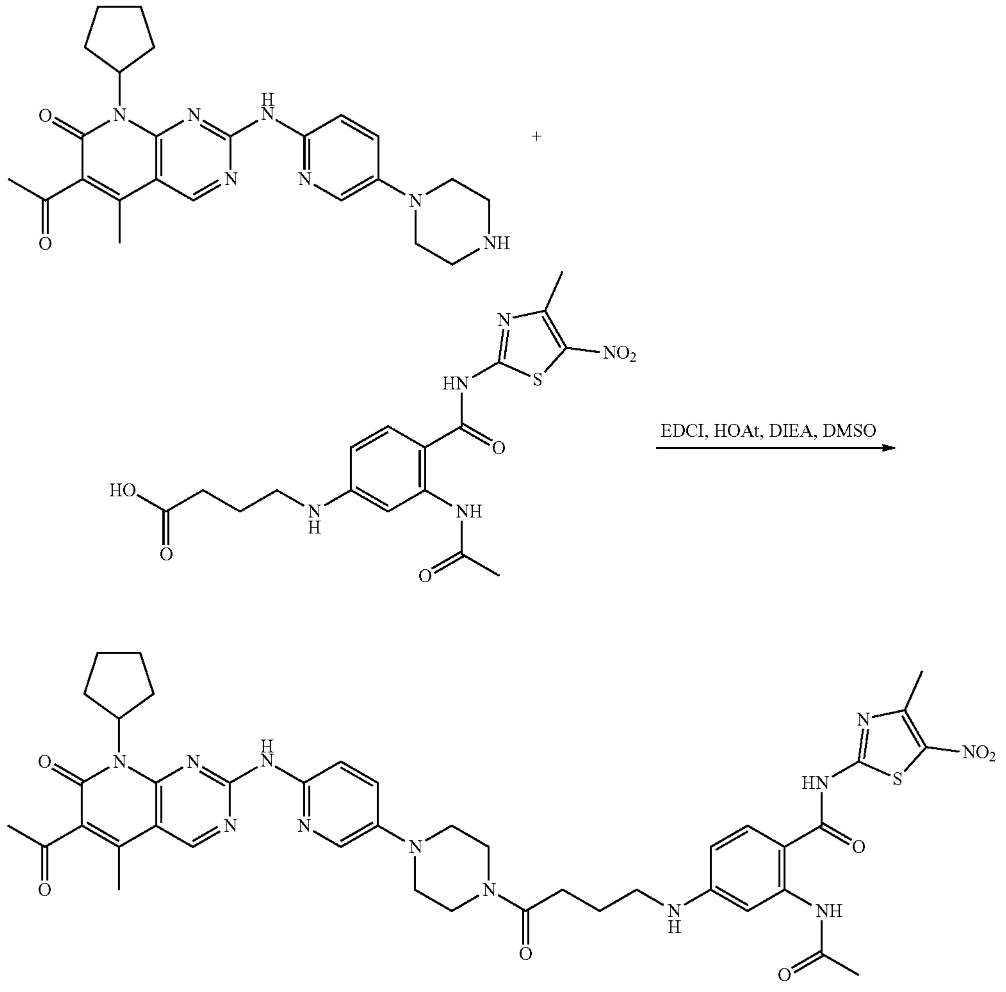

D-080 was synthesized following the same procedure as D-78. (3.45 mg, yield: 18.4%). MS (ESI) m/z: 851.6 $[M+H]^+$.

Example 247. 2-Acetamido-4-((5-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-5-oxopentyl)amino)-N-(4-methyl-5-nitrothiazol-2-yl)benzamide (D-81)

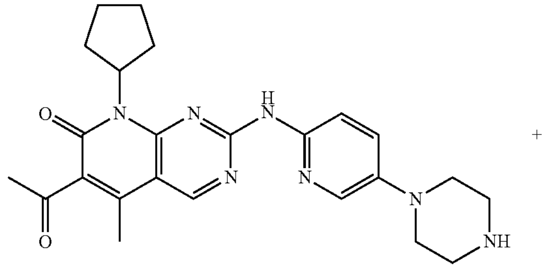

-continued
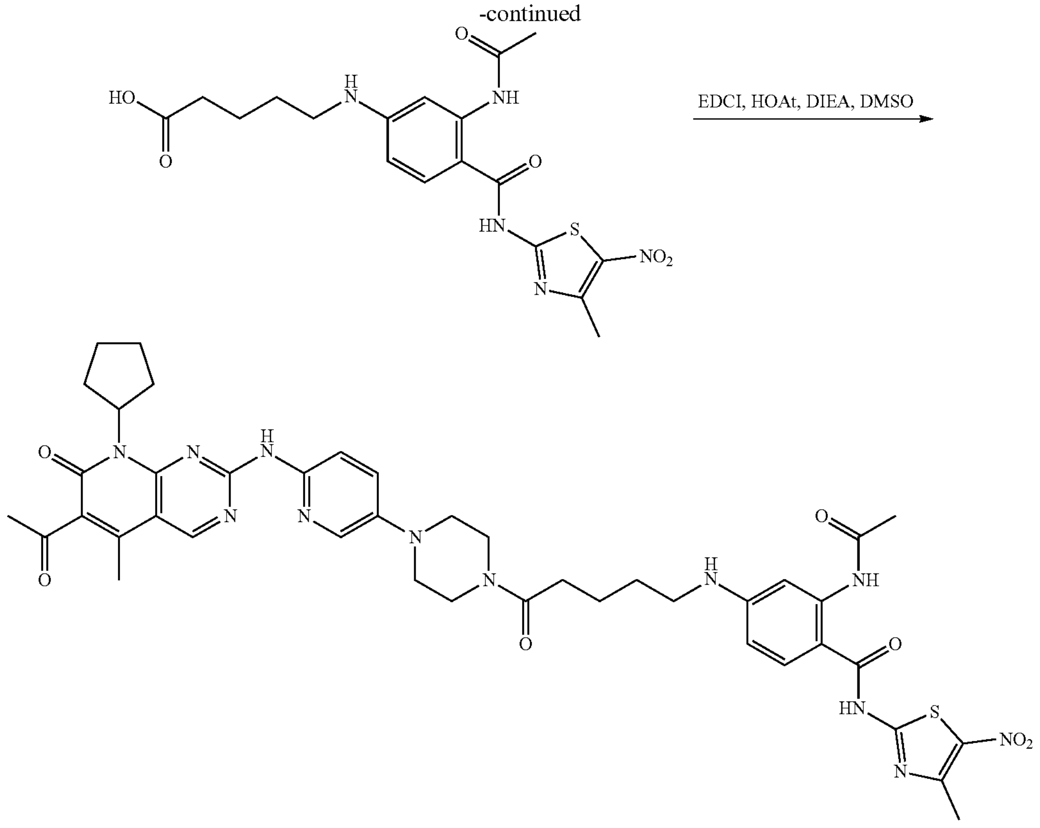
D-81 was synthesized following the same procedure as D-78. (1.2 mg, yield: 6.3%). MS (ESI) m/z: 865.5 $[M+H]^+$.
Example 248. 2-Acetamido-4-((6-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-6-oxohexyl)amino)-N-(4-methyl-5-nitrothiazol-2-yl)benzamide (D-82)
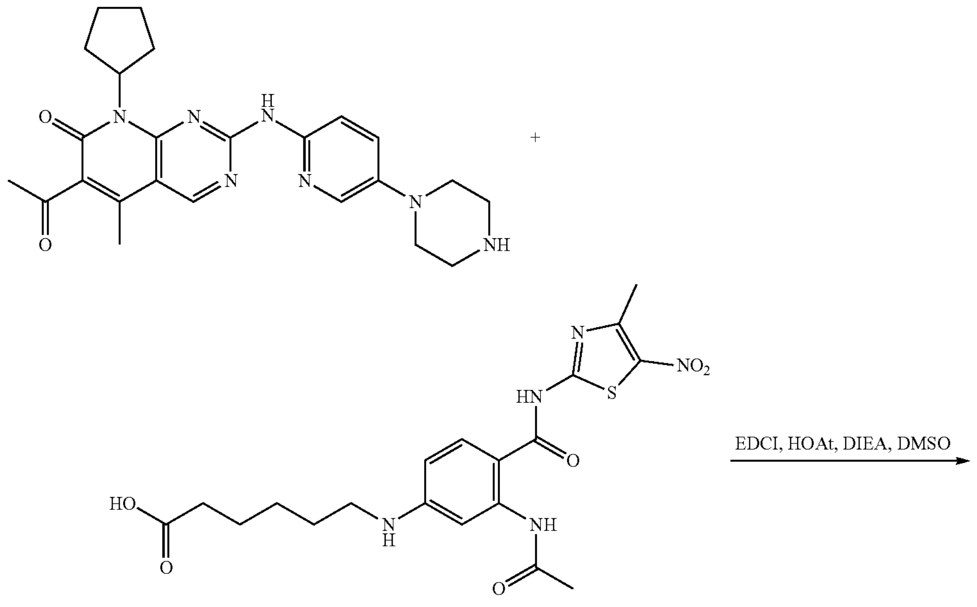

-continued
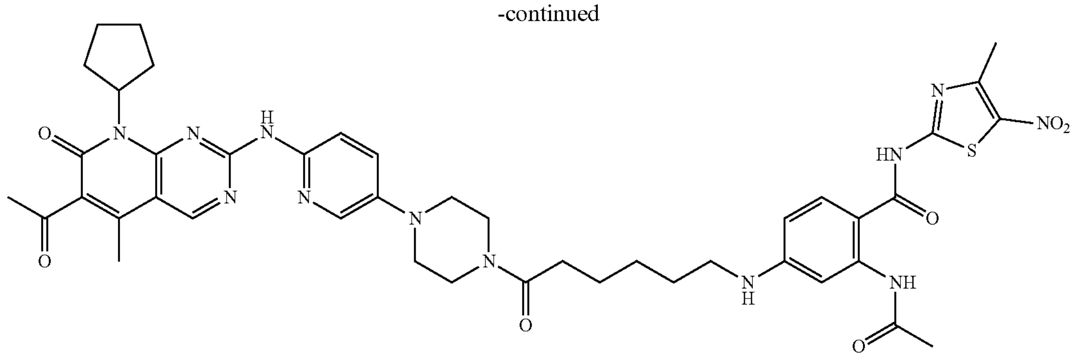
D-82 was synthesized following the same procedure as D-78. (4.98 mg, yield: 25.8%). MS (ESI) m/z: 879.6 $[M+H]^+$.
Example 249. 2-Acetamido-4-((7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxoheptyl)amino)-N-(4-methyl-5-nitrothiazol-2-yl)benzamide (D-83)
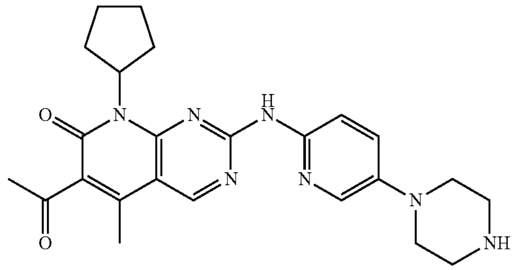
+
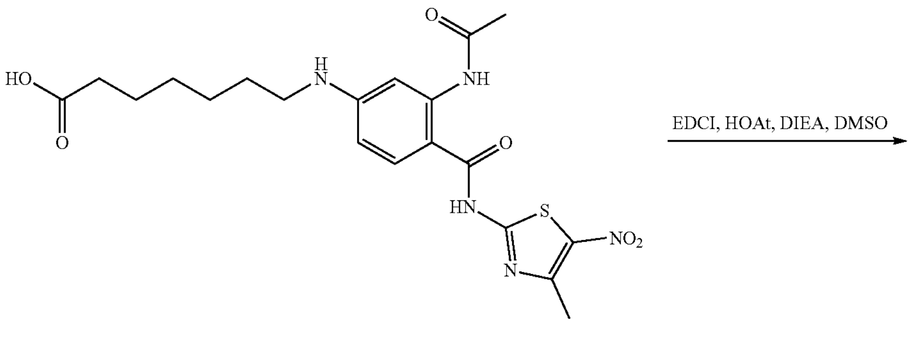

-continued
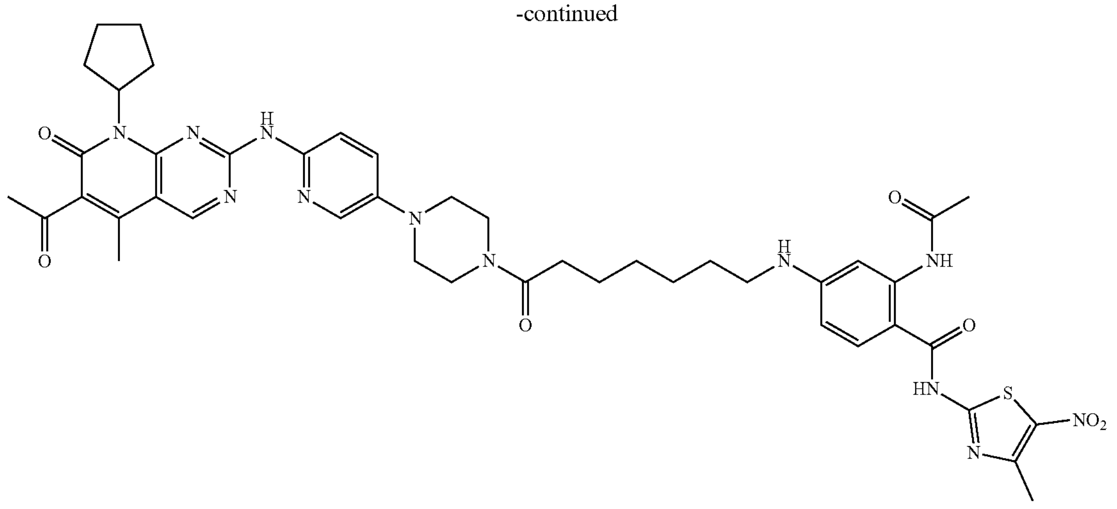
D-83 was synthesized following the same procedure as D-78. (6.24 mg, yield: 31.8%). MS (ESI) m/z: 893.6 $[M+H]^+$
Example 250. 2-Acetamido-4-((10-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-10-oxodecyl)amino)-N-(4-methyl-5-nitrothiazol-2-yl)benzamide (D-86)
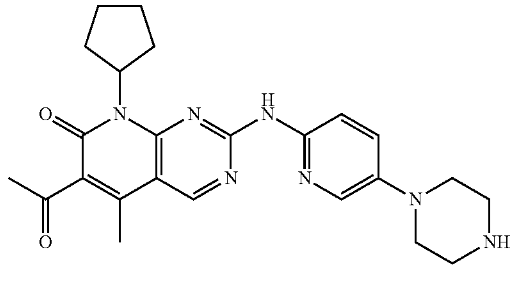
+
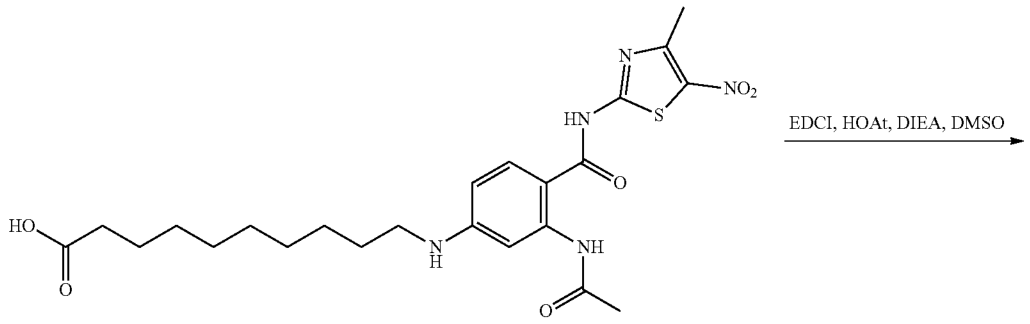

-continued
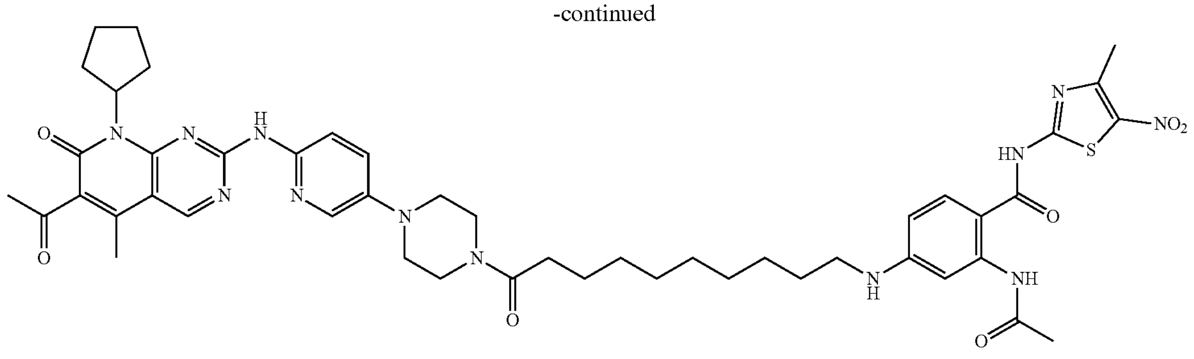
D-86 was synthesized following the same procedure as D-78. (4.51 mg, yield: 22%). MS (ESI) m/z: 935.6 $[M+H]^+$.
Example 251. 2-Acetamido-4-((11-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-11-oxoundecyl)amino)-N-(4-methyl-5-nitrothiazol-2-yl)benzamide (D-87)
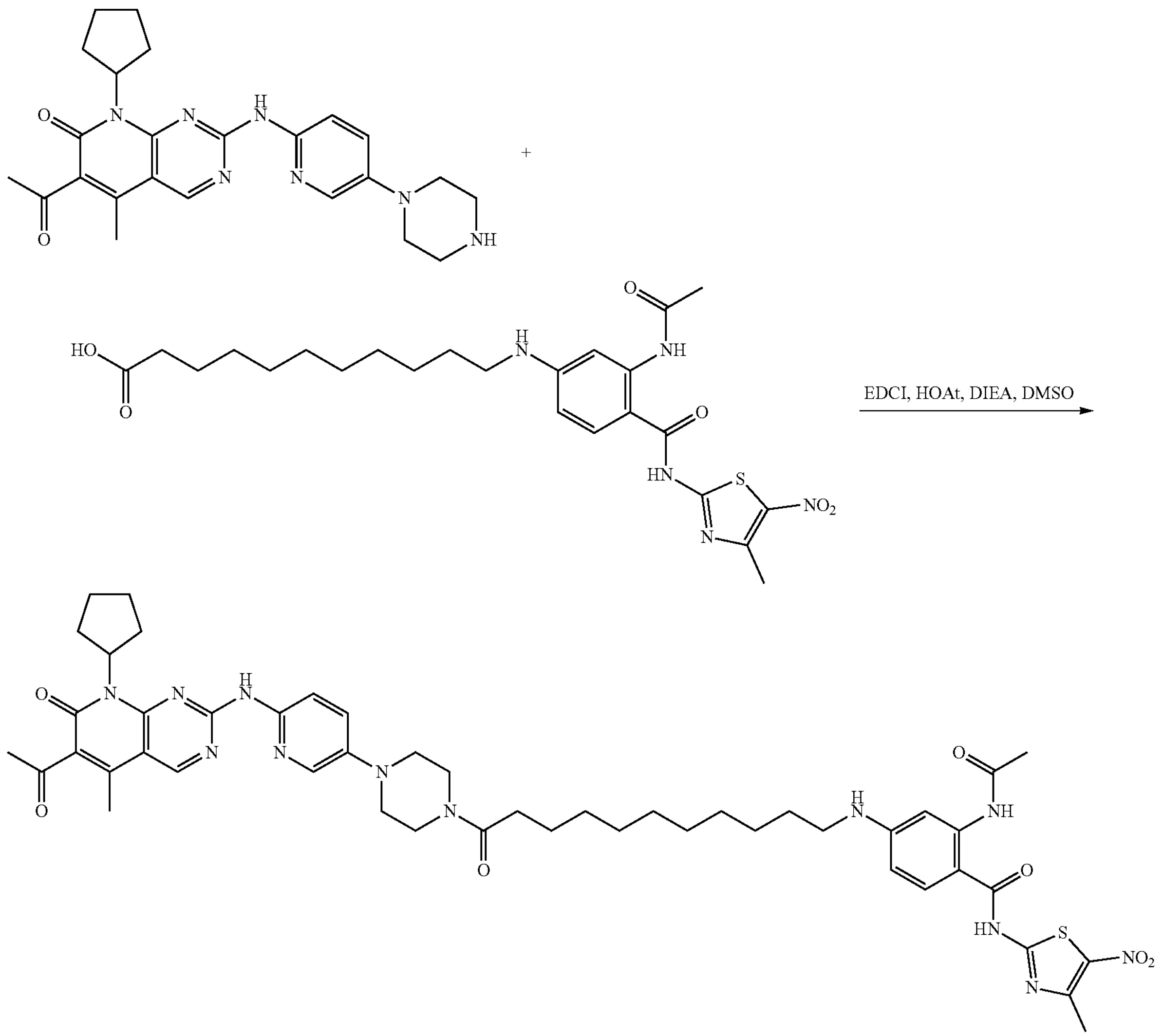

D-87 was synthesized following the same procedure as D-78. (4.12 mg, yield: 19.8%). MS (ESI) m/z: 949.7 $[M+H]^+$.
Example 252. 2-Acetamido-4-((2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethyl)amino)-N-(4-methyl-5-nitrothiazol-2-yl)benzamide (D-88)
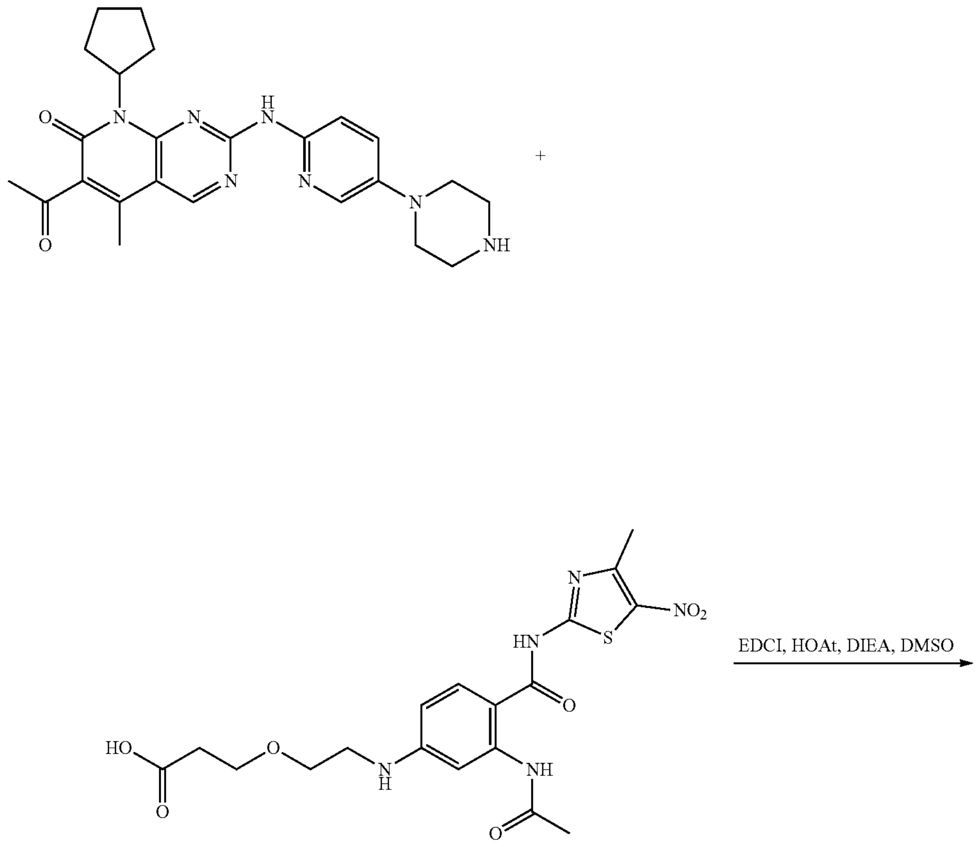
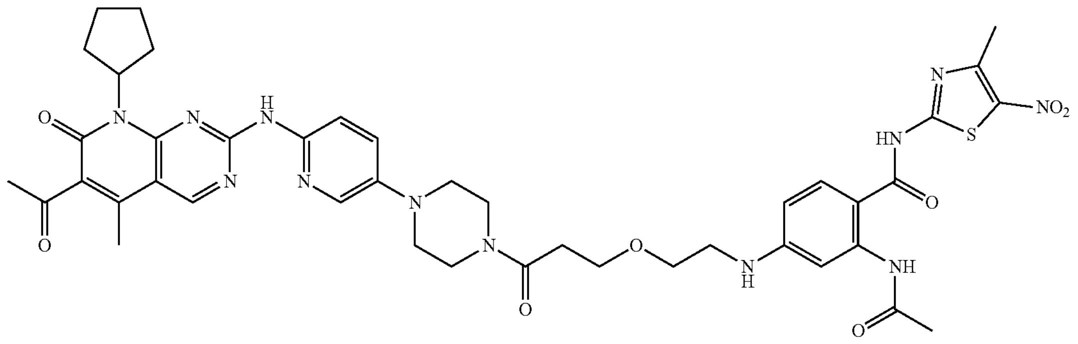
D-88 was synthesized following the same procedure as D-78. (5.7 mg, yield: 29.4%). MS (ESI) m/z: 881.6 $[M+H]^+$.

Example 253. 2-Acetamido-4-((2-(2-(3-(4-(6-((6-acetyl-8-cyclopentyl-5-methyl-7-oxo-7,8-dihydro-pyrido[2,3-d]pyrimidin-2-yl)amino)pyridin-3-yl) piperazin-1-yl)-3-oxopropoxy)ethoxy)ethyl)amino)-N-(4-methyl-5-nitrothiazol-2-yl)benzamide (D-89)
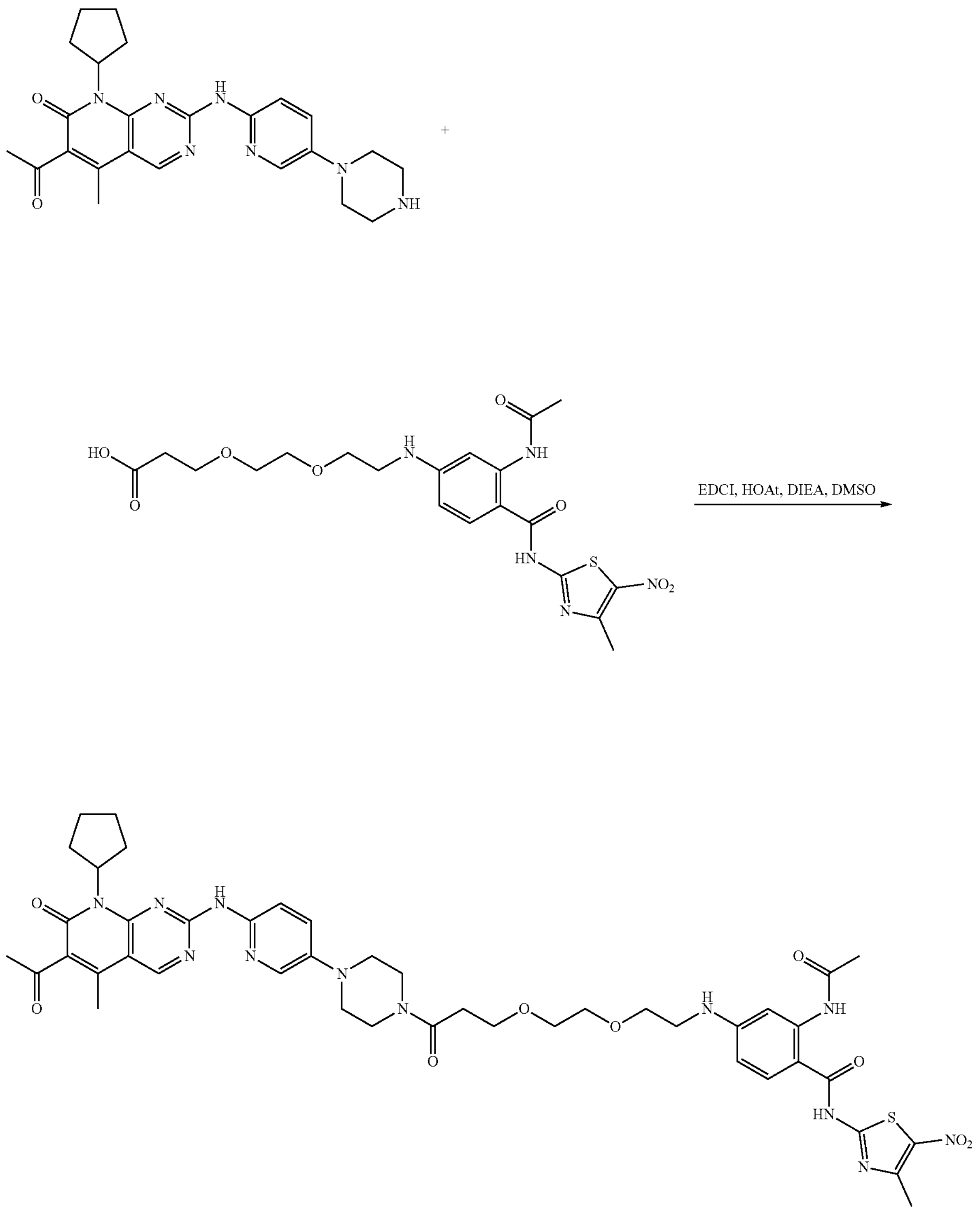
D-89 was synthesized following the same procedure as D-78. (3.72 mg, yield: 18.3%). MS (ESI) m/z: 925.7 $[M+H]^+$.

Example 254. 2-Acetamido-4-((2-(2-(2-(3-(4-(6-((6-acetyl-8-cyclopentyl-5-methyl-7-oxo-7,8-dihydro-pyrido[2,3-d]pyrimidin-2-yl)amino)pyridin-3-yl) piperazin-1-yl)-3-oxopropoxy)ethoxy)ethoxy)ethyl) amino)-N-(4-methyl-5-nitrothiazol-2-yl)benzamide (D-90)

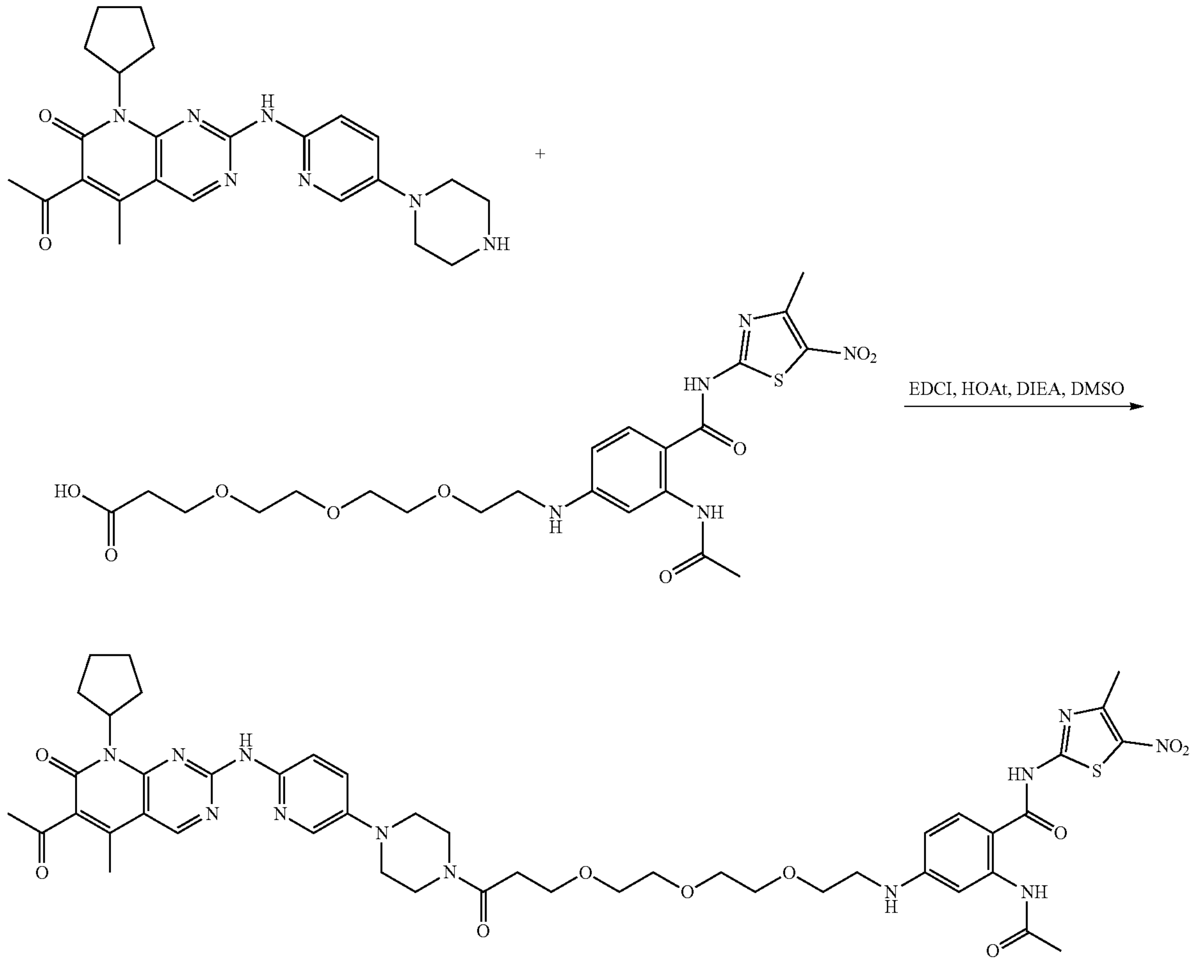

D-90 was synthesized following the same procedure as D-78. (3.51 mg, yield: 16.5%). MS (ESI) m/z: 969.7 $[M+H]^+$ Example 255. 2-Acetamido-4-((15-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-15-oxo-3,6,9,12-tetraoxapentadecyl)amino)-N-(4-methyl-5-nitrothiazol-2-yl)benzamide (D-91)

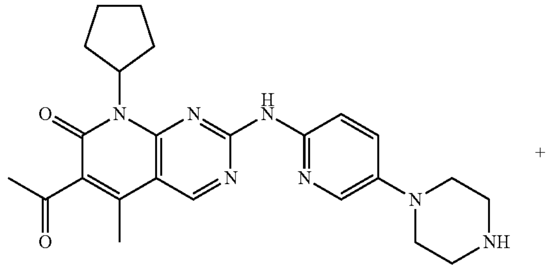

-continued
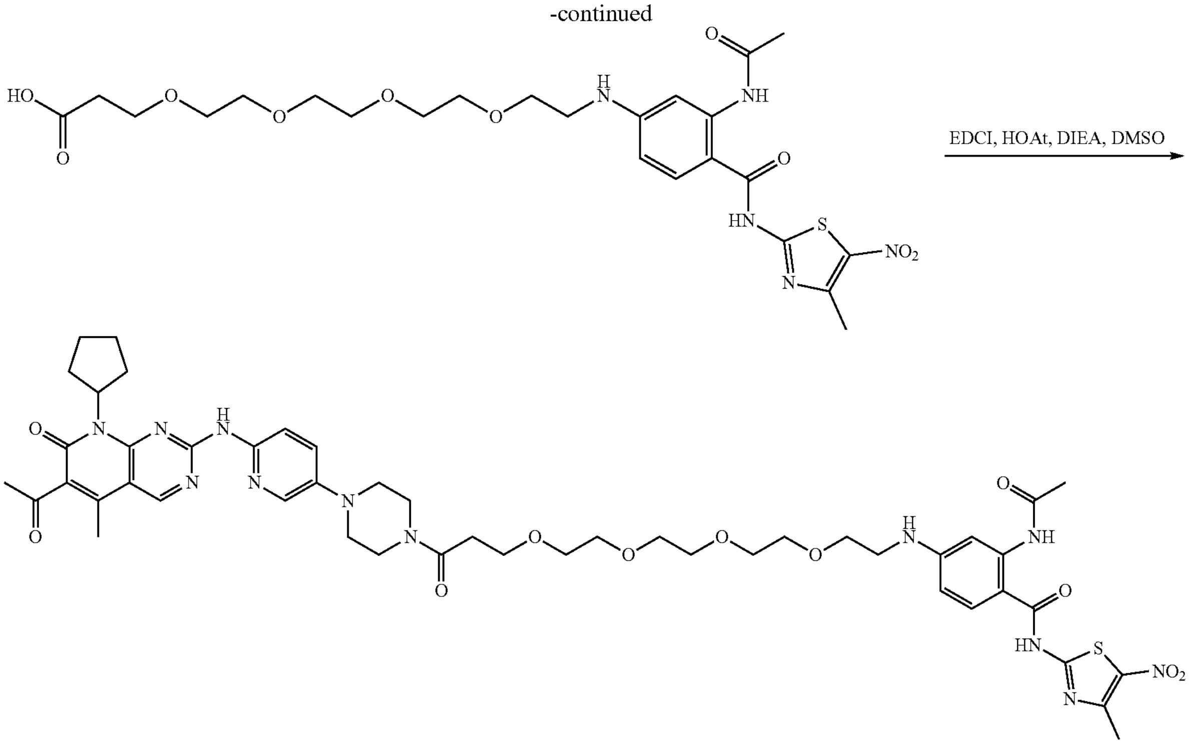
D-91 was synthesized following the same procedure as D-78. (4.62 mg, yield: 20.7%). MS (ESI) m/z: 1013.7 $[M+H]^+$
Example 256. 2-Acetamido-4-((18-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-18-oxo-3,6,9,12,15-pentaoxaoctadecyl)amino)-N-(4-methyl-5-nitrothiazol-2-yl)benzamide (D-92)
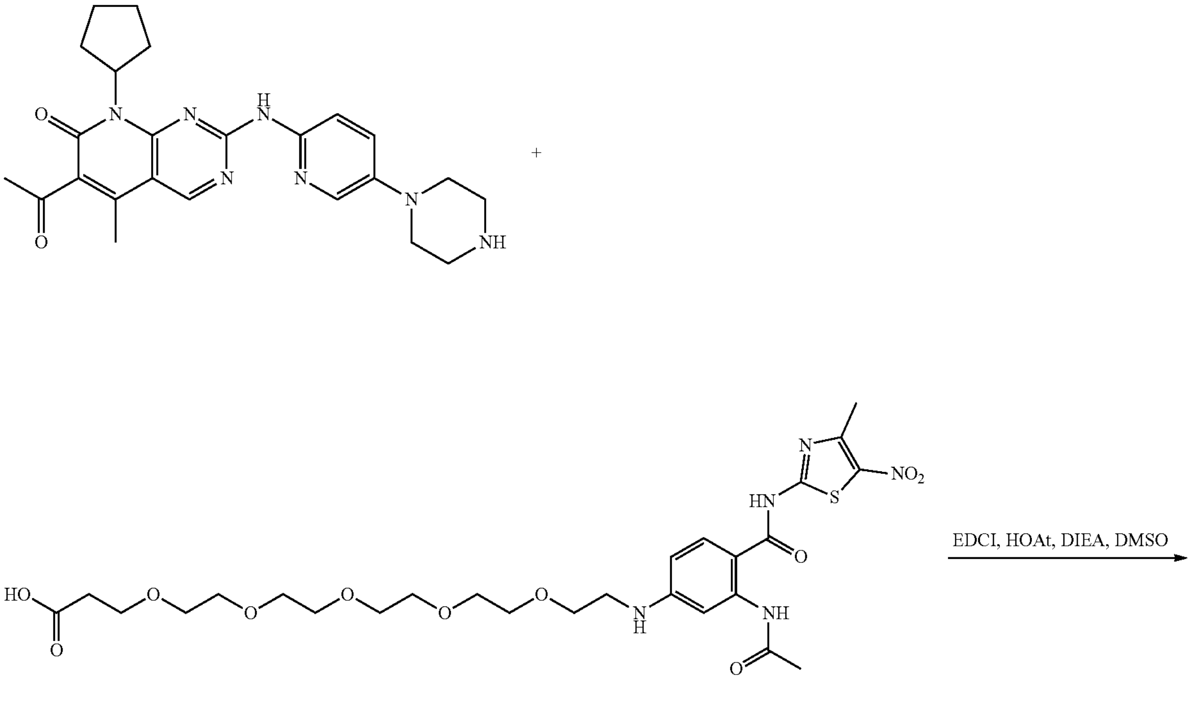

-continued
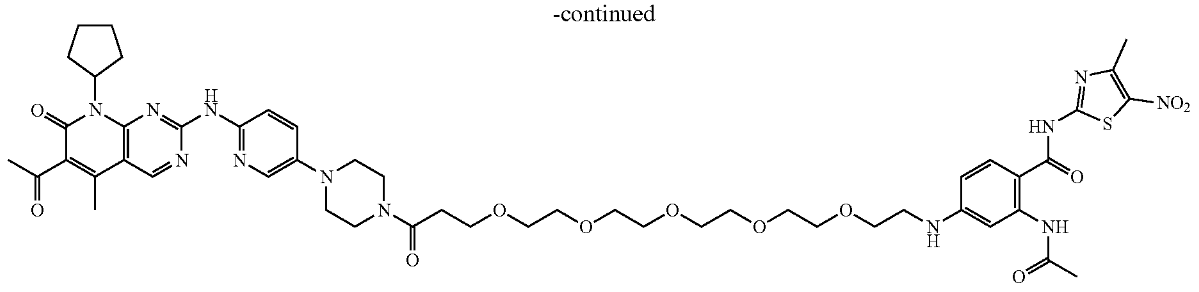
D-92 was synthesized following the same procedure as D-78. (5.42 mg, yield: 23.4%). MS (ESI) m/z: 1057.8 $[M+H]^+$.
Example 257. 2-Acetamido-4-((3-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)propyl)amino)-N-(4-methyl-5-nitrothiazol-2-yl)benzamide (D-93)
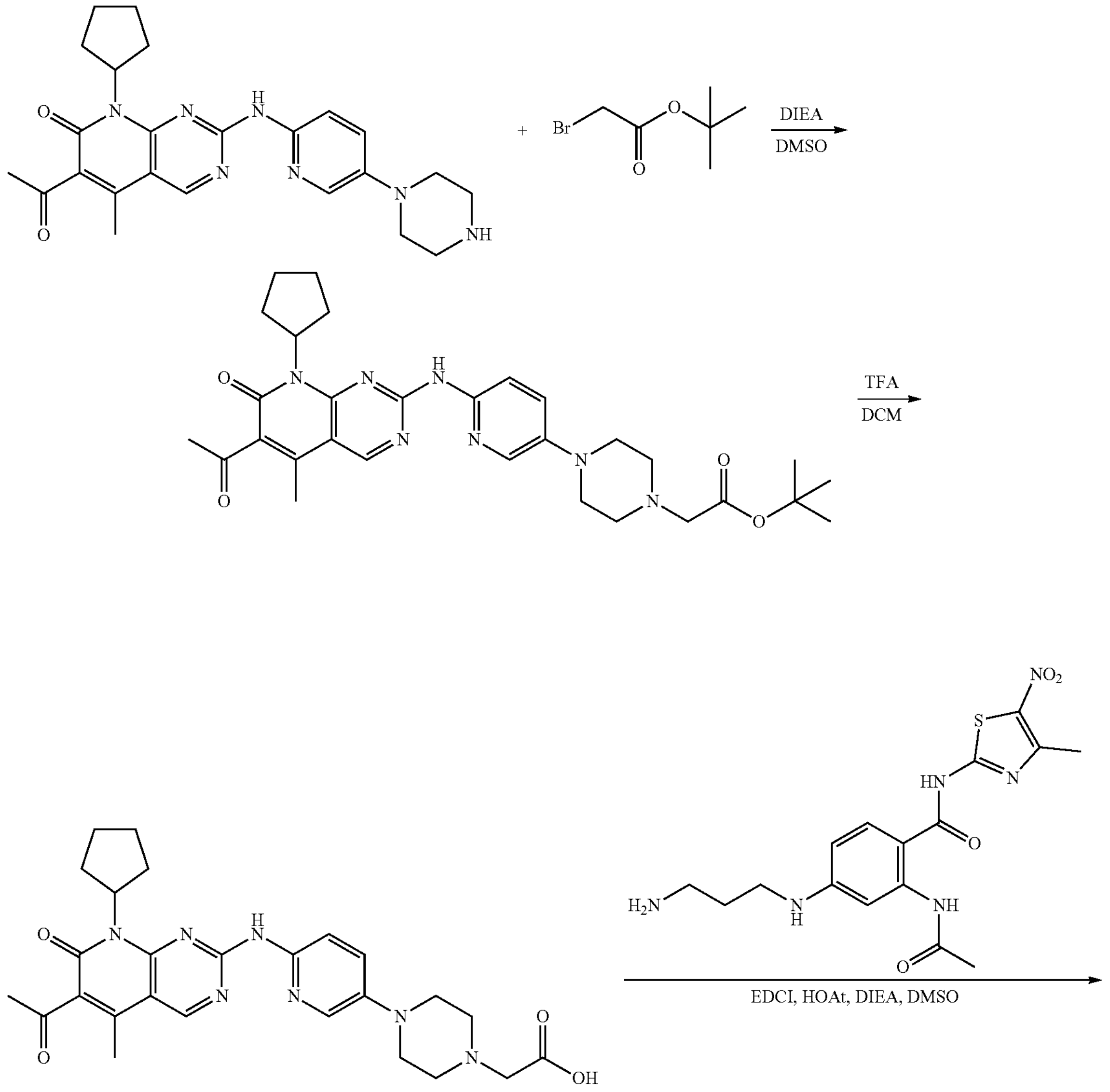

-continued

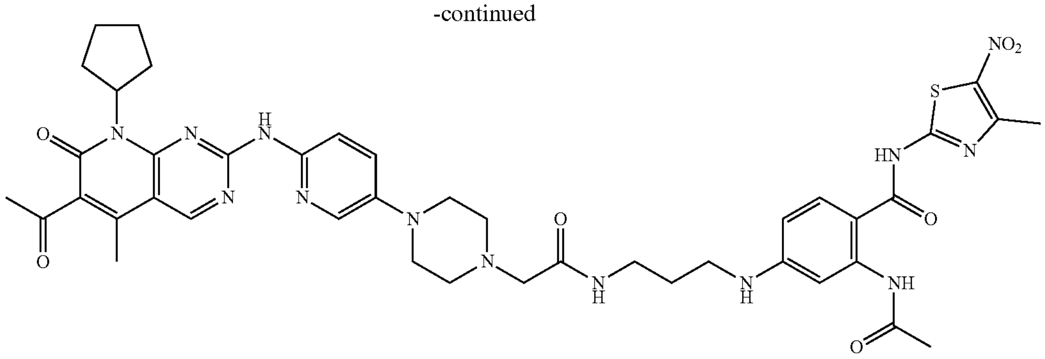

Step 1. Synthesis of tert-butyl 2-(4-(6-((6-acetyl-8-cyclopentyl-5-methyl-7-oxo-7,8-dibydropyrido[2,3-d]pyrimidin-2-yl)amino)pyridin-3-yl)piperazin-1-yl) acetate

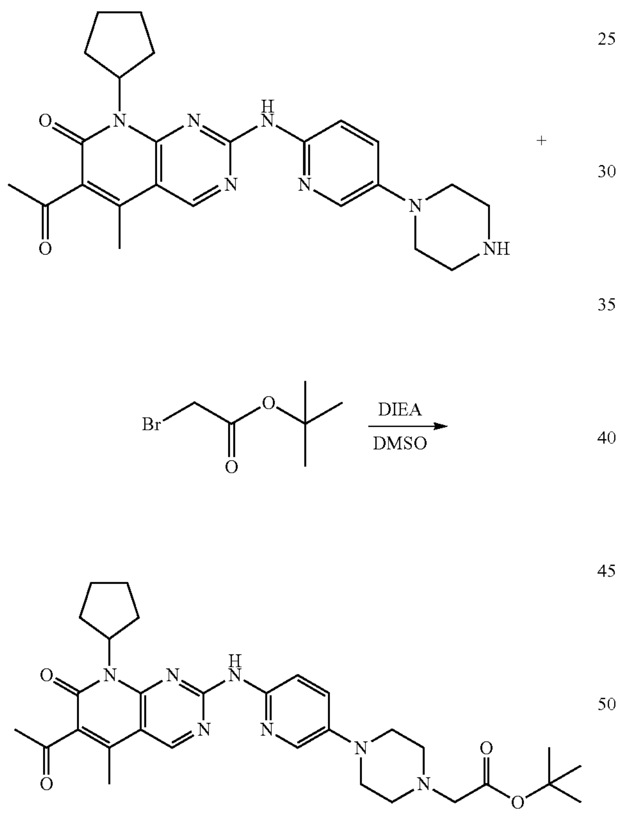

To a mixture of 6-acetyl-8-cyclopentyl-5-methyl-2-((5-(piperazin-1-yl)pyridin-2-yl)amino)pyrido[2,3-d]pyrimidin-7 (8H)-one (200 mg, 0.45 mmol) and DIEA (284 mg, 1.8 mmol) in DMSO (20 mL) was added tert-butyl 2-bromoacetate (88 mg, 0.45 mmol). The resulting mixture was stirred at 25° C. for 16 h. The mixture was quenched with water and extracted with DCM (3x30 mL). The organic phases were combined and washed with brine (2x40 mL), dried over $Na_2SO_4$ and concentrated in vacuum to give the title compound (230 mg, yield: 91.6%) as yellow solid. MS (ESI) m/z: 562.6 $[M+H]^+$.

Step 2. Synthesis of 2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetic acid

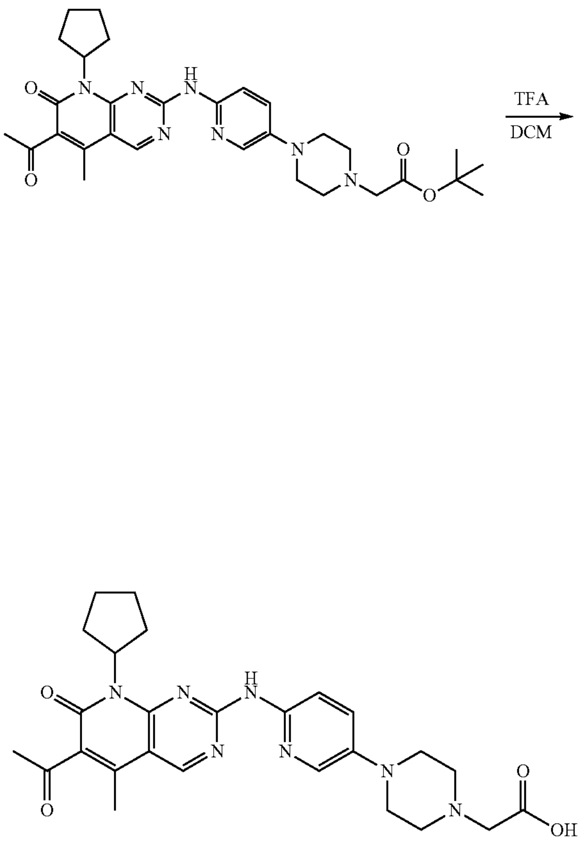

To a mixture of tert-butyl 2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetate (230 mg, 0.41 mmol) in DCM (10 mL) was added TFA (10 mL). The resulting mixture was stirred at 25° C. for 16 h. The solvent was removed under reduced pressure. The residue was purified with reverse-phase chromatography to give the title compound (180 mg, yield: 86.7%) as yellow solid. MS (ESI) m/z: 506.6 $[M+H]^+$.

Step 3. Synthesis of 2-acetamido-4-((3-(2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)acetamido)propyl)amino)-N-(4-methyl-5-nitrothiazol-2-yl)benzamide

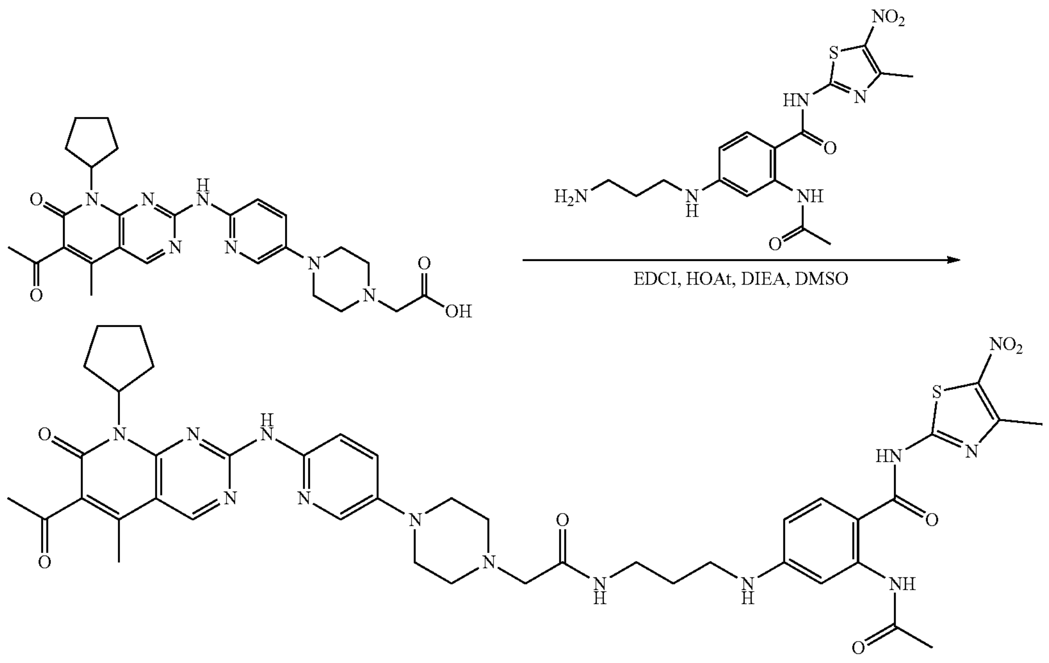

D-93 was synthesized following the same procedure as last step of D-78. (3.11 mg, yield: 35.4%). MS (ESI) m/z: 880.6 $[M+H]^+$.

Example 258. 2-Acetamido-4-((5-(2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)acetamido)pentyl)amino)-N-(4-methyl-5-nitrothiazol-2-yl)benzamide (D-94)

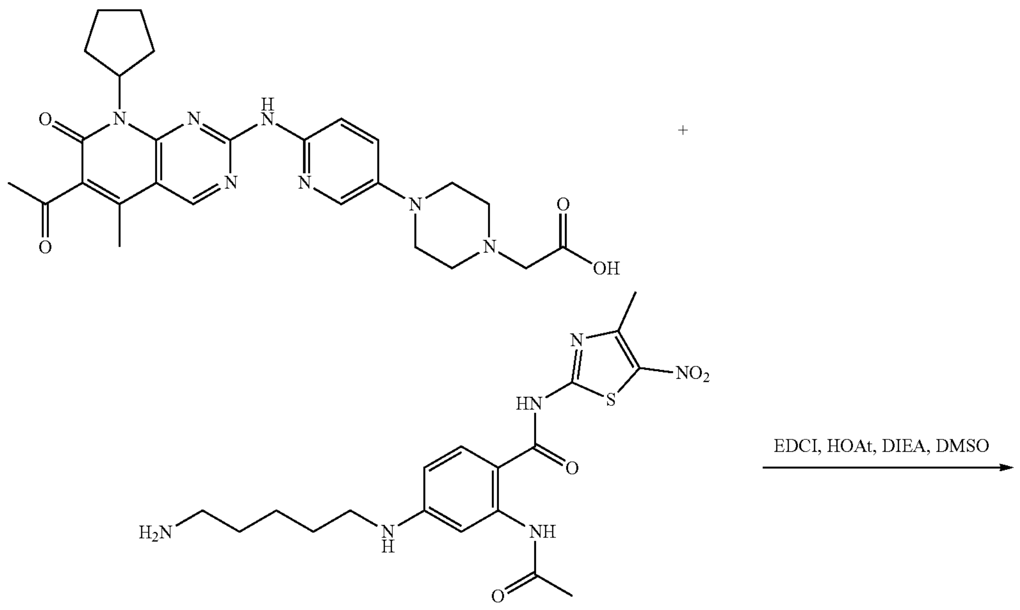

-continued
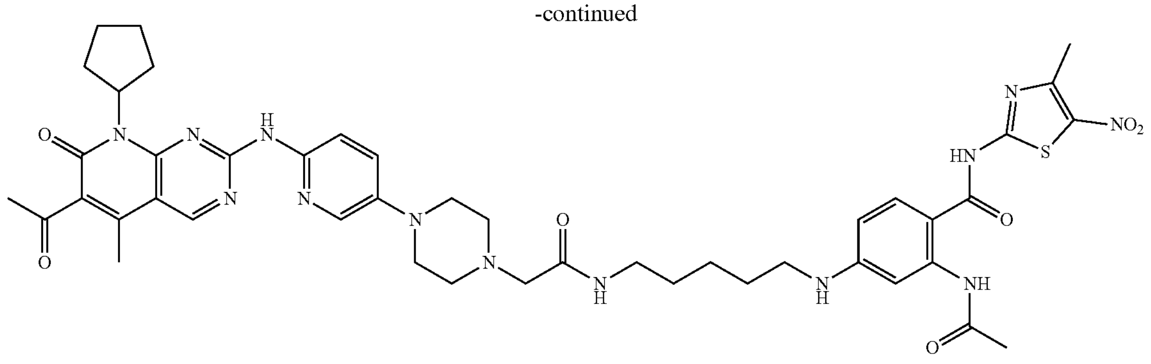
D-94 was synthesized following the same procedure as D-93. (2.95 mg, yield: 32.5%). MS (ESI) m/z: 908.6 $[M+H]^+$.
Example 259. 2-Acetamido-4-((9-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)nonyl)amino)-N-(4-methyl-5-nitrothiazol-2-yl)benzamide (D-95)
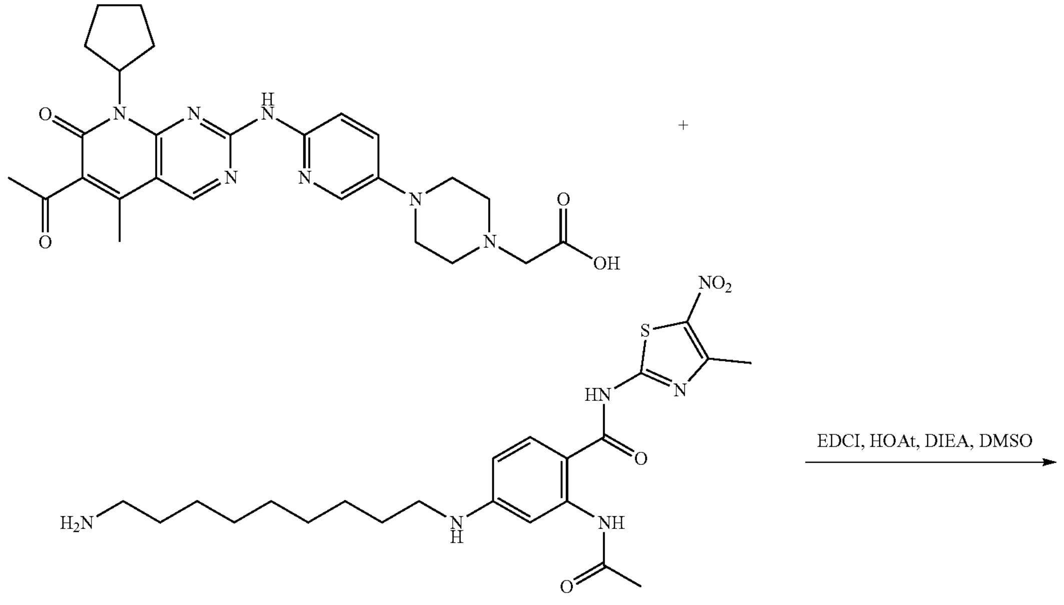
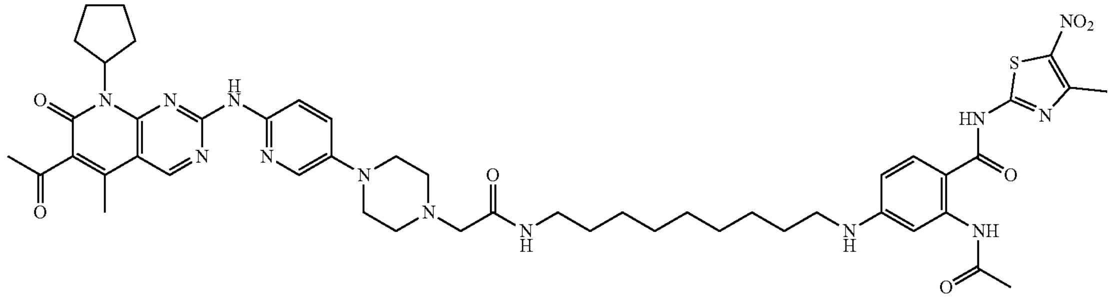
D-95 was synthesized following the same procedure as D-93. (3.08 mg, yield: 32%). MS (ESI) m/z: 964.7 $[M+H]^+$.

Example 260. 2-Acetamido-4-((11-(2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)acetamido)undecyl)amino)-N-(4-methyl-5-nitrothiazol-2-yl)benzamide (D-96)

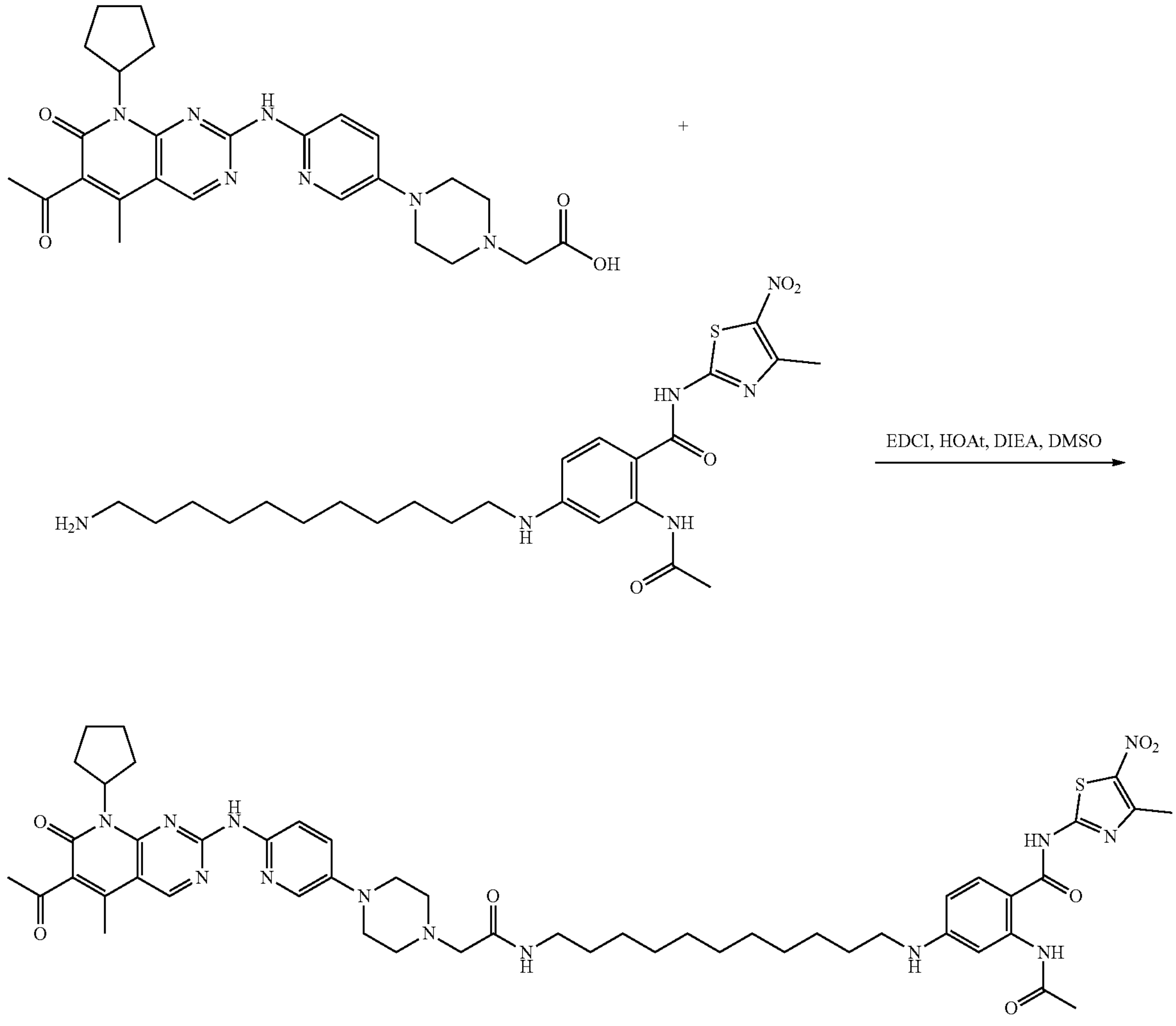

D-96 was synthesized following the same procedure as D-93. (1.97 mg, yield: 19.9%). MS (ESI) m/z: 992.7 $[M+H]^+$.

Example 261: 2-(4-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-4-oxobutanamido)-N-(4-methyl-5-nitrothiazol-2-yl)benzamide (D-97)

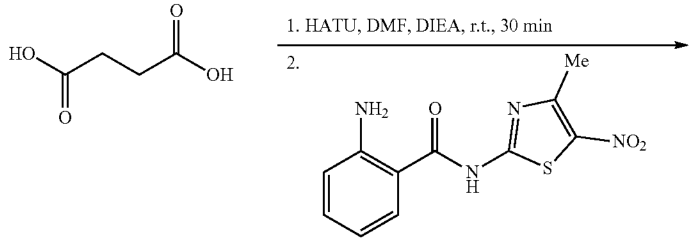

-continued

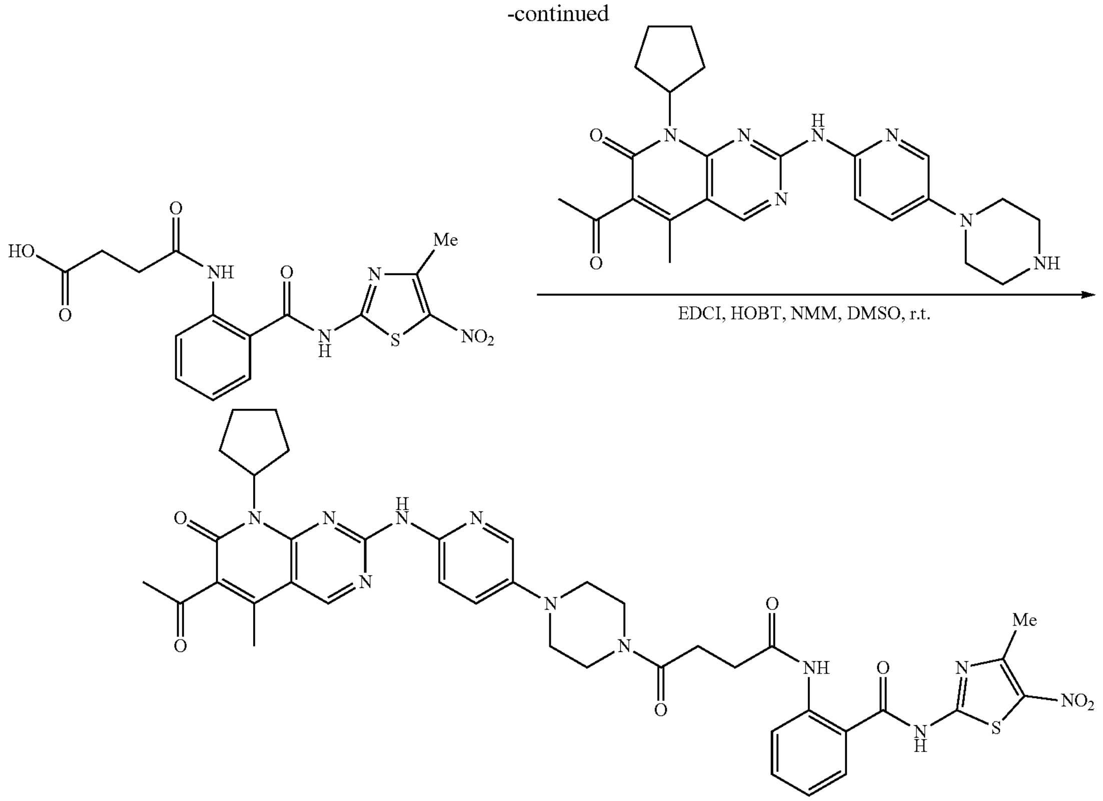

Step 1. Synthesis of 4-((2-((4-methyl-5-nitrothiazol-2-yl)carbamoyl)phenyl)amino)-4-oxobutanoic acid

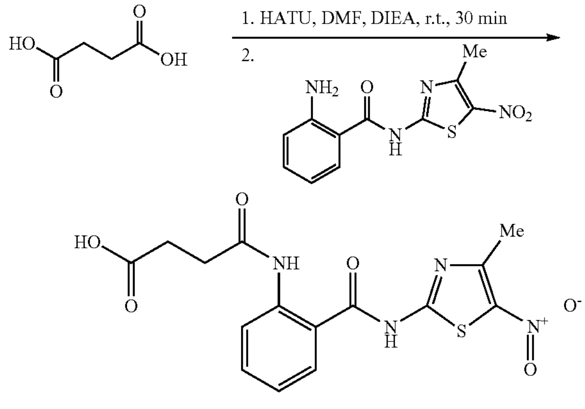

A solution of succinic acid (700 mg, 5.40 mmol), HATU (615 mg, 1.62 mmol) and DIEA (418 mg, 3.24 mmol) in DMF (10 mL) was stirred at room temperature for 30 minutes, before 2-amino-N-(4-methyl-5-nitrothiazol-2-yl)benzamide (300 mg, 1.08 mmol) was added. After the mixture was stirred at room temperature overnight, the mixture was purified by prep-HPLC to give the title compound (120 mg, 32% yield) as white solid. $^1H$ NMR (400 MHz, DMSO-$d_6$): δ 13.45 (brs, 1H), 12.24 (brs, 1H), 10.25 (brs, 1H), 7.75-7.71 (m, 2H), 7.57 (dt, J=1.2, 8.0 Hz, 1H), 7.25 (dt, J=1.2, 8.0 Hz, 1H), 2.70 (s, 3H), 2.55-2.51 (m, 2H), 2.49-2.44 (m, 2H). MS (ESI) m/z: 379.0 $[M+H]^+$.

Step 2. Synthesis of 2-(4-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-4-oxobutanamido)-N-(4-methyl-5-nitrothiazol-2-yl)benzamide

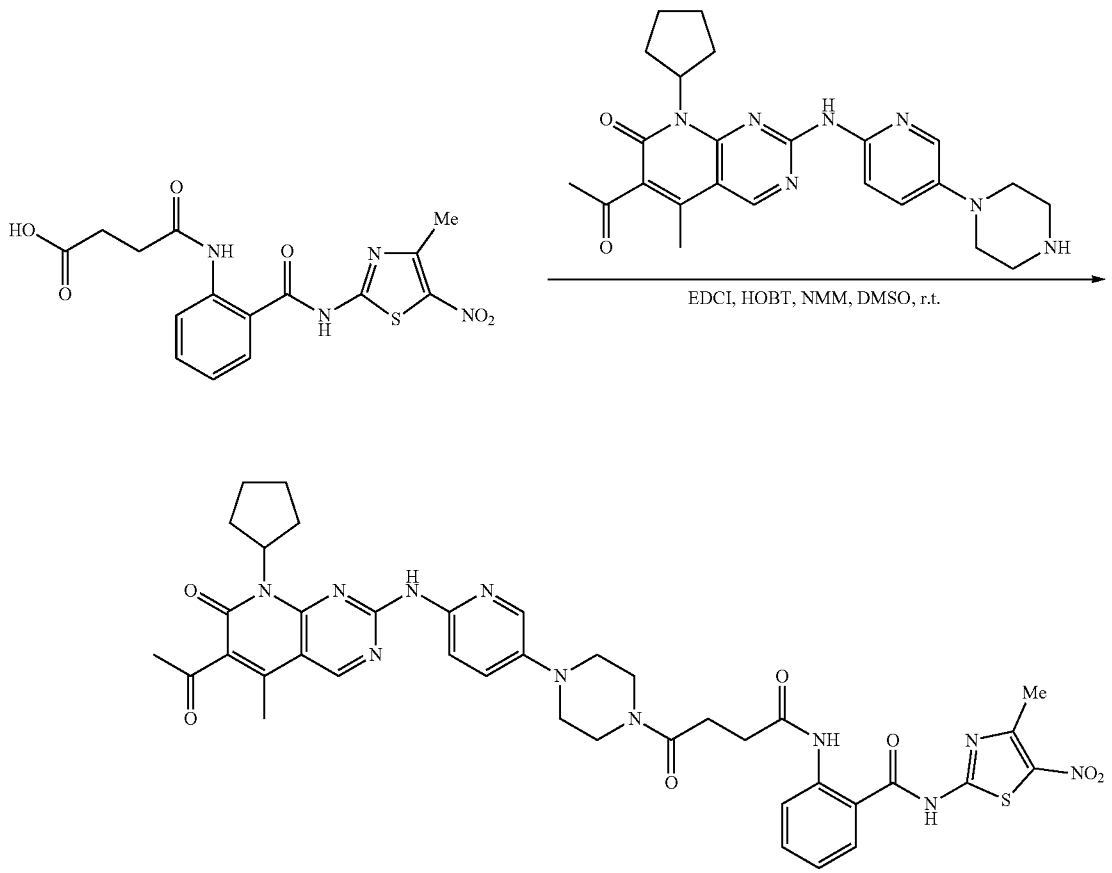

To a solution of 4-((2-((4-methyl-5-nitrothiazol-2-yl)carbamoyl)phenyl)amino)-4-oxobutanoic acid (6.0 mg, 0.015 mmol) and 6-acetyl-8-cyclopentyl-5-methyl-2-((5-(piperazin-1-yl)pyridin-2-yl)amino)pyrido[2,3-d]pyrimidin-7(8H)-one (7.0 mg, 0.015 mmol) in DMSO (1 mL) were added EDCI (4.5 mg, 0.023 mmol), HOBT (3.1 mg, 0.023 mmol) and NMM (5 μL, 0.047 mmol). Then the reaction mixture was stirred at room temperature overnight. The resulting mixture was purified by prep-HPLC to give the title compound (10.6 mg, 75% yield) as white solid. MS (ESI) m/z: 808.4 $[M+H]^+$.

Example 262: 2-(5-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-5-oxopentanamido)-N-(4-methyl-5-nitrothiazol-2-yl)benzamide (D-98)

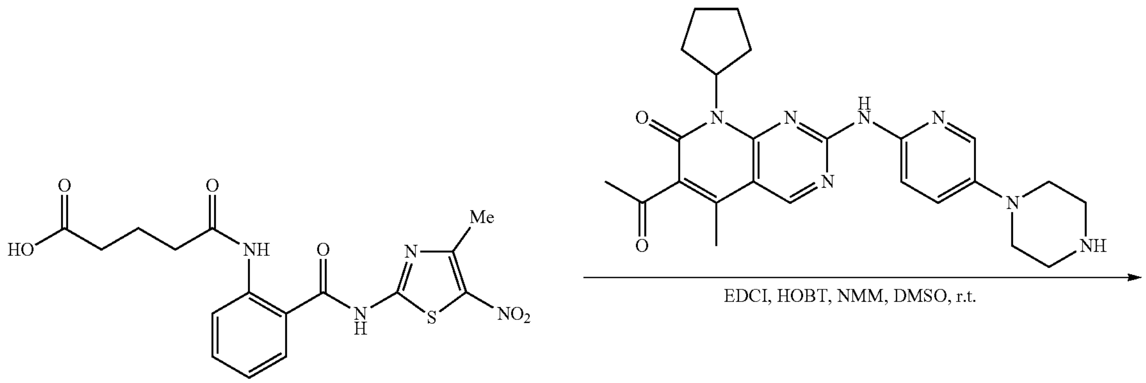

-continued
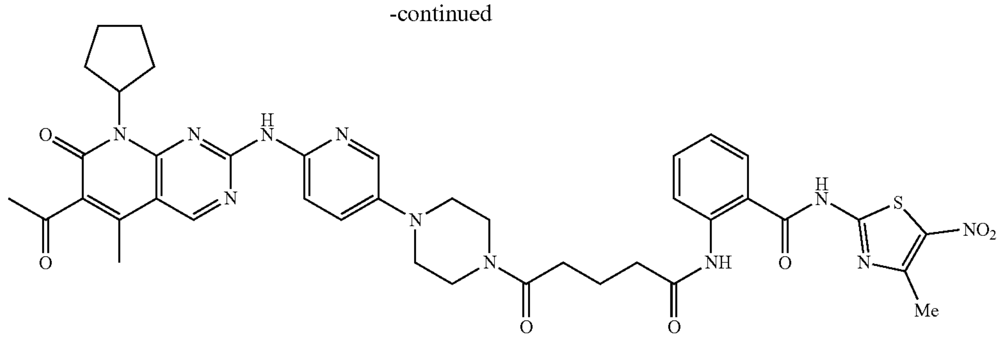
D-98 was synthesized following the standard procedure for preparing D-97 (11.4 mg, 79% yield). MS (EST) m/z: 822.4 [M+H]$^+$.
Example 263: 2-(6-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-6-oxohexanamido)-N-(4-methyl-5-nitrothiazol-2-yl)benzamide (D-99)
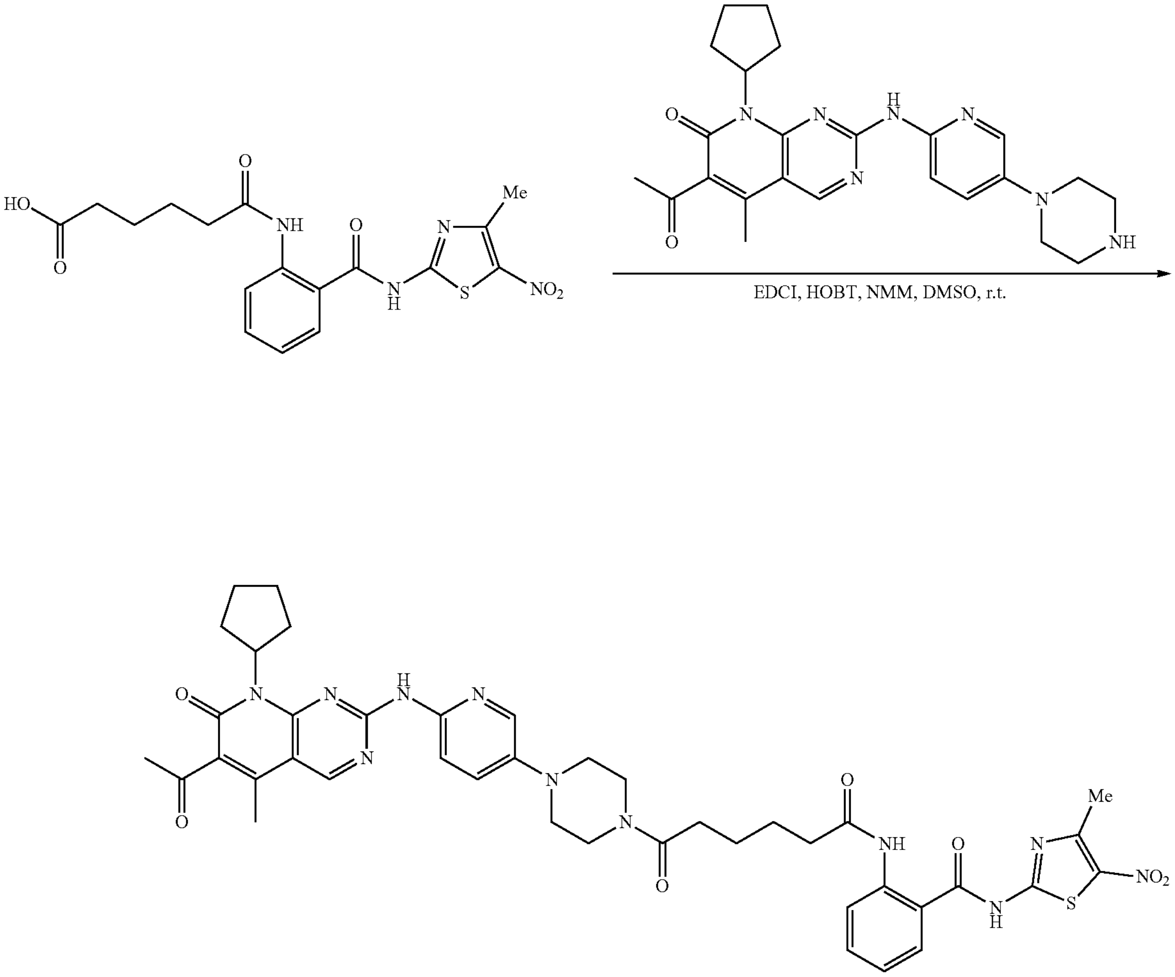
D-99 was synthesized following the standard procedure for preparing D-97 (12.7 mg, 86% yield). MS (EST) m/z: 836.4 [M+H]$^+$.

Example 264: 2-(7-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-7-oxoheptanamido)-N-(4-methyl-5-nitrothiazol-2-yl)benzamide (D-100)

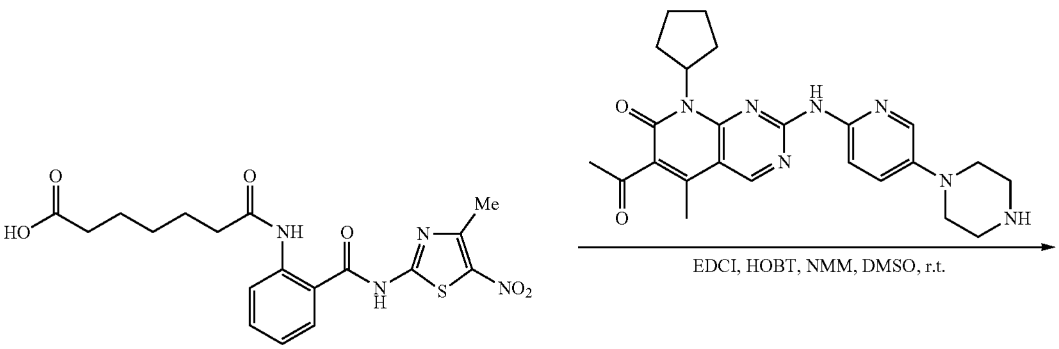

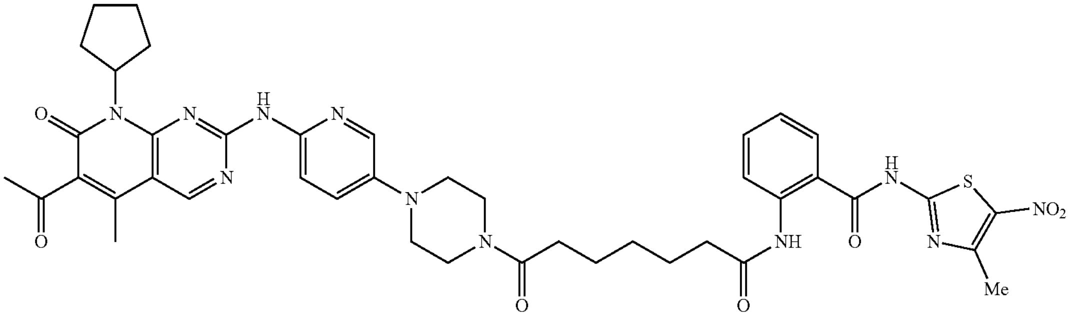

D-100 was synthesized following the standard procedure for preparing D-97 (13.1 mg, 88% yield). MS (EST) m/z: 850.5 $[M+H]^+$.

Example 265: 2-(8-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-8-oxooctanamido)-N-(4-methyl-5-nitrothiazol-2-yl)benzamide (D-101)

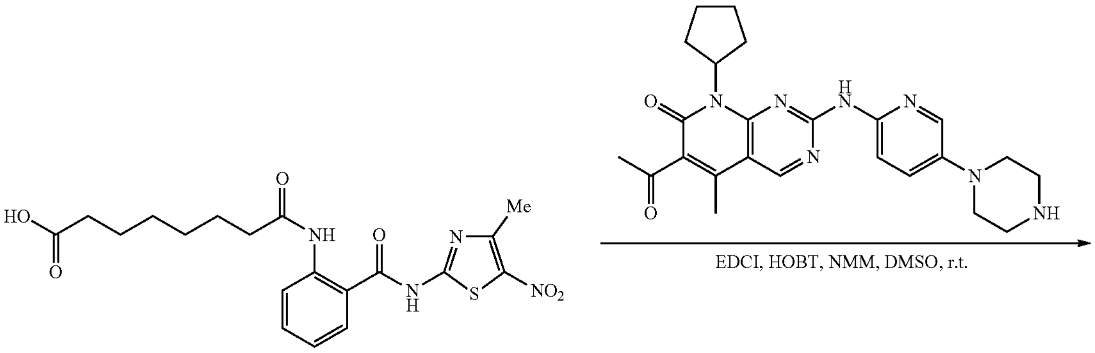

-continued
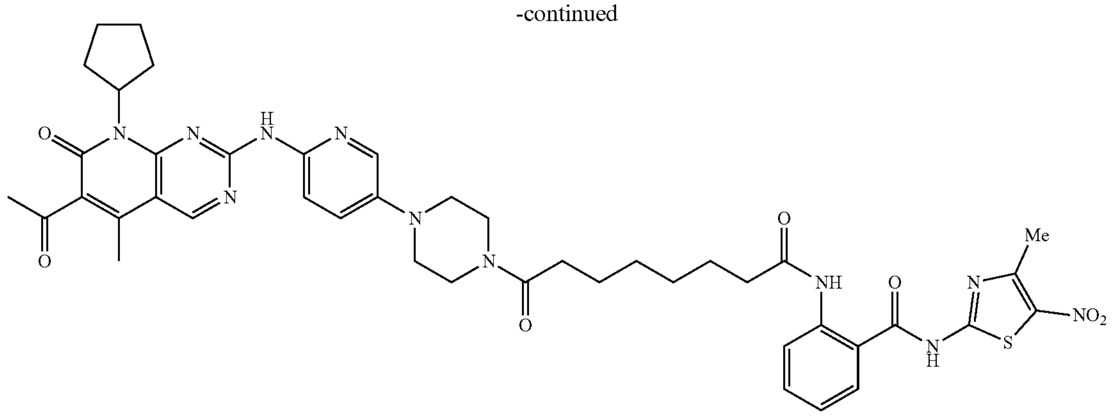
D-101 was synthesized following the standard procedure for preparing D-97 (12.3 mg, 81% yield). MS (EST) m/z: 864.5 $[M+H]^+$.
Example 266: 2-(9-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-9-oxononanamido)-N-(4-methyl-5-nitrothiazol-2-yl)benzamide (D-102)
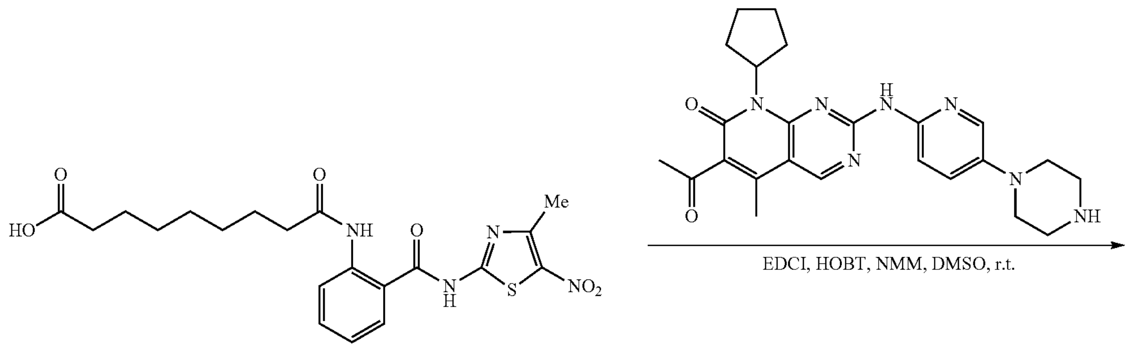
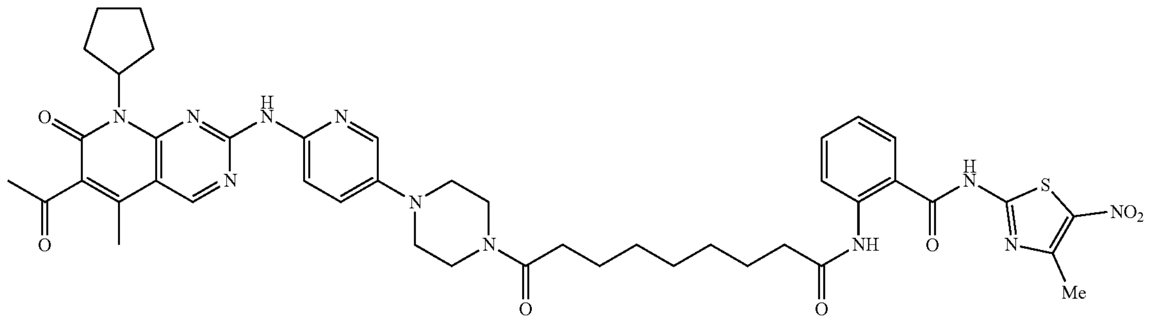
D-102 was synthesized following the standard procedure for preparing D-97 (13.7 mg, 89% yield). MS (EST) m/z: 878.5 $[M+H]^+$.

Example 267: 2-(10-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-10-oxodecanamido)-N-(4-methyl-5-nitrothiazol-2-yl) benzamide (D-103)

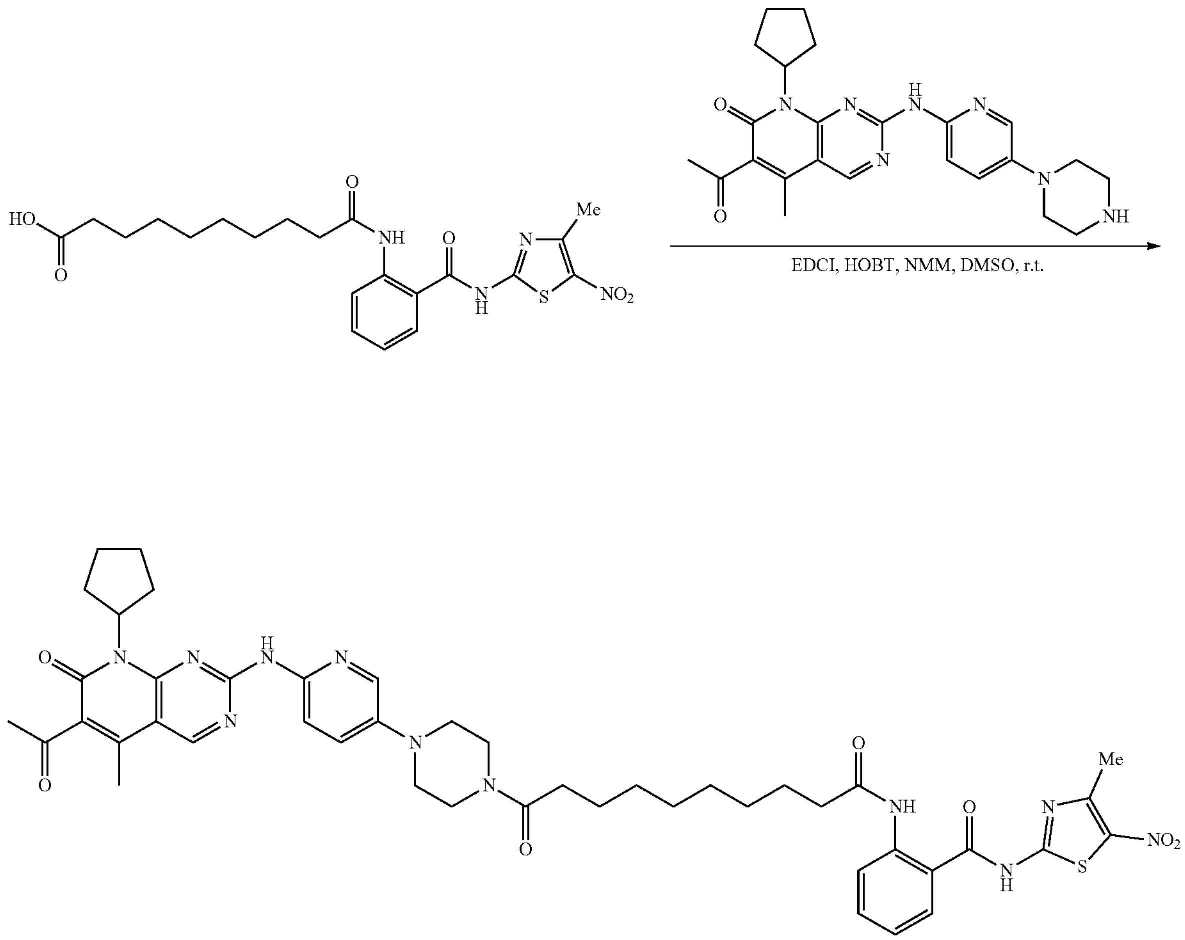

D-103 was synthesized following the standard procedure for preparing D-97 (12.4 mg, 79% yield). MS (EST) m/z: 892.5 $[M+H]^+$.

Example 268: 2-(11-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-11-oxoundecanamido)-N-(4-methyl-5-nitrothiazol-2-yl) benzamide (D-104)

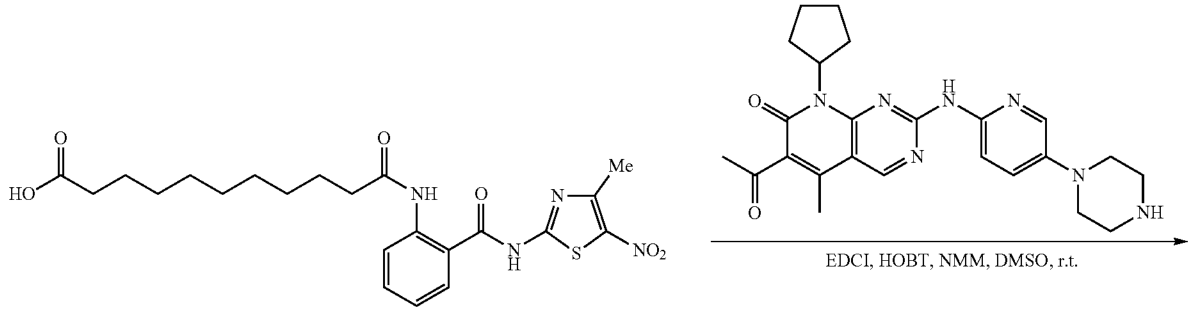

-continued
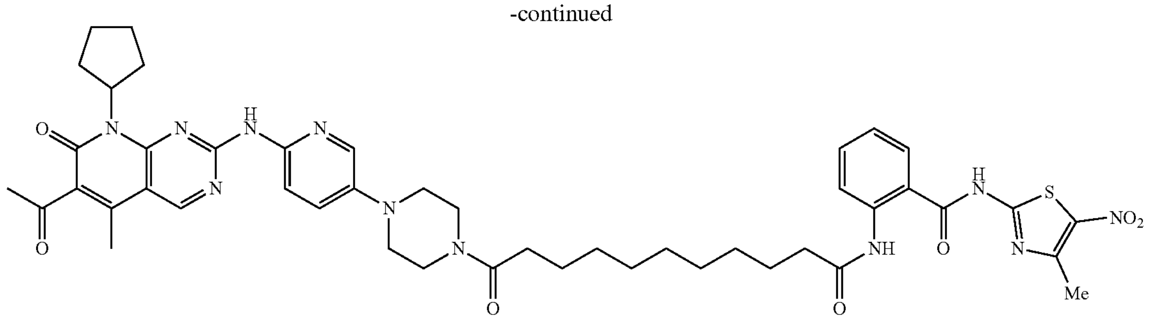
D-104 was synthesized following the standard procedure for preparing D-97 (13.1 mg, 82% yield). MS (EST) m/z: 906.6 [M+H]$^+$.
Example 269: 2-(12-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-12-oxododccanamido)-N-(4-methyl-5-nitrothiazol-2-yl) benzamide (D-105)
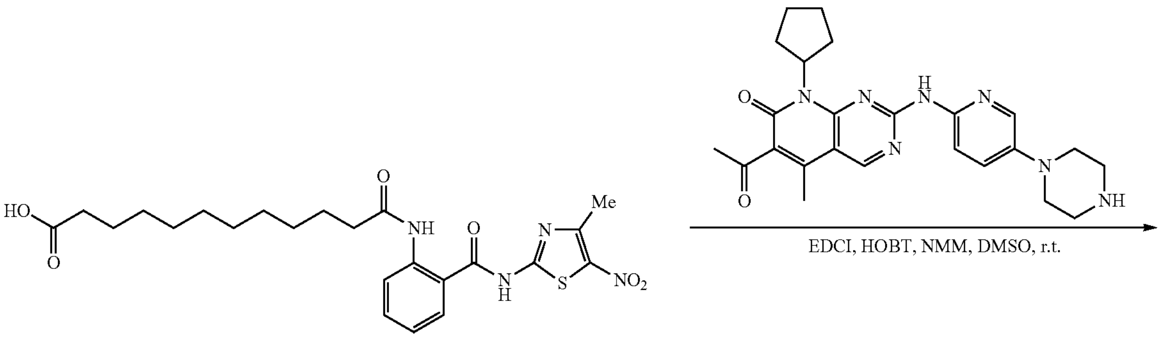
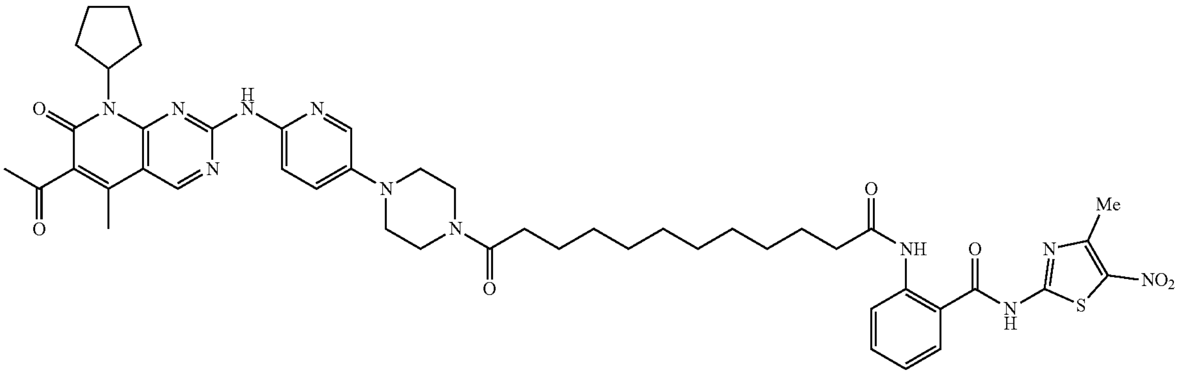
D-105 was synthesized following the standard procedure for preparing D-97 (13.8 mg, 85% yield). MS (EST) m/z: 920.6 [M+H]$^+$.

Example 270: 2-(13-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-13-oxotridecanamido)-N-(4-methyl-5-nitrothiazol-2-yl)benzamide (D-106)

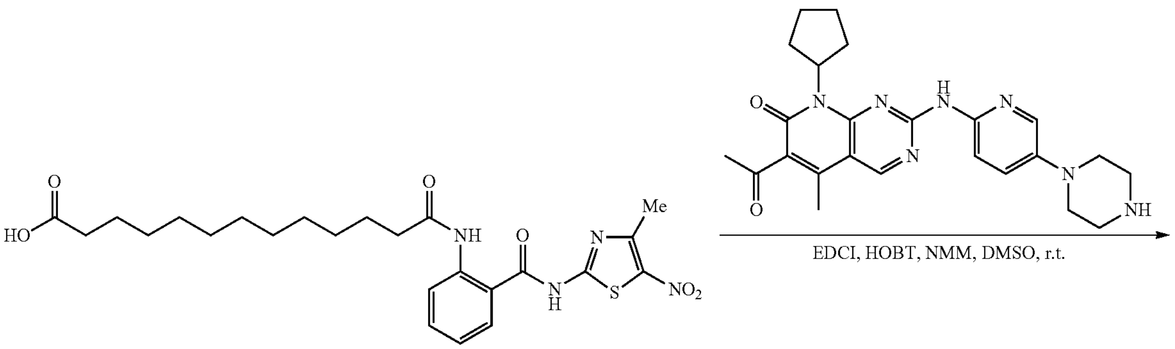

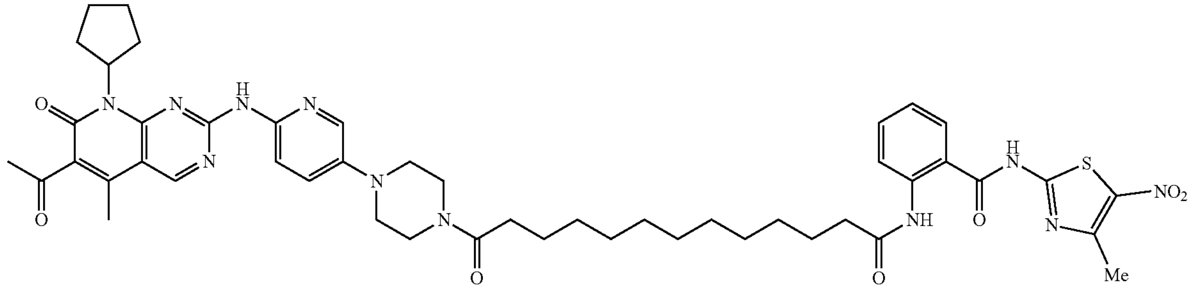

D-106 was synthesized following the standard procedure for preparing D-97 (12.6 mg, 77% yield). MS (EST) m/z: 934.6 $[M+H]^+$.

Example 271: 2-(3-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)propanamido)-N-(4-methyl-5-nitrothiazol-2-yl)benzamide (D-107)

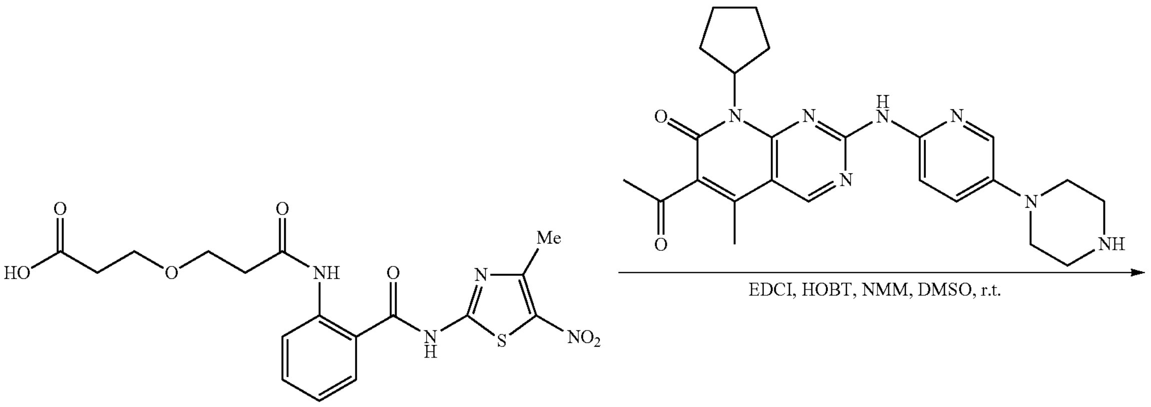

-continued

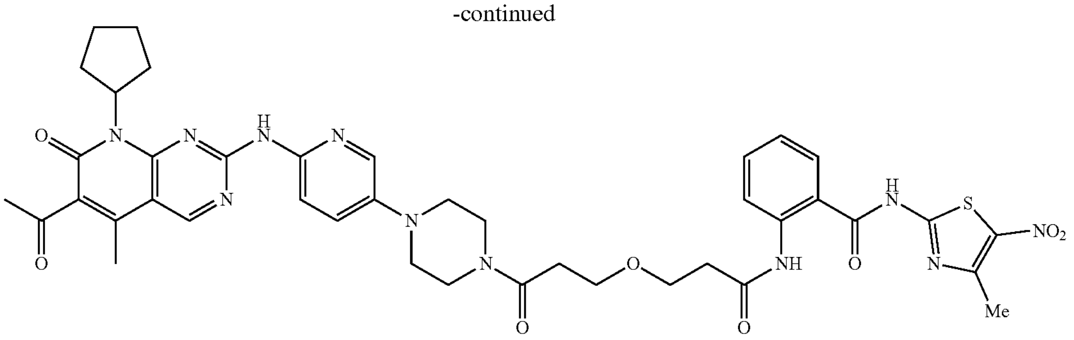

D-107 was synthesized following the standard procedure for preparing D-97 (5.8 mg, 68% yield). MS (EST) m/z: 852.4 $[M+H]^+$.

Example 272: 2-(3-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)propanamido)-N-(4-methyl-5-nitrothiazol-2-yl)benzamide (D-108)

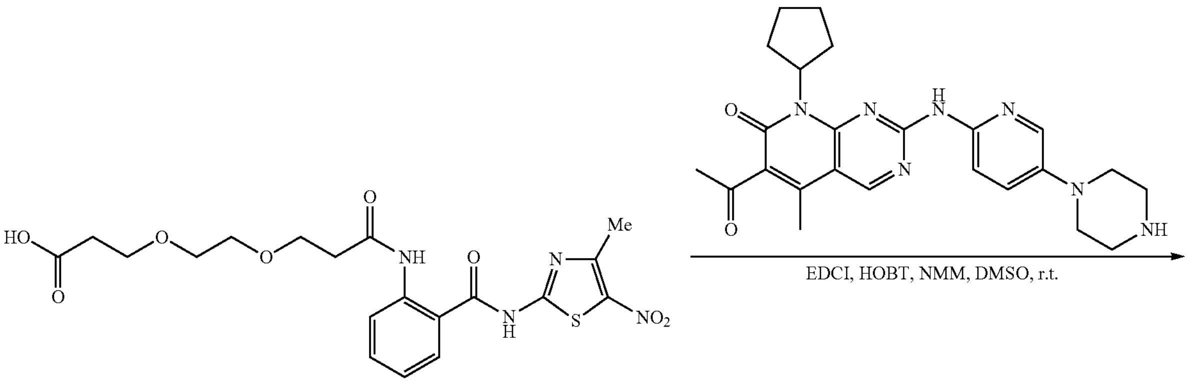

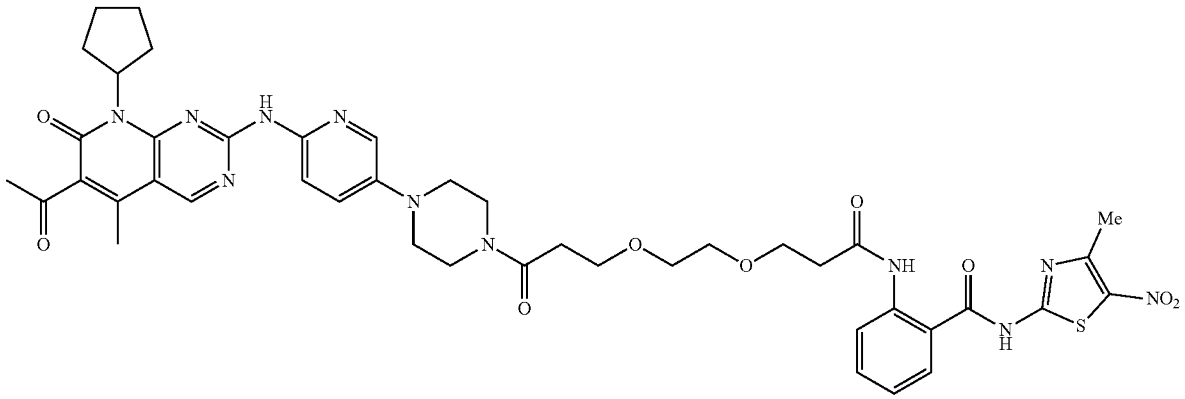

D-108 was synthesized following the standard procedure for preparing D-97 (6.9 mg, 77% yield). MS (EST) m/z: 896.4 $[M+H]^+$.

Example 273: 2-(3-(2-(2-(3-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-3-oxopropoxy)ethoxy)ethoxy)propanamido)-N-(4-methyl-5-nitrothiazol-2-yl)benzamide (D-109)

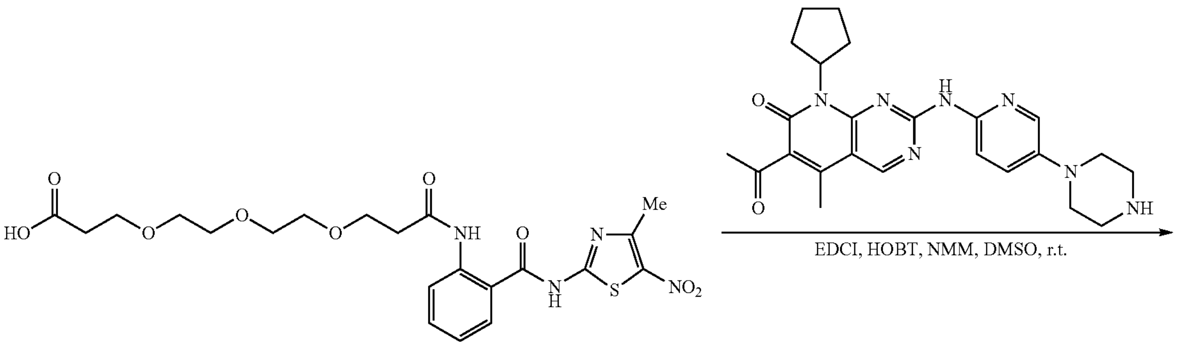

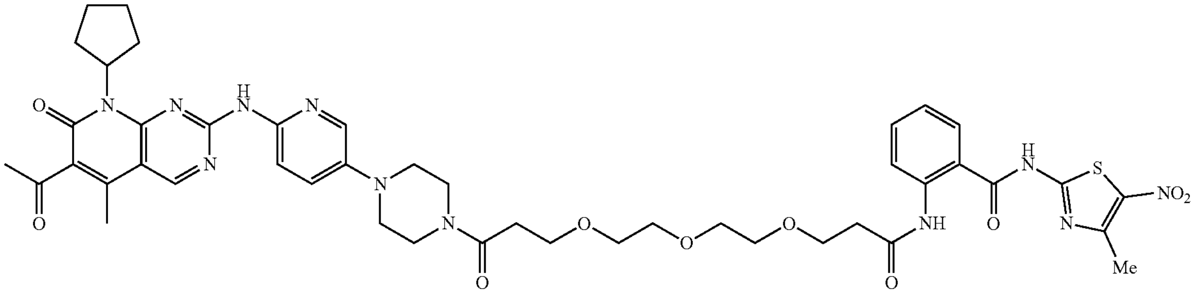

D-109 was synthesized following the standard procedure for preparing D-97 (5.3 mg, 57% yield). MS (ESI) m/z: 940.5 $[M+H]^+$.

Example 274: 16-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-N-(2-((4-methyl-5-nitrothiazol-2-yl)carbamoyl)phenyl)-16-oxo-4,7,10,13-tetraoxahexadecanamide (D-110)

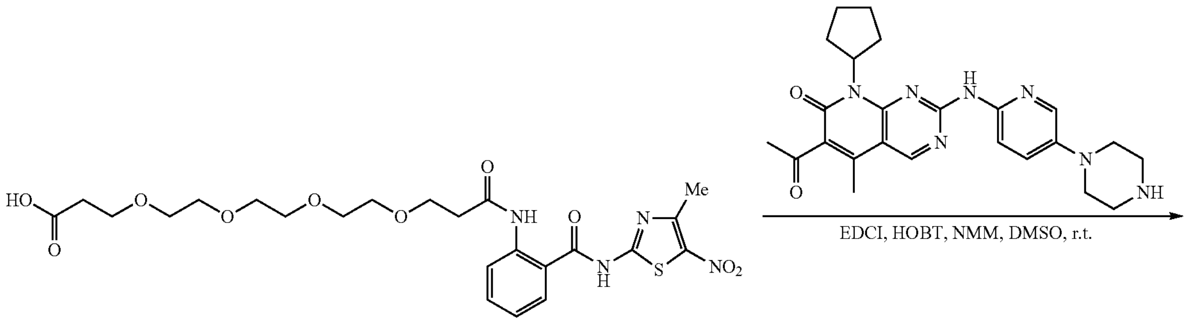

-continued

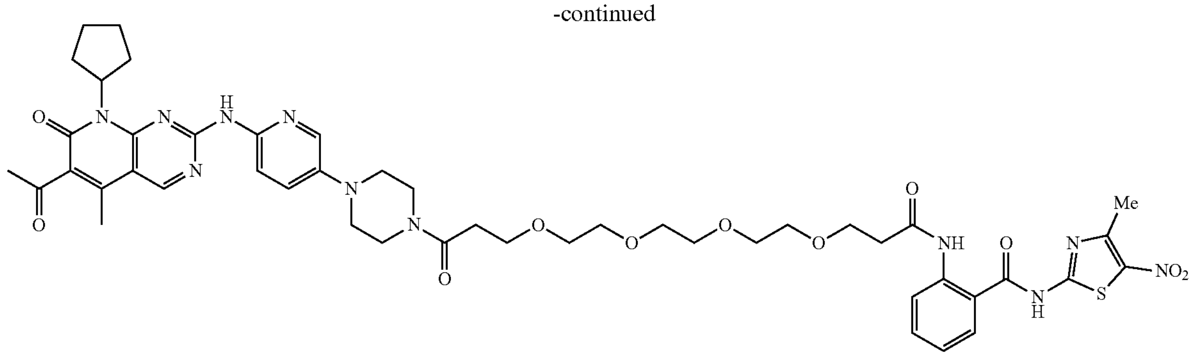

D-110 was synthesized following the standard procedure for preparing D-97 (5.3 mg, 57% yield). MS (EST) m/z: 984.5 [M+H]$^+$.

Example 275: 19-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-N-(2-((4-methyl-5-nitrothiazol-2-yl)carbamoyl)phenyl)-19-oxo-4,7,10,13,16-pentaoxanonadecanamide (D-111)

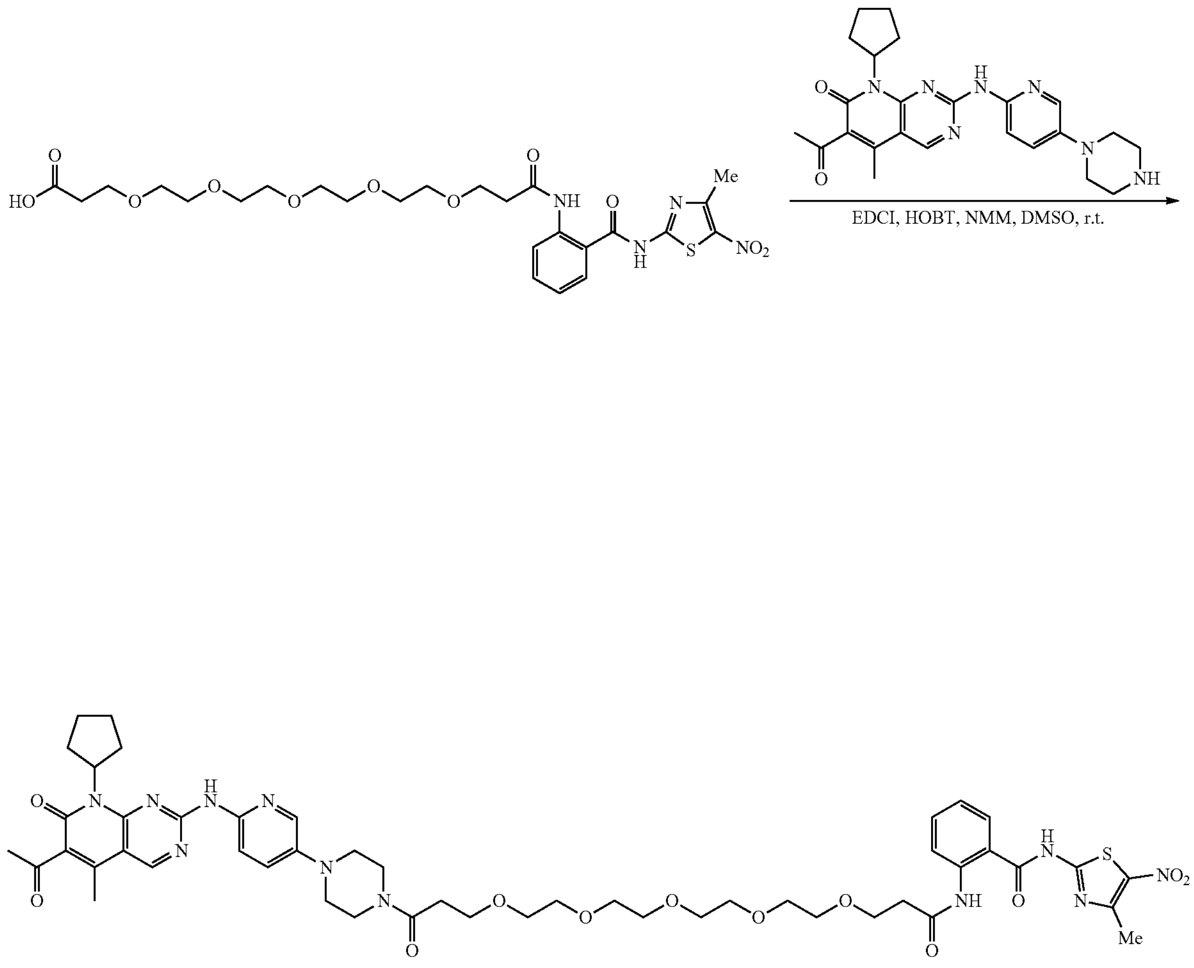

D-111 was synthesized following the standard procedure for preparing D-97 (4.3 mg, 42% yield). MS (EST) m/z: 1028.5 [M+H]$^+$.

Example 276: 2-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)acetamido)-N-(4-methyl-5-nitrothiazol-2-yl)benzamide (D-112)

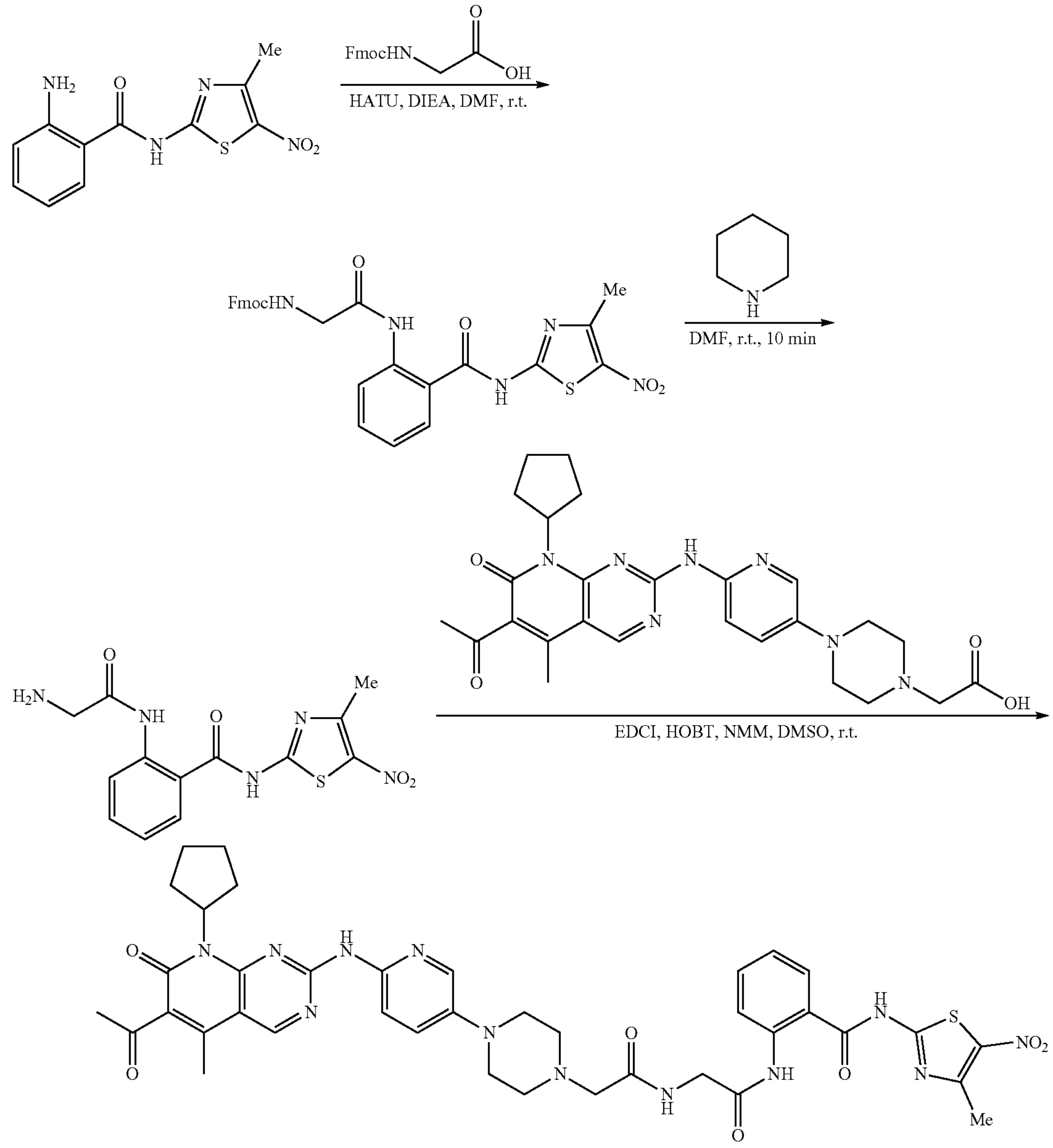

Step 1. Synthesis of (9H-fluoren-9-yl)methyl (2-((2-((4-methyl-5-nitrothiazol-2-yl)carbamoyl)phenyl)amino)-2-oxoethyl)carbamate

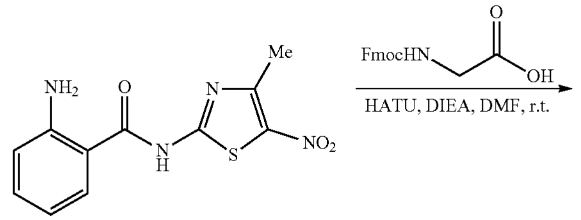

-continued

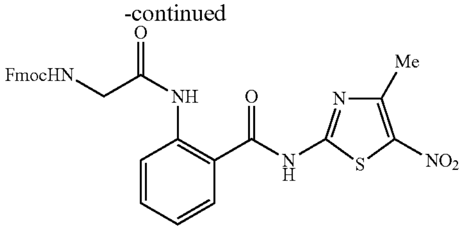

A solution of (((9H-fluoren-9-yl)methoxy)carbonyl)glycine (427 mg, 1.43 mmol), 2-amino-N-(4-methyl-5-nitrothiazol-2-yl)benzamide (400 mg, 1.43 mmol), HATU (815 mg, 2.15 mmol) and DIEA (553 mg, 4.29 mmol) in DMF (10 mL) was stirred at room temperature overnight. Then, the mixture was poured into water (100 mL) and acidified to pH=6 by 1N HCl, before being extracted with EtOAc (3×50 mL). The combined organic layers were washed with brine (2×100 mL), dried over $Na_2SO_4$, filtered and concentrated in vacuum to give the crude desired product (500 mg), which was used directly for next step without further purification. MS (ESI) m/z: 556.0 $[M-H]^-$.

Step 2. Synthesis of 2-(2-aminoacetamido)-N-(4-methyl-5-nitrothiazol-2-yl)benzamide

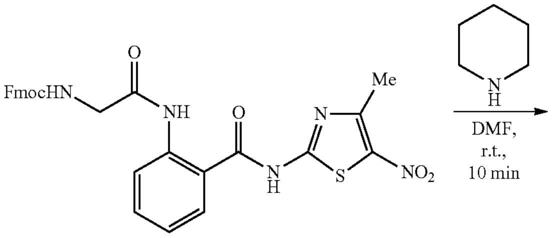

-continued

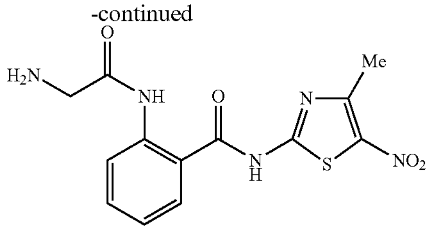

A solution of (9H-fluoren-9-yl)methyl (2-((2-((4-methyl-5-nitrothiazol-2-yl)carbamoyl)phenyl)amino)-2-oxoethyl) carbamate (500 mg, crude) and piperidine (1 mL) in DMF (3 mL) was stirred at room temperature for 10 min. Then, the mixture was purified by prep-HPLC to give the title compound (100 mg, 21% yield over two steps) as a yellow formic acid salt. $^1H$ NMR (400 MHz, DMSO-$d_6$): δ 14.4 (brs, 1H), 8.67 (brs, 2H), 8.50 (d, J=8.0 Hz, 1H), 8.24 (dd, J=8.0, 1.6 Hz, 1H), 7.50-7.46 (m, 1H), 7.18-7.14 (m, 1H), 3.91 (s, 2H), 2.63 (s, 3H). MS (ESI) m/z: 336.1 $[M+H]^+$.

Step 3. Synthesis of 2-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)acetamido)-N-(4-methyl-5-nitrothiazol-2-yl)benzamide

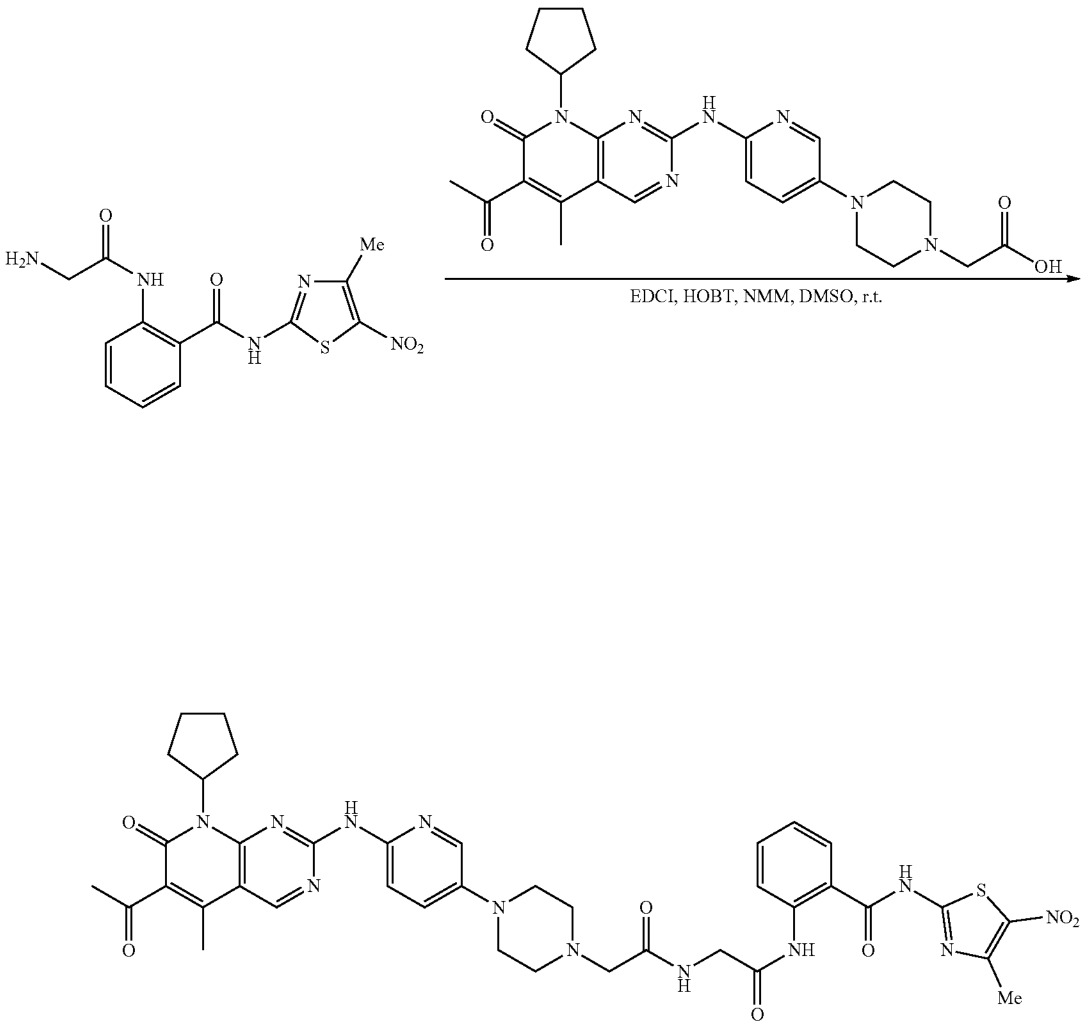

To a solution of 2-(2-aminoacetamido)-N-(4-methyl-5-nitrothiazol-2-yl)benzamide (6.1 mg, 0.018 mmol) and 2-(4-(6-((6-acetyl-8-cyclopentyl-5-methyl-7-oxo-7,8-dihydro-pyrido[2,3-d]pyrimidin-2-yl)amino)pyridin-3-yl)piperazin-1-yl)acetic acid (9.1 mg, 0.018 mmol) in DMSO (1 mL) were added EDCI (6.9 mg, 0.036 mmol), HOBT (5.5 mg, 0.036 mmol) and NMM (10 μL, 0.09 mmol). Then the reaction mixture was stirred at room temperature overnight. The resulting mixture was purified by prep-HPLC to give the title compound (10 mg, 62% yield) as white solid. MS (ESI) m/z: 823.4 $[M+H]^+$.

Example 277: 2-(3-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)propanamido)-N-(4-methyl-5-nitrothiazol-2-yl)benzamide (D-113)

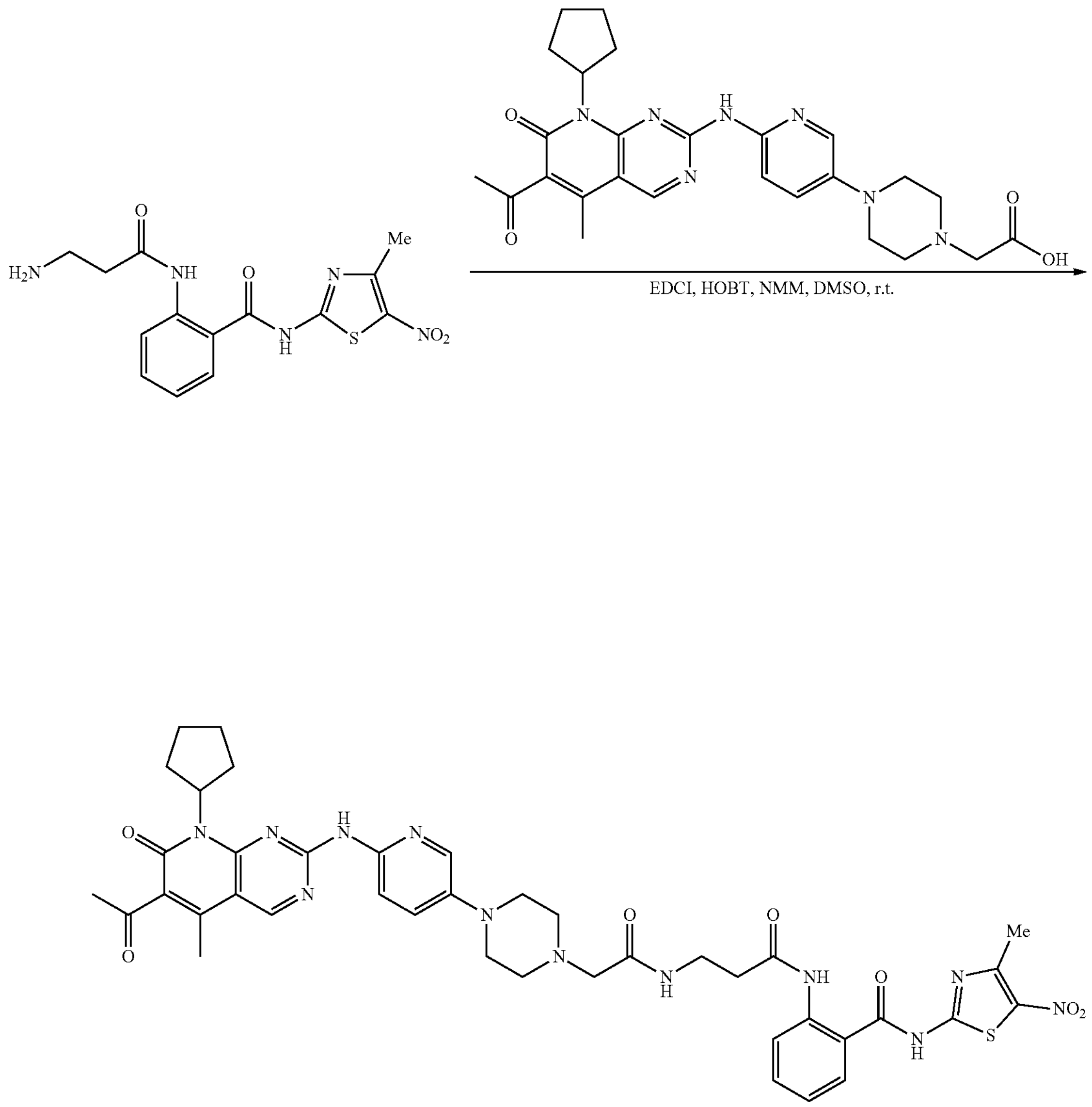

D-113 was synthesized following the standard procedure for preparing D-112 (5 mg, 27% yield). MS (EST) m/z: 837.4 $[M+H]^+$.

Example 278: 2-(4-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)butanamido)-N-(4-methyl-5-nitrothiazol-2-yl)benzamide (D-114)

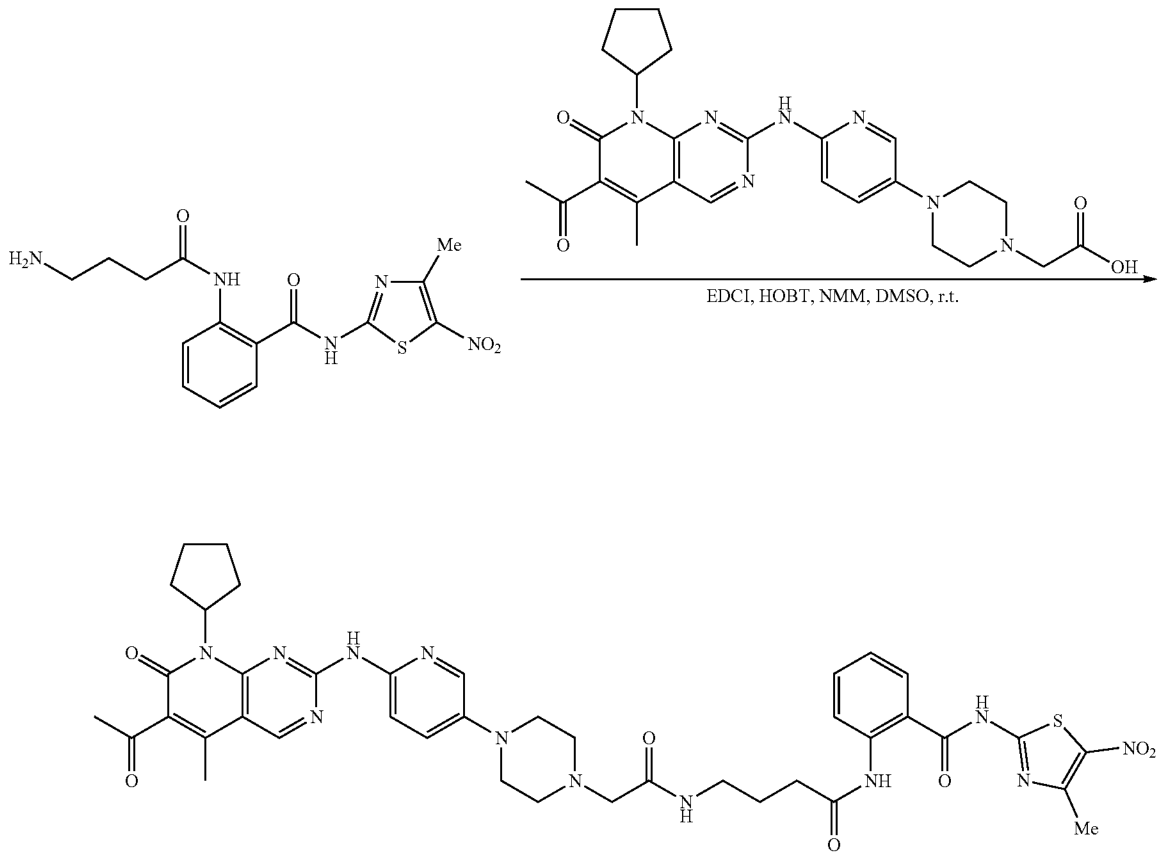

D-114 was synthesized following the standard procedure for preparing D-112 (12 mg, 69% yield). MS (EST) m/z: 851.4 [M+H]$^+$.

Example 279: 2-(5-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)pentanamido)-N-(4-methyl-5-nitrothiazol-2-yl)benzamide (D-115)

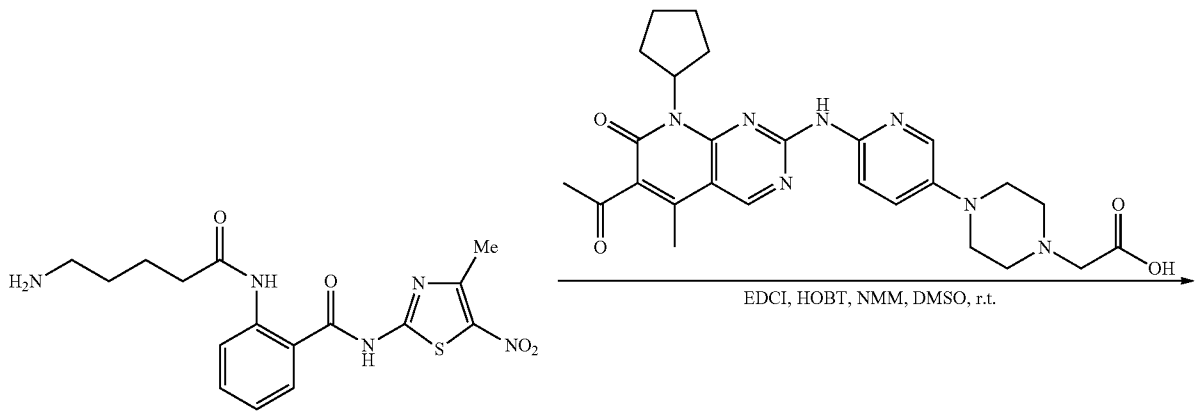

-continued

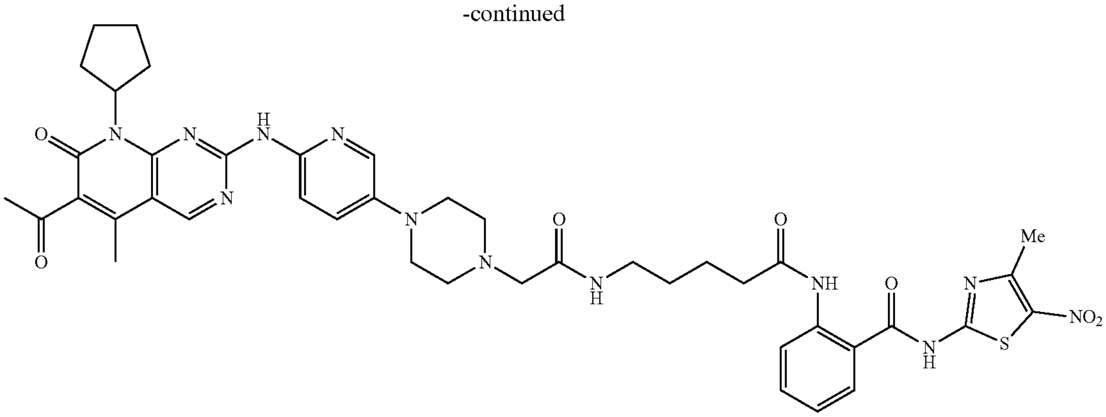

D-115 was synthesized following the standard procedure for preparing D-112 (8 mg, 44% yield). MS (EST) m/z: 865.4 [M+H]$^+$.

Example 280: 2-(6-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)hexanamido)-N-(4-methyl-5-nitrothiazol-2-yl)benzamide (D-116)

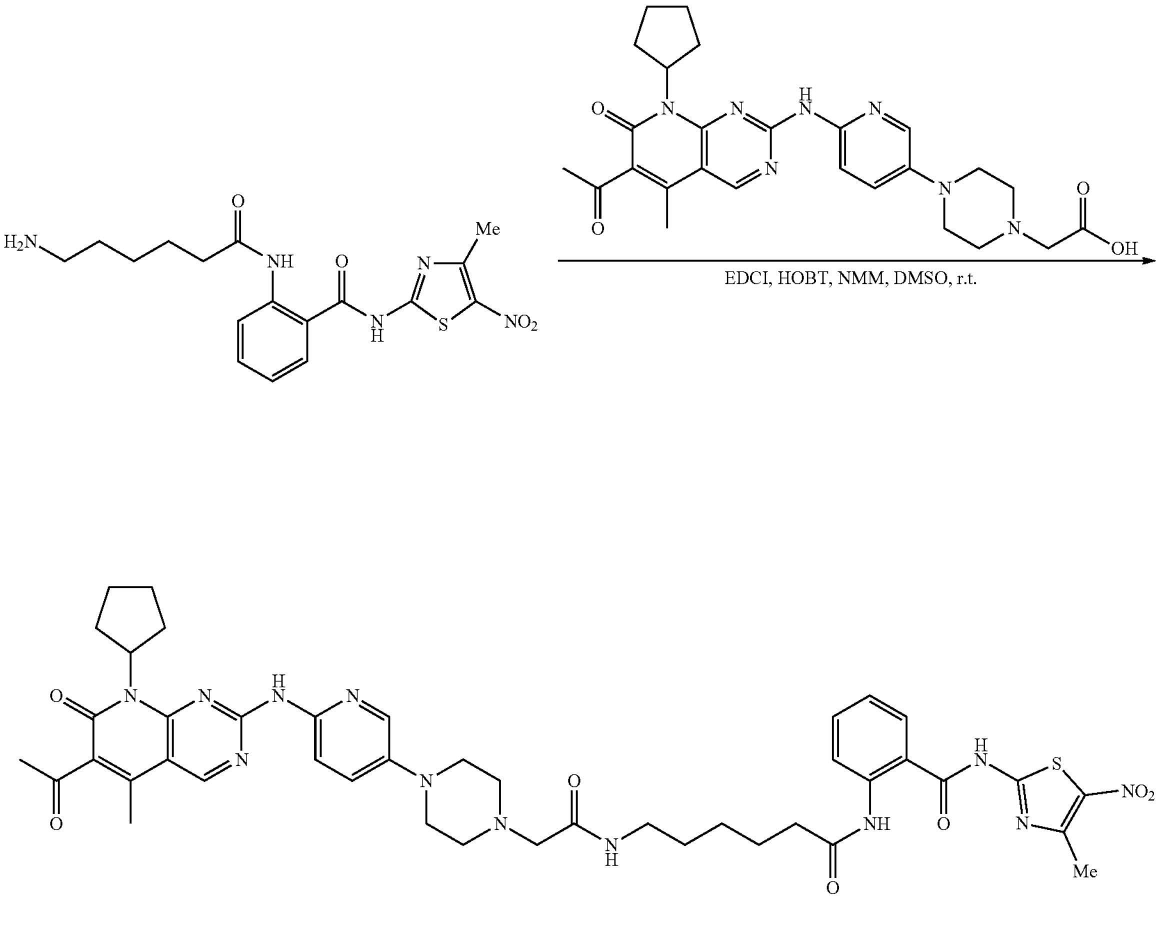

D-116 was synthesized following the standard procedure for preparing D-112 (10 mg, 56% yield). MS (EST) m/z: 879.5 [M+H]$^+$.

Example 281: 2-(7-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)heptanamido)-N-(4-methyl-5-nitrothiazol-2-yl)benzamide (D-117)

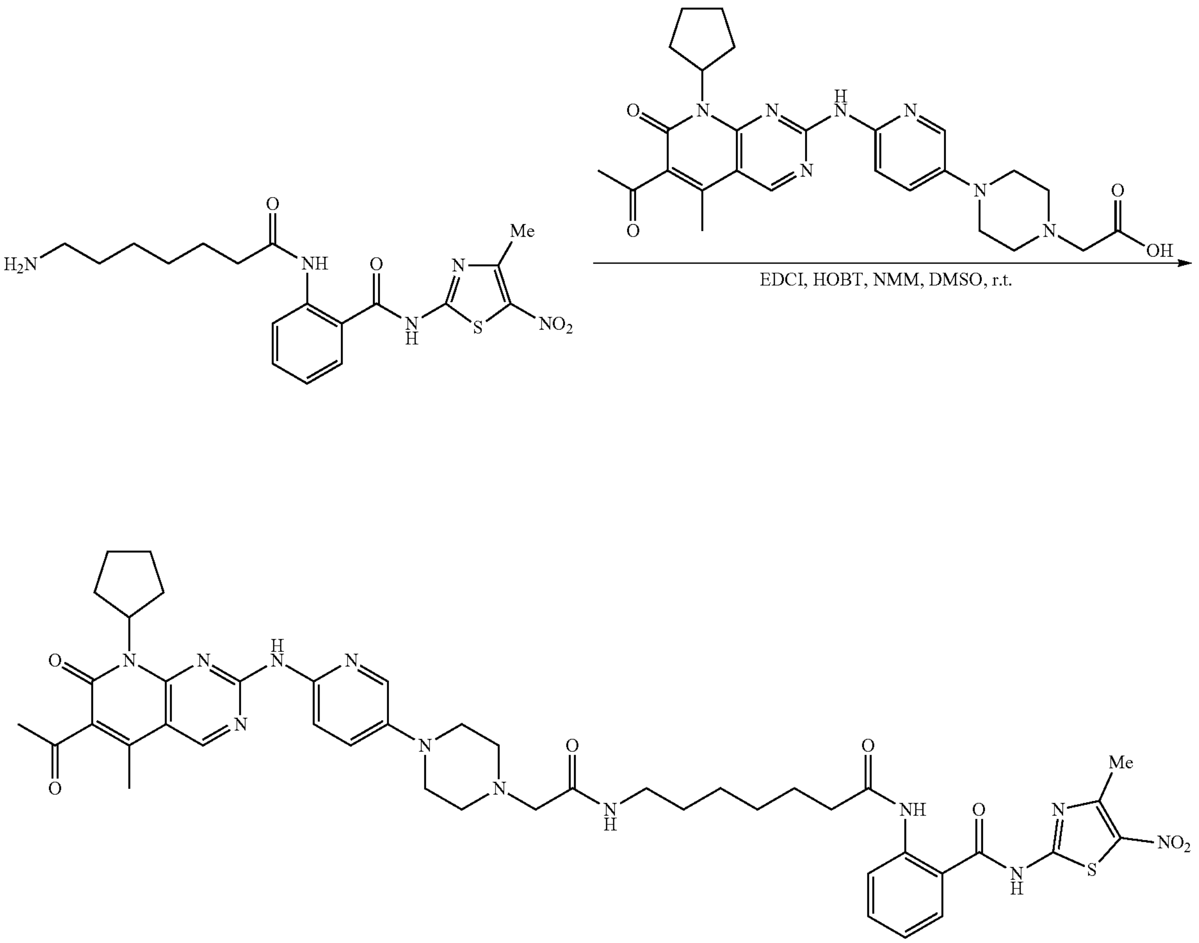

D-117 was synthesized following the standard procedure for preparing D-112 (8 mg, 43% yield). MS (EST) m/z: 893.5 $[M+H]^+$.

Example 282: 2-(8-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)octanamido)-N-(4-methyl-5-nitrothiazol-2-yl)benzamide (D-118)

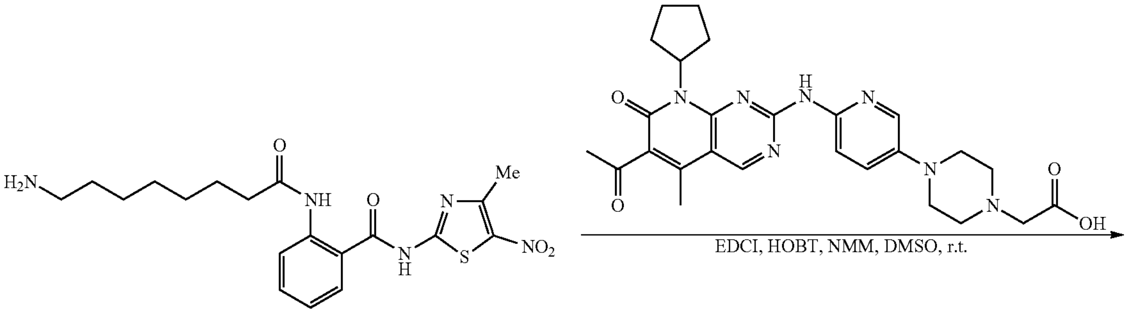

-continued
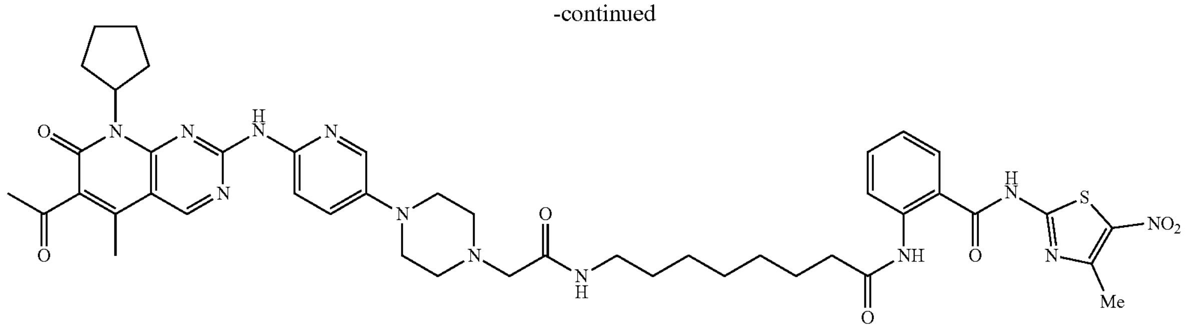
D-118 was synthesized following the standard procedure for preparing D-112 (7 mg, 39% yield). MS (EST) m/z: 907.5 [M+H]+.
Example 283: 2-(9-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)nonanamido)-N-(4-methyl-5-nitrothiazol-2-yl)benzamide (D-119)
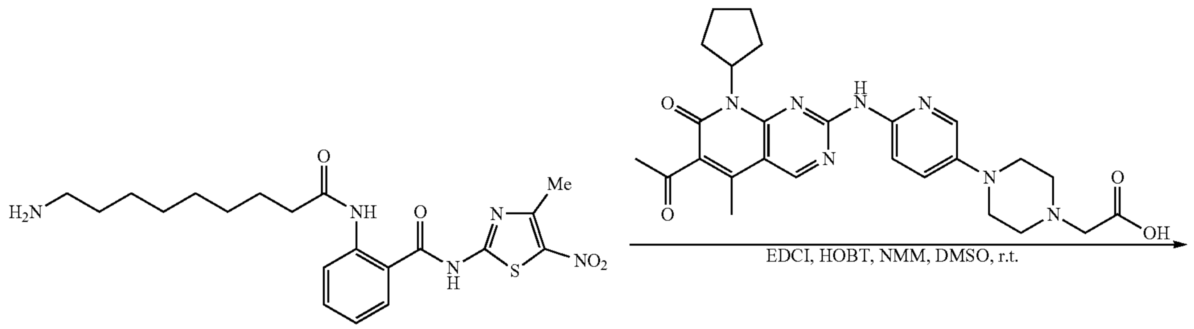
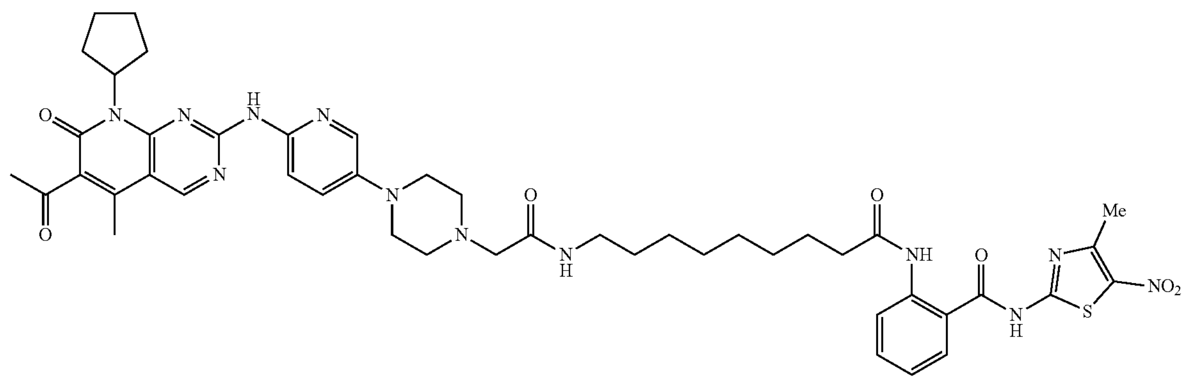
D-119 was synthesized following the standard procedure for preparing D-112 (11 mg, 63% yield). MS (EST) m/z: 921.6 [M+H]+.

Example 284: 2-(10-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)decanamido)-N-(4-methyl-5-nitrothiazol-2-yl)benzamide (D-120)

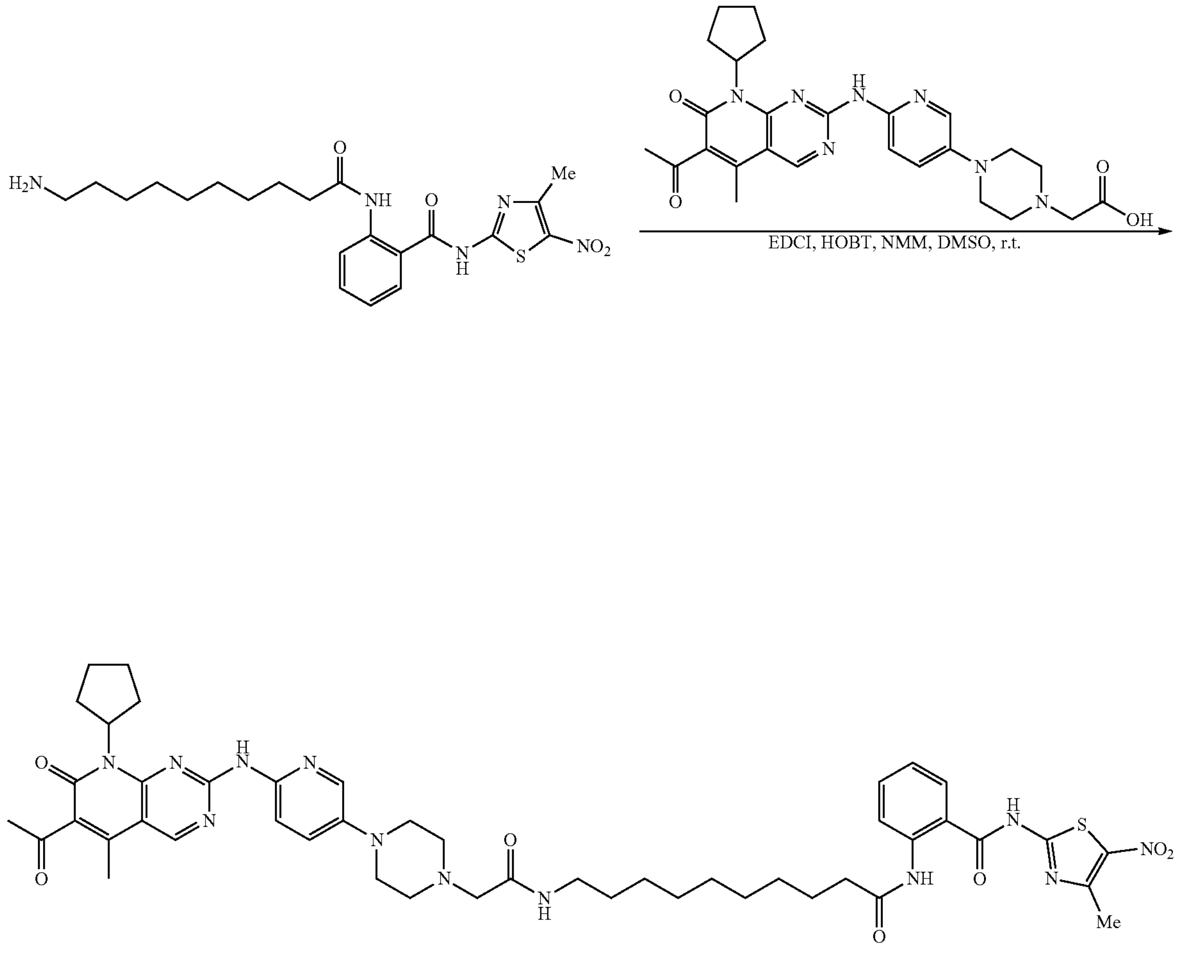

D-120 was synthesized following the standard procedure for preparing D-112 (10 mg, 57% yield). MS (EST) m/z: 935.6 $[M+H]^+$.

Example 285: 2-(11-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)undecanamido)-N-(4-methyl-5-nitrothiazol-2-yl)benzamide (D-121)

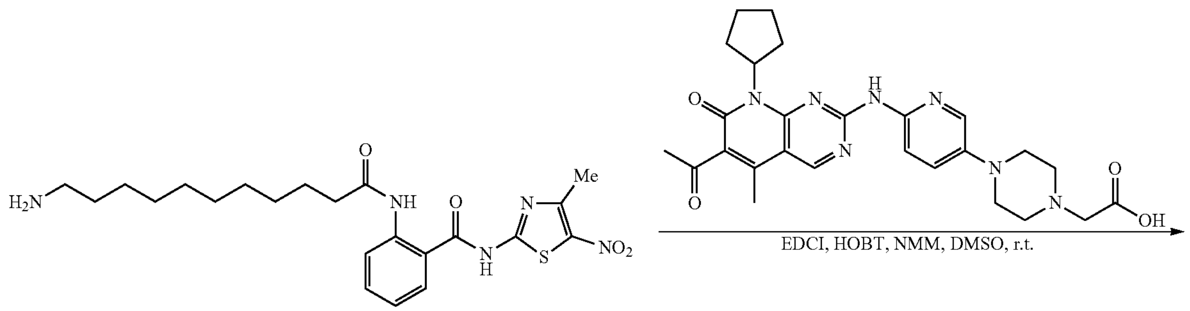

-continued
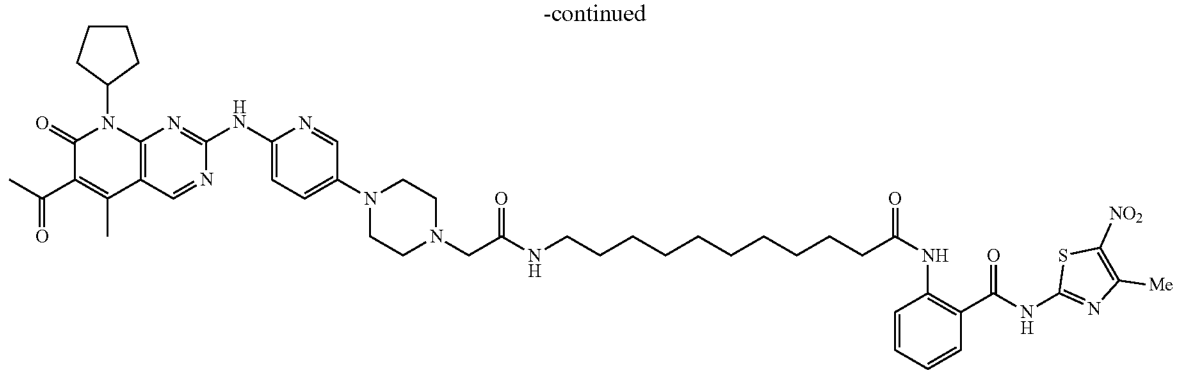
D-121 was synthesized following the standard procedure for preparing D-112 (11 mg, 58% yield). MS (EST) m/z: 949.6 [M+H]+.
Example 286: 2-(3-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)ethoxy)propanamido)-N-(4-methyl-5-nitrothiazol-2-yl)benzamide (D-122)
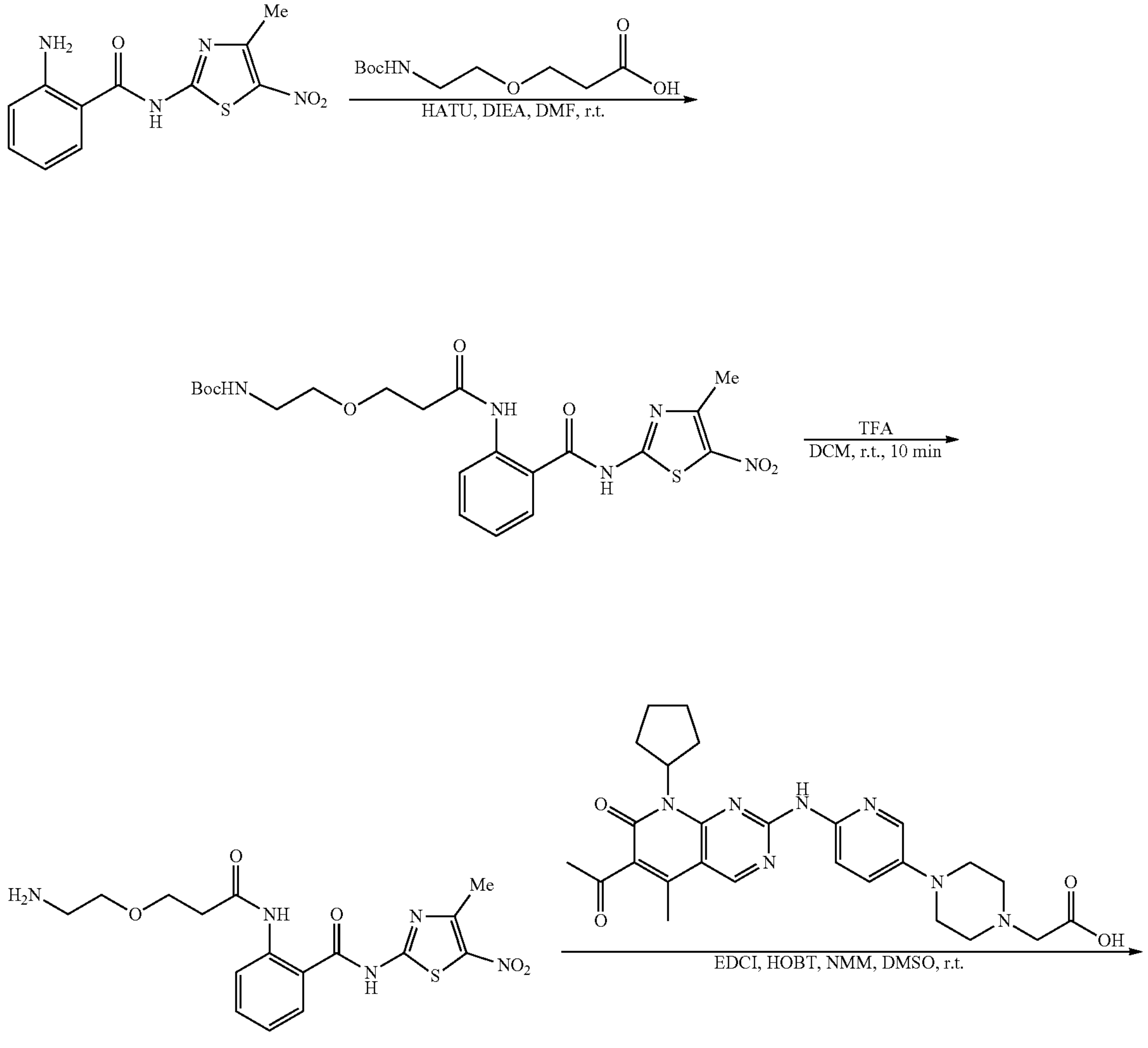

-continued

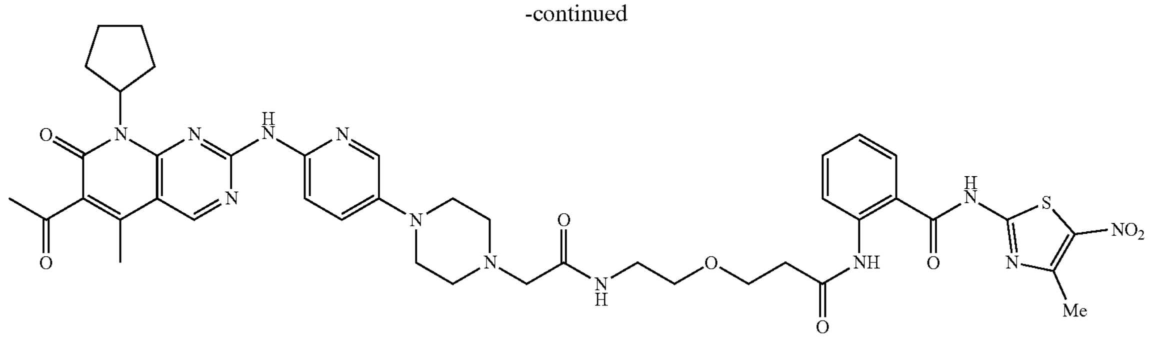

D-122 was synthesized following the standard procedure for preparing D-112 (2.7 mg, 31% yield). MS (EST) m/z: 881.4 [M+H]+.

Example 287: 2-(3-(2-(2-(2-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)acetamido)ethoxy)ethoxy)propanamido)-N-(4-methyl-5-nitrothiazol-2-yl)benzamide (D-123)

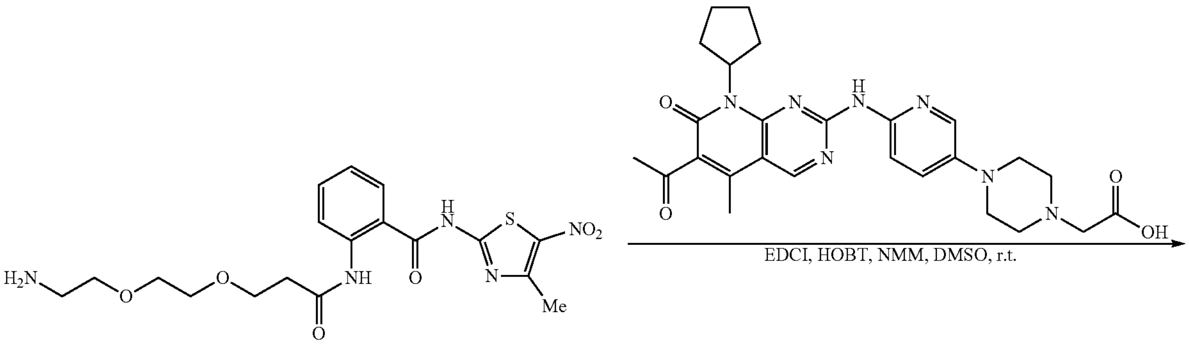

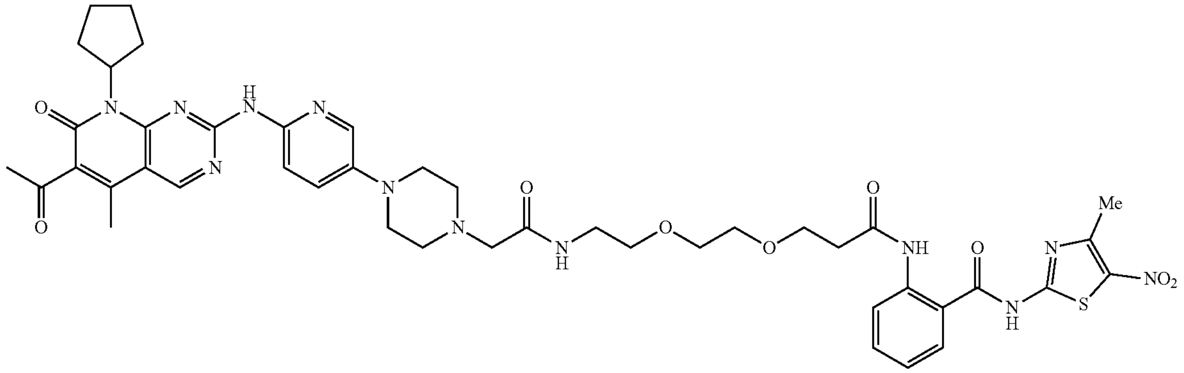

D-123 was synthesized following the standard procedure for preparing D-112 (5.7 mg, 62% yield). MS (EST) m/z: 925.5 [M+H]+.

Example 288: 2-(1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12-trioxa-3-azapentadecan-15-amido)-N-(4-methyl-5-nitrothiazol-2-yl)benzamide (D-124)

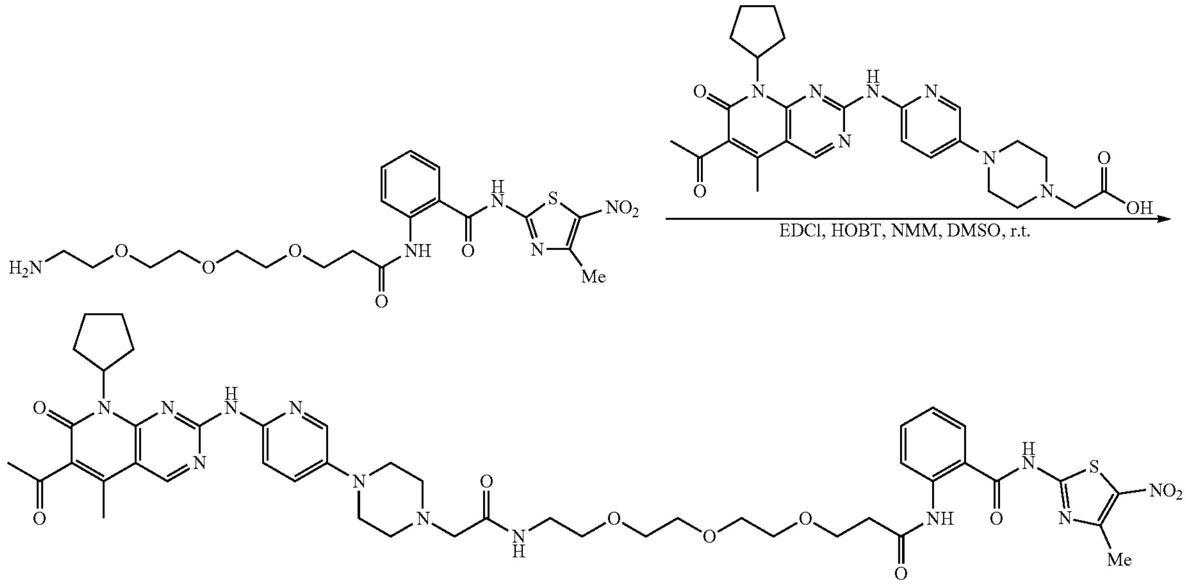

D-124 was synthesized following the standard procedure for preparing D-112 (4.3 mg, 45% yield). MS (EST) m/z: 969.5 [M+H]+.

Example 289: 2-(1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15-tetraoxa-3-azaoctadecan-18-amido)-N-(4-methyl-5-nitrothiazol-2-yl)benzamide (D-125)

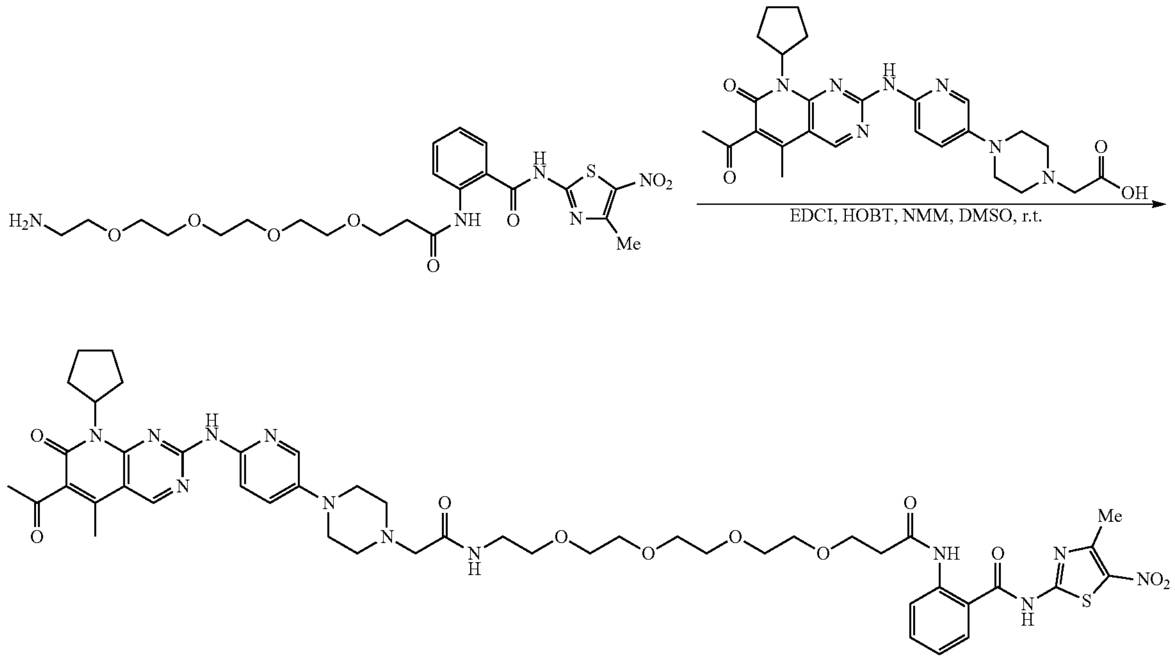

D-125 was synthesized following the standard procedure for preparing D-112 (5.2 mg, 51% yield). MS (EST) m/z: 1013.5 $[M+H]^+$.

Example 290: 2-(1-(4-(6-((6-acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15,18-pentaoxa-3-azahenicosan-21-amido)-N-(4-methyl-5-nitrothiazol-2-yl)benzamide (D-126)

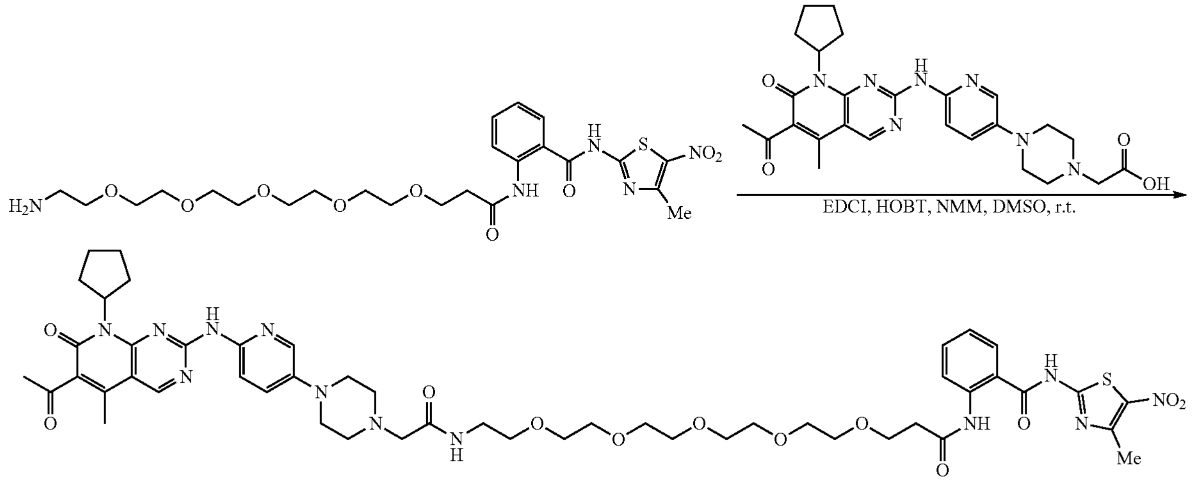

D-126 was synthesized following the standard procedure for preparing D-112 (4.8 mg, 46% yield). MS (EST) m/z: 1057.5 $[M+H]^+$.

Example 291. 4-((2-(2-(2-(2-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)acetamido)ethoxy)ethoxy)ethyl)amino)-2-methyl-N-(5-nitrothiazol-2-yl)benzamide (D-127)

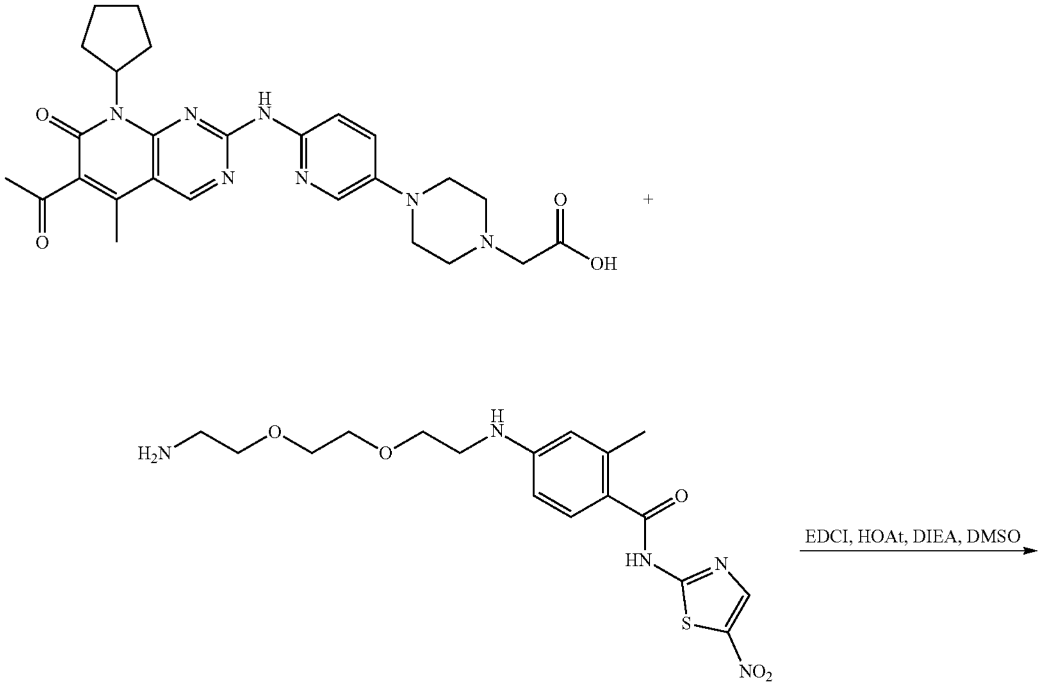

-continued
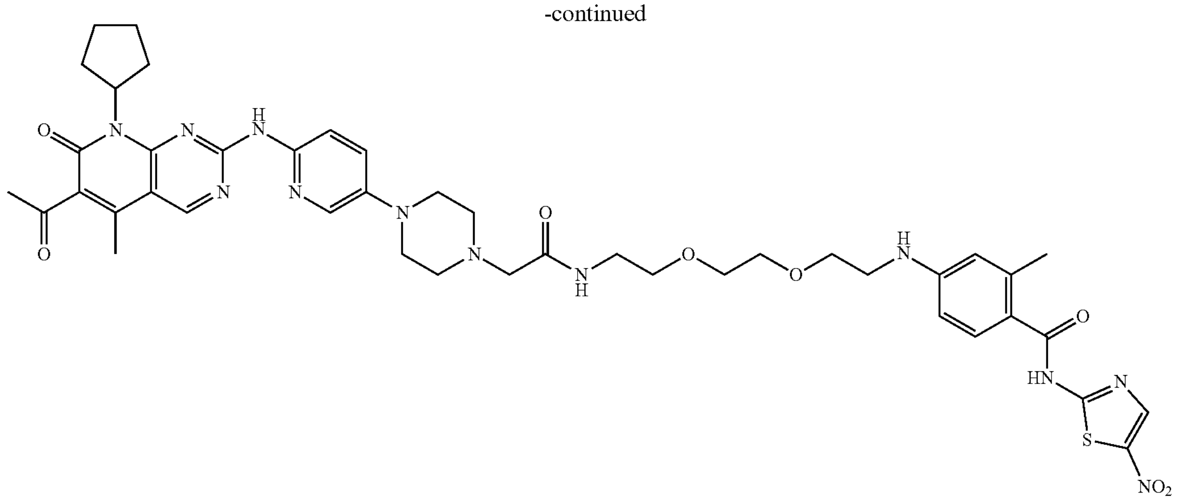
D-127 was synthesized following the same procedure as D-93. (2.29 mg, yield: 25.6%). MS (ESI) m/z: 897.8 $[M+H]^+$.
Example 292. 4-((1-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15-tetraoxa-3-azaheptadecan-17-yl)amino)-2-methyl-N-(5-nitrothiazol-2-yl)benzamide (D-128)
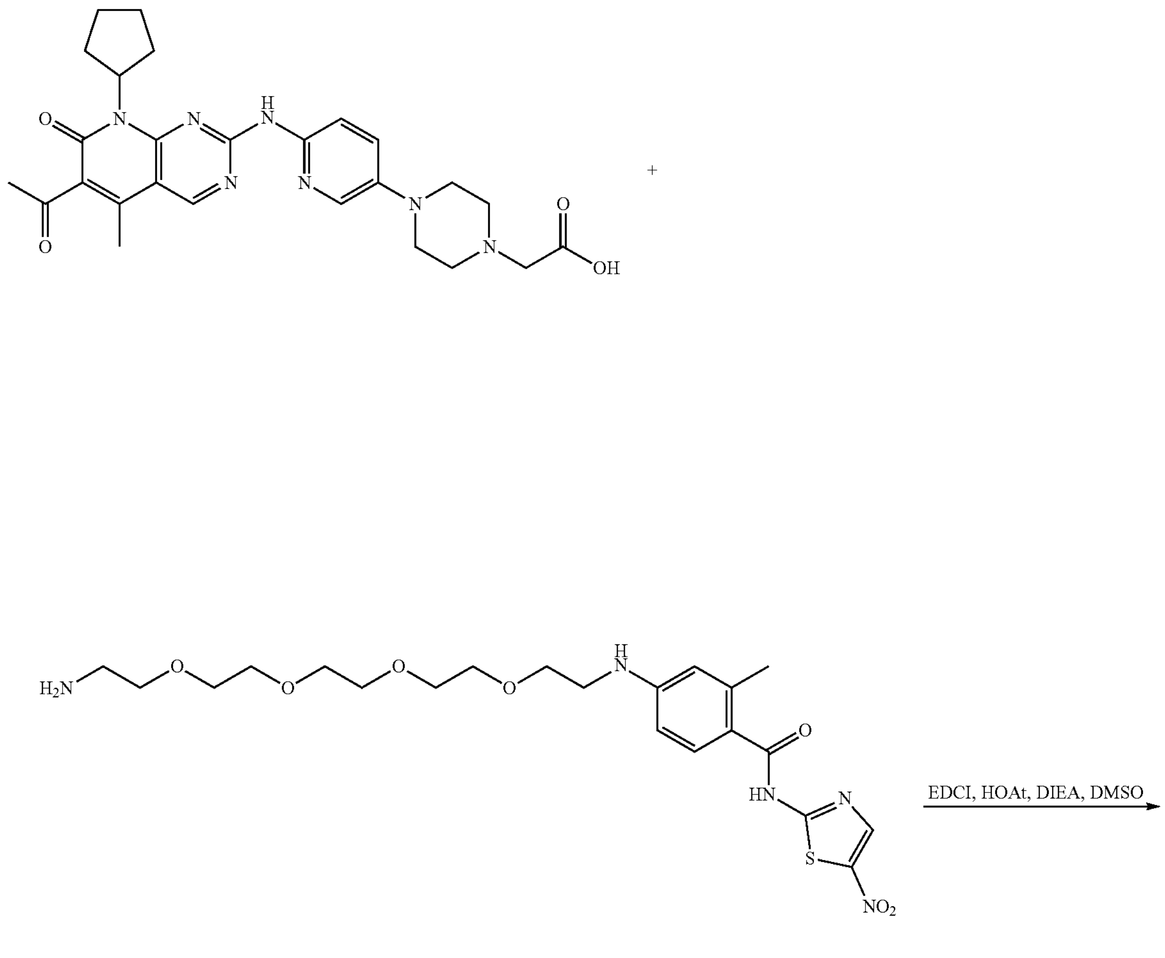

-continued
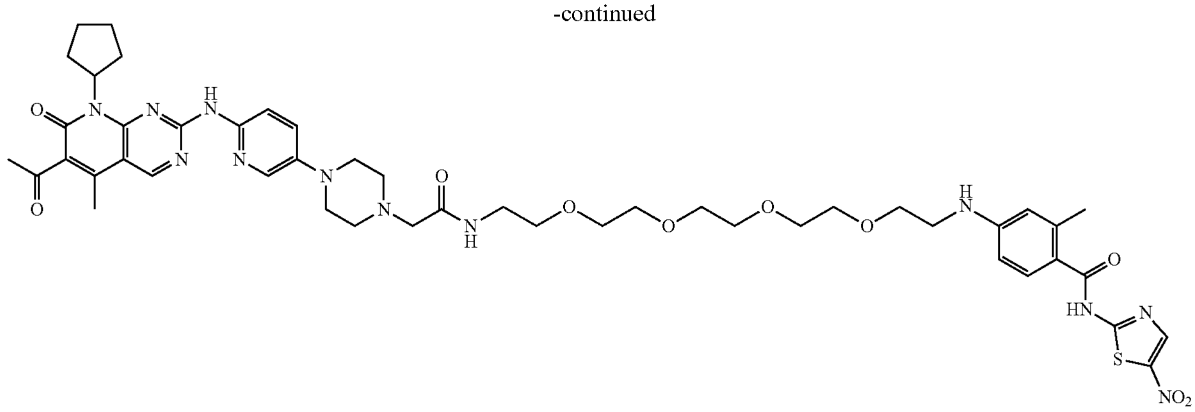
D-128 was synthesized following the same procedure as D-93. (2.85 mg, yield: 28.9%). MS (ESI) m/z: 985.9 $[M+H]^+$.
Example 293. 4-((1-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15,18-pentaoxa-3-azaicosan-20-yl)amino)-2-methyl-N-(5-nitrothiazol-2-yl)benzamide (D-129)
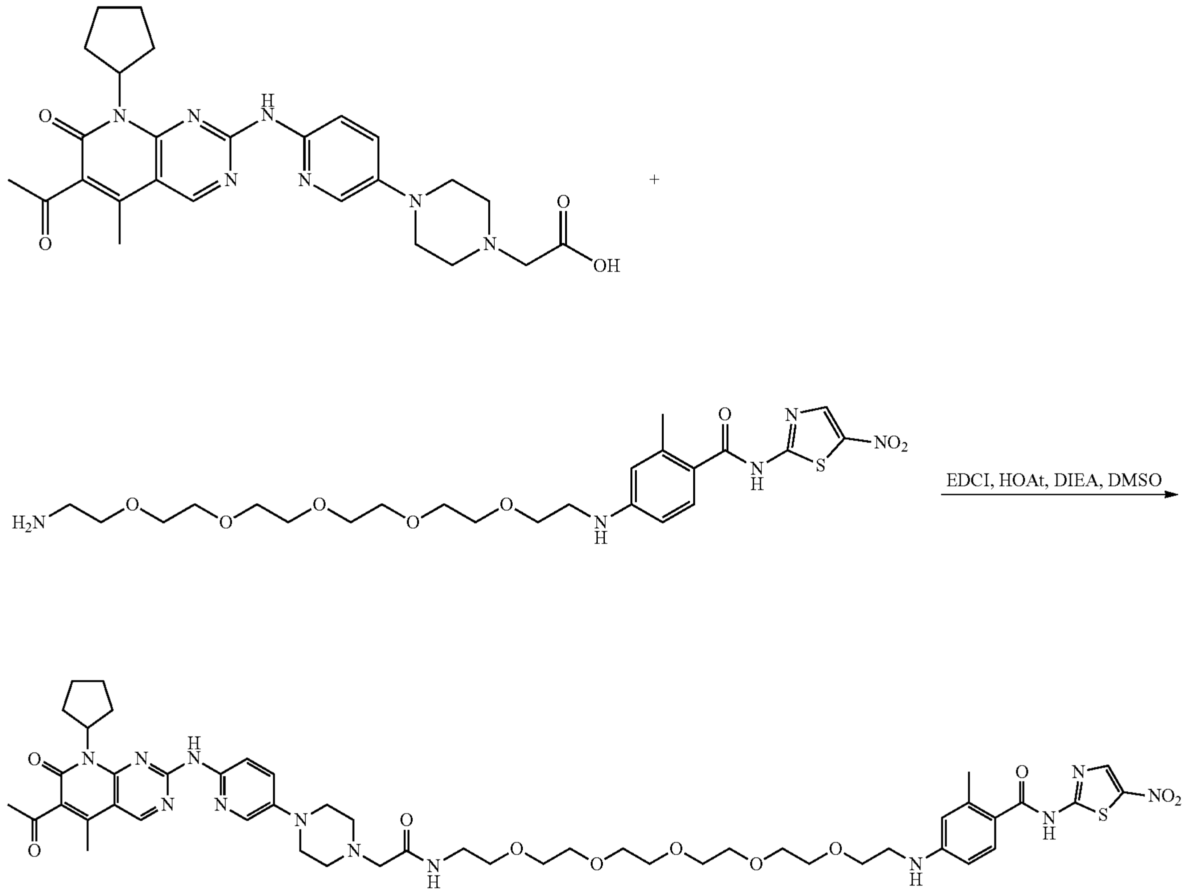
D-129 was synthesized following the same procedure as D-93. (2.64 mg, yield: 22.6%). MS (ESI) m/z: 1030.1 $[M+H]^+$.

Example 294. 4-((1-(4-(6-((6-Acetyl-8-cyclopentyl-5-methyl-7-oxo-7,8-dihydropyrido[2,3-d]pyrimidin-2-yl)amino)pyridin-3-yl)piperazin-1-yl)-2-oxo-6,9,12,15,18,21-hexaoxa-3-azatricosan-23-yl)amino)-2-methyl-N-(5-nitrothiazol-2-yl)benzamide (D-130)
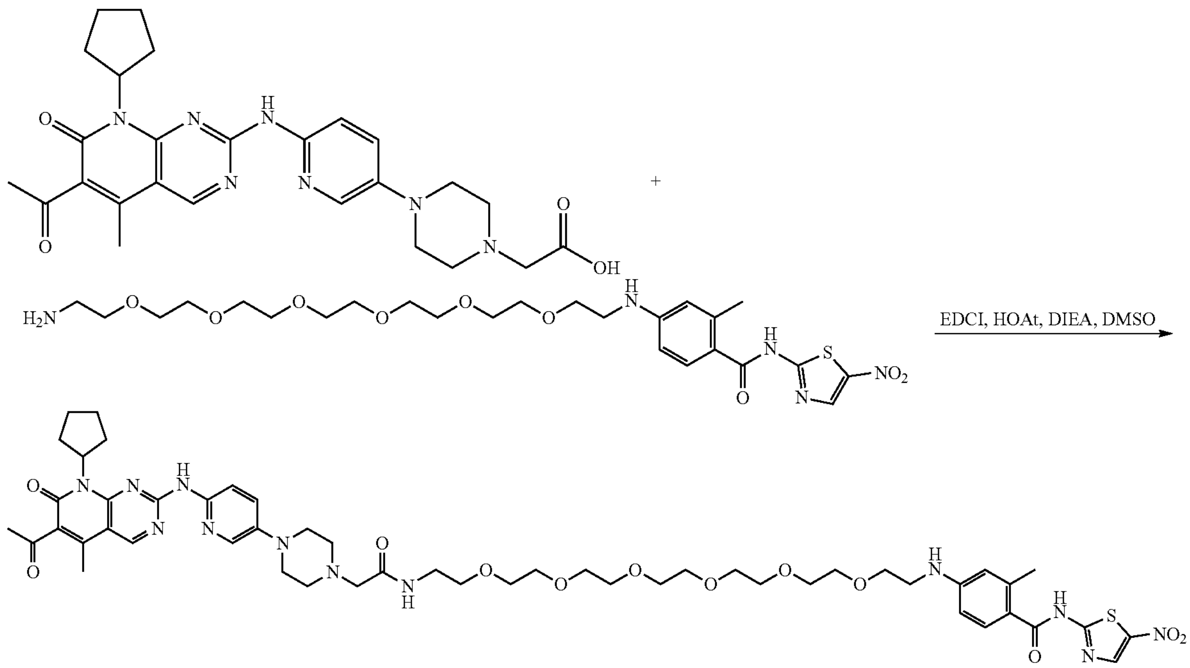
D-130 was synthesized following the same procedure as D-93. (2.81 mg, yield: 26.2%). MS (ESI) m/z: 1074.0 $[M+H]^+$.
Example 295. 5-(Butylamino)-2-methyl-N-(5-nitrothiazol-2-yl)benzamide (B-148)
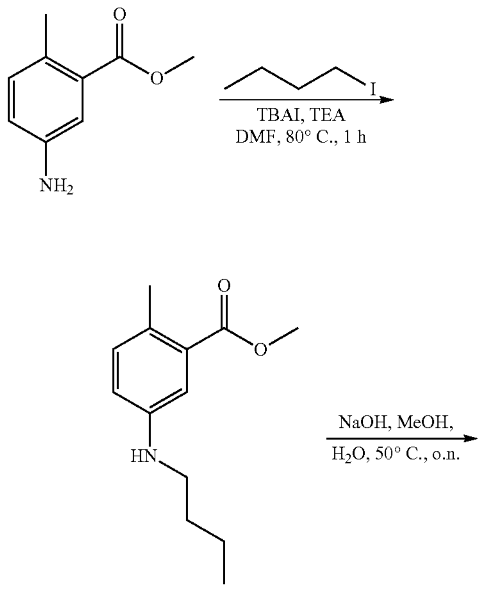
-continued
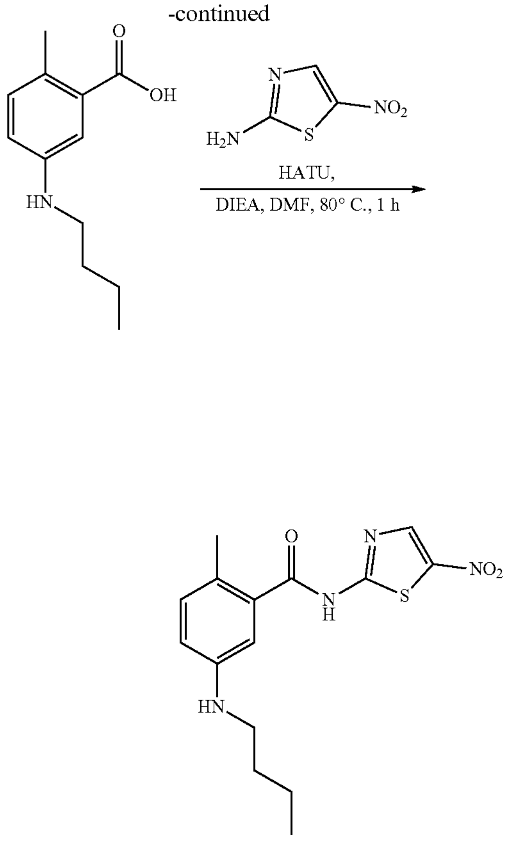

Step 1. Synthesis of methyl 5-(butylamino)-2-methylbenzoate

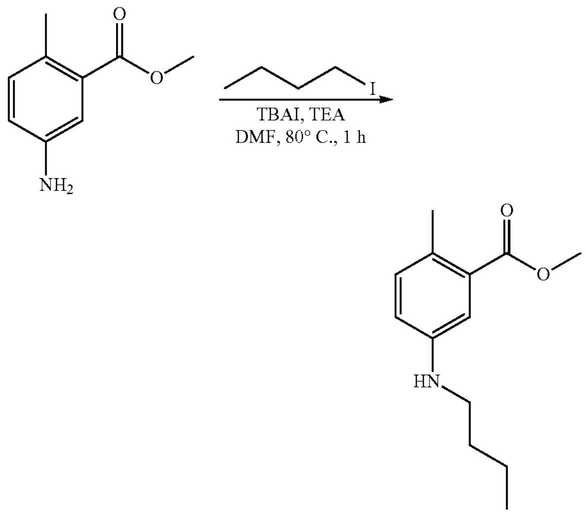

A solution of methyl 5-amino-2-methylbenzoate (500 mg, 3.03 mmol), 1-iodobutane (1.67 g, 9.09 mmol), TBAI (1.12 g, 3.03 mmol) and TEA (1.23 g, 12.2 mmol) in DMF (8 mL) was stirred at 80° C. for 1 hour. The mixture was diluted with water (100 mL) and extracted with EtOAc (3×50 mL). The combined organic phase was washed with brine (2×100 mL), dried over $Na_2SO_4$, filtered and concentrated in vacuum to give a residue, which was purified by silica gel column chromatography (petroleum ether:EtOAc=3:1) to give the title compound (270 mg, yield: 40%) as a yellow solid. MS (ESI) m/z: 222.1 $[M+H]^+$.

Step 2. Synthesis of 5-(butylamino)-2-methylbenzoic acid

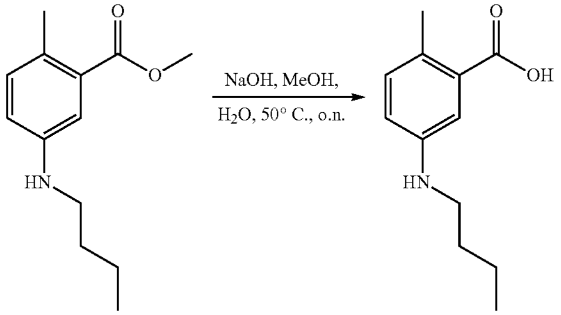 [SMILES: CCCCNc1ccc(C)c(C(=O)OC)c1 ; CCCCNc1ccc(C)c(C(=O)O)c1]

A solution of methyl 5-(butylamino)-2-methylbenzoate (200 mg, 0.91 mmol) and NaOH (181 mg, 4.52 mmol) in MeOH (5 mL)/$H_2O$ (5 mL) was stirred at 50° C. overnight. Then, the mixture was diluted with water (20 mL) and acidified (pH=2) with HCl (1 N). The mixture was extracted with EtOAc (3×50 mL). The combined organic phase was washed with brine (2×50 mL), dried over $Na_2SO_4$, filtered and concentrated in vacuum to give the title compound (76 mg, yield: 40%) as a yellow oil. MS (ESI) m/z: 208.2 $[M+H]^+$.

Step 3. Synthesis of 5-(butylamino)-2-methyl-N-(5-nitrothiazol-2-yl)benzamide

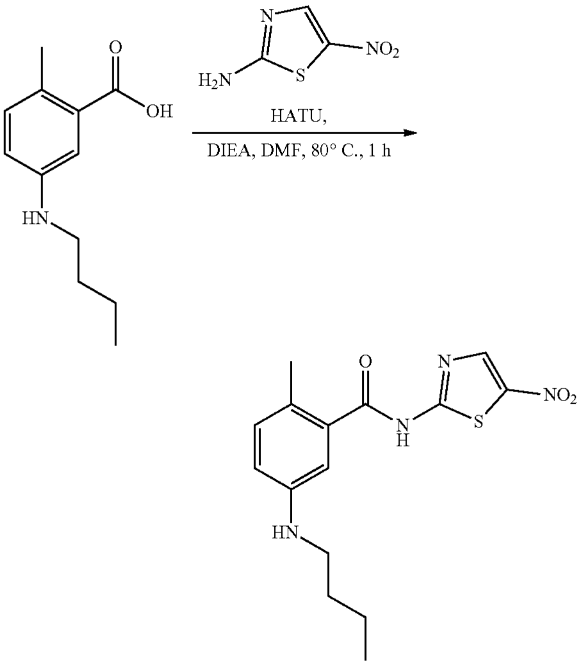

To a solution of 5-(butylamino)-2-methylbenzoic acid (40 mg, 0.193 mmol), 5-nitrothiazol-2-amine (56 mg, 0.386 mmol) and HATU (147 mg, 0.386 mmol) in DMF (2 mL) at 80° C., was added DIEA (75 mg, 0.579 mmol). After being stirred at 80° C. for 1 hour, the mixture was cooled to room temperature. Then the mixture was purified by prep-HPLC (0.1% formic acid) to give the title compound (16.5 mg, yield: 25.8%) as a yellow solid. $^1H$ NMR (400 MHz, DMSO-$d_6$): δ 13.38 (s, 1H), 8.69 (s, 1H), 7.05 (d, J=8.4 Hz, 1H), 6.81 (s, 1H), 6.74-6.72 (m, 1H), 5.78 (brs, 1H), 3.04 (t, J=6.8 Hz, 2H), 2.25 (s, 3H), 1.57-1.50 (m, 2H), 1.43-1.36 (m, 2H), 0.91 (t, J=7.6 Hz, 31-1). MS (ESI) m/z: 335.0 $[M+H]^+$.

Example 296. 2-Acetamido-5-(butylamino)-N-(5-nitrothiazol-2-yl)benzamide (B-149)

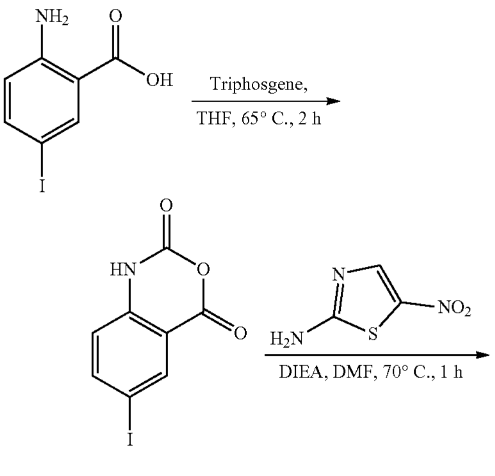

-continued

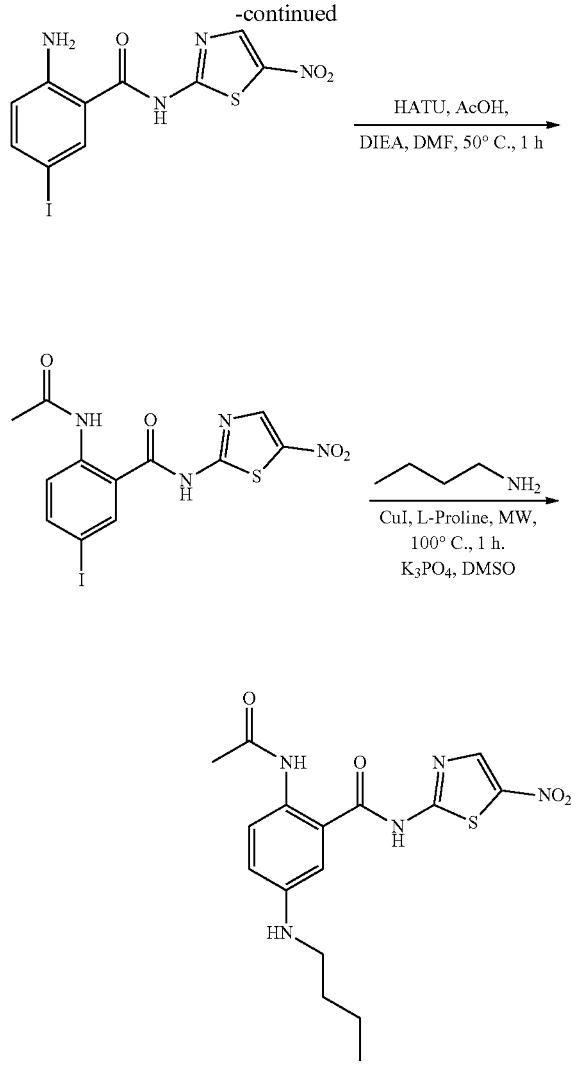

Step 1. Synthesis of 6-iodo-2H-benzo[d][1,3]oxazine-2,4 (1H)-dione

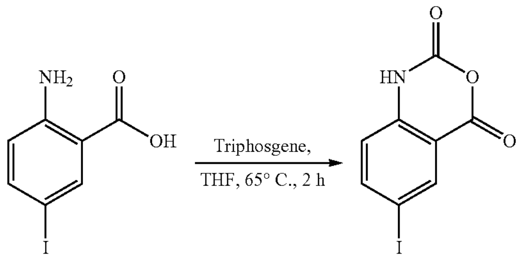 [SMILES: Nc1ccc(I)cc1C(=O)O ; O=c1[nH]c2ccc(I)cc2c(=O)o1]

A solution of 2-amino-5-iodobenzoic acid (1.00 g, 3.80 mmol) and triphosgene (1.69 g, 5.70 mmol) in THF (15 mL) was stirred at 65° C. for 2 hours. After being cooled to room temperature, the mixture was filtered and the cake was washed by petroleum ether (100 mL) to give the title compound (800 mg, yield: 72.8%) as a white solid. MS (ESI) m/z: 287.8 $[M-H]^-$.

Step 2. Synthesis of 2-acetamido-5-iodo-N-(5-nitrothiazol-2-yl)benzamide

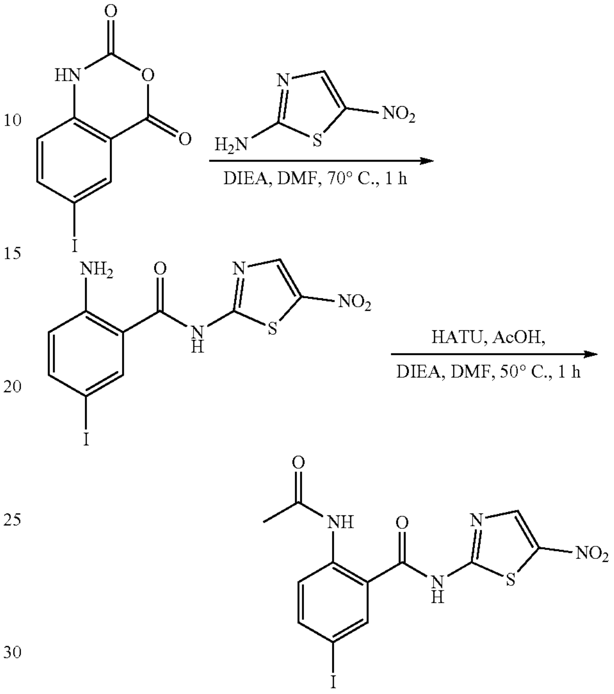

A solution of 6-iodo-2H-benzo[d][1,3]oxazine-2,4 (1H)-dione (800 mg, 2.77 mmol), 5-nitrothiazol-2-amine (803 mg, 5.54 mmol) and DIEA (1.40 g, 11.1 mmol) in DMF (8 mL) was stirred at 70° C. for 1 hour. Then, HATU (1.29 g, 3.41 mmol), AcOH (272 mg, 4.54 mmol) and DIEA (878 mg, 6.81 mmol) were added to the mixture. After being stirred at 50° C. for 1 hour, the mixture was diluted with water (100 mL) and extracted with EtOAc (3×100 mL). The combined organic phase was washed with brine (2×100 mL), dried over $Na_2SO_4$, filtered and concentrated in vacuum to give a residue, which was purified by silica gel column chromatography (petroleum ether:EtOAc=1:1) to give the title compound (200 mg, yield: 20.4%) as a yellow solid. MS (ESI) m/z: 432.9 $[M+H]^+$.

Step 3. Synthesis of 2-acetamido-5-(butylamino)-N-(5-nitrothiazol-2-yl)benzamide

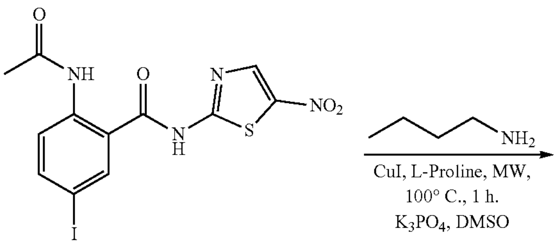

-continued

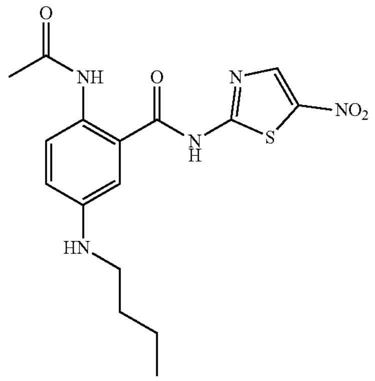

To a solution of 2-acetamido-5-iodo-N-(5-nitrothiazol-2-yl)benzamide (40 mg, 0.092 mmol), butan-1-amine (20 mg, 0.277 mmol), CuI (18 mg, 0.092 mmol), L-proline (11 mg, 0.092 mmol) and $K_3PO_4$ (59 mg, 0.277 mmol) in DMSO (2 mL) was heated at 100° C. under microwave for 1 hour under argon atmosphere. After being cooled to room temperature, the mixture was purified by prep-HPLC (0.1% formic acid) to give the tide compound (2.35 mg, yield: 6.77%) as a yellow solid. $^1$H NMR (400 MHz, DMSO-$d_6$): δ 8.44 (s, 1H), 7.47 (d, J=8.0 Hz, 1H), 6.96 (s, 1H), 6.82 (dd, J=8.8 Hz, 2.8 Hz, 1H), 3.13 (t, J=6.8 Hz, 2H), 2.09 (s, 3H), 1.64-1.58 (m, 2H), 1.49-1.43 (m, 2H), 0.98 (t, J=7.6 Hz, 3H). MS (ESI) m/z: 378.2 $[M+H]^+$.

Example 297. 4-chloro-2-methyl-N-(5-nitrothiazol-2-yl)benzamide (B-150)

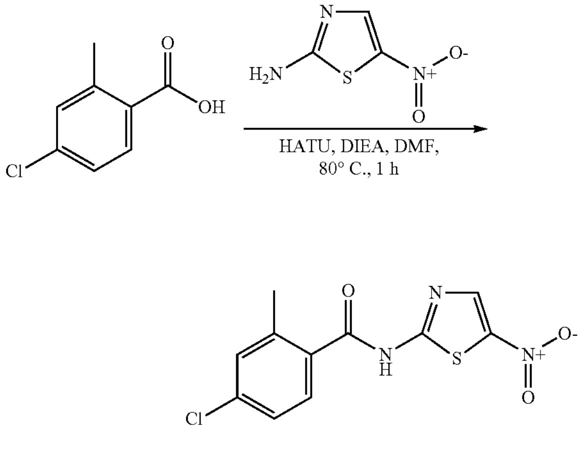

To a solution of 4-chloro-2-methylbenzoic acid (100 mg, 0.586 mmol), 5-nitrothiazol-2-amine (127 mg, 0.879 mmol) and HATU (446 mg, 1.17 mmol) in DMF (5 mL) at 80° C. was added DIEA (227 mg, 1.76 mmol). After being stirred at 80° C. for 1 hour, the mixture was cooled to room temperature, and purified by prep-HPLC (0.1% formic acid) to give the title compound (36.0 mg, yield: 20.6%) as a yellow solid. $^1$H NMR (400 MHz, DMSO-$d_6$): δ 13.61 (s, 1H), 8.69 (s, 1H), 7.70 (d, J=8.4 Hz, 1H), 7.48 (s, 1H), 7.48-7.41 (m, 1H), 2.44 (s, 3H). MS (ESI) m/z: 298.0 $[M+H]^+$.

Example 298. 4-Cyano-2-methyl-N-(5-nitrothiazol-2-yl)benzamide (B-151)

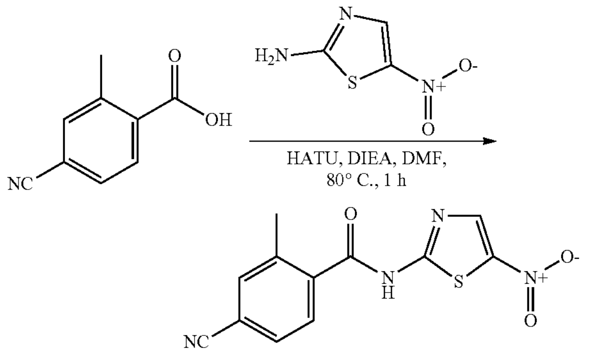

To a solution of 4-cyano-2-methylbenzoic acid (50 mg, 0.310 mmol), 5-nitrothiazol-2-amine (90 mg, 0.620 mmol) and HATU (236 mg, 0.620 mmol) in DMF (2 mL) at 80° C. was added DIEA (120 mg, 0.930 mmol). After being stirred at 80° C. for 1 hour, the mixture was cooled to room temperature and purified by prep-HPLC (0.1% formic acid) to give the title compound (34.5 mg, yield: 38.8%) as a yellow solid. $^1$H NMR (400 MHz, DMSO-$d_6$): δ 13.72 (brs, 1H), 8.72 (s, 1H), 7.89 (s, 1H), 7.86-7.80 (m, 2H), 2.44 (s, 3H). MS (ESI) m/z: 289.0 $[M+H]^+$.

Example 299. 4-Bromo-2-methyl-N-(5-nitrothiazol-2-yl)benzamide (B-152)

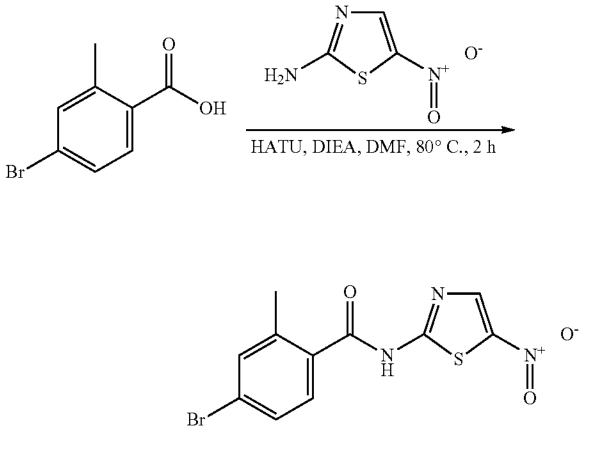

A solution of 4-bromo-2-methylbenzoic acid (100 mg, 0.465 mmol), 5-nitrothiazol-2-amine (67 mg, 0.465 mmol), HATU (353 mg, 0.930 mmol) and DIEA (120 mg, 0.930 mmol) in DMF (5 mL) was stirred at 80° C. for 2 hours. The mixture was concentrated under reduced pressure, and the resulting residue was purified by prep-HPLC (0.1% formic acid) to give the title compound (21.2 mg, yield: 13.3%) as a yellow solid. $^1$H NMR (400 MHz, DMSO-$d_6$): 13.59 (brs, 1H), 8.65 (s, 1H), 7.67 (d, J=8.4 Hz, 1H), 7.59 (s, 1H), 7.54-7.52 (m, 1H), 2.45 (s, 3H). MS (EST) m/z: 343.9 $[M+H]^+$.

Example 300. 3-Methyl-N-(5-nitrothiazol-2-yl)-[1,1'-biphenyl]-4-carboxamide (B-153)

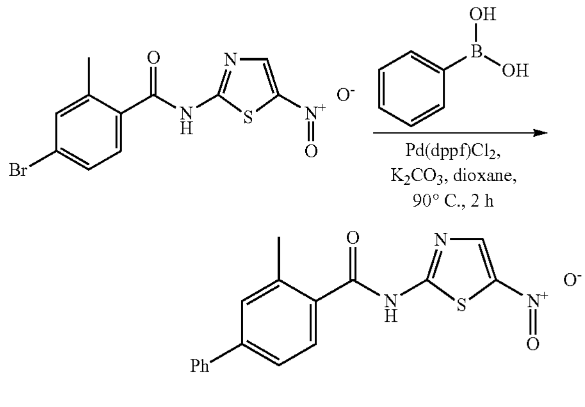

A solution of 4-bromo-2-methyl-N-(5-nitrothiazol-2-yl)benzamide (100 mg, 0.292 mmol), phenylboronic acid (70 mg, 0.584 mmol), $K_2CO_3$ (80 mg, 0.584 mmol) and $Pd(dppf)Cl_2$ (21 mg, 0.0292 mmol) in dioxane (5 mL) were stirred at 90° C. for 2 hours. The mixture was filtered and concentrated under reduced pressure, and the resulting residue was purified by prep-HPLC (0.1% formic acid) to give the title compound (11.3 mg, yield: 11.4%) as a yellow solid. $^1H$ NMR (400 MHz, DMSO-$d_6$): 8.56 (s, 1H), 8.14 (s, 1H), 7.96 (d, J=8.4 Hz, 1H), 7.73 (d, J=7.6 Hz, 2H), 7.57-7.56 (m, 2H), 7.50-7.46 (m, 2H), 7.41-7.39 (m, 1H), 2.60 (s, 3H). MS (ESI) m/z: 340.1 $[M+H]^+$.

Example 301. 2-Methyl-6-nitro-N-(5-nitrothiazol-2-yl)benzamide (B-154)

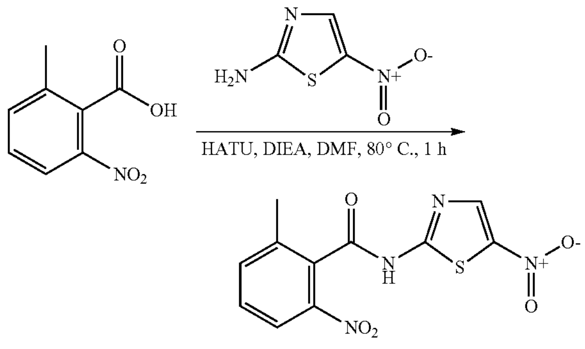

To a solution of 2-methyl-6-nitrobenzoic acid (100 mg, 0.552 mmol), 5-nitrothiazol-2-amine (160 mg, 1.10 mmol) and HATU (420 mg, 1.10 mmol) in DMF (5 mL) was added DIEA (214 mg, 1.66 mmol). The mixture was stirred at 80° C. for 1 hour. After being cooled to room temperature, the mixture was purified by prep-HPLC (0.1% formic acid) to give the title compound (75.0 mg, yield: 44.1%) as a yellow solid. $^1H$ NMR (400 MHz, DMSO-$d_6$): δ 13.72 (s, 1H), 8.69 (s, 1H), 8.15 (d, J=8.0 Hz, 1H), 7.84 (d, J=7.6 Hz, 1H), 7.73 (t, J=8 Hz, 1H), 2.35 (s, 3H). MS (ESI) m/z: 308.9 $[M+H]^+$.

Example 302. 5-(Butylamino)-2-ethoxy-N-(5-nitrothiazol-2-yl)benzamide (B-155)

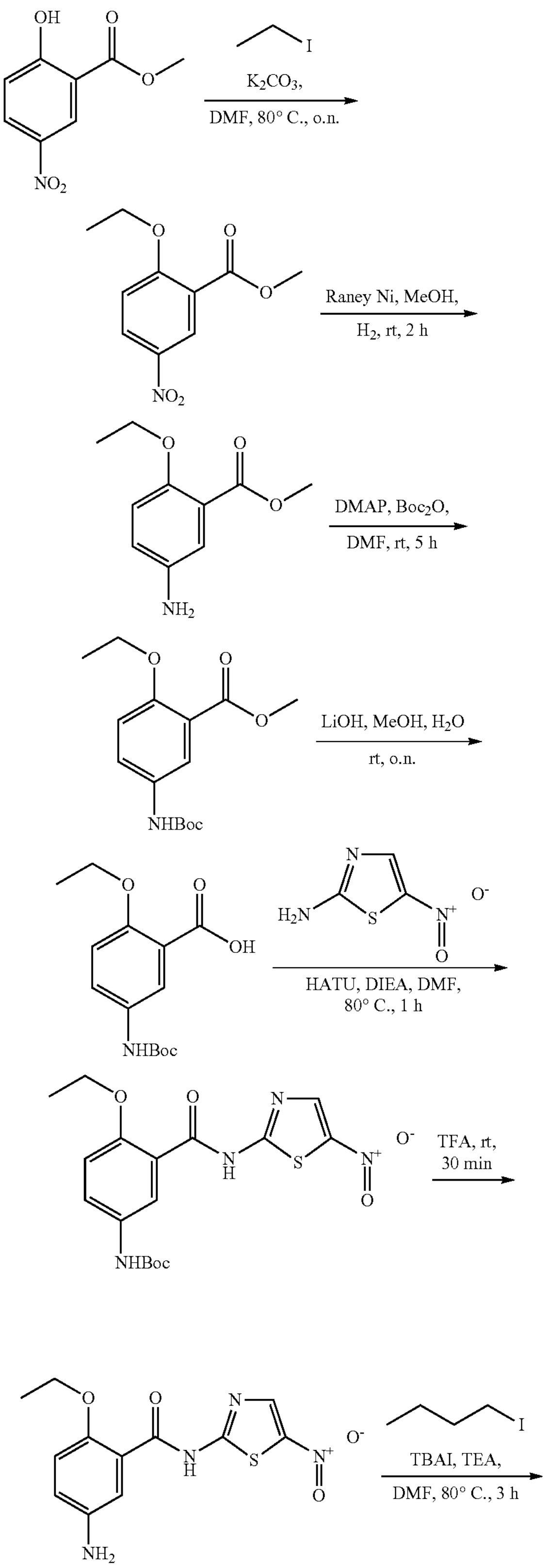

-continued

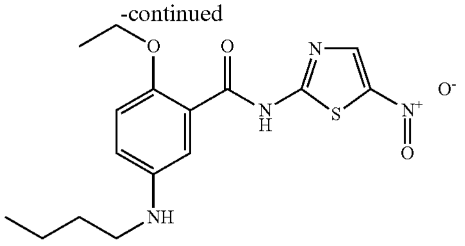

Step 1. Synthesis of methyl 2-ethoxy-5-nitrobenzoate

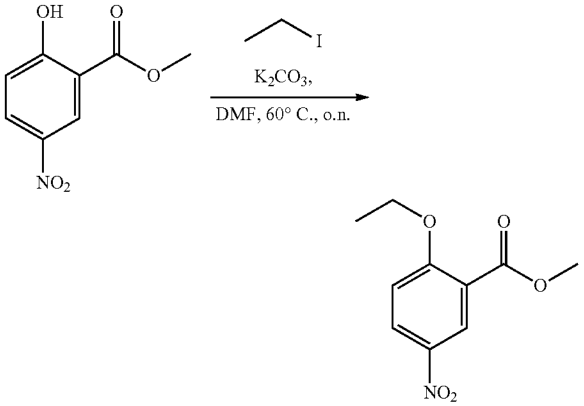

A solution of methyl 2-hydroxy-5-nitrobenzoate (2.00 g, 10.2 mmol), iodoethane (3.17 g, 20.3 mmol) and $K_2CO_3$ (2.80 g, 20.3 mmol) in DMF (30 mL) was stirred at 60° C. overnight. The mixture was diluted with water (100 mL) and extracted with EtOAc (3×100 mL). The combined organic phase was washed with brine (2×100 mL), dried over $Na_2SO_4$, filtered and concentrated in vacuum to give the title compound (1.80 g, yield: 78.4%) as a white solid. MS (ESI) m/z: 226.1 $[M+H]^+$.

Step 2. Synthesis of methyl 5-amino-2-ethoxybenzoate

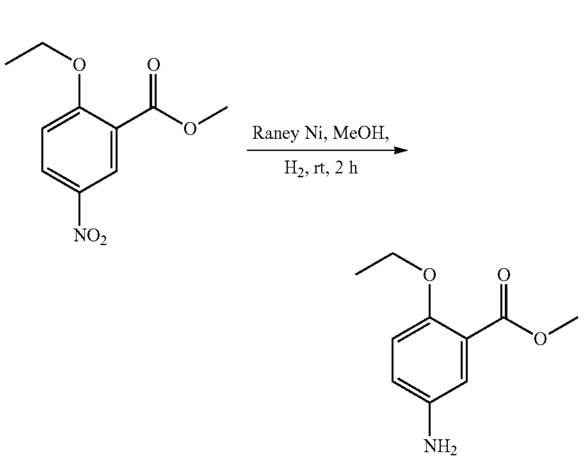

A solution of methyl 2-ethoxy-5-nitrobenzoate (1.80 g, 8.00 mmol) and Raney Ni (200 mg) in MeOH (20 mL) was stirred at room temperature for 2 hours under hydrogen atmosphere. The mixture was filtered and the filtrate was concentrated in vacuum to give the title compound (1.40 g, yield: 89.7%) as white solid. MS (ESI) m/z: 196.2 $[M+H]^+$.

Step 3. Synthesis of methyl 5-((tert-butoxycarbonyl)amino)-2-ethoxybenzoate

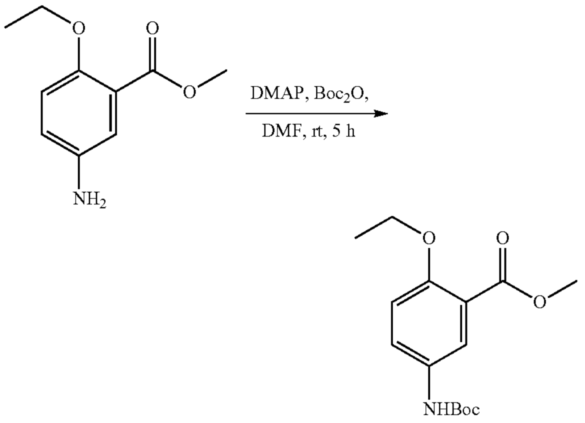

A solution of methyl 5-amino-2-ethoxybenzoate (400 mg, 2.05 mmol), $Boc_2O$ (670 mg, 3.07 mmol) and DMAP (500 mg, 4.10 mmol) in DMF (5 mL) was stirred at room temperature for 5 hours. The mixture was diluted with water (50 mL) and extracted with EtOAc (3×50 mL). The combined organic phase was washed with brine (2×100 mL), dried over $Na_2SO_4$, filtered and concentrated in vacuum to give a residue, which was purified by silica gel column chromatography (petroleum ether:EtOAc=2:1) to give the title compound (300 mg, yield: 49.7%) as a white solid. MS (ESI) m/z: 296.5 $[M+H]^+$.

Step 4. Synthesis of 5-((tert-butoxycarbonyl)amino)-2-ethoxybenzoic acid

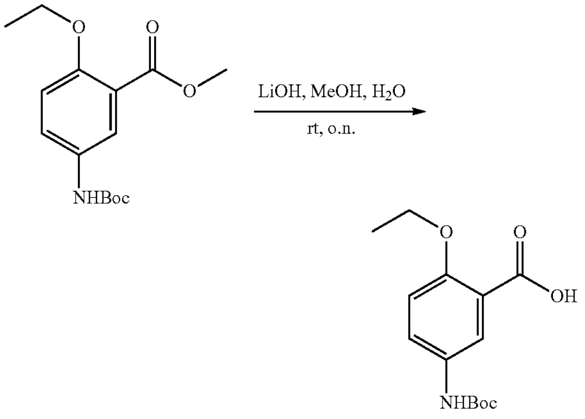

A solution of methyl 5-((tert-butoxycarbonyl)amino)-2-ethoxybenzoate (300 mg, 1.02 mmol) and $LiOH{\cdot}H_2O$ (213 mg, 5.08 mmol) in MeOH (5 mL)/$H_2O$ (5 mL) was stirred at room temperature overnight. The mixture was diluted with water (20 mL) and acidified (pH=2) with HCl (1N).

The mixture was extracted with EtOAc (3×50 mL). The combined organic phase was washed with brine (2×50 mL), dried over $Na_2SO_4$, filtered and concentrated in vacuum to give the title compound (240 mg, yield: 83.6%) as a white solid which was used for next step directly. MS (EST) m/z: 280.1 $[M-1]^-$.

Step 5. Synthesis of tert-butyl (4-ethoxy-3-((5-nitrothiazol-2-yl)carbamoyl)phenyl)carbamate

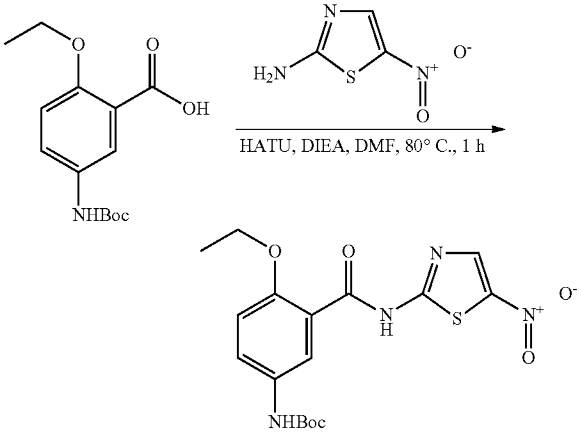

To a solution of 5-((tert-butoxycarbonyl)amino)-2-ethoxybenzoic acid (200 mg, 0.712 mmol), 5-nitrothiazol-2-amine (206 mg, 1.42 mmol) and HATU (540 mg, 1.42 mmol) in DMF (2 mL) at 80° C. was added DIEA (75 mg, 0.579 mmol). After being stirred at 80° C. for 1 hour, the mixture was diluted with water (100 mL) and filtered, the filtrate cake was washed by EtOAc (10 mL) to give the title compound (200 mg, yield: 69.0%) as a yellow solid. MS (ESI) m/z: 409.1 $[M+H]^+$.

Step 6. Synthesis of 5-amino-2-ethoxy-N-(5-nitrothiazol-2-yl)benzamide

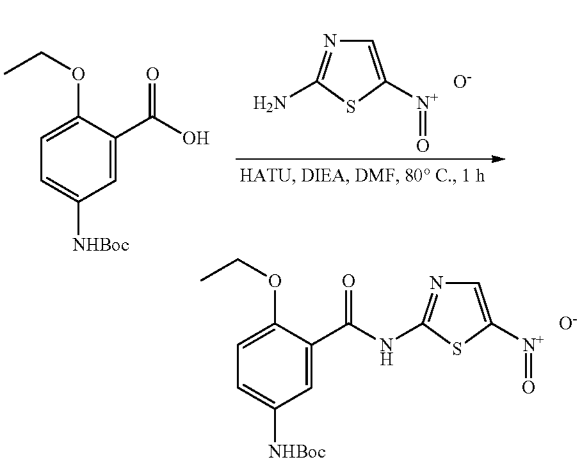

A solution of tert-butyl (4-ethoxy-3-((5-nitrothiazol-2-yl)carbamoyl)phenyl)carbamate (55 mg, 0.135 mmol) in TFA (5 mL) was stirred at room temperature for 30 minutes, the mixture was concentrated in vacuum to give the title compound (60.0 mg, crude) as a white solid, which was used for next step directly. MS (ESI) m/z: 309.0 $[M+H]^+$.

Step 7. Synthesis of 5-(butylamino)-2-ethoxy-N-(5-nitrothiazol-2-yl)benzamide

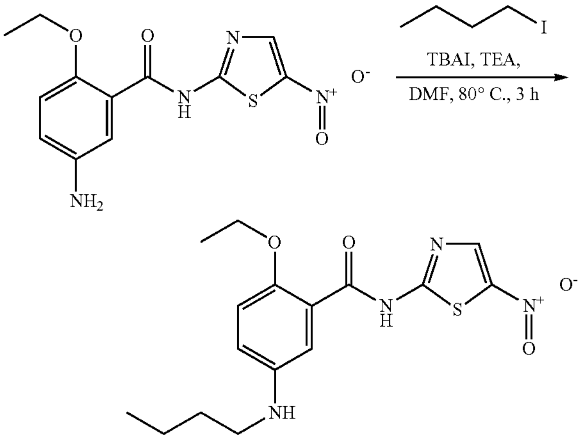

A solution of 5-amino-2-ethoxy-N-(5-nitrothiazol-2-yl)benzamide (60 mg, crude), 1-iodobutane (270 mg, 1.47 mmol), TBAI (108 mg, 0.294 mmol) and TEA (60 mg, 0.588 mmol) in DMF (3 mL) was stirred at 80° C. for 3 hours. After being cooed to room temperature, the mixture was purified by prep-HPLC (0.1% formic acid) to give the title compound (9.27 mg, yield: 18.9% over two steps) as a yellow solid. $^1H$ NMR (400 MHz, DMSO-$d_6$): δ 12.50 (brs, 1H), 8.69 (s, 1H), 7.07-7.05 (m, 2H), 6.90-6.88 (m, 1H), 4.12 (q, J=6.8 Hz, 2H), 2.99 (t, J=6.8 Hz, 2H), 1.54-1.51 (m, 2H), 1.41-1.36 (m, 5H), 0.92 (t, J=7.2 Hz, 3H). MS (ESI) m/z: 365.1 $[M+H]^+$.

Example 303. 4-Methoxy-2-methyl-N-(5-nitrothiazol-2-yl)benzamide (B-156)

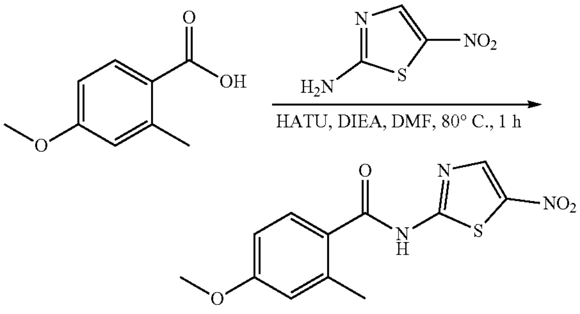

Step 7. Synthesis of 5-(butylamino)-2-ethoxy-N-(5-nitrothiazol-2-yl)benzamide

To a solution of 4-methoxy-2-methylbenzoic acid (100 mg, 0.602 mmol), 5-nitrothiazol-2-amine (175 mg, 1.20 mmol) and HATU (458 mg, 1.20 mmol) in DMF (4 mL) at 80° C. was added DIEA (233 mg, 1.81 mmol). After being stirred for 1 hour, the mixture was cooled to room temperature. Then the mixture was purified by prep-HPLC (0.1% formic acid) to give the title compound (26.9 mg, yield: 15.2%) as a yellow solid. $^{1}H$ NMR (400 MHz, DMSO-$d_6$): δ 13.33 (brs, 1H), 8.69 (s, 1H), 7.70 (d, J=8.8 Hz, 1H), 6.94-6.89 (m, 2H), 3.82 (s, 3H), 2.46 (s, 3H). MS (ESI) m/z: 294.0 $[M+H]^+$.

Example 304. 2,6-Dimethyl-N-(5-nitrothiazol-2-yl) benzamide (B-157)

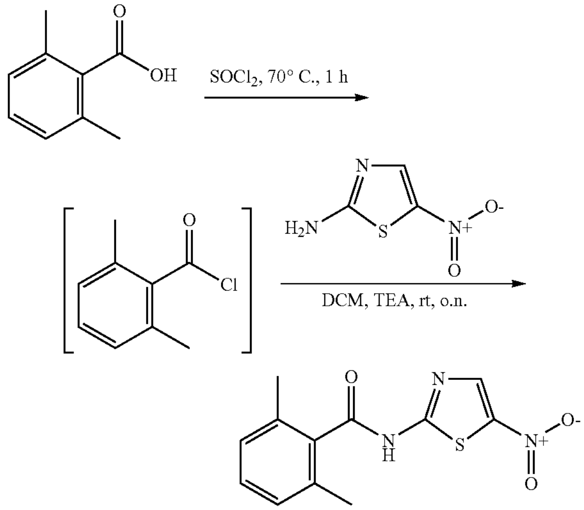

A solution of 2,6-dimethylbenzoic acid (200 mg, 1.33 mmol) in $SOCl_2$ (5 mL) was stirred at 70° C. for 1 hour. After being concentrated in vacuum to remove $SOCl_2$, the crude was diluted with DCM (5 mL). The solution was cooled to 0° C., before TEA (670 mg, 6.65 mmol) and 5-nitrothiazol-2-amine (290 mg, 2.00 mmol) were added. After the mixture was stirred at room temperature overnight, the mixture was concentrated to give a residue, which was purified by prep-HPLC (0.1% formic acid) to give the title compound (2.18 mg, yield: 0.59%) as a yellow solid. $^{1}H$ NMR (400 MHz, DMSO-$d_6$): δ 13.56 (brs, 1H), 8.68 (s, 1H), 7.32 (t, J=7.60 Hz, 1H), 7.16 (d, J=7.60 Hz, 2H), 2.23 (s, 6H). MS (ESI) m/z: 278.0 $[M+H]^+$.

Example 305. 4-Ethyl-2-methyl-N-(5-nitrothiazol-2-yl)benzamide (B-158)

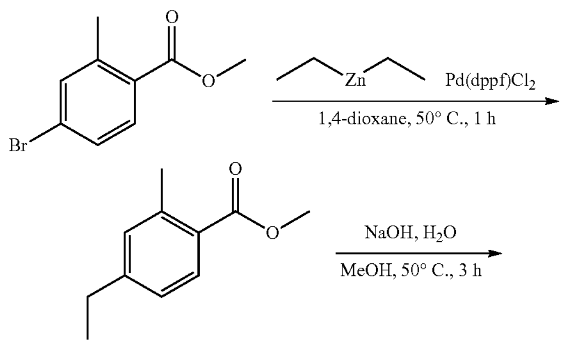

-continued

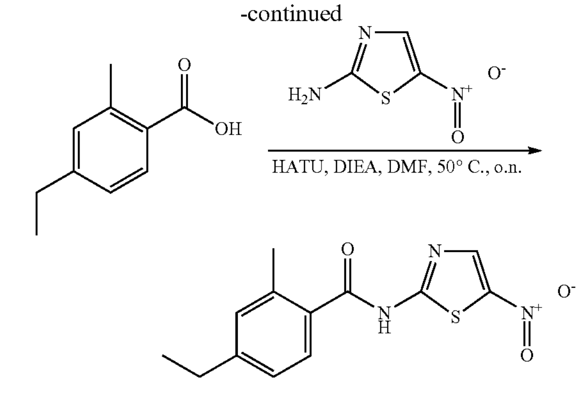

Step 1. Synthesis of methyl 4-ethyl-2-methylbenzoate

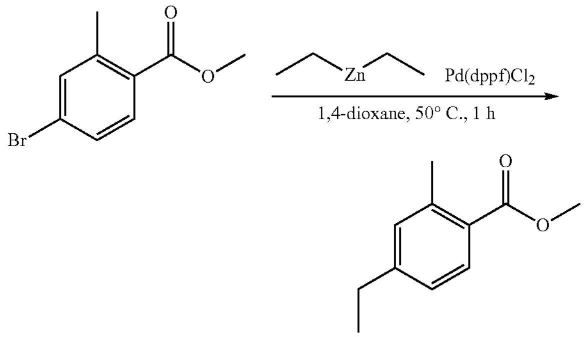

A solution of methyl 4-bromo-2-methylbenzoate (500 mg, 2.18 mmol), diethylzinc (5 mL, 1M in hexane) and Pd(dppf)$Cl_2$ (159 mg, 0.218 mmol) in 1,4-dioxane (10 mL) was stirred at 50° C. for 1 hour in argon atmosphere. The mixture was diluted with water (50 mL) and extracted with EtOAc (2×50 mL). The combined organic phase was washed with brine (2×50 mL), dried over $Na_2SO_4$, filtered and concentrated in vacuum to give a residue, which was purified by silica gel column chromatography (petroleum ether: EtOAc=10:1) to give the title compound (300 mg, yield: 77.3%) as a colorless oil.

Step 2. Synthesis of 4-ethyl-2-methylbenzoic acid

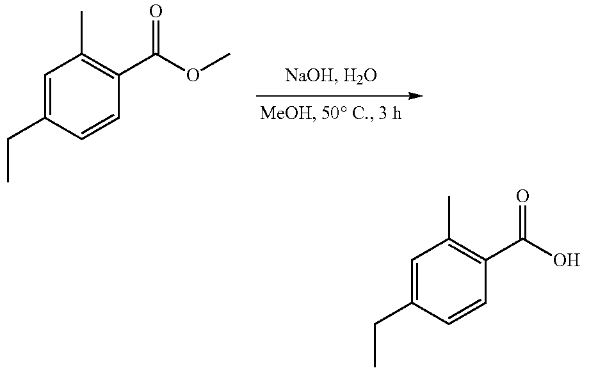

A solution of methyl 4-ethyl-2-methylbenzoate (150 mg, 0.840 mmol) and NaOH (101 mg, 2.53 mmol) in MeOH (3 mL)/water (1 mL) was stirred at 50° C. for 3 hours. The mixture was diluted with water (20 mL) and acidified (pH=5) with 1N HCl. The mixture was extracted with EtOAc (2×20 mL). The combined organic phase was washed with brine (2×20 mL), dried over $Na_2SO_4$, filtered and concentrated in vacuum to give the title compound (130 mg, yield: 94.5%) as a white solid. MS (ESI) m/z: 165.2 $[M+H]^+$.

Step 3. Synthesis of 4-ethyl-2-methyl-N-(5-nitrothiazol-2-yl)benzamide

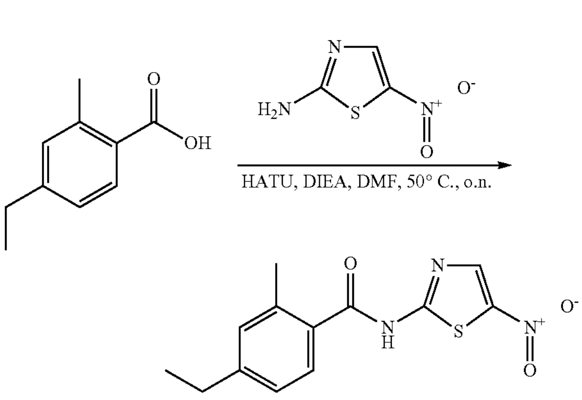

To a solution of 4-ethyl-2-methylbenzoic acid (50 mg, 0.305 mmol), 5-nitrothiazol-2-amine (88 mg, 0.610 mmol) and HATU (174 mg, 0.458 mmol) in DMF (3 mL) at 80° C. was added DIEA (79 mg, 0.610 mmol). After being was stirred at 80° C. for 1 hour, the mixture was cooled to room temperature. The mixture was purified by prep-HPLC (0.1% formic acid) to give the title compound (21.1 mg, yield: 23.8%) as a yellow solid. $^1H$ NMR (400 MHz, DMSO-$d_6$): δ 13.41 (s, 1H), 8.70 (s, 1H), 7.59 (d, J=7.6 Hz, 1H), 7.22-7.18 (m, 2H), 2.64 (q, J=7.6 Hz, 2H), 2.43 (s, 3H), 1.20 (t, J=7.6 Hz, 3H). MS (ESI) m/z: 292.1 $[M+H]^+$.

Example 306. 2-Ethoxy-6-methyl-N-(5-nitrothiazol-2-yl)benzamide (B-159)

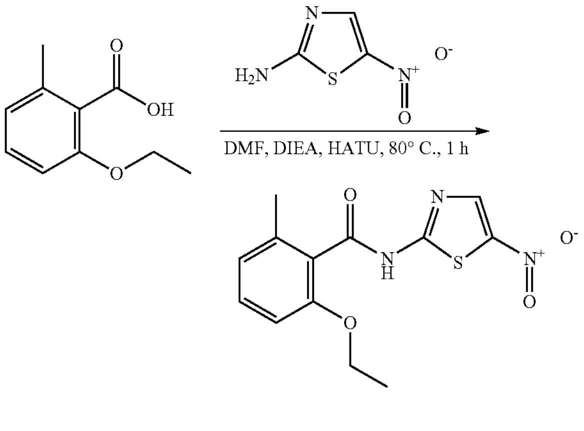

To solution of 2-ethoxy-6-methylbenzoic acid (140 mg, crude), HATU (304 mg, 0.80 mmol) and 5-nitrothiazol-2-amine (116 mg, 0.80 mmol) in DMF (10 mL) at 80° C. was added DIEA (206 mg, 1.60 mmol). After being stirred at 80° C. for 1 hour, the mixture was cooled to room temperature and purified by prep-HPLC (0.1% $NH_3H_2O$) to give the title compound (58.8 mg, 23.9% yield) as a brown solid. $^1H$ NMR (400 MHz, DMSO-$d_6$) δ 13.40 (s, 1H), 8.66 (s, 1H), 7.36 (t, J=8.0 Hz, 1H), 6.97 (d, J=8.0 Hz, 1H), 7.36 (t, J=8.0 Hz, 1H), 4.06 (q, J=6.8 Hz, 2H), 2.21 (s, 3H), 1.23 (t, J=6.8 Hz, 3H). MS (ESI) m/z: 308.3 $[M+H]^+$.

Example 307. 4-(Butylamino)-2-ethoxy-N-(5-nitrothiazol-2-yl)benzamide (B-160)

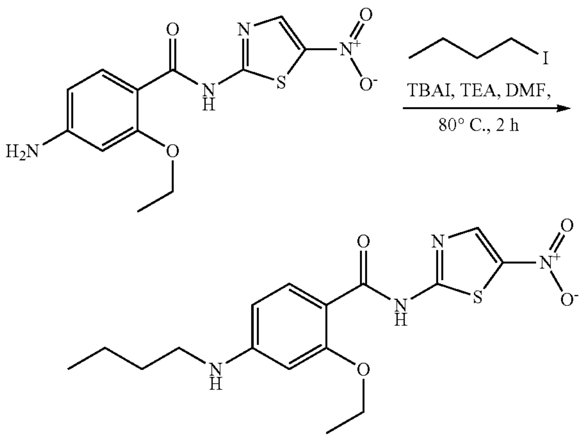

A solution of 4-amino-2-ethoxy-N-(5-nitrothiazol-2-yl) benzamide (50 mg, crude), 1-iodobutane (178 mg, 0.971 mmol), TBAI (90 mg, 0.243 mmol) and TEA (60 mg, 0.648 mmol) in DMF (3 mL) was stirred at 80° C. for 2 hours. After being cooled to room temperature, the mixture was purified by prep-HPLC (0.1% formic acid) to give the title compound (1.90 mg, yield: 4.41%) as a yellow solid. $^1H$ NMR (400 MHz, DMSO-$d_6$): δ 12.48 (brs, 1H), 8.69 (s, 1H), 7.07-7.03 (m, 2H), 6.85 (dd, J=9.2 Hz, 2.4 Hz, 1H), 5.62 (brs, 1H), 4.12 (q, J=6.4 Hz, 2H), 2.99 (t, J=6.8 Hz, 2H), 1.54-1.51 (m, 2H), 1.49-1.34 (m, 5H), 0.92 (t, J=7.2 Hz, 31-1). MS (ESI) m/z: 365.1 $[M+H]^+$.

Example 308. 4-(Isopropylamino)-2-methyl-N-(5-nitrothiazol-2-yl)benzamide (B-161)

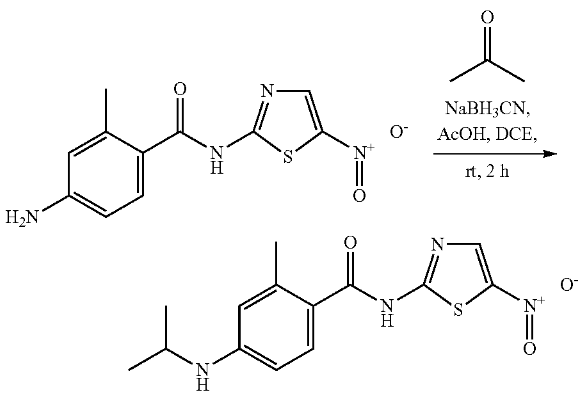

To a solution of 4-amino-2-methyl-N-(5-nitrothiazol-2-yl)benzamide (100 mg, 0.360 mmol), propan-2-one (63 mg, 1.08 mmol) and acetic acid (1 drops) in DCE (3 mL) was added $NaBH_3CN$ (45 mg, 0.720 mmol). After being stirred at room temperature for 2 hours, the mixture was concentrated. The residue was purified by prep-HPLC (0.1% formic acid) to give the title compound (5.85 mg, yield: 5.09%) as a yellow solid. $^1H$ NMR (400 MHz, DMSO-$d_6$): δ 12.99 (s, 1H), 8.66 (s, 1H), 7.61 (d, J=8.4 Hz, 1H), 6.46-6.43 (m, 2H), 6.32 (d, J=8.8 Hz, 1H), 3.70-3.61 (m, 1H), 2.41 (s, 3H), 1.14 (d, J=6.4 Hz, 6H). MS (ESI) m/z: 321.1 $[M+H]^+$.

Example 309. 2-Methyl-4-morpholino-N-(5-nitrothiazol-2-yl)benzamide (B-162)

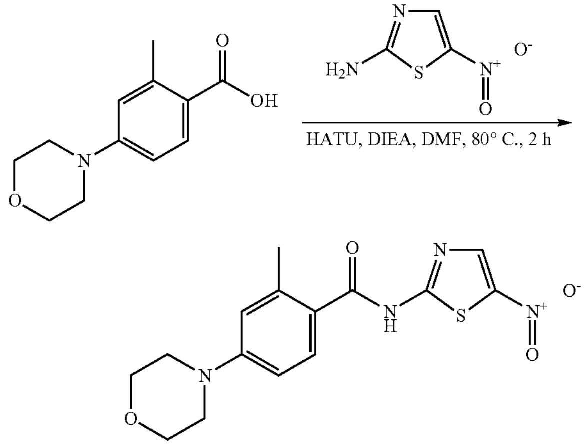

A solution of 2-methyl-4-morpholinobenzoic acid (140 mg, 0.633 mmol), 5-nitrothiazol-2-amine (91 mg, 0.633 mmol), HATU (361 mg, 0.95 mmol) and DIEA (126 mg, 0.95 mmol) in DMF (5 mL) were stirred at 80° C. for 2 hours. The mixture was filtered and concentrated under reduced pressure, and the resulting residue was purified by prep-HPLC (0.1% $NH_3 \cdot H_2O$) to give the title compound (20.1 mg, yield: 10.2%) as a yellow solid. $^1H$ NMR (400 MHz, DMSO-$d_6$): 8.46 (s, 1H), 8.05 (d, J=8.8 Hz, 1H), 6.79-6.72 (m, 2H), 3.74-3.72 (m, 4H), 3.22-3.18 (m, 4H), 2.58 (s, 3H), MS (ESI) m/z: 349.1 $[M+H]^+$.

Example 310. 2-Methyl-4-(4-methylpiperazin-1-yl)-N-(5-nitrothiazol-2-yl)benzamide (B-163)

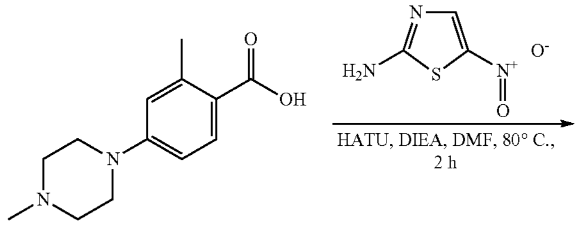

-continued

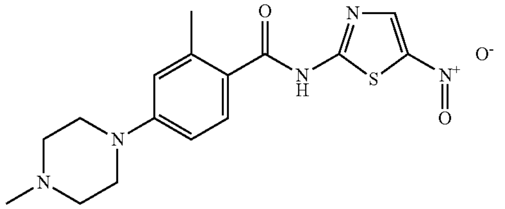

A solution of 2-methyl-4-(4-methylpiperazin-1-yl)benzoic acid (50 mg, 0.213 mmol), 5-nitrothiazol-2-amine (37 mg, 0.256 mmol) and HATU (121 mg, 0.32 mmol) in DMF (5 mL) at 80° C. was added DIEA (55 mg, 0.426 mmol). After being stirred at 80° C. for 2 hours, the mixture was cooled to room temperature and purified by prep-HPLC (0.1% TFA) to give the title compound (3.67 mg, yield: 3.62%) as a yellow solid. $^1H$ NMR (400 MHz, DMSO-$d_6$): 13.21 (brs, 1H), 9.84 (brs, 1H), 8.69 (s, 1H), 7.71 (s, J=8.8 Hz, 1H), 6.96-6.92 (m, 2H), 4.13-3.96 (m, 2H), 3.58-3.53 (m, 2H), 3.16-3.12 (m, 2H), 2.85 (s, 3H), 2.47 (s, 3H). MS (EST) m/z: 362.1 $[M+H]^+$.

Example 311. 4-Isopropyl-2-methyl-N-(5-nitrothiazol-2-yl)benzamide (B-164)

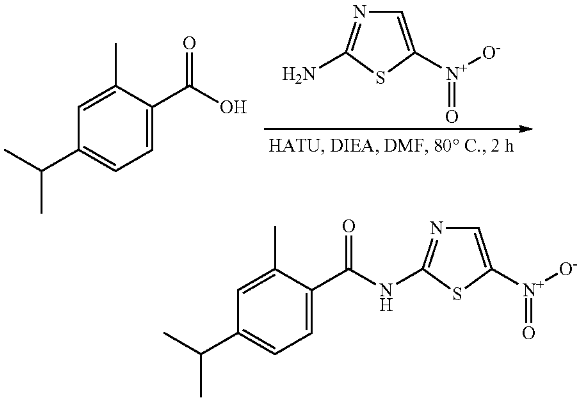

A solution of 4-isopropyl-2-methylbenzoic acid (100 mg, 0.562 mmol), 5-nitrothiazol-2-amine (81 mg, 0.562 mmol), HATU (320 mg, 0.843 mmol) and DIEA (109 mg, 0.843 mmol) in DMF (5 mL) was stirred at 80° C. for 2 hours. The mixture was concentrated under reduced pressure, and the resulting residue was purified by prep-HPLC (0.1% $NH_3 \cdot H_2O$) to give the tide compound (5.57 mg, yield: 3.26%) as a yellow solid. $^1H$ NMR (400 MHz, DMSO-$d_6$): 13.40 (s, 1H), 8.67 (s, 1H), 7.62 (d, J=7.6 Hz, 1H), 7.23-7.21 (m, 2H), 2.94-2.90 (m, 1H), 2.44 (s, 3H), 1.22 (d, J=6.8 Hz, 6H). MS (ESI) m/z: 306.1 $[M+H]^+$.

Example 312. 4-(Butylamino)-2-methyl-N-(5-nitrothiazol-2-yl)benzamide (B-165)

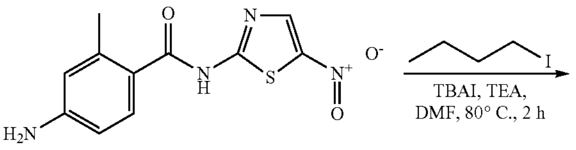

-continued

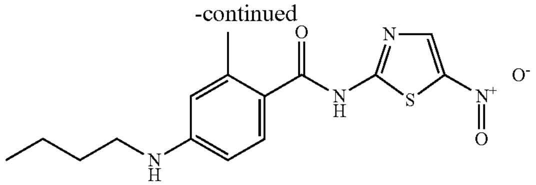

A solution of 4-amino-2-methyl-N-(5-nitrothiazol-2-yl) benzamide (100 mg, 0.36 mmol), 1-iodobutane (66 mg, 0.36 mmol), TBAI (265 mg, 0.720 mmol) and TEA (72 mg, 0.720 mmol) in DMF (5 mL) was stirred at 80° C. for 2 hours. The mixture was filtered and concentrated under reduced pressure. The residue was purified by prep-HPLC (0.1% formic acid) to give the title compound (19.8 mg, yield: 16.5%) as a yellow solid. $^1$H NMR (400 MHz, DMSO-$d_6$): 9.13 (s, 1H), 8.09 (d, J=8.4 Hz, 1H), 6.45-6.41 (m, 2H), 5.94 (brs, 1H), 4.28 (t, J=6.8 Hz, 2H), 2.54 (s, 3H), 1.82 (t, J=7.6 Hz, 2H), 1.34 (t, J=7.2 Hz, 2H), 0.92 (t, J=7.2 Hz, 3H). MS (EST) m/z: 335.4 [M+H]$^+$.

Example 313. 2-Methyl-4-(methylamino)-N-(5-nitrothiazol-2-yl)benzamide (B-166)

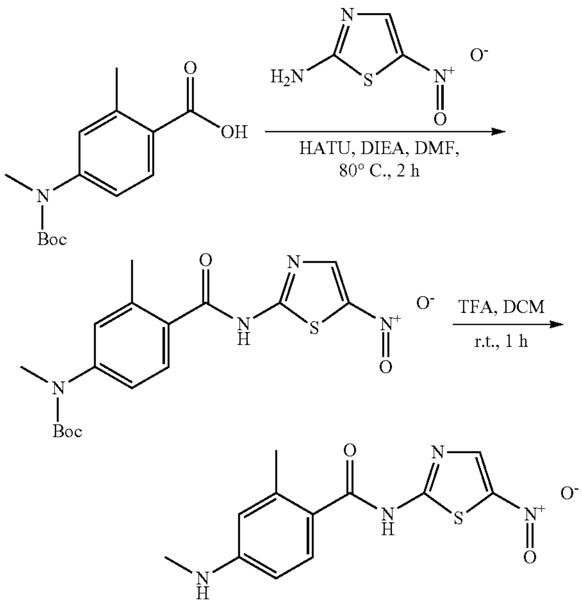

Step 1. Synthesis of tert-butyl methyl(3-methyl-4-((5-nitrothiazol-2-yl)carbamoyl)phenyl)carbamate

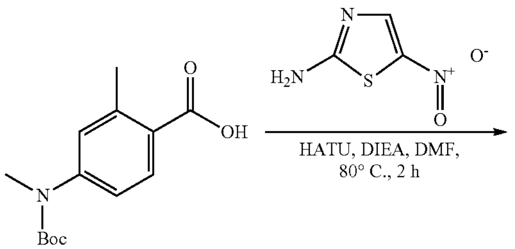

-continued

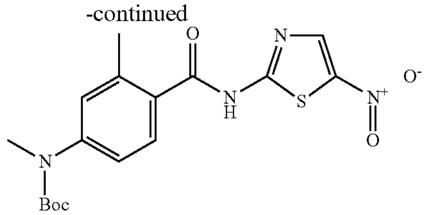

To a solution of 4-((tert-butoxycarbonyl)(methyl)amino)-2-methylbenzoic acid (200 mg, 0.750 mmol), 5-nitrothiazol-2-amine (218 mg, 1.51 mmol) and HATU (574 mg, 1.51 mmol) in DMF (3 mL) was added DIEA (292 mg, 2.25 mmol) at 80° C. After being stirred at 80° C. for 2 hours, the mixture was cooled to room temperature and diluted with water (20 mL). The mixture was extracted with EtOAc (2×20 mL). The combined organic phase was washed with brine (2×20 mL), and dried over $Na_2SO_4$, filtered and concentrated in vacuum to give the title compound (250 mg, crude) as a colorless oil which was used for the next step directly. MS (ESI) m/z: 337.0 [M+H−56]$^+$.

Step 2. Synthesis of 2-methyl-4-(methylamino)-N-(5-nitrothiazol-2-yl)benzamide

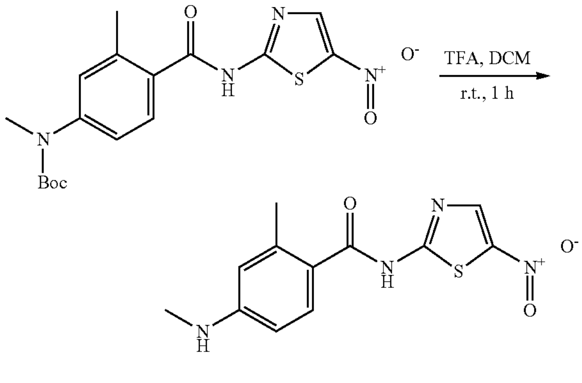

A solution of tert-butyl methyl(3-methyl-4-((5-nitrothiazol-2-yl)carbamoyl)phenyl)carbamate (250 mg, 0.638 mmol) in DCM (2 ml)/TFA (1 ml) was stirred at room temperature for 1 hour. The mixture was concentrated in vacuum to give a residue, which was purified by prep-HPLC (0.1% formic acid) to give the title compound (29.4 mg, yield: 15.8%) as a yellow solid. $^1$H NMR (400 MHz, DMSO-$d_6$): δ 12.9 (s, 1H), 8.66 (s, 1H), 7.63 (d, J=8.4 Hz, 1H), 6.51 (d, J=4.8 Hz, 1H), 6.44-6.41 (m, 2H), 2.74 (d, J=4.8 Hz, 3H), 2.43 (s, 3H). MS (ESI) m/z: 293.0 [M+H]$^+$.

Example 314. 4-(Dimethylamino)-2-methyl-N-(5-nitrothiazol-2-yl)benzamide (B-167)

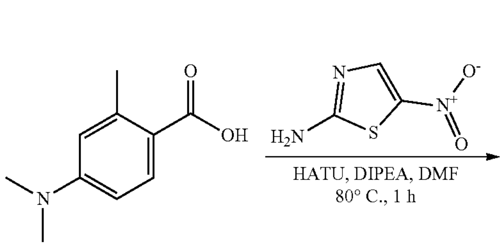

-continued

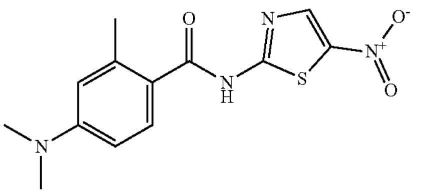

To a solution of 4-(dimethylamino)-2-methylbenzoic acid (50 mg, crude), HATU (117 mg, 0.31 mmol) and 5-nitrothiazol-2-amine (40 mg, 0.279 mmol) in DMF (3 mL) was added DIPEA (72 mg, 0.558 mmol) at 80° C. After being stirred at 80° C. for 1 h, the mixture was cooled to room temperature. Then the mixture was purified by prep-HPLC (0.1% formic acid) to give the desired compound (8.96 mg, yield: 11.2%) as a yellow solid. $^1$H NMR (400 MHz, DMSO-$d_6$) δ 13.06 (s, 1H), 8.67 (s, 1H), 7.70 (d, J=8.4 Hz, 1H), 6.62-6.58 (m, 2H), 3.00 (s, 6H), 2.48 (s, 3H). MS (EST) m/z: 307.0 [M+H]$^+$.

Example 315. 2-Ethoxy-6-(ethylamino)-N-(5-nitrothiazol-2-yl)benzamide (B-168)

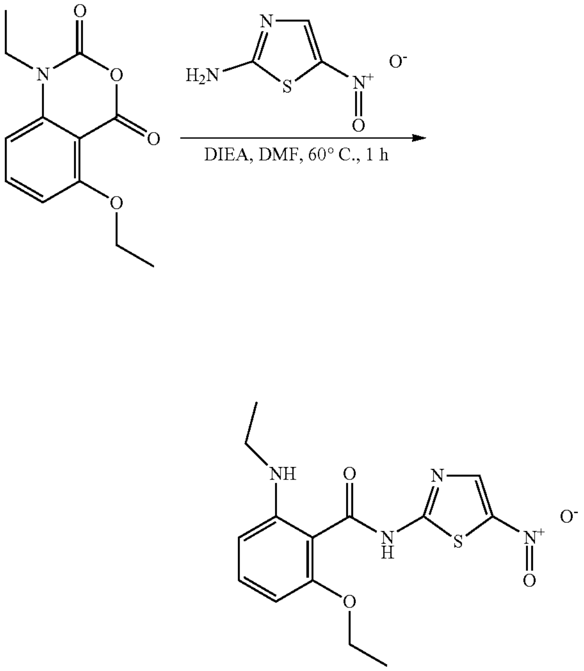

A solution of 5-ethoxy-1-ethyl-2H-benzo[d][1,3]oxazine-2,4 (1H)-dione (200 mg, 0.851 mmol), 5-nitrothiazol-2-amine (123 mg, 0.851 mmol) and DIPEA (220 mg, 1.70 mmol) in DMF (5 mL) was stirred at 60° C. for 1 h. After being cooled to room temperature, the mixture was purified by prep-HPLC (0.1% formic acid) to give desired compound (14.3 mg, yield: 4.72%) as a yellow solid. $^1$H NMR (400 MHz, DMSO-$d_6$) δ 12.51 (brs, 1H), 8.65 (s, 1H), 7.27 (t, J=21.2 Hz, 8.4 Hz, 1H), 6.39-6.31 (m, 2H), 4.10 (q, J=6.8 Hz, 2H), 3.16 (q, J=7.2 Hz, 2H), 1.35 (t, J=7.2 Hz, 3H), 1.18 (t, J=7.2 Hz, 3H) MS (ESI) m/z: 337.2 [M+H]$^+$.

Example 316. 2-(Ethylamino)-6-methyl-N-(5-nitrothiazol-2-yl)benzamide (B-169)

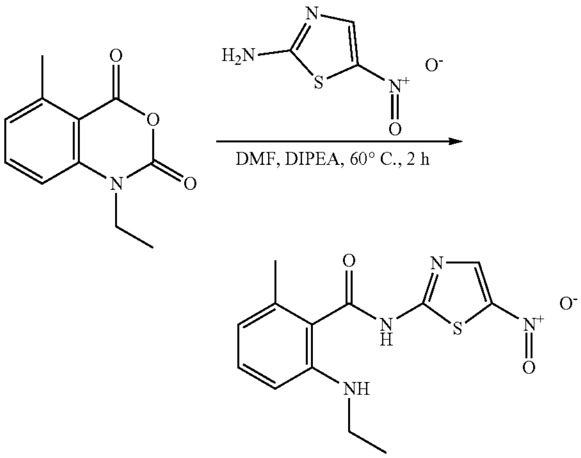

A solution of 1-ethyl-5-methyl-2H-benzo[d][1,3]oxazine-2,4 (1H)-dione (300 mg, crude), 5-nitrothiazol-2-amine (318 mg, 2.19 mmol) and DIPEA (378 mg, 2.92 mmol) in DMF (3 mL) was stirred at 60° C. for 2 h. After being cooled to room temperature, the mixture was purified by prep-HPLC (0.1% TFA) to give the desired compound (4.23 mg, yield: 0.15%) as a yellow solid. $^1$H NMR (400 MHz, DMSO-$d_6$) δ 9.31 (brs, 1H), 8.66 (s, 1H), 7.17 (t, J=8.0 Hz, 1H), 6.55 (d, J=8.4 Hz, 1H), 6.50 (d, J=7.6 Hz, 1H), 3.09 (q, J=7.2 Hz, 2H), 2.15 (s, 3H), 1.11 (t, J=7.2 Hz, 3H). MS (ESI) m/z: 306.7 [M+H]$^+$.

Example 317. 3-Methyl-2-((5-nitrothiazol-2-yl)carbamoyl)phenyl acetate (B-170)

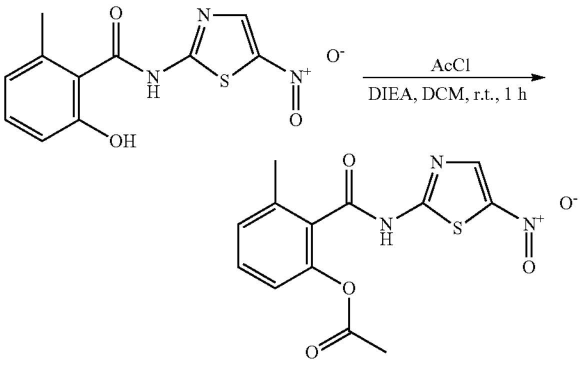

To a solution of 2-hydroxy-6-methyl-N-(5-nitrothiazol-2-yl)benzamide (50 mg, 0.179 mmol) and DIEA (mg, 0.179 mmol) in DCM (5 mL) was added acetyl chloride (15 mg, 0.197 mmol). After being stirred at room temperature for 1 h, the mixture was purified by column chromatography (petroleum ether:EtOAc=1:1) to afford the tide compound (9.42 mg, yield: 16.4%) as a yellow solid. $^1$H NMR (400 MHz, DMSO-$d_6$): δ 13.65 (s, 1H), 8.68 (s, 1H), 7.62 (t, J=8.0 Hz, 1H), 7.25 (d, J=7.2 Hz, 1H), 7.15 (t, J=8.0 Hz, 1H), 2.30 (s, 3H), 2.14 (s, 3H). MS (ESI) m/z: 322.2 [M+H]$^+$.

Example 318. 4-Fluoro-2-methyl-N-(5-nitrothiazol-2-yl)benzamide (B-171)

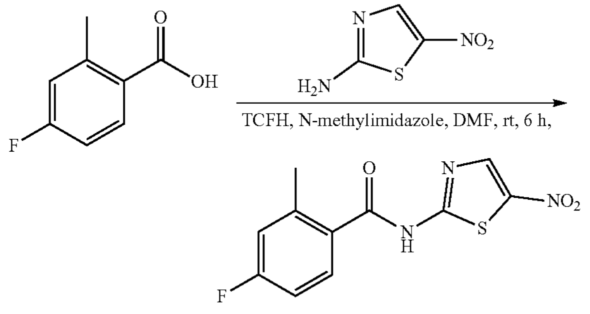

To a solution of 4-fluoro-2-methylbenzoic acid (200 mg, 1.30 mmol) and 5-nitrothiazol-2-amine (188.5 mg, 1.30 mmol) in DMF (3 mL) were added TCFH (364 mg, 1.30 mmol) and N-methylimidazole (319.8 mg, 3.90 mmol). After the mixture was stirred at rt for 6 hours, it was purified by prep-HPLC (0.1% TFA) to give the title compound (127 mg, yield: 77.0%) as a white solid. $^1$H NMR (400 MHz, DMSO-$d_6$) δ 13.52 (s, 1H), 8.70 (s, 1H), 7.77-7.70 (m, 1H), 7.29-7.18 (m, 2H), 2.48 (s, 3H). MS (EST) m/z: 282.2 [M+H]$^+$.

Example 319. 2,4-Dimethyl-N-(5-nitrothiazol-2-yl) benzamide (B-172)

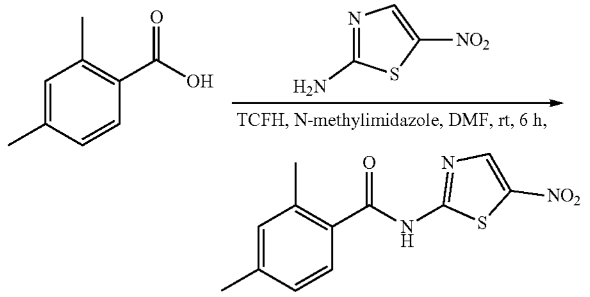

To a solution of 2,4-dimethylbenzoic acid (200 mg, 1.33 mmol) and 5-nitrothiazol-2-amine (193 mg, 1.33 mmol) in DMF (3 mL) were added TCFH (372 mg, 1.33 mmol) and N-methylimidazole (327 mg, 3.99 mmol). After the mixture was stirred at rt for 6 hours, the mixture was purified by prep-HPLC (0.1% TFA) to give the title compound (90.3 mg, yield: 75.2%) as a white solid. $^1$H NMR (400 MHz, DMSO-$d_6$) δ 13.43 (s, 1H), 8.70 (s, 1H), 7.58 (d, J=7.8 Hz, 1H), 7.22-7.12 (m, 2H), 2.41 (s, 3H), 2.34 (s, 3H). MS (ESI) m/z: 278.2 [M+H]$^+$.

Example 320. 2-Methyl-4-nitro-N-(5-nitrothiazol-2-yl)benzamide (B-173)

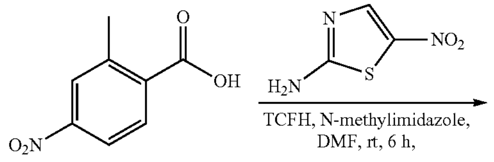

-continued

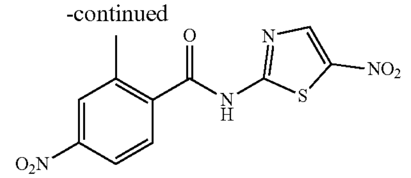

To a solution of 2-methyl-4-nitrobenzoic acid (200 mg, 1.10 mmol) and 5-nitrothiazol-2-amine (160 mg, 1.10 mmol) in DMF (3 mL) were added TCFH (308 mg, 1.10 mmol) and N-methylimidazole (270 mg, 3.3 mmol). After the mixture was stirred at rt for 16 hours, the mixture was purified by prep-HPLC (0.1% TFA) to give the title compound (87.5 mg, yield 91.1%) as a white solid. $^1$H NMR (400 MHz, DMSO-$d_6$) δ 13.80 (s, 1H), 8.73 (s, 1H), 8.25 (d, J=2.4 Hz, 1H), 8.18 (dd, J=8.4, 2.4 Hz, 1H), 7.90 (d, J=8.4 Hz, 1H), 2.52 (s, 3H). MS (EST) m/z: 309.1 [M+H]$^+$.

Example 321. 2,5-Dimethyl-N-(5-nitrothiazol-2-yl) benzamide (B-174)

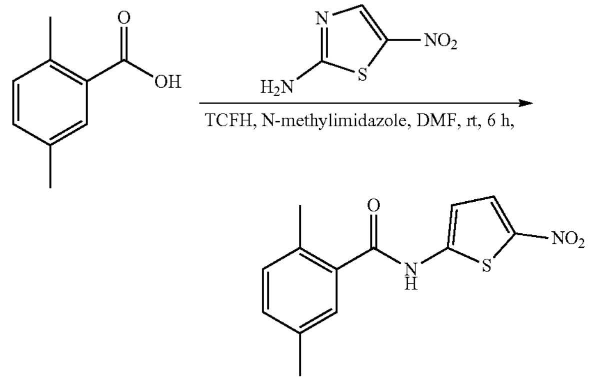

To a solution of 2,5-dimethylbenzoic acid (200 mg, 1.33 mmol) and 5-nitrothiazol-2-amine (193 mg, 1.33 mmol) in DMF (3 mL) were added TCFH (372 mg, 1.33 mmol) and N-methylimidazole (327 mg, 3.99 mmol). After the mixture was stirred at rt for 16 hours, the mixture was purified by prep-HPLC (0.1% TFA) to give the title compound (97.1 mg, yield: 75.2%) as a white solid. $^1$H NMR (400 MHz, DMSO-$d_6$) δ 13.44 (s, 1H), 8.70 (s, 1H), 7.49 (s, 1H), 7.32-7.30 (m, 1H), 7.25 (d, J=7.6 Hz, 1H), 2.38 (s, 3H), 2.33 (s, 3H). MS (ESI) m/z: 278.2 [M+H]$^+$.

Example 322. 2-Methyl-N-(5-methylthiazol-2-yl) benzamide (B-175)

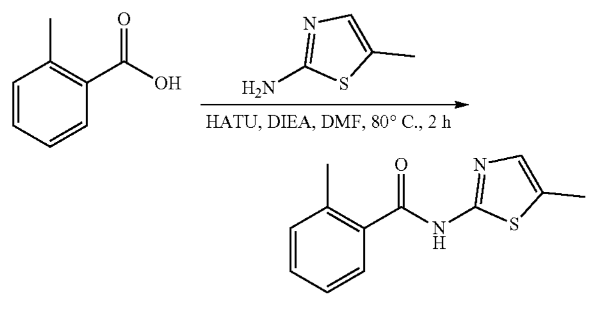

A solution of 2-methylbenzoic acid (100 mg, 0.735 mmol), 5-methylthiazol-2-amine (125 mg, 1.10 mmol), HATU (418 mg, 1.10 mmol) and DIEA (285 mg, 2.21 mmol) in DMF (8 mL) was stirred at 80° C. for 2 hours. The mixture was diluted with water (50 mL) and extracted with EtOAc (3×50 mL). The combined organic phase was washed with brine (2×100 mL), dried over $Na_2SO_4$, filtered and concentrated in vacuum to give a residue, which was purified by prep-HPLC (0.1% formic acid) to give the title compound (50.0 mg, yield: 29.4%) as a white solid. $^1H$ NMR (400 MHz, DMSO-$d_6$): δ 12.3 (brs, 1H), 7.51 (d, J=7.6 Hz, 1H), 7.42 (t, J=7.6 Hz, 1H), 7.32-7.27 (m, 2H), 7.18 (s, 1H), 2.38 (s, 6H). MS (ESI) m/z: 233.1 $[M+H]^+$.

Example 323. 2-Methyl-N-(thiazol-2-yl)benzamide (B-176)

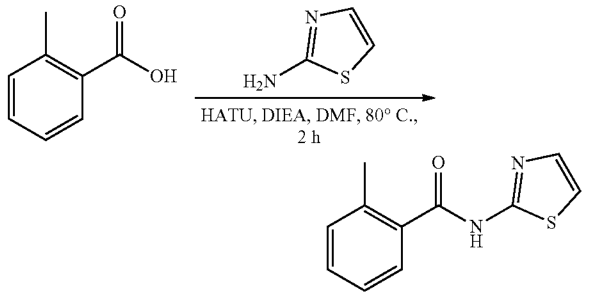

A solution of 2-methylbenzoic acid (100 mg, 0.735 mmol), 5-methylthiazol-2-amine (110 mg, 1.10 mmol), HATU (418 mg, 1.10 mmol) and DIEA (285 mg, 2.21 mmol) in DMF (8 mL) was stirred at 80° C. for 2 hours. The mixture was diluted with water (50 mL) and extracted with EtOAc (3×50 mL). The combined organic phase was washed with brine (2×100 mL), dried over $Na_2SO_4$, filtered and concentrated in vacuum to give a residue. The residue was recrystallized with MeOH (50 mL) to give the title compound (72.0 mg, yield: 45.0%) as a pale-yellow solid. $^1H$ NMR (400 MHz, DMSO-$d_6$): δ 12.48 (brs, 1H), 7.54-7.53 (m, 2H), 7.43 (dd, J=7.6 Hz, 0.8 Hz, 1H), 7.33-7.30 (m, 2H), 7.28 (d, J=3.6 Hz, 1H), 2.39 (s, 3H). MS (ESI) m/z: 219.1 $[M+H]^+$.

Example 324. Heterobifunctional Compounds Bind to DDB1 (FIG. 2)

The binding affinities of heterobifunctional compounds to DDB1 were determined by SPR assay. Purified His-DDB1 proteins were immobilized on a CM5 sensor chip, and a dose range of compound solutions were injected in multi-cycle kinetic format. Data were fit to steady state model and gave equivalent dissociation constants ($K_D$). Data showed that all heterobifunctional compounds bind to DDB1 in a concentration-dependent manner, and the binding affinities ($K_D$) are from 5 μM to 60 μM.

Example 325. Heterobifunctional Compounds Concentration Dependently Reduced P300 and CBP Protein Levels (FIG. 3A and FIG. 3B)

LNCaP cells were treated with selected heterobifunctional compounds at indicated concentrations for 8 hours. Data showed that P300 and CBP proteins levels were reduced in a concentration-dependent manner.

Example 326. Heterobifunctional Compounds Rapidly Reduced P300 and CBP Protein Levels (FIG. 4)

LNCaP cells were treated with selected heterobifunctional compounds at 500 nM for indicated period of time. Data showed that P300 and CBP protein levels were significantly reduced as early as 2-4 hours following treatment.

Figure 5A:
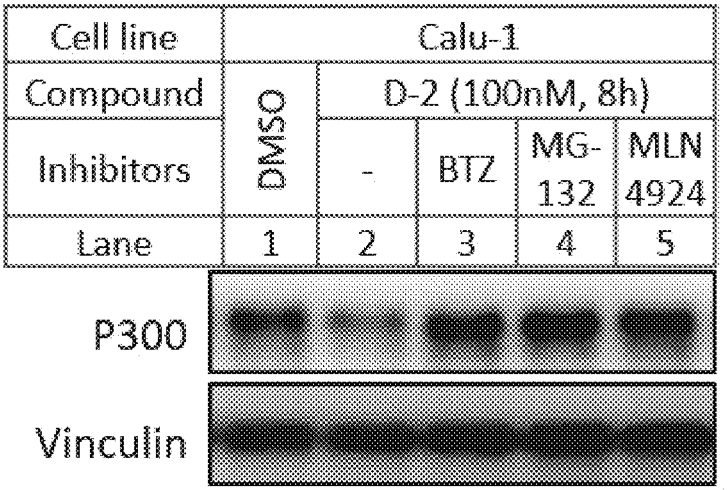
FIG. 5A shows immunoblots of P300 protein expressed by Calu-1 cells after treatment with heterobifunctional compound D-2 in the presence or absence of Bortezomib (BTZ), MG-132, or MLN4924.
Figure 5B:
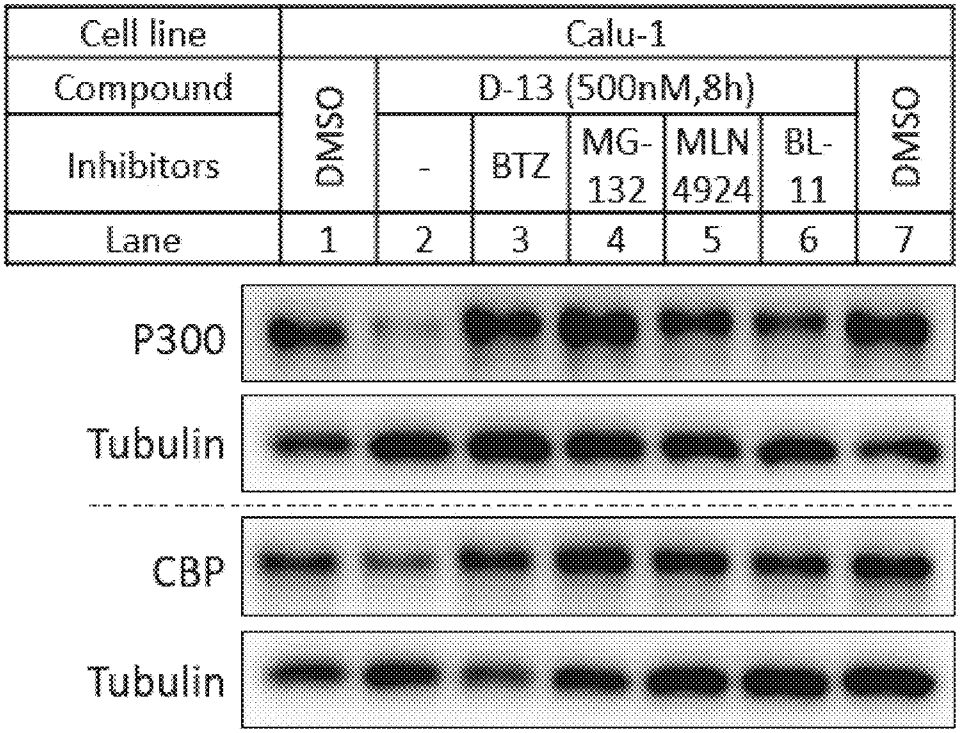
FIG. 5B shows immunoblots of P300 protein expressed by Calu-1 cells after treatment with heterobifunctional compound D-13 in the presence or absence of BTZ, MG-132, MLN4924, or BL-11.

Example 327. Heterobifunctional Compound-Mediated Degradation of P300 is Dependent on the Ubiquitin-Proteasome System and the Interaction with DDB1 (FIG. 5A and FIG. 5B)

Calu-1 cells were treated with a single dose of heterobifunctional compounds in the presence or absence of 200 nM Bortczomib (BTZ), 10 μM MG-132 (MG), 5 μM MLN4924 (MLN), or 10 μM BL-11. Data showed that heterobifunctional compound-mediated degradation of P300 is compromised by a proteasome inhibitor, MG-132 or Bortezomib, or a cullin E3 ligase inhibitor, MLN4924, or an excessive DDB1 ligand, BL-11.

Example 328. Heterobifunctional Compounds Suppressed Viability of LNCaP Prostate Cancer Cells (FIG. 6)

LNCaP cells were treated with GNE-781 or selected heterobifunctional compounds for 3 days at indicated concentrations following a 3-fold serial dilution. Data showed that cell viability was significantly reduced in the presence of heterobifunctional compounds in a concentration-dependent manner.

Example 329. Heterobifunctional Compounds Concentration Dependently Reduced CDK4 and CDK6 Protein Levels (FIG. 7A and FIG. 7B)

Calu-1 cells were treated with selected heterobifunctional compounds at indicated concentrations for 16 hours. Data showed that CDK4 and CDK6 proteins levels were reduced in a concentration-dependent manner.

Example 330. Heterobifunctional Compounds Reduced CDK4 and CDK6 Protein Levels 16 Hours after Treatment (FIG. 8)

Calu-1 cells were treated with selected heterobifunctional compounds at 1 BM for indicated period of time. Data showed that CDK4 and CDK6 protein levels were significantly reduced 16 hours after treatment.

Example 331. DDB1 Binding

The binding affinities ($K_D$ values) of selected heterobifunctional compounds and peptides are set forth in Table 6 and Table 7.

TABLE 6

DDB1 binder activities

| Compound | Binding |
|---|---|
| B-1 | B |
| B-2 | B |
| B-3 | B |
| B-4 | A |
| B-5 | C |
| B-6 | A |
| B-7 | A |
| B-8 | A |
| B-9 | B |
| B-10 | B |
| B-11 | B |
| B-12 | A |
| B-13 | B |
| B-14 | B |
| B-15 | B |
| B-17 | A |
| B-18 | B |
| B-19 | B |
| B-21 | C |
| B-22 | B |
| B-23 | B |
| B-24 | B |
| B-25 | B |
| B-27 | B |
| B-29 | B |
| B-30 | B |
| B-31 | B |
| B-32 | B |
| B-33 | A |
| B-34 | A |
| B-35 | B |
| B-36 | B |
| B-37 | C |
| B-38 | A |
| B-39 | B |
| B-40 | B |
| B-41 | C |
| B-42 | B |
| B-43 | B |
| B-45 | A |
| B-46 | B |
| B-47 | C |
| B-48 | C |
| B-51 | B |
| B-53 | B |
| B-54 | B |
| B-55 | B |
| B-56 | C |
| B-57 | B |
| B-58 | B |
| B-59 | B |
| B-60 | B |
| B-61 | B |
| B-62 | B |
| B-63 | C |
| B-64 | B |
| B-65 | B |
| B-66 | A |
| B-67 | B |
| B-68 | B |
| B-69 | C |
| B-70 | A |
| B-71 | B |
| B-72 | A |
| B-73 | C |
| B-74 | A |
| B-75 | C |
| B-76 | C |
| B-77 | C |
| B-78 | B |
| B-80 | B |
| B-81 | B |
| B-82 | B |
| B-83 | C |
| B-84 | A |
| B-85 | B |

TABLE 6-continued

DDB1 binder activities

| Compound | Binding |
|---|---|
| B-86 | A |
| B-88 | B |
| B-89 | B |
| B-91 | B |
| B-92 | B |
| B-93 | B |
| B-96 | B |
| B-97 | C |
| B-98 | B |
| B-99 | B |
| B-100 | B |
| B-101 | B |
| B-102 | A |
| B-103 | B |
| B-104 | B |
| B-105 | C |
| B-106 | A |
| B-107 | B |
| B-108 | B |
| B-109 | B |
| B-110 | A |
| B-111 | B |
| B-112 | A |
| B-113 | B |
| B-114 | A |
| B-115 | C |
| B-116 | B |
| B-117 | B |
| B-118 | B |
| B-119 | B |
| B-120 | B |
| B-121 | B |
| B-122 | C |
| B-123 | A |
| B-124 | A |
| B-125 | A |
| B-128 | B |
| B-129 | B |
| B-130 | C |
| B-131 | A |
| B-134 | C |
| B-135 | B |
| B-136 | B |
| B-137 | B |
| B-138 | B |
| B-139 | A |
| B-140 | B |
| B-141 | B |
| B-142 | B |
| B-143 | B |
| B-144 | B |
| B-145 | B |
| B-146 | B |
| B-148 | B |
| B-149 | B |
| B-150 | B |
| B-151 | C |
| B-152 | A |
| B-153 | B |
| B-154 | C |
| B-155 | C |
| B-156 | C |
| B-157 | C |
| B-158 | B |
| B-159 | C |
| B-160 | B |
| B-161 | C |
| B-162 | C |
| B-163 | C |
| B-164 | C |
| B-165 | B |
| B-166 | B |
| B-167 | C |
| B-168 | C |
| B-169 | B |
| B-170 | C |

TABLE 6-continued

| DDB1 binder activities | |
|---|---|
| Compound | Binding |
| B-171 | B |
| B-172 | B |
| B-173 | C |
| B-174 | A |
| B-175 | A |
| B-176 | A |
| Peptide 1 (SEQ ID NO: 1) | A |
| Peptide 2 (SEQ ID NO: 2) | A |
| Peptide 3 (SEQ ID NO: 3) | A |
| Peptide 4 (SEQ ID NO: 4) | A |
| Peptide 5 (SEQ ID NO: 5) | A |
| Peptide 6 (SEQ ID NO: 6) | A |
| Peptide 7 (SEQ ID NO: 7) | B |

Table 6 key:
A: Kd < 20 uM;
B: Kd 20-100 uM;
C: Kd > 100 uM.

TABLE 7

| Activity of DDB1 binding moieties with linkers and/or target protein binding moiety | |
|---|---|
| Compound | Binding ($K_d$) |
| BL-1 | A |
| BL-2 | B |
| BL-3 | B |
| BL-4 | D |
| BL-5 | B |
| BL-6 | B |
| BL-7 | B |
| BL-8 | B |
| BL-9 | A |
| BL-11 | B |
| BL-20 | B |
| D-2 | B |
| D-7 | B |
| D-13 | B |
| D-23 | B |
| D-26 | B |
| D-29 | B |
| D-31 | B |
| D-32 | B |
| D-35 | B |
| D-37 | B |
| D-45 | A |
| D-46 | A |
| D-47 | A |
| D-48 | A |
| D-49 | A |

Table 7 key:
A: Kd < 20 uM;
B: Kd 20-100 uM;
C: Kd > 100 uM.

Figure 9:
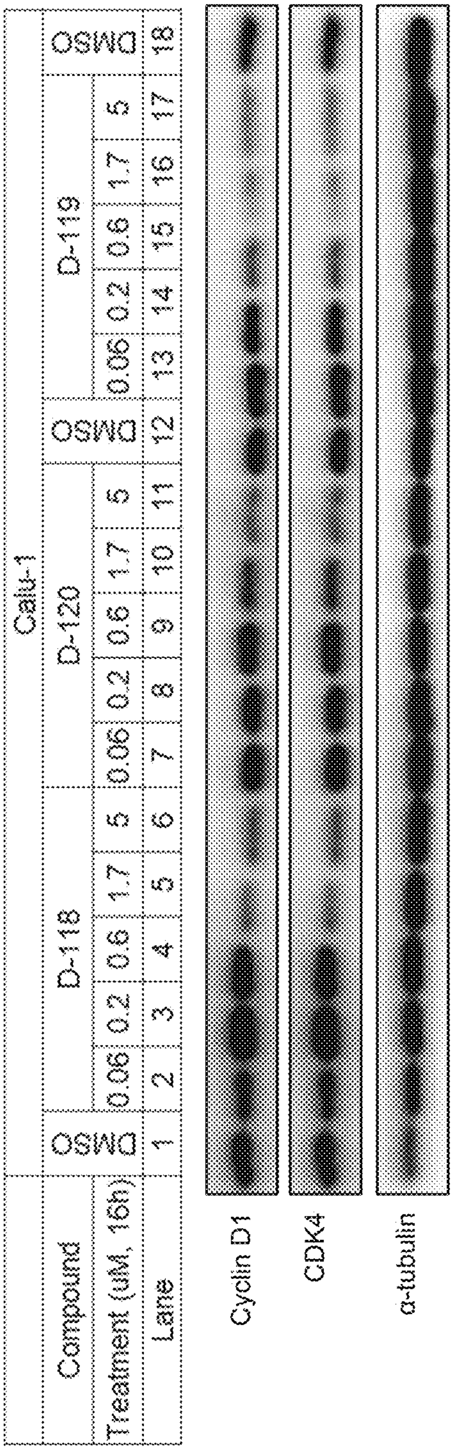
FIG. 9 shows immunoblots of a cyclin and a cyclin dependent kinase expressed by Calu-1 cells after treatment with heterobifunctional compound D-118, D-119, or D-120 at indicated concentrations for 16 hours.

Example 332. Heterobifunctional Compounds Concentration Dependently Reduced CDK4 and CyclinD1 Protein Levels (FIG. 9)

Calu-1 cells were treated with selected heterobifunctional compounds at indicated concentrations for 16 hours. Data showed that CDK4 and cyclinD1 proteins levels were reduced in a concentration-dependent manner.

Figure 10:
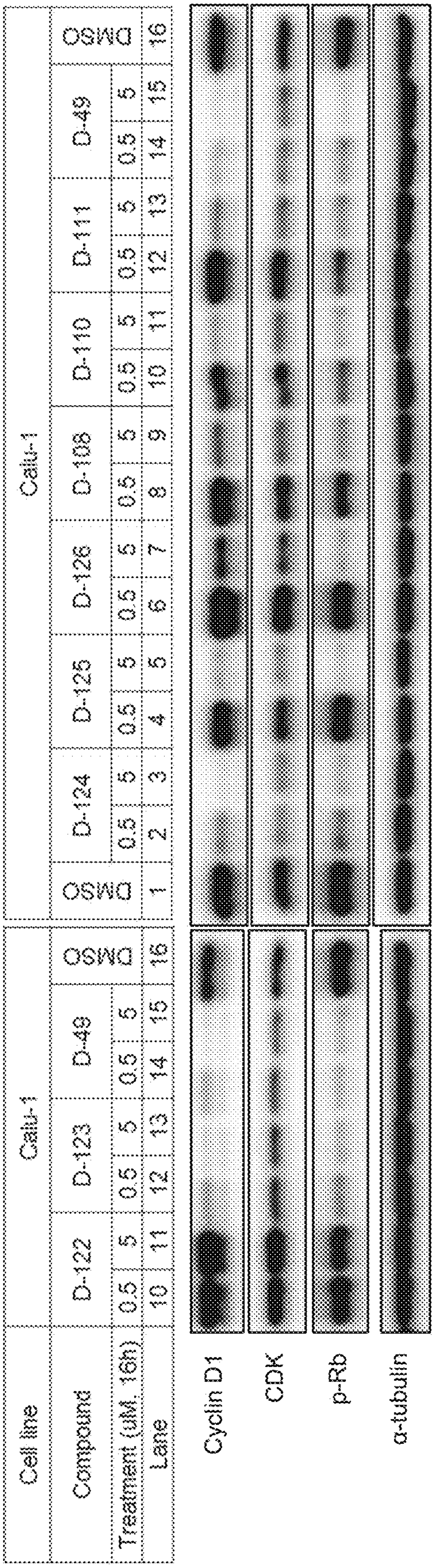
FIG. 10 shows immunoblots of a cyclin, a cyclin dependent kinase, and phospho-Rb expressed by Calu-1 cells after treatment with various amounts of heterobifunctional compound D-49, D-108, D-110, D-111, D-122, D-123, D-124, D-125, or D-126 for 16 hours.

Example 333. Heterobifunctional Compounds Concentration Dependently Reduced CDK4 and CyclinD1 Protein Levels (FIG. 10)

Calu-1 cells were treated with selected heterobifunctional compounds at indicated concentrations for 16 hours. Data showed that CDK4 and cyclinD1 proteins levels and CDK4/6 activity (as evidenced by Rb phosphorylation) were reduced in a concentration-dependent manner, so did the CDK4/6 activity.

Figure 11:
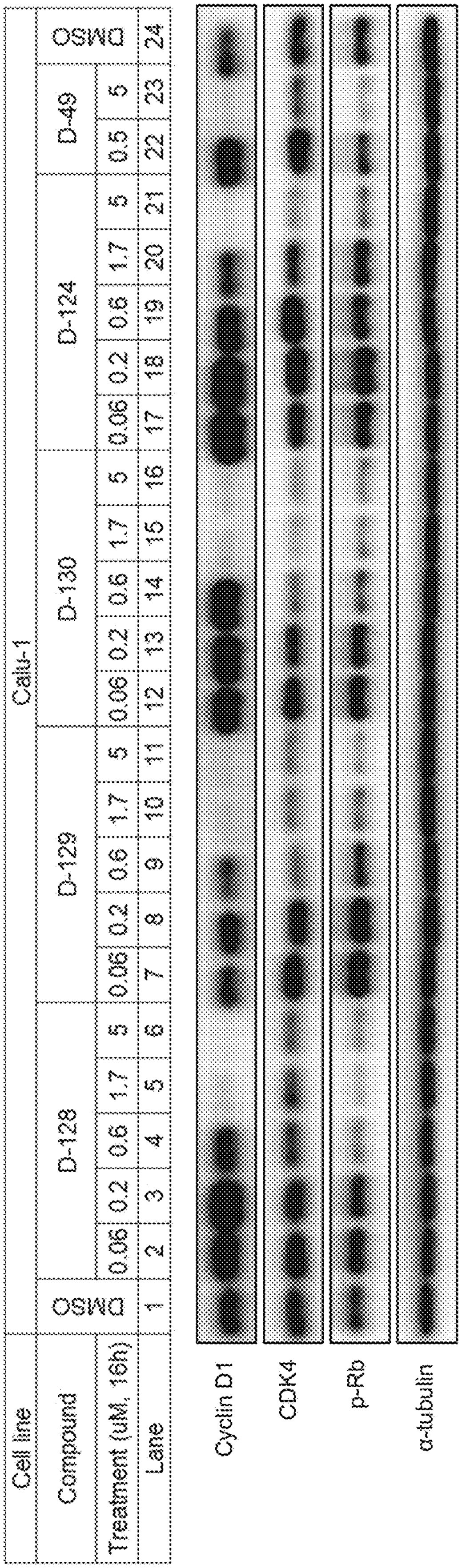
FIG. 11 shows immunoblots of a cyclin, a cyclin dependent kinase, and phospho-Rb expressed by Calu-1 cells after treatment with various amounts of heterobifunctional compound D-49, D-124, D-128, D-129, and D-130 for 16 hours.

Example 334. Heterobifunctional Compounds Concentration Dependently Reduced CDK4 and cyclinD1 Protein Levels (FIG. 11)

Calu-1 cells were treated with selected heterobifunctional compounds at indicated concentrations for 16 hours. Data showed that CDK4 and cyclinD1 proteins levels and Rb phosphorylation were reduced in a concentration-dependent manner.

Example 335. Heterobifunctional Compounds Suppressed Viability of Calu-1, MDA-MB-453 and MIA PaCa-2 Cancer Cells (FIG. 12)

Calu-1, MDA-MB-453 or MIA PaCa-2 cancer cells were treated with Palbociclib or selected heterobifunctional compounds for 5 days at indicated concentrations following a 2-fold serial dilution. Data showed that cell viability was significantly reduced in the presence of heterobifunctional compounds in a concentration-dependent manner.

Example 336. Heterobifunctional Compounds Suppressed Cell Viability (Table 8)

A variety of cancer cell lines were treated with Palbociclib or selected heterobifunctional compounds for 5 days at indicated concentrations in FIG. 12. The cell viability inhibitory effects ($IC_{50}$ values) of selected heterobifunctional compounds are set forth in Table 8.

TABLE 8

| Activity of DDB1 binding moieties with linkers and target protein binding moiety at the inhibition of multiple cancer lines. | | | | |
|---|---|---|---|---|
| | $IC_{50}$ (uM) | | | |
| Cell line | Palbociclib | D-128 | D-129 | D-130 |
| MDAMB-468 | C | B | B | B |
| MDAMB-453 | C | A | A | A |
| Hs 578T | B | A | A | A |
| BT-549 | C | A | A | A |
| HCC1937 | C | A | A | A |
| HCT116 | C | A | A | A |
| A375 | B | A | A | B |
| SK-MEL-28 | B | A | A | A |
| SK-N-SH | C | A | A | A |
| NCI-H358 | C | A | A | A |
| Calu-1 | C | A | A | A |
| HCC827 | C | A | A | A |
| MIA PaCa-2 | B | A | A | A |

Table 8 key:
A: Kd < 2 uM;
B: Kd 2-10 uM;
C: Kd > 10 uM

Figure 13:
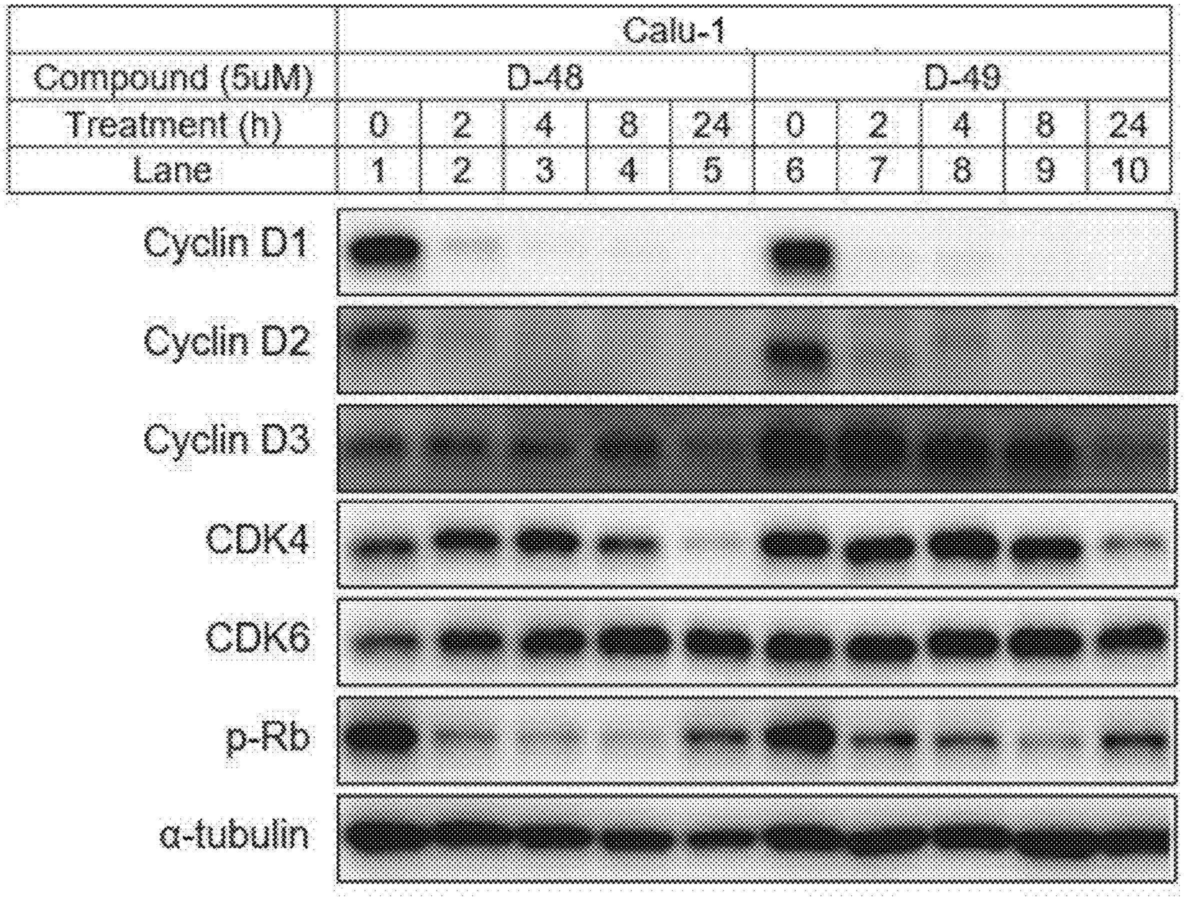
FIG. 13 immunoblots of cyclins, cyclin dependent kinases, and phospho-Rb proteins after treatment with 5 uM of heterobifunctional compound D-48 or D-49 for various amounts of time.

Example 337. Heterobifunctional Compounds Reduced CyclinD1/D2 Earlier than CDK4/6 Protein Levels (FIG. 13)

Calu-1 cells were treated with selected heterobifunctional compounds at 5 μM for indicated period of time. Data showed that cyclinD1/D2 protein levels were significantly reduced as early as 2 hours following treatment, while CDK4 protein levels were reduced 8 hours after treatment.

Figure 14:
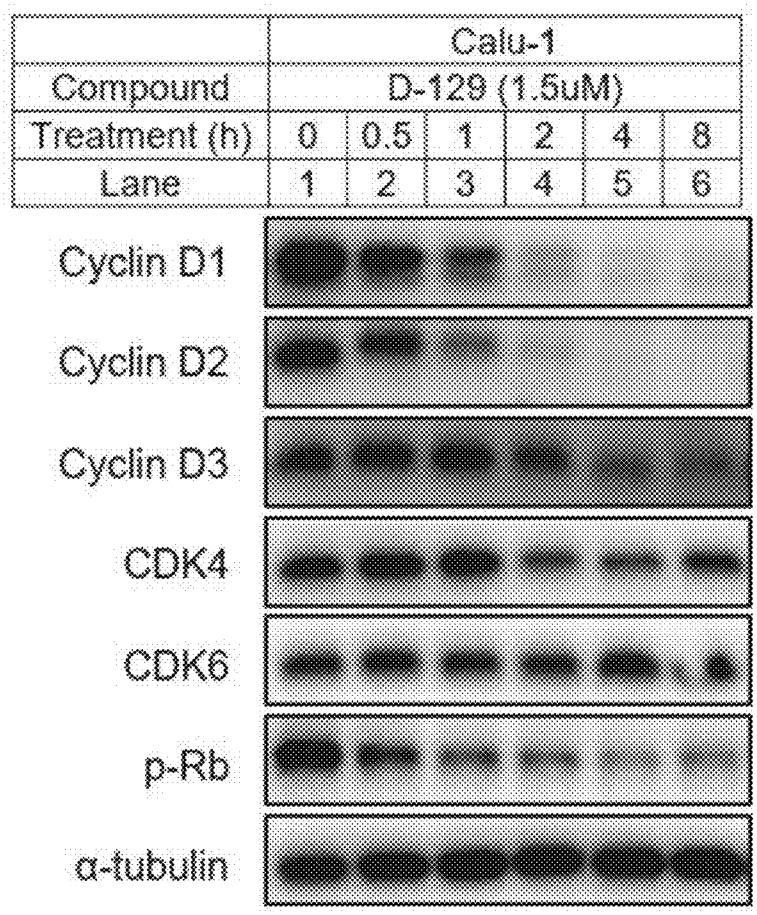
FIG. 14 shows immunoblots of cyclins, cyclin dependent kinases, and phospho-Rb after treatment with 1.5 uM of heterobifunctional compound D-129 for various amounts of time.

Example 338. Heterobifunctional Compounds Reduced CyclinD1/D2 Earlier than CDK4/6 Protein Levels (FIG. 14)

Calu-1 cells were treated with selected heterobifunctional compounds at 1.5 μM for indicated period of time. Data showed that cyclinD1/D2 protein levels were significantly reduced as early as 1 hour following treatment, while CDK4 protein levels were reduced 2 hours after treatment.

Example 339. Materials and Methods of Experiments Described Herein

Protein Expression and Purification. Human DDB1 (UniPro: Q16531) coding sequences were cloned into pFastBacHTB vector and were expressed in High5 cells using Bac-to-Bac baculovirus expression system (Thermo Fisher Scientific). The expression construct for DDB1 includes a N-terminal His6-tag (SEQ ID NO: 8) to facilitate the purification. DDB1 proteins were obtained from supernatant of cell lysates and purified through sequential application of Ni affinity (Ni-NTA column. Bio-Rad), and size-exclusion (Superdex 200 16/600GL column, GE Healthcare) column chromatography.

Surface plasmon resonance (SPR) binding assay. All SPR studies were performed on a Biacore X100 plus or T200 instrument (GE Healthcare). Immobilization of purified His-DDB1 was carried out at 25° C. using a CM5 sensor chip. The surface was pre-equilibrated in HBS-EP running buffer (10 mM HEPES, pH7.4, 150 mM NaCl, 3 mM EDTA, 0.05% P20), then activated with EDC/NHS. His-DDB1 proteins were immobilized by amine coupling to a density of 11,000-13,000 resonance units (RUs) on flow cell FC2, whereas flow cell FC1 was used as reference. Both DDB1 immobilized and reference surfaces were deactivated with 1M ethanolamine.

All interaction experiments were performed at 25° C. Heterobifunctional compounds were prepared and serially diluted in HBS-EP running buffer containing final 5% DMSO (6-point two-fold serial dilution, 100 μM-3.125 μM final concentration of compounds). Compound Solutions were injected individually in multi-cycle kinetic format without regeneration (flow rate 30 td/min, association time 120 s, dissociation time 120 s). Sensorgrams from reference surfaces and blank injections were subtracted from the raw data (double-referencing) and the data was solvent-corrected prior to analysis. All data were fit to steady state affinity model using Biacore Evaluation Software and gave equivalent dissociation constants ($K_D$).

Cell Culture. LNCaP (clone FGC), Calu-1, MDA-MB-468, MDA-MB-453, NCI-H358, HCC1937, BT-549, HCT116, A375, SK-MEL-28, SK—N-SH, MIA PaCa-2, HS 578T, HCC827, MIA PaCa-2, and other cells were cultured at 37° C. with 5% $CO_2$ in DMEM or RPMI 1640 Medium supplemented with 10% fetal bovine serum. Cells were authenticated using the short tandem repeat (STR) assays. *Mycoplasma* test results were negative.

Antibodies and reagents. Anti-P300 (86377), anti-CBP (7389), anti-CDK4 (12790), anti-CDK6 (3136), anti-phospho-Rb (8516), anti-Cyclin D1 (2978), anti-Cyclin D2 (3741), anti-CyclinD3 (2936) and anti-vinculin (18799) antibodies were purchased from Cell Signaling Technology. Anti-DDB1 antibody (ab109027) was purchased from abcam. HRP-conjugated anti-α-tubulin antibody (GN14310-AT-S) was purchased from GNI. Media and other cell culture reagents were purchased from Thermo Fisher Scientific. CellTiter-Glo Luminescent Assay kit was purchased from Promega.

Immunoblotting. Cultured cells were washed with cold PBS once and lysed in cold RIPA buffer supplemented with protease inhibitors and phosphatase inhibitors (Beyotime Biotechnology). The solutions were then incubated at 4° C. for 30 minutes with gentle agitation to fully lyse cells. Cell lysates were centrifuged at 13,000 rpm for 10 minutes at 4° C. and pellets were discarded. Total protein concentrations in the lysates were determined by BCA assays (Beyotime Biotechnology). Cell lysates were mixed with Laemmli loading buffer to 1× and heated at 99° C. for 5 min. Proteins were resolved on SDS-PAGE and visualized by chemiluminescence. Images were taken by a ChemiDoc MP Imaging system (Bio-Rad). Protein bands were quantitated using the accompanied software provided by Bio-Rad.

Cell viability assay. Cells were seeded at a density of 5000 cells per well in 96-well assay plates and treated with test compounds following a 11-point 3-fold serial dilution for 3-5 days. Three days later, cell viability was determined using the CellTiter-Glo Assay Kit according to the manufacturer's instructions. The dose-response curves were determined and $IC_{50}$ values were calculated using the GraphPad Prism software following a nonlinear regression (least squares fit) method.

Example 340. Clinical Trials

The compounds described herein will be tested in human clinical studies to determine their efficacy for degrading the target proteins described herein. For example, clinical tests including the degradation of a TRK, cyclin, CDK, CREB, CBP, or P300 using compounds described herein din humans will be performed. In some cases, compounds that perform best in in vivo cell culture experiments or in vivo animal studies will be chosen for clinical tests.

While preferred embodiments of the present invention have been shown and described herein, it will be obvious to those skilled in the art that such embodiments are provided by way of example only.

Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

```
Sequence total quantity: 8
SEQ ID NO: 1             moltype = AA  length = 14
FEATURE                  Location/Qualifiers
REGION                   1..14
                         note = Description of Artificial Sequence: Synthetic peptide
source                   1..14
```

```
                        mol_type = protein
                        organism = synthetic construct
SEQUENCE: 1
ILPKVLHKRT LGLS                                              14

SEQ ID NO: 2            moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 2
ILPKVWHKRE LGLS                                              14

SEQ ID NO: 3            moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 3
ILPKVLHKRT LGL                                               13

SEQ ID NO: 4            moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 4
ILPKVLHKRT FGL                                               13

SEQ ID NO: 5            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 5
KVLHKRTLG                                                    9

SEQ ID NO: 6            moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 6
NFTSRLNRRA SFP                                               13

SEQ ID NO: 7            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 7
SRLNRRASF                                                    9

SEQ ID NO: 8            moltype = AA  length = 6
FEATURE                 Location/Qualifiers
REGION                  1..6
                        note = Description of Artificial Sequence: Synthetic 6xHis
                         tag
source                  1..6
                        mol_type = protein
                        organism = synthetic construct
SEQUENCE: 8
HHHHHH                                                       6
```

What is claimed:

1. A ligand comprising a DNA damage-binding protein 1 (DDB1) binding moiety, wherein the ligand is a heterobifunctional ligand comprising the structure of Formula (IIc), Formula (IId), or Formula (IIe):

Formula (IIc)

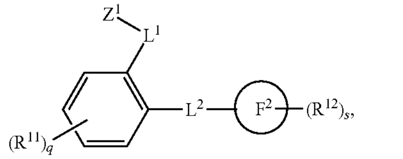

Formula (IId)

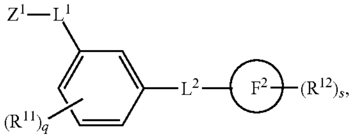

or

Formula (IIe)

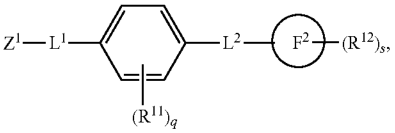

or a pharmaceutically acceptable salt thereof, wherein:

$F^2$ is a 5-membered heteroaryl;

$L^2$ is a bond, —C(═O)$NR^{13}$—, —$NR^{13}$C(═O)—, —C(═O)—, —C(═S)—, —S—, —S(═O), —$S(═O)_2$—, —S(═O)$NR^{13}$—, —$NR^{13}$S(═O)—, —$S(═O)_2NR^{13}$—, —$NR^{13}S(═O)_2$—, —O—, $C_1$-$C_4$ alkyl, C1-$C_4$ haloalkyl, $C_1$-$C_4$ heteroalkyl, $C_1$-$C_4$ alkoxy, $C_1$-$C_4$ alkylamino, $C_1$-$C_4$ alkenyl, or $C_1$-$C_4$ alkynyl, wherein each $R^{13}$ is independently hydrogen, —S(═O)$R^b$, —$S(═O)_2R^d$, —$S(═O)_2NR^cR^d$, —C(═O)$R^b$, —$CO_2R^a$, —C(═O)$NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl; wherein the alkyl, alkenyl, alkynyl, and heteroalkyl is optionally substituted with one, two, or three of halogen, —$OR^a$, or —$NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

each $R^{11}$ and $R^{12}$ is independently hydrogen, halogen, —CN, —$R^a$, —$OR^a$, —$SR^a$, —S(═O)$R^b$, —$NO_2$, —$NR^cR^d$, —$S(═O)_2R^d$, —$NR^aS(═O)_2R^d$, —$S(═O)_2NR^cR^d$, —C(═O)$R^b$, —OC(═O)$R^b$, —$CO_2R^a$, —$OCO_2R^a$, —C(═O)$NR^cR^d$, —OC(═O) $NR^cR^d$, —$NR^a$C(═O)$NR^cR^d$, —$NR^a$C(═O)$R^b$, —$NR^a$C(═O)$OR^a$$C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —$R^a$, —$OR^a$, or $NR^cR^d$; and the carbocyclyl, heterocyclyl, aryl, and heteroaryl is optionally substituted with one, two, or three of halogen, $C_1$-$C_6$ alkyl, $C_1$-$C_6$ haloalkyl, —$R^a$, —$OR^a$, or —$NR^cR^d$;

each $R^a$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ carbocyclyl, $C_2$-$C_8$ heterocyclyl, aryl, or heteroaryl, wherein the alkyl, alkenyl, alkynyl, and heteroalkyl is optionally substituted with one, two, or three of halogen, —OH, —OMe, or —$NH_2$; and the carbocyclyl, heterocyclyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$, together with the nitrogen atom to which they are attached, form a heterocyclyl or heteroaryl, wherein the heterocyclyl and heteroaryl is optionally substituted with one, two, or three of halogen, $C_1$-$C_6$ alkyl, $C_1$-$C_6$ haloalkyl, —OH, —OMe, or —$NH_2$;

q is an integer of 1-4;

s is an integer of 1-5;

$L^1$ is a linker; and $Z^1$ is a target protein binding moiety.

2. The ligand of claim 1, or a pharmaceutically acceptable salt thereof, wherein the linker comprises —$(CH_2)_{p2}NH(CH_2)_{p1}$NH—, —$(CH_2)_{p2}NH(CH_2)_{p1}$C(═O)NH—, —$(CH_2)_{p2}NH(CH_2)_{p1}$NHC(═O)—, —$(CH_2)_{p2}NH(CH_2CH_2)(OCH_2CH_2)_{p1}$NH—, —$(CH_2)_{p2}NH(CH_2CH_2)(OCH_2CH_2)_{p1}$C(═O)NH—, or —$(CH_2)_{p2}NH(CH_2CH_2)(OCH_2CH_2)_{p1}$NHC(═O)—, wherein pl is 1-15, and p2 is 0-15.

3. The ligand of claim 1, or a pharmaceutically acceptable salt thereof, wherein $L^2$ is —C(═O)NH—.

4. The ligand of claim 1, or a pharmaceutically acceptable salt thereof, wherein $L^2$ is —C(═O)N($C_1$-$C_5$ alkyl)-.

5. The ligand of claim 1, or a pharmaceutically acceptable salt thereof, wherein $F^2$ is triazolyl, tetrazolyl, furanyl, pyrrolyl, thiazolyl, oxazolyl, isoxazolyl, imidazolyl, pyrazolyl, thiadiazolyl, or oxadiazolyl.

6. The ligand of claim 1, or a pharmaceutically acceptable salt thereof, wherein $F^2$ is thiazolyl, oxazolyl, furyl, or thiophenyl.

7. The ligand of claim 1, or a pharmaceutically acceptable salt thereof, wherein $F^2$ is thiazolyl.

8. The ligand of claim 1, or a pharmaceutically acceptable salt thereof, wherein $F^2$ is thiophenyl.

9. The ligand of claim 1, or a pharmaceutically acceptable salt thereof, wherein q is 1 or 2.

10. The ligand of claim 1, or a pharmaceutically acceptable salt thereof, wherein s is 1 or 2.

11. The ligand of claim 1, or a pharmaceutically acceptable salt thereof, wherein each $R^{11}$ is independently hydrogen, —$NR^a$C(═O)$R^b$, or $C_1$-$C_3$ alkyl.

12. The ligand of claim 1, or a pharmaceutically acceptable salt thereof, wherein each $R^a$ is independently hydrogen.

13. The ligand of claim 1, or a pharmaceutically acceptable salt thereof, wherein each $R^b$ is independently $C_1$-$C_3$ alkyl.

14. The ligand of claim 1, or a pharmaceutically acceptable salt thereof, wherein each $R^b$ is independently methyl.

15. The ligand of claim 1, or a pharmaceutically acceptable salt thereof, wherein each $R^{12}$ is independently —$NO_2$ or $C_1$-$C_6$ alkyl.

16. The ligand of claim 1, or a pharmaceutically acceptable salt thereof, wherein each $R^{12}$ is independently —$NO_2$ or methyl.

17. The ligand of claim 1, or a pharmaceutically acceptable salt thereof, wherein Zi is a target protein binding moiety that binds to CBP or P300.

18. The ligand of claim 1, selected from the group consisting of:

2-(6-aminohexanamido)-N-(4-methyl-5-nitrothiazol-2-yl)benzamide;

2-(3-(2-(3-(2-aminoethoxy)propoxy)ethoxy)propanamido)-N-(4-methyl-5-nitrothiazol-2-yl)benzamide;

2-acetamido-N4-(6-aminohexyl)-N1-(4-methyl-5-nitrothiazol-2-yl)terephthalamide;

2-acetamido-N4-(2-(2-(2-(2-aminoethoxy)ethoxy)ethoxy)ethyl)-N1-(4-methyl-5-nitrothiazol-2-yl)terephthalamide;

2-acetamido-N4-(2-(2-(2-(2-aminoethoxy)ethoxy)ethoxy)ethyl)-N1-(5-nitrothiazol-2-yl)terephthalamide;

2-acetamido-4-((7-aminoheptyl)amino)-N-(4-methyl-5-nitrothiazol-2-yl)benzamide;

2-acetamido-4-((2-(2-(2-(2-aminoethoxy)ethoxy)ethoxy)ethyl)amino)-N-(4-methyl-5-nitrothiazol-2-yl)benzamide;

2-acetamido-4-((2-(2-(2-(2-aminoethoxy)ethoxy)ethoxy)ethyl)amino)-N-(5-nitrothiazol-2-yl)benzamide;

2-acetamido-4-((2-aminoethyl)amino)-N-(4-methyl-5-nitrothiazol-2-yl)benzamide;

2-acetamido-4-((4-aminobutyl)amino)-N-(4-methyl-5-nitrothiazol-2-yl)benzamide;

2-acetamido-4-((6-aminohexyl)amino)-N-(4-methyl-5-nitrothiazol-2-yl)benzamide;

2-acetamido-4-((8-aminooctyl)amino)-N-(4-methyl-5-nitrothiazol-2-yl)benzamide;

2-acetamido-4-((10-aminodecyl)amino)-N-(4-methyl-5-nitrothiazol-2-yl)benzamide;

2-acetamido-4-((2-(2-aminoethoxy)ethyl)amino)-N-(4-methyl-5-nitrothiazol-2-yl)benzamide;

2-acetamido-4-((2-(2-(2-aminoethoxy)ethoxy)ethyl)amino)-N-(4-methyl-5-nitrothiazol-2-yl)benzamide;

2-acetamido-4-((14-amino-3,6,9,12-tetraoxatetradecyl)amino)-N-(4-methyl-5-nitrothiazol-2-yl)benzamide;

2-acetamido-4-((17-amino-3,6,9,12, 15-pentaoxaheptadecyl)amino)-N-(4-methyl-5-nitrothiazol-2-yl)benzamide;

2-acetamido-4-((20-amino-3,6,9,12,15,18-hexaoxaicosyl)amino)-N-(4-methyl-5-nitrothiazol-2-yl)benzamide;

2-acetamido-4-((4-aminobutyl)amino)-N-(5-nitrothiophen-2-yl)benzamide;

2-acetamido-4-((3-aminopropyl)amino)-N-(4-methyl-5-nitrothiazol-2-yl)benzamide;

2-acetamido-4-((5-aminopentyl)amino)-N-(4-methyl-5-nitrothiazol-2-yl)benzamide;

2-acetamido-4-((11-aminoundecyl)amino)-N-(4-methyl-5-nitrothiazol-2-yl)benzamide;

3-((3-acetamido-4-((4-methyl-5-nitrothiazol-2-yl)carbamoyl)phenyl)amino)propanoic acid;

7-((3-acetamido-4-((4-methyl-5-nitrothiazol-2-yl)carbamoyl)phenyl)amino)heptanoic acid;

3-(2-(2-(2-((3-acetamido-4-((4-methyl-5-nitrothiazol-2-yl)carbamoyl)phenyl)amino)ethoxy)ethoxy)ethoxy)propanoic acid;

(3-acetamido-4-((4-methyl-5-nitrothiazol-2-yl)carbamoyl)phenyl) glycine;

6-((3-acetamido-4-((4-methyl-5-nitrothiazol-2-yl)carbamoyl)phenyl)amino)hexanoic acid;

10-((3-acetamido-4-((4-methyl-5-nitrothiazol-2-yl)carbamoyl)phenyl)amino)decanoic acid;

11-((3-acetamido-4-((4-methyl-5-nitrothiazol-2-yl)carbamoyl)phenyl)amino)undecanoic acid;

3-(2-(2-((3-acetamido-4-((4-methyl-5-nitrothiazol-2-yl)carbamoyl)phenyl)amino)ethoxy)ethoxy)propanoic acid;

2-acetamido-4-((9-aminononyl)amino)-N-(4-methyl-5-nitrothiazol-2-yl)benzamide;

4-((3-acetamido-4-((4-methyl-5-nitrothiazol-2-yl)carbamoyl)phenyl)amino)butanoic acid;

5-((3-acetamido-4-((4-methyl-5-nitrothiazol-2-yl)carbamoyl)phenyl)amino)pentanoic acid;

3-(2-((3-acetamido-4-((4-methyl-5-nitrothiazol-2-yl)carbamoyl)phenyl)amino)ethoxy)propanoic acid;

1-((3-acetamido-4-((4-methyl-5-nitrothiazol-2-yl)carbamoyl)phenyl)amino)-3,6,9,12-tetraoxapentadecan-15-oic acid;

1-((3-acetamido-4-((4-methyl-5-nitrothiazol-2-yl)carbamoyl)phenyl)amino)-3,6,9,12,15-pentaoxaoctadecan-18-oic acid;

8-((3-acetamido-4-((4-methyl-5-nitrothiazol-2-yl)carbamoyl)phenyl)amino)octanoic acid;

9-((3-acetamido-4-((4-methyl-5-nitrothiazol-2-yl)carbamoyl)phenyl)amino)nonanoic acid;

4-((2-(2-(2-aminoethoxy)ethoxy)ethyl)amino)-2-methyl-N-(5-nitrothiazol-2-yl)benzamide;

4-((14-amino-3,6,9,12-tetraoxatetradecyl)amino)-2-methyl-N-(5-nitrothiazol-2-yl)benzamide;

4-((17-amino-3,6,9,12,15-pentaoxaheptadecyl)amino)-2-methyl-N-(5-nitrothiazol-2-yl)benzamide;

4-((20-amino-3,6,9,12,15,18-hexaoxaicosyl)amino)-2-methyl-N-(5-nitrothiazol-2-yl)benzamide;

4-((2-((4-methyl-5-nitrothiazol-2-yl)carbamoyl)phenyl)amino)-4-oxobutanoic acid;

5-((2-((4-methyl-5-nitrothiazol-2-yl)carbamoyl)phenyl)amino)-5-oxopentanoic acid;

6-((2-((4-methyl-5-nitrothiazol-2-yl)carbamoyl)phenyl)amino)-6-oxohexanoic acid;

7-((2-((4-methyl-5-nitrothiazol-2-yl)carbamoyl)phenyl)amino)-7-oxoheptanoic acid;

8-((2-((4-methyl-5-nitrothiazol-2-yl)carbamoyl)phenyl)amino)-8-oxooctanoic acid;

9-((2-((4-methyl-5-nitrothiazol-2-yl)carbamoyl)phenyl)amino)-9-oxononanoic acid;

10-((2-((4-methyl-5-nitrothiazol-2-yl)carbamoyl)phenyl)amino)-10-oxodecanoic acid;

11-((2-((4-methyl-5-nitrothiazol-2-yl)carbamoyl)phenyl)amino)-11-oxoundecanoic acid;

12-((2-((4-methyl-5-nitrothiazol-2-yl)carbamoyl)phenyl)amino)-12-oxododecanoic acid;

13-((2-((4-methyl-5-nitrothiazol-2-yl)carbamoyl)phenyl)amino)-13-oxotridecanoic acid;

3-(3-((2-((4-methyl-5-nitrothiazol-2-yl)carbamoyl)phenyl)amino)-3-oxopropoxy)propanoic acid;

3-(2-(3-((2-((4-methyl-5-nitrothiazol-2-yl)carbamoyl)phenyl)amino)-3-oxopropoxy) ethoxy)propanoic acid;

3-(2-(2-(3-((2-((4-methyl-5-nitrothiazol-2-yl)carbamoyl)phenyl)amino)-3-oxopropoxy) ethoxy)ethoxy)propanoic acid;

16-((2-((4-methyl-5-nitrothiazol-2-yl)carbamoyl)phenyl)amino)-16-oxo-4,7,10,13-tetraoxahexadecanoic acid;

19-((2-((4-methyl-5-nitrothiazol-2-yl)carbamoyl)phenyl)amino)-19-oxo-4,7,10, 13, 16-pentaoxanonadecanoic acid;

2-(2-aminoacetamido)-N-(4-methyl-5-nitrothiazol-2-yl)benzamide;

2-(3-aminopropanamido)-N-(4-methyl-5-nitrothiazol-2-yl)benzamide;

2-(4-aminobutanamido)-N-(4-methyl-5-nitrothiazol-2-yl)benzamide;

2-(5-aminopentanamido)-N-(4-methyl-5-nitrothiazol-2-yl)benzamide;

2-(7-aminoheptanamido)-N-(4-methyl-5-nitrothiazol-2-yl)benzamide;

2-(8-aminooctanamido)-N-(4-methyl-5-nitrothiazol-2-yl)benzamide;

2-(9-aminononanamido)-N-(4-methyl-5-nitrothiazol-2-yl)benzamide;

2-(10-aminodecanamido)-N-(4-methyl-5-nitrothiazol-2-yl)benzamide;

2-(11-aminoundecanamido)-N-(4-methyl-5-nitrothiazol-2-yl)benzamide;

2-(3-(2-aminoethoxy) propanamido)-N-(4-methyl-5-nitrothiazol-2-yl)benzamide;

2-(3-(2-(2-aminoethoxy)ethoxy) propanamido)-N-(4-methyl-5-nitrothiazol-2-yl)benzamide;

1-amino-N-(2-((4-methyl-5-nitrothiazol-2-yl)carbamoyl)phenyl)-3,6,9,12-tetraoxapentadecan-15-amide; and 1-amino-N-(2-((4-methyl-5-nitrothiazol-2-yl)carbamoyl)phenyl)-3,6,9,12,15-pentaoxaoctadecan-18-amide;

or a pharmaceutically acceptable salt thereof.

19. A heterobifunctional compound selected from the group consisting of:

2-acetamido-4-((2-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)ethyl)amino)-N-(4-methyl-5-nitrothiazol-2-yl)benzamide;

2-acetamido-4-((4-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)butyl)amino)-N-(4-methyl-5-nitrothiazol-2-yl)benzamide;

2-acetamido-4-((6-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)hexyl)amino)-N-(4-methyl-5-nitrothiazol-2-yl)benzamide;

2-acetamido-4-((7-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)heptyl)amino)-N-(4-methyl-5-nitrothiazol-2-yl)benzamide;

2-acetamido-4-((8-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)octyl)amino)-N-(4-methyl-5-nitrothiazol-2-yl)benzamide;

2-acetamido-4-((10-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)decyl)amino)-N-(4-methyl-5-nitrothiazol-2-yl)benzamide;

2-acetamido-4-((2-(2-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)ethoxy)ethyl)amino)-N-(4-methyl-5-nitrothiazol-2-yl)benzamide;

2-acetamido-4-((2-(2-(2-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)ethoxy)ethoxy)ethyl)amino)-N-(4-methyl-5-nitrothiazol-2-yl)benzamide;

2-acetamido-4-((1-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)-2-oxo-6,9,12-trioxa-3-azatetradecan-14-yl)amino)-N-(4-methyl-5-nitrothiazol-2-yl)benzamide;

2-acetamido-4-((1-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)-2-oxo-6,9,12,15-tetraoxa-3-azaheptadecan-17-yl)amino)-N-(4-methyl-5-nitrothiazol-2-yl)benzamide;

2-acetamido-4-((1-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)-2-oxo-6,9,12,15,18-pentaoxa-3-azaicosan-20-yl)amino)-N-(4-methyl-5-nitrothiazol-2-yl)benzamide;

2-acetamido-4-((1-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)-2-oxo-6,9,12,15,18,21-hexaoxa-3-azatricosan-23-yl)amino)-N-(4-methyl-5-nitrothiazol-2-yl)benzamide; and 2-acetamido-4-((4-(2-(4-(5-acetyl-3-(7-(difluoromethyl)-6-(1-methyl-1H-pyrazol-4-yl)-3,4-dihydroquinolin-1(2H)-yl)-4,5,6,7-tetrahydro-1H-pyrazolo[4,3-c]pyridin-1-yl)piperidin-1-yl)acetamido)butyl)amino)-N-(5-nitrothiophen-2-yl)benzamide;

or a pharmaceutically acceptable salt thereof.

20. A pharmaceutical composition comprising the ligand of claim 1, or a pharmaceutically acceptable salt thereof, and a pharmaceutically acceptable excipient.

* * * * *